US007167802B2

(12) United States Patent
Parris et al.

(10) Patent No.: US 7,167,802 B2
(45) Date of Patent: Jan. 23, 2007

(54) METHODS FOR IDENTIFYING AGENTS THAT INTERACT WITH MAP KINASE ACTIVATED PROTEIN KINASE 2

(75) Inventors: Kevin D. Parris, Auburndale, MA (US); Kathryn W. Underwood, Quincy, MA (US); Mark L. Stahl, Lexington, MA (US); Lidia Mosyak, Newton, MA (US); Kristine Svenson, Andover, MA (US); Tania Shane, Newton, MA (US); Meggin L. Taylor, Wakefield, MA (US)

(73) Assignee: Wyeth, Madison, NJ (US)

( * ) Notice: Subject to any disclaimer, the term of this patent is extended or adjusted under 35 U.S.C. 154(b) by 317 days.

(21) Appl. No.: 10/294,027

(22) Filed: Nov. 13, 2002

(65) Prior Publication Data

US 2004/0091872 A1 May 13, 2004

(51) Int. Cl.
*G06F 19/00* (2006.01)
(52) U.S. Cl. ...................................... 702/27
(58) Field of Classification Search .................. 702/27
See application file for complete search history.

(56) References Cited

U.S. PATENT DOCUMENTS 6,820,011 B2 * 11/2004 Chen et al. .................... 702/19

FOREIGN PATENT DOCUMENTS

WO  WO 03/048340  6/2003
WO  WO 03/076333  9/2003

OTHER PUBLICATIONS

Meng, Wuyi, et al., entitled "Structure of Mitogen-activated Protein Kinase-activated Protein (MAPKAP) Kinase 2 Suggests a Bifunctional Switch That Couples Kinase Activation with Nuclear Export," The Journal of Biological Chemistry, vol. 277, No. 40 Issue of Oct. 4, pp. 37401-37405, 2002. Published JBC papers in press, Aug. 8, 2002.
Ben-Levy, R., Hooper, S., Wilson, R., Paterson, H.F., Marshall, C.J. (1998) Nuclear export of the stress-activated protein kinase p38 mediated by its substrate MAPKAP kinase-2. *Curr. Biol.* 8, 1049-1057.
Ben-Levy, R., Leighton, I., Doza, Y., Attwood, P., Morrice, N., Marshall, C., Cohen, P. (1995) Identification of novel phosphorylation sites required for activation of MAPKAP kinase-2. *EMBO J.* 14, 5920-5930.
Clifton, A.D., Young, P.R., Cohen, P. (1996) A comparison of the substrate specificity of MAPKAP kinase-2 and MAPKAP kinase-3 and their activation by cytokines and cellular stress. *FEBS Letters* 392, 209-214.
Cuenda, A., Rouse, J., Doza, Y.N., Meier, R., Cohen, P., Gallagher, T.F., Young, P.R., Lee, J.C. (1995) SB 203580 is a specific inhibitor of a MAP kinase homologue which is stimulated by cellular stresses and interleukin-1. *FEBS Letters* 364, 229-233.

Engel, K., Kotlyarov, A., Gaestel, M. (1998) Leptomycin B-sensitive nuclear export of MAPKAP kinase 2 is regulated by phosphorylation. *EMBO J.* 17, 3363-3371.
Engel, K., Plath, K., Gaestel, M. (1993) The MAP kinase-activated protein kinase 2 contains a proline-rich SH3-binding domain. *FEBS Letters* 336, 143-147.
Engel, K., Schultz, H., Martin, F., Kotlyarov, A., Plath, K., Hahn, M., Heinemann, U., Gaestel, M. (1995) Constitutive Activation of Mitogen-activated Protein Kinase-activated Protein Kinase 2 by Mutation of Phosphorylation Sites and an A-helix Motif. *J. Biol. Chem.* 270, 27213-27221.
Goldberg, J., Nairn, A.C., Kuriyan, J. (1996) Structural basis for the autoinhibition of calcium/calmodulin-dependent protein kinase I. *Cell* 84, 875-87.
Hedges, J.C., Dechert, M.A., Yamboliev, I.A., Martin, J.L., Hickey, E., Weber, L.A., Gerthoffer, W.T. (1999) A Role for p38MAPK/HSP27 Pathway in Smooth Muscle Cell Migration. *J. Biol. Chem.* 274, 24211-24219.
Huse, M., Kuriyan, J. (2002) The Conformational Plasticity of Protein Kinase. *Cell* 109, 275-282.
Johnson, L.N., Noble, M.E.M., Owen, D.J. (1996) Active and Inactive Protein Kinases: Structural Basis for Regulation. *Cell* 85, 149-158.
Komatsu, S., Murai, N., Totsukawa, G., Abe, M., Akasaka, K., Shimada, H., Hosoya, H. (1997) Identification of MAPKAPK homolog (MAPKAPK-4) as a myosin II regulatory light-chain kinase in sea urchin egg extracts. Arch. *Biochem. Biophys.* 343, 55-62.
Kotlyarov, A., Neininger, A., Schubert, C., Eckert, R., Birchmeier, C., Volk, H.-D., Gaestel, M. (1999) MAPKAP kinase 2 is essential for LPS-induced TNF- biosynthesis. *Nat. Cell. Biol.* 1, 94-97.
Kotlyarov, A., Yannoni, Y., Fritz, S., Laass, K., Telliez, J.-B., Pitman, D., Lin, L.-L., Gaestel, M. (2002) Distinct Cellular Function of MK2. *Mol. Cell Biol.* 22, 4827-4835.
Lavoie, J., Hickey, E., Weber, L., Landry, J. (1993) Modulation of actin microfilament dynamics and fluid phase pinocytosis by phosphorylation of heat shock protein 27. *J. Biol. Chem.* 268, 24210-24214.
Lee, J.C., Laydon, J.T., McDonnel, P.C., Gallagher, T.F., Kumar, S., Green, D., McNulty, D., Blumenthal, M.J., Heys, J.R., Landvatter, S.W., et al. (1994) A protein kinase involved in the regulation of inflammatory cytokine biosynthesis. *Nature* 372, 739-746.
Mayans, O., van der Ven, P.F.M., Wilm, M., Mues, A., Young, P., Furst, D.O., Wilmanns, M., Gautel, M. (1998) Structural basis for activation of the titin kinase domain during myofibrillogenesis. *Nature* 395, 863-869.
McLaughlin, M.M., Kumar, S., McDonnell, P.C., Van Horn, S., Lee, J.C., Livi, G.P., Young, P.R. (1996) Identification of Mitogen-activated Protein (MAP) Kinase-activated Protein Kinase-3, a Novel Substrate of CSBP p38 MAP Kinase. *J. Biol. Chem.* 271, 8488-8492.
Neininger, A., Kontoyiannis, D., Kotlyarov, A., Winzen, R., Eckert, R., Volk, H.-D., Holtmann, H., Kollias, G., Gaestel, M. (2002) MK2 Targets AU-rich Elements and Regulates Biosynthesis of Tumor Necrosis Factor and Interleukin-6 Independently at Different Post-transcriptional Levels. *J. Biol. Chem.* 277, 3065-3068.

(Continued)

*Primary Examiner*—Andrew Wang
*Assistant Examiner*—Pablo Whaley
(74) *Attorney, Agent, or Firm*—Fish & Richardson P.C.

(57) ABSTRACT

This invention is directed to the crystal structures of MK2, and to the use of these structures in rational drug design methods to identify agents that may interact with active sites of MK2 proteins. Such agents may be useful as therapeutic agents.

18 Claims, 249 Drawing Sheets

OTHER PUBLICATIONS

Ni, H., Wang, X.S., Diener, K., Yao, Z. (1998) MAPKAPK5, a Novel Mitogen-Activated Protein Kinase (MAPK)-Activated Protein Kinase, Is a Substrate of the Extracellular-Regulated Kinase (ERK) and p38 Kinase. *Biochem. Biophys. Res. Commun.* 243, 492-496.

Prade, L., Engh, R.A., Girod, A., Kinzel, V., Huber, R., Bossemeyer, D. (1997) Staurosporine-induced conformational changes of cAMP-dependent protein kinase catalytic subunit explain inhibitory potential. *Structure* 5, 1627-37.

Stokoe, D., Campbell, D., Nakielny, S., Hidaka, H., Leevers, S., Marshall, C., Cohen, P. (1992) MAPKAP kinase-2; a novel protein kinase activated by mitogen-activated protein kinase. *EMBO J.* 11, 3985-3994.

Stokoe, D., Caudwell, B., Cohen, P.T., Cohen, P. (1993) The substrate specificity and structure of mitogen-activated protein (MAP) kinase-activated protein kinase-2. *Biochem. J* 296, 843-849.

Stokoe, D., Engel, K., Campbell, D.G., Cohen, P., Gaestel, M. (1992) Identification of MAPKAP kinase 2 as a major enzyme responsible for the phosphorylation of the small mammalian heat shock proteins. *FEBS Letters* 313, 307-313.

Tan, Y., Rouse, J., Zhang, A., Cariati, S., Cohen, P., Comb, M. (1996) FGF and stress regulate CREB and ATF-1 via a pathway involving p38 MAP kinase and MAPKAP kinase-2. *EMBO J.* 15, 4629-4642.

Tanoue, T., Adachi, M. Moriguchi, T., Nishida, E. (2000) A conserved docking motif in MAP kinases common to substrates, activators and regulators. *Nat. Cell. Biol.* 2, 110-116.

Veron, M., Radzio-Andzelm, E., Tsigelny, I., Eyck, L., Taylor, S. (1993) A Conserved Helix Motif Complements the Protein Kinase Core. *Proc. Natl. Acad. Sci.* 90, 10618-10622.

Zheng, J.H., Trafny, E.A., Knighton, D.R., Xuong, N.H., Taylor, S.S., Teneyck, L.F., Sowadski, J.M. (1993) Crystal structure of the catalytic subunit of cAMP-dependent protein kinase complexed with magnesium-ATP and peptide inhibitor. *Biochemistry* 32, 2154-61.

Zu, Y.-L., Wu, F., Gilchrist, A., Ai, Y., Labadia, M.E., Huang, C.-K. (1994) The Primary Structure of a Human MAP Kinase Activated Protein Kinase 2. *Biochem. Biophys. Res. Commun.* 200, 1118-1124.

\* cited by examiner

FIGURE 1

```
MK2   1   MLSNSQGQSP PVPFPAPAPP PQPPTPALPH PPAQPPPPPP QQFPQFHVKS
MK3   1   -MDGETAEEQ GGPVPPPVAP GGPGLGGAPG GRREP----- ----------
MK5   1   -MS-EESDMD K--------- ---------- ---------- -------AI-

MK2  51   GLQIKKNAII DDYKVT-SQV LGLGINGKVL QIFNKRTQEK FALKMLQDCP
MK3  34   ----KKYKVT DDYQLS-KQV LGLGVNGKVL ECFHRRTGQK CALKLLYDSP
MK5  11   ----KETSIL EEYSINWTQK LGAGISGPVR VCVKKSTQER FALKILLDRP

MK2 100   KARREVELHW RASQCPHIVR IVDVYEN--- ---LYAGRKC LLIVMECLDG
MK3  80   KARQEVDHHW QASGGPHIVC ILDVYEN--- ---MHHGKRC LLIIMECMEG
MK5  58   KARNEVRLHM MCATHPNIVQ IIEVFANSVQ FPHESSPRAR LLIVMEMMEG

MK2 144   GELFSRIQDR GDQAFTEREA SEIMKSIGEA IQYLHSINIA HRDVKPENLL
MK3 124   GELFSRIQER GDQAFTEREA AEIMRDIGTA IQFLHSHNIA HRDVKPENLL
MK5 108   GELFHRISQH --RHFTEKQA SQVTKQIALA LRHCHLLNIA HRDLKPENLL

MK2 194   YTSKRPNAIL KLTDFGFAKE TTSHNSLTTP CYTPYYVAPE VLGPEK----
MK3 174   YTSKEKDAVL KLTDFGFAKE TT-QNALQTP CYTPYYVAPE VLGPEK----
MK5 156   FKDNSLDAPV KLCDFGFAKI DQ--GDLMTP QFTPYYVAPQ VLEAQRRHQK

MK2 239   ---------- ----YDKSCD MWSLGVIMYI LLCGYPPFYS NHG-LAISPG
MK3 218   ---------- ----YDKSCD MWSLGVIMYI LLCGFPPFYS NTG-QAISPG
MK5 204   EKSGIIPTSP TPYTYNKSCD LWSLGVIIYV MLCGYPPFYS KHHSRTIPKD

MK2 275   MKTRIRMGQY EFPNPEWSEV SEEVKMLIRN LLKTEPTQRM TITEFMNHPW
MK3 254   MKRRIRLGQY GFPNPEWSEV SEDAKQLIRL LLKTDPTERL TITQFMNHPW
MK5 254   MRRKIMTGSF EFPEEEWSQI SEMAKDVVRK LLKVKPEERL TIEGVLDHPW

MK2 325   IMQSTKVPQT PLHTSRVLKE DKERWEDVKE EMTSALATMR VDYEQIKIKK
MK3 304   INQSMVVPQT PLHTARVLQE DKDHWDEVKE EMTSALATMR VDYDQVKIKD
MK5 304   LNSTEALDN- -VLPSAQLMM DKAVVAGIQQ AHAEQLANMR IQDLKVSLKP

MK2 375   IEDASNPLLL KR-------- -----RKKAR ALEAAALAH- ----------
MK3 354   LKTSNNRLLN KR-------- -----RKKQA GSSSASQGCN NQ--------
MK5 352   LHSVNNPILR KRKLLGTKPK DSVYIHDHEN GAEDSNVALE KLRDVIAQCI

MK2 400   ---------- ---------- ---------- ---------- ----------
MK3 382   ---------- ---------- ---------- ---------- ----------
MK5 402   LPQAGKGENE DEKLNEVMQE AWKYNRECKL LRDTLQSFSW NGRGFTDKVD

MK2 400   ---------- ----------  --
MK3 382   ---------- ----------  --
MK5 452   RLKLAEIVKQ VIEEQTTSHE  SQ
```

FIG. 2

|  |  | Atom Type | Res. | Mol. | Res. No. | X | Y | Z | OCC | B |  |
|---|---|---|---|---|---|---|---|---|---|---|---|
| ATOM | 1 | N | GLN | A | 42 | 103.342 | -4.478 | 31.810 | 1.00 | 83.90 | N |
| ATOM | 2 | CA | GLN | A | 42 | 103.732 | -3.298 | 31.046 | 1.00 | 83.00 | C |
| ATOM | 3 | CB | GLN | A | 42 | 103.053 | -3.373 | 29.679 | 1.00 | 84.44 | C |
| ATOM | 4 | CG | GLN | A | 42 | 102.455 | -2.030 | 29.255 | 1.00 | 87.23 | C |
| ATOM | 5 | CD | GLN | A | 42 | 102.751 | -1.781 | 27.796 | 1.00 | 99.12 | C |
| ATOM | 6 | OE1 | GLN | A | 42 | 103.106 | -0.696 | 27.363 | 1.00 | 103.07 | O |
| ATOM | 7 | NE2 | GLN | A | 42 | 102.566 | -2.864 | 27.014 | 1.00 | 101.31 | N |
| ATOM | 8 | C | GLN | A | 42 | 103.315 | -2.010 | 31.762 | 1.00 | 80.05 | C |
| ATOM | 9 | O | GLN | A | 42 | 103.711 | -0.906 | 31.410 | 1.00 | 81.72 | O |
| ATOM | 10 | N | PHE | A | 43 | 102.465 | -2.188 | 32.787 | 1.00 | 73.10 | N |
| ATOM | 11 | CA | PHE | A | 43 | 101.892 | -1.041 | 33.486 | 1.00 | 66.71 | C |
| ATOM | 12 | CB | PHE | A | 43 | 100.616 | -1.533 | 34.172 | 1.00 | 65.82 | C |
| ATOM | 13 | CG | PHE | A | 43 | 99.888 | -0.397 | 34.826 | 1.00 | 63.46 | C |
| ATOM | 14 | CD1 | PHE | A | 43 | 99.133 | 0.473 | 34.047 | 1.00 | 62.52 | C |
| ATOM | 15 | CE1 | PHE | A | 43 | 98.255 | 1.356 | 34.656 | 1.00 | 62.52 | C |
| ATOM | 16 | CZ | PHE | A | 43 | 98.130 | 1.381 | 36.038 | 1.00 | 60.07 | C |
| ATOM | 17 | CE2 | PHE | A | 43 | 98.904 | 0.525 | 36.809 | 1.00 | 59.63 | C |
| ATOM | 18 | CD2 | PHE | A | 43 | 99.789 | -0.361 | 36.206 | 1.00 | 61.05 | C |
| ATOM | 19 | C | PHE | A | 43 | 102.859 | -0.452 | 34.521 | 1.00 | 63.59 | C |
| ATOM | 20 | O | PHE | A | 43 | 103.620 | -1.153 | 35.176 | 1.00 | 63.03 | O |
| ATOM | 21 | N | PRO | A | 44 | 102.837 | 0.892 | 34.618 | 1.00 | 60.33 | N |
| ATOM | 22 | CA | PRO | A | 44 | 103.723 | 1.620 | 35.519 | 1.00 | 56.96 | C |
| ATOM | 23 | CB | PRO | A | 44 | 103.732 | 3.077 | 35.060 | 1.00 | 56.42 | C |
| ATOM | 24 | CG | PRO | A | 44 | 102.466 | 3.318 | 34.243 | 1.00 | 58.10 | C |
| ATOM | 25 | CD | PRO | A | 44 | 101.999 | 1.828 | 33.885 | 1.00 | 60.41 | C |
| ATOM | 26 | C | PRO | A | 44 | 103.267 | 1.534 | 36.982 | 1.00 | 54.28 | C |
| ATOM | 27 | O | PRO | A | 44 | 103.035 | 2.538 | 37.644 | 1.00 | 55.12 | O |
| ATOM | 28 | N | GLN | A | 45 | 103.053 | 0.263 | 37.355 | 1.00 | 50.50 | N |
| ATOM | 29 | CA | GLN | A | 45 | 102.599 | -0.003 | 38.711 | 1.00 | 46.92 | C |
| ATOM | 30 | CB | GLN | A | 45 | 102.598 | -1.516 | 38.933 | 1.00 | 47.23 | C |
| ATOM | 31 | CG | GLN | A | 45 | 101.239 | -2.035 | 39.406 | 1.00 | 47.17 | C |
| ATOM | 32 | CD | GLN | A | 45 | 101.057 | -3.466 | 38.956 | 1.00 | 46.13 | C |
| ATOM | 33 | OE1 | GLN | A | 45 | 100.215 | -4.208 | 39.432 | 1.00 | 41.65 | O |
| ATOM | 34 | NE2 | GLN | A | 45 | 101.912 | -3.845 | 37.986 | 1.00 | 49.23 | N |
| ATOM | 35 | C | GLN | A | 45 | 103.502 | 0.682 | 39.738 | 1.00 | 44.74 | C |
| ATOM | 36 | O | GLN | A | 45 | 103.114 | 0.947 | 40.868 | 1.00 | 45.06 | O |
| ATOM | 37 | N | PHE | A | 46 | 104.774 | 0.771 | 39.350 | 1.00 | 43.02 | N |
| ATOM | 38 | CA | PHE | A | 46 | 105.831 | 1.205 | 40.256 | 1.00 | 40.94 | C |
| ATOM | 39 | CB | PHE | A | 46 | 107.227 | 1.013 | 39.648 | 1.00 | 40.94 | C |
| ATOM | 40 | CG | PHE | A | 46 | 107.473 | 1.830 | 38.406 | 1.00 | 38.62 | C |
| ATOM | 41 | CD1 | PHE | A | 46 | 107.215 | 1.305 | 37.150 | 1.00 | 39.74 | C |
| ATOM | 42 | CE1 | PHE | A | 46 | 107.498 | 2.028 | 35.999 | 1.00 | 42.01 | C |
| ATOM | 43 | CZ | PHE | A | 46 | 108.047 | 3.299 | 36.097 | 1.00 | 41.49 | C |
| ATOM | 44 | CE2 | PHE | A | 46 | 108.301 | 3.836 | 37.337 | 1.00 | 42.85 | C |

FIG. 2A-1

| ATOM | 45 | CD2 | PHE | A | 46 | 108.012 | 3.099 | 38.489 | 1.00 | 40.40 | C |
| --- | --- | --- | --- | --- | --- | --- | --- | --- | --- | --- | --- |
| ATOM | 46 | C | PHE | A | 46 | 105.602 | 2.683 | 40.503 | 1.00 | 40.26 | C |
| ATOM | 47 | O | PHE | A | 46 | 106.278 | 3.297 | 41.312 | 1.00 | 41.33 | O |
| ATOM | 48 | N | HIS | A | 47 | 104.654 | 3.259 | 39.779 | 1.00 | 38.21 | N |
| ATOM | 49 | CA | HIS | A | 47 | 104.356 | 4.656 | 39.986 | 1.00 | 36.87 | C |
| ATOM | 50 | CB | HIS | A | 47 | 104.084 | 5.371 | 38.662 | 1.00 | 36.18 | C |
| ATOM | 51 | CG | HIS | A | 47 | 105.327 | 5.859 | 37.987 | 1.00 | 36.33 | C |
| ATOM | 52 | ND1 | HIS | A | 47 | 106.374 | 6.424 | 38.687 | 1.00 | 37.15 | N |
| ATOM | 53 | CE1 | HIS | A | 47 | 107.317 | 6.783 | 37.838 | 1.00 | 37.62 | C |
| ATOM | 54 | NE2 | HIS | A | 47 | 106.922 | 6.471 | 36.616 | 1.00 | 38.11 | N |
| ATOM | 55 | CD2 | HIS | A | 47 | 105.680 | 5.891 | 36.682 | 1.00 | 35.90 | C |
| ATOM | 56 | C | HIS | A | 47 | 103.162 | 4.786 | 40.892 | 1.00 | 35.48 | C |
| ATOM | 57 | O | HIS | A | 47 | 102.723 | 5.896 | 41.192 | 1.00 | 36.39 | O |
| ATOM | 58 | N | VAL | A | 48 | 102.629 | 3.659 | 41.336 | 1.00 | 32.27 | N |
| ATOM | 59 | CA | VAL | A | 48 | 101.474 | 3.724 | 42.200 | 1.00 | 29.83 | C |
| ATOM | 60 | CB | VAL | A | 48 | 100.457 | 2.623 | 41.919 | 1.00 | 28.67 | C |
| ATOM | 61 | CG1 | VAL | A | 48 | 99.470 | 2.532 | 43.060 | 1.00 | 24.67 | C |
| ATOM | 62 | CG2 | VAL | A | 48 | 99.729 | 2.936 | 40.645 | 1.00 | 29.20 | C |
| ATOM | 63 | C | VAL | A | 48 | 101.887 | 3.604 | 43.620 | 1.00 | 30.06 | C |
| ATOM | 64 | O | VAL | A | 48 | 102.465 | 2.592 | 44.008 | 1.00 | 30.90 | O |
| ATOM | 65 | N | LYS | A | 49 | 101.585 | 4.640 | 44.399 | 1.00 | 29.52 | N |
| ATOM | 66 | CA | LYS | A | 49 | 101.889 | 4.728 | 45.827 | 1.00 | 29.87 | C |
| ATOM | 67 | CB | LYS | A | 49 | 102.905 | 5.851 | 46.042 | 1.00 | 30.94 | C |
| ATOM | 68 | CG | LYS | A | 49 | 103.057 | 6.239 | 47.518 | 1.00 | 43.43 | C |
| ATOM | 69 | CD | LYS | A | 49 | 104.209 | 7.227 | 47.732 | 1.00 | 51.12 | C |
| ATOM | 70 | CE | LYS | A | 49 | 104.229 | 7.848 | 49.131 | 1.00 | 49.24 | C |
| ATOM | 71 | NZ | LYS | A | 49 | 105.365 | 8.763 | 49.238 | 1.00 | 47.47 | N |
| ATOM | 72 | C | LYS | A | 49 | 100.642 | 4.993 | 46.676 | 1.00 | 27.58 | C |
| ATOM | 73 | O | LYS | A | 49 | 99.678 | 5.617 | 46.251 | 1.00 | 28.13 | O |
| ATOM | 74 | N | SER | A | 50 | 100.676 | 4.451 | 47.905 | 1.00 | 25.19 | N |
| ATOM | 75 | CA | SER | A | 50 | 99.532 | 4.601 | 48.785 | 1.00 | 26.74 | C |
| ATOM | 76 | CB | SER | A | 50 | 99.757 | 3.706 | 50.004 | 1.00 | 25.06 | C |
| ATOM | 77 | OG | SER | A | 50 | 100.846 | 4.217 | 50.769 | 1.00 | 29.02 | O |
| ATOM | 78 | C | SER | A | 50 | 99.328 | 6.052 | 49.237 | 1.00 | 26.64 | C |
| ATOM | 79 | O | SER | A | 50 | 100.257 | 6.839 | 49.357 | 1.00 | 26.58 | O |
| ATOM | 80 | N | GLY | A | 51 | 98.050 | 6.410 | 49.446 | 1.00 | 26.18 | N |
| ATOM | 81 | CA | GLY | A | 51 | 97.761 | 7.710 | 50.030 | 1.00 | 25.75 | C |
| ATOM | 82 | C | GLY | A | 51 | 98.083 | 7.710 | 51.525 | 1.00 | 25.11 | C |
| ATOM | 83 | O | GLY | A | 51 | 98.614 | 6.754 | 52.078 | 1.00 | 23.55 | O |
| ATOM | 84 | N | LEU | A | 52 | 97.843 | 8.821 | 52.218 | 1.00 | 25.42 | N |
| ATOM | 85 | CA | LEU | A | 52 | 98.194 | 8.955 | 53.625 | 1.00 | 25.43 | C |
| ATOM | 86 | CB | LEU | A | 52 | 98.797 | 10.329 | 53.862 | 1.00 | 24.62 | C |
| ATOM | 87 | CG | LEU | A | 52 | 98.955 | 10.746 | 55.324 | 1.00 | 30.89 | C |
| ATOM | 88 | CD1 | LEU | A | 52 | 100.084 | 9.930 | 55.966 | 1.00 | 32.12 | C |
| ATOM | 89 | CD2 | LEU | A | 52 | 99.258 | 12.220 | 55.402 | 1.00 | 25.99 | C |
| ATOM | 90 | C | LEU | A | 52 | 96.987 | 8.804 | 54.535 | 1.00 | 27.08 | C |

FIG. 2A-2

| | | | | | | | | | |
|---|---|---|---|---|---|---|---|---|---|
| ATOM | 91 | O | LEU | A | 52 | 96.110 | 9.662 | 54.498 | 1.00 | 28.74 | O |
| ATOM | 92 | N | GLN | A | 53 | 96.927 | 7.733 | 55.336 | 1.00 | 28.31 | N |
| ATOM | 93 | CA | GLN | A | 53 | 95.808 | 7.543 | 56.268 | 1.00 | 30.13 | C |
| ATOM | 94 | CB | GLN | A | 53 | 95.481 | 6.056 | 56.431 | 1.00 | 31.33 | C |
| ATOM | 95 | CG | GLN | A | 53 | 94.448 | 5.705 | 57.518 | 1.00 | 33.15 | C |
| ATOM | 96 | CD | GLN | A | 53 | 93.029 | 6.200 | 57.204 | 1.00 | 42.41 | C |
| ATOM | 97 | OE1 | GLN | A | 53 | 92.450 | 5.888 | 56.154 | 1.00 | 44.13 | O |
| ATOM | 98 | NE2 | GLN | A | 53 | 92.459 | 6.965 | 58.129 | 1.00 | 46.23 | N |
| ATOM | 99 | C | GLN | A | 53 | 96.191 | 8.144 | 57.628 | 1.00 | 30.94 | C |
| ATOM | 100 | O | GLN | A | 53 | 97.117 | 7.680 | 58.294 | 1.00 | 30.42 | O |
| ATOM | 101 | N | ILE | A | 54 | 95.467 | 9.187 | 58.022 | 1.00 | 31.07 | N |
| ATOM | 102 | CA | ILE | A | 54 | 95.705 | 9.894 | 59.272 | 1.00 | 30.99 | C |
| ATOM | 103 | CB | ILE | A | 54 | 95.082 | 11.300 | 59.182 | 1.00 | 32.10 | C |
| ATOM | 104 | CG1 | ILE | A | 54 | 95.782 | 12.070 | 58.054 | 1.00 | 31.12 | C |
| ATOM | 105 | CD1 | ILE | A | 54 | 95.246 | 13.440 | 57.793 | 1.00 | 34.97 | C |
| ATOM | 106 | CG2 | ILE | A | 54 | 95.195 | 12.020 | 60.506 | 1.00 | 30.55 | C |
| ATOM | 107 | C | ILE | A | 54 | 95.104 | 9.149 | 60.440 | 1.00 | 31.18 | C |
| ATOM | 108 | O | ILE | A | 54 | 93.923 | 8.852 | 60.406 | 1.00 | 33.98 | O |
| ATOM | 109 | N | LYS | A | 55 | 95.893 | 8.852 | 61.473 | 1.00 | 29.56 | N |
| ATOM | 110 | CA | LYS | A | 55 | 95.381 | 8.123 | 62.624 | 1.00 | 29.27 | C |
| ATOM | 111 | CB | LYS | A | 55 | 96.485 | 7.393 | 63.309 | 1.00 | 30.75 | C |
| ATOM | 112 | CG | LYS | A | 55 | 96.986 | 6.291 | 62.488 | 1.00 | 36.06 | C |
| ATOM | 113 | CD | LYS | A | 55 | 98.061 | 5.547 | 63.198 | 1.00 | 41.89 | C |
| ATOM | 114 | CE | LYS | A | 55 | 98.501 | 4.474 | 62.318 | 1.00 | 52.94 | C |
| ATOM | 115 | NZ | LYS | A | 55 | 99.554 | 3.760 | 63.036 | 1.00 | 59.15 | N |
| ATOM | 116 | C | LYS | A | 55 | 94.751 | 9.040 | 63.637 | 1.00 | 28.71 | C |
| ATOM | 117 | O | LYS | A | 55 | 95.256 | 10.131 | 63.874 | 1.00 | 28.12 | O |
| ATOM | 118 | N | LYS | A | 56 | 93.656 | 8.593 | 64.250 | 1.00 | 28.22 | N |
| ATOM | 119 | CA | LYS | A | 56 | 92.988 | 9.408 | 65.242 | 1.00 | 26.02 | C |
| ATOM | 120 | CB | LYS | A | 56 | 91.490 | 9.277 | 65.120 | 1.00 | 26.93 | C |
| ATOM | 121 | CG | LYS | A | 56 | 90.992 | 9.466 | 63.733 | 1.00 | 29.70 | C |
| ATOM | 122 | CD | LYS | A | 56 | 91.263 | 10.858 | 63.240 | 1.00 | 31.17 | C |
| ATOM | 123 | CE | LYS | A | 56 | 90.457 | 11.107 | 61.976 | 1.00 | 33.99 | C |
| ATOM | 124 | NZ | LYS | A | 56 | 90.534 | 12.527 | 61.551 | 1.00 | 40.40 | N |
| ATOM | 125 | C | LYS | A | 56 | 93.390 | 9.006 | 66.639 | 1.00 | 24.60 | C |
| ATOM | 126 | O | LYS | A | 56 | 93.275 | 9.811 | 67.583 | 1.00 | 27.04 | O |
| ATOM | 127 | N | ASN | A | 57 | 93.895 | 7.783 | 66.813 | 1.00 | 21.92 | N |
| ATOM | 128 | CA | ASN | A | 57 | 94.247 | 7.426 | 68.173 | 1.00 | 20.94 | C |
| ATOM | 129 | CB | ASN | A | 57 | 94.684 | 5.981 | 68.248 | 1.00 | 20.31 | C |
| ATOM | 130 | CG | ASN | A | 57 | 96.018 | 5.753 | 67.668 | 1.00 | 22.66 | C |
| ATOM | 131 | OD1 | ASN | A | 57 | 96.173 | 5.839 | 66.470 | 1.00 | 32.54 | O |
| ATOM | 132 | ND2 | ASN | A | 57 | 97.009 | 5.450 | 68.504 | 1.00 | 19.88 | N |
| ATOM | 133 | C | ASN | A | 57 | 95.283 | 8.376 | 68.809 | 1.00 | 19.43 | C |
| ATOM | 134 | O | ASN | A | 57 | 96.103 | 8.962 | 68.146 | 1.00 | 18.22 | O |
| ATOM | 135 | N | ALA | A | 58 | 95.219 | 8.560 | 70.106 | 1.00 | 20.01 | N |
| ATOM | 136 | CA | ALA | A | 58 | 96.182 | 9.456 | 70.720 | 1.00 | 20.84 | C |

FIG. 2A-3

| ATOM | 137 | CB | ALA | A | 58 | 95.992 | 9.503 | 72.219 | 1.00 | 18.95 | C |
|---|---|---|---|---|---|---|---|---|---|---|---|
| ATOM | 138 | C | ALA | A | 58 | 97.585 | 8.994 | 70.395 | 1.00 | 20.82 | C |
| ATOM | 139 | O | ALA | A | 58 | 97.911 | 7.832 | 70.536 | 1.00 | 23.61 | O |
| ATOM | 140 | N | ILE | A | 59 | 98.416 | 9.925 | 69.953 | 1.00 | 17.79 | N |
| ATOM | 141 | CA | ILE | A | 59 | 99.781 | 9.605 | 69.626 | 1.00 | 17.84 | C |
| ATOM | 142 | CB | ILE | A | 59 | 100.515 | 10.882 | 69.118 | 1.00 | 19.61 | C |
| ATOM | 143 | CG1 | ILE | A | 59 | 101.861 | 10.488 | 68.468 | 1.00 | 15.39 | C |
| ATOM | 144 | CD1 | ILE | A | 59 | 102.557 | 11.622 | 67.747 | 1.00 | 15.32 | C |
| ATOM | 145 | CG2 | ILE | A | 59 | 100.688 | 11.906 | 70.299 | 1.00 | 13.34 | C |
| ATOM | 146 | C | ILE | A | 59 | 100.495 | 9.025 | 70.883 | 1.00 | 20.98 | C |
| ATOM | 147 | O | ILE | A | 59 | 101.416 | 8.199 | 70.771 | 1.00 | 22.84 | O |
| ATOM | 148 | N | ILE | A | 60 | 100.076 | 9.443 | 72.076 | 1.00 | 20.59 | N |
| ATOM | 149 | CA | ILE | A | 60 | 100.718 | 8.931 | 73.279 | 1.00 | 19.01 | C |
| ATOM | 150 | CB | ILE | A | 60 | 100.270 | 9.706 | 74.530 | 1.00 | 18.89 | C |
| ATOM | 151 | CG1 | ILE | A | 60 | 98.769 | 9.722 | 74.653 | 1.00 | 18.01 | C |
| ATOM | 152 | CD1 | ILE | A | 60 | 98.330 | 10.686 | 75.700 | 1.00 | 15.95 | C |
| ATOM | 153 | CG2 | ILE | A | 60 | 100.748 | 11.140 | 74.456 | 1.00 | 18.65 | C |
| ATOM | 154 | C | ILE | A | 60 | 100.535 | 7.406 | 73.498 | 1.00 | 19.94 | C |
| ATOM | 155 | O | ILE | A | 60 | 101.152 | 6.815 | 74.406 | 1.00 | 19.51 | O |
| ATOM | 156 | N | ASP | A | 61 | 99.716 | 6.766 | 72.661 | 1.00 | 20.95 | N |
| ATOM | 157 | CA | ASP | A | 61 | 99.548 | 5.319 | 72.764 | 1.00 | 23.00 | C |
| ATOM | 158 | CB | ASP | A | 61 | 98.356 | 4.795 | 71.990 | 1.00 | 24.39 | C |
| ATOM | 159 | CG | ASP | A | 61 | 97.051 | 5.275 | 72.522 | 1.00 | 29.70 | C |
| ATOM | 160 | OD1 | ASP | A | 61 | 96.034 | 5.116 | 71.802 | 1.00 | 36.00 | O |
| ATOM | 161 | OD2 | ASP | A | 61 | 97.033 | 5.812 | 73.655 | 1.00 | 33.74 | O |
| ATOM | 162 | C | ASP | A | 61 | 100.734 | 4.677 | 72.113 | 1.00 | 22.47 | C |
| ATOM | 163 | O | ASP | A | 61 | 101.178 | 3.621 | 72.543 | 1.00 | 22.18 | O |
| ATOM | 164 | N | ASP | A | 62 | 101.258 | 5.327 | 71.077 | 1.00 | 21.14 | N |
| ATOM | 165 | CA | ASP | A | 62 | 102.322 | 4.736 | 70.301 | 1.00 | 21.87 | C |
| ATOM | 166 | CB | ASP | A | 62 | 101.977 | 4.843 | 68.830 | 1.00 | 23.17 | C |
| ATOM | 167 | CG | ASP | A | 62 | 100.651 | 4.254 | 68.527 | 1.00 | 26.50 | C |
| ATOM | 168 | OD1 | ASP | A | 62 | 99.972 | 4.730 | 67.610 | 1.00 | 28.51 | O |
| ATOM | 169 | OD2 | ASP | A | 62 | 100.272 | 3.300 | 69.225 | 1.00 | 26.98 | O |
| ATOM | 170 | C | ASP | A | 62 | 103.715 | 5.226 | 70.501 | 1.00 | 21.47 | C |
| ATOM | 171 | O | ASP | A | 62 | 104.676 | 4.540 | 70.116 | 1.00 | 22.04 | O |
| ATOM | 172 | N | TYR | A | 63 | 103.849 | 6.391 | 71.103 | 1.00 | 21.12 | N |
| ATOM | 173 | CA | TYR | A | 63 | 105.175 | 6.923 | 71.298 | 1.00 | 19.62 | C |
| ATOM | 174 | CB | TYR | A | 63 | 105.487 | 8.024 | 70.266 | 1.00 | 20.13 | C |
| ATOM | 175 | CG | TYR | A | 63 | 105.441 | 7.619 | 68.825 | 1.00 | 20.06 | C |
| ATOM | 176 | CD1 | TYR | A | 63 | 106.552 | 7.064 | 68.214 | 1.00 | 22.61 | C |
| ATOM | 177 | CE1 | TYR | A | 63 | 106.504 | 6.632 | 66.922 | 1.00 | 25.72 | C |
| ATOM | 178 | CZ | TYR | A | 63 | 105.340 | 6.744 | 66.227 | 1.00 | 28.78 | C |
| ATOM | 179 | OH | TYR | A | 63 | 105.283 | 6.245 | 64.947 | 1.00 | 32.87 | O |
| ATOM | 180 | CE2 | TYR | A | 63 | 104.216 | 7.298 | 66.806 | 1.00 | 28.81 | C |
| ATOM | 181 | CD2 | TYR | A | 63 | 104.270 | 7.733 | 68.089 | 1.00 | 26.82 | C |
| ATOM | 182 | C | TYR | A | 63 | 105.218 | 7.571 | 72.637 | 1.00 | 19.14 | C |

FIG. 2A-4

| ATOM | 183 | O | TYR | A | 63 | 104.199 | 7.949 | 73.201 | 1.00 | 18.21 | O |
|---|---|---|---|---|---|---|---|---|---|---|---|
| ATOM | 184 | N | LYS | A | 64 | 106.427 | 7.720 | 73.131 | 1.00 | 19.14 | N |
| ATOM | 185 | CA | LYS | A | 64 | 106.632 | 8.418 | 74.362 | 1.00 | 19.65 | C |
| ATOM | 186 | CB | LYS | A | 64 | 107.808 | 7.816 | 75.125 | 1.00 | 18.66 | C |
| ATOM | 187 | CG | LYS | A | 64 | 108.157 | 8.591 | 76.350 | 1.00 | 20.33 | C |
| ATOM | 188 | CD | LYS | A | 64 | 109.520 | 8.235 | 76.844 | 1.00 | 18.73 | C |
| ATOM | 189 | CE | LYS | A | 64 | 109.785 | 9.070 | 78.084 | 1.00 | 23.39 | C |
| ATOM | 190 | NZ | LYS | A | 64 | 111.051 | 8.681 | 78.815 | 1.00 | 28.07 | N |
| ATOM | 191 | C | LYS | A | 64 | 107.014 | 9.767 | 73.763 | 1.00 | 19.58 | C |
| ATOM | 192 | O | LYS | A | 64 | 107.858 | 9.834 | 72.882 | 1.00 | 19.21 | O |
| ATOM | 193 | N | VAL | A | 65 | 106.365 | 10.836 | 74.198 | 1.00 | 20.61 | N |
| ATOM | 194 | CA | VAL | A | 65 | 106.693 | 12.160 | 73.680 | 1.00 | 20.31 | C |
| ATOM | 195 | CB | VAL | A | 65 | 105.421 | 12.948 | 73.265 | 1.00 | 19.70 | C |
| ATOM | 196 | CG1 | VAL | A | 65 | 105.787 | 14.380 | 72.820 | 1.00 | 19.25 | C |
| ATOM | 197 | CG2 | VAL | A | 65 | 104.747 | 12.207 | 72.132 | 1.00 | 14.96 | C |
| ATOM | 198 | C | VAL | A | 65 | 107.483 | 12.944 | 74.712 | 1.00 | 22.65 | C |
| ATOM | 199 | O | VAL | A | 65 | 106.930 | 13.574 | 75.621 | 1.00 | 23.68 | O |
| ATOM | 200 | N | THR | A | 66 | 108.798 | 12.885 | 74.575 | 1.00 | 24.00 | N |
| ATOM | 201 | CA | THR | A | 66 | 109.598 | 13.660 | 75.515 | 1.00 | 25.27 | C |
| ATOM | 202 | CB | THR | A | 66 | 111.074 | 13.389 | 75.221 | 1.00 | 24.96 | C |
| ATOM | 203 | OG1 | THR | A | 66 | 111.524 | 14.308 | 74.224 | 1.00 | 22.48 | O |
| ATOM | 204 | CG2 | THR | A | 66 | 111.255 | 11.963 | 74.696 | 1.00 | 24.29 | C |
| ATOM | 205 | C | THR | A | 66 | 109.309 | 15.158 | 75.398 | 1.00 | 26.63 | C |
| ATOM | 206 | O | THR | A | 66 | 108.815 | 15.653 | 74.392 | 1.00 | 26.18 | O |
| ATOM | 207 | N | SER | A | 67 | 109.598 | 15.882 | 76.495 | 1.00 | 30.45 | N |
| ATOM | 208 | CA | SER | A | 67 | 109.358 | 17.320 | 76.492 | 1.00 | 34.28 | C |
| ATOM | 209 | CB | SER | A | 67 | 109.033 | 17.751 | 77.920 | 1.00 | 35.87 | C |
| ATOM | 210 | OG | SER | A | 67 | 109.302 | 19.145 | 78.069 | 1.00 | 39.91 | O |
| ATOM | 211 | C | SER | A | 67 | 110.578 | 18.093 | 75.984 | 1.00 | 34.30 | C |
| ATOM | 212 | O | SER | A | 67 | 110.825 | 19.236 | 76.340 | 1.00 | 34.88 | O |
| ATOM | 213 | N | GLN | A | 68 | 111.371 | 17.407 | 75.143 | 1.00 | 33.82 | N |
| ATOM | 214 | CA | GLN | A | 68 | 112.597 | 18.021 | 74.654 | 1.00 | 33.31 | C |
| ATOM | 215 | CB | GLN | A | 68 | 113.706 | 16.975 | 74.755 | 1.00 | 34.87 | C |
| ATOM | 216 | CG | GLN | A | 68 | 114.985 | 17.374 | 74.027 | 1.00 | 43.65 | C |
| ATOM | 217 | CD | GLN | A | 68 | 115.847 | 16.147 | 73.874 | 1.00 | 51.57 | C |
| ATOM | 218 | OE1 | GLN | A | 68 | 116.993 | 16.184 | 73.469 | 1.00 | 50.43 | O |
| ATOM | 219 | NE2 | GLN | A | 68 | 115.238 | 15.011 | 74.265 | 1.00 | 55.62 | N |
| ATOM | 220 | C | GLN | A | 68 | 112.444 | 18.506 | 73.212 | 1.00 | 32.26 | C |
| ATOM | 221 | O | GLN | A | 68 | 111.948 | 17.812 | 72.338 | 1.00 | 34.08 | O |
| ATOM | 222 | N | VAL | A | 69 | 112.860 | 19.770 | 72.992 | 1.00 | 30.62 | N |
| ATOM | 223 | CA | VAL | A | 69 | 112.665 | 20.374 | 71.680 | 1.00 | 29.45 | C |
| ATOM | 224 | CB | VAL | A | 69 | 112.350 | 21.859 | 71.890 | 1.00 | 28.80 | C |
| ATOM | 225 | CG1 | VAL | A | 69 | 112.093 | 22.527 | 70.540 | 1.00 | 29.52 | C |
| ATOM | 226 | CG2 | VAL | A | 69 | 111.128 | 22.020 | 72.773 | 1.00 | 30.06 | C |
| ATOM | 227 | C | VAL | A | 69 | 113.903 | 20.231 | 70.789 | 1.00 | 28.14 | C |
| ATOM | 228 | O | VAL | A | 69 | 115.026 | 20.510 | 71.182 | 1.00 | 29.18 | O |

FIG. 2A-5

| ATOM | 229 | N | LEU | A | 70 | 113.667 | 19.737 | 69.557 | 1.00 | 26.38 | N |
|---|---|---|---|---|---|---|---|---|---|---|---|
| ATOM | 230 | CA | LEU | A | 70 | 114.752 | 19.666 | 68.590 | 1.00 | 26.57 | C |
| ATOM | 231 | CB | LEU | A | 70 | 114.368 | 18.647 | 67.514 | 1.00 | 25.28 | C |
| ATOM | 232 | CG | LEU | A | 70 | 114.377 | 17.208 | 68.039 | 1.00 | 24.48 | C |
| ATOM | 233 | CD1 | LEU | A | 70 | 114.219 | 16.178 | 66.919 | 1.00 | 18.25 | C |
| ATOM | 234 | CD2 | LEU | A | 70 | 115.674 | 16.852 | 68.767 | 1.00 | 21.62 | C |
| ATOM | 235 | C | LEU | A | 70 | 114.994 | 21.032 | 67.945 | 1.00 | 27.92 | C |
| ATOM | 236 | O | LEU | A | 70 | 116.088 | 21.358 | 67.506 | 1.00 | 27.18 | O |
| ATOM | 237 | N | GLY | A | 71 | 113.899 | 21.790 | 67.861 | 1.00 | 29.31 | N |
| ATOM | 238 | CA | GLY | A | 71 | 113.887 | 23.132 | 67.285 | 1.00 | 27.75 | C |
| ATOM | 239 | C | GLY | A | 71 | 112.477 | 23.570 | 66.874 | 1.00 | 29.10 | C |
| ATOM | 240 | O | GLY | A | 71 | 111.495 | 22.865 | 67.058 | 1.00 | 28.06 | O |
| ATOM | 241 | N | LEU | A | 72 | 112.394 | 24.805 | 66.335 | 1.00 | 30.22 | N |
| ATOM | 242 | CA | LEU | A | 72 | 111.099 | 25.323 | 65.903 | 1.00 | 32.18 | C |
| ATOM | 243 | CB | LEU | A | 72 | 110.914 | 26.725 | 66.489 | 1.00 | 31.39 | C |
| ATOM | 244 | CG | LEU | A | 72 | 111.346 | 26.819 | 67.954 | 1.00 | 36.66 | C |
| ATOM | 245 | CD1 | LEU | A | 72 | 111.527 | 28.268 | 68.414 | 1.00 | 42.42 | C |
| ATOM | 246 | CD2 | LEU | A | 72 | 110.334 | 26.193 | 68.910 | 1.00 | 41.86 | C |
| ATOM | 247 | C | LEU | A | 72 | 110.991 | 25.388 | 64.379 | 1.00 | 32.94 | C |
| ATOM | 248 | O | LEU | A | 72 | 111.667 | 26.155 | 63.709 | 1.00 | 33.72 | O |
| ATOM | 249 | N | GLY | A | 73 | 110.129 | 24.516 | 63.832 | 1.00 | 34.51 | N |
| ATOM | 250 | CA | GLY | A | 73 | 109.868 | 24.568 | 62.402 | 1.00 | 33.90 | C |
| ATOM | 251 | C | GLY | A | 73 | 108.731 | 25.542 | 62.092 | 1.00 | 34.50 | C |
| ATOM | 252 | O | GLY | A | 73 | 108.164 | 26.185 | 62.966 | 1.00 | 35.49 | O |
| ATOM | 253 | N | ILE | A | 74 | 108.427 | 25.673 | 60.789 | 1.00 | 35.12 | N |
| ATOM | 254 | CA | ILE | A | 74 | 107.375 | 26.602 | 60.396 | 1.00 | 35.88 | C |
| ATOM | 255 | CB | ILE | A | 74 | 107.374 | 26.711 | 58.874 | 1.00 | 35.92 | C |
| ATOM | 256 | CG1 | ILE | A | 74 | 108.727 | 27.215 | 58.374 | 1.00 | 35.91 | C |
| ATOM | 257 | CD1 | ILE | A | 74 | 108.735 | 27.455 | 56.863 | 1.00 | 35.71 | C |
| ATOM | 258 | CG2 | ILE | A | 74 | 106.301 | 27.724 | 58.428 | 1.00 | 35.99 | C |
| ATOM | 259 | C | ILE | A | 74 | 105.999 | 26.150 | 60.883 | 1.00 | 36.05 | C |
| ATOM | 260 | O | ILE | A | 74 | 105.443 | 25.155 | 60.440 | 1.00 | 36.40 | O |
| ATOM | 261 | N | ASN | A | 75 | 105.469 | 26.900 | 61.868 | 1.00 | 35.76 | N |
| ATOM | 262 | CA | ASN | A | 75 | 104.081 | 26.685 | 62.248 | 1.00 | 37.59 | C |
| ATOM | 263 | CB | ASN | A | 75 | 103.314 | 26.254 | 61.002 | 1.00 | 39.37 | C |
| ATOM | 264 | CG | ASN | A | 75 | 102.880 | 27.479 | 60.242 | 1.00 | 44.82 | C |
| ATOM | 265 | OD1 | ASN | A | 75 | 102.674 | 28.552 | 60.803 | 1.00 | 51.44 | O |
| ATOM | 266 | ND2 | ASN | A | 75 | 102.760 | 27.310 | 58.918 | 1.00 | 47.51 | N |
| ATOM | 267 | C | ASN | A | 75 | 103.946 | 25.618 | 63.335 | 1.00 | 36.34 | C |
| ATOM | 268 | O | ASN | A | 75 | 102.856 | 25.203 | 63.704 | 1.00 | 39.70 | O |
| ATOM | 269 | N | GLY | A | 76 | 105.104 | 25.139 | 63.822 | 1.00 | 33.28 | N |
| ATOM | 270 | CA | GLY | A | 76 | 105.062 | 24.105 | 64.848 | 1.00 | 34.25 | C |
| ATOM | 271 | C | GLY | A | 76 | 106.448 | 23.791 | 65.413 | 1.00 | 32.95 | C |
| ATOM | 272 | O | GLY | A | 76 | 107.479 | 23.994 | 64.785 | 1.00 | 30.57 | O |
| ATOM | 273 | N | LYS | A | 77 | 106.443 | 23.311 | 66.668 | 1.00 | 33.11 | N |
| ATOM | 274 | CA | LYS | A | 77 | 107.692 | 22.887 | 67.281 | 1.00 | 32.56 | C |

FIG. 2A-6

| | | | | | | | | | | |
|---|---|---|---|---|---|---|---|---|---|---|
| ATOM | 275 | CB | LYS | A | 77 | 107.529 | 22.963 | 68.799 | 1.00 | 34.66 | C |
| ATOM | 276 | CG | LYS | A | 77 | 106.493 | 24.008 | 69.220 | 1.00 | 42.88 | C |
| ATOM | 277 | CD | LYS | A | 77 | 105.924 | 23.731 | 70.613 | 1.00 | 46.90 | C |
| ATOM | 278 | CE | LYS | A | 77 | 106.314 | 24.808 | 71.631 | 1.00 | 52.32 | C |
| ATOM | 279 | NZ | LYS | A | 77 | 106.322 | 26.119 | 70.985 | 1.00 | 57.21 | N |
| ATOM | 280 | C | LYS | A | 77 | 108.052 | 21.462 | 66.867 | 1.00 | 29.54 | C |
| ATOM | 281 | O | LYS | A | 77 | 107.244 | 20.722 | 66.322 | 1.00 | 28.47 | O |
| ATOM | 282 | N | VAL | A | 78 | 109.324 | 21.099 | 67.109 | 1.00 | 27.89 | N |
| ATOM | 283 | CA | VAL | A | 78 | 109.761 | 19.755 | 66.755 | 1.00 | 25.71 | C |
| ATOM | 284 | CB | VAL | A | 78 | 110.791 | 19.864 | 65.631 | 1.00 | 26.82 | C |
| ATOM | 285 | CG1 | VAL | A | 78 | 111.343 | 18.481 | 65.295 | 1.00 | 24.63 | C |
| ATOM | 286 | CG2 | VAL | A | 78 | 110.153 | 20.460 | 64.391 | 1.00 | 25.85 | C |
| ATOM | 287 | C | VAL | A | 78 | 110.375 | 19.032 | 67.955 | 1.00 | 25.65 | C |
| ATOM | 288 | O | VAL | A | 78 | 111.514 | 19.257 | 68.341 | 1.00 | 21.62 | O |
| ATOM | 289 | N | LEU | A | 79 | 109.557 | 18.165 | 68.575 | 1.00 | 25.95 | N |
| ATOM | 290 | CA | LEU | A | 79 | 110.042 | 17.414 | 69.728 | 1.00 | 24.51 | C |
| ATOM | 291 | CB | LEU | A | 79 | 108.867 | 17.198 | 70.686 | 1.00 | 22.30 | C |
| ATOM | 292 | CG | LEU | A | 79 | 108.278 | 18.515 | 71.205 | 1.00 | 23.16 | C |
| ATOM | 293 | CD1 | LEU | A | 79 | 107.033 | 18.299 | 72.068 | 1.00 | 30.98 | C |
| ATOM | 294 | CD2 | LEU | A | 79 | 109.258 | 19.310 | 72.067 | 1.00 | 31.63 | C |
| ATOM | 295 | C | LEU | A | 79 | 110.636 | 16.066 | 69.307 | 1.00 | 24.72 | C |
| ATOM | 296 | O | LEU | A | 79 | 110.435 | 15.590 | 68.198 | 1.00 | 26.49 | O |
| ATOM | 297 | N | GLN | A | 80 | 111.352 | 15.477 | 70.252 | 1.00 | 24.76 | N |
| ATOM | 298 | CA | GLN | A | 80 | 111.864 | 14.145 | 70.058 | 1.00 | 24.30 | C |
| ATOM | 299 | CB | GLN | A | 80 | 113.238 | 13.995 | 70.650 | 1.00 | 25.13 | C |
| ATOM | 300 | CG | GLN | A | 80 | 113.845 | 12.681 | 70.264 | 1.00 | 31.74 | C |
| ATOM | 301 | CD | GLN | A | 80 | 115.166 | 12.865 | 69.542 | 1.00 | 40.68 | C |
| ATOM | 302 | OE1 | GLN | A | 80 | 116.187 | 13.229 | 70.168 | 1.00 | 42.36 | O |
| ATOM | 303 | NE2 | GLN | A | 80 | 115.163 | 12.635 | 68.211 | 1.00 | 40.44 | N |
| ATOM | 304 | C | GLN | A | 80 | 110.905 | 13.206 | 70.766 | 1.00 | 22.54 | C |
| ATOM | 305 | O | GLN | A | 80 | 110.488 | 13.447 | 71.913 | 1.00 | 20.06 | O |
| ATOM | 306 | N | ILE | A | 81 | 110.525 | 12.158 | 70.054 | 1.00 | 21.73 | N |
| ATOM | 307 | CA | ILE | A | 81 | 109.631 | 11.170 | 70.594 | 1.00 | 21.81 | C |
| ATOM | 308 | CB | ILE | A | 81 | 108.241 | 11.215 | 69.890 | 1.00 | 22.66 | C |
| ATOM | 309 | CG1 | ILE | A | 81 | 108.369 | 10.810 | 68.423 | 1.00 | 16.53 | C |
| ATOM | 310 | CD1 | ILE | A | 81 | 107.031 | 10.795 | 67.713 | 1.00 | 21.07 | C |
| ATOM | 311 | CG2 | ILE | A | 81 | 107.640 | 12.610 | 69.970 | 1.00 | 23.46 | C |
| ATOM | 312 | C | ILE | A | 81 | 110.262 | 9.787 | 70.401 | 1.00 | 22.49 | C |
| ATOM | 313 | O | ILE | A | 81 | 111.147 | 9.601 | 69.557 | 1.00 | 24.97 | O |
| ATOM | 314 | N | PHE | A | 82 | 109.798 | 8.821 | 71.188 | 1.00 | 22.30 | N |
| ATOM | 315 | CA | PHE | A | 82 | 110.297 | 7.456 | 71.118 | 1.00 | 20.52 | C |
| ATOM | 316 | CB | PHE | A | 82 | 111.009 | 7.073 | 72.405 | 1.00 | 20.99 | C |
| ATOM | 317 | CG | PHE | A | 82 | 112.281 | 7.762 | 72.588 | 1.00 | 21.28 | C |
| ATOM | 318 | CD1 | PHE | A | 82 | 112.336 | 8.955 | 73.271 | 1.00 | 25.45 | C |
| ATOM | 319 | CE1 | PHE | A | 82 | 113.540 | 9.646 | 73.377 | 1.00 | 26.87 | C |
| ATOM | 320 | CZ | PHE | A | 82 | 114.693 | 9.130 | 72.792 | 1.00 | 23.96 | C |

FIG. 2A-7

| ATOM | 321 | CE2 | PHE | A | 82 | 114.629 | 7.938 | 72.117 | 1.00 | 24.75 | C |
|---|---|---|---|---|---|---|---|---|---|---|---|
| ATOM | 322 | CD2 | PHE | A | 82 | 113.422 | 7.261 | 72.018 | 1.00 | 21.71 | C |
| ATOM | 323 | C | PHE | A | 82 | 109.159 | 6.505 | 70.888 | 1.00 | 21.11 | C |
| ATOM | 324 | O | PHE | A | 82 | 108.060 | 6.667 | 71.427 | 1.00 | 21.70 | O |
| ATOM | 325 | N | ASN | A | 83 | 109.448 | 5.495 | 70.092 | 1.00 | 20.41 | N |
| ATOM | 326 | CA | ASN | A | 83 | 108.498 | 4.484 | 69.735 | 1.00 | 19.43 | C |
| ATOM | 327 | CB | ASN | A | 83 | 109.033 | 3.816 | 68.490 | 1.00 | 18.81 | C |
| ATOM | 328 | CG | ASN | A | 83 | 108.065 | 2.897 | 67.877 | 1.00 | 19.17 | C |
| ATOM | 329 | OD1 | ASN | A | 83 | 107.728 | 1.865 | 68.447 | 1.00 | 19.03 | O |
| ATOM | 330 | ND2 | ASN | A | 83 | 107.587 | 3.258 | 66.691 | 1.00 | 20.78 | N |
| ATOM | 331 | C | ASN | A | 83 | 108.327 | 3.465 | 70.882 | 1.00 | 20.54 | C |
| ATOM | 332 | O | ASN | A | 83 | 109.223 | 2.660 | 71.129 | 1.00 | 19.97 | O |
| ATOM | 333 | N | LYS | A | 84 | 107.181 | 3.492 | 71.562 | 1.00 | 20.24 | N |
| ATOM | 334 | CA | LYS | A | 84 | 106.899 | 2.590 | 72.680 | 1.00 | 19.59 | C |
| ATOM | 335 | CB | LYS | A | 84 | 105.507 | 2.872 | 73.247 | 1.00 | 20.13 | C |
| ATOM | 336 | CG | LYS | A | 84 | 105.327 | 4.200 | 73.930 | 1.00 | 13.91 | C |
| ATOM | 337 | CD | LYS | A | 84 | 103.857 | 4.400 | 74.200 | 1.00 | 26.19 | C |
| ATOM | 338 | CE | LYS | A | 84 | 103.576 | 4.760 | 75.645 | 1.00 | 28.09 | C |
| ATOM | 339 | NZ | LYS | A | 84 | 103.731 | 6.220 | 75.974 | 1.00 | 34.25 | N |
| ATOM | 340 | C | LYS | A | 84 | 107.009 | 1.085 | 72.356 | 1.00 | 21.23 | C |
| ATOM | 341 | O | LYS | A | 84 | 107.360 | 0.274 | 73.219 | 1.00 | 20.96 | O |
| ATOM | 342 | N | ARG | A | 85 | 106.698 | 0.700 | 71.124 | 1.00 | 22.17 | N |
| ATOM | 343 | CA | ARG | A | 85 | 106.812 | -0.707 | 70.763 | 1.00 | 20.64 | C |
| ATOM | 344 | CB | ARG | A | 85 | 105.886 | -1.092 | 69.606 | 1.00 | 18.79 | C |
| ATOM | 345 | CG | ARG | A | 85 | 104.402 | -1.132 | 69.941 | 1.00 | 17.17 | C |
| ATOM | 346 | CD | ARG | A | 85 | 103.538 | -1.417 | 68.705 | 1.00 | 22.54 | C |
| ATOM | 347 | NE | ARG | A | 85 | 102.097 | -1.271 | 68.957 | 1.00 | 26.34 | N |
| ATOM | 348 | CZ | ARG | A | 85 | 101.455 | -0.113 | 69.129 | 1.00 | 30.06 | C |
| ATOM | 349 | NH1AR | G | A | 85 | 102.094 | 1.060 | 69.074 | 1.00 | 25.87 | N |
| ATOM | 350 | NH2AR | G | A | 85 | 100.155 | -0.131 | 69.396 | 1.00 | 31.06 | N |
| ATOM | 351 | C | ARG | A | 85 | 108.228 | -1.046 | 70.364 | 1.00 | 20.57 | C |
| ATOM | 352 | O | ARG | A | 85 | 108.733 | -2.067 | 70.776 | 1.00 | 19.98 | O |
| ATOM | 353 | N | THR | A | 86 | 108.900 | -0.198 | 69.596 | 1.00 | 22.66 | N |
| ATOM | 354 | CA | THR | A | 86 | 110.252 | -0.561 | 69.157 | 1.00 | 23.98 | C |
| ATOM | 355 | CB | THR | A | 86 | 110.368 | -0.503 | 67.634 | 1.00 | 23.15 | C |
| ATOM | 356 | OG1 | THR | A | 86 | 110.432 | 0.873 | 67.206 | 1.00 | 24.39 | O |
| ATOM | 357 | CG2 | THR | A | 86 | 109.164 | -1.188 | 66.988 | 1.00 | 23.75 | C |
| ATOM | 358 | C | THR | A | 86 | 111.420 | 0.219 | 69.727 | 1.00 | 25.17 | C |
| ATOM | 359 | O | THR | A | 86 | 112.570 | -0.102 | 69.441 | 1.00 | 24.93 | O |
| ATOM | 360 | N | ALA | A | 87 | 111.126 | 1.245 | 70.516 | 1.00 | 26.46 | N |
| ATOM | 361 | CA | ALA | A | 87 | 112.148 | 2.074 | 71.142 | 1.00 | 26.46 | C |
| ATOM | 362 | CB | ALA | A | 87 | 113.059 | 1.198 | 72.058 | 1.00 | 25.09 | C |
| ATOM | 363 | C | ALA | A | 87 | 112.997 | 2.916 | 70.193 | 1.00 | 26.06 | C |
| ATOM | 364 | O | ALA | A | 87 | 113.957 | 3.545 | 70.623 | 1.00 | 25.79 | O |
| ATOM | 365 | N | GLU | A | 88 | 112.662 | 2.941 | 68.908 | 1.00 | 26.57 | N |
| ATOM | 366 | CA | GLU | A | 88 | 113.427 | 3.753 | 67.960 | 1.00 | 28.12 | C |

FIG. 2A-8

| | | | | | | | | | | |
|---|---|---|---|---|---|---|---|---|---|---|
| ATOM | 367 | CB | GLU | A | 88 | 113.032 | 3.463 | 66.528 | 1.00 | 30.71 | C |
| ATOM | 368 | CG | GLU | A | 88 | 113.355 | 2.130 | 65.996 | 1.00 | 36.35 | C |
| ATOM | 369 | CD | GLU | A | 88 | 113.076 | 2.111 | 64.516 | 1.00 | 47.80 | C |
| ATOM | 370 | OE1 | GLU | A | 88 | 113.794 | 2.819 | 63.750 | 1.00 | 45.08 | O |
| ATOM | 371 | OE2 | GLU | A | 88 | 112.112 | 1.403 | 64.134 | 1.00 | 50.96 | O |
| ATOM | 372 | C | GLU | A | 88 | 113.131 | 5.221 | 68.203 | 1.00 | 27.12 | C |
| ATOM | 373 | O | GLU | A | 88 | 112.090 | 5.554 | 68.752 | 1.00 | 26.75 | O |
| ATOM | 374 | N | LYS | A | 89 | 114.024 | 6.090 | 67.749 | 1.00 | 25.97 | N |
| ATOM | 375 | CA | LYS | A | 89 | 113.844 | 7.522 | 67.948 | 1.00 | 25.02 | C |
| ATOM | 376 | CB | LYS | A | 89 | 115.172 | 8.134 | 68.335 | 1.00 | 26.07 | C |
| ATOM | 377 | CG | LYS | A | 89 | 115.087 | 9.545 | 68.883 | 1.00 | 30.75 | C |
| ATOM | 378 | CD | LYS | A | 89 | 116.496 | 10.026 | 69.176 | 1.00 | 35.35 | C |
| ATOM | 379 | CE | LYS | A | 89 | 117.466 | 9.386 | 68.169 | 1.00 | 38.18 | C |
| ATOM | 380 | NZ | LYS | A | 89 | 118.798 | 10.031 | 68.129 | 1.00 | 38.38 | N |
| ATOM | 381 | C | LYS | A | 89 | 113.262 | 8.272 | 66.740 | 1.00 | 24.28 | C |
| ATOM | 382 | O | LYS | A | 89 | 113.660 | 8.041 | 65.591 | 1.00 | 24.36 | O |
| ATOM | 383 | N | PHE | A | 90 | 112.311 | 9.169 | 66.994 | 1.00 | 23.13 | N |
| ATOM | 384 | CA | PHE | A | 90 | 111.727 | 9.902 | 65.892 | 1.00 | 22.74 | C |
| ATOM | 385 | CB | PHE | A | 90 | 110.370 | 9.333 | 65.548 | 1.00 | 21.97 | C |
| ATOM | 386 | CG | PHE | A | 90 | 110.424 | 7.952 | 65.014 | 1.00 | 19.55 | C |
| ATOM | 387 | CD1 | PHE | A | 90 | 110.625 | 6.866 | 65.860 | 1.00 | 22.04 | C |
| ATOM | 388 | CE1 | PHE | A | 90 | 110.670 | 5.582 | 65.364 | 1.00 | 16.30 | C |
| ATOM | 389 | CZ | PHE | A | 90 | 110.521 | 5.368 | 64.042 | 1.00 | 15.82 | C |
| ATOM | 390 | CE2 | PHE | A | 90 | 110.321 | 6.431 | 63.178 | 1.00 | 15.24 | C |
| ATOM | 391 | CD2 | PHE | A | 90 | 110.272 | 7.718 | 63.662 | 1.00 | 16.84 | C |
| ATOM | 392 | C | PHE | A | 90 | 111.565 | 11.373 | 66.171 | 1.00 | 22.93 | C |
| ATOM | 393 | O | PHE | A | 90 | 111.600 | 11.807 | 67.326 | 1.00 | 25.53 | O |
| ATOM | 394 | N | ALA | A | 91 | 111.382 | 12.150 | 65.107 | 1.00 | 21.84 | N |
| ATOM | 395 | CA | ALA | A | 91 | 111.155 | 13.574 | 65.253 | 1.00 | 22.54 | C |
| ATOM | 396 | CB | ALA | A | 91 | 111.912 | 14.327 | 64.210 | 1.00 | 21.03 | C |
| ATOM | 397 | C | ALA | A | 91 | 109.644 | 13.786 | 65.074 | 1.00 | 23.32 | C |
| ATOM | 398 | O | ALA | A | 91 | 108.970 | 13.093 | 64.293 | 1.00 | 23.50 | O |
| ATOM | 399 | N | LEU | A | 92 | 109.113 | 14.753 | 65.806 | 1.00 | 23.62 | N |
| ATOM | 400 | CA | LEU | A | 92 | 107.705 | 15.043 | 65.751 | 1.00 | 24.72 | C |
| ATOM | 401 | CB | LEU | A | 92 | 107.076 | 14.572 | 67.045 | 1.00 | 23.74 | C |
| ATOM | 402 | CG | LEU | A | 92 | 105.582 | 14.771 | 67.097 | 1.00 | 23.50 | C |
| ATOM | 403 | CD1 | LEU | A | 92 | 104.981 | 13.730 | 66.126 | 1.00 | 28.27 | C |
| ATOM | 404 | CD2 | LEU | A | 92 | 105.067 | 14.585 | 68.507 | 1.00 | 23.14 | C |
| ATOM | 405 | C | LEU | A | 92 | 107.418 | 16.535 | 65.600 | 1.00 | 25.54 | C |
| ATOM | 406 | O | LEU | A | 92 | 107.789 | 17.332 | 66.468 | 1.00 | 26.18 | O |
| ATOM | 407 | N | LYS | A | 93 | 106.752 | 16.907 | 64.512 | 1.00 | 24.48 | N |
| ATOM | 408 | CA | LYS | A | 93 | 106.361 | 18.296 | 64.304 | 1.00 | 24.95 | C |
| ATOM | 409 | CB | LYS | A | 93 | 106.500 | 18.693 | 62.849 | 1.00 | 25.35 | C |
| ATOM | 410 | CG | LYS | A | 93 | 106.201 | 20.143 | 62.594 | 1.00 | 24.17 | C |
| ATOM | 411 | CD | LYS | A | 93 | 106.406 | 20.502 | 61.141 | 1.00 | 28.19 | C |
| ATOM | 412 | CE | LYS | A | 93 | 106.616 | 22.015 | 61.042 | 1.00 | 32.20 | C |

FIG. 2A-9

| | | | | | | | | | | |
|---|---|---|---|---|---|---|---|---|---|---|
| ATOM | 413 | NZ | LYS | A | 93 | 106.320 | 22.558 | 59.692 | 1.00 | 31.60 | N |
| ATOM | 414 | C | LYS | A | 93 | 104.901 | 18.424 | 64.708 | 1.00 | 25.15 | C |
| ATOM | 415 | O | LYS | A | 93 | 104.072 | 17.642 | 64.289 | 1.00 | 25.08 | O |
| ATOM | 416 | N | MSE | A | 94 | 104.583 | 19.395 | 65.544 | 1.00 | 27.01 | N |
| ATOM | 417 | CA | MSE | A | 94 | 103.215 | 19.590 | 65.964 | 1.00 | 27.80 | C |
| ATOM | 418 | CB | MSE | A | 94 | 103.194 | 19.860 | 67.439 | 1.00 | 28.23 | C |
| ATOM | 419 | CG | MSE | A | 94 | 104.129 | 18.973 | 68.201 | 1.00 | 35.52 | C |
| ATOM | 420 | SE | MSE | A | 94 | 103.764 | 19.165 | 70.092 | 1.00 | 56.16 | S |
| ATOM | 421 | CE | MSE | A | 94 | 101.842 | 19.633 | 69.974 | 1.00 | 43.88 | C |
| ATOM | 422 | C | MSE | A | 94 | 102.605 | 20.776 | 65.226 | 1.00 | 27.67 | C |
| ATOM | 423 | O | MSE | A | 94 | 103.052 | 21.914 | 65.378 | 1.00 | 27.03 | O |
| ATOM | 424 | N | LEU | A | 95 | 101.594 | 20.525 | 64.412 | 1.00 | 26.60 | N |
| ATOM | 425 | CA | LEU | A | 95 | 100.955 | 21.610 | 63.696 | 1.00 | 24.73 | C |
| ATOM | 426 | CB | LEU | A | 95 | 100.890 | 21.271 | 62.204 | 1.00 | 25.87 | C |
| ATOM | 427 | CG | LEU | A | 95 | 102.231 | 21.341 | 61.459 | 1.00 | 28.73 | C |
| ATOM | 428 | CD1 | LEU | A | 95 | 102.129 | 20.855 | 60.025 | 1.00 | 27.05 | C |
| ATOM | 429 | CD2 | LEU | A | 95 | 102.708 | 22.779 | 61.495 | 1.00 | 26.68 | C |
| ATOM | 430 | C | LEU | A | 95 | 99.561 | 21.796 | 64.243 | 1.00 | 23.71 | C |
| ATOM | 431 | O | LEU | A | 95 | 98.981 | 20.844 | 64.734 | 1.00 | 24.90 | O |
| ATOM | 432 | N | ALA | A | 96 | 99.024 | 23.009 | 64.216 | 1.00 | 23.22 | N |
| ATOM | 433 | CA | ALA | A | 96 | 97.641 | 23.200 | 64.648 | 1.00 | 23.38 | C |
| ATOM | 434 | CB | ALA | A | 96 | 97.412 | 24.615 | 65.141 | 1.00 | 23.16 | C |
| ATOM | 435 | C | ALA | A | 96 | 96.821 | 22.951 | 63.380 | 1.00 | 24.18 | C |
| ATOM | 436 | O | ALA | A | 96 | 97.114 | 23.500 | 62.310 | 1.00 | 23.60 | O |
| ATOM | 437 | N | ASP | A | 97 | 95.799 | 22.120 | 63.485 | 1.00 | 24.28 | N |
| ATOM | 438 | CA | ASP | A | 97 | 94.990 | 21.786 | 62.309 | 1.00 | 26.26 | C |
| ATOM | 439 | CB | ASP | A | 97 | 93.917 | 20.737 | 62.691 | 1.00 | 26.49 | C |
| ATOM | 440 | CG | ASP | A | 97 | 93.334 | 20.043 | 61.480 | 1.00 | 32.74 | C |
| ATOM | 441 | OD1 | ASP | A | 97 | 93.320 | 20.661 | 60.409 | 1.00 | 33.35 | O |
| ATOM | 442 | OD2 | ASP | A | 97 | 92.867 | 18.887 | 61.574 | 1.00 | 46.73 | O |
| ATOM | 443 | C | ASP | A | 97 | 94.349 | 23.037 | 61.643 | 1.00 | 24.53 | C |
| ATOM | 444 | O | ASP | A | 97 | 93.688 | 23.844 | 62.278 | 1.00 | 23.53 | O |
| ATOM | 445 | N | CYS | A | 98 | 94.569 | 23.209 | 60.355 | 1.00 | 23.53 | N |
| ATOM | 446 | CA | CYS | A | 98 | 93.999 | 24.346 | 59.659 | 1.00 | 23.90 | C |
| ATOM | 447 | CB | CYS | A | 98 | 94.579 | 25.655 | 60.174 | 1.00 | 24.81 | C |
| ATOM | 448 | SG | CYS | A | 98 | 96.319 | 25.834 | 59.871 | 1.00 | 24.39 | S |
| ATOM | 449 | C | CYS | A | 98 | 94.374 | 24.128 | 58.239 | 1.00 | 23.55 | C |
| ATOM | 450 | O | CYS | A | 98 | 95.221 | 23.282 | 57.955 | 1.00 | 20.82 | O |
| ATOM | 451 | N | PRO | A | 99 | 93.760 | 24.885 | 57.314 | 1.00 | 23.88 | N |
| ATOM | 452 | CA | PRO | A | 99 | 94.052 | 24.733 | 55.880 | 1.00 | 24.54 | C |
| ATOM | 453 | CB | PRO | A | 99 | 93.270 | 25.870 | 55.250 | 1.00 | 24.89 | C |
| ATOM | 454 | CG | PRO | A | 99 | 92.040 | 25.904 | 56.113 | 1.00 | 24.87 | C |
| ATOM | 455 | CD | PRO | A | 99 | 92.671 | 25.852 | 57.515 | 1.00 | 23.07 | C |
| ATOM | 456 | C | PRO | A | 99 | 95.519 | 24.697 | 55.486 | 1.00 | 25.61 | C |
| ATOM | 457 | O | PRO | A | 99 | 95.910 | 23.817 | 54.721 | 1.00 | 27.86 | O |
| ATOM | 458 | N | LYS | A | 100 | 96.330 | 25.613 | 56.001 | 1.00 | 26.59 | N |

FIG. 2A-10

| | | | | | | | | | | | |
|---|---|---|---|---|---|---|---|---|---|---|---|
| ATOM | 459 | CA | LYS | A | 100 | 97.754 | 25.586 | 55.683 | 1.00 | 25.52 | C |
| ATOM | 460 | CB | LYS | A | 100 | 98.508 | 26.738 | 56.347 | 1.00 | 26.30 | C |
| ATOM | 461 | CG | LYS | A | 100 | 98.243 | 28.121 | 55.758 | 1.00 | 33.53 | C |
| ATOM | 462 | CD | LYS | A | 100 | 99.324 | 29.127 | 56.178 | 1.00 | 44.24 | C |
| ATOM | 463 | CE | LYS | A | 100 | 98.984 | 30.578 | 55.757 | 1.00 | 46.86 | C |
| ATOM | 464 | NZ | LYS | A | 100 | 98.204 | 31.361 | 56.809 | 1.00 | 47.71 | N |
| ATOM | 465 | C | LYS | A | 100 | 98.312 | 24.270 | 56.196 | 1.00 | 23.87 | C |
| ATOM | 466 | O | LYS | A | 100 | 98.986 | 23.555 | 55.459 | 1.00 | 25.01 | O |
| ATOM | 467 | N | ALA | A | 101 | 97.997 | 23.940 | 57.446 | 1.00 | 23.10 | N |
| ATOM | 468 | CA | ALA | A | 101 | 98.397 | 22.653 | 58.012 | 1.00 | 23.31 | C |
| ATOM | 469 | CB | ALA | A | 101 | 97.754 | 22.515 | 59.385 | 1.00 | 24.30 | C |
| ATOM | 470 | C | ALA | A | 101 | 98.054 | 21.443 | 57.132 | 1.00 | 23.39 | C |
| ATOM | 471 | O | ALA | A | 101 | 98.853 | 20.522 | 56.938 | 1.00 | 22.01 | O |
| ATOM | 472 | N | ARG | A | 102 | 96.810 | 21.413 | 56.631 | 1.00 | 25.91 | N |
| ATOM | 473 | CA | ARG | A | 102 | 96.437 | 20.258 | 55.830 | 1.00 | 27.32 | C |
| ATOM | 474 | CB | ARG | A | 102 | 94.913 | 20.152 | 55.764 | 1.00 | 26.23 | C |
| ATOM | 475 | CG | ARG | A | 102 | 94.281 | 19.828 | 57.124 | 1.00 | 30.31 | C |
| ATOM | 476 | CD | ARG | A | 102 | 93.714 | 18.396 | 57.164 | 1.00 | 36.01 | C |
| ATOM | 477 | NE | ARG | A | 102 | 93.115 | 18.103 | 58.474 | 1.00 | 35.36 | N |
| ATOM | 478 | CZ | ARG | A | 102 | 93.101 | 16.814 | 58.865 | 1.00 | 39.39 | C |
| ATOM | 479 | NH1AR | G | A | 102 | 93.222 | 16.508 | 60.146 | 1.00 | 42.47 | N |
| ATOM | 480 | NH2AR | G | A | 102 | 93.139 | 15.852 | 57.946 | 1.00 | 39.52 | N |
| ATOM | 481 | C | ARG | A | 102 | 97.120 | 20.270 | 54.448 | 1.00 | 29.83 | C |
| ATOM | 482 | O | ARG | A | 102 | 97.228 | 19.259 | 53.758 | 1.00 | 32.68 | O |
| ATOM | 483 | N | ARG | A | 103 | 97.602 | 21.483 | 54.052 | 1.00 | 30.12 | N |
| ATOM | 484 | CA | ARG | A | 103 | 98.403 | 21.581 | 52.829 | 1.00 | 29.72 | C |
| ATOM | 485 | CB | ARG | A | 103 | 98.448 | 23.050 | 52.362 | 1.00 | 31.52 | C |
| ATOM | 486 | CG | ARG | A | 103 | 99.056 | 23.228 | 50.964 | 1.00 | 38.61 | C |
| ATOM | 487 | CD | ARG | A | 103 | 99.132 | 24.701 | 50.515 | 1.00 | 51.19 | C |
| ATOM | 488 | NE | ARG | A | 103 | 99.748 | 25.550 | 51.545 | 1.00 | 55.90 | N |
| ATOM | 489 | CZ | ARG | A | 103 | 99.792 | 26.879 | 51.301 | 1.00 | 58.13 | C |
| ATOM | 490 | NH1AR | G | A | 103 | 100.750 | 27.616 | 51.832 | 1.00 | 56.70 | N |
| ATOM | 491 | NH2AR | G | A | 103 | 98.905 | 27.436 | 50.469 | 1.00 | 62.64 | N |
| ATOM | 492 | C | ARG | A | 103 | 99.830 | 21.019 | 53.044 | 1.00 | 28.75 | C |
| ATOM | 493 | O | ARG | A | 103 | 100.373 | 20.283 | 52.231 | 1.00 | 26.98 | O |
| ATOM | 494 | N | GLU | A | 104 | 100.443 | 21.428 | 54.172 | 1.00 | 27.35 | N |
| ATOM | 495 | CA | GLU | A | 104 | 101.809 | 20.965 | 54.447 | 1.00 | 25.86 | C |
| ATOM | 496 | CB | GLU | A | 104 | 102.269 | 21.548 | 55.784 | 1.00 | 26.80 | C |
| ATOM | 497 | CG | GLU | A | 104 | 103.708 | 21.139 | 56.123 | 1.00 | 24.59 | C |
| ATOM | 498 | CD | GLU | A | 104 | 104.148 | 21.781 | 57.426 | 1.00 | 31.47 | C |
| ATOM | 499 | OE1 | GLU | A | 104 | 103.686 | 22.868 | 57.736 | 1.00 | 32.23 | O |
| ATOM | 500 | OE2 | GLU | A | 104 | 104.996 | 21.202 | 58.104 | 1.00 | 29.78 | O |
| ATOM | 501 | C | GLU | A | 104 | 101.911 | 19.439 | 54.499 | 1.00 | 27.03 | C |
| ATOM | 502 | O | GLU | A | 104 | 102.846 | 18.832 | 53.993 | 1.00 | 27.95 | O |
| ATOM | 503 | N | VAL | A | 105 | 100.959 | 18.763 | 55.137 | 1.00 | 25.95 | N |
| ATOM | 504 | CA | VAL | A | 105 | 101.005 | 17.315 | 55.280 | 1.00 | 23.97 | C |

FIG. 2A-11

| ATOM | 505 | CB | VAL | A | 105 | 99.877 | 16.817 | 56.268 | 1.00 | 24.18 | C |
|---|---|---|---|---|---|---|---|---|---|---|---|
| ATOM | 506 | CG1 | VAL | A | 105 | 99.651 | 15.308 | 56.161 | 1.00 | 19.54 | C |
| ATOM | 507 | CG2 | VAL | A | 105 | 100.248 | 17.204 | 57.689 | 1.00 | 22.58 | C |
| ATOM | 508 | C | VAL | A | 105 | 100.892 | 16.641 | 53.935 | 1.00 | 26.38 | C |
| ATOM | 509 | O | VAL | A | 105 | 101.710 | 15.786 | 53.576 | 1.00 | 24.95 | O |
| ATOM | 510 | N | GLU | A | 106 | 99.889 | 17.037 | 53.177 | 1.00 | 26.86 | N |
| ATOM | 511 | CA | GLU | A | 106 | 99.705 | 16.453 | 51.858 | 1.00 | 28.82 | C |
| ATOM | 512 | CB | GLU | A | 106 | 98.499 | 17.081 | 51.194 | 1.00 | 28.76 | C |
| ATOM | 513 | CG | GLU | A | 106 | 97.470 | 16.089 | 50.841 | 1.00 | 43.13 | C |
| ATOM | 514 | CD | GLU | A | 106 | 96.908 | 16.349 | 49.474 | 1.00 | 57.35 | C |
| ATOM | 515 | OE1 | GLU | A | 106 | 97.717 | 16.608 | 48.529 | 1.00 | 58.11 | O |
| ATOM | 516 | OE2 | GLU | A | 106 | 95.655 | 16.285 | 49.356 | 1.00 | 61.47 | O |
| ATOM | 517 | C | GLU | A | 106 | 100.949 | 16.655 | 50.973 | 1.00 | 27.59 | C |
| ATOM | 518 | O | GLU | A | 106 | 101.474 | 15.713 | 50.413 | 1.00 | 27.99 | O |
| ATOM | 519 | N | LEU | A | 107 | 101.404 | 17.900 | 50.853 | 1.00 | 26.48 | N |
| ATOM | 520 | CA | LEU | A | 107 | 102.580 | 18.214 | 50.075 | 1.00 | 26.25 | C |
| ATOM | 521 | CB | LEU | A | 107 | 102.942 | 19.691 | 50.226 | 1.00 | 26.54 | C |
| ATOM | 522 | CG | LEU | A | 107 | 101.884 | 20.629 | 49.653 | 1.00 | 26.67 | C |
| ATOM | 523 | CD1 | LEU | A | 107 | 102.308 | 22.009 | 49.948 | 1.00 | 27.79 | C |
| ATOM | 524 | CD2 | LEU | A | 107 | 101.681 | 20.426 | 48.174 | 1.00 | 18.11 | C |
| ATOM | 525 | C | LEU | A | 107 | 103.752 | 17.383 | 50.551 | 1.00 | 26.64 | C |
| ATOM | 526 | O | LEU | A | 107 | 104.450 | 16.722 | 49.763 | 1.00 | 27.08 | O |
| ATOM | 527 | N | HIS | A | 108 | 103.986 | 17.421 | 51.842 | 1.00 | 25.75 | N |
| ATOM | 528 | CA | HIS | A | 108 | 105.119 | 16.693 | 52.395 | 1.00 | 26.30 | C |
| ATOM | 529 | CB | HIS | A | 108 | 105.259 | 17.085 | 53.866 | 1.00 | 26.98 | C |
| ATOM | 530 | CG | HIS | A | 108 | 106.522 | 16.645 | 54.511 | 1.00 | 29.02 | C |
| ATOM | 531 | ND1 | HIS | A | 108 | 106.959 | 17.153 | 55.706 | 1.00 | 34.00 | N |
| ATOM | 532 | CE1 | HIS | A | 108 | 108.140 | 16.632 | 56.001 | 1.00 | 32.24 | C |
| ATOM | 533 | NE2 | HIS | A | 108 | 108.478 | 15.804 | 55.036 | 1.00 | 20.28 | N |
| ATOM | 534 | CD2 | HIS | A | 108 | 107.485 | 15.790 | 54.091 | 1.00 | 27.65 | C |
| ATOM | 535 | C | HIS | A | 108 | 104.920 | 15.175 | 52.196 | 1.00 | 25.60 | C |
| ATOM | 536 | O | HIS | A | 108 | 105.885 | 14.450 | 51.985 | 1.00 | 22.39 | O |
| ATOM | 537 | N | TRP | A | 109 | 103.677 | 14.698 | 52.223 | 1.00 | 25.72 | N |
| ATOM | 538 | CA | TRP | A | 109 | 103.454 | 13.261 | 52.040 | 1.00 | 25.39 | C |
| ATOM | 539 | CB | TRP | A | 109 | 101.969 | 12.917 | 52.220 | 1.00 | 25.44 | C |
| ATOM | 540 | CG | TRP | A | 109 | 101.752 | 11.432 | 52.094 | 1.00 | 22.72 | C |
| ATOM | 541 | CD1 | TRP | A | 109 | 100.914 | 10.804 | 51.129 | 1.00 | 21.39 | C |
| ATOM | 542 | NE1 | TRP | A | 109 | 100.906 | 9.446 | 51.228 | 1.00 | 20.30 | N |
| ATOM | 543 | CE2 | TRP | A | 109 | 101.803 | 9.132 | 52.367 | 1.00 | 16.73 | C |
| ATOM | 544 | CD2 | TRP | A | 109 | 102.311 | 10.350 | 52.889 | 1.00 | 20.60 | C |
| ATOM | 545 | CE3 | TRP | A | 109 | 103.176 | 10.298 | 53.977 | 1.00 | 21.28 | C |
| ATOM | 546 | CZ3 | TRP | A | 109 | 103.538 | 9.075 | 54.514 | 1.00 | 25.04 | C |
| ATOM | 547 | CH2 | TRP | A | 109 | 103.038 | 7.879 | 53.990 | 1.00 | 20.33 | C |
| ATOM | 548 | CZ2 | TRP | A | 109 | 102.176 | 7.911 | 52.914 | 1.00 | 18.97 | C |
| ATOM | 549 | C | TRP | A | 109 | 103.902 | 12.849 | 50.655 | 1.00 | 27.03 | C |
| ATOM | 550 | O | TRP | A | 109 | 104.553 | 11.826 | 50.474 | 1.00 | 28.67 | O |

FIG. 2A-12

| ATOM | 551 | N | ARG | A | 110 | 103.495 | 13.672 | 49.665 | 1.00 | 28.04 | N |
|---|---|---|---|---|---|---|---|---|---|---|---|
| ATOM | 552 | CA | ARG | A | 110 | 103.860 | 13.392 | 48.276 | 1.00 | 26.58 | C |
| ATOM | 553 | CB | ARG | A | 110 | 103.152 | 14.407 | 47.379 | 1.00 | 24.71 | C |
| ATOM | 554 | CG | ARG | A | 110 | 101.647 | 14.151 | 47.293 | 1.00 | 24.82 | C |
| ATOM | 555 | CD | ARG | A | 110 | 101.042 | 14.673 | 45.986 | 1.00 | 25.23 | C |
| ATOM | 556 | NE | ARG | A | 110 | 100.475 | 16.013 | 46.177 | 1.00 | 32.15 | N |
| ATOM | 557 | CZ | ARG | A | 110 | 100.862 | 16.969 | 45.315 | 1.00 | 42.79 | C |
| ATOM | 558 | NH1AR | G | A | 110 | 101.705 | 16.677 | 44.340 | 1.00 | 38.39 | N |
| ATOM | 559 | NH2AR | G | A | 110 | 100.421 | 18.221 | 45.471 | 1.00 | 49.56 | N |
| ATOM | 560 | C | ARG | A | 110 | 105.372 | 13.460 | 48.041 | 1.00 | 26.16 | C |
| ATOM | 561 | O | ARG | A | 110 | 105.961 | 12.652 | 47.334 | 1.00 | 25.68 | O |
| ATOM | 562 | N | ALA | A | 111 | 105.993 | 14.499 | 48.623 | 1.00 | 27.24 | N |
| ATOM | 563 | CA | ALA | A | 111 | 107.426 | 14.680 | 48.435 | 1.00 | 28.37 | C |
| ATOM | 564 | CB | ALA | A | 111 | 107.820 | 16.016 | 49.058 | 1.00 | 26.74 | C |
| ATOM | 565 | C | ALA | A | 111 | 108.233 | 13.548 | 49.079 | 1.00 | 29.83 | C |
| ATOM | 566 | O | ALA | A | 111 | 109.383 | 13.299 | 48.745 | 1.00 | 31.61 | O |
| ATOM | 567 | N | SER | A | 112 | 107.591 | 12.880 | 50.056 | 1.00 | 31.50 | N |
| ATOM | 568 | CA | SER | A | 112 | 108.296 | 11.873 | 50.845 | 1.00 | 31.49 | C |
| ATOM | 569 | CB | SER | A | 112 | 107.348 | 11.396 | 51.941 | 1.00 | 32.52 | C |
| ATOM | 570 | OG | SER | A | 112 | 107.884 | 10.224 | 52.558 | 1.00 | 45.68 | O |
| ATOM | 571 | C | SER | A | 112 | 108.768 | 10.681 | 50.002 | 1.00 | 31.45 | C |
| ATOM | 572 | O | SER | A | 112 | 109.668 | 9.941 | 50.370 | 1.00 | 31.01 | O |
| ATOM | 573 | N | GLN | A | 113 | 108.093 | 10.482 | 48.855 | 1.00 | 32.87 | N |
| ATOM | 574 | CA | GLN | A | 113 | 108.462 | 9.360 | 47.992 | 1.00 | 33.81 | C |
| ATOM | 575 | CB | GLN | A | 113 | 107.520 | 9.350 | 46.785 | 1.00 | 34.68 | C |
| ATOM | 576 | CG | GLN | A | 113 | 107.732 | 8.153 | 45.855 | 1.00 | 43.51 | C |
| ATOM | 577 | CD | GLN | A | 113 | 107.900 | 6.879 | 46.653 | 1.00 | 57.00 | C |
| ATOM | 578 | OE1 | GLN | A | 113 | 107.136 | 6.540 | 47.544 | 1.00 | 60.59 | O |
| ATOM | 579 | NE2 | GLN | A | 113 | 108.941 | 6.125 | 46.249 | 1.00 | 57.32 | N |
| ATOM | 580 | C | GLN | A | 113 | 109.916 | 9.458 | 47.524 | 1.00 | 32.46 | C |
| ATOM | 581 | O | GLN | A | 113 | 110.489 | 8.507 | 47.007 | 1.00 | 32.66 | O |
| ATOM | 582 | N | CYS | A | 114 | 110.507 | 10.666 | 47.641 | 1.00 | 31.09 | N |
| ATOM | 583 | CA | CYS | A | 114 | 111.884 | 10.880 | 47.182 | 1.00 | 30.18 | C |
| ATOM | 584 | CB | CYS | A | 114 | 111.964 | 12.300 | 46.583 | 1.00 | 30.42 | C |
| ATOM | 585 | SG | CYS | A | 114 | 113.626 | 12.984 | 46.346 | 1.00 | 34.49 | S |
| ATOM | 586 | C | CYS | A | 114 | 112.854 | 10.732 | 48.363 | 1.00 | 30.11 | C |
| ATOM | 587 | O | CYS | A | 114 | 112.700 | 11.332 | 49.400 | 1.00 | 30.99 | O |
| ATOM | 588 | N | PRO | A | 115 | 113.844 | 9.873 | 48.126 | 1.00 | 29.36 | N |
| ATOM | 589 | CA | PRO | A | 115 | 114.853 | 9.472 | 49.127 | 1.00 | 28.66 | C |
| ATOM | 590 | CB | PRO | A | 115 | 115.824 | 8.544 | 48.375 | 1.00 | 27.51 | C |
| ATOM | 591 | CG | PRO | A | 115 | 114.987 | 7.895 | 47.281 | 1.00 | 28.30 | C |
| ATOM | 592 | CD | PRO | A | 115 | 114.104 | 9.178 | 46.889 | 1.00 | 30.48 | C |
| ATOM | 593 | C | PRO | A | 115 | 115.629 | 10.629 | 49.736 | 1.00 | 27.87 | C |
| ATOM | 594 | O | PRO | A | 115 | 116.400 | 10.478 | 50.688 | 1.00 | 27.94 | O |
| ATOM | 595 | N | HIS | A | 116 | 115.484 | 11.825 | 49.164 | 1.00 | 26.17 | N |
| ATOM | 596 | CA | HIS | A | 116 | 116.253 | 12.924 | 49.736 | 1.00 | 26.93 | C |

FIG. 2A-13

| ATOM | 597 | CB | HIS | A | 116 | 116.955 | 13.686 | 48.628 | 1.00 | 27.73 | C |
|---|---|---|---|---|---|---|---|---|---|---|---|
| ATOM | 598 | CG | HIS | A | 116 | 118.168 | 12.919 | 48.203 | 1.00 | 30.95 | C |
| ATOM | 599 | ND1 | HIS | A | 116 | 119.274 | 12.771 | 48.983 | 1.00 | 36.20 | N |
| ATOM | 600 | CE1 | HIS | A | 116 | 120.112 | 12.007 | 48.247 | 1.00 | 33.74 | C |
| ATOM | 601 | NE2 | HIS | A | 116 | 119.599 | 11.672 | 47.052 | 1.00 | 33.04 | N |
| ATOM | 602 | CD2 | HIS | A | 116 | 118.376 | 12.238 | 46.996 | 1.00 | 33.25 | C |
| ATOM | 603 | C | HIS | A | 116 | 115.381 | 13.881 | 50.515 | 1.00 | 26.87 | C |
| ATOM | 604 | O | HIS | A | 116 | 115.717 | 15.041 | 50.713 | 1.00 | 26.24 | O |
| ATOM | 605 | N | ILE | A | 117 | 114.201 | 13.388 | 50.891 | 1.00 | 28.48 | N |
| ATOM | 606 | CA | ILE | A | 117 | 113.305 | 14.183 | 51.709 | 1.00 | 28.70 | C |
| ATOM | 607 | CB | ILE | A | 117 | 112.106 | 14.578 | 50.840 | 1.00 | 27.02 | C |
| ATOM | 608 | CG1 | ILE | A | 117 | 112.546 | 15.607 | 49.794 | 1.00 | 25.94 | C |
| ATOM | 609 | CD1 | ILE | A | 117 | 111.417 | 15.991 | 48.836 | 1.00 | 32.19 | C |
| ATOM | 610 | CG2 | ILE | A | 117 | 111.006 | 15.217 | 51.715 | 1.00 | 23.99 | C |
| ATOM | 611 | C | ILE | A | 117 | 112.855 | 13.395 | 52.932 | 1.00 | 29.01 | C |
| ATOM | 612 | O | ILE | A | 117 | 112.456 | 12.241 | 52.854 | 1.00 | 32.36 | O |
| ATOM | 613 | N | VAL | A | 118 | 112.972 | 14.051 | 54.101 | 1.00 | 28.14 | N |
| ATOM | 614 | CA | VAL | A | 118 | 112.659 | 13.360 | 55.340 | 1.00 | 27.17 | C |
| ATOM | 615 | CB | VAL | A | 118 | 112.561 | 14.399 | 56.456 | 1.00 | 26.03 | C |
| ATOM | 616 | CG1 | VAL | A | 118 | 111.257 | 15.187 | 56.337 | 1.00 | 29.60 | C |
| ATOM | 617 | CG2 | VAL | A | 118 | 112.621 | 13.717 | 57.811 | 1.00 | 27.74 | C |
| ATOM | 618 | C | VAL | A | 118 | 111.367 | 12.550 | 55.227 | 1.00 | 26.20 | C |
| ATOM | 619 | O | VAL | A | 118 | 110.327 | 13.030 | 54.805 | 1.00 | 27.56 | O |
| ATOM | 620 | N | ARG | A | 119 | 111.482 | 11.249 | 55.567 | 1.00 | 26.07 | N |
| ATOM | 621 | CA | ARG | A | 119 | 110.368 | 10.323 | 55.475 | 1.00 | 26.99 | C |
| ATOM | 622 | CB | ARG | A | 119 | 110.903 | 8.908 | 55.702 | 1.00 | 25.69 | C |
| ATOM | 623 | CG | ARG | A | 119 | 110.010 | 7.839 | 55.073 | 1.00 | 26.99 | C |
| ATOM | 624 | CD | ARG | A | 119 | 110.332 | 6.435 | 55.599 | 1.00 | 38.98 | C |
| ATOM | 625 | NE | ARG | A | 119 | 109.366 | 6.037 | 56.627 | 1.00 | 51.75 | N |
| ATOM | 626 | CZ | ARG | A | 119 | 109.686 | 4.983 | 57.400 | 1.00 | 53.47 | C |
| ATOM | 627 | NH1AR | G | A | 119 | 110.952 | 4.710 | 57.665 | 1.00 | 51.10 | N |
| ATOM | 628 | NH2AR | G | A | 119 | 108.715 | 4.214 | 57.902 | 1.00 | 57.80 | N |
| ATOM | 629 | C | ARG | A | 119 | 109.303 | 10.651 | 56.517 | 1.00 | 27.01 | C |
| ATOM | 630 | O | ARG | A | 119 | 109.595 | 10.958 | 57.665 | 1.00 | 26.85 | O |
| ATOM | 631 | N | ILE | A | 120 | 108.023 | 10.578 | 56.114 | 1.00 | 25.77 | N |
| ATOM | 632 | CA | ILE | A | 120 | 106.960 | 10.617 | 57.108 | 1.00 | 24.67 | C |
| ATOM | 633 | CB | ILE | A | 120 | 105.746 | 11.326 | 56.500 | 1.00 | 25.43 | C |
| ATOM | 634 | CG1 | ILE | A | 120 | 105.928 | 12.845 | 56.573 | 1.00 | 22.97 | C |
| ATOM | 635 | CD1 | ILE | A | 120 | 104.745 | 13.594 | 55.954 | 1.00 | 25.39 | C |
| ATOM | 636 | CG2 | ILE | A | 120 | 104.476 | 10.971 | 57.294 | 1.00 | 24.30 | C |
| ATOM | 637 | C | ILE | A | 120 | 106.565 | 9.206 | 57.524 | 1.00 | 26.14 | C |
| ATOM | 638 | O | ILE | A | 120 | 106.181 | 8.371 | 56.716 | 1.00 | 29.28 | O |
| ATOM | 639 | N | VAL | A | 121 | 106.723 | 8.932 | 58.832 | 1.00 | 24.87 | N |
| ATOM | 640 | CA | VAL | A | 121 | 106.218 | 7.670 | 59.352 | 1.00 | 24.33 | C |
| ATOM | 641 | CB | VAL | A | 121 | 106.957 | 7.339 | 60.647 | 1.00 | 26.19 | C |
| ATOM | 642 | CG1 | VAL | A | 121 | 106.313 | 6.119 | 61.305 | 1.00 | 26.23 | C |

FIG. 2A-14

| ATOM | 643 | CG2 | VAL | A | 121 | 108.416 | 7.036 | 60.354 | 1.00 | 23.97 | C |
|---|---|---|---|---|---|---|---|---|---|---|---|
| ATOM | 644 | C | VAL | A | 121 | 104.720 | 7.768 | 59.628 | 1.00 | 23.47 | C |
| ATOM | 645 | O | VAL | A | 121 | 103.938 | 6.898 | 59.276 | 1.00 | 22.70 | O |
| ATOM | 646 | N | ASP | A | 122 | 104.213 | 8.786 | 60.273 | 1.00 | 24.42 | N |
| ATOM | 647 | CA | ASP | A | 122 | 102.781 | 8.795 | 60.467 | 1.00 | 26.76 | C |
| ATOM | 648 | CB | ASP | A | 122 | 102.353 | 7.935 | 61.663 | 1.00 | 28.05 | C |
| ATOM | 649 | CG | ASP | A | 122 | 102.353 | 6.453 | 61.365 | 1.00 | 34.08 | C |
| ATOM | 650 | OD1 | ASP | A | 122 | 101.606 | 6.028 | 60.446 | 1.00 | 36.37 | O |
| ATOM | 651 | OD2 | ASP | A | 122 | 103.101 | 5.726 | 62.074 | 1.00 | 34.73 | O |
| ATOM | 652 | C | ASP | A | 122 | 102.273 | 10.174 | 60.729 | 1.00 | 26.57 | C |
| ATOM | 653 | O | ASP | A | 122 | 103.006 | 11.053 | 61.170 | 1.00 | 27.48 | O |
| ATOM | 654 | N | VAL | A | 123 | 100.994 | 10.359 | 60.469 | 1.00 | 25.62 | N |
| ATOM | 655 | CA | VAL | A | 123 | 100.392 | 11.621 | 60.777 | 1.00 | 24.49 | C |
| ATOM | 656 | CB | VAL | A | 123 | 99.886 | 12.363 | 59.526 | 1.00 | 25.87 | C |
| ATOM | 657 | CG1 | VAL | A | 123 | 99.432 | 13.798 | 59.934 | 1.00 | 25.94 | C |
| ATOM | 658 | CG2 | VAL | A | 123 | 100.985 | 12.418 | 58.475 | 1.00 | 23.38 | C |
| ATOM | 659 | C | VAL | A | 123 | 99.227 | 11.334 | 61.693 | 1.00 | 24.14 | C |
| ATOM | 660 | O | VAL | A | 123 | 98.418 | 10.452 | 61.446 | 1.00 | 24.67 | O |
| ATOM | 661 | N | TYR | A | 124 | 99.162 | 12.088 | 62.776 | 1.00 | 24.23 | N |
| ATOM | 662 | CA | TYR | A | 124 | 98.068 | 11.962 | 63.734 | 1.00 | 23.26 | C |
| ATOM | 663 | CB | TYR | A | 124 | 98.620 | 11.710 | 65.131 | 1.00 | 24.36 | C |
| ATOM | 664 | CG | TYR | A | 124 | 99.201 | 10.339 | 65.329 | 1.00 | 20.81 | C |
| ATOM | 665 | CD1 | TYR | A | 124 | 100.445 | 10.015 | 64.831 | 1.00 | 23.23 | C |
| ATOM | 666 | CE1 | TYR | A | 124 | 100.981 | 8.778 | 65.026 | 1.00 | 14.79 | C |
| ATOM | 667 | CZ | TYR | A | 124 | 100.272 | 7.829 | 65.731 | 1.00 | 16.97 | C |
| ATOM | 668 | OH | TYR | A | 124 | 100.829 | 6.602 | 65.982 | 1.00 | 18.90 | O |
| ATOM | 669 | CE2 | TYR | A | 124 | 99.031 | 8.118 | 66.229 | 1.00 | 23.32 | C |
| ATOM | 670 | CD2 | TYR | A | 124 | 98.503 | 9.365 | 66.030 | 1.00 | 23.05 | C |
| ATOM | 671 | C | TYR | A | 124 | 97.189 | 13.225 | 63.778 | 1.00 | 23.42 | C |
| ATOM | 672 | O | TYR | A | 124 | 97.654 | 14.341 | 63.626 | 1.00 | 22.92 | O |
| ATOM | 673 | N | GLU | A | 125 | 95.907 | 13.037 | 63.981 | 1.00 | 23.60 | N |
| ATOM | 674 | CA | GLU | A | 125 | 95.000 | 14.155 | 64.116 | 1.00 | 22.70 | C |
| ATOM | 675 | CB | GLU | A | 125 | 93.846 | 14.040 | 63.149 | 1.00 | 22.52 | C |
| ATOM | 676 | CG | GLU | A | 125 | 92.985 | 15.286 | 63.059 | 1.00 | 29.06 | C |
| ATOM | 677 | CD | GLU | A | 125 | 91.643 | 14.984 | 62.465 | 1.00 | 35.72 | C |
| ATOM | 678 | OE1 | GLU | A | 125 | 90.673 | 14.886 | 63.251 | 1.00 | 38.41 | O |
| ATOM | 679 | OE2 | GLU | A | 125 | 91.552 | 14.822 | 61.230 | 1.00 | 33.66 | O |
| ATOM | 680 | C | GLU | A | 125 | 94.478 | 13.906 | 65.504 | 1.00 | 22.02 | C |
| ATOM | 681 | O | GLU | A | 125 | 93.658 | 13.009 | 65.685 | 1.00 | 22.53 | O |
| ATOM | 682 | N | ASN | A | 126 | 94.976 | 14.651 | 66.487 | 1.00 | 20.76 | N |
| ATOM | 683 | CA | ASN | A | 126 | 94.530 | 14.488 | 67.858 | 1.00 | 20.64 | C |
| ATOM | 684 | CB | ASN | A | 126 | 95.652 | 14.039 | 68.763 | 1.00 | 21.01 | C |
| ATOM | 685 | CG | ASN | A | 126 | 96.157 | 12.643 | 68.458 | 1.00 | 23.19 | C |
| ATOM | 686 | OD1 | ASN | A | 126 | 97.219 | 12.266 | 68.934 | 1.00 | 22.44 | O |
| ATOM | 687 | ND2 | ASN | A | 126 | 95.406 | 11.867 | 67.692 | 1.00 | 27.78 | N |
| ATOM | 688 | C | ASN | A | 126 | 94.011 | 15.800 | 68.370 | 1.00 | 20.55 | C |

FIG. 2A-15

| ATOM | 689 | O   | ASN | A | 126 | 93.831  | 16.756 | 67.612 | 1.00 | 24.82 | O |
|------|-----|-----|-----|---|-----|---------|--------|--------|------|-------|---|
| ATOM | 690 | N   | LEU | A | 127 | 93.793  | 15.834 | 69.684 | 1.00 | 19.63 | N |
| ATOM | 691 | CA  | LEU | A | 127 | 93.253  | 16.993 | 70.397 | 1.00 | 17.61 | C |
| ATOM | 692 | CB  | LEU | A | 127 | 91.975  | 16.566 | 71.093 | 1.00 | 16.23 | C |
| ATOM | 693 | CG  | LEU | A | 127 | 90.666  | 17.261 | 70.735 | 1.00 | 18.36 | C |
| ATOM | 694 | CD1 | LEU | A | 127 | 90.691  | 17.814 | 69.332 | 1.00 | 14.30 | C |
| ATOM | 695 | CD2 | LEU | A | 127 | 89.505  | 16.272 | 70.946 | 1.00 | 19.19 | C |
| ATOM | 696 | C   | LEU | A | 127 | 94.256  | 17.448 | 71.438 | 1.00 | 18.63 | C |
| ATOM | 697 | O   | LEU | A | 127 | 94.375  | 16.838 | 72.488 | 1.00 | 20.26 | O |
| ATOM | 698 | N   | TYR | A | 128 | 95.008  | 18.506 | 71.160 | 1.00 | 20.33 | N |
| ATOM | 699 | CA  | TYR | A | 128 | 95.931  | 18.991 | 72.176 | 1.00 | 21.42 | C |
| ATOM | 700 | CB  | TYR | A | 128 | 97.199  | 19.472 | 71.477 | 1.00 | 21.95 | C |
| ATOM | 701 | CG  | TYR | A | 128 | 98.194  | 19.902 | 72.494 | 1.00 | 29.52 | C |
| ATOM | 702 | CD1 | TYR | A | 128 | 99.098  | 18.979 | 73.009 | 1.00 | 35.32 | C |
| ATOM | 703 | CE1 | TYR | A | 128 | 100.002 | 19.362 | 73.988 | 1.00 | 38.26 | C |
| ATOM | 704 | CZ  | TYR | A | 128 | 99.987  | 20.674 | 74.467 | 1.00 | 43.41 | C |
| ATOM | 705 | OH  | TYR | A | 128 | 100.887 | 21.045 | 75.446 | 1.00 | 50.43 | O |
| ATOM | 706 | CE2 | TYR | A | 128 | 99.091  | 21.597 | 73.955 | 1.00 | 42.89 | C |
| ATOM | 707 | CD2 | TYR | A | 128 | 98.195  | 21.215 | 72.968 | 1.00 | 39.64 | C |
| ATOM | 708 | C   | TYR | A | 128 | 95.324  | 20.133 | 72.995 | 1.00 | 21.81 | C |
| ATOM | 709 | O   | TYR | A | 128 | 95.163  | 21.258 | 72.537 | 1.00 | 21.09 | O |
| ATOM | 710 | N   | ALA | A | 129 | 94.948  | 19.797 | 74.241 | 1.00 | 25.95 | N |
| ATOM | 711 | CA  | ALA | A | 129 | 94.398  | 20.815 | 75.129 | 1.00 | 28.19 | C |
| ATOM | 712 | CB  | ALA | A | 129 | 95.492  | 21.845 | 75.411 | 1.00 | 29.13 | C |
| ATOM | 713 | C   | ALA | A | 129 | 93.175  | 21.510 | 74.521 | 1.00 | 28.80 | C |
| ATOM | 714 | O   | ALA | A | 129 | 93.061  | 22.729 | 74.487 | 1.00 | 29.09 | O |
| ATOM | 715 | N   | GLY | A | 130 | 92.258  | 20.682 | 73.989 | 1.00 | 28.52 | N |
| ATOM | 716 | CA  | GLY | A | 130 | 91.023  | 21.237 | 73.446 | 1.00 | 29.86 | C |
| ATOM | 717 | C   | GLY | A | 130 | 91.125  | 21.511 | 71.945 | 1.00 | 30.27 | C |
| ATOM | 718 | O   | GLY | A | 130 | 90.160  | 21.412 | 71.198 | 1.00 | 31.39 | O |
| ATOM | 719 | N   | ALA | A | 131 | 92.334  | 21.907 | 71.513 | 1.00 | 29.99 | N |
| ATOM | 720 | CA  | ALA | A | 131 | 92.609  | 22.303 | 70.137 | 1.00 | 30.64 | C |
| ATOM | 721 | CB  | ALA | A | 131 | 93.783  | 23.282 | 70.139 | 1.00 | 31.81 | C |
| ATOM | 722 | C   | ALA | A | 131 | 92.929  | 21.104 | 69.234 | 1.00 | 29.62 | C |
| ATOM | 723 | O   | ALA | A | 131 | 93.492  | 20.095 | 69.646 | 1.00 | 29.98 | O |
| ATOM | 724 | N   | LYS | A | 132 | 92.505  | 21.237 | 67.963 | 1.00 | 30.04 | N |
| ATOM | 725 | CA  | LYS | A | 132 | 92.804  | 20.203 | 66.974 | 1.00 | 30.63 | C |
| ATOM | 726 | CB  | LYS | A | 132 | 91.704  | 20.266 | 65.913 | 1.00 | 31.89 | C |
| ATOM | 727 | CG  | LYS | A | 132 | 91.439  | 18.928 | 65.225 | 1.00 | 37.27 | C |
| ATOM | 728 | CD  | LYS | A | 132 | 90.196  | 19.001 | 64.336 | 1.00 | 43.24 | C |
| ATOM | 729 | CE  | LYS | A | 132 | 89.966  | 17.717 | 63.539 | 1.00 | 45.62 | C |
| ATOM | 730 | NZ  | LYS | A | 132 | 88.894  | 17.945 | 62.572 | 1.00 | 53.09 | N |
| ATOM | 731 | C   | LYS | A | 132 | 94.160  | 20.466 | 66.313 | 1.00 | 30.63 | C |
| ATOM | 732 | O   | LYS | A | 132 | 94.481  | 21.579 | 65.927 | 1.00 | 31.35 | O |
| ATOM | 733 | N   | CYS | A | 133 | 94.988  | 19.405 | 66.223 | 1.00 | 29.19 | N |
| ATOM | 734 | CA  | CYS | A | 133 | 96.306  | 19.585 | 65.612 | 1.00 | 31.80 | C |

FIG. 2A-16

| ATOM | 735 | CB | CYS | A | 133 | 97.288 | 19.980 | 66.709 | 1.00 | 31.04 | C |
|---|---|---|---|---|---|---|---|---|---|---|---|
| ATOM | 736 | SG | CYS | A | 133 | 97.228 | 18.849 | 68.116 | 1.00 | 44.40 | S |
| ATOM | 737 | C | CYS | A | 133 | 96.803 | 18.309 | 64.927 | 1.00 | 29.24 | C |
| ATOM | 738 | O | CYS | A | 133 | 96.369 | 17.204 | 65.228 | 1.00 | 28.00 | O |
| ATOM | 739 | N | LEU | A | 134 | 97.699 | 18.584 | 63.977 | 1.00 | 28.05 | N |
| ATOM | 740 | CA | LEU | A | 134 | 98.318 | 17.523 | 63.173 | 1.00 | 26.68 | C |
| ATOM | 741 | CB | LEU | A | 134 | 98.416 | 17.939 | 61.696 | 1.00 | 25.58 | C |
| ATOM | 742 | CG | LEU | A | 134 | 97.274 | 17.758 | 60.672 | 1.00 | 25.61 | C |
| ATOM | 743 | CD1 | LEU | A | 134 | 96.332 | 16.633 | 61.053 | 1.00 | 19.83 | C |
| ATOM | 744 | CD2 | LEU | A | 134 | 96.496 | 19.033 | 60.569 | 1.00 | 34.11 | C |
| ATOM | 745 | C | LEU | A | 134 | 99.703 | 17.191 | 63.713 | 1.00 | 26.37 | C |
| ATOM | 746 | O | LEU | A | 134 | 100.553 | 18.057 | 63.822 | 1.00 | 28.01 | O |
| ATOM | 747 | N | LEU | A | 135 | 99.920 | 15.934 | 64.068 | 1.00 | 25.54 | N |
| ATOM | 748 | CA | LEU | A | 135 | 101.189 | 15.491 | 64.626 | 1.00 | 25.28 | C |
| ATOM | 749 | CB | LEU | A | 135 | 100.926 | 14.647 | 65.880 | 1.00 | 25.77 | C |
| ATOM | 750 | CG | LEU | A | 135 | 100.008 | 15.335 | 66.915 | 1.00 | 23.21 | C |
| ATOM | 751 | CD1 | LEU | A | 135 | 99.951 | 14.523 | 68.175 | 1.00 | 20.11 | C |
| ATOM | 752 | CD2 | LEU | A | 135 | 100.514 | 16.737 | 67.223 | 1.00 | 24.65 | C |
| ATOM | 753 | C | LEU | A | 135 | 101.909 | 14.699 | 63.563 | 1.00 | 26.69 | C |
| ATOM | 754 | O | LEU | A | 135 | 101.480 | 13.599 | 63.154 | 1.00 | 28.81 | O |
| ATOM | 755 | N | ILE | A | 136 | 103.006 | 15.259 | 63.089 | 1.00 | 25.62 | N |
| ATOM | 756 | CA | ILE | A | 136 | 103.740 | 14.612 | 62.014 | 1.00 | 25.59 | C |
| ATOM | 757 | CB | ILE | A | 136 | 104.244 | 15.650 | 60.972 | 1.00 | 26.18 | C |
| ATOM | 758 | CG1 | ILE | A | 136 | 103.088 | 16.488 | 60.436 | 1.00 | 26.15 | C |
| ATOM | 759 | CD1 | ILE | A | 136 | 103.501 | 17.345 | 59.221 | 1.00 | 27.07 | C |
| ATOM | 760 | CG2 | ILE | A | 136 | 104.930 | 14.949 | 59.827 | 1.00 | 22.73 | C |
| ATOM | 761 | C | ILE | A | 136 | 104.931 | 13.840 | 62.526 | 1.00 | 25.09 | C |
| ATOM | 762 | O | ILE | A | 136 | 105.884 | 14.431 | 63.053 | 1.00 | 25.07 | O |
| ATOM | 763 | N | VAL | A | 137 | 104.887 | 12.521 | 62.386 | 1.00 | 23.86 | N |
| ATOM | 764 | CA | VAL | A | 137 | 106.007 | 11.724 | 62.831 | 1.00 | 21.71 | C |
| ATOM | 765 | CB | VAL | A | 137 | 105.565 | 10.315 | 63.310 | 1.00 | 23.93 | C |
| ATOM | 766 | CG1 | VAL | A | 137 | 106.779 | 9.466 | 63.683 | 1.00 | 23.87 | C |
| ATOM | 767 | CG2 | VAL | A | 137 | 104.666 | 10.450 | 64.537 | 1.00 | 21.32 | C |
| ATOM | 768 | C | VAL | A | 137 | 107.020 | 11.577 | 61.717 | 1.00 | 21.14 | C |
| ATOM | 769 | O | VAL | A | 137 | 106.730 | 11.023 | 60.672 | 1.00 | 21.65 | O |
| ATOM | 770 | N | MSE | A | 138 | 108.224 | 12.078 | 61.949 | 1.00 | 20.76 | N |
| ATOM | 771 | CA | MSE | A | 138 | 109.276 | 11.942 | 60.960 | 1.00 | 20.97 | C |
| ATOM | 772 | CB | MSE | A | 138 | 109.798 | 13.311 | 60.543 | 1.00 | 20.45 | C |
| ATOM | 773 | CG | MSE | A | 138 | 108.874 | 14.010 | 59.619 | 1.00 | 20.95 | C |
| ATOM | 774 | SE | MSE | A | 138 | 109.060 | 15.871 | 59.744 | 1.00 | 32.61 | S |
| ATOM | 775 | CE | MSE | A | 138 | 108.756 | 16.127 | 61.569 | 1.00 | 30.55 | C |
| ATOM | 776 | C | MSE | A | 138 | 110.440 | 11.101 | 61.439 | 1.00 | 20.80 | C |
| ATOM | 777 | O | MSE | A | 138 | 110.731 | 11.041 | 62.629 | 1.00 | 20.14 | O |
| ATOM | 778 | N | GLU | A | 139 | 111.095 | 10.472 | 60.471 | 1.00 | 22.66 | N |
| ATOM | 779 | CA | GLU | A | 139 | 112.286 | 9.652 | 60.674 | 1.00 | 23.46 | C |
| ATOM | 780 | CB | GLU | A | 139 | 112.765 | 9.151 | 59.324 | 1.00 | 23.19 | C |

FIG. 2A-17

| ATOM | 781 | CG | GLU | A | 139 | 113.791 | 10.050 | 58.707 | 1.00 | 26.85 | C |
| --- | --- | --- | --- | --- | --- | --- | --- | --- | --- | --- | --- |
| ATOM | 782 | CD | GLU | A | 139 | 114.247 | 9.542 | 57.353 | 1.00 | 29.70 | C |
| ATOM | 783 | OE1 | GLU | A | 139 | 113.874 | 10.147 | 56.310 | 1.00 | 29.35 | O |
| ATOM | 784 | OE2 | GLU | A | 139 | 114.976 | 8.518 | 57.333 | 1.00 | 29.64 | O |
| ATOM | 785 | C | GLU | A | 139 | 113.393 | 10.500 | 61.330 | 1.00 | 24.62 | C |
| ATOM | 786 | O | GLU | A | 139 | 113.471 | 11.685 | 61.135 | 1.00 | 24.98 | O |
| ATOM | 787 | N | CYS | A | 140 | 114.262 | 9.902 | 62.115 | 1.00 | 26.72 | N |
| ATOM | 788 | CA | CYS | A | 140 | 115.291 | 10.698 | 62.768 | 1.00 | 29.61 | C |
| ATOM | 789 | CB | CYS | A | 140 | 115.803 | 9.978 | 64.010 | 1.00 | 29.95 | C |
| ATOM | 790 | SG | CYS | A | 140 | 116.298 | 11.081 | 65.338 | 1.00 | 42.52 | S |
| ATOM | 791 | C | CYS | A | 140 | 116.449 | 10.995 | 61.824 | 1.00 | 29.25 | C |
| ATOM | 792 | O | CYS | A | 140 | 116.886 | 10.136 | 61.057 | 1.00 | 29.64 | O |
| ATOM | 793 | N | LEU | A | 141 | 116.925 | 12.227 | 61.864 | 1.00 | 28.57 | N |
| ATOM | 794 | CA | LEU | A | 141 | 118.122 | 12.760 | 61.211 | 1.00 | 27.72 | C |
| ATOM | 795 | CB | LEU | A | 141 | 117.683 | 13.875 | 60.263 | 1.00 | 27.02 | C |
| ATOM | 796 | CG | LEU | A | 141 | 116.679 | 13.383 | 59.217 | 1.00 | 26.53 | C |
| ATOM | 797 | CD1 | LEU | A | 141 | 115.998 | 14.534 | 58.468 | 1.00 | 33.12 | C |
| ATOM | 798 | CD2 | LEU | A | 141 | 117.330 | 12.500 | 58.155 | 1.00 | 21.60 | C |
| ATOM | 799 | C | LEU | A | 141 | 119.157 | 13.291 | 62.216 | 1.00 | 29.71 | C |
| ATOM | 800 | O | LEU | A | 141 | 119.077 | 14.409 | 62.710 | 1.00 | 32.31 | O |
| ATOM | 801 | N | ASP | A | 142 | 120.151 | 12.425 | 62.518 | 1.00 | 30.99 | N |
| ATOM | 802 | CA | ASP | A | 142 | 121.136 | 12.745 | 63.544 | 1.00 | 33.03 | C |
| ATOM | 803 | CB | ASP | A | 142 | 121.312 | 11.512 | 64.428 | 1.00 | 35.08 | C |
| ATOM | 804 | CG | ASP | A | 142 | 120.407 | 11.636 | 65.643 | 1.00 | 44.56 | C |
| ATOM | 805 | OD1 | ASP | A | 142 | 119.201 | 11.449 | 65.480 | 1.00 | 52.85 | O |
| ATOM | 806 | OD2 | ASP | A | 142 | 120.911 | 11.910 | 66.728 | 1.00 | 54.52 | O |
| ATOM | 807 | C | ASP | A | 142 | 122.485 | 13.132 | 62.936 | 1.00 | 30.90 | C |
| ATOM | 808 | O | ASP | A | 142 | 123.483 | 13.305 | 63.621 | 1.00 | 29.77 | O |
| ATOM | 809 | N | GLY | A | 143 | 122.502 | 13.230 | 61.594 | 1.00 | 29.16 | N |
| ATOM | 810 | CA | GLY | A | 143 | 123.760 | 13.502 | 60.908 | 1.00 | 26.83 | C |
| ATOM | 811 | C | GLY | A | 143 | 124.230 | 14.944 | 61.118 | 1.00 | 24.13 | C |
| ATOM | 812 | O | GLY | A | 143 | 125.388 | 15.289 | 60.917 | 1.00 | 23.45 | O |
| ATOM | 813 | N | GLY | A | 144 | 123.269 | 15.806 | 61.493 | 1.00 | 23.73 | N |
| ATOM | 814 | CA | GLY | A | 144 | 123.604 | 17.210 | 61.696 | 1.00 | 21.81 | C |
| ATOM | 815 | C | GLY | A | 144 | 123.454 | 18.007 | 60.400 | 1.00 | 21.40 | C |
| ATOM | 816 | O | GLY | A | 144 | 123.257 | 17.464 | 59.321 | 1.00 | 18.10 | O |
| ATOM | 817 | N | GLU | A | 145 | 123.505 | 19.344 | 60.542 | 1.00 | 23.39 | N |
| ATOM | 818 | CA | GLU | A | 145 | 123.384 | 20.203 | 59.372 | 1.00 | 25.60 | C |
| ATOM | 819 | CB | GLU | A | 145 | 123.614 | 21.646 | 59.818 | 1.00 | 27.39 | C |
| ATOM | 820 | CG | GLU | A | 145 | 122.496 | 22.170 | 60.716 | 1.00 | 30.89 | C |
| ATOM | 821 | CD | GLU | A | 145 | 122.727 | 23.637 | 60.993 | 1.00 | 43.97 | C |
| ATOM | 822 | OE1 | GLU | A | 145 | 123.828 | 24.108 | 60.753 | 1.00 | 47.70 | O |
| ATOM | 823 | OE2 | GLU | A | 145 | 121.806 | 24.296 | 61.473 | 1.00 | 47.22 | O |
| ATOM | 824 | C | GLU | A | 145 | 124.403 | 19.824 | 58.293 | 1.00 | 26.27 | C |
| ATOM | 825 | O | GLU | A | 145 | 125.410 | 19.176 | 58.544 | 1.00 | 26.74 | O |
| ATOM | 826 | N | LEU | A | 146 | 124.085 | 20.221 | 57.045 | 1.00 | 26.08 | N |

FIG. 2A-18

| ATOM | 827 | CA | LEU | A | 146 | 125.017 | 19.973 | 55.948 | 1.00 | 25.18 | C |
|---|---|---|---|---|---|---|---|---|---|---|---|
| ATOM | 828 | CB | LEU | A | 146 | 124.426 | 20.592 | 54.678 | 1.00 | 25.14 | C |
| ATOM | 829 | CG | LEU | A | 146 | 125.496 | 20.907 | 53.631 | 1.00 | 20.97 | C |
| ATOM | 830 | CD1 | LEU | A | 146 | 126.215 | 19.650 | 53.138 | 1.00 | 22.41 | C |
| ATOM | 831 | CD2 | LEU | A | 146 | 124.922 | 21.585 | 52.385 | 1.00 | 17.99 | C |
| ATOM | 832 | C | LEU | A | 146 | 126.389 | 20.589 | 56.228 | 1.00 | 25.36 | C |
| ATOM | 833 | O | LEU | A | 146 | 127.432 | 20.007 | 55.961 | 1.00 | 24.62 | O |
| ATOM | 834 | N | PHE | A | 147 | 126.358 | 21.829 | 56.758 | 1.00 | 26.07 | N |
| ATOM | 835 | CA | PHE | A | 147 | 127.598 | 22.565 | 56.965 | 1.00 | 26.88 | C |
| ATOM | 836 | CB | PHE | A | 147 | 127.263 | 24.058 | 56.976 | 1.00 | 27.81 | C |
| ATOM | 837 | CG | PHE | A | 147 | 127.049 | 24.538 | 55.570 | 1.00 | 30.53 | C |
| ATOM | 838 | CD1 | PHE | A | 147 | 126.602 | 25.835 | 55.342 | 1.00 | 36.01 | C |
| ATOM | 839 | CE1 | PHE | A | 147 | 126.412 | 26.282 | 54.042 | 1.00 | 40.89 | C |
| ATOM | 840 | CZ | PHE | A | 147 | 126.667 | 25.439 | 52.966 | 1.00 | 37.24 | C |
| ATOM | 841 | CE2 | PHE | A | 147 | 127.109 | 24.142 | 53.203 | 1.00 | 35.18 | C |
| ATOM | 842 | CD2 | PHE | A | 147 | 127.302 | 23.686 | 54.506 | 1.00 | 34.23 | C |
| ATOM | 843 | C | PHE | A | 147 | 128.291 | 22.166 | 58.269 | 1.00 | 26.71 | C |
| ATOM | 844 | O | PHE | A | 147 | 129.447 | 22.485 | 58.511 | 1.00 | 25.96 | O |
| ATOM | 845 | N | SER | A | 148 | 127.612 | 21.537 | 59.220 | 1.00 | 28.98 | N |
| ATOM | 846 | CA | SER | A | 148 | 128.246 | 21.145 | 60.470 | 1.00 | 29.32 | C |
| ATOM | 847 | CB | SER | A | 148 | 127.211 | 20.630 | 61.441 | 1.00 | 30.34 | C |
| ATOM | 848 | OG | SER | A | 148 | 126.390 | 21.700 | 61.873 | 1.00 | 34.35 | O |
| ATOM | 849 | C | SER | A | 148 | 129.169 | 20.013 | 60.089 | 1.00 | 29.33 | C |
| ATOM | 850 | O | SER | A | 148 | 130.333 | 19.990 | 60.470 | 1.00 | 28.38 | O |
| ATOM | 851 | N | ARG | A | 149 | 128.635 | 19.067 | 59.330 | 1.00 | 31.08 | N |
| ATOM | 852 | CA | ARG | A | 149 | 129.430 | 17.949 | 58.867 | 1.00 | 32.71 | C |
| ATOM | 853 | CB | ARG | A | 149 | 128.592 | 17.088 | 57.920 | 1.00 | 34.94 | C |
| ATOM | 854 | CG | ARG | A | 149 | 129.124 | 15.684 | 57.675 | 1.00 | 38.97 | C |
| ATOM | 855 | CD | ARG | A | 149 | 128.043 | 14.624 | 57.974 | 1.00 | 44.17 | C |
| ATOM | 856 | NE | ARG | A | 149 | 128.412 | 13.268 | 57.550 | 1.00 | 46.48 | N |
| ATOM | 857 | CZ | ARG | A | 149 | 128.792 | 12.937 | 56.313 | 1.00 | 51.23 | C |
| ATOM | 858 | NH1AR | G | A | 149 | 128.862 | 13.854 | 55.349 | 1.00 | 51.70 | N |
| ATOM | 859 | NH2AR | G | A | 149 | 129.111 | 11.678 | 56.035 | 1.00 | 52.42 | N |
| ATOM | 860 | C | ARG | A | 149 | 130.674 | 18.530 | 58.164 | 1.00 | 32.75 | C |
| ATOM | 861 | O | ARG | A | 149 | 131.807 | 18.259 | 58.566 | 1.00 | 33.81 | O |
| ATOM | 862 | N | ILE | A | 150 | 130.468 | 19.357 | 57.143 | 1.00 | 33.32 | N |
| ATOM | 863 | CA | ILE | A | 150 | 131.591 | 19.962 | 56.434 | 1.00 | 32.66 | C |
| ATOM | 864 | CB | ILE | A | 150 | 131.149 | 21.087 | 55.453 | 1.00 | 32.75 | C |
| ATOM | 865 | CG1 | ILE | A | 150 | 130.962 | 20.549 | 54.032 | 1.00 | 33.98 | C |
| ATOM | 866 | CD1 | ILE | A | 150 | 129.644 | 19.843 | 53.790 | 1.00 | 36.90 | C |
| ATOM | 867 | CG2 | ILE | A | 150 | 132.190 | 22.183 | 55.430 | 1.00 | 30.68 | C |
| ATOM | 868 | C | ILE | A | 150 | 132.554 | 20.597 | 57.420 | 1.00 | 32.79 | C |
| ATOM | 869 | O | ILE | A | 150 | 133.749 | 20.361 | 57.373 | 1.00 | 33.41 | O |
| ATOM | 870 | N | GLN | A | 151 | 132.028 | 21.410 | 58.318 | 1.00 | 33.82 | N |
| ATOM | 871 | CA | GLN | A | 151 | 132.855 | 22.102 | 59.297 | 1.00 | 35.23 | C |
| ATOM | 872 | CB | GLN | A | 151 | 131.957 | 22.941 | 60.200 | 1.00 | 35.06 | C |

FIG. 2A-19

| ATOM | 873 | CG | GLN | A | 151 | 132.632 | 24.059 | 60.921 | 1.00 | 36.73 | C |
| ATOM | 874 | CD | GLN | A | 151 | 131.619 | 24.945 | 61.613 | 1.00 | 39.43 | C |
| ATOM | 875 | OE1 | GLN | A | 151 | 131.942 | 26.014 | 62.122 | 1.00 | 42.72 | O |
| ATOM | 876 | NE2 | GLN | A | 151 | 130.376 | 24.498 | 61.634 | 1.00 | 42.22 | N |
| ATOM | 877 | C | GLN | A | 151 | 133.734 | 21.165 | 60.142 | 1.00 | 36.39 | C |
| ATOM | 878 | O | GLN | A | 151 | 134.880 | 21.486 | 60.459 | 1.00 | 37.18 | O |
| ATOM | 879 | N | ALA | A | 152 | 133.206 | 20.001 | 60.498 | 1.00 | 37.66 | N |
| ATOM | 880 | CA | ALA | A | 152 | 133.959 | 19.062 | 61.317 | 1.00 | 39.35 | C |
| ATOM | 881 | CB | ALA | A | 152 | 132.996 | 18.175 | 62.110 | 1.00 | 39.69 | C |
| ATOM | 882 | C | ALA | A | 152 | 134.904 | 18.199 | 60.485 | 1.00 | 40.85 | C |
| ATOM | 883 | O | ALA | A | 152 | 134.498 | 17.155 | 59.977 | 1.00 | 41.72 | O |
| ATOM | 884 | N | ARG | A | 153 | 136.155 | 18.629 | 60.343 | 1.00 | 41.82 | N |
| ATOM | 885 | CA | ARG | A | 153 | 137.149 | 17.870 | 59.578 | 1.00 | 42.65 | C |
| ATOM | 886 | CB | ARG | A | 153 | 136.992 | 18.132 | 58.075 | 1.00 | 42.17 | C |
| ATOM | 887 | CG | ARG | A | 153 | 135.708 | 17.578 | 57.464 | 1.00 | 43.98 | C |
| ATOM | 888 | CD | ARG | A | 153 | 135.576 | 17.935 | 55.991 | 1.00 | 46.18 | C |
| ATOM | 889 | NE | ARG | A | 153 | 134.460 | 17.252 | 55.354 | 1.00 | 51.51 | N |
| ATOM | 890 | CZ | ARG | A | 153 | 134.554 | 16.567 | 54.220 | 1.00 | 51.97 | C |
| ATOM | 891 | NH1AR | G | A | 153 | 133.499 | 15.929 | 53.733 | 1.00 | 52.01 | N |
| ATOM | 892 | NH2AR | G | A | 153 | 135.709 | 16.521 | 53.564 | 1.00 | 45.29 | N |
| ATOM | 893 | C | ARG | A | 153 | 138.566 | 18.243 | 60.014 | 1.00 | 44.12 | C |
| ATOM | 894 | O | ARG | A | 153 | 139.227 | 18.990 | 59.255 | 1.00 | 46.20 | O |
| ATOM | 895 | OXT | ARG | A | 153 | 138.979 | 17.775 | 61.105 | 1.00 | 44.22 | O |
| ATOM | 896 | N | ALA | A | 157 | 140.631 | 18.338 | 53.059 | 1.00 | 38.68 | N |
| ATOM | 897 | CA | ALA | A | 157 | 139.307 | 18.491 | 53.650 | 1.00 | 39.69 | C |
| ATOM | 898 | CB | ALA | A | 157 | 139.197 | 19.909 | 54.213 | 1.00 | 40.14 | C |
| ATOM | 899 | C | ALA | A | 157 | 138.199 | 18.250 | 52.624 | 1.00 | 39.28 | C |
| ATOM | 900 | O | ALA | A | 157 | 138.003 | 17.151 | 52.119 | 1.00 | 40.82 | O |
| ATOM | 901 | N | PHE | A | 158 | 137.431 | 19.322 | 52.354 | 1.00 | 37.34 | N |
| ATOM | 902 | CA | PHE | A | 158 | 136.356 | 19.214 | 51.374 | 1.00 | 35.79 | C |
| ATOM | 903 | CB | PHE | A | 158 | 135.214 | 20.122 | 51.832 | 1.00 | 35.71 | C |
| ATOM | 904 | CG | PHE | A | 158 | 133.972 | 19.826 | 51.048 | 1.00 | 34.23 | C |
| ATOM | 905 | CD1 | PHE | A | 158 | 133.463 | 18.534 | 51.030 | 1.00 | 35.52 | C |
| ATOM | 906 | CE1 | PHE | A | 158 | 132.254 | 18.278 | 50.399 | 1.00 | 40.81 | C |
| ATOM | 907 | CZ | PHE | A | 158 | 131.553 | 19.306 | 49.783 | 1.00 | 40.96 | C |
| ATOM | 908 | CE2 | PHE | A | 158 | 132.073 | 20.594 | 49.798 | 1.00 | 38.85 | C |
| ATOM | 909 | CD2 | PHE | A | 158 | 133.284 | 20.858 | 50.428 | 1.00 | 33.38 | C |
| ATOM | 910 | C | PHE | A | 158 | 136.830 | 19.646 | 49.985 | 1.00 | 35.16 | C |
| ATOM | 911 | O | PHE | A | 158 | 137.278 | 20.762 | 49.772 | 1.00 | 35.08 | O |
| ATOM | 912 | N | THR | A | 159 | 136.759 | 18.700 | 49.030 | 1.00 | 34.22 | N |
| ATOM | 913 | CA | THR | A | 159 | 137.156 | 19.034 | 47.667 | 1.00 | 33.38 | C |
| ATOM | 914 | CB | THR | A | 159 | 137.650 | 17.757 | 46.979 | 1.00 | 33.20 | C |
| ATOM | 915 | OG1 | THR | A | 159 | 136.554 | 16.859 | 46.814 | 1.00 | 38.19 | O |
| ATOM | 916 | CG2 | THR | A | 159 | 138.724 | 17.079 | 47.835 | 1.00 | 34.85 | C |
| ATOM | 917 | C | THR | A | 159 | 135.990 | 19.638 | 46.879 | 1.00 | 32.21 | C |
| ATOM | 918 | O | THR | A | 159 | 134.923 | 19.919 | 47.407 | 1.00 | 32.07 | O |

FIG. 2A-20

| ATOM | 919 | N   | GLU | A | 160 | 136.240 | 19.873 | 45.580 | 1.00 | 30.49 | N |
| --- | --- | --- | --- | --- | --- | --- | --- | --- | --- | --- | --- |
| ATOM | 920 | CA  | GLU | A | 160 | 135.188 | 20.436 | 44.741 | 1.00 | 30.11 | C |
| ATOM | 921 | CB  | GLU | A | 160 | 135.846 | 21.238 | 43.617 | 1.00 | 29.35 | C |
| ATOM | 922 | CG  | GLU | A | 160 | 134.844 | 21.664 | 42.544 | 1.00 | 33.72 | C |
| ATOM | 923 | CD  | GLU | A | 160 | 135.552 | 22.468 | 41.482 | 1.00 | 39.52 | C |
| ATOM | 924 | OE1 | GLU | A | 160 | 136.244 | 23.414 | 41.827 | 1.00 | 42.21 | O |
| ATOM | 925 | OE2 | GLU | A | 160 | 135.387 | 22.153 | 40.305 | 1.00 | 41.48 | O |
| ATOM | 926 | C   | GLU | A | 160 | 134.300 | 19.342 | 44.149 | 1.00 | 28.93 | C |
| ATOM | 927 | O   | GLU | A | 160 | 133.087 | 19.472 | 44.058 | 1.00 | 30.25 | O |
| ATOM | 928 | N   | ALA | A | 161 | 134.833 | 18.189 | 43.778 | 1.00 | 27.83 | N |
| ATOM | 929 | CA  | ALA | A | 161 | 133.960 | 17.121 | 43.306 | 1.00 | 27.01 | C |
| ATOM | 930 | CB  | ALA | A | 161 | 134.779 | 15.940 | 42.791 | 1.00 | 26.14 | C |
| ATOM | 931 | C   | ALA | A | 161 | 133.074 | 16.687 | 44.478 | 1.00 | 26.44 | C |
| ATOM | 932 | O   | ALA | A | 161 | 132.004 | 16.111 | 44.275 | 1.00 | 26.90 | O |
| ATOM | 933 | N   | GLU | A | 162 | 133.526 | 16.945 | 45.704 | 1.00 | 25.98 | N |
| ATOM | 934 | CA  | GLU | A | 162 | 132.713 | 16.588 | 46.860 | 1.00 | 27.24 | C |
| ATOM | 935 | CB  | GLU | A | 162 | 133.475 | 16.792 | 48.176 | 1.00 | 27.77 | C |
| ATOM | 936 | CG  | GLU | A | 162 | 134.012 | 15.485 | 48.801 | 1.00 | 31.65 | C |
| ATOM | 937 | CD  | GLU | A | 162 | 134.947 | 15.699 | 50.005 | 1.00 | 31.10 | C |
| ATOM | 938 | OE1 | GLU | A | 162 | 134.618 | 15.234 | 51.117 | 1.00 | 35.10 | O |
| ATOM | 939 | OE2 | GLU | A | 162 | 136.012 | 16.335 | 49.830 | 1.00 | 25.44 | O |
| ATOM | 940 | C   | GLU | A | 162 | 131.499 | 17.510 | 46.797 | 1.00 | 26.29 | C |
| ATOM | 941 | O   | GLU | A | 162 | 130.363 | 17.039 | 46.716 | 1.00 | 26.67 | O |
| ATOM | 942 | N   | ALA | A | 163 | 131.762 | 18.820 | 46.798 | 1.00 | 25.04 | N |
| ATOM | 943 | CA  | ALA | A | 163 | 130.738 | 19.845 | 46.721 | 1.00 | 24.41 | C |
| ATOM | 944 | CB  | ALA | A | 163 | 131.382 | 21.178 | 46.567 | 1.00 | 23.72 | C |
| ATOM | 945 | C   | ALA | A | 163 | 129.792 | 19.593 | 45.555 | 1.00 | 24.30 | C |
| ATOM | 946 | O   | ALA | A | 163 | 128.603 | 19.868 | 45.627 | 1.00 | 24.81 | O |
| ATOM | 947 | N   | SER | A | 164 | 130.323 | 19.068 | 44.472 | 1.00 | 22.33 | N |
| ATOM | 948 | CA  | SER | A | 164 | 129.515 | 18.784 | 43.309 | 1.00 | 22.73 | C |
| ATOM | 949 | CB  | SER | A | 164 | 130.401 | 18.359 | 42.137 | 1.00 | 21.65 | C |
| ATOM | 950 | OG  | SER | A | 164 | 129.633 | 18.066 | 40.989 | 1.00 | 21.45 | O |
| ATOM | 951 | C   | SER | A | 164 | 128.571 | 17.661 | 43.633 | 1.00 | 24.79 | C |
| ATOM | 952 | O   | SER | A | 164 | 127.397 | 17.706 | 43.290 | 1.00 | 26.29 | O |
| ATOM | 953 | N   | GLU | A | 165 | 129.108 | 16.637 | 44.286 | 1.00 | 26.31 | N |
| ATOM | 954 | CA  | GLU | A | 165 | 128.328 | 15.471 | 44.646 | 1.00 | 26.41 | C |
| ATOM | 955 | CB  | GLU | A | 165 | 129.244 | 14.412 | 45.257 | 1.00 | 27.89 | C |
| ATOM | 956 | CG  | GLU | A | 165 | 129.709 | 13.354 | 44.249 | 1.00 | 33.10 | C |
| ATOM | 957 | CD  | GLU | A | 165 | 130.884 | 12.509 | 44.779 | 1.00 | 45.73 | C |
| ATOM | 958 | OE1 | GLU | A | 165 | 132.038 | 13.018 | 44.801 | 1.00 | 45.86 | O |
| ATOM | 959 | OE2 | GLU | A | 165 | 130.643 | 11.339 | 45.184 | 1.00 | 52.68 | O |
| ATOM | 960 | C   | GLU | A | 165 | 127.205 | 15.845 | 45.592 | 1.00 | 25.24 | C |
| ATOM | 961 | O   | GLU | A | 165 | 126.099 | 15.323 | 45.486 | 1.00 | 26.14 | O |
| ATOM | 962 | N   | ILE | A | 166 | 127.495 | 16.756 | 46.508 | 1.00 | 24.26 | N |
| ATOM | 963 | CA  | ILE | A | 166 | 126.496 | 17.234 | 47.450 | 1.00 | 23.46 | C |
| ATOM | 964 | CB  | ILE | A | 166 | 127.111 | 18.134 | 48.491 | 1.00 | 22.48 | C |

FIG. 2A-21

| | | | | | | | | | | |
|---|---|---|---|---|---|---|---|---|---|---|
| ATOM | 965 | CG1 | ILE | A | 166 | 128.000 | 17.322 | 49.425 | 1.00 | 23.12 | C |
| ATOM | 966 | CD1 | ILE | A | 166 | 128.578 | 18.136 | 50.570 | 1.00 | 22.22 | C |
| ATOM | 967 | CG2 | ILE | A | 166 | 126.037 | 18.825 | 49.252 | 1.00 | 19.63 | C |
| ATOM | 968 | C | ILE | A | 166 | 125.450 | 18.039 | 46.684 | 1.00 | 23.46 | C |
| ATOM | 969 | O | ILE | A | 166 | 124.265 | 17.765 | 46.778 | 1.00 | 23.35 | O |
| ATOM | 970 | N | MSEA | | 167 | 125.895 | 19.016 | 45.905 | 1.00 | 23.96 | N |
| ATOM | 971 | CA | MSEA | | 167 | 124.975 | 19.840 | 45.136 | 1.00 | 24.49 | C |
| ATOM | 972 | CB | MSEA | | 167 | 125.726 | 20.830 | 44.257 | 1.00 | 21.85 | C |
| ATOM | 973 | CG | MSEA | | 167 | 126.303 | 21.980 | 45.026 | 1.00 | 19.47 | C |
| ATOM | 974 | SE | MSEA | | 167 | 125.040 | 22.756 | 46.278 | 1.00 | 26.21 | S |
| ATOM | 975 | CE | MSEA | | 167 | 123.724 | 23.344 | 45.011 | 1.00 | 31.94 | C |
| ATOM | 976 | C | MSEA | | 167 | 124.051 | 19.008 | 44.274 | 1.00 | 26.21 | C |
| ATOM | 977 | O | MSEA | | 167 | 122.958 | 19.442 | 43.925 | 1.00 | 29.26 | O |
| ATOM | 978 | N | LYS | A | 168 | 124.470 | 17.800 | 43.931 | 1.00 | 25.31 | N |
| ATOM | 979 | CA | LYS | A | 168 | 123.632 | 16.964 | 43.091 | 1.00 | 25.87 | C |
| ATOM | 980 | CB | LYS | A | 168 | 124.499 | 16.003 | 42.289 | 1.00 | 25.02 | C |
| ATOM | 981 | CG | LYS | A | 168 | 123.727 | 15.184 | 41.331 | 1.00 | 28.19 | C |
| ATOM | 982 | CD | LYS | A | 168 | 124.465 | 13.930 | 41.022 | 1.00 | 31.25 | C |
| ATOM | 983 | CE | LYS | A | 168 | 123.784 | 13.218 | 39.879 | 1.00 | 39.53 | C |
| ATOM | 984 | NZ | LYS | A | 168 | 124.471 | 11.920 | 39.553 | 1.00 | 44.70 | N |
| ATOM | 985 | C | LYS | A | 168 | 122.608 | 16.181 | 43.921 | 1.00 | 26.26 | C |
| ATOM | 986 | O | LYS | A | 168 | 121.560 | 15.777 | 43.420 | 1.00 | 26.56 | O |
| ATOM | 987 | N | SER | A | 169 | 122.892 | 15.946 | 45.187 | 1.00 | 26.76 | N |
| ATOM | 988 | CA | SER | A | 169 | 121.902 | 15.227 | 45.938 | 1.00 | 28.87 | C |
| ATOM | 989 | CB | SER | A | 169 | 122.493 | 14.685 | 47.242 | 1.00 | 29.86 | C |
| ATOM | 990 | OG | SER | A | 169 | 123.441 | 15.576 | 47.801 | 1.00 | 34.66 | O |
| ATOM | 991 | C | SER | A | 169 | 120.773 | 16.204 | 46.215 | 1.00 | 27.92 | C |
| ATOM | 992 | O | SER | A | 169 | 119.599 | 15.874 | 46.097 | 1.00 | 30.68 | O |
| ATOM | 993 | N | ILE | A | 170 | 121.139 | 17.426 | 46.574 | 1.00 | 27.00 | N |
| ATOM | 994 | CA | ILE | A | 170 | 120.156 | 18.437 | 46.888 | 1.00 | 24.81 | C |
| ATOM | 995 | CB | ILE | A | 170 | 120.823 | 19.725 | 47.248 | 1.00 | 24.70 | C |
| ATOM | 996 | CG1 | ILE | A | 170 | 121.843 | 19.462 | 48.344 | 1.00 | 22.68 | C |
| ATOM | 997 | CD1 | ILE | A | 170 | 122.550 | 20.718 | 48.798 | 1.00 | 24.18 | C |
| ATOM | 998 | CG2 | ILE | A | 170 | 119.778 | 20.743 | 47.661 | 1.00 | 17.95 | C |
| ATOM | 999 | C | ILE | A | 170 | 119.288 | 18.661 | 45.674 | 1.00 | 25.36 | C |
| ATOM | 1000 | O | ILE | A | 170 | 118.058 | 18.726 | 45.774 | 1.00 | 26.21 | O |
| ATOM | 1001 | N | GLY | A | 171 | 119.944 | 18.762 | 44.528 | 1.00 | 23.14 | N |
| ATOM | 1002 | CA | GLY | A | 171 | 119.245 | 18.978 | 43.291 | 1.00 | 22.40 | C |
| ATOM | 1003 | C | GLY | A | 171 | 118.275 | 17.860 | 43.041 | 1.00 | 21.55 | C |
| ATOM | 1004 | O | GLY | A | 171 | 117.275 | 18.043 | 42.341 | 1.00 | 22.25 | O |
| ATOM | 1005 | N | GLU | A | 172 | 118.555 | 16.696 | 43.612 | 1.00 | 21.64 | N |
| ATOM | 1006 | CA | GLU | A | 172 | 117.665 | 15.553 | 43.415 | 1.00 | 24.18 | C |
| ATOM | 1007 | CB | GLU | A | 172 | 118.327 | 14.243 | 43.825 | 1.00 | 23.98 | C |
| ATOM | 1008 | CG | GLU | A | 172 | 119.173 | 13.748 | 42.705 | 1.00 | 29.72 | C |
| ATOM | 1009 | CD | GLU | A | 172 | 119.691 | 12.363 | 42.934 | 1.00 | 41.98 | C |
| ATOM | 1010 | OE1 | GLU | A | 172 | 118.851 | 11.443 | 43.107 | 1.00 | 48.85 | O |

FIG. 2A-22

| ATOM | 1011 | OE2 | GLU | A | 172 | 120.944 | 12.201 | 42.935 | 1.00 | 44.51 | O |
|------|------|-----|-----|---|-----|---------|--------|--------|------|-------|---|
| ATOM | 1012 | C | GLU | A | 172 | 116.342 | 15.715 | 44.120 | 1.00 | 24.51 | C |
| ATOM | 1013 | O | GLU | A | 172 | 115.289 | 15.351 | 43.560 | 1.00 | 25.79 | O |
| ATOM | 1014 | N | ALA | A | 173 | 116.374 | 16.255 | 45.336 | 1.00 | 23.34 | N |
| ATOM | 1015 | CA | ALA | A | 173 | 115.116 | 16.476 | 46.007 | 1.00 | 22.84 | C |
| ATOM | 1016 | CB | ALA | A | 173 | 115.324 | 16.860 | 47.433 | 1.00 | 22.05 | C |
| ATOM | 1017 | C | ALA | A | 173 | 114.403 | 17.599 | 45.253 | 1.00 | 22.08 | C |
| ATOM | 1018 | O | ALA | A | 173 | 113.238 | 17.501 | 44.942 | 1.00 | 23.50 | O |
| ATOM | 1019 | N | ILE | A | 174 | 115.116 | 18.665 | 44.933 | 1.00 | 21.53 | N |
| ATOM | 1020 | CA | ILE | A | 174 | 114.487 | 19.753 | 44.236 | 1.00 | 21.96 | C |
| ATOM | 1021 | CB | ILE | A | 174 | 115.462 | 20.901 | 43.969 | 1.00 | 22.21 | C |
| ATOM | 1022 | CG1 | ILE | A | 174 | 115.946 | 21.440 | 45.300 | 1.00 | 20.55 | C |
| ATOM | 1023 | CD1 | ILE | A | 174 | 114.849 | 21.465 | 46.300 | 1.00 | 22.80 | C |
| ATOM | 1024 | CG2 | ILE | A | 174 | 114.749 | 22.036 | 43.155 | 1.00 | 19.16 | C |
| ATOM | 1025 | C | ILE | A | 174 | 113.898 | 19.301 | 42.924 | 1.00 | 23.52 | C |
| ATOM | 1026 | O | ILE | A | 174 | 112.790 | 19.698 | 42.563 | 1.00 | 26.08 | O |
| ATOM | 1027 | N | GLN | A | 175 | 114.618 | 18.466 | 42.195 | 1.00 | 23.33 | N |
| ATOM | 1028 | CA | GLN | A | 175 | 114.083 | 18.022 | 40.924 | 1.00 | 23.17 | C |
| ATOM | 1029 | CB | GLN | A | 175 | 115.072 | 17.173 | 40.157 | 1.00 | 23.86 | C |
| ATOM | 1030 | CG | GLN | A | 175 | 114.375 | 16.346 | 39.139 | 1.00 | 28.72 | C |
| ATOM | 1031 | CD | GLN | A | 175 | 115.328 | 15.706 | 38.165 | 1.00 | 37.29 | C |
| ATOM | 1032 | OE1 | GLN | A | 175 | 116.333 | 15.103 | 38.568 | 1.00 | 41.07 | O |
| ATOM | 1033 | NE2 | GLN | A | 175 | 115.023 | 15.817 | 36.871 | 1.00 | 39.66 | N |
| ATOM | 1034 | C | GLN | A | 175 | 112.829 | 17.223 | 41.090 | 1.00 | 22.75 | C |
| ATOM | 1035 | O | GLN | A | 175 | 111.910 | 17.363 | 40.288 | 1.00 | 25.66 | O |
| ATOM | 1036 | N | TYR | A | 176 | 112.778 | 16.381 | 42.125 | 1.00 | 20.56 | N |
| ATOM | 1037 | CA | TYR | A | 176 | 111.602 | 15.551 | 42.330 | 1.00 | 20.70 | C |
| ATOM | 1038 | CB | TYR | A | 176 | 111.799 | 14.530 | 43.459 | 1.00 | 20.65 | C |
| ATOM | 1039 | CG | TYR | A | 176 | 110.572 | 13.652 | 43.577 | 1.00 | 19.86 | C |
| ATOM | 1040 | CD1 | TYR | A | 176 | 110.221 | 12.781 | 42.566 | 1.00 | 18.72 | C |
| ATOM | 1041 | CE1 | TYR | A | 176 | 109.005 | 12.112 | 42.598 | 1.00 | 27.00 | C |
| ATOM | 1042 | CZ | TYR | A | 176 | 108.126 | 12.320 | 43.660 | 1.00 | 28.85 | C |
| ATOM | 1043 | OH | TYR | A | 176 | 106.868 | 11.723 | 43.701 | 1.00 | 34.76 | O |
| ATOM | 1044 | CE2 | TYR | A | 176 | 108.479 | 13.174 | 44.675 | 1.00 | 27.37 | C |
| ATOM | 1045 | CD2 | TYR | A | 176 | 109.686 | 13.823 | 44.630 | 1.00 | 25.75 | C |
| ATOM | 1046 | C | TYR | A | 176 | 110.374 | 16.385 | 42.631 | 1.00 | 21.54 | C |
| ATOM | 1047 | O | TYR | A | 176 | 109.286 | 16.139 | 42.093 | 1.00 | 23.90 | O |
| ATOM | 1048 | N | LEU | A | 177 | 110.560 | 17.368 | 43.501 | 1.00 | 19.28 | N |
| ATOM | 1049 | CA | LEU | A | 177 | 109.490 | 18.243 | 43.870 | 1.00 | 20.23 | C |
| ATOM | 1050 | CB | LEU | A | 177 | 109.951 | 19.187 | 44.988 | 1.00 | 22.00 | C |
| ATOM | 1051 | CG | LEU | A | 177 | 110.348 | 18.573 | 46.350 | 1.00 | 20.95 | C |
| ATOM | 1052 | CD1 | LEU | A | 177 | 110.765 | 19.639 | 47.306 | 1.00 | 17.92 | C |
| ATOM | 1053 | CD2 | LEU | A | 177 | 109.186 | 17.830 | 46.968 | 1.00 | 24.32 | C |
| ATOM | 1054 | C | LEU | A | 177 | 108.954 | 19.028 | 42.658 | 1.00 | 22.33 | C |
| ATOM | 1055 | O | LEU | A | 177 | 107.739 | 19.007 | 42.403 | 1.00 | 25.68 | O |
| ATOM | 1056 | N | HIS | A | 178 | 109.804 | 19.696 | 41.883 | 1.00 | 20.42 | N |

FIG. 2A-23

| | | | | | | | | | | | |
|---|---|---|---|---|---|---|---|---|---|---|---|
| ATOM | 1057 | CA | HIS | A | 178 | 109.248 | 20.440 | 40.755 | 1.00 | 18.27 | C |
| ATOM | 1058 | CB | HIS | A | 178 | 110.302 | 21.299 | 40.057 | 1.00 | 18.50 | C |
| ATOM | 1059 | CG | HIS | A | 178 | 110.855 | 22.377 | 40.936 | 1.00 | 18.26 | C |
| ATOM | 1060 | ND1 | HIS | A | 178 | 111.845 | 23.237 | 40.528 | 1.00 | 14.61 | N |
| ATOM | 1061 | CE1 | HIS | A | 178 | 112.178 | 24.030 | 41.531 | 1.00 | 13.10 | C |
| ATOM | 1062 | NE2 | HIS | A | 178 | 111.436 | 23.718 | 42.572 | 1.00 | 18.14 | N |
| ATOM | 1063 | CD2 | HIS | A | 178 | 110.597 | 22.688 | 42.226 | 1.00 | 13.99 | C |
| ATOM | 1064 | C | HIS | A | 178 | 108.552 | 19.563 | 39.744 | 1.00 | 17.22 | C |
| ATOM | 1065 | O | HIS | A | 178 | 107.630 | 20.010 | 39.058 | 1.00 | 17.21 | O |
| ATOM | 1066 | N | SER | A | 179 | 108.972 | 18.312 | 39.643 | 1.00 | 16.49 | N |
| ATOM | 1067 | CA | SER | A | 179 | 108.350 | 17.442 | 38.693 | 1.00 | 17.01 | C |
| ATOM | 1068 | CB | SER | A | 179 | 109.197 | 16.219 | 38.426 | 1.00 | 16.13 | C |
| ATOM | 1069 | OG | SER | A | 179 | 109.482 | 15.530 | 39.628 | 1.00 | 23.22 | O |
| ATOM | 1070 | C | SER | A | 179 | 107.023 | 17.033 | 39.200 | 1.00 | 19.16 | C |
| ATOM | 1071 | O | SER | A | 179 | 106.222 | 16.573 | 38.427 | 1.00 | 23.20 | O |
| ATOM | 1072 | N | ILE | A | 180 | 106.753 | 17.109 | 40.494 | 1.00 | 17.31 | N |
| ATOM | 1073 | CA | ILE | A | 180 | 105.384 | 16.757 | 40.881 | 1.00 | 19.74 | C |
| ATOM | 1074 | CB | ILE | A | 180 | 105.249 | 15.772 | 42.115 | 1.00 | 19.39 | C |
| ATOM | 1075 | CG1 | ILE | A | 180 | 105.957 | 16.348 | 43.345 | 1.00 | 18.59 | C |
| ATOM | 1076 | CD1 | ILE | A | 180 | 105.737 | 15.578 | 44.614 | 1.00 | 15.33 | C |
| ATOM | 1077 | CG2 | ILE | A | 180 | 105.684 | 14.345 | 41.708 | 1.00 | 20.22 | C |
| ATOM | 1078 | C | ILE | A | 180 | 104.653 | 18.046 | 41.199 | 1.00 | 20.64 | C |
| ATOM | 1079 | O | ILE | A | 180 | 103.638 | 18.048 | 41.891 | 1.00 | 20.86 | O |
| ATOM | 1080 | N | ASN | A | 181 | 105.197 | 19.145 | 40.696 | 1.00 | 19.51 | N |
| ATOM | 1081 | CA | ASN | A | 181 | 104.616 | 20.463 | 40.894 | 1.00 | 20.64 | C |
| ATOM | 1082 | CB | ASN | A | 181 | 103.207 | 20.478 | 40.363 | 1.00 | 21.90 | C |
| ATOM | 1083 | CG | ASN | A | 181 | 103.164 | 20.772 | 38.910 | 1.00 | 28.71 | C |
| ATOM | 1084 | OD1 | ASN | A | 181 | 103.950 | 20.237 | 38.147 | 1.00 | 40.24 | O |
| ATOM | 1085 | ND2 | ASN | A | 181 | 102.253 | 21.641 | 38.506 | 1.00 | 40.00 | N |
| ATOM | 1086 | C | ASN | A | 181 | 104.608 | 21.063 | 42.282 | 1.00 | 20.23 | C |
| ATOM | 1087 | O | ASN | A | 181 | 103.598 | 21.628 | 42.702 | 1.00 | 19.29 | O |
| ATOM | 1088 | N | ILE | A | 182 | 105.723 | 20.948 | 42.992 | 1.00 | 19.36 | N |
| ATOM | 1089 | CA | ILE | A | 182 | 105.810 | 21.543 | 44.302 | 1.00 | 18.59 | C |
| ATOM | 1090 | CB | ILE | A | 182 | 105.891 | 20.486 | 45.434 | 1.00 | 20.23 | C |
| ATOM | 1091 | CG1 | ILE | A | 182 | 104.641 | 19.638 | 45.464 | 1.00 | 18.74 | C |
| ATOM | 1092 | CD1 | ILE | A | 182 | 104.838 | 18.436 | 46.249 | 1.00 | 18.91 | C |
| ATOM | 1093 | CG2 | ILE | A | 182 | 106.015 | 21.191 | 46.781 | 1.00 | 16.51 | C |
| ATOM | 1094 | C | ILE | A | 182 | 107.046 | 22.407 | 44.399 | 1.00 | 18.22 | C |
| ATOM | 1095 | O | ILE | A | 182 | 108.126 | 22.026 | 43.971 | 1.00 | 18.34 | O |
| ATOM | 1096 | N | ALA | A | 183 | 106.872 | 23.578 | 44.976 | 1.00 | 17.59 | N |
| ATOM | 1097 | CA | ALA | A | 183 | 107.967 | 24.483 | 45.164 | 1.00 | 17.46 | C |
| ATOM | 1098 | CB | ALA | A | 183 | 107.574 | 25.887 | 44.724 | 1.00 | 17.12 | C |
| ATOM | 1099 | C | ALA | A | 183 | 108.099 | 24.398 | 46.675 | 1.00 | 19.89 | C |
| ATOM | 1100 | O | ALA | A | 183 | 107.092 | 24.487 | 47.383 | 1.00 | 21.70 | O |
| ATOM | 1101 | N | HIS | A | 184 | 109.320 | 24.223 | 47.173 | 1.00 | 19.39 | N |
| ATOM | 1102 | CA | HIS | A | 184 | 109.524 | 24.083 | 48.592 | 1.00 | 20.41 | C |

FIG. 2A-24

| ATOM | 1103 | CB | HIS | A | 184 | 110.837 | 23.368 | 48.812 | 1.00 | 19.72 | C |
|---|---|---|---|---|---|---|---|---|---|---|---|
| ATOM | 1104 | CG | HIS | A | 184 | 111.239 | 23.275 | 50.239 | 1.00 | 23.36 | C |
| ATOM | 1105 | ND1 | HIS | A | 184 | 111.577 | 24.389 | 50.985 | 1.00 | 22.33 | N |
| ATOM | 1106 | CE1 | HIS | A | 184 | 111.854 | 23.998 | 52.223 | 1.00 | 25.33 | C |
| ATOM | 1107 | NE2 | HIS | A | 184 | 111.705 | 22.683 | 52.303 | 1.00 | 25.20 | N |
| ATOM | 1108 | CD2 | HIS | A | 184 | 111.321 | 22.206 | 51.073 | 1.00 | 24.12 | C |
| ATOM | 1109 | C | HIS | A | 184 | 109.495 | 25.438 | 49.278 | 1.00 | 21.68 | C |
| ATOM | 1110 | O | HIS | A | 184 | 108.945 | 25.620 | 50.370 | 1.00 | 22.86 | O |
| ATOM | 1111 | N | ARG | A | 185 | 110.093 | 26.403 | 48.601 | 1.00 | 22.24 | N |
| ATOM | 1112 | CA | ARG | A | 185 | 110.182 | 27.786 | 49.082 | 1.00 | 22.07 | C |
| ATOM | 1113 | CB | ARG | A | 185 | 108.813 | 28.411 | 49.033 | 1.00 | 22.13 | C |
| ATOM | 1114 | CG | ARG | A | 185 | 108.382 | 28.419 | 47.598 | 1.00 | 22.95 | C |
| ATOM | 1115 | CD | ARG | A | 185 | 107.203 | 29.265 | 47.410 | 1.00 | 26.08 | C |
| ATOM | 1116 | NE | ARG | A | 185 | 106.338 | 29.209 | 48.567 | 1.00 | 25.84 | N |
| ATOM | 1117 | CZ | ARG | A | 185 | 105.250 | 29.944 | 48.680 | 1.00 | 34.67 | C |
| ATOM | 1118 | NH1AR | G | A | 185 | 104.915 | 30.782 | 47.705 | 1.00 | 34.60 | N |
| ATOM | 1119 | NH2AR | G | A | 185 | 104.492 | 29.830 | 49.748 | 1.00 | 36.42 | N |
| ATOM | 1120 | C | ARG | A | 185 | 110.926 | 28.136 | 50.384 | 1.00 | 22.84 | C |
| ATOM | 1121 | O | ARG | A | 185 | 110.985 | 29.323 | 50.752 | 1.00 | 20.49 | O |
| ATOM | 1122 | N | ASP | A | 186 | 111.508 | 27.131 | 51.059 | 1.00 | 23.14 | N |
| ATOM | 1123 | CA | ASP | A | 186 | 112.328 | 27.442 | 52.215 | 1.00 | 23.02 | C |
| ATOM | 1124 | CB | ASP | A | 186 | 111.530 | 27.425 | 53.507 | 1.00 | 22.89 | C |
| ATOM | 1125 | CG | ASP | A | 186 | 112.305 | 28.042 | 54.655 | 1.00 | 22.97 | C |
| ATOM | 1126 | OD1 | ASP | A | 186 | 112.878 | 29.119 | 54.450 | 1.00 | 24.02 | O |
| ATOM | 1127 | OD2 | ASP | A | 186 | 112.366 | 27.449 | 55.763 | 1.00 | 38.27 | O |
| ATOM | 1128 | C | ASP | A | 186 | 113.552 | 26.525 | 52.278 | 1.00 | 23.08 | C |
| ATOM | 1129 | O | ASP | A | 186 | 113.919 | 25.947 | 53.306 | 1.00 | 24.22 | O |
| ATOM | 1130 | N | VAL | A | 187 | 114.183 | 26.395 | 51.124 | 1.00 | 22.27 | N |
| ATOM | 1131 | CA | VAL | A | 187 | 115.385 | 25.602 | 50.993 | 1.00 | 22.20 | C |
| ATOM | 1132 | CB | VAL | A | 187 | 115.671 | 25.259 | 49.552 | 1.00 | 21.35 | C |
| ATOM | 1133 | CG1 | VAL | A | 187 | 117.024 | 24.535 | 49.467 | 1.00 | 21.48 | C |
| ATOM | 1134 | CG2 | VAL | A | 187 | 114.539 | 24.448 | 48.978 | 1.00 | 18.60 | C |
| ATOM | 1135 | C | VAL | A | 187 | 116.538 | 26.436 | 51.497 | 1.00 | 23.13 | C |
| ATOM | 1136 | O | VAL | A | 187 | 116.831 | 27.501 | 50.984 | 1.00 | 25.14 | O |
| ATOM | 1137 | N | LYS | A | 188 | 117.215 | 25.943 | 52.499 | 1.00 | 22.55 | N |
| ATOM | 1138 | CA | LYS | A | 188 | 118.301 | 26.690 | 53.044 | 1.00 | 20.87 | C |
| ATOM | 1139 | CB | LYS | A | 188 | 117.769 | 27.761 | 54.005 | 1.00 | 18.69 | C |
| ATOM | 1140 | CG | LYS | A | 188 | 117.274 | 27.268 | 55.304 | 1.00 | 23.10 | C |
| ATOM | 1141 | CD | LYS | A | 188 | 116.373 | 28.274 | 55.910 | 1.00 | 30.96 | C |
| ATOM | 1142 | CE | LYS | A | 188 | 115.724 | 27.688 | 57.134 | 1.00 | 33.17 | C |
| ATOM | 1143 | NZ | LYS | A | 188 | 114.656 | 28.594 | 57.668 | 1.00 | 40.82 | N |
| ATOM | 1144 | C | LYS | A | 188 | 119.190 | 25.666 | 53.706 | 1.00 | 21.35 | C |
| ATOM | 1145 | O | LYS | A | 188 | 118.736 | 24.605 | 54.134 | 1.00 | 21.12 | O |
| ATOM | 1146 | N | PRO | A | 189 | 120.477 | 25.971 | 53.795 | 1.00 | 21.95 | N |
| ATOM | 1147 | CA | PRO | A | 189 | 121.426 | 25.046 | 54.388 | 1.00 | 21.88 | C |
| ATOM | 1148 | CB | PRO | A | 189 | 122.662 | 25.916 | 54.577 | 1.00 | 22.87 | C |

FIG. 2A-25

| ATOM | 1149 | CG | PRO | A | 189 | 122.089 | 27.221 | 54.843 | 1.00 | 24.54 | C |
|---|---|---|---|---|---|---|---|---|---|---|---|
| ATOM | 1150 | CD | PRO | A | 189 | 121.025 | 27.333 | 53.799 | 1.00 | 21.78 | C |
| ATOM | 1151 | C | PRO | A | 189 | 120.934 | 24.416 | 55.655 | 1.00 | 22.17 | C |
| ATOM | 1152 | O | PRO | A | 189 | 121.115 | 23.221 | 55.880 | 1.00 | 22.74 | O |
| ATOM | 1153 | N | GLU | A | 190 | 120.283 | 25.200 | 56.487 | 1.00 | 22.71 | N |
| ATOM | 1154 | CA | GLU | A | 190 | 119.837 | 24.646 | 57.749 | 1.00 | 22.45 | C |
| ATOM | 1155 | CB | GLU | A | 190 | 119.458 | 25.772 | 58.702 | 1.00 | 21.48 | C |
| ATOM | 1156 | CG | GLU | A | 190 | 120.546 | 26.814 | 58.937 | 1.00 | 24.64 | C |
| ATOM | 1157 | CD | GLU | A | 190 | 120.674 | 27.913 | 57.830 | 1.00 | 30.27 | C |
| ATOM | 1158 | OE1 | GLU | A | 190 | 119.813 | 28.003 | 56.919 | 1.00 | 34.23 | O |
| ATOM | 1159 | OE2 | GLU | A | 190 | 121.641 | 28.715 | 57.899 | 1.00 | 33.26 | O |
| ATOM | 1160 | C | GLU | A | 190 | 118.702 | 23.612 | 57.677 | 1.00 | 22.75 | C |
| ATOM | 1161 | O | GLU | A | 190 | 118.446 | 22.944 | 58.667 | 1.00 | 23.94 | O |
| ATOM | 1162 | N | ASN | A | 191 | 118.005 | 23.488 | 56.543 | 1.00 | 22.71 | N |
| ATOM | 1163 | CA | ASN | A | 191 | 116.941 | 22.500 | 56.444 | 1.00 | 24.50 | C |
| ATOM | 1164 | CB | ASN | A | 191 | 115.752 | 23.033 | 55.655 | 1.00 | 23.71 | C |
| ATOM | 1165 | CG | ASN | A | 191 | 114.904 | 23.945 | 56.475 | 1.00 | 28.00 | C |
| ATOM | 1166 | OD1 | ASN | A | 191 | 114.909 | 23.833 | 57.694 | 1.00 | 32.87 | O |
| ATOM | 1167 | ND2 | ASN | A | 191 | 114.165 | 24.865 | 55.830 | 1.00 | 28.18 | N |
| ATOM | 1168 | C | ASN | A | 191 | 117.431 | 21.217 | 55.799 | 1.00 | 25.28 | C |
| ATOM | 1169 | O | ASN | A | 191 | 116.654 | 20.304 | 55.517 | 1.00 | 28.96 | O |
| ATOM | 1170 | N | LEU | A | 192 | 118.723 | 21.155 | 55.540 | 1.00 | 23.41 | N |
| ATOM | 1171 | CA | LEU | A | 192 | 119.307 | 19.979 | 54.948 | 1.00 | 24.15 | C |
| ATOM | 1172 | CB | LEU | A | 192 | 120.243 | 20.399 | 53.818 | 1.00 | 23.15 | C |
| ATOM | 1173 | CG | LEU | A | 192 | 119.579 | 20.980 | 52.573 | 1.00 | 25.97 | C |
| ATOM | 1174 | CD1 | LEU | A | 192 | 120.584 | 21.843 | 51.778 | 1.00 | 28.10 | C |
| ATOM | 1175 | CD2 | LEU | A | 192 | 119.049 | 19.834 | 51.736 | 1.00 | 24.32 | C |
| ATOM | 1176 | C | LEU | A | 192 | 120.066 | 19.302 | 56.082 | 1.00 | 24.75 | C |
| ATOM | 1177 | O | LEU | A | 192 | 121.098 | 19.818 | 56.530 | 1.00 | 25.10 | O |
| ATOM | 1178 | N | LEU | A | 193 | 119.540 | 18.170 | 56.554 | 1.00 | 23.88 | N |
| ATOM | 1179 | CA | LEU | A | 193 | 120.129 | 17.419 | 57.669 | 1.00 | 25.42 | C |
| ATOM | 1180 | CB | LEU | A | 193 | 119.123 | 17.201 | 58.783 | 1.00 | 26.74 | C |
| ATOM | 1181 | CG | LEU | A | 193 | 118.568 | 18.449 | 59.436 | 1.00 | 28.01 | C |
| ATOM | 1182 | CD1 | LEU | A | 193 | 117.960 | 18.064 | 60.785 | 1.00 | 31.36 | C |
| ATOM | 1183 | CD2 | LEU | A | 193 | 119.693 | 19.449 | 59.619 | 1.00 | 24.49 | C |
| ATOM | 1184 | C | LEU | A | 193 | 120.546 | 16.063 | 57.230 | 1.00 | 26.42 | C |
| ATOM | 1185 | O | LEU | A | 193 | 119.846 | 15.438 | 56.446 | 1.00 | 28.72 | O |
| ATOM | 1186 | N | TYR | A | 194 | 121.661 | 15.577 | 57.764 | 1.00 | 26.30 | N |
| ATOM | 1187 | CA | TYR | A | 194 | 122.140 | 14.236 | 57.395 | 1.00 | 25.94 | C |
| ATOM | 1188 | CB | TYR | A | 194 | 123.650 | 14.156 | 57.561 | 1.00 | 25.40 | C |
| ATOM | 1189 | CG | TYR | A | 194 | 124.437 | 14.595 | 56.362 | 1.00 | 28.23 | C |
| ATOM | 1190 | CD1 | TYR | A | 194 | 124.412 | 13.868 | 55.190 | 1.00 | 28.01 | C |
| ATOM | 1191 | CE1 | TYR | A | 194 | 125.175 | 14.233 | 54.140 | 1.00 | 25.13 | C |
| ATOM | 1192 | CZ | TYR | A | 194 | 125.992 | 15.348 | 54.235 | 1.00 | 26.52 | C |
| ATOM | 1193 | OH | TYR | A | 194 | 126.796 | 15.707 | 53.168 | 1.00 | 23.15 | O |
| ATOM | 1194 | CE2 | TYR | A | 194 | 126.030 | 16.088 | 55.373 | 1.00 | 25.96 | C |

FIG. 2A-26

| ATOM | 1195 | CD2 | TYR | A | 194 | 125.261 | 15.717 | 56.424 | 1.00 | 29.63 | C |
|---|---|---|---|---|---|---|---|---|---|---|---|
| ATOM | 1196 | C | TYR | A | 194 | 121.491 | 13.152 | 58.247 | 1.00 | 26.36 | C |
| ATOM | 1197 | O | TYR | A | 194 | 121.246 | 13.374 | 59.439 | 1.00 | 26.76 | O |
| ATOM | 1198 | N | THR | A | 195 | 121.225 | 11.994 | 57.639 | 1.00 | 27.52 | N |
| ATOM | 1199 | CA | THR | A | 195 | 120.629 | 10.850 | 58.349 | 1.00 | 27.93 | C |
| ATOM | 1200 | CB | THR | A | 195 | 120.479 | 9.635 | 57.442 | 1.00 | 27.70 | C |
| ATOM | 1201 | OG1 | THR | A | 195 | 121.742 | 9.328 | 56.824 | 1.00 | 26.26 | O |
| ATOM | 1202 | CG2 | THR | A | 195 | 119.423 | 9.902 | 56.390 | 1.00 | 27.06 | C |
| ATOM | 1203 | C | THR | A | 195 | 121.459 | 10.401 | 59.551 | 1.00 | 28.45 | C |
| ATOM | 1204 | O | THR | A | 195 | 121.043 | 10.536 | 60.709 | 1.00 | 29.42 | O |
| ATOM | 1205 | N | SER | A | 196 | 122.634 | 9.857 | 59.278 | 1.00 | 29.47 | N |
| ATOM | 1206 | CA | SER | A | 196 | 123.526 | 9.415 | 60.348 | 1.00 | 32.09 | C |
| ATOM | 1207 | CB | SER | A | 196 | 123.829 | 7.933 | 60.199 | 1.00 | 31.27 | C |
| ATOM | 1208 | OG | SER | A | 196 | 124.276 | 7.645 | 58.886 | 1.00 | 33.35 | O |
| ATOM | 1209 | C | SER | A | 196 | 124.817 | 10.185 | 60.226 | 1.00 | 33.68 | C |
| ATOM | 1210 | O | SER | A | 196 | 124.933 | 11.075 | 59.377 | 1.00 | 33.80 | O |
| ATOM | 1211 | N | ALA | A | 197 | 125.794 | 9.846 | 61.069 | 1.00 | 35.59 | N |
| ATOM | 1212 | CA | ALA | A | 197 | 127.093 | 10.505 | 60.993 | 1.00 | 37.62 | C |
| ATOM | 1213 | CB | ALA | A | 197 | 127.669 | 10.730 | 62.366 | 1.00 | 35.43 | C |
| ATOM | 1214 | C | ALA | A | 197 | 128.016 | 9.624 | 60.159 | 1.00 | 39.22 | C |
| ATOM | 1215 | O | ALA | A | 197 | 129.197 | 9.915 | 60.011 | 1.00 | 39.06 | O |
| ATOM | 1216 | N | ARG | A | 198 | 127.471 | 8.546 | 59.604 | 1.00 | 42.00 | N |
| ATOM | 1217 | CA | ARG | A | 198 | 128.260 | 7.647 | 58.771 | 1.00 | 43.94 | C |
| ATOM | 1218 | CB | ARG | A | 198 | 127.410 | 6.506 | 58.234 | 1.00 | 45.92 | C |
| ATOM | 1219 | CG | ARG | A | 198 | 128.166 | 5.607 | 57.249 | 1.00 | 51.15 | C |
| ATOM | 1220 | CD | ARG | A | 198 | 127.341 | 5.278 | 56.032 | 1.00 | 58.60 | C |
| ATOM | 1221 | NE | ARG | A | 198 | 125.947 | 5.049 | 56.399 | 1.00 | 64.47 | N |
| ATOM | 1222 | CZ | ARG | A | 198 | 125.067 | 4.400 | 55.645 | 1.00 | 67.58 | C |
| ATOM | 1223 | NH1AR | G | A | 198 | 125.424 | 3.901 | 54.465 | 1.00 | 67.78 | N |
| ATOM | 1224 | NH2AR | G | A | 198 | 123.824 | 4.250 | 56.081 | 1.00 | 70.33 | N |
| ATOM | 1225 | C | ARG | A | 198 | 128.846 | 8.395 | 57.579 | 1.00 | 42.65 | C |
| ATOM | 1226 | O | ARG | A | 198 | 128.386 | 9.480 | 57.214 | 1.00 | 43.27 | O |
| ATOM | 1227 | N | PRO | A | 199 | 129.885 | 7.824 | 56.960 | 1.00 | 41.41 | N |
| ATOM | 1228 | CA | PRO | A | 199 | 130.449 | 8.528 | 55.808 | 1.00 | 40.84 | C |
| ATOM | 1229 | CB | PRO | A | 199 | 131.691 | 7.701 | 55.474 | 1.00 | 41.50 | C |
| ATOM | 1230 | CG | PRO | A | 199 | 132.135 | 7.217 | 56.822 | 1.00 | 41.36 | C |
| ATOM | 1231 | CD | PRO | A | 199 | 130.811 | 6.780 | 57.440 | 1.00 | 41.13 | C |
| ATOM | 1232 | C | PRO | A | 199 | 129.459 | 8.542 | 54.661 | 1.00 | 40.17 | C |
| ATOM | 1233 | O | PRO | A | 199 | 129.483 | 9.442 | 53.830 | 1.00 | 41.86 | O |
| ATOM | 1234 | N | ALA | A | 200 | 128.588 | 7.539 | 54.620 | 1.00 | 38.28 | N |
| ATOM | 1235 | CA | ALA | A | 200 | 127.606 | 7.434 | 53.547 | 1.00 | 36.41 | C |
| ATOM | 1236 | CB | ALA | A | 200 | 127.673 | 6.045 | 52.930 | 1.00 | 36.67 | C |
| ATOM | 1237 | C | ALA | A | 200 | 126.167 | 7.752 | 53.973 | 1.00 | 35.63 | C |
| ATOM | 1238 | O | ALA | A | 200 | 125.200 | 7.183 | 53.437 | 1.00 | 36.10 | O |
| ATOM | 1239 | N | ALA | A | 201 | 126.016 | 8.647 | 54.946 | 1.00 | 32.98 | N |
| ATOM | 1240 | CA | ALA | A | 201 | 124.687 | 9.036 | 55.371 | 1.00 | 31.46 | C |

FIG. 2A-27

| ATOM | 1241 | CB | ALA | A | 201 | 124.770 | 9.873 | 56.618 | 1.00 | 31.84 | C |
| --- | --- | --- | --- | --- | --- | --- | --- | --- | --- | --- | --- |
| ATOM | 1242 | C | ALA | A | 201 | 124.130 | 9.861 | 54.208 | 1.00 | 30.41 | C |
| ATOM | 1243 | O | ALA | A | 201 | 124.893 | 10.449 | 53.438 | 1.00 | 29.98 | O |
| ATOM | 1244 | N | ILE | A | 202 | 122.814 | 9.902 | 54.065 | 1.00 | 28.40 | N |
| ATOM | 1245 | CA | ILE | A | 202 | 122.230 | 10.666 | 52.977 | 1.00 | 27.77 | C |
| ATOM | 1246 | CB | ILE | A | 202 | 121.174 | 9.822 | 52.246 | 1.00 | 28.79 | C |
| ATOM | 1247 | CG1 | ILE | A | 202 | 120.072 | 10.719 | 51.718 | 1.00 | 33.40 | C |
| ATOM | 1248 | CD1 | ILE | A | 202 | 119.135 | 9.988 | 50.801 | 1.00 | 46.77 | C |
| ATOM | 1249 | CG2 | ILE | A | 202 | 120.602 | 8.772 | 53.156 | 1.00 | 28.09 | C |
| ATOM | 1250 | C | ILE | A | 202 | 121.630 | 11.999 | 53.421 | 1.00 | 26.00 | C |
| ATOM | 1251 | O | ILE | A | 202 | 121.051 | 12.072 | 54.499 | 1.00 | 26.56 | O |
| ATOM | 1252 | N | LEU | A | 203 | 121.800 | 13.053 | 52.614 | 1.00 | 23.71 | N |
| ATOM | 1253 | CA | LEU | A | 203 | 121.243 | 14.370 | 52.936 | 1.00 | 23.04 | C |
| ATOM | 1254 | CB | LEU | A | 203 | 121.908 | 15.482 | 52.130 | 1.00 | 24.41 | C |
| ATOM | 1255 | CG | LEU | A | 203 | 121.623 | 16.984 | 52.274 | 1.00 | 31.91 | C |
| ATOM | 1256 | CD1 | LEU | A | 203 | 122.022 | 17.406 | 53.668 | 1.00 | 33.38 | C |
| ATOM | 1257 | CD2 | LEU | A | 203 | 122.381 | 17.809 | 51.263 | 1.00 | 32.63 | C |
| ATOM | 1258 | C | LEU | A | 203 | 119.746 | 14.461 | 52.629 | 1.00 | 22.04 | C |
| ATOM | 1259 | O | LEU | A | 203 | 119.288 | 14.069 | 51.555 | 1.00 | 21.87 | O |
| ATOM | 1260 | N | LYS | A | 204 | 118.973 | 14.993 | 53.566 | 1.00 | 21.34 | N |
| ATOM | 1261 | CA | LYS | A | 204 | 117.552 | 15.140 | 53.326 | 1.00 | 21.71 | C |
| ATOM | 1262 | CB | LYS | A | 204 | 116.797 | 14.084 | 54.115 | 1.00 | 22.50 | C |
| ATOM | 1263 | CG | LYS | A | 204 | 117.194 | 12.696 | 53.708 | 1.00 | 21.20 | C |
| ATOM | 1264 | CD | LYS | A | 204 | 116.452 | 11.677 | 54.496 | 1.00 | 24.64 | C |
| ATOM | 1265 | CE | LYS | A | 204 | 116.755 | 10.311 | 53.965 | 1.00 | 24.02 | C |
| ATOM | 1266 | NZ | LYS | A | 204 | 115.649 | 9.397 | 54.324 | 1.00 | 30.04 | N |
| ATOM | 1267 | C | LYS | A | 204 | 116.961 | 16.514 | 53.613 | 1.00 | 21.53 | C |
| ATOM | 1268 | O | LYS | A | 204 | 117.272 | 17.142 | 54.617 | 1.00 | 20.50 | O |
| ATOM | 1269 | N | LEU | A | 205 | 116.107 | 16.966 | 52.692 | 1.00 | 21.61 | N |
| ATOM | 1270 | CA | LEU | A | 205 | 115.386 | 18.244 | 52.813 | 1.00 | 22.04 | C |
| ATOM | 1271 | CB | LEU | A | 205 | 114.732 | 18.598 | 51.476 | 1.00 | 21.38 | C |
| ATOM | 1272 | CG | LEU | A | 205 | 114.215 | 19.996 | 51.091 | 1.00 | 23.27 | C |
| ATOM | 1273 | CD1 | LEU | A | 205 | 115.048 | 21.027 | 51.825 | 1.00 | 23.55 | C |
| ATOM | 1274 | CD2 | LEU | A | 205 | 114.283 | 20.269 | 49.617 | 1.00 | 21.27 | C |
| ATOM | 1275 | C | LEU | A | 205 | 114.268 | 18.034 | 53.868 | 1.00 | 23.83 | C |
| ATOM | 1276 | O | LEU | A | 205 | 113.572 | 16.985 | 53.861 | 1.00 | 23.50 | O |
| ATOM | 1277 | N | THR | A | 206 | 114.110 | 19.009 | 54.765 | 1.00 | 23.62 | N |
| ATOM | 1278 | CA | THR | A | 206 | 113.067 | 18.961 | 55.773 | 1.00 | 24.59 | C |
| ATOM | 1279 | CB | THR | A | 206 | 113.628 | 19.010 | 57.171 | 1.00 | 23.90 | C |
| ATOM | 1280 | OG1 | THR | A | 206 | 114.163 | 20.315 | 57.393 | 1.00 | 25.60 | O |
| ATOM | 1281 | CG2 | THR | A | 206 | 114.713 | 17.954 | 57.386 | 1.00 | 23.22 | C |
| ATOM | 1282 | C | THR | A | 206 | 112.172 | 20.197 | 55.641 | 1.00 | 26.12 | C |
| ATOM | 1283 | O | THR | A | 206 | 112.305 | 20.989 | 54.712 | 1.00 | 28.51 | O |
| ATOM | 1284 | N | ASP | A | 207 | 111.294 | 20.377 | 56.621 | 1.00 | 27.05 | N |
| ATOM | 1285 | CA | ASP | A | 207 | 110.331 | 21.484 | 56.705 | 1.00 | 24.64 | C |
| ATOM | 1286 | CB | ASP | A | 207 | 110.960 | 22.708 | 57.306 | 1.00 | 23.45 | C |

FIG. 2A-28

| ATOM | 1287 | CG  | ASP | A | 207 | 109.963 | 23.495 | 58.137 | 1.00 | 28.29 | C |
| --- | --- | --- | --- | --- | --- | --- | --- | --- | --- | --- | --- |
| ATOM | 1288 | OD1 | ASP | A | 207 | 108.752 | 23.393 | 57.838 | 1.00 | 33.54 | O |
| ATOM | 1289 | OD2 | ASP | A | 207 | 110.369 | 24.212 | 59.081 | 1.00 | 28.37 | O |
| ATOM | 1290 | C   | ASP | A | 207 | 109.602 | 21.905 | 55.463 | 1.00 | 23.12 | C |
| ATOM | 1291 | O   | ASP | A | 207 | 110.151 | 22.604 | 54.665 | 1.00 | 24.92 | O |
| ATOM | 1292 | N   | PHE | A | 208 | 108.344 | 21.490 | 55.332 | 1.00 | 23.71 | N |
| ATOM | 1293 | CA  | PHE | A | 208 | 107.474 | 21.808 | 54.192 | 1.00 | 20.55 | C |
| ATOM | 1294 | CB  | PHE | A | 208 | 106.762 | 20.552 | 53.677 | 1.00 | 18.43 | C |
| ATOM | 1295 | CG  | PHE | A | 208 | 107.645 | 19.695 | 52.848 | 1.00 | 20.52 | C |
| ATOM | 1296 | CD1 | PHE | A | 208 | 108.742 | 19.077 | 53.407 | 1.00 | 24.17 | C |
| ATOM | 1297 | CE1 | PHE | A | 208 | 109.668 | 18.421 | 52.626 | 1.00 | 27.42 | C |
| ATOM | 1298 | CZ  | PHE | A | 208 | 109.497 | 18.377 | 51.248 | 1.00 | 28.23 | C |
| ATOM | 1299 | CE2 | PHE | A | 208 | 108.400 | 18.981 | 50.675 | 1.00 | 24.59 | C |
| ATOM | 1300 | CD2 | PHE | A | 208 | 107.480 | 19.631 | 51.478 | 1.00 | 23.54 | C |
| ATOM | 1301 | C   | PHE | A | 208 | 106.449 | 22.882 | 54.529 | 1.00 | 20.32 | C |
| ATOM | 1302 | O   | PHE | A | 208 | 105.444 | 23.042 | 53.829 | 1.00 | 21.89 | O |
| ATOM | 1303 | N   | GLY | A | 209 | 106.739 | 23.624 | 55.594 | 1.00 | 19.54 | N |
| ATOM | 1304 | CA  | GLY | A | 209 | 105.881 | 24.703 | 56.033 | 1.00 | 19.83 | C |
| ATOM | 1305 | C   | GLY | A | 209 | 105.597 | 25.818 | 55.036 | 1.00 | 21.41 | C |
| ATOM | 1306 | O   | GLY | A | 209 | 104.618 | 26.504 | 55.209 | 1.00 | 21.83 | O |
| ATOM | 1307 | N   | PHE | A | 210 | 106.447 | 26.038 | 54.031 | 1.00 | 21.80 | N |
| ATOM | 1308 | CA  | PHE | A | 210 | 106.181 | 27.074 | 53.027 | 1.00 | 22.97 | C |
| ATOM | 1309 | CB  | PHE | A | 210 | 107.340 | 28.062 | 52.820 | 1.00 | 25.17 | C |
| ATOM | 1310 | CG  | PHE | A | 210 | 107.542 | 29.027 | 53.924 | 1.00 | 28.60 | C |
| ATOM | 1311 | CD1 | PHE | A | 210 | 106.481 | 29.692 | 54.503 | 1.00 | 35.95 | C |
| ATOM | 1312 | CE1 | PHE | A | 210 | 106.693 | 30.631 | 55.540 | 1.00 | 38.68 | C |
| ATOM | 1313 | CZ  | PHE | A | 210 | 107.961 | 30.895 | 55.988 | 1.00 | 35.66 | C |
| ATOM | 1314 | CE2 | PHE | A | 210 | 109.036 | 30.236 | 55.415 | 1.00 | 39.10 | C |
| ATOM | 1315 | CD2 | PHE | A | 210 | 108.821 | 29.299 | 54.379 | 1.00 | 33.11 | C |
| ATOM | 1316 | C   | PHE | A | 210 | 106.013 | 26.389 | 51.695 | 1.00 | 22.43 | C |
| ATOM | 1317 | O   | PHE | A | 210 | 105.941 | 27.067 | 50.662 | 1.00 | 24.13 | O |
| ATOM | 1318 | N   | ALA | A | 211 | 105.991 | 25.058 | 51.677 | 1.00 | 22.31 | N |
| ATOM | 1319 | CA  | ALA | A | 211 | 105.845 | 24.389 | 50.389 | 1.00 | 23.18 | C |
| ATOM | 1320 | CB  | ALA | A | 211 | 105.786 | 22.894 | 50.570 | 1.00 | 22.21 | C |
| ATOM | 1321 | C   | ALA | A | 211 | 104.603 | 24.891 | 49.661 | 1.00 | 26.14 | C |
| ATOM | 1322 | O   | ALA | A | 211 | 103.637 | 25.368 | 50.259 | 1.00 | 27.47 | O |
| ATOM | 1323 | N   | LYS | A | 212 | 104.609 | 24.798 | 48.351 | 1.00 | 28.70 | N |
| ATOM | 1324 | CA  | LYS | A | 212 | 103.435 | 25.257 | 47.615 | 1.00 | 29.61 | C |
| ATOM | 1325 | CB  | LYS | A | 212 | 103.518 | 26.765 | 47.366 | 1.00 | 28.23 | C |
| ATOM | 1326 | CG  | LYS | A | 212 | 102.260 | 27.359 | 46.850 | 1.00 | 31.65 | C |
| ATOM | 1327 | CD  | LYS | A | 212 | 102.145 | 28.825 | 47.285 | 1.00 | 40.20 | C |
| ATOM | 1328 | CE  | LYS | A | 212 | 101.167 | 29.618 | 46.363 | 1.00 | 45.07 | C |
| ATOM | 1329 | NZ  | LYS | A | 212 | 100.685 | 30.861 | 47.059 | 1.00 | 41.42 | N |
| ATOM | 1330 | C   | LYS | A | 212 | 103.207 | 24.525 | 46.315 | 1.00 | 29.56 | C |
| ATOM | 1331 | O   | LYS | A | 212 | 104.135 | 24.155 | 45.607 | 1.00 | 27.99 | O |
| ATOM | 1332 | N   | GLU | A | 213 | 101.946 | 24.273 | 46.043 | 1.00 | 30.27 | N |

FIG. 2A-29

| ATOM | 1333 | CA | GLU | A | 213 | 101.574 | 23.592 | 44.837 | 1.00 | 31.49 | C |
|---|---|---|---|---|---|---|---|---|---|---|---|
| ATOM | 1334 | CB | GLU | A | 213 | 100.166 | 23.088 | 44.990 | 1.00 | 33.16 | C |
| ATOM | 1335 | CG | GLU | A | 213 | 99.653 | 22.379 | 43.801 | 1.00 | 42.75 | C |
| ATOM | 1336 | CD | GLU | A | 213 | 98.706 | 21.297 | 44.231 | 1.00 | 54.56 | C |
| ATOM | 1337 | OE1 | GLU | A | 213 | 98.368 | 21.311 | 45.444 | 1.00 | 55.69 | O |
| ATOM | 1338 | OE2 | GLU | A | 213 | 98.311 | 20.446 | 43.381 | 1.00 | 60.45 | O |
| ATOM | 1339 | C | GLU | A | 213 | 101.686 | 24.646 | 43.749 | 1.00 | 31.25 | C |
| ATOM | 1340 | O | GLU | A | 213 | 101.401 | 25.815 | 43.968 | 1.00 | 31.54 | O |
| ATOM | 1341 | N | THR | A | 214 | 102.124 | 24.248 | 42.575 | 1.00 | 32.19 | N |
| ATOM | 1342 | CA | THR | A | 214 | 102.307 | 25.221 | 41.531 | 1.00 | 34.43 | C |
| ATOM | 1343 | CB | THR | A | 214 | 103.764 | 25.175 | 41.037 | 1.00 | 32.87 | C |
| ATOM | 1344 | OG1 | THR | A | 214 | 104.078 | 23.847 | 40.619 | 1.00 | 33.99 | O |
| ATOM | 1345 | CG2 | THR | A | 214 | 104.726 | 25.583 | 42.129 | 1.00 | 28.75 | C |
| ATOM | 1346 | C | THR | A | 214 | 101.367 | 24.984 | 40.364 | 1.00 | 38.31 | C |
| ATOM | 1347 | O | THR | A | 214 | 101.821 | 24.673 | 39.279 | 1.00 | 40.12 | O |
| ATOM | 1348 | N | THR | A | 215 | 100.064 | 25.131 | 40.573 | 1.00 | 42.24 | N |
| ATOM | 1349 | CA | THR | A | 215 | 99.097 | 24.901 | 39.496 | 1.00 | 45.08 | C |
| ATOM | 1350 | CB | THR | A | 215 | 99.287 | 23.513 | 38.895 | 1.00 | 45.12 | C |
| ATOM | 1351 | OG1 | THR | A | 215 | 99.830 | 22.642 | 39.900 | 1.00 | 43.07 | O |
| ATOM | 1352 | CG2 | THR | A | 215 | 100.184 | 23.572 | 37.660 | 1.00 | 39.60 | C |
| ATOM | 1353 | C | THR | A | 215 | 97.623 | 25.020 | 39.913 | 1.00 | 49.23 | C |
| ATOM | 1354 | O | THR | A | 215 | 97.207 | 26.116 | 40.394 | 1.00 | 52.48 | O |
| ATOM | 1355 | OXT | THR | A | 215 | 96.892 | 24.003 | 39.740 | 1.00 | 50.73 | O |
| ATOM | 1356 | N | PRO | A | 227 | 98.557 | 18.349 | 22.574 | 1.00 | 29.51 | N |
| ATOM | 1357 | CA | PRO | A | 227 | 99.415 | 18.161 | 21.408 | 1.00 | 28.87 | C |
| ATOM | 1358 | CB | PRO | A | 227 | 99.181 | 19.329 | 20.454 | 1.00 | 29.96 | C |
| ATOM | 1359 | CG | PRO | A | 227 | 97.857 | 19.975 | 20.835 | 1.00 | 31.02 | C |
| ATOM | 1360 | CD | PRO | A | 227 | 97.709 | 19.518 | 22.361 | 1.00 | 30.26 | C |
| ATOM | 1361 | C | PRO | A | 227 | 100.894 | 18.088 | 21.797 | 1.00 | 27.07 | C |
| ATOM | 1362 | O | PRO | A | 227 | 101.344 | 18.667 | 22.777 | 1.00 | 25.54 | O |
| ATOM | 1363 | N | TYR | A | 228 | 101.650 | 17.306 | 21.001 | 1.00 | 24.87 | N |
| ATOM | 1364 | CA | TYR | A | 228 | 103.073 | 17.158 | 21.276 | 1.00 | 22.41 | C |
| ATOM | 1365 | CB | TYR | A | 228 | 103.608 | 16.000 | 20.430 | 1.00 | 21.93 | C |
| ATOM | 1366 | CG | TYR | A | 228 | 103.460 | 16.313 | 18.982 | 1.00 | 19.07 | C |
| ATOM | 1367 | CD1 | TYR | A | 228 | 104.538 | 16.827 | 18.269 | 1.00 | 16.34 | C |
| ATOM | 1368 | CE1 | TYR | A | 228 | 104.434 | 17.041 | 16.902 | 1.00 | 17.00 | C |
| ATOM | 1369 | CZ | TYR | A | 228 | 103.234 | 16.759 | 16.247 | 1.00 | 16.07 | C |
| ATOM | 1370 | OH | TYR | A | 228 | 103.135 | 16.972 | 14.886 | 1.00 | 10.36 | O |
| ATOM | 1371 | CE2 | TYR | A | 228 | 102.157 | 16.255 | 16.953 | 1.00 | 18.49 | C |
| ATOM | 1372 | CD2 | TYR | A | 228 | 102.265 | 16.033 | 18.318 | 1.00 | 19.40 | C |
| ATOM | 1373 | C | TYR | A | 228 | 103.845 | 18.439 | 20.954 | 1.00 | 21.08 | C |
| ATOM | 1374 | O | TYR | A | 228 | 105.068 | 18.483 | 20.989 | 1.00 | 21.42 | O |
| ATOM | 1375 | N | TYR | A | 229 | 103.033 | 19.439 | 20.551 | 1.00 | 18.37 | N |
| ATOM | 1376 | CA | TYR | A | 229 | 103.685 | 20.683 | 20.140 | 1.00 | 16.23 | C |
| ATOM | 1377 | CB | TYR | A | 229 | 103.431 | 20.884 | 18.647 | 1.00 | 15.50 | C |
| ATOM | 1378 | CG | TYR | A | 229 | 101.981 | 21.109 | 18.408 | 1.00 | 16.29 | C |

FIG. 2A-30

| ATOM | 1379 | CD1 | TYR | A | 229 | 101.443 | 22.386 | 18.553 | 1.00 | 16.41 | C |
| --- | --- | --- | --- | --- | --- | --- | --- | --- | --- | --- | --- |
| ATOM | 1380 | CE1 | TYR | A | 229 | 100.094 | 22.605 | 18.318 | 1.00 | 15.76 | C |
| ATOM | 1381 | CZ | TYR | A | 229 | 99.274 | 21.537 | 17.953 | 1.00 | 15.83 | C |
| ATOM | 1382 | OH | TYR | A | 229 | 97.934 | 21.765 | 17.709 | 1.00 | 16.12 | O |
| ATOM | 1383 | CE2 | TYR | A | 229 | 99.806 | 20.266 | 17.809 | 1.00 | 16.43 | C |
| ATOM | 1384 | CD2 | TYR | A | 229 | 101.157 | 20.049 | 18.036 | 1.00 | 17.76 | C |
| ATOM | 1385 | C | TYR | A | 229 | 103.173 | 21.905 | 20.924 | 1.00 | 15.50 | C |
| ATOM | 1386 | O | TYR | A | 229 | 103.604 | 23.032 | 20.721 | 1.00 | 15.37 | O |
| ATOM | 1387 | N | VAL | A | 230 | 102.281 | 21.617 | 21.866 | 1.00 | 14.23 | N |
| ATOM | 1388 | CA | VAL | A | 230 | 101.746 | 22.631 | 22.764 | 1.00 | 12.97 | C |
| ATOM | 1389 | CB | VAL | A | 230 | 100.639 | 22.041 | 23.660 | 1.00 | 14.22 | C |
| ATOM | 1390 | CG1 | VAL | A | 230 | 101.191 | 20.890 | 24.460 | 1.00 | 16.17 | C |
| ATOM | 1391 | CG2 | VAL | A | 230 | 100.102 | 23.101 | 24.612 | 1.00 | 16.22 | C |
| ATOM | 1392 | C | VAL | A | 230 | 102.850 | 23.160 | 23.659 | 1.00 | 11.20 | C |
| ATOM | 1393 | O | VAL | A | 230 | 103.622 | 22.386 | 24.192 | 1.00 | 10.44 | O |
| ATOM | 1394 | N | ALA | A | 231 | 102.920 | 24.479 | 23.812 | 1.00 | 9.76 | N |
| ATOM | 1395 | CA | ALA | A | 231 | 103.904 | 25.118 | 24.682 | 1.00 | 8.60 | C |
| ATOM | 1396 | CB | ALA | A | 231 | 104.026 | 26.585 | 24.267 | 1.00 | 8.07 | C |
| ATOM | 1397 | C | ALA | A | 231 | 103.491 | 25.023 | 26.154 | 1.00 | 10.01 | C |
| ATOM | 1398 | O | ALA | A | 231 | 102.319 | 24.954 | 26.497 | 1.00 | 9.19 | O |
| ATOM | 1399 | N | PRO | A | 232 | 104.505 | 24.989 | 27.039 | 1.00 | 11.91 | N |
| ATOM | 1400 | CA | PRO | A | 232 | 104.271 | 24.783 | 28.462 | 1.00 | 13.19 | C |
| ATOM | 1401 | CB | PRO | A | 232 | 105.614 | 24.878 | 29.181 | 1.00 | 10.92 | C |
| ATOM | 1402 | CG | PRO | A | 232 | 106.642 | 25.426 | 28.198 | 1.00 | 13.47 | C |
| ATOM | 1403 | CD | PRO | A | 232 | 105.928 | 25.159 | 26.788 | 1.00 | 12.72 | C |
| ATOM | 1404 | C | PRO | A | 232 | 103.295 | 25.815 | 29.023 | 1.00 | 16.16 | C |
| ATOM | 1405 | O | PRO | A | 232 | 102.486 | 25.544 | 29.899 | 1.00 | 20.46 | O |
| ATOM | 1406 | N | GLU | A | 233 | 103.417 | 27.051 | 28.511 | 1.00 | 19.06 | N |
| ATOM | 1407 | CA | GLU | A | 233 | 102.633 | 28.168 | 29.025 | 1.00 | 21.79 | C |
| ATOM | 1408 | CB | GLU | A | 233 | 103.133 | 29.451 | 28.365 | 1.00 | 21.87 | C |
| ATOM | 1409 | CG | GLU | A | 233 | 104.573 | 29.322 | 27.868 | 1.00 | 21.97 | C |
| ATOM | 1410 | CD | GLU | A | 233 | 104.603 | 29.507 | 26.367 | 1.00 | 19.44 | C |
| ATOM | 1411 | OE1 | GLU | A | 233 | 103.543 | 29.632 | 25.771 | 1.00 | 19.87 | O |
| ATOM | 1412 | OE2 | GLU | A | 233 | 105.694 | 29.524 | 25.802 | 1.00 | 25.19 | O |
| ATOM | 1413 | C | GLU | A | 233 | 101.138 | 27.987 | 28.747 | 1.00 | 23.27 | C |
| ATOM | 1414 | O | GLU | A | 233 | 100.290 | 28.722 | 29.236 | 1.00 | 24.80 | O |
| ATOM | 1415 | N | VAL | A | 234 | 100.832 | 26.988 | 27.898 | 1.00 | 25.05 | N |
| ATOM | 1416 | CA | VAL | A | 234 | 99.433 | 26.788 | 27.538 | 1.00 | 27.01 | C |
| ATOM | 1417 | CB | VAL | A | 234 | 99.354 | 26.552 | 26.029 | 1.00 | 26.24 | C |
| ATOM | 1418 | CG1 | VAL | A | 234 | 98.088 | 25.774 | 25.685 | 1.00 | 27.00 | C |
| ATOM | 1419 | CG2 | VAL | A | 234 | 99.336 | 27.883 | 25.296 | 1.00 | 25.38 | C |
| ATOM | 1420 | C | VAL | A | 234 | 98.826 | 25.601 | 28.290 | 1.00 | 29.40 | C |
| ATOM | 1421 | O | VAL | A | 234 | 97.614 | 25.466 | 28.431 | 1.00 | 30.42 | O |
| ATOM | 1422 | N | LEU | A | 235 | 99.714 | 24.702 | 28.748 | 1.00 | 31.77 | N |
| ATOM | 1423 | CA | LEU | A | 235 | 99.246 | 23.535 | 29.492 | 1.00 | 35.67 | C |
| ATOM | 1424 | CB | LEU | A | 235 | 100.279 | 22.417 | 29.328 | 1.00 | 34.12 | C |

FIG. 2A-31

| ATOM | 1425 | CG  | LEU | A | 235 | 100.214 | 21.737 | 27.958 | 1.00 | 36.69 | C |
| ATOM | 1426 | CD1 | LEU | A | 235 | 100.541 | 20.240 | 28.021 | 1.00 | 40.66 | C |
| ATOM | 1427 | CD2 | LEU | A | 235 | 98.834  | 21.847 | 27.310 | 1.00 | 38.02 | C |
| ATOM | 1428 | C   | LEU | A | 235 | 99.050  | 23.854 | 30.981 | 1.00 | 38.93 | C |
| ATOM | 1429 | O   | LEU | A | 235 | 98.720  | 23.004 | 31.796 | 1.00 | 42.19 | O |
| ATOM | 1430 | N   | GLY | A | 236 | 99.303  | 25.132 | 31.335 | 1.00 | 41.46 | N |
| ATOM | 1431 | CA  | GLY | A | 236 | 99.155  | 25.535 | 32.733 | 1.00 | 44.44 | C |
| ATOM | 1432 | C   | GLY | A | 236 | 99.997  | 26.771 | 33.059 | 1.00 | 45.76 | C |
| ATOM | 1433 | O   | GLY | A | 236 | 101.185 | 26.841 | 32.779 | 1.00 | 44.97 | O |
| ATOM | 1434 | N   | PRO | A | 237 | 99.324  | 27.788 | 33.637 | 1.00 | 47.18 | N |
| ATOM | 1435 | CA  | PRO | A | 237 | 99.958  | 29.046 | 34.020 | 1.00 | 48.05 | C |
| ATOM | 1436 | CB  | PRO | A | 237 | 98.971  | 29.837 | 34.880 | 1.00 | 48.94 | C |
| ATOM | 1437 | CG  | PRO | A | 237 | 97.683  | 29.032 | 34.995 | 1.00 | 49.91 | C |
| ATOM | 1438 | CD  | PRO | A | 237 | 97.897  | 27.901 | 33.884 | 1.00 | 48.10 | C |
| ATOM | 1439 | C   | PRO | A | 237 | 101.262 | 28.821 | 34.793 | 1.00 | 48.74 | C |
| ATOM | 1440 | O   | PRO | A | 237 | 102.355 | 28.818 | 34.245 | 1.00 | 49.46 | O |
| ATOM | 1441 | N   | ALA | A | 238 | 101.118 | 28.676 | 36.126 | 1.00 | 48.25 | N |
| ATOM | 1442 | CA  | ALA | A | 238 | 102.290 | 28.458 | 36.969 | 1.00 | 48.68 | C |
| ATOM | 1443 | CB  | ALA | A | 238 | 103.045 | 27.233 | 36.446 | 1.00 | 48.60 | C |
| ATOM | 1444 | C   | ALA | A | 238 | 103.217 | 29.676 | 36.998 | 1.00 | 48.62 | C |
| ATOM | 1445 | O   | ALA | A | 238 | 103.869 | 30.027 | 36.023 | 1.00 | 48.54 | O |
| ATOM | 1446 | N   | ALA | A | 239 | 103.235 | 30.352 | 38.162 | 1.00 | 48.38 | N |
| ATOM | 1447 | CA  | ALA | A | 239 | 104.056 | 31.550 | 38.299 | 1.00 | 48.42 | C |
| ATOM | 1448 | CB  | ALA | A | 239 | 103.601 | 32.299 | 39.551 | 1.00 | 48.49 | C |
| ATOM | 1449 | C   | ALA | A | 239 | 105.548 | 31.212 | 38.408 | 1.00 | 48.02 | C |
| ATOM | 1450 | O   | ALA | A | 239 | 106.099 | 30.418 | 37.655 | 1.00 | 49.71 | O |
| ATOM | 1451 | N   | TYR | A | 240 | 106.217 | 31.885 | 39.365 | 1.00 | 45.53 | N |
| ATOM | 1452 | CA  | TYR | A | 240 | 107.647 | 31.655 | 39.521 | 1.00 | 44.34 | C |
| ATOM | 1453 | CB  | TYR | A | 240 | 108.383 | 32.913 | 39.062 | 1.00 | 45.06 | C |
| ATOM | 1454 | CG  | TYR | A | 240 | 107.829 | 33.357 | 37.755 | 1.00 | 45.21 | C |
| ATOM | 1455 | CD1 | TYR | A | 240 | 106.770 | 34.260 | 37.722 | 1.00 | 48.21 | C |
| ATOM | 1456 | CE1 | TYR | A | 240 | 106.220 | 34.645 | 36.508 | 1.00 | 49.09 | C |
| ATOM | 1457 | CZ  | TYR | A | 240 | 106.719 | 34.106 | 35.321 | 1.00 | 49.59 | C |
| ATOM | 1458 | OH  | TYR | A | 240 | 106.161 | 34.486 | 34.114 | 1.00 | 51.00 | O |
| ATOM | 1459 | CE2 | TYR | A | 240 | 107.776 | 33.213 | 35.350 | 1.00 | 44.72 | C |
| ATOM | 1460 | CD2 | TYR | A | 240 | 108.332 | 32.836 | 36.564 | 1.00 | 43.61 | C |
| ATOM | 1461 | C   | TYR | A | 240 | 108.006 | 31.326 | 40.970 | 1.00 | 43.90 | C |
| ATOM | 1462 | O   | TYR | A | 240 | 108.881 | 31.921 | 41.579 | 1.00 | 44.41 | O |
| ATOM | 1463 | N   | ASP | A | 241 | 107.250 | 30.364 | 41.532 | 1.00 | 42.53 | N |
| ATOM | 1464 | CA  | ASP | A | 241 | 107.534 | 29.923 | 42.891 | 1.00 | 39.94 | C |
| ATOM | 1465 | CB  | ASP | A | 241 | 106.239 | 29.397 | 43.508 | 1.00 | 41.14 | C |
| ATOM | 1466 | CG  | ASP | A | 241 | 105.631 | 30.482 | 44.382 | 1.00 | 45.89 | C |
| ATOM | 1467 | OD1 | ASP | A | 241 | 106.401 | 31.189 | 45.035 | 1.00 | 45.82 | O |
| ATOM | 1468 | OD2 | ASP | A | 241 | 104.411 | 30.618 | 44.396 | 1.00 | 55.86 | O |
| ATOM | 1469 | C   | ASP | A | 241 | 108.604 | 28.835 | 42.914 | 1.00 | 37.32 | C |
| ATOM | 1470 | O   | ASP | A | 241 | 109.235 | 28.558 | 43.925 | 1.00 | 37.89 | O |

FIG. 2A-32

| ATOM | 1471 | N | LYS | A | 242 | 108.766 | 28.171 | 41.757 | 1.00 | 34.41 | N |
|------|------|----|-----|---|-----|---------|--------|--------|------|-------|---|
| ATOM | 1472 | CA | LYS | A | 242 | 109.829 | 27.183 | 41.660 | 1.00 | 32.24 | C |
| ATOM | 1473 | CB | LYS | A | 242 | 109.647 | 26.395 | 40.360 | 1.00 | 31.16 | C |
| ATOM | 1474 | CG | LYS | A | 242 | 108.455 | 25.434 | 40.424 | 1.00 | 30.43 | C |
| ATOM | 1475 | CD | LYS | A | 242 | 108.544 | 24.313 | 39.385 | 1.00 | 22.36 | C |
| ATOM | 1476 | CE | LYS | A | 242 | 107.502 | 23.213 | 39.618 | 1.00 | 32.05 | C |
| ATOM | 1477 | NZ | LYS | A | 242 | 106.265 | 23.548 | 38.913 | 1.00 | 39.64 | N |
| ATOM | 1478 | C | LYS | A | 242 | 111.192 | 27.871 | 41.673 | 1.00 | 31.15 | C |
| ATOM | 1479 | O | LYS | A | 242 | 112.158 | 27.383 | 42.244 | 1.00 | 33.08 | O |
| ATOM | 1480 | N | SER | A | 243 | 111.077 | 28.975 | 40.977 | 1.00 | 30.00 | N |
| ATOM | 1481 | CA | SER | A | 243 | 112.186 | 29.834 | 40.718 | 1.00 | 28.11 | C |
| ATOM | 1482 | CB | SER | A | 243 | 111.697 | 31.080 | 40.001 | 1.00 | 28.35 | C |
| ATOM | 1483 | OG | SER | A | 243 | 112.727 | 32.039 | 39.973 | 1.00 | 38.49 | O |
| ATOM | 1484 | C | SER | A | 243 | 113.009 | 30.195 | 41.921 | 1.00 | 25.69 | C |
| ATOM | 1485 | O | SER | A | 243 | 114.218 | 30.285 | 41.818 | 1.00 | 23.84 | O |
| ATOM | 1486 | N | CYS | A | 244 | 112.404 | 30.406 | 43.075 | 1.00 | 26.22 | N |
| ATOM | 1487 | CA | CYS | A | 244 | 113.264 | 30.753 | 44.181 | 1.00 | 26.90 | C |
| ATOM | 1488 | CB | CYS | A | 244 | 112.551 | 31.650 | 45.168 | 1.00 | 27.03 | C |
| ATOM | 1489 | SG | CYS | A | 244 | 111.295 | 30.848 | 46.026 | 1.00 | 37.51 | S |
| ATOM | 1490 | C | CYS | A | 244 | 113.897 | 29.539 | 44.866 | 1.00 | 25.90 | C |
| ATOM | 1491 | O | CYS | A | 244 | 114.795 | 29.700 | 45.675 | 1.00 | 24.86 | O |
| ATOM | 1492 | N | ASP | A | 245 | 113.448 | 28.329 | 44.546 | 1.00 | 25.89 | N |
| ATOM | 1493 | CA | ASP | A | 245 | 114.097 | 27.146 | 45.101 | 1.00 | 22.62 | C |
| ATOM | 1494 | CB | ASP | A | 245 | 113.393 | 25.831 | 44.682 | 1.00 | 20.89 | C |
| ATOM | 1495 | CG | ASP | A | 245 | 112.169 | 25.481 | 45.557 | 1.00 | 24.01 | C |
| ATOM | 1496 | OD1 | ASP | A | 245 | 112.028 | 26.047 | 46.661 | 1.00 | 29.59 | O |
| ATOM | 1497 | OD2 | ASP | A | 245 | 111.345 | 24.627 | 45.139 | 1.00 | 24.34 | O |
| ATOM | 1498 | C | ASP | A | 245 | 115.493 | 27.213 | 44.434 | 1.00 | 22.82 | C |
| ATOM | 1499 | O | ASP | A | 245 | 116.531 | 26.961 | 45.064 | 1.00 | 22.72 | O |
| ATOM | 1500 | N | MSE | A | 246 | 115.497 | 27.575 | 43.151 | 1.00 | 22.20 | N |
| ATOM | 1501 | CA | MSE | A | 246 | 116.723 | 27.692 | 42.365 | 1.00 | 23.90 | C |
| ATOM | 1502 | CB | MSE | A | 246 | 116.389 | 27.989 | 40.910 | 1.00 | 23.59 | C |
| ATOM | 1503 | CG | MSE | A | 246 | 115.480 | 26.934 | 40.263 | 1.00 | 24.02 | C |
| ATOM | 1504 | SE | MSE | A | 246 | 116.087 | 25.113 | 40.541 | 1.00 | 28.55 | S |
| ATOM | 1505 | CE | MSE | A | 246 | 117.920 | 25.337 | 40.044 | 1.00 | 26.58 | C |
| ATOM | 1506 | C | MSE | A | 246 | 117.645 | 28.769 | 42.900 | 1.00 | 23.66 | C |
| ATOM | 1507 | O | MSE | A | 246 | 118.861 | 28.622 | 42.877 | 1.00 | 23.35 | O |
| ATOM | 1508 | N | TRP | A | 247 | 117.070 | 29.868 | 43.370 | 1.00 | 24.54 | N |
| ATOM | 1509 | CA | TRP | A | 247 | 117.899 | 30.902 | 43.939 | 1.00 | 21.80 | C |
| ATOM | 1510 | CB | TRP | A | 247 | 117.055 | 32.108 | 44.343 | 1.00 | 21.27 | C |
| ATOM | 1511 | CG | TRP | A | 247 | 117.836 | 33.112 | 45.154 | 1.00 | 20.00 | C |
| ATOM | 1512 | CD1 | TRP | A | 247 | 118.071 | 33.059 | 46.468 | 1.00 | 15.90 | C |
| ATOM | 1513 | NE1 | TRP | A | 247 | 118.896 | 34.074 | 46.853 | 1.00 | 15.57 | N |
| ATOM | 1514 | CE2 | TRP | A | 247 | 119.218 | 34.823 | 45.760 | 1.00 | 15.93 | C |
| ATOM | 1515 | CD2 | TRP | A | 247 | 118.563 | 34.249 | 44.665 | 1.00 | 16.27 | C |
| ATOM | 1516 | CE3 | TRP | A | 247 | 118.729 | 34.828 | 43.405 | 1.00 | 16.80 | C |

FIG. 2A-33

| ATOM | 1517 | CZ3 | TRP | A | 247 | 119.535 | 35.952 | 43.292 | 1.00 | 21.42 | C |
|---|---|---|---|---|---|---|---|---|---|---|---|
| ATOM | 1518 | CH2 | TRP | A | 247 | 120.170 | 36.495 | 44.403 | 1.00 | 17.48 | C |
| ATOM | 1519 | CZ2 | TRP | A | 247 | 120.025 | 35.949 | 45.643 | 1.00 | 17.23 | C |
| ATOM | 1520 | C | TRP | A | 247 | 118.592 | 30.247 | 45.156 | 1.00 | 22.75 | C |
| ATOM | 1521 | O | TRP | A | 247 | 119.812 | 30.333 | 45.317 | 1.00 | 22.25 | O |
| ATOM | 1522 | N | SER | A | 248 | 117.815 | 29.563 | 45.991 | 1.00 | 23.72 | N |
| ATOM | 1523 | CA | SER | A | 248 | 118.349 | 28.886 | 47.160 | 1.00 | 23.47 | C |
| ATOM | 1524 | CB | SER | A | 248 | 117.289 | 28.017 | 47.784 | 1.00 | 23.04 | C |
| ATOM | 1525 | OG | SER | A | 248 | 116.429 | 28.833 | 48.532 | 1.00 | 30.70 | O |
| ATOM | 1526 | C | SER | A | 248 | 119.536 | 28.023 | 46.824 | 1.00 | 23.04 | C |
| ATOM | 1527 | O | SER | A | 248 | 120.568 | 28.086 | 47.518 | 1.00 | 21.70 | O |
| ATOM | 1528 | N | LEU | A | 249 | 119.370 | 27.188 | 45.795 | 1.00 | 22.51 | N |
| ATOM | 1529 | CA | LEU | A | 249 | 120.423 | 26.297 | 45.318 | 1.00 | 23.44 | C |
| ATOM | 1530 | CB | LEU | A | 249 | 119.981 | 25.668 | 43.999 | 1.00 | 24.68 | C |
| ATOM | 1531 | CG | LEU | A | 249 | 119.742 | 24.159 | 43.911 | 1.00 | 22.30 | C |
| ATOM | 1532 | CD1 | LEU | A | 249 | 118.920 | 23.696 | 45.116 | 1.00 | 24.02 | C |
| ATOM | 1533 | CD2 | LEU | A | 249 | 119.048 | 23.813 | 42.590 | 1.00 | 26.75 | C |
| ATOM | 1534 | C | LEU | A | 249 | 121.691 | 27.162 | 45.101 | 1.00 | 22.74 | C |
| ATOM | 1535 | O | LEU | A | 249 | 122.805 | 26.798 | 45.490 | 1.00 | 19.55 | O |
| ATOM | 1536 | N | GLY | A | 250 | 121.491 | 28.326 | 44.494 | 1.00 | 22.17 | N |
| ATOM | 1537 | CA | GLY | A | 250 | 122.595 | 29.223 | 44.264 | 1.00 | 21.05 | C |
| ATOM | 1538 | C | GLY | A | 250 | 123.354 | 29.550 | 45.538 | 1.00 | 21.46 | C |
| ATOM | 1539 | O | GLY | A | 250 | 124.573 | 29.326 | 45.613 | 1.00 | 19.99 | O |
| ATOM | 1540 | N | VAL | A | 251 | 122.661 | 30.101 | 46.526 | 1.00 | 20.25 | N |
| ATOM | 1541 | CA | VAL | A | 251 | 123.302 | 30.432 | 47.803 | 1.00 | 18.36 | C |
| ATOM | 1542 | CB | VAL | A | 251 | 122.251 | 31.054 | 48.747 | 1.00 | 16.01 | C |
| ATOM | 1543 | CG1 | VAL | A | 251 | 122.805 | 31.293 | 50.127 | 1.00 | 13.89 | C |
| ATOM | 1544 | CG2 | VAL | A | 251 | 121.764 | 32.298 | 48.164 | 1.00 | 16.28 | C |
| ATOM | 1545 | C | VAL | A | 251 | 123.978 | 29.194 | 48.483 | 1.00 | 19.83 | C |
| ATOM | 1546 | O | VAL | A | 251 | 125.062 | 29.288 | 49.057 | 1.00 | 19.67 | O |
| ATOM | 1547 | N | ILE | A | 252 | 123.360 | 28.030 | 48.428 | 1.00 | 20.14 | N |
| ATOM | 1548 | CA | ILE | A | 252 | 124.005 | 26.900 | 49.065 | 1.00 | 20.56 | C |
| ATOM | 1549 | CB | ILE | A | 252 | 123.063 | 25.645 | 49.071 | 1.00 | 19.67 | C |
| ATOM | 1550 | CG1 | ILE | A | 252 | 121.863 | 25.913 | 49.982 | 1.00 | 18.16 | C |
| ATOM | 1551 | CD1 | ILE | A | 252 | 120.702 | 25.005 | 49.693 | 1.00 | 18.71 | C |
| ATOM | 1552 | CG2 | ILE | A | 252 | 123.777 | 24.432 | 49.581 | 1.00 | 15.69 | C |
| ATOM | 1553 | C | ILE | A | 252 | 125.339 | 26.624 | 48.336 | 1.00 | 22.24 | C |
| ATOM | 1554 | O | ILE | A | 252 | 126.399 | 26.608 | 48.960 | 1.00 | 22.22 | O |
| ATOM | 1555 | N | MSE | A | 253 | 125.288 | 26.431 | 47.021 | 1.00 | 21.83 | N |
| ATOM | 1556 | CA | MSE | A | 253 | 126.502 | 26.182 | 46.232 | 1.00 | 21.44 | C |
| ATOM | 1557 | CB | MSE | A | 253 | 126.188 | 26.235 | 44.732 | 1.00 | 21.85 | C |
| ATOM | 1558 | CG | MSE | A | 253 | 127.161 | 25.478 | 43.880 | 1.00 | 24.39 | C |
| ATOM | 1559 | SE | MSE | A | 253 | 126.551 | 25.413 | 42.066 | 1.00 | 31.40 | S |
| ATOM | 1560 | CE | MSE | A | 253 | 125.707 | 23.724 | 42.060 | 1.00 | 35.78 | C |
| ATOM | 1561 | C | MSE | A | 253 | 127.621 | 27.191 | 46.564 | 1.00 | 20.28 | C |
| ATOM | 1562 | O | MSE | A | 253 | 128.754 | 26.800 | 46.878 | 1.00 | 20.51 | O |

FIG. 2A-34

| ATOM | 1563 | N   | TYR | A | 254 | 127.308 | 28.480 | 46.492 | 1.00 | 19.78 | N |
| ---- | ---- | --- | --- | - | --- | ------- | ------ | ------ | ---- | ----- | - |
| ATOM | 1564 | CA  | TYR | A | 254 | 128.288 | 29.478 | 46.810 | 1.00 | 19.20 | C |
| ATOM | 1565 | CB  | TYR | A | 254 | 127.619 | 30.848 | 46.911 | 1.00 | 20.37 | C |
| ATOM | 1566 | CG  | TYR | A | 254 | 128.559 | 32.011 | 47.105 | 1.00 | 18.09 | C |
| ATOM | 1567 | CD1 | TYR | A | 254 | 129.139 | 32.255 | 48.335 | 1.00 | 18.64 | C |
| ATOM | 1568 | CE1 | TYR | A | 254 | 130.001 | 33.320 | 48.520 | 1.00 | 24.57 | C |
| ATOM | 1569 | CZ  | TYR | A | 254 | 130.295 | 34.166 | 47.457 | 1.00 | 24.25 | C |
| ATOM | 1570 | OH  | TYR | A | 254 | 131.148 | 35.232 | 47.656 | 1.00 | 24.10 | O |
| ATOM | 1571 | CE2 | TYR | A | 254 | 129.732 | 33.942 | 46.221 | 1.00 | 22.23 | C |
| ATOM | 1572 | CD2 | TYR | A | 254 | 128.863 | 32.864 | 46.058 | 1.00 | 22.18 | C |
| ATOM | 1573 | C   | TYR | A | 254 | 128.933 | 29.059 | 48.127 | 1.00 | 20.80 | C |
| ATOM | 1574 | O   | TYR | A | 254 | 130.096 | 28.643 | 48.143 | 1.00 | 21.64 | O |
| ATOM | 1575 | N   | ILE | A | 255 | 128.199 | 29.121 | 49.232 | 1.00 | 21.28 | N |
| ATOM | 1576 | CA  | ILE | A | 255 | 128.779 | 28.724 | 50.509 | 1.00 | 20.52 | C |
| ATOM | 1577 | CB  | ILE | A | 255 | 127.720 | 28.635 | 51.571 | 1.00 | 20.04 | C |
| ATOM | 1578 | CG1 | ILE | A | 255 | 126.903 | 29.928 | 51.583 | 1.00 | 20.60 | C |
| ATOM | 1579 | CD1 | ILE | A | 255 | 125.670 | 29.887 | 52.484 | 1.00 | 18.86 | C |
| ATOM | 1580 | CG2 | ILE | A | 255 | 128.376 | 28.355 | 52.913 | 1.00 | 18.76 | C |
| ATOM | 1581 | C   | ILE | A | 255 | 129.532 | 27.374 | 50.477 | 1.00 | 20.58 | C |
| ATOM | 1582 | O   | ILE | A | 255 | 130.505 | 27.184 | 51.184 | 1.00 | 18.59 | O |
| ATOM | 1583 | N   | LEU | A | 256 | 129.102 | 26.431 | 49.660 | 1.00 | 21.32 | N |
| ATOM | 1584 | CA  | LEU | A | 256 | 129.802 | 25.160 | 49.627 | 1.00 | 21.88 | C |
| ATOM | 1585 | CB  | LEU | A | 256 | 129.072 | 24.133 | 48.763 | 1.00 | 22.50 | C |
| ATOM | 1586 | CG  | LEU | A | 256 | 128.071 | 23.187 | 49.430 | 1.00 | 23.30 | C |
| ATOM | 1587 | CD1 | LEU | A | 256 | 127.708 | 22.087 | 48.436 | 1.00 | 26.75 | C |
| ATOM | 1588 | CD2 | LEU | A | 256 | 128.664 | 22.610 | 50.682 | 1.00 | 15.45 | C |
| ATOM | 1589 | C   | LEU | A | 256 | 131.212 | 25.269 | 49.092 | 1.00 | 22.50 | C |
| ATOM | 1590 | O   | LEU | A | 256 | 132.042 | 24.377 | 49.329 | 1.00 | 22.94 | O |
| ATOM | 1591 | N   | LEU | A | 257 | 131.504 | 26.338 | 48.362 | 1.00 | 22.70 | N |
| ATOM | 1592 | CA  | LEU | A | 257 | 132.838 | 26.452 | 47.804 | 1.00 | 21.98 | C |
| ATOM | 1593 | CB  | LEU | A | 257 | 132.771 | 26.909 | 46.356 | 1.00 | 20.81 | C |
| ATOM | 1594 | CG  | LEU | A | 257 | 131.804 | 26.114 | 45.517 | 1.00 | 22.21 | C |
| ATOM | 1595 | CD1 | LEU | A | 257 | 131.731 | 26.707 | 44.148 | 1.00 | 22.37 | C |
| ATOM | 1596 | CD2 | LEU | A | 257 | 132.239 | 24.680 | 45.454 | 1.00 | 25.19 | C |
| ATOM | 1597 | C   | LEU | A | 257 | 133.758 | 27.374 | 48.567 | 1.00 | 22.35 | C |
| ATOM | 1598 | O   | LEU | A | 257 | 134.951 | 27.386 | 48.282 | 1.00 | 23.92 | O |
| ATOM | 1599 | N   | CYS | A | 258 | 133.257 | 28.146 | 49.524 | 1.00 | 22.29 | N |
| ATOM | 1600 | CA  | CYS | A | 258 | 134.171 | 29.037 | 50.216 | 1.00 | 21.73 | C |
| ATOM | 1601 | CB  | CYS | A | 258 | 134.222 | 30.371 | 49.484 | 1.00 | 21.11 | C |
| ATOM | 1602 | SG  | CYS | A | 258 | 132.823 | 31.427 | 49.854 | 1.00 | 21.19 | S |
| ATOM | 1603 | C   | CYS | A | 258 | 133.898 | 29.288 | 51.700 | 1.00 | 22.99 | C |
| ATOM | 1604 | O   | CYS | A | 258 | 134.619 | 30.033 | 52.346 | 1.00 | 22.76 | O |
| ATOM | 1605 | N   | GLY | A | 259 | 132.851 | 28.686 | 52.242 | 1.00 | 23.75 | N |
| ATOM | 1606 | CA  | GLY | A | 259 | 132.560 | 28.874 | 53.646 | 1.00 | 24.59 | C |
| ATOM | 1607 | C   | GLY | A | 259 | 131.758 | 30.094 | 54.053 | 1.00 | 24.84 | C |
| ATOM | 1608 | O   | GLY | A | 259 | 131.445 | 30.246 | 55.228 | 1.00 | 24.95 | O |

FIG. 2A-35

| ATOM | 1609 | N | TYR | A | 260 | 131.420 | 30.982 | 53.131 | 1.00 | 24.50 | N |
|---|---|---|---|---|---|---|---|---|---|---|---|
| ATOM | 1610 | CA | TYR | A | 260 | 130.631 | 32.145 | 53.536 | 1.00 | 25.17 | C |
| ATOM | 1611 | CB | TYR | A | 260 | 131.549 | 33.344 | 53.778 | 1.00 | 24.66 | C |
| ATOM | 1612 | CG | TYR | A | 260 | 132.423 | 33.726 | 52.606 | 1.00 | 25.88 | C |
| ATOM | 1613 | CD1 | TYR | A | 260 | 131.998 | 34.673 | 51.680 | 1.00 | 28.72 | C |
| ATOM | 1614 | CE1 | TYR | A | 260 | 132.789 | 35.013 | 50.587 | 1.00 | 31.88 | C |
| ATOM | 1615 | CZ | TYR | A | 260 | 134.024 | 34.390 | 50.411 | 1.00 | 31.46 | C |
| ATOM | 1616 | OH | TYR | A | 260 | 134.799 | 34.699 | 49.303 | 1.00 | 36.72 | O |
| ATOM | 1617 | CE2 | TYR | A | 260 | 134.460 | 33.440 | 51.329 | 1.00 | 25.82 | C |
| ATOM | 1618 | CD2 | TYR | A | 260 | 133.663 | 33.122 | 52.415 | 1.00 | 25.68 | C |
| ATOM | 1619 | C | TYR | A | 260 | 129.581 | 32.439 | 52.475 | 1.00 | 25.97 | C |
| ATOM | 1620 | O | TYR | A | 260 | 129.661 | 31.912 | 51.371 | 1.00 | 27.46 | O |
| ATOM | 1621 | N | PRO | A | 261 | 128.567 | 33.251 | 52.802 | 1.00 | 25.50 | N |
| ATOM | 1622 | CA | PRO | A | 261 | 127.481 | 33.616 | 51.882 | 1.00 | 24.58 | C |
| ATOM | 1623 | CB | PRO | A | 261 | 126.336 | 33.907 | 52.827 | 1.00 | 25.41 | C |
| ATOM | 1624 | CG | PRO | A | 261 | 127.050 | 34.657 | 53.925 | 1.00 | 25.45 | C |
| ATOM | 1625 | CD | PRO | A | 261 | 128.329 | 33.833 | 54.133 | 1.00 | 24.74 | C |
| ATOM | 1626 | C | PRO | A | 261 | 127.824 | 34.842 | 51.050 | 1.00 | 23.43 | C |
| ATOM | 1627 | O | PRO | A | 261 | 128.654 | 35.646 | 51.445 | 1.00 | 24.92 | O |
| ATOM | 1628 | N | PRO | A | 262 | 127.175 | 34.998 | 49.891 | 1.00 | 21.46 | N |
| ATOM | 1629 | CA | PRO | A | 262 | 127.353 | 36.097 | 48.943 | 1.00 | 20.62 | C |
| ATOM | 1630 | CB | PRO | A | 262 | 126.759 | 35.531 | 47.665 | 1.00 | 19.82 | C |
| ATOM | 1631 | CG | PRO | A | 262 | 125.622 | 34.734 | 48.194 | 1.00 | 20.68 | C |
| ATOM | 1632 | CD | PRO | A | 262 | 126.249 | 33.991 | 49.348 | 1.00 | 19.93 | C |
| ATOM | 1633 | C | PRO | A | 262 | 126.662 | 37.375 | 49.403 | 1.00 | 22.09 | C |
| ATOM | 1634 | O | PRO | A | 262 | 127.085 | 38.482 | 49.089 | 1.00 | 24.53 | O |
| ATOM | 1635 | N | PHE | A | 263 | 125.520 | 37.226 | 50.041 | 1.00 | 25.16 | N |
| ATOM | 1636 | CA | PHE | A | 263 | 125.020 | 38.514 | 50.552 | 1.00 | 27.70 | C |
| ATOM | 1637 | CB | PHE | A | 263 | 123.544 | 38.648 | 50.148 | 1.00 | 26.11 | C |
| ATOM | 1638 | CG | PHE | A | 263 | 123.410 | 38.478 | 48.666 | 1.00 | 22.67 | C |
| ATOM | 1639 | CD1 | PHE | A | 263 | 123.138 | 37.217 | 48.155 | 1.00 | 16.62 | C |
| ATOM | 1640 | CE1 | PHE | A | 263 | 123.189 | 37.006 | 46.789 | 1.00 | 15.07 | C |
| ATOM | 1641 | CZ | PHE | A | 263 | 123.496 | 38.053 | 45.931 | 1.00 | 14.84 | C |
| ATOM | 1642 | CE2 | PHE | A | 263 | 123.772 | 39.313 | 46.448 | 1.00 | 14.79 | C |
| ATOM | 1643 | CD2 | PHE | A | 263 | 123.725 | 39.531 | 47.819 | 1.00 | 21.81 | C |
| ATOM | 1644 | C | PHE | A | 263 | 125.162 | 38.650 | 52.076 | 1.00 | 31.15 | C |
| ATOM | 1645 | O | PHE | A | 263 | 124.997 | 37.711 | 52.830 | 1.00 | 31.15 | O |
| ATOM | 1646 | N | TYR | A | 264 | 125.521 | 39.881 | 52.526 | 1.00 | 35.53 | N |
| ATOM | 1647 | CA | TYR | A | 264 | 125.675 | 40.128 | 53.972 | 1.00 | 40.48 | C |
| ATOM | 1648 | CB | TYR | A | 264 | 127.090 | 39.726 | 54.377 | 1.00 | 41.04 | C |
| ATOM | 1649 | CG | TYR | A | 264 | 128.065 | 40.597 | 53.674 | 1.00 | 44.86 | C |
| ATOM | 1650 | CD1 | TYR | A | 264 | 128.107 | 40.603 | 52.285 | 1.00 | 46.31 | C |
| ATOM | 1651 | CE1 | TYR | A | 264 | 129.101 | 41.303 | 51.618 | 1.00 | 49.78 | C |
| ATOM | 1652 | CZ | TYR | A | 264 | 130.072 | 41.993 | 52.346 | 1.00 | 52.81 | C |
| ATOM | 1653 | OH | TYR | A | 264 | 131.036 | 42.713 | 51.672 | 1.00 | 55.00 | O |
| ATOM | 1654 | CE2 | TYR | A | 264 | 130.028 | 42.003 | 53.727 | 1.00 | 53.26 | C |

FIG. 2A-36

| ATOM | 1655 | CD2 | TYR | A | 264 | 129.027 | 41.308 | 54.397 | 1.00 | 51.21 | C |
| --- | --- | --- | --- | --- | --- | --- | --- | --- | --- | --- | --- |
| ATOM | 1656 | C | TYR | A | 264 | 125.411 | 41.598 | 54.340 | 1.00 | 43.14 | C |
| ATOM | 1657 | O | TYR | A | 264 | 124.940 | 42.389 | 53.530 | 1.00 | 43.60 | O |
| ATOM | 1658 | N | SER | A | 265 | 125.686 | 41.940 | 55.635 | 1.00 | 46.17 | N |
| ATOM | 1659 | CA | SER | A | 265 | 125.480 | 43.308 | 56.122 | 1.00 | 48.55 | C |
| ATOM | 1660 | CB | SER | A | 265 | 124.932 | 43.228 | 57.551 | 1.00 | 49.30 | C |
| ATOM | 1661 | OG | SER | A | 265 | 124.198 | 44.416 | 57.846 | 1.00 | 51.57 | O |
| ATOM | 1662 | C | SER | A | 265 | 126.777 | 44.137 | 56.117 | 1.00 | 49.54 | C |
| ATOM | 1663 | O | SER | A | 265 | 127.813 | 43.741 | 56.644 | 1.00 | 49.66 | O |
| ATOM | 1664 | N | ASN | A | 266 | 126.696 | 45.325 | 55.490 | 1.00 | 50.15 | N |
| ATOM | 1665 | CA | ASN | A | 266 | 127.886 | 46.163 | 55.367 | 1.00 | 50.94 | C |
| ATOM | 1666 | CB | ASN | A | 266 | 128.677 | 45.688 | 54.147 | 1.00 | 51.35 | C |
| ATOM | 1667 | CG | ASN | A | 266 | 130.153 | 45.851 | 54.404 | 1.00 | 53.17 | C |
| ATOM | 1668 | OD1 | ASN | A | 266 | 130.804 | 45.009 | 55.018 | 1.00 | 56.15 | O |
| ATOM | 1669 | ND2 | ASN | A | 266 | 130.700 | 46.962 | 53.882 | 1.00 | 50.91 | N |
| ATOM | 1670 | C | ASN | A | 266 | 127.523 | 47.643 | 55.202 | 1.00 | 51.32 | C |
| ATOM | 1671 | O | ASN | A | 266 | 127.361 | 48.157 | 54.105 | 1.00 | 51.75 | O |
| ATOM | 1672 | N | HIS | A | 267 | 127.348 | 48.323 | 56.351 | 1.00 | 51.89 | N |
| ATOM | 1673 | CA | HIS | A | 267 | 126.996 | 49.739 | 56.297 | 1.00 | 52.60 | C |
| ATOM | 1674 | CB | HIS | A | 267 | 126.473 | 50.153 | 57.674 | 1.00 | 53.71 | C |
| ATOM | 1675 | CG | HIS | A | 267 | 125.008 | 49.816 | 57.779 | 1.00 | 58.87 | C |
| ATOM | 1676 | ND1 | HIS | A | 267 | 124.074 | 50.278 | 56.911 | 1.00 | 61.61 | N |
| ATOM | 1677 | CE1 | HIS | A | 267 | 122.903 | 49.758 | 57.328 | 1.00 | 64.00 | C |
| ATOM | 1678 | NE2 | HIS | A | 267 | 123.052 | 48.997 | 58.415 | 1.00 | 66.06 | N |
| ATOM | 1679 | CD2 | HIS | A | 267 | 124.371 | 49.011 | 58.730 | 1.00 | 63.17 | C |
| ATOM | 1680 | C | HIS | A | 267 | 128.199 | 50.602 | 55.913 | 1.00 | 51.44 | C |
| ATOM | 1681 | O | HIS | A | 267 | 128.086 | 51.774 | 55.573 | 1.00 | 50.82 | O |
| ATOM | 1682 | N | GLY | A | 268 | 129.390 | 49.987 | 56.019 | 1.00 | 50.98 | N |
| ATOM | 1683 | CA | GLY | A | 268 | 130.604 | 50.709 | 55.660 | 1.00 | 50.09 | C |
| ATOM | 1684 | C | GLY | A | 268 | 130.671 | 50.974 | 54.156 | 1.00 | 49.63 | C |
| ATOM | 1685 | O | GLY | A | 268 | 131.499 | 51.724 | 53.660 | 1.00 | 49.33 | O |
| ATOM | 1686 | N | LEU | A | 269 | 129.778 | 50.287 | 53.421 | 1.00 | 48.85 | N |
| ATOM | 1687 | CA | LEU | A | 269 | 129.753 | 50.452 | 51.973 | 1.00 | 48.04 | C |
| ATOM | 1688 | CB | LEU | A | 269 | 128.823 | 49.386 | 51.392 | 1.00 | 47.95 | C |
| ATOM | 1689 | CG | LEU | A | 269 | 129.455 | 47.993 | 51.374 | 1.00 | 48.23 | C |
| ATOM | 1690 | CD1 | LEU | A | 269 | 128.492 | 46.925 | 50.851 | 1.00 | 48.44 | C |
| ATOM | 1691 | CD2 | LEU | A | 269 | 130.698 | 47.916 | 50.489 | 1.00 | 49.41 | C |
| ATOM | 1692 | C | LEU | A | 269 | 129.246 | 51.839 | 51.571 | 1.00 | 48.05 | C |
| ATOM | 1693 | O | LEU | A | 269 | 128.776 | 52.627 | 52.381 | 1.00 | 49.10 | O |
| ATOM | 1694 | N | ALA | A | 270 | 129.397 | 52.137 | 50.269 | 1.00 | 47.49 | N |
| ATOM | 1695 | CA | ALA | A | 270 | 128.825 | 53.366 | 49.737 | 1.00 | 46.63 | C |
| ATOM | 1696 | CB | ALA | A | 270 | 129.814 | 53.959 | 48.735 | 1.00 | 45.98 | C |
| ATOM | 1697 | C | ALA | A | 270 | 127.496 | 53.082 | 49.043 | 1.00 | 46.25 | C |
| ATOM | 1698 | O | ALA | A | 270 | 126.486 | 53.744 | 49.256 | 1.00 | 46.54 | O |
| ATOM | 1699 | N | ILE | A | 271 | 127.533 | 52.075 | 48.151 | 1.00 | 45.02 | N |
| ATOM | 1700 | CA | ILE | A | 271 | 126.314 | 51.697 | 47.456 | 1.00 | 44.28 | C |

FIG. 2A-37

| ATOM | 1701 | CB | ILE | A | 271 | 126.636 | 51.467 | 45.985 | 1.00 | 44.31 | C |
|---|---|---|---|---|---|---|---|---|---|---|---|
| ATOM | 1702 | CG1 | ILE | A | 271 | 126.446 | 52.771 | 45.211 | 1.00 | 43.07 | C |
| ATOM | 1703 | CD1 | ILE | A | 271 | 125.603 | 53.784 | 45.989 | 1.00 | 43.18 | C |
| ATOM | 1704 | CG2 | ILE | A | 271 | 125.654 | 50.432 | 45.404 | 1.00 | 42.61 | C |
| ATOM | 1705 | C | ILE | A | 271 | 125.708 | 50.432 | 48.044 | 1.00 | 44.22 | C |
| ATOM | 1706 | O | ILE | A | 271 | 126.388 | 49.521 | 48.509 | 1.00 | 44.64 | O |
| ATOM | 1707 | N | SER | A | 272 | 124.372 | 50.406 | 48.039 | 1.00 | 43.65 | N |
| ATOM | 1708 | CA | SER | A | 272 | 123.709 | 49.260 | 48.621 | 1.00 | 43.00 | C |
| ATOM | 1709 | CB | SER | A | 272 | 123.684 | 48.137 | 47.582 | 1.00 | 43.58 | C |
| ATOM | 1710 | OG | SER | A | 272 | 122.862 | 48.516 | 46.476 | 1.00 | 46.92 | O |
| ATOM | 1711 | C | SER | A | 272 | 124.465 | 48.778 | 49.856 | 1.00 | 41.10 | C |
| ATOM | 1712 | O | SER | A | 272 | 125.009 | 47.678 | 49.875 | 1.00 | 41.38 | O |
| ATOM | 1713 | N | PRO | A | 273 | 124.548 | 49.633 | 50.888 | 1.00 | 39.22 | N |
| ATOM | 1714 | CA | PRO | A | 273 | 124.904 | 49.135 | 52.187 | 1.00 | 38.32 | C |
| ATOM | 1715 | CB | PRO | A | 273 | 124.556 | 50.201 | 53.216 | 1.00 | 38.38 | C |
| ATOM | 1716 | CG | PRO | A | 273 | 124.409 | 51.533 | 52.481 | 1.00 | 38.17 | C |
| ATOM | 1717 | CD | PRO | A | 273 | 124.338 | 51.074 | 50.942 | 1.00 | 38.62 | C |
| ATOM | 1718 | C | PRO | A | 273 | 124.061 | 47.898 | 52.439 | 1.00 | 37.89 | C |
| ATOM | 1719 | O | PRO | A | 273 | 124.561 | 46.791 | 52.595 | 1.00 | 38.80 | O |
| ATOM | 1720 | N | GLY | A | 274 | 122.763 | 48.190 | 52.661 | 1.00 | 35.93 | N |
| ATOM | 1721 | CA | GLY | A | 274 | 121.862 | 47.146 | 53.150 | 1.00 | 31.62 | C |
| ATOM | 1722 | C | GLY | A | 274 | 121.978 | 45.850 | 52.341 | 1.00 | 29.40 | C |
| ATOM | 1723 | O | GLY | A | 274 | 122.148 | 45.863 | 51.129 | 1.00 | 28.18 | O |
| ATOM | 1724 | N | MSEA | | 275 | 121.910 | 44.740 | 53.070 | 1.00 | 27.60 | N |
| ATOM | 1725 | CA | MSEA | | 275 | 121.994 | 43.404 | 52.491 | 1.00 | 24.63 | C |
| ATOM | 1726 | CB | MSEA | | 275 | 122.029 | 42.351 | 53.591 | 1.00 | 25.47 | C |
| ATOM | 1727 | CG | MSEA | | 275 | 122.209 | 40.927 | 53.103 | 1.00 | 27.92 | C |
| ATOM | 1728 | SE | MSEA | | 275 | 121.897 | 39.739 | 54.582 | 1.00 | 35.40 | S |
| ATOM | 1729 | CE | MSEA | | 275 | 119.986 | 40.060 | 54.775 | 1.00 | 36.64 | C |
| ATOM | 1730 | C | MSEA | | 275 | 120.760 | 43.213 | 51.631 | 1.00 | 22.37 | C |
| ATOM | 1731 | O | MSEA | | 275 | 120.824 | 42.609 | 50.566 | 1.00 | 23.17 | O |
| ATOM | 1732 | N | ALA | A | 276 | 119.632 | 43.726 | 52.098 | 1.00 | 19.15 | N |
| ATOM | 1733 | CA | ALA | A | 276 | 118.426 | 43.626 | 51.305 | 1.00 | 19.06 | C |
| ATOM | 1734 | CB | ALA | A | 276 | 117.242 | 44.356 | 52.008 | 1.00 | 17.46 | C |
| ATOM | 1735 | C | ALA | A | 276 | 118.728 | 44.258 | 49.940 | 1.00 | 18.21 | C |
| ATOM | 1736 | O | ALA | A | 276 | 118.487 | 43.650 | 48.904 | 1.00 | 18.72 | O |
| ATOM | 1737 | N | THR | A | 277 | 119.288 | 45.463 | 49.948 | 1.00 | 17.64 | N |
| ATOM | 1738 | CA | THR | A | 277 | 119.627 | 46.170 | 48.713 | 1.00 | 18.09 | C |
| ATOM | 1739 | CB | THR | A | 277 | 120.174 | 47.600 | 49.017 | 1.00 | 18.52 | C |
| ATOM | 1740 | OG1 | THR | A | 277 | 119.106 | 48.390 | 49.564 | 1.00 | 20.68 | O |
| ATOM | 1741 | CG2 | THR | A | 277 | 120.688 | 48.290 | 47.762 | 1.00 | 18.58 | C |
| ATOM | 1742 | C | THR | A | 277 | 120.609 | 45.360 | 47.899 | 1.00 | 17.35 | C |
| ATOM | 1743 | O | THR | A | 277 | 120.360 | 45.119 | 46.737 | 1.00 | 18.00 | O |
| ATOM | 1744 | N | ARG | A | 278 | 121.708 | 44.923 | 48.496 | 1.00 | 16.47 | N |
| ATOM | 1745 | CA | ARG | A | 278 | 122.662 | 44.086 | 47.764 | 1.00 | 17.00 | C |
| ATOM | 1746 | CB | ARG | A | 278 | 123.753 | 43.591 | 48.710 | 1.00 | 17.11 | C |

FIG. 2A-38

| ATOM | 1747 | CG | ARG | A | 278 | 124.275 | 44.650 | 49.648 | 1.00 | 24.34 | C |
|---|---|---|---|---|---|---|---|---|---|---|---|
| ATOM | 1748 | CD | ARG | A | 278 | 125.720 | 44.395 | 49.913 | 1.00 | 34.04 | C |
| ATOM | 1749 | NE | ARG | A | 278 | 126.449 | 44.492 | 48.649 | 1.00 | 47.37 | N |
| ATOM | 1750 | CZ | ARG | A | 278 | 127.765 | 44.304 | 48.513 | 1.00 | 54.40 | C |
| ATOM | 1751 | NH1AR | G | A | 278 | 128.517 | 43.996 | 49.570 | 1.00 | 58.62 | N |
| ATOM | 1752 | NH2AR | G | A | 278 | 128.343 | 44.454 | 47.326 | 1.00 | 53.89 | N |
| ATOM | 1753 | C | ARG | A | 278 | 121.990 | 42.857 | 47.072 | 1.00 | 15.52 | C |
| ATOM | 1754 | O | ARG | A | 278 | 122.351 | 42.464 | 45.984 | 1.00 | 15.18 | O |
| ATOM | 1755 | N | ILE | A | 279 | 121.017 | 42.247 | 47.715 | 1.00 | 15.09 | N |
| ATOM | 1756 | CA | ILE | A | 279 | 120.337 | 41.118 | 47.105 | 1.00 | 14.25 | C |
| ATOM | 1757 | CB | ILE | A | 279 | 119.471 | 40.345 | 48.153 | 1.00 | 14.76 | C |
| ATOM | 1758 | CG1 | ILE | A | 279 | 120.367 | 39.606 | 49.152 | 1.00 | 9.29 | C |
| ATOM | 1759 | CD1 | ILE | A | 279 | 119.685 | 39.310 | 50.432 | 1.00 | 9.93 | C |
| ATOM | 1760 | CG2 | ILE | A | 279 | 118.571 | 39.390 | 47.452 | 1.00 | 11.00 | C |
| ATOM | 1761 | C | ILE | A | 279 | 119.448 | 41.603 | 45.967 | 1.00 | 14.95 | C |
| ATOM | 1762 | O | ILE | A | 279 | 119.436 | 41.013 | 44.900 | 1.00 | 14.45 | O |
| ATOM | 1763 | N | ARG | A | 280 | 118.685 | 42.665 | 46.184 | 1.00 | 14.54 | N |
| ATOM | 1764 | CA | ARG | A | 280 | 117.768 | 43.172 | 45.163 | 1.00 | 16.36 | C |
| ATOM | 1765 | CB | ARG | A | 280 | 117.061 | 44.419 | 45.709 | 1.00 | 16.98 | C |
| ATOM | 1766 | CG | ARG | A | 280 | 115.665 | 44.122 | 46.266 | 1.00 | 23.87 | C |
| ATOM | 1767 | CD | ARG | A | 280 | 114.720 | 45.328 | 46.155 | 1.00 | 34.40 | C |
| ATOM | 1768 | NE | ARG | A | 280 | 113.783 | 45.368 | 47.281 | 1.00 | 43.12 | N |
| ATOM | 1769 | CZ | ARG | A | 280 | 114.181 | 46.017 | 48.388 | 1.00 | 47.75 | C |
| ATOM | 1770 | NH1AR | G | A | 280 | 115.384 | 46.560 | 48.438 | 1.00 | 48.45 | N |
| ATOM | 1771 | NH2AR | G | A | 280 | 113.336 | 46.159 | 49.409 | 1.00 | 48.51 | N |
| ATOM | 1772 | C | ARG | A | 280 | 118.557 | 43.550 | 43.914 | 1.00 | 15.85 | C |
| ATOM | 1773 | O | ARG | A | 280 | 118.257 | 43.157 | 42.795 | 1.00 | 15.60 | O |
| ATOM | 1774 | N | MSEA | | 281 | 119.583 | 44.383 | 44.159 | 1.00 | 17.58 | N |
| ATOM | 1775 | CA | MSEA | | 281 | 120.498 | 44.673 | 43.066 | 1.00 | 20.25 | C |
| ATOM | 1776 | CB | MSEA | | 281 | 121.572 | 45.629 | 43.596 | 1.00 | 18.73 | C |
| ATOM | 1777 | CG | MSEA | | 281 | 120.967 | 46.971 | 43.997 | 1.00 | 16.76 | C |
| ATOM | 1778 | SE | MSEA | | 281 | 120.376 | 47.910 | 42.584 | 1.00 | 24.70 | S |
| ATOM | 1779 | CE | MSEA | | 281 | 121.966 | 48.463 | 41.955 | 1.00 | 17.70 | C |
| ATOM | 1780 | C | MSEA | | 281 | 121.018 | 43.339 | 42.518 | 1.00 | 22.42 | C |
| ATOM | 1781 | O | MSEA | | 281 | 120.881 | 43.026 | 41.344 | 1.00 | 25.11 | O |
| ATOM | 1782 | N | GLY | A | 282 | 121.672 | 42.609 | 43.439 | 1.00 | 22.68 | N |
| ATOM | 1783 | CA | GLY | A | 282 | 122.151 | 41.299 | 43.043 | 1.00 | 22.92 | C |
| ATOM | 1784 | C | GLY | A | 282 | 123.653 | 41.541 | 43.161 | 1.00 | 23.55 | C |
| ATOM | 1785 | O | GLY | A | 282 | 124.438 | 41.222 | 42.277 | 1.00 | 23.01 | O |
| ATOM | 1786 | N | GLN | A | 283 | 124.013 | 42.202 | 44.281 | 1.00 | 24.03 | N |
| ATOM | 1787 | CA | GLN | A | 283 | 125.401 | 42.618 | 44.467 | 1.00 | 23.03 | C |
| ATOM | 1788 | CB | GLN | A | 283 | 125.400 | 43.961 | 45.212 | 1.00 | 23.51 | C |
| ATOM | 1789 | CG | GLN | A | 283 | 124.832 | 45.107 | 44.371 | 1.00 | 29.50 | C |
| ATOM | 1790 | CD | GLN | A | 283 | 124.810 | 46.378 | 45.194 | 1.00 | 37.64 | C |
| ATOM | 1791 | OE1 | GLN | A | 283 | 124.283 | 47.412 | 44.810 | 1.00 | 40.05 | O |
| ATOM | 1792 | NE2 | GLN | A | 283 | 125.446 | 46.270 | 46.376 | 1.00 | 39.79 | N |

FIG. 2A-39

| ATOM | 1793 | C   | GLN | A | 283 | 126.222 | 41.591 | 45.259 | 1.00 | 23.11 | C |
| ATOM | 1794 | O   | GLN | A | 283 | 126.181 | 41.523 | 46.477 | 1.00 | 25.11 | O |
| ATOM | 1795 | N   | TYR | A | 284 | 126.962 | 40.750 | 44.511 | 1.00 | 23.40 | N |
| ATOM | 1796 | CA  | TYR | A | 284 | 127.885 | 39.823 | 45.165 | 1.00 | 22.80 | C |
| ATOM | 1797 | CB  | TYR | A | 284 | 127.143 | 38.522 | 45.478 | 1.00 | 21.90 | C |
| ATOM | 1798 | CG  | TYR | A | 284 | 126.784 | 37.820 | 44.216 | 1.00 | 19.01 | C |
| ATOM | 1799 | CD1 | TYR | A | 284 | 125.666 | 38.226 | 43.494 | 1.00 | 22.55 | C |
| ATOM | 1800 | CE1 | TYR | A | 284 | 125.360 | 37.625 | 42.283 | 1.00 | 25.29 | C |
| ATOM | 1801 | CZ  | TYR | A | 284 | 126.167 | 36.590 | 41.799 | 1.00 | 22.97 | C |
| ATOM | 1802 | OH  | TYR | A | 284 | 125.861 | 36.012 | 40.584 | 1.00 | 28.19 | O |
| ATOM | 1803 | CE2 | TYR | A | 284 | 127.272 | 36.171 | 42.521 | 1.00 | 13.30 | C |
| ATOM | 1804 | CD2 | TYR | A | 284 | 127.581 | 36.780 | 43.729 | 1.00 | 10.34 | C |
| ATOM | 1805 | C   | TYR | A | 284 | 129.105 | 39.549 | 44.286 | 1.00 | 24.22 | C |
| ATOM | 1806 | O   | TYR | A | 284 | 129.261 | 40.089 | 43.199 | 1.00 | 24.25 | O |
| ATOM | 1807 | N   | GLU | A | 285 | 130.020 | 38.710 | 44.807 | 1.00 | 26.24 | N |
| ATOM | 1808 | CA  | GLU | A | 285 | 131.236 | 38.441 | 44.052 | 1.00 | 26.36 | C |
| ATOM | 1809 | CB  | GLU | A | 285 | 132.106 | 39.695 | 44.102 | 1.00 | 27.63 | C |
| ATOM | 1810 | CG  | GLU | A | 285 | 133.155 | 39.619 | 45.206 | 1.00 | 35.64 | C |
| ATOM | 1811 | CD  | GLU | A | 285 | 132.986 | 40.799 | 46.139 | 1.00 | 50.45 | C |
| ATOM | 1812 | OE1 | GLU | A | 285 | 132.256 | 41.721 | 45.801 | 1.00 | 54.26 | O |
| ATOM | 1813 | OE2 | GLU | A | 285 | 133.603 | 40.788 | 47.200 | 1.00 | 55.93 | O |
| ATOM | 1814 | C   | GLU | A | 285 | 132.006 | 37.237 | 44.609 | 1.00 | 26.06 | C |
| ATOM | 1815 | O   | GLU | A | 285 | 131.678 | 36.672 | 45.643 | 1.00 | 27.93 | O |
| ATOM | 1816 | N   | PHE | A | 286 | 133.043 | 36.826 | 43.851 | 1.00 | 25.59 | N |
| ATOM | 1817 | CA  | PHE | A | 286 | 133.846 | 35.681 | 44.275 | 1.00 | 25.76 | C |
| ATOM | 1818 | CB  | PHE | A | 286 | 133.924 | 34.696 | 43.106 | 1.00 | 24.15 | C |
| ATOM | 1819 | CG  | PHE | A | 286 | 132.562 | 34.457 | 42.523 | 1.00 | 23.18 | C |
| ATOM | 1820 | CD1 | PHE | A | 286 | 132.189 | 35.139 | 41.371 | 1.00 | 21.19 | C |
| ATOM | 1821 | CE1 | PHE | A | 286 | 131.061 | 34.744 | 40.671 | 1.00 | 20.63 | C |
| ATOM | 1822 | CZ  | PHE | A | 286 | 130.294 | 33.674 | 41.117 | 1.00 | 20.87 | C |
| ATOM | 1823 | CE2 | PHE | A | 286 | 130.657 | 33.016 | 42.281 | 1.00 | 23.55 | C |
| ATOM | 1824 | CD2 | PHE | A | 286 | 131.788 | 33.406 | 42.993 | 1.00 | 22.98 | C |
| ATOM | 1825 | C   | PHE | A | 286 | 135.259 | 36.103 | 44.678 | 1.00 | 26.91 | C |
| ATOM | 1826 | O   | PHE | A | 286 | 136.235 | 35.828 | 43.992 | 1.00 | 27.43 | O |
| ATOM | 1827 | N   | PRO | A | 287 | 135.404 | 36.810 | 45.808 | 1.00 | 28.39 | N |
| ATOM | 1828 | CA  | PRO | A | 287 | 136.716 | 37.282 | 46.249 | 1.00 | 28.99 | C |
| ATOM | 1829 | CB  | PRO | A | 287 | 136.392 | 37.933 | 47.600 | 1.00 | 28.01 | C |
| ATOM | 1830 | CG  | PRO | A | 287 | 135.253 | 37.153 | 48.080 | 1.00 | 27.80 | C |
| ATOM | 1831 | CD  | PRO | A | 287 | 134.401 | 37.043 | 46.857 | 1.00 | 28.29 | C |
| ATOM | 1832 | C   | PRO | A | 287 | 137.821 | 36.222 | 46.349 | 1.00 | 30.03 | C |
| ATOM | 1833 | O   | PRO | A | 287 | 137.594 | 35.037 | 46.117 | 1.00 | 31.16 | O |
| ATOM | 1834 | N   | ASN | A | 288 | 139.026 | 36.670 | 46.685 | 1.00 | 31.18 | N |
| ATOM | 1835 | CA  | ASN | A | 288 | 140.101 | 35.730 | 46.960 | 1.00 | 32.27 | C |
| ATOM | 1836 | CB  | ASN | A | 288 | 141.331 | 36.174 | 46.172 | 1.00 | 32.42 | C |
| ATOM | 1837 | CG  | ASN | A | 288 | 141.160 | 35.779 | 44.728 | 1.00 | 34.48 | C |
| ATOM | 1838 | OD1 | ASN | A | 288 | 141.289 | 36.587 | 43.812 | 1.00 | 33.42 | O |

FIG. 2A-40

| | | | | | | | | | | |
|---|---|---|---|---|---|---|---|---|---|---|
| ATOM | 1839 | ND2 | ASN | A | 288 | 140.837 | 34.491 | 44.529 | 1.00 | 37.33 | N |
| ATOM | 1840 | C | ASN | A | 288 | 140.417 | 35.660 | 48.456 | 1.00 | 32.53 | C |
| ATOM | 1841 | O | ASN | A | 288 | 140.015 | 36.499 | 49.253 | 1.00 | 34.43 | O |
| ATOM | 1842 | N | PRO | A | 289 | 141.127 | 34.584 | 48.833 | 1.00 | 31.69 | N |
| ATOM | 1843 | CA | PRO | A | 289 | 141.563 | 33.571 | 47.886 | 1.00 | 31.11 | C |
| ATOM | 1844 | CB | PRO | A | 289 | 142.837 | 32.965 | 48.465 | 1.00 | 31.76 | C |
| ATOM | 1845 | CG | PRO | A | 289 | 142.829 | 33.210 | 49.977 | 1.00 | 31.46 | C |
| ATOM | 1846 | CD | PRO | A | 289 | 141.605 | 34.237 | 50.158 | 1.00 | 31.81 | C |
| ATOM | 1847 | C | PRO | A | 289 | 140.515 | 32.469 | 47.692 | 1.00 | 31.35 | C |
| ATOM | 1848 | O | PRO | A | 289 | 140.639 | 31.595 | 46.844 | 1.00 | 32.36 | O |
| ATOM | 1849 | N | GLU | A | 290 | 139.476 | 32.515 | 48.547 | 1.00 | 30.10 | N |
| ATOM | 1850 | CA | GLU | A | 290 | 138.470 | 31.459 | 48.537 | 1.00 | 28.53 | C |
| ATOM | 1851 | CB | GLU | A | 290 | 137.186 | 32.027 | 49.145 | 1.00 | 29.66 | C |
| ATOM | 1852 | CG | GLU | A | 290 | 137.158 | 31.908 | 50.667 | 1.00 | 30.44 | C |
| ATOM | 1853 | CD | GLU | A | 290 | 138.359 | 32.616 | 51.248 | 1.00 | 28.98 | C |
| ATOM | 1854 | OE1 | GLU | A | 290 | 138.481 | 33.816 | 51.051 | 1.00 | 23.00 | O |
| ATOM | 1855 | OE2 | GLU | A | 290 | 139.170 | 31.955 | 51.896 | 1.00 | 28.35 | O |
| ATOM | 1856 | C | GLU | A | 290 | 138.186 | 30.907 | 47.135 | 1.00 | 27.79 | C |
| ATOM | 1857 | O | GLU | A | 290 | 138.098 | 29.705 | 46.915 | 1.00 | 28.62 | O |
| ATOM | 1858 | N | TRP | A | 291 | 137.997 | 31.833 | 46.178 | 1.00 | 25.62 | N |
| ATOM | 1859 | CA | TRP | A | 291 | 137.556 | 31.414 | 44.853 | 1.00 | 25.12 | C |
| ATOM | 1860 | CB | TRP | A | 291 | 136.568 | 32.459 | 44.336 | 1.00 | 24.82 | C |
| ATOM | 1861 | CG | TRP | A | 291 | 135.307 | 32.384 | 45.108 | 1.00 | 23.56 | C |
| ATOM | 1862 | CD1 | TRP | A | 291 | 134.983 | 33.113 | 46.271 | 1.00 | 20.32 | C |
| ATOM | 1863 | NE1 | TRP | A | 291 | 133.775 | 32.765 | 46.784 | 1.00 | 23.69 | N |
| ATOM | 1864 | CE2 | TRP | A | 291 | 133.247 | 31.709 | 45.886 | 1.00 | 23.01 | C |
| ATOM | 1865 | CD2 | TRP | A | 291 | 134.199 | 31.487 | 44.861 | 1.00 | 21.46 | C |
| ATOM | 1866 | CE3 | TRP | A | 291 | 133.943 | 30.527 | 43.884 | 1.00 | 18.51 | C |
| ATOM | 1867 | CZ3 | TRP | A | 291 | 132.764 | 29.803 | 43.900 | 1.00 | 20.10 | C |
| ATOM | 1868 | CH2 | TRP | A | 291 | 131.821 | 30.033 | 44.917 | 1.00 | 22.17 | C |
| ATOM | 1869 | CZ2 | TRP | A | 291 | 132.067 | 30.986 | 45.901 | 1.00 | 20.99 | C |
| ATOM | 1870 | C | TRP | A | 291 | 138.718 | 31.254 | 43.870 | 1.00 | 25.10 | C |
| ATOM | 1871 | O | TRP | A | 291 | 138.537 | 30.934 | 42.702 | 1.00 | 25.17 | O |
| ATOM | 1872 | N | SER | A | 292 | 139.933 | 31.490 | 44.321 | 1.00 | 25.49 | N |
| ATOM | 1873 | CA | SER | A | 292 | 141.101 | 31.460 | 43.448 | 1.00 | 26.33 | C |
| ATOM | 1874 | CB | SER | A | 292 | 142.349 | 31.495 | 44.316 | 1.00 | 25.71 | C |
| ATOM | 1875 | OG | SER | A | 292 | 142.247 | 32.599 | 45.203 | 1.00 | 26.15 | O |
| ATOM | 1876 | C | SER | A | 292 | 141.205 | 30.351 | 42.407 | 1.00 | 25.96 | C |
| ATOM | 1877 | O | SER | A | 292 | 141.433 | 30.620 | 41.248 | 1.00 | 25.12 | O |
| ATOM | 1878 | N | GLU | A | 293 | 141.025 | 29.109 | 42.803 | 1.00 | 26.41 | N |
| ATOM | 1879 | CA | GLU | A | 293 | 141.146 | 28.043 | 41.826 | 1.00 | 27.95 | C |
| ATOM | 1880 | CB | GLU | A | 293 | 142.008 | 26.908 | 42.362 | 1.00 | 29.25 | C |
| ATOM | 1881 | CG | GLU | A | 293 | 143.451 | 27.242 | 42.643 | 1.00 | 36.44 | C |
| ATOM | 1882 | CD | GLU | A | 293 | 144.001 | 26.228 | 43.590 | 1.00 | 44.56 | C |
| ATOM | 1883 | OE1 | GLU | A | 293 | 144.179 | 25.056 | 43.176 | 1.00 | 45.78 | O |
| ATOM | 1884 | OE2 | GLU | A | 293 | 144.210 | 26.591 | 44.770 | 1.00 | 49.83 | O |

FIG. 2A-41

| | | | | | | | | | | | |
|---|---|---|---|---|---|---|---|---|---|---|---|
| ATOM | 1885 | C | GLU | A | 293 | 139.827 | 27.452 | 41.406 | 1.00 | 27.74 | C |
| ATOM | 1886 | O | GLU | A | 293 | 139.805 | 26.423 | 40.727 | 1.00 | 28.49 | O |
| ATOM | 1887 | N | VAL | A | 294 | 138.730 | 28.076 | 41.829 | 1.00 | 26.83 | N |
| ATOM | 1888 | CA | VAL | A | 294 | 137.415 | 27.590 | 41.458 | 1.00 | 25.58 | C |
| ATOM | 1889 | CB | VAL | A | 294 | 136.326 | 28.286 | 42.265 | 1.00 | 26.06 | C |
| ATOM | 1890 | CG1 | VAL | A | 294 | 134.988 | 27.574 | 42.035 | 1.00 | 26.14 | C |
| ATOM | 1891 | CG2 | VAL | A | 294 | 136.708 | 28.277 | 43.738 | 1.00 | 25.14 | C |
| ATOM | 1892 | C | VAL | A | 294 | 137.255 | 27.916 | 39.988 | 1.00 | 24.91 | C |
| ATOM | 1893 | O | VAL | A | 294 | 137.601 | 29.002 | 39.552 | 1.00 | 24.37 | O |
| ATOM | 1894 | N | SER | A | 295 | 136.733 | 26.970 | 39.226 | 1.00 | 25.36 | N |
| ATOM | 1895 | CA | SER | A | 295 | 136.580 | 27.171 | 37.798 | 1.00 | 26.21 | C |
| ATOM | 1896 | CB | SER | A | 295 | 136.271 | 25.850 | 37.110 | 1.00 | 26.35 | C |
| ATOM | 1897 | OG | SER | A | 295 | 134.972 | 25.402 | 37.430 | 1.00 | 28.21 | O |
| ATOM | 1898 | C | SER | A | 295 | 135.535 | 28.180 | 37.375 | 1.00 | 27.50 | C |
| ATOM | 1899 | O | SER | A | 295 | 134.511 | 28.360 | 38.030 | 1.00 | 27.80 | O |
| ATOM | 1900 | N | GLU | A | 296 | 135.816 | 28.828 | 36.252 | 1.00 | 28.55 | N |
| ATOM | 1901 | CA | GLU | A | 296 | 134.915 | 29.805 | 35.668 | 1.00 | 29.64 | C |
| ATOM | 1902 | CB | GLU | A | 296 | 135.480 | 30.292 | 34.332 | 1.00 | 30.44 | C |
| ATOM | 1903 | CG | GLU | A | 296 | 134.706 | 31.423 | 33.667 | 1.00 | 38.18 | C |
| ATOM | 1904 | CD | GLU | A | 296 | 134.750 | 32.709 | 34.466 | 1.00 | 46.74 | C |
| ATOM | 1905 | OE1 | GLU | A | 296 | 135.704 | 32.881 | 35.258 | 1.00 | 52.48 | O |
| ATOM | 1906 | OE2 | GLU | A | 296 | 133.843 | 33.557 | 34.294 | 1.00 | 49.10 | O |
| ATOM | 1907 | C | GLU | A | 296 | 133.620 | 29.034 | 35.447 | 1.00 | 28.74 | C |
| ATOM | 1908 | O | GLU | A | 296 | 132.523 | 29.564 | 35.653 | 1.00 | 31.12 | O |
| ATOM | 1909 | N | GLU | A | 297 | 133.764 | 27.773 | 35.038 | 1.00 | 26.61 | N |
| ATOM | 1910 | CA | GLU | A | 297 | 132.612 | 26.919 | 34.812 | 1.00 | 24.90 | C |
| ATOM | 1911 | CB | GLU | A | 297 | 133.060 | 25.498 | 34.514 | 1.00 | 24.89 | C |
| ATOM | 1912 | CG | GLU | A | 297 | 132.044 | 24.473 | 34.878 | 1.00 | 27.80 | C |
| ATOM | 1913 | CD | GLU | A | 297 | 132.018 | 23.306 | 33.922 | 1.00 | 31.75 | C |
| ATOM | 1914 | OE1 | GLU | A | 297 | 131.429 | 23.457 | 32.828 | 1.00 | 34.82 | O |
| ATOM | 1915 | OE2 | GLU | A | 297 | 132.588 | 22.241 | 34.257 | 1.00 | 32.11 | O |
| ATOM | 1916 | C | GLU | A | 297 | 131.685 | 26.922 | 36.033 | 1.00 | 24.40 | C |
| ATOM | 1917 | O | GLU | A | 297 | 130.475 | 27.153 | 35.917 | 1.00 | 24.32 | O |
| ATOM | 1918 | N | VAL | A | 298 | 132.244 | 26.675 | 37.204 | 1.00 | 22.49 | N |
| ATOM | 1919 | CA | VAL | A | 298 | 131.427 | 26.669 | 38.376 | 1.00 | 22.01 | C |
| ATOM | 1920 | CB | VAL | A | 298 | 132.225 | 26.270 | 39.632 | 1.00 | 21.55 | C |
| ATOM | 1921 | CG1 | VAL | A | 298 | 131.280 | 26.113 | 40.833 | 1.00 | 17.80 | C |
| ATOM | 1922 | CG2 | VAL | A | 298 | 132.955 | 24.968 | 39.374 | 1.00 | 23.91 | C |
| ATOM | 1923 | C | VAL | A | 298 | 130.833 | 28.047 | 38.591 | 1.00 | 22.20 | C |
| ATOM | 1924 | O | VAL | A | 298 | 129.616 | 28.171 | 38.693 | 1.00 | 22.53 | O |
| ATOM | 1925 | N | ALA | A | 299 | 131.679 | 29.073 | 38.653 | 1.00 | 22.07 | N |
| ATOM | 1926 | CA | ALA | A | 299 | 131.213 | 30.439 | 38.906 | 1.00 | 22.85 | C |
| ATOM | 1927 | CB | ALA | A | 299 | 132.401 | 31.400 | 38.886 | 1.00 | 21.04 | C |
| ATOM | 1928 | C | ALA | A | 299 | 130.106 | 30.921 | 37.957 | 1.00 | 23.77 | C |
| ATOM | 1929 | O | ALA | A | 299 | 129.218 | 31.677 | 38.331 | 1.00 | 24.34 | O |
| ATOM | 1930 | N | MSE | A | 300 | 130.145 | 30.438 | 36.731 | 1.00 | 25.14 | N |

FIG. 2A-42

| ATOM | 1931 | CA | MSEA |   | 300 | 129.143 | 30.808 | 35.756 | 1.00 | 28.53 | C |
| --- | --- | --- | --- | --- | --- | --- | --- | --- | --- | --- | --- |
| ATOM | 1932 | CB | MSEA |   | 300 | 129.561 | 30.343 | 34.377 | 1.00 | 31.17 | C |
| ATOM | 1933 | CG | MSEA |   | 300 | 128.781 | 31.001 | 33.258 | 1.00 | 42.25 | C |
| ATOM | 1934 | SE | MSEA |   | 300 | 128.782 | 32.934 | 33.431 | 1.00 | 61.79 | S |
| ATOM | 1935 | CE | MSEA |   | 300 | 126.850 | 33.105 | 33.666 | 1.00 | 43.85 | C |
| ATOM | 1936 | C | MSEA |   | 300 | 127.836 | 30.171 | 36.120 | 1.00 | 27.73 | C |
| ATOM | 1937 | O | MSEA |   | 300 | 126.783 | 30.730 | 35.833 | 1.00 | 30.18 | O |
| ATOM | 1938 | N | LEU | A | 301 | 127.912 | 28.993 | 36.742 | 1.00 | 26.38 | N |
| ATOM | 1939 | CA | LEU | A | 301 | 126.731 | 28.252 | 37.183 | 1.00 | 24.65 | C |
| ATOM | 1940 | CB | LEU | A | 301 | 127.104 | 26.834 | 37.598 | 1.00 | 23.00 | C |
| ATOM | 1941 | CG | LEU | A | 301 | 125.934 | 25.942 | 38.030 | 1.00 | 24.25 | C |
| ATOM | 1942 | CD1 | LEU | A | 301 | 124.937 | 25.762 | 36.919 | 1.00 | 30.34 | C |
| ATOM | 1943 | CD2 | LEU | A | 301 | 126.481 | 24.615 | 38.462 | 1.00 | 25.01 | C |
| ATOM | 1944 | C | LEU | A | 301 | 126.059 | 28.984 | 38.349 | 1.00 | 24.59 | C |
| ATOM | 1945 | O | LEU | A | 301 | 124.835 | 29.054 | 38.444 | 1.00 | 26.13 | O |
| ATOM | 1946 | N | ILE | A | 302 | 126.859 | 29.527 | 39.244 | 1.00 | 23.39 | N |
| ATOM | 1947 | CA | ILE | A | 302 | 126.310 | 30.278 | 40.334 | 1.00 | 23.14 | C |
| ATOM | 1948 | CB | ILE | A | 302 | 127.389 | 30.581 | 41.352 | 1.00 | 22.73 | C |
| ATOM | 1949 | CG1 | ILE | A | 302 | 127.774 | 29.279 | 42.038 | 1.00 | 23.38 | C |
| ATOM | 1950 | CD1 | ILE | A | 302 | 128.871 | 29.472 | 43.076 | 1.00 | 21.84 | C |
| ATOM | 1951 | CG2 | ILE | A | 302 | 126.938 | 31.693 | 42.331 | 1.00 | 18.89 | C |
| ATOM | 1952 | C | ILE | A | 302 | 125.740 | 31.576 | 39.748 | 1.00 | 24.32 | C |
| ATOM | 1953 | O | ILE | A | 302 | 124.702 | 32.067 | 40.203 | 1.00 | 24.22 | O |
| ATOM | 1954 | N | ARG | A | 303 | 126.410 | 32.127 | 38.732 | 1.00 | 24.85 | N |
| ATOM | 1955 | CA | ARG | A | 303 | 125.936 | 33.365 | 38.107 | 1.00 | 26.11 | C |
| ATOM | 1956 | CB | ARG | A | 303 | 126.890 | 33.831 | 36.978 | 1.00 | 25.40 | C |
| ATOM | 1957 | CG | ARG | A | 303 | 128.164 | 34.599 | 37.421 | 1.00 | 31.73 | C |
| ATOM | 1958 | CD | ARG | A | 303 | 128.071 | 36.165 | 37.404 | 1.00 | 44.67 | C |
| ATOM | 1959 | NE | ARG | A | 303 | 128.809 | 36.785 | 38.526 | 1.00 | 53.65 | N |
| ATOM | 1960 | CZ | ARG | A | 303 | 128.589 | 38.011 | 39.039 | 1.00 | 51.90 | C |
| ATOM | 1961 | NH1AR | G | A | 303 | 127.650 | 38.806 | 38.539 | 1.00 | 52.31 | N |
| ATOM | 1962 | NH2AR | G | A | 303 | 129.282 | 38.436 | 40.089 | 1.00 | 44.68 | N |
| ATOM | 1963 | C | ARG | A | 303 | 124.534 | 33.119 | 37.539 | 1.00 | 26.31 | C |
| ATOM | 1964 | O | ARG | A | 303 | 123.669 | 34.001 | 37.548 | 1.00 | 25.44 | O |
| ATOM | 1965 | N | ASN | A | 304 | 124.290 | 31.913 | 37.056 | 1.00 | 26.94 | N |
| ATOM | 1966 | CA | ASN | A | 304 | 122.999 | 31.683 | 36.481 | 1.00 | 29.95 | C |
| ATOM | 1967 | CB | ASN | A | 304 | 123.113 | 30.744 | 35.303 | 1.00 | 30.95 | C |
| ATOM | 1968 | CG | ASN | A | 304 | 122.601 | 31.389 | 34.048 | 1.00 | 42.78 | C |
| ATOM | 1969 | OD1 | ASN | A | 304 | 123.343 | 32.120 | 33.366 | 1.00 | 46.52 | O |
| ATOM | 1970 | ND2 | ASN | A | 304 | 121.303 | 31.175 | 33.749 | 1.00 | 48.26 | N |
| ATOM | 1971 | C | ASN | A | 304 | 121.888 | 31.208 | 37.392 | 1.00 | 28.87 | C |
| ATOM | 1972 | O | ASN | A | 304 | 120.748 | 31.041 | 36.940 | 1.00 | 31.75 | O |
| ATOM | 1973 | N | LEU | A | 305 | 122.221 | 30.970 | 38.657 | 1.00 | 25.85 | N |
| ATOM | 1974 | CA | LEU | A | 305 | 121.254 | 30.536 | 39.639 | 1.00 | 23.76 | C |
| ATOM | 1975 | CB | LEU | A | 305 | 121.851 | 29.492 | 40.571 | 1.00 | 24.67 | C |
| ATOM | 1976 | CG | LEU | A | 305 | 121.901 | 28.089 | 40.004 | 1.00 | 20.78 | C |

FIG. 2A-43

| ATOM | 1977 | CD1 | LEU | A | 305 | 122.743 | 27.168 | 40.892 | 1.00 | 16.89 | C |
| --- | --- | --- | --- | --- | --- | --- | --- | --- | --- | --- | --- |
| ATOM | 1978 | CD2 | LEU | A | 305 | 120.471 | 27.606 | 39.841 | 1.00 | 26.69 | C |
| ATOM | 1979 | C | LEU | A | 305 | 120.920 | 31.757 | 40.452 | 1.00 | 23.07 | C |
| ATOM | 1980 | O | LEU | A | 305 | 119.772 | 31.956 | 40.844 | 1.00 | 25.04 | O |
| ATOM | 1981 | N | LEU | A | 306 | 121.935 | 32.579 | 40.705 | 1.00 | 21.42 | N |
| ATOM | 1982 | CA | LEU | A | 306 | 121.747 | 33.765 | 41.489 | 1.00 | 21.14 | C |
| ATOM | 1983 | CB | LEU | A | 306 | 123.008 | 34.092 | 42.251 | 1.00 | 20.21 | C |
| ATOM | 1984 | CG | LEU | A | 306 | 123.389 | 33.234 | 43.460 | 1.00 | 21.16 | C |
| ATOM | 1985 | CD1 | LEU | A | 306 | 124.669 | 33.762 | 44.084 | 1.00 | 14.68 | C |
| ATOM | 1986 | CD2 | LEU | A | 306 | 122.280 | 33.316 | 44.476 | 1.00 | 20.42 | C |
| ATOM | 1987 | C | LEU | A | 306 | 121.294 | 34.986 | 40.726 | 1.00 | 22.97 | C |
| ATOM | 1988 | O | LEU | A | 306 | 121.538 | 36.100 | 41.179 | 1.00 | 25.22 | O |
| ATOM | 1989 | N | LYS | A | 307 | 120.606 | 34.825 | 39.600 | 1.00 | 22.66 | N |
| ATOM | 1990 | CA | LYS | A | 307 | 120.167 | 36.013 | 38.869 | 1.00 | 21.68 | C |
| ATOM | 1991 | CB | LYS | A | 307 | 119.936 | 35.617 | 37.410 | 1.00 | 21.98 | C |
| ATOM | 1992 | CG | LYS | A | 307 | 121.237 | 35.631 | 36.608 | 1.00 | 25.46 | C |
| ATOM | 1993 | CD | LYS | A | 307 | 120.998 | 35.754 | 35.101 | 1.00 | 29.75 | C |
| ATOM | 1994 | CE | LYS | A | 307 | 121.724 | 36.957 | 34.482 | 1.00 | 36.42 | C |
| ATOM | 1995 | NZ | LYS | A | 307 | 123.167 | 36.814 | 34.669 | 1.00 | 39.65 | N |
| ATOM | 1996 | C | LYS | A | 307 | 118.895 | 36.620 | 39.477 | 1.00 | 21.95 | C |
| ATOM | 1997 | O | LYS | A | 307 | 117.941 | 35.934 | 39.801 | 1.00 | 25.30 | O |
| ATOM | 1998 | N | THR | A | 308 | 118.935 | 37.959 | 39.651 | 1.00 | 21.76 | N |
| ATOM | 1999 | CA | THR | A | 308 | 117.846 | 38.665 | 40.335 | 1.00 | 21.80 | C |
| ATOM | 2000 | CB | THR | A | 308 | 118.138 | 40.167 | 40.273 | 1.00 | 20.75 | C |
| ATOM | 2001 | OG1 | THR | A | 308 | 119.238 | 40.471 | 41.129 | 1.00 | 21.02 | O |
| ATOM | 2002 | CG2 | THR | A | 308 | 116.904 | 40.946 | 40.748 | 1.00 | 31.64 | C |
| ATOM | 2003 | C | THR | A | 308 | 116.489 | 38.413 | 39.690 | 1.00 | 21.24 | C |
| ATOM | 2004 | O | THR | A | 308 | 115.466 | 38.285 | 40.351 | 1.00 | 22.09 | O |
| ATOM | 2005 | N | GLU | A | 309 | 116.496 | 38.413 | 38.342 | 1.00 | 20.81 | N |
| ATOM | 2006 | CA | GLU | A | 309 | 115.245 | 38.300 | 37.600 | 1.00 | 20.46 | C |
| ATOM | 2007 | CB | GLU | A | 309 | 115.512 | 38.740 | 36.165 | 1.00 | 19.87 | C |
| ATOM | 2008 | CG | GLU | A | 309 | 114.264 | 38.673 | 35.283 | 1.00 | 23.65 | C |
| ATOM | 2009 | CD | GLU | A | 309 | 113.027 | 38.932 | 36.117 | 1.00 | 26.75 | C |
| ATOM | 2010 | OE1 | GLU | A | 309 | 112.844 | 40.055 | 36.573 | 1.00 | 25.16 | O |
| ATOM | 2011 | OE2 | GLU | A | 309 | 112.229 | 38.008 | 36.268 | 1.00 | 17.02 | O |
| ATOM | 2012 | C | GLU | A | 309 | 114.726 | 36.866 | 37.606 | 1.00 | 19.35 | C |
| ATOM | 2013 | O | GLU | A | 309 | 114.993 | 36.069 | 36.719 | 1.00 | 18.31 | O |
| ATOM | 2014 | N | PRO | A | 310 | 113.850 | 36.459 | 38.531 | 1.00 | 19.69 | N |
| ATOM | 2015 | CA | PRO | A | 310 | 113.349 | 35.072 | 38.465 | 1.00 | 19.88 | C |
| ATOM | 2016 | CB | PRO | A | 310 | 111.916 | 35.190 | 38.991 | 1.00 | 19.15 | C |
| ATOM | 2017 | CG | PRO | A | 310 | 111.996 | 36.327 | 39.923 | 1.00 | 18.62 | C |
| ATOM | 2018 | CD | PRO | A | 310 | 112.880 | 37.327 | 39.224 | 1.00 | 19.33 | C |
| ATOM | 2019 | C | PRO | A | 310 | 113.426 | 34.389 | 37.088 | 1.00 | 21.02 | C |
| ATOM | 2020 | O | PRO | A | 310 | 114.160 | 33.435 | 36.898 | 1.00 | 18.74 | O |
| ATOM | 2021 | N | THR | A | 311 | 112.710 | 34.912 | 36.106 | 1.00 | 22.98 | N |
| ATOM | 2022 | CA | THR | A | 311 | 112.699 | 34.274 | 34.796 | 1.00 | 24.07 | C |

FIG. 2A-44

| | | | | | | | | | | |
|---|---|---|---|---|---|---|---|---|---|---|
| ATOM | 2023 | CB | THR | A | 311 | 111.708 | 34.963 | 33.886 | 1.00 | 24.17 | C |
| ATOM | 2024 | OG1 | THR | A | 311 | 111.973 | 36.363 | 33.878 | 1.00 | 23.78 | O |
| ATOM | 2025 | CG2 | THR | A | 311 | 110.307 | 34.732 | 34.400 | 1.00 | 25.88 | C |
| ATOM | 2026 | C | THR | A | 311 | 114.040 | 34.073 | 34.070 | 1.00 | 25.17 | C |
| ATOM | 2027 | O | THR | A | 311 | 114.153 | 33.213 | 33.192 | 1.00 | 26.62 | O |
| ATOM | 2028 | N | GLN | A | 312 | 115.059 | 34.837 | 34.415 | 1.00 | 24.14 | N |
| ATOM | 2029 | CA | GLN | A | 312 | 116.334 | 34.613 | 33.776 | 1.00 | 22.70 | C |
| ATOM | 2030 | CB | GLN | A | 312 | 117.267 | 35.820 | 33.925 | 1.00 | 20.76 | C |
| ATOM | 2031 | CG | GLN | A | 312 | 117.064 | 36.958 | 32.949 | 1.00 | 24.70 | C |
| ATOM | 2032 | CD | GLN | A | 312 | 118.103 | 38.075 | 33.139 | 1.00 | 31.99 | C |
| ATOM | 2033 | OE1 | GLN | A | 312 | 119.309 | 37.825 | 33.079 | 1.00 | 36.29 | O |
| ATOM | 2034 | NE2 | GLN | A | 312 | 117.641 | 39.306 | 33.374 | 1.00 | 32.98 | N |
| ATOM | 2035 | C | GLN | A | 312 | 116.988 | 33.420 | 34.473 | 1.00 | 21.56 | C |
| ATOM | 2036 | O | GLN | A | 312 | 117.986 | 32.885 | 33.974 | 1.00 | 21.97 | O |
| ATOM | 2037 | N | ARG | A | 313 | 116.445 | 32.988 | 35.614 | 1.00 | 21.66 | N |
| ATOM | 2038 | CA | ARG | A | 313 | 117.079 | 31.904 | 36.384 | 1.00 | 21.12 | C |
| ATOM | 2039 | CB | ARG | A | 313 | 116.546 | 31.922 | 37.782 | 1.00 | 21.46 | C |
| ATOM | 2040 | CG | ARG | A | 313 | 117.593 | 31.915 | 38.826 | 1.00 | 21.28 | C |
| ATOM | 2041 | CD | ARG | A | 313 | 116.959 | 32.155 | 40.159 | 1.00 | 18.87 | C |
| ATOM | 2042 | NE | ARG | A | 313 | 116.588 | 33.547 | 40.382 | 1.00 | 20.37 | N |
| ATOM | 2043 | CZ | ARG | A | 313 | 115.692 | 33.934 | 41.280 | 1.00 | 18.59 | C |
| ATOM | 2044 | NH1AR | G | A | 313 | 115.077 | 33.029 | 42.013 | 1.00 | 22.60 | N |
| ATOM | 2045 | NH2AR | G | A | 313 | 115.441 | 35.211 | 41.470 | 1.00 | 19.66 | N |
| ATOM | 2046 | C | ARG | A | 313 | 116.986 | 30.514 | 35.816 | 1.00 | 21.61 | C |
| ATOM | 2047 | O | ARG | A | 313 | 116.009 | 30.163 | 35.204 | 1.00 | 25.24 | O |
| ATOM | 2048 | N | MSE | A | 314 | 118.018 | 29.718 | 36.012 | 1.00 | 22.66 | N |
| ATOM | 2049 | CA | MSE | A | 314 | 118.089 | 28.348 | 35.481 | 1.00 | 23.64 | C |
| ATOM | 2050 | CB | MSE | A | 314 | 119.519 | 27.839 | 35.691 | 1.00 | 24.65 | C |
| ATOM | 2051 | CG | MSE | A | 314 | 119.850 | 26.446 | 35.136 | 1.00 | 33.63 | C |
| ATOM | 2052 | SE | MSE | A | 314 | 121.682 | 25.966 | 35.629 | 1.00 | 41.76 | S |
| ATOM | 2053 | CE | MSE | A | 314 | 121.841 | 27.166 | 37.068 | 1.00 | 38.05 | C |
| ATOM | 2054 | C | MSE | A | 314 | 117.079 | 27.369 | 36.115 | 1.00 | 22.51 | C |
| ATOM | 2055 | O | MSE | A | 314 | 116.902 | 27.327 | 37.338 | 1.00 | 25.02 | O |
| ATOM | 2056 | N | THR | A | 315 | 116.420 | 26.568 | 35.298 | 1.00 | 21.26 | N |
| ATOM | 2057 | CA | THR | A | 315 | 115.449 | 25.622 | 35.819 | 1.00 | 19.58 | C |
| ATOM | 2058 | CB | THR | A | 315 | 114.579 | 25.101 | 34.746 | 1.00 | 18.89 | C |
| ATOM | 2059 | OG1 | THR | A | 315 | 115.347 | 24.211 | 33.922 | 1.00 | 17.18 | O |
| ATOM | 2060 | CG2 | THR | A | 315 | 113.996 | 26.243 | 33.964 | 1.00 | 14.53 | C |
| ATOM | 2061 | C | THR | A | 315 | 116.149 | 24.423 | 36.429 | 1.00 | 19.30 | C |
| ATOM | 2062 | O | THR | A | 315 | 117.338 | 24.240 | 36.215 | 1.00 | 19.17 | O |
| ATOM | 2063 | N | ILE | A | 316 | 115.409 | 23.594 | 37.170 | 1.00 | 19.01 | N |
| ATOM | 2064 | CA | ILE | A | 316 | 116.026 | 22.448 | 37.805 | 1.00 | 18.97 | C |
| ATOM | 2065 | CB | ILE | A | 316 | 115.123 | 21.847 | 38.934 | 1.00 | 17.12 | C |
| ATOM | 2066 | CG1 | ILE | A | 316 | 115.966 | 20.919 | 39.809 | 1.00 | 16.98 | C |
| ATOM | 2067 | CD1 | ILE | A | 316 | 117.078 | 21.636 | 40.537 | 1.00 | 15.94 | C |
| ATOM | 2068 | CG2 | ILE | A | 316 | 113.979 | 21.069 | 38.387 | 1.00 | 13.24 | C |

FIG. 2A-45

| | | | | | | | | | | |
|---|---|---|---|---|---|---|---|---|---|---|
| ATOM | 2069 | C | ILE | A | 316 | 116.486 | 21.363 | 36.811 | 1.00 | 22.24 | C |
| ATOM | 2070 | O | ILE | A | 316 | 117.406 | 20.577 | 37.116 | 1.00 | 22.49 | O |
| ATOM | 2071 | N | THR | A | 317 | 115.897 | 21.329 | 35.618 | 1.00 | 23.79 | N |
| ATOM | 2072 | CA | THR | A | 317 | 116.320 | 20.343 | 34.630 | 1.00 | 23.58 | C |
| ATOM | 2073 | CB | THR | A | 317 | 115.283 | 20.153 | 33.536 | 1.00 | 22.70 | C |
| ATOM | 2074 | OG1 | THR | A | 317 | 114.101 | 19.581 | 34.116 | 1.00 | 26.44 | O |
| ATOM | 2075 | CG2 | THR | A | 317 | 115.807 | 19.226 | 32.474 | 1.00 | 17.42 | C |
| ATOM | 2076 | C | THR | A | 317 | 117.628 | 20.799 | 34.012 | 1.00 | 24.56 | C |
| ATOM | 2077 | O | THR | A | 317 | 118.503 | 19.992 | 33.690 | 1.00 | 24.35 | O |
| ATOM | 2078 | N | GLU | A | 318 | 117.761 | 22.106 | 33.850 | 1.00 | 25.45 | N |
| ATOM | 2079 | CA | GLU | A | 318 | 118.984 | 22.665 | 33.314 | 1.00 | 27.15 | C |
| ATOM | 2080 | CB | GLU | A | 318 | 118.803 | 24.164 | 33.076 | 1.00 | 28.75 | C |
| ATOM | 2081 | CG | GLU | A | 318 | 118.053 | 24.469 | 31.778 | 1.00 | 29.69 | C |
| ATOM | 2082 | CD | GLU | A | 318 | 117.379 | 25.826 | 31.781 | 1.00 | 35.60 | C |
| ATOM | 2083 | OE1 | GLU | A | 318 | 117.116 | 26.346 | 30.676 | 1.00 | 36.11 | O |
| ATOM | 2084 | OE2 | GLU | A | 318 | 117.096 | 26.365 | 32.872 | 1.00 | 38.58 | O |
| ATOM | 2085 | C | GLU | A | 318 | 120.066 | 22.408 | 34.336 | 1.00 | 26.31 | C |
| ATOM | 2086 | O | GLU | A | 318 | 121.141 | 21.941 | 34.026 | 1.00 | 26.30 | O |
| ATOM | 2087 | N | PHE | A | 319 | 119.763 | 22.700 | 35.576 | 1.00 | 26.62 | N |
| ATOM | 2088 | CA | PHE | A | 319 | 120.719 | 22.457 | 36.638 | 1.00 | 25.80 | C |
| ATOM | 2089 | CB | PHE | A | 319 | 120.070 | 22.734 | 37.994 | 1.00 | 26.67 | C |
| ATOM | 2090 | CG | PHE | A | 319 | 121.005 | 22.569 | 39.150 | 1.00 | 26.61 | C |
| ATOM | 2091 | CD1 | PHE | A | 319 | 121.801 | 23.613 | 39.559 | 1.00 | 28.67 | C |
| ATOM | 2092 | CE1 | PHE | A | 319 | 122.662 | 23.454 | 40.626 | 1.00 | 26.11 | C |
| ATOM | 2093 | CZ | PHE | A | 319 | 122.724 | 22.254 | 41.279 | 1.00 | 20.29 | C |
| ATOM | 2094 | CE2 | PHE | A | 319 | 121.935 | 21.206 | 40.873 | 1.00 | 19.69 | C |
| ATOM | 2095 | CD2 | PHE | A | 319 | 121.088 | 21.359 | 39.826 | 1.00 | 25.79 | C |
| ATOM | 2096 | C | PHE | A | 319 | 121.216 | 21.003 | 36.625 | 1.00 | 24.69 | C |
| ATOM | 2097 | O | PHE | A | 319 | 122.426 | 20.739 | 36.634 | 1.00 | 23.68 | O |
| ATOM | 2098 | N | MSE | A | 320 | 120.277 | 20.059 | 36.620 | 1.00 | 23.73 | N |
| ATOM | 2099 | CA | MSE | A | 320 | 120.658 | 18.660 | 36.654 | 1.00 | 23.64 | C |
| ATOM | 2100 | CB | MSE | A | 320 | 119.434 | 17.764 | 36.784 | 1.00 | 24.62 | C |
| ATOM | 2101 | CG | MSE | A | 320 | 118.791 | 17.821 | 38.140 | 1.00 | 26.00 | C |
| ATOM | 2102 | SE | MSE | A | 320 | 120.088 | 17.534 | 39.516 | 1.00 | 21.29 | S |
| ATOM | 2103 | CE | MSE | A | 320 | 119.693 | 15.688 | 39.831 | 1.00 | 14.01 | C |
| ATOM | 2104 | C | MSE | A | 320 | 121.463 | 18.249 | 35.454 | 1.00 | 24.35 | C |
| ATOM | 2105 | O | MSE | A | 320 | 122.364 | 17.441 | 35.570 | 1.00 | 23.86 | O |
| ATOM | 2106 | N | ASN | A | 321 | 121.154 | 18.800 | 34.292 | 1.00 | 25.34 | N |
| ATOM | 2107 | CA | ASN | A | 321 | 121.896 | 18.436 | 33.105 | 1.00 | 23.77 | C |
| ATOM | 2108 | CB | ASN | A | 321 | 121.067 | 18.659 | 31.872 | 1.00 | 24.16 | C |
| ATOM | 2109 | CG | ASN | A | 321 | 120.191 | 17.499 | 31.576 | 1.00 | 29.26 | C |
| ATOM | 2110 | OD1 | ASN | A | 321 | 119.452 | 17.039 | 32.438 | 1.00 | 36.01 | O |
| ATOM | 2111 | ND2 | ASN | A | 321 | 120.268 | 16.998 | 30.351 | 1.00 | 37.15 | N |
| ATOM | 2112 | C | ASN | A | 321 | 123.182 | 19.175 | 32.962 | 1.00 | 22.95 | C |
| ATOM | 2113 | O | ASN | A | 321 | 123.938 | 18.893 | 32.054 | 1.00 | 23.42 | O |
| ATOM | 2114 | N | HIS | A | 322 | 123.446 | 20.130 | 33.831 | 1.00 | 21.13 | N |

FIG. 2A-46

| ATOM | 2115 | CA | HIS | A | 322 | 124.704 | 20.829 | 33.722 | 1.00 | 20.12 | C |
|---|---|---|---|---|---|---|---|---|---|---|---|
| ATOM | 2116 | CB | HIS | A | 322 | 124.835 | 21.890 | 34.793 | 1.00 | 20.91 | C |
| ATOM | 2117 | CG | HIS | A | 322 | 125.947 | 22.853 | 34.542 | 1.00 | 23.04 | C |
| ATOM | 2118 | ND1 | HIS | A | 322 | 127.271 | 22.512 | 34.703 | 1.00 | 20.29 | N |
| ATOM | 2119 | CE1 | HIS | A | 322 | 128.028 | 23.542 | 34.383 | 1.00 | 17.26 | C |
| ATOM | 2120 | NE2 | HIS | A | 322 | 127.240 | 24.540 | 34.020 | 1.00 | 23.89 | N |
| ATOM | 2121 | CD2 | HIS | A | 322 | 125.933 | 24.134 | 34.110 | 1.00 | 23.38 | C |
| ATOM | 2122 | C | HIS | A | 322 | 125.780 | 19.797 | 33.914 | 1.00 | 19.19 | C |
| ATOM | 2123 | O | HIS | A | 322 | 125.628 | 18.891 | 34.702 | 1.00 | 21.15 | O |
| ATOM | 2124 | N | PRO | A | 323 | 126.888 | 19.919 | 33.185 | 1.00 | 18.84 | N |
| ATOM | 2125 | CA | PRO | A | 323 | 128.032 | 19.007 | 33.238 | 1.00 | 19.17 | C |
| ATOM | 2126 | CB | PRO | A | 323 | 128.996 | 19.612 | 32.225 | 1.00 | 18.22 | C |
| ATOM | 2127 | CG | PRO | A | 323 | 128.097 | 20.252 | 31.234 | 1.00 | 18.49 | C |
| ATOM | 2128 | CD | PRO | A | 323 | 127.094 | 20.936 | 32.143 | 1.00 | 19.43 | C |
| ATOM | 2129 | C | PRO | A | 323 | 128.687 | 18.881 | 34.607 | 1.00 | 19.30 | C |
| ATOM | 2130 | O | PRO | A | 323 | 129.138 | 17.810 | 34.996 | 1.00 | 18.93 | O |
| ATOM | 2131 | N | TRP | A | 324 | 128.731 | 19.976 | 35.346 | 1.00 | 20.13 | N |
| ATOM | 2132 | CA | TRP | A | 324 | 129.392 | 19.962 | 36.638 | 1.00 | 20.37 | C |
| ATOM | 2133 | CB | TRP | A | 324 | 129.512 | 21.380 | 37.147 | 1.00 | 19.93 | C |
| ATOM | 2134 | CG | TRP | A | 324 | 130.409 | 21.558 | 38.272 | 1.00 | 17.37 | C |
| ATOM | 2135 | CD1 | TRP | A | 324 | 131.705 | 21.872 | 38.210 | 1.00 | 13.37 | C |
| ATOM | 2136 | NE1 | TRP | A | 324 | 132.201 | 22.139 | 39.467 | 1.00 | 13.45 | N |
| ATOM | 2137 | CE2 | TRP | A | 324 | 131.199 | 21.980 | 40.378 | 1.00 | 18.23 | C |
| ATOM | 2138 | CD2 | TRP | A | 324 | 130.048 | 21.604 | 39.657 | 1.00 | 18.62 | C |
| ATOM | 2139 | CE3 | TRP | A | 324 | 128.861 | 21.375 | 40.355 | 1.00 | 17.14 | C |
| ATOM | 2140 | CZ3 | TRP | A | 324 | 128.865 | 21.533 | 41.723 | 1.00 | 17.63 | C |
| ATOM | 2141 | CH2 | TRP | A | 324 | 130.029 | 21.914 | 42.418 | 1.00 | 15.74 | C |
| ATOM | 2142 | CZ2 | TRP | A | 324 | 131.203 | 22.138 | 41.767 | 1.00 | 19.43 | C |
| ATOM | 2143 | C | TRP | A | 324 | 128.656 | 19.102 | 37.637 | 1.00 | 22.16 | C |
| ATOM | 2144 | O | TRP | A | 324 | 129.269 | 18.412 | 38.451 | 1.00 | 22.85 | O |
| ATOM | 2145 | N | ILE | A | 325 | 127.332 | 19.147 | 37.593 | 1.00 | 23.63 | N |
| ATOM | 2146 | CA | ILE | A | 325 | 126.584 | 18.336 | 38.519 | 1.00 | 26.45 | C |
| ATOM | 2147 | CB | ILE | A | 325 | 125.177 | 18.920 | 38.804 | 1.00 | 25.88 | C |
| ATOM | 2148 | CG1 | ILE | A | 325 | 125.201 | 19.739 | 40.102 | 1.00 | 26.03 | C |
| ATOM | 2149 | CD1 | ILE | A | 325 | 125.415 | 21.194 | 39.920 | 1.00 | 31.00 | C |
| ATOM | 2150 | CG2 | ILE | A | 325 | 124.172 | 17.799 | 38.968 | 1.00 | 26.70 | C |
| ATOM | 2151 | C | ILE | A | 325 | 126.474 | 16.962 | 37.899 | 1.00 | 28.50 | C |
| ATOM | 2152 | O | ILE | A | 325 | 126.576 | 15.935 | 38.581 | 1.00 | 28.87 | O |
| ATOM | 2153 | N | MSE | A | 326 | 126.310 | 16.936 | 36.591 | 1.00 | 30.83 | N |
| ATOM | 2154 | CA | MSE | A | 326 | 126.173 | 15.661 | 35.922 | 1.00 | 34.24 | C |
| ATOM | 2155 | CB | MSE | A | 326 | 125.680 | 15.875 | 34.492 | 1.00 | 35.03 | C |
| ATOM | 2156 | CG | MSE | A | 326 | 125.063 | 14.630 | 33.915 | 1.00 | 41.14 | C |
| ATOM | 2157 | SE | MSE | A | 326 | 124.005 | 14.960 | 32.351 | 1.00 | 53.94 | S |
| ATOM | 2158 | CE | MSE | A | 326 | 122.293 | 14.394 | 33.032 | 1.00 | 55.40 | C |
| ATOM | 2159 | C | MSE | A | 326 | 127.456 | 14.808 | 35.964 | 1.00 | 35.54 | C |
| ATOM | 2160 | O | MSE | A | 326 | 127.405 | 13.625 | 36.327 | 1.00 | 36.79 | O |

FIG. 2A-47

| ATOM | 2161 | N | ALA | A | 327 | 128.603 | 15.393 | 35.632 | 1.00 | 36.92 | N |
|---|---|---|---|---|---|---|---|---|---|---|---|
| ATOM | 2162 | CA | ALA | A | 327 | 129.859 | 14.648 | 35.654 | 1.00 | 37.61 | C |
| ATOM | 2163 | CB | ALA | A | 327 | 130.741 | 15.146 | 34.515 | 1.00 | 37.55 | C |
| ATOM | 2164 | C | ALA | A | 327 | 130.580 | 14.852 | 36.981 | 1.00 | 38.50 | C |
| ATOM | 2165 | O | ALA | A | 327 | 131.780 | 15.087 | 36.994 | 1.00 | 38.79 | O |
| ATOM | 2166 | N | SER | A | 328 | 129.860 | 14.760 | 38.091 | 1.00 | 39.81 | N |
| ATOM | 2167 | CA | SER | A | 328 | 130.468 | 14.961 | 39.414 | 1.00 | 41.22 | C |
| ATOM | 2168 | CB | SER | A | 328 | 129.405 | 14.871 | 40.525 | 1.00 | 41.91 | C |
| ATOM | 2169 | OG | SER | A | 328 | 128.466 | 15.935 | 40.488 | 1.00 | 44.71 | O |
| ATOM | 2170 | C | SER | A | 328 | 131.574 | 13.951 | 39.733 | 1.00 | 41.53 | C |
| ATOM | 2171 | O | SER | A | 328 | 131.872 | 13.703 | 40.900 | 1.00 | 42.57 | O |
| ATOM | 2172 | N | THR | A | 329 | 132.179 | 13.366 | 38.708 | 1.00 | 41.16 | N |
| ATOM | 2173 | CA | THR | A | 329 | 133.223 | 12.367 | 38.914 | 1.00 | 41.28 | C |
| ATOM | 2174 | CB | THR | A | 329 | 132.660 | 10.931 | 38.809 | 1.00 | 41.85 | C |
| ATOM | 2175 | OG1 | THR | A | 329 | 132.184 | 10.694 | 37.472 | 1.00 | 42.10 | O |
| ATOM | 2176 | CG2 | THR | A | 329 | 131.520 | 10.735 | 39.812 | 1.00 | 42.05 | C |
| ATOM | 2177 | C | THR | A | 329 | 134.274 | 12.537 | 37.849 | 1.00 | 40.79 | C |
| ATOM | 2178 | O | THR | A | 329 | 134.844 | 11.571 | 37.352 | 1.00 | 39.29 | O |
| ATOM | 2179 | N | ALA | A | 330 | 134.503 | 13.785 | 37.492 | 1.00 | 40.39 | N |
| ATOM | 2180 | CA | ALA | A | 330 | 135.485 | 14.129 | 36.491 | 1.00 | 40.21 | C |
| ATOM | 2181 | CB | ALA | A | 330 | 134.857 | 14.075 | 35.101 | 1.00 | 40.53 | C |
| ATOM | 2182 | C | ALA | A | 330 | 135.852 | 15.553 | 36.876 | 1.00 | 39.31 | C |
| ATOM | 2183 | O | ALA | A | 330 | 136.704 | 16.206 | 36.263 | 1.00 | 40.20 | O |
| ATOM | 2184 | N | VAL | A | 331 | 135.189 | 16.020 | 37.921 | 1.00 | 37.03 | N |
| ATOM | 2185 | CA | VAL | A | 331 | 135.417 | 17.352 | 38.426 | 1.00 | 35.38 | C |
| ATOM | 2186 | CB | VAL | A | 331 | 134.178 | 17.852 | 39.228 | 1.00 | 34.67 | C |
| ATOM | 2187 | CG1 | VAL | A | 331 | 133.415 | 16.661 | 39.792 | 1.00 | 35.66 | C |
| ATOM | 2188 | CG2 | VAL | A | 331 | 134.606 | 18.790 | 40.358 | 1.00 | 33.24 | C |
| ATOM | 2189 | C | VAL | A | 331 | 136.658 | 17.335 | 39.299 | 1.00 | 35.09 | C |
| ATOM | 2190 | O | VAL | A | 331 | 136.871 | 16.412 | 40.087 | 1.00 | 34.68 | O |
| ATOM | 2191 | N | PRO | A | 332 | 137.512 | 18.349 | 39.130 | 1.00 | 35.13 | N |
| ATOM | 2192 | CA | PRO | A | 332 | 138.771 | 18.594 | 39.830 | 1.00 | 34.04 | C |
| ATOM | 2193 | CB | PRO | A | 332 | 139.072 | 20.042 | 39.490 | 1.00 | 34.38 | C |
| ATOM | 2194 | CG | PRO | A | 332 | 138.593 | 20.143 | 38.097 | 1.00 | 36.49 | C |
| ATOM | 2195 | CD | PRO | A | 332 | 137.269 | 19.389 | 38.116 | 1.00 | 35.45 | C |
| ATOM | 2196 | C | PRO | A | 332 | 138.572 | 18.411 | 41.315 | 1.00 | 33.12 | C |
| ATOM | 2197 | O | PRO | A | 332 | 137.644 | 18.960 | 41.898 | 1.00 | 33.28 | O |
| ATOM | 2198 | N | ALA | A | 333 | 139.439 | 17.632 | 41.934 | 1.00 | 31.79 | N |
| ATOM | 2199 | CA | ALA | A | 333 | 139.302 | 17.418 | 43.351 | 1.00 | 30.71 | C |
| ATOM | 2200 | CB | ALA | A | 333 | 139.843 | 16.053 | 43.713 | 1.00 | 30.37 | C |
| ATOM | 2201 | C | ALA | A | 333 | 140.128 | 18.494 | 44.023 | 1.00 | 29.31 | C |
| ATOM | 2202 | O | ALA | A | 333 | 140.806 | 18.268 | 45.013 | 1.00 | 28.39 | O |
| ATOM | 2203 | N | THR | A | 334 | 140.044 | 19.687 | 43.441 | 1.00 | 27.92 | N |
| ATOM | 2204 | CA | THR | A | 334 | 140.729 | 20.853 | 43.967 | 1.00 | 26.60 | C |
| ATOM | 2205 | CB | THR | A | 334 | 140.543 | 22.096 | 43.071 | 1.00 | 26.63 | C |
| ATOM | 2206 | OG1 | THR | A | 334 | 140.366 | 23.245 | 43.901 | 1.00 | 25.57 | O |

FIG. 2A-48

| | | | | | | | | | | |
|---|---|---|---|---|---|---|---|---|---|---|
| ATOM | 2207 | CG2 | THR | A | 334 | 139.359 | 21.949 | 42.160 | 1.00 | 26.79 | C |
| ATOM | 2208 | C | THR | A | 334 | 140.174 | 21.194 | 45.334 | 1.00 | 25.58 | C |
| ATOM | 2209 | O | THR | A | 334 | 138.968 | 21.113 | 45.563 | 1.00 | 26.24 | O |
| ATOM | 2210 | N | PRO | A | 335 | 141.051 | 21.561 | 46.267 | 1.00 | 24.00 | N |
| ATOM | 2211 | CA | PRO | A | 335 | 140.738 | 21.931 | 47.655 | 1.00 | 23.77 | C |
| ATOM | 2212 | CB | PRO | A | 335 | 142.101 | 21.888 | 48.325 | 1.00 | 24.39 | C |
| ATOM | 2213 | CG | PRO | A | 335 | 142.822 | 20.847 | 47.537 | 1.00 | 24.27 | C |
| ATOM | 2214 | CD | PRO | A | 335 | 142.465 | 21.198 | 46.133 | 1.00 | 23.48 | C |
| ATOM | 2215 | C | PRO | A | 335 | 140.035 | 23.286 | 47.865 | 1.00 | 24.38 | C |
| ATOM | 2216 | O | PRO | A | 335 | 140.310 | 24.256 | 47.170 | 1.00 | 24.40 | O |
| ATOM | 2217 | N | LEU | A | 336 | 139.132 | 23.354 | 48.838 | 1.00 | 25.56 | N |
| ATOM | 2218 | CA | LEU | A | 336 | 138.409 | 24.596 | 49.122 | 1.00 | 25.99 | C |
| ATOM | 2219 | CB | LEU | A | 336 | 136.904 | 24.395 | 48.926 | 1.00 | 25.51 | C |
| ATOM | 2220 | CG | LEU | A | 336 | 136.318 | 24.081 | 47.544 | 1.00 | 25.78 | C |
| ATOM | 2221 | CD1 | LEU | A | 336 | 134.845 | 23.829 | 47.592 | 1.00 | 31.98 | C |
| ATOM | 2222 | CD2 | LEU | A | 336 | 136.574 | 25.267 | 46.668 | 1.00 | 30.44 | C |
| ATOM | 2223 | C | LEU | A | 336 | 138.669 | 25.082 | 50.543 | 1.00 | 26.44 | C |
| ATOM | 2224 | O | LEU | A | 336 | 139.079 | 24.314 | 51.401 | 1.00 | 25.76 | O |
| ATOM | 2225 | N | HIS | A | 337 | 138.418 | 26.358 | 50.794 | 1.00 | 27.48 | N |
| ATOM | 2226 | CA | HIS | A | 337 | 138.640 | 26.905 | 52.133 | 1.00 | 28.55 | C |
| ATOM | 2227 | CB | HIS | A | 337 | 139.102 | 28.365 | 52.049 | 1.00 | 28.50 | C |
| ATOM | 2228 | CG | HIS | A | 337 | 140.235 | 28.585 | 51.103 | 1.00 | 28.45 | C |
| ATOM | 2229 | ND1 | HIS | A | 337 | 141.202 | 29.538 | 51.318 | 1.00 | 26.10 | N |
| ATOM | 2230 | CE1 | HIS | A | 337 | 142.060 | 29.519 | 50.315 | 1.00 | 28.61 | C |
| ATOM | 2231 | NE2 | HIS | A | 337 | 141.686 | 28.589 | 49.457 | 1.00 | 27.95 | N |
| ATOM | 2232 | CD2 | HIS | A | 337 | 140.547 | 27.990 | 49.927 | 1.00 | 28.92 | C |
| ATOM | 2233 | C | HIS | A | 337 | 137.364 | 26.849 | 52.967 | 1.00 | 29.50 | C |
| ATOM | 2234 | O | HIS | A | 337 | 137.266 | 27.500 | 54.016 | 1.00 | 30.69 | O |
| ATOM | 2235 | N | THR | A | 338 | 136.395 | 26.071 | 52.486 | 1.00 | 28.57 | N |
| ATOM | 2236 | CA | THR | A | 338 | 135.097 | 25.931 | 53.131 | 1.00 | 27.10 | C |
| ATOM | 2237 | CB | THR | A | 338 | 134.241 | 24.899 | 52.397 | 1.00 | 27.68 | C |
| ATOM | 2238 | OG1 | THR | A | 338 | 134.188 | 25.226 | 51.004 | 1.00 | 26.96 | O |
| ATOM | 2239 | CG2 | THR | A | 338 | 132.838 | 24.891 | 52.960 | 1.00 | 24.62 | C |
| ATOM | 2240 | C | THR | A | 338 | 135.237 | 25.491 | 54.568 | 1.00 | 26.97 | C |
| ATOM | 2241 | O | THR | A | 338 | 134.832 | 26.196 | 55.493 | 1.00 | 25.96 | O |
| ATOM | 2242 | N | SER | A | 339 | 135.820 | 24.311 | 54.741 | 1.00 | 27.49 | N |
| ATOM | 2243 | CA | SER | A | 339 | 136.015 | 23.751 | 56.059 | 1.00 | 29.08 | C |
| ATOM | 2244 | CB | SER | A | 339 | 136.838 | 22.463 | 55.968 | 1.00 | 29.43 | C |
| ATOM | 2245 | OG | SER | A | 339 | 136.677 | 21.661 | 57.139 | 1.00 | 32.29 | O |
| ATOM | 2246 | C | SER | A | 339 | 136.702 | 24.761 | 56.956 | 1.00 | 28.87 | C |
| ATOM | 2247 | O | SER | A | 339 | 136.194 | 25.102 | 58.011 | 1.00 | 28.71 | O |
| ATOM | 2248 | N | ARG | A | 340 | 137.857 | 25.249 | 56.533 | 1.00 | 30.01 | N |
| ATOM | 2249 | CA | ARG | A | 340 | 138.568 | 26.223 | 57.346 | 1.00 | 31.66 | C |
| ATOM | 2250 | CB | ARG | A | 340 | 139.820 | 26.725 | 56.638 | 1.00 | 32.70 | C |
| ATOM | 2251 | CG | ARG | A | 340 | 140.580 | 25.728 | 55.796 | 1.00 | 36.51 | C |
| ATOM | 2252 | CD | ARG | A | 340 | 141.728 | 26.488 | 55.136 | 1.00 | 41.01 | C |

FIG. 2A-49

| ATOM | 2253 | NE | ARG | A | 340 | 141.922 | 26.149 | 53.730 | 1.00 | 44.09 | N |
|---|---|---|---|---|---|---|---|---|---|---|---|
| ATOM | 2254 | CZ | ARG | A | 340 | 142.732 | 26.817 | 52.916 | 1.00 | 44.87 | C |
| ATOM | 2255 | NH1AR | G | A | 340 | 143.413 | 27.859 | 53.386 | 1.00 | 46.00 | N |
| ATOM | 2256 | NH2AR | G | A | 340 | 142.869 | 26.445 | 51.643 | 1.00 | 45.60 | N |
| ATOM | 2257 | C | ARG | A | 340 | 137.683 | 27.438 | 57.641 | 1.00 | 31.36 | C |
| ATOM | 2258 | O | ARG | A | 340 | 137.383 | 27.726 | 58.796 | 1.00 | 32.74 | O |
| ATOM | 2259 | N | VAL | A | 341 | 137.300 | 28.163 | 56.589 | 1.00 | 29.57 | N |
| ATOM | 2260 | CA | VAL | A | 341 | 136.467 | 29.357 | 56.709 | 1.00 | 28.19 | C |
| ATOM | 2261 | CB | VAL | A | 341 | 135.949 | 29.800 | 55.317 | 1.00 | 28.38 | C |
| ATOM | 2262 | CG1 | VAL | A | 341 | 135.030 | 30.988 | 55.435 | 1.00 | 26.83 | C |
| ATOM | 2263 | CG2 | VAL | A | 341 | 137.104 | 30.149 | 54.437 | 1.00 | 26.91 | C |
| ATOM | 2264 | C | VAL | A | 341 | 135.275 | 29.132 | 57.641 | 1.00 | 28.28 | C |
| ATOM | 2265 | O | VAL | A | 341 | 134.960 | 29.971 | 58.506 | 1.00 | 28.39 | O |
| ATOM | 2266 | N | LEU | A | 342 | 134.625 | 27.989 | 57.473 | 1.00 | 27.59 | N |
| ATOM | 2267 | CA | LEU | A | 342 | 133.463 | 27.654 | 58.273 | 1.00 | 27.57 | C |
| ATOM | 2268 | CB | LEU | A | 342 | 132.937 | 26.277 | 57.831 | 1.00 | 26.70 | C |
| ATOM | 2269 | CG | LEU | A | 342 | 131.488 | 26.178 | 57.330 | 1.00 | 25.26 | C |
| ATOM | 2270 | CD1 | LEU | A | 342 | 131.026 | 27.537 | 56.812 | 1.00 | 22.22 | C |
| ATOM | 2271 | CD2 | LEU | A | 342 | 131.376 | 25.111 | 56.255 | 1.00 | 19.58 | C |
| ATOM | 2272 | C | LEU | A | 342 | 133.749 | 27.689 | 59.775 | 1.00 | 28.53 | C |
| ATOM | 2273 | O | LEU | A | 342 | 132.973 | 28.263 | 60.538 | 1.00 | 28.68 | O |
| ATOM | 2274 | N | ALA | A | 343 | 134.871 | 27.094 | 60.187 | 1.00 | 30.18 | N |
| ATOM | 2275 | CA | ALA | A | 343 | 135.294 | 27.028 | 61.601 | 1.00 | 33.39 | C |
| ATOM | 2276 | CB | ALA | A | 343 | 136.548 | 26.151 | 61.741 | 1.00 | 32.45 | C |
| ATOM | 2277 | C | ALA | A | 343 | 135.561 | 28.391 | 62.241 | 1.00 | 35.63 | C |
| ATOM | 2278 | O | ALA | A | 343 | 135.200 | 28.629 | 63.395 | 1.00 | 36.73 | O |
| ATOM | 2279 | N | ALA | A | 344 | 136.218 | 29.276 | 61.505 | 1.00 | 37.95 | N |
| ATOM | 2280 | CA | ALA | A | 344 | 136.498 | 30.601 | 62.029 | 1.00 | 39.78 | C |
| ATOM | 2281 | CB | ALA | A | 344 | 137.560 | 31.265 | 61.191 | 1.00 | 39.70 | C |
| ATOM | 2282 | C | ALA | A | 344 | 135.206 | 31.418 | 61.989 | 1.00 | 41.48 | C |
| ATOM | 2283 | O | ALA | A | 344 | 135.066 | 32.427 | 62.687 | 1.00 | 41.03 | O |
| ATOM | 2284 | N | ASP | A | 345 | 134.261 | 30.957 | 61.174 | 1.00 | 44.14 | N |
| ATOM | 2285 | CA | ASP | A | 345 | 132.969 | 31.621 | 61.004 | 1.00 | 46.73 | C |
| ATOM | 2286 | CB | ASP | A | 345 | 132.423 | 32.106 | 62.348 | 1.00 | 46.79 | C |
| ATOM | 2287 | CG | ASP | A | 345 | 131.939 | 30.975 | 63.224 | 1.00 | 49.82 | C |
| ATOM | 2288 | OD1 | ASP | A | 345 | 132.619 | 29.918 | 63.284 | 1.00 | 50.22 | O |
| ATOM | 2289 | OD2 | ASP | A | 345 | 130.878 | 31.155 | 63.861 | 1.00 | 54.07 | O |
| ATOM | 2290 | C | ASP | A | 345 | 133.145 | 32.816 | 60.078 | 1.00 | 47.94 | C |
| ATOM | 2291 | O | ASP | A | 345 | 132.907 | 32.663 | 58.864 | 1.00 | 48.74 | O |
| ATOM | 2292 | OXT | ASP | A | 345 | 133.548 | 33.886 | 60.582 | 1.00 | 48.78 | O |
| ATOM | 2293 | N | PRO | B | 44 | 105.405 | 17.433 | 80.194 | 1.00 | 53.10 | N |
| ATOM | 2294 | CA | PRO | B | 44 | 104.476 | 16.315 | 80.258 | 1.00 | 51.29 | C |
| ATOM | 2295 | CB | PRO | B | 44 | 103.880 | 16.277 | 81.663 | 1.00 | 51.94 | C |
| ATOM | 2296 | CG | PRO | B | 44 | 104.583 | 17.331 | 82.514 | 1.00 | 53.76 | C |
| ATOM | 2297 | CD | PRO | B | 44 | 105.770 | 17.795 | 81.551 | 1.00 | 54.31 | C |
| ATOM | 2298 | C | PRO | B | 44 | 103.362 | 16.451 | 79.221 | 1.00 | 49.30 | C |

FIG. 2A-50

| ATOM | 2299 | O | PRO | B | 44 | 102.549 | 17.368 | 79.248 | 1.00 | 48.91 | O |
|---|---|---|---|---|---|---|---|---|---|---|---|
| ATOM | 2300 | N | GLN | B | 45 | 103.365 | 15.514 | 78.255 | 1.00 | 47.98 | N |
| ATOM | 2301 | CA | GLN | B | 45 | 102.297 | 15.466 | 77.268 | 1.00 | 46.63 | C |
| ATOM | 2302 | CB | GLN | B | 45 | 102.855 | 14.872 | 75.977 | 1.00 | 46.62 | C |
| ATOM | 2303 | CG | GLN | B | 45 | 103.434 | 15.936 | 75.048 | 1.00 | 43.54 | C |
| ATOM | 2304 | CD | GLN | B | 45 | 102.768 | 15.835 | 73.695 | 1.00 | 46.14 | C |
| ATOM | 2305 | OE1 | GLN | B | 45 | 102.545 | 16.806 | 72.990 | 1.00 | 47.72 | O |
| ATOM | 2306 | NE2 | GLN | B | 45 | 102.399 | 14.581 | 73.367 | 1.00 | 40.88 | N |
| ATOM | 2307 | C | GLN | B | 45 | 101.139 | 14.607 | 77.765 | 1.00 | 46.67 | C |
| ATOM | 2308 | O | GLN | B | 45 | 101.230 | 13.394 | 77.899 | 1.00 | 46.15 | O |
| ATOM | 2309 | N | ALA | B | 46 | 100.031 | 15.299 | 78.079 | 1.00 | 47.05 | N |
| ATOM | 2310 | CA | ALA | B | 46 | 98.880 | 14.598 | 78.621 | 1.00 | 47.29 | C |
| ATOM | 2311 | CB | ALA | B | 46 | 98.976 | 14.646 | 80.146 | 1.00 | 48.71 | C |
| ATOM | 2312 | C | ALA | B | 46 | 97.567 | 15.230 | 78.156 | 1.00 | 47.52 | C |
| ATOM | 2313 | O | ALA | B | 46 | 96.579 | 14.553 | 77.914 | 1.00 | 48.87 | O |
| ATOM | 2314 | N | HIS | B | 47 | 97.553 | 16.578 | 78.063 | 1.00 | 48.73 | N |
| ATOM | 2315 | CA | HIS | B | 47 | 96.334 | 17.218 | 77.580 | 1.00 | 49.49 | C |
| ATOM | 2316 | CB | HIS | B | 47 | 96.402 | 18.737 | 77.784 | 1.00 | 50.42 | C |
| ATOM | 2317 | CG | HIS | B | 47 | 97.758 | 19.158 | 78.282 | 1.00 | 52.08 | C |
| ATOM | 2318 | ND1 | HIS | B | 47 | 98.872 | 19.147 | 77.508 | 1.00 | 56.37 | N |
| ATOM | 2319 | CE1 | HIS | B | 47 | 99.822 | 19.761 | 78.237 | 1.00 | 56.60 | C |
| ATOM | 2320 | NE2 | HIS | B | 47 | 99.370 | 20.150 | 79.429 | 1.00 | 58.87 | N |
| ATOM | 2321 | CD2 | HIS | B | 47 | 98.069 | 19.781 | 79.497 | 1.00 | 54.81 | C |
| ATOM | 2322 | C | HIS | B | 47 | 96.095 | 16.902 | 76.109 | 1.00 | 47.56 | C |
| ATOM | 2323 | O | HIS | B | 47 | 95.659 | 17.735 | 75.323 | 1.00 | 48.82 | O |
| ATOM | 2324 | N | VAL | B | 48 | 96.548 | 15.681 | 75.809 | 1.00 | 43.23 | N |
| ATOM | 2325 | CA | VAL | B | 48 | 96.566 | 15.094 | 74.494 | 1.00 | 36.75 | C |
| ATOM | 2326 | CB | VAL | B | 48 | 97.881 | 14.464 | 74.279 | 1.00 | 36.54 | C |
| ATOM | 2327 | CG1 | VAL | B | 48 | 98.150 | 14.320 | 72.759 | 1.00 | 32.40 | C |
| ATOM | 2328 | CG2 | VAL | B | 48 | 98.913 | 15.293 | 75.059 | 1.00 | 34.32 | C |
| ATOM | 2329 | C | VAL | B | 48 | 95.529 | 14.016 | 74.339 | 1.00 | 34.52 | C |
| ATOM | 2330 | O | VAL | B | 48 | 95.771 | 12.889 | 74.720 | 1.00 | 33.38 | O |
| ATOM | 2331 | N | LYS | B | 49 | 94.389 | 14.374 | 73.771 | 1.00 | 32.31 | N |
| ATOM | 2332 | CA | LYS | B | 49 | 93.293 | 13.451 | 73.548 | 1.00 | 31.57 | C |
| ATOM | 2333 | CB | LYS | B | 49 | 91.996 | 14.154 | 73.924 | 1.00 | 33.93 | C |
| ATOM | 2334 | CG | LYS | B | 49 | 90.768 | 13.270 | 73.700 | 1.00 | 41.21 | C |
| ATOM | 2335 | CD | LYS | B | 49 | 89.464 | 13.971 | 74.091 | 1.00 | 48.89 | C |
| ATOM | 2336 | CE | LYS | B | 49 | 88.236 | 13.087 | 73.867 | 1.00 | 46.52 | C |
| ATOM | 2337 | NZ | LYS | B | 49 | 87.028 | 13.813 | 74.262 | 1.00 | 54.22 | N |
| ATOM | 2338 | C | LYS | B | 49 | 93.234 | 13.025 | 72.093 | 1.00 | 29.51 | C |
| ATOM | 2339 | O | LYS | B | 49 | 93.648 | 13.735 | 71.186 | 1.00 | 29.62 | O |
| ATOM | 2340 | N | SER | B | 50 | 92.700 | 11.855 | 71.855 | 1.00 | 27.01 | N |
| ATOM | 2341 | CA | SER | B | 50 | 92.612 | 11.373 | 70.494 | 1.00 | 25.18 | C |
| ATOM | 2342 | CB | SER | B | 50 | 92.391 | 9.875 | 70.472 | 1.00 | 23.51 | C |
| ATOM | 2343 | OG | SER | B | 50 | 91.033 | 9.680 | 70.762 | 1.00 | 24.42 | O |
| ATOM | 2344 | C | SER | B | 50 | 91.478 | 12.013 | 69.716 | 1.00 | 24.43 | C |

FIG. 2A-51

| ATOM | 2345 | O | SER | B | 50 | 90.533 | 12.583 | 70.269 | 1.00 | 22.79 | O |
| --- | --- | --- | --- | --- | --- | --- | --- | --- | --- | --- | --- |
| ATOM | 2346 | N | GLY | B | 51 | 91.588 | 11.894 | 68.405 | 1.00 | 23.45 | N |
| ATOM | 2347 | CA | GLY | B | 51 | 90.560 | 12.420 | 67.555 | 1.00 | 23.92 | C |
| ATOM | 2348 | C | GLY | B | 51 | 89.481 | 11.375 | 67.451 | 1.00 | 22.74 | C |
| ATOM | 2349 | O | GLY | B | 51 | 89.584 | 10.262 | 67.975 | 1.00 | 21.54 | O |
| ATOM | 2350 | N | LEU | B | 52 | 88.429 | 11.766 | 66.759 | 1.00 | 24.61 | N |
| ATOM | 2351 | CA | LEU | B | 52 | 87.265 | 10.912 | 66.530 | 1.00 | 27.59 | C |
| ATOM | 2352 | CB | LEU | B | 52 | 86.006 | 11.766 | 66.623 | 1.00 | 27.25 | C |
| ATOM | 2353 | CG | LEU | B | 52 | 84.834 | 11.174 | 65.885 | 1.00 | 30.59 | C |
| ATOM | 2354 | CD1 | LEU | B | 52 | 84.157 | 10.200 | 66.826 | 1.00 | 34.59 | C |
| ATOM | 2355 | CD2 | LEU | B | 52 | 83.894 | 12.288 | 65.433 | 1.00 | 36.43 | C |
| ATOM | 2356 | C | LEU | B | 52 | 87.311 | 10.252 | 65.151 | 1.00 | 27.06 | C |
| ATOM | 2357 | O | LEU | B | 52 | 87.195 | 10.928 | 64.156 | 1.00 | 25.97 | O |
| ATOM | 2358 | N | GLN | B | 53 | 87.509 | 8.944 | 65.089 | 1.00 | 28.21 | N |
| ATOM | 2359 | CA | GLN | B | 53 | 87.526 | 8.267 | 63.800 | 1.00 | 28.50 | C |
| ATOM | 2360 | CB | GLN | B | 53 | 88.442 | 7.039 | 63.816 | 1.00 | 28.78 | C |
| ATOM | 2361 | CG | GLN | B | 53 | 88.431 | 6.245 | 62.519 | 1.00 | 33.77 | C |
| ATOM | 2362 | CD | GLN | B | 53 | 89.052 | 7.020 | 61.346 | 1.00 | 40.78 | C |
| ATOM | 2363 | OE1 | GLN | B | 53 | 90.285 | 7.054 | 61.192 | 1.00 | 38.58 | O |
| ATOM | 2364 | NE2 | GLN | B | 53 | 88.202 | 7.664 | 60.526 | 1.00 | 42.72 | N |
| ATOM | 2365 | C | GLN | B | 53 | 86.108 | 7.819 | 63.531 | 1.00 | 27.32 | C |
| ATOM | 2366 | O | GLN | B | 53 | 85.555 | 7.012 | 64.241 | 1.00 | 29.78 | O |
| ATOM | 2367 | N | ILE | B | 54 | 85.510 | 8.354 | 62.501 | 1.00 | 25.80 | N |
| ATOM | 2368 | CA | ILE | B | 54 | 84.151 | 7.978 | 62.152 | 1.00 | 24.54 | C |
| ATOM | 2369 | CB | ILE | B | 54 | 83.589 | 9.080 | 61.233 | 1.00 | 23.63 | C |
| ATOM | 2370 | CG1 | ILE | B | 54 | 83.244 | 10.299 | 62.088 | 1.00 | 24.87 | C |
| ATOM | 2371 | CD1 | ILE | B | 54 | 82.929 | 11.497 | 61.300 | 1.00 | 22.40 | C |
| ATOM | 2372 | CG2 | ILE | B | 54 | 82.497 | 8.546 | 60.390 | 1.00 | 25.36 | C |
| ATOM | 2373 | C | ILE | B | 54 | 84.068 | 6.583 | 61.486 | 1.00 | 23.22 | C |
| ATOM | 2374 | O | ILE | B | 54 | 84.810 | 6.274 | 60.592 | 1.00 | 24.02 | O |
| ATOM | 2375 | N | LYS | B | 55 | 83.176 | 5.728 | 61.924 | 1.00 | 22.50 | N |
| ATOM | 2376 | CA | LYS | B | 55 | 83.085 | 4.404 | 61.314 | 1.00 | 21.35 | C |
| ATOM | 2377 | CB | LYS | B | 55 | 82.608 | 3.350 | 62.325 | 1.00 | 22.75 | C |
| ATOM | 2378 | CG | LYS | B | 55 | 83.576 | 3.098 | 63.432 | 1.00 | 21.75 | C |
| ATOM | 2379 | CD | LYS | B | 55 | 82.975 | 2.307 | 64.563 | 1.00 | 27.27 | C |
| ATOM | 2380 | CE | LYS | B | 55 | 84.095 | 2.023 | 65.514 | 1.00 | 35.90 | C |
| ATOM | 2381 | NZ | LYS | B | 55 | 83.694 | 1.263 | 66.711 | 1.00 | 48.49 | N |
| ATOM | 2382 | C | LYS | B | 55 | 82.120 | 4.398 | 60.167 | 1.00 | 19.67 | C |
| ATOM | 2383 | O | LYS | B | 55 | 81.037 | 4.986 | 60.258 | 1.00 | 19.20 | O |
| ATOM | 2384 | N | LYS | B | 56 | 82.488 | 3.680 | 59.113 | 1.00 | 18.30 | N |
| ATOM | 2385 | CA | LYS | B | 56 | 81.647 | 3.580 | 57.920 | 1.00 | 19.10 | C |
| ATOM | 2386 | CB | LYS | B | 56 | 82.503 | 3.605 | 56.671 | 1.00 | 18.18 | C |
| ATOM | 2387 | CG | LYS | B | 56 | 83.275 | 4.866 | 56.484 | 1.00 | 20.72 | C |
| ATOM | 2388 | CD | LYS | B | 56 | 82.349 | 6.079 | 56.419 | 1.00 | 21.94 | C |
| ATOM | 2389 | CE | LYS | B | 56 | 83.204 | 7.260 | 56.082 | 1.00 | 26.76 | C |
| ATOM | 2390 | NZ | LYS | B | 56 | 84.487 | 6.941 | 56.779 | 1.00 | 26.61 | N |

FIG. 2A-52

| ATOM | 2391 | C | LYS | B | 56 | 80.765 | 2.346 | 57.874 | 1.00 | 19.55 | C |
| ATOM | 2392 | O | LYS | B | 56 | 79.792 | 2.316 | 57.141 | 1.00 | 22.10 | O |
| ATOM | 2393 | N | ASN | B | 57 | 81.079 | 1.333 | 58.665 | 1.00 | 17.47 | N |
| ATOM | 2394 | CA | ASN | B | 57 | 80.269 | 0.146 | 58.642 | 1.00 | 17.13 | C |
| ATOM | 2395 | CB | ASN | B | 57 | 80.952 | -0.983 | 59.385 | 1.00 | 18.71 | C |
| ATOM | 2396 | CG | ASN | B | 57 | 80.883 | -0.817 | 60.821 | 1.00 | 20.61 | C |
| ATOM | 2397 | OD1 | ASN | B | 57 | 81.805 | -0.278 | 61.429 | 1.00 | 28.52 | O |
| ATOM | 2398 | ND2 | ASN | B | 57 | 79.796 | -1.299 | 61.419 | 1.00 | 23.76 | N |
| ATOM | 2399 | C | ASN | B | 57 | 78.880 | 0.361 | 59.188 | 1.00 | 16.58 | C |
| ATOM | 2400 | O | ASN | B | 57 | 78.660 | 1.233 | 59.998 | 1.00 | 16.51 | O |
| ATOM | 2401 | N | ALA | B | 58 | 77.940 | -0.460 | 58.721 | 1.00 | 18.11 | N |
| ATOM | 2402 | CA | ALA | B | 58 | 76.536 | -0.385 | 59.091 | 1.00 | 18.16 | C |
| ATOM | 2403 | CB | ALA | B | 58 | 75.806 | -1.543 | 58.416 | 1.00 | 16.80 | C |
| ATOM | 2404 | C | ALA | B | 58 | 76.371 | -0.479 | 60.604 | 1.00 | 17.53 | C |
| ATOM | 2405 | O | ALA | B | 58 | 76.869 | -1.389 | 61.259 | 1.00 | 18.40 | O |
| ATOM | 2406 | N | ILE | B | 59 | 75.683 | 0.533 | 61.162 | 1.00 | 15.89 | N |
| ATOM | 2407 | CA | ILE | B | 59 | 75.550 | 0.597 | 62.612 | 1.00 | 16.16 | C |
| ATOM | 2408 | CB | ILE | B | 59 | 74.671 | 1.802 | 62.971 | 1.00 | 17.10 | C |
| ATOM | 2409 | CG1 | ILE | B | 59 | 74.659 | 2.022 | 64.482 | 1.00 | 18.43 | C |
| ATOM | 2410 | CD1 | ILE | B | 59 | 74.388 | 3.480 | 64.856 | 1.00 | 29.41 | C |
| ATOM | 2411 | CG2 | ILE | B | 59 | 73.222 | 1.527 | 62.534 | 1.00 | 16.87 | C |
| ATOM | 2412 | C | ILE | B | 59 | 74.952 | -0.691 | 63.194 | 1.00 | 16.99 | C |
| ATOM | 2413 | O | ILE | B | 59 | 75.269 | -1.116 | 64.292 | 1.00 | 14.97 | O |
| ATOM | 2414 | N | ILE | B | 60 | 74.020 | -1.290 | 62.424 | 1.00 | 17.80 | N |
| ATOM | 2415 | CA | ILE | B | 60 | 73.396 | -2.528 | 62.887 | 1.00 | 19.85 | C |
| ATOM | 2416 | CB | ILE | B | 60 | 72.281 | -2.914 | 61.913 | 1.00 | 18.84 | C |
| ATOM | 2417 | CG1 | ILE | B | 60 | 72.819 | -2.983 | 60.482 | 1.00 | 19.35 | C |
| ATOM | 2418 | CD1 | ILE | B | 60 | 71.697 | -3.052 | 59.441 | 1.00 | 22.24 | C |
| ATOM | 2419 | CG2 | ILE | B | 60 | 71.175 | -1.846 | 61.938 | 1.00 | 16.48 | C |
| ATOM | 2420 | C | ILE | B | 60 | 74.399 | -3.678 | 62.995 | 1.00 | 23.02 | C |
| ATOM | 2421 | O | ILE | B | 60 | 74.195 | -4.636 | 63.728 | 1.00 | 24.87 | O |
| ATOM | 2422 | N | ASP | B | 61 | 75.555 | -3.634 | 62.343 | 1.00 | 25.17 | N |
| ATOM | 2423 | CA | ASP | B | 61 | 76.540 | -4.694 | 62.572 | 1.00 | 27.45 | C |
| ATOM | 2424 | CB | ASP | B | 61 | 77.804 | -4.531 | 61.713 | 1.00 | 28.72 | C |
| ATOM | 2425 | CG | ASP | B | 61 | 77.524 | -4.493 | 60.215 | 1.00 | 33.24 | C |
| ATOM | 2426 | OD1 | ASP | B | 61 | 78.470 | -4.132 | 59.464 | 1.00 | 40.44 | O |
| ATOM | 2427 | OD2 | ASP | B | 61 | 76.389 | -4.810 | 59.784 | 1.00 | 37.70 | O |
| ATOM | 2428 | C | ASP | B | 61 | 77.100 | -4.695 | 63.995 | 1.00 | 27.48 | C |
| ATOM | 2429 | O | ASP | B | 61 | 77.821 | -5.595 | 64.407 | 1.00 | 28.03 | O |
| ATOM | 2430 | N | ASP | B | 62 | 76.669 | -3.655 | 64.730 | 1.00 | 26.93 | N |
| ATOM | 2431 | CA | ASP | B | 62 | 77.187 | -3.523 | 66.078 | 1.00 | 26.17 | C |
| ATOM | 2432 | CB | ASP | B | 62 | 78.194 | -2.346 | 66.280 | 1.00 | 27.77 | C |
| ATOM | 2433 | CG | ASP | B | 62 | 79.361 | -2.472 | 65.341 | 1.00 | 29.00 | C |
| ATOM | 2434 | OD1 | ASP | B | 62 | 79.987 | -3.545 | 65.297 | 1.00 | 20.97 | O |
| ATOM | 2435 | OD2 | ASP | B | 62 | 79.662 | -1.480 | 64.646 | 1.00 | 32.73 | O |
| ATOM | 2436 | C | ASP | B | 62 | 76.164 | -3.295 | 67.227 | 1.00 | 26.35 | C |

FIG. 2A-53

| ATOM | 2437 | O | ASP | B | 62 | 76.431 | -3.513 | 68.409 | 1.00 | 25.46 | O |
| ATOM | 2438 | N | TYR | B | 63 | 74.990 | -2.837 | 66.813 | 1.00 | 26.78 | N |
| ATOM | 2439 | CA | TYR | B | 63 | 73.915 | -2.555 | 67.759 | 1.00 | 26.61 | C |
| ATOM | 2440 | CB | TYR | B | 63 | 73.803 | -1.033 | 68.024 | 1.00 | 24.94 | C |
| ATOM | 2441 | CG | TYR | B | 63 | 75.060 | -0.384 | 68.570 | 1.00 | 25.78 | C |
| ATOM | 2442 | CD1 | TYR | B | 63 | 75.303 | -0.325 | 69.946 | 1.00 | 21.68 | C |
| ATOM | 2443 | CE1 | TYR | B | 63 | 76.465 | 0.244 | 70.444 | 1.00 | 18.28 | C |
| ATOM | 2444 | CZ | TYR | B | 63 | 77.400 | 0.757 | 69.572 | 1.00 | 22.27 | C |
| ATOM | 2445 | OH | TYR | B | 63 | 78.555 | 1.311 | 70.058 | 1.00 | 22.33 | O |
| ATOM | 2446 | CE2 | TYR | B | 63 | 77.195 | 0.715 | 68.208 | 1.00 | 26.01 | C |
| ATOM | 2447 | CD2 | TYR | B | 63 | 76.027 | 0.149 | 67.711 | 1.00 | 25.11 | C |
| ATOM | 2448 | C | TYR | B | 63 | 72.577 | -3.013 | 67.201 | 1.00 | 27.19 | C |
| ATOM | 2449 | O | TYR | B | 63 | 72.415 | -3.192 | 65.977 | 1.00 | 27.96 | O |
| ATOM | 2450 | N | ALA | B | 64 | 71.640 | -3.243 | 68.117 | 1.00 | 25.63 | N |
| ATOM | 2451 | CA | ALA | B | 64 | 70.209 | -3.353 | 67.833 | 1.00 | 25.39 | C |
| ATOM | 2452 | CB | ALA | B | 64 | 69.599 | -4.338 | 68.829 | 1.00 | 25.56 | C |
| ATOM | 2453 | C | ALA | B | 64 | 69.488 | -2.004 | 67.937 | 1.00 | 25.11 | C |
| ATOM | 2454 | O | ALA | B | 64 | 69.259 | -1.466 | 69.011 | 1.00 | 27.17 | O |
| ATOM | 2455 | N | VAL | B | 65 | 69.148 | -1.437 | 66.764 | 1.00 | 24.74 | N |
| ATOM | 2456 | CA | VAL | B | 65 | 68.454 | -0.152 | 66.769 | 1.00 | 26.58 | C |
| ATOM | 2457 | CB | VAL | B | 65 | 68.777 | 0.585 | 65.470 | 1.00 | 26.29 | C |
| ATOM | 2458 | CG1 | VAL | B | 65 | 68.159 | 1.984 | 65.502 | 1.00 | 23.68 | C |
| ATOM | 2459 | CG2 | VAL | B | 65 | 70.281 | 0.701 | 65.304 | 1.00 | 23.98 | C |
| ATOM | 2460 | C | VAL | B | 65 | 66.939 | -0.313 | 66.905 | 1.00 | 28.75 | C |
| ATOM | 2461 | O | VAL | B | 65 | 66.204 | -0.418 | 65.931 | 1.00 | 30.40 | O |
| ATOM | 2462 | N | THR | B | 66 | 66.477 | -0.371 | 68.169 | 1.00 | 30.52 | N |
| ATOM | 2463 | CA | THR | B | 66 | 65.040 | -0.430 | 68.411 | 1.00 | 31.42 | C |
| ATOM | 2464 | CB | THR | B | 66 | 64.801 | -0.390 | 69.918 | 1.00 | 31.56 | C |
| ATOM | 2465 | OG1 | THR | B | 66 | 64.406 | 0.933 | 70.295 | 1.00 | 33.24 | O |
| ATOM | 2466 | CG2 | THR | B | 66 | 66.085 | -0.766 | 70.666 | 1.00 | 31.54 | C |
| ATOM | 2467 | C | THR | B | 66 | 64.315 | 0.740 | 67.741 | 1.00 | 32.70 | C |
| ATOM | 2468 | O | THR | B | 66 | 64.883 | 1.500 | 66.969 | 1.00 | 32.69 | O |
| ATOM | 2469 | N | SER | B | 67 | 63.007 | 0.858 | 68.029 | 1.00 | 34.85 | N |
| ATOM | 2470 | CA | SER | B | 67 | 62.253 | 1.952 | 67.414 | 1.00 | 37.00 | C |
| ATOM | 2471 | CB | SER | B | 67 | 61.171 | 1.360 | 66.509 | 1.00 | 38.06 | C |
| ATOM | 2472 | OG | SER | B | 67 | 60.672 | 2.389 | 65.647 | 1.00 | 45.19 | O |
| ATOM | 2473 | C | SER | B | 67 | 61.633 | 2.893 | 68.450 | 1.00 | 36.32 | C |
| ATOM | 2474 | O | SER | B | 67 | 60.877 | 3.802 | 68.131 | 1.00 | 36.34 | O |
| ATOM | 2475 | N | GLN | B | 68 | 61.936 | 2.638 | 69.737 | 1.00 | 36.19 | N |
| ATOM | 2476 | CA | GLN | B | 68 | 61.473 | 3.590 | 70.744 | 1.00 | 37.84 | C |
| ATOM | 2477 | CB | GLN | B | 68 | 61.493 | 2.934 | 72.126 | 1.00 | 39.47 | C |
| ATOM | 2478 | CG | GLN | B | 68 | 61.633 | 3.976 | 73.237 | 1.00 | 48.28 | C |
| ATOM | 2479 | CD | GLN | B | 68 | 61.419 | 3.326 | 74.585 | 1.00 | 59.36 | C |
| ATOM | 2480 | OE1 | GLN | B | 68 | 60.760 | 3.843 | 75.473 | 1.00 | 62.56 | O |
| ATOM | 2481 | NE2 | GLN | B | 68 | 62.028 | 2.131 | 74.716 | 1.00 | 60.96 | N |
| ATOM | 2482 | C | GLN | B | 68 | 62.357 | 4.834 | 70.767 | 1.00 | 36.34 | C |

FIG. 2A-54

| ATOM | 2483 | O   | GLN | B | 68 | 63.522 | 4.796  | 71.140 | 1.00  | 37.20 | O |
|------|------|-----|-----|---|----|--------|--------|--------|-------|-------|---|
| ATOM | 2484 | N   | VAL | B | 69 | 61.776 | 5.959  | 70.304 | 1.00  | 34.12 | N |
| ATOM | 2485 | CA  | VAL | B | 69 | 62.518 | 7.210  | 70.349 | 1.00  | 32.32 | C |
| ATOM | 2486 | CB  | VAL | B | 69 | 61.838 | 8.201  | 69.399 | 1.00  | 32.81 | C |
| ATOM | 2487 | CG1 | VAL | B | 69 | 62.485 | 9.577  | 69.534 | 1.00  | 30.99 | C |
| ATOM | 2488 | CG2 | VAL | B | 69 | 61.968 | 7.724  | 67.964 | 1.00  | 35.48 | C |
| ATOM | 2489 | C   | VAL | B | 69 | 62.553 | 7.778  | 71.771 | 1.00  | 29.76 | C |
| ATOM | 2490 | O   | VAL | B | 69 | 61.556 | 7.805  | 72.481 | 1.00  | 29.19 | O |
| ATOM | 2491 | N   | LEU | B | 70 | 63.741 | 8.225  | 72.178 | 1.00  | 27.71 | N |
| ATOM | 2492 | CA  | LEU | B | 70 | 63.905 | 8.867  | 73.462 | 1.00  | 26.62 | C |
| ATOM | 2493 | CB  | LEU | B | 70 | 65.365 | 8.798  | 73.907 | 1.00  | 27.65 | C |
| ATOM | 2494 | CG  | LEU | B | 70 | 65.937 | 7.418  | 74.292 | 1.00  | 27.86 | C |
| ATOM | 2495 | CD1 | LEU | B | 70 | 67.459 | 7.480  | 74.430 | 1.00  | 29.36 | C |
| ATOM | 2496 | CD2 | LEU | B | 70 | 65.302 | 6.969  | 75.589 | 1.00  | 27.08 | C |
| ATOM | 2497 | C   | LEU | B | 70 | 63.458 | 10.308 | 73.309 | 1.00* | 26.23 | C |
| ATOM | 2498 | O   | LEU | B | 70 | 62.869 | 10.882 | 74.191 | 1.00  | 27.21 | O |
| ATOM | 2499 | N   | GLY | B | 71 | 63.719 | 10.904 | 72.170 | 1.00  | 26.56 | N |
| ATOM | 2500 | CA  | GLY | B | 71 | 63.292 | 12.274 | 72.012 | 1.00  | 27.14 | C |
| ATOM | 2501 | C   | GLY | B | 71 | 63.656 | 12.876 | 70.683 | 1.00  | 28.29 | C |
| ATOM | 2502 | O   | GLY | B | 71 | 64.107 | 12.201 | 69.768 | 1.00  | 27.82 | O |
| ATOM | 2503 | N   | LEU | B | 72 | 63.406 | 14.168 | 70.574 | 1.00  | 29.09 | N |
| ATOM | 2504 | CA  | LEU | B | 72 | 63.743 | 14.920 | 69.380 | 1.00  | 29.63 | C |
| ATOM | 2505 | CB  | LEU | B | 72 | 62.509 | 15.597 | 68.794 | 1.00  | 27.99 | C |
| ATOM | 2506 | CG  | LEU | B | 72 | 61.303 | 14.726 | 68.441 | 1.00  | 31.07 | C |
| ATOM | 2507 | CD1 | LEU | B | 72 | 60.444 | 15.571 | 67.540 | 1.00  | 37.65 | C |
| ATOM | 2508 | CD2 | LEU | B | 72 | 61.658 | 13.442 | 67.703 | 1.00  | 31.96 | C |
| ATOM | 2509 | C   | LEU | B | 72 | 64.744 | 15.981 | 69.829 | 1.00  | 31.30 | C |
| ATOM | 2510 | O   | LEU | B | 72 | 64.437 | 16.796 | 70.700 | 1.00  | 30.66 | O |
| ATOM | 2511 | N   | GLY | B | 73 | 65.949 | 15.935 | 69.269 | 1.00  | 32.28 | N |
| ATOM | 2512 | CA  | GLY | B | 73 | 66.957 | 16.918 | 69.609 | 1.00  | 31.11 | C |
| ATOM | 2513 | C   | GLY | B | 73 | 67.140 | 17.894 | 68.463 | 1.00  | 33.35 | C |
| ATOM | 2514 | O   | GLY | B | 73 | 66.545 | 17.757 | 67.376 | 1.00  | 32.32 | O |
| ATOM | 2515 | N   | ILE | B | 74 | 67.948 | 18.906 | 68.707 | 1.00  | 33.59 | N |
| ATOM | 2516 | CA  | ILE | B | 74 | 68.217 | 19.880 | 67.673 | 1.00  | 34.98 | C |
| ATOM | 2517 | CB  | ILE | B | 74 | 69.294 | 20.858 | 68.131 | 1.00  | 34.59 | C |
| ATOM | 2518 | CG1 | ILE | B | 74 | 68.855 | 21.484 | 69.444 | 1.00  | 33.72 | C |
| ATOM | 2519 | CD1 | ILE | B | 74 | 69.937 | 22.222 | 70.128 | 1.00  | 34.06 | C |
| ATOM | 2520 | CG2 | ILE | B | 74 | 69.564 | 21.912 | 67.052 | 1.00  | 32.31 | C |
| ATOM | 2521 | C   | ILE | B | 74 | 68.696 | 19.156 | 66.404 | 1.00  | 36.21 | C |
| ATOM | 2522 | O   | ILE | B | 74 | 69.801 | 18.592 | 66.340 | 1.00  | 34.75 | O |
| ATOM | 2523 | N   | ASN | B | 75 | 67.836 | 19.147 | 65.398 | 1.00  | 37.98 | N |
| ATOM | 2524 | CA  | ASN | B | 75 | 68.169 | 18.531 | 64.119 | 1.00  | 38.57 | C |
| ATOM | 2525 | CB  | ASN | B | 75 | 69.516 | 19.067 | 63.641 | 1.00  | 38.49 | C |
| ATOM | 2526 | CG  | ASN | B | 75 | 69.600 | 20.591 | 63.731 | 1.00  | 43.53 | C |
| ATOM | 2527 | OD1 | ASN | B | 75 | 68.756 | 21.311 | 63.188 | 1.00  | 46.01 | O |
| ATOM | 2528 | ND2 | ASN | B | 75 | 70.614 | 21.089 | 64.421 | 1.00  | 42.28 | N |

FIG. 2A-55

| ATOM | 2529 | C | ASN | B | 75 | 68.172 | 17.006 | 64.089 | 1.00 | 37.40 | C |
|---|---|---|---|---|---|---|---|---|---|---|---|
| ATOM | 2530 | O | ASN | B | 75 | 68.677 | 16.433 | 63.151 | 1.00 | 39.35 | O |
| ATOM | 2531 | N | GLY | B | 76 | 67.600 | 16.337 | 65.082 | 1.00 | 36.48 | N |
| ATOM | 2532 | CA | GLY | B | 76 | 67.601 | 14.880 | 65.043 | 1.00 | 32.98 | C |
| ATOM | 2533 | C | GLY | B | 76 | 66.936 | 14.118 | 66.185 | 1.00 | 31.26 | C |
| ATOM | 2534 | O | GLY | B | 76 | 67.005 | 14.493 | 67.362 | 1.00 | 31.56 | O |
| ATOM | 2535 | N | ALA | B | 77 | 66.292 | 13.021 | 65.826 | 1.00 | 27.96 | N |
| ATOM | 2536 | CA | ALA | B | 77 | 65.626 | 12.172 | 66.790 | 1.00 | 25.89 | C |
| ATOM | 2537 | CB | ALA | B | 77 | 64.653 | 11.245 | 66.061 | 1.00 | 26.99 | C |
| ATOM | 2538 | C | ALA | B | 77 | 66.684 | 11.343 | 67.525 | 1.00 | 25.14 | C |
| ATOM | 2539 | O | ALA | B | 77 | 67.768 | 11.085 | 66.992 | 1.00 | 24.05 | O |
| ATOM | 2540 | N | VAL | B | 78 | 66.368 | 10.938 | 68.748 | 1.00 | 24.34 | N |
| ATOM | 2541 | CA | VAL | B | 78 | 67.276 | 10.120 | 69.542 | 1.00 | 23.96 | C |
| ATOM | 2542 | CB | VAL | B | 78 | 67.710 | 10.842 | 70.839 | 1.00 | 25.14 | C |
| ATOM | 2543 | CG1 | VAL | B | 78 | 68.613 | 9.940 | 71.640 | 1.00 | 25.01 | C |
| ATOM | 2544 | CG2 | VAL | B | 78 | 68.434 | 12.113 | 70.501 | 1.00 | 24.05 | C |
| ATOM | 2545 | C | VAL | B | 78 | 66.604 | 8.797 | 69.904 | 1.00 | 23.27 | C |
| ATOM | 2546 | O | VAL | B | 78 | 65.573 | 8.782 | 70.582 | 1.00 | 20.51 | O |
| ATOM | 2547 | N | LEU | B | 79 | 67.220 | 7.695 | 69.470 | 1.00 | 23.61 | N |
| ATOM | 2548 | CA | LEU | B | 79 | 66.687 | 6.347 | 69.697 | 1.00 | 24.68 | C |
| ATOM | 2549 | CB | LEU | B | 79 | 66.687 | 5.548 | 68.384 | 1.00 | 24.38 | C |
| ATOM | 2550 | CG | LEU | B | 79 | 65.794 | 5.997 | 67.224 | 1.00 | 28.37 | C |
| ATOM | 2551 | CD1 | LEU | B | 79 | 66.048 | 5.114 | 66.035 | 1.00 | 31.06 | C |
| ATOM | 2552 | CD2 | LEU | B | 79 | 64.325 | 5.865 | 67.600 | 1.00 | 39.59 | C |
| ATOM | 2553 | C | LEU | B | 79 | 67.447 | 5.522 | 70.732 | 1.00 | 24.73 | C |
| ATOM | 2554 | O | LEU | B | 79 | 68.588 | 5.809 | 71.055 | 1.00 | 23.57 | O |
| ATOM | 2555 | N | GLN | B | 80 | 66.801 | 4.487 | 71.262 | 1.00 | 25.65 | N |
| ATOM | 2556 | CA | GLN | B | 80 | 67.488 | 3.622 | 72.208 | 1.00 | 26.21 | C |
| ATOM | 2557 | CB | GLN | B | 80 | 66.513 | 3.053 | 73.238 | 1.00 | 24.26 | C |
| ATOM | 2558 | CG | GLN | B | 80 | 67.186 | 2.304 | 74.385 | 1.00 | 31.14 | C |
| ATOM | 2559 | CD | GLN | B | 80 | 67.682 | 3.224 | 75.540 | 1.00 | 43.25 | C |
| ATOM | 2560 | OE1 | GLN | B | 80 | 66.888 | 3.692 | 76.379 | 1.00 | 47.13 | O |
| ATOM | 2561 | NE2 | GLN | B | 80 | 69.006 | 3.471 | 75.586 | 1.00 | 46.35 | N |
| ATOM | 2562 | C | GLN | B | 80 | 68.105 | 2.496 | 71.365 | 1.00 | 25.99 | C |
| ATOM | 2563 | O | GLN | B | 80 | 67.546 | 2.098 | 70.338 | 1.00 | 28.15 | O |
| ATOM | 2564 | N | ILE | B | 81 | 69.270 | 2.008 | 71.758 | 1.00 | 25.92 | N |
| ATOM | 2565 | CA | ILE | B | 81 | 69.897 | 0.910 | 71.021 | 1.00 | 26.01 | C |
| ATOM | 2566 | CB | ILE | B | 81 | 70.818 | 1.423 | 69.847 | 1.00 | 26.76 | C |
| ATOM | 2567 | CG1 | ILE | B | 81 | 72.033 | 2.198 | 70.357 | 1.00 | 23.37 | C |
| ATOM | 2568 | CD1 | ILE | B | 81 | 72.956 | 2.588 | 69.202 | 1.00 | 15.18 | C |
| ATOM | 2569 | CG2 | ILE | B | 81 | 70.034 | 2.352 | 68.930 | 1.00 | 26.56 | C |
| ATOM | 2570 | C | ILE | B | 81 | 70.708 | 0.040 | 71.983 | 1.00 | 25.35 | C |
| ATOM | 2571 | O | ILE | B | 81 | 70.897 | 0.416 | 73.160 | 1.00 | 26.02 | O |
| ATOM | 2572 | N | PHE | B | 82 | 71.159 | -1.131 | 71.519 | 1.00 | 23.65 | N |
| ATOM | 2573 | CA | PHE | B | 82 | 71.953 | -2.009 | 72.391 | 1.00 | 22.36 | C |
| ATOM | 2574 | CB | PHE | B | 82 | 71.136 | -3.164 | 72.895 | 1.00 | 22.62 | C |

FIG. 2A-56

| ATOM | 2575 | CG | PHE | B | 82 | 69.908 | -2.760 | 73.591 | 1.00 | 23.87 | C |
|---|---|---|---|---|---|---|---|---|---|---|---|
| ATOM | 2576 | CD1 | PHE | B | 82 | 68.794 | -2.394 | 72.873 | 1.00 | 25.23 | C |
| ATOM | 2577 | CE1 | PHE | B | 82 | 67.647 | -2.005 | 73.520 | 1.00 | 26.81 | C |
| ATOM | 2578 | CZ | PHE | B | 82 | 67.604 | -1.979 | 74.906 | 1.00 | 25.26 | C |
| ATOM | 2579 | CE2 | PHE | B | 82 | 68.719 | -2.347 | 75.623 | 1.00 | 23.52 | C |
| ATOM | 2580 | CD2 | PHE | B | 82 | 69.865 | -2.736 | 74.957 | 1.00 | 23.37 | C |
| ATOM | 2581 | C | PHE | B | 82 | 73.149 | -2.587 | 71.705 | 1.00 | 21.83 | C |
| ATOM | 2582 | O | PHE | B | 82 | 73.113 | -2.860 | 70.508 | 1.00 | 21.48 | O |
| ATOM | 2583 | N | ASN | B | 83 | 74.215 | -2.779 | 72.472 | 1.00 | 21.50 | N |
| ATOM | 2584 | CA | ASN | B | 83 | 75.441 | -3.346 | 71.944 | 1.00 | 20.90 | C |
| ATOM | 2585 | CB | ASN | B | 83 | 76.589 | -3.053 | 72.888 | 1.00 | 19.92 | C |
| ATOM | 2586 | CG | ASN | B | 83 | 77.891 | -3.673 | 72.432 | 1.00 | 20.30 | C |
| ATOM | 2587 | OD1 | ASN | B | 83 | 78.072 | -4.889 | 72.489 | 1.00 | 25.22 | O |
| ATOM | 2588 | ND2 | ASN | B | 83 | 78.810 | -2.841 | 71.970 | 1.00 | 24.42 | N |
| ATOM | 2589 | C | ASN | B | 83 | 75.202 | -4.840 | 71.811 | 1.00 | 22.26 | C |
| ATOM | 2590 | O | ASN | B | 83 | 75.045 | -5.564 | 72.780 | 1.00 | 21.17 | O |
| ATOM | 2591 | N | LYS | B | 84 | 75.131 | -5.306 | 70.580 | 1.00 | 24.63 | N |
| ATOM | 2592 | CA | LYS | B | 84 | 74.882 | -6.709 | 70.332 | 1.00 | 26.60 | C |
| ATOM | 2593 | CB | LYS | B | 84 | 75.117 | -7.044 | 68.845 | 1.00 | 27.47 | C |
| ATOM | 2594 | CG | LYS | B | 84 | 74.012 | -6.602 | 67.881 | 1.00 | 29.69 | C |
| ATOM | 2595 | CD | LYS | B | 84 | 74.453 | -6.909 | 66.452 | 1.00 | 38.80 | C |
| ATOM | 2596 | CE | LYS | B | 84 | 73.297 | -7.125 | 65.453 | 1.00 | 44.26 | C |
| ATOM | 2597 | NZ | LYS | B | 84 | 72.315 | -5.988 | 65.193 | 1.00 | 48.10 | N |
| ATOM | 2598 | C | LYS | B | 84 | 75.696 | -7.648 | 71.220 | 1.00 | 26.98 | C |
| ATOM | 2599 | O | LYS | B | 84 | 75.134 | -8.572 | 71.777 | 1.00 | 27.71 | O |
| ATOM | 2600 | N | ARG | B | 85 | 76.996 | -7.415 | 71.381 | 1.00 | 27.79 | N |
| ATOM | 2601 | CA | ARG | B | 85 | 77.901 | -8.209 | 72.201 | 1.00 | 29.03 | C |
| ATOM | 2602 | CB | ARG | B | 85 | 79.322 | -7.717 | 71.940 | 1.00 | 30.67 | C |
| ATOM | 2603 | CG | ARG | B | 85 | 79.862 | -8.233 | 70.608 | 1.00 | 32.80 | C |
| ATOM | 2604 | CD | ARG | B | 85 | 81.391 | -8.177 | 70.548 | 1.00 | 37.34 | C |
| ATOM | 2605 | NE | ARG | B | 85 | 81.977 | -9.153 | 71.471 | 1.00 | 38.87 | N |
| ATOM | 2606 | CZ | ARG | B | 85 | 83.221 | -8.903 | 71.916 | 1.00 | 40.68 | C |
| ATOM | 2607 | NH1AR | G | B | 85 | 83.854 | -7.808 | 71.527 | 1.00 | 37.67 | N |
| ATOM | 2608 | NH2AR | G | B | 85 | 83.824 | -9.779 | 72.722 | 1.00 | 38.29 | N |
| ATOM | 2609 | C | ARG | B | 85 | 77.570 | -8.124 | 73.695 | 1.00 | 29.53 | C |
| ATOM | 2610 | O | ARG | B | 85 | 77.398 | -9.126 | 74.378 | 1.00 | 29.53 | O |
| ATOM | 2611 | N | THR | B | 86 | 77.523 | -6.880 | 74.215 | 1.00 | 27.98 | N |
| ATOM | 2612 | CA | THR | B | 86 | 77.295 | -6.715 | 75.651 | 1.00 | 28.24 | C |
| ATOM | 2613 | CB | THR | B | 86 | 77.974 | -5.428 | 76.115 | 1.00 | 28.56 | C |
| ATOM | 2614 | OG1 | THR | B | 86 | 77.340 | -4.305 | 75.493 | 1.00 | 30.68 | O |
| ATOM | 2615 | CG2 | THR | B | 86 | 79.450 | -5.444 | 75.720 | 1.00 | 29.43 | C |
| ATOM | 2616 | C | THR | B | 86 | 75.808 | -6.678 | 76.005 | 1.00 | 28.85 | C |
| ATOM | 2617 | O | THR | B | 86 | 75.368 | -7.197 | 77.018 | 1.00 | 29.18 | O |
| ATOM | 2618 | N | GLN | B | 87 | 75.020 | -5.999 | 75.148 | 1.00 | 31.43 | N |
| ATOM | 2619 | CA | GLN | B | 87 | 73.580 | -5.970 | 75.374 | 1.00 | 33.06 | C |
| ATOM | 2620 | CB | GLN | B | 87 | 73.197 | -7.252 | 76.113 | 1.00 | 34.30 | C |

FIG. 2A-57

| ATOM | 2621 | CG | GLN | B | 87 | 71.689 | -7.492 | 76.120 | 1.00 | 40.48 | C |
|------|------|-----|-----|---|----|--------|--------|--------|------|-------|---|
| ATOM | 2622 | CD | GLN | B | 87 | 71.389 | -8.787 | 75.404 | 1.00 | 52.24 | C |
| ATOM | 2623 | OE1 | GLN | B | 87 | 70.259 | -9.220 | 75.264 | 1.00 | 56.74 | O |
| ATOM | 2624 | NE2 | GLN | B | 87 | 72.485 | -9.417 | 74.937 | 1.00 | 54.43 | N |
| ATOM | 2625 | C | GLN | B | 87 | 73.146 | -4.752 | 76.198 | 1.00 | 32.36 | C |
| ATOM | 2626 | O | GLN | B | 87 | 71.986 | -4.581 | 76.557 | 1.00 | 32.47 | O |
| ATOM | 2627 | N | GLU | B | 88 | 74.138 | -3.910 | 76.536 | 1.00 | 31.86 | N |
| ATOM | 2628 | CA | GLU | B | 88 | 73.829 | -2.726 | 77.326 | 1.00 | 32.58 | C |
| ATOM | 2629 | CB | GLU | B | 88 | 75.075 | -2.349 | 78.124 | 1.00 | 33.66 | C |
| ATOM | 2630 | CG | GLU | B | 88 | 76.206 | -1.840 | 77.230 | 1.00 | 42.92 | C |
| ATOM | 2631 | CD | GLU | B | 88 | 77.455 | -1.660 | 78.060 | 1.00 | 51.15 | C |
| ATOM | 2632 | OE1 | GLU | B | 88 | 77.369 | -1.753 | 79.276 | 1.00 | 51.85 | O |
| ATOM | 2633 | OE2 | GLU | B | 88 | 78.510 | -1.425 | 77.477 | 1.00 | 52.70 | O |
| ATOM | 2634 | C | GLU | B | 88 | 73.396 | -1.550 | 76.448 | 1.00 | 31.16 | C |
| ATOM | 2635 | O | GLU | B | 88 | 73.590 | -1.544 | 75.239 | 1.00 | 31.32 | O |
| ATOM | 2636 | N | LYS | B | 89 | 72.591 | -0.652 | 77.010 | 1.00 | 30.93 | N |
| ATOM | 2637 | CA | LYS | B | 89 | 71.959 | 0.354 | 76.143 | 1.00 | 29.74 | C |
| ATOM | 2638 | CB | LYS | B | 89 | 70.458 | 0.465 | 76.450 | 1.00 | 29.11 | C |
| ATOM | 2639 | CG | LYS | B | 89 | 70.123 | 0.636 | 77.880 | 1.00 | 30.03 | C |
| ATOM | 2640 | CD | LYS | B | 89 | 68.800 | 1.349 | 78.002 | 1.00 | 38.43 | C |
| ATOM | 2641 | CE | LYS | B | 89 | 68.638 | 1.999 | 79.383 | 1.00 | 40.78 | C |
| ATOM | 2642 | NZ | LYS | B | 89 | 67.682 | 3.154 | 79.300 | 1.00 | 46.24 | N |
| ATOM | 2643 | C | LYS | B | 89 | 72.555 | 1.767 | 76.040 | 1.00 | 29.06 | C |
| ATOM | 2644 | O | LYS | B | 89 | 73.004 | 2.366 | 77.025 | 1.00 | 29.67 | O |
| ATOM | 2645 | N | PHE | B | 90 | 72.540 | 2.275 | 74.816 | 1.00 | 26.99 | N |
| ATOM | 2646 | CA | PHE | B | 90 | 73.052 | 3.595 | 74.519 | 1.00 | 25.61 | C |
| ATOM | 2647 | CB | PHE | B | 90 | 74.299 | 3.498 | 73.634 | 1.00 | 25.64 | C |
| ATOM | 2648 | CG | PHE | B | 90 | 75.427 | 2.694 | 74.234 | 1.00 | 22.17 | C |
| ATOM | 2649 | CD1 | PHE | B | 90 | 75.339 | 1.312 | 74.336 | 1.00 | 19.57 | C |
| ATOM | 2650 | CE1 | PHE | B | 90 | 76.421 | 0.557 | 74.798 | 1.00 | 17.08 | C |
| ATOM | 2651 | CZ | PHE | B | 90 | 77.603 | 1.179 | 75.169 | 1.00 | 18.02 | C |
| ATOM | 2652 | CE2 | PHE | B | 90 | 77.704 | 2.564 | 75.087 | 1.00 | 20.94 | C |
| ATOM | 2653 | CD2 | PHE | B | 90 | 76.616 | 3.317 | 74.621 | 1.00 | 21.93 | C |
| ATOM | 2654 | C | PHE | B | 90 | 71.981 | 4.393 | 73.789 | 1.00 | 24.90 | C |
| ATOM | 2655 | O | PHE | B | 90 | 70.979 | 3.834 | 73.357 | 1.00 | 25.74 | O |
| ATOM | 2656 | N | ALA | B | 91 | 72.171 | 5.702 | 73.682 | 1.00 | 22.21 | N |
| ATOM | 2657 | CA | ALA | B | 91 | 71.227 | 6.523 | 72.951 | 1.00 | 23.16 | C |
| ATOM | 2658 | CB | ALA | B | 91 | 71.016 | 7.801 | 73.640 | 1.00 | 25.12 | C |
| ATOM | 2659 | C | ALA | B | 91 | 71.881 | 6.769 | 71.616 | 1.00 | 23.30 | C |
| ATOM | 2660 | O | ALA | B | 91 | 73.090 | 6.718 | 71.493 | 1.00 | 26.79 | O |
| ATOM | 2661 | N | LEU | B | 92 | 71.098 | 7.043 | 70.602 | 1.00 | 22.44 | N |
| ATOM | 2662 | CA | LEU | B | 92 | 71.658 | 7.259 | 69.288 | 1.00 | 22.64 | C |
| ATOM | 2663 | CB | LEU | B | 92 | 71.436 | 6.047 | 68.393 | 1.00 | 21.83 | C |
| ATOM | 2664 | CG | LEU | B | 92 | 71.845 | 6.352 | 66.956 | 1.00 | 24.47 | C |
| ATOM | 2665 | CD1 | LEU | B | 92 | 73.371 | 6.326 | 66.874 | 1.00 | 27.29 | C |
| ATOM | 2666 | CD2 | LEU | B | 92 | 71.246 | 5.340 | 65.984 | 1.00 | 24.25 | C |

FIG. 2A-58

| | | | | | | | | | | |
|---|---|---|---|---|---|---|---|---|---|---|
| ATOM | 2667 | C | LEU | B | 92 | 70.971 | 8.434 | 68.667 | 1.00 | 23.71 C |
| ATOM | 2668 | O | LEU | B | 92 | 69.730 | 8.471 | 68.597 | 1.00 | 23.60 O |
| ATOM | 2669 | N | LYS | B | 93 | 71.774 | 9.408 | 68.240 | 1.00 | 24.64 N |
| ATOM | 2670 | CA | LYS | B | 93 | 71.216 | 10.580 | 67.590 | 1.00 | 25.65 C |
| ATOM | 2671 | CB | LYS | B | 93 | 71.825 | 11.878 | 68.120 | 1.00 | 24.01 C |
| ATOM | 2672 | CG | LYS | B | 93 | 71.135 | 13.133 | 67.585 | 1.00 | 25.11 C |
| ATOM | 2673 | CD | LYS | B | 93 | 71.710 | 14.374 | 68.229 | 1.00 | 25.99 C |
| ATOM | 2674 | CE | LYS | B | 93 | 71.004 | 15.652 | 67.790 | 1.00 | 28.63 C |
| ATOM | 2675 | NZ | LYS | B | 93 | 71.660 | 16.885 | 68.350 | 1.00 | 30.77 N |
| ATOM | 2676 | C | LYS | B | 93 | 71.488 | 10.451 | 66.121 | 1.00 | 25.58 C |
| ATOM | 2677 | O | LYS | B | 93 | 72.592 | 10.123 | 65.712 | 1.00 | 26.99 O |
| ATOM | 2678 | N | MSE | B | 94 | 70.461 | 10.673 | 65.326 | 1.00 | 25.19 N |
| ATOM | 2679 | CA | MSE | B | 94 | 70.609 | 10.595 | 63.894 | 1.00 | 25.82 C |
| ATOM | 2680 | CB | MSE | B | 94 | 69.533 | 9.718 | 63.317 | 1.00 | 23.85 C |
| ATOM | 2681 | CG | MSE | B | 94 | 69.401 | 8.381 | 63.992 | 1.00 | 29.52 C |
| ATOM | 2682 | SE | MSE | B | 94 | 68.113 | 7.313 | 62.982 | 1.00 | 48.35 S |
| ATOM | 2683 | CE | MSE | B | 94 | 68.928 | 7.480 | 61.191 | 1.00 | 28.08 C |
| ATOM | 2684 | C | MSE | B | 94 | 70.529 | 11.988 | 63.257 | 1.00 | 26.51 C |
| ATOM | 2685 | O | MSE | B | 94 | 69.593 | 12.765 | 63.460 | 1.00 | 27.66 O |
| ATOM | 2686 | N | LEU | B | 95 | 71.542 | 12.306 | 62.487 | 1.00 | 26.47 N |
| ATOM | 2687 | CA | LEU | B | 95 | 71.575 | 13.569 | 61.810 | 1.00 | 28.10 C |
| ATOM | 2688 | CB | LEU | B | 95 | 72.757 | 14.415 | 62.290 | 1.00 | 27.10 C |
| ATOM | 2689 | CG | LEU | B | 95 | 72.890 | 14.806 | 63.745 | 1.00 | 27.10 C |
| ATOM | 2690 | CD1 | LEU | B | 95 | 74.117 | 15.677 | 63.937 | 1.00 | 23.82 C |
| ATOM | 2691 | CD2 | LEU | B | 95 | 71.630 | 15.525 | 64.150 | 1.00 | 28.63 C |
| ATOM | 2692 | C | LEU | B | 95 | 71.803 | 13.262 | 60.339 | 1.00 | 28.25 C |
| ATOM | 2693 | O | LEU | B | 95 | 72.479 | 12.280 | 59.998 | 1.00 | 27.05 O |
| ATOM | 2694 | N | GLN | B | 96 | 71.228 | 14.094 | 59.479 | 1.00 | 28.48 N |
| ATOM | 2695 | CA | GLN | B | 96 | 71.471 | 13.957 | 58.074 | 1.00 | 30.59 C |
| ATOM | 2696 | CB | GLN | B | 96 | 70.432 | 14.741 | 57.286 | 1.00 | 31.83 C |
| ATOM | 2697 | CG | GLN | B | 96 | 69.085 | -14.013 | 57.214 | 1.00 | 40.49 C |
| ATOM | 2698 | CD | GLN | B | 96 | 67.995 | 14.795 | 56.458 | 1.00 | 46.51 C |
| ATOM | 2699 | OE1 | GLN | B | 96 | 68.086 | 14.972 | 55.247 | 1.00 | 47.20 O |
| ATOM | 2700 | NE2 | GLN | B | 96 | 66.966 | 15.262 | 57.184 | 1.00 | 48.54 N |
| ATOM | 2701 | C | GLN | B | 96 | 72.867 | 14.573 | 57.937 | 1.00 | 29.67 C |
| ATOM | 2702 | O | GLN | B | 96 | 73.176 | 15.589 | 58.570 | 1.00 | 28.46 O |
| ATOM | 2703 | N | ASP | B | 97 | 73.727 | 13.944 | 57.146 | 1.00 | 29.73 N |
| ATOM | 2704 | CA | ASP | B | 97 | 75.088 | 14.451 | 57.025 | 1.00 | 31.44 C |
| ATOM | 2705 | CB | ASP | B | 97 | 75.903 | 13.432 | 56.229 | 1.00 | 32.65 C |
| ATOM | 2706 | CG | ASP | B | 97 | 77.386 | 13.722 | 56.404 | 1.00 | 40.60 C |
| ATOM | 2707 | OD1 | ASP | B | 97 | 77.710 | 14.870 | 56.716 | 1.00 | 45.48 O |
| ATOM | 2708 | OD2 | ASP | B | 97 | 78.192 | 12.812 | 56.232 | 1.00 | 49.59 O |
| ATOM | 2709 | C | ASP | B | 97 | 75.137 | 15.817 | 56.329 | 1.00 | 30.19 C |
| ATOM | 2710 | O | ASP | B | 97 | 74.523 | 16.051 | 55.296 | 1.00 | 31.64 O |
| ATOM | 2711 | N | CYS | B | 98 | 75.875 | 16.747 | 56.961 | 1.00 | 29.93 N |
| ATOM | 2712 | CA | CYS | B | 98 | 76.052 | 18.067 | 56.365 | 1.00 | 27.73 C |

FIG. 2A-59

| ATOM | 2713 | CB | CYS | B | 98 | 74.683 | 18.743 | 56.264 | 1.00 | 25.06 | C |
|---|---|---|---|---|---|---|---|---|---|---|---|
| ATOM | 2714 | SG | CYS | B | 98 | 73.878 | 18.914 | 57.873 | 1.00 | 25.94 | S |
| ATOM | 2715 | C | CYS | B | 98 | 77.001 | 18.926 | 57.200 | 1.00 | 27.81 | C |
| ATOM | 2716 | O | CYS | B | 98 | 77.490 | 18.529 | 58.250 | 1.00 | 27.66 | O |
| ATOM | 2717 | N | PRO | B | 99 | 77.295 | 20.128 | 56.677 | 1.00 | 27.92 | N |
| ATOM | 2718 | CA | PRO | B | 99 | 78.186 | 21.056 | 57.356 | 1.00 | 28.19 | C |
| ATOM | 2719 | CB | PRO | B | 99 | 78.097 | 22.393 | 56.625 | 1.00 | 28.94 | C |
| ATOM | 2720 | CG | PRO | B | 99 | 77.550 | 22.118 | 55.227 | 1.00 | 28.34 | C |
| ATOM | 2721 | CD | PRO | B | 99 | 76.821 | 20.704 | 55.427 | 1.00 | 27.05 | C |
| ATOM | 2722 | C | PRO | B | 99 | 77.805 | 21.239 | 58.830 | 1.00 | 28.28 | C |
| ATOM | 2723 | O | PRO | B | 99 | 78.611 | 21.083 | 59.734 | 1.00 | 28.26 | O |
| ATOM | 2724 | N | LYS | B | 100 | 76.530 | 21.612 | 59.049 | 1.00 | 28.75 | N |
| ATOM | 2725 | CA | LYS | B | 100 | 76.063 | 21.842 | 60.410 | 1.00 | 27.98 | C |
| ATOM | 2726 | CB | LYS | B | 100 | 74.595 | 22.261 | 60.341 | 1.00 | 28.93 | C |
| ATOM | 2727 | CG | LYS | B | 100 | 74.334 | 23.596 | 61.043 | 1.00 | 33.18 | C |
| ATOM | 2728 | CD | LYS | B | 100 | 73.101 | 24.313 | 60.492 | 1.00 | 44.32 | C |
| ATOM | 2729 | CE | LYS | B | 100 | 73.393 | 25.762 | 60.088 | 1.00 | 52.70 | C |
| ATOM | 2730 | NZ | LYS | B | 100 | 72.153 | 26.429 | 59.694 | 1.00 | 53.68 | N |
| ATOM | 2731 | C | LYS | B | 100 | 76.208 | 20.591 | 61.285 | 1.00 | 27.47 | C |
| ATOM | 2732 | O | LYS | B | 100 | 76.770 | 20.620 | 62.371 | 1.00 | 31.42 | O |
| ATOM | 2733 | N | ALA | B | 101 | 75.705 | 19.438 | 60.865 | 1.00 | 26.69 | N |
| ATOM | 2734 | CA | ALA | B | 101 | 75.827 | 18.210 | 61.649 | 1.00 | 24.02 | C |
| ATOM | 2735 | CB | ALA | B | 101 | 75.178 | 17.049 | 60.942 | 1.00 | 22.89 | C |
| ATOM | 2736 | C | ALA | B | 101 | 77.271 | 17.873 | 61.868 | 1.00 | 23.86 | C |
| ATOM | 2737 | O | ALA | B | 101 | 77.633 | 17.366 | 62.925 | 1.00 | 25.91 | O |
| ATOM | 2738 | N | ARG | B | 102 | 78.121 | 18.125 | 60.880 | 1.00 | 25.46 | N |
| ATOM | 2739 | CA | ARG | B | 102 | 79.509 | 17.795 | 61.083 | 1.00 | 25.70 | C |
| ATOM | 2740 | CB | ARG | B | 102 | 80.263 | 17.739 | 59.764 | 1.00 | 23.93 | C |
| ATOM | 2741 | CG | ARG | B | 102 | 81.201 | 16.528 | 59.766 | 1.00 | 32.57 | C |
| ATOM | 2742 | CD | ARG | B | 102 | 80.791 | 15.588 | 58.710 | 1.00 | 32.81 | C |
| ATOM | 2743 | NE | ARG | B | 102 | 81.460 | 14.280 | 58.680 | 1.00 | 33.20 | N |
| ATOM | 2744 | CZ | ARG | B | 102 | 81.302 | 13.343 | 57.752 | 1.00 | 33.71 | C |
| ATOM | 2745 | NH1AR | G | B | 102 | 81.962 | 12.200 | 57.833 | 1.00 | 41.03 | N |
| ATOM | 2746 | NH2AR | G | B | 102 | 80.524 | 13.594 | 56.703 | 1.00 | 38.32 | N |
| ATOM | 2747 | C | ARG | B | 102 | 80.145 | 18.729 | 62.077 | 1.00 | 26.24 | C |
| ATOM | 2748 | O | ARG | B | 102 | 81.176 | 18.426 | 62.679 | 1.00 | 25.37 | O |
| ATOM | 2749 | N | ARG | B | 103 | 79.478 | 19.856 | 62.288 | 1.00 | 27.67 | N |
| ATOM | 2750 | CA | ARG | B | 103 | 79.936 | 20.843 | 63.237 | 1.00 | 27.70 | C |
| ATOM | 2751 | CB | ARG | B | 103 | 79.222 | 22.175 | 62.988 | 1.00 | 30.24 | C |
| ATOM | 2752 | CG | ARG | B | 103 | 79.673 | 23.314 | 63.913 | 1.00 | 37.39 | C |
| ATOM | 2753 | CD | ARG | B | 103 | 79.028 | 24.680 | 63.561 | 1.00 | 51.63 | C |
| ATOM | 2754 | NE | ARG | B | 103 | 77.602 | 24.751 | 63.872 | 1.00 | 60.79 | N |
| ATOM | 2755 | CZ | ARG | B | 103 | 76.903 | 25.889 | 63.925 | 1.00 | 66.03 | C |
| ATOM | 2756 | NH1AR | G | B | 103 | 77.513 | 27.043 | 63.675 | 1.00 | 67.33 | N |
| ATOM | 2757 | NH2AR | G | B | 103 | 75.607 | 25.880 | 64.251 | 1.00 | 67.32 | N |
| ATOM | 2758 | C | ARG | B | 103 | 79.584 | 20.317 | 64.604 | 1.00 | 26.31 | C |

FIG. 2A-60

| ATOM | 2759 | O | ARG | B | 103 | 80.348 | 20.398 | 65.533 | 1.00 | 25.87 | O |
|---|---|---|---|---|---|---|---|---|---|---|---|
| ATOM | 2760 | N | GLU | B | 104 | 78.405 | 19.762 | 64.733 | 1.00 | 25.59 | N |
| ATOM | 2761 | CA | GLU | B | 104 | 77.987 | 19.267 | 66.021 | 1.00 | 25.43 | C |
| ATOM | 2762 | CB | GLU | B | 104 | 76.550 | 18.780 | 65.926 | 1.00 | 24.30 | C |
| ATOM | 2763 | CG | GLU | B | 104 | 75.903 | 18.441 | 67.223 | 1.00 | 30.02 | C |
| ATOM | 2764 | CD | GLU | B | 104 | 74.502 | 17.874 | 67.029 | 1.00 | 37.80 | C |
| ATOM | 2765 | OE1 | GLU | B | 104 | 73.753 | 18.442 | 66.209 | 1.00 | 40.19 | O |
| ATOM | 2766 | OE2 | GLU | B | 104 | 74.137 | 16.871 | 67.690 | 1.00 | 38.01 | O |
| ATOM | 2767 | C | GLU | B | 104 | 78.900 | 18.136 | 66.502 | 1.00 | 25.50 | C |
| ATOM | 2768 | O | GLU | B | 104 | 79.394 | 18.165 | 67.634 | 1.00 | 26.84 | O |
| ATOM | 2769 | N | VAL | B | 105 | 79.150 | 17.154 | 65.634 | 1.00 | 25.42 | N |
| ATOM | 2770 | CA | VAL | B | 105 | 79.929 | 16.004 | 66.030 | 1.00 | 25.72 | C |
| ATOM | 2771 | CB | VAL | B | 105 | 80.044 | 15.006 | 64.902 | 1.00 | 25.92 | C |
| ATOM | 2772 | CG1 | VAL | B | 105 | 81.154 | 14.008 | 65.185 | 1.00 | 27.20 | C |
| ATOM | 2773 | CG2 | VAL | B | 105 | 78.729 | 14.269 | 64.781 | 1.00 | 26.18 | C |
| ATOM | 2774 | C | VAL | B | 105 | 81.256 | 16.398 | 66.506 | 1.00 | 25.99 | C |
| ATOM | 2775 | O | VAL | B | 105 | 81.680 | 16.007 | 67.591 | 1.00 | 27.42 | O |
| ATOM | 2776 | N | GLU | B | 106 | 81.905 | 17.217 | 65.706 | 1.00 | 26.85 | N |
| ATOM | 2777 | CA | GLU | B | 106 | 83.224 | 17.717 | 66.045 | 1.00 | 28.41 | C |
| ATOM | 2778 | CB | GLU | B | 106 | 83.712 | 18.654 | 64.959 | 1.00 | 29.19 | C |
| ATOM | 2779 | CG | GLU | B | 106 | 85.129 | 19.081 | 65.114 | 1.00 | 41.17 | C |
| ATOM | 2780 | CD | GLU | B | 106 | 85.652 | 19.691 | 63.826 | 1.00 | 61.61 | C |
| ATOM | 2781 | OE1 | GLU | B | 106 | 84.861 | 20.415 | 63.155 | 1.00 | 67.60 | O |
| ATOM | 2782 | OE2 | GLU | B | 106 | 86.846 | 19.452 | 63.485 | 1.00 | 66.00 | O |
| ATOM | 2783 | C | GLU | B | 106 | 83.227 | 18.455 | 67.364 | 1.00 | 28.17 | C |
| ATOM | 2784 | O | GLU | B | 106 | 84.089 | 18.211 | 68.182 | 1.00 | 27.98 | O |
| ATOM | 2785 | N | LEU | B | 107 | 82.273 | 19.354 | 67.581 | 1.00 | 26.24 | N |
| ATOM | 2786 | CA | LEU | B | 107 | 82.264 | 20.095 | 68.821 | 1.00 | 24.35 | C |
| ATOM | 2787 | CB | LEU | B | 107 | 81.302 | 21.308 | 68.764 | 1.00 | 23.56 | C |
| ATOM | 2788 | CG | LEU | B | 107 | 81.648 | 22.427 | 67.776 | 1.00 | 24.50 | C |
| ATOM | 2789 | CD1 | LEU | B | 107 | 80.557 | 23.469 | 67.788 | 1.00 | 23.86 | C |
| ATOM | 2790 | CD2 | LEU | B | 107 | 83.012 | 23.061 | 68.149 | 1.00 | 21.45 | C |
| ATOM | 2791 | C | LEU | B | 107 | 81.868 | 19.186 | 69.966 | 1.00 | 24.70 | C |
| ATOM | 2792 | O | LEU | B | 107 | 82.429 | 19.287 | 71.056 | 1.00 | 25.03 | O |
| ATOM | 2793 | N | HIS | B | 108 | 80.897 | 18.304 | 69.743 | 1.00 | 23.92 | N |
| ATOM | 2794 | CA | HIS | B | 108 | 80.486 | 17.433 | 70.823 | 1.00 | 23.72 | C |
| ATOM | 2795 | CB | HIS | B | 108 | 79.270 | 16.613 | 70.424 | 1.00 | 23.90 | C |
| ATOM | 2796 | CG | HIS | B | 108 | 78.633 | 15.887 | 71.561 | 1.00 | 22.80 | C |
| ATOM | 2797 | ND1 | HIS | B | 108 | 77.363 | 15.366 | 71.483 | 1.00 | 29.69 | N |
| ATOM | 2798 | CE1 | HIS | B | 108 | 77.083 | 14.717 | 72.601 | 1.00 | 32.73 | C |
| ATOM | 2799 | NE2 | HIS | B | 108 | 78.127 | 14.801 | 73.405 | 1.00 | 27.69 | N |
| ATOM | 2800 | CD2 | HIS | B | 108 | 79.108 | 15.534 | 72.775 | 1.00 | 19.18 | C |
| ATOM | 2801 | C | HIS | B | 108 | 81.671 | 16.545 | 71.139 | 1.00 | 23.78 | C |
| ATOM | 2802 | O | HIS | B | 108 | 81.965 | 16.333 | 72.309 | 1.00 | 21.61 | O |
| ATOM | 2803 | N | TRP | B | 109 | 82.376 | 16.056 | 70.113 | 1.00 | 23.70 | N |
| ATOM | 2804 | CA | TRP | B | 109 | 83.529 | 15.220 | 70.380 | 1.00 | 22.99 | C |

FIG. 2A-61

| ATOM | 2805 | CB | TRP | B | 109 | 84.279 | 14.860 | 69.103 | 1.00 | 23.16 | C |
| --- | --- | --- | --- | --- | --- | --- | --- | --- | --- | --- | --- |
| ATOM | 2806 | CG | TRP | B | 109 | 85.483 | 13.944 | 69.370 | 1.00 | 20.15 | C |
| ATOM | 2807 | CD1 | TRP | B | 109 | 86.804 | 14.229 | 69.157 | 1.00 | 20.22 | C |
| ATOM | 2808 | NE1 | TRP | B | 109 | 87.597 | 13.172 | 69.548 | 1.00 | 12.02 | N |
| ATOM | 2809 | CE2 | TRP | B | 109 | 86.785 | 12.175 | 70.023 | 1.00 | 17.64 | C |
| ATOM | 2810 | CD2 | TRP | B | 109 | 85.448 | 12.628 | 69.925 | 1.00 | 18.02 | C |
| ATOM | 2811 | CE3 | TRP | B | 109 | 84.419 | 11.787 | 70.351 | 1.00 | 16.93 | C |
| ATOM | 2812 | CZ3 | TRP | B | 109 | 84.749 | 10.538 | 70.863 | 1.00 | 17.52 | C |
| ATOM | 2813 | CH2 | TRP | B | 109 | 86.086 | 10.112 | 70.955 | 1.00 | 14.17 | C |
| ATOM | 2814 | CZ2 | TRP | B | 109 | 87.115 | 10.904 | 70.539 | 1.00 | 16.22 | C |
| ATOM | 2815 | C | TRP | B | 109 | 84.492 | 15.907 | 71.366 | 1.00 | 24.78 | C |
| ATOM | 2816 | O | TRP | B | 109 | 84.777 | 15.351 | 72.429 | 1.00 | 27.79 | O |
| ATOM | 2817 | N | ARG | B | 110 | 84.984 | 17.099 | 71.035 | 1.00 | 22.84 | N |
| ATOM | 2818 | CA | ARG | B | 110 | 85.900 | 17.797 | 71.920 | 1.00 | 22.19 | C |
| ATOM | 2819 | CB | ARG | B | 110 | 86.304 | 19.124 | 71.307 | 1.00 | 21.28 | C |
| ATOM | 2820 | CG | ARG | B | 110 | 86.910 | 18.994 | 69.981 | 1.00 | 21.94 | C |
| ATOM | 2821 | CD | ARG | B | 110 | 87.877 | 20.099 | 69.718 | 1.00 | 22.73 | C |
| ATOM | 2822 | NE | ARG | B | 110 | 87.259 | 21.217 | 69.028 | 1.00 | 25.57 | N |
| ATOM | 2823 | CZ | ARG | B | 110 | 87.283 | 22.486 | 69.450 | 1.00 | 32.91 | C |
| ATOM | 2824 | NH1AR | G | B | 110 | 87.877 | 22.863 | 70.586 | 1.00 | 30.14 | N |
| ATOM | 2825 | NH2AR | G | B | 110 | 86.743 | 23.412 | 68.681 | 1.00 | 39.32 | N |
| ATOM | 2826 | C | ARG | B | 110 | 85.336 | 18.056 | 73.328 | 1.00 | 24.85 | C |
| ATOM | 2827 | O | ARG | B | 110 | 86.034 | 17.850 | 74.331 | 1.00 | 27.61 | O |
| ATOM | 2828 | N | ALA | B | 111 | 84.098 | 18.524 | 73.424 | 1.00 | 26.06 | N |
| ATOM | 2829 | CA | ALA | B | 111 | 83.516 | 18.793 | 74.728 | 1.00 | 25.47 | C |
| ATOM | 2830 | CB | ALA | B | 111 | 82.082 | 19.293 | 74.579 | 1.00 | 24.92 | C |
| ATOM | 2831 | C | ALA | B | 111 | 83.530 | 17.515 | 75.556 | 1.00 | 26.80 | C |
| ATOM | 2832 | O | ALA | B | 111 | 83.475 | 17.562 | 76.784 | 1.00 | 26.36 | O |
| ATOM | 2833 | N | SER | B | 112 | 83.591 | 16.379 | 74.869 | 1.00 | 27.21 | N |
| ATOM | 2834 | CA | SER | B | 112 | 83.583 | 15.082 | 75.514 | 1.00 | 28.83 | C |
| ATOM | 2835 | CB | SER | B | 112 | 83.564 | 13.982 | 74.481 | 1.00 | 27.66 | C |
| ATOM | 2836 | OG | SER | B | 112 | 83.465 | 12.735 | 75.128 | 1.00 | 48.15 | O |
| ATOM | 2837 | C | SER | B | 112 | 84.707 | 14.810 | 76.484 | 1.00 | 27.92 | C |
| ATOM | 2838 | O | SER | B | 112 | 84.593 | 13.906 | 77.322 | 1.00 | 26.64 | O |
| ATOM | 2839 | N | ALA | B | 113 | 85.805 | 15.542 | 76.373 | 1.00 | 29.12 | N |
| ATOM | 2840 | CA | ALA | B | 113 | 86.856 | 15.306 | 77.342 | 1.00 | 29.88 | C |
| ATOM | 2841 | CB | ALA | B | 113 | 87.978 | 16.311 | 77.196 | 1.00 | 31.07 | C |
| ATOM | 2842 | C | ALA | B | 113 | 86.210 | 15.459 | 78.715 | 1.00 | 30.89 | C |
| ATOM | 2843 | O | ALA | B | 113 | 86.358 | 14.596 | 79.549 | 1.00 | 30.79 | O |
| ATOM | 2844 | N | CYS | B | 114 | 85.465 | 16.543 | 78.927 | 1.00 | 29.60 | N |
| ATOM | 2845 | CA | CYS | B | 114 | 84.843 | 16.800 | 80.202 | 1.00 | 28.77 | C |
| ATOM | 2846 | CB | CYS | B | 114 | 84.227 | 18.204 | 80.204 | 1.00 | 27.24 | C |
| ATOM | 2847 | SG | CYS | B | 114 | 83.223 | 18.585 | 81.669 | 1.00 | 35.81 | S |
| ATOM | 2848 | C | CYS | B | 114 | 83.806 | 15.758 | 80.552 | 1.00 | 27.65 | C |
| ATOM | 2849 | O | CYS | B | 114 | 82.828 | 15.571 | 79.835 | 1.00 | 28.99 | O |
| ATOM | 2850 | N | PRO | B | 115 | 83.983 | 15.091 | 81.698 | 1.00 | 26.98 | N |

FIG. 2A-62

| ATOM | 2851 | CA | PRO | B | 115 | 83.058 | 14.047 | 82.153 | 1.00 | 27.45 | C |
| ATOM | 2852 | CB | PRO | B | 115 | 83.777 | 13.451 | 83.371 | 1.00 | 26.81 | C |
| ATOM | 2853 | CG | PRO | B | 115 | 84.439 | 14.633 | 83.947 | 1.00 | 24.68 | C |
| ATOM | 2854 | CD | PRO | B | 115 | 84.953 | 15.428 | 82.751 | 1.00 | 25.08 | C |
| ATOM | 2855 | C | PRO | B | 115 | 81.682 | 14.590 | 82.501 | 1.00 | 27.47 | C |
| ATOM | 2856 | O | PRO | B | 115 | 80.798 | 13.850 | 82.887 | 1.00 | 28.86 | O |
| ATOM | 2857 | N | HIS | B | 116 | 81.490 | 15.890 | 82.394 | 1.00 | 26.11 | N |
| ATOM | 2858 | CA | HIS | B | 116 | 80.180 | 16.422 | 82.735 | 1.00 | 27.43 | C |
| ATOM | 2859 | CB | HIS | B | 116 | 80.332 | 17.696 | 83.514 | 1.00 | 27.69 | C |
| ATOM | 2860 | CG | HIS | B | 116 | 80.362 | 17.464 | 84.977 | 1.00 | 33.15 | C |
| ATOM | 2861 | ND1 | HIS | B | 116 | 79.271 | 16.983 | 85.665 | 1.00 | 34.21 | N |
| ATOM | 2862 | CE1 | HIS | B | 116 | 79.603 | 16.817 | 86.927 | 1.00 | 36.25 | C |
| ATOM | 2863 | NE2 | HIS | B | 116 | 80.866 | 17.174 | 87.082 | 1.00 | 31.01 | N |
| ATOM | 2864 | CD2 | HIS | B | 116 | 81.362 | 17.584 | 85.875 | 1.00 | 32.74 | C |
| ATOM | 2865 | C | HIS | B | 116 | 79.344 | 16.652 | 81.496 | 1.00 | 27.69 | C |
| ATOM | 2866 | O | HIS | B | 116 | 78.229 | 17.221 | 81.532 | 1.00 | 26.82 | O |
| ATOM | 2867 | N | ILE | B | 117 | 79.916 | 16.157 | 80.410 | 1.00 | 26.35 | N |
| ATOM | 2868 | CA | ILE | B | 117 | 79.311 | 16.259 | 79.126 | 1.00 | 27.14 | C |
| ATOM | 2869 | CB | ILE | B | 117 | 80.205 | 17.114 | 78.213 | 1.00 | 25.55 | C |
| ATOM | 2870 | CG1 | ILE | B | 117 | 79.833 | 18.582 | 78.461 | 1.00 | 27.38 | C |
| ATOM | 2871 | CD1 | ILE | B | 117 | 80.949 | 19.477 | 78.314 | 1.00 | 29.79 | C |
| ATOM | 2872 | CG2 | ILE | B | 117 | 80.094 | 16.664 | 76.759 | 1.00 | 25.07 | C |
| ATOM | 2873 | C | ILE | B | 117 | 79.145 | 14.846 | 78.646 | 1.00 | 26.46 | C |
| ATOM | 2874 | O | ILE | B | 117 | 80.055 | 14.056 | 78.702 | 1.00 | 27.27 | O |
| ATOM | 2875 | N | VAL | B | 118 | 77.957 | 14.535 | 78.181 | 1.00 | 25.36 | N |
| ATOM | 2876 | CA | VAL | B | 118 | 77.631 | 13.207 | 77.739 | 1.00 | 23.18 | C |
| ATOM | 2877 | CB | VAL | B | 118 | 76.220 | 13.190 | 77.102 | 1.00 | 22.42 | C |
| ATOM | 2878 | CG1 | VAL | B | 118 | 76.274 | 13.742 | 75.671 | 1.00 | 21.48 | C |
| ATOM | 2879 | CG2 | VAL | B | 118 | 75.685 | 11.800 | 77.153 | 1.00 | 20.14 | C |
| ATOM | 2880 | C | VAL | B | 118 | 78.648 | 12.611 | 76.795 | 1.00 | 23.94 | C |
| ATOM | 2881 | O | VAL | B | 118 | 79.057 | 13.241 | 75.803 | 1.00 | 26.40 | O |
| ATOM | 2882 | N | ARG | B | 119 | 79.035 | 11.373 | 77.093 | 1.00 | 23.34 | N |
| ATOM | 2883 | CA | ARG | B | 119 | 80.008 | 10.645 | 76.300 | 1.00 | 24.18 | C |
| ATOM | 2884 | CB | ARG | B | 119 | 80.504 | 9.422 | 77.055 | 1.00 | 24.43 | C |
| ATOM | 2885 | CG | ARG | B | 119 | 81.938 | 9.003 | 76.703 | 1.00 | 24.60 | C |
| ATOM | 2886 | CD | ARG | B | 119 | 82.355 | 7.790 | 77.526 | 1.00 | 26.65 | C |
| ATOM | 2887 | NE | ARG | B | 119 | 82.905 | 6.741 | 76.667 | 1.00 | 33.24 | N |
| ATOM | 2888 | CZ | ARG | B | 119 | 82.458 | 5.491 | 76.618 | 1.00 | 37.00 | C |
| ATOM | 2889 | NH1AR | G | B | 119 | 81.442 | 5.120 | 77.396 | 1.00 | 38.10 | N |
| ATOM | 2890 | NH2AR | G | B | 119 | 82.989 | 4.623 | 75.744 | 1.00 | 36.65 | N |
| ATOM | 2891 | C | ARG | B | 119 | 79.521 | 10.174 | 74.944 | 1.00 | 24.09 | C |
| ATOM | 2892 | O | ARG | B | 119 | 78.376 | 9.733 | 74.797 | 1.00 | 25.45 | O |
| ATOM | 2893 | N | ILE | B | 120 | 80.412 | 10.298 | 73.961 | 1.00 | 23.45 | N |
| ATOM | 2894 | CA | ILE | B | 120 | 80.188 | 9.856 | 72.600 | 1.00 | 22.61 | C |
| ATOM | 2895 | CB | ILE | B | 120 | 80.756 | 10.817 | 71.542 | 1.00 | 21.81 | C |
| ATOM | 2896 | CG1 | ILE | B | 120 | 79.838 | 12.062 | 71.404 | 1.00 | 20.80 | C |

FIG. 2A-63

| ATOM | 2897 | CD1 | ILE | B | 120 | 80.041 | 12.897 | 70.156 | 1.00 | 16.80 | C |
|---|---|---|---|---|---|---|---|---|---|---|---|
| ATOM | 2898 | CG2 | ILE | B | 120 | 80.952 | 10.051 | 70.208 | 1.00 | 15.98 | C |
| ATOM | 2899 | C | ILE | B | 120 | 80.963 | 8.564 | 72.484 | 1.00 | 24.40 | C |
| ATOM | 2900 | O | ILE | B | 120 | 82.184 | 8.565 | 72.537 | 1.00 | 24.75 | O |
| ATOM | 2901 | N | VAL | B | 121 | 80.246 | 7.462 | 72.335 | 1.00 | 23.41 | N |
| ATOM | 2902 | CA | VAL | B | 121 | 80.849 | 6.156 | 72.202 | 1.00 | 23.57 | C |
| ATOM | 2903 | CB | VAL | B | 121 | 79.776 | 5.045 | 72.520 | 1.00 | 26.16 | C |
| ATOM | 2904 | CG1 | VAL | B | 121 | 80.277 | 3.663 | 72.094 | 1.00 | 23.54 | C |
| ATOM | 2905 | CG2 | VAL | B | 121 | 79.424 | 5.063 | 74.026 | 1.00 | 21.76 | C |
| ATOM | 2906 | C | VAL | B | 121 | 81.396 | 5.950 | 70.791 | 1.00 | 23.77 | C |
| ATOM | 2907 | O | VAL | B | 121 | 82.482 | 5.452 | 70.610 | 1.00 | 20.05 | O |
| ATOM | 2908 | N | ASP | B | 122 | 80.621 | 6.337 | 69.791 | 1.00 | 24.78 | N |
| ATOM | 2909 | CA | ASP | B | 122 | 80.989 | 6.173 | 68.390 | 1.00 | 24.63 | C |
| ATOM | 2910 | CB | ASP | B | 122 | 80.691 | 4.728 | 67.915 | 1.00 | 26.18 | C |
| ATOM | 2911 | CG | ASP | B | 122 | 81.784 | 3.704 | 68.279 | 1.00 | 31.55 | C |
| ATOM | 2912 | OD1 | ASP | B | 122 | 82.994 | 3.986 | 68.093 | 1.00 | 35.06 | O |
| ATOM | 2913 | OD2 | ASP | B | 122 | 81.417 | 2.584 | 68.719 | 1.00 | 36.24 | O |
| ATOM | 2914 | C | ASP | B | 122 | 80.162 | 7.103 | 67.491 | 1.00 | 25.38 | C |
| ATOM | 2915 | O | ASP | B | 122 | 79.057 | 7.520 | 67.833 | 1.00 | 25.49 | O |
| ATOM | 2916 | N | VAL | B | 123 | 80.704 | 7.409 | 66.323 | 1.00 | 26.19 | N |
| ATOM | 2917 | CA | VAL | B | 123 | 79.971 | 8.183 | 65.347 | 1.00 | 26.22 | C |
| ATOM | 2918 | CB | VAL | B | 123 | 80.592 | 9.498 | 65.073 | 1.00 | 26.18 | C |
| ATOM | 2919 | CG1 | VAL | B | 123 | 79.725 | 10.259 | 64.090 | 1.00 | 26.56 | C |
| ATOM | 2920 | CG2 | VAL | B | 123 | 80.761 | 10.227 | 66.325 | 1.00 | 21.91 | C |
| ATOM | 2921 | C | VAL | B | 123 | 80.085 | 7.355 | 64.069 | 1.00 | 28.80 | C |
| ATOM | 2922 | O | VAL | B | 123 | 81.189 | 6.911 | 63.694 | 1.00 | 31.54 | O |
| ATOM | 2923 | N | TYR | B | 124 | 78.948 | 7.140 | 63.416 | 1.00 | 29.27 | N |
| ATOM | 2924 | CA | TYR | B | 124 | 78.891 | 6.348 | 62.196 | 1.00 | 26.94 | C |
| ATOM | 2925 | CB | TYR | B | 124 | 77.889 | 5.205 | 62.349 | 1.00 | 27.11 | C |
| ATOM | 2926 | CG | TYR | B | 124 | 78.361 | 4.059 | 63.185 | 1.00 | 26.63 | C |
| ATOM | 2927 | CD1 | TYR | B | 124 | 77.971 | 3.941 | 64.510 | 1.00 | 28.94 | C |
| ATOM | 2928 | CE1 | TYR | B | 124 | 78.428 | 2.899 | 65.316 | 1.00 | 29.55 | C |
| ATOM | 2929 | CZ | TYR | B | 124 | 79.284 | 1.955 | 64.785 | 1.00 | 29.77 | C |
| ATOM | 2930 | OH | TYR | B | 124 | 79.726 | 0.913 | 65.576 | 1.00 | 27.62 | O |
| ATOM | 2931 | CE2 | TYR | B | 124 | 79.684 | 2.051 | 63.454 | 1.00 | 32.04 | C |
| ATOM | 2932 | CD2 | TYR | B | 124 | 79.224 | 3.101 | 62.663 | 1.00 | 27.90 | C |
| ATOM | 2933 | C | TYR | B | 124 | 78.454 | 7.144 | 60.989 | 1.00 | 27.18 | C |
| ATOM | 2934 | O | TYR | B | 124 | 77.522 | 7.945 | 61.053 | 1.00 | 28.54 | O |
| ATOM | 2935 | N | GLU | B | 125 | 79.114 | 6.915 | 59.869 | 1.00 | 26.24 | N |
| ATOM | 2936 | CA | GLU | B | 125 | 78.697 | 7.554 | 58.638 | 1.00 | 23.48 | C |
| ATOM | 2937 | CB | GLU | B | 125 | 79.884 | 8.033 | 57.854 | 1.00 | 22.14 | C |
| ATOM | 2938 | CG | GLU | B | 125 | 79.512 | 8.842 | 56.671 | 1.00 | 26.18 | C |
| ATOM | 2939 | CD | GLU | B | 125 | 80.711 | 9.063 | 55.803 | 1.00 | 37.57 | C |
| ATOM | 2940 | OE1 | GLU | B | 125 | 80.881 | 8.312 | 54.803 | 1.00 | 38.17 | O |
| ATOM | 2941 | OE2 | GLU | B | 125 | 81.509 | 9.967 | 56.137 | 1.00 | 34.88 | O |
| ATOM | 2942 | C | GLU | B | 125 | 78.036 | 6.406 | 57.890 | 1.00 | 23.44 | C |

FIG. 2A-64

| ATOM | 2943 | O   | GLU | B | 125 | 78.710 | 5.508  | 57.385 | 1.00 | 21.36 | O |
| ---- | ---- | --- | --- | - | --- | ------ | ------ | ------ | ---- | ----- | - |
| ATOM | 2944 | N   | ASN | B | 126 | 76.718 | 6.390  | 57.869 | 1.00 | 22.25 | N |
| ATOM | 2945 | CA  | ASN | B | 126 | 76.026 | 5.334  | 57.156 | 1.00 | 20.82 | C |
| ATOM | 2946 | CB  | ASN | B | 126 | 75.218 | 4.453  | 58.096 | 1.00 | 22.09 | C |
| ATOM | 2947 | CG  | ASN | B | 126 | 76.076 | 3.530  | 58.939 | 1.00 | 23.89 | C |
| ATOM | 2948 | OD1 | ASN | B | 126 | 75.557 | 2.870  | 59.861 | 1.00 | 23.11 | O |
| ATOM | 2949 | ND2 | ASN | B | 126 | 77.385 | 3.463  | 58.635 | 1.00 | 18.63 | N |
| ATOM | 2950 | C   | ASN | B | 126 | 75.060 | 5.916  | 56.161 | 1.00 | 20.20 | C |
| ATOM | 2951 | O   | ASN | B | 126 | 74.759 | 7.123  | 56.134 | 1.00 | 19.00 | O |
| ATOM | 2952 | N   | LEU | B | 127 | 74.570 | 5.013  | 55.336 | 1.00 | 21.36 | N |
| ATOM | 2953 | CA  | LEU | B | 127 | 73.597 | 5.344  | 54.336 | 1.00 | 20.94 | C |
| ATOM | 2954 | CB  | LEU | B | 127 | 73.945 | 4.619  | 53.055 | 1.00 | 19.99 | C |
| ATOM | 2955 | CG  | LEU | B | 127 | 73.914 | 5.426  | 51.760 | 1.00 | 20.05 | C |
| ATOM | 2956 | CD1 | LEU | B | 127 | 74.501 | 6.807  | 51.915 | 1.00 | 14.99 | C |
| ATOM | 2957 | CD2 | LEU | B | 127 | 74.671 | 4.621  | 50.736 | 1.00 | 18.36 | C |
| ATOM | 2958 | C   | LEU | B | 127 | 72.293 | 4.819  | 54.919 | 1.00 | 22.51 | C |
| ATOM | 2959 | O   | LEU | B | 127 | 72.208 | 3.661  | 55.340 | 1.00 | 24.52 | O |
| ATOM | 2960 | N   | TYR | B | 128 | 71.296 | 5.697  | 54.999 | 1.00 | 23.54 | N |
| ATOM | 2961 | CA  | TYR | B | 128 | 69.994 | 5.317  | 55.507 | 1.00 | 24.30 | C |
| ATOM | 2962 | CB  | TYR | B | 128 | 69.726 | 5.901  | 56.888 | 1.00 | 26.10 | C |
| ATOM | 2963 | CG  | TYR | B | 128 | 68.274 | 5.756  | 57.266 | 1.00 | 31.29 | C |
| ATOM | 2964 | CD1 | TYR | B | 128 | 67.827 | 4.647  | 57.969 | 1.00 | 33.21 | C |
| ATOM | 2965 | CE1 | TYR | B | 128 | 66.490 | 4.453  | 58.199 | 1.00 | 38.46 | C |
| ATOM | 2966 | CZ  | TYR | B | 128 | 65.574 | 5.376  | 57.725 | 1.00 | 43.82 | C |
| ATOM | 2967 | OH  | TYR | B | 128 | 64.227 | 5.184  | 57.921 | 1.00 | 46.03 | O |
| ATOM | 2968 | CE2 | TYR | B | 128 | 65.991 | 6.492  | 57.032 | 1.00 | 42.24 | C |
| ATOM | 2969 | CD2 | TYR | B | 128 | 67.329 | 6.676  | 56.810 | 1.00 | 37.53 | C |
| ATOM | 2970 | C   | TYR | B | 128 | 69.003 | 5.885  | 54.532 | 1.00 | 24.23 | C |
| ATOM | 2971 | O   | TYR | B | 128 | 68.927 | 7.103  | 54.355 | 1.00 | 23.44 | O |
| ATOM | 2972 | N   | ALA | B | 129 | 68.255 | 5.002  | 53.878 | 1.00 | 26.08 | N |
| ATOM | 2973 | CA  | ALA | B | 129 | 67.279 | 5.445  | 52.891 | 1.00 | 27.73 | C |
| ATOM | 2974 | CB  | ALA | B | 129 | 66.277 | 6.346  | 53.560 | 1.00 | 27.77 | C |
| ATOM | 2975 | C   | ALA | B | 129 | 67.957 | 6.200  | 51.740 | 1.00 | 28.35 | C |
| ATOM | 2976 | O   | ALA | B | 129 | 67.438 | 7.210  | 51.273 | 1.00 | 28.86 | O |
| ATOM | 2977 | N   | GLY | B | 130 | 69.113 | 5.721  | 51.295 | 1.00 | 28.13 | N |
| ATOM | 2978 | CA  | GLY | B | 130 | 69.816 | 6.404  | 50.228 | 1.00 | 27.57 | C |
| ATOM | 2979 | C   | GLY | B | 130 | 70.453 | 7.755  | 50.583 | 1.00 | 26.36 | C |
| ATOM | 2980 | O   | GLY | B | 130 | 71.127 | 8.390  | 49.734 | 1.00 | 26.06 | O |
| ATOM | 2981 | N   | ALA | B | 131 | 70.247 | 8.200  | 51.832 | 1.00 | 24.87 | N |
| ATOM | 2982 | CA  | ALA | B | 131 | 70.785 | 9.485  | 52.305 | 1.00 | 24.22 | C |
| ATOM | 2983 | CB  | ALA | B | 131 | 69.709 | 10.290 | 53.007 | 1.00 | 24.42 | C |
| ATOM | 2984 | C   | ALA | B | 131 | 71.949 | 9.294  | 53.242 | 1.00 | 23.15 | C |
| ATOM | 2985 | O   | ALA | B | 131 | 71.939 | 8.381  | 54.070 | 1.00 | 23.37 | O |
| ATOM | 2986 | N   | ALA | B | 132 | 72.958 | 10.143 | 53.105 | 1.00 | 22.45 | N |
| ATOM | 2987 | CA  | ALA | B | 132 | 74.110 | 10.065 | 53.984 | 1.00 | 21.19 | C |
| ATOM | 2988 | CB  | ALA | B | 132 | 75.265 | 10.864 | 53.414 | 1.00 | 21.26 | C |

FIG. 2A-65

| ATOM | 2989 | C | ALA | B | 132 | 73.668 | 10.645 | 55.325 | 1.00 | 23.56 | C |
|---|---|---|---|---|---|---|---|---|---|---|---|
| ATOM | 2990 | O | ALA | B | 132 | 72.959 | 11.652 | 55.367 | 1.00 | 24.60 | O |
| ATOM | 2991 | N | CYS | B | 133 | 74.056 | 10.006 | 56.426 | 1.00 | 24.48 | N |
| ATOM | 2992 | CA | CYS | B | 133 | 73.687 | 10.524 | 57.736 | 1.00 | 24.88 | C |
| ATOM | 2993 | CB | CYS | B | 133 | 72.330 | 9.955 | 58.136 | 1.00 | 25.15 | C |
| ATOM | 2994 | SG | CYS | B | 133 | 72.380 | 8.185 | 58.414 | 1.00 | 34.98 | S |
| ATOM | 2995 | C | CYS | B | 133 | 74.757 | 10.180 | 58.770 | 1.00 | 23.53 | C |
| ATOM | 2996 | O | CYS | B | 133 | 75.565 | 9.290 | 58.546 | 1.00 | 24.70 | O |
| ATOM | 2997 | N | LEU | B | 134 | 74.765 | 10.921 | 59.878 | 1.00 | 23.82 | N |
| ATOM | 2998 | CA | LEU | B | 134 | 75.704 | 10.761 | 61.002 | 1.00 | 23.15 | C |
| ATOM | 2999 | CB | LEU | B | 134 | 76.248 | 12.112 | 61.436 | 1.00 | 23.36 | C |
| ATOM | 3000 | CG | LEU | B | 134 | 77.643 | 12.537 | 60.978 | 1.00 | 23.87 | C |
| ATOM | 3001 | CD1 | LEU | B | 134 | 78.234 | 11.566 | 59.974 | 1.00 | 22.01 | C |
| ATOM | 3002 | CD2 | LEU | B | 134 | 77.540 | 13.930 | 60.383 | 1.00 | 29.07 | C |
| ATOM | 3003 | C | LEU | B | 134 | 74.946 | 10.181 | 62.184 | 1.00 | 24.16 | C |
| ATOM | 3004 | O | LEU | B | 134 | 73.965 | 10.751 | 62.629 | 1.00 | 25.67 | O |
| ATOM | 3005 | N | LEU | B | 135 | 75.409 | 9.053 | 62.698 | 1.00 | 23.26 | N |
| ATOM | 3006 | CA | LEU | B | 135 | 74.775 | 8.389 | 63.813 | 1.00 | 23.15 | C |
| ATOM | 3007 | CB | LEU | B | 135 | 74.562 | 6.918 | 63.449 | 1.00 | 22.67 | C |
| ATOM | 3008 | CG | LEU | B | 135 | 73.697 | 6.710 | 62.190 | 1.00 | 23.42 | C |
| ATOM | 3009 | CD1 | LEU | B | 135 | 73.652 | 5.242 | 61.772 | 1.00 | 27.00 | C |
| ATOM | 3010 | CD2 | LEU | B | 135 | 72.296 | 7.230 | 62.479 | 1.00 | 25.37 | C |
| ATOM | 3011 | C | LEU | B | 135 | 75.732 | 8.532 | 64.978 | 1.00 | 24.70 | C |
| ATOM | 3012 | O | LEU | B | 135 | 76.846 | 8.001 | 64.962 | 1.00 | 27.22 | O |
| ATOM | 3013 | N | ILE | B | 136 | 75.305 | 9.269 | 65.989 | 1.00 | 24.90 | N |
| ATOM | 3014 | CA | ILE | B | 136 | 76.124 | 9.535 | 67.168 | 1.00 | 25.05 | C |
| ATOM | 3015 | CB | ILE | B | 136 | 75.945 | 11.011 | 67.643 | 1.00 | 25.13 | C |
| ATOM | 3016 | CG1 | ILE | B | 136 | 76.210 | 11.973 | 66.484 | 1.00 | 24.11 | C |
| ATOM | 3017 | CD1 | ILE | B | 136 | 76.370 | 13.403 | 66.936 | 1.00 | 30.34 | C |
| ATOM | 3018 | CG2 | ILE | B | 136 | 76.872 | 11.322 | 68.757 | 1.00 | 24.05 | C |
| ATOM | 3019 | C | ILE | B | 136 | 75.706 | 8.610 | 68.283 | 1.00 | 24.80 | C |
| ATOM | 3020 | O | ILE | B | 136 | 74.605 | 8.754 | 68.826 | 1.00 | 26.53 | O |
| ATOM | 3021 | N | VAL | B | 137 | 76.570 | 7.654 | 68.624 | 1.00 | 23.57 | N |
| ATOM | 3022 | CA | VAL | B | 137 | 76.239 | 6.732 | 69.696 | 1.00 | 24.33 | C |
| ATOM | 3023 | CB | VAL | B | 137 | 76.959 | 5.369 | 69.534 | 1.00 | 24.68 | C |
| ATOM | 3024 | CG1 | VAL | B | 137 | 76.667 | 4.476 | 70.742 | 1.00 | 23.23 | C |
| ATOM | 3025 | CG2 | VAL | B | 137 | 76.458 | 4.660 | 68.258 | 1.00 | 27.10 | C |
| ATOM | 3026 | C | VAL | B | 137 | 76.635 | 7.355 | 71.022 | 1.00 | 25.11 | C |
| ATOM | 3027 | O | VAL | B | 137 | 77.796 | 7.716 | 71.211 | 1.00 | 26.07 | O |
| ATOM | 3028 | N | MSE | B | 138 | 75.684 | 7.479 | 71.945 | 1.00 | 23.93 | N |
| ATOM | 3029 | CA | MSE | B | 138 | 75.996 | 8.080 | 73.229 | 1.00 | 22.24 | C |
| ATOM | 3030 | CB | MSE | B | 138 | 75.268 | 9.422 | 73.343 | 1.00 | 22.81 | C |
| ATOM | 3031 | CG | MSE | B | 138 | 75.784 | 10.480 | 72.418 | 1.00 | 22.09 | C |
| ATOM | 3032 | SE | MSE | B | 138 | 74.557 | 11.929 | 72.196 | 1.00 | 33.02 | S |
| ATOM | 3033 | CE | MSE | B | 138 | 73.103 | 11.031 | 71.385 | 1.00 | 37.03 | C |
| ATOM | 3034 | C | MSE | B | 138 | 75.689 | 7.237 | 74.465 | 1.00 | 22.51 | C |

FIG. 2A-66

| | | | | | | | | | | | |
|---|---|---|---|---|---|---|---|---|---|---|---|
| ATOM | 3035 | O | MSEB | | 138 | 74.793 | 6.398 | 74.436 | 1.00 | 22.38 | O |
| ATOM | 3036 | N | GLU | B | 139 | 76.442 | 7.464 | 75.546 | 1.00 | 21.81 | N |
| ATOM | 3037 | CA | GLU | B | 139 | 76.193 | 6.770 | 76.816 | 1.00 | 22.17 | C |
| ATOM | 3038 | CB | GLU | B | 139 | 77.147 | 7.254 | 77.916 | 1.00 | 19.93 | C |
| ATOM | 3039 | CG | GLU | B | 139 | 77.068 | 8.747 | 78.181 | 1.00 | 30.51 | C |
| ATOM | 3040 | CD | GLU | B | 139 | 77.900 | 9.219 | 79.363 | 1.00 | 29.99 | C |
| ATOM | 3041 | OE1 | GLU | B | 139 | 78.105 | 10.437 | 79.542 | 1.00 | 33.95 | O |
| ATOM | 3042 | OE2 | GLU | B | 139 | 78.345 | 8.360 | 80.132 | 1.00 | 31.88 | O |
| ATOM | 3043 | C | GLU | B | 139 | 74.732 | 7.006 | 77.247 | 1.00 | 21.38 | C |
| ATOM | 3044 | O | GLU | B | 139 | 74.114 | 8.009 | 76.923 | 1.00 | 19.35 | O |
| ATOM | 3045 | N | CYS | B | 140 | 74.164 | 6.056 | 77.960 | 1.00 | 25.90 | N |
| ATOM | 3046 | CA | CYS | B | 140 | 72.793 | 6.216 | 78.403 | 1.00 | 29.88 | C |
| ATOM | 3047 | CB | CYS | B | 140 | 72.151 | 4.833 | 78.639 | 1.00 | 29.32 | C |
| ATOM | 3048 | SG | CYS | B | 140 | 70.311 | 4.778 | 78.543 | 1.00 | 43.66 | S |
| ATOM | 3049 | C | CYS | B | 140 | 72.789 | 7.018 | 79.700 | 1.00 | 29.86 | C |
| ATOM | 3050 | O | CYS | B | 140 | 73.666 | 6.855 | 80.551 | 1.00 | 32.08 | O |
| ATOM | 3051 | N | LEU | B | 141 | 71.824 | 7.912 | 79.843 | 1.00 | 28.50 | N |
| ATOM | 3052 | CA | LEU | B | 141 | 71.697 | 8.681 | 81.068 | 1.00 | 27.85 | C |
| ATOM | 3053 | CB | LEU | B | 141 | 71.884 | 10.145 | 80.779 | 1.00 | 28.47 | C |
| ATOM | 3054 | CG | LEU | B | 141 | 73.158 | 10.482 | 80.027 | 1.00 | 28.22 | C |
| ATOM | 3055 | CD1 | LEU | B | 141 | 73.038 | 11.935 | 79.620 | 1.00 | 28.84 | C |
| ATOM | 3056 | CD2 | LEU | B | 141 | 74.396 | 10.248 | 80.870 | 1.00 | 24.13 | C |
| ATOM | 3057 | C | LEU | B | 141 | 70.282 | 8.411 | 81.547 | 1.00 | 27.86 | C |
| ATOM | 3058 | O | LEU | B | 141 | 69.315 | 8.996 | 81.061 | 1.00 | 26.83 | O |
| ATOM | 3059 | N | ASP | B | 142 | 70.155 | 7.512 | 82.511 | 1.00 | 26.63 | N |
| ATOM | 3060 | CA | ASP | B | 142 | 68.840 | 7.151 | 82.980 | 1.00 | 27.89 | C |
| ATOM | 3061 | CB | ASP | B | 142 | 68.724 | 5.642 | 83.099 | 1.00 | 29.12 | C |
| ATOM | 3062 | CG | ASP | B | 142 | 68.783 | 4.961 | 81.768 | 1.00 | 39.42 | C |
| ATOM | 3063 | OD1 | ASP | B | 142 | 68.520 | 5.615 | 80.730 | 1.00 | 47.28 | O |
| ATOM | 3064 | OD2 | ASP | B | 142 | 69.082 | 3.752 | 81.752 | 1.00 | 51.71 | O |
| ATOM | 3065 | C | ASP | B | 142 | 68.375 | 7.751 | 84.263 | 1.00 | 25.95 | C |
| ATOM | 3066 | O | ASP | B | 142 | 67.307 | 7.390 | 84.733 | 1.00 | 27.90 | O |
| ATOM | 3067 | N | GLY | B | 143 | 69.136 | 8.667 | 84.837 | 1.00 | 23.04 | N |
| ATOM | 3068 | CA | GLY | B | 143 | 68.715 | 9.239 | 86.097 | 1.00 | 21.02 | C |
| ATOM | 3069 | C | GLY | B | 143 | 67.654 | 10.304 | 86.039 | 1.00 | 19.24 | C |
| ATOM | 3070 | O | GLY | B | 143 | 67.299 | 10.854 | 87.044 | 1.00 | 21.01 | O |
| ATOM | 3071 | N | GLY | B | 144 | 67.137 | 10.603 | 84.874 | 1.00 | 19.17 | N |
| ATOM | 3072 | CA | GLY | B | 144 | 66.142 | 11.650 | 84.792 | 1.00 | 18.38 | C |
| ATOM | 3073 | C | GLY | B | 144 | 66.763 | 13.009 | 84.547 | 1.00 | 19.34 | C |
| ATOM | 3074 | O | GLY | B | 144 | 67.985 | 13.160 | 84.606 | 1.00 | 20.82 | O |
| ATOM | 3075 | N | GLU | B | 145 | 65.942 | 14.007 | 84.251 | 1.00 | 20.91 | N |
| ATOM | 3076 | CA | GLU | B | 145 | 66.504 | 15.327 | 84.023 | 1.00 | 22.33 | C |
| ATOM | 3077 | CB | GLU | B | 145 | 65.724 | 16.113 | 82.954 | 1.00 | 21.98 | C |
| ATOM | 3078 | CG | GLU | B | 145 | 64.274 | 16.323 | 83.245 | 1.00 | 31.02 | C |
| ATOM | 3079 | CD | GLU | B | 145 | 63.495 | 16.804 | 82.013 | 1.00 | 40.55 | C |
| ATOM | 3080 | OE1 | GLU | B | 145 | 63.774 | 16.324 | 80.878 | 1.00 | 36.56 | O |

FIG. 2A-67

| ATOM | 3081 | OE2 | GLU | B | 145 | 62.585 | 17.657 | 82.186 | 1.00 | 46.95 | O |
| --- | --- | --- | --- | --- | --- | --- | --- | --- | --- | --- | --- |
| ATOM | 3082 | C | GLU | B | 145 | 66.519 | 16.050 | 85.340 | 1.00 | 20.90 | C |
| ATOM | 3083 | O | GLU | B | 145 | 65.698 | 15.793 | 86.188 | 1.00 | 21.45 | O |
| ATOM | 3084 | N | LEU | B | 146 | 67.495 | 16.924 | 85.510 | 1.00 | 21.22 | N |
| ATOM | 3085 | CA | LEU | B | 146 | 67.656 | 17.701 | 86.730 | 1.00 | 21.40 | C |
| ATOM | 3086 | CB | LEU | B | 146 | 68.159 | 19.088 | 86.371 | 1.00 | 21.62 | C |
| ATOM | 3087 | CG | LEU | B | 146 | 68.614 | 19.984 | 87.505 | 1.00 | 22.15 | C |
| ATOM | 3088 | CD1 | LEU | B | 146 | 69.730 | 19.321 | 88.255 | 1.00 | 19.94 | C |
| ATOM | 3089 | CD2 | LEU | B | 146 | 69.105 | 21.301 | 86.906 | 1.00 | 31.14 | C |
| ATOM | 3090 | C | LEU | B | 146 | 66.423 | 17.857 | 87.604 | 1.00 | 22.86 | C |
| ATOM | 3091 | O | LEU | B | 146 | 66.268 | 17.199 | 88.618 | 1.00 | 24.66 | O |
| ATOM | 3092 | N | PHE | B | 147 | 65.529 | 18.733 | 87.191 | 1.00 | 23.80 | N |
| ATOM | 3093 | CA | PHE | B | 147 | 64.340 | 19.005 | 87.974 | 1.00 | 24.82 | C |
| ATOM | 3094 | CB | PHE | B | 147 | 63.598 | 20.177 | 87.339 | 1.00 | 25.34 | C |
| ATOM | 3095 | CG | PHE | B | 147 | 64.346 | 21.449 | 87.493 | 1.00 | 27.67 | C |
| ATOM | 3096 | CD1 | PHE | B | 147 | 64.371 | 22.390 | 86.502 | 1.00 | 29.99 | C |
| ATOM | 3097 | CE1 | PHE | B | 147 | 65.162 | 23.496 | 86.625 | 1.00 | 27.01 | C |
| ATOM | 3098 | CZ | PHE | B | 147 | 65.930 | 23.662 | 87.747 | 1.00 | 29.48 | C |
| ATOM | 3099 | CE2 | PHE | B | 147 | 65.899 | 22.737 | 88.738 | 1.00 | 30.61 | C |
| ATOM | 3100 | CD2 | PHE | B | 147 | 65.117 | 21.644 | 88.613 | 1.00 | 29.55 | C |
| ATOM | 3101 | C | PHE | B | 147 | 63.423 | 17.852 | 88.325 | 1.00 | 25.18 | C |
| ATOM | 3102 | O | PHE | B | 147 | 62.843 | 17.848 | 89.409 | 1.00 | 26.61 | O |
| ATOM | 3103 | N | SER | B | 148 | 63.289 | 16.878 | 87.439 | 1.00 | 25.94 | N |
| ATOM | 3104 | CA | SER | B | 148 | 62.474 | 15.721 | 87.759 | 1.00 | 26.96 | C |
| ATOM | 3105 | CB | SER | B | 148 | 62.525 | 14.697 | 86.637 | 1.00 | 26.70 | C |
| ATOM | 3106 | OG | SER | B | 148 | 61.964 | 15.263 | 85.458 | 1.00 | 31.33 | O |
| ATOM | 3107 | C | SER | B | 148 | 63.101 | 15.143 | 89.004 | 1.00 | 27.08 | C |
| ATOM | 3108 | O | SER | B | 148 | 62.441 | 14.987 | 90.012 | 1.00 | 25.90 | O |
| ATOM | 3109 | N | ARG | B | 149 | 64.394 | 14.854 | 88.944 | 1.00 | 28.91 | N |
| ATOM | 3110 | CA | ARG | B | 149 | 65.088 | 14.309 | 90.107 | 1.00 | 30.28 | C |
| ATOM | 3111 | CB | ARG | B | 149 | 66.607 | 14.330 | 89.884 | 1.00 | 31.03 | C |
| ATOM | 3112 | CG | ARG | B | 149 | 67.452 | 13.573 | ·90.931 | 1.00 | 35.99 | C |
| ATOM | 3113 | CD | ARG | B | 149 | 67.201 | 12.056 | 90.905 | 1.00 | 42.91 | C |
| ATOM | 3114 | NE | ARG | B | 149 | 68.211 | 11.260 | 90.199 | 1.00 | 39.67 | N |
| ATOM | 3115 | CZ | ARG | B | 149 | 69.486 | 11.184 | 90.562 | 1.00 | 36.60 | C |
| ATOM | 3116 | NH1AR | G | B | 149 | 69.950 | 11.869 | 91.618 | 1.00 | 34.25 | N |
| ATOM | 3117 | NH2AR | G | B | 149 | 70.290 | 10.369 | 89.910 | 1.00 | 35.23 | N |
| ATOM | 3118 | C | ARG | B | 149 | 64.716 | 15.132 | 91.341 | 1.00 | 30.28 | C |
| ATOM | 3119 | O | ARG | B | 149 | 64.297 | 14.570 | 92.353 | 1.00 | 31.28 | O |
| ATOM | 3120 | N | ILE | B | 150 | 64.848 | 16.454 | 91.261 | 1.00 | 30.21 | N |
| ATOM | 3121 | CA | ILE | B | 150 | 64.501 | 17.307 | 92.393 | 1.00 | 29.95 | C |
| ATOM | 3122 | CB | ILE | B | 150 | 64.691 | 18.817 | 92.072 | 1.00 | 30.69 | C |
| ATOM | 3123 | CG1 | ILE | B | 150 | 66.128 | 19.088 | 91.663 | 1.00 | 32.37 | C |
| ATOM | 3124 | CD1 | ILE | B | 150 | 67.100 | 18.850 | 92.778 | 1.00 | 38.44 | C |
| ATOM | 3125 | CG2 | ILE | B | 150 | 64.453 | 19.657 | 93.312 | 1.00 | 26.11 | C |
| ATOM | 3126 | C | ILE | B | 150 | 63.044 | 17.074 | 92.741 | 1.00 | 29.31 | C |

FIG. 2A-68

| ATOM | 3127 | O | ILE | B | 150 | 62.690 | 16.896 | 93.889 | 1.00 | 30.08 | O |
|---|---|---|---|---|---|---|---|---|---|---|---|
| ATOM | 3128 | N | GLN | B | 151 | 62.191 | 17.061 | 91.737 | 1.00 | 30.46 | N |
| ATOM | 3129 | CA | GLN | B | 151 | 60.772 | 16.854 | 91.976 | 1.00 | 32.42 | C |
| ATOM | 3130 | CB | GLN | B | 151 | 59.993 | 17.096 | 90.694 | 1.00 | 31.59 | C |
| ATOM | 3131 | CG | GLN | B | 151 | 58.634 | 16.530 | 90.743 | 1.00 | 34.88 | C |
| ATOM | 3132 | CD | GLN | B | 151 | 57.686 | 17.299 | 89.887 | 1.00 | 37.00 | C |
| ATOM | 3133 | OE1 | GLN | B | 151 | 57.970 | 17.595 | 88.727 | 1.00 | 38.34 | O |
| ATOM | 3134 | NE2 | GLN | B | 151 | 56.536 | 17.631 | 90.444 | 1.00 | 41.56 | N |
| ATOM | 3135 | C | GLN | B | 151 | 60.384 | 15.480 | 92.542 | 1.00 | 34.61 | C |
| ATOM | 3136 | O | GLN | B | 151 | 59.807 | 15.395 | 93.631 | 1.00 | 33.48 | O |
| ATOM | 3137 | N | ALA | B | 152 | 60.677 | 14.414 | 91.793 | 1.00 | 37.33 | N |
| ATOM | 3138 | CA | ALA | B | 152 | 60.361 | 13.049 | 92.215 | 1.00 | 40.00 | C |
| ATOM | 3139 | CB | ALA | B | 152 | 61.246 | 12.037 | 91.476 | 1.00 | 39.79 | C |
| ATOM | 3140 | C | ALA | B | 152 | 60.588 | 12.934 | 93.710 | 1.00 | 41.90 | C |
| ATOM | 3141 | O | ALA | B | 152 | 59.850 | 12.242 | 94.413 | 1.00 | 42.14 | O |
| ATOM | 3142 | N | ARG | B | 153 | 61.617 | 13.618 | 94.191 | 1.00 | 43.83 | N |
| ATOM | 3143 | CA | ARG | B | 153 | 61.884 | 13.629 | 95.606 | 1.00 | 45.74 | C |
| ATOM | 3144 | CB | ARG | B | 153 | 63.047 | 14.580 | 95.880 | 1.00 | 45.37 | C |
| ATOM | 3145 | CG | ARG | B | 153 | 63.065 | 15.058 | 97.328 | 1.00 | 42.02 | C |
| ATOM | 3146 | CD | ARG | B | 153 | 64.299 | 15.898 | 97.650 | 1.00 | 43.22 | C |
| ATOM | 3147 | NE | ARG | B | 153 | 65.408 | 15.537 | 96.760 | 1.00 | 40.04 | N |
| ATOM | 3148 | CZ | ARG | B | 153 | 66.631 | 15.989 | 97.090 | 1.00 | 38.57 | C |
| ATOM | 3149 | NH1AR | G | B | 153 | 66.789 | 16.728 | 98.172 | 1.00 | 35.47 | N |
| ATOM | 3150 | NH2AR | G | B | 153 | 67.684 | 15.651 | 96.343 | 1.00 | 39.69 | N |
| ATOM | 3151 | C | ARG | B | 153 | 60.659 | 14.012 | 96.429 | 1.00 | 47.65 | C |
| ATOM | 3152 | O | ARG | B | 153 | 59.740 | 14.710 | 95.994 | 1.00 | 49.27 | O |
| ATOM | 3153 | N | GLY | B | 154 | 60.675 | 13.450 | 97.636 | 1.00 | 48.92 | N |
| ATOM | 3154 | CA | GLY | B | 154 | 59.655 | 13.674 | 98.636 | 1.00 | 50.63 | C |
| ATOM | 3155 | C | GLY | B | 154 | 60.316 | 13.320 | 99.952 | 1.00 | 52.15 | C |
| ATOM | 3156 | O | GLY | B | 154 | 59.705 | 13.206 | 101.001 | 1.00 | 51.34 | O |
| ATOM | 3157 | N | ASP | B | 155 | 61.630 | 13.077 | 99.811 | 1.00 | 53.71 | N |
| ATOM | 3158 | CA | ASP | B | 155 | 62.473 | 12.809 | 100.959 | 1.00 | 54.41 | C |
| ATOM | 3159 | CB | ASP | B | 155 | 63.735 | 12.110 | 100.446 | 1.00 | 55.21 | C |
| ATOM | 3160 | CG | ASP | B | 155 | 63.356 | 11.131 | 99.338 | 1.00 | 55.97 | C |
| ATOM | 3161 | OD1 | ASP | B | 155 | 62.354 | 10.435 | 99.507 | 1.00 | 55.47 | O |
| ATOM | 3162 | OD2 | ASP | B | 155 | 64.031 | 11.103 | 98.319 | 1.00 | 57.05 | O |
| ATOM | 3163 | C | ASP | B | 155 | 62.817 | 14.124 | 101.662 | 1.00 | 53.41 | C |
| ATOM | 3164 | O | ASP | B | 155 | 63.970 | 14.495 | 101.841 | 1.00 | 53.10 | O |
| ATOM | 3165 | N | GLN | B | 156 | 61.751 | 14.879 | 101.972 | 1.00 | 51.46 | N |
| ATOM | 3166 | CA | GLN | B | 156 | 61.929 | 16.075 | 102.776 | 1.00 | 50.51 | C |
| ATOM | 3167 | CB | GLN | B | 156 | 62.345 | 15.620 | 104.169 | 1.00 | 51.07 | C |
| ATOM | 3168 | CG | GLN | B | 156 | 61.170 | 15.518 | 105.135 | 1.00 | 57.00 | C |
| ATOM | 3169 | CD | GLN | B | 156 | 60.261 | 14.397 | 104.699 | 1.00 | 62.92 | C |
| ATOM | 3170 | OE1 | GLN | B | 156 | 60.307 | 13.274 | 105.178 | 1.00 | 64.73 | O |
| ATOM | 3171 | NE2 | GLN | B | 156 | 59.397 | 14.760 | 103.732 | 1.00 | 64.62 | N |
| ATOM | 3172 | C | GLN | B | 156 | 62.991 | 17.027 | 102.217 | 1.00 | 47.87 | C |

FIG. 2A-69

| ATOM | 3173 | O | GLN | B | 156 | 62.977 | 17.436 | 101.058 | 1.00 | 46.97 | O |
|---|---|---|---|---|---|---|---|---|---|---|---|
| ATOM | 3174 | N | ALA | B | 157 | 63.918 | 17.396 | 103.122 | 1.00 | 44.80 | N |
| ATOM | 3175 | CA | ALA | B | 157 | 64.785 | 18.552 | 102.893 | 1.00 | 40.80 | C |
| ATOM | 3176 | CB | ALA | B | 157 | 65.785 | 18.650 | 104.048 | 1.00 | 42.01 | C |
| ATOM | 3177 | C | ALA | B | 157 | 65.538 | 18.530 | 101.561 | 1.00 | 38.43 | C |
| ATOM | 3178 | O | ALA | B | 157 | 66.272 | 17.607 | 101.230 | 1.00 | 38.65 | O |
| ATOM | 3179 | N | PHE | B | 158 | 65.306 | 19.601 | 100.778 | 1.00 | 34.59 | N |
| ATOM | 3180 | CA | PHE | B | 158 | 66.159 | 19.859 | 99.626 | 1.00 | 28.74 | C |
| ATOM | 3181 | CB | PHE | B | 158 | 65.281 | 20.009 | 98.384 | 1.00 | 28.40 | C |
| ATOM | 3182 | CG | PHE | B | 158 | 66.125 | 20.458 | 97.228 | 1.00 | 24.76 | C |
| ATOM | 3183 | CD1 | PHE | B | 158 | 67.238 | 19.710 | 96.865 | 1.00 | 25.70 | C |
| ATOM | 3184 | CE1 | PHE | B | 158 | 68.094 | 20.179 | 95.878 | 1.00 | 23.76 | C |
| ATOM | 3185 | CZ | PHE | B | 158 | 67.839 | 21.392 | 95.247 | 1.00 | 17.80 | C |
| ATOM | 3186 | CE2 | PHE | B | 158 | 66.720 | 22.131 | 95.611 | 1.00 | 22.79 | C |
| ATOM | 3187 | CD2 | PHE | B | 158 | 65.858 | 21.668 | 96.602 | 1.00 | 24.11 | C |
| ATOM | 3188 | C | PHE | B | 158 | 66.964 | 21.142 | 99.839 | 1.00 | 26.91 | C |
| ATOM | 3189 | O | PHE | B | 158 | 66.440 | 22.180 | 100.221 | 1.00 | 25.67 | O |
| ATOM | 3190 | N | THR | B | 159 | 68.270 | 21.189 | 100.029 | 1.00 | 25.97 | N |
| ATOM | 3191 | CA | THR | B | 159 | 68.862 | 22.368 | 100.643 | 1.00 | 25.08 | C |
| ATOM | 3192 | CB | THR | B | 159 | 69.690 | 21.952 | 101.863 | 1.00 | 24.86 | C |
| ATOM | 3193 | OG1 | THR | B | 159 | 70.668 | 20.972 | 101.463 | 1.00 | 28.44 | O |
| ATOM | 3194 | CG2 | THR | B | 159 | 68.767 | 21.376 | 102.939 | 1.00 | 24.34 | C |
| ATOM | 3195 | C | THR | B | 159 | 69.718 | 23.259 | 99.762 | 1.00 | 24.21 | C |
| ATOM | 3196 | O | THR | B | 159 | 70.221 | 22.828 | 98.736 | 1.00 | 22.26 | O |
| ATOM | 3197 | N | GLU | B | 160 | 69.879 | 24.504 | 100.207 | 1.00 | 24.19 | N |
| ATOM | 3198 | CA | GLU | B | 160 | 70.666 | 25.523 | 99.514 | 1.00 | 25.71 | C |
| ATOM | 3199 | CB | GLU | B | 160 | 70.781 | 26.800 | 100.366 | 1.00 | 25.34 | C |
| ATOM | 3200 | CG | GLU | B | 160 | 71.184 | 28.046 | 99.579 | 1.00 | 29.09 | C |
| ATOM | 3201 | CD | GLU | B | 160 | 71.481 | 29.273 | 100.456 | 1.00 | 35.80 | C |
| ATOM | 3202 | OE1 | GLU | B | 160 | 70.592 | 29.701 | 101.242 | 1.00 | 42.13 | O |
| ATOM | 3203 | OE2 | GLU | B | 160 | 72.607 | 29.822 | 100.351 | 1.00 | 34.96 | O |
| ATOM | 3204 | C | GLU | B | 160 | 72.057 | 24.989 | 99.229 | 1.00 | 26.09 | C |
| ATOM | 3205 | O | GLU | B | 160 | 72.747 | 25.489 | 98.346 | 1.00 | 27.15 | O |
| ATOM | 3206 | N | ARG | B | 161 | 72.445 | 23.963 | 99.987 | 1.00 | 27.16 | N |
| ATOM | 3207 | CA | ARG | B | 161 | 73.744 | 23.332 | 99.865 | 1.00 | 28.08 | C |
| ATOM | 3208 | CB | ARG | B | 161 | 74.080 | 22.570 | 101.135 | 1.00 | 29.06 | C |
| ATOM | 3209 | CG | ARG | B | 161 | 75.177 | 23.191 | 101.951 | 1.00 | 35.23 | C |
| ATOM | 3210 | CD | ARG | B | 161 | 76.449 | 22.360 | 101.943 | 1.00 | 40.84 | C |
| ATOM | 3211 | NE | ARG | B | 161 | 77.192 | 22.607 | 103.177 | 1.00 | 47.69 | N |
| ATOM | 3212 | CZ | ARG | B | 161 | 76.976 | 21.971 | 104.333 | 1.00 | 46.86 | C |
| ATOM | 3213 | NH1AR | G | B | 161 | 76.049 | 21.020 | 104.431 | 1.00 | 47.04 | N |
| ATOM | 3214 | NH2AR | G | B | 161 | 77.660 | 22.320 | 105.414 | 1.00 | 42.59 | N |
| ATOM | 3215 | C | ARG | B | 161 | 73.852 | 22.383 | 98.691 | 1.00 | 29.12 | C |
| ATOM | 3216 | O | ARG | B | 161 | 74.892 | 22.335 | 98.039 | 1.00 | 31.16 | O |
| ATOM | 3217 | N | GLU | B | 162 | 72.809 | 21.611 | 98.420 | 1.00 | 28.73 | N |
| ATOM | 3218 | CA | GLU | B | 162 | 72.878 | 20.705 | 97.287 | 1.00 | 28.19 | C |

FIG. 2A-70

| ATOM | 3219 | CB | GLU | B | 162 | 71.870 | 19.569 | 97.406 | 1.00 | 29.82 | C |
| --- | --- | --- | --- | --- | --- | --- | --- | --- | --- | --- | --- |
| ATOM | 3220 | CG | GLU | B | 162 | 71.266 | 19.364 | 98.794 | 1.00 | 36.04 | C |
| ATOM | 3221 | CD | GLU | B | 162 | 70.100 | 18.380 | 98.767 | 1.00 | 42.39 | C |
| ATOM | 3222 | OE1 | GLU | B | 162 | 69.318 | 18.385 | 99.745 | 1.00 | 41.12 | O |
| ATOM | 3223 | OE2 | GLU | B | 162 | 69.980 | 17.618 | 97.766 | 1.00 | 42.33 | O |
| ATOM | 3224 | C | GLU | B | 162 | 72.581 | 21.512 | 96.025 | 1.00 | 27.18 | C |
| ATOM | 3225 | O | GLU | B | 162 | 72.931 | 21.092 | 94.927 | 1.00 | 28.45 | O |
| ATOM | 3226 | N | ALA | B | 163 | 71.912 | 22.655 | 96.178 | 1.00 | 26.15 | N |
| ATOM | 3227 | CA | ALA | B | 163 | 71.626 | 23.521 | 95.037 | 1.00 | 24.41 | C |
| ATOM | 3228 | CB | ALA | B | 163 | 70.841 | 24.709 | 95.477 | 1.00 | 22.22 | C |
| ATOM | 3229 | C | ALA | B | 163 | 72.990 | 23.962 | 94.513 | 1.00 | 25.09 | C |
| ATOM | 3230 | O | ALA | B | 163 | 73.293 | 23.857 | 93.321 | 1.00 | 23.62 | O |
| ATOM | 3231 | N | SER | B | 164 | 73.816 | 24.446 | 95.424 | 1.00 | 25.80 | N |
| ATOM | 3232 | CA | SER | B | 164 | 75.155 | 24.856 | 95.079 | 1.00 | 26.67 | C |
| ATOM | 3233 | CB | SER | B | 164 | 75.876 | 25.418 | 96.306 | 1.00 | 26.93 | C |
| ATOM | 3234 | OG | SER | B | 164 | 77.285 | 25.399 | 96.142 | 1.00 | 25.18 | O |
| ATOM | 3235 | C | SER | B | 164 | 75.918 | 23.655 | 94.582 | 1.00 | 26.56 | C |
| ATOM | 3236 | O | SER | B | 164 | 76.673 | 23.759 | 93.645 | 1.00 | 27.50 | O |
| ATOM | 3237 | N | GLU | B | 165 | 75.744 | 22.503 | 95.205 | 1.00 | 26.59 | N |
| ATOM | 3238 | CA | GLU | B | 165 | 76.494 | 21.351 | 94.744 | 1.00 | 26.74 | C |
| ATOM | 3239 | CB | GLU | B | 165 | 76.170 | 20.126 | 95.603 | 1.00 | 28.35 | C |
| ATOM | 3240 | CG | GLU | B | 165 | 76.946 | 20.003 | 96.904 | 1.00 | 31.55 | C |
| ATOM | 3241 | CD | GLU | B | 165 | 76.146 | 19.218 | 97.962 | 1.00 | 44.38 | C |
| ATOM | 3242 | OE1 | GLU | B | 165 | 75.355 | 18.327 | 97.532 | 1.00 | 51.03 | O |
| ATOM | 3243 | OE2 | GLU | B | 165 | 76.300 | 19.483 | 99.197 | 1.00 | 41.47 | O |
| ATOM | 3244 | C | GLU | B | 165 | 76.148 | 21.092 | 93.280 | 1.00 | 25.61 | C |
| ATOM | 3245 | O | GLU | B | 165 | 77.010 | 20.775 | 92.460 | 1.00 | 27.25 | O |
| ATOM | 3246 | N | ILE | B | 166 | 74.878 | 21.244 | 92.947 | 1.00 | 24.18 | N |
| ATOM | 3247 | CA | ILE | B | 166 | 74.420 | 21.022 | 91.593 | 1.00 | 21.56 | C |
| ATOM | 3248 | CB | ILE | B | 166 | 72.920 | 21.043 | 91.570 | 1.00 | 22.92 | C |
| ATOM | 3249 | CG1 | ILE | B | 166 | 72.405 | 19.881 | 92.422 | 1.00 | 21.00 | C |
| ATOM | 3250 | CD1 | ILE | B | 166 | 70.881 | 19.754 | 92.481 | 1.00 | 31.37 | C |
| ATOM | 3251 | CG2 | ILE | B | 166 | 72.430 | 21.067 | 90.160 | 1.00 | 16.12 | C |
| ATOM | 3252 | C | ILE | B | 166 | 74.954 | 22.118 | 90.693 | 1.00 | 22.03 | C |
| ATOM | 3253 | O | ILE | B | 166 | 75.608 | 21.836 | 89.687 | 1.00 | 19.98 | O |
| ATOM | 3254 | N | MSE | B | 167 | 74.704 | 23.370 | 91.080 | 1.00 | 22.79 | N |
| ATOM | 3255 | CA | MSE | B | 167 | 75.157 | 24.496 | 90.293 | 1.00 | 22.92 | C |
| ATOM | 3256 | CB | MSE | B | 167 | 74.884 | 25.826 | 91.010 | 1.00 | 23.37 | C |
| ATOM | 3257 | CG | MSE | B | 167 | 73.435 | 26.316 | 90.962 | 1.00 | 23.14 | C |
| ATOM | 3258 | SE | MSE | B | 167 | 72.623 | 25.969 | 89.269 | 1.00 | 29.38 | S |
| ATOM | 3259 | CE | MSE | B | 167 | 73.840 | 26.962 | 88.158 | 1.00 | 22.08 | C |
| ATOM | 3260 | C | MSE | B | 167 | 76.619 | 24.375 | 89.936 | 1.00 | 23.59 | C |
| ATOM | 3261 | O | MSE | B | 167 | 77.014 | 24.697 | 88.807 | 1.00 | 23.14 | O |
| ATOM | 3262 | N | LYS | B | 168 | 77.436 | 23.906 | 90.867 | 1.00 | 25.07 | N |
| ATOM | 3263 | CA | LYS | B | 168 | 78.837 | 23.752 | 90.573 | 1.00 | 26.15 | C |
| ATOM | 3264 | CB | LYS | B | 168 | 79.608 | 23.410 | 91.831 | 1.00 | 26.95 | C |

FIG. 2A-71

| ATOM | 3265 | CG | LYS | B | 168 | 81.138 | 23.405 | 91.664 | 1.00 | 31.71 | C |
| --- | --- | --- | --- | --- | --- | --- | --- | --- | --- | --- | --- |
| ATOM | 3266 | CD | LYS | B | 168 | 81.830 | 22.924 | 92.949 | 1.00 | 36.53 | C |
| ATOM | 3267 | CE | LYS | B | 168 | 83.310 | 22.944 | 92.805 | 1.00 | 40.33 | C |
| ATOM | 3268 | NZ | LYS | B | 168 | 83.627 | 22.423 | 91.427 | 1.00 | 51.04 | N |
| ATOM | 3269 | C | LYS | B | 168 | 79.045 | 22.668 | 89.519 | 1.00 | 26.96 | C |
| ATOM | 3270 | O | LYS | B | 168 | 79.889 | 22.789 | 88.629 | 1.00 | 27.78 | O |
| ATOM | 3271 | N | SER | B | 169 | 78.255 | 21.616 | 89.563 | 1.00 | 28.36 | N |
| ATOM | 3272 | CA | SER | B | 169 | 78.464 | 20.575 | 88.573 | 1.00 | 28.98 | C |
| ATOM | 3273 | CB | SER | B | 169 | 77.596 | 19.387 | 88.874 | 1.00 | 29.90 | C |
| ATOM | 3274 | OG | SER | B | 169 | 76.379 | 19.585 | 88.173 | 1.00 | 44.76 | O |
| ATOM | 3275 | C | SER | B | 169 | 78.140 | 21.060 | 87.162 | 1.00 | 27.37 | C |
| ATOM | 3276 | O | SER | B | 169 | 78.888 | 20.759 | 86.222 | 1.00 | 28.74 | O |
| ATOM | 3277 | N | ILE | B | 170 | 77.011 | 21.774 | 87.009 | 1.00 | 23.08 | N |
| ATOM | 3278 | CA | ILE | B | 170 | 76.624 | 22.309 | 85.693 | 1.00 | 20.60 | C |
| ATOM | 3279 | CB | ILE | B | 170 | 75.255 | 23.074 | 85.715 | 1.00 | 20.19 | C |
| ATOM | 3280 | CG1 | ILE | B | 170 | 74.132 | 22.154 | 86.165 | 1.00 | 18.43 | C |
| ATOM | 3281 | CD1 | ILE | B | 170 | 72.874 | 22.860 | 86.549 | 1.00 | 24.08 | C |
| ATOM | 3282 | CG2 | ILE | B | 170 | 74.901 | 23.548 | 84.360 | 1.00 | 15.78 | C |
| ATOM | 3283 | C | ILE | B | 170 | 77.725 | 23.283 | 85.284 | 1.00 | 21.66 | C |
| ATOM | 3284 | O | ILE | B | 170 | 78.135 | 23.324 | 84.123 | 1.00 | 20.56 | O |
| ATOM | 3285 | N | GLY | B | 171 | 78.206 | 24.049 | 86.272 | 1.00 | 23.57 | N |
| ATOM | 3286 | CA | GLY | B | 171 | 79.273 | 25.002 | 86.052 | 1.00 | 22.66 | C |
| ATOM | 3287 | C | GLY | B | 171 | 80.513 | 24.346 | 85.477 | 1.00 | 25.36 | C |
| ATOM | 3288 | O | GLY | B | 171 | 81.179 | 24.949 | 84.635 | 1.00 | 24.24 | O |
| ATOM | 3289 | N | GLU | B | 172 | 80.824 | 23.118 | 85.902 | 1.00 | 26.53 | N |
| ATOM | 3290 | CA | GLU | B | 172 | 82.006 | 22.419 | 85.392 | 1.00 | 28.76 | C |
| ATOM | 3291 | CB | GLU | B | 172 | 82.273 | 21.152 | 86.196 | 1.00 | 29.24 | C |
| ATOM | 3292 | CG | GLU | B | 172 | 82.468 | 21.463 | 87.670 | 1.00 | 39.39 | C |
| ATOM | 3293 | CD | GLU | B | 172 | 83.200 | 20.392 | 88.458 | 1.00 | 53.09 | C |
| ATOM | 3294 | OE1 | GLU | B | 172 | 82.615 | 19.309 | 88.709 | 1.00 | 61.48 | O |
| ATOM | 3295 | OE2 | GLU | B | 172 | 84.368 | 20.657 | 88.835 | 1.00 | 54.85 | O |
| ATOM | 3296 | C | GLU | B | 172 | 81.905 | 22.099 | 83.906 | 1.00 | 28.31 | C |
| ATOM | 3297 | O | GLU | B | 172 | 82.922 | 22.150 | 83.150 | 1.00 | 28.32 | O |
| ATOM | 3298 | N | ALA | B | 173 | 80.691 | 21.809 | 83.454 | 1.00 | 26.30 | N |
| ATOM | 3299 | CA | ALA | B | 173 | 80.563 | 21.527 | 82.035 | 1.00 | 24.98 | C |
| ATOM | 3300 | CB | ALA | B | 173 | 79.207 | 20.935 | 81.703 | 1.00 | 23.23 | C |
| ATOM | 3301 | C | ALA | B | 173 | 80.798 | 22.827 | 81.279 | 1.00 | 25.19 | C |
| ATOM | 3302 | O | ALA | B | 173 | 81.535 | 22.843 | 80.308 | 1.00 | 28.31 | O |
| ATOM | 3303 | N | ILE | B | 174 | 80.225 | 23.930 | 81.743 | 1.00 | 23.98 | N |
| ATOM | 3304 | CA | ILE | B | 174 | 80.395 | 25.189 | 81.041 | 1.00 | 22.56 | C |
| ATOM | 3305 | CB | ILE | B | 174 | 79.467 | 26.290 | 81.593 | 1.00 | 23.16 | C |
| ATOM | 3306 | CG1 | ILE | B | 174 | 78.020 | 25.801 | 81.571 | 1.00 | 22.90 | C |
| ATOM | 3307 | CD1 | ILE | B | 174 | 77.627 | 25.265 | 80.240 | 1.00 | 26.86 | C |
| ATOM | 3308 | CG2 | ILE | B | 174 | 79.643 | 27.564 | 80.785 | 1.00 | 16.36 | C |
| ATOM | 3309 | C | ILE | B | 174 | 81.827 | 25.738 | 81.057 | 1.00 | 23.28 | C |
| ATOM | 3310 | O | ILE | B | 174 | 82.270 | 26.294 | 80.077 | 1.00 | 24.66 | O |

FIG. 2A-72

| ATOM | 3311 | N | GLN | B | 175 | 82.547 | 25.598 | 82.153 | 1.00 | 22.15 | N |
|---|---|---|---|---|---|---|---|---|---|---|---|
| ATOM | 3312 | CA | GLN | B | 175 | 83.875 | 26.129 | 82.194 | 1.00 | 21.80 | C |
| ATOM | 3313 | CB | GLN | B | 175 | 84.427 | 25.989 | 83.591 | 1.00 | 20.66 | C |
| ATOM | 3314 | CG | GLN | B | 175 | 85.908 | 26.264 | 83.713 | 1.00 | 23.39 | C |
| ATOM | 3315 | CD | GLN | B | 175 | 86.362 | 26.124 | 85.157 | 1.00 | 33.38 | C |
| ATOM | 3316 | OE1 | GLN | B | 175 | 86.168 | 25.075 | 85.780 | 1.00 | 32.86 | O |
| ATOM | 3317 | NE2 | GLN | B | 175 | 86.958 | 27.191 | 85.708 | 1.00 | 37.86 | N |
| ATOM | 3318 | C | GLN | B | 175 | 84.768 | 25.437 | 81.202 | 1.00 | 21.77 | C |
| ATOM | 3319 | O | GLN | B | 175 | 85.688 | 26.040 | 80.635 | 1.00 | 20.44 | O |
| ATOM | 3320 | N | TYR | B | 176 | 84.503 | 24.157 | 80.964 | 1.00 | 22.25 | N |
| ATOM | 3321 | CA | TYR | B | 176 | 85.336 | 23.414 | 80.021 | 1.00 | 22.12 | C |
| ATOM | 3322 | CB | TYR | B | 176 | 85.150 | 21.904 | 80.220 | 1.00 | 22.06 | C |
| ATOM | 3323 | CG | TYR | B | 176 | 86.022 | 21.125 | 79.307 | 1.00 | 21.41 | C |
| ATOM | 3324 | CD1 | TYR | B | 176 | 87.396 | 21.115 | 79.473 | 1.00 | 23.65 | C |
| ATOM | 3325 | CE1 | TYR | B | 176 | 88.215 | 20.502 | 78.569 | 1.00 | 26.17 | C |
| ATOM | 3326 | CZ | TYR | B | 176 | 87.657 | 19.889 | 77.457 | 1.00 | 29.71 | C |
| ATOM | 3327 | OH | TYR | B | 176 | 88.469 | 19.399 | 76.438 | 1.00 | 37.29 | O |
| ATOM | 3328 | CE2 | TYR | B | 176 | 86.288 | 19.877 | 77.286 | 1.00 | 29.51 | C |
| ATOM | 3329 | CD2 | TYR | B | 176 | 85.487 | 20.488 | 78.206 | 1.00 | 25.70 | C |
| ATOM | 3330 | C | TYR | B | 176 | 85.040 | 23.794 | 78.569 | 1.00 | 24.20 | C |
| ATOM | 3331 | O | TYR | B | 176 | 85.953 | 23.874 | 77.718 | 1.00 | 26.10 | O |
| ATOM | 3332 | N | LEU | B | 177 | 83.765 | 24.031 | 78.280 | 1.00 | 23.07 | N |
| ATOM | 3333 | CA | LEU | B | 177 | 83.406 | 24.379 | 76.936 | 1.00 | 23.62 | C |
| ATOM | 3334 | CB | LEU | B | 177 | 81.901 | 24.493 | 76.781 | 1.00 | 24.61 | C |
| ATOM | 3335 | CG | LEU | B | 177 | 80.955 | 23.294 | 76.825 | 1.00 | 26.52 | C |
| ATOM | 3336 | CD1 | LEU | B | 177 | 79.691 | 23.744 | 76.123 | 1.00 | 26.81 | C |
| ATOM | 3337 | CD2 | LEU | B | 177 | 81.519 | 22.090 | 76.111 | 1.00 | 26.29 | C |
| ATOM | 3338 | C | LEU | B | 177 | 84.044 | 25.699 | 76.608 | 1.00 | 25.20 | C |
| ATOM | 3339 | O | LEU | B | 177 | 84.758 | 25.805 | 75.612 | 1.00 | 24.83 | O |
| ATOM | 3340 | N | HIS | B | 178 | 83.789 | 26.707 | 77.443 | 1.00 | 23.98 | N |
| ATOM | 3341 | CA | HIS | B | 178 | 84.356 | 28.037 | 77.245 | 1.00 | 23.56 | C |
| ATOM | 3342 | CB | HIS | B | 178 | 83.796 | 28.983 | 78.286 | 1.00 | 20.81 | C |
| ATOM | 3343 | CG | HIS | B | 178 | 82.326 | 29.252 | 78.119 | 1.00 | 19.73 | C |
| ATOM | 3344 | ND1 | HIS | B | 178 | 81.596 | 30.024 | 78.997 | 1.00 | 16.99 | N |
| ATOM | 3345 | CE1 | HIS | B | 178 | 80.343 | 30.104 | 78.592 | 1.00 | 15.02 | C |
| ATOM | 3346 | NE2 | HIS | B | 178 | 80.221 | 29.410 | 77.485 | 1.00 | 21.75 | N |
| ATOM | 3347 | CD2 | HIS | B | 178 | 81.446 | 28.861 | 77.167 | 1.00 | 19.43 | C |
| ATOM | 3348 | C | HIS | B | 178 | 85.909 | 28.021 | 77.211 | 1.00 | 24.19 | C |
| ATOM | 3349 | O | HIS | B | 178 | 86.546 | 28.759 | 76.444 | 1.00 | 23.74 | O |
| ATOM | 3350 | N | SER | B | 179 | 86.539 | 27.148 | 77.983 | 1.00 | 23.83 | N |
| ATOM | 3351 | CA | SER | B | 179 | 87.983 | 27.095 | 77.897 | 1.00 | 22.99 | C |
| ATOM | 3352 | CB | SER | B | 179 | 88.571 | 26.208 | 78.979 | 1.00 | 21.83 | C |
| ATOM | 3353 | OG | SER | B | 179 | 87.874 | 24.982 | 79.053 | 1.00 | 26.44 | O |
| ATOM | 3354 | C | SER | B | 179 | 88.421 | 26.576 | 76.547 | 1.00 | 23.92 | C |
| ATOM | 3355 | O | SER | B | 179 | 89.572 | 26.786 | 76.159 | 1.00 | 24.60 | O |
| ATOM | 3356 | N | ILE | B | 180 | 87.550 | 25.890 | 75.811 | 1.00 | 22.24 | N |

FIG. 2A-73

| ATOM | 3357 | CA | ILE | B | 180 | 87.982 | 25.408 | 74.512 | 1.00 | 21.23 | C |
| --- | --- | --- | --- | --- | --- | --- | --- | --- | --- | --- | --- |
| ATOM | 3358 | CB | ILE | B | 180 | 87.952 | 23.842 | 74.413 | 1.00 | 21.63 | C |
| ATOM | 3359 | CG1 | ILE | B | 180 | 86.521 | 23.285 | 74.486 | 1.00 | 19.92 | C |
| ATOM | 3360 | CD1 | ILE | B | 180 | 86.434 | 21.782 | 74.472 | 1.00 | 13.71 | C |
| ATOM | 3361 | CG2 | ILE | B | 180 | 88.782 | 23.269 | 75.538 | 1.00 | 21.02 | C |
| ATOM | 3362 | C | ILE | B | 180 | 87.147 | 26.072 | 73.447 | 1.00 | 23.10 | C |
| ATOM | 3363 | O | ILE | B | 180 | 86.821 | 25.514 | 72.405 | 1.00 | 25.67 | O |
| ATOM | 3364 | N | ASN | B | 181 | 86.785 | 27.297 | 73.751 | 1.00 | 21.90 | N |
| ATOM | 3365 | CA | ASN | B | 181 | 86.017 | 28.138 | 72.848 | 1.00 | 22.54 | C |
| ATOM | 3366 | CB | ASN | B | 181 | 86.981 | 28.771 | 71.860 | 1.00 | 22.88 | C |
| ATOM | 3367 | CG | ASN | B | 181 | 88.049 | 29.555 | 72.584 | 1.00 | 27.88 | C |
| ATOM | 3368 | OD1 | ASN | B | 181 | 87.753 | 30.485 | 73.327 | 1.00 | 33.71 | O |
| ATOM | 3369 | ND2 | ASN | B | 181 | 89.315 | 29.212 | 72.324 | 1.00 | 31.73 | N |
| ATOM | 3370 | C | ASN | B | 181 | 84.764 | 27.636 | 72.154 | 1.00 | 22.14 | C |
| ATOM | 3371 | O | ASN | B | 181 | 84.530 | 27.914 | 70.992 | 1.00 | 22.66 | O |
| ATOM | 3372 | N | ILE | B | 182 | 83.937 | 26.955 | 72.923 | 1.00 | 21.19 | N |
| ATOM | 3373 | CA | ILE | B | 182 | 82.665 | 26.481 | 72.463 | 1.00 | 20.02 | C |
| ATOM | 3374 | CB | ILE | B | 182 | 82.596 | 24.934 | 72.550 | 1.00 | 18.83 | C |
| ATOM | 3375 | CG1 | ILE | B | 182 | 83.632 | 24.318 | 71.645 | 1.00 | 18.97 | C |
| ATOM | 3376 | CD1 | ILE | B | 182 | 83.718 | 22.860 | 71.856 | 1.00 | 22.28 | C |
| ATOM | 3377 | CG2 | ILE | B | 182 | 81.243 | 24.420 | 72.143 | 1.00 | 16.61 | C |
| ATOM | 3378 | C | ILE | B | 182 | 81.555 | 27.096 | 73.342 | 1.00 | 20.75 | C |
| ATOM | 3379 | O | ILE | B | 182 | 81.664 | 27.220 | 74.574 | 1.00 | 20.65 | O |
| ATOM | 3380 | N | ALA | B | 183 | 80.489 | 27.518 | 72.690 | 1.00 | 22.59 | N |
| ATOM | 3381 | CA | ALA | B | 183 | 79.330 | 28.044 | 73.388 | 1.00 | 23.22 | C |
| ATOM | 3382 | CB | ALA | B | 183 | 78.931 | 29.376 | 72.803 | 1.00 | 23.28 | C |
| ATOM | 3383 | C | ALA | B | 183 | 78.228 | 26.987 | 73.153 | 1.00 | 24.42 | C |
| ATOM | 3384 | O | ALA | B | 183 | 77.904 | 26.661 | 72.034 | 1.00 | 25.35 | O |
| ATOM | 3385 | N | HIS | B | 184 | 77.681 | 26.425 | 74.212 | 1.00 | 25.21 | N |
| ATOM | 3386 | CA | HIS | B | 184 | 76.645 | 25.436 | 74.039 | 1.00 | 24.82 | C |
| ATOM | 3387 | CB | HIS | B | 184 | 76.246 | 24.824 | 75.383 | 1.00 | 23.11 | C |
| ATOM | 3388 | CG | HIS | B | 184 | 75.313 | 23.657 | 75.260 | 1.00 | 25.75 | C |
| ATOM | 3389 | ND1 | HIS | B | 184 | 73.942 | 23.798 | 75.257 | 1.00 | 25.27 | N |
| ATOM | 3390 | CE1 | HIS | B | 184 | 73.384 | 22.617 | 75.072 | 1.00 | 30.64 | C |
| ATOM | 3391 | NE2 | HIS | B | 184 | 74.342 | 21.714 | 74.959 | 1.00 | 30.56 | N |
| ATOM | 3392 | CD2 | HIS | B | 184 | 75.559 | 22.337 | 75.072 | 1.00 | 21.81 | C |
| ATOM | 3393 | C | HIS | B | 184 | 75.446 | 26.115 | 73.390 | 1.00 | 26.46 | C |
| ATOM | 3394 | O | HIS | B | 184 | 74.858 | 25.601 | 72.453 | 1.00 | 27.92 | O |
| ATOM | 3395 | N | ARG | B | 185 | 75.092 | 27.277 | 73.912 | 1.00 | 25.83 | N |
| ATOM | 3396 | CA | ARG | B | 185 | 73.995 | 28.054 | 73.386 | 1.00 | 26.52 | C |
| ATOM | 3397 | CB | ARG | B | 185 | 74.256 | 28.423 | 71.935 | 1.00 | 25.93 | C |
| ATOM | 3398 | CG | ARG | B | 185 | 75.556 | 29.156 | 71.797 | 1.00 | 26.82 | C |
| ATOM | 3399 | CD | ARG | B | 185 | 75.566 | 29.996 | 70.586 | 1.00 | 30.35 | C |
| ATOM | 3400 | NE | ARG | B | 185 | 75.442 | 29.208 | 69.372 | 1.00 | 28.00 | N |
| ATOM | 3401 | CZ | ARG | B | 185 | 74.939 | 29.689 | 68.240 | 1.00 | 28.26 | C |
| ATOM | 3402 | NH1AR | G | B | 185 | 74.519 | 30.958 | 68.203 | 1.00 | 25.81 | N |

FIG. 2A-74

| ATOM | 3403 | NH2AR | G | B | 185 | 74.849 | 28.911 | 67.164 | 1.00 | 29.36 | N |
|---|---|---|---|---|---|---|---|---|---|---|---|
| ATOM | 3404 | C | ARG | B | 185 | 72.623 | 27.449 | 73.537 | 1.00 | 26.83 | C |
| ATOM | 3405 | O | ARG | B | 185 | 71.651 | 28.051 | 73.082 | 1.00 | 27.68 | O |
| ATOM | 3406 | N | ASP | B | 186 | 72.515 | 26.280 | 74.153 | 1.00 | 24.94 | N |
| ATOM | 3407 | CA | ASP | B | 186 | 71.197 | 25.733 | 74.404 | 1.00 | 25.52 | C |
| ATOM | 3408 | CB | ASP | B | 186 | 70.746 | 24.758 | 73.321 | 1.00 | 26.13 | C |
| ATOM | 3409 | CG | ASP | B | 186 | 69.261 | 24.375 | 73.455 | 1.00 | 30.08 | C |
| ATOM | 3410 | OD1 | ASP | B | 186 | 68.406 | 25.288 | 73.678 | 1.00 | 24.53 | O |
| ATOM | 3411 | OD2 | ASP | B | 186 | 68.952 | 23.159 | 73.335 | 1.00 | 35.02 | O |
| ATOM | 3412 | C | ASP | B | 186 | 71.178 | 25.061 | 75.762 | 1.00 | 27.24 | C |
| ATOM | 3413 | O | ASP | B | 186 | 70.694 | 23.960 | 75.913 | 1.00 | 28.09 | O |
| ATOM | 3414 | N | VAL | B | 187 | 71.709 | 25.750 | 76.762 | 1.00 | 28.11 | N |
| ATOM | 3415 | CA | VAL | B | 187 | 71.733 | 25.219 | 78.106 | 1.00 | 26.26 | C |
| ATOM | 3416 | CB | VAL | B | 187 | 72.913 | 25.789 | 78.970 | 1.00 | 26.41 | C |
| ATOM | 3417 | CG1 | VAL | B | 187 | 72.849 | 25.178 | 80.372 | 1.00 | 22.24 | C |
| ATOM | 3418 | CG2 | VAL | B | 187 | 74.269 | 25.469 | 78.320 | 1.00 | 21.28 | C |
| ATOM | 3419 | C | VAL | B | 187 | 70.428 | 25.506 | 78.824 | 1.00 | 26.69 | C |
| ATOM | 3420 | O | VAL | B | 187 | 70.230 | 26.568 | 79.403 | 1.00 | 25.92 | O |
| ATOM | 3421 | N | LYS | B | 188 | 69.535 | 24.540 | 78.784 | 1.00 | 27.83 | N |
| ATOM | 3422 | CA | LYS | B | 188 | 68.246 | 24.649 | 79.458 | 1.00 | 29.15 | C |
| ATOM | 3423 | CB | LYS | B | 188 | 67.107 | 24.580 | 78.433 | 1.00 | 29.69 | C |
| ATOM | 3424 | CG | LYS | B | 188 | 67.170 | 23.336 | 77.587 | 1.00 | 31.75 | C |
| ATOM | 3425 | CD | LYS | B | 188 | 66.382 | 23.485 | 76.339 | 1.00 | 37.82 | C |
| ATOM | 3426 | CE | LYS | B | 188 | 66.463 | 22.199 | 75.500 | 1.00 | 44.27 | C |
| ATOM | 3427 | NZ | LYS | B | 188 | 66.051 | 22.374 | 74.037 | 1.00 | 44.31 | N |
| ATOM | 3428 | C | LYS | B | 188 | 68.207 | 23.441 | 80.387 | 1.00 | 27.77 | C |
| ATOM | 3429 | O | LYS | B | 188 | 68.991 | 22.515 | 80.248 | 1.00 | 25.17 | O |
| ATOM | 3430 | N | PRO | B | 189 | 67.297 | 23.451 | 81.355 | 1.00 | 27.76 | N |
| ATOM | 3431 | CA | PRO | B | 189 | 67.120 | 22.385 | 82.345 | 1.00 | 26.62 | C |
| ATOM | 3432 | CB | PRO | B | 189 | 65.849 | 22.780 | 83.070 | 1.00 | 23.96 | C |
| ATOM | 3433 | CG | PRO | B | 189 | 65.970 | 24.207 | 83.122 | 1.00 | 27.39 | C |
| ATOM | 3434 | CD | PRO | B | 189 | 66.529 | 24.644 | 81.738 | 1.00 | 28.48 | C |
| ATOM | 3435 | C | PRO | B | 189 | 66.991 | 21.037 | 81.733 | 1.00 | 27.08 | C |
| ATOM | 3436 | O | PRO | B | 189 | 67.702 | 20.116 | 82.114 | 1.00 | 28.06 | O |
| ATOM | 3437 | N | GLU | B | 190 | 66.085 | 20.935 | 80.774 | 1.00 | 26.29 | N |
| ATOM | 3438 | CA | GLU | B | 190 | 65.784 | 19.695 | 80.073 | 1.00 | 25.34 | C |
| ATOM | 3439 | CB | GLU | B | 190 | 64.700 | 19.973 | 79.024 | 1.00 | 23.87 | C |
| ATOM | 3440 | CG | GLU | B | 190 | 63.389 | 20.536 | 79.597 | 1.00 | 30.79 | C |
| ATOM | 3441 | CD | GLU | B | 190 | 63.479 | 22.001 | 80.109 | 1.00 | 34.69 | C |
| ATOM | 3442 | OE1 | GLU | B | 190 | 64.323 | 22.769 | 79.586 | 1.00 | 32.40 | O |
| ATOM | 3443 | OE2 | GLU | B | 190 | 62.689 | 22.389 | 81.022 | 1.00 | 34.82 | O |
| ATOM | 3444 | C | GLU | B | 190 | 66.981 | 19.006 | 79.410 | 1.00 | 25.68 | C |
| ATOM | 3445 | O | GLU | B | 190 | 66.888 | 17.830 | 79.052 | 1.00 | 27.63 | O |
| ATOM | 3446 | N | ASN | B | 191 | 68.086 | 19.732 | 79.224 | 1.00 | 25.41 | N |
| ATOM | 3447 | CA | ASN | B | 191 | 69.301 | 19.187 | 78.614 | 1.00 | 26.14 | C |
| ATOM | 3448 | CB | ASN | B | 191 | 70.015 | 20.213 | 77.742 | 1.00 | 26.38 | C |

FIG. 2A-75

| ATOM | 3449 | CG  | ASN | B | 191 | 69.450 | 20.281 | 76.381 | 1.00 | 29.24 | C |
| ATOM | 3450 | OD1 | ASN | B | 191 | 68.781 | 19.348 | 75.948 | 1.00 | 35.94 | O |
| ATOM | 3451 | ND2 | ASN | B | 191 | 69.705 | 21.375 | 75.674 | 1.00 | 27.69 | N |
| ATOM | 3452 | C   | ASN | B | 191 | 70.308 | 18.707 | 79.620 | 1.00 | 26.52 | C |
| ATOM | 3453 | O   | ASN | B | 191 | 71.441 | 18.408 | 79.247 | 1.00 | 27.97 | O |
| ATOM | 3454 | N   | LEU | B | 192 | 69.920 | 18.676 | 80.891 | 1.00 | 24.76 | N |
| ATOM | 3455 | CA  | LEU | B | 192 | 70.791 | 18.202 | 81.954 | 1.00 | 23.44 | C |
| ATOM | 3456 | CB  | LEU | B | 192 | 70.885 | 19.272 | 83.047 | 1.00 | 23.84 | C |
| ATOM | 3457 | CG  | LEU | B | 192 | 71.433 | 20.612 | 82.520 | 1.00 | 22.93 | C |
| ATOM | 3458 | CD1 | LEU | B | 192 | 71.467 | 21.717 | 83.584 | 1.00 | 19.67 | C |
| ATOM | 3459 | CD2 | LEU | B | 192 | 72.840 | 20.362 | 81.982 | 1.00 | 23.52 | C |
| ATOM | 3460 | C   | LEU | B | 192 | 70.216 | 16.874 | 82.498 | 1.00 | 23.78 | C |
| ATOM | 3461 | O   | LEU | B | 192 | 69.254 | 16.876 | 83.294 | 1.00 | 25.87 | O |
| ATOM | 3462 | N   | LEU | B | 193 | 70.771 | 15.744 | 82.047 | 1.00 | 22.24 | N |
| ATOM | 3463 | CA  | LEU | B | 193 | 70.313 | 14.419 | 82.490 | 1.00 | 22.98 | C |
| ATOM | 3464 | CB  | LEU | B | 193 | 70.166 | 13.469 | 81.313 | 1.00 | 22.72 | C |
| ATOM | 3465 | CG  | LEU | B | 193 | 69.331 | 14.041 | 80.181 | 1.00 | 23.90 | C |
| ATOM | 3466 | CD1 | LEU | B | 193 | 68.939 | 12.955 | 79.137 | 1.00 | 21.62 | C |
| ATOM | 3467 | CD2 | LEU | B | 193 | 68.120 | 14.656 | 80.827 | 1.00 | 22.28 | C |
| ATOM | 3468 | C   | LEU | B | 193 | 71.264 | 13.758 | 83.455 | 1.00 | 22.51 | C |
| ATOM | 3469 | O   | LEU | B | 193 | 72.484 | 13.917 | 83.347 | 1.00 | 20.68 | O |
| ATOM | 3470 | N   | TYR | B | 194 | 70.698 | 12.980 | 84.380 | 1.00 | 22.74 | N |
| ATOM | 3471 | CA  | TYR | B | 194 | 71.497 | 12.207 | 85.357 | 1.00 | 21.25 | C |
| ATOM | 3472 | CB  | TYR | B | 194 | 70.680 | 11.952 | 86.582 | 1.00 | 20.46 | C |
| ATOM | 3473 | CG  | TYR | B | 194 | 70.825 | 13.067 | 87.565 | 1.00 | 22.99 | C |
| ATOM | 3474 | CD1 | TYR | B | 194 | 72.056 | 13.302 | 88.182 | 1.00 | 23.53 | C |
| ATOM | 3475 | CE1 | TYR | B | 194 | 72.200 | 14.314 | 89.055 | 1.00 | 20.20 | C |
| ATOM | 3476 | CZ  | TYR | B | 194 | 71.121 | 15.143 | 89.340 | 1.00 | 22.67 | C |
| ATOM | 3477 | OH  | TYR | B | 194 | 71.277 | 16.157 | 90.255 | 1.00 | 21.53 | O |
| ATOM | 3478 | CE2 | TYR | B | 194 | 69.902 | 14.949 | 88.748 | 1.00 | 23.02 | C |
| ATOM | 3479 | CD2 | TYR | B | 194 | 69.755 | 13.906 | 87.869 | 1.00 | 24.82 | C |
| ATOM | 3480 | C   | TYR | B | 194 | 71.969 | 10.877 | 84.773 | 1.00 | 20.35 | C |
| ATOM | 3481 | O   | TYR | B | 194 | 71.247 | 10.265 | 84.001 | 1.00 | 19.17 | O |
| ATOM | 3482 | N   | THR | B | 195 | 73.188 | 10.458 | 85.106 | 1.00 | 20.81 | N |
| ATOM | 3483 | CA  | THR | B | 195 | 73.716 | 9.194  | 84.599 | 1.00 | 20.05 | C |
| ATOM | 3484 | CB  | THR | B | 195 | 75.052 | 8.905  | 85.110 | 1.00 | 17.81 | C |
| ATOM | 3485 | OG1 | THR | B | 195 | 75.046 | 9.126  | 86.511 | 1.00 | 22.71 | O |
| ATOM | 3486 | CG2 | THR | B | 195 | 76.075 | 9.798  | 84.462 | 1.00 | 22.44 | C |
| ATOM | 3487 | C   | THR | B | 195 | 72.884 | 8.046  | 85.056 | 1.00 | 19.54 | C |
| ATOM | 3488 | O   | THR | B | 195 | 72.624 | 7.117  | 84.292 | 1.00 | 22.35 | O |
| ATOM | 3489 | N   | SER | B | 196 | 72.466 | 8.093  | 86.309 | 1.00 | 18.31 | N |
| ATOM | 3490 | CA  | SER | B | 196 | 71.646 | 7.030  | 86.864 | 1.00 | 20.11 | C |
| ATOM | 3491 | CB  | SER | B | 196 | 72.516 | 5.919  | 87.470 | 1.00 | 20.10 | C |
| ATOM | 3492 | OG  | SER | B | 196 | 73.160 | 6.369  | 88.641 | 1.00 | 25.70 | O |
| ATOM | 3493 | C   | SER | B | 196 | 70.781 | 7.620  | 87.934 | 1.00 | 19.98 | C |
| ATOM | 3494 | O   | SER | B | 196 | 70.748 | 8.816  | 88.085 | 1.00 | 20.81 | O |

FIG. 2A-76

| ATOM | 3495 | N | ALA | B | 197 | 70.073 | 6.795 | 88.695 | 1.00 | 22.07 | N |
|------|------|---|-----|---|-----|--------|-------|--------|------|-------|---|
| ATOM | 3496 | CA | ALA | B | 197 | 69.234 | 7.369 | 89.731 | 1.00 | 22.21 | C |
| ATOM | 3497 | CB | ALA | B | 197 | 67.848 | 6.773 | 89.708 | 1.00 | 21.59 | C |
| ATOM | 3498 | C | ALA | B | 197 | 69.855 | 7.197 | 91.085 | 1.00 | 22.06 | C |
| ATOM | 3499 | O | ALA | B | 197 | 69.271 | 7.614 | 92.079 | 1.00 | 22.28 | O |
| ATOM | 3500 | N | ARG | B | 198 | 71.050 | 6.629 | 91.168 | 1.00 | 22.15 | N |
| ATOM | 3501 | CA | ARG | B | 198 | 71.553 | 6.507 | 92.511 | 1.00 | 24.15 | C |
| ATOM | 3502 | CB | ARG | B | 198 | 72.124 | 5.101 | 92.790 | 1.00 | 25.25 | C |
| ATOM | 3503 | CG | ARG | B | 198 | 72.933 | 4.505 | 91.736 | 1.00 | 28.06 | C |
| ATOM | 3504 | CD | ARG | B | 198 | 72.380 | 3.185 | 91.294 | 1.00 | 31.97 | C |
| ATOM | 3505 | NE | ARG | B | 198 | 73.164 | 2.883 | 90.122 | 1.00 | 38.33 | N |
| ATOM | 3506 | CZ | ARG | B | 198 | 72.734 | 2.271 | 89.040 | 1.00 | 39.55 | C |
| ATOM | 3507 | NH1AR | G | B | 198 | 71.496 | 1.851 | 88.950 | 1.00 | 40.56 | N |
| ATOM | 3508 | NH2AR | G | B | 198 | 73.559 | 2.134 | 88.024 | 1.00 | 39.84 | N |
| ATOM | 3509 | C | ARG | B | 198 | 72.471 | 7.605 | 92.996 | 1.00 | 24.54 | C |
| ATOM | 3510 | O | ARG | B | 198 | 73.005 | 8.402 | 92.213 | 1.00 | 22.90 | O |
| ATOM | 3511 | N | PRO | B | 199 | 72.650 | 7.667 | 94.331 | 1.00 | 26.20 | N |
| ATOM | 3512 | CA | PRO | B | 199 | 73.476 | 8.670 | 94.987 | 1.00 | 26.00 | C |
| ATOM | 3513 | CB | PRO | B | 199 | 73.934 | 7.959 | 96.271 | 1.00 | 27.08 | C |
| ATOM | 3514 | CG | PRO | B | 199 | 72.760 | 7.141 | 96.621 | 1.00 | 27.47 | C |
| ATOM | 3515 | CD | PRO | B | 199 | 72.402 | 6.544 | 95.262 | 1.00 | 25.89 | C |
| ATOM | 3516 | C | PRO | B | 199 | 74.615 | 9.171 | 94.176 | 1.00 | 25.30 | C |
| ATOM | 3517 | O | PRO | B | 199 | 74.681 | 10.337 | 93.904 | 1.00 | 25.60 | O |
| ATOM | 3518 | N | ASN | B | 200 | 75.509 | 8.301 | 93.748 | 1.00 | 25.61 | N |
| ATOM | 3519 | CA | ASN | B | 200 | 76.669 | 8.810 | 93.033 | 1.00 | 26.07 | C |
| ATOM | 3520 | CB | ASN | B | 200 | 77.732 | 7.734 | 93.025 | 1.00 | 26.79 | C |
| ATOM | 3521 | CG | ASN | B | 200 | 77.389 | 6.623 | 92.061 | 1.00 | 30.69 | C |
| ATOM | 3522 | OD1 | ASN | B | 200 | 76.252 | 6.110 | 92.049 | 1.00 | 29.62 | O |
| ATOM | 3523 | ND2 | ASN | B | 200 | 78.358 | 6.253 | 91.232 | 1.00 | 36.36 | N |
| ATOM | 3524 | C | ASN | B | 200 | 76.442 | 9.282 | 91.588 | 1.00 | 24.32 | C |
| ATOM | 3525 | O | ASN | B | 200 | 77.403 | 9.409 | 90.847 | 1.00 | 25.12 | O |
| ATOM | 3526 | N | ALA | B | 201 | 75.204 | 9.529 | 91.170 | 1.00 | 22.85 | N |
| ATOM | 3527 | CA | ALA | B | 201 | 75.010 | 9.940 | 89.786 | 1.00 | 23.10 | C |
| ATOM | 3528 | CB | ALA | B | 201 | 73.520 | 9.937 | 89.407 | 1.00 | 22.97 | C |
| ATOM | 3529 | C | ALA | B | 201 | 75.596 | 11.303 | 89.505 | 1.00 | 23.11 | C |
| ATOM | 3530 | O | ALA | B | 201 | 75.575 | 12.188 | 90.350 | 1.00 | 25.36 | O |
| ATOM | 3531 | N | ILE | B | 202 | 76.115 | 11.466 | 88.300 | 1.00 | 21.79 | N |
| ATOM | 3532 | CA | ILE | B | 202 | 76.680 | 12.725 | 87.860 | 1.00 | 21.55 | C |
| ATOM | 3533 | CB | ILE | B | 202 | 78.117 | 12.498 | 87.374 | 1.00 | 22.60 | C |
| ATOM | 3534 | CG1 | ILE | B | 202 | 78.357 | 13.266 | 86.099 | 1.00 | 22.74 | C |
| ATOM | 3535 | CD1 | ILE | B | 202 | 79.712 | 12.916 | 85.494 | 1.00 | 31.26 | C |
| ATOM | 3536 | CG2 | ILE | B | 202 | 78.399 | 11.018 | 87.134 | 1.00 | 19.19 | C |
| ATOM | 3537 | C | ILE | B | 202 | 75.805 | 13.339 | 86.750 | 1.00 | 19.65 | C |
| ATOM | 3538 | O | ILE | B | 202 | 75.361 | 12.632 | 85.870 | 1.00 | 19.30 | O |
| ATOM | 3539 | N | LEU | B | 203 | 75.511 | 14.643 | 86.841 | 1.00 | 19.08 | N |
| ATOM | 3540 | CA | LEU | B | 203 | 74.686 | 15.395 | 85.843 | 1.00 | 18.67 | C |

FIG. 2A-77

| ATOM | 3541 | CB | LEU | B | 203 | 74.284 | 16.777 | 86.340 | 1.00 | 18.52 | C |
| --- | --- | --- | --- | --- | --- | --- | --- | --- | --- | --- | --- |
| ATOM | 3542 | CG | LEU | B | 203 | 72.961 | 17.454 | 85.983 | 1.00 | 20.04 | C |
| ATOM | 3543 | CD1 | LEU | B | 203 | 71.915 | 16.328 | 85.851 | 1.00 | 18.62 | C |
| ATOM | 3544 | CD2 | LEU | B | 203 | 72.540 | 18.479 | 87.006 | 1.00 | 25.93 | C |
| ATOM | 3545 | C | LEU | B | 203 | 75.467 | 15.640 | 84.588 | 1.00 | 18.73 | C |
| ATOM | 3546 | O | LEU | B | 203 | 76.614 | 15.995 | 84.680 | 1.00 | 20.25 | O |
| ATOM | 3547 | N | LYS | B | 204 | 74.843 | 15.495 | 83.429 | 1.00 | 19.01 | N |
| ATOM | 3548 | CA | LYS | B | 204 | 75.552 | 15.709 | 82.199 | 1.00 | 20.42 | C |
| ATOM | 3549 | CB | LYS | B | 204 | 75.886 | 14.349 | 81.615 | 1.00 | 21.89 | C |
| ATOM | 3550 | CG | LYS | B | 204 | 76.901 | 13.592 | 82.462 | 1.00 | 21.39 | C |
| ATOM | 3551 | CD | LYS | B | 204 | 77.631 | 12.581 | 81.623 | 1.00 | 24.18 | C |
| ATOM | 3552 | CE | LYS | B | 204 | 78.701 | 11.920 | 82.450 | 1.00 | 21.71 | C |
| ATOM | 3553 | NZ | LYS | B | 204 | 79.699 | 11.265 | 81.571 | 1.00 | 20.97 | N |
| ATOM | 3554 | C | LYS | B | 204 | 74.859 | 16.603 | 81.146 | 1.00 | 22.82 | C |
| ATOM | 3555 | O | LYS | B | 204 | 73.643 | 16.514 | 80.969 | 1.00 | 23.76 | O |
| ATOM | 3556 | N | LEU | B | 205 | 75.625 | 17.482 | 80.471 | 1.00 | 23.67 | N |
| ATOM | 3557 | CA | LEU | B | 205 | 75.069 | 18.355 | 79.422 | 1.00 | 25.67 | C |
| ATOM | 3558 | CB | LEU | B | 205 | 75.986 | 19.512 | 79.028 | 1.00 | 24.02 | C |
| ATOM | 3559 | CG | LEU | B | 205 | 75.494 | 20.797 | 78.339 | 1.00 | 28.74 | C |
| ATOM | 3560 | CD1 | LEU | B | 205 | 74.121 | 21.184 | 78.907 | 1.00 | 27.24 | C |
| ATOM | 3561 | CD2 | LEU | B | 205 | 76.494 | 21.922 | 78.517 | 1.00 | 24.32 | C |
| ATOM | 3562 | C | LEU | B | 205 | 74.976 | 17.497 | 78.198 | 1.00 | 26.95 | C |
| ATOM | 3563 | O | LEU | B | 205 | 75.900 | 16.731 | 77.907 | 1.00 | 28.74 | O |
| ATOM | 3564 | N | THR | B | 206 | 73.879 | 17.670 | 77.462 | 1.00 | 26.03 | N |
| ATOM | 3565 | CA | THR | B | 206 | 73.618 | 16.935 | 76.230 | 1.00 | 26.60 | C |
| ATOM | 3566 | CB | THR | B | 206 | 72.408 | 16.035 | 76.392 | 1.00 | 25.09 | C |
| ATOM | 3567 | OG1 | THR | B | 206 | 71.237 | 16.854 | 76.572 | 1.00 | 31.32 | O |
| ATOM | 3568 | CG2 | THR | B | 206 | 72.568 | 15.154 | 77.577 | 1.00 | 20.18 | C |
| ATOM | 3569 | C | THR | B | 206 | 73.277 | 17.926 | 75.109 | 1.00 | 26.80 | C |
| ATOM | 3570 | O | THR | B | 206 | 73.168 | 19.134 | 75.329 | 1.00 | 29.53 | O |
| ATOM | 3571 | N | ASP | B | 207 | 73.063 | 17.377 | 73.920 | 1.00 | 27.03 | N |
| ATOM | 3572 | CA | ASP | B | 207 | 72.711 | 18.126 | 72.714 | 1.00 | 27.91 | C |
| ATOM | 3573 | CB | ASP | B | 207 | 71.293 | 18.639 | 72.792 | 1.00 | 27.85 | C |
| ATOM | 3574 | CG | ASP | B | 207 | 70.647 | 18.692 | 71.424 | 1.00 | 30.94 | C |
| ATOM | 3575 | OD1 | ASP | B | 207 | 71.377 | 18.851 | 70.417 | 1.00 | 30.55 | O |
| ATOM | 3576 | OD2 | ASP | B | 207 | 69.412 | 18.568 | 71.338 | 1.00 | 37.69 | O |
| ATOM | 3577 | C | ASP | B | 207 | 73.583 | 19.286 | 72.287 | 1.00 | 25.84 | C |
| ATOM | 3578 | O | ASP | B | 207 | 73.479 | 20.360 | 72.846 | 1.00 | 26.36 | O |
| ATOM | 3579 | N | PHE | B | 208 | 74.415 | 19.074 | 71.275 | 1.00 | 25.05 | N |
| ATOM | 3580 | CA | PHE | B | 208 | 75.273 | 20.136 | 70.789 | 1.00 | 25.76 | C |
| ATOM | 3581 | CB | PHE | B | 208 | 76.720 | 19.638 | 70.678 | 1.00 | 25.29 | C |
| ATOM | 3582 | CG | PHE | B | 208 | 77.487 | 19.697 | 71.967 | 1.00 | 26.72 | C |
| ATOM | 3583 | CD1 | PHE | B | 208 | 77.151 | 18.877 | 73.035 | 1.00 | 25.88 | C |
| ATOM | 3584 | CE1 | PHE | B | 208 | 77.854 | 18.931 | 74.249 | 1.00 | 27.34 | C |
| ATOM | 3585 | CZ | PHE | B | 208 | 78.913 | 19.828 | 74.392 | 1.00 | 29.07 | C |
| ATOM | 3586 | CE2 | PHE | B | 208 | 79.254 | 20.651 | 73.318 | 1.00 | 27.20 | C |

FIG. 2A-78

| | | | | | | | | | | |
|---|---|---|---|---|---|---|---|---|---|---|
| ATOM | 3587 | CD2 | PHE | B | 208 | 78.539 | 20.576 | 72.116 | 1.00 | 29.03 | C |
| ATOM | 3588 | C | PHE | B | 208 | 74.795 | 20.748 | 69.442 | 1.00 | 25.04 | C |
| ATOM | 3589 | O | PHE | B | 208 | 75.560 | 21.396 | 68.726 | 1.00 | 25.80 | O |
| ATOM | 3590 | N | GLY | B | 209 | 73.519 | 20.556 | 69.127 | 1.00 | 24.05 | N |
| ATOM | 3591 | CA | GLY | B | 209 | 72.942 | 21.087 | 67.914 | 1.00 | 21.13 | C |
| ATOM | 3592 | C | GLY | B | 209 | 73.021 | 22.585 | 67.673 | 1.00 | 21.86 | C |
| ATOM | 3593 | O | GLY | B | 209 | 72.777 | 23.021 | 66.586 | 1.00 | 23.81 | O |
| ATOM | 3594 | N | PHE | B | 210 | 73.340 | 23.385 | 68.669 | 1.00 | 21.29 | N |
| ATOM | 3595 | CA | PHE | B | 210 | 73.454 | 24.836 | 68.491 | 1.00 | 21.63 | C |
| ATOM | 3596 | CB | PHE | B | 210 | 72.453 | 25.611 | 69.367 | 1.00 | 21.23 | C |
| ATOM | 3597 | CG | PHE | B | 210 | 71.022 | 25.407 | 69.009 | 1.00 | 26.63 | C |
| ATOM | 3598 | CD1 | PHE | B | 210 | 70.592 | 25.494 | 67.714 | 1.00 | 32.92 | C |
| ATOM | 3599 | CE1 | PHE | B | 210 | 69.260 | 25.383 | 67.402 | 1.00 | 38.98 | C |
| ATOM | 3600 | CZ | PHE | B | 210 | 68.344 | 25.180 | 68.363 | 1.00 | 40.40 | C |
| ATOM | 3601 | CE2 | PHE | B | 210 | 68.751 | 25.084 | 69.656 | 1.00 | 43.23 | C |
| ATOM | 3602 | CD2 | PHE | B | 210 | 70.093 | 25.198 | 69.980 | 1.00 | 37.12 | C |
| ATOM | 3603 | C | PHE | B | 210 | 74.842 | 25.297 | 68.921 | 1.00 | 20.90 | C |
| ATOM | 3604 | O | PHE | B | 210 | 75.129 | 26.487 | 68.864 | 1.00 | 19.31 | O |
| ATOM | 3605 | N | ALA | B | 211 | 75.673 | 24.364 | 69.404 | 1.00 | 21.10 | N |
| ATOM | 3606 | CA | ALA | B | 211 | 77.005 | 24.699 | 69.844 | 1.00 | 21.53 | C |
| ATOM | 3607 | CB | ALA | B | 211 | 77.762 | 23.452 | 70.217 | 1.00 | 20.27 | C |
| ATOM | 3608 | C | ALA | B | 211 | 77.749 | 25.454 | 68.763 | 1.00 | 23.63 | C |
| ATOM | 3609 | O | ALA | B | 211 | 77.624 | 25.162 | 67.582 | 1.00 | 25.98 | O |
| ATOM | 3610 | N | LYS | B | 212 | 78.541 | 26.427 | 69.194 | 1.00 | 26.31 | N |
| ATOM | 3611 | CA | LYS | B | 212 | 79.327 | 27.251 | 68.294 | 1.00 | 27.39 | C |
| ATOM | 3612 | CB | LYS | B | 212 | 78.656 | 28.615 | 68.180 | 1.00 | 29.02 | C |
| ATOM | 3613 | CG | LYS | B | 212 | 78.185 | 29.015 | 66.799 | 1.00 | 29.21 | C |
| ATOM | 3614 | CD | LYS | B | 212 | 77.809 | 30.500 | 66.842 | 1.00 | 41.43 | C |
| ATOM | 3615 | CE | LYS | B | 212 | 78.710 | 31.378 | 65.926 | 1.00 | 47.98 | C |
| ATOM | 3616 | NZ | LYS | B | 212 | 78.262 | 31.401 | 64.476 | 1.00 | 49.69 | N |
| ATOM | 3617 | C | LYS | B | 212 | 80.780 | 27.449 | 68.756 | 1.00 | 27.76 | C |
| ATOM | 3618 | O | LYS | B | 212 | 81.027 | 27.641 | 69.925 | 1.00 | 27.54 | O |
| ATOM | 3619 | N | GLU | B | 213 | 81.719 | 27.395 | 67.822 | 1.00 | 28.36 | N |
| ATOM | 3620 | CA | GLU | B | 213 | 83.136 | 27.638 | 68.078 | 1.00 | 29.21 | C |
| ATOM | 3621 | CB | GLU | B | 213 | 83.980 | 27.220 | 66.870 | 1.00 | 30.40 | C |
| ATOM | 3622 | CG | GLU | B | 213 | 84.698 | 25.899 | 66.997 | 1.00 | 37.79 | C |
| ATOM | 3623 | CD | GLU | B | 213 | 85.888 | 25.761 | 66.039 | 1.00 | 49.07 | C |
| ATOM | 3624 | OE1 | GLU | B | 213 | 85.681 | 25.676 | 64.813 | 1.00 | 48.64 | O |
| ATOM | 3625 | OE2 | GLU | B | 213 | 87.045 | 25.743 | 66.521 | 1.00 | 52.48 | O |
| ATOM | 3626 | C | GLU | B | 213 | 83.311 | 29.146 | 68.234 | 1.00 | 29.42 | C |
| ATOM | 3627 | O | GLU | B | 213 | 83.308 | 29.845 | 67.255 | 1.00 | 30.99 | O |
| ATOM | 3628 | N | THR | B | 214 | 83.487 | 29.672 | 69.434 | 1.00 | 31.10 | N |
| ATOM | 3629 | CA | THR | B | 214 | 83.582 | 31.133 | 69.519 | 1.00 | 32.09 | C |
| ATOM | 3630 | CB | THR | B | 214 | 83.556 | 31.532 | 70.994 | 1.00 | 30.64 | C |
| ATOM | 3631 | OG1 | THR | B | 214 | 84.474 | 30.699 | 71.711 | 1.00 | 28.81 | O |
| ATOM | 3632 | CG2 | THR | B | 214 | 82.153 | 31.323 | 71.562 | 1.00 | 31.10 | C |

FIG. 2A-79

| ATOM | 3633 | C   | THR | B | 214 | 84.847  | 31.682 | 68.853 | 1.00 | 35.84 | C |
|------|------|-----|-----|---|-----|---------|--------|--------|------|-------|---|
| ATOM | 3634 | O   | THR | B | 214 | 85.077  | 32.883 | 68.799 | 1.00 | 34.49 | O |
| ATOM | 3635 | N   | THR | B | 215 | 85.705  | 30.767 | 68.369 | 1.00 | 41.14 | N |
| ATOM | 3636 | CA  | THR | B | 215 | 86.889  | 31.222 | 67.649 | 1.00 | 45.50 | C |
| ATOM | 3637 | CB  | THR | B | 215 | 88.081  | 31.201 | 68.605 | 1.00 | 44.79 | C |
| ATOM | 3638 | OG1 | THR | B | 215 | 88.026  | 30.007 | 69.390 | 1.00 | 53.23 | O |
| ATOM | 3639 | CG2 | THR | B | 215 | 88.009  | 32.405 | 69.548 | 1.00 | 46.02 | C |
| ATOM | 3640 | C   | THR | B | 215 | 87.175  | 30.357 | 66.421 | 1.00 | 48.58 | C |
| ATOM | 3641 | O   | THR | B | 215 | 86.686  | 30.619 | 65.331 | 1.00 | 53.24 | O |
| ATOM | 3642 | OXT | THR | B | 215 | 87.902  | 29.375 | 66.486 | 1.00 | 48.62 | O |
| ATOM | 3643 | N   | PRO | B | 227 | 103.453 | 36.813 | 75.032 | 1.00 | 25.36 | N |
| ATOM | 3644 | CA  | PRO | B | 227 | 103.587 | 38.104 | 75.777 | 1.00 | 24.26 | C |
| ATOM | 3645 | CB  | PRO | B | 227 | 103.206 | 39.239 | 74.826 | 1.00 | 24.04 | C |
| ATOM | 3646 | CG  | PRO | B | 227 | 103.284 | 38.549 | 73.464 | 1.00 | 25.16 | C |
| ATOM | 3647 | CD  | PRO | B | 227 | 102.882 | 37.074 | 73.703 | 1.00 | 26.03 | C |
| ATOM | 3648 | C   | PRO | B | 227 | 102.647 | 38.077 | 76.990 | 1.00 | 23.01 | C |
| ATOM | 3649 | O   | PRO | B | 227 | 101.412 | 38.103 | 76.865 | 1.00 | 23.49 | O |
| ATOM | 3650 | N   | TYR | B | 228 | 103.247 | 38.019 | 78.167 | 1.00 | 20.29 | N |
| ATOM | 3651 | CA  | TYR | B | 228 | 102.514 | 37.957 | 79.410 | 1.00 | 17.71 | C |
| ATOM | 3652 | CB  | TYR | B | 228 | 103.518 | 37.794 | 80.552 | 1.00 | 18.34 | C |
| ATOM | 3653 | CG  | TYR | B | 228 | 104.295 | 39.051 | 80.861 | 1.00 | 17.01 | C |
| ATOM | 3654 | CD1 | TYR | B | 228 | 103.802 | 39.992 | 81.757 | 1.00 | 21.77 | C |
| ATOM | 3655 | CE1 | TYR | B | 228 | 104.516 | 41.159 | 82.062 | 1.00 | 21.41 | C |
| ATOM | 3656 | CZ  | TYR | B | 228 | 105.741 | 41.384 | 81.464 | 1.00 | 19.28 | C |
| ATOM | 3657 | OH  | TYR | B | 228 | 106.479 | 42.494 | 81.811 | 1.00 | 14.00 | O |
| ATOM | 3658 | CE2 | TYR | B | 228 | 106.245 | 40.458 | 80.561 | 1.00 | 19.48 | C |
| ATOM | 3659 | CD2 | TYR | B | 228 | 105.521 | 39.298 | 80.266 | 1.00 | 17.32 | C |
| ATOM | 3660 | C   | TYR | B | 228 | 101.596 | 39.148 | 79.711 | 1.00 | 15.51 | C |
| ATOM | 3661 | O   | TYR | B | 228 | 100.697 | 39.027 | 80.514 | 1.00 | 16.51 | O |
| ATOM | 3662 | N   | TYR | B | 229 | 101.802 | 40.293 | 79.085 | 1.00 | 13.15 | N |
| ATOM | 3663 | CA  | TYR | B | 229 | 100.982 | 41.445 | 79.402 | 1.00 | 12.16 | C |
| ATOM | 3664 | CB  | TYR | B | 229 | 101.899 | 42.605 | 79.669 | 1.00 | 10.93 | C |
| ATOM | 3665 | CG  | TYR | B | 229 | 102.593 | 43.017 | 78.418 | 1.00 | 15.26 | C |
| ATOM | 3666 | CD1 | TYR | B | 229 | 102.005 | 43.931 | 77.546 | 1.00 | 20.20 | C |
| ATOM | 3667 | CE1 | TYR | B | 229 | 102.617 | 44.277 | 76.363 | 1.00 | 22.78 | C |
| ATOM | 3668 | CZ  | TYR | B | 229 | 103.842 | 43.703 | 76.034 | 1.00 | 23.69 | C |
| ATOM | 3669 | OH  | TYR | B | 229 | 104.490 | 44.096 | 74.875 | 1.00 | 25.32 | O |
| ATOM | 3670 | CE2 | TYR | B | 229 | 104.431 | 42.795 | 76.881 | 1.00 | 20.77 | C |
| ATOM | 3671 | CD2 | TYR | B | 229 | 103.810 | 42.462 | 78.067 | 1.00 | 16.67 | C |
| ATOM | 3672 | C   | TYR | B | 229 | 99.915  | 41.857 | 78.388 | 1.00 | 11.63 | C |
| ATOM | 3673 | O   | TYR | B | 229 | 99.247  | 42.885 | 78.576 | 1.00 | 11.67 | O |
| ATOM | 3674 | N   | VAL | B | 230 | 99.739  | 41.062 | 77.333 | 1.00 | 11.67 | N |
| ATOM | 3675 | CA  | VAL | B | 230 | 98.749  | 41.325 | 76.285 | 1.00 | 12.09 | C |
| ATOM | 3676 | CB  | VAL | B | 230 | 99.022  | 40.402 | 75.033 | 1.00 | 12.81 | C |
| ATOM | 3677 | CG1 | VAL | B | 230 | 99.128  | 38.962 | 75.466 | 1.00 | 11.64 | C |
| ATOM | 3678 | CG2 | VAL | B | 230 | 97.903  | 40.551 | 73.971 | 1.00 | 14.92 | C |

FIG. 2A-80

| ATOM | 3679 | C | VAL | B | 230 | 97.334 | 41.076 | 76.817 | 1.00 | 12.07 | C |
| --- | --- | --- | --- | --- | --- | --- | --- | --- | --- | --- | --- |
| ATOM | 3680 | O | VAL | B | 230 | 97.127 | 40.108 | 77.536 | 1.00 | 11.54 | O |
| ATOM | 3681 | N | ALA | B | 231 | 96.382 | 41.949 | 76.453 | 1.00 | 12.55 | N |
| ATOM | 3682 | CA | ALA | B | 231 | 94.975 | 41.866 | 76.881 | 1.00 | 12.70 | C |
| ATOM | 3683 | CB | ALA | B | 231 | 94.343 | 43.187 | 76.790 | 1.00 | 13.20 | C |
| ATOM | 3684 | C | ALA | B | 231 | 94.166 | 40.886 | 76.070 | 1.00 | 13.47 | C |
| ATOM | 3685 | O | ALA | B | 231 | 94.280 | 40.816 | 74.840 | 1.00 | 13.74 | O |
| ATOM | 3686 | N | PRO | B | 232 | 93.310 | 40.118 | 76.745 | 1.00 | 14.79 | N |
| ATOM | 3687 | CA | PRO | B | 232 | 92.461 | 39.116 | 76.123 | 1.00 | 15.04 | C |
| ATOM | 3688 | CB | PRO | B | 232 | 91.360 | 38.928 | 77.139 | 1.00 | 15.20 | C |
| ATOM | 3689 | CG | PRO | B | 232 | 91.522 | 40.036 | 78.090 | 1.00 | 17.05 | C |
| ATOM | 3690 | CD | PRO | B | 232 | 92.966 | 40.258 | 78.153 | 1.00 | 16.05 | C |
| ATOM | 3691 | C | PRO | B | 232 | 91.957 | 39.471 | 74.753 | 1.00 | 16.54 | C |
| ATOM | 3692 | O | PRO | B | 232 | 92.131 | 38.723 | 73.805 | 1.00 | 17.22 | O |
| ATOM | 3693 | N | GLU | B | 233 | 91.364 | 40.644 | 74.645 | 1.00 | 19.14 | N |
| ATOM | 3694 | CA | GLU | B | 233 | 90.806 | 41.135 | 73.382 | 1.00 | 21.12 | C |
| ATOM | 3695 | CB | GLU | B | 233 | 90.149 | 42.480 | 73.648 | 1.00 | 20.77 | C |
| ATOM | 3696 | CG | GLU | B | 233 | 90.269 | 42.795 | 75.115 | 1.00 | 22.00 | C |
| ATOM | 3697 | CD | GLU | B | 233 | 90.943 | 44.074 | 75.364 | 1.00 | 19.70 | C |
| ATOM | 3698 | OE1 | GLU | B | 233 | 91.308 | 44.328 | 76.509 | 1.00 | 27.15 | O |
| ATOM | 3699 | OE2 | GLU | B | 233 | 91.094 | 44.844 | 74.415 | 1.00 | 23.69 | O |
| ATOM | 3700 | C | GLU | B | 233 | 91.868 | 41.282 | 72.315 | 1.00 | 22.02 | C |
| ATOM | 3701 | O | GLU | B | 233 | 91.599 | 41.100 | 71.138 | 1.00 | 23.71 | O |
| ATOM | 3702 | N | VAL | B | 234 | 93.082 | 41.620 | 72.712 | 1.00 | 24.48 | N |
| ATOM | 3703 | CA | VAL | B | 234 | 94.118 | 41.687 | 71.689 | 1.00 | 26.13 | C |
| ATOM | 3704 | CB | VAL | B | 234 | 95.255 | 42.561 | 72.216 | 1.00 | 24.46 | C |
| ATOM | 3705 | CG1 | VAL | B | 234 | 96.280 | 42.800 | 71.110 | 1.00 | 23.98 | C |
| ATOM | 3706 | CG2 | VAL | B | 234 | 94.705 | 43.897 | 72.679 | 1.00 | 24.80 | C |
| ATOM | 3707 | C | VAL | B | 234 | 94.649 | 40.298 | 71.319 | 1.00 | 28.47 | C |
| ATOM | 3708 | O | VAL | B | 234 | 95.721 | 40.139 | 70.751 | 1.00 | 28.50 | O |
| ATOM | 3709 | N | LEU | B | 235 | 93.869 | 39.268 | 71.697 | 1.00 | 32.53 | N |
| ATOM | 3710 | CA | LEU | B | 235 | 94.266 | 37.903 | 71.365 | 1.00 | 36.29 | C |
| ATOM | 3711 | CB | LEU | B | 235 | 94.309 | 37.093 | 72.660 | 1.00 | 35.18 | C |
| ATOM | 3712 | CG | LEU | B | 235 | 95.666 | 37.176 | 73.360 | 1.00 | 33.37 | C |
| ATOM | 3713 | CD1 | LEU | B | 235 | 96.002 | 35.899 | 74.133 | 1.00 | 29.75 | C |
| ATOM | 3714 | CD2 | LEU | B | 235 | 96.820 | 37.403 | 72.386 | 1.00 | 34.09 | C |
| ATOM | 3715 | C | LEU | B | 235 | 93.279 | 37.261 | 70.387 | 1.00 | 40.94 | C |
| ATOM | 3716 | O | LEU | B | 235 | 93.507 | 36.196 | 69.827 | 1.00 | 44.02 | O |
| ATOM | 3717 | N | GLY | B | 236 | 92.127 | 37.938 | 70.228 | 1.00 | 43.80 | N |
| ATOM | 3718 | CA | GLY | B | 236 | 91.094 | 37.414 | 69.347 | 1.00 | 46.01 | C |
| ATOM | 3719 | C | GLY | B | 236 | 89.719 | 37.960 | 69.733 | 1.00 | 48.46 | C |
| ATOM | 3720 | O | GLY | B | 236 | 89.251 | 37.819 | 70.856 | 1.00 | 48.71 | O |
| ATOM | 3721 | N | PRO | B | 237 | 89.082 | 38.639 | 68.761 | 1.00 | 50.46 | N |
| ATOM | 3722 | CA | PRO | B | 237 | 87.794 | 39.272 | 68.983 | 1.00 | 52.28 | C |
| ATOM | 3723 | CB | PRO | B | 237 | 87.127 | 39.428 | 67.619 | 1.00 | 52.96 | C |
| ATOM | 3724 | CG | PRO | B | 237 | 88.175 | 39.162 | 66.534 | 1.00 | 52.92 | C |

FIG. 2A-81

| ATOM | 3725 | CD  | PRO | B | 237 | 89.494 | 38.850 | 67.388 | 1.00 | 51.58 | C |
| --- | --- | --- | --- | --- | --- | --- | --- | --- | --- | --- | --- |
| ATOM | 3726 | C   | PRO | B | 237 | 86.907 | 38.445 | 69.916 | 1.00 | 53.10 | C |
| ATOM | 3727 | O   | PRO | B | 237 | 86.728 | 38.759 | 71.085 | 1.00 | 54.34 | O |
| ATOM | 3728 | N   | GLU | B | 238 | 86.320 | 37.444 | 69.242 | 1.00 | 52.81 | N |
| ATOM | 3729 | CA  | GLU | B | 238 | 85.308 | 36.640 | 69.904 | 1.00 | 54.18 | C |
| ATOM | 3730 | CB  | GLU | B | 238 | 85.946 | 35.971 | 71.114 | 1.00 | 54.15 | C |
| ATOM | 3731 | CG  | GLU | B | 238 | 84.947 | 35.117 | 71.903 | 1.00 | 55.36 | C |
| ATOM | 3732 | CD  | GLU | B | 238 | 85.651 | 34.471 | 73.074 | 1.00 | 60.76 | C |
| ATOM | 3733 | OE1 | GLU | B | 238 | 85.007 | 33.743 | 73.817 | 1.00 | 64.68 | O |
| ATOM | 3734 | OE2 | GLU | B | 238 | 86.848 | 34.704 | 73.235 | 1.00 | 66.39 | O |
| ATOM | 3735 | C   | GLU | B | 238 | 84.136 | 37.512 | 70.358 | 1.00 | 53.74 | C |
| ATOM | 3736 | O   | GLU | B | 238 | 84.280 | 38.458 | 71.118 | 1.00 | 53.39 | O |
| ATOM | 3737 | N   | ALA | B | 239 | 82.951 | 37.192 | 69.830 | 1.00 | 53.57 | N |
| ATOM | 3738 | CA  | ALA | B | 239 | 81.806 | 38.020 | 70.175 | 1.00 | 52.65 | C |
| ATOM | 3739 | CB  | ALA | B | 239 | 80.668 | 37.700 | 69.202 | 1.00 | 53.60 | C |
| ATOM | 3740 | C   | ALA | B | 239 | 81.349 | 37.770 | 71.615 | 1.00 | 51.65 | C |
| ATOM | 3741 | O   | ALA | B | 239 | 82.110 | 37.846 | 72.572 | 1.00 | 53.16 | O |
| ATOM | 3742 | N   | ALA | B | 240 | 80.041 | 37.505 | 71.748 | 1.00 | 49.33 | N |
| ATOM | 3743 | CA  | ALA | B | 240 | 79.499 | 37.146 | 73.047 | 1.00 | 48.78 | C |
| ATOM | 3744 | CB  | ALA | B | 240 | 78.768 | 38.370 | 73.614 | 1.00 | 49.66 | C |
| ATOM | 3745 | C   | ALA | B | 240 | 78.535 | 35.973 | 72.910 | 1.00 | 47.69 | C |
| ATOM | 3746 | O   | ALA | B | 240 | 77.324 | 36.120 | 72.983 | 1.00 | 49.07 | O |
| ATOM | 3747 | N   | ASP | B | 241 | 79.112 | 34.781 | 72.674 | 1.00 | 44.64 | N |
| ATOM | 3748 | CA  | ASP | B | 241 | 78.284 | 33.581 | 72.645 | 1.00 | 40.89 | C |
| ATOM | 3749 | CB  | ASP | B | 241 | 78.858 | 32.623 | 71.595 | 1.00 | 41.89 | C |
| ATOM | 3750 | CG  | ASP | B | 241 | 78.411 | 33.075 | 70.211 | 1.00 | 46.26 | C |
| ATOM | 3751 | OD1 | ASP | B | 241 | 77.232 | 32.894 | 69.902 | 1.00 | 47.04 | O |
| ATOM | 3752 | OD2 | ASP | B | 241 | 79.224 | 33.621 | 69.475 | 1.00 | 48.56 | O |
| ATOM | 3753 | C   | ASP | B | 241 | 78.241 | 32.903 | 74.021 | 1.00 | 38.42 | C |
| ATOM | 3754 | O   | ASP | B | 241 | 77.204 | 32.454 | 74.487 | 1.00 | 39.98 | O |
| ATOM | 3755 | N   | LYS | B | 242 | 79.431 | 32.830 | 74.607 | 1.00 | 33.18 | N |
| ATOM | 3756 | CA  | LYS | B | 242 | 79.575 | 32.212 | 75.916 | 1.00 | 29.29 | C |
| ATOM | 3757 | CB  | LYS | B | 242 | 80.993 | 32.410 | 76.446 | 1.00 | 26.43 | C |
| ATOM | 3758 | CG  | LYS | B | 242 | 82.045 | 31.948 | 75.525 | 1.00 | 22.79 | C |
| ATOM | 3759 | CD  | LYS | B | 242 | 83.393 | 32.035 | 76.139 | 1.00 | 24.08 | C |
| ATOM | 3760 | CE  | LYS | B | 242 | 84.407 | 31.274 | 75.281 | 1.00 | 33.35 | C |
| ATOM | 3761 | NZ  | LYS | B | 242 | 85.583 | 32.111 | 74.805 | 1.00 | 43.38 | N |
| ATOM | 3762 | C   | LYS | B | 242 | 78.589 | 32.913 | 76.840 | 1.00 | 28.34 | C |
| ATOM | 3763 | O   | LYS | B | 242 | 78.026 | 32.315 | 77.746 | 1.00 | 30.94 | O |
| ATOM | 3764 | N   | SER | B | 243 | 78.380 | 34.193 | 76.581 | 1.00 | 27.18 | N |
| ATOM | 3765 | CA  | SER | B | 243 | 77.499 | 35.013 | 77.370 | 1.00 | 26.58 | C |
| ATOM | 3766 | CB  | SER | B | 243 | 77.327 | 36.360 | 76.714 | 1.00 | 27.87 | C |
| ATOM | 3767 | OG  | SER | B | 243 | 78.041 | 37.330 | 77.423 | 1.00 | 28.17 | O |
| ATOM | 3768 | C   | SER | B | 243 | 76.140 | 34.441 | 77.602 | 1.00 | 27.20 | C |
| ATOM | 3769 | O   | SER | B | 243 | 75.603 | 34.563 | 78.690 | 1.00 | 26.73 | O |
| ATOM | 3770 | N   | CYS | B | 244 | 75.561 | 33.800 | 76.598 | 1.00 | 27.68 | N |

FIG. 2A-82

| ATOM | 3771 | CA | CYS | B | 244 | 74.221 | 33.331 | 76.812 | 1.00 | 29.36 | C |
|---|---|---|---|---|---|---|---|---|---|---|---|
| ATOM | 3772 | CB | CYS | B | 244 | 73.476 | 33.109 | 75.498 | 1.00 | 29.68 | C |
| ATOM | 3773 | SG | CYS | B | 244 | 74.220 | 31.956 | 74.416 | 1.00 | 45.03 | S |
| ATOM | 3774 | C | CYS | B | 244 | 74.171 | 32.141 | 77.693 | 1.00 | 25.85 | C |
| ATOM | 3775 | O | CYS | B | 244 | 73.174 | 31.970 | 78.376 | 1.00 | 27.83 | O |
| ATOM | 3776 | N | ASP | B | 245 | 75.240 | 31.337 | 77.714 | 1.00 | 23.75 | N |
| ATOM | 3777 | CA | ASP | B | 245 | 75.299 | 30.185 | 78.619 | 1.00 | 21.17 | C |
| ATOM | 3778 | CB | ASP | B | 245 | 76.572 | 29.373 | 78.453 | 1.00 | 17.24 | C |
| ATOM | 3779 | CG | ASP | B | 245 | 76.746 | 28.784 | 77.042 | 1.00 | 20.01 | C |
| ATOM | 3780 | OD1 | ASP | B | 245 | 75.776 | 28.594 | 76.281 | 1.00 | 21.33 | O |
| ATOM | 3781 | OD2 | ASP | B | 245 | 77.894 | 28.483 | 76.680 | 1.00 | 18.01 | O |
| ATOM | 3782 | C | ASP | B | 245 | 75.241 | 30.740 | 80.052 | 1.00 | 20.45 | C |
| ATOM | 3783 | O | ASP | B | 245 | 74.559 | 30.200 | 80.903 | 1.00 | 21.57 | O |
| ATOM | 3784 | N | MSE | B | 246 | 75.906 | 31.861 | 80.312 | 1.00 | 19.47 | N |
| ATOM | 3785 | CA | MSE | B | 246 | 75.878 | 32.423 | 81.653 | 1.00 | 19.18 | C |
| ATOM | 3786 | CB | MSE | B | 246 | 76.901 | 33.547 | 81.796 | 1.00 | 18.58 | C |
| ATOM | 3787 | CG | MSE | B | 246 | 78.353 | 33.096 | 81.524 | 1.00 | 19.10 | C |
| ATOM | 3788 | SE | MSE | B | 246 | 78.946 | 31.455 | 82.415 | 1.00 | 27.59 | S |
| ATOM | 3789 | CE | MSE | B | 246 | 78.265 | 31.832 | 84.138 | 1.00 | 36.19 | C |
| ATOM | 3790 | C | MSE | B | 246 | 74.494 | 32.893 | 82.015 | 1.00 | 19.54 | C |
| ATOM | 3791 | O | MSE | B | 246 | 74.098 | 32.786 | 83.169 | 1.00 | 21.06 | O |
| ATOM | 3792 | N | TRP | B | 247 | 73.740 | 33.414 | 81.049 | 1.00 | 18.95 | N |
| ATOM | 3793 | CA | TRP | B | 247 | 72.357 | 33.766 | 81.376 | 1.00 | 18.69 | C |
| ATOM | 3794 | CB | TRP | B | 247 | 71.750 | 34.512 | 80.179 | 1.00 | 18.44 | C |
| ATOM | 3795 | CG | TRP | B | 247 | 70.296 | 34.738 | 80.370 | 1.00 | 12.88 | C |
| ATOM | 3796 | CD1 | TRP | B | 247 | 69.255 | 33.857 | 80.000 | 1.00 | 11.17 | C |
| ATOM | 3797 | NE1 | TRP | B | 247 | 68.023 | 34.394 | 80.208 | 1.00 | 20.21 | N |
| ATOM | 3798 | CE2 | TRP | B | 247 | 68.259 | 35.750 | 80.761 | 1.00 | 17.33 | C |
| ATOM | 3799 | CD2 | TRP | B | 247 | 69.658 | 35.951 | 80.851 | 1.00 | 19.45 | C |
| ATOM | 3800 | CE3 | TRP | B | 247 | 70.140 | 37.162 | 81.336 | 1.00 | 22.06 | C |
| ATOM | 3801 | CZ3 | TRP | B | 247 | 69.270 | 38.160 | 81.750 | 1.00 | 22.82 | C |
| ATOM | 3802 | CH2 | TRP | B | 247 | 67.884 | 37.947 | 81.670 | 1.00 | 24.35 | C |
| ATOM | 3803 | CZ2 | TRP | B | 247 | 67.389 | 36.744 | 81.178 | 1.00 | 17.06 | C |
| ATOM | 3804 | C | TRP | B | 247 | 71.529 | 32.522 | 81.704 | 1.00 | 20.88 | C |
| ATOM | 3805 | O | TRP | B | 247 | 70.705 | 32.505 | 82.606 | 1.00 | 22.42 | O |
| ATOM | 3806 | N | SER | B | 248 | 71.746 | 31.460 | 80.907 | 1.00 | 22.00 | N |
| ATOM | 3807 | CA | SER | B | 248 | 71.060 | 30.203 | 81.183 | 1.00 | 24.69 | C |
| ATOM | 3808 | CB | SER | B | 248 | 71.535 | 29.158 | 80.173 | 1.00 | 23.58 | C |
| ATOM | 3809 | OG | SER | B | 248 | 70.649 | 29.148 | 79.053 | 1.00 | 35.84 | O |
| ATOM | 3810 | C | SER | B | 248 | 71.354 | 29.725 | 82.603 | 1.00 | 26.17 | C |
| ATOM | 3811 | O | SER | B | 248 | 70.478 | 29.311 | 83.347 | 1.00 | 29.50 | O |
| ATOM | 3812 | N | LEU | B | 249 | 72.652 | 29.757 | 82.955 | 1.00 | 23.56 | N |
| ATOM | 3813 | CA | LEU | B | 249 | 73.060 | 29.354 | 84.296 | 1.00 | 22.90 | C |
| ATOM | 3814 | CB | LEU | B | 249 | 74.538 | 29.710 | 84.469 | 1.00 | 23.49 | C |
| ATOM | 3815 | CG | LEU | B | 249 | 75.428 | 28.475 | 84.654 | 1.00 | 20.49 | C |
| ATOM | 3816 | CD1 | LEU | B | 249 | 75.077 | 27.343 | 83.688 | 1.00 | 25.45 | C |

FIG. 2A-83

| ATOM | 3817 | CD2 | LEU | B | 249 | 76.911 | 28.771 | 84.439 | 1.00 | 19.28 | C |
| ATOM | 3818 | C | LEU | B | 249 | 72.217 | 30.034 | 85.387 | 1.00 | 25.44 | C |
| ATOM | 3819 | O | LEU | B | 249 | 71.857 | 29.426 | 86.385 | 1.00 | 28.46 | O |
| ATOM | 3820 | N | GLY | B | 250 | 71.942 | 31.316 | 85.146 | 1.00 | 23.36 | N |
| ATOM | 3821 | CA | GLY | B | 250 | 71.166 | 32.085 | 86.102 | 1.00 | 20.71 | C |
| ATOM | 3822 | C | GLY | B | 250 | 69.709 | 31.676 | 86.137 | 1.00 | 19.54 | C |
| ATOM | 3823 | O | GLY | B | 250 | 69.083 | 31.625 | 87.192 | 1.00 | 16.87 | O |
| ATOM | 3824 | N | VAL | B | 251 | 69.150 | 31.392 | 84.978 | 1.00 | 17.78 | N |
| ATOM | 3825 | CA | VAL | B | 251 | 67.769 | 30.977 | 84.949 | 1.00 | 18.56 | C |
| ATOM | 3826 | CB | VAL | B | 251 | 67.259 | 30.653 | 83.516 | 1.00 | 18.20 | C |
| ATOM | 3827 | CG1 | VAL | B | 251 | 65.861 | 30.037 | 83.605 | 1.00 | 17.04 | C |
| ATOM | 3828 | CG2 | VAL | B | 251 | 67.221 | 31.907 | 82.671 | 1.00 | 15.20 | C |
| ATOM | 3829 | C | VAL | B | 251 | 67.660 | 29.701 | 85.754 | 1.00 | 19.88 | C |
| ATOM | 3830 | O | VAL | B | 251 | 66.714 | 29.538 | 86.506 | 1.00 | 20.34 | O |
| ATOM | 3831 | N | ILE | B | 252 | 68.639 | 28.806 | 85.573 | 1.00 | 19.76 | N |
| ATOM | 3832 | CA | ILE | B | 252 | 68.673 | 27.516 | 86.244 | 1.00 | 21.44 | C |
| ATOM | 3833 | CB | ILE | B | 252 | 69.755 | 26.605 | 85.606 | 1.00 | 21.07 | C |
| ATOM | 3834 | CG1 | ILE | B | 252 | 69.319 | 26.211 | 84.189 | 1.00 | 19.91 | C |
| ATOM | 3835 | CD1 | ILE | B | 252 | 70.334 | 25.411 | 83.440 | 1.00 | 12.62 | C |
| ATOM | 3836 | CG2 | ILE | B | 252 | 69.959 | 25.330 | 86.414 | 1.00 | 19.62 | C |
| ATOM | 3837 | C | ILE | B | 252 | 68.879 | 27.626 | 87.753 | 1.00 | 22.23 | C |
| ATOM | 3838 | O | ILE | B | 252 | 68.162 | 26.997 | 88.530 | 1.00 | 22.92 | O |
| ATOM | 3839 | N | MSEB | | 253 | 69.845 | 28.418 | 88.190 | 1.00 | 22.51 | N |
| ATOM | 3840 | CA | MSEB | | 253 | 70.072 | 28.572 | 89.627 | 1.00 | 22.43 | C |
| ATOM | 3841 | CB | MSEB | | 253 | 71.174 | 29.597 | 89.849 | 1.00 | 21.57 | C |
| ATOM | 3842 | CG | MSEB | | 253 | 71.675 | 29.651 | 91.224 | 1.00 | 24.61 | C |
| ATOM | 3843 | SE | MSEB | | 253 | 73.237 | 30.709 | 91.281 | 1.00 | 30.25 | S |
| ATOM | 3844 | CE | MSEB | | 253 | 74.422 | 29.560 | 90.367 | 1.00 | 32.18 | C |
| ATOM | 3845 | C | MSEB | | 253 | 68.763 | 29.068 | 90.258 | 1.00 | 22.22 | C |
| ATOM | 3846 | O | MSEB | | 253 | 68.277 | 28.536 | 91.255 | 1.00 | 23.25 | O |
| ATOM | 3847 | N | TYR | B | 254 | 68.194 | 30.092 | 89.646 | 1.00 | 22.32 | N |
| ATOM | 3848 | CA | TYR | B | 254 | 66.961 | 30.659 | 90.109 | 1.00 | 24.13 | C |
| ATOM | 3849 | CB | TYR | B | 254 | 66.453 | 31.683 | 89.085 | 1.00 | 23.31 | C |
| ATOM | 3850 | CG | TYR | B | 254 | 65.286 | 32.497 | 89.569 | 1.00 | 24.84 | C |
| ATOM | 3851 | CD1 | TYR | B | 254 | 63.985 | 32.040 | 89.404 | 1.00 | 28.36 | C |
| ATOM | 3852 | CE1 | TYR | B | 254 | 62.902 | 32.758 | 89.881 | 1.00 | 25.93 | C |
| ATOM | 3853 | CZ | TYR | B | 254 | 63.119 | 33.962 | 90.539 | 1.00 | 25.17 | C |
| ATOM | 3854 | OH | TYR | B | 254 | 62.035 | 34.660 | 91.037 | 1.00 | 26.49 | O |
| ATOM | 3855 | CE2 | TYR | B | 254 | 64.416 | 34.447 | 90.715 | 1.00 | 26.26 | C |
| ATOM | 3856 | CD2 | TYR | B | 254 | 65.485 | 33.711 | 90.229 | 1.00 | 24.69 | C |
| ATOM | 3857 | C | TYR | B | 254 | 65.908 | 29.581 | 90.338 | 1.00 | 25.01 | C |
| ATOM | 3858 | O | TYR | B | 254 | 65.360 | 29.483 | 91.421 | 1.00 | 27.01 | O |
| ATOM | 3859 | N | ILE | B | 255 | 65.621 | 28.774 | 89.330 | 1.00 | 24.08 | N |
| ATOM | 3860 | CA | ILE | B | 255 | 64.609 | 27.746 | 89.467 | 1.00 | 23.69 | C |
| ATOM | 3861 | CB | ILE | B | 255 | 64.373 | 27.046 | 88.137 | 1.00 | 23.70 | C |
| ATOM | 3862 | CG1 | ILE | B | 255 | 63.759 | 28.049 | 87.151 | 1.00 | 23.69 | C |

FIG. 2A-84

| ATOM | 3863 | CD1 | ILE | B | 255 | 63.725 | 27.582 | 85.710 | 1.00 | 21.07 | C |
|---|---|---|---|---|---|---|---|---|---|---|---|
| ATOM | 3864 | CG2 | ILE | B | 255 | 63.464 | 25.833 | 88.351 | 1.00 | 18.46 | C |
| ATOM | 3865 | C | ILE | B | 255 | 65.023 | 26.723 | 90.514 | 1.00 | 23.68 | C |
| ATOM | 3866 | O | ILE | B | 255 | 64.272 | 26.397 | 91.443 | 1.00 | 25.80 | O |
| ATOM | 3867 | N | LEU | B | 256 | 66.231 | 26.223 | 90.355 | 1.00 | 23.05 | N |
| ATOM | 3868 | CA | LEU | B | 256 | 66.769 | 25.287 | 91.299 | 1.00 | 22.71 | C |
| ATOM | 3869 | CB | LEU | B | 256 | 68.289 | 25.262 | 91.184 | 1.00 | 23.80 | C |
| ATOM | 3870 | CG | LEU | B | 256 | 68.929 | 23.892 | 91.038 | 1.00 | 25.36 | C |
| ATOM | 3871 | CD1 | LEU | B | 256 | 70.234 | 23.866 | 91.826 | 1.00 | 25.94 | C |
| ATOM | 3872 | CD2 | LEU | B | 256 | 67.965 | 22.839 | 91.559 | 1.00 | 28.22 | C |
| ATOM | 3873 | C | LEU | B | 256 | 66.398 | 25.776 | 92.692 | 1.00 | 22.59 | C |
| ATOM | 3874 | O | LEU | B | 256 | 65.996 | 24.991 | 93.535 | 1.00 | 22.57 | O |
| ATOM | 3875 | N | LEU | B | 257 | 66.520 | 27.079 | 92.926 | 1.00 | 22.61 | N |
| ATOM | 3876 | CA | LEU | B | 257 | 66.246 | 27.655 | 94.248 | 1.00 | 23.15 | C |
| ATOM | 3877 | CB | LEU | B | 257 | 67.103 | 28.905 | 94.461 | 1.00 | 22.12 | C |
| ATOM | 3878 | CG | LEU | B | 257 | 68.600 | 28.723 | 94.666 | 1.00 | 19.54 | C |
| ATOM | 3879 | CD1 | LEU | B | 257 | 69.307 | 30.023 | 94.446 | 1.00 | 19.05 | C |
| ATOM | 3880 | CD2 | LEU | B | 257 | 68.847 | 28.221 | 96.048 | 1.00 | 15.14 | C |
| ATOM | 3881 | C | LEU | B | 257 | 64.854 | 28.003 | 94.753 | 1.00 | 23.46 | C |
| ATOM | 3882 | O | LEU | B | 257 | 64.768 | 28.426 | 95.891 | 1.00 | 23.43 | O |
| ATOM | 3883 | N | CYS | B | 258 | 63.788 | 27.843 | 93.966 | 1.00 | 22.80 | N |
| ATOM | 3884 | CA | CYS | B | 258 | 62.437 | 28.199 | 94.433 | 1.00 | 22.48 | C |
| ATOM | 3885 | CB | CYS | B | 258 | 62.176 | 29.712 | 94.313 | 1.00 | 21.66 | C |
| ATOM | 3886 | SG | CYS | B | 258 | 61.748 | 30.316 | 92.626 | 1.00 | 26.69 | S |
| ATOM | 3887 | C | CYS | B | 258 | 61.300 | 27.481 | 93.715 | 1.00 | 21.78 | C |
| ATOM | 3888 | O | CYS | B | 258 | 60.127 | 27.659 | 94.099 | 1.00 | 21.82 | O |
| ATOM | 3889 | N | GLY | B | 259 | 61.626 | 26.723 | 92.655 | 1.00 | 22.10 | N |
| ATOM | 3890 | CA | GLY | B | 259 | 60.607 | 25.973 | 91.933 | 1.00 | 22.52 | C |
| ATOM | 3891 | C | GLY | B | 259 | 59.941 | 26.622 | 90.729 | 1.00 | 22.68 | C |
| ATOM | 3892 | O | GLY | B | 259 | 59.110 | 25.989 | 90.063 | 1.00 | 22.40 | O |
| ATOM | 3893 | N | TYR | B | 260 | 60.259 | 27.886 | 90.445 | 1.00 | 22.79 | N |
| ATOM | 3894 | CA | TYR | B | 260 | 59.677 | 28.540 | 89.271 | 1.00 | 22.74 | C |
| ATOM | 3895 | CB | TYR | B | 260 | 58.434 | 29.350 | 89.636 | 1.00 | 21.71 | C |
| ATOM | 3896 | CG | TYR | B | 260 | 58.525 | 30.150 | 90.893 | 1.00 | 18.72 | C |
| ATOM | 3897 | CD1 | TYR | B | 260 | 58.905 | 31.480 | 90.855 | 1.00 | 19.63 | C |
| ATOM | 3898 | CE1 | TYR | B | 260 | 59.035 | 32.214 | 91.999 | 1.00 | 17.01 | C |
| ATOM | 3899 | CZ | TYR | B | 260 | 58.790 | 31.631 | 93.201 | 1.00 | 20.70 | C |
| ATOM | 3900 | OH | TYR | B | 260 | 59.011 | 32.373 | 94.327 | 1.00 | 24.60 | O |
| ATOM | 3901 | CE2 | TYR | B | 260 | 58.393 | 30.302 | 93.284 | 1.00 | 22.22 | C |
| ATOM | 3902 | CD2 | TYR | B | 260 | 58.266 | 29.571 | 92.128 | 1.00 | 18.55 | C |
| ATOM | 3903 | C | TYR | B | 260 | 60.690 | 29.390 | 88.546 | 1.00 | 23.51 | C |
| ATOM | 3904 | O | TYR | B | 260 | 61.726 | 29.724 | 89.093 | 1.00 | 24.95 | O |
| ATOM | 3905 | N | PRO | B | 261 | 60.416 | 29.737 | 87.295 | 1.00 | 23.62 | N |
| ATOM | 3906 | CA | PRO | B | 261 | 61.370 | 30.548 | 86.543 | 1.00 | 22.62 | C |
| ATOM | 3907 | CB | PRO | B | 261 | 61.009 | 30.222 | 85.093 | 1.00 | 21.56 | C |
| ATOM | 3908 | CG | PRO | B | 261 | 59.573 | 30.054 | 85.138 | 1.00 | 23.29 | C |

FIG. 2A-85

| ATOM | 3909 | CD | PRO | B | 261 | 59.288 | 29.327 | 86.444 | 1.00 | 23.95 | C |
|---|---|---|---|---|---|---|---|---|---|---|---|
| ATOM | 3910 | C | PRO | B | 261 | 61.316 | 32.039 | 86.869 | 1.00 | 22.79 | C |
| ATOM | 3911 | O | PRO | B | 261 | 60.297 | 32.541 | 87.327 | 1.00 | 23.71 | O |
| ATOM | 3912 | N | PRO | B | 262 | 62.429 | 32.760 | 86.670 | 1.00 | 23.45 | N |
| ATOM | 3913 | CA | PRO | B | 262 | 62.389 | 34.187 | 86.975 | 1.00 | 23.66 | C |
| ATOM | 3914 | CB | PRO | B | 262 | 63.853 | 34.580 | 86.931 | 1.00 | 22.02 | C |
| ATOM | 3915 | CG | PRO | B | 262 | 64.362 | 33.736 | 85.841 | 1.00 | 22.10 | C |
| ATOM | 3916 | CD | PRO | B | 262 | 63.748 | 32.379 | 86.148 | 1.00 | 22.73 | C |
| ATOM | 3917 | C | PRO | B | 262 | 61.527 | 34.925 | 85.950 | 1.00 | 24.74 | C |
| ATOM | 3918 | O | PRO | B | 262 | 60.914 | 35.936 | 86.252 | 1.00 | 27.05 | O |
| ATOM | 3919 | N | PHE | B | 263 | 61.470 | 34.439 | 84.726 | 1.00 | 27.22 | N |
| ATOM | 3920 | CA | PHE | B | 263 | 60.613 | 35.111 | 83.762 | 1.00 | 30.42 | C |
| ATOM | 3921 | CB | PHE | B | 263 | 61.396 | 35.670 | 82.562 | 1.00 | 28.10 | C |
| ATOM | 3922 | CG | PHE | B | 263 | 62.582 | 36.464 | 82.932 | 1.00 | 24.79 | C |
| ATOM | 3923 | CD1 | PHE | B | 263 | 63.838 | 35.888 | 82.922 | 1.00 | 21.26 | C |
| ATOM | 3924 | CE1 | PHE | B | 263 | 64.945 | 36.586 | 83.329 | 1.00 | 16.30 | C |
| ATOM | 3925 | CZ | PHE | B | 263 | 64.817 | 37.881 | 83.758 | 1.00 | 19.05 | C |
| ATOM | 3926 | CE2 | PHE | B | 263 | 63.575 | 38.490 | 83.778 | 1.00 | 21.26 | C |
| ATOM | 3927 | CD2 | PHE | B | 263 | 62.453 | 37.773 | 83.358 | 1.00 | 25.72 | C |
| ATOM | 3928 | C | PHE | B | 263 | 59.664 | 34.042 | 83.273 | 1.00 | 33.95 | C |
| ATOM | 3929 | O | PHE | B | 263 | 60.066 | 32.893 | 83.066 | 1.00 | 34.76 | O |
| ATOM | 3930 | N | TYR | B | 264 | 58.405 | 34.414 | 83.108 | 1.00 | 37.44 | N |
| ATOM | 3931 | CA | TYR | B | 264 | 57.377 | 33.557 | 82.542 | 1.00 | 41.21 | C |
| ATOM | 3932 | CB | TYR | B | 264 | 57.090 | 32.427 | 83.535 | 1.00 | 42.02 | C |
| ATOM | 3933 | CG | TYR | B | 264 | 56.689 | 32.988 | 84.855 | 1.00 | 47.54 | C |
| ATOM | 3934 | CD1 | TYR | B | 264 | 55.394 | 33.466 | 85.042 | 1.00 | 51.62 | C |
| ATOM | 3935 | CE1 | TYR | B | 264 | 54.962 | 33.841 | 86.305 | 1.00 | 55.17 | C |
| ATOM | 3936 | CZ | TYR | B | 264 | 55.841 | 33.766 | 87.388 | 1.00 | 54.96 | C |
| ATOM | 3937 | OH | TYR | B | 264 | 55.425 | 34.210 | 88.630 | 1.00 | 50.85 | O |
| ATOM | 3938 | CE2 | TYR | B | 264 | 57.130 | 33.303 | 87.208 | 1.00 | 51.85 | C |
| ATOM | 3939 | CD2 | TYR | B | 264 | 57.558 | 32.917 | 85.945 | 1.00 | 50.27 | C |
| ATOM | 3940 | C | TYR | B | 264 | 56.097 | 34.344 | 82.255 | 1.00 | 41.29 | C |
| ATOM | 3941 | O | TYR | B | 264 | 56.028 | 35.558 | 82.408 | 1.00 | 41.26 | O |
| ATOM | 3942 | N | SER | B | 265 | 55.079 | 33.612 | 81.779 | 1.00 | 41.35 | N |
| ATOM | 3943 | CA | SER | B | 265 | 53.802 | 34.258 | 81.513 | 1.00 | 42.83 | C |
| ATOM | 3944 | CB | SER | B | 265 | 53.266 | 33.718 | 80.187 | 1.00 | 42.83 | C |
| ATOM | 3945 | OG | SER | B | 265 | 51.839 | 33.681 | 80.238 | 1.00 | 46.53 | O |
| ATOM | 3946 | C | SER | B | 265 | 52.800 | 33.973 | 82.632 | 1.00 | 43.05 | C |
| ATOM | 3947 | O | SER | B | 265 | 52.667 | 32.852 | 83.107 | 1.00 | 43.32 | O |
| ATOM | 3948 | N | GLY | B | 274 | 54.873 | 40.589 | 76.728 | 1.00 | 22.69 | N |
| ATOM | 3949 | CA | GLY | B | 274 | 54.589 | 39.990 | 78.016 | 1.00 | 22.54 | C |
| ATOM | 3950 | C | GLY | B | 274 | 55.865 | 39.521 | 78.663 | 1.00 | 23.72 | C |
| ATOM | 3951 | O | GLY | B | 274 | 56.513 | 40.233 | 79.420 | 1.00 | 23.66 | O |
| ATOM | 3952 | N | MSEB | | 275 | 56.256 | 38.310 | 78.335 | 1.00 | 24.52 | N |
| ATOM | 3953 | CA | MSEB | | 275 | 57.448 | 37.750 | 78.915 | 1.00 | 24.15 | C |
| ATOM | 3954 | CB | MSEB | | 275 | 57.416 | 36.246 | 78.733 | 1.00 | 24.50 | C |

FIG. 2A-86

| ATOM | 3955 | CG | MSEB | | 275 | 58.328 | 35.467 | 79.615 | 1.00 | 31.29 | C |
|---|---|---|---|---|---|---|---|---|---|---|---|
| ATOM | 3956 | SE | MSEB | | 275 | 57.904 | 33.668 | 79.192 | 1.00 | 37.14 | S |
| ATOM | 3957 | CE | MSEB | | 275 | 59.048 | 33.306 | 77.702 | 1.00 | 36.86 | C |
| ATOM | 3958 | C | MSEB | | 275 | 58.674 | 38.344 | 78.253 | 1.00 | 23.59 | C |
| ATOM | 3959 | O | MSEB | | 275 | 59.678 | 38.617 | 78.911 | 1.00 | 23.18 | O |
| ATOM | 3960 | N | ALA | B | 276 | 58.600 | 38.555 | 76.951 | 1.00 | 24.07 | N |
| ATOM | 3961 | CA | ALA | B | 276 | 59.750 | 39.116 | 76.258 | 1.00 | 23.42 | C |
| ATOM | 3962 | CB | ALA | B | 276 | 59.477 | 39.241 | 74.742 | 1.00 | 21.89 | C |
| ATOM | 3963 | C | ALA | B | 276 | 60.125 | 40.466 | 76.867 | 1.00 | 22.57 | C |
| ATOM | 3964 | O | ALA | B | 276 | 61.293 | 40.694 | 77.179 | 1.00 | 22.69 | O |
| ATOM | 3965 | N | THR | B | 277 | 59.144 | 41.349 | 77.072 | 1.00 | 22.48 | N |
| ATOM | 3966 | CA | THR | B | 277 | 59.438 | 42.671 | 77.631 | 1.00 | 23.10 | C |
| ATOM | 3967 | CB | THR | B | 277 | 58.178 | 43.540 | 77.848 | 1.00 | 22.33 | C |
| ATOM | 3968 | OG1 | THR | B | 277 | 57.551 | 43.780 | 76.596 | 1.00 | 26.17 | O |
| ATOM | 3969 | CG2 | THR | B | 277 | 58.547 | 44.890 | 78.427 | 1.00 | 24.10 | C |
| ATOM | 3970 | C | THR | B | 277 | 60.115 | 42.484 | 78.951 | 1.00 | 23.00 | C |
| ATOM | 3971 | O | THR | B | 277 | 61.181 | 43.052 | 79.181 | 1.00 | 23.95 | O |
| ATOM | 3972 | N | ARG | B | 278 | 59.494 | 41.685 | 79.816 | 1.00 | 21.65 | N |
| ATOM | 3973 | CA | ARG | B | 278 | 60.071 | 41.411 | 81.125 | 1.00 | 22.23 | C |
| ATOM | 3974 | CB | ARG | B | 278 | 59.155 | 40.473 | 81.927 | 1.00 | 21.95 | C |
| ATOM | 3975 | CG | ARG | B | 278 | 58.422 | 41.210 | 83.045 | 1.00 | 25.24 | C |
| ATOM | 3976 | CD | ARG | B | 278 | 57.284 | 40.423 | 83.540 | 1.00 | 31.62 | C |
| ATOM | 3977 | NE | ARG | B | 278 | 56.487 | 40.024 | 82.401 | 1.00 | 38.54 | N |
| ATOM | 3978 | CZ | ARG | B | 278 | 55.731 | 38.935 | 82.362 | 1.00 | 39.83 | C |
| ATOM | 3979 | NH1AR | G | B | 278 | 55.667 | 38.135 | 83.416 | 1.00 | 44.26 | N |
| ATOM | 3980 | NH2AR | G | B | 278 | 55.065 | 38.628 | 81.262 | 1.00 | 39.40 | N |
| ATOM | 3981 | C | ARG | B | 278 | 61.496 | 40.843 | 80.980 | 1.00 | 21.16 | C |
| ATOM | 3982 | O | ARG | B | 278 | 62.373 | 41.145 | 81.791 | 1.00 | 22.00 | O |
| ATOM | 3983 | N | ILE | B | 279 | 61.753 | 40.039 | 79.950 | 1.00 | 20.62 | N |
| ATOM | 3984 | CA | ILE | B | 279 | 63.127 | 39.603 | 79.739 | 1.00 | 20.22 | C |
| ATOM | 3985 | CB | ILE | B | 279 | 63.121 | 38.453 | 78.729 | 1.00 | 22.05 | C |
| ATOM | 3986 | CG1 | ILE | B | 279 | 62.306 | 37.276 | 79.274 | 1.00 | 20.07 | C |
| ATOM | 3987 | CD1 | ILE | B | 279 | 62.018 | 36.224 | 78.202 | 1.00 | 24.61 | C |
| ATOM | 3988 | CG2 | ILE | B | 279 | 64.561 | 37.957 | 78.492 | 1.00 | 15.26 | C |
| ATOM | 3989 | C | ILE | B | 279 | 64.005 | 40.748 | 79.234 | 1.00 | 22.12 | C |
| ATOM | 3990 | O | ILE | B | 279 | 64.982 | 41.147 | 79.853 | 1.00 | 22.71 | O |
| ATOM | 3991 | N | ARG | B | 280 | 63.650 | 41.252 | 78.039 | 1.00 | 21.58 | N |
| ATOM | 3992 | CA | ARG | B | 280 | 64.382 | 42.393 | 77.506 | 1.00 | 22.44 | C |
| ATOM | 3993 | CB | ARG | B | 280 | 63.520 | 43.041 | 76.420 | 1.00 | 24.13 | C |
| ATOM | 3994 | CG | ARG | B | 280 | 63.360 | 42.146 | 75.192 | 1.00 | 33.13 | C |
| ATOM | 3995 | CD | ARG | B | 280 | 62.434 | 42.767 | 74.139 | 1.00 | 43.48 | C |
| ATOM | 3996 | NE | ARG | B | 280 | 62.300 | 41.885 | 72.973 | 1.00 | 52.54 | N |
| ATOM | 3997 | CZ | ARG | B | 280 | 61.512 | 42.305 | 71.964 | 1.00 | 60.55 | C |
| ATOM | 3998 | NH1AR | G | B | 280 | 61.260 | 41.505 | 70.941 | 1.00 | 66.84 | N |
| ATOM | 3999 | NH2AR | G | B | 280 | 61.003 | 43.538 | 71.993 | 1.00 | 63.26 | N |
| ATOM | 4000 | C | ARG | B | 280 | 64.681 | 43.415 | 78.606 | 1.00 | 21.50 | C |

FIG. 2A-87

| ATOM | 4001 | O | ARG | B | 280 | 65.761 | 43.983 | 78.706 | 1.00 | 21.21 | O |
|---|---|---|---|---|---|---|---|---|---|---|---|
| ATOM | 4002 | N | MSE | B | 281 | 63.649 | 43.666 | 79.433 | 1.00 | 19.05 | N |
| ATOM | 4003 | CA | MSE | B | 281 | 63.801 | 44.633 | 80.512 | 1.00 | 18.00 | C |
| ATOM | 4004 | CB | MSE | B | 281 | 62.406 | 45.126 | 80.906 | 1.00 | 18.15 | C |
| ATOM | 4005 | CG | MSE | B | 281 | 61.771 | 46.016 | 79.831 | 1.00 | 16.25 | C |
| ATOM | 4006 | SE | MSE | B | 281 | 62.548 | 47.634 | 79.736 | 1.00 | 33.67 | S |
| ATOM | 4007 | CE | MSE | B | 281 | 61.623 | 48.433 | 81.056 | 1.00 | 13.00 | C |
| ATOM | 4008 | C | MSE | B | 281 | 64.502 | 44.019 | 81.726 | 1.00 | 18.92 | C |
| ATOM | 4009 | O | MSE | B | 281 | 65.077 | 44.699 | 82.562 | 1.00 | 18.78 | O |
| ATOM | 4010 | N | GLY | B | 282 | 64.401 | 42.679 | 81.825 | 1.00 | 21.24 | N |
| ATOM | 4011 | CA | GLY | B | 282 | 65.087 | 41.986 | 82.908 | 1.00 | 20.49 | C |
| ATOM | 4012 | C | GLY | B | 282 | 64.440 | 42.255 | 84.269 | 1.00 | 22.22 | C |
| ATOM | 4013 | O | GLY | B | 282 | 65.103 | 42.422 | 85.286 | 1.00 | 22.77 | O |
| ATOM | 4014 | N | GLN | B | 283 | 63.097 | 42.342 | 84.262 | 1.00 | 22.21 | N |
| ATOM | 4015 | CA | GLN | B | 283 | 62.407 | 42.495 | 85.531 | 1.00 | 24.15 | C |
| ATOM | 4016 | CB | GLN | B | 283 | 61.283 | 43.527 | 85.395 | 1.00 | 23.99 | C |
| ATOM | 4017 | CG | GLN | B | 283 | 60.345 | 43.255 | 84.219 | 1.00 | 27.93 | C |
| ATOM | 4018 | CD | GLN | B | 283 | 59.550 | 44.510 | 83.933 | 1.00 | 35.08 | C |
| ATOM | 4019 | OE1 | GLN | B | 283 | 58.597 | 44.538 | 83.172 | 1.00 | 34.95 | O |
| ATOM | 4020 | NE2 | GLN | B | 283 | 60.002 | 45.597 | 84.591 | 1.00 | 33.68 | N |
| ATOM | 4021 | C | GLN | B | 283 | 61.849 | 41.162 | 86.024 | 1.00 | 24.78 | C |
| ATOM | 4022 | O | GLN | B | 283 | 60.875 | 40.625 | 85.523 | 1.00 | 25.24 | O |
| ATOM | 4023 | N | TYR | B | 284 | 62.570 | 40.606 | 86.998 | 1.00 | 24.51 | N |
| ATOM | 4024 | CA | TYR | B | 284 | 62.076 | 39.455 | 87.730 | 1.00 | 25.01 | C |
| ATOM | 4025 | CB | TYR | B | 284 | 63.032 | 38.299 | 87.457 | 1.00 | 24.01 | C |
| ATOM | 4026 | CG | TYR | B | 284 | 64.411 | 38.714 | 87.814 | 1.00 | 23.19 | C |
| ATOM | 4027 | CD1 | TYR | B | 284 | 65.178 | 39.442 | 86.911 | 1.00 | 23.54 | C |
| ATOM | 4028 | CE1 | TYR | B | 284 | 66.485 | 39.787 | 87.223 | 1.00 | 20.74 | C |
| ATOM | 4029 | CZ | TYR | B | 284 | 67.037 | 39.384 | 88.440 | 1.00 | 25.05 | C |
| ATOM | 4030 | OH | TYR | B | 284 | 68.349 | 39.697 | 88.726 | 1.00 | 25.49 | O |
| ATOM | 4031 | CE2 | TYR | B | 284 | 66.271 | 38.676 | 89.348 | 1.00 | 25.99 | C |
| ATOM | 4032 | CD2 | TYR | B | 284 | 64.961 | 38.340 | 89.039 | 1.00 | 24.67 | C |
| ATOM | 4033 | C | TYR | B | 284 | 62.093 | 39.809 | 89.216 | 1.00 | 25.19 | C |
| ATOM | 4034 | O | TYR | B | 284 | 62.169 | 40.971 | 89.586 | 1.00 | 25.64 | O |
| ATOM | 4035 | N | GLU | B | 285 | 61.980 | 38.791 | 90.086 | 1.00 | 27.07 | N |
| ATOM | 4036 | CA | GLU | B | 285 | 62.087 | 39.117 | 91.504 | 1.00 | 27.88 | C |
| ATOM | 4037 | CB | GLU | B | 285 | 60.982 | 40.106 | 91.890 | 1.00 | 28.21 | C |
| ATOM | 4038 | CG | GLU | B | 285 | 59.587 | 39.478 | 91.969 | 1.00 | 34.76 | C |
| ATOM | 4039 | CD | GLU | B | 285 | 58.595 | 40.545 | 92.380 | 1.00 | 50.74 | C |
| ATOM | 4040 | OE1 | GLU | B | 285 | 58.984 | 41.706 | 92.447 | 1.00 | 55.15 | O |
| ATOM | 4041 | OE2 | GLU | B | 285 | 57.437 | 40.205 | 92.637 | 1.00 | 54.65 | O |
| ATOM | 4042 | C | GLU | B | 285 | 62.095 | 37.909 | 92.431 | 1.00 | 27.98 | C |
| ATOM | 4043 | O | GLU | B | 285 | 61.817 | 36.775 | 92.064 | 1.00 | 30.10 | O |
| ATOM | 4044 | N | PHE | B | 286 | 62.470 | 38.200 | 93.684 | 1.00 | 27.59 | N |
| ATOM | 4045 | CA | PHE | B | 286 | 62.665 | 37.137 | 94.657 | 1.00 | 24.53 | C |
| ATOM | 4046 | CB | PHE | B | 286 | 64.001 | 37.421 | 95.345 | 1.00 | 24.09 | C |

FIG. 2A-88

| | | | | | | | | | | |
|---|---|---|---|---|---|---|---|---|---|---|
| ATOM | 4047 | CG  | PHE | B | 286 | 65.092 | 37.433 | 94.315  | 1.00 | 18.63 C |
| ATOM | 4048 | CD1 | PHE | B | 286 | 66.017 | 38.470 | 94.305  | 1.00 | 16.90 C |
| ATOM | 4049 | CE1 | PHE | B | 286 | 67.129 | 38.389 | 93.479  | 1.00 | 11.90 C |
| ATOM | 4050 | CZ  | PHE | B | 286 | 67.331 | 37.285 | 92.666  | 1.00 | 14.18 C |
| ATOM | 4051 | CE2 | PHE | B | 286 | 66.390 | 36.261 | 92.666  | 1.00 | 17.08 C |
| ATOM | 4052 | CD2 | PHE | B | 286 | 65.265 | 36.336 | 93.487  | 1.00 | 17.25 C |
| ATOM | 4053 | C   | PHE | B | 286 | 61.527 | 37.086 | 95.689  | 1.00 | 24.38 C |
| ATOM | 4054 | O   | PHE | B | 286 | 61.659 | 37.498 | 96.833  | 1.00 | 24.94 O |
| ATOM | 4055 | N   | PRO | B | 287 | 60.371 | 36.568 | 95.231  | 1.00 | 24.05 N |
| ATOM | 4056 | CA  | PRO | B | 287 | 59.155 | 36.566 | 96.036  | 1.00 | 24.48 C |
| ATOM | 4057 | CB  | PRO | B | 287 | 58.006 | 36.068 | 95.162  | 1.00 | 23.64 C |
| ATOM | 4058 | CG  | PRO | B | 287 | 58.520 | 35.947 | 93.731  | 1.00 | 23.94 C |
| ATOM | 4059 | CD  | PRO | B | 287 | 60.106 | 35.949 | 93.948  | 1.00 | 23.22 C |
| ATOM | 4060 | C   | PRO | B | 287 | 59.258 | 35.702 | 97.295  | 1.00 | 24.78 C |
| ATOM | 4061 | O   | PRO | B | 287 | 60.121 | 34.847 | 97.441  | 1.00 | 23.92 O |
| ATOM | 4062 | N   | ASN | B | 288 | 58.336 | 35.997 | 98.236  | 1.00 | 26.45 N |
| ATOM | 4063 | CA  | ASN | B | 288 | 58.208 | 35.177 | 99.442  | 1.00 | 26.91 C |
| ATOM | 4064 | CB  | ASN | B | 288 | 57.887 | 36.111 | 100.611 | 1.00 | 27.53 C |
| ATOM | 4065 | CG  | ASN | B | 288 | 59.029 | 37.060 | 100.844 | 1.00 | 29.42 C |
| ATOM | 4066 | OD1 | ASN | B | 288 | 60.144 | 36.666 | 101.166 | 1.00 | 28.47 O |
| ATOM | 4067 | ND2 | ASN | B | 288 | 58.705 | 38.364 | 100.758 | 1.00 | 31.17 N |
| ATOM | 4068 | C   | ASN | B | 288 | 57.073 | 34.165 | 99.290  | 1.00 | 27.33 C |
| ATOM | 4069 | O   | ASN | B | 288 | 56.123 | 34.376 | 98.549  | 1.00 | 26.00 O |
| ATOM | 4070 | N   | PRO | B | 289 | 57.216 | 33.011 | 99.971  | 1.00 | 28.31 N |
| ATOM | 4071 | CA  | PRO | B | 289 | 58.280 | 32.808 | 100.938 | 1.00 | 29.69 C |
| ATOM | 4072 | CB  | PRO | B | 289 | 57.773 | 31.760 | 101.923 | 1.00 | 30.60 C |
| ATOM | 4073 | CG  | PRO | B | 289 | 56.673 | 30.954 | 101.227 | 1.00 | 31.67 C |
| ATOM | 4074 | CD  | PRO | B | 289 | 56.394 | 31.817 | 99.903  | 1.00 | 28.53 C |
| ATOM | 4075 | C   | PRO | B | 289 | 59.571 | 32.304 | 100.284 | 1.00 | 30.31 C |
| ATOM | 4076 | O   | PRO | B | 289 | 60.673 | 32.521 | 100.766 | 1.00 | 33.95 O |
| ATOM | 4077 | N   | GLU | B | 290 | 59.398 | 31.566 | 99.176  | 1.00 | 27.92 N |
| ATOM | 4078 | CA  | GLU | B | 290 | 60.540 | 30.890 | 98.561  | 1.00 | 26.41 C |
| ATOM | 4079 | CB  | GLU | B | 290 | 60.352 | 30.899 | 97.043  | 1.00 | 27.43 C |
| ATOM | 4080 | CG  | GLU | B | 290 | 59.216 | 29.977 | 96.595  | 1.00 | 29.20 C |
| ATOM | 4081 | CD  | GLU | B | 290 | 57.896 | 30.562 | 97.043  | 1.00 | 32.50 C |
| ATOM | 4082 | OE1 | GLU | B | 290 | 57.904 | 31.562 | 97.748  | 1.00 | 34.34 O |
| ATOM | 4083 | OE2 | GLU | B | 290 | 56.861 | 30.017 | 96.669  | 1.00 | 33.15 O |
| ATOM | 4084 | C   | GLU | B | 290 | 61.885 | 31.527 | 98.923  | 1.00 | 25.50 C |
| ATOM | 4085 | O   | GLU | B | 290 | 62.809 | 30.870 | 99.384  | 1.00 | 26.84 O |
| ATOM | 4086 | N   | TRP | B | 291 | 61.991 | 32.843 | 98.663  | 1.00 | 24.90 N |
| ATOM | 4087 | CA  | TRP | B | 291 | 63.299 | 33.479 | 98.765  | 1.00 | 23.79 C |
| ATOM | 4088 | CB  | TRP | B | 291 | 63.380 | 34.561 | 97.687  | 1.00 | 23.38 C |
| ATOM | 4089 | CG  | TRP | B | 291 | 63.176 | 33.946 | 96.351  | 1.00 | 24.33 C |
| ATOM | 4090 | CD1 | TRP | B | 291 | 61.942 | 33.725 | 95.702  | 1.00 | 22.02 C |
| ATOM | 4091 | NE1 | TRP | B | 291 | 62.087 | 33.065 | 94.521  | 1.00 | 24.93 N |
| ATOM | 4092 | CE2 | TRP | B | 291 | 63.543 | 32.813 | 94.374  | 1.00 | 23.99 C |

FIG. 2A-89

| ATOM | 4093 | CD2 | TRP | B | 291 | 64.197 | 33.368 | 95.503 | 1.00 | 23.55 | C |
| --- | --- | --- | --- | --- | --- | --- | --- | --- | --- | --- | --- |
| ATOM | 4094 | CE3 | TRP | B | 291 | 65.582 | 33.261 | 95.606 | 1.00 | 23.66 | C |
| ATOM | 4095 | CZ3 | TRP | B | 291 | 66.321 | 32.631 | 94.617 | 1.00 | 26.36 | C |
| ATOM | 4096 | CH2 | TRP | B | 291 | 65.664 | 32.081 | 93.504 | 1.00 | 22.92 | C |
| ATOM | 4097 | CZ2 | TRP | B | 291 | 64.282 | 32.180 | 93.387 | 1.00 | 24.37 | C |
| ATOM | 4098 | C | TRP | B | 291 | 63.561 | 34.081 | 100.148 | 1.00 | 23.55 | C |
| ATOM | 4099 | O | TRP | B | 291 | 64.670 | 34.473 | 100.481 | 1.00 | 22.90 | O |
| ATOM | 4100 | N | SER | B | 292 | 62.489 | 34.158 | 100.931 | 1.00 | 25.30 | N |
| ATOM | 4101 | CA | SER | B | 292 | 62.521 | 34.750 | 102.270 | 1.00 | 27.91 | C |
| ATOM | 4102 | CB | SER | B | 292 | 61.292 | 34.306 | 103.037 | 1.00 | 26.73 | C |
| ATOM | 4103 | OG | SER | B | 292 | 60.206 | 34.139 | 102.130 | 1.00 | 33.46 | O |
| ATOM | 4104 | C | SER | B | 292 | 63.771 | 34.374 | 103.037 | 1.00 | 28.45 | C |
| ATOM | 4105 | O | SER | B | 292 | 64.559 | 35.227 | 103.433 | 1.00 | 28.53 | O |
| ATOM | 4106 | N | GLU | B | 293 | 63.974 | 33.078 | 103.203 | 1.00 | 29.85 | N |
| ATOM | 4107 | CA | GLU | B | 293 | 65.120 | 32.617 | 103.948 | 1.00 | 31.26 | C |
| ATOM | 4108 | CB | GLU | B | 293 | 64.750 | 31.382 | 104.779 | 1.00 | 31.81 | C |
| ATOM | 4109 | CG | GLU | B | 293 | 64.399 | 31.716 | 106.214 | 1.00 | 39.38 | C |
| ATOM | 4110 | CD | GLU | B | 293 | 65.596 | 32.321 | 106.949 | 1.00 | 50.63 | C |
| ATOM | 4111 | OE1 | GLU | B | 293 | 66.680 | 31.677 | 106.932 | 1.00 | 56.36 | O |
| ATOM | 4112 | OE2 | GLU | B | 293 | 65.465 | 33.428 | 107.536 | 1.00 | 50.08 | O |
| ATOM | 4113 | C | GLU | B | 293 | 66.325 | 32.336 | 103.093 | 1.00 | 30.35 | C |
| ATOM | 4114 | O | GLU | B | 293 | 67.249 | 31.650 | 103.537 | 1.00 | 30.30 | O |
| ATOM | 4115 | N | VAL | B | 294 | 66.329 | 32.876 | 101.873 | 1.00 | 30.36 | N |
| ATOM | 4116 | CA | VAL | B | 294 | 67.476 | 32.676 | 100.971 | 1.00 | 29.64 | C |
| ATOM | 4117 | CB | VAL | B | 294 | 67.006 | 32.506 | 99.524 | 1.00 | 27.37 | C |
| ATOM | 4118 | CG1 | VAL | B | 294 | 68.196 | 32.481 | 98.578 | 1.00 | 25.39 | C |
| ATOM | 4119 | CG2 | VAL | B | 294 | 66.229 | 31.217 | 99.424 | 1.00 | 24.73 | C |
| ATOM | 4120 | C | VAL | B | 294 | 68.562 | 33.774 | 101.062 | 1.00 | 31.14 | C |
| ATOM | 4121 | O | VAL | B | 294 | 68.269 | 34.973 | 101.097 | 1.00 | 31.33 | O |
| ATOM | 4122 | N | SER | B | 295 | 69.815 | 33.343 | 101.126 | 1.00 | 31.84 | N |
| ATOM | 4123 | CA | SER | B | 295 | 70.931 | 34.265 | 101.256 | 1.00 | 33.80 | C |
| ATOM | 4124 | CB | SER | B | 295 | 72.230 | 33.505 | 101.052 | 1.00 | 34.38 | C |
| ATOM | 4125 | OG | SER | B | 295 | 71.993 | 32.128 | 101.286 | 1.00 | 40.50 | O |
| ATOM | 4126 | C | SER | B | 295 | 70.874 | 35.440 | 100.299 | 1.00 | 34.17 | C |
| ATOM | 4127 | O | SER | B | 295 | 70.377 | 35.339 | 99.183 | 1.00 | 34.16 | O |
| ATOM | 4128 | N | GLU | B | 296 | 71.387 | 36.570 | 100.732 | 1.00 | 34.17 | N |
| ATOM | 4129 | CA | GLU | B | 296 | 71.371 | 37.733 | 99.872 | 1.00 | 35.21 | C |
| ATOM | 4130 | CB | GLU | B | 296 | 71.485 | 39.022 | 100.703 | 1.00 | 35.79 | C |
| ATOM | 4131 | CG | GLU | B | 296 | 71.884 | 40.283 | 99.959 | 1.00 | 41.29 | C |
| ATOM | 4132 | CD | GLU | B | 296 | 70.805 | 40.787 | 99.037 | 1.00 | 52.44 | C |
| ATOM | 4133 | OE1 | GLU | B | 296 | 69.623 | 40.690 | 99.429 | 1.00 | 56.50 | O |
| ATOM | 4134 | OE2 | GLU | B | 296 | 71.131 | 41.292 | 97.929 | 1.00 | 58.09 | O |
| ATOM | 4135 | C | GLU | B | 296 | 72.531 | 37.603 | 98.920 | 1.00 | 35.34 | C |
| ATOM | 4136 | O | GLU | B | 296 | 72.528 | 38.236 | 97.870 | 1.00 | 37.22 | O |
| ATOM | 4137 | N | GLU | B | 297 | 73.513 | 36.763 | 99.266 | 1.00 | 33.54 | N |
| ATOM | 4138 | CA | GLU | B | 297 | 74.689 | 36.590 | 98.412 | 1.00 | 31.53 | C |

FIG. 2A-90

| ATOM | 4139 | CB | GLU | B | 297 | 75.873 | 36.090 | 99.234 | 1.00 | 33.17 | C |
| --- | --- | --- | --- | --- | --- | --- | --- | --- | --- | --- | --- |
| ATOM | 4140 | CG | GLU | B | 297 | 76.195 | 34.626 | 99.107 | 1.00 | 35.33 | C |
| ATOM | 4141 | CD | GLU | B | 297 | 77.614 | 34.345 | 99.523 | 1.00 | 37.83 | C |
| ATOM | 4142 | OE1 | GLU | B | 297 | 78.508 | 35.124 | 99.115 | 1.00 | 39.94 | O |
| ATOM | 4143 | OE2 | GLU | B | 297 | 77.844 | 33.352 | 100.239 | 1.00 | 36.02 | O |
| ATOM | 4144 | C | GLU | B | 297 | 74.440 | 35.664 | 97.224 | 1.00 | 29.50 | C |
| ATOM | 4145 | O | GLU | B | 297 | 75.182 | 35.643 | 96.251 | 1.00 | 29.65 | O |
| ATOM | 4146 | N | VAL | B | 298 | 73.368 | 34.910 | 97.330 | 1.00 | 28.03 | N |
| ATOM | 4147 | CA | VAL | B | 298 | 72.940 | 34.000 | 96.305 | 1.00 | 26.26 | C |
| ATOM | 4148 | CB | VAL | B | 298 | 72.103 | 32.849 | 96.930 | 1.00 | 25.24 | C |
| ATOM | 4149 | CG1 | VAL | B | 298 | 71.722 | 31.827 | 95.883 | 1.00 | 24.36 | C |
| ATOM | 4150 | CG2 | VAL | B | 298 | 72.922 | 32.181 | 98.001 | 1.00 | 27.23 | C |
| ATOM | 4151 | C | VAL | B | 298 | 72.098 | 34.852 | 95.352 | 1.00 | 25.96 | C |
| ATOM | 4152 | O | VAL | B | 298 | 72.231 | 34.751 | 94.137 | 1.00 | 25.96 | O |
| ATOM | 4153 | N | LYS | B | 299 | 71.239 | 35.691 | 95.917 | 1.00 | 25.07 | N |
| ATOM | 4154 | CA | LYS | B | 299 | 70.396 | 36.570 | 95.127 | 1.00 | 24.95 | C |
| ATOM | 4155 | CB | LYS | B | 299 | 69.517 | 37.394 | 96.062 | 1.00 | 24.80 | C |
| ATOM | 4156 | CG | LYS | B | 299 | 68.368 | 36.629 | 96.601 | 1.00 | 26.66 | C |
| ATOM | 4157 | CD | LYS | B | 299 | 67.681 | 37.355 | 97.722 | 1.00 | 26.52 | C |
| ATOM | 4158 | CE | LYS | B | 299 | 66.650 | 36.436 | 98.365 | 1.00 | 32.66 | C |
| ATOM | 4159 | NZ | LYS | B | 299 | 66.083 | 36.940 | 99.663 | 1.00 | 32.53 | N |
| ATOM | 4160 | C | LYS | B | 299 | 71.258 | 37.513 | 94.271 | 1.00 | 26.04 | C |
| ATOM | 4161 | O | LYS | B | 299 | 70.962 | 37.813 | 93.098 | 1.00 | 26.91 | O |
| ATOM | 4162 | N | MSEB | | 300 | 72.340 | 37.960 | 94.882 | 1.00 | 25.55 | N |
| ATOM | 4163 | CA | MSEB | | 300 | 73.243 | 38.867 | 94.252 | 1.00 | 28.61 | C |
| ATOM | 4164 | CB | MSEB | | 300 | 74.227 | 39.374 | 95.307 | 1.00 | 30.49 | C |
| ATOM | 4165 | CG | MSEB | | 300 | 74.866 | 40.744 | 95.027 | 1.00 | 41.62 | C |
| ATOM | 4166 | SE | MSEB | | 300 | 73.681 | 42.051 | 94.187 | 1.00 | 62.37 | S |
| ATOM | 4167 | CE | MSEB | | 300 | 74.532 | 42.096 | 92.455 | 1.00 | 45.12 | C |
| ATOM | 4168 | C | MSEB | | 300 | 73.931 | 38.107 | 93.144 | 1.00 | 28.46 | C |
| ATOM | 4169 | O | MSEB | | 300 | 74.267 | 38.674 | 92.100 | 1.00 | 29.96 | O |
| ATOM | 4170 | N | LEU | B | 301 | 74.118 | 36.801 | 93.374 | 1.00 | 27.96 | N |
| ATOM | 4171 | CA | LEU | B | 301 | 74.766 | 35.901 | 92.411 | 1.00 | 26.00 | C |
| ATOM | 4172 | CB | LEU | B | 301 | 75.074 | 34.550 | 93.100 | 1.00 | 25.99 | C |
| ATOM | 4173 | CG | LEU | B | 301 | 75.850 | 33.467 | 92.319 | 1.00 | 27.07 | C |
| ATOM | 4174 | CD1 | LEU | B | 301 | 77.082 | 34.034 | 91.646 | 1.00 | 21.85 | C |
| ATOM | 4175 | CD2 | LEU | B | 301 | 76.204 | 32.364 | 93.237 | 1.00 | 22.88 | C |
| ATOM | 4176 | C | LEU | B | 301 | 73.879 | 35.715 | 91.156 | 1.00 | 25.65 | C |
| ATOM | 4177 | O | LEU | B | 301 | 74.349 | 35.685 | 90.014 | 1.00 | 25.60 | O |
| ATOM | 4178 | N | ILE | B | 302 | 72.589 | 35.613 | 91.374 | 1.00 | 25.70 | N |
| ATOM | 4179 | CA | ILE | B | 302 | 71.703 | 35.474 | 90.268 | 1.00 | 24.96 | C |
| ATOM | 4180 | CB | ILE | B | 302 | 70.369 | 34.993 | 90.762 | 1.00 | 25.79 | C |
| ATOM | 4181 | CG1 | ILE | B | 302 | 70.508 | 33.495 | 91.102 | 1.00 | 22.86 | C |
| ATOM | 4182 | CD1 | ILE | B | 302 | 69.568 | 33.029 | 92.235 | 1.00 | 23.18 | C |
| ATOM | 4183 | CG2 | ILE | B | 302 | 69.269 | 35.327 | 89.754 | 1.00 | 21.28 | C |
| ATOM | 4184 | C | ILE | B | 302 | 71.583 | 36.811 | 89.555 | 1.00 | 24.48 | C |

FIG. 2A-91

| ATOM | 4185 | O | ILE | B | 302 | 71.430 | 36.868 | 88.337 | 1.00 | 23.19 | O |
|---|---|---|---|---|---|---|---|---|---|---|---|
| ATOM | 4186 | N | ARG | B | 303 | 71.689 | 37.894 | 90.308 | 1.00 | 24.86 | N |
| ATOM | 4187 | CA | ARG | B | 303 | 71.581 | 39.235 | 89.749 | 1.00 | 25.67 | C |
| ATOM | 4188 | CB | ARG | B | 303 | 71.616 | 40.268 | 90.855 | 1.00 | 24.81 | C |
| ATOM | 4189 | CG | ARG | B | 303 | 70.394 | 40.298 | 91.689 | 1.00 | 22.92 | C |
| ATOM | 4190 | CD | ARG | B | 303 | 70.216 | 41.658 | 92.261 | 1.00 | 20.21 | C |
| ATOM | 4191 | NE | ARG | B | 303 | 69.194 | 41.597 | 93.282 | 1.00 | 28.46 | N |
| ATOM | 4192 | CZ | ARG | B | 303 | 69.427 | 41.382 | 94.574 | 1.00 | 30.35 | C |
| ATOM | 4193 | NH1AR | G | B | 303 | 70.685 | 41.222 | 95.065 | 1.00 | 25.25 | N |
| ATOM | 4194 | NH2AR | G | B | 303 | 68.370 | 41.272 | 95.359 | 1.00 | 32.47 | N |
| ATOM | 4195 | C | ARG | B | 303 | 72.674 | 39.571 | 88.770 | 1.00 | 27.30 | C |
| ATOM | 4196 | O | ARG | B | 303 | 72.513 | 40.436 | 87.928 | 1.00 | 28.08 | O |
| ATOM | 4197 | N | ASN | B | 304 | 73.794 | 38.885 | 88.896 | 1.00 | 28.92 | N |
| ATOM | 4198 | CA | ASN | B | 304 | 74.925 | 39.127 | 88.040 | 1.00 | 32.03 | C |
| ATOM | 4199 | CB | ASN | B | 304 | 76.202 | 38.920 | 88.823 | 1.00 | 33.75 | C |
| ATOM | 4200 | CG | ASN | B | 304 | 77.005 | 40.150 | 88.910 | 1.00 | 39.82 | C |
| ATOM | 4201 | OD1 | ASN | B | 304 | 77.474 | 40.651 | 87.879 | 1.00 | 50.66 | O |
| ATOM | 4202 | ND2 | ASN | B | 304 | 77.180 | 40.675 | 90.126 | 1.00 | 37.17 | N |
| ATOM | 4203 | C | ASN | B | 304 | 74.920 | 38.179 | 86.870 | 1.00 | 32.67 | C |
| ATOM | 4204 | O | ASN | B | 304 | 75.610 | 38.394 | 85.877 | 1.00 | 35.96 | O |
| ATOM | 4205 | N | LEU | B | 305 | 74.167 | 37.100 | 87.010 | 1.00 | 31.16 | N |
| ATOM | 4206 | CA | LEU | B | 305 | 74.066 | 36.120 | 85.967 | 1.00 | 25.65 | C |
| ATOM | 4207 | CB | LEU | B | 305 | 73.612 | 34.821 | 86.575 | 1.00 | 26.38 | C |
| ATOM | 4208 | CG | LEU | B | 305 | 74.767 | 34.153 | 87.275 | 1.00 | 27.27 | C |
| ATOM | 4209 | CD1 | LEU | B | 305 | 74.392 | 32.769 | 87.923 | 1.00 | 23.34 | C |
| ATOM | 4210 | CD2 | LEU | B | 305 | 75.809 | 34.013 | 86.171 | 1.00 | 28.00 | C |
| ATOM | 4211 | C | LEU | B | 305 | 72.994 | 36.630 | 85.050 | 1.00 | 26.35 | C |
| ATOM | 4212 | O | LEU | B | 305 | 73.115 | 36.585 | 83.810 | 1.00 | 26.07 | O |
| ATOM | 4213 | N | LEU | B | 306 | 71.931 | 37.112 | 85.688 | 1.00 | 25.39 | N |
| ATOM | 4214 | CA | LEU | B | 306 | 70.770 | 37.598 | 84.982 | 1.00 | 24.60 | C |
| ATOM | 4215 | CB | LEU | B | 306 | 69.552 | 37.453 | 85.861 | 1.00 | 23.79 | C |
| ATOM | 4216 | CG | LEU | B | 306 | 69.079 | 36.026 | 85.991 | 1.00 | 24.39 | C |
| ATOM | 4217 | CD1 | LEU | B | 306 | 67.729 | 36.096 | 86.676 | 1.00 | 20.76 | C |
| ATOM | 4218 | CD2 | LEU | B | 306 | 69.025 | 35.324 | 84.632 | 1.00 | 20.20 | C |
| ATOM | 4219 | C | LEU | B | 306 | 70.819 | 39.009 | 84.445 | 1.00 | 25.49 | C |
| ATOM | 4220 | O | LEU | B | 306 | 69.795 | 39.671 | 84.328 | 1.00 | 27.01 | O |
| ATOM | 4221 | N | LYS | B | 307 | 71.998 | 39.470 | 84.100 | 1.00 | 25.36 | N |
| ATOM | 4222 | CA | LYS | B | 307 | 72.101 | 40.807 | 83.590 | 1.00 | 26.26 | C |
| ATOM | 4223 | CB | LYS | B | 307 | 73.461 | 41.395 | 83.895 | 1.00 | 25.60 | C |
| ATOM | 4224 | CG | LYS | B | 307 | 73.420 | 42.086 | 85.197 | 1.00 | 27.79 | C |
| ATOM | 4225 | CD | LYS | B | 307 | 74.739 | 42.619 | 85.558 | 1.00 | 32.28 | C |
| ATOM | 4226 | CE | LYS | B | 307 | 74.584 | 43.356 | 86.867 | 1.00 | 35.58 | C |
| ATOM | 4227 | NZ | LYS | B | 307 | 73.208 | 43.852 | 86.933 | 1.00 | 32.38 | N |
| ATOM | 4228 | C | LYS | B | 307 | 71.801 | 40.938 | 82.139 | 1.00 | 26.28 | C |
| ATOM | 4229 | O | LYS | B | 307 | 72.290 | 40.199 | 81.303 | 1.00 | 28.36 | O |
| ATOM | 4230 | N | THR | B | 308 | 70.965 | 41.924 | 81.870 | 1.00 | 26.14 | N |

FIG. 2A-92

| ATOM | 4231 | CA | THR | B | 308 | 70.515 | 42.286 | 80.546 | 1.00 | 23.70 | C |
| ATOM | 4232 | CB | THR | B | 308 | 69.650 | 43.502 | 80.710 | 1.00 | 22.36 | C |
| ATOM | 4233 | OG1 | THR | B | 308 | 68.313 | 43.065 | 80.933 | 1.00 | 26.95 | O |
| ATOM | 4234 | CG2 | THR | B | 308 | 69.742 | 44.393 | 79.552 | 1.00 | 25.43 | C |
| ATOM | 4235 | C | THR | B | 308 | 71.624 | 42.517 | 79.521 | 1.00 | 22.24 | C |
| ATOM | 4236 | O | THR | B | 308 | 71.531 | 42.067 | 78.399 | 1.00 | 23.14 | O |
| ATOM | 4237 | N | GLU | B | 309 | 72.682 | 43.204 | 79.893 | 1.00 | 20.64 | N |
| ATOM | 4238 | CA | GLU | B | 309 | 73.725 | 43.419 | 78.926 | 1.00 | 19.66 | C |
| ATOM | 4239 | CB | GLU | B | 309 | 74.417 | 44.779 | 79.173 | 1.00 | 19.81 | C |
| ATOM | 4240 | CG | GLU | B | 309 | 75.131 | 45.370 | 77.926 | 1.00 | 22.05 | C |
| ATOM | 4241 | CD | GLU | B | 309 | 74.155 | 45.918 | 76.836 | 1.00 | 32.20 | C |
| ATOM | 4242 | OE1 | GLU | B | 309 | 73.267 | 46.765 | 77.148 | 1.00 | 34.54 | O |
| ATOM | 4243 | OE2 | GLU | B | 309 | 74.289 | 45.503 | 75.653 | 1.00 | 36.86 | O |
| ATOM | 4244 | C | GLU | B | 309 | 74.743 | 42.250 | 78.972 | 1.00 | 20.34 | C |
| ATOM | 4245 | O | GLU | B | 309 | 75.365 | 41.981 | 80.003 | 1.00 | 17.99 | O |
| ATOM | 4246 | N | PRO | B | 310 | 74.881 | 41.510 | 77.853 | 1.00 | 19.13 | N |
| ATOM | 4247 | CA | PRO | B | 310 | 75.816 | 40.391 | 77.791 | 1.00 | 18.89 | C |
| ATOM | 4248 | CB | PRO | B | 310 | 75.941 | 40.153 | 76.293 | 1.00 | 18.07 | C |
| ATOM | 4249 | CG | PRO | B | 310 | 74.689 | 40.550 | 75.768 | 1.00 | 14.08 | C |
| ATOM | 4250 | CD | PRO | B | 310 | 74.281 | 41.748 | 76.540 | 1.00 | 17.26 | C |
| ATOM | 4251 | C | PRO | B | 310 | 77.193 | 40.738 | 78.439 | 1.00 | 20.08 | C |
| ATOM | 4252 | O | PRO | B | 310 | 77.685 | 39.995 | 79.281 | 1.00 | 22.05 | O |
| ATOM | 4253 | N | THR | B | 311 | 77.794 | 41.872 | 78.068 | 1.00 | 19.59 | N |
| ATOM | 4254 | CA | THR | B | 311 | 79.107 | 42.232 | 78.588 | 1.00 | 17.45 | C |
| ATOM | 4255 | CB | THR | B | 311 | 79.759 | 43.375 | 77.776 | 1.00 | 16.47 | C |
| ATOM | 4256 | OG1 | THR | B | 311 | 78.958 | 44.559 | 77.852 | 1.00 | 20.11 | O |
| ATOM | 4257 | CG2 | THR | B | 311 | 79.928 | 42.968 | 76.316 | 1.00 | 17.41 | C |
| ATOM | 4258 | C | THR | B | 311 | 79.181 | 42.616 | 80.038 | 1.00 | 17.39 | C |
| ATOM | 4259 | O | THR | B | 311 | 80.252 | 42.746 | 80.594 | 1.00 | 18.07 | O |
| ATOM | 4260 | N | GLN | B | 312 | 78.040 | 42.767 | 80.667 | 1.00 | 19.80 | N |
| ATOM | 4261 | CA | GLN | B | 312 | 77.983 | 43.177 | 82.068 | 1.00 | 18.00 | C |
| ATOM | 4262 | CB | GLN | B | 312 | 76.725 | 44.077 | 82.260 | 1.00 | 16.55 | C |
| ATOM | 4263 | CG | GLN | B | 312 | 76.700 | 44.944 | 83.482 | 1.00 | 22.06 | C |
| ATOM | 4264 | CD | GLN | B | 312 | 75.732 | 46.154 | 83.390 | 1.00 | 34.75 | C |
| ATOM | 4265 | OE1 | GLN | B | 312 | 74.572 | 46.098 | 83.845 | 1.00 | 41.42 | O |
| ATOM | 4266 | NE2 | GLN | B | 312 | 76.219 | 47.262 | 82.806 | 1.00 | 35.23 | N |
| ATOM | 4267 | C | GLN | B | 312 | 77.904 | 41.918 | 82.900 | 1.00 | 16.30 | C |
| ATOM | 4268 | O | GLN | B | 312 | 78.115 | 41.926 | 84.088 | 1.00 | 16.03 | O |
| ATOM | 4269 | N | ARG | B | 313 | 77.641 | 40.810 | 82.233 | 1.00 | 17.41 | N |
| ATOM | 4270 | CA | ARG | B | 313 | 77.426 | 39.518 | 82.871 | 1.00 | 19.37 | C |
| ATOM | 4271 | CB | ARG | B | 313 | 76.739 | 38.622 | 81.870 | 1.00 | 19.40 | C |
| ATOM | 4272 | CG | ARG | B | 313 | 75.811 | 37.639 | 82.418 | 1.00 | 21.42 | C |
| ATOM | 4273 | CD | ARG | B | 313 | 75.056 | 37.071 | 81.253 | 1.00 | 20.74 | C |
| ATOM | 4274 | NE | ARG | B | 313 | 74.008 | 37.977 | 80.816 | 1.00 | 19.97 | N |
| ATOM | 4275 | CZ | ARG | B | 313 | 73.545 | 38.024 | 79.582 | 1.00 | 24.48 | C |
| ATOM | 4276 | NH1AR | G | B | 313 | 74.048 | 37.209 | 78.660 | 1.00 | 29.25 | N |

FIG. 2A-93

| ATOM | 4277 | NH2AR | G    | B | 313 | 72.594 | 38.880 | 79.261 | 1.00 | 26.55 | N |
|------|------|-------|------|---|-----|--------|--------|--------|------|-------|---|
| ATOM | 4278 | C     | ARG  | B | 313 | 78.648 | 38.847 | 83.409 | 1.00 | 20.51 | C |
| ATOM | 4279 | O     | ARG  | B | 313 | 79.746 | 39.143 | 83.014 | 1.00 | 24.04 | O |
| ATOM | 4280 | N     | MSEB |   | 314 | 78.451 | 37.916 | 84.314 | 1.00 | 22.83 | N |
| ATOM | 4281 | CA    | MSEB |   | 314 | 79.560 | 37.210 | 84.928 | 1.00 | 24.88 | C |
| ATOM | 4282 | CB    | MSEB |   | 314 | 79.056 | 36.518 | 86.186 | 1.00 | 25.77 | C |
| ATOM | 4283 | CG    | MSEB |   | 314 | 80.120 | 35.912 | 87.047 | 1.00 | 32.45 | C |
| ATOM | 4284 | SE    | MSEB |   | 314 | 79.335 | 35.376 | 88.754 | 1.00 | 40.91 | S |
| ATOM | 4285 | CE    | MSEB |   | 314 | 77.796 | 34.596 | 88.045 | 1.00 | 40.04 | C |
| ATOM | 4286 | C     | MSEB |   | 314 | 80.193 | 36.190 | 83.990 | 1.00 | 25.68 | C |
| ATOM | 4287 | O     | MSEB |   | 314 | 79.536 | 35.632 | 83.095 | 1.00 | 30.06 | O |
| ATOM | 4288 | N     | THR  | B | 315 | 81.484 | 35.949 | 84.180 | 1.00 | 24.71 | N |
| ATOM | 4289 | CA    | THR  | B | 315 | 82.164 | 34.942 | 83.362 | 1.00 | 22.64 | C |
| ATOM | 4290 | CB    | THR  | B | 315 | 83.596 | 35.318 | 83.107 | 1.00 | 21.55 | C |
| ATOM | 4291 | OG1   | THR  | B | 315 | 84.341 | 35.245 | 84.328 | 1.00 | 21.31 | O |
| ATOM | 4292 | CG2   | THR  | B | 315 | 83.639 | 36.695 | 82.566 | 1.00 | 18.74 | C |
| ATOM | 4293 | C     | THR  | B | 315 | 82.135 | 33.599 | 84.110 | 1.00 | 23.05 | C |
| ATOM | 4294 | O     | THR  | B | 315 | 82.011 | 33.582 | 85.345 | 1.00 | 22.30 | O |
| ATOM | 4295 | N     | ILE  | B | 316 | 82.233 | 32.490 | 83.369 | 1.00 | 21.14 | N |
| ATOM | 4296 | CA    | ILE  | B | 316 | 82.221 | 31.163 | 83.982 | 1.00 | 19.15 | C |
| ATOM | 4297 | CB    | ILE  | B | 316 | 82.332 | 30.001 | 82.928 | 1.00 | 19.59 | C |
| ATOM | 4298 | CG1   | ILE  | B | 316 | 81.809 | 28.720 | 83.570 | 1.00 | 18.16 | C |
| ATOM | 4299 | CD1   | ILE  | B | 316 | 80.586 | 28.923 | 84.416 | 1.00 | 12.29 | C |
| ATOM | 4300 | CG2   | ILE  | B | 316 | 83.781 | 29.806 | 82.427 | 1.00 | 13.62 | C |
| ATOM | 4301 | C     | ILE  | B | 316 | 83.350 | 31.046 | 84.991 | 1.00 | 19.35 | C |
| ATOM | 4302 | O     | ILE  | B | 316 | 83.216 | 30.386 | 86.003 | 1.00 | 21.37 | O |
| ATOM | 4303 | N     | THR  | B | 317 | 84.446 | 31.733 | 84.734 | 1.00 | 19.36 | N |
| ATOM | 4304 | CA    | THR  | B | 317 | 85.588 | 31.701 | 85.655 | 1.00 | 19.86 | C |
| ATOM | 4305 | CB    | THR  | B | 317 | 86.807 | 32.428 | 85.055 | 1.00 | 20.71 | C |
| ATOM | 4306 | OG1   | THR  | B | 317 | 86.990 | 31.999 | 83.689 | 1.00 | 24.69 | O |
| ATOM | 4307 | CG2   | THR  | B | 317 | 88.050 | 32.157 | 85.857 | 1.00 | 15.66 | C |
| ATOM | 4308 | C     | THR  | B | 317 | 85.229 | 32.356 | 86.975 | 1.00 | 20.65 | C |
| ATOM | 4309 | O     | THR  | B | 317 | 85.496 | 31.809 | 88.021 | 1.00 | 21.38 | O |
| ATOM | 4310 | N     | GLU  | B | 318 | 84.621 | 33.532 | 86.922 | 1.00 | 20.07 | N |
| ATOM | 4311 | CA    | GLU  | B | 318 | 84.230 | 34.223 | 88.132 | 1.00 | 19.74 | C |
| ATOM | 4312 | CB    | GLU  | B | 318 | 83.687 | 35.626 | 87.830 | 1.00 | 17.22 | C |
| ATOM | 4313 | CG    | GLU  | B | 318 | 84.698 | 36.491 | 87.175 | 1.00 | 18.98 | C |
| ATOM | 4314 | CD    | GLU  | B | 318 | 84.168 | 37.795 | 86.601 | 1.00 | 25.63 | C |
| ATOM | 4315 | OE1   | GLU  | B | 318 | 84.706 | 38.832 | 87.020 | 1.00 | 28.27 | O |
| ATOM | 4316 | OE2   | GLU  | B | 318 | 83.250 | 37.802 | 85.723 | 1.00 | 30.49 | O |
| ATOM | 4317 | C     | GLU  | B | 318 | 83.148 | 33.391 | 88.771 | 1.00 | 21.43 | C |
| ATOM | 4318 | O     | GLU  | B | 318 | 83.051 | 33.304 | 89.980 | 1.00 | 22.51 | O |
| ATOM | 4319 | N     | PHE  | B | 319 | 82.309 | 32.764 | 87.979 | 1.00 | 22.60 | N |
| ATOM | 4320 | CA    | PHE  | B | 319 | 81.258 | 32.007 | 88.612 | 1.00 | 22.48 | C |
| ATOM | 4321 | CB    | PHE  | B | 319 | 80.257 | 31.573 | 87.553 | 1.00 | 21.63 | C |
| ATOM | 4322 | CG    | PHE  | B | 319 | 79.257 | 30.590 | 88.047 | 1.00 | 20.30 | C |

FIG. 2A-94

| ATOM | 4323 | CD1 | PHE | B | 319 | 78.047 | 31.009 | 88.501 | 1.00 | 24.30 | C |
|---|---|---|---|---|---|---|---|---|---|---|---|
| ATOM | 4324 | CE1 | PHE | B | 319 | 77.120 | 30.093 | 88.901 | 1.00 | 25.26 | C |
| ATOM | 4325 | CZ | PHE | B | 319 | 77.383 | 28.753 | 88.858 | 1.00 | 22.34 | C |
| ATOM | 4326 | CE2 | PHE | B | 319 | 78.597 | 28.314 | 88.415 | 1.00 | 20.07 | C |
| ATOM | 4327 | CD2 | PHE | B | 319 | 79.526 | 29.223 | 88.015 | 1.00 | 20.21 | C |
| ATOM | 4328 | C | PHE | B | 319 | 81.843 | 30.800 | 89.395 | 1.00 | 21.60 | C |
| ATOM | 4329 | O | PHE | B | 319 | 81.399 | 30.478 | 90.489 | 1.00 | 20.87 | O |
| ATOM | 4330 | N | MSE | B | 320 | 82.850 | 30.139 | 88.851 | 1.00 | 20.46 | N |
| ATOM | 4331 | CA | MSE | B | 320 | 83.417 | 29.010 | 89.567 | 1.00 | 20.30 | C |
| ATOM | 4332 | CB | MSE | B | 320 | 84.374 | 28.218 | 88.653 | 1.00 | 20.94 | C |
| ATOM | 4333 | CG | MSE | B | 320 | 83.679 | 27.392 | 87.574 | 1.00 | 17.01 | C |
| ATOM | 4334 | SE | MSE | B | 320 | 82.257 | 26.266 | 88.275 | 1.00 | 26.59 | S |
| ATOM | 4335 | CE | MSE | B | 320 | 83.369 | 24.749 | 88.593 | 1.00 | 6.91 | C |
| ATOM | 4336 | C | MSE | B | 320 | 84.139 | 29.493 | 90.812 | 1.00 | 20.15 | C |
| ATOM | 4337 | O | MSE | B | 320 | 84.141 | 28.838 | 91.830 | 1.00 | 20.08 | O |
| ATOM | 4338 | N | ASN | B | 321 | 84.749 | 30.660 | 90.725 | 1.00 | 21.51 | N |
| ATOM | 4339 | CA | ASN | B | 321 | 85.474 | 31.218 | 91.839 | 1.00 | 19.53 | C |
| ATOM | 4340 | CB | ASN | B | 321 | 86.480 | 32.206 | 91.349 | 1.00 | 20.56 | C |
| ATOM | 4341 | CG | ASN | B | 321 | 87.675 | 31.541 | 90.841 | 1.00 | 25.63 | C |
| ATOM | 4342 | OD1 | ASN | B | 321 | 88.107 | 30.544 | 91.412 | 1.00 | 32.28 | O |
| ATOM | 4343 | ND2 | ASN | B | 321 | 88.244 | 32.053 | 89.779 | 1.00 | 35.64 | N |
| ATOM | 4344 | C | ASN | B | 321 | 84.624 | 31.885 | 92.850 | 1.00 | 18.42 | C |
| ATOM | 4345 | O | ASN | B | 321 | 85.112 | 32.286 | 93.900 | 1.00 | 18.87 | O |
| ATOM | 4346 | N | HIS | B | 322 | 83.346 | 32.026 | 92.551 | 1.00 | 19.09 | N |
| ATOM | 4347 | CA | HIS | B | 322 | 82.461 | 32.678 | 93.491 | 1.00 | 19.15 | C |
| ATOM | 4348 | CB | HIS | B | 322 | 81.100 | 32.921 | 92.871 | 1.00 | 17.90 | C |
| ATOM | 4349 | CG | HIS | B | 322 | 80.177 | 33.651 | 93.769 | 1.00 | 18.67 | C |
| ATOM | 4350 | ND1 | HIS | B | 322 | 80.005 | 33.295 | 95.084 | 1.00 | 20.65 | N |
| ATOM | 4351 | CE1 | HIS | B | 322 | 79.129 | 34.105 | 95.642 | 1.00 | 20.97 | C |
| ATOM | 4352 | NE2 | HIS | B | 322 | 78.729 | 34.973 | 94.734 | 1.00 | 21.37 | N |
| ATOM | 4353 | CD2 | HIS | B | 322 | 79.375 | 34.712 | 93.554 | 1.00 | 21.41 | C |
| ATOM | 4354 | C | HIS | B | 322 | 82.338 | 31.789 | 94.716 | 1.00 | 20.44 | C |
| ATOM | 4355 | O | HIS | B | 322 | 82.318 | 30.561 | 94.620 | 1.00 | 20.62 | O |
| ATOM | 4356 | N | PRO | B | 323 | 82.275 | 32.407 | 95.894 | 1.00 | 21.45 | N |
| ATOM | 4357 | CA | PRO | B | 323 | 82.171 | 31.725 | 97.179 | 1.00 | 21.53 | C |
| ATOM | 4358 | CB | PRO | B | 323 | 82.114 | 32.890 | 98.162 | 1.00 | 21.82 | C |
| ATOM | 4359 | CG | PRO | B | 323 | 83.066 | 33.816 | 97.574 | 1.00 | 21.43 | C |
| ATOM | 4360 | CD | PRO | B | 323 | 82.637 | 33.815 | 96.102 | 1.00 | 22.31 | C |
| ATOM | 4361 | C | PRO | B | 323 | 81.036 | 30.756 | 97.358 | 1.00 | 20.46 | C |
| ATOM | 4362 | O | PRO | B | 323 | 81.202 | 29.680 | 97.940 | 1.00 | 17.32 | O |
| ATOM | 4363 | N | TRP | B | 324 | 79.870 | 31.118 | 96.873 | 1.00 | 20.59 | N |
| ATOM | 4364 | CA | TRP | B | 324 | 78.750 | 30.212 | 97.080 | 1.00 | 22.69 | C |
| ATOM | 4365 | CB | TRP | B | 324 | 77.476 | 30.913 | 96.629 | 1.00 | 22.79 | C |
| ATOM | 4366 | CG | TRP | B | 324 | 76.245 | 30.237 | 96.953 | 1.00 | 21.31 | C |
| ATOM | 4367 | CD1 | TRP | B | 324 | 75.588 | 30.292 | 98.120 | 1.00 | 15.93 | C |
| ATOM | 4368 | NE1 | TRP | B | 324 | 74.416 | 29.585 | 98.033 | 1.00 | 20.69 | N |

FIG. 2A-95

| ATOM | 4369 | CE2 | TRP | B | 324 | 74.313 | 29.046 | 96.777 | 1.00 | 22.29 | C |
|---|---|---|---|---|---|---|---|---|---|---|---|
| ATOM | 4370 | CD2 | TRP | B | 324 | 75.460 | 29.442 | 96.065 | 1.00 | 17.98 | C |
| ATOM | 4371 | CE3 | TRP | B | 324 | 75.614 | 29.031 | 94.732 | 1.00 | 16.86 | C |
| ATOM | 4372 | CZ3 | TRP | B | 324 | 74.626 | 28.245 | 94.151 | 1.00 | 23.12 | C |
| ATOM | 4373 | CH2 | TRP | B | 324 | 73.479 | 27.860 | 94.887 | 1.00 | 23.89 | C |
| ATOM | 4374 | CZ2 | TRP | B | 324 | 73.307 | 28.248 | 96.202 | 1.00 | 23.55 | C |
| ATOM | 4375 | C | TRP | B | 324 | 78.971 | 28.897 | 96.330 | 1.00 | 24.02 | C |
| ATOM | 4376 | O | TRP | B | 324 | 78.561 | 27.840 | 96.770 | 1.00 | 23.94 | O |
| ATOM | 4377 | N | ILE | B | 325 | 79.643 | 28.986 | 95.191 | 1.00 | 24.28 | N |
| ATOM | 4378 | CA | ILE | B | 325 | 79.914 | 27.822 | 94.372 | 1.00 | 24.72 | C |
| ATOM | 4379 | CB | ILE | B | 325 | 80.054 | 28.236 | 92.866 | 1.00 | 23.39 | C |
| ATOM | 4380 | CG1 | ILE | B | 325 | 78.869 | 27.761 | 92.057 | 1.00 | 25.80 | C |
| ATOM | 4381 | CD1 | ILE | B | 325 | 77.613 | 28.370 | 92.434 | 1.00 | 28.77 | C |
| ATOM | 4382 | CG2 | ILE | B | 325 | 81.217 | 27.541 | 92.245 | 1.00 | 24.11 | C |
| ATOM | 4383 | C | ILE | B | 325 | 81.175 | 27.052 | 94.818 | 1.00 | 25.56 | C |
| ATOM | 4384 | O | ILE | B | 325 | 81.188 | 25.830 | 94.885 | 1.00 | 26.00 | O |
| ATOM | 4385 | N | MSE | B | 326 | 82.233 | 27.772 | 95.127 | 1.00 | 27.64 | N |
| ATOM | 4386 | CA | MSE | B | 326 | 83.469 | 27.139 | 95.526 | 1.00 | 31.85 | C |
| ATOM | 4387 | CB | MSE | B | 326 | 84.554 | 28.192 | 95.576 | 1.00 | 31.87 | C |
| ATOM | 4388 | CG | MSE | B | 326 | 85.924 | 27.639 | 95.657 | 1.00 | 38.26 | C |
| ATOM | 4389 | SE | MSE | B | 326 | 87.132 | 29.080 | 95.257 | 1.00 | 53.96 | S |
| ATOM | 4390 | CE | MSE | B | 326 | 88.119 | 28.219 | 93.823 | 1.00 | 48.71 | C |
| ATOM | 4391 | C | MSE | B | 326 | 83.329 | 26.438 | 96.876 | 1.00 | 34.56 | C |
| ATOM | 4392 | O | MSE | B | 326 | 83.386 | 25.205 | 96.954 | 1.00 | 37.13 | O |
| ATOM | 4393 | N | GLN | B | 327 | 83.132 | 27.225 | 97.933 | 1.00 | 36.37 | N |
| ATOM | 4394 | CA | GLN | B | 327 | 82.976 | 26.710 | 99.285 | 1.00 | 37.47 | C |
| ATOM | 4395 | CB | GLN | B | 327 | 83.299 | 27.822 | 100.291 | 1.00 | 38.93 | C |
| ATOM | 4396 | CG | GLN | B | 327 | 84.750 | 28.321 | 100.308 | 1.00 | 43.21 | C |
| ATOM | 4397 | CD | GLN | B | 327 | 85.753 | 27.228 | 100.695 | 1.00 | 52.53 | C |
| ATOM | 4398 | OE1 | GLN | B | 327 | 85.437 | 26.316 | 101.481 | 1.00 | 53.20 | O |
| ATOM | 4399 | NE2 | GLN | B | 327 | 86.973 | 27.317 | 100.152 | 1.00 | 53.60 | N |
| ATOM | 4400 | C | GLN | B | 327 | 81.560 | 26.198 | 99.555 | 1.00 | 37.19 | C |
| ATOM | 4401 | O | GLN | B | 327 | 80.839 | 26.802 | 100.347 | 1.00 | 38.54 | O |
| ATOM | 4402 | N | SER | B | 328 | 81.155 | 25.097 | 98.925 | 1.00 | 36.62 | N |
| ATOM | 4403 | CA | SER | B | 328 | 79.806 | 24.570 | 99.147 | 1.00 | 36.36 | C |
| ATOM | 4404 | CB | SER | B | 328 | 79.476 | 23.461 | 98.147 | 1.00 | 36.75 | C |
| ATOM | 4405 | OG | SER | B | 328 | 79.433 | 23.940 | 96.814 | 1.00 | 37.23 | O |
| ATOM | 4406 | C | SER | B | 328 | 79.649 | 24.006 | 100.558 | 1.00 | 36.12 | C |
| ATOM | 4407 | O | SER | B | 328 | 78.719 | 24.356 | 101.304 | 1.00 | 35.48 | O |
| ATOM | 4408 | N | THR | B | 329 | 80.571 | 23.118 | 100.913 | 1.00 | 37.04 | N |
| ATOM | 4409 | CA | THR | B | 329 | 80.587 | 22.477 | 102.224 | 1.00 | 38.39 | C |
| ATOM | 4410 | CB | THR | B | 329 | 81.967 | 21.881 | 102.543 | 1.00 | 39.17 | C |
| ATOM | 4411 | OG1 | THR | B | 329 | 82.880 | 22.949 | 102.817 | 1.00 | 41.66 | O |
| ATOM | 4412 | CG2 | THR | B | 329 | 82.497 | 21.057 | 101.360 | 1.00 | 41.27 | C |
| ATOM | 4413 | C | THR | B | 329 | 80.307 | 23.512 | 103.291 | 1.00 | 37.09 | C |
| ATOM | 4414 | O | THR | B | 329 | 79.937 | 23.173 | 104.408 | 1.00 | 38.03 | O |

FIG. 2A-96

| ATOM | 4415 | N | ALA | B | 330 | 80.492 | 24.779 | 102.932 | 1.00 | 35.52 | N |
| --- | --- | --- | --- | --- | --- | --- | --- | --- | --- | --- | --- |
| ATOM | 4416 | CA | ALA | B | 330 | 80.306 | 25.874 | 103.860 | 1.00 | 34.17 | C |
| ATOM | 4417 | CB | ALA | B | 330 | 81.527 | 26.779 | 103.798 | 1.00 | 34.54 | C |
| ATOM | 4418 | C | ALA | B | 330 | 79.024 | 26.709 | 103.723 | 1.00 | 32.85 | C |
| ATOM | 4419 | O | ALA | B | 330 | 78.916 | 27.771 | 104.339 | 1.00 | 32.97 | O |
| ATOM | 4420 | N | VAL | B | 331 | 78.054 | 26.260 | 102.931 | 1.00 | 31.06 | N |
| ATOM | 4421 | CA | VAL | B | 331 | 76.821 | 27.039 | 102.791 | 1.00 | 30.01 | C |
| ATOM | 4422 | CB | VAL | B | 331 | 76.325 | 27.137 | 101.301 | 1.00 | 30.01 | C |
| ATOM | 4423 | CG1 | VAL | B | 331 | 76.677 | 25.905 | 100.554 | 1.00 | 28.26 | C |
| ATOM | 4424 | CG2 | VAL | B | 331 | 74.824 | 27.331 | 101.246 | 1.00 | 33.42 | C |
| ATOM | 4425 | C | VAL | B | 331 | 75.791 | 26.353 | 103.630 | 1.00 | 29.74 | C |
| ATOM | 4426 | O | VAL | B | 331 | 75.801 | 25.129 | 103.735 | 1.00 | 30.83 | O |
| ATOM | 4427 | N | PRO | B | 332 | 74.901 | 27.134 | 104.268 | 1.00 | 29.52 | N |
| ATOM | 4428 | CA | PRO | B | 332 | 73.848 | 26.599 | 105.124 | 1.00 | 29.30 | C |
| ATOM | 4429 | CB | PRO | B | 332 | 72.926 | 27.803 | 105.349 | 1.00 | 29.35 | C |
| ATOM | 4430 | CG | PRO | B | 332 | 73.244 | 28.732 | 104.245 | 1.00 | 29.21 | C |
| ATOM | 4431 | CD | PRO | B | 332 | 74.741 | 28.588 | 104.125 | 1.00 | 29.95 | C |
| ATOM | 4432 | C | PRO | B | 332 | 73.147 | 25.450 | 104.473 | 1.00 | 28.63 | C |
| ATOM | 4433 | O | PRO | B | 332 | 73.288 | 25.247 | 103.288 | 1.00 | 28.49 | O |
| ATOM | 4434 | N | ALA | B | 333 | 72.414 | 24.681 | 105.262 | 1.00 | 28.71 | N |
| ATOM | 4435 | CA | ALA | B | 333 | 71.669 | 23.553 | 104.732 | 1.00 | 28.28 | C |
| ATOM | 4436 | CB | ALA | B | 333 | 72.067 | 22.275 | 105.469 | 1.00 | 27.59 | C |
| ATOM | 4437 | C | ALA | B | 333 | 70.173 | 23.853 | 104.894 | 1.00 | 27.75 | C |
| ATOM | 4438 | O | ALA | B | 333 | 69.404 | 23.009 | 105.320 | 1.00 | 28.13 | O |
| ATOM | 4439 | N | THR | B | 334 | 69.783 | 25.075 | 104.534 | 1.00 | 25.88 | N |
| ATOM | 4440 | CA | THR | B | 334 | 68.410 | 25.539 | 104.629 | 1.00 | 25.13 | C |
| ATOM | 4441 | CB | THR | B | 334 | 68.338 | 27.049 | 104.489 | 1.00 | 25.97 | C |
| ATOM | 4442 | OG1 | THR | B | 334 | 67.470 | 27.379 | 103.395 | 1.00 | 29.29 | O |
| ATOM | 4443 | CG2 | THR | B | 334 | 69.714 | 27.626 | 104.238 | 1.00 | 25.87 | C |
| ATOM | 4444 | C | THR | B | 334 | 67.479 | 24.947 | 103.589 | 1.00 | 24.26 | C |
| ATOM | 4445 | O | THR | B | 334 | 67.777 | 24.892 | 102.402 | 1.00 | 22.10 | O |
| ATOM | 4446 | N | PRO | B | 335 | 66.302 | 24.530 | 104.028 | 1.00 | 23.90 | N |
| ATOM | 4447 | CA | PRO | B | 335 | 65.295 | 23.928 | 103.169 | 1.00 | 24.60 | C |
| ATOM | 4448 | CB | PRO | B | 335 | 64.218 | 23.504 | 104.145 | 1.00 | 25.05 | C |
| ATOM | 4449 | CG | PRO | B | 335 | 64.944 | 23.340 | 105.421 | 1.00 | 25.81 | C |
| ATOM | 4450 | CD | PRO | B | 335 | 65.844 | 24.549 | 105.416 | 1.00 | 24.58 | C |
| ATOM | 4451 | C | PRO | B | 335 | 64.769 | 24.944 | 102.199 | 1.00 | 25.43 | C |
| ATOM | 4452 | O | PRO | B | 335 | 64.498 | 26.062 | 102.596 | 1.00 | 27.49 | O |
| ATOM | 4453 | N | LEU | B | 336 | 64.631 | 24.554 | 100.936 | 1.00 | 24.34 | N |
| ATOM | 4454 | CA | LEU | B | 336 | 64.112 | 25.423 | 99.888 | 1.00 | 23.02 | C |
| ATOM | 4455 | CB | LEU | B | 336 | 65.006 | 25.368 | 98.639 | 1.00 | 23.82 | C |
| ATOM | 4456 | CG | LEU | B | 336 | 66.361 | 26.070 | 98.477 | 1.00 | 23.67 | C |
| ATOM | 4457 | CD1 | LEU | B | 336 | 66.754 | 26.883 | 99.700 | 1.00 | 26.25 | C |
| ATOM | 4458 | CD2 | LEU | B | 336 | 67.394 | 25.005 | 98.159 | 1.00 | 20.03 | C |
| ATOM | 4459 | C | LEU | B | 336 | 62.755 | 24.859 | 99.541 | 1.00 | 22.74 | C |
| ATOM | 4460 | O | LEU | B | 336 | 62.509 | 23.697 | 99.773 | 1.00 | 22.25 | O |

FIG. 2A-97

| ATOM | 4461 | N | HIS | B | 337 | 61.885 | 25.656 | 98.950 | 1.00 | 23.73 | N |
| --- | --- | --- | --- | --- | --- | --- | --- | --- | --- | --- | --- |
| ATOM | 4462 | CA | HIS | B | 337 | 60.559 | 25.179 | 98.598 | 1.00 | 22.95 | C |
| ATOM | 4463 | CB | HIS | B | 337 | 59.586 | 26.352 | 98.612 | 1.00 | 23.21 | C |
| ATOM | 4464 | CG | HIS | B | 337 | 59.565 | 27.111 | 99.901 | 1.00 | 23.93 | C |
| ATOM | 4465 | ND1 | HIS | B | 337 | 58.398 | 27.572 | 100.472 | 1.00 | 25.12 | N |
| ATOM | 4466 | CE1 | HIS | B | 337 | 58.682 | 28.239 | 101.578 | 1.00 | 27.29 | C |
| ATOM | 4467 | NE2 | HIS | B | 337 | 59.991 | 28.227 | 101.747 | 1.00 | 24.86 | N |
| ATOM | 4468 | CD2 | HIS | B | 337 | 60.566 | 27.523 | 100.713 | 1.00 | 24.31 | C |
| ATOM | 4469 | C | HIS | B | 337 | 60.476 | 24.497 | 97.241 | 1.00 | 22.60 | C |
| ATOM | 4470 | O | HIS | B | 337 | 59.380 | 24.235 | 96.742 | 1.00 | 22.74 | O |
| ATOM | 4471 | N | THR | B | 338 | 61.635 | 24.197 | 96.664 | 1.00 | 21.42 | N |
| ATOM | 4472 | CA | THR | B | 338 | 61.799 | 23.751 | 95.285 | 1.00 | 20.95 | C |
| ATOM | 4473 | CB | THR | B | 338 | 63.271 | 23.398 | 95.072 | 1.00 | 20.75 | C |
| ATOM | 4474 | OG1 | THR | B | 338 | 64.071 | 24.544 | 95.368 | 1.00 | 21.44 | O |
| ATOM | 4475 | CG2 | THR | B | 338 | 63.507 | 22.991 | 93.615 | 1.00 | 12.20 | C |
| ATOM | 4476 | C | THR | B | 338 | 60.926 | 22.530 | 94.993 | 1.00 | 22.21 | C |
| ATOM | 4477 | O | THR | B | 338 | 59.971 | 22.575 | 94.231 | 1.00 | 22.65 | O |
| ATOM | 4478 | N | SER | B | 339 | 61.314 | 21.397 | 95.609 | 1.00 | 23.33 | N |
| ATOM | 4479 | CA | SER | B | 339 | 60.527 | 20.183 | 95.441 | 1.00 | 26.90 | C |
| ATOM | 4480 | CB | SER | B | 339 | 60.950 | 19.192 | 96.527 | 1.00 | 27.59 | C |
| ATOM | 4481 | OG | SER | B | 339 | 62.128 | 18.502 | 96.107 | 1.00 | 34.42 | O |
| ATOM | 4482 | C | SER | B | 339 | 59.030 | 20.471 | 95.565 | 1.00 | 27.75 | C |
| ATOM | 4483 | O | SER | B | 339 | 58.204 | 19.994 | 94.798 | 1.00 | 26.25 | O |
| ATOM | 4484 | N | ARG | B | 340 | 58.691 | 21.261 | 96.603 | 1.00 | 30.68 | N |
| ATOM | 4485 | CA | ARG | B | 340 | 57.287 | 21.535 | 96.890 | 1.00 | 33.83 | C |
| ATOM | 4486 | CB | ARG | B | 340 | 57.222 | 22.383 | 98.159 | 1.00 | 35.55 | C |
| ATOM | 4487 | CG | ARG | B | 340 | 58.322 | 22.010 | 99.154 | 1.00 | 44.18 | C |
| ATOM | 4488 | CD | ARG | B | 340 | 57.995 | 22.475 | 100.578 | 1.00 | 52.25 | C |
| ATOM | 4489 | NE | ARG | B | 340 | 58.893 | 23.560 | 100.979 | 1.00 | 55.12 | N |
| ATOM | 4490 | CZ | ARG | B | 340 | 59.108 | 23.728 | 102.296 | 1.00 | 53.75 | C |
| ATOM | 4491 | NH1AR | G | B | 340 | 58.524 | 22.928 | 103.172 | 1.00 | 51.16 | N |
| ATOM | 4492 | NH2AR | G | B | 340 | 59.942 | 24.682 | 102.713 | 1.00 | 51.90 | N |
| ATOM | 4493 | C | ARG | B | 340 | 56.587 | 22.255 | 95.735 | 1.00 | 33.10 | C |
| ATOM | 4494 | O | ARG | B | 340 | 55.535 | 21.852 | 95.259 | 1.00 | 33.81 | O |
| ATOM | 4495 | N | VAL | B | 341 | 57.181 | 23.387 | 95.314 | 1.00 | 31.68 | N |
| ATOM | 4496 | CA | VAL | B | 341 | 56.587 | 24.127 | 94.206 | 1.00 | 31.27 | C |
| ATOM | 4497 | CB | VAL | B | 341 | 57.394 | 25.411 | 93.989 | 1.00 | 31.10 | C |
| ATOM | 4498 | CG1 | VAL | B | 341 | 56.800 | 26.212 | 92.831 | 1.00 | 31.66 | C |
| ATOM | 4499 | CG2 | VAL | B | 341 | 57.364 | 26.261 | 95.245 | 1.00 | 31.72 | C |
| ATOM | 4500 | C | VAL | B | 341 | 56.572 | 23.291 | 92.925 | 1.00 | 32.27 | C |
| ATOM | 4501 | O | VAL | B | 341 | 55.618 | 23.283 | 92.158 | 1.00 | 33.19 | O |
| ATOM | 4502 | N | LEU | B | 342 | 57.697 | 22.595 | 92.690 | 1.00 | 33.76 | N |
| ATOM | 4503 | CA | LEU | B | 342 | 57.785 | 21.750 | 91.506 | 1.00 | 33.81 | C |
| ATOM | 4504 | CB | LEU | B | 342 | 59.067 | 20.922 | 91.602 | 1.00 | 33.34 | C |
| ATOM | 4505 | CG | LEU | B | 342 | 60.097 | 21.318 | 90.541 | 1.00 | 31.91 | C |
| ATOM | 4506 | CD1 | LEU | B | 342 | 59.780 | 22.671 | 89.901 | 1.00 | 34.37 | C |

FIG. 2A-98

| ATOM | 4507 | CD2 | LEU | B | 342 | 61.514 | 21.429 | 91.102 | 1.00 | 28.82 | C |
|---|---|---|---|---|---|---|---|---|---|---|---|
| ATOM | 4508 | C | LEU | B | 342 | 56.573 | 20.824 | 91.386 | 1.00 | 35.69 | C |
| ATOM | 4509 | O | LEU | B | 342 | 55.824 | 20.863 | 90.419 | 1.00 | 34.85 | O |
| ATOM | 4510 | N | ALA | B | 343 | 56.471 | 19.994 | 92.442 | 1.00 | 37.92 | N |
| ATOM | 4511 | CA | ALA | B | 343 | 55.321 | 19.107 | 92.551 | 1.00 | 41.19 | C |
| ATOM | 4512 | CB | ALA | B | 343 | 55.377 | 18.409 | 93.910 | 1.00 | 40.33 | C |
| ATOM | 4513 | C | ALA | B | 343 | 54.009 | 19.886 | 92.418 | 1.00 | 44.34 | C |
| ATOM | 4514 | O | ALA | B | 343 | 53.039 | 19.438 | 91.820 | 1.00 | 44.71 | O |
| ATOM | 4515 | N | GLU | B | 344 | 53.985 | 21.079 | 93.043 | 1.00 | 48.72 | N |
| ATOM | 4516 | CA | GLU | B | 344 | 52.825 | 21.950 | 92.873 | 1.00 | 52.30 | C |
| ATOM | 4517 | CB | GLU | B | 344 | 53.090 | 23.253 | 93.631 | 1.00 | 53.07 | C |
| ATOM | 4518 | CG | GLU | B | 344 | 52.717 | 23.159 | 95.109 | 1.00 | 56.65 | C |
| ATOM | 4519 | CD | GLU | B | 344 | 52.878 | 24.516 | 95.761 | 1.00 | 61.60 | C |
| ATOM | 4520 | OE1 | GLU | B | 344 | 52.282 | 25.471 | 95.290 | 1.00 | 64.14 | O |
| ATOM | 4521 | OE2 | GLU | B | 344 | 53.594 | 24.600 | 96.758 | 1.00 | 62.66 | O |
| ATOM | 4522 | C | GLU | B | 344 | 52.583 | 22.250 | 91.391 | 1.00 | 53.80 | C |
| ATOM | 4523 | O | GLU | B | 344 | 51.628 | 21.794 | 90.779 | 1.00 | 53.12 | O |
| ATOM | 4524 | N | ASP | B | 345 | 53.478 | 23.077 | 90.823 | 1.00 | 57.27 | N |
| ATOM | 4525 | CA | ASP | B | 345 | 53.361 | 23.404 | 89.409 | 1.00 | 61.15 | C |
| ATOM | 4526 | CB | ASP | B | 345 | 52.616 | 22.262 | 88.719 | 1.00 | 60.98 | C |
| ATOM | 4527 | CG | ASP | B | 345 | 52.831 | 22.350 | 87.213 | 1.00 | 63.28 | C |
| ATOM | 4528 | OD1 | ASP | B | 345 | 53.586 | 23.225 | 86.790 | 1.00 | 63.66 | O |
| ATOM | 4529 | OD2 | ASP | B | 345 | 52.247 | 21.552 | 86.487 | 1.00 | 64.73 | O |
| ATOM | 4530 | C | ASP | B | 345 | 52.610 | 24.725 | 89.194 | 1.00 | 63.41 | C |
| ATOM | 4531 | O | ASP | B | 345 | 51.993 | 24.959 | 88.163 | 1.00 | 65.21 | O |
| ATOM | 4532 | OXT | ASP | B | 345 | 52.594 | 25.606 | 90.043 | 1.00 | 64.70 | O |
| ATOM | 4533 | N | GLN | C | 41 | 65.761 | -3.925 | 67.530 | 1.00 | 60.43 | N |
| ATOM | 4534 | CA | GLN | C | 41 | 64.821 | -4.626 | 66.666 | 1.00 | 59.79 | C |
| ATOM | 4535 | CB | GLN | C | 41 | 64.739 | -6.077 | 67.147 | 1.00 | 60.56 | C |
| ATOM | 4536 | CG | GLN | C | 41 | 63.933 | -6.966 | 66.201 | 1.00 | 61.64 | C |
| ATOM | 4537 | CD | GLN | C | 41 | 64.065 | -8.410 | 66.631 | 1.00 | 62.71 | C |
| ATOM | 4538 | OE1 | GLN | C | 41 | 63.729 | -8.807 | 67.733 | 1.00 | 59.30 | O |
| ATOM | 4539 | NE2 | GLN | C | 41 | 64.549 | -9.219 | 65.667 | 1.00 | 63.04 | N |
| ATOM | 4540 | C | GLN | C | 41 | 63.434 | -3.980 | 66.703 | 1.00 | 58.55 | C |
| ATOM | 4541 | O | GLN | C | 41 | 62.692 | -4.084 | 67.672 | 1.00 | 57.30 | O |
| ATOM | 4542 | N | GLN | C | 42 | 63.102 | -3.254 | 65.614 | 1.00 | 57.17 | N |
| ATOM | 4543 | CA | GLN | C | 42 | 61.786 | -2.624 | 65.556 | 1.00 | 55.71 | C |
| ATOM | 4544 | CB | GLN | C | 42 | 61.617 | -1.767 | 66.809 | 1.00 | 55.07 | C |
| ATOM | 4545 | CG | GLN | C | 42 | 60.171 | -1.730 | 67.300 | 1.00 | 54.89 | C |
| ATOM | 4546 | CD | GLN | C | 42 | 60.100 | -2.341 | 68.675 | 1.00 | 55.53 | C |
| ATOM | 4547 | OE1 | GLN | C | 42 | 59.056 | -2.502 | 69.279 | 1.00 | 56.48 | O |
| ATOM | 4548 | NE2 | GLN | C | 42 | 61.304 | -2.683 | 69.175 | 1.00 | 55.29 | N |
| ATOM | 4549 | C | GLN | C | 42 | 61.596 | -1.745 | 64.318 | 1.00 | 55.03 | C |
| ATOM | 4550 | O | GLN | C | 42 | 60.492 | -1.509 | 63.850 | 1.00 | 54.97 | O |
| ATOM | 4551 | N | ALA | C | 43 | 62.722 | -1.208 | 63.806 | 1.00 | 53.46 | N |
| ATOM | 4552 | CA | ALA | C | 43 | 62.603 | -0.176 | 62.780 | 1.00 | 52.20 | C |

FIG. 2A-99

| ATOM | 4553 | CB | ALA | C | 43 | 63.409 | 1.043 | 63.229 | 1.00 | 52.00 | C |
| ATOM | 4554 | C | ALA | C | 43 | 63.084 | -0.635 | 61.403 | 1.00 | 51.50 | C |
| ATOM | 4555 | O | ALA | C | 43 | 63.360 | -1.804 | 61.151 | 1.00 | 51.40 | O |
| ATOM | 4556 | N | PRO | C | 44 | 63.151 | 0.349 | 60.488 | 1.00 | 50.87 | N |
| ATOM | 4557 | CA | PRO | C | 44 | 63.485 | 0.096 | 59.097 | 1.00 | 49.81 | C |
| ATOM | 4558 | CB | PRO | C | 44 | 63.005 | 1.307 | 58.306 | 1.00 | 50.01 | C |
| ATOM | 4559 | CG | PRO | C | 44 | 62.946 | 2.496 | 59.262 | 1.00 | 50.88 | C |
| ATOM | 4560 | CD | PRO | C | 44 | 62.934 | 1.776 | 60.691 | 1.00 | 51.11 | C |
| ATOM | 4561 | C | PRO | C | 44 | 64.991 | -0.061 | 58.913 | 1.00 | 49.01 | C |
| ATOM | 4562 | O | PRO | C | 44 | 65.624 | 0.622 | 58.121 | 1.00 | 48.57 | O |
| ATOM | 4563 | N | GLN | C | 45 | 65.445 | -1.012 | 59.748 | 1.00 | 47.33 | N |
| ATOM | 4564 | CA | GLN | C | 45 | 66.865 | -1.347 | 59.782 | 1.00 | 45.83 | C |
| ATOM | 4565 | CB | GLN | C | 45 | 67.052 | -2.581 | 60.666 | 1.00 | 46.06 | C |
| ATOM | 4566 | CG | GLN | C | 45 | 68.127 | -2.381 | 61.735 | 1.00 | 48.49 | C |
| ATOM | 4567 | CD | GLN | C | 45 | 67.725 | -3.114 | 62.992 | 1.00 | 49.64 | C |
| ATOM | 4568 | OE1 | GLN | C | 45 | 66.566 | -3.213 | 63.362 | 1.00 | 51.76 | O |
| ATOM | 4569 | NE2 | GLN | C | 45 | 68.767 | -3.605 | 63.689 | 1.00 | 47.12 | N |
| ATOM | 4570 | C | GLN | C | 45 | 67.442 | -1.635 | 58.396 | 1.00 | 44.59 | C |
| ATOM | 4571 | O | GLN | C | 45 | 68.527 | -1.196 | 58.042 | 1.00 | 44.44 | O |
| ATOM | 4572 | N | PHE | C | 46 | 66.710 | -2.450 | 57.616 | 1.00 | 44.13 | N |
| ATOM | 4573 | CA | PHE | C | 46 | 67.219 | -2.788 | 56.294 | 1.00 | 42.05 | C |
| ATOM | 4574 | CB | PHE | C | 46 | 66.162 | -3.614 | 55.568 | 1.00 | 42.11 | C |
| ATOM | 4575 | CG | PHE | C | 46 | 65.098 | -2.719 | 55.007 | 1.00 | 39.48 | C |
| ATOM | 4576 | CD1 | PHE | C | 46 | 63.923 | -2.525 | 55.720 | 1.00 | 36.60 | C |
| ATOM | 4577 | CE1 | PHE | C | 46 | 62.864 | -1.847 | 55.136 | 1.00 | 37.46 | C |
| ATOM | 4578 | CZ | PHE | C | 46 | 62.976 | -1.347 | 53.846 | 1.00 | 37.24 | C |
| ATOM | 4579 | CE2 | PHE | C | 46 | 64.160 | -1.532 | 53.144 | 1.00 | 38.88 | C |
| ATOM | 4580 | CD2 | PHE | C | 46 | 65.227 | -2.215 | 53.724 | 1.00 | 39.75 | C |
| ATOM | 4581 | C | PHE | C | 46 | 67.542 | -1.527 | 55.486 | 1.00 | 41.59 | C |
| ATOM | 4582 | O | PHE | C | 46 | 68.364 | -1.527 | 54.582 | 1.00 | 41.70 | O |
| ATOM | 4583 | N | HIS | C | 47 | 66.826 | -0.439 | 55.822 | 1.00 | 41.13 | N |
| ATOM | 4584 | CA | HIS | C | 47 | 67.067 | 0.826 | 55.146 | 1.00 | 40.12 | C |
| ATOM | 4585 | CB | HIS | C | 47 | 65.930 | 1.783 | 55.513 | 1.00 | 41.18 | C |
| ATOM | 4586 | CG | HIS | C | 47 | 64.981 | 1.914 | 54.353 | 1.00 | 40.99 | C |
| ATOM | 4587 | ND1 | HIS | C | 47 | 65.386 | 1.946 | 53.060 | 1.00 | 42.76 | N |
| ATOM | 4588 | CE1 | HIS | C | 47 | 64.264 | 2.060 | 52.330 | 1.00 | 45.10 | C |
| ATOM | 4589 | NE2 | HIS | C | 47 | 63.170 | 2.107 | 53.094 | 1.00 | 45.40 | N |
| ATOM | 4590 | CD2 | HIS | C | 47 | 63.586 | 2.019 | 54.382 | 1.00 | 41.11 | C |
| ATOM | 4591 | C | HIS | C | 47 | 68.404 | 1.429 | 55.571 | 1.00 | 37.98 | C |
| ATOM | 4592 | O | HIS | C | 47 | 68.805 | 2.493 | 55.113 | 1.00 | 38.77 | O |
| ATOM | 4593 | N | VAL | C | 48 | 69.168 | 0.774 | 56.438 | 1.00 | 34.01 | N |
| ATOM | 4594 | CA | VAL | C | 48 | 70.449 | 1.297 | 56.851 | 1.00 | 30.45 | C |
| ATOM | 4595 | CB | VAL | C | 48 | 70.567 | 1.225 | 58.381 | 1.00 | 30.15 | C |
| ATOM | 4596 | CG1 | VAL | C | 48 | 72.013 | 1.342 | 58.838 | 1.00 | 26.60 | C |
| ATOM | 4597 | CG2 | VAL | C | 48 | 69.764 | 2.348 | 58.976 | 1.00 | 32.72 | C |
| ATOM | 4598 | C | VAL | C | 48 | 71.628 | 0.591 | 56.226 | 1.00 | 29.26 | C |

FIG. 2A-100

| ATOM | 4599 | O | VAL | C | 48 | 71.817 | -0.577 | 56.460 | 1.00 | 28.47 | O |
| --- | --- | --- | --- | --- | --- | --- | --- | --- | --- | --- | --- |
| ATOM | 4600 | N | LYS | C | 49 | 72.421 | 1.292 | 55.426 | 1.00 | 29.05 | N |
| ATOM | 4601 | CA | LYS | C | 49 | 73.609 | 0.670 | 54.834 | 1.00 | 28.75 | C |
| ATOM | 4602 | CB | LYS | C | 49 | 73.533 | 0.647 | 53.302 | 1.00 | 28.62 | C |
| ATOM | 4603 | CG | LYS | C | 49 | 74.809 | 0.301 | 52.561 | 1.00 | 42.26 | C |
| ATOM | 4604 | CD | LYS | C | 49 | 74.618 | -0.148 | 51.131 | 1.00 | 53.99 | C |
| ATOM | 4605 | CE | LYS | C | 49 | 75.897 | -0.156 | 50.324 | 1.00 | 52.81 | C |
| ATOM | 4606 | NZ | LYS | C | 49 | 75.611 | 0.064 | 48.850 | 1.00 | 56.37 | N |
| ATOM | 4607 | C | LYS | C | 49 | 74.905 | 1.392 | 55.255 | 1.00 | 26.23 | C |
| ATOM | 4608 | O | LYS | C | 49 | 74.897 | 2.552 | 55.652 | 1.00 | 28.02 | O |
| ATOM | 4609 | N | SER | C | 50 | 76.031 | 0.708 | 55.141 | 1.00 | 22.78 | N |
| ATOM | 4610 | CA | SER | C | 50 | 77.303 | 1.281 | 55.528 | 1.00 | 20.71 | C |
| ATOM | 4611 | CB | SER | C | 50 | 78.360 | 0.222 | 55.599 | 1.00 | 19.50 | C |
| ATOM | 4612 | OG | SER | C | 50 | 78.834 | 0.035 | 54.301 | 1.00 | 13.40 | O |
| ATOM | 4613 | C | SER | C | 50 | 77.794 | 2.309 | 54.555 | 1.00 | 21.59 | C |
| ATOM | 4614 | O | SER | C | 50 | 77.434 | 2.290 | 53.386 | 1.00 | 22.27 | O |
| ATOM | 4615 | N | GLY | C | 51 | 78.673 | 3.178 | 55.036 | 1.00 | 21.97 | N |
| ATOM | 4616 | CA | GLY | C | 51 | 79.226 | 4.215 | 54.199 | 1.00 | 22.42 | C |
| ATOM | 4617 | C | GLY | C | 51 | 80.455 | 3.730 | 53.476 | 1.00 | 23.44 | C |
| ATOM | 4618 | O | GLY | C | 51 | 80.907 | 2.606 | 53.653 | 1.00 | 25.52 | O |
| ATOM | 4619 | N | LEU | C | 52 | 81.001 | 4.586 | 52.635 | 1.00 | 25.71 | N |
| ATOM | 4620 | CA | LEU | C | 52 | 82.186 | 4.233 | 51.891 | 1.00 | 26.16 | C |
| ATOM | 4621 | CB | LEU | C | 52 | 82.228 | 5.045 | 50.604 | 1.00 | 25.89 | C |
| ATOM | 4622 | CG | LEU | C | 52 | 83.414 | 4.652 | 49.720 | 1.00 | 32.29 | C |
| ATOM | 4623 | CD1 | LEU | C | 52 | 83.419 | 3.127 | 49.554 | 1.00 | 33.21 | C |
| ATOM | 4624 | CD2 | LEU | C | 52 | 83.338 | 5.382 | 48.385 | 1.00 | 32.87 | C |
| ATOM | 4625 | C | LEU | C | 52 | 83.397 | 4.531 | 52.767 | 1.00 | 26.58 | C |
| ATOM | 4626 | O | LEU | C | 52 | 83.424 | 5.512 | 53.474 | 1.00 | 27.43 | O |
| ATOM | 4627 | N | GLN | C | 53 | 84.388 | 3.662 | 52.751 | 1.00 | 27.96 | N |
| ATOM | 4628 | CA | GLN | C | 53 | 85.568 | 3.880 | 53.533 | 1.00 | 26.63 | C |
| ATOM | 4629 | CB | GLN | C | 53 | 85.765 | 2.791 | 54.559 | 1.00 | 24.58 | C |
| ATOM | 4630 | CG | GLN | C | 53 | 87.029 | 2.940 | 55.424 | 1.00 | 31.70 | C |
| ATOM | 4631 | CD | GLN | C | 53 | 87.209 | 4.335 | 56.109 | 1.00 | 39.41 | C |
| ATOM | 4632 | OE1 | GLN | C | 53 | 86.300 | 4.873 | 56.784 | 1.00 | 41.30 | O |
| ATOM | 4633 | NE2 | GLN | C | 53 | 88.399 | 4.905 | 55.944 | 1.00 | 36.43 | N |
| ATOM | 4634 | C | GLN | C | 53 | 86.714 | 3.846 | 52.581 | 1.00 | 27.39 | C |
| ATOM | 4635 | O | GLN | C | 53 | 87.283 | 2.795 | 52.352 | 1.00 | 30.34 | O |
| ATOM | 4636 | N | ILE | C | 54 | 87.062 | 4.993 | 52.013 | 1.00 | 26.62 | N |
| ATOM | 4637 | CA | ILE | C | 54 | 88.188 | 5.055 | 51.099 | 1.00 | 23.94 | C |
| ATOM | 4638 | CB | ILE | C | 54 | 88.479 | 6.472 | 50.736 | 1.00 | 24.60 | C |
| ATOM | 4639 | CG1 | ILE | C | 54 | 87.276 | 7.057 | 50.010 | 1.00 | 22.86 | C |
| ATOM | 4640 | CD1 | ILE | C | 54 | 87.633 | 8.061 | 48.960 | 1.00 | 26.15 | C |
| ATOM | 4641 | CG2 | ILE | C | 54 | 89.799 | 6.519 | 50.013 | 1.00 | 23.57 | C |
| ATOM | 4642 | C | ILE | C | 54 | 89.491 | 4.470 | 51.671 | 1.00 | 22.90 | C |
| ATOM | 4643 | O | ILE | C | 54 | 89.883 | 4.805 | 52.756 | 1.00 | 21.92 | O |
| ATOM | 4644 | N | LYS | C | 55 | 90.161 | 3.605 | 50.925 | 1.00 | 23.63 | N |

FIG. 2A-101

| ATOM | 4645 | CA  | LYS | C | 55 | 91.418  | 3.012  | 51.362 | 1.00 | 21.93 | C |
| ---- | ---- | --- | --- | - | -- | ------- | ------ | ------ | ---- | ----- | - |
| ATOM | 4646 | CB  | LYS | C | 55 | 91.526  | 1.589  | 50.851 | 1.00 | 21.06 | C |
| ATOM | 4647 | CG  | LYS | C | 55 | 90.415  | 0.760  | 51.343 | 1.00 | 22.39 | C |
| ATOM | 4648 | CD  | LYS | C | 55 | 90.454  | -0.665 | 50.834 | 1.00 | 25.94 | C |
| ATOM | 4649 | CE  | LYS | C | 55 | 89.398  | -1.441 | 51.616 | 1.00 | 30.75 | C |
| ATOM | 4650 | NZ  | LYS | C | 55 | 89.062  | -2.746 | 51.031 | 1.00 | 36.46 | N |
| ATOM | 4651 | C   | LYS | C | 55 | 92.595  | 3.812  | 50.867 | 1.00 | 21.44 | C |
| ATOM | 4652 | O   | LYS | C | 55 | 92.535  | 4.387  | 49.790 | 1.00 | 21.14 | O |
| ATOM | 4653 | N   | LYS | C | 56 | 93.680  | 3.849  | 51.644 | 1.00 | 21.63 | N |
| ATOM | 4654 | CA  | LYS | C | 56 | 94.831  | 4.620  | 51.193 | 1.00 | 21.59 | C |
| ATOM | 4655 | CB  | LYS | C | 56 | 95.275  | 5.670  | 52.216 | 1.00 | 22.20 | C |
| ATOM | 4656 | CG  | LYS | C | 56 | 94.194  | 6.209  | 53.085 | 1.00 | 26.07 | C |
| ATOM | 4657 | CD  | LYS | C | 56 | 92.989  | 6.618  | 52.289 | 1.00 | 28.51 | C |
| ATOM | 4658 | CE  | LYS | C | 56 | 92.453  | 7.891  | 52.862 | 1.00 | 34.20 | C |
| ATOM | 4659 | NZ  | LYS | C | 56 | 93.468  | 8.974  | 52.621 | 1.00 | 41.19 | N |
| ATOM | 4660 | C   | LYS | C | 56 | 96.003  | 3.734  | 50.874 | 1.00 | 19.87 | C |
| ATOM | 4661 | O   | LYS | C | 56 | 96.937  | 4.165  | 50.223 | 1.00 | 22.33 | O |
| ATOM | 4662 | N   | ASN | C | 57 | 95.974  | 2.496  | 51.315 | 1.00 | 16.40 | N |
| ATOM | 4663 | CA  | ASN | C | 57 | 97.077  | 1.627  | 50.994 | 1.00 | 14.60 | C |
| ATOM | 4664 | CB  | ASN | C | 57 | 96.839  | 0.260  | 51.561 | 1.00 | 13.93 | C |
| ATOM | 4665 | CG  | ASN | C | 57 | 95.611  | -0.366 | 51.023 | 1.00 | 17.12 | C |
| ATOM | 4666 | OD1 | ASN | C | 57 | 95.679  | -1.279 | 50.209 | 1.00 | 26.11 | O |
| ATOM | 4667 | ND2 | ASN | C | 57 | 94.465  | 0.115  | 51.467 | 1.00 | 25.47 | N |
| ATOM | 4668 | C   | ASN | C | 57 | 97.198  | 1.516  | 49.503 | 1.00 | 13.41 | C |
| ATOM | 4669 | O   | ASN | C | 57 | 96.216  | 1.651  | 48.779 | 1.00 | 11.36 | O |
| ATOM | 4670 | N   | ALA | C | 58 | 98.403  | 1.262  | 49.023 | 1.00 | 13.15 | N |
| ATOM | 4671 | CA  | ALA | C | 58 | 98.591  | 1.125  | 47.593 | 1.00 | 14.07 | C |
| ATOM | 4672 | CB  | ALA | C | 58 | 100.008 | 0.777  | 47.312 | 1.00 | 13.79 | C |
| ATOM | 4673 | C   | ALA | C | 58 | 97.655  | 0.027  | 47.053 | 1.00 | 15.47 | C |
| ATOM | 4674 | O   | ALA | C | 58 | 97.633  | -1.084 | 47.554 | 1.00 | 15.29 | O |
| ATOM | 4675 | N   | ILE | C | 59 | 96.876  | 0.340  | 46.036 | 1.00 | 17.68 | N |
| ATOM | 4676 | CA  | ILE | C | 59 | 95.955  | -0.636 | 45.492 | 1.00 | 18.73 | C |
| ATOM | 4677 | CB  | ILE | C | 59 | 95.152  | -0.054 | 44.340 | 1.00 | 19.94 | C |
| ATOM | 4678 | CG1 | ILE | C | 59 | 94.110  | -1.057 | 43.879 | 1.00 | 18.52 | C |
| ATOM | 4679 | CD1 | ILE | C | 59 | 92.989  | -0.419 | 43.118 | 1.00 | 18.64 | C |
| ATOM | 4680 | CG2 | ILE | C | 59 | 96.069  | 0.284  | 43.210 | 1.00 | 17.41 | C |
| ATOM | 4681 | C   | ILE | C | 59 | 96.687  | -1.872 | 44.979 | 1.00 | 19.51 | C |
| ATOM | 4682 | O   | ILE | C | 59 | 96.170  | -2.992 | 45.066 | 1.00 | 22.14 | O |
| ATOM | 4683 | N   | ILE | C | 60 | 97.895  | -1.682 | 44.455 | 1.00 | 20.82 | N |
| ATOM | 4684 | CA  | ILE | C | 60 | 98.618  | -2.833 | 43.938 | 1.00 | 20.48 | C |
| ATOM | 4685 | CB  | ILE | C | 60 | 99.936  | -2.452 | 43.238 | 1.00 | 20.32 | C |
| ATOM | 4686 | CG1 | ILE | C | 60 | 100.910 | -1.892 | 44.259 | 1.00 | 21.31 | C |
| ATOM | 4687 | CD1 | ILE | C | 60 | 102.022 | -1.146 | 43.626 | 1.00 | 20.56 | C |
| ATOM | 4688 | CG2 | ILE | C | 60 | 99.670  | -1.481 | 42.102 | 1.00 | 14.31 | C |
| ATOM | 4689 | C   | ILE | C | 60 | 98.887  | -3.863 | 45.020 | 1.00 | 20.68 | C |
| ATOM | 4690 | O   | ILE | C | 60 | 99.264  | -4.963 | 44.691 | 1.00 | 21.83 | O |

FIG. 2A-102

| ATOM | 4691 | N   | ASP | C | 61 | 98.710  | -3.531 | 46.295 | 1.00 | 22.05 | N |
|------|------|-----|-----|---|----|---------|--------|--------|------|-------|---|
| ATOM | 4692 | CA  | ASP | C | 61 | 98.868  | -4.538 | 47.364 | 1.00 | 23.13 | C |
| ATOM | 4693 | CB  | ASP | C | 61 | 98.694  | -3.957 | 48.761 | 1.00 | 24.29 | C |
| ATOM | 4694 | CG  | ASP | C | 61 | 99.873  | -3.151 | 49.241 | 1.00 | 31.46 | C |
| ATOM | 4695 | OD1 | ASP | C | 61 | 99.802  | -2.697 | 50.423 | 1.00 | 37.08 | O |
| ATOM | 4696 | OD2 | ASP | C | 61 | 100.842 | -2.966 | 48.463 | 1.00 | 35.20 | O |
| ATOM | 4697 | C   | ASP | C | 61 | 97.693  | -5.517 | 47.262 | 1.00 | 22.98 | C |
| ATOM | 4698 | O   | ASP | C | 61 | 97.730  | -6.592 | 47.822 | 1.00 | 20.88 | O |
| ATOM | 4699 | N   | ASP | C | 62 | 96.628  | -5.121 | 46.577 | 1.00 | 22.82 | N |
| ATOM | 4700 | CA  | ASP | C | 62 | 95.446  | -5.954 | 46.515 | 1.00 | 24.39 | C |
| ATOM | 4701 | CB  | ASP | C | 62 | 94.255  | -5.165 | 47.045 | 1.00 | 23.92 | C |
| ATOM | 4702 | CG  | ASP | C | 62 | 94.406  | -4.787 | 48.481 | 1.00 | 25.11 | C |
| ATOM | 4703 | OD1 | ASP | C | 62 | 95.214  | -5.446 | 49.175 | 1.00 | 26.27 | O |
| ATOM | 4704 | OD2 | ASP | C | 62 | 93.704  | -3.858 | 48.922 | 1.00 | 24.44 | O |
| ATOM | 4705 | C   | ASP | C | 62 | 95.058  | -6.486 | 45.166 | 1.00 | 26.20 | C |
| ATOM | 4706 | O   | ASP | C | 62 | 94.307  | -7.449 | 45.058 | 1.00 | 28.30 | O |
| ATOM | 4707 | N   | TYR | C | 63 | 95.560  | -5.844 | 44.136 | 1.00 | 26.76 | N |
| ATOM | 4708 | CA  | TYR | C | 63 | 95.183  | -6.198 | 42.793 | 1.00 | 26.06 | C |
| ATOM | 4709 | CB  | TYR | C | 63 | 94.136  | -5.186 | 42.280 | 1.00 | 24.25 | C |
| ATOM | 4710 | CG  | TYR | C | 63 | 92.803  | -5.220 | 42.974 | 1.00 | 24.28 | C |
| ATOM | 4711 | CD1 | TYR | C | 63 | 91.760  | -5.993 | 42.475 | 1.00 | 23.80 | C |
| ATOM | 4712 | CE1 | TYR | C | 63 | 90.540  | -6.011 | 43.095 | 1.00 | 24.44 | C |
| ATOM | 4713 | CZ  | TYR | C | 63 | 90.342  | -5.252 | 44.235 | 1.00 | 26.17 | C |
| ATOM | 4714 | OH  | TYR | C | 63 | 89.137  | -5.278 | 44.887 | 1.00 | 31.44 | O |
| ATOM | 4715 | CE2 | TYR | C | 63 | 91.358  | -4.475 | 44.748 | 1.00 | 25.20 | C |
| ATOM | 4716 | CD2 | TYR | C | 63 | 92.581  | -4.464 | 44.115 | 1.00 | 23.08 | C |
| ATOM | 4717 | C   | TYR | C | 63 | 96.374  | -6.111 | 41.875 | 1.00 | 25.70 | C |
| ATOM | 4718 | O   | TYR | C | 63 | 97.362  | -5.442 | 42.207 | 1.00 | 26.61 | O |
| ATOM | 4719 | N   | LYS | C | 64 | 96.276  | -6.785 | 40.729 | 1.00 | 24.45 | N |
| ATOM | 4720 | CA  | LYS | C | 64 | 97.310  | -6.691 | 39.731 | 1.00 | 24.29 | C |
| ATOM | 4721 | CB  | LYS | C | 64 | 97.617  | -8.030 | 39.067 | 1.00 | 25.94 | C |
| ATOM | 4722 | CG  | LYS | C | 64 | 98.410  | -7.920 | 37.747 | 1.00 | 32.24 | C |
| ATOM | 4723 | CD  | LYS | C | 64 | 99.711  | -7.185 | 37.932 | 1.00 | 44.03 | C |
| ATOM | 4724 | CE  | LYS | C | 64 | 100.654 | -7.365 | 36.739 | 1.00 | 48.39 | C |
| ATOM | 4725 | NZ  | LYS | C | 64 | 100.505 | -6.367 | 35.612 | 1.00 | 53.35 | N |
| ATOM | 4726 | C   | LYS | C | 64 | 96.570  | -5.811 | 38.783 | 1.00 | 23.89 | C |
| ATOM | 4727 | O   | LYS | C | 64 | 95.443  | -6.100 | 38.406 | 1.00 | 24.50 | O |
| ATOM | 4728 | N   | VAL | C | 65 | 97.192  | -4.702 | 38.431 | 1.00 | 23.75 | N |
| ATOM | 4729 | CA  | VAL | C | 65 | 96.581  | -3.739 | 37.532 | 1.00 | 22.43 | C |
| ATOM | 4730 | CB  | VAL | C | 65 | 96.790  | -2.298 | 38.043 | 1.00 | 22.66 | C |
| ATOM | 4731 | CG1 | VAL | C | 65 | 96.134  | -1.312 | 37.083 | 1.00 | 24.26 | C |
| ATOM | 4732 | CG2 | VAL | C | 65 | 96.204  | -2.152 | 39.474 | 1.00 | 20.89 | C |
| ATOM | 4733 | C   | VAL | C | 65 | 97.291  | -3.919 | 36.225 | 1.00 | 22.38 | C |
| ATOM | 4734 | O   | VAL | C | 65 | 98.521  | -3.945 | 36.174 | 1.00 | 22.60 | O |
| ATOM | 4735 | N   | THR | C | 66 | 96.517  | -4.059 | 35.161 | 1.00 | 21.79 | N |
| ATOM | 4736 | CA  | THR | C | 66 | 97.111  | -4.261 | 33.863 | 1.00 | 21.58 | C |

FIG. 2A-103

| | | | | | | | | | | |
|---|---|---|---|---|---|---|---|---|---|---|
| ATOM | 4737 | CB | THR | C | 66 | 96.457 | -5.410 | 33.154 | 1.00 | 20.80 | C |
| ATOM | 4738 | OG1 | THR | C | 66 | 95.308 | -4.927 | 32.469 | 1.00 | 24.25 | O |
| ATOM | 4739 | CG2 | THR | C | 66 | 96.021 | -6.448 | 34.140 | 1.00 | 20.12 | C |
| ATOM | 4740 | C | THR | C | 66 | 96.967 | -3.034 | 33.003 | 1.00 | 21.81 | C |
| ATOM | 4741 | O | THR | C | 66 | 96.368 | -2.052 | 33.397 | 1.00 | 20.43 | O |
| ATOM | 4742 | N | SER | C | 67 | 97.510 | -3.103 | 31.805 | 1.00 | 21.54 | N |
| ATOM | 4743 | CA | SER | C | 67 | 97.420 | -1.987 | 30.903 | 1.00 | 23.96 | C |
| ATOM | 4744 | CB | SER | C | 67 | 98.744 | -1.813 | 30.190 | 1.00 | 25.20 | C |
| ATOM | 4745 | OG | SER | C | 67 | 99.087 | -3.026 | 29.527 | 1.00 | 33.85 | O |
| ATOM | 4746 | C | SER | C | 67 | 96.294 | -2.187 | 29.886 | 1.00 | 24.54 | C |
| ATOM | 4747 | O | SER | C | 67 | 96.185 | -1.451 | 28.919 | 1.00 | 25.24 | O |
| ATOM | 4748 | N | ALA | C | 68 | 95.467 | -3.196 | 30.100 | 1.00 | 25.48 | N |
| ATOM | 4749 | CA | ALA | C | 68 | 94.390 | -3.437 | 29.150 | 1.00 | 25.77 | C |
| ATOM | 4750 | CB | ALA | C | 68 | 93.874 | -4.859 | 29.362 | 1.00 | 25.87 | C |
| ATOM | 4751 | C | ALA | C | 68 | 93.253 | -2.433 | 29.339 | 1.00 | 26.41 | C |
| ATOM | 4752 | O | ALA | C | 68 | 92.420 | -2.547 | 30.228 | 1.00 | 29.25 | O |
| ATOM | 4753 | N | VAL | C | 69 | 93.263 | -1.398 | 28.479 | 1.00 | 26.47 | N |
| ATOM | 4754 | CA | VAL | C | 69 | 92.280 | -0.333 | 28.622 | 1.00 | 25.97 | C |
| ATOM | 4755 | CB | VAL | C | 69 | 92.724 | 0.849 | 27.761 | 1.00 | 25.02 | C |
| ATOM | 4756 | CG1 | VAL | C | 69 | 91.524 | 1.732 | 27.426 | 1.00 | 25.01 | C |
| ATOM | 4757 | CG2 | VAL | C | 69 | 93.754 | 1.674 | 28.507 | 1.00 | 30.01 | C |
| ATOM | 4758 | C | VAL | C | 69 | 90.882 | -0.788 | 28.207 | 1.00 | 25.01 | C |
| ATOM | 4759 | O | VAL | C | 69 | 90.618 | -1.129 | 27.059 | 1.00 | 28.03 | O |
| ATOM | 4760 | N | LEU | C | 70 | 89.976 | -0.826 | 29.202 | 1.00 | 23.98 | N |
| ATOM | 4761 | CA | LEU | C | 70 | 88.602 | -1.203 | 28.906 | 1.00 | 24.51 | C |
| ATOM | 4762 | CB | LEU | C | 70 | 87.860 | -1.398 | 30.230 | 1.00 | 26.07 | C |
| ATOM | 4763 | CG | LEU | C | 70 | 88.307 | -2.661 | 30.974 | 1.00 | 26.57 | C |
| ATOM | 4764 | CD1 | LEU | C | 70 | 87.282 | -3.123 | 32.012 | 1.00 | 30.54 | C |
| ATOM | 4765 | CD2 | LEU | C | 70 | 88.537 | -3.849 | 30.040 | 1.00 | 26.48 | C |
| ATOM | 4766 | C | LEU | C | 70 | 87.903 | -0.132 | 28.066 | 1.00 | 26.01 | C |
| ATOM | 4767 | O | LEU | C | 70 | 87.111 | -0.422 | 27.181 | 1.00 | 28.42 | O |
| ATOM | 4768 | N | GLY | C | 71 | 88.236 | 1.103 | 28.439 | 1.00 | 27.87 | N |
| ATOM | 4769 | CA | GLY | C | 71 | 87.627 | 2.256 | 27.787 | 1.00 | 28.69 | C |
| ATOM | 4770 | C | GLY | C | 71 | 87.852 | 3.578 | 28.477 | 1.00 | 29.65 | C |
| ATOM | 4771 | O | GLY | C | 71 | 88.406 | 3.614 | 29.575 | 1.00 | 30.25 | O |
| ATOM | 4772 | N | LEU | C | 72 | 87.435 | 4.669 | 27.837 | 1.00 | 30.17 | N |
| ATOM | 4773 | CA | LEU | C | 72 | 87.574 | 6.003 | 28.430 | 1.00 | 29.55 | C |
| ATOM | 4774 | CB | LEU | C | 72 | 88.090 | 7.002 | 27.410 | 1.00 | 28.96 | C |
| ATOM | 4775 | CG | LEU | C | 72 | 89.335 | 6.522 | 26.673 | 1.00 | 32.75 | C |
| ATOM | 4776 | CD1 | LEU | C | 72 | 89.830 | 7.636 | 25.740 | 1.00 | 39.57 | C |
| ATOM | 4777 | CD2 | LEU | C | 72 | 90.424 | 6.114 | 27.654 | 1.00 | 37.79 | C |
| ATOM | 4778 | C | LEU | C | 72 | 86.252 | 6.527 | 28.991 | 1.00 | 28.84 | C |
| ATOM | 4779 | O | LEU | C | 72 | 85.366 | 6.904 | 28.245 | 1.00 | 30.32 | O |
| ATOM | 4780 | N | GLY | C | 73 | 86.128 | 6.542 | 30.320 | 1.00 | 28.86 | N |
| ATOM | 4781 | CA | GLY | C | 73 | 84.919 | 7.035 | 30.954 | 1.00 | 28.41 | C |
| ATOM | 4782 | C | GLY | C | 73 | 84.969 | 8.539 | 31.101 | 1.00 | 28.20 | C |

FIG. 2A-104

| ATOM | 4783 | O | GLY | C | 73 | 86.003 | 9.141 | 30.786 | 1.00 | 26.67 | O |
|---|---|---|---|---|---|---|---|---|---|---|---|
| ATOM | 4784 | N | ILE | C | 74 | 83.871 | 9.156 | 31.538 | 1.00 | 28.32 | N |
| ATOM | 4785 | CA | ILE | C | 74 | 83.865 | 10.602 | 31.747 | 1.00 | 28.77 | C |
| ATOM | 4786 | CB | ILE | C | 74 | 82.479 | 11.060 | 32.271 | 1.00 | 29.97 | C |
| ATOM | 4787 | CG1 | ILE | C | 74 | 81.449 | 10.883 | 31.178 | 1.00 | 29.66 | C |
| ATOM | 4788 | CD1 | ILE | C | 74 | 80.027 | 10.986 | 31.712 | 1.00 | 28.19 | C |
| ATOM | 4789 | CG2 | ILE | C | 74 | 82.486 | 12.532 | 32.747 | 1.00 | 24.77 | C |
| ATOM | 4790 | C | ILE | C | 74 | 84.977 | 10.942 | 32.773 | 1.00 | 29.03 | C |
| ATOM | 4791 | O | ILE | C | 74 | 84.997 | 10.436 | 33.905 | 1.00 | 27.43 | O |
| ATOM | 4792 | N | ASN | C | 75 | 85.922 | 11.777 | 32.359 | 1.00 | 29.27 | N |
| ATOM | 4793 | CA | ASN | C | 75 | 87.024 | 12.163 | 33.231 | 1.00 | 30.86 | C |
| ATOM | 4794 | CB | ASN | C | 75 | 86.533 | 12.823 | 34.505 | 1.00 | 30.68 | C |
| ATOM | 4795 | CG | ASN | C | 75 | 85.740 | 14.092 | 34.254 | 1.00 | 34.36 | C |
| ATOM | 4796 | OD1 | ASN | C | 75 | 86.066 | 14.885 | 33.373 | 1.00 | 32.78 | O |
| ATOM | 4797 | ND2 | ASN | C | 75 | 84.700 | 14.305 | 35.053 | 1.00 | 37.29 | N |
| ATOM | 4798 | C | ASN | C | 75 | 87.938 | 11.039 | 33.653 | 1.00 | 31.88 | C |
| ATOM | 4799 | O | ASN | C | 75 | 88.814 | 11.273 | 34.475 | 1.00 | 34.18 | O |
| ATOM | 4800 | N | GLY | C | 76 | 87.783 | 9.826 | 33.131 | 1.00 | 32.80 | N |
| ATOM | 4801 | CA | GLY | C | 76 | 88.684 | 8.770 | 33.566 | 1.00 | 30.30 | C |
| ATOM | 4802 | C | GLY | C | 76 | 88.774 | 7.545 | 32.685 | 1.00 | 30.08 | C |
| ATOM | 4803 | O | GLY | C | 76 | 87.790 | 7.141 | 32.070 | 1.00 | 32.04 | O |
| ATOM | 4804 | N | ALA | C | 77 | 89.969 | 6.959 | 32.626 | 1.00 | 28.37 | N |
| ATOM | 4805 | CA | ALA | C | 77 | 90.222 | 5.754 | 31.859 | 1.00 | 26.97 | C |
| ATOM | 4806 | CB | ALA | C | 77 | 91.724 | 5.608 | 31.573 | 1.00 | 25.35 | C |
| ATOM | 4807 | C | ALA | C | 77 | 89.752 | 4.556 | 32.696 | 1.00 | 26.86 | C |
| ATOM | 4808 | O | ALA | C | 77 | 89.831 | 4.591 | 33.930 | 1.00 | 26.52 | O |
| ATOM | 4809 | N | VAL | C | 78 | 89.267 | 3.499 | 32.043 | 1.00 | 24.10 | N |
| ATOM | 4810 | CA | VAL | C | 78 | 88.868 | 2.346 | 32.804 | 1.00 | 22.82 | C |
| ATOM | 4811 | CB | VAL | C | 78 | 87.435 | 2.026 | 32.564 | 1.00 | 23.45 | C |
| ATOM | 4812 | CG1 | VAL | C | 78 | 87.032 | 0.821 | 33.407 | 1.00 | 20.47 | C |
| ATOM | 4813 | CG2 | VAL | C | 78 | 86.596 | 3.281 | 32.870 | 1.00 | 20.40 | C |
| ATOM | 4814 | C | VAL | C | 78 | 89.738 | 1.153 | 32.472 | 1.00 | 23.83 | C |
| ATOM | 4815 | O | VAL | C | 78 | 89.746 | 0.653 | 31.379 | 1.00 | 24.08 | O |
| ATOM | 4816 | N | LEU | C | 79 | 90.502 | 0.711 | 33.438 | 1.00 | 24.50 | N |
| ATOM | 4817 | CA | LEU | C | 79 | 91.386 | -0.407 | 33.240 | 1.00 | 25.79 | C |
| ATOM | 4818 | CB | LEU | C | 79 | 92.722 | -0.136 | 33.955 | 1.00 | 24.89 | C |
| ATOM | 4819 | CG | LEU | C | 79 | 93.664 | 0.989 | 33.545 | 1.00 | 22.27 | C |
| ATOM | 4820 | CD1 | LEU | C | 79 | 94.802 | 1.028 | 34.496 | 1.00 | 18.78 | C |
| ATOM | 4821 | CD2 | LEU | C | 79 | 94.126 | 0.788 | 32.128 | 1.00 | 26.29 | C |
| ATOM | 4822 | C | LEU | C | 79 | 90.791 | -1.704 | 33.789 | 1.00 | 27.47 | C |
| ATOM | 4823 | O | LEU | C | 79 | 89.862 | -1.694 | 34.586 | 1.00 | 29.21 | O |
| ATOM | 4824 | N | GLN | C | 80 | 91.370 | -2.820 | 33.361 | 1.00 | 27.65 | N |
| ATOM | 4825 | CA | GLN | C | 80 | 90.966 | -4.138 | 33.803 | 1.00 | 27.68 | C |
| ATOM | 4826 | CB | GLN | C | 80 | 90.947 | -5.097 | 32.618 | 1.00 | 28.28 | C |
| ATOM | 4827 | CG | GLN | C | 80 | 90.752 | -6.545 | 33.026 | 1.00 | 33.97 | C |
| ATOM | 4828 | CD | GLN | C | 80 | 90.217 | -7.389 | 31.896 | 1.00 | 48.37 | C |

FIG. 2A-105

| ATOM | 4829 | OE1 | GLN | C | 80 | 89.238 | -8.143 | 32.074 | 1.00 | 55.64 | O |
| --- | --- | --- | --- | --- | --- | --- | --- | --- | --- | --- | --- |
| ATOM | 4830 | NE2 | GLN | C | 80 | 90.844 | -7.274 | 30.713 | 1.00 | 46.74 | N |
| ATOM | 4831 | C | GLN | C | 80 | 91.954 | -4.640 | 34.847 | 1.00 | 26.45 | C |
| ATOM | 4832 | O | GLN | C | 80 | 93.144 | -4.718 | 34.579 | 1.00 | 26.09 | O |
| ATOM | 4833 | N | ILE | C | 81 | 91.481 | -4.977 | 36.039 | 1.00 | 24.77 | N |
| ATOM | 4834 | CA | ILE | C | 81 | 92.400 | -5.473 | 37.053 | 1.00 | 22.99 | C |
| ATOM | 4835 | CB | ILE | C | 81 | 92.517 | -4.507 | 38.282 | 1.00 | 24.23 | C |
| ATOM | 4836 | CG1 | ILE | C | 81 | 91.150 | -4.288 | 38.909 | 1.00 | 20.59 | C |
| ATOM | 4837 | CD1 | ILE | C | 81 | 91.244 | -3.564 | 40.178 | 1.00 | 23.58 | C |
| ATOM | 4838 | CG2 | ILE | C | 81 | 93.174 | -3.174 | 37.870 | 1.00 | 23.41 | C |
| ATOM | 4839 | C | ILE | C | 81 | 92.014 | -6.848 | 37.557 | 1.00 | 22.73 | C |
| ATOM | 4840 | O | ILE | C | 81 | 90.908 | -7.325 | 37.309 | 1.00 | 24.00 | O |
| ATOM | 4841 | N | PHE | C | 82 | 92.935 | -7.462 | 38.293 | 1.00 | 22.42 | N |
| ATOM | 4842 | CA | PHE | C | 82 | 92.756 | -8.803 | 38.834 | 1.00 | 23.53 | C |
| ATOM | 4843 | CB | PHE | C | 82 | 93.690 | -9.799 | 38.131 | 1.00 | 22.70 | C |
| ATOM | 4844 | CG | PHE | C | 82 | 93.484 | -9.865 | 36.660 | 1.00 | 23.73 | C |
| ATOM | 4845 | CD1 | PHE | C | 82 | 92.422 | -10.552 | 36.135 | 1.00 | 28.63 | C |
| ATOM | 4846 | CE1 | PHE | C | 82 | 92.189 | -10.539 | 34.775 | 1.00 | 32.13 | C |
| ATOM | 4847 | CZ | PHE | C | 82 | 93.023 | -9.836 | 33.945 | 1.00 | 32.09 | C |
| ATOM | 4848 | CE2 | PHE | C | 82 | 94.086 | -9.153 | 34.474 | 1.00 | 28.54 | C |
| ATOM | 4849 | CD2 | PHE | C | 82 | 94.307 | -9.175 | 35.809 | 1.00 | 25.73 | C |
| ATOM | 4850 | C | PHE | C | 82 | 93.074 | -8.794 | 40.300 | 1.00 | 24.80 | C |
| ATOM | 4851 | O | PHE | C | 82 | 94.102 | -8.225 | 40.713 | 1.00 | 22.82 | O |
| ATOM | 4852 | N | ASN | C | 83 | 92.203 | -9.442 | 41.072 | 1.00 | 27.55 | N |
| ATOM | 4853 | CA | ASN | C | 83 | 92.356 | -9.533 | 42.510 | 1.00 | 29.32 | C |
| ATOM | 4854 | CB | ASN | C | 83 | 91.032 | -9.932 | 43.134 | 1.00 | 30.16 | C |
| ATOM | 4855 | CG | ASN | C | 83 | 91.131 | -10.093 | 44.643 | 1.00 | 32.02 | C |
| ATOM | 4856 | OD1 | ASN | C | 83 | 91.835 | -10.979 | 45.146 | 1.00 | 29.40 | O |
| ATOM | 4857 | ND2 | ASN | C | 83 | 90.431 | -9.223 | 45.379 | 1.00 | 35.15 | N |
| ATOM | 4858 | C | ASN | C | 83 | 93.417 | -10.554 | 42.918 | 1.00 | 29.58 | C |
| ATOM | 4859 | O | ASN | C | 83 | 93.133 | -11.733 | 43.023 | 1.00 | 29.53 | O |
| ATOM | 4860 | N | LYS | C | 84 | 94.631 | -10.098 | 43.175 | 1.00 | 30.97 | N |
| ATOM | 4861 | CA | LYS | C | 84 | 95.721 | -10.987 | 43.567 | 1.00 | 31.50 | C |
| ATOM | 4862 | CB | LYS | C | 84 | 96.809 | -10.183 | 44.271 | 1.00 | 31.52 | C |
| ATOM | 4863 | CG | LYS | C | 84 | 97.522 | -9.238 | 43.336 | 1.00 | 32.32 | C |
| ATOM | 4864 | CD | LYS | C | 84 | 98.746 | -8.634 | 43.989 | 1.00 | 37.13 | C |
| ATOM | 4865 | CE | LYS | C | 84 | 99.527 | -7.850 | 42.964 | 1.00 | 40.48 | C |
| ATOM | 4866 | NZ | LYS | C | 84 | 100.709 | -7.174 | 43.560 | 1.00 | 41.75 | N |
| ATOM | 4867 | C | LYS | C | 84 | 95.372 | -12.217 | 44.409 | 1.00 | 32.44 | C |
| ATOM | 4868 | O | LYS | C | 84 | 95.877 | -13.304 | 44.153 | 1.00 | 32.74 | O |
| ATOM | 4869 | N | ARG | C | 85 | 94.517 | -12.075 | 45.403 | 1.00 | 34.14 | N |
| ATOM | 4870 | CA | ARG | C | 85 | 94.192 | -13.226 | 46.214 | 1.00 | 36.18 | C |
| ATOM | 4871 | CB | ARG | C | 85 | 93.517 | -12.783 | 47.501 | 1.00 | 37.86 | C |
| ATOM | 4872 | CG | ARG | C | 85 | 93.073 | -13.932 | 48.398 | 1.00 | 44.56 | C |
| ATOM | 4873 | CD | ARG | C | 85 | 92.335 | -13.424 | 49.645 | 1.00 | 53.35 | C |
| ATOM | 4874 | NE | ARG | C | 85 | 91.017 | -12.894 | 49.299 | 1.00 | 59.58 | N |

FIG. 2A-106

| ATOM | 4875 | CZ | ARG | C | 85 | 89.879 | -13.553 | 49.481 | 1.00 | 61.55 | C |
|---|---|---|---|---|---|---|---|---|---|---|---|
| ATOM | 4876 | NH1AR | G | C | 85 | 89.898 | -14.774 | 50.016 | 1.00 | 57.70 | N |
| ATOM | 4877 | NH2AR | G | C | 85 | 88.721 | -12.996 | 49.121 | 1.00 | 63.68 | N |
| ATOM | 4878 | C | ARG | C | 85 | 93.295 | -14.237 | 45.517 | 1.00 | 35.69 | C |
| ATOM | 4879 | O | ARG | C | 85 | 93.654 | -15.401 | 45.401 | 1.00 | 36.07 | O |
| ATOM | 4880 | N | THR | C | 86 | 92.129 | -13.783 | 45.059 | 1.00 | 35.64 | N |
| ATOM | 4881 | CA | THR | C | 86 | 91.129 | -14.630 | 44.395 | 1.00 | 35.77 | C |
| ATOM | 4882 | CB | THR | C | 86 | 89.726 | -14.125 | 44.669 | 1.00 | 36.03 | C |
| ATOM | 4883 | OG1 | THR | C | 86 | 89.518 | -12.910 | 43.929 | 1.00 | 36.55 | O |
| ATOM | 4884 | CG2 | THR | C | 86 | 89.535 | -13.867 | 46.167 | 1.00 | 38.26 | C |
| ATOM | 4885 | C | THR | C | 86 | 91.245 | -14.728 | 42.884 | 1.00 | 35.94 | C |
| ATOM | 4886 | O | THR | C | 86 | 90.579 | -15.558 | 42.265 | 1.00 | 36.33 | O |
| ATOM | 4887 | N | GLN | C | 87 | 92.037 | -13.856 | 42.275 | 1.00 | 36.79 | N |
| ATOM | 4888 | CA | GLN | C | 87 | 92.228 | -13.911 | 40.829 | 1.00 | 36.23 | C |
| ATOM | 4889 | CB | GLN | C | 87 | 92.488 | -15.360 | 40.435 | 1.00 | 36.18 | C |
| ATOM | 4890 | CG | GLN | C | 87 | 93.342 | -15.505 | 39.206 | 1.00 | 42.92 | C |
| ATOM | 4891 | CD | GLN | C | 87 | 94.786 | -15.536 | 39.573 | 1.00 | 48.54 | C |
| ATOM | 4892 | OE1 | GLN | C | 87 | 95.662 | -15.503 | 38.711 | 1.00 | 48.90 | O |
| ATOM | 4893 | NE2 | GLN | C | 87 | 95.054 | -15.604 | 40.877 | 1.00 | 50.74 | N |
| ATOM | 4894 | C | GLN | C | 87 | 91.103 | -13.354 | 39.919 | 1.00 | 35.13 | C |
| ATOM | 4895 | O | GLN | C | 87 | 91.259 | -13.344 | 38.689 | 1.00 | 34.18 | O |
| ATOM | 4896 | N | GLU | C | 88 | 89.990 | -12.890 | 40.501 | 1.00 | 34.31 | N |
| ATOM | 4897 | CA | GLU | C | 88 | 88.878 | -12.374 | 39.699 | 1.00 | 35.07 | C |
| ATOM | 4898 | CB | GLU | C | 88 | 87.682 | -11.998 | 40.552 | 1.00 | 35.82 | C |
| ATOM | 4899 | CG | GLU | C | 88 | 87.423 | -12.838 | 41.753 | 1.00 | 41.93 | C |
| ATOM | 4900 | CD | GLU | C | 88 | 86.202 | -12.318 | 42.485 | 1.00 | 49.03 | C |
| ATOM | 4901 | OE1 | GLU | C | 88 | 86.166 | -12.388 | 43.740 | 1.00 | 52.51 | O |
| ATOM | 4902 | OE2 | GLU | C | 88 | 85.271 | -11.839 | 41.792 | 1.00 | 46.41 | O |
| ATOM | 4903 | C | GLU | C | 88 | 89.200 | -11.149 | 38.862 | 1.00 | 33.44 | C |
| ATOM | 4904 | O | GLU | C | 88 | 90.169 | -10.437 | 39.117 | 1.00 | 33.56 | O |
| ATOM | 4905 | N | LYS | C | 89 | 88.356 | -10.908 | 37.865 | 1.00 | 32.52 | N |
| ATOM | 4906 | CA | LYS | C | 89 | 88.513 | -9.771 | 36.974 | 1.00 | 30.71 | C |
| ATOM | 4907 | CB | LYS | C | 89 | 87.922 | -10.066 | 35.586 | 1.00 | 31.11 | C |
| ATOM | 4908 | CG | LYS | C | 89 | 88.870 | -10.749 | 34.603 | 1.00 | 36.10 | C |
| ATOM | 4909 | CD | LYS | C | 89 | 88.205 | -11.886 | 33.780 | 1.00 | 42.40 | C |
| ATOM | 4910 | CE | LYS | C | 89 | 89.222 | -12.514 | 32.777 | 1.00 | 43.44 | C |
| ATOM | 4911 | NZ | LYS | C | 89 | 88.978 | -13.959 | 32.430 | 1.00 | 36.83 | N |
| ATOM | 4912 | C | LYS | C | 89 | 87.735 | -8.641 | 37.596 | 1.00 | 29.42 | C |
| ATOM | 4913 | O | LYS | C | 89 | 86.639 | -8.855 | 38.135 | 1.00 | 28.24 | O |
| ATOM | 4914 | N | PHE | C | 90 | 88.306 | -7.441 | 37.552 | 1.00 | 27.45 | N |
| ATOM | 4915 | CA | PHE | C | 90 | 87.616 | -6.289 | 38.093 | 1.00 | 26.10 | C |
| ATOM | 4916 | CB | PHE | C | 90 | 88.046 | -6.035 | 39.533 | 1.00 | 25.28 | C |
| ATOM | 4917 | CG | PHE | C | 90 | 87.301 | -6.862 | 40.558 | 1.00 | 20.29 | C |
| ATOM | 4918 | CD1 | PHE | C | 90 | 87.885 | -7.963 | 41.132 | 1.00 | 16.72 | C |
| ATOM | 4919 | CE1 | PHE | C | 90 | 87.245 | -8.684 | 42.126 | 1.00 | 17.91 | C |
| ATOM | 4920 | CZ | PHE | C | 90 | 86.009 | -8.302 | 42.548 | 1.00 | 19.15 | C |

FIG. 2A-107

| ATOM | 4921 | CE2 | PHE | C | 90 | 85.399 | -7.188 | 41.968 | 1.00 | 17.58 | C |
|---|---|---|---|---|---|---|---|---|---|---|---|
| ATOM | 4922 | CD2 | PHE | C | 90 | 86.048 | -6.483 | 40.983 | 1.00 | 17.79 | C |
| ATOM | 4923 | C | PHE | C | 90 | 87.898 | -5.090 | 37.232 | 1.00 | 26.01 | C |
| ATOM | 4924 | O | PHE | C | 90 | 88.961 | -5.012 | 36.600 | 1.00 | 26.35 | O |
| ATOM | 4925 | N | ALA | C | 91 | 86.943 | -4.163 | 37.170 | 1.00 | 24.06 | N |
| ATOM | 4926 | CA | ALA | C | 91 | 87.155 | -2.971 | 36.366 | 1.00 | 23.07 | C |
| ATOM | 4927 | CB | ALA | C | 91 | 85.872 | -2.533 | 35.697 | 1.00 | 21.45 | C |
| ATOM | 4928 | C | ALA | C | 91 | 87.696 | -1.864 | 37.267 | 1.00 | 24.49 | C |
| ATOM | 4929 | O | ALA | C | 91 | 87.461 | -1.845 | 38.474 | 1.00 | 25.39 | O |
| ATOM | 4930 | N | LEU | C | 92 | 88.427 | -0.936 | 36.672 | 1.00 | 23.64 | N |
| ATOM | 4931 | CA | LEU | C | 92 | 88.999 | 0.129 | 37.438 | 1.00 | 22.74 | C |
| ATOM | 4932 | CB | LEU | C | 92 | 90.421 | -0.237 | 37.790 | 1.00 | 20.96 | C |
| ATOM | 4933 | CG | LEU | C | 92 | 91.129 | 0.871 | 38.545 | 1.00 | 22.22 | C |
| ATOM | 4934 | CD1 | LEU | C | 92 | 90.539 | 0.932 | 39.955 | 1.00 | 19.16 | C |
| ATOM | 4935 | CD2 | LEU | C | 92 | 92.662 | 0.646 | 38.548 | 1.00 | 20.48 | C |
| ATOM | 4936 | C | LEU | C | 92 | 88.993 | 1.463 | 36.735 | 1.00 | 23.69 | C |
| ATOM | 4937 | O | LEU | C | 92 | 89.608 | 1.606 | 35.696 | 1.00 | 26.01 | O |
| ATOM | 4938 | N | LYS | C | 93 | 88.287 | 2.444 | 37.295 | 1.00 | 23.10 | N |
| ATOM | 4939 | CA | LYS | C | 93 | 88.281 | 3.796 | 36.738 | 1.00 | 23.77 | C |
| ATOM | 4940 | CB | LYS | C | 93 | 86.917 | 4.443 | 36.868 | 1.00 | 23.28 | C |
| ATOM | 4941 | CG | LYS | C | 93 | 86.835 | 5.788 | 36.206 | 1.00 | 24.70 | C |
| ATOM | 4942 | CD | LYS | C | 93 | 85.442 | 6.330 | 36.384 | 1.00 | 27.24 | C |
| ATOM | 4943 | CE | LYS | C | 93 | 85.197 | 7.518 | 35.458 | 1.00 | 28.35 | C |
| ATOM | 4944 | NZ | LYS | C | 93 | 83.816 | 8.093 | 35.610 | 1.00 | 30.17 | N |
| ATOM | 4945 | C | LYS | C | 93 | 89.271 | 4.618 | 37.559 | 1.00 | 25.00 | C |
| ATOM | 4946 | O | LYS | C | 93 | 89.240 | 4.616 | 38.800 | 1.00 | 24.23 | O |
| ATOM | 4947 | N | MSEC | | 94 | 90.152 | 5.315 | 36.865 | 1.00 | 26.03 | N |
| ATOM | 4948 | CA | MSEC | | 94 | 91.150 | 6.145 | 37.494 | 1.00 | 26.38 | C |
| ATOM | 4949 | CB | MSEC | | 94 | 92.471 | 5.938 | 36.821 | 1.00 | 27.18 | C |
| ATOM | 4950 | CG | MSEC | | 94 | 92.890 | 4.491 | 36.813 | 1.00 | 33.00 | C |
| ATOM | 4951 | SE | MSEC | | 94 | 94.739 | 4.361 | 36.296 | 1.00 | 49.41 | S |
| ATOM | 4952 | CE | MSEC | | 94 | 95.456 | 5.450 | 37.765 | 1.00 | 40.00 | C |
| ATOM | 4953 | C | MSEC | | 94 | 90.749 | 7.578 | 37.327 | 1.00 | 26.46 | C |
| ATOM | 4954 | O | MSEC | | 94 | 90.693 | 8.054 | 36.212 | 1.00 | 27.43 | O |
| ATOM | 4955 | N | LEU | C | 95 | 90.461 | 8.261 | 38.430 | 1.00 | 26.35 | N |
| ATOM | 4956 | CA | LEU | C | 95 | 90.074 | 9.670 | 38.410 | 1.00 | 24.90 | C |
| ATOM | 4957 | CB | LEU | C | 95 | 88.752 | 9.887 | 39.150 | 1.00 | 24.05 | C |
| ATOM | 4958 | CG | LEU | C | 95 | 87.460 | 9.221 | 38.711 | 1.00 | 23.40 | C |
| ATOM | 4959 | CD1 | LEU | C | 95 | 86.414 | 9.409 | 39.746 | 1.00 | 28.79 | C |
| ATOM | 4960 | CD2 | LEU | C | 95 | 87.004 | 9.817 | 37.428 | 1.00 | 22.88 | C |
| ATOM | 4961 | C | LEU | C | 95 | 91.120 | 10.491 | 39.146 | 1.00 | 25.68 | C |
| ATOM | 4962 | O | LEU | C | 95 | 91.690 | 10.033 | 40.130 | 1.00 | 25.83 | O |
| ATOM | 4963 | N | ALA | C | 96 | 91.372 | 11.715 | 38.696 | 1.00 | 27.72 | N |
| ATOM | 4964 | CA | ALA | C | 96 | 92.308 | 12.575 | 39.419 | 1.00 | 27.12 | C |
| ATOM | 4965 | CB | ALA | C | 96 | 92.641 | 13.812 | 38.574 | 1.00 | 26.61 | C |
| ATOM | 4966 | C | ALA | C | 96 | 91.575 | 13.001 | 40.712 | 1.00 | 27.55 | C |

FIG. 2A-108

| ATOM | 4967 | O | ALA | C | 96 | 90.381 | 13.314 | 40.668 | 1.00 | 28.91 | O |
|---|---|---|---|---|---|---|---|---|---|---|---|
| ATOM | 4968 | N | ASP | C | 97 | 92.242 | 13.010 | 41.860 | 1.00 | 27.68 | N |
| ATOM | 4969 | CA | ASP | C | 97 | 91.527 | 13.452 | 43.065 | 1.00 | 27.75 | C |
| ATOM | 4970 | CB | ASP | C | 97 | 92.400 | 13.366 | 44.307 | 1.00 | 27.14 | C |
| ATOM | 4971 | CG | ASP | C | 97 | 91.582 | 13.151 | 45.564 | 1.00 | 32.28 | C |
| ATOM | 4972 | OD1 | ASP | C | 97 | 90.415 | 13.594 | 45.582 | 1.00 | 34.48 | O |
| ATOM | 4973 | OD2 | ASP | C | 97 | 92.100 | 12.536 | 46.527 | 1.00 | 36.88 | O |
| ATOM | 4974 | C | ASP | C | 97 | 91.080 | 14.912 | 42.914 | 1.00 | 27.19 | C |
| ATOM | 4975 | O | ASP | C | 97 | 91.872 | 15.774 | 42.529 | 1.00 | 27.64 | O |
| ATOM | 4976 | N | CYS | C | 98 | 89.818 | 15.186 | 43.210 | 1.00 | 25.34 | N |
| ATOM | 4977 | CA | CYS | C | 98 | 89.306 | 16.537 | 43.123 | 1.00 | 24.34 | C |
| ATOM | 4978 | CB | CYS | C | 98 | 89.571 | 17.111 | 41.751 | 1.00 | 22.85 | C |
| ATOM | 4979 | SG | CYS | C | 98 | 88.678 | 16.364 | 40.454 | 1.00 | 24.37 | S |
| ATOM | 4980 | C | CYS | C | 98 | 87.837 | 16.646 | 43.483 | 1.00 | 23.91 | C |
| ATOM | 4981 | O | CYS | C | 98 | 87.151 | 15.648 | 43.618 | 1.00 | 23.73 | O |
| ATOM | 4982 | N | PRO | C | 99 | 87.330 | 17.878 | 43.658 | 1.00 | 24.47 | N |
| ATOM | 4983 | CA | PRO | C | 99 | 85.912 | 18.018 | 44.030 | 1.00 | 24.69 | C |
| ATOM | 4984 | CB | PRO | C | 99 | 85.680 | 19.530 | 43.948 | 1.00 | 24.92 | C |
| ATOM | 4985 | CG | PRO | C | 99 | 87.041 | 20.090 | 44.197 | 1.00 | 22.49 | C |
| ATOM | 4986 | CD | PRO | C | 99 | 87.923 | 19.203 | 43.384 | 1.00 | 24.42 | C |
| ATOM | 4987 | C | PRO | C | 99 | 84.993 | 17.199 | 43.134 | 1.00 | 25.02 | C |
| ATOM | 4988 | O | PRO | C | 99 | 84.258 | 16.350 | 43.613 | 1.00 | 26.50 | O |
| ATOM | 4989 | N | LYS | C | 100 | 85.037 | 17.447 | 41.831 | 1.00 | 25.02 | N |
| ATOM | 4990 | CA | LYS | C | 100 | 84.227 | 16.678 | 40.904 | 1.00 | 25.48 | C |
| ATOM | 4991 | CB | LYS | C | 100 | 84.539 | 17.070 | 39.475 | 1.00 | 24.80 | C |
| ATOM | 4992 | CG | LYS | C | 100 | 83.648 | 18.125 | 38.935 | 1.00 | 30.29 | C |
| ATOM | 4993 | CD | LYS | C | 100 | 83.782 | 18.142 | 37.424 | 1.00 | 40.75 | C |
| ATOM | 4994 | CE | LYS | C | 100 | 83.523 | 19.533 | 36.867 | 1.00 | 53.21 | C |
| ATOM | 4995 | NZ | LYS | C | 100 | 82.331 | 20.135 | 37.559 | 1.00 | 59.35 | N |
| ATOM | 4996 | C | LYS | C | 100 | 84.462 | 15.156 | 41.069 | 1.00 | 25.59 | C |
| ATOM | 4997 | O | LYS | C | 100 | 83.520 | 14.371 | 40.994 | 1.00 | 27.74 | O |
| ATOM | 4998 | N | ALA | C | 101 | 85.709 | 14.740 | 41.276 | 1.00 | 24.38 | N |
| ATOM | 4999 | CA | ALA | C | 101 | 85.988 | 13.336 | 41.456 | 1.00 | 24.79 | C |
| ATOM | 5000 | CB | ALA | C | 101 | 87.447 | 13.111 | 41.663 | 1.00 | 24.30 | C |
| ATOM | 5001 | C | ALA | C | 101 | 85.236 | 12.868 | 42.660 | 1.00 | 26.59 | C |
| ATOM | 5002 | O | ALA | C | 101 | 84.450 | 11.916 | 42.590 | 1.00 | 28.28 | O |
| ATOM | 5003 | N | ARG | C | 102 | 85.451 | 13.562 | 43.771 | 1.00 | 27.16 | N |
| ATOM | 5004 | CA | ARG | C | 102 | 84.857 | 13.186 | 45.042 | 1.00 | 26.56 | C |
| ATOM | 5005 | CB | ARG | C | 102 | 85.332 | 14.113 | 46.141 | 1.00 | 25.52 | C |
| ATOM | 5006 | CG | ARG | C | 102 | 86.803 | 14.032 | 46.346 | 1.00 | 27.72 | C |
| ATOM | 5007 | CD | ARG | C | 102 | 87.133 | 13.072 | 47.473 | 1.00 | 30.33 | C |
| ATOM | 5008 | NE | ARG | C | 102 | 88.565 | 12.810 | 47.574 | 1.00 | 29.78 | N |
| ATOM | 5009 | CZ | ARG | C | 102 | 89.121 | 12.006 | 48.473 | 1.00 | 28.08 | C |
| ATOM | 5010 | NH1AR | G | C | 102 | 88.378 | 11.379 | 49.368 | 1.00 | 30.88 | N |
| ATOM | 5011 | NH2AR | G | C | 102 | 90.432 | 11.814 | 48.453 | 1.00 | 26.26 | N |
| ATOM | 5012 | C | ARG | C | 102 | 83.378 | 13.176 | 44.984 | 1.00 | 26.85 | C |

FIG. 2A-109

| ATOM | 5013 | O | ARG | C | 102 | 82.734 | 12.462 | 45.750 | 1.00 | 28.83 | O |
|---|---|---|---|---|---|---|---|---|---|---|---|
| ATOM | 5014 | N | ARG | C | 103 | 82.834 | 13.972 | 44.077 | 1.00 | 27.01 | N |
| ATOM | 5015 | CA | ARG | C | 103 | 81.413 | 14.060 | 43.837 | 1.00 | 28.42 | C |
| ATOM | 5016 | CB | ARG | C | 103 | 81.166 | 15.195 | 42.839 | 1.00 | 30.19 | C |
| ATOM | 5017 | CG | ARG | C | 103 | 79.713 | 15.668 | 42.840 | 1.00 | 40.29 | C |
| ATOM | 5018 | CD | ARG | C | 103 | 79.595 | 17.164 | 42.527 | 1.00 | 61.85 | C |
| ATOM | 5019 | NE | ARG | C | 103 | 79.219 | 17.370 | 41.127 | 1.00 | 68.06 | N |
| ATOM | 5020 | CZ | ARG | C | 103 | 79.891 | 18.314 | 40.441 | 1.00 | 74.49 | C |
| ATOM | 5021 | NH1AR | G | C | 103 | 80.856 | 18.998 | 41.027 | 1.00 | 72.62 | N |
| ATOM | 5022 | NH2AR | G | C | 103 | 79.568 | 18.562 | 39.169 | 1.00 | 71.87 | N |
| ATOM | 5023 | C | ARG | C | 103 | 80.918 | 12.748 | 43.263 | 1.00 | 27.28 | C |
| ATOM | 5024 | O | ARG | C | 103 | 79.960 | 12.156 | 43.738 | 1.00 | 26.34 | O |
| ATOM | 5025 | N | GLU | C | 104 | 81.628 | 12.350 | 42.214 | 1.00 | 27.19 | N |
| ATOM | 5026 | CA | GLU | C | 104 | 81.320 | 11.168 | 41.467 | 1.00 | 28.99 | C |
| ATOM | 5027 | CB | GLU | C | 104 | 82.355 | 10.949 | 40.372 | 1.00 | 28.09 | C |
| ATOM | 5028 | CG | GLU | C | 104 | 82.033 | 9.758 | 39.483 | 1.00 | 31.61 | C |
| ATOM | 5029 | CD | GLU | C | 104 | 82.952 | 9.627 | 38.282 | 1.00 | 34.28 | C |
| ATOM | 5030 | OE1 | GLU | C | 104 | 83.181 | 8.483 | 37.828 | 1.00 | 35.97 | O |
| ATOM | 5031 | OE2 | GLU | C | 104 | 83.440 | 10.669 | 37.780 | 1.00 | 39.51 | O |
| ATOM | 5032 | C | GLU | C | 104 | 81.289 | 9.957 | 42.376 | 1.00 | 30.58 | C |
| ATOM | 5033 | O | GLU | C | 104 | 80.301 | 9.217 | 42.392 | 1.00 | 29.85 | O |
| ATOM | 5034 | N | VAL | C | 105 | 82.370 | 9.745 | 43.129 | 1.00 | 31.17 | N |
| ATOM | 5035 | CA | VAL | C | 105 | 82.465 | 8.606 | 44.027 | 1.00 | 28.75 | C |
| ATOM | 5036 | CB | VAL | C | 105 | 83.803 | 8.636 | 44.802 | 1.00 | 28.78 | C |
| ATOM | 5037 | CG1 | VAL | C | 105 | 83.731 | 7.786 | 46.031 | 1.00 | 29.70 | C |
| ATOM | 5038 | CG2 | VAL | C | 105 | 84.922 | 8.126 | 43.916 | 1.00 | 28.61 | C |
| ATOM | 5039 | C | VAL | C | 105 | 81.291 | 8.618 | 44.978 | 1.00 | 30.20 | C |
| ATOM | 5040 | O | VAL | C | 105 | 80.657 | 7.590 | 45.230 | 1.00 | 30.57 | O |
| ATOM | 5041 | N | GLU | C | 106 | 80.981 | 9.788 | 45.502 | 1.00 | 28.74 | N |
| ATOM | 5042 | CA | GLU | C | 106 | 79.877 | 9.869 | 46.424 | 1.00 | 29.17 | C |
| ATOM | 5043 | CB | GLU | C | 106 | 79.784 | 11.278 | 47.011 | 1.00 | 30.75 | C |
| ATOM | 5044 | CG | GLU | C | 106 | 80.117 | 11.334 | 48.492 | 1.00 | 44.14 | C |
| ATOM | 5045 | CD | GLU | C | 106 | 81.603 | 11.675 | 48.777 | 1.00 | 57.51 | C |
| ATOM | 5046 | OE1 | GLU | C | 106 | 82.526 | 11.010 | 48.205 | 1.00 | 56.66 | O |
| ATOM | 5047 | OE2 | GLU | C | 106 | 81.828 | 12.623 | 49.592 | 1.00 | 58.06 | O |
| ATOM | 5048 | C | GLU | C | 106 | 78.556 | 9.497 | 45.771 | 1.00 | 27.98 | C |
| ATOM | 5049 | O | GLU | C | 106 | 77.798 | 8.671 | 46.269 | 1.00 | 28.50 | O |
| ATOM | 5050 | N | LEU | C | 107 | 78.262 | 10.130 | 44.654 | 1.00 | 26.69 | N |
| ATOM | 5051 | CA | LEU | C | 107 | 77.007 | 9.875 | 43.986 | 1.00 | 25.94 | C |
| ATOM | 5052 | CB | LEU | C | 107 | 76.906 | 10.767 | 42.741 | 1.00 | 25.81 | C |
| ATOM | 5053 | CG | LEU | C | 107 | 76.840 | 12.287 | 42.970 | 1.00 | 23.89 | C |
| ATOM | 5054 | CD1 | LEU | C | 107 | 76.840 | 13.044 | 41.694 | 1.00 | 29.86 | C |
| ATOM | 5055 | CD2 | LEU | C | 107 | 75.636 | 12.601 | 43.826 | 1.00 | 15.42 | C |
| ATOM | 5056 | C | LEU | C | 107 | 76.902 | 8.390 | 43.622 | 1.00 | 25.37 | C |
| ATOM | 5057 | O | LEU | C | 107 | 75.898 | 7.733 | 43.891 | 1.00 | 24.95 | O |
| ATOM | 5058 | N | HIS | C | 108 | 77.969 | 7.858 | 43.035 | 1.00 | 26.08 | N |

FIG. 2A-110

| ATOM | 5059 | CA | HIS | C | 108 | 78.016 | 6.480 | 42.628 | 1.00 | 27.00 | C |
|---|---|---|---|---|---|---|---|---|---|---|---|
| ATOM | 5060 | CB | HIS | C | 108 | 79.380 | 6.178 | 42.038 | 1.00 | 27.01 | C |
| ATOM | 5061 | CG | HIS | C | 108 | 79.382 | 5.018 | 41.102 | 1.00 | 31.46 | C |
| ATOM | 5062 | ND1 | HIS | C | 108 | 80.307 | 4.885 | 40.088 | 1.00 | 35.24 | N |
| ATOM | 5063 | CE1 | HIS | C | 108 | 80.059 | 3.779 | 39.411 | 1.00 | 32.31 | C |
| ATOM | 5064 | NE2 | HIS | C | 108 | 79.004 | 3.192 | 39.947 | 1.00 | 26.43 | N |
| ATOM | 5065 | CD2 | HIS | C | 108 | 78.563 | 3.945 | 41.008 | 1.00 | 29.47 | C |
| ATOM | 5066 | C | HIS | C | 108 | 77.727 | 5.568 | 43.799 | 1.00 | 28.09 | C |
| ATOM | 5067 | O | HIS | C | 108 | 76.821 | 4.761 | 43.719 | 1.00 | 31.16 | O |
| ATOM | 5068 | N | TRP | C | 109 | 78.481 | 5.696 | 44.893 | 1.00 | 27.74 | N |
| ATOM | 5069 | CA | TRP | C | 109 | 78.278 | 4.869 | 46.098 | 1.00 | 26.25 | C |
| ATOM | 5070 | CB | TRP | C | 109 | 79.152 | 5.378 | 47.246 | 1.00 | 25.53 | C |
| ATOM | 5071 | CG | TRP | C | 109 | 79.032 | 4.547 | 48.519 | 1.00 | 23.42 | C |
| ATOM | 5072 | CD1 | TRP | C | 109 | 78.457 | 4.924 | 49.683 | 1.00 | 19.39 | C |
| ATOM | 5073 | NE1 | TRP | C | 109 | 78.568 | 3.918 | 50.614 | 1.00 | 18.85 | N |
| ATOM | 5074 | CE2 | TRP | C | 109 | 79.223 | 2.861 | 50.052 | 1.00 | 21.42 | C |
| ATOM | 5075 | CD2 | TRP | C | 109 | 79.528 | 3.218 | 48.723 | 1.00 | 22.71 | C |
| ATOM | 5076 | CE3 | TRP | C | 109 | 80.210 | 2.292 | 47.902 | 1.00 | 27.55 | C |
| ATOM | 5077 | CZ3 | TRP | C | 109 | 80.559 | 1.059 | 48.432 | 1.00 | 27.04 | C |
| ATOM | 5078 | CH2 | TRP | C | 109 | 80.235 | 0.735 | 49.770 | 1.00 | 27.83 | C |
| ATOM | 5079 | CZ2 | TRP | C | 109 | 79.569 | 1.623 | 50.590 | 1.00 | 26.36 | C |
| ATOM | 5080 | C | TRP | C | 109 | 76.815 | 4.808 | 46.589 | 1.00 | 26.67 | C |
| ATOM | 5081 | O | TRP | C | 109 | 76.306 | 3.729 | 46.961 | 1.00 | 28.01 | O |
| ATOM | 5082 | N | ARG | C | 110 | 76.151 | 5.966 | 46.632 | 1.00 | 25.12 | N |
| ATOM | 5083 | CA | ARG | C | 110 | 74.766 | 6.007 | 47.045 | 1.00 | 22.91 | C |
| ATOM | 5084 | CB | ARG | C | 110 | 74.262 | 7.455 | 47.074 | 1.00 | 21.38 | C |
| ATOM | 5085 | CG | ARG | C | 110 | 74.787 | 8.277 | 48.209 | 1.00 | 21.38 | C |
| ATOM | 5086 | CD | ARG | C | 110 | 73.741 | 9.195 | 48.706 | 1.00 | 26.05 | C |
| ATOM | 5087 | NE | ARG | C | 110 | 73.648 | 10.401 | 47.900 | 1.00 | 29.39 | N |
| ATOM | 5088 | CZ | ARG | C | 110 | 72.489 | 10.955 | 47.517 | 1.00 | 37.24 | C |
| ATOM | 5089 | NH1AR | G | C | 110 | 71.306 | 10.398 | 47.848 | 1.00 | 36.22 | N |
| ATOM | 5090 | NH2AR | G | C | 110 | 72.501 | 12.114 | 46.853 | 1.00 | 41.73 | N |
| ATOM | 5091 | C | ARG | C | 110 | 73.933 | 5.223 | 46.033 | 1.00 | 22.55 | C |
| ATOM | 5092 | O | ARG | C | 110 | 72.975 | 4.562 | 46.381 | 1.00 | 23.37 | O |
| ATOM | 5093 | N | ALA | C | 111 | 74.302 | 5.334 | 44.761 | 1.00 | 21.97 | N |
| ATOM | 5094 | CA | ALA | C | 111 | 73.592 | 4.689 | 43.665 | 1.00 | 24.73 | C |
| ATOM | 5095 | CB | ALA | C | 111 | 74.061 | 5.274 | 42.370 | 1.00 | 21.61 | C |
| ATOM | 5096 | C | ALA | C | 111 | 73.796 | 3.184 | 43.657 | 1.00 | 25.65 | C |
| ATOM | 5097 | O | ALA | C | 111 | 72.878 | 2.414 | 43.376 | 1.00 | 25.44 | O |
| ATOM | 5098 | N | SER | C | 112 | 75.017 | 2.800 | 43.999 | 1.00 | 26.90 | N |
| ATOM | 5099 | CA | SER | C | 112 | 75.474 | 1.431 | 44.030 | 1.00 | 28.54 | C |
| ATOM | 5100 | CB | SER | C | 112 | 76.864 | 1.453 | 44.634 | 1.00 | 27.27 | C |
| ATOM | 5101 | OG | SER | C | 112 | 77.442 | 0.157 | 44.729 | 1.00 | 38.27 | O |
| ATOM | 5102 | C | SER | C | 112 | 74.571 | 0.443 | 44.765 | 1.00 | 28.69 | C |
| ATOM | 5103 | O | SER | C | 112 | 74.735 | -0.771 | 44.674 | 1.00 | 30.25 | O |
| ATOM | 5104 | N | GLN | C | 113 | 73.604 | 0.962 | 45.490 | 1.00 | 28.68 | N |

FIG. 2A-111

| ATOM | 5105 | CA | GLN | C | 113 | 72.696 | 0.129 | 46.259 | 1.00 | 29.96 | C |
| ATOM | 5106 | CB | GLN | C | 113 | 72.055 | 1.017 | 47.343 | 1.00 | 30.71 | C |
| ATOM | 5107 | CG | GLN | C | 113 | 70.857 | 0.435 | 48.059 | 1.00 | 38.01 | C |
| ATOM | 5108 | CD | GLN | C | 113 | 71.237 | -0.353 | 49.298 | 1.00 | 45.84 | C |
| ATOM | 5109 | OE1 | GLN | C | 113 | 72.423 | -0.649 | 49.539 | 1.00 | 46.48 | O |
| ATOM | 5110 | NE2 | GLN | C | 113 | 70.234 | -0.713 | 50.089 | 1.00 | 45.85 | N |
| ATOM | 5111 | C | GLN | C | 113 | 71.636 | -0.501 | 45.350 | 1.00 | 29.75 | C |
| ATOM | 5112 | O | GLN | C | 113 | 70.953 | -1.440 | 45.713 | 1.00 | 29.94 | O |
| ATOM | 5113 | N | CYS | C | 114 | 71.490 | 0.031 | 44.155 | 1.00 | 29.26 | N |
| ATOM | 5114 | CA | CYS | C | 114 | 70.505 | -0.492 | 43.247 | 1.00 | 27.88 | C |
| ATOM | 5115 | CB | CYS | C | 114 | 69.986 | 0.649 | 42.382 | 1.00 | 27.81 | C |
| ATOM | 5116 | SG | CYS | C | 114 | 68.932 | 0.180 | 41.002 | 1.00 | 27.17 | S |
| ATOM | 5117 | C | CYS | C | 114 | 71.174 | -1.576 | 42.409 | 1.00 | 28.47 | C |
| ATOM | 5118 | O | CYS | C | 114 | 72.291 | -1.420 | 41.942 | 1.00 | 30.08 | O |
| ATOM | 5119 | N | PRO | C | 115 | 70.502 | -2.708 | 42.228 | 1.00 | 29.30 | N |
| ATOM | 5120 | CA | PRO | C | 115 | 70.999 | -3.851 | 41.461 | 1.00 | 29.28 | C |
| ATOM | 5121 | CB | PRO | C | 115 | 69.839 | -4.832 | 41.520 | 1.00 | 30.32 | C |
| ATOM | 5122 | CG | PRO | C | 115 | 69.177 | -4.482 | 42.812 | 1.00 | 31.38 | C |
| ATOM | 5123 | CD | PRO | C | 115 | 69.173 | -2.987 | 42.778 | 1.00 | 29.71 | C |
| ATOM | 5124 | C | PRO | C | 115 | 71.340 | -3.510 | 40.036 | 1.00 | 27.89 | C |
| ATOM | 5125 | O | PRO | C | 115 | 72.271 | -4.068 | 39.461 | 1.00 | 28.61 | O |
| ATOM | 5126 | N | HIS | C | 116 | 70.568 | -2.591 | 39.465 | 1.00 | 27.25 | N |
| ATOM | 5127 | CA | HIS | C | 116 | 70.754 | -2.173 | 38.086 | 1.00 | 26.48 | C |
| ATOM | 5128 | CB | HIS | C | 116 | 69.439 | -1.675 | 37.539 | 1.00 | 25.63 | C |
| ATOM | 5129 | CG | HIS | C | 116 | 68.435 | -2.770 | 37.366 | 1.00 | 30.85 | C |
| ATOM | 5130 | ND1 | HIS | C | 116 | 68.589 | -3.770 | 36.428 | 1.00 | 28.78 | N |
| ATOM | 5131 | CE1 | HIS | C | 116 | 67.639 | -4.668 | 36.593 | 1.00 | 31.93 | C |
| ATOM | 5132 | NE2 | HIS | C | 116 | 66.869 | -4.284 | 37.594 | 1.00 | 28.91 | N |
| ATOM | 5133 | CD2 | HIS | C | 116 | 67.343 | -3.099 | 38.093 | 1.00 | 33.57 | C |
| ATOM | 5134 | C | HIS | C | 116 | 71.817 | -1.142 | 37.888 | 1.00 | 25.15 | C |
| ATOM | 5135 | O | HIS | C | 116 | 71.860 | -0.471 | 36.874 | 1.00 | 26.57 | O |
| ATOM | 5136 | N | ILE | C | 117 | 72.694 | -1.026 | 38.862 | 1.00 | 25.03 | N |
| ATOM | 5137 | CA | ILE | C | 117 | 73.796 | -0.077 | 38.819 | 1.00 | 25.74 | C |
| ATOM | 5138 | CB | ILE | C | 117 | 73.445 | 1.105 | 39.720 | 1.00 | 25.90 | C |
| ATOM | 5139 | CG1 | ILE | C | 117 | 72.226 | 1.842 | 39.145 | 1.00 | 29.11 | C |
| ATOM | 5140 | CD1 | ILE | C | 117 | 72.207 | 3.322 | 39.521 | 1.00 | 29.45 | C |
| ATOM | 5141 | CG2 | ILE | C | 117 | 74.614 | 2.106 | 39.746 | 1.00 | 26.27 | C |
| ATOM | 5142 | C | ILE | C | 117 | 75.112 | -0.717 | 39.262 | 1.00 | 25.81 | C |
| ATOM | 5143 | O | ILE | C | 117 | 75.228 | -1.303 | 40.333 | 1.00 | 27.68 | O |
| ATOM | 5144 | N | VAL | C | 118 | 76.113 | -0.618 | 38.362 | 1.00 | 25.88 | N |
| ATOM | 5145 | CA | VAL | C | 118 | 77.408 | -1.241 | 38.604 | 1.00 | 26.85 | C |
| ATOM | 5146 | CB | VAL | C | 118 | 78.408 | -0.622 | 37.621 | 1.00 | 27.36 | C |
| ATOM | 5147 | CG1 | VAL | C | 118 | 78.715 | 0.822 | 38.015 | 1.00 | 25.54 | C |
| ATOM | 5148 | CG2 | VAL | C | 118 | 79.701 | -1.423 | 37.588 | 1.00 | 28.35 | C |
| ATOM | 5149 | C | VAL | C | 118 | 77.883 | -1.072 | 40.058 | 1.00 | 25.76 | C |
| ATOM | 5150 | O | VAL | C | 118 | 77.993 | 0.023 | 40.590 | 1.00 | 26.95 | O |

FIG. 2A-112

| ATOM | 5151 | N | ARG | C | 119 | 78.134 | -2.222 | 40.715 | 1.00 | 25.98 | N |
|------|------|------|------|---|-----|--------|--------|--------|------|-------|---|
| ATOM | 5152 | CA | ARG | C | 119 | 78.494 | -2.177 | 42.127 | 1.00 | 25.35 | C |
| ATOM | 5153 | CB | ARG | C | 119 | 78.303 | -3.575 | 42.704 | 1.00 | 26.61 | C |
| ATOM | 5154 | CG | ARG | C | 119 | 79.268 | -3.871 | 43.846 | 1.00 | 26.27 | C |
| ATOM | 5155 | CD | ARG | C | 119 | 79.286 | -5.368 | 44.185 | 1.00 | 33.13 | C |
| ATOM | 5156 | NE | ARG | C | 119 | 80.213 | -5.642 | 45.283 | 1.00 | 38.88 | N |
| ATOM | 5157 | CZ | ARG | C | 119 | 80.964 | -6.756 | 45.196 | 1.00 | 40.23 | C |
| ATOM | 5158 | NH1AR | G | C | 119 | 80.831 | -7.569 | 44.159 | 1.00 | 34.83 | N |
| ATOM | 5159 | NH2AR | G | C | 119 | 81.836 | -7.042 | 46.164 | 1.00 | 44.65 | N |
| ATOM | 5160 | C | ARG | C | 119 | 79.936 | -1.712 | 42.342 | 1.00 | 25.66 | C |
| ATOM | 5161 | O | ARG | C | 119 | 80.862 | -2.160 | 41.681 | 1.00 | 25.19 | O |
| ATOM | 5162 | N | ILE | C | 120 | 80.166 | -0.738 | 43.229 | 1.00 | 23.03 | N |
| ATOM | 5163 | CA | ILE | C | 120 | 81.526 | -0.271 | 43.495 | 1.00 | 21.80 | C |
| ATOM | 5164 | CB | ILE | C | 120 | 81.588 | 1.199 | 44.061 | 1.00 | 22.80 | C |
| ATOM | 5165 | CG1 | ILE | C | 120 | 81.213 | 2.231 | 42.993 | 1.00 | 23.79 | C |
| ATOM | 5166 | CD1 | ILE | C | 120 | 81.185 | 3.617 | 43.509 | 1.00 | 23.66 | C |
| ATOM | 5167 | CG2 | ILE | C | 120 | 82.988 | 1.498 | 44.546 | 1.00 | 21.12 | C |
| ATOM | 5168 | C | ILE | C | 120 | 81.996 | -1.242 | 44.584 | 1.00 | 21.25 | C |
| ATOM | 5169 | O | ILE | C | 120 | 81.321 | -1.423 | 45.576 | 1.00 | 22.09 | O |
| ATOM | 5170 | N | VAL | C | 121 | 83.148 | -1.864 | 44.377 | 1.00 | 19.62 | N |
| ATOM | 5171 | CA | VAL | C | 121 | 83.718 | -2.844 | 45.310 | 1.00 | 20.21 | C |
| ATOM | 5172 | CB | VAL | C | 121 | 84.538 | -3.947 | 44.541 | 1.00 | 19.39 | C |
| ATOM | 5173 | CG1 | VAL | C | 121 | 85.406 | -4.708 | 45.502 | 1.00 | 17.67 | C |
| ATOM | 5174 | CG2 | VAL | C | 121 | 83.606 | -4.870 | 43.787 | 1.00 | 18.77 | C |
| ATOM | 5175 | C | VAL | C | 121 | 84.641 | -2.189 | 46.335 | 1.00 | 20.91 | C |
| ATOM | 5176 | O | VAL | C | 121 | 84.581 | -2.497 | 47.513 | 1.00 | 21.23 | O |
| ATOM | 5177 | N | ASP | C | 122 | 85.513 | -1.302 | 45.880 | 1.00 | 21.88 | N |
| ATOM | 5178 | CA | ASP | C | 122 | 86.419 | -0.605 | 46.768 | 1.00 | 22.38 | C |
| ATOM | 5179 | CB | ASP | C | 122 | 87.725 | -1.375 | 46.968 | 1.00 | 22.88 | C |
| ATOM | 5180 | CG | ASP | C | 122 | 87.637 | -2.433 | 48.063 | 1.00 | 29.13 | C |
| ATOM | 5181 | OD1 | ASP | C | 122 | 86.932 | -2.214 | 49.100 | 1.00 | 36.24 | O |
| ATOM | 5182 | OD2 | ASP | C | 122 | 88.309 | -3.481 | 47.888 | 1.00 | 31.00 | O |
| ATOM | 5183 | C | ASP | C | 122 | 86.767 | 0.704 | 46.137 | 1.00 | 21.30 | C |
| ATOM | 5184 | O | ASP | C | 122 | 86.642 | 0.866 | 44.934 | 1.00 | 21.12 | O |
| ATOM | 5185 | N | VAL | C | 123 | 87.191 | 1.657 | 46.944 | 1.00 | 21.57 | N |
| ATOM | 5186 | CA | VAL | C | 123 | 87.626 | 2.928 | 46.403 | 1.00 | 22.19 | C |
| ATOM | 5187 | CB | VAL | C | 123 | 86.605 | 4.053 | 46.649 | 1.00 | 21.37 | C |
| ATOM | 5188 | CG1 | VAL | C | 123 | 87.159 | 5.371 | 46.098 | 1.00 | 25.32 | C |
| ATOM | 5189 | CG2 | VAL | C | 123 | 85.289 | 3.721 | 45.941 | 1.00 | 22.64 | C |
| ATOM | 5190 | C | VAL | C | 123 | 88.966 | 3.211 | 47.075 | 1.00 | 22.46 | C |
| ATOM | 5191 | O | VAL | C | 123 | 89.100 | 3.058 | 48.288 | 1.00 | 24.47 | O |
| ATOM | 5192 | N | TYR | C | 124 | 89.972 | 3.554 | 46.281 | 1.00 | 20.65 | N |
| ATOM | 5193 | CA | TYR | C | 124 | 91.283 | 3.837 | 46.824 | 1.00 | 19.99 | C |
| ATOM | 5194 | CB | TYR | C | 124 | 92.327 | 2.922 | 46.211 | 1.00 | 19.59 | C |
| ATOM | 5195 | CG | TYR | C | 124 | 92.248 | 1.490 | 46.607 | 1.00 | 22.33 | C |
| ATOM | 5196 | CD1 | TYR | C | 124 | 91.357 | 0.634 | 46.009 | 1.00 | 23.74 | C |

FIG. 2A-113

| ATOM | 5197 | CE1 | TYR | C | 124 | 91.314 | -0.704 | 46.368 | 1.00 | 18.51 | C |
| ATOM | 5198 | CZ | TYR | C | 124 | 92.163 | -1.177 | 47.347 | 1.00 | 21.26 | C |
| ATOM | 5199 | OH | TYR | C | 124 | 92.085 | -2.479 | 47.763 | 1.00 | 22.36 | O |
| ATOM | 5200 | CE2 | TYR | C | 124 | 93.061 | -0.341 | 47.954 | 1.00 | 24.67 | C |
| ATOM | 5201 | CD2 | TYR | C | 124 | 93.102 | 0.979 | 47.584 | 1.00 | 28.24 | C |
| ATOM | 5202 | C | TYR | C | 124 | 91.738 | 5.270 | 46.580 | 1.00 | 19.40 | C |
| ATOM | 5203 | O | TYR | C | 124 | 91.360 | 5.910 | 45.603 | 1.00 | 20.67 | O |
| ATOM | 5204 | N | GLU | C | 125 | 92.579 | 5.757 | 47.474 | 1.00 | 19.91 | N |
| ATOM | 5205 | CA | GLU | C | 125 | 93.131 | 7.101 | 47.358 | 1.00 | 20.59 | C |
| ATOM | 5206 | CB | GLU | C | 125 | 92.791 | 7.951 | 48.582 | 1.00 | 19.26 | C |
| ATOM | 5207 | CG | GLU | C | 125 | 93.078 | 9.426 | 48.419 | 1.00 | 22.43 | C |
| ATOM | 5208 | CD | GLU | C | 125 | 93.046 | 10.175 | 49.727 | 1.00 | 26.07 | C |
| ATOM | 5209 | OE1 | GLU | C | 125 | 94.113 | 10.234 | 50.369 | 1.00 | 30.47 | O |
| ATOM | 5210 | OE2 | GLU | C | 125 | 91.979 | 10.692 | 50.130 | 1.00 | 26.63 | O |
| ATOM | 5211 | C | GLU | C | 125 | 94.601 | 6.809 | 47.336 | 1.00 | 21.22 | C |
| ATOM | 5212 | O | GLU | C | 125 | 95.166 | 6.395 | 48.346 | 1.00 | 21.37 | O |
| ATOM | 5213 | N | ASN | C | 126 | 95.224 | 6.951 | 46.181 | 1.00 | 20.78 | N |
| ATOM | 5214 | CA | ASN | C | 126 | 96.645 | 6.667 | 46.093 | 1.00 | 20.76 | C |
| ATOM | 5215 | CB | ASN | C | 126 | 96.921 | 5.379 | 45.305 | 1.00 | 20.62 | C |
| ATOM | 5216 | CG | ASN | C | 126 | 96.528 | 4.085 | 46.055 | 1.00 | 24.40 | C |
| ATOM | 5217 | OD1 | ASN | C | 126 | 96.645 | 3.000 | 45.490 | 1.00 | 26.32 | O |
| ATOM | 5218 | ND2 | ASN | C | 126 | 96.078 | 4.195 | 47.303 | 1.00 | 21.19 | N |
| ATOM | 5219 | C | ASN | C | 126 | 97.314 | 7.798 | 45.360 | 1.00 | 20.68 | C |
| ATOM | 5220 | O | ASN | C | 126 | 96.673 | 8.729 | 44.882 | 1.00 | 21.27 | O |
| ATOM | 5221 | N | LEU | C | 127 | 98.627 | 7.700 | 45.289 | 1.00 | 19.57 | N |
| ATOM | 5222 | CA | LEU | C | 127 | 99.435 | 8.657 | 44.580 | 1.00 | 18.05 | C |
| ATOM | 5223 | CB | LEU | C | 127 | 100.602 | 9.081 | 45.460 | 1.00 | 16.22 | C |
| ATOM | 5224 | CG | LEU | C | 127 | 100.700 | 10.498 | 46.052 | 1.00 | 16.80 | C |
| ATOM | 5225 | CD1 | LEU | C | 127 | 99.369 | 11.216 | 46.164 | 1.00 | 15.18 | C |
| ATOM | 5226 | CD2 | LEU | C | 127 | 101.326 | 10.353 | 47.411 | 1.00 | 11.31 | C |
| ATOM | 5227 | C | LEU | C | 127 | 99.926 | 7.900 | 43.333 | 1.00 | 20.10 | C |
| ATOM | 5228 | O | LEU | C | 127 | 100.473 | 6.782 | 43.420 | 1.00 | 21.05 | O |
| ATOM | 5229 | N | TYR | C | 128 | 99.658 | 8.477 | 42.168 | 1.00 | 20.82 | N |
| ATOM | 5230 | CA | TYR | C | 128 | 100.125 | 7.887 | 40.936 | 1.00 | 21.92 | C |
| ATOM | 5231 | CB | TYR | C | 128 | 98.996 | 7.604 | 39.956 | 1.00 | 23.54 | C |
| ATOM | 5232 | CG | TYR | C | 128 | 99.539 | 6.960 | 38.713 | 1.00 | 27.39 | C |
| ATOM | 5233 | CD1 | TYR | C | 128 | 99.957 | 5.642 | 38.727 | 1.00 | 31.36 | C |
| ATOM | 5234 | CE1 | TYR | C | 128 | 100.605 | 5.096 | 37.641 | 1.00 | 37.53 | C |
| ATOM | 5235 | CZ | TYR | C | 128 | 100.843 | 5.869 | 36.522 | 1.00 | 38.55 | C |
| ATOM | 5236 | OH | TYR | C | 128 | 101.528 | 5.336 | 35.444 | 1.00 | 35.91 | O |
| ATOM | 5237 | CE2 | TYR | C | 128 | 100.425 | 7.177 | 36.484 | 1.00 | 36.69 | C |
| ATOM | 5238 | CD2 | TYR | C | 128 | 99.774 | 7.709 | 37.572 | 1.00 | 31.37 | C |
| ATOM | 5239 | C | TYR | C | 128 | 101.054 | 8.906 | 40.311 | 1.00 | 23.32 | C |
| ATOM | 5240 | O | TYR | C | 128 | 100.622 | 9.978 | 39.860 | 1.00 | 21.34 | O |
| ATOM | 5241 | N | ALA | C | 129 | 102.338 | 8.561 | 40.309 | 1.00 | 26.16 | N |
| ATOM | 5242 | CA | ALA | C | 129 | 103.383 | 9.410 | 39.748 | 1.00 | 27.46 | C |

FIG. 2A-114

| ATOM | 5243 | CB | ALA | C | 129 | 103.140 | 9.531 | 38.243 | 1.00 | 27.81 | C |
|---|---|---|---|---|---|---|---|---|---|---|---|
| ATOM | 5244 | C | ALA | C | 129 | 103.376 | 10.795 | 40.388 | 1.00 | 28.47 | C |
| ATOM | 5245 | O | ALA | C | 129 | 103.467 | 11.823 | 39.728 | 1.00 | 30.16 | O |
| ATOM | 5246 | N | GLY | C | 130 | 103.223 | 10.802 | 41.724 | 1.00 | 28.06 | N |
| ATOM | 5247 | CA | GLY | C | 130 | 103.182 | 12.077 | 42.430 | 1.00 | 29.90 | C |
| ATOM | 5248 | C | GLY | C | 130 | 101.763 | 12.651 | 42.479 | 1.00 | 31.08 | C |
| ATOM | 5249 | O | GLY | C | 130 | 101.437 | 13.521 | 43.273 | 1.00 | 31.75 | O |
| ATOM | 5250 | N | ARG | C | 131 | 100.917 | 12.152 | 41.561 | 1.00 | 32.00 | N |
| ATOM | 5251 | CA | ARG | C | 131 | 99.540 | 12.630 | 41.521 | 1.00 | 32.72 | C |
| ATOM | 5252 | CB | ARG | C | 131 | 98.938 | 12.230 | 40.169 | 1.00 | 35.36 | C |
| ATOM | 5253 | CG | ARG | C | 131 | 99.207 | 13.254 | 39.066 | 1.00 | 42.81 | C |
| ATOM | 5254 | CD | ARG | C | 131 | 100.122 | 14.385 | 39.538 | 1.00 | 50.64 | C |
| ATOM | 5255 | NE | ARG | C | 131 | 101.236 | 14.562 | 38.605 | 1.00 | 57.07 | N |
| ATOM | 5256 | CZ | ARG | C | 131 | 101.943 | 15.705 | 38.691 | 1.00 | 60.25 | C |
| ATOM | 5257 | NH1AR | G | C | 131 | 101.806 | 16.492 | 39.744 | 1.00 | 58.94 | N |
| ATOM | 5258 | NH2AR | G | C | 131 | 102.866 | 15.978 | 37.764 | 1.00 | 58.53 | N |
| ATOM | 5259 | C | ARG | C | 131 | 98.705 | 12.011 | 42.640 | 1.00 | 30.95 | C |
| ATOM | 5260 | O | ARG | C | 131 | 98.884 | 10.861 | 43.028 | 1.00 | 32.30 | O |
| ATOM | 5261 | N | LYS | C | 132 | 97.793 | 12.828 | 43.195 | 1.00 | 30.09 | N |
| ATOM | 5262 | CA | LYS | C | 132 | 96.790 | 12.262 | 44.085 | 1.00 | 29.13 | C |
| ATOM | 5263 | CB | LYS | C | 132 | 96.379 | 13.321 | 45.115 | 1.00 | 29.68 | C |
| ATOM | 5264 | CG | LYS | C | 132 | 95.786 | 12.696 | 46.382 | 1.00 | 36.82 | C |
| ATOM | 5265 | CD | LYS | C | 132 | 95.146 | 13.734 | 47.308 | 1.00 | 44.80 | C |
| ATOM | 5266 | CE | LYS | C | 132 | 94.404 | 13.087 | 48.484 | 1.00 | 47.33 | C |
| ATOM | 5267 | NZ | LYS | C | 132 | 93.792 | 14.120 | 49.319 | 1.00 | 47.09 | N |
| ATOM | 5268 | C | LYS | C | 132 | 95.571 | 11.800 | 43.286 | 1.00 | 28.51 | C |
| ATOM | 5269 | O | LYS | C | 132 | 94.909 | 12.580 | 42.614 | 1.00 | 28.87 | O |
| ATOM | 5270 | N | CYS | C | 133 | 95.314 | 10.500 | 43.278 | 1.00 | 29.12 | N |
| ATOM | 5271 | CA | CYS | C | 133 | 94.257 | 9.981 | 42.421 | 1.00 | 30.78 | C |
| ATOM | 5272 | CB | CYS | C | 133 | 94.867 | 9.178 | 41.263 | 1.00 | 31.51 | C |
| ATOM | 5273 | SG | CYS | C | 133 | 94.958 | 7.381 | 41.560 | 1.00 | 54.68 | S |
| ATOM | 5274 | C | CYS | C | 133 | 93.249 | 9.142 | 43.174 | 1.00 | 27.51 | C |
| ATOM | 5275 | O | CYS | C | 133 | 93.545 | 8.581 | 44.223 | 1.00 | 29.11 | O |
| ATOM | 5276 | N | LEU | C | 134 | 92.047 | 9.065 | 42.627 | 1.00 | 25.39 | N |
| ATOM | 5277 | CA | LEU | C | 134 | 90.961 | 8.304 | 43.242 | 1.00 | 23.73 | C |
| ATOM | 5278 | CB | LEU | C | 134 | 89.764 | 9.238 | 43.402 | 1.00 | 24.25 | C |
| ATOM | 5279 | CG | LEU | C | 134 | 88.981 | 9.186 | 44.696 | 1.00 | 24.16 | C |
| ATOM | 5280 | CD1 | LEU | C | 134 | 89.873 | 9.406 | 45.894 | 1.00 | 24.55 | C |
| ATOM | 5281 | CD2 | LEU | C | 134 | 87.925 | 10.258 | 44.629 | 1.00 | 32.72 | C |
| ATOM | 5282 | C | LEU | C | 134 | 90.630 | 7.076 | 42.348 | 1.00 | 22.93 | C |
| ATOM | 5283 | O | LEU | C | 134 | 90.123 | 7.229 | 41.234 | 1.00 | 21.18 | O |
| ATOM | 5284 | N | LEU | C | 135 | 90.946 | 5.878 | 42.850 | 1.00 | 23.47 | N |
| ATOM | 5285 | CA | LEU | C | 135 | 90.739 | 4.622 | 42.122 | 1.00 | 23.47 | C |
| ATOM | 5286 | CB | LEU | C | 135 | 91.969 | 3.743 | 42.292 | 1.00 | 22.05 | C |
| ATOM | 5287 | CG | LEU | C | 135 | 93.203 | 4.379 | 41.637 | 1.00 | 21.21 | C |
| ATOM | 5288 | CD1 | LEU | C | 135 | 94.450 | 3.523 | 41.905 | 1.00 | 24.33 | C |

FIG. 2A-115

| ATOM | 5289 | CD2 | LEU | C | 135 | 92.999 | 4.496 | 40.130 | 1.00 | 35.97 | C |
|------|------|-----|-----|---|-----|--------|-------|--------|------|-------|---|
| ATOM | 5290 | C | LEU | C | 135 | 89.490 | 3.844 | 42.506 | 1.00 | 23.55 | C |
| ATOM | 5291 | O | LEU | C | 135 | 89.390 | 3.321 | 43.597 | 1.00 | 25.35 | O |
| ATOM | 5292 | N | ILE | C | 136 | 88.526 | 3.768 | 41.600 | 1.00 | 24.58 | N |
| ATOM | 5293 | CA | ILE | C | 136 | 87.277 | 3.046 | 41.872 | 1.00 | 24.20 | C |
| ATOM | 5294 | CB | ILE | C | 136 | 86.096 | 3.746 | 41.247 | 1.00 | 23.58 | C |
| ATOM | 5295 | CG1 | ILE | C | 136 | 85.969 | 5.144 | 41.832 | 1.00 | 23.87 | C |
| ATOM | 5296 | CD1 | ILE | C | 136 | 85.003 | 5.986 | 41.082 | 1.00 | 31.33 | C |
| ATOM | 5297 | CG2 | ILE | C | 136 | 84.854 | 2.915 | 41.434 | 1.00 | 24.09 | C |
| ATOM | 5298 | C | ILE | C | 136 | 87.268 | 1.633 | 41.300 | 1.00 | 22.62 | C |
| ATOM | 5299 | O | ILE | C | 136 | 87.216 | 1.467 | 40.077 | 1.00 | 22.93 | O |
| ATOM | 5300 | N | VAL | C | 137 | 87.321 | 0.629 | 42.167 | 1.00 | 20.37 | N |
| ATOM | 5301 | CA | VAL | C | 137 | 87.300 | -0.753 | 41.713 | 1.00 | 19.96 | C |
| ATOM | 5302 | CB | VAL | C | 137 | 88.028 | -1.705 | 42.723 | 1.00 | 20.69 | C |
| ATOM | 5303 | CG1 | VAL | C | 137 | 87.952 | -3.158 | 42.257 | 1.00 | 19.76 | C |
| ATOM | 5304 | CG2 | VAL | C | 137 | 89.485 | -1.297 | 42.859 | 1.00 | 20.68 | C |
| ATOM | 5305 | C | VAL | C | 137 | 85.850 | -1.171 | 41.562 | 1.00 | 19.95 | C |
| ATOM | 5306 | O | VAL | C | 137 | 85.058 | -1.093 | 42.510 | 1.00 | 19.15 | O |
| ATOM | 5307 | N | MSE | C | 138 | 85.510 | -1.608 | 40.356 | 1.00 | 19.75 | N |
| ATOM | 5308 | CA | MSE | C | 138 | 84.142 | -2.035 | 40.029 | 1.00 | 20.03 | C |
| ATOM | 5309 | CB | MSE | C | 138 | 83.551 | -1.091 | 38.980 | 1.00 | 21.74 | C |
| ATOM | 5310 | CG | MSE | C | 138 | 83.429 | 0.325 | 39.441 | 1.00 | 23.03 | C |
| ATOM | 5311 | SE | MSE | C | 138 | 82.966 | 1.541 | 38.089 | 1.00 | 31.61 | S |
| ATOM | 5312 | CE | MSE | C | 138 | 84.680 | 1.717 | 37.270 | 1.00 | 22.09 | C |
| ATOM | 5313 | C | MSE | C | 138 | 83.962 | -3.469 | 39.516 | 1.00 | 19.72 | C |
| ATOM | 5314 | O | MSE | C | 138 | 84.865 | -4.080 | 38.903 | 1.00 | 18.77 | O |
| ATOM | 5315 | N | GLU | C | 139 | 82.762 | -3.988 | 39.748 | 1.00 | 20.71 | N |
| ATOM | 5316 | CA | GLU | C | 139 | 82.407 | -5.327 | 39.280 | 1.00 | 21.29 | C |
| ATOM | 5317 | CB | GLU | C | 139 | 80.980 | -5.684 | 39.744 | 1.00 | 19.72 | C |
| ATOM | 5318 | CG | GLU | C | 139 | 79.911 | -5.522 | 38.699 | 1.00 | 24.97 | C |
| ATOM | 5319 | CD | GLU | C | 139 | 78.485 | -5.653 | 39.249 | 1.00 | 30.14 | C |
| ATOM | 5320 | OE1 | GLU | C | 139 | 77.904 | -4.640 | 39.693 | 1.00 | 25.97 | O |
| ATOM | 5321 | OE2 | GLU | C | 139 | 77.923 | -6.766 | 39.231 | 1.00 | 30.29 | O |
| ATOM | 5322 | C | GLU | C | 139 | 82.527 | -5.344 | 37.742 | 1.00 | 22.51 | C |
| ATOM | 5323 | O | GLU | C | 139 | 82.187 | -4.377 | 37.052 | 1.00 | 21.67 | O |
| ATOM | 5324 | N | CYS | C | 140 | 83.047 | -6.433 | 37.187 | 1.00 | 23.97 | N |
| ATOM | 5325 | CA | CYS | C | 140 | 83.160 | -6.480 | 35.730 | 1.00 | 26.13 | C |
| ATOM | 5326 | CB | CYS | C | 140 | 84.213 | -7.500 | 35.274 | 1.00 | 27.73 | C |
| ATOM | 5327 | SG | CYS | C | 140 | 84.961 | -7.049 | 33.662 | 1.00 | 40.05 | S |
| ATOM | 5328 | C | CYS | C | 140 | 81.800 | -6.849 | 35.170 | 1.00 | 24.91 | C |
| ATOM | 5329 | O | CYS | C | 140 | 81.027 | -7.570 | 35.810 | 1.00 | 25.65 | O |
| ATOM | 5330 | N | LEU | C | 141 | 81.489 | -6.308 | 34.006 | 1.00 | 23.09 | N |
| ATOM | 5331 | CA | LEU | C | 141 | 80.230 | -6.584 | 33.355 | 1.00 | 24.96 | C |
| ATOM | 5332 | CB | LEU | C | 141 | 79.348 | -5.346 | 33.371 | 1.00 | 24.37 | C |
| ATOM | 5333 | CG | LEU | C | 141 | 79.163 | -4.692 | 34.740 | 1.00 | 25.54 | C |
| ATOM | 5334 | CD1 | LEU | C | 141 | 78.191 | -3.534 | 34.669 | 1.00 | 22.81 | C |

FIG. 2A-116

| ATOM | 5335 | CD2 | LEU | C | 141 | 78.658 | -5.762 | 35.695 | 1.00 | 27.78 | C |
|---|---|---|---|---|---|---|---|---|---|---|---|
| ATOM | 5336 | C | LEU | C | 141 | 80.655 | -6.909 | 31.954 | 1.00 | 26.55 | C |
| ATOM | 5337 | O | LEU | C | 141 | 80.777 | -6.023 | 31.118 | 1.00 | 29.70 | O |
| ATOM | 5338 | N | ASP | C | 142 | 80.888 | -8.197 | 31.705 | 1.00 | 25.88 | N |
| ATOM | 5339 | CA | ASP | C | 142 | 81.380 | -8.677 | 30.413 | 1.00 | 26.61 | C |
| ATOM | 5340 | CB | ASP | C | 142 | 82.297 | -9.855 | 30.665 | 1.00 | 30.21 | C |
| ATOM | 5341 | CG | ASP | C | 142 | 81.659 | -10.850 | 31.577 | 1.00 | 44.29 | C |
| ATOM | 5342 | OD1 | ASP | C | 142 | 80.471 | -11.174 | 31.315 | 1.00 | 59.84 | O |
| ATOM | 5343 | OD2 | ASP | C | 142 | 82.335 | -11.319 | 32.537 | 1.00 | 60.03 | O |
| ATOM | 5344 | C | ASP | C | 142 | 80.355 | -9.063 | 29.349 | 1.00 | 24.31 | C |
| ATOM | 5345 | O | ASP | C | 142 | 80.731 | -9.435 | 28.264 | 1.00 | 22.87 | O |
| ATOM | 5346 | N | GLY | C | 143 | 79.074 | -8.947 | 29.647 | 1.00 | 23.08 | N |
| ATOM | 5347 | CA | GLY | C | 143 | 78.066 | -9.293 | 28.675 | 1.00 | 21.94 | C |
| ATOM | 5348 | C | GLY | C | 143 | 77.815 | -8.330 | 27.537 | 1.00 | 20.27 | C |
| ATOM | 5349 | O | GLY | C | 143 | 76.967 | -8.598 | 26.710 | 1.00 | 19.63 | O |
| ATOM | 5350 | N | GLY | C | 144 | 78.519 | -7.204 | 27.478 | 1.00 | 22.51 | N |
| ATOM | 5351 | CA | GLY | C | 144 | 78.322 | -6.265 | 26.372 | 1.00 | 23.22 | C |
| ATOM | 5352 | C | GLY | C | 144 | 77.312 | -5.142 | 26.542 | 1.00 | 25.12 | C |
| ATOM | 5353 | O | GLY | C | 144 | 76.547 | -5.122 | 27.525 | 1.00 | 25.07 | O |
| ATOM | 5354 | N | GLU | C | 145 | 77.310 | -4.194 | 25.595 | 1.00 | 26.37 | N |
| ATOM | 5355 | CA | GLU | C | 145 | 76.374 | -3.069 | 25.657 | 1.00 | 26.97 | C |
| ATOM | 5356 | CB | GLU | C | 145 | 76.821 | -1.893 | 24.799 | 1.00 | 27.60 | C |
| ATOM | 5357 | CG | GLU | C | 145 | 78.172 | -2.041 | 24.165 | 1.00 | 38.00 | C |
| ATOM | 5358 | CD | GLU | C | 145 | 78.897 | -0.686 | 23.988 | 1.00 | 50.33 | C |
| ATOM | 5359 | OE1 | GLU | C | 145 | 79.676 | -0.263 | 24.906 | 1.00 | 50.29 | O |
| ATOM | 5360 | OE2 | GLU | C | 145 | 78.668 | -0.045 | 22.924 | 1.00 | 52.39 | O |
| ATOM | 5361 | C | GLU | C | 145 | 75.000 | -3.520 | 25.191 | 1.00 | 25.44 | C |
| ATOM | 5362 | O | GLU | C | 145 | 74.880 | -4.302 | 24.257 | 1.00 | 24.44 | O |
| ATOM | 5363 | N | LEU | C | 146 | 73.960 | -3.029 | 25.855 | 1.00 | 22.78 | N |
| ATOM | 5364 | CA | LEU | C | 146 | 72.603 | -3.385 | 25.489 | 1.00 | 21.86 | C |
| ATOM | 5365 | CB | LEU | C | 146 | 71.627 | -2.273 | 25.905 | 1.00 | 21.83 | C |
| ATOM | 5366 | CG | LEU | C | 146 | 70.215 | -2.523 | 25.377 | 1.00 | 21.09 | C |
| ATOM | 5367 | CD1 | LEU | C | 146 | 69.554 | -3.667 | 26.147 | 1.00 | 19.63 | C |
| ATOM | 5368 | CD2 | LEU | C | 146 | 69.417 | -1.278 | 25.498 | 1.00 | 19.55 | C |
| ATOM | 5369 | C | LEU | C | 146 | 72.398 | -3.690 | 23.997 | 1.00 | 20.30 | C |
| ATOM | 5370 | O | LEU | C | 146 | 71.837 | -4.697 | 23.675 | 1.00 | 20.75 | O |
| ATOM | 5371 | N | PHE | C | 147 | 72.845 | -2.835 | 23.090 | 1.00 | 19.74 | N |
| ATOM | 5372 | CA | PHE | C | 147 | 72.613 | -3.088 | 21.681 | 1.00 | 21.86 | C |
| ATOM | 5373 | CB | PHE | C | 147 | 72.790 | -1.814 | 20.849 | 1.00 | 22.83 | C |
| ATOM | 5374 | CG | PHE | C | 147 | 71.746 | -0.774 | 21.109 | 1.00 | 23.66 | C |
| ATOM | 5375 | CD1 | PHE | C | 147 | 71.927 | 0.520 | 20.713 | 1.00 | 21.67 | C |
| ATOM | 5376 | CE1 | PHE | C | 147 | 71.000 | 1.489 | 21.018 | 1.00 | 23.61 | C |
| ATOM | 5377 | CZ | PHE | C | 147 | 69.883 | 1.177 | 21.714 | 1.00 | 22.51 | C |
| ATOM | 5378 | CE2 | PHE | C | 147 | 69.679 | -0.102 | 22.106 | 1.00 | 23.96 | C |
| ATOM | 5379 | CD2 | PHE | C | 147 | 70.609 | -1.080 | 21.806 | 1.00 | 26.32 | C |
| ATOM | 5380 | C | PHE | C | 147 | 73.436 | -4.222 | 21.076 | 1.00 | 23.15 | C |

FIG. 2A-117

| ATOM | 5381 | O | PHE | C | 147 | 72.988 | -4.864 | 20.129 | 1.00 | 24.87 | O |
| ATOM | 5382 | N | SER | C | 148 | 74.634 | -4.481 | 21.566 | 1.00 | 22.76 | N |
| ATOM | 5383 | CA | SER | C | 148 | 75.365 | -5.606 | 21.008 | 1.00 | 24.83 | C |
| ATOM | 5384 | CB | SER | C | 148 | 76.664 | -5.788 | 21.732 | 1.00 | 25.33 | C |
| ATOM | 5385 | OG | SER | C | 148 | 77.226 | -4.523 | 21.928 | 1.00 | 35.32 | O |
| ATOM | 5386 | C | SER | C | 148 | 74.538 | -6.867 | 21.225 | 1.00 | 24.94 | C |
| ATOM | 5387 | O | SER | C | 148 | 74.451 | -7.722 | 20.356 | 1.00 | 25.33 | O |
| ATOM | 5388 | N | ARG | C | 149 | 73.934 | -6.980 | 22.399 | 1.00 | 24.85 | N |
| ATOM | 5389 | CA | ARG | C | 149 | 73.166 | -8.154 | 22.706 | 1.00 | 25.74 | C |
| ATOM | 5390 | CB | ARG | C | 149 | 72.853 | -8.228 | 24.203 | 1.00 | 26.70 | C |
| ATOM | 5391 | CG | ARG | C | 149 | 74.102 | -8.323 | 25.082 | 1.00 | 33.60 | C |
| ATOM | 5392 | CD | ARG | C | 149 | 74.696 | -9.748 | 25.160 | 1.00 | 42.66 | C |
| ATOM | 5393 | NE | ARG | C | 149 | 74.478 | -10.390 | 26.465 | 1.00 | 46.72 | N |
| ATOM | 5394 | CZ | ARG | C | 149 | 73.285 | -10.530 | 27.029 | 1.00 | 49.24 | C |
| ATOM | 5395 | NH1AR | G | C | 149 | 72.195 | -10.062 | 26.411 | 1.00 | 49.14 | N |
| ATOM | 5396 | NH2AR | G | C | 149 | 73.169 | -11.166 | 28.188 | 1.00 | 44.44 | N |
| ATOM | 5397 | C | ARG | C | 149 | 71.897 | -8.195 | 21.926 | 1.00 | 25.90 | C |
| ATOM | 5398 | O | ARG | C | 149 | 71.472 | -9.261 | 21.502 | 1.00 | 25.40 | O |
| ATOM | 5399 | N | ILE | C | 150 | 71.270 | -7.051 | 21.717 | 1.00 | 25.47 | N |
| ATOM | 5400 | CA | ILE | C | 150 | 70.023 | -7.123 | 20.997 | 1.00 | 26.53 | C |
| ATOM | 5401 | CB | ILE | C | 150 | 69.363 | -5.755 | 20.772 | 1.00 | 26.50 | C |
| ATOM | 5402 | CG1 | ILE | C | 150 | 68.415 | -5.395 | 21.921 | 1.00 | 24.99 | C |
| ATOM | 5403 | CD1 | ILE | C | 150 | 68.967 | -5.676 | 23.271 | 1.00 | 28.15 | C |
| ATOM | 5404 | CG2 | ILE | C | 150 | 68.579 | -5.805 | 19.487 | 1.00 | 28.95 | C |
| ATOM | 5405 | C | ILE | C | 150 | 70.300 | -7.734 | 19.656 | 1.00 | 26.79 | C |
| ATOM | 5406 | O | ILE | C | 150 | 69.572 | -8.581 | 19.204 | 1.00 | 26.12 | O |
| ATOM | 5407 | N | GLN | C | 151 | 71.392 | -7.336 | 19.031 | 1.00 | 29.09 | N |
| ATOM | 5408 | CA | GLN | C | 151 | 71.687 | -7.846 | 17.712 | 1.00 | 32.90 | C |
| ATOM | 5409 | CB | GLN | C | 151 | 72.632 | -6.904 | 16.983 | 1.00 | 33.14 | C |
| ATOM | 5410 | CG | GLN | C | 151 | 73.894 | -6.632 | 17.692 | 1.00 | 37.37 | C |
| ATOM | 5411 | CD | GLN | C | 151 | 74.774 | -5.730 | 16.894 | 1.00 | 43.46 | C |
| ATOM | 5412 | OE1 | GLN | C | 151 | 75.990 | -5.781 | 17.031 | 1.00 | 47.86 | O |
| ATOM | 5413 | NE2 | GLN | C | 151 | 74.178 | -4.885 | 16.052 | 1.00 | 46.49 | N |
| ATOM | 5414 | C | GLN | C | 151 | 72.201 | -9.267 | 17.636 | 1.00 | 35.14 | C |
| ATOM | 5415 | O | GLN | C | 151 | 71.764 | -10.029 | 16.787 | 1.00 | 34.73 | O |
| ATOM | 5416 | N | ASP | C | 152 | 73.117 | -9.661 | 18.499 | 1.00 | 37.32 | N |
| ATOM | 5417 | CA | ASP | C | 152 | 73.565 | -11.036 | 18.396 | 1.00 | 40.22 | C |
| ATOM | 5418 | CB | ASP | C | 152 | 74.829 | -11.275 | 19.223 | 1.00 | 39.75 | C |
| ATOM | 5419 | CG | ASP | C | 152 | 76.020 | -10.485 | 18.698 | 1.00 | 41.77 | C |
| ATOM | 5420 | OD1 | ASP | C | 152 | 76.095 | -10.279 | 17.456 | 1.00 | 47.18 | O |
| ATOM | 5421 | OD2 | ASP | C | 152 | 76.876 | -10.078 | 19.520 | 1.00 | 38.70 | O |
| ATOM | 5422 | C | ASP | C | 152 | 72.450 | -11.954 | 18.852 | 1.00 | 41.89 | C |
| ATOM | 5423 | O | ASP | C | 152 | 72.681 | -13.130 | 19.091 | 1.00 | 42.89 | O |
| ATOM | 5424 | N | ARG | C | 153 | 71.240 | -11.407 | 18.968 | 1.00 | 44.11 | N |
| ATOM | 5425 | CA | ARG | C | 153 | 70.083 | -12.181 | 19.397 | 1.00 | 45.18 | C |
| ATOM | 5426 | CB | ARG | C | 153 | 68.806 | -11.349 | 19.326 | 1.00 | 45.77 | C |

FIG. 2A-118

| ATOM | 5427 | CG | ARG | C | 153 | 67.993 | -11.286 | 20.619 | 1.00 | 49.92 | C |
|------|------|------|------|---|-----|--------|---------|--------|------|-------|---|
| ATOM | 5428 | CD | ARG | C | 153 | 68.795 | -10.736 | 21.798 | 1.00 | 55.51 | C |
| ATOM | 5429 | NE | ARG | C | 153 | 69.702 | -11.745 | 22.359 | 1.00 | 65.42 | N |
| ATOM | 5430 | CZ | ARG | C | 153 | 70.598 | -11.529 | 23.328 | 1.00 | 70.46 | C |
| ATOM | 5431 | NH1AR | G | C | 153 | 70.739 | -10.314 | 23.875 | 1.00 | 67.88 | N |
| ATOM | 5432 | NH2AR | G | C | 153 | 71.356 | -12.543 | 23.765 | 1.00 | 68.79 | N |
| ATOM | 5433 | C | ARG | C | 153 | 69.978 | -13.345 | 18.442 | 1.00 | 46.49 | C |
| ATOM | 5434 | O | ARG | C | 153 | 70.182 | -13.194 | 17.230 | 1.00 | 46.68 | O |
| ATOM | 5435 | N | GLY | C | 154 | 69.682 | -14.514 | 18.998 | 1.00 | 47.61 | N |
| ATOM | 5436 | CA | GLY | C | 154 | 69.565 | -15.705 | 18.182 | 1.00 | 46.57 | C |
| ATOM | 5437 | C | GLY | C | 154 | 68.447 | -15.556 | 17.167 | 1.00 | 47.00 | C |
| ATOM | 5438 | O | GLY | C | 154 | 67.300 | -15.311 | 17.539 | 1.00 | 47.76 | O |
| ATOM | 5439 | N | ALA | C | 155 | 68.799 | -15.692 | 15.888 | 1.00 | 46.04 | N |
| ATOM | 5440 | CA | ALA | C | 155 | 67.847 | -15.592 | 14.802 | 1.00 | 44.86 | C |
| ATOM | 5441 | CB | ALA | C | 155 | 66.593 | -16.370 | 15.144 | 1.00 | 43.67 | C |
| ATOM | 5442 | C | ALA | C | 155 | 67.507 | -14.141 | 14.463 | 1.00 | 45.85 | C |
| ATOM | 5443 | O | ALA | C | 155 | 66.903 | -13.869 | 13.423 | 1.00 | 45.59 | O |
| ATOM | 5444 | N | GLN | C | 156 | 67.907 | -13.205 | 15.324 | 1.00 | 46.95 | N |
| ATOM | 5445 | CA | GLN | C | 156 | 67.636 | -11.784 | 15.091 | 1.00 | 47.22 | C |
| ATOM | 5446 | CB | GLN | C | 156 | 68.218 | -11.336 | 13.746 | 1.00 | 48.00 | C |
| ATOM | 5447 | CG | GLN | C | 156 | 69.532 | -11.997 | 13.401 | 1.00 | 51.80 | C |
| ATOM | 5448 | CD | GLN | C | 156 | 70.632 | -11.597 | 14.346 | 1.00 | 55.97 | C |
| ATOM | 5449 | OE1 | GLN | C | 156 | 71.075 | -10.444 | 14.336 | 1.00 | 59.94 | O |
| ATOM | 5450 | NE2 | GLN | C | 156 | 71.080 | -12.537 | 15.177 | 1.00 | 56.65 | N |
| ATOM | 5451 | C | GLN | C | 156 | 66.138 | -11.520 | 15.054 | 1.00 | 46.33 | C |
| ATOM | 5452 | O | GLN | C | 156 | 65.616 | -11.136 | 13.999 | 1.00 | 46.24 | O |
| ATOM | 5453 | N | ALA | C | 157 | 65.456 | -11.716 | 16.182 | 1.00 | 44.32 | N |
| ATOM | 5454 | CA | ALA | C | 157 | 64.009 | -11.488 | 16.269 | 1.00 | 41.58 | C |
| ATOM | 5455 | CB | ALA | C | 157 | 63.288 | -12.803 | 16.017 | 1.00 | 40.38 | C |
| ATOM | 5456 | C | ALA | C | 157 | 63.648 | -10.902 | 17.667 | 1.00 | 39.10 | C |
| ATOM | 5457 | O | ALA | C | 157 | 63.519 | -11.626 | 18.670 | 1.00 | 40.32 | O |
| ATOM | 5458 | N | PHE | C | 158 | 63.477 | -9.587 | 17.725 | 1.00 | 35.11 | N |
| ATOM | 5459 | CA | PHE | C | 158 | 63.206 | -8.883 | 18.983 | 1.00 | 29.49 | C |
| ATOM | 5460 | CB | PHE | C | 158 | 64.100 | -7.619 | 19.001 | 1.00 | 28.67 | C |
| ATOM | 5461 | CG | PHE | C | 158 | 64.270 | -6.981 | 20.341 | 1.00 | 26.36 | C |
| ATOM | 5462 | CD1 | PHE | C | 158 | 64.901 | -7.644 | 21.367 | 1.00 | 23.88 | C |
| ATOM | 5463 | CE1 | PHE | C | 158 | 65.071 | -7.051 | 22.602 | 1.00 | 20.56 | C |
| ATOM | 5464 | CZ | PHE | C | 158 | 64.606 | -5.791 | 22.813 | 1.00 | 23.27 | C |
| ATOM | 5465 | CE2 | PHE | C | 158 | 63.970 | -5.119 | 21.786 | 1.00 | 25.32 | C |
| ATOM | 5466 | CD2 | PHE | C | 158 | 63.807 | -5.708 | 20.569 | 1.00 | 21.07 | C |
| ATOM | 5467 | C | PHE | C | 158 | 61.717 | -8.522 | 19.065 | 1.00 | 27.43 | C |
| ATOM | 5468 | O | PHE | C | 158 | 61.143 | -7.924 | 18.128 | 1.00 | 26.19 | O |
| ATOM | 5469 | N | THR | C | 159 | 61.088 | -8.880 | 20.180 | 1.00 | 24.63 | N |
| ATOM | 5470 | CA | THR | C | 159 | 59.665 | -8.591 | 20.360 | 1.00 | 23.27 | C |
| ATOM | 5471 | CB | THR | C | 159 | 58.909 | -9.766 | 20.990 | 1.00 | 23.07 | C |
| ATOM | 5472 | OG1 | THR | C | 159 | 59.505 | -10.126 | 22.256 | 1.00 | 29.26 | O |

FIG. 2A-119

| ATOM | 5473 | CG2 | THR | C | 159 | 58.917 | -10.935 | 20.051 | 1.00 | 21.61 | C |
| ATOM | 5474 | C | THR | C | 159 | 59.414 | -7.385 | 21.238 | 1.00 | 21.34 | C |
| ATOM | 5475 | O | THR | C | 159 | 60.227 | -7.047 | 22.081 | 1.00 | 18.66 | O |
| ATOM | 5476 | N | GLU | C | 160 | 58.268 | -6.754 | 21.018 | 1.00 | 20.67 | N |
| ATOM | 5477 | CA | GLU | C | 160 | 57.852 | -5.591 | 21.769 | 1.00 | 20.68 | C |
| ATOM | 5478 | CB | GLU | C | 160 | 56.423 | -5.195 | 21.362 | 1.00 | 19.70 | C |
| ATOM | 5479 | CG | GLU | C | 160 | 55.847 | -4.015 | 22.117 | 1.00 | 21.04 | C |
| ATOM | 5480 | CD | GLU | C | 160 | 54.450 | -3.643 | 21.679 | 1.00 | 26.44 | C |
| ATOM | 5481 | OE1 | GLU | C | 160 | 54.216 | -3.598 | 20.470 | 1.00 | 29.16 | O |
| ATOM | 5482 | OE2 | GLU | C | 160 | 53.574 | -3.366 | 22.519 | 1.00 | 31.34 | O |
| ATOM | 5483 | C | GLU | C | 160 | 57.930 | -5.918 | 23.258 | 1.00 | 21.39 | C |
| ATOM | 5484 | O | GLU | C | 160 | 58.434 | -5.124 | 24.047 | 1.00 | 21.79 | O |
| ATOM | 5485 | N | ARG | C | 161 | 57.452 | -7.089 | 23.656 | 1.00 | 21.44 | N |
| ATOM | 5486 | CA | ARG | C | 161 | 57.505 | -7.443 | 25.060 | 1.00 | 22.61 | C |
| ATOM | 5487 | CB | ARG | C | 161 | 56.864 | -8.803 | 25.301 | 1.00 | 21.62 | C |
| ATOM | 5488 | CG | ARG | C | 161 | 57.115 | -9.313 | 26.716 | 1.00 | 21.74 | C |
| ATOM | 5489 | CD | ARG | C | 161 | 56.438 | -10.608 | 26.956 | 1.00 | 21.51 | C |
| ATOM | 5490 | NE | ARG | C | 161 | 55.065 | -10.552 | 26.486 | 1.00 | 20.34 | N |
| ATOM | 5491 | CZ | ARG | C | 161 | 54.267 | -11.613 | 26.433 | 1.00 | 21.57 | C |
| ATOM | 5492 | NH1AR | G | C | 161 | 54.726 | -12.795 | 26.838 | 1.00 | 17.87 | N |
| ATOM | 5493 | NH2AR | G | C | 161 | 53.030 | -11.493 | 25.954 | 1.00 | 9.78 | N |
| ATOM | 5494 | C | ARG | C | 161 | 58.937 | -7.453 | 25.606 | 1.00 | 23.97 | C |
| ATOM | 5495 | O | ARG | C | 161 | 59.166 | -7.184 | 26.785 | 1.00 | 25.79 | O |
| ATOM | 5496 | N | GLU | C | 162 | 59.892 | -7.781 | 24.753 | 1.00 | 25.39 | N |
| ATOM | 5497 | CA | GLU | C | 162 | 61.289 | -7.794 | 25.155 | 1.00 | 25.97 | C |
| ATOM | 5498 | CB | GLU | C | 162 | 62.139 | -8.388 | 24.045 | 1.00 | 28.08 | C |
| ATOM | 5499 | CG | GLU | C | 162 | 62.789 | -9.695 | 24.374 | 1.00 | 35.37 | C |
| ATOM | 5500 | CD | GLU | C | 162 | 62.953 | -10.552 | 23.142 | 1.00 | 44.35 | C |
| ATOM | 5501 | OE1 | GLU | C | 162 | 63.452 | -11.697 | 23.303 | 1.00 | 51.84 | O |
| ATOM | 5502 | OE2 | GLU | C | 162 | 62.572 | -10.087 | 22.019 | 1.00 | 46.48 | O |
| ATOM | 5503 | C | GLU | C | 162 | 61.733 | -6.351 | 25.393 | 1.00 | 23.78 | C |
| ATOM | 5504 | O | GLU | C | 162 | 62.447 | -6.060 | 26.338 | 1.00 | 24.85 | O |
| ATOM | 5505 | N | ALA | C | 163 | 61.307 | -5.465 | 24.507 | 1.00 | 21.50 | N |
| ATOM | 5506 | CA | ALA | C | 163 | 61.610 | -4.071 | 24.589 | 1.00 | 19.63 | C |
| ATOM | 5507 | CB | ALA | C | 163 | 60.879 | -3.363 | 23.533 | 1.00 | 19.24 | C |
| ATOM | 5508 | C | ALA | C | 163 | 61.161 | -3.594 | 25.945 | 1.00 | 20.95 | C |
| ATOM | 5509 | O | ALA | C | 163 | 61.905 | -2.953 | 26.679 | 1.00 | 21.13 | O |
| ATOM | 5510 | N | SER | C | 164 | 59.934 | -3.925 | 26.289 | 1.00 | 21.66 | N |
| ATOM | 5511 | CA | SER | C | 164 | 59.376 | -3.549 | 27.573 | 1.00 | 22.51 | C |
| ATOM | 5512 | CB | SER | C | 164 | 58.015 | -4.195 | 27.743 | 1.00 | 22.30 | C |
| ATOM | 5513 | OG | SER | C | 164 | 57.396 | -3.799 | 28.953 | 1.00 | 27.91 | O |
| ATOM | 5514 | C | SER | C | 164 | 60.245 | -3.990 | 28.724 | 1.00 | 22.16 | C |
| ATOM | 5515 | O | SER | C | 164 | 60.766 | -3.187 | 29.470 | 1.00 | 20.20 | O |
| ATOM | 5516 | N | GLU | C | 165 | 60.395 | -5.292 | 28.890 | 1.00 | 21.68 | N |
| ATOM | 5517 | CA | GLU | C | 165 | 61.185 | -5.772 | 30.007 | 1.00 | 22.61 | C |
| ATOM | 5518 | CB | GLU | C | 165 | 61.382 | -7.287 | 29.884 | 1.00 | 19.93 | C |

FIG. 2A-120

| | | | | | | | | | | |
|---|---|---|---|---|---|---|---|---|---|---|
| ATOM | 5519 | CG | GLU | C | 165 | 60.079 | -7.975 | 29.580 | 1.00 | 27.87 | C |
| ATOM | 5520 | CD | GLU | C | 165 | 60.233 | -9.426 | 29.123 | 1.00 | 38.11 | C |
| ATOM | 5521 | OE1 | GLU | C | 165 | 61.081 | -9.712 | 28.234 | 1.00 | 41.13 | O |
| ATOM | 5522 | OE2 | GLU | C | 165 | 59.485 | -10.276 | 29.662 | 1.00 | 41.26 | O |
| ATOM | 5523 | C | GLU | C | 165 | 62.522 | -5.012 | 30.107 | 1.00 | 22.91 | C |
| ATOM | 5524 | O | GLU | C | 165 | 62.952 | -4.614 | 31.200 | 1.00 | 24.01 | O |
| ATOM | 5525 | N | ILE | C | 166 | 63.184 | -4.788 | 28.984 | 1.00 | 21.96 | N |
| ATOM | 5526 | CA | ILE | C | 166 | 64.427 | -4.065 | 29.082 | 1.00 | 20.99 | C |
| ATOM | 5527 | CB | ILE | C | 166 | 65.157 | -4.017 | 27.760 | 1.00 | 20.98 | C |
| ATOM | 5528 | CG1 | ILE | C | 166 | 65.800 | -5.381 | 27.482 | 1.00 | 20.81 | C |
| ATOM | 5529 | CD1 | ILE | C | 166 | 66.494 | -5.507 | 26.119 | 1.00 | 17.02 | C |
| ATOM | 5530 | CG2 | ILE | C | 166 | 66.144 | -2.875 | 27.772 | 1.00 | 18.77 | C |
| ATOM | 5531 | C | ILE | C | 166 | 64.141 | -2.640 | 29.563 | 1.00 | 22.26 | C |
| ATOM | 5532 | O | ILE | C | 166 | 64.787 | -2.183 | 30.526 | 1.00 | 22.56 | O |
| ATOM | 5533 | N | MSEC | | 167 | 63.182 | -1.945 | 28.931 | 1.00 | 22.01 | N |
| ATOM | 5534 | CA | MSEC | | 167 | 62.869 | -0.588 | 29.365 | 1.00 | 21.30 | C |
| ATOM | 5535 | CB | MSEC | | 167 | 61.706 | 0.012 | 28.596 | 1.00 | 20.71 | C |
| ATOM | 5536 | CG | MSEC | | 167 | 62.065 | 0.504 | 27.194 | 1.00 | 24.04 | C |
| ATOM | 5537 | SE | MSEC | | 167 | 63.712 | 1.494 | 27.046 | 1.00 | 28.77 | S |
| ATOM | 5538 | CE | MSEC | | 167 | 63.178 | 2.913 | 28.291 | 1.00 | 20.46 | C |
| ATOM | 5539 | C | MSEC | | 167 | 62.553 | -0.498 | 30.855 | 1.00 | 21.24 | C |
| ATOM | 5540 | O | MSEC | | 167 | 62.864 | 0.493 | 31.511 | 1.00 | 20.60 | O |
| ATOM | 5541 | N | LYS | C | 168 | 61.962 | -1.544 | 31.399 | 1.00 | 20.39 | N |
| ATOM | 5542 | CA | LYS | C | 168 | 61.596 | -1.533 | 32.796 | 1.00 | 21.33 | C |
| ATOM | 5543 | CB | LYS | C | 168 | 60.552 | -2.620 | 33.060 | 1.00 | 20.02 | C |
| ATOM | 5544 | CG | LYS | C | 168 | 60.089 | -2.632 | 34.490 | 1.00 | 15.10 | C |
| ATOM | 5545 | CD | LYS | C | 168 | 59.025 | -3.647 | 34.704 | 1.00 | 26.38 | C |
| ATOM | 5546 | CE | LYS | C | 168 | 58.880 | -3.961 | 36.185 | 1.00 | 32.12 | C |
| ATOM | 5547 | NZ | LYS | C | 168 | 57.586 | -4.698 | 36.399 | 1.00 | 38.05 | N |
| ATOM | 5548 | C | LYS | C | 168 | 62.781 | -1.660 | 33.756 | 1.00 | 23.28 | C |
| ATOM | 5549 | O | LYS | C | 168 | 62.732 | -1.172 | 34.882 | 1.00 | 24.13 | O |
| ATOM | 5550 | N | SER | C | 169 | 63.862 | -2.298 | 33.336 | 1.00 | 24.77 | N |
| ATOM | 5551 | CA | SER | C | 169 | 64.990 | -2.382 | 34.251 | 1.00 | 27.16 | C |
| ATOM | 5552 | CB | SER | C | 169 | 65.843 | -3.604 | 33.958 | 1.00 | 26.52 | C |
| ATOM | 5553 | OG | SER | C | 169 | 65.898 | -3.750 | 32.574 | 1.00 | 29.01 | O |
| ATOM | 5554 | C | SER | C | 169 | 65.815 | -1.116 | 34.117 | 1.00 | 28.05 | C |
| ATOM | 5555 | O | SER | C | 169 | 66.441 | -0.705 | 35.075 | 1.00 | 30.45 | O |
| ATOM | 5556 | N | ILE | C | 170 | 65.836 | -0.514 | 32.934 | 1.00 | 26.75 | N |
| ATOM | 5557 | CA | ILE | C | 170 | 66.580 | 0.712 | 32.789 | 1.00 | 26.86 | C |
| ATOM | 5558 | CB | ILE | C | 170 | 66.503 | 1.250 | 31.355 | 1.00 | 29.06 | C |
| ATOM | 5559 | CG1 | ILE | C | 170 | 67.079 | 0.241 | 30.370 | 1.00 | 27.34 | C |
| ATOM | 5560 | CD1 | ILE | C | 170 | 66.872 | 0.654 | 28.924 | 1.00 | 25.53 | C |
| ATOM | 5561 | CG2 | ILE | C | 170 | 67.308 | 2.529 | 31.240 | 1.00 | 24.68 | C |
| ATOM | 5562 | C | ILE | C | 170 | 65.819 | 1.685 | 33.698 | 1.00 | 28.22 | C |
| ATOM | 5563 | O | ILE | C | 170 | 66.401 | 2.452 | 34.492 | 1.00 | 25.37 | O |
| ATOM | 5564 | N | GLY | C | 171 | 64.497 | 1.623 | 33.569 | 1.00 | 28.78 | N |

FIG. 2A-121

| ATOM | 5565 | CA  | GLY | C | 171 | 63.617 | 2.460  | 34.360 | 1.00 | 28.11 | C |
|------|------|-----|-----|---|-----|--------|--------|--------|------|-------|---|
| ATOM | 5566 | C   | GLY | C | 171 | 63.857 | 2.268  | 35.831 | 1.00 | 28.34 | C |
| ATOM | 5567 | O   | GLY | C | 171 | 63.701 | 3.206  | 36.588 | 1.00 | 28.12 | O |
| ATOM | 5568 | N   | GLU | C | 172 | 64.226 | 1.062  | 36.255 | 1.00 | 27.78 | N |
| ATOM | 5569 | CA  | GLU | C | 172 | 64.501 | 0.817  | 37.671 | 1.00 | 28.83 | C |
| ATOM | 5570 | CB  | GLU | C | 172 | 64.762 | -0.648 | 37.929 | 1.00 | 30.52 | C |
| ATOM | 5571 | CG  | GLU | C | 172 | 63.524 | -1.469 | 37.915 | 1.00 | 40.18 | C |
| ATOM | 5572 | CD  | GLU | C | 172 | 63.820 | -2.878 | 38.340 | 1.00 | 57.65 | C |
| ATOM | 5573 | OE1 | GLU | C | 172 | 64.279 | -3.031 | 39.505 | 1.00 | 61.48 | O |
| ATOM | 5574 | OE2 | GLU | C | 172 | 63.609 | -3.814 | 37.516 | 1.00 | 64.26 | O |
| ATOM | 5575 | C   | GLU | C | 172 | 65.699 | 1.590  | 38.171 | 1.00 | 28.06 | C |
| ATOM | 5576 | O   | GLU | C | 172 | 65.679 | 2.132  | 39.258 | 1.00 | 29.44 | O |
| ATOM | 5577 | N   | ALA | C | 173 | 66.762 | 1.612  | 37.391 | 1.00 | 27.02 | N |
| ATOM | 5578 | CA  | ALA | C | 173 | 67.918 | 2.354  | 37.790 | 1.00 | 27.17 | C |
| ATOM | 5579 | CB  | ALA | C | 173 | 69.051 | 2.081  | 36.823 | 1.00 | 26.82 | C |
| ATOM | 5580 | C   | ALA | C | 173 | 67.591 | 3.881  | 37.852 | 1.00 | 27.36 | C |
| ATOM | 5581 | O   | ALA | C | 173 | 67.991 | 4.566  | 38.797 | 1.00 | 29.28 | O |
| ATOM | 5582 | N   | ILE | C | 174 | 66.883 | 4.417  | 36.860 | 1.00 | 26.57 | N |
| ATOM | 5583 | CA  | ILE | C | 174 | 66.549 | 5.830  | 36.901 | 1.00 | 25.19 | C |
| ATOM | 5584 | CB  | ILE | C | 174 | 65.845 | 6.312  | 35.616 | 1.00 | 25.03 | C |
| ATOM | 5585 | CG1 | ILE | C | 174 | 66.783 | 6.207  | 34.407 | 1.00 | 23.76 | C |
| ATOM | 5586 | CD1 | ILE | C | 174 | 68.256 | 6.353  | 34.732 | 1.00 | 20.30 | C |
| ATOM | 5587 | CG2 | ILE | C | 174 | 65.278 | 7.715  | 35.845 | 1.00 | 21.30 | C |
| ATOM | 5588 | C   | ILE | C | 174 | 65.613 | 6.167  | 38.079 | 1.00 | 26.21 | C |
| ATOM | 5589 | O   | ILE | C | 174 | 65.748 | 7.226  | 38.726 | 1.00 | 27.76 | O |
| ATOM | 5590 | N   | GLN | C | 175 | 64.669 | 5.282  | 38.371 | 1.00 | 22.80 | N |
| ATOM | 5591 | CA  | GLN | C | 175 | 63.753 | 5.543  | 39.453 | 1.00 | 21.40 | C |
| ATOM | 5592 | CB  | GLN | C | 175 | 62.670 | 4.478  | 39.513 | 1.00 | 19.06 | C |
| ATOM | 5593 | CG  | GLN | C | 175 | 61.647 | 4.712  | 40.612 | 1.00 | 24.06 | C |
| ATOM | 5594 | CD  | GLN | C | 175 | 60.726 | 3.546  | 40.748 | 1.00 | 30.54 | C |
| ATOM | 5595 | OE1 | GLN | C | 175 | 61.179 | 2.436  | 40.955 | 1.00 | 33.42 | O |
| ATOM | 5596 | NE2 | GLN | C | 175 | 59.426 | 3.774  | 40.626 | 1.00 | 34.46 | N |
| ATOM | 5597 | C   | GLN | C | 175 | 64.485 | 5.587  | 40.774 | 1.00 | 21.38 | C |
| ATOM | 5598 | O   | GLN | C | 175 | 64.247 | 6.464  | 41.600 | 1.00 | 21.54 | O |
| ATOM | 5599 | N   | TYR | C | 176 | 65.396 | 4.650  | 40.981 | 1.00 | 21.02 | N |
| ATOM | 5600 | CA  | TYR | C | 176 | 66.105 | 4.627  | 42.236 | 1.00 | 21.65 | C |
| ATOM | 5601 | CB  | TYR | C | 176 | 67.106 | 3.499  | 42.290 | 1.00 | 20.39 | C |
| ATOM | 5602 | CG  | TYR | C | 176 | 67.702 | 3.427  | 43.653 | 1.00 | 20.37 | C |
| ATOM | 5603 | CD1 | TYR | C | 176 | 66.891 | 3.225  | 44.757 | 1.00 | 22.07 | C |
| ATOM | 5604 | CE1 | TYR | C | 176 | 67.406 | 3.249  | 46.021 | 1.00 | 25.19 | C |
| ATOM | 5605 | CZ  | TYR | C | 176 | 68.756 | 3.468  | 46.198 | 1.00 | 27.12 | C |
| ATOM | 5606 | OH  | TYR | C | 176 | 69.267 | 3.524  | 47.465 | 1.00 | 30.45 | O |
| ATOM | 5607 | CE2 | TYR | C | 176 | 69.591 | 3.664  | 45.112 | 1.00 | 26.88 | C |
| ATOM | 5608 | CD2 | TYR | C | 176 | 69.061 | 3.645  | 43.852 | 1.00 | 23.21 | C |
| ATOM | 5609 | C   | TYR | C | 176 | 66.858 | 5.907  | 42.399 | 1.00 | 23.10 | C |
| ATOM | 5610 | O   | TYR | C | 176 | 66.752 | 6.584  | 43.422 | 1.00 | 22.85 | O |

FIG. 2A-122

| | | | | | | | | | | |
|---|---|---|---|---|---|---|---|---|---|---|
| ATOM | 5611 | N | LEU | C | 177 | 67.638 | 6.209 | 41.373 | 1.00 | 22.46 | N |
| ATOM | 5612 | CA | LEU | C | 177 | 68.442 | 7.396 | 41.340 | 1.00 | 22.48 | C |
| ATOM | 5613 | CB | LEU | C | 177 | 69.095 | 7.547 | 39.982 | 1.00 | 23.55 | C |
| ATOM | 5614 | CG | LEU | C | 177 | 70.394 | 6.820 | 39.675 | 1.00 | 20.89 | C |
| ATOM | 5615 | CD1 | LEU | C | 177 | 70.841 | 7.272 | 38.318 | 1.00 | 17.78 | C |
| ATOM | 5616 | CD2 | LEU | C | 177 | 71.452 | 7.138 | 40.716 | 1.00 | 25.12 | C |
| ATOM | 5617 | C | LEU | C | 177 | 67.628 | 8.645 | 41.627 | 1.00 | 24.32 | C |
| ATOM | 5618 | O | LEU | C | 177 | 67.974 | 9.436 | 42.509 | 1.00 | 25.87 | O |
| ATOM | 5619 | N | HIS | C | 178 | 66.543 | 8.840 | 40.895 | 1.00 | 23.47 | N |
| ATOM | 5620 | CA | HIS | C | 178 | 65.769 | 10.050 | 41.143 | 1.00 | 22.81 | C |
| ATOM | 5621 | CB | HIS | C | 178 | 64.700 | 10.225 | 40.070 | 1.00 | 22.74 | C |
| ATOM | 5622 | CG | HIS | C | 178 | 65.283 | 10.529 | 38.731 | 1.00 | 20.40 | C |
| ATOM | 5623 | ND1 | HIS | C | 178 | 64.522 | 10.715 | 37.602 | 1.00 | 18.18 | N |
| ATOM | 5624 | CE1 | HIS | C | 178 | 65.318 | 10.979 | 36.582 | 1.00 | 16.20 | C |
| ATOM | 5625 | NE2 | HIS | C | 178 | 66.567 | 10.968 | 37.008 | 1.00 | 17.88 | N |
| ATOM | 5626 | CD2 | HIS | C | 178 | 66.573 | 10.692 | 38.349 | 1.00 | 19.95 | C |
| ATOM | 5627 | C | HIS | C | 178 | 65.170 | 10.154 | 42.516 | 1.00 | 21.81 | C |
| ATOM | 5628 | O | HIS | C | 178 | 65.018 | 11.244 | 43.031 | 1.00 | 20.31 | O |
| ATOM | 5629 | N | SER | C | 179 | 64.855 | 9.027 | 43.141 | 1.00 | 22.63 | N |
| ATOM | 5630 | CA | SER | C | 179 | 64.262 | 9.085 | 44.460 | 1.00 | 21.04 | C |
| ATOM | 5631 | CB | SER | C | 179 | 63.635 | 7.772 | 44.818 | 1.00 | 19.72 | C |
| ATOM | 5632 | OG | SER | C | 179 | 64.666 | 6.819 | 44.893 | 1.00 | 21.07 | O |
| ATOM | 5633 | C | SER | C | 179 | 65.284 | 9.440 | 45.507 | 1.00 | 19.65 | C |
| ATOM | 5634 | O | SER | C | 179 | 64.914 | 9.739 | 46.622 | 1.00 | 22.11 | O |
| ATOM | 5635 | N | ILE | C | 180 | 66.568 | 9.389 | 45.202 | 1.00 | 18.35 | N |
| ATOM | 5636 | CA | ILE | C | 180 | 67.507 | 9.787 | 46.219 | 1.00 | 19.32 | C |
| ATOM | 5637 | CB | ILE | C | 180 | 68.509 | 8.675 | 46.539 | 1.00 | 18.39 | C |
| ATOM | 5638 | CG1 | ILE | C | 180 | 69.407 | 8.406 | 45.342 | 1.00 | 20.04 | C |
| ATOM | 5639 | CD1 | ILE | C | 180 | 70.545 | 7.416 | 45.662 | 1.00 | 18.99 | C |
| ATOM | 5640 | CG2 | ILE | C | 180 | 67.791 | 7.423 | 46.906 | 1.00 | 12.78 | C |
| ATOM | 5641 | C | ILE | C | 180 | 68.218 | 11.047 | 45.711 | 1.00 | 21.24 | C |
| ATOM | 5642 | O | ILE | C | 180 | 69.348 | 11.358 | 46.089 | 1.00 | 22.47 | O |
| ATOM | 5643 | N | ASN | C | 181 | 67.504 | 11.757 | 44.844 | 1.00 | 21.14 | N |
| ATOM | 5644 | CA | ASN | C | 181 | 67.924 | 12.992 | 44.219 | 1.00 | 20.75 | C |
| ATOM | 5645 | CB | ASN | C | 181 | 67.898 | 14.132 | 45.208 | 1.00 | 22.67 | C |
| ATOM | 5646 | CG | ASN | C | 181 | 66.507 | 14.429 | 45.691 | 1.00 | 25.33 | C |
| ATOM | 5647 | OD1 | ASN | C | 181 | 66.198 | 14.215 | 46.856 | 1.00 | 28.37 | O |
| ATOM | 5648 | ND2 | ASN | C | 181 | 65.646 | 14.899 | 44.786 | 1.00 | 26.28 | N |
| ATOM | 5649 | C | ASN | C | 181 | 69.227 | 13.022 | 43.506 | 1.00 | 22.27 | C |
| ATOM | 5650 | O | ASN | C | 181 | 70.076 | 13.853 | 43.791 | 1.00 | 23.02 | O |
| ATOM | 5651 | N | ILE | C | 182 | 69.362 | 12.123 | 42.544 | 1.00 | 23.03 | N |
| ATOM | 5652 | CA | ILE | C | 182 | 70.528 | 12.024 | 41.713 | 1.00 | 22.78 | C |
| ATOM | 5653 | CB | ILE | C | 182 | 71.374 | 10.770 | 42.071 | 1.00 | 24.15 | C |
| ATOM | 5654 | CG1 | ILE | C | 182 | 71.841 | 10.878 | 43.516 | 1.00 | 22.92 | C |
| ATOM | 5655 | CD1 | ILE | C | 182 | 72.397 | 9.634 | 44.082 | 1.00 | 26.51 | C |
| ATOM | 5656 | CG2 | ILE | C | 182 | 72.593 | 10.658 | 41.156 | 1.00 | 20.80 | C |

FIG. 2A-123

| ATOM | 5657 | C | ILE | C | 182 | 69.950 | 11.907 | 40.301 | 1.00 | 25.36 | C |
| --- | --- | --- | --- | --- | --- | --- | --- | --- | --- | --- | --- |
| ATOM | 5658 | O | ILE | C | 182 | 68.936 | 11.207 | 40.056 | 1.00 | 25.45 | O |
| ATOM | 5659 | N | ALA | C | 183 | 70.559 | 12.658 | 39.394 | 1.00 | 25.51 | N |
| ATOM | 5660 | CA | ALA | C | 183 | 70.171 | 12.664 | 38.008 | 1.00 | 25.34 | C |
| ATOM | 5661 | CB | ALA | C | 183 | 69.889 | 14.070 | 37.541 | 1.00 | 23.30 | C |
| ATOM | 5662 | C | ALA | C | 183 | 71.482 | 12.161 | 37.456 | 1.00 | 25.65 | C |
| ATOM | 5663 | O | ALA | C | 183 | 72.538 | 12.649 | 37.855 | 1.00 | 26.56 | O |
| ATOM | 5664 | N | HIS | C | 184 | 71.405 | 11.170 | 36.563 | 1.00 | 25.36 | N |
| ATOM | 5665 | CA | HIS | C | 184 | 72.560 | 10.550 | 35.958 | 1.00 | 24.74 | C |
| ATOM | 5666 | CB | HIS | C | 184 | 72.167 | 9.219 | 35.324 | 1.00 | 25.59 | C |
| ATOM | 5667 | CG | HIS | C | 184 | 73.316 | 8.508 | 34.698 | 1.00 | 26.77 | C |
| ATOM | 5668 | ND1 | HIS | C | 184 | 74.166 | 7.699 | 35.428 | 1.00 | 31.30 | N |
| ATOM | 5669 | CE1 | HIS | C | 184 | 75.206 | 7.357 | 34.686 | 1.00 | 25.89 | C |
| ATOM | 5670 | NE2 | HIS | C | 184 | 75.057 | 7.910 | 33.499 | 1.00 | 26.75 | N |
| ATOM | 5671 | CD2 | HIS | C | 184 | 73.879 | 8.628 | 33.473 | 1.00 | 25.59 | C |
| ATOM | 5672 | C | HIS | C | 184 | 73.155 | 11.463 | 34.908 | 1.00 | 26.39 | C |
| ATOM | 5673 | O | HIS | C | 184 | 74.347 | 11.678 | 34.853 | 1.00 | 26.14 | O |
| ATOM | 5674 | N | ARG | C | 185 | 72.305 | 11.985 | 34.056 | 1.00 | 27.35 | N |
| ATOM | 5675 | CA | ARG | C | 185 | 72.732 | 12.876 | 33.005 | 1.00 | 28.49 | C |
| ATOM | 5676 | CB | ARG | C | 185 | 73.279 | 14.134 | 33.609 | 1.00 | 26.07 | C |
| ATOM | 5677 | CG | ARG | C | 185 | 72.199 | 14.772 | 34.455 | 1.00 | 28.87 | C |
| ATOM | 5678 | CD | ARG | C | 185 | 72.547 | 16.156 | 34.861 | 1.00 | 26.09 | C |
| ATOM | 5679 | NE | ARG | C | 185 | 73.989 | 16.288 | 34.982 | 1.00 | 25.39 | N |
| ATOM | 5680 | CZ | ARG | C | 185 | 74.590 | 17.460 | 35.074 | 1.00 | 28.97 | C |
| ATOM | 5681 | NH1AR | G | C | 185 | 73.842 | 18.572 | 35.050 | 1.00 | 24.16 | N |
| ATOM | 5682 | NH2AR | G | C | 185 | 75.913 | 17.512 | 35.199 | 1.00 | 28.44 | N |
| ATOM | 5683 | C | ARG | C | 185 | 73.638 | 12.354 | 31.898 | 1.00 | 30.22 | C |
| ATOM | 5684 | O | ARG | C | 185 | 74.140 | 13.140 | 31.095 | 1.00 | 30.18 | O |
| ATOM | 5685 | N | ASP | C | 186 | 73.881 | 11.040 | 31.838 | 1.00 | 30.38 | N |
| ATOM | 5686 | CA | ASP | C | 186 | 74.598 | 10.539 | 30.677 | 1.00 | 30.26 | C |
| ATOM | 5687 | CB | ASP | C | 186 | 76.107 | 10.590 | 30.835 | 1.00 | 31.08 | C |
| ATOM | 5688 | CG | ASP | C | 186 | 76.825 | 10.544 | 29.494 | 1.00 | 34.42 | C |
| ATOM | 5689 | OD1 | ASP | C | 186 | 76.336 | 11.163 | 28.526 | 1.00 | 30.19 | O |
| ATOM | 5690 | OD2 | ASP | C | 186 | 77.894 | 9.894 | 29.412 | 1.00 | 39.21 | O |
| ATOM | 5691 | C | ASP | C | 186 | 74.095 | 9.149 | 30.342 | 1.00 | 30.16 | C |
| ATOM | 5692 | O | ASP | C | 186 | 74.823 | 8.297 | 29.860 | 1.00 | 29.93 | O |
| ATOM | 5693 | N | VAL | C | 187 | 72.802 | 8.961 | 30.608 | 1.00 | 29.89 | N |
| ATOM | 5694 | CA | VAL | C | 187 | 72.064 | 7.728 | 30.304 | 1.00 | 29.57 | C |
| ATOM | 5695 | CB | VAL | C | 187 | 70.602 | 7.817 | 30.790 | 1.00 | 31.18 | C |
| ATOM | 5696 | CG1 | VAL | C | 187 | 69.812 | 6.589 | 30.272 | 1.00 | 27.65 | C |
| ATOM | 5697 | CG2 | VAL | C | 187 | 70.550 | 7.932 | 32.312 | 1.00 | 25.83 | C |
| ATOM | 5698 | C | VAL | C | 187 | 72.000 | 7.541 | 28.781 | 1.00 | 29.28 | C |
| ATOM | 5699 | O | VAL | C | 187 | 71.233 | 8.192 | 28.100 | 1.00 | 29.98 | O |
| ATOM | 5700 | N | LYS | C | 188 | 72.800 | 6.655 | 28.243 | 1.00 | 27.48 | N |
| ATOM | 5701 | CA | LYS | C | 188 | 72.792 | 6.465 | 26.812 | 1.00 | 25.89 | C |
| ATOM | 5702 | CB | LYS | C | 188 | 73.872 | 7.313 | 26.155 | 1.00 | 25.74 | C |

FIG. 2A-124

| ATOM | 5703 | CG | LYS | C | 188 | 75.192 | 7.062 | 26.793 | 1.00 | 23.64 | C |
|---|---|---|---|---|---|---|---|---|---|---|---|
| ATOM | 5704 | CD | LYS | C | 188 | 76.280 | 7.757 | 26.105 | 1.00 | 26.04 | C |
| ATOM | 5705 | CE | LYS | C | 188 | 77.545 | 7.534 | 26.893 | 1.00 | 31.30 | C |
| ATOM | 5706 | NZ | LYS | C | 188 | 78.671 | 8.280 | 26.272 | 1.00 | 34.87 | N |
| ATOM | 5707 | C | LYS | C | 188 | 73.132 | 5.019 | 26.663 | 1.00 | 24.57 | C |
| ATOM | 5708 | O | LYS | C | 188 | 73.683 | 4.422 | 27.580 | 1.00 | 25.60 | O |
| ATOM | 5709 | N | PRO | C | 189 | 72.826 | 4.440 | 25.497 | 1.00 | 23.17 | N |
| ATOM | 5710 | CA | PRO | C | 189 | 73.051 | 3.055 | 25.117 | 1.00 | 22.78 | C |
| ATOM | 5711 | CB | PRO | C | 189 | 72.949 | 3.132 | 23.600 | 1.00 | 22.65 | C |
| ATOM | 5712 | CG | PRO | C | 189 | 71.866 | 4.094 | 23.408 | 1.00 | 20.39 | C |
| ATOM | 5713 | CD | PRO | C | 189 | 72.265 | 5.189 | 24.352 | 1.00 | 24.29 | C |
| ATOM | 5714 | C | PRO | C | 189 | 74.366 | 2.430 | 25.589 | 1.00 | 22.21 | C |
| ATOM | 5715 | O | PRO | C | 189 | 74.393 | 1.409 | 26.301 | 1.00 | 22.20 | O |
| ATOM | 5716 | N | GLU | C | 190 | 75.460 | 3.065 | 25.212 | 1.00 | 20.68 | N |
| ATOM | 5717 | CA | GLU | C | 190 | 76.763 | 2.550 | 25.523 | 1.00 | 21.18 | C |
| ATOM | 5718 | CB | GLU | C | 190 | 77.765 | 3.296 | 24.674 | 1.00 | 20.66 | C |
| ATOM | 5719 | CG | GLU | C | 190 | 77.339 | 3.468 | 23.201 | 1.00 | 28.76 | C |
| ATOM | 5720 | CD | GLU | C | 190 | 76.065 | 4.369 | 22.974 | 1.00 | 41.00 | C |
| ATOM | 5721 | OE1 | GLU | C | 190 | 75.569 | 4.987 | 23.941 | 1.00 | 43.25 | O |
| ATOM | 5722 | OE2 | GLU | C | 190 | 75.553 | 4.459 | 21.817 | 1.00 | 40.15 | O |
| ATOM | 5723 | C | GLU | C | 190 | 77.158 | 2.537 | 27.001 | 1.00 | 22.66 | C |
| ATOM | 5724 | O | GLU | C | 190 | 78.213 | 1.992 | 27.344 | 1.00 | 25.55 | O |
| ATOM | 5725 | N | ASN | C | 191 | 76.334 | 3.136 | 27.872 | 1.00 | 21.02 | N |
| ATOM | 5726 | CA | ASN | C | 191 | 76.595 | 3.133 | 29.309 | 1.00 | 22.68 | C |
| ATOM | 5727 | CB | ASN | C | 191 | 76.252 | 4.479 | 29.972 | 1.00 | 23.88 | C |
| ATOM | 5728 | CG | ASN | C | 191 | 77.338 | 5.545 | 29.824 | 1.00 | 26.13 | C |
| ATOM | 5729 | OD1 | ASN | C | 191 | 78.479 | 5.261 | 29.491 | 1.00 | 27.90 | O |
| ATOM | 5730 | ND2 | ASN | C | 191 | 76.973 | 6.788 | 30.108 | 1.00 | 34.17 | N |
| ATOM | 5731 | C | ASN | C | 191 | 75.732 | 2.042 | 29.965 | 1.00 | 23.78 | C |
| ATOM | 5732 | O | ASN | C | 191 | 75.650 | 1.939 | 31.209 | 1.00 | 23.40 | O |
| ATOM | 5733 | N | LEU | C | 192 | 75.053 | 1.242 | 29.144 | 1.00 | 23.24 | N |
| ATOM | 5734 | CA | LEU | C | 192 | 74.254 | 0.138 | 29.681 | 1.00 | 22.69 | C |
| ATOM | 5735 | CB | LEU | C | 192 | 72.823 | 0.227 | 29.142 | 1.00 | 24.16 | C |
| ATOM | 5736 | CG | LEU | C | 192 | 72.032 | 1.385 | 29.789 | 1.00 | 21.84 | C |
| ATOM | 5737 | CD1 | LEU | C | 192 | 70.771 | 1.707 | 29.009 | 1.00 | 22.04 | C |
| ATOM | 5738 | CD2 | LEU | C | 192 | 71.714 | 0.998 | 31.209 | 1.00 | 20.28 | C |
| ATOM | 5739 | C | LEU | C | 192 | 74.948 | -1.189 | 29.303 | 1.00 | 22.86 | C |
| ATOM | 5740 | O | LEU | C | 192 | 74.969 | -1.594 | 28.150 | 1.00 | 25.82 | O |
| ATOM | 5741 | N | LEU | C | 193 | 75.537 | -1.855 | 30.288 | 1.00 | 21.75 | N |
| ATOM | 5742 | CA | LEU | C | 193 | 76.276 | -3.076 | 30.034 | 1.00 | 21.66 | C |
| ATOM | 5743 | CB | LEU | C | 193 | 77.720 | -2.972 | 30.502 | 1.00 | 22.86 | C |
| ATOM | 5744 | CG | LEU | C | 193 | 78.535 | -1.785 | 30.036 | 1.00 | 23.50 | C |
| ATOM | 5745 | CD1 | LEU | C | 193 | 79.990 | -1.981 | 30.462 | 1.00 | 23.48 | C |
| ATOM | 5746 | CD2 | LEU | C | 193 | 78.387 | -1.630 | 28.585 | 1.00 | 22.44 | C |
| ATOM | 5747 | C | LEU | C | 193 | 75.701 | -4.209 | 30.802 | 1.00 | 21.62 | C |
| ATOM | 5748 | O | LEU | C | 193 | 75.343 | -4.036 | 31.988 | 1.00 | 22.89 | O |

FIG. 2A-125

| ATOM | 5749 | N | TYR | C | 194 | 75.690 | -5.384 | 30.134 | 1.00 | 19.19 | N |
|---|---|---|---|---|---|---|---|---|---|---|---|
| ATOM | 5750 | CA | TYR | C | 194 | 75.189 | -6.628 | 30.710 | 1.00 | 18.14 | C |
| ATOM | 5751 | CB | TYR | C | 194 | 74.811 | -7.576 | 29.603 | 1.00 | 17.95 | C |
| ATOM | 5752 | CG | TYR | C | 194 | 73.386 | -7.393 | 29.190 | 1.00 | 20.27 | C |
| ATOM | 5753 | CD1 | TYR | C | 194 | 72.342 | -7.694 | 30.063 | 1.00 | 22.11 | C |
| ATOM | 5754 | CE1 | TYR | C | 194 | 71.037 | -7.455 | 29.716 | 1.00 | 17.92 | C |
| ATOM | 5755 | CZ | TYR | C | 194 | 70.768 | -6.914 | 28.493 | 1.00 | 21.17 | C |
| ATOM | 5756 | OH | TYR | C | 194 | 69.478 | -6.682 | 28.089 | 1.00 | 21.13 | O |
| ATOM | 5757 | CE2 | TYR | C | 194 | 71.776 | -6.610 | 27.617 | 1.00 | 24.27 | C |
| ATOM | 5758 | CD2 | TYR | C | 194 | 73.071 | -6.854 | 27.965 | 1.00 | 20.96 | C |
| ATOM | 5759 | C | TYR | C | 194 | 76.213 | -7.235 | 31.634 | 1.00 | 17.60 | C |
| ATOM | 5760 | O | TYR | C | 194 | 77.393 | -7.031 | 31.469 | 1.00 | 16.73 | O |
| ATOM | 5761 | N | THR | C | 195 | 75.762 | -7.963 | 32.632 | 1.00 | 17.86 | N |
| ATOM | 5762 | CA | THR | C | 195 | 76.670 | -8.560 | 33.590 | 1.00 | 19.72 | C |
| ATOM | 5763 | CB | THR | C | 195 | 75.921 | -9.171 | 34.756 | 1.00 | 20.17 | C |
| ATOM | 5764 | OG1 | THR | C | 195 | 74.751 | -9.844 | 34.254 | 1.00 | 25.48 | O |
| ATOM | 5765 | CG2 | THR | C | 195 | 75.545 | -8.075 | 35.802 | 1.00 | 20.31 | C |
| ATOM | 5766 | C | THR | C | 195 | 77.469 | -9.648 | 32.976 | 1.00 | 22.06 | C |
| ATOM | 5767 | O | THR | C | 195 | 78.684 | -9.698 | 33.121 | 1.00 | 23.36 | O |
| ATOM | 5768 | N | SER | C | 196 | 76.786 | -10.537 | 32.273 | 1.00 | 22.22 | N |
| ATOM | 5769 | CA | SER | C | 196 | 77.480 | -11.651 | 31.649 | 1.00 | 24.94 | C |
| ATOM | 5770 | CB | SER | C | 196 | 77.385 | -12.887 | 32.534 | 1.00 | 25.49 | C |
| ATOM | 5771 | OG | SER | C | 196 | 76.047 | -13.362 | 32.486 | 1.00 | 28.57 | O |
| ATOM | 5772 | C | SER | C | 196 | 76.809 | -11.967 | 30.338 | 1.00 | 27.03 | C |
| ATOM | 5773 | O | SER | C | 196 | 75.790 | -11.361 | 30.004 | 1.00 | 28.56 | O |
| ATOM | 5774 | N | LYS | C | 197 | 77.384 | -12.945 | 29.626 | 1.00 | 28.05 | N |
| ATOM | 5775 | CA | LYS | C | 197 | 76.871 | -13.399 | 28.348 | 1.00 | 28.15 | C |
| ATOM | 5776 | CB | LYS | C | 197 | 77.954 | -14.111 | 27.545 | 1.00 | 28.14 | C |
| ATOM | 5777 | CG | LYS | C | 197 | 79.383 | -13.647 | 27.811 | 1.00 | 32.42 | C |
| ATOM | 5778 | CD | LYS | C | 197 | 79.991 | -12.911 | 26.607 | 1.00 | 37.50 | C |
| ATOM | 5779 | CE | LYS | C | 197 | 81.536 | -13.037 | 26.571 | 1.00 | 40.86 | C |
| ATOM | 5780 | NZ | LYS | C | 197 | 82.153 | -12.798 | 27.914 | 1.00 | 44.31 | N |
| ATOM | 5781 | C | LYS | C | 197 | 75.738 | -14.354 | 28.644 | 1.00 | 28.53 | C |
| ATOM | 5782 | O | LYS | C | 197 | 74.900 | -14.612 | 27.787 | 1.00 | 28.55 | O |
| ATOM | 5783 | N | ARG | C | 198 | 75.699 | -14.878 | 29.863 | 1.00 | 29.38 | N |
| ATOM | 5784 | CA | ARG | C | 198 | 74.614 | -15.783 | 30.233 | 1.00 | 31.16 | C |
| ATOM | 5785 | CB | ARG | C | 198 | 74.546 | -15.986 | 31.736 | 1.00 | 31.30 | C |
| ATOM | 5786 | CG | ARG | C | 198 | 74.688 | -17.420 | 32.157 | 1.00 | 35.63 | C |
| ATOM | 5787 | CD | ARG | C | 198 | 76.049 | -17.632 | 32.792 | 1.00 | 40.03 | C |
| ATOM | 5788 | NE | ARG | C | 198 | 76.257 | -16.623 | 33.814 | 1.00 | 38.38 | N |
| ATOM | 5789 | CZ | ARG | C | 198 | 77.366 | -16.508 | 34.520 | 1.00 | 41.96 | C |
| ATOM | 5790 | NH1AR | G | C | 198 | 78.355 | -17.360 | 34.309 | 1.00 | 45.96 | N |
| ATOM | 5791 | NH2AR | G | C | 198 | 77.488 | -15.524 | 35.412 | 1.00 | 44.49 | N |
| ATOM | 5792 | C | ARG | C | 198 | 73.275 | -15.226 | 29.786 | 1.00 | 31.31 | C |
| ATOM | 5793 | O | ARG | C | 198 | 73.106 | -14.028 | 29.653 | 1.00 | 29.44 | O |
| ATOM | 5794 | N | PRO | C | 199 | 72.285 | -16.095 | 29.569 | 1.00 | 31.92 | N |

FIG. 2A-126

| ATOM | 5795 | CA | PRO | C | 199 | 71.007 | -15.539 | 29.135 | 1.00 | 32.36 | C |
| --- | --- | --- | --- | --- | --- | --- | --- | --- | --- | --- | --- |
| ATOM | 5796 | CB | PRO | C | 199 | 70.228 | -16.773 | 28.664 | 1.00 | 31.03 | C |
| ATOM | 5797 | CG | PRO | C | 199 | 70.771 | -17.844 | 29.509 | 1.00 | 33.69 | C |
| ATOM | 5798 | CD | PRO | C | 199 | 72.263 | -17.564 | 29.470 | 1.00 | 33.10 | C |
| ATOM | 5799 | C | PRO | C | 199 | 70.258 | -14.711 | 30.155 | 1.00 | 32.94 | C |
| ATOM | 5800 | O | PRO | C | 199 | 69.426 | -13.886 | 29.777 | 1.00 | 34.40 | O |
| ATOM | 5801 | N | ALA | C | 200 | 70.528 | -14.883 | 31.437 | 1.00 | 32.06 | N |
| ATOM | 5802 | CA | ALA | C | 200 | 69.771 | -14.071 | 32.377 | 1.00 | 31.28 | C |
| ATOM | 5803 | CB | ALA | C | 200 | 69.116 | -14.960 | 33.391 | 1.00 | 31.28 | C |
| ATOM | 5804 | C | ALA | C | 200 | 70.575 | -12.972 | 33.064 | 1.00 | 31.22 | C |
| ATOM | 5805 | O | ALA | C | 200 | 70.214 | -12.510 | 34.157 | 1.00 | 31.02 | O |
| ATOM | 5806 | N | ALA | C | 201 | 71.656 | -12.543 | 32.415 | 1.00 | 30.52 | N |
| ATOM | 5807 | CA | ALA | C | 201 | 72.515 | -11.491 | 32.955 | 1.00 | 30.15 | C |
| ATOM | 5808 | CB | ALA | C | 201 | 73.628 | -11.143 | 31.958 | 1.00 | 29.47 | C |
| ATOM | 5809 | C | ALA | C | 201 | 71.656 | -10.272 | 33.193 | 1.00 | 30.18 | C |
| ATOM | 5810 | O | ALA | C | 201 | 70.701 | -10.046 | 32.451 | 1.00 | 29.84 | O |
| ATOM | 5811 | N | ILE | C | 202 | 71.975 | -9.496 | 34.226 | 1.00 | 29.98 | N |
| ATOM | 5812 | CA | ILE | C | 202 | 71.196 | -8.290 | 34.478 | 1.00 | 32.04 | C |
| ATOM | 5813 | CB | ILE | C | 202 | 70.948 | -8.048 | 35.970 | 1.00 | 33.67 | C |
| ATOM | 5814 | CG1 | ILE | C | 202 | 71.117 | -6.571 | 36.280 | 1.00 | 37.59 | C |
| ATOM | 5815 | CD1 | ILE | C | 202 | 70.813 | -6.246 | 37.761 | 1.00 | 49.90 | C |
| ATOM | 5816 | CG2 | ILE | C | 202 | 71.892 | -8.874 | 36.826 | 1.00 | 33.26 | C |
| ATOM | 5817 | C | ILE | C | 202 | 71.911 | -7.061 | 33.908 | 1.00 | 31.25 | C |
| ATOM | 5818 | O | ILE | C | 202 | 73.128 | -6.955 | 34.004 | 1.00 | 32.99 | O |
| ATOM | 5819 | N | LEU | C | 203 | 71.135 | -6.163 | 33.294 | 1.00 | 28.81 | N |
| ATOM | 5820 | CA | LEU | C | 203 | 71.595 | -4.907 | 32.691 | 1.00 | 26.66 | C |
| ATOM | 5821 | CB | LEU | C | 203 | 70.493 | -4.349 | 31.827 | 1.00 | 26.74 | C |
| ATOM | 5822 | CG | LEU | C | 203 | 70.733 | -3.100 | 31.022 | 1.00 | 28.82 | C |
| ATOM | 5823 | CD1 | LEU | C | 203 | 71.826 | -3.386 | 30.017 | 1.00 | 26.80 | C |
| ATOM | 5824 | CD2 | LEU | C | 203 | 69.441 | -2.676 | 30.385 | 1.00 | 33.22 | C |
| ATOM | 5825 | C | LEU | C | 203 | 71.912 | -3.832 | 33.755 | 1.00 | 26.58 | C |
| ATOM | 5826 | O | LEU | C | 203 | 71.173 | -3.650 | 34.727 | 1.00 | 26.40 | O |
| ATOM | 5827 | N | LYS | C | 204 | 72.987 | -3.085 | 33.549 | 1.00 | 27.18 | N |
| ATOM | 5828 | CA | LYS | C | 204 | 73.368 | -2.077 | 34.516 | 1.00 | 27.37 | C |
| ATOM | 5829 | CB | LYS | C | 204 | 74.421 | -2.673 | 35.413 | 1.00 | 27.16 | C |
| ATOM | 5830 | CG | LYS | C | 204 | 73.859 | -3.802 | 36.242 | 1.00 | 27.25 | C |
| ATOM | 5831 | CD | LYS | C | 204 | 74.949 | -4.452 | 37.043 | 1.00 | 30.68 | C |
| ATOM | 5832 | CE | LYS | C | 204 | 74.392 | -5.140 | 38.244 | 1.00 | 27.04 | C |
| ATOM | 5833 | NZ | LYS | C | 204 | 75.512 | -5.320 | 39.198 | 1.00 | 27.55 | N |
| ATOM | 5834 | C | LYS | C | 204 | 73.830 | -0.737 | 33.966 | 1.00 | 26.31 | C |
| ATOM | 5835 | O | LYS | C | 204 | 74.482 | -0.669 | 32.900 | 1.00 | 26.72 | O |
| ATOM | 5836 | N | LEU | C | 205 | 73.453 | 0.336 | 34.683 | 1.00 | 26.22 | N |
| ATOM | 5837 | CA | LEU | C | 205 | 73.834 | 1.707 | 34.304 | 1.00 | 25.45 | C |
| ATOM | 5838 | CB | LEU | C | 205 | 72.799 | 2.685 | 34.774 | 1.00 | 23.20 | C |
| ATOM | 5839 | CG | LEU | C | 205 | 73.087 | 4.129 | 34.428 | 1.00 | 22.88 | C |
| ATOM | 5840 | CD1 | LEU | C | 205 | 73.288 | 4.305 | 32.973 | 1.00 | 19.01 | C |

FIG. 2A-127

| ATOM | 5841 | CD2 | LEU | C | 205 | 71.928 | 4.957 | 34.905 | 1.00 | 23.93 | C |
|---|---|---|---|---|---|---|---|---|---|---|---|
| ATOM | 5842 | C | LEU | C | 205 | 75.207 | 2.024 | 34.920 | 1.00 | 27.09 | C |
| ATOM | 5843 | O | LEU | C | 205 | 75.514 | 1.650 | 36.048 | 1.00 | 26.96 | O |
| ATOM | 5844 | N | THR | C | 206 | 76.039 | 2.687 | 34.138 | 1.00 | 27.83 | N |
| ATOM | 5845 | CA | THR | C | 206 | 77.393 | 2.987 | 34.546 | 1.00 | 29.12 | C |
| ATOM | 5846 | CB | THR | C | 206 | 78.372 | 2.112 | 33.742 | 1.00 | 28.73 | C |
| ATOM | 5847 | OG1 | THR | C | 206 | 78.273 | 2.474 | 32.362 | 1.00 | 27.21 | O |
| ATOM | 5848 | CG2 | THR | C | 206 | 78.028 | 0.645 | 33.891 | 1.00 | 29.58 | C |
| ATOM | 5849 | C | THR | C | 206 | 77.748 | 4.450 | 34.276 | 1.00 | 30.31 | C |
| ATOM | 5850 | O | THR | C | 206 | 76.957 | 5.191 | 33.685 | 1.00 | 35.17 | O |
| ATOM | 5851 | N | ASP | C | 207 | 78.964 | 4.829 | 34.655 | 1.00 | 28.37 | N |
| ATOM | 5852 | CA | ASP | C | 207 | 79.484 | 6.184 | 34.520 | 1.00 | 27.81 | C |
| ATOM | 5853 | CB | ASP | C | 207 | 79.754 | 6.534 | 33.075 | 1.00 | 26.53 | C |
| ATOM | 5854 | CG | ASP | C | 207 | 80.985 | 7.424 | 32.953 | 1.00 | 31.95 | C |
| ATOM | 5855 | OD1 | ASP | C | 207 | 81.207 | 8.213 | 33.893 | 1.00 | 37.14 | O |
| ATOM | 5856 | OD2 | ASP | C | 207 | 81.733 | 7.358 | 31.951 | 1.00 | 37.50 | O |
| ATOM | 5857 | C | ASP | C | 207 | 78.698 | 7.343 | 35.201 | 1.00 | 27.91 | C |
| ATOM | 5858 | O | ASP | C | 207 | 77.749 | 7.927 | 34.654 | 1.00 | 30.48 | O |
| ATOM | 5859 | N | PHE | C | 208 | 79.108 | 7.670 | 36.419 | 1.00 | 26.02 | N |
| ATOM | 5860 | CA | PHE | C | 208 | 78.453 | 8.741 | 37.123 | 1.00 | 25.96 | C |
| ATOM | 5861 | CB | PHE | C | 208 | 78.179 | 8.325 | 38.565 | 1.00 | 24.95 | C |
| ATOM | 5862 | CG | PHE | C | 208 | 77.010 | 7.387 | 38.705 | 1.00 | 28.19 | C |
| ATOM | 5863 | CD1 | PHE | C | 208 | 77.051 | 6.119 | 38.165 | 1.00 | 26.07 | C |
| ATOM | 5864 | CE1 | PHE | C | 208 | 75.972 | 5.264 | 38.271 | 1.00 | 25.14 | C |
| ATOM | 5865 | CZ | PHE | C | 208 | 74.811 | 5.663 | 38.928 | 1.00 | 26.81 | C |
| ATOM | 5866 | CE2 | PHE | C | 208 | 74.746 | 6.929 | 39.473 | 1.00 | 26.38 | C |
| ATOM | 5867 | CD2 | PHE | C | 208 | 75.855 | 7.787 | 39.358 | 1.00 | 30.09 | C |
| ATOM | 5868 | C | PHE | C | 208 | 79.276 | 10.032 | 37.034 | 1.00 | 24.77 | C |
| ATOM | 5869 | O | PHE | C | 208 | 79.147 | 10.921 | 37.865 | 1.00 | 27.37 | O |
| ATOM | 5870 | N | GLY | C | 209 | 80.087 | 10.144 | 35.981 | 1.00 | 24.65 | N |
| ATOM | 5871 | CA | GLY | C | 209 | 80.898 | 11.327 | 35.814 | 1.00 | 22.55 | C |
| ATOM | 5872 | C | GLY | C | 209 | 80.150 | 12.603 | 35.441 | 1.00 | 22.74 | C |
| ATOM | 5873 | O | GLY | C | 209 | 80.768 | 13.575 | 35.056 | 1.00 | 23.37 | O |
| ATOM | 5874 | N | PHE | C | 210 | 78.827 | 12.602 | 35.522 | 1.00 | 23.56 | N |
| ATOM | 5875 | CA | PHE | C | 210 | 78.045 | 13.778 | 35.192 | 1.00 | 23.99 | C |
| ATOM | 5876 | CB | PHE | C | 210 | 77.423 | 13.718 | 33.801 | 1.00 | 26.34 | C |
| ATOM | 5877 | CG | PHE | C | 210 | 78.335 | 14.063 | 32.680 | 1.00 | 29.51 | C |
| ATOM | 5878 | CD1 | PHE | C | 210 | 79.461 | 14.841 | 32.874 | 1.00 | 32.49 | C |
| ATOM | 5879 | CE1 | PHE | C | 210 | 80.237 | 15.251 | 31.800 | 1.00 | 35.26 | C |
| ATOM | 5880 | CZ | PHE | C | 210 | 79.891 | 14.885 | 30.522 | 1.00 | 34.83 | C |
| ATOM | 5881 | CE2 | PHE | C | 210 | 78.783 | 14.104 | 30.309 | 1.00 | 37.18 | C |
| ATOM | 5882 | CD2 | PHE | C | 210 | 78.006 | 13.693 | 31.391 | 1.00 | 36.43 | C |
| ATOM | 5883 | C | PHE | C | 210 | 76.904 | 13.764 | 36.134 | 1.00 | 23.28 | C |
| ATOM | 5884 | O | PHE | C | 210 | 76.046 | 14.613 | 36.064 | 1.00 | 22.72 | O |
| ATOM | 5885 | N | ALA | C | 211 | 76.833 | 12.742 | 36.970 | 1.00 | 21.67 | N |
| ATOM | 5886 | CA | ALA | C | 211 | 75.729 | 12.678 | 37.918 | 1.00 | 21.73 | C |

FIG. 2A-128

| ATOM | 5887 | CB | ALA | C | 211 | 75.823 | 11.398 | 38.811 | 1.00 | 19.47 | C |
|---|---|---|---|---|---|---|---|---|---|---|---|
| ATOM | 5888 | C | ALA | C | 211 | 75.774 | 13.936 | 38.785 | 1.00 | 22.87 | C |
| ATOM | 5889 | O | ALA | C | 211 | 76.843 | 14.454 | 39.148 | 1.00 | 21.27 | O |
| ATOM | 5890 | N | LYS | C | 212 | 74.586 | 14.406 | 39.124 | 1.00 | 24.65 | N |
| ATOM | 5891 | CA | LYS | C | 212 | 74.429 | 15.589 | 39.934 | 1.00 | 27.00 | C |
| ATOM | 5892 | CB | LYS | C | 212 | 74.130 | 16.775 | 39.009 | 1.00 | 25.79 | C |
| ATOM | 5893 | CG | LYS | C | 212 | 73.664 | 18.009 | 39.711 | 1.00 | 34.75 | C |
| ATOM | 5894 | CD | LYS | C | 212 | 74.250 | 19.254 | 39.072 | 1.00 | 44.08 | C |
| ATOM | 5895 | CE | LYS | C | 212 | 73.749 | 20.525 | 39.761 | 1.00 | 46.90 | C |
| ATOM | 5896 | NZ | LYS | C | 212 | 74.340 | 21.723 | 39.103 | 1.00 | 48.87 | N |
| ATOM | 5897 | C | LYS | C | 212 | 73.339 | 15.393 | 40.978 | 1.00 | 27.44 | C |
| ATOM | 5898 | O | LYS | C | 212 | 72.378 | 14.685 | 40.756 | 1.00 | 28.92 | O |
| ATOM | 5899 | N | GLU | C | 213 | 73.530 | 15.997 | 42.145 | 1.00 | 30.07 | N |
| ATOM | 5900 | CA | GLU | C | 213 | 72.557 | 15.943 | 43.226 | 1.00 | 31.68 | C |
| ATOM | 5901 | CB | GLU | C | 213 | 73.212 | 16.321 | 44.532 | 1.00 | 32.49 | C |
| ATOM | 5902 | CG | GLU | C | 213 | 72.786 | 15.437 | 45.645 | 1.00 | 41.12 | C |
| ATOM | 5903 | CD | GLU | C | 213 | 73.672 | 15.576 | 46.851 | 1.00 | 53.98 | C |
| ATOM | 5904 | OE1 | GLU | C | 213 | 74.907 | 15.688 | 46.662 | 1.00 | 54.17 | O |
| ATOM | 5905 | OE2 | GLU | C | 213 | 73.128 | 15.551 | 47.989 | 1.00 | 61.09 | O |
| ATOM | 5906 | C | GLU | C | 213 | 71.511 | 16.969 | 42.824 | 1.00 | 31.64 | C |
| ATOM | 5907 | O | GLU | C | 213 | 71.842 | 18.066 | 42.389 | 1.00 | 29.98 | O |
| ATOM | 5908 | N | THR | C | 214 | 70.247 | 16.621 | 42.944 | 1.00 | 33.53 | N |
| ATOM | 5909 | CA | THR | C | 214 | 69.216 | 17.527 | 42.490 | 1.00 | 34.53 | C |
| ATOM | 5910 | CB | THR | C | 214 | 68.019 | 16.740 | 41.987 | 1.00 | 34.92 | C |
| ATOM | 5911 | OG1 | THR | C | 214 | 67.690 | 15.708 | 42.930 | 1.00 | 37.18 | O |
| ATOM | 5912 | CG2 | THR | C | 214 | 68.343 | 16.132 | 40.639 | 1.00 | 37.01 | C |
| ATOM | 5913 | C | THR | C | 214 | 68.752 | 18.575 | 43.464 | 1.00 | 35.80 | C |
| ATOM | 5914 | O | THR | C | 214 | 68.297 | 19.642 | 43.073 | 1.00 | 35.85 | O |
| ATOM | 5915 | N | THR | C | 215 | 68.850 | 18.266 | 44.738 | 1.00 | 38.15 | N |
| ATOM | 5916 | CA | THR | C | 215 | 68.447 | 19.221 | 45.741 | 1.00 | 41.51 | C |
| ATOM | 5917 | CB | THR | C | 215 | 67.648 | 18.557 | 46.825 | 1.00 | 42.22 | C |
| ATOM | 5918 | OG1 | THR | C | 215 | 68.448 | 17.517 | 47.410 | 1.00 | 41.67 | O |
| ATOM | 5919 | CG2 | THR | C | 215 | 66.363 | 17.967 | 46.251 | 1.00 | 42.20 | C |
| ATOM | 5920 | C | THR | C | 215 | 69.749 | 19.702 | 46.331 | 1.00 | 42.54 | C |
| ATOM | 5921 | O | THR | C | 215 | 70.460 | 18.823 | 46.876 | 1.00 | 44.12 | O |
| ATOM | 5922 | OXT | THR | C | 215 | 70.040 | 20.916 | 46.218 | 1.00 | 41.66 | O |
| ATOM | 5923 | N | PRO | C | 227 | 53.881 | 18.738 | 56.097 | 1.00 | 20.13 | N |
| ATOM | 5924 | CA | PRO | C | 227 | 52.438 | 18.874 | 55.783 | 1.00 | 19.20 | C |
| ATOM | 5925 | CB | PRO | C | 227 | 52.146 | 20.366 | 55.599 | 1.00 | 19.49 | C |
| ATOM | 5926 | CG | PRO | C | 227 | 53.215 | 20.970 | 56.468 | 1.00 | 20.47 | C |
| ATOM | 5927 | CD | PRO | C | 227 | 54.469 | 20.083 | 56.188 | 1.00 | 21.02 | C |
| ATOM | 5928 | C | PRO | C | 227 | 52.006 | 18.057 | 54.557 | 1.00 | 17.93 | C |
| ATOM | 5929 | O | PRO | C | 227 | 52.413 | 18.296 | 53.401 | 1.00 | 18.18 | O |
| ATOM | 5930 | N | TYR | C | 228 | 51.146 | 17.097 | 54.862 | 1.00 | 16.44 | N |
| ATOM | 5931 | CA | TYR | C | 228 | 50.596 | 16.169 | 53.920 | 1.00 | 15.34 | C |
| ATOM | 5932 | CB | TYR | C | 228 | 49.620 | 15.281 | 54.658 | 1.00 | 14.66 | C |

FIG. 2A-129

| ATOM | 5933 | CG | TYR | C | 228 | 48.306 | 15.969 | 54.894 | 1.00 | 9.44 | C |
|---|---|---|---|---|---|---|---|---|---|---|---|
| ATOM | 5934 | CD1 | TYR | C | 228 | 47.262 | 15.850 | 53.978 | 1.00 | 6.87 | C |
| ATOM | 5935 | CE1 | TYR | C | 228 | 46.043 | 16.481 | 54.191 | 1.00 | 5.18 | C |
| ATOM | 5936 | CZ | TYR | C | 228 | 45.867 | 17.229 | 55.337 | 1.00 | 4.49 | C |
| ATOM | 5937 | OH | TYR | C | 228 | 44.665 | 17.802 | 55.596 | 1.00 | 2.16 | O |
| ATOM | 5938 | CE2 | TYR | C | 228 | 46.886 | 17.362 | 56.253 | 1.00 | 6.67 | C |
| ATOM | 5939 | CD2 | TYR | C | 228 | 48.099 | 16.737 | 56.026 | 1.00 | 8.01 | C |
| ATOM | 5940 | C | TYR | C | 228 | 49.867 | 16.831 | 52.767 | 1.00 | 15.15 | C |
| ATOM | 5941 | O | TYR | C | 228 | 49.306 | 16.128 | 51.926 | 1.00 | 16.47 | O |
| ATOM | 5942 | N | TYR | C | 229 | 49.850 | 18.158 | 52.715 | 1.00 | 13.86 | N |
| ATOM | 5943 | CA | TYR | C | 229 | 49.141 | 18.849 | 51.647 | 1.00 | 11.78 | C |
| ATOM | 5944 | CB | TYR | C | 229 | 47.919 | 19.588 | 52.220 | 1.00 | 10.01 | C |
| ATOM | 5945 | CG | TYR | C | 229 | 48.279 | 20.733 | 53.149 | 1.00 | 8.47 | C |
| ATOM | 5946 | CD1 | TYR | C | 229 | 48.510 | 22.020 | 52.659 | 1.00 | 9.24 | C |
| ATOM | 5947 | CE1 | TYR | C | 229 | 48.916 | 23.053 | 53.513 | 1.00 | 10.51 | C |
| ATOM | 5948 | CZ | TYR | C | 229 | 49.088 | 22.792 | 54.869 | 1.00 | 6.88 | C |
| ATOM | 5949 | OH | TYR | C | 229 | 49.470 | 23.775 | 55.733 | 1.00 | 5.15 | O |
| ATOM | 5950 | CE2 | TYR | C | 229 | 48.861 | 21.534 | 55.372 | 1.00 | 10.79 | C |
| ATOM | 5951 | CD2 | TYR | C | 229 | 48.456 | 20.512 | 54.515 | 1.00 | 12.63 | C |
| ATOM | 5952 | C | TYR | C | 229 | 50.042 | 19.831 | 50.921 | 1.00 | 11.26 | C |
| ATOM | 5953 | O | TYR | C | 229 | 49.623 | 20.471 | 49.967 | 1.00 | 9.22 | O |
| ATOM | 5954 | N | VAL | C | 230 | 51.278 | 19.965 | 51.363 | 1.00 | 11.58 | N |
| ATOM | 5955 | CA | VAL | C | 230 | 52.166 | 20.898 | 50.693 | 1.00 | 13.39 | C |
| ATOM | 5956 | CB | VAL | C | 230 | 53.477 | 21.119 | 51.527 | 1.00 | 14.81 | C |
| ATOM | 5957 | CG1 | VAL | C | 230 | 54.319 | 19.833 | 51.528 | 1.00 | 13.50 | C |
| ATOM | 5958 | CG2 | VAL | C | 230 | 54.279 | 22.316 | 50.964 | 1.00 | 17.45 | C |
| ATOM | 5959 | C | VAL | C | 230 | 52.525 | 20.412 | 49.276 | 1.00 | 12.50 | C |
| ATOM | 5960 | O | VAL | C | 230 | 52.681 | 19.218 | 49.029 | 1.00 | 12.34 | O |
| ATOM | 5961 | N | ALA | C | 231 | 52.657 | 21.343 | 48.341 | 1.00 | 13.57 | N |
| ATOM | 5962 | CA | ALA | C | 231 | 52.984 | 20.979 | 46.973 | 1.00 | 14.18 | C |
| ATOM | 5963 | CB | ALA | C | 231 | 52.583 | 22.107 | 46.053 | 1.00 | 14.23 | C |
| ATOM | 5964 | C | ALA | C | 231 | 54.470 | 20.646 | 46.804 | 1.00 | 14.65 | C |
| ATOM | 5965 | O | ALA | C | 231 | 55.312 | 21.195 | 47.476 | 1.00 | 15.53 | O |
| ATOM | 5966 | N | PRO | C | 232 | 54.809 | 19.735 | 45.884 | 1.00 | 15.87 | N |
| ATOM | 5967 | CA | PRO | C | 232 | 56.220 | 19.403 | 45.713 | 1.00 | 17.22 | C |
| ATOM | 5968 | CB | PRO | C | 232 | 56.197 | 18.375 | 44.573 | 1.00 | 15.49 | C |
| ATOM | 5969 | CG | PRO | C | 232 | 54.971 | 18.716 | 43.827 | 1.00 | 17.42 | C |
| ATOM | 5970 | CD | PRO | C | 232 | 53.974 | 19.019 | 44.907 | 1.00 | 15.55 | C |
| ATOM | 5971 | C | PRO | C | 232 | 57.136 | 20.603 | 45.445 | 1.00 | 19.05 | C |
| ATOM | 5972 | O | PRO | C | 232 | 58.257 | 20.641 | 45.918 | 1.00 | 20.55 | O |
| ATOM | 5973 | N | GLU | C | 233 | 56.661 | 21.587 | 44.697 | 1.00 | 21.82 | N |
| ATOM | 5974 | CA | GLU | C | 233 | 57.444 | 22.793 | 44.365 | 1.00 | 23.66 | C |
| ATOM | 5975 | CB | GLU | C | 233 | 56.570 | 23.709 | 43.551 | 1.00 | 22.57 | C |
| ATOM | 5976 | CG | GLU | C | 233 | 55.252 | 23.032 | 43.360 | 1.00 | 23.80 | C |
| ATOM | 5977 | CD | GLU | C | 233 | 54.125 | 23.978 | 43.167 | 1.00 | 31.51 | C |
| ATOM | 5978 | OE1 | GLU | C | 233 | 53.002 | 23.464 | 43.136 | 1.00 | 36.16 | O |

FIG. 2A-130

| ATOM | 5979 | OE2 | GLU | C | 233 | 54.330 | 25.221 | 43.036 | 1.00 | 37.02 | O |
|---|---|---|---|---|---|---|---|---|---|---|---|
| ATOM | 5980 | C | GLU | C | 233 | 57.851 | 23.510 | 45.627 | 1.00 | 25.39 | C |
| ATOM | 5981 | O | GLU | C | 233 | 58.919 | 24.100 | 45.703 | 1.00 | 27.93 | O |
| ATOM | 5982 | N | VAL | C | 234 | 56.969 | 23.467 | 46.616 | 1.00 | 26.69 | N |
| ATOM | 5983 | CA | VAL | C | 234 | 57.219 | 24.096 | 47.908 | 1.00 | 27.51 | C |
| ATOM | 5984 | CB | VAL | C | 234 | 55.924 | 24.173 | 48.706 | 1.00 | 26.23 | C |
| ATOM | 5985 | CG1 | VAL | C | 234 | 56.175 | 24.749 | 50.047 | 1.00 | 23.56 | C |
| ATOM | 5986 | CG2 | VAL | C | 234 | 54.907 | 24.973 | 47.924 | 1.00 | 25.76 | C |
| ATOM | 5987 | C | VAL | C | 234 | 58.282 | 23.331 | 48.711 | 1.00 | 30.00 | C |
| ATOM | 5988 | O | VAL | C | 234 | 59.157 | 23.938 | 49.302 | 1.00 | 30.62 | O |
| ATOM | 5989 | N | LEU | C | 235 | 58.193 | 22.006 | 48.724 | 1.00 | 33.10 | N |
| ATOM | 5990 | CA | LEU | C | 235 | 59.151 | 21.166 | 49.419 | 1.00 | 36.11 | C |
| ATOM | 5991 | CB | LEU | C | 235 | 58.978 | 19.708 | 49.025 | 1.00 | 35.12 | C |
| ATOM | 5992 | CG | LEU | C | 235 | 58.195 | 18.792 | 49.953 | 1.00 | 32.18 | C |
| ATOM | 5993 | CD1 | LEU | C | 235 | 59.115 | 17.701 | 50.449 | 1.00 | 32.45 | C |
| ATOM | 5994 | CD2 | LEU | C | 235 | 57.643 | 19.581 | 51.093 | 1.00 | 25.62 | C |
| ATOM | 5995 | C | LEU | C | 235 | 60.561 | 21.573 | 49.078 | 1.00 | 39.84 | C |
| ATOM | 5996 | O | LEU | C | 235 | 61.491 | 21.287 | 49.827 | 1.00 | 42.44 | O |
| ATOM | 5997 | N | GLY | C | 236 | 60.739 | 22.221 | 47.938 | 1.00 | 42.84 | N |
| ATOM | 5998 | CA | GLY | C | 236 | 62.076 | 22.657 | 47.583 | 1.00 | 45.67 | C |
| ATOM | 5999 | C | GLY | C | 236 | 62.229 | 22.929 | 46.110 | 1.00 | 48.17 | C |
| ATOM | 6000 | O | GLY | C | 236 | 61.639 | 22.224 | 45.292 | 1.00 | 48.15 | O |
| ATOM | 6001 | N | PRO | C | 237 | 63.047 | 23.920 | 45.734 | 1.00 | 49.67 | N |
| ATOM | 6002 | CA | PRO | C | 237 | 63.280 | 24.283 | 44.332 | 1.00 | 50.00 | C |
| ATOM | 6003 | CB | PRO | C | 237 | 64.492 | 25.220 | 44.405 | 1.00 | 50.48 | C |
| ATOM | 6004 | CG | PRO | C | 237 | 65.232 | 24.747 | 45.634 | 1.00 | 51.91 | C |
| ATOM | 6005 | CD | PRO | C | 237 | 64.080 | 24.514 | 46.604 | 1.00 | 51.05 | C |
| ATOM | 6006 | C | PRO | C | 237 | 63.521 | 23.104 | 43.401 | 1.00 | 50.25 | C |
| ATOM | 6007 | O | PRO | C | 237 | 62.566 | 22.479 | 42.931 | 1.00 | 50.85 | O |
| ATOM | 6008 | N | ALA | C | 238 | 64.796 | 22.815 | 43.141 | 1.00 | 49.70 | N |
| ATOM | 6009 | CA | ALA | C | 238 | 65.215 | 21.734 | 42.240 | 1.00 | 50.30 | C |
| ATOM | 6010 | CB | ALA | C | 238 | 64.548 | 20.412 | 42.634 | 1.00 | 49.92 | C |
| ATOM | 6011 | C | ALA | C | 238 | 64.936 | 22.047 | 40.762 | 1.00 | 50.32 | C |
| ATOM | 6012 | O | ALA | C | 238 | 63.785 | 22.054 | 40.316 | 1.00 | 50.15 | O |
| ATOM | 6013 | N | ALA | C | 239 | 66.005 | 22.301 | 40.009 | 1.00 | 50.28 | N |
| ATOM | 6014 | CA | ALA | C | 239 | 65.896 | 22.610 | 38.582 | 1.00 | 49.01 | C |
| ATOM | 6015 | CB | ALA | C | 239 | 67.285 | 22.881 | 37.999 | 1.00 | 49.24 | C |
| ATOM | 6016 | C | ALA | C | 239 | 65.205 | 21.486 | 37.805 | 1.00 | 47.33 | C |
| ATOM | 6017 | O | ALA | C | 239 | 64.175 | 20.960 | 38.245 | 1.00 | 47.11 | O |
| ATOM | 6018 | N | TYR | C | 240 | 65.755 | 21.115 | 36.653 | 1.00 | 46.09 | N |
| ATOM | 6019 | CA | TYR | C | 240 | 65.145 | 20.050 | 35.855 | 1.00 | 45.48 | C |
| ATOM | 6020 | CB | TYR | C | 240 | 64.201 | 20.661 | 34.801 | 1.00 | 47.00 | C |
| ATOM | 6021 | CG | TYR | C | 240 | 63.066 | 21.476 | 35.401 | 1.00 | 50.24 | C |
| ATOM | 6022 | CD1 | TYR | C | 240 | 63.068 | 22.866 | 35.339 | 1.00 | 48.86 | C |
| ATOM | 6023 | CE1 | TYR | C | 240 | 62.071 | 23.617 | 35.937 | 1.00 | 52.08 | C |
| ATOM | 6024 | CZ | TYR | C | 240 | 61.050 | 22.978 | 36.614 | 1.00 | 54.42 | C |

FIG. 2A-131

| ATOM | 6025 | OH  | TYR  | C | 240 | 60.033 | 23.711 | 37.196 | 1.00 | 51.07 | O |
|------|------|-----|------|---|-----|--------|--------|--------|------|-------|---|
| ATOM | 6026 | CE2 | TYR  | C | 240 | 61.028 | 21.597 | 36.691 | 1.00 | 56.89 | C |
| ATOM | 6027 | CD2 | TYR  | C | 240 | 62.031 | 20.854 | 36.081 | 1.00 | 56.50 | C |
| ATOM | 6028 | C   | TYR  | C | 240 | 66.126 | 19.076 | 35.182 | 1.00 | 43.96 | C |
| ATOM | 6029 | O   | TYR  | C | 240 | 65.992 | 18.765 | 34.000 | 1.00 | 44.77 | O |
| ATOM | 6030 | N   | ASP  | C | 241 | 67.099 | 18.579 | 35.943 | 1.00 | 40.33 | N |
| ATOM | 6031 | CA  | ASP  | C | 241 | 68.067 | 17.643 | 35.405 | 1.00 | 35.39 | C |
| ATOM | 6032 | CB  | ASP  | C | 241 | 69.280 | 17.592 | 36.284 | 1.00 | 36.57 | C |
| ATOM | 6033 | CG  | ASP  | C | 241 | 69.921 | 18.936 | 36.428 | 1.00 | 40.53 | C |
| ATOM | 6034 | OD1 | ASP  | C | 241 | 70.571 | 19.377 | 35.449 | 1.00 | 45.35 | O |
| ATOM | 6035 | OD2 | ASP  | C | 241 | 69.758 | 19.542 | 37.515 | 1.00 | 39.24 | O |
| ATOM | 6036 | C   | ASP  | C | 241 | 67.492 | 16.269 | 35.295 | 1.00 | 33.24 | C |
| ATOM | 6037 | O   | ASP  | C | 241 | 67.740 | 15.582 | 34.322 | 1.00 | 34.16 | O |
| ATOM | 6038 | N   | LYS  | C | 242 | 66.725 | 15.842 | 36.287 | 1.00 | 31.02 | N |
| ATOM | 6039 | CA  | LYS  | C | 242 | 66.130 | 14.509 | 36.211 | 1.00 | 27.53 | C |
| ATOM | 6040 | CB  | LYS  | C | 242 | 65.087 | 14.335 | 37.294 | 1.00 | 26.63 | C |
| ATOM | 6041 | CG  | LYS  | C | 242 | 65.712 | 14.242 | 38.641 | 1.00 | 26.17 | C |
| ATOM | 6042 | CD  | LYS  | C | 242 | 64.676 | 13.978 | 39.696 | 1.00 | 30.13 | C |
| ATOM | 6043 | CE  | LYS  | C | 242 | 65.268 | 13.999 | 41.080 | 1.00 | 33.31 | C |
| ATOM | 6044 | NZ  | LYS  | C | 242 | 64.183 | 13.857 | 42.106 | 1.00 | 35.28 | N |
| ATOM | 6045 | C   | LYS  | C | 242 | 65.482 | 14.341 | 34.847 | 1.00 | 26.90 | C |
| ATOM | 6046 | O   | LYS  | C | 242 | 65.371 | 13.240 | 34.306 | 1.00 | 26.96 | O |
| ATOM | 6047 | N   | SER  | C | 243 | 65.111 | 15.483 | 34.288 | 1.00 | 25.07 | N |
| ATOM | 6048 | CA  | SER  | C | 243 | 64.438 | 15.569 | 33.034 | 1.00 | 25.77 | C |
| ATOM | 6049 | CB  | SER  | C | 243 | 64.016 | 16.997 | 32.823 | 1.00 | 25.77 | C |
| ATOM | 6050 | OG  | SER  | C | 243 | 62.649 | 17.021 | 32.549 | 1.00 | 31.33 | O |
| ATOM | 6051 | C   | SER  | C | 243 | 65.193 | 15.080 | 31.830 | 1.00 | 24.51 | C |
| ATOM | 6052 | O   | SER  | C | 243 | 64.637 | 14.419 | 30.962 | 1.00 | 22.62 | O |
| ATOM | 6053 | N   | CYS  | C | 244 | 66.457 | 15.418 | 31.740 | 1.00 | 25.27 | N |
| ATOM | 6054 | CA  | CYS  | C | 244 | 67.170 | 14.969 | 30.581 | 1.00 | 27.74 | C |
| ATOM | 6055 | CB  | CYS  | C | 244 | 68.509 | 15.710 | 30.469 | 1.00 | 29.09 | C |
| ATOM | 6056 | SG  | CYS  | C | 244 | 69.714 | 15.197 | 31.622 | 1.00 | 40.09 | S |
| ATOM | 6057 | C   | CYS  | C | 244 | 67.298 | 13.440 | 30.701 | 1.00 | 24.18 | C |
| ATOM | 6058 | O   | CYS  | C | 244 | 67.231 | 12.745 | 29.701 | 1.00 | 26.47 | O |
| ATOM | 6059 | N   | ASP  | C | 245 | 67.438 | 12.923 | 31.922 | 1.00 | 22.03 | N |
| ATOM | 6060 | CA  | ASP  | C | 245 | 67.492 | 11.481 | 32.144 | 1.00 | 19.00 | C |
| ATOM | 6061 | CB  | ASP  | C | 245 | 67.454 | 11.144 | 33.641 | 1.00 | 18.37 | C |
| ATOM | 6062 | CG  | ASP  | C | 245 | 68.831 | 11.216 | 34.341 | 1.00 | 19.07 | C |
| ATOM | 6063 | OD1 | ASP  | C | 245 | 69.872 | 11.454 | 33.717 | 1.00 | 16.89 | O |
| ATOM | 6064 | OD2 | ASP  | C | 245 | 68.867 | 11.018 | 35.566 | 1.00 | 22.45 | O |
| ATOM | 6065 | C   | ASP  | C | 245 | 66.236 | 10.864 | 31.480 | 1.00 | 19.29 | C |
| ATOM | 6066 | O   | ASP  | C | 245 | 66.312 | 9.808  | 30.856 | 1.00 | 17.28 | O |
| ATOM | 6067 | N   | MSEC |   | 246 | 65.071 | 11.518 | 31.610 | 1.00 | 18.67 | N |
| ATOM | 6068 | CA  | MSEC |   | 246 | 63.845 | 10.983 | 30.993 | 1.00 | 17.91 | C |
| ATOM | 6069 | CB  | MSEC |   | 246 | 62.590 | 11.688 | 31.500 | 1.00 | 16.54 | C |
| ATOM | 6070 | CG  | MSEC |   | 246 | 62.326 | 11.495 | 32.931 | 1.00 | 13.94 | C |

FIG. 2A-132

| ATOM | 6071 | SE | MSEC | | 246 | 62.547 | 9.714 | 33.542 | 1.00 | 27.23 | S |
|---|---|---|---|---|---|---|---|---|---|---|---|
| ATOM | 6072 | CE | MSEC | | 246 | 60.999 | 8.971 | 32.644 | 1.00 | 18.74 | C |
| ATOM | 6073 | C | MSEC | | 246 | 63.820 | 11.057 | 29.467 | 1.00 | 18.15 | C |
| ATOM | 6074 | O | MSEC | | 246 | 63.127 | 10.277 | 28.829 | 1.00 | 18.66 | O |
| ATOM | 6075 | N | TRP | C | 247 | 64.548 | 12.003 | 28.889 | 1.00 | 18.70 | N |
| ATOM | 6076 | CA | TRP | C | 247 | 64.596 | 12.137 | 27.449 | 1.00 | 19.34 | C |
| ATOM | 6077 | CB | TRP | C | 247 | 65.218 | 13.473 | 27.078 | 1.00 | 18.96 | C |
| ATOM | 6078 | CG | TRP | C | 247 | 65.641 | 13.612 | 25.647 | 1.00 | 19.33 | C |
| ATOM | 6079 | CD1 | TRP | C | 247 | 66.829 | 13.228 | 25.109 | 1.00 | 14.73 | C |
| ATOM | 6080 | NE1 | TRP | C | 247 | 66.914 | 13.633 | 23.818 | 1.00 | 13.20 | N |
| ATOM | 6081 | CE2 | TRP | C | 247 | 65.765 | 14.283 | 23.474 | 1.00 | 14.02 | C |
| ATOM | 6082 | CD2 | TRP | C | 247 | 64.932 | 14.288 | 24.605 | 1.00 | 19.08 | C |
| ATOM | 6083 | CE3 | TRP | C | 247 | 63.677 | 14.903 | 24.528 | 1.00 | 17.30 | C |
| ATOM | 6084 | CZ3 | TRP | C | 247 | 63.298 | 15.483 | 23.337 | 1.00 | 23.40 | C |
| ATOM | 6085 | CH2 | TRP | C | 247 | 64.165 | 15.456 | 22.210 | 1.00 | 21.79 | C |
| ATOM | 6086 | CZ2 | TRP | C | 247 | 65.399 | 14.861 | 22.270 | 1.00 | 15.83 | C |
| ATOM | 6087 | C | TRP | C | 247 | 65.442 | 10.971 | 26.948 | 1.00 | 21.74 | C |
| ATOM | 6088 | O | TRP | C | 247 | 65.123 | 10.320 | 25.937 | 1.00 | 21.02 | O |
| ATOM | 6089 | N | SER | C | 248 | 66.506 | 10.678 | 27.682 | 1.00 | 22.45 | N |
| ATOM | 6090 | CA | SER | C | 248 | 67.350 | 9.573 | 27.287 | 1.00 | 22.68 | C |
| ATOM | 6091 | CB | SER | C | 248 | 68.479 | 9.393 | 28.266 | 1.00 | 20.77 | C |
| ATOM | 6092 | OG | SER | C | 248 | 69.420 | 10.382 | 27.957 | 1.00 | 20.89 | O |
| ATOM | 6093 | C | SER | C | 248 | 66.521 | 8.326 | 27.212 | 1.00 | 24.65 | C |
| ATOM | 6094 | O | SER | C | 248 | 66.615 | 7.564 | 26.256 | 1.00 | 28.48 | O |
| ATOM | 6095 | N | LEU | C | 249 | 65.684 | 8.133 | 28.219 | 1.00 | 25.18 | N |
| ATOM | 6096 | CA | LEU | C | 249 | 64.827 | 6.987 | 28.274 | 1.00 | 24.52 | C |
| ATOM | 6097 | CB | LEU | C | 249 | 63.866 | 7.144 | 29.449 | 1.00 | 25.71 | C |
| ATOM | 6098 | CG | LEU | C | 249 | 63.958 | 5.969 | 30.454 | 1.00 | 24.18 | C |
| ATOM | 6099 | CD1 | LEU | C | 249 | 65.418 | 5.492 | 30.622 | 1.00 | 20.38 | C |
| ATOM | 6100 | CD2 | LEU | C | 249 | 63.324 | 6.368 | 31.786 | 1.00 | 29.59 | C |
| ATOM | 6101 | C | LEU | C | 249 | 64.098 | 6.927 | 26.946 | 1.00 | 24.75 | C |
| ATOM | 6102 | O | LEU | C | 249 | 63.911 | 5.860 | 26.374 | 1.00 | 23.80 | O |
| ATOM | 6103 | N | GLY | C | 250 | 63.729 | 8.093 | 26.436 | 1.00 | 24.61 | N |
| ATOM | 6104 | CA | GLY | C | 250 | 63.014 | 8.149 | 25.177 | 1.00 | 24.64 | C |
| ATOM | 6105 | C | GLY | C | 250 | 63.878 | 7.803 | 23.976 | 1.00 | 24.87 | C |
| ATOM | 6106 | O | GLY | C | 250 | 63.453 | 7.095 | 23.072 | 1.00 | 23.34 | O |
| ATOM | 6107 | N | VAL | C | 251 | 65.092 | 8.317 | 23.917 | 1.00 | 22.86 | N |
| ATOM | 6108 | CA | VAL | C | 251 | 65.901 | 7.978 | 22.766 | 1.00 | 19.92 | C |
| ATOM | 6109 | CB | VAL | C | 251 | 67.212 | 8.799 | 22.738 | 1.00 | 19.39 | C |
| ATOM | 6110 | CG1 | VAL | C | 251 | 68.155 | 8.270 | 21.669 | 1.00 | 13.98 | C |
| ATOM | 6111 | CG2 | VAL | C | 251 | 66.893 | 10.216 | 22.483 | 1.00 | 14.48 | C |
| ATOM | 6112 | C | VAL | C | 251 | 66.190 | 6.461 | 22.797 | 1.00 | 21.55 | C |
| ATOM | 6113 | O | VAL | C | 251 | 66.184 | 5.803 | 21.750 | 1.00 | 21.10 | O |
| ATOM | 6114 | N | ILE | C | 252 | 66.417 | 5.895 | 23.984 | 1.00 | 21.17 | N |
| ATOM | 6115 | CA | ILE | C | 252 | 66.688 | 4.466 | 24.052 | 1.00 | 19.60 | C |
| ATOM | 6116 | CB | ILE | C | 252 | 67.168 | 4.075 | 25.426 | 1.00 | 18.82 | C |

FIG. 2A-133

| | | | | | | | | | | | |
|---|---|---|---|---|---|---|---|---|---|---|---|
| ATOM | 6117 | CG1 | ILE | C | 252 | 68.610 | 4.575 | 25.593 | 1.00 | 19.56 | C |
| ATOM | 6118 | CD1 | ILE | C | 252 | 69.176 | 4.487 | 27.047 | 1.00 | 10.45 | C |
| ATOM | 6119 | CG2 | ILE | C | 252 | 67.014 | 2.583 | 25.625 | 1.00 | 16.81 | C |
| ATOM | 6120 | C | ILE | C | 252 | 65.491 | 3.588 | 23.641 | 1.00 | 20.81 | C |
| ATOM | 6121 | O | ILE | C | 252 | 65.631 | 2.615 | 22.881 | 1.00 | 18.63 | O |
| ATOM | 6122 | N | MSEC | | 253 | 64.311 | 3.948 | 24.128 | 1.00 | 21.35 | N |
| ATOM | 6123 | CA | MSEC | | 253 | 63.121 | 3.186 | 23.817 | 1.00 | 22.49 | C |
| ATOM | 6124 | CB | MSEC | | 253 | 61.916 | 3.758 | 24.557 | 1.00 | 22.39 | C |
| ATOM | 6125 | CG | MSEC | | 253 | 60.701 | 2.908 | 24.441 | 1.00 | 27.61 | C |
| ATOM | 6126 | SE | MSEC | | 253 | 59.189 | 3.431 | 25.516 | 1.00 | 31.69 | S |
| ATOM | 6127 | CE | MSEC | | 253 | 60.014 | 3.055 | 27.172 | 1.00 | 34.81 | C |
| ATOM | 6128 | C | MSEC | | 253 | 62.923 | 3.243 | 22.311 | 1.00 | 23.03 | C |
| ATOM | 6129 | O | MSEC | | 253 | 62.814 | 2.226 | 21.632 | 1.00 | 25.60 | O |
| ATOM | 6130 | N | TYR | C | 254 | 62.923 | 4.444 | 21.774 | 1.00 | 23.82 | N |
| ATOM | 6131 | CA | TYR | C | 254 | 62.722 | 4.608 | 20.348 | 1.00 | 22.52 | C |
| ATOM | 6132 | CB | TYR | C | 254 | 62.901 | 6.057 | 19.997 | 1.00 | 22.10 | C |
| ATOM | 6133 | CG | TYR | C | 254 | 62.754 | 6.366 | 18.573 | 1.00 | 20.37 | C |
| ATOM | 6134 | CD1 | TYR | C | 254 | 63.705 | 5.942 | 17.667 | 1.00 | 13.54 | C |
| ATOM | 6135 | CE1 | TYR | C | 254 | 63.541 | 6.192 | 16.306 | 1.00 | 13.37 | C |
| ATOM | 6136 | CZ | TYR | C | 254 | 62.407 | 6.867 | 15.864 | 1.00 | 18.33 | C |
| ATOM | 6137 | OH | TYR | C | 254 | 62.180 | 6.956 | 14.510 | 1.00 | 21.56 | O |
| ATOM | 6138 | CE2 | TYR | C | 254 | 61.448 | 7.326 | 16.763 | 1.00 | 17.40 | C |
| ATOM | 6139 | CD2 | TYR | C | 254 | 61.627 | 7.071 | 18.109 | 1.00 | 18.28 | C |
| ATOM | 6140 | C | TYR | C | 254 | 63.679 | 3.715 | 19.563 | 1.00 | 22.54 | C |
| ATOM | 6141 | O | TYR | C | 254 | 63.257 | 3.041 | 18.636 | 1.00 | 24.49 | O |
| ATOM | 6142 | N | ILE | C | 255 | 64.951 | 3.664 | 19.933 | 1.00 | 21.35 | N |
| ATOM | 6143 | CA | ILE | C | 255 | 65.846 | 2.814 | 19.184 | 1.00 | 20.18 | C |
| ATOM | 6144 | CB | ILE | C | 255 | 67.317 | 3.025 | 19.597 | 1.00 | 19.47 | C |
| ATOM | 6145 | CG1 | ILE | C | 255 | 67.747 | 4.443 | 19.209 | 1.00 | 20.36 | C |
| ATOM | 6146 | CD1 | ILE | C | 255 | 69.094 | 4.905 | 19.754 | 1.00 | 8.81 | C |
| ATOM | 6147 | CG2 | ILE | C | 255 | 68.210 | 1.979 | 18.935 | 1.00 | 13.95 | C |
| ATOM | 6148 | C | ILE | C | 255 | 65.422 | 1.370 | 19.427 | 1.00 | 22.65 | C |
| ATOM | 6149 | O | ILE | C | 255 | 65.294 | 0.595 | 18.494 | 1.00 | 24.25 | O |
| ATOM | 6150 | N | LEU | C | 256 | 65.155 | 1.009 | 20.672 | 1.00 | 22.88 | N |
| ATOM | 6151 | CA | LEU | C | 256 | 64.752 | -0.357 | 20.979 | 1.00 | 20.73 | C |
| ATOM | 6152 | CB | LEU | C | 256 | 64.318 | -0.500 | 22.426 | 1.00 | 20.70 | C |
| ATOM | 6153 | CG | LEU | C | 256 | 65.408 | -0.649 | 23.452 | 1.00 | 20.96 | C |
| ATOM | 6154 | CD1 | LEU | C | 256 | 64.798 | -1.155 | 24.773 | 1.00 | 17.67 | C |
| ATOM | 6155 | CD2 | LEU | C | 256 | 66.427 | -1.633 | 22.899 | 1.00 | 12.49 | C |
| ATOM | 6156 | C | LEU | C | 256 | 63.612 | -0.875 | 20.155 | 1.00 | 21.95 | C |
| ATOM | 6157 | O | LEU | C | 256 | 63.430 | -2.063 | 20.064 | 1.00 | 22.55 | O |
| ATOM | 6158 | N | LEU | C | 257 | 62.825 | -0.013 | 19.559 | 1.00 | 22.51 | N |
| ATOM | 6159 | CA | LEU | C | 257 | 61.690 | -0.540 | 18.836 | 1.00 | 23.53 | C |
| ATOM | 6160 | CB | LEU | C | 257 | 60.426 | 0.205 | 19.265 | 1.00 | 24.09 | C |
| ATOM | 6161 | CG | LEU | C | 257 | 59.962 | 0.057 | 20.695 | 1.00 | 22.10 | C |
| ATOM | 6162 | CD1 | LEU | C | 257 | 58.811 | 0.923 | 20.886 | 1.00 | 32.67 | C |

FIG. 2A-134

| ATOM | 6163 | CD2 | LEU | C | 257 | 59.580 | -1.373 | 20.976 | 1.00 | 32.95 | C |
|---|---|---|---|---|---|---|---|---|---|---|---|
| ATOM | 6164 | C | LEU | C | 257 | 61.747 | -0.543 | 17.334 | 1.00 | 23.24 | C |
| ATOM | 6165 | O | LEU | C | 257 | 60.889 | -1.132 | 16.706 | 1.00 | 25.62 | O |
| ATOM | 6166 | N | CYS | C | 258 | 62.722 | 0.122 | 16.737 | 1.00 | 22.29 | N |
| ATOM | 6167 | CA | CYS | C | 258 | 62.774 | 0.173 | 15.292 | 1.00 | 21.27 | C |
| ATOM | 6168 | CB | CYS | C | 258 | 62.286 | 1.558 | 14.795 | 1.00 | 20.78 | C |
| ATOM | 6169 | SG | CYS | C | 258 | 63.576 | 2.912 | 14.880 | 1.00 | 25.33 | S |
| ATOM | 6170 | C | CYS | C | 258 | 64.205 | -0.092 | 14.861 | 1.00 | 20.21 | C |
| ATOM | 6171 | O | CYS | C | 258 | 64.478 | -0.351 | 13.700 | 1.00 | 20.05 | O |
| ATOM | 6172 | N | GLY | C | 259 | 65.127 | -0.001 | 15.801 | 1.00 | 20.61 | N |
| ATOM | 6173 | CA | GLY | C | 259 | 66.514 | -0.250 | 15.472 | 1.00 | 21.19 | C |
| ATOM | 6174 | C | GLY | C | 259 | 67.357 | 0.953 | 15.089 | 1.00 | 21.12 | C |
| ATOM | 6175 | O | GLY | C | 259 | 68.570 | 0.826 | 14.943 | 1.00 | 19.85 | O |
| ATOM | 6176 | N | TYR | C | 260 | 66.748 | 2.115 | 14.894 | 1.00 | 21.42 | N |
| ATOM | 6177 | CA | TYR | C | 260 | 67.550 | 3.286 | 14.560 | 1.00 | 24.65 | C |
| ATOM | 6178 | CB | TYR | C | 260 | 67.423 | 3.615 | 13.060 | 1.00 | 24.50 | C |
| ATOM | 6179 | CG | TYR | C | 260 | 66.023 | 3.723 | 12.532 | 1.00 | 28.90 | C |
| ATOM | 6180 | CD1 | TYR | C | 260 | 65.314 | 4.904 | 12.650 | 1.00 | 29.65 | C |
| ATOM | 6181 | CE1 | TYR | C | 260 | 64.006 | 4.995 | 12.214 | 1.00 | 33.76 | C |
| ATOM | 6182 | CZ | TYR | C | 260 | 63.395 | 3.895 | 11.657 | 1.00 | 34.33 | C |
| ATOM | 6183 | OH | TYR | C | 260 | 62.082 | 4.014 | 11.283 | 1.00 | 46.01 | O |
| ATOM | 6184 | CE2 | TYR | C | 260 | 64.078 | 2.708 | 11.520 | 1.00 | 27.82 | C |
| ATOM | 6185 | CD2 | TYR | C | 260 | 65.388 | 2.625 | 11.954 | 1.00 | 29.38 | C |
| ATOM | 6186 | C | TYR | C | 260 | 67.216 | 4.493 | 15.449 | 1.00 | 24.74 | C |
| ATOM | 6187 | O | TYR | C | 260 | 66.210 | 4.488 | 16.140 | 1.00 | 26.18 | O |
| ATOM | 6188 | N | PRO | C | 261 | 68.072 | 5.525 | 15.466 | 1.00 | 24.13 | N |
| ATOM | 6189 | CA | PRO | C | 261 | 67.893 | 6.742 | 16.270 | 1.00 | 23.17 | C |
| ATOM | 6190 | CB | PRO | C | 261 | 69.289 | 7.342 | 16.280 | 1.00 | 23.98 | C |
| ATOM | 6191 | CG | PRO | C | 261 | 69.723 | 7.082 | 14.922 | 1.00 | 25.60 | C |
| ATOM | 6192 | CD | PRO | C | 261 | 69.336 | 5.602 | 14.717 | 1.00 | 23.99 | C |
| ATOM | 6193 | C | PRO | C | 261 | 66.859 | 7.709 | 15.700 | 1.00 | 22.83 | C |
| ATOM | 6194 | O | PRO | C | 261 | 66.790 | 7.931 | 14.496 | 1.00 | 23.22 | O |
| ATOM | 6195 | N | PRO | C | 262 | 66.078 | 8.351 | 16.579 | 1.00 | 22.50 | N |
| ATOM | 6196 | CA | PRO | C | 262 | 65.038 | 9.300 | 16.148 | 1.00 | 21.87 | C |
| ATOM | 6197 | CB | PRO | C | 262 | 64.241 | 9.530 | 17.420 | 1.00 | 20.01 | C |
| ATOM | 6198 | CG | PRO | C | 262 | 65.320 | 9.475 | 18.483 | 1.00 | 22.04 | C |
| ATOM | 6199 | CD | PRO | C | 262 | 66.206 | 8.312 | 18.049 | 1.00 | 21.20 | C |
| ATOM | 6200 | C | PRO | C | 262 | 65.526 | 10.612 | 15.512 | 1.00 | 24.24 | C |
| ATOM | 6201 | O | PRO | C | 262 | 64.826 | 11.214 | 14.663 | 1.00 | 26.61 | O |
| ATOM | 6202 | N | PHE | C | 263 | 66.708 | 11.077 | 15.905 | 1.00 | 23.31 | N |
| ATOM | 6203 | CA | PHE | C | 263 | 67.187 | 12.316 | 15.322 | 1.00 | 23.30 | C |
| ATOM | 6204 | CB | PHE | C | 263 | 67.301 | 13.421 | 16.385 | 1.00 | 22.03 | C |
| ATOM | 6205 | CG | PHE | C | 263 | 66.083 | 13.596 | 17.225 | 1.00 | 20.27 | C |
| ATOM | 6206 | CD1 | PHE | C | 263 | 66.014 | 13.045 | 18.474 | 1.00 | 21.37 | C |
| ATOM | 6207 | CE1 | PHE | C | 263 | 64.936 | 13.241 | 19.267 | 1.00 | 20.63 | C |
| ATOM | 6208 | CZ | PHE | C | 263 | 63.889 | 14.001 | 18.814 | 1.00 | 28.57 | C |

FIG. 2A-135

| ATOM | 6209 | CE2 | PHE | C | 263 | 63.928 | 14.559 | 17.561 | 1.00 | 26.71 | C |
| --- | --- | --- | --- | --- | --- | --- | --- | --- | --- | --- | --- |
| ATOM | 6210 | CD2 | PHE | C | 263 | 65.021 | 14.351 | 16.777 | 1.00 | 24.10 | C |
| ATOM | 6211 | C | PHE | C | 263 | 68.538 | 12.121 | 14.670 | 1.00 | 24.45 | C |
| ATOM | 6212 | O | PHE | C | 263 | 69.384 | 11.411 | 15.193 | 1.00 | 26.27 | O |
| ATOM | 6213 | N | TYR | C | 264 | 68.729 | 12.765 | 13.529 | 1.00 | 24.71 | N |
| ATOM | 6214 | CA | TYR | C | 264 | 69.983 | 12.717 | 12.813 | 1.00 | 27.15 | C |
| ATOM | 6215 | CB | TYR | C | 264 | 70.184 | 11.359 | 12.152 | 1.00 | 29.68 | C |
| ATOM | 6216 | CG | TYR | C | 264 | 69.042 | 10.980 | 11.269 | 1.00 | 34.57 | C |
| ATOM | 6217 | CD1 | TYR | C | 264 | 67.869 | 10.476 | 11.808 | 1.00 | 42.59 | C |
| ATOM | 6218 | CE1 | TYR | C | 264 | 66.784 | 10.222 | 11.025 | 1.00 | 49.04 | C |
| ATOM | 6219 | CZ | TYR | C | 264 | 66.867 | 10.456 | 9.678 | 1.00 | 56.15 | C |
| ATOM | 6220 | OH | TYR | C | 264 | 65.802 | 10.158 | 8.866 | 1.00 | 63.36 | O |
| ATOM | 6221 | CE2 | TYR | C | 264 | 68.019 | 10.948 | 9.122 | 1.00 | 52.10 | C |
| ATOM | 6222 | CD2 | TYR | C | 264 | 69.095 | 11.206 | 9.918 | 1.00 | 43.11 | C |
| ATOM | 6223 | C | TYR | C | 264 | 69.959 | 13.800 | 11.748 | 1.00 | 26.94 | C |
| ATOM | 6224 | O | TYR | C | 264 | 69.006 | 14.581 | 11.653 | 1.00 | 28.39 | O |
| ATOM | 6225 | N | SER | C | 265 | 71.020 | 13.856 | 10.950 | 1.00 | 26.17 | N |
| ATOM | 6226 | CA | SER | C | 265 | 71.106 | 14.847 | 9.884 | 1.00 | 25.40 | C |
| ATOM | 6227 | CB | SER | C | 265 | 72.506 | 15.454 | 9.817 | 1.00 | 24.47 | C |
| ATOM | 6228 | OG | SER | C | 265 | 72.762 | 16.322 | 10.898 | 1.00 | 20.86 | O |
| ATOM | 6229 | C | SER | C | 265 | 70.781 | 14.246 | 8.533 | 1.00 | 26.05 | C |
| ATOM | 6230 | O | SER | C | 265 | 71.131 | 13.110 | 8.244 | 1.00 | 25.68 | O |
| ATOM | 6231 | N | ASN | C | 266 | 70.101 | 15.031 | 7.713 | 1.00 | 27.60 | N |
| ATOM | 6232 | CA | ASN | C | 266 | 69.743 | 14.634 | 6.370 | 1.00 | 29.48 | C |
| ATOM | 6233 | CB | ASN | C | 266 | 68.398 | 13.914 | 6.337 | 1.00 | 30.15 | C |
| ATOM | 6234 | CG | ASN | C | 266 | 67.882 | 13.698 | 4.902 | 1.00 | 32.89 | C |
| ATOM | 6235 | OD1 | ASN | C | 266 | 68.658 | 13.494 | 3.963 | 1.00 | 35.21 | O |
| ATOM | 6236 | ND2 | ASN | C | 266 | 66.571 | 13.726 | 4.742 | 1.00 | 37.61 | N |
| ATOM | 6237 | C | ASN | C | 266 | 69.667 | 15.868 | 5.492 | 1.00 | 29.43 | C |
| ATOM | 6238 | O | ASN | C | 266 | 68.578 | 16.294 | 5.093 | 1.00 | 30.05 | O |
| ATOM | 6239 | N | HIS | C | 267 | 70.826 | 16.437 | 5.186 | 1.00 | 30.19 | N |
| ATOM | 6240 | CA | HIS | C | 267 | 70.883 | 17.632 | 4.343 | 1.00 | 31.93 | C |
| ATOM | 6241 | CB | HIS | C | 267 | 72.331 | 18.035 | 4.109 | 1.00 | 33.37 | C |
| ATOM | 6242 | CG | HIS | C | 267 | 73.011 | 18.501 | 5.353 | 1.00 | 41.56 | C |
| ATOM | 6243 | ND1 | HIS | C | 267 | 72.522 | 19.540 | 6.117 | 1.00 | 46.15 | N |
| ATOM | 6244 | CE1 | HIS | C | 267 | 73.275 | 19.684 | 7.189 | 1.00 | 47.90 | C |
| ATOM | 6245 | NE2 | HIS | C | 267 | 74.240 | 18.780 | 7.146 | 1.00 | 49.17 | N |
| ATOM | 6246 | CD2 | HIS | C | 267 | 74.099 | 18.029 | 6.006 | 1.00 | 47.11 | C |
| ATOM | 6247 | C | HIS | C | 267 | 70.145 | 17.566 | 3.007 | 1.00 | 30.59 | C |
| ATOM | 6248 | O | HIS | C | 267 | 70.059 | 18.557 | 2.293 | 1.00 | 30.50 | O |
| ATOM | 6249 | N | GLY | C | 268 | 69.599 | 16.420 | 2.655 | 1.00 | 30.10 | N |
| ATOM | 6250 | CA | GLY | C | 268 | 68.887 | 16.393 | 1.413 | 1.00 | 29.83 | C |
| ATOM | 6251 | C | GLY | C | 268 | 67.601 | 17.145 | 1.636 | 1.00 | 29.35 | C |
| ATOM | 6252 | O | GLY | C | 268 | 67.105 | 17.800 | 0.727 | 1.00 | 29.25 | O |
| ATOM | 6253 | N | LEU | C | 269 | 67.073 | 17.068 | 2.853 | 1.00 | 28.91 | N |
| ATOM | 6254 | CA | LEU | C | 269 | 65.811 | 17.737 | 3.193 | 1.00 | 28.73 | C |

FIG. 2A-136

| | | | | | | | | | | |
|---|---|---|---|---|---|---|---|---|---|---|
| ATOM | 6255 | CB | LEU | C | 269 | 65.356 | 17.396 | 4.612 | 1.00 | 29.20 | C |
| ATOM | 6256 | CG | LEU | C | 269 | 65.154 | 15.930 | 5.003 | 1.00 | 31.25 | C |
| ATOM | 6257 | CD1 | LEU | C | 269 | 64.839 | 15.811 | 6.503 | 1.00 | 21.22 | C |
| ATOM | 6258 | CD2 | LEU | C | 269 | 64.067 | 15.334 | 4.133 | 1.00 | 32.16 | C |
| ATOM | 6259 | C | LEU | C | 269 | 65.873 | 19.251 | 3.072 | 1.00 | 29.15 | C |
| ATOM | 6260 | O | LEU | C | 269 | 66.931 | 19.871 | 3.193 | 1.00 | 28.52 | O |
| ATOM | 6261 | N | ALA | C | 270 | 64.695 | 19.828 | 2.862 | 1.00 | 29.74 | N |
| ATOM | 6262 | CA | ALA | C | 270 | 64.523 | 21.256 | 2.683 | 1.00 | 29.42 | C |
| ATOM | 6263 | CB | ALA | C | 270 | 63.349 | 21.499 | 1.769 | 1.00 | 29.95 | C |
| ATOM | 6264 | C | ALA | C | 270 | 64.315 | 22.003 | 3.994 | 1.00 | 29.12 | C |
| ATOM | 6265 | O | ALA | C | 270 | 64.456 | 23.224 | 4.050 | 1.00 | 29.00 | O |
| ATOM | 6266 | N | ILE | C | 271 | 63.953 | 21.288 | 5.048 | 1.00 | 27.43 | N |
| ATOM | 6267 | CA | ILE | C | 271 | 63.741 | 21.952 | 6.319 | 1.00 | 28.03 | C |
| ATOM | 6268 | CB | ILE | C | 271 | 62.256 | 22.238 | 6.575 | 1.00 | 28.12 | C |
| ATOM | 6269 | CG1 | ILE | C | 271 | 61.821 | 23.432 | 5.728 | 1.00 | 28.37 | C |
| ATOM | 6270 | CD1 | ILE | C | 271 | 60.655 | 24.199 | 6.300 | 1.00 | 29.55 | C |
| ATOM | 6271 | CG2 | ILE | C | 271 | 62.024 | 22.497 | 8.044 | 1.00 | 30.12 | C |
| ATOM | 6272 | C | ILE | C | 271 | 64.296 | 21.121 | 7.441 | 1.00 | 27.69 | C |
| ATOM | 6273 | O | ILE | C | 271 | 63.995 | 19.925 | 7.532 | 1.00 | 29.64 | O |
| ATOM | 6274 | N | SER | C | 272 | 65.100 | 21.760 | 8.286 | 1.00 | 26.11 | N |
| ATOM | 6275 | CA | SER | C | 272 | 65.741 | 21.082 | 9.408 | 1.00 | 24.34 | C |
| ATOM | 6276 | CB | SER | C | 272 | 64.692 | 20.505 | 10.368 | 1.00 | 25.48 | C |
| ATOM | 6277 | OG | SER | C | 272 | 63.975 | 21.541 | 11.037 | 1.00 | 28.78 | O |
| ATOM | 6278 | C | SER | C | 272 | 66.686 | 19.970 | 8.944 | 1.00 | 21.74 | C |
| ATOM | 6279 | O | SER | C | 272 | 66.478 | 18.803 | 9.227 | 1.00 | 20.06 | O |
| ATOM | 6280 | N | PRO | C | 273 | 67.731 | 20.334 | 8.201 | 1.00 | 20.39 | N |
| ATOM | 6281 | CA | PRO | C | 273 | 68.730 | 19.400 | 7.683 | 1.00 | 19.61 | C |
| ATOM | 6282 | CB | PRO | C | 273 | 69.605 | 20.279 | 6.781 | 1.00 | 17.95 | C |
| ATOM | 6283 | CG | PRO | C | 273 | 68.794 | 21.476 | 6.527 | 1.00 | 17.95 | C |
| ATOM | 6284 | CD | PRO | C | 273 | 68.031 | 21.705 | 7.773 | 1.00 | 20.08 | C |
| ATOM | 6285 | C | PRO | C | 273 | 69.571 | 18.806 | 8.829 | 1.00 | 19.40 | C |
| ATOM | 6286 | O | PRO | C | 273 | 69.785 | 17.606 | 8.903 | 1.00 | 22.09 | O |
| ATOM | 6287 | N | GLY | C | 274 | 70.046 | 19.656 | 9.727 | 1.00 | 18.39 | N |
| ATOM | 6288 | CA | GLY | C | 274 | 70.878 | 19.163 | 10.791 | 1.00 | 16.80 | C |
| ATOM | 6289 | C | GLY | C | 274 | 70.247 | 18.577 | 12.030 | 1.00 | 17.40 | C |
| ATOM | 6290 | O | GLY | C | 274 | 69.222 | 19.017 | 12.538 | 1.00 | 18.56 | O |
| ATOM | 6291 | N | MSEC | | 275 | 70.944 | 17.592 | 12.568 | 1.00 | 18.89 | N |
| ATOM | 6292 | CA | MSEC | | 275 | 70.490 | 16.903 | 13.740 | 1.00 | 19.64 | C |
| ATOM | 6293 | CB | MSEC | | 275 | 71.519 | 15.854 | 14.130 | 1.00 | 20.29 | C |
| ATOM | 6294 | CG | MSEC | | 275 | 71.047 | 15.010 | 15.263 | 1.00 | 25.16 | C |
| ATOM | 6295 | SE | MSEC | | 275 | 72.255 | 13.619 | 15.597 | 1.00 | 34.56 | S |
| ATOM | 6296 | CE | MSEC | | 275 | 73.669 | 14.596 | 16.460 | 1.00 | 25.47 | C |
| ATOM | 6297 | C | MSEC | | 275 | 70.143 | 17.810 | 14.926 | 1.00 | 18.24 | C |
| ATOM | 6298 | O | MSEC | | 275 | 69.051 | 17.699 | 15.466 | 1.00 | 16.95 | O |
| ATOM | 6299 | N | ALA | C | 276 | 71.051 | 18.701 | 15.326 | 1.00 | 19.28 | N |
| ATOM | 6300 | CA | ALA | C | 276 | 70.779 | 19.597 | 16.456 | 1.00 | 20.63 | C |

FIG. 2A-137

| ATOM | 6301 | CB | ALA | C | 276 | 71.936 | 20.583 | 16.654 | 1.00 | 16.57 | C |
| --- | --- | --- | --- | --- | --- | --- | --- | --- | --- | --- | --- |
| ATOM | 6302 | C | ALA | C | 276 | 69.447 | 20.343 | 16.244 | 1.00 | 21.54 | C |
| ATOM | 6303 | O | ALA | C | 276 | 68.628 | 20.482 | 17.168 | 1.00 | 22.68 | O |
| ATOM | 6304 | N | THR | C | 277 | 69.201 | 20.783 | 15.020 | 1.00 | 21.90 | N |
| ATOM | 6305 | CA | THR | C | 277 | 67.950 | 21.478 | 14.738 | 1.00 | 22.64 | C |
| ATOM | 6306 | CB | THR | C | 277 | 67.952 | 22.024 | 13.343 | 1.00 | 23.23 | C |
| ATOM | 6307 | OG1 | THR | C | 277 | 68.983 | 23.005 | 13.257 | 1.00 | 25.92 | O |
| ATOM | 6308 | CG2 | THR | C | 277 | 66.604 | 22.646 | 13.005 | 1.00 | 22.94 | C |
| ATOM | 6309 | C | THR | C | 277 | 66.720 | 20.586 | 14.900 | 1.00 | 22.50 | C |
| ATOM | 6310 | O | THR | C | 277 | 65.705 | 21.018 | 15.465 | 1.00 | 23.51 | O |
| ATOM | 6311 | N | ARG | C | 278 | 66.814 | 19.360 | 14.375 | 1.00 | 21.21 | N |
| ATOM | 6312 | CA | ARG | C | 278 | 65.744 | 18.382 | 14.489 | 1.00 | 22.40 | C |
| ATOM | 6313 | CB | ARG | C | 278 | 66.187 | 17.059 | 13.892 | 1.00 | 22.66 | C |
| ATOM | 6314 | CG | ARG | C | 278 | 67.202 | 17.151 | 12.763 | 1.00 | 28.34 | C |
| ATOM | 6315 | CD | ARG | C | 278 | 66.756 | 16.299 | 11.579 | 1.00 | 33.85 | C |
| ATOM | 6316 | NE | ARG | C | 278 | 65.526 | 16.869 | 11.066 | 1.00 | 38.69 | N |
| ATOM | 6317 | CZ | ARG | C | 278 | 64.648 | 16.208 | 10.342 | 1.00 | 42.67 | C |
| ATOM | 6318 | NH1AR | G | C | 278 | 64.867 | 14.938 | 10.057 | 1.00 | 45.58 | N |
| ATOM | 6319 | NH2AR | G | C | 278 | 63.568 | 16.830 | 9.880 | 1.00 | 43.48 | N |
| ATOM | 6320 | C | ARG | C | 278 | 65.410 | 18.131 | 15.967 | 1.00 | 21.09 | C |
| ATOM | 6321 | O | ARG | C | 278 | 64.250 | 17.937 | 16.316 | 1.00 | 23.07 | O |
| ATOM | 6322 | N | ILE | C | 279 | 66.437 | 18.117 | 16.829 | 1.00 | 20.25 | N |
| ATOM | 6323 | CA | ILE | C | 279 | 66.234 | 17.877 | 18.259 | 1.00 | 19.67 | C |
| ATOM | 6324 | CB | ILE | C | 279 | 67.542 | 17.622 | 18.967 | 1.00 | 19.30 | C |
| ATOM | 6325 | CG1 | ILE | C | 279 | 68.151 | 16.321 | 18.499 | 1.00 | 18.16 | C |
| ATOM | 6326 | CD1 | ILE | C | 279 | 69.552 | 16.091 | 19.081 | 1.00 | 17.69 | C |
| ATOM | 6327 | CG2 | ILE | C | 279 | 67.305 | 17.477 | 20.437 | 1.00 | 19.21 | C |
| ATOM | 6328 | C | ILE | C | 279 | 65.506 | 19.038 | 18.962 | 1.00 | 20.61 | C |
| ATOM | 6329 | O | ILE | C | 279 | 64.530 | 18.819 | 19.683 | 1.00 | 20.52 | O |
| ATOM | 6330 | N | ARG | C | 280 | 65.982 | 20.267 | 18.767 | 1.00 | 19.30 | N |
| ATOM | 6331 | CA | ARG | C | 280 | 65.296 | 21.416 | 19.355 | 1.00 | 18.67 | C |
| ATOM | 6332 | CB | ARG | C | 280 | 65.850 | 22.751 | 18.864 | 1.00 | 19.36 | C |
| ATOM | 6333 | CG | ARG | C | 280 | 67.218 | 23.130 | 19.253 | 1.00 | 23.05 | C |
| ATOM | 6334 | CD | ARG | C | 280 | 67.425 | 24.535 | 18.741 | 1.00 | 35.28 | C |
| ATOM | 6335 | NE | ARG | C | 280 | 68.835 | 24.902 | 18.596 | 1.00 | 45.28 | N |
| ATOM | 6336 | CZ | ARG | C | 280 | 69.438 | 25.117 | 17.423 | 1.00 | 49.98 | C |
| ATOM | 6337 | NH1AR | G | C | 280 | 68.778 | 24.998 | 16.260 | 1.00 | 46.03 | N |
| ATOM | 6338 | NH2AR | G | C | 280 | 70.715 | 25.496 | 17.414 | 1.00 | 50.55 | N |
| ATOM | 6339 | C | ARG | C | 280 | 63.861 | 21.375 | 18.866 | 1.00 | 17.50 | C |
| ATOM | 6340 | O | ARG | C | 280 | 62.940 | 21.448 | 19.651 | 1.00 | 18.38 | O |
| ATOM | 6341 | N | MSE | C | 281 | 63.703 | 21.321 | 17.543 | 1.00 | 16.41 | N |
| ATOM | 6342 | CA | MSE | C | 281 | 62.406 | 21.304 | 16.904 | 1.00 | 17.16 | C |
| ATOM | 6343 | CB | MSE | C | 281 | 62.527 | 21.145 | 15.399 | 1.00 | 18.81 | C |
| ATOM | 6344 | CG | MSE | C | 281 | 63.033 | 22.345 | 14.625 | 1.00 | 14.41 | C |
| ATOM | 6345 | SE | MSE | C | 281 | 61.868 | 23.838 | 14.892 | 1.00 | 33.56 | S |
| ATOM | 6346 | CE | MSE | C | 281 | 60.869 | 23.668 | 13.265 | 1.00 | 21.06 | C |

FIG. 2A-138

| ATOM | 6347 | C   | MSEC |   | 281 | 61.610 | 20.148 | 17.407 | 1.00 | 17.98 | C |
|------|------|-----|------|---|-----|--------|--------|--------|------|-------|---|
| ATOM | 6348 | O   | MSEC |   | 281 | 60.394 | 20.224 | 17.478 | 1.00 | 18.66 | O |
| ATOM | 6349 | N   | GLY  | C | 282 | 62.305 | 19.073 | 17.778 | 1.00 | 18.93 | N |
| ATOM | 6350 | CA  | GLY  | C | 282 | 61.618 | 17.867 | 18.221 | 1.00 | 20.70 | C |
| ATOM | 6351 | C   | GLY  | C | 282 | 60.995 | 17.143 | 17.015 | 1.00 | 22.07 | C |
| ATOM | 6352 | O   | GLY  | C | 282 | 59.859 | 16.696 | 17.042 | 1.00 | 23.15 | O |
| ATOM | 6353 | N   | GLN  | C | 283 | 61.711 | 17.053 | 15.916 | 1.00 | 21.77 | N |
| ATOM | 6354 | CA  | GLN  | C | 283 | 61.111 | 16.367 | 14.841 | 1.00 | 22.31 | C |
| ATOM | 6355 | CB  | GLN  | C | 283 | 60.973 | 17.262 | 13.625 | 1.00 | 23.19 | C |
| ATOM | 6356 | CG  | GLN  | C | 283 | 62.194 | 17.949 | 13.181 | 1.00 | 26.30 | C |
| ATOM | 6357 | CD  | GLN  | C | 283 | 61.900 | 18.763 | 11.946 | 1.00 | 34.00 | C |
| ATOM | 6358 | OE1 | GLN  | C | 283 | 61.463 | 18.216 | 10.944 | 1.00 | 35.15 | O |
| ATOM | 6359 | NE2 | GLN  | C | 283 | 62.122 | 20.080 | 12.013 | 1.00 | 41.26 | N |
| ATOM | 6360 | C   | GLN  | C | 283 | 61.734 | 15.049 | 14.453 | 1.00 | 22.01 | C |
| ATOM | 6361 | O   | GLN  | C | 283 | 62.777 | 14.969 | 13.816 | 1.00 | 21.94 | O |
| ATOM | 6362 | N   | TYR  | C | 284 | 61.047 | 14.011 | 14.896 | 1.00 | 22.63 | N |
| ATOM | 6363 | CA  | TYR  | C | 284 | 61.356 | 12.640 | 14.598 | 1.00 | 22.37 | C |
| ATOM | 6364 | CB  | TYR  | C | 284 | 61.676 | 11.856 | 15.857 | 1.00 | 20.77 | C |
| ATOM | 6365 | CG  | TYR  | C | 284 | 60.621 | 11.924 | 16.898 | 1.00 | 19.15 | C |
| ATOM | 6366 | CD1 | TYR  | C | 284 | 60.509 | 13.030 | 17.707 | 1.00 | 18.25 | C |
| ATOM | 6367 | CE1 | TYR  | C | 284 | 59.595 | 13.079 | 18.718 | 1.00 | 22.22 | C |
| ATOM | 6368 | CZ  | TYR  | C | 284 | 58.746 | 12.010 | 18.947 | 1.00 | 23.35 | C |
| ATOM | 6369 | OH  | TYR  | C | 284 | 57.832 | 12.095 | 19.977 | 1.00 | 24.45 | O |
| ATOM | 6370 | CE2 | TYR  | C | 284 | 58.821 | 10.877 | 18.142 | 1.00 | 18.97 | C |
| ATOM | 6371 | CD2 | TYR  | C | 284 | 59.767 | 10.848 | 17.117 | 1.00 | 19.94 | C |
| ATOM | 6372 | C   | TYR  | C | 284 | 60.028 | 12.185 | 14.005 | 1.00 | 22.17 | C |
| ATOM | 6373 | O   | TYR  | C | 284 | 59.098 | 12.969 | 13.897 | 1.00 | 21.99 | O |
| ATOM | 6374 | N   | ALA  | C | 285 | 59.941 | 10.924 | 13.622 | 1.00 | 22.96 | N |
| ATOM | 6375 | CA  | ALA  | C | 285 | 58.733 | 10.397 | 13.024 | 1.00 | 22.74 | C |
| ATOM | 6376 | CB  | ALA  | C | 285 | 58.813 | 10.541 | 11.507 | 1.00 | 22.26 | C |
| ATOM | 6377 | C   | ALA  | C | 285 | 58.700 | 8.940  | 13.406 | 1.00 | 22.86 | C |
| ATOM | 6378 | O   | ALA  | C | 285 | 59.704 | 8.414  | 13.858 | 1.00 | 23.47 | O |
| ATOM | 6379 | N   | PHE  | C | 286 | 57.542 | 8.312  | 13.261 | 1.00 | 23.86 | N |
| ATOM | 6380 | CA  | PHE  | C | 286 | 57.383 | 6.888  | 13.534 | 1.00 | 24.52 | C |
| ATOM | 6381 | CB  | PHE  | C | 286 | 56.279 | 6.607  | 14.559 | 1.00 | 22.62 | C |
| ATOM | 6382 | CG  | PHE  | C | 286 | 56.589 | 7.040  | 15.959 | 1.00 | 21.78 | C |
| ATOM | 6383 | CD1 | PHE  | C | 286 | 55.849 | 8.032  | 16.569 | 1.00 | 24.34 | C |
| ATOM | 6384 | CE1 | PHE  | C | 286 | 56.092 | 8.370  | 17.902 | 1.00 | 26.91 | C |
| ATOM | 6385 | CZ  | PHE  | C | 286 | 57.083 | 7.712  | 18.626 | 1.00 | 25.40 | C |
| ATOM | 6386 | CE2 | PHE  | C | 286 | 57.813 | 6.741  | 18.027 | 1.00 | 25.07 | C |
| ATOM | 6387 | CD2 | PHE  | C | 286 | 57.571 | 6.404  | 16.699 | 1.00 | 25.69 | C |
| ATOM | 6388 | C   | PHE  | C | 286 | 56.900 | 6.391  | 12.187 | 1.00 | 26.11 | C |
| ATOM | 6389 | O   | PHE  | C | 286 | 55.732 | 6.053  | 12.037 | 1.00 | 27.78 | O |
| ATOM | 6390 | N   | PRO  | C | 287 | 57.782 | 6.325  | 11.193 | 1.00 | 25.18 | N |
| ATOM | 6391 | CA  | PRO  | C | 287 | 57.510 | 5.888  | 9.825  | 1.00 | 24.47 | C |
| ATOM | 6392 | CB  | PRO  | C | 287 | 58.675 | 6.486  | 9.082  | 1.00 | 23.96 | C |

FIG. 2A-139

| ATOM | 6393 | CG | PRO | C | 287 | 59.799 | 6.098 | 10.021 | 1.00 | 23.11 | C |
| --- | --- | --- | --- | --- | --- | --- | --- | --- | --- | --- | --- |
| ATOM | 6394 | CD | PRO | C | 287 | 59.225 | 6.568 | 11.363 | 1.00 | 25.55 | C |
| ATOM | 6395 | C | PRO | C | 287 | 57.386 | 4.374 | 9.506 | 1.00 | 25.01 | C |
| ATOM | 6396 | O | PRO | C | 287 | 58.023 | 3.520 | 10.157 | 1.00 | 23.14 | O |
| ATOM | 6397 | N | ASN | C | 288 | 56.566 | 4.050 | 8.494 | 1.00 | 25.06 | N |
| ATOM | 6398 | CA | ASN | C | 288 | 56.454 | 2.651 | 8.047 | 1.00 | 27.14 | C |
| ATOM | 6399 | CB | ASN | C | 288 | 55.244 | 2.395 | 7.170 | 1.00 | 27.52 | C |
| ATOM | 6400 | CG | ASN | C | 288 | 53.992 | 2.782 | 7.810 | 1.00 | 28.00 | C |
| ATOM | 6401 | OD1 | ASN | C | 288 | 53.767 | 2.507 | 8.998 | 1.00 | 25.24 | O |
| ATOM | 6402 | ND2 | ASN | C | 288 | 53.123 | 3.416 | 7.027 | 1.00 | 28.88 | N |
| ATOM | 6403 | C | ASN | C | 288 | 57.660 | 2.462 | 7.145 | 1.00 | 28.99 | C |
| ATOM | 6404 | O | ASN | C | 288 | 58.086 | 3.413 | 6.496 | 1.00 | 29.90 | O |
| ATOM | 6405 | N | PRO | C | 289 | 58.157 | 1.226 | 7.000 | 1.00 | 29.59 | N |
| ATOM | 6406 | CA | PRO | C | 289 | 57.697 | -0.024 | 7.590 | 1.00 | 28.96 | C |
| ATOM | 6407 | CB | PRO | C | 289 | 58.534 | -1.051 | 6.864 | 1.00 | 31.77 | C |
| ATOM | 6408 | CG | PRO | C | 289 | 59.834 | -0.321 | 6.718 | 1.00 | 32.59 | C |
| ATOM | 6409 | CD | PRO | C | 289 | 59.367 | 0.995 | 6.201 | 1.00 | 29.25 | C |
| ATOM | 6410 | C | PRO | C | 289 | 57.840 | -0.121 | 9.082 | 1.00 | 26.75 | C |
| ATOM | 6411 | O | PRO | C | 289 | 56.871 | 0.058 | 9.768 | 1.00 | 29.77 | O |
| ATOM | 6412 | N | GLU | C | 290 | 59.047 | -0.403 | 9.568 | 1.00 | 24.91 | N |
| ATOM | 6413 | CA | GLU | C | 290 | 59.384 | -0.553 | 11.003 | 1.00 | 24.91 | C |
| ATOM | 6414 | CB | GLU | C | 290 | 60.718 | 0.140 | 11.335 | 1.00 | 25.74 | C |
| ATOM | 6415 | CG | GLU | C | 290 | 61.660 | 0.416 | 10.175 | 1.00 | 32.96 | C |
| ATOM | 6416 | CD | GLU | C | 290 | 61.282 | 1.689 | 9.383 | 1.00 | 44.09 | C |
| ATOM | 6417 | OE1 | GLU | C | 290 | 60.065 | 1.992 | 9.207 | 1.00 | 48.52 | O |
| ATOM | 6418 | OE2 | GLU | C | 290 | 62.216 | 2.381 | 8.916 | 1.00 | 48.53 | O |
| ATOM | 6419 | C | GLU | C | 290 | 58.399 | -0.187 | 12.132 | 1.00 | 22.37 | C |
| ATOM | 6420 | O | GLU | C | 290 | 58.338 | -0.906 | 13.128 | 1.00 | 22.65 | O |
| ATOM | 6421 | N | TRP | C | 291 | 57.646 | 0.904 | 12.017 | 1.00 | 21.40 | N |
| ATOM | 6422 | CA | TRP | C | 291 | 56.744 | 1.258 | 13.109 | 1.00 | 22.90 | C |
| ATOM | 6423 | CB | TRP | C | 291 | 56.713 | 2.782 | 13.351 | 1.00 | 23.09 | C |
| ATOM | 6424 | CG | TRP | C | 291 | 57.991 | 3.327 | 13.914 | 1.00 | 27.61 | C |
| ATOM | 6425 | CD1 | TRP | C | 291 | 59.051 | 3.764 | 13.204 | 1.00 | 30.69 | C |
| ATOM | 6426 | NE1 | TRP | C | 291 | 60.080 | 4.098 | 14.039 | 1.00 | 36.60 | N |
| ATOM | 6427 | CE2 | TRP | C | 291 | 59.694 | 3.889 | 15.334 | 1.00 | 33.73 | C |
| ATOM | 6428 | CD2 | TRP | C | 291 | 58.373 | 3.398 | 15.297 | 1.00 | 29.74 | C |
| ATOM | 6429 | CE3 | TRP | C | 291 | 57.735 | 3.089 | 16.504 | 1.00 | 30.81 | C |
| ATOM | 6430 | CZ3 | TRP | C | 291 | 58.434 | 3.282 | 17.702 | 1.00 | 27.40 | C |
| ATOM | 6431 | CH2 | TRP | C | 291 | 59.747 | 3.777 | 17.703 | 1.00 | 32.82 | C |
| ATOM | 6432 | CZ2 | TRP | C | 291 | 60.394 | 4.088 | 16.534 | 1.00 | 33.39 | C |
| ATOM | 6433 | C | TRP | C | 291 | 55.338 | 0.777 | 12.908 | 1.00 | 22.32 | C |
| ATOM | 6434 | O | TRP | C | 291 | 54.520 | 0.768 | 13.847 | 1.00 | 23.67 | O |
| ATOM | 6435 | N | SER | C | 292 | 55.063 | 0.361 | 11.681 | 1.00 | 20.67 | N |
| ATOM | 6436 | CA | SER | C | 292 | 53.745 | -0.098 | 11.278 | 1.00 | 19.56 | C |
| ATOM | 6437 | CB | SER | C | 292 | 53.793 | -0.795 | 9.924 | 1.00 | 18.21 | C |
| ATOM | 6438 | OG | SER | C | 292 | 53.894 | -2.196 | 10.109 | 1.00 | 22.82 | O |

FIG. 2A-140

| ATOM | 6439 | C | SER | C | 292 | 53.070 | -1.022 | 12.240 | 1.00 | 18.56 | C |
|---|---|---|---|---|---|---|---|---|---|---|---|
| ATOM | 6440 | O | SER | C | 292 | 51.911 | -0.850 | 12.528 | 1.00 | 19.35 | O |
| ATOM | 6441 | N | ALA | C | 293 | 53.759 | -2.024 | 12.745 | 1.00 | 19.20 | N |
| ATOM | 6442 | CA | ALA | C | 293 | 53.051 | -2.928 | 13.638 | 1.00 | 19.48 | C |
| ATOM | 6443 | CB | ALA | C | 293 | 53.537 | -4.370 | 13.402 | 1.00 | 20.37 | C |
| ATOM | 6444 | C | ALA | C | 293 | 53.177 | -2.539 | 15.097 | 1.00 | 19.02 | C |
| ATOM | 6445 | O | ALA | C | 293 | 52.962 | -3.344 | 15.981 | 1.00 | 19.45 | O |
| ATOM | 6446 | N | VAL | C | 294 | 53.532 | -1.285 | 15.343 | 1.00 | 19.87 | N |
| ATOM | 6447 | CA | VAL | C | 294 | 53.706 | -0.811 | 16.691 | 1.00 | 21.14 | C |
| ATOM | 6448 | CB | VAL | C | 294 | 54.958 | 0.017 | 16.765 | 1.00 | 22.18 | C |
| ATOM | 6449 | CG1 | VAL | C | 294 | 54.950 | 0.844 | 18.049 | 1.00 | 24.01 | C |
| ATOM | 6450 | CG2 | VAL | C | 294 | 56.178 | -0.916 | 16.695 | 1.00 | 23.33 | C |
| ATOM | 6451 | C | VAL | C | 294 | 52.530 | 0.021 | 17.144 | 1.00 | 22.08 | C |
| ATOM | 6452 | O | VAL | C | 294 | 52.172 | 0.953 | 16.458 | 1.00 | 24.64 | O |
| ATOM | 6453 | N | SER | C | 295 | 51.933 | -0.292 | 18.292 | 1.00 | 21.62 | N |
| ATOM | 6454 | CA | SER | C | 295 | 50.771 | 0.481 | 18.757 | 1.00 | 22.77 | C |
| ATOM | 6455 | CB | SER | C | 295 | 50.152 | -0.122 | 20.001 | 1.00 | 24.39 | C |
| ATOM | 6456 | OG | SER | C | 295 | 51.080 | -0.194 | 21.068 | 1.00 | 22.13 | O |
| ATOM | 6457 | C | SER | C | 295 | 50.932 | 1.958 | 19.060 | 1.00 | 23.20 | C |
| ATOM | 6458 | O | SER | C | 295 | 52.022 | 2.472 | 19.325 | 1.00 | 22.10 | O |
| ATOM | 6459 | N | GLU | C | 296 | 49.786 | 2.615 | 19.059 | 1.00 | 24.59 | N |
| ATOM | 6460 | CA | GLU | C | 296 | 49.687 | 4.029 | 19.322 | 1.00 | 26.99 | C |
| ATOM | 6461 | CB | GLU | C | 296 | 48.289 | 4.518 | 19.025 | 1.00 | 26.34 | C |
| ATOM | 6462 | CG | GLU | C | 296 | 48.191 | 5.982 | 19.062 | 1.00 | 36.33 | C |
| ATOM | 6463 | CD | GLU | C | 296 | 48.986 | 6.609 | 17.945 | 1.00 | 46.11 | C |
| ATOM | 6464 | OE1 | GLU | C | 296 | 49.010 | 6.015 | 16.839 | 1.00 | 47.25 | O |
| ATOM | 6465 | OE2 | GLU | C | 296 | 49.567 | 7.693 | 18.154 | 1.00 | 46.26 | O |
| ATOM | 6466 | C | GLU | C | 296 | 50.025 | 4.351 | 20.760 | 1.00 | 26.45 | C |
| ATOM | 6467 | O | GLU | C | 296 | 50.514 | 5.438 | 21.050 | 1.00 | 28.76 | O |
| ATOM | 6468 | N | GLU | C | 297 | 49.768 | 3.413 | 21.662 | 1.00 | 25.71 | N |
| ATOM | 6469 | CA | GLU | C | 297 | 50.048 | 3.658 | 23.074 | 1.00 | 24.41 | C |
| ATOM | 6470 | CB | GLU | C | 297 | 49.465 | 2.557 | 23.945 | 1.00 | 24.33 | C |
| ATOM | 6471 | CG | GLU | C | 297 | 50.479 | 1.810 | 24.707 | 1.00 | 29.22 | C |
| ATOM | 6472 | CD | GLU | C | 297 | 49.846 | 0.917 | 25.726 | 1.00 | 38.62 | C |
| ATOM | 6473 | OE1 | GLU | C | 297 | 49.007 | 1.429 | 26.491 | 1.00 | 37.58 | O |
| ATOM | 6474 | OE2 | GLU | C | 297 | 50.177 | -0.289 | 25.773 | 1.00 | 40.96 | O |
| ATOM | 6475 | C | GLU | C | 297 | 51.540 | 3.725 | 23.293 | 1.00 | 23.83 | C |
| ATOM | 6476 | O | GLU | C | 297 | 52.035 | 4.592 | 24.012 | 1.00 | 24.19 | O |
| ATOM | 6477 | N | VAL | C | 298 | 52.248 | 2.797 | 22.664 | 1.00 | 23.63 | N |
| ATOM | 6478 | CA | VAL | C | 298 | 53.679 | 2.740 | 22.765 | 1.00 | 23.44 | C |
| ATOM | 6479 | CB | VAL | C | 298 | 54.202 | 1.497 | 22.061 | 1.00 | 22.43 | C |
| ATOM | 6480 | CG1 | VAL | C | 298 | 55.724 | 1.499 | 22.017 | 1.00 | 20.85 | C |
| ATOM | 6481 | CG2 | VAL | C | 298 | 53.725 | 0.288 | 22.788 | 1.00 | 27.39 | C |
| ATOM | 6482 | C | VAL | C | 298 | 54.309 | 3.970 | 22.143 | 1.00 | 24.62 | C |
| ATOM | 6483 | O | VAL | C | 298 | 55.286 | 4.507 | 22.645 | 1.00 | 25.02 | O |
| ATOM | 6484 | N | LYS | C | 299 | 53.745 | 4.439 | 21.051 | 1.00 | 25.46 | N |

FIG. 2A-141

| ATOM | 6485 | CA | LYS | C | 299 | 54.332 | 5.581 | 20.405 | 1.00 | 25.90 | C |
| --- | --- | --- | --- | --- | --- | --- | --- | --- | --- | --- | --- |
| ATOM | 6486 | CB | LYS | C | 299 | 53.723 | 5.765 | 19.033 | 1.00 | 25.38 | C |
| ATOM | 6487 | CG | LYS | C | 299 | 54.135 | 4.729 | 18.034 | 1.00 | 27.16 | C |
| ATOM | 6488 | CD | LYS | C | 299 | 53.542 | 5.128 | 16.722 | 1.00 | 29.25 | C |
| ATOM | 6489 | CE | LYS | C | 299 | 53.108 | 3.955 | 15.900 | 1.00 | 33.73 | C |
| ATOM | 6490 | NZ | LYS | C | 299 | 52.042 | 4.422 | 14.943 | 1.00 | 36.12 | N |
| ATOM | 6491 | C | LYS | C | 299 | 54.113 | 6.832 | 21.208 | 1.00 | 27.02 | C |
| ATOM | 6492 | O | LYS | C | 299 | 54.944 | 7.754 | 21.223 | 1.00 | 27.77 | O |
| ATOM | 6493 | N | MSEC | | 300 | 52.957 | 6.840 | 21.859 | 1.00 | 28.92 | N |
| ATOM | 6494 | CA | MSEC | | 300 | 52.482 | 7.940 | 22.664 | 1.00 | 28.25 | C |
| ATOM | 6495 | CB | MSEC | | 300 | 51.012 | 7.687 | 22.981 | 1.00 | 28.43 | C |
| ATOM | 6496 | CG | MSEC | | 300 | 50.171 | 8.922 | 23.344 | 1.00 | 41.89 | C |
| ATOM | 6497 | SE | MSEC | | 300 | 50.298 | 10.514 | 22.201 | 1.00 | 64.28 | S |
| ATOM | 6498 | CE | MSEC | | 300 | 51.142 | 11.664 | 23.502 | 1.00 | 39.07 | C |
| ATOM | 6499 | C | MSEC | | 300 | 53.344 | 8.003 | 23.902 | 1.00 | 26.35 | C |
| ATOM | 6500 | O | MSEC | | 300 | 53.607 | 9.076 | 24.440 | 1.00 | 27.95 | O |
| ATOM | 6501 | N | LEU | C | 301 | 53.806 | 6.845 | 24.343 | 1.00 | 24.13 | N |
| ATOM | 6502 | CA | LEU | C | 301 | 54.666 | 6.786 | 25.497 | 1.00 | 24.20 | C |
| ATOM | 6503 | CB | LEU | C | 301 | 54.867 | 5.337 | 25.887 | 1.00 | 23.02 | C |
| ATOM | 6504 | CG | LEU | C | 301 | 55.804 | 5.199 | 27.071 | 1.00 | 22.19 | C |
| ATOM | 6505 | CD1 | LEU | C | 301 | 55.246 | 6.024 | 28.232 | 1.00 | 22.53 | C |
| ATOM | 6506 | CD2 | LEU | C | 301 | 55.958 | 3.734 | 27.425 | 1.00 | 12.24 | C |
| ATOM | 6507 | C | LEU | C | 301 | 56.000 | 7.445 | 25.104 | 1.00 | 26.62 | C |
| ATOM | 6508 | O | LEU | C | 301 | 56.577 | 8.225 | 25.851 | 1.00 | 27.91 | O |
| ATOM | 6509 | N | ILE | C | 302 | 56.493 | 7.137 | 23.921 | 1.00 | 27.32 | N |
| ATOM | 6510 | CA | ILE | C | 302 | 57.705 | 7.742 | 23.446 | 1.00 | 26.14 | C |
| ATOM | 6511 | CB | ILE | C | 302 | 58.104 | 7.082 | 22.117 | 1.00 | 28.10 | C |
| ATOM | 6512 | CG1 | ILE | C | 302 | 58.503 | 5.632 | 22.407 | 1.00 | 29.70 | C |
| ATOM | 6513 | CD1 | ILE | C | 302 | 58.974 | 4.845 | 21.205 | 1.00 | 30.73 | C |
| ATOM | 6514 | CG2 | ILE | C | 302 | 59.175 | 7.908 | 21.396 | 1.00 | 24.48 | C |
| ATOM | 6515 | C | ILE | C | 302 | 57.517 | 9.271 | 23.272 | 1.00 | 26.61 | C |
| ATOM | 6516 | O | ILE | C | 302 | 58.406 | 10.056 | 23.584 | 1.00 | 26.79 | O |
| ATOM | 6517 | N | ARG | C | 303 | 56.360 | 9.698 | 22.780 | 1.00 | 26.64 | N |
| ATOM | 6518 | CA | ARG | C | 303 | 56.103 | 11.123 | 22.597 | 1.00 | 27.72 | C |
| ATOM | 6519 | CB | ARG | C | 303 | 54.782 | 11.329 | 21.861 | 1.00 | 26.99 | C |
| ATOM | 6520 | CG | ARG | C | 303 | 54.857 | 10.965 | 20.386 | 1.00 | 28.96 | C |
| ATOM | 6521 | CD | ARG | C | 303 | 53.681 | 11.566 | 19.646 | 1.00 | 29.44 | C |
| ATOM | 6522 | NE | ARG | C | 303 | 52.827 | 10.556 | 19.032 | 1.00 | 35.82 | N |
| ATOM | 6523 | CZ | ARG | C | 303 | 52.708 | 10.391 | 17.719 | 1.00 | 39.92 | C |
| ATOM | 6524 | NH1AR | G | C | 303 | 53.391 | 11.172 | 16.880 | 1.00 | 42.80 | N |
| ATOM | 6525 | NH2AR | G | C | 303 | 51.911 | 9.448 | 17.246 | 1.00 | 38.78 | N |
| ATOM | 6526 | C | ARG | C | 303 | 56.104 | 11.931 | 23.902 | 1.00 | 28.91 | C |
| ATOM | 6527 | O | ARG | C | 303 | 56.513 | 13.084 | 23.915 | 1.00 | 30.51 | O |
| ATOM | 6528 | N | ASN | C | 304 | 55.640 | 11.343 | 24.994 | 1.00 | 28.09 | N |
| ATOM | 6529 | CA | ASN | C | 304 | 55.668 | 12.053 | 26.246 | 1.00 | 29.85 | C |
| ATOM | 6530 | CB | ASN | C | 304 | 54.661 | 11.456 | 27.218 | 1.00 | 29.55 | C |

FIG. 2A-142

| ATOM | 6531 | CG | ASN | C | 304 | 53.240 | 11.942 | 26.930 | 1.00 | 36.29 | C |
| --- | --- | --- | --- | --- | --- | --- | --- | --- | --- | --- | --- |
| ATOM | 6532 | OD1 | ASN | C | 304 | 52.255 | 11.282 | 27.279 | 1.00 | 37.90 | O |
| ATOM | 6533 | ND2 | ASN | C | 304 | 53.131 | 13.119 | 26.284 | 1.00 | 42.74 | N |
| ATOM | 6534 | C | ASN | C | 304 | 57.085 | 12.019 | 26.805 | 1.00 | 28.81 | C |
| ATOM | 6535 | O | ASN | C | 304 | 57.478 | 12.887 | 27.592 | 1.00 | 29.42 | O |
| ATOM | 6536 | N | LEU | C | 305 | 57.875 | 11.027 | 26.412 | 1.00 | 25.18 | N |
| ATOM | 6537 | CA | LEU | C | 305 | 59.243 | 11.013 | 26.890 | 1.00 | 24.20 | C |
| ATOM | 6538 | CB | LEU | C | 305 | 59.842 | 9.612 | 26.836 | 1.00 | 23.19 | C |
| ATOM | 6539 | CG | LEU | C | 305 | 59.339 | 8.731 | 27.968 | 1.00 | 21.49 | C |
| ATOM | 6540 | CD1 | LEU | C | 305 | 59.640 | 7.283 | 27.670 | 1.00 | 23.67 | C |
| ATOM | 6541 | CD2 | LEU | C | 305 | 59.952 | 9.153 | 29.257 | 1.00 | 24.08 | C |
| ATOM | 6542 | C | LEU | C | 305 | 60.063 | 11.954 | 26.033 | 1.00 | 25.23 | C |
| ATOM | 6543 | O | LEU | C | 305 | 60.933 | 12.595 | 26.540 | 1.00 | 26.09 | O |
| ATOM | 6544 | N | LEU | C | 306 | 59.788 | 12.042 | 24.734 | 1.00 | 25.62 | N |
| ATOM | 6545 | CA | LEU | C | 306 | 60.564 | 12.924 | 23.852 | 1.00 | 24.88 | C |
| ATOM | 6546 | CB | LEU | C | 306 | 60.765 | 12.283 | 22.470 | 1.00 | 24.71 | C |
| ATOM | 6547 | CG | LEU | C | 306 | 61.768 | 11.127 | 22.464 | 1.00 | 22.23 | C |
| ATOM | 6548 | CD1 | LEU | C | 306 | 61.797 | 10.432 | 21.120 | 1.00 | 17.85 | C |
| ATOM | 6549 | CD2 | LEU | C | 306 | 63.124 | 11.681 | 22.861 | 1.00 | 23.00 | C |
| ATOM | 6550 | C | LEU | C | 306 | 59.950 | 14.303 | 23.675 | 1.00 | 26.57 | C |
| ATOM | 6551 | O | LEU | C | 306 | 59.868 | 14.819 | 22.572 | 1.00 | 28.67 | O |
| ATOM | 6552 | N | LYS | C | 307 | 59.478 | 14.894 | 24.764 | 1.00 | 28.02 | N |
| ATOM | 6553 | CA | LYS | C | 307 | 58.918 | 16.239 | 24.687 | 1.00 | 26.25 | C |
| ATOM | 6554 | CB | LYS | C | 307 | 57.956 | 16.502 | 25.834 | 1.00 | 24.63 | C |
| ATOM | 6555 | CG | LYS | C | 307 | 56.822 | 15.505 | 25.914 | 1.00 | 28.56 | C |
| ATOM | 6556 | CD | LYS | C | 307 | 55.499 | 16.148 | 25.585 | 1.00 | 35.59 | C |
| ATOM | 6557 | CE | LYS | C | 307 | 55.411 | 16.554 | 24.152 | 1.00 | 32.33 | C |
| ATOM | 6558 | NZ | LYS | C | 307 | 54.213 | 17.389 | 23.931 | 1.00 | 36.36 | N |
| ATOM | 6559 | C | LYS | C | 307 | 60.113 | 17.177 | 24.769 | 1.00 | 24.94 | C |
| ATOM | 6560 | O | LYS | C | 307 | 61.049 | 17.029 | 25.571 | 1.00 | 25.71 | O |
| ATOM | 6561 | N | THR | C | 308 | 60.060 | 18.152 | 23.906 | 1.00 | 24.41 | N |
| ATOM | 6562 | CA | THR | C | 308 | 61.092 | 19.138 | 23.776 | 1.00 | 22.80 | C |
| ATOM | 6563 | CB | THR | C | 308 | 60.753 | 19.876 | 22.511 | 1.00 | 20.98 | C |
| ATOM | 6564 | OG1 | THR | C | 308 | 61.809 | 19.666 | 21.588 | 1.00 | 25.62 | O |
| ATOM | 6565 | CG2 | THR | C | 308 | 60.461 | 21.305 | 22.746 | 1.00 | 17.66 | C |
| ATOM | 6566 | C | THR | C | 308 | 61.237 | 20.068 | 24.978 | 1.00 | 23.91 | C |
| ATOM | 6567 | O | THR | C | 308 | 62.309 | 20.519 | 25.327 | 1.00 | 25.22 | O |
| ATOM | 6568 | N | GLU | C | 309 | 60.127 | 20.331 | 25.634 | 1.00 | 24.39 | N |
| ATOM | 6569 | CA | GLU | C | 309 | 60.073 | 21.221 | 26.750 | 1.00 | 21.68 | C |
| ATOM | 6570 | CB | GLU | C | 309 | 58.715 | 21.888 | 26.653 | 1.00 | 22.58 | C |
| ATOM | 6571 | CG | GLU | C | 309 | 58.558 | 23.216 | 27.360 | 1.00 | 28.81 | C |
| ATOM | 6572 | CD | GLU | C | 309 | 59.577 | 24.245 | 26.936 | 1.00 | 31.36 | C |
| ATOM | 6573 | OE1 | GLU | C | 309 | 59.592 | 24.571 | 25.732 | 1.00 | 32.86 | O |
| ATOM | 6574 | OE2 | GLU | C | 309 | 60.357 | 24.714 | 27.821 | 1.00 | 31.33 | O |
| ATOM | 6575 | C | GLU | C | 309 | 60.224 | 20.359 | 27.998 | 1.00 | 20.57 | C |
| ATOM | 6576 | O | GLU | C | 309 | 59.318 | 19.613 | 28.322 | 1.00 | 20.14 | O |

FIG. 2A-143

| ATOM | 6577 | N | PRO | C | 310 | 61.360 | 20.468 | 28.734 | 1.00 | 20.20 | N |
|---|---|---|---|---|---|---|---|---|---|---|---|
| ATOM | 6578 | CA | PRO | C | 310 | 61.535 | 19.635 | 29.939 | 1.00 | 20.00 | C |
| ATOM | 6579 | CB | PRO | C | 310 | 62.638 | 20.361 | 30.719 | 1.00 | 18.80 | C |
| ATOM | 6580 | CG | PRO | C | 310 | 63.455 | 20.942 | 29.681 | 1.00 | 16.32 | C |
| ATOM | 6581 | CD | PRO | C | 310 | 62.448 | 21.462 | 28.646 | 1.00 | 20.44 | C |
| ATOM | 6582 | C | PRO | C | 310 | 60.280 | 19.458 | 30.758 | 1.00 | 21.52 | C |
| ATOM | 6583 | O | PRO | C | 310 | 59.837 | 18.361 | 31.000 | 1.00 | 21.98 | O |
| ATOM | 6584 | N | THR | C | 311 | 59.697 | 20.561 | 31.179 | 1.00 | 22.07 | N |
| ATOM | 6585 | CA | THR | C | 311 | 58.507 | 20.538 | 32.007 | 1.00 | 22.34 | C |
| ATOM | 6586 | CB | THR | C | 311 | 58.048 | 21.973 | 32.246 | 1.00 | 21.99 | C |
| ATOM | 6587 | OG1 | THR | C | 311 | 58.362 | 22.766 | 31.083 | 1.00 | 27.67 | O |
| ATOM | 6588 | CG2 | THR | C | 311 | 58.785 | 22.554 | 33.425 | 1.00 | 18.58 | C |
| ATOM | 6589 | C | THR | C | 311 | 57.348 | 19.677 | 31.524 | 1.00 | 24.50 | C |
| ATOM | 6590 | O | THR | C | 311 | 56.539 | 19.292 | 32.343 | 1.00 | 27.76 | O |
| ATOM | 6591 | N | GLN | C | 312 | 57.266 | 19.357 | 30.228 | 1.00 | 24.13 | N |
| ATOM | 6592 | CA | GLN | C | 312 | 56.172 | 18.527 | 29.681 | 1.00 | 24.91 | C |
| ATOM | 6593 | CB | GLN | C | 312 | 55.919 | 18.764 | 28.191 | 1.00 | 25.66 | C |
| ATOM | 6594 | CG | GLN | C | 312 | 55.212 | 20.019 | 27.768 | 1.00 | 31.19 | C |
| ATOM | 6595 | CD | GLN | C | 312 | 54.626 | 19.860 | 26.350 | 1.00 | 42.36 | C |
| ATOM | 6596 | OE1 | GLN | C | 312 | 53.785 | 18.996 | 26.139 | 1.00 | 44.87 | O |
| ATOM | 6597 | NE2 | GLN | C | 312 | 55.079 | 20.677 | 25.378 | 1.00 | 47.40 | N |
| ATOM | 6598 | C | GLN | C | 312 | 56.478 | 17.059 | 29.776 | 1.00 | 23.70 | C |
| ATOM | 6599 | O | GLN | C | 312 | 55.604 | 16.220 | 29.649 | 1.00 | 23.91 | O |
| ATOM | 6600 | N | ARG | C | 313 | 57.741 | 16.749 | 29.953 | 1.00 | 22.97 | N |
| ATOM | 6601 | CA | ARG | C | 313 | 58.175 | 15.377 | 30.020 | 1.00 | 22.85 | C |
| ATOM | 6602 | CB | ARG | C | 313 | 59.671 | 15.338 | 30.099 | 1.00 | 22.10 | C |
| ATOM | 6603 | CG | ARG | C | 313 | 60.272 | 14.763 | 28.909 | 1.00 | 21.47 | C |
| ATOM | 6604 | CD | ARG | C | 313 | 61.716 | 14.982 | 28.948 | 1.00 | 19.24 | C |
| ATOM | 6605 | NE | ARG | C | 313 | 62.095 | 15.988 | 27.972 | 1.00 | 19.86 | N |
| ATOM | 6606 | CZ | ARG | C | 313 | 63.253 | 16.614 | 28.019 | 1.00 | 17.82 | C |
| ATOM | 6607 | NH1AR | G | C | 313 | 64.095 | 16.304 | 28.992 | 1.00 | 18.57 | N |
| ATOM | 6608 | NH2AR | G | C | 313 | 63.562 | 17.551 | 27.130 | 1.00 | 19.58 | N |
| ATOM | 6609 | C | ARG | C | 313 | 57.602 | 14.508 | 31.103 | 1.00 | 24.22 | C |
| ATOM | 6610 | O | ARG | C | 313 | 57.368 | 14.943 | 32.217 | 1.00 | 26.73 | O |
| ATOM | 6611 | N | MSEC | | 314 | 57.375 | 13.252 | 30.763 | 1.00 | 27.25 | N |
| ATOM | 6612 | CA | MSEC | | 314 | 56.843 | 12.290 | 31.713 | 1.00 | 28.99 | C |
| ATOM | 6613 | CB | MSEC | | 314 | 56.630 | 10.965 | 30.994 | 1.00 | 30.63 | C |
| ATOM | 6614 | CG | MSEC | | 314 | 55.641 | 10.030 | 31.644 | 1.00 | 38.47 | C |
| ATOM | 6615 | SE | MSEC | | 314 | 55.687 | 8.393 | 30.645 | 1.00 | 38.81 | S |
| ATOM | 6616 | CE | MSEC | | 314 | 54.058 | 8.642 | 29.738 | 1.00 | 50.04 | C |
| ATOM | 6617 | C | MSEC | | 314 | 57.883 | 12.128 | 32.830 | 1.00 | 28.38 | C |
| ATOM | 6618 | O | MSEC | | 314 | 59.080 | 12.244 | 32.588 | 1.00 | 28.17 | O |
| ATOM | 6619 | N | THR | C | 315 | 57.433 | 11.880 | 34.050 | 1.00 | 26.47 | N |
| ATOM | 6620 | CA | THR | C | 315 | 58.373 | 11.710 | 35.150 | 1.00 | 24.22 | C |
| ATOM | 6621 | CB | THR | C | 315 | 57.814 | 12.262 | 36.428 | 1.00 | 22.09 | C |
| ATOM | 6622 | OG1 | THR | C | 315 | 56.662 | 11.503 | 36.812 | 1.00 | 24.47 | O |

FIG. 2A-144

| ATOM | 6623 | CG2 | THR | C | 315 | 57.464 | 13.707 | 36.236 | 1.00 | 22.77 | C |
| ATOM | 6624 | C | THR | C | 315 | 58.687 | 10.239 | 35.356 | 1.00 | 23.75 | C |
| ATOM | 6625 | O | THR | C | 315 | 57.891 | 9.385 | 34.972 | 1.00 | 24.76 | O |
| ATOM | 6626 | N | ILE | C | 316 | 59.833 | 9.931 | 35.958 | 1.00 | 22.38 | N |
| ATOM | 6627 | CA | ILE | C | 316 | 60.176 | 8.540 | 36.150 | 1.00 | 19.34 | C |
| ATOM | 6628 | CB | ILE | C | 316 | 61.566 | 8.406 | 36.906 | 1.00 | 19.68 | C |
| ATOM | 6629 | CG1 | ILE | C | 316 | 62.250 | 7.039 | 36.630 | 1.00 | 16.47 | C |
| ATOM | 6630 | CD1 | ILE | C | 316 | 61.901 | 6.347 | 35.323 | 1.00 | 14.39 | C |
| ATOM | 6631 | CG2 | ILE | C | 316 | 61.369 | 8.419 | 38.388 | 1.00 | 18.75 | C |
| ATOM | 6632 | C | ILE | C | 316 | 59.048 | 7.752 | 36.854 | 1.00 | 19.01 | C |
| ATOM | 6633 | O | ILE | C | 316 | 58.926 | 6.563 | 36.670 | 1.00 | 19.18 | O |
| ATOM | 6634 | N | THR | C | 317 | 58.176 | 8.415 | 37.604 | 1.00 | 18.95 | N |
| ATOM | 6635 | CA | THR | C | 317 | 57.144 | 7.677 | 38.333 | 1.00 | 17.66 | C |
| ATOM | 6636 | CB | THR | C | 317 | 56.597 | 8.450 | 39.563 | 1.00 | 18.33 | C |
| ATOM | 6637 | OG1 | THR | C | 317 | 57.676 | 8.900 | 40.418 | 1.00 | 20.29 | O |
| ATOM | 6638 | CG2 | THR | C | 317 | 55.660 | 7.555 | 40.326 | 1.00 | 12.39 | C |
| ATOM | 6639 | C | THR | C | 317 | 55.983 | 7.352 | 37.462 | 1.00 | 19.25 | C |
| ATOM | 6640 | O | THR | C | 317 | 55.315 | 6.352 | 37.644 | 1.00 | 19.85 | O |
| ATOM | 6641 | N | GLU | C | 318 | 55.712 | 8.227 | 36.517 | 1.00 | 20.66 | N |
| ATOM | 6642 | CA | GLU | C | 318 | 54.622 | 7.984 | 35.597 | 1.00 | 20.24 | C |
| ATOM | 6643 | CB | GLU | C | 318 | 54.305 | 9.269 | 34.846 | 1.00 | 20.62 | C |
| ATOM | 6644 | CG | GLU | C | 318 | 53.703 | 10.286 | 35.752 | 1.00 | 22.71 | C |
| ATOM | 6645 | CD | GLU | C | 318 | 53.643 | 11.671 | 35.142 | 1.00 | 25.30 | C |
| ATOM | 6646 | OE1 | GLU | C | 318 | 52.700 | 12.414 | 35.480 | 1.00 | 33.33 | O |
| ATOM | 6647 | OE2 | GLU | C | 318 | 54.537 | 12.024 | 34.333 | 1.00 | 26.12 | O |
| ATOM | 6648 | C | GLU | C | 318 | 55.106 | 6.860 | 34.678 | 1.00 | 19.65 | C |
| ATOM | 6649 | O | GLU | C | 318 | 54.415 | 5.871 | 34.499 | 1.00 | 19.44 | O |
| ATOM | 6650 | N | PHE | C | 319 | 56.297 | 7.012 | 34.116 | 1.00 | 20.43 | N |
| ATOM | 6651 | CA | PHE | C | 319 | 56.879 | 5.977 | 33.288 | 1.00 | 20.52 | C |
| ATOM | 6652 | CB | PHE | C | 319 | 58.364 | 6.203 | 33.144 | 1.00 | 21.07 | C |
| ATOM | 6653 | CG | PHE | C | 319 | 59.059 | 5.145 | 32.348 | 1.00 | 20.27 | C |
| ATOM | 6654 | CD1 | PHE | C | 319 | 59.016 | 5.171 | 30.957 | 1.00 | 21.77 | C |
| ATOM | 6655 | CE1 | PHE | C | 319 | 59.688 | 4.212 | 30.229 | 1.00 | 19.19 | C |
| ATOM | 6656 | CZ | PHE | C | 319 | 60.415 | 3.213 | 30.890 | 1.00 | 18.75 | C |
| ATOM | 6657 | CE2 | PHE | C | 319 | 60.460 | 3.175 | 32.268 | 1.00 | 17.24 | C |
| ATOM | 6658 | CD2 | PHE | C | 319 | 59.785 | 4.131 | 32.990 | 1.00 | 19.57 | C |
| ATOM | 6659 | C | PHE | C | 319 | 56.684 | 4.624 | 33.977 | 1.00 | 19.54 | C |
| ATOM | 6660 | O | PHE | C | 319 | 55.978 | 3.752 | 33.481 | 1.00 | 18.89 | O |
| ATOM | 6661 | N | MSEC | | 320 | 57.323 | 4.446 | 35.121 | 1.00 | 20.11 | N |
| ATOM | 6662 | CA | MSEC | | 320 | 57.191 | 3.189 | 35.814 | 1.00 | 19.75 | C |
| ATOM | 6663 | CB | MSEC | | 320 | 57.983 | 3.211 | 37.119 | 1.00 | 18.81 | C |
| ATOM | 6664 | CG | MSEC | | 320 | 59.497 | 3.308 | 36.933 | 1.00 | 22.14 | C |
| ATOM | 6665 | SE | MSEC | | 320 | 60.338 | 1.922 | 35.854 | 1.00 | 26.07 | S |
| ATOM | 6666 | CE | MSEC | | 320 | 60.279 | 0.595 | 37.194 | 1.00 | 12.09 | C |
| ATOM | 6667 | C | MSEC | | 320 | 55.745 | 2.787 | 36.093 | 1.00 | 19.79 | C |
| ATOM | 6668 | O | MSEC | | 320 | 55.465 | 1.616 | 36.342 | 1.00 | 20.19 | O |

FIG. 2A-145

| | | | | | | | | | | |
|---|---|---|---|---|---|---|---|---|---|---|
| ATOM | 6669 | N | ASN | C | 321 | 54.814 | 3.730 | 36.061 | 1.00 | 21.91 | N |
| ATOM | 6670 | CA | ASN | C | 321 | 53.433 | 3.365 | 36.328 | 1.00 | 21.25 | C |
| ATOM | 6671 | CB | ASN | C | 321 | 52.725 | 4.442 | 37.138 | 1.00 | 21.83 | C |
| ATOM | 6672 | CG | ASN | C | 321 | 52.987 | 4.302 | 38.611 | 1.00 | 26.36 | C |
| ATOM | 6673 | OD1 | ASN | C | 321 | 52.886 | 3.199 | 39.170 | 1.00 | 29.73 | O |
| ATOM | 6674 | ND2 | ASN | C | 321 | 53.319 | 5.415 | 39.263 | 1.00 | 29.21 | N |
| ATOM | 6675 | C | ASN | C | 321 | 52.624 | 3.079 | 35.090 | 1.00 | 21.56 | C |
| ATOM | 6676 | O | ASN | C | 321 | 51.481 | 2.646 | 35.187 | 1.00 | 22.05 | O |
| ATOM | 6677 | N | HIS | C | 322 | 53.214 | 3.323 | 33.925 | 1.00 | 20.95 | N |
| ATOM | 6678 | CA | HIS | C | 322 | 52.582 | 3.051 | 32.641 | 1.00 | 20.38 | C |
| ATOM | 6679 | CB | HIS | C | 322 | 53.503 | 3.569 | 31.535 | 1.00 | 21.05 | C |
| ATOM | 6680 | CG | HIS | C | 322 | 52.722 | 3.727 | 30.257 | 1.00 | 25.37 | C |
| ATOM | 6681 | ND1 | HIS | C | 322 | 52.145 | 2.688 | 29.603 | 1.00 | 27.92 | N |
| ATOM | 6682 | CE1 | HIS | C | 322 | 51.600 | 3.217 | 28.491 | 1.00 | 26.81 | C |
| ATOM | 6683 | NE2 | HIS | C | 322 | 51.802 | 4.535 | 28.412 | 1.00 | 24.35 | N |
| ATOM | 6684 | CD2 | HIS | C | 322 | 52.508 | 4.894 | 29.513 | 1.00 | 24.87 | C |
| ATOM | 6685 | C | HIS | C | 322 | 52.331 | 1.552 | 32.456 | 1.00 | 21.38 | C |
| ATOM | 6686 | O | HIS | C | 322 | 53.160 | 0.707 | 32.765 | 1.00 | 23.55 | O |
| ATOM | 6687 | N | PRO | C | 323 | 51.120 | 1.234 | 31.967 | 1.00 | 20.30 | N |
| ATOM | 6688 | CA | PRO | C | 323 | 50.720 | -0.153 | 31.777 | 1.00 | 18.94 | C |
| ATOM | 6689 | CB | PRO | C | 323 | 49.373 | -0.152 | 31.059 | 1.00 | 18.34 | C |
| ATOM | 6690 | CG | PRO | C | 323 | 48.770 | 1.245 | 31.187 | 1.00 | 20.67 | C |
| ATOM | 6691 | CD | PRO | C | 323 | 50.052 | 2.133 | 31.549 | 1.00 | 20.93 | C |
| ATOM | 6692 | C | PRO | C | 323 | 51.748 | -0.930 | 30.953 | 1.00 | 19.61 | C |
| ATOM | 6693 | O | PRO | C | 323 | 52.040 | -2.095 | 31.197 | 1.00 | 19.71 | O |
| ATOM | 6694 | N | TRP | C | 324 | 52.275 | -0.250 | 29.919 | 1.00 | 22.04 | N |
| ATOM | 6695 | CA | TRP | C | 324 | 53.222 | -0.906 | 29.024 | 1.00 | 20.76 | C |
| ATOM | 6696 | CB | TRP | C | 324 | 53.571 | 0.075 | 27.905 | 1.00 | 21.26 | C |
| ATOM | 6697 | CG | TRP | C | 324 | 54.264 | -0.633 | 26.805 | 1.00 | 16.57 | C |
| ATOM | 6698 | CD1 | TRP | C | 324 | 53.672 | -1.461 | 25.827 | 1.00 | 19.22 | C |
| ATOM | 6699 | NE1 | TRP | C | 324 | 54.581 | -1.963 | 24.949 | 1.00 | 20.95 | N |
| ATOM | 6700 | CE2 | TRP | C | 324 | 55.895 | -1.429 | 25.384 | 1.00 | 13.85 | C |
| ATOM | 6701 | CD2 | TRP | C | 324 | 55.684 | -0.610 | 26.522 | 1.00 | 16.99 | C |
| ATOM | 6702 | CE3 | TRP | C | 324 | 56.770 | 0.013 | 27.127 | 1.00 | 20.23 | C |
| ATOM | 6703 | CZ3 | TRP | C | 324 | 58.048 | -0.152 | 26.623 | 1.00 | 20.33 | C |
| ATOM | 6704 | CH2 | TRP | C | 324 | 58.252 | -0.966 | 25.494 | 1.00 | 12.96 | C |
| ATOM | 6705 | CZ2 | TRP | C | 324 | 57.176 | -1.595 | 24.880 | 1.00 | 12.61 | C |
| ATOM | 6706 | C | TRP | C | 324 | 54.497 | -1.346 | 29.750 | 1.00 | 22.16 | C |
| ATOM | 6707 | O | TRP | C | 324 | 55.167 | -2.299 | 29.371 | 1.00 | 20.75 | O |
| ATOM | 6708 | N | ILE | C | 325 | 54.849 | -0.588 | 30.804 | 1.00 | 24.34 | N |
| ATOM | 6709 | CA | ILE | C | 325 | 56.058 | -0.942 | 31.539 | 1.00 | 26.75 | C |
| ATOM | 6710 | CB | ILE | C | 325 | 56.716 | 0.354 | 32.009 | 1.00 | 25.21 | C |
| ATOM | 6711 | CG1 | ILE | C | 325 | 57.971 | 0.640 | 31.182 | 1.00 | 29.16 | C |
| ATOM | 6712 | CD1 | ILE | C | 325 | 57.664 | 1.451 | 29.921 | 1.00 | 34.45 | C |
| ATOM | 6713 | CG2 | ILE | C | 325 | 57.142 | 0.219 | 33.481 | 1.00 | 30.80 | C |
| ATOM | 6714 | C | ILE | C | 325 | 55.736 | -1.833 | 32.742 | 1.00 | 28.72 | C |

FIG. 2A-146

| ATOM | 6715 | O | ILE | C | 325 | 56.462 | -2.755 | 33.088 | 1.00 | 30.61 | O |
|---|---|---|---|---|---|---|---|---|---|---|---|
| ATOM | 6716 | N | MSEC | | 326 | 54.612 | -1.498 | 33.402 | 1.00 | 31.12 | N |
| ATOM | 6717 | CA | MSEC | | 326 | 54.201 | -2.265 | 34.572 | 1.00 | 35.18 | C |
| ATOM | 6718 | CB | MSEC | | 326 | 52.912 | -1.644 | 35.111 | 1.00 | 36.08 | C |
| ATOM | 6719 | CG | MSEC | | 326 | 52.686 | -1.943 | 36.594 | 1.00 | 43.51 | C |
| ATOM | 6720 | SE | MSEC | | 326 | 51.880 | -0.577 | 37.444 | 1.00 | 61.42 | S |
| ATOM | 6721 | CE | MSEC | | 326 | 53.235 | -0.136 | 38.541 | 1.00 | 58.75 | C |
| ATOM | 6722 | C | MSEC | | 326 | 53.961 | -3.738 | 34.230 | 1.00 | 36.31 | C |
| ATOM | 6723 | O | MSEC | | 326 | 54.520 | -4.648 | 34.829 | 1.00 | 36.98 | O |
| ATOM | 6724 | N | GLN | C | 327 | 53.059 | -3.960 | 33.256 | 1.00 | 36.91 | N |
| ATOM | 6725 | CA | GLN | C | 327 | 52.690 | -5.330 | 32.920 | 1.00 | 38.71 | C |
| ATOM | 6726 | CB | GLN | C | 327 | 51.174 | -5.383 | 32.745 | 1.00 | 39.76 | C |
| ATOM | 6727 | CG | GLN | C | 327 | 50.427 | -5.216 | 34.066 | 1.00 | 46.36 | C |
| ATOM | 6728 | CD | GLN | C | 327 | 49.351 | -4.168 | 33.899 | 1.00 | 54.74 | C |
| ATOM | 6729 | OE1 | GLN | C | 327 | 48.963 | -3.460 | 34.814 | 1.00 | 59.11 | O |
| ATOM | 6730 | NE2 | GLN | C | 327 | 48.855 | -4.092 | 32.648 | 1.00 | 50.83 | N |
| ATOM | 6731 | C | GLN | C | 327 | 53.374 | -5.806 | 31.640 | 1.00 | 38.73 | C |
| ATOM | 6732 | O | GLN | C | 327 | 52.739 | -6.050 | 30.623 | 1.00 | 39.30 | O |
| ATOM | 6733 | N | SER | C | 328 | 54.692 | -5.980 | 31.626 | 1.00 | 38.90 | N |
| ATOM | 6734 | CA | SER | C | 328 | 55.373 | -6.465 | 30.416 | 1.00 | 38.95 | C |
| ATOM | 6735 | CB | SER | C | 328 | 56.858 | -6.766 | 30.699 | 1.00 | 40.06 | C |
| ATOM | 6736 | OG | SER | C | 328 | 57.584 | -5.608 | 31.138 | 1.00 | 42.45 | O |
| ATOM | 6737 | C | SER | C | 328 | 54.644 | -7.740 | 30.095 | 1.00 | 37.52 | C |
| ATOM | 6738 | O | SER | C | 328 | 54.297 | -8.016 | 28.959 | 1.00 | 37.98 | O |
| ATOM | 6739 | N | THR | C | 329 | 54.414 | -8.512 | 31.152 | 1.00 | 37.43 | N |
| ATOM | 6740 | CA | THR | C | 329 | 53.673 | -9.772 | 31.126 | 1.00 | 37.14 | C |
| ATOM | 6741 | CB | THR | C | 329 | 52.988 | -10.009 | 32.522 | 1.00 | 37.08 | C |
| ATOM | 6742 | OG1 | THR | C | 329 | 52.203 | -11.204 | 32.497 | 1.00 | 38.31 | O |
| ATOM | 6743 | CG2 | THR | C | 329 | 52.056 | -8.832 | 32.881 | 1.00 | 36.94 | C |
| ATOM | 6744 | C | THR | C | 329 | 52.583 | -9.771 | 30.041 | 1.00 | 36.13 | C |
| ATOM | 6745 | O | THR | C | 329 | 52.453 | -10.732 | 29.281 | 1.00 | 34.66 | O |
| ATOM | 6746 | N | ALA | C | 330 | 51.818 | -8.684 | 29.969 | 1.00 | 36.10 | N |
| ATOM | 6747 | CA | ALA | C | 330 | 50.724 | -8.557 | 29.010 | 1.00 | 34.55 | C |
| ATOM | 6748 | CB | ALA | C | 330 | 49.469 | -8.016 | 29.753 | 1.00 | 35.93 | C |
| ATOM | 6749 | C | ALA | C | 330 | 50.975 | -7.726 | 27.727 | 1.00 | 32.41 | C |
| ATOM | 6750 | O | ALA | C | 330 | 50.026 | -7.300 | 27.056 | 1.00 | 30.31 | O |
| ATOM | 6751 | N | VAL | C | 331 | 52.235 | -7.478 | 27.383 | 1.00 | 31.10 | N |
| ATOM | 6752 | CA | VAL | C | 331 | 52.516 | -6.732 | 26.160 | 1.00 | 30.03 | C |
| ATOM | 6753 | CB | VAL | C | 331 | 53.750 | -5.787 | 26.326 | 1.00 | 30.16 | C |
| ATOM | 6754 | CG1 | VAL | C | 331 | 54.877 | -6.533 | 26.924 | 1.00 | 34.12 | C |
| ATOM | 6755 | CG2 | VAL | C | 331 | 54.194 | -5.243 | 25.008 | 1.00 | 29.08 | C |
| ATOM | 6756 | C | VAL | C | 331 | 52.737 | -7.802 | 25.088 | 1.00 | 28.30 | C |
| ATOM | 6757 | O | VAL | C | 331 | 53.257 | -8.887 | 25.371 | 1.00 | 27.77 | O |
| ATOM | 6758 | N | PRO | C | 332 | 52.297 | -7.526 | 23.857 | 1.00 | 27.89 | N |
| ATOM | 6759 | CA | PRO | C | 332 | 52.409 | -8.422 | 22.702 | 1.00 | 27.22 | C |
| ATOM | 6760 | CB | PRO | C | 332 | 51.780 | -7.606 | 21.565 | 1.00 | 28.04 | C |

FIG. 2A-147

| ATOM | 6761 | CG | PRO | C | 332 | 50.909 | -6.639 | 22.254 | 1.00 | 29.72 | C |
|---|---|---|---|---|---|---|---|---|---|---|---|
| ATOM | 6762 | CD | PRO | C | 332 | 51.714 | -6.242 | 23.446 | 1.00 | 27.95 | C |
| ATOM | 6763 | C | PRO | C | 332 | 53.832 | -8.826 | 22.343 | 1.00 | 26.50 | C |
| ATOM | 6764 | O | PRO | C | 332 | 54.740 | -7.990 | 22.350 | 1.00 | 26.65 | O |
| ATOM | 6765 | N | GLN | C | 333 | 54.023 | -10.102 | 22.017 | 1.00 | 24.53 | N |
| ATOM | 6766 | CA | GLN | C | 333 | 55.333 | -10.581 | 21.602 | 1.00 | 24.13 | C |
| ATOM | 6767 | CB | GLN | C | 333 | 55.405 | -12.098 | 21.638 | 1.00 | 26.22 | C |
| ATOM | 6768 | CG | GLN | C | 333 | 55.138 | -12.715 | 22.974 | 1.00 | 32.66 | C |
| ATOM | 6769 | CD | GLN | C | 333 | 56.376 | -13.345 | 23.589 | 1.00 | 43.39 | C |
| ATOM | 6770 | OE1 | GLN | C | 333 | 56.273 | -14.148 | 24.508 | 1.00 | 50.19 | O |
| ATOM | 6771 | NE2 | GLN | C | 333 | 57.555 | -12.969 | 23.097 | 1.00 | 46.03 | N |
| ATOM | 6772 | C | GLN | C | 333 | 55.518 | -10.132 | 20.164 | 1.00 | 22.34 | C |
| ATOM | 6773 | O | GLN | C | 333 | 56.075 | -10.862 | 19.379 | 1.00 | 23.54 | O |
| ATOM | 6774 | N | THR | C | 334 | 55.060 | -8.932 | 19.829 | 1.00 | 19.07 | N |
| ATOM | 6775 | CA | THR | C | 334 | 55.183 | -8.455 | 18.474 | 1.00 | 18.49 | C |
| ATOM | 6776 | CB | THR | C | 334 | 54.346 | -7.183 | 18.272 | 1.00 | 18.21 | C |
| ATOM | 6777 | OG1 | THR | C | 334 | 54.979 | -6.312 | 17.327 | 1.00 | 13.98 | O |
| ATOM | 6778 | CG2 | THR | C | 334 | 54.128 | -6.513 | 19.581 | 1.00 | 22.23 | C |
| ATOM | 6779 | C | THR | C | 334 | 56.593 | -8.246 | 17.968 | 1.00 | 19.44 | C |
| ATOM | 6780 | O | THR | C | 334 | 57.454 | -7.686 | 18.639 | 1.00 | 19.40 | O |
| ATOM | 6781 | N | PRO | C | 335 | 56.844 | -8.710 | 16.743 | 1.00 | 19.33 | N |
| ATOM | 6782 | CA | PRO | C | 335 | 58.091 | -8.673 | 15.989 | 1.00 | 20.04 | C |
| ATOM | 6783 | CB | PRO | C | 335 | 57.768 | -9.511 | 14.762 | 1.00 | 16.19 | C |
| ATOM | 6784 | CG | PRO | C | 335 | 56.779 | -10.398 | 15.239 | 1.00 | 19.21 | C |
| ATOM | 6785 | CD | PRO | C | 335 | 55.868 | -9.507 | 16.007 | 1.00 | 18.97 | C |
| ATOM | 6786 | C | PRO | C | 335 | 58.611 | -7.293 | 15.612 | 1.00 | 22.52 | C |
| ATOM | 6787 | O | PRO | C | 335 | 57.924 | -6.510 | 14.923 | 1.00 | 25.35 | O |
| ATOM | 6788 | N | LEU | C | 336 | 59.854 | -7.045 | 16.007 | 1.00 | 22.69 | N |
| ATOM | 6789 | CA | LEU | C | 336 | 60.508 | -5.781 | 15.744 | 1.00 | 23.82 | C |
| ATOM | 6790 | CB | LEU | C | 336 | 61.064 | -5.242 | 17.073 | 1.00 | 23.23 | C |
| ATOM | 6791 | CG | LEU | C | 336 | 60.155 | -4.490 | 18.053 | 1.00 | 26.08 | C |
| ATOM | 6792 | CD1 | LEU | C | 336 | 58.769 | -4.361 | 17.510 | 1.00 | 25.46 | C |
| ATOM | 6793 | CD2 | LEU | C | 336 | 60.167 | -5.185 | 19.363 | 1.00 | 27.91 | C |
| ATOM | 6794 | C | LEU | C | 336 | 61.646 | -5.865 | 14.713 | 1.00 | 23.43 | C |
| ATOM | 6795 | O | LEU | C | 336 | 62.481 | -6.738 | 14.818 | 1.00 | 23.52 | O |
| ATOM | 6796 | N | HIS | C | 337 | 61.686 | -4.948 | 13.750 | 1.00 | 23.33 | N |
| ATOM | 6797 | CA | HIS | C | 337 | 62.755 | -4.890 | 12.752 | 1.00 | 23.30 | C |
| ATOM | 6798 | CB | HIS | C | 337 | 62.561 | -3.697 | 11.803 | 1.00 | 25.39 | C |
| ATOM | 6799 | CG | HIS | C | 337 | 61.378 | -3.775 | 10.878 | 1.00 | 28.45 | C |
| ATOM | 6800 | ND1 | HIS | C | 337 | 60.205 | -4.424 | 11.195 | 1.00 | 34.90 | N |
| ATOM | 6801 | CE1 | HIS | C | 337 | 59.279 | -4.127 | 10.302 | 1.00 | 35.02 | C |
| ATOM | 6802 | NE2 | HIS | C | 337 | 59.812 | -3.322 | 9.401 | 1.00 | 32.33 | N |
| ATOM | 6803 | CD2 | HIS | C | 337 | 61.128 | -3.102 | 9.727 | 1.00 | 29.00 | C |
| ATOM | 6804 | C | HIS | C | 337 | 64.078 | -4.580 | 13.476 | 1.00 | 22.57 | C |
| ATOM | 6805 | O | HIS | C | 337 | 65.142 | -4.496 | 12.848 | 1.00 | 21.56 | O |
| ATOM | 6806 | N | THR | C | 338 | 64.001 | -4.380 | 14.790 | 1.00 | 20.99 | N |

FIG. 2A-148

| ATOM | 6807 | CA | THR | C | 338 | 65.140 | -3.980 | 15.610 | 1.00 | 19.30 | C |
|---|---|---|---|---|---|---|---|---|---|---|---|
| ATOM | 6808 | CB | THR | C | 338 | 64.675 | -3.916 | 17.094 | 1.00 | 18.98 | C |
| ATOM | 6809 | OG1 | THR | C | 338 | 63.536 | -3.061 | 17.145 | 1.00 | 18.49 | O |
| ATOM | 6810 | CG2 | THR | C | 338 | 65.748 | -3.364 | 18.046 | 1.00 | 17.72 | C |
| ATOM | 6811 | C | THR | C | 338 | 66.495 | -4.668 | 15.445 | 1.00 | 19.50 | C |
| ATOM | 6812 | O | THR | C | 338 | 67.436 | -3.983 | 15.046 | 1.00 | 20.86 | O |
| ATOM | 6813 | N | SER | C | 339 | 66.633 | -5.968 | 15.730 | 1.00 | 19.55 | N |
| ATOM | 6814 | CA | SER | C | 339 | 67.941 | -6.658 | 15.555 | 1.00 | 19.76 | C |
| ATOM | 6815 | CB | SER | C | 339 | 67.851 | -8.163 | 15.831 | 1.00 | 20.50 | C |
| ATOM | 6816 | OG | SER | C | 339 | 67.978 | -8.484 | 17.189 | 1.00 | 26.28 | O |
| ATOM | 6817 | C | SER | C | 339 | 68.576 | -6.553 | 14.173 | 1.00 | 20.05 | C |
| ATOM | 6818 | O | SER | C | 339 | 69.773 | -6.356 | 14.071 | 1.00 | 18.93 | O |
| ATOM | 6819 | N | ARG | C | 340 | 67.774 | -6.723 | 13.115 | 1.00 | 20.55 | N |
| ATOM | 6820 | CA | ARG | C | 340 | 68.309 | -6.677 | 11.755 | 1.00 | 21.52 | C |
| ATOM | 6821 | CB | ARG | C | 340 | 67.236 | -6.848 | 10.684 | 1.00 | 22.21 | C |
| ATOM | 6822 | CG | ARG | C | 340 | 66.452 | -8.150 | 10.620 | 1.00 | 29.71 | C |
| ATOM | 6823 | CD | ARG | C | 340 | 65.051 | -7.902 | 9.936 | 1.00 | 34.40 | C |
| ATOM | 6824 | NE | ARG | C | 340 | 63.862 | -7.750 | 10.801 | 1.00 | 44.02 | N |
| ATOM | 6825 | CZ | ARG | C | 340 | 62.715 | -7.150 | 10.430 | 1.00 | 41.08 | C |
| ATOM | 6826 | NH1AR | G | C | 340 | 61.557 | -7.539 | 10.971 | 1.00 | 43.68 | N |
| ATOM | 6827 | NH2AR | G | C | 340 | 62.704 | -6.221 | 9.462 | 1.00 | 35.97 | N |
| ATOM | 6828 | C | ARG | C | 340 | 68.932 | -5.326 | 11.517 | 1.00 | 21.13 | C |
| ATOM | 6829 | O | ARG | C | 340 | 70.036 | -5.214 | 11.023 | 1.00 | 21.08 | O |
| ATOM | 6830 | N | VAL | C | 341 | 68.174 | -4.288 | 11.844 | 1.00 | 20.49 | N |
| ATOM | 6831 | CA | VAL | C | 341 | 68.611 | -2.916 | 11.648 | 1.00 | 20.36 | C |
| ATOM | 6832 | CB | VAL | C | 341 | 67.463 | -1.963 | 11.969 | 1.00 | 19.96 | C |
| ATOM | 6833 | CG1 | VAL | C | 341 | 67.854 | -0.558 | 11.713 | 1.00 | 15.68 | C |
| ATOM | 6834 | CG2 | VAL | C | 341 | 66.269 | -2.347 | 11.152 | 1.00 | 19.17 | C |
| ATOM | 6835 | C | VAL | C | 341 | 69.838 | -2.586 | 12.480 | 1.00 | 21.21 | C |
| ATOM | 6836 | O | VAL | C | 341 | 70.775 | -1.981 | 11.989 | 1.00 | 21.29 | O |
| ATOM | 6837 | N | LEU | C | 342 | 69.835 | -2.989 | 13.737 | 1.00 | 23.09 | N |
| ATOM | 6838 | CA | LEU | C | 342 | 70.980 | -2.745 | 14.597 | 1.00 | 23.93 | C |
| ATOM | 6839 | CB | LEU | C | 342 | 70.729 | -3.341 | 15.983 | 1.00 | 22.88 | C |
| ATOM | 6840 | CG | LEU | C | 342 | 70.737 | -2.395 | 17.198 | 1.00 | 23.22 | C |
| ATOM | 6841 | CD1 | LEU | C | 342 | 70.565 | -0.966 | 16.767 | 1.00 | 16.75 | C |
| ATOM | 6842 | CD2 | LEU | C | 342 | 69.650 | -2.811 | 18.184 | 1.00 | 20.27 | C |
| ATOM | 6843 | C | LEU | C | 342 | 72.214 | -3.390 | 13.960 | 1.00 | 24.33 | C |
| ATOM | 6844 | O | LEU | C | 342 | 73.237 | -2.738 | 13.775 | 1.00 | 25.50 | O |
| ATOM | 6845 | N | LYS | C | 343 | 72.095 | -4.662 | 13.585 | 1.00 | 24.60 | N |
| ATOM | 6846 | CA | LYS | C | 343 | 73.202 | -5.399 | 12.991 | 1.00 | 26.56 | C |
| ATOM | 6847 | CB | LYS | C | 343 | 72.825 | -6.866 | 12.843 | 1.00 | 26.48 | C |
| ATOM | 6848 | CG | LYS | C | 343 | 73.993 | -7.796 | 12.557 | 1.00 | 25.69 | C |
| ATOM | 6849 | CD | LYS | C | 343 | 73.504 | -9.216 | 12.380 | 1.00 | 25.78 | C |
| ATOM | 6850 | CE | LYS | C | 343 | 74.573 | -10.116 | 11.751 | 1.00 | 32.23 | C |
| ATOM | 6851 | NZ | LYS | C | 343 | 73.986 | -11.388 | 11.131 | 1.00 | 34.69 | N |
| ATOM | 6852 | C | LYS | C | 343 | 73.723 | -4.866 | 11.658 | 1.00 | 28.21 | C |

FIG. 2A-149

| ATOM | 6853 | O | LYS | C | 343 | 74.919 | -4.786 | 11.452 | 1.00 | 28.11 | O |
|------|------|---|-----|---|-----|--------|--------|--------|------|-------|---|
| ATOM | 6854 | N | GLU | C | 344 | 72.859 | -4.495 | 10.743 | 1.00 | 31.28 | N |
| ATOM | 6855 | CA | GLU | C | 344 | 73.383 | -4.012 | 9.493 | 1.00 | 35.52 | C |
| ATOM | 6856 | CB | GLU | C | 344 | 72.266 | -3.818 | 8.480 | 1.00 | 34.53 | C |
| ATOM | 6857 | CG | GLU | C | 344 | 72.163 | -4.928 | 7.472 | 1.00 | 44.44 | C |
| ATOM | 6858 | CD | GLU | C | 344 | 71.288 | -6.085 | 7.932 | 1.00 | 53.67 | C |
| ATOM | 6859 | OE1 | GLU | C | 344 | 70.046 | -5.866 | 8.009 | 1.00 | 57.58 | O |
| ATOM | 6860 | OE2 | GLU | C | 344 | 71.830 | -7.198 | 8.207 | 1.00 | 52.20 | O |
| ATOM | 6861 | C | GLU | C | 344 | 74.163 | -2.710 | 9.596 | 1.00 | 38.55 | C |
| ATOM | 6862 | O | GLU | C | 344 | 75.187 | -2.535 | 8.921 | 1.00 | 39.89 | O |
| ATOM | 6863 | N | ASP | C | 345 | 73.678 | -1.813 | 10.458 | 1.00 | 42.46 | N |
| ATOM | 6864 | CA | ASP | C | 345 | 74.213 | -0.453 | 10.618 | 1.00 | 45.11 | C |
| ATOM | 6865 | CB | ASP | C | 345 | 75.720 | -0.423 | 10.482 | 1.00 | 45.23 | C |
| ATOM | 6866 | CG | ASP | C | 345 | 76.395 | -0.854 | 11.734 | 1.00 | 47.62 | C |
| ATOM | 6867 | OD1 | ASP | C | 345 | 76.436 | -0.050 | 12.699 | 1.00 | 48.03 | O |
| ATOM | 6868 | OD2 | ASP | C | 345 | 76.863 | -2.012 | 11.757 | 1.00 | 50.29 | O |
| ATOM | 6869 | C | ASP | C | 345 | 73.571 | 0.373 | 9.502 | 1.00 | 46.05 | C |
| ATOM | 6870 | O | ASP | C | 345 | 74.194 | 0.688 | 8.480 | 1.00 | 43.64 | O |
| ATOM | 6871 | N | ALA | C | 346 | 72.291 | 0.670 | 9.708 | 1.00 | 47.22 | N |
| ATOM | 6872 | CA | ALA | C | 346 | 71.497 | 1.435 | 8.761 | 1.00 | 48.38 | C |
| ATOM | 6873 | CB | ALA | C | 346 | 70.229 | 1.966 | 9.454 | 1.00 | 47.56 | C |
| ATOM | 6874 | C | ALA | C | 346 | 72.247 | 2.599 | 8.126 | 1.00 | 47.77 | C |
| ATOM | 6875 | O | ALA | C | 346 | 73.467 | 2.704 | 8.194 | 1.00 | 47.00 | O |
| ATOM | 6876 | N | ALA | C | 347 | 71.475 | 3.460 | 7.484 | 1.00 | 46.78 | N |
| ATOM | 6877 | CA | ALA | C | 347 | 71.993 | 4.655 | 6.856 | 1.00 | 44.58 | C |
| ATOM | 6878 | CB | ALA | C | 347 | 71.015 | 5.137 | 5.770 | 1.00 | 46.37 | C |
| ATOM | 6879 | C | ALA | C | 347 | 72.080 | 5.696 | 7.978 | 1.00 | 41.98 | C |
| ATOM | 6880 | O | ALA | C | 347 | 73.065 | 6.415 | 8.102 | 1.00 | 40.39 | O |
| ATOM | 6881 | N | ARG | C | 348 | 71.036 | 5.753 | 8.799 | 1.00 | 38.53 | N |
| ATOM | 6882 | CA | ARG | C | 348 | 71.009 | 6.700 | 9.896 | 1.00 | 36.57 | C |
| ATOM | 6883 | CB | ARG | C | 348 | 69.664 | 6.611 | 10.630 | 1.00 | 35.65 | C |
| ATOM | 6884 | CG | ARG | C | 348 | 68.567 | 7.423 | 9.973 | 1.00 | 38.77 | C |
| ATOM | 6885 | CD | ARG | C | 348 | 67.241 | 7.227 | 10.678 | 1.00 | 47.31 | C |
| ATOM | 6886 | NE | ARG | C | 348 | 66.148 | 7.886 | 9.965 | 1.00 | 52.14 | N |
| ATOM | 6887 | CZ | ARG | C | 348 | 64.917 | 8.053 | 10.442 | 1.00 | 54.33 | C |
| ATOM | 6888 | NH1AR | G | C | 348 | 64.593 | 7.606 | 11.647 | 1.00 | 51.57 | N |
| ATOM | 6889 | NH2AR | G | C | 348 | 64.011 | 8.696 | 9.720 | 1.00 | 56.72 | N |
| ATOM | 6890 | C | ARG | C | 348 | 72.169 | 6.494 | 10.867 | 1.00 | 33.98 | C |
| ATOM | 6891 | O | ARG | C | 348 | 72.735 | 7.450 | 11.390 | 1.00 | 33.83 | O |
| ATOM | 6892 | N | TRP | C | 349 | 72.518 | 5.239 | 11.106 | 1.00 | 31.45 | N |
| ATOM | 6893 | CA | TRP | C | 349 | 73.617 | 4.950 | 12.002 | 1.00 | 28.80 | C |
| ATOM | 6894 | CB | TRP | C | 349 | 73.682 | 3.449 | 12.296 | 1.00 | 28.79 | C |
| ATOM | 6895 | CG | TRP | C | 349 | 72.740 | 3.035 | 13.384 | 1.00 | 29.65 | C |
| ATOM | 6896 | CD1 | TRP | C | 349 | 71.730 | 2.112 | 13.304 | 1.00 | 26.69 | C |
| ATOM | 6897 | NE1 | TRP | C | 349 | 71.055 | 2.047 | 14.487 | 1.00 | 24.59 | N |
| ATOM | 6898 | CE2 | TRP | C | 349 | 71.623 | 2.931 | 15.367 | 1.00 | 26.10 | C |

FIG. 2A-150

| | | | | | | | | | | |
|---|---|---|---|---|---|---|---|---|---|---|
| ATOM | 6899 | CD2 | TRP | C | 349 | 72.685 | 3.568 | 14.703 | 1.00 | 26.38 | C |
| ATOM | 6900 | CE3 | TRP | C | 349 | 73.428 | 4.524 | 15.385 | 1.00 | 24.32 | C |
| ATOM | 6901 | CZ3 | TRP | C | 349 | 73.095 | 4.815 | 16.683 | 1.00 | 26.29 | C |
| ATOM | 6902 | CH2 | TRP | C | 349 | 72.037 | 4.169 | 17.322 | 1.00 | 30.34 | C |
| ATOM | 6903 | CZ2 | TRP | C | 349 | 71.289 | 3.223 | 16.682 | 1.00 | 28.18 | C |
| ATOM | 6904 | C | TRP | C | 349 | 74.911 | 5.426 | 11.374 | 1.00 | 26.82 | C |
| ATOM | 6905 | O | TRP | C | 349 | 75.810 | 5.891 | 12.057 | 1.00 | 25.01 | O |
| ATOM | 6906 | N | GLU | C | 350 | 75.009 | 5.314 | 10.062 | 1.00 | 25.86 | N |
| ATOM | 6907 | CA | GLU | C | 350 | 76.221 | 5.750 | 9.402 | 1.00 | 26.28 | C |
| ATOM | 6908 | CB | GLU | C | 350 | 76.257 | 5.253 | 7.970 | 1.00 | 25.53 | C |
| ATOM | 6909 | CG | GLU | C | 350 | 77.589 | 5.495 | 7.349 | 1.00 | 28.31 | C |
| ATOM | 6910 | CD | GLU | C | 350 | 77.981 | 4.409 | 6.388 | 1.00 | 34.21 | C |
| ATOM | 6911 | OE1 | GLU | C | 350 | 77.440 | 4.374 | 5.265 | 1.00 | 35.60 | O |
| ATOM | 6912 | OE2 | GLU | C | 350 | 78.834 | 3.581 | 6.764 | 1.00 | 39.90 | O |
| ATOM | 6913 | C | GLU | C | 350 | 76.287 | 7.270 | 9.449 | 1.00 | 26.16 | C |
| ATOM | 6914 | O | GLU | C | 350 | 77.324 | 7.847 | 9.764 | 1.00 | 26.15 | O |
| ATOM | 6915 | N | ASP | C | 351 | 75.156 | 7.903 | 9.152 | 1.00 | 27.37 | N |
| ATOM | 6916 | CA | ASP | C | 351 | 75.022 | 9.354 | 9.173 | 1.00 | 27.87 | C |
| ATOM | 6917 | CB | ASP | C | 351 | 73.569 | 9.760 | 8.902 | 1.00 | 29.13 | C |
| ATOM | 6918 | CG | ASP | C | 351 | 73.168 | 9.535 | 7.454 | 1.00 | 33.17 | C |
| ATOM | 6919 | OD1 | ASP | C | 351 | 74.086 | 9.338 | 6.621 | 1.00 | 36.89 | O |
| ATOM | 6920 | OD2 | ASP | C | 351 | 71.948 | 9.564 | 7.148 | 1.00 | 35.06 | O |
| ATOM | 6921 | C | ASP | C | 351 | 75.468 | 9.934 | 10.500 | 1.00 | 26.83 | C |
| ATOM | 6922 | O | ASP | C | 351 | 76.172 | 10.940 | 10.536 | 1.00 | 26.67 | O |
| ATOM | 6923 | N | VAL | C | 352 | 75.060 | 9.298 | 11.587 | 1.00 | 25.64 | N |
| ATOM | 6924 | CA | VAL | C | 352 | 75.438 | 9.767 | 12.906 | 1.00 | 25.14 | C |
| ATOM | 6925 | CB | VAL | C | 352 | 74.393 | 9.317 | 14.016 | 1.00 | 24.97 | C |
| ATOM | 6926 | CG1 | VAL | C | 352 | 72.997 | 9.659 | 13.572 | 1.00 | 25.74 | C |
| ATOM | 6927 | CG2 | VAL | C | 352 | 74.486 | 7.857 | 14.315 | 1.00 | 24.03 | C |
| ATOM | 6928 | C | VAL | C | 352 | 76.856 | 9.313 | 13.262 | 1.00 | 24.65 | C |
| ATOM | 6929 | O | VAL | C | 352 | 77.562 | 10.015 | 13.951 | 1.00 | 22.94 | O |
| ATOM | 6930 | N | LYS | C | 353 | 77.281 | 8.149 | 12.787 | 1.00 | 26.10 | N |
| ATOM | 6931 | CA | LYS | C | 353 | 78.623 | 7.685 | 13.075 | 1.00 | 28.70 | C |
| ATOM | 6932 | CB | LYS | C | 353 | 78.814 | 6.234 | 12.600 | 1.00 | 29.13 | C |
| ATOM | 6933 | CG | LYS | C | 353 | 78.088 | 5.196 | 13.468 | 1.00 | 34.19 | C |
| ATOM | 6934 | CD | LYS | C | 353 | 78.139 | 3.762 | 12.911 | 1.00 | 38.48 | C |
| ATOM | 6935 | CE | LYS | C | 353 | 79.433 | 3.022 | 13.248 | 1.00 | 43.43 | C |
| ATOM | 6936 | NZ | LYS | C | 353 | 79.336 | 1.564 | 12.885 | 1.00 | 45.32 | N |
| ATOM | 6937 | C | LYS | C | 353 | 79.588 | 8.624 | 12.355 | 1.00 | 30.01 | C |
| ATOM | 6938 | O | LYS | C | 353 | 80.721 | 8.831 | 12.794 | 1.00 | 30.62 | O |
| ATOM | 6939 | N | GLU | C | 354 | 79.139 | 9.191 | 11.243 | 1.00 | 31.28 | N |
| ATOM | 6940 | CA | GLU | C | 354 | 79.972 | 10.126 | 10.501 | 1.00 | 33.49 | C |
| ATOM | 6941 | CB | GLU | C | 354 | 79.529 | 10.238 | 9.052 | 1.00 | 32.99 | C |
| ATOM | 6942 | CG | GLU | C | 354 | 79.544 | 11.664 | 8.562 | 1.00 | 32.98 | C |
| ATOM | 6943 | CD | GLU | C | 354 | 79.513 | 11.761 | 7.055 | 1.00 | 33.72 | C |
| ATOM | 6944 | OE1 | GLU | C | 354 | 80.593 | 11.643 | 6.449 | 1.00 | 31.90 | O |

FIG. 2A-151

| | | | | | | | | | | |
|---|---|---|---|---|---|---|---|---|---|---|
| ATOM | 6945 | OE2 | GLU | C | 354 | 78.415 | 11.941 | 6.478 | 1.00 | 36.38 | O |
| ATOM | 6946 | C | GLU | C | 354 | 79.915 | 11.510 | 11.132 | 1.00 | 34.74 | C |
| ATOM | 6947 | O | GLU | C | 354 | 80.908 | 12.222 | 11.180 | 1.00 | 33.12 | O |
| ATOM | 6948 | N | GLU | C | 355 | 78.749 | 11.898 | 11.616 | 1.00 | 37.61 | N |
| ATOM | 6949 | CA | GLU | C | 355 | 78.638 | 13.188 | 12.247 | 1.00 | 40.48 | C |
| ATOM | 6950 | CB | GLU | C | 355 | 77.257 | 13.363 | 12.851 | 1.00 | 42.03 | C |
| ATOM | 6951 | CG | GLU | C | 355 | 76.890 | 14.797 | 13.112 | 1.00 | 44.35 | C |
| ATOM | 6952 | CD | GLU | C | 355 | 75.562 | 15.156 | 12.494 | 1.00 | 51.19 | C |
| ATOM | 6953 | OE1 | GLU | C | 355 | 75.235 | 16.354 | 12.466 | 1.00 | 54.28 | O |
| ATOM | 6954 | OE2 | GLU | C | 355 | 74.839 | 14.243 | 12.037 | 1.00 | 55.51 | O |
| ATOM | 6955 | C | GLU | C | 355 | 79.701 | 13.337 | 13.330 | 1.00 | 42.22 | C |
| ATOM | 6956 | O | GLU | C | 355 | 80.003 | 14.458 | 13.715 | 1.00 | 43.05 | O |
| ATOM | 6957 | N | MSEC | | 356 | 80.258 | 12.224 | 13.826 | 1.00 | 44.57 | N |
| ATOM | 6958 | CA | MSEC | | 356 | 81.321 | 12.271 | 14.848 | 1.00 | 46.84 | C |
| ATOM | 6959 | CB | MSEC | | 356 | 81.578 | 10.892 | 15.477 | 1.00 | 49.00 | C |
| ATOM | 6960 | CG | MSEC | | 356 | 80.468 | 10.359 | 16.391 | 1.00 | 59.45 | C |
| ATOM | 6961 | SE | MSEC | | 356 | 80.742 | 8.478 | 17.002 | 1.00 | 87.47 | S |
| ATOM | 6962 | CE | MSEC | | 356 | 81.575 | 8.829 | 18.742 | 1.00 | 75.19 | C |
| ATOM | 6963 | C | MSEC | | 356 | 82.587 | 12.743 | 14.137 | 1.00 | 45.60 | C |
| ATOM | 6964 | O | MSEC | | 356 | 83.338 | 11.953 | 13.554 | 1.00 | 45.05 | O |
| ATOM | 6965 | N | THR | C | 357 | 82.796 | 14.052 | 14.191 | 1.00 | 45.40 | N |
| ATOM | 6966 | CA | THR | C | 357 | 83.913 | 14.733 | 13.543 | 1.00 | 44.25 | C |
| ATOM | 6967 | CB | THR | C | 357 | 83.475 | 15.316 | 12.181 | 1.00 | 43.71 | C |
| ATOM | 6968 | OG1 | THR | C | 357 | 83.168 | 14.250 | 11.272 | 1.00 | 40.57 | O |
| ATOM | 6969 | CG2 | THR | C | 357 | 84.553 | 16.185 | 11.607 | 1.00 | 42.61 | C |
| ATOM | 6970 | C | THR | C | 357 | 84.345 | 15.903 | 14.418 | 1.00 | 45.25 | C |
| ATOM | 6971 | O | THR | C | 357 | 84.027 | 17.042 | 14.014 | 1.00 | 46.75 | O |
| ATOM | 6972 | OXT | THR | C | 357 | 84.960 | 15.686 | 15.484 | 1.00 | 44.66 | O |
| ATOM | 6973 | N | PHE | D | 43 | 106.822 | 58.132 | -2.416 | 1.00 | 36.80 | N |
| ATOM | 6974 | CA | PHE | D | 43 | 105.791 | 57.458 | -1.642 | 1.00 | 36.43 | C |
| ATOM | 6975 | CB | PHE | D | 43 | 104.424 | 57.931 | -2.145 | 1.00 | 35.63 | C |
| ATOM | 6976 | CG | PHE | D | 43 | 103.343 | 57.318 | -1.307 | 1.00 | 35.47 | C |
| ATOM | 6977 | CD1 | PHE | D | 43 | 102.854 | 58.008 | -0.206 | 1.00 | 35.70 | C |
| ATOM | 6978 | CE1 | PHE | D | 43 | 101.873 | 57.433 | 0.591 | 1.00 | 35.43 | C |
| ATOM | 6979 | CZ | PHE | D | 43 | 101.382 | 56.168 | 0.291 | 1.00 | 36.01 | C |
| ATOM | 6980 | CE2 | PHE | D | 43 | 101.877 | 55.484 | -0.812 | 1.00 | 36.01 | C |
| ATOM | 6981 | CD2 | PHE | D | 43 | 102.861 | 56.055 | -1.613 | 1.00 | 35.35 | C |
| ATOM | 6982 | C | PHE | D | 43 | 105.894 | 55.937 | -1.768 | 1.00 | 36.62 | C |
| ATOM | 6983 | O | PHE | D | 43 | 106.273 | 55.385 | -2.793 | 1.00 | 36.22 | O |
| ATOM | 6984 | N | PRO | D | 44 | 105.589 | 55.254 | -0.652 | 1.00 | 37.03 | N |
| ATOM | 6985 | CA | PRO | D | 44 | 105.628 | 53.805 | -0.602 | 1.00 | 36.40 | C |
| ATOM | 6986 | CB | PRO | D | 44 | 105.822 | 53.417 | 0.862 | 1.00 | 36.92 | C |
| ATOM | 6987 | CG | PRO | D | 44 | 105.508 | 54.638 | 1.732 | 1.00 | 37.99 | C |
| ATOM | 6988 | CD | PRO | D | 44 | 105.206 | 55.776 | 0.647 | 1.00 | 37.24 | C |
| ATOM | 6989 | C | PRO | D | 44 | 104.342 | 53.176 | -1.139 | 1.00 | 36.60 | C |
| ATOM | 6990 | O | PRO | D | 44 | 103.667 | 52.408 | -0.473 | 1.00 | 37.31 | O |

FIG. 2A-152

| ATOM | 6991 | N | GLN | D | 45 | 103.982 | 53.563 | -2.376 | 1.00 | 35.77 | N |
|---|---|---|---|---|---|---|---|---|---|---|---|
| ATOM | 6992 | CA | GLN | D | 45 | 102.780 | 52.998 | -2.972 | 1.00 | 34.63 | C |
| ATOM | 6993 | CB | GLN | D | 45 | 102.752 | 53.392 | -4.453 | 1.00 | 34.13 | C |
| ATOM | 6994 | CG | GLN | D | 45 | 101.660 | 54.408 | -4.791 | 1.00 | 36.61 | C |
| ATOM | 6995 | CD | GLN | D | 45 | 102.055 | 55.157 | -6.045 | 1.00 | 39.19 | C |
| ATOM | 6996 | OE1 | GLN | D | 45 | 101.265 | 55.792 | -6.720 | 1.00 | 39.23 | O |
| ATOM | 6997 | NE2 | GLN | D | 45 | 103.358 | 55.023 | -6.365 | 1.00 | 41.64 | N |
| ATOM | 6998 | C | GLN | D | 45 | 102.776 | 51.470 | -2.851 | 1.00 | 33.88 | C |
| ATOM | 6999 | O | GLN | D | 45 | 101.776 | 50.834 | -2.554 | 1.00 | 35.00 | O |
| ATOM | 7000 | N | PHE | D | 46 | 103.960 | 50.887 | -3.123 | 1.00 | 32.14 | N |
| ATOM | 7001 | CA | PHE | D | 46 | 104.071 | 49.431 | -3.217 | 1.00 | 30.74 | C |
| ATOM | 7002 | CB | PHE | D | 46 | 105.530 | 49.077 | -3.505 | 1.00 | 30.96 | C |
| ATOM | 7003 | CG | PHE | D | 46 | 106.296 | 48.927 | -2.220 | 1.00 | 30.64 | C |
| ATOM | 7004 | CD1 | PHE | D | 46 | 107.018 | 50.007 | -1.726 | 1.00 | 29.90 | C |
| ATOM | 7005 | CE1 | PHE | D | 46 | 107.853 | 49.831 | -0.633 | 1.00 | 30.66 | C |
| ATOM | 7006 | CZ | PHE | D | 46 | 107.969 | 48.588 | -0.026 | 1.00 | 30.38 | C |
| ATOM | 7007 | CE2 | PHE | D | 46 | 107.239 | 47.517 | -0.522 | 1.00 | 33.84 | C |
| ATOM | 7008 | CD2 | PHE | D | 46 | 106.397 | 47.684 | -1.618 | 1.00 | 33.26 | C |
| ATOM | 7009 | C | PHE | D | 46 | 103.598 | 48.719 | -1.954 | 1.00 | 29.90 | C |
| ATOM | 7010 | O | PHE | D | 46 | 102.993 | 47.657 | -2.002 | 1.00 | 29.55 | O |
| ATOM | 7011 | N | HIS | D | 47 | 103.736 | 49.436 | -0.848 | 1.00 | 28.39 | N |
| ATOM | 7012 | CA | HIS | D | 47 | 103.174 | 48.976 | 0.414 | 1.00 | 26.33 | C |
| ATOM | 7013 | CB | HIS | D | 47 | 103.843 | 49.706 | 1.601 | 1.00 | 26.77 | C |
| ATOM | 7014 | CG | HIS | D | 47 | 105.033 | 48.983 | 2.170 | 1.00 | 25.25 | C |
| ATOM | 7015 | ND1 | HIS | D | 47 | 105.045 | 47.615 | 2.390 | 1.00 | 28.42 | N |
| ATOM | 7016 | CE1 | HIS | D | 47 | 106.195 | 47.268 | 2.941 | 1.00 | 22.81 | C |
| ATOM | 7017 | NE2 | HIS | D | 47 | 106.931 | 48.356 | 3.085 | 1.00 | 17.27 | N |
| ATOM | 7018 | CD2 | HIS | D | 47 | 106.227 | 49.443 | 2.611 | 1.00 | 18.81 | C |
| ATOM | 7019 | C | HIS | D | 47 | 101.640 | 49.106 | 0.516 | 1.00 | 23.90 | C |
| ATOM | 7020 | O | HIS | D | 47 | 101.065 | 48.798 | 1.538 | 1.00 | 25.30 | O |
| ATOM | 7021 | N | VAL | D | 48 | 100.980 | 49.531 | -0.544 | 1.00 | 21.24 | N |
| ATOM | 7022 | CA | VAL | D | 48 | 99.524 | 49.620 | -0.505 | 1.00 | 20.01 | C |
| ATOM | 7023 | CB | VAL | D | 48 | 99.109 | 50.903 | -1.228 | 1.00 | 18.78 | C |
| ATOM | 7024 | CG1 | VAL | D | 48 | 97.591 | 51.066 | -1.162 | 1.00 | 18.57 | C |
| ATOM | 7025 | CG2 | VAL | D | 48 | 99.768 | 52.105 | -0.582 | 1.00 | 19.47 | C |
| ATOM | 7026 | C | VAL | D | 48 | 98.845 | 48.416 | -1.164 | 1.00 | 20.73 | C |
| ATOM | 7027 | O | VAL | D | 48 | 98.768 | 48.290 | -2.378 | 1.00 | 21.10 | O |
| ATOM | 7028 | N | LYS | D | 49 | 98.375 | 47.487 | -0.311 | 1.00 | 22.15 | N |
| ATOM | 7029 | CA | LYS | D | 49 | 97.532 | 46.408 | -0.816 | 1.00 | 24.46 | C |
| ATOM | 7030 | CB | LYS | D | 49 | 97.884 | 45.122 | -0.066 | 1.00 | 25.54 | C |
| ATOM | 7031 | CG | LYS | D | 49 | 97.142 | 43.906 | -0.625 | 1.00 | 38.18 | C |
| ATOM | 7032 | CD | LYS | D | 49 | 97.136 | 42.727 | 0.354 | 1.00 | 45.91 | C |
| ATOM | 7033 | CE | LYS | D | 49 | 96.318 | 41.536 | -0.157 | 1.00 | 43.07 | C |
| ATOM | 7034 | NZ | LYS | D | 49 | 96.352 | 40.455 | 0.829 | 1.00 | 46.60 | N |
| ATOM | 7035 | C | LYS | D | 49 | 96.054 | 46.745 | -0.602 | 1.00 | 23.89 | C |
| ATOM | 7036 | O | LYS | D | 49 | 95.688 | 47.577 | 0.219 | 1.00 | 25.38 | O |

FIG. 2A-153

| ATOM | 7037 | N | SER | D | 50 | 95.193 | 46.098 | -1.404 | 1.00 | 22.70 | N |
|---|---|---|---|---|---|---|---|---|---|---|---|
| ATOM | 7038 | CA | SER | D | 50 | 93.767 | 46.397 | -1.308 | 1.00 | 23.02 | C |
| ATOM | 7039 | CB | SER | D | 50 | 93.113 | 46.057 | -2.645 | 1.00 | 22.39 | C |
| ATOM | 7040 | OG | SER | D | 50 | 92.796 | 44.667 | -2.677 | 1.00 | 23.81 | O |
| ATOM | 7041 | C | SER | D | 50 | 93.094 | 45.618 | -0.176 | 1.00 | 24.10 | C |
| ATOM | 7042 | O | SER | D | 50 | 93.496 | 44.518 | 0.182 | 1.00 | 25.01 | O |
| ATOM | 7043 | N | GLY | D | 51 | 92.022 | 46.197 | 0.353 | 1.00 | 24.20 | N |
| ATOM | 7044 | CA | GLY | D | 51 | 91.281 | 45.548 | 1.419 | 1.00 | 24.76 | C |
| ATOM | 7045 | C | GLY | D | 51 | 90.517 | 44.342 | 0.944 | 1.00 | 25.31 | C |
| ATOM | 7046 | O | GLY | D | 51 | 90.688 | 43.918 | -0.185 | 1.00 | 26.22 | O |
| ATOM | 7047 | N | LEU | D | 52 | 89.663 | 43.794 | 1.797 | 1.00 | 25.39 | N |
| ATOM | 7048 | CA | LEU | D | 52 | 88.886 | 42.617 | 1.437 | 1.00 | 25.57 | C |
| ATOM | 7049 | CB | LEU | D | 52 | 88.982 | 41.577 | 2.562 | 1.00 | 25.26 | C |
| ATOM | 7050 | CG | LEU | D | 52 | 88.164 | 40.292 | 2.403 | 1.00 | 24.46 | C |
| ATOM | 7051 | CD1 | LEU | D | 52 | 88.574 | 39.603 | 1.119 | 1.00 | 22.23 | C |
| ATOM | 7052 | CD2 | LEU | D | 52 | 88.362 | 39.378 | 3.614 | 1.00 | 19.20 | C |
| ATOM | 7053 | C | LEU | D | 52 | 87.408 | 42.915 | 1.141 | 1.00 | 26.35 | C |
| ATOM | 7054 | O | LEU | D | 52 | 86.670 | 43.293 | 2.029 | 1.00 | 26.63 | O |
| ATOM | 7055 | N | GLN | D | 53 | 86.965 | 42.736 | -0.100 | 1.00 | 28.40 | N |
| ATOM | 7056 | CA | GLN | D | 53 | 85.570 | 42.993 | -0.412 | 1.00 | 30.66 | C |
| ATOM | 7057 | CB | GLN | D | 53 | 85.425 | 43.667 | -1.766 | 1.00 | 29.98 | C |
| ATOM | 7058 | CG | GLN | D | 53 | 83.986 | 44.045 | -2.130 | 1.00 | 37.78 | C |
| ATOM | 7059 | CD | GLN | D | 53 | 83.308 | 45.027 | -1.129 | 1.00 | 45.47 | C |
| ATOM | 7060 | OE1 | GLN | D | 53 | 83.941 | 45.926 | -0.576 | 1.00 | 48.43 | O |
| ATOM | 7061 | NE2 | GLN | D | 53 | 82.003 | 44.859 | -0.932 | 1.00 | 46.69 | N |
| ATOM | 7062 | C | GLN | D | 53 | 84.762 | 41.714 | -0.420 | 1.00 | 30.81 | C |
| ATOM | 7063 | O | GLN | D | 53 | 84.658 | 41.063 | -1.430 | 1.00 | 33.90 | O |
| ATOM | 7064 | N | ILE | D | 54 | 84.166 | 41.353 | 0.701 | 1.00 | 29.60 | N |
| ATOM | 7065 | CA | ILE | D | 54 | 83.359 | 40.144 | 0.738 | 1.00 | 27.06 | C |
| ATOM | 7066 | CB | ILE | D | 54 | 82.838 | 39.923 | 2.166 | 1.00 | 27.46 | C |
| ATOM | 7067 | CG1 | ILE | D | 54 | 84.022 | 39.757 | 3.098 | 1.00 | 24.24 | C |
| ATOM | 7068 | CD1 | ILE | D | 54 | 83.667 | 39.173 | 4.387 | 1.00 | 32.05 | C |
| ATOM | 7069 | CG2 | ILE | D | 54 | 81.963 | 38.704 | 2.229 | 1.00 | 28.72 | C |
| ATOM | 7070 | C | ILE | D | 54 | 82.184 | 40.168 | -0.268 | 1.00 | 26.48 | C |
| ATOM | 7071 | O | ILE | D | 54 | 81.632 | 41.218 | -0.564 | 1.00 | 27.16 | O |
| ATOM | 7072 | N | LYS | D | 55 | 81.836 | 39.001 | -0.801 | 1.00 | 25.39 | N |
| ATOM | 7073 | CA | LYS | D | 55 | 80.751 | 38.855 | -1.760 | 1.00 | 23.97 | C |
| ATOM | 7074 | CB | LYS | D | 55 | 81.153 | 37.925 | -2.865 | 1.00 | 23.69 | C |
| ATOM | 7075 | CG | LYS | D | 55 | 82.357 | 38.329 | -3.630 | 1.00 | 24.78 | C |
| ATOM | 7076 | CD | LYS | D | 55 | 82.581 | 37.194 | -4.581 | 1.00 | 28.09 | C |
| ATOM | 7077 | CE | LYS | D | 55 | 83.655 | 37.439 | -5.551 | 1.00 | 29.38 | C |
| ATOM | 7078 | NZ | LYS | D | 55 | 83.633 | 36.166 | -6.313 | 1.00 | 42.83 | N |
| ATOM | 7079 | C | LYS | D | 55 | 79.500 | 38.259 | -1.128 | 1.00 | 24.72 | C |
| ATOM | 7080 | O | LYS | D | 55 | 79.603 | 37.373 | -0.255 | 1.00 | 26.12 | O |
| ATOM | 7081 | N | LYS | D | 56 | 78.327 | 38.689 | -1.610 | 1.00 | 22.76 | N |
| ATOM | 7082 | CA | LYS | D | 56 | 77.065 | 38.202 | -1.062 | 1.00 | 21.60 | C |

FIG. 2A-154

| ATOM | 7083 | CB | LYS | D | 56 | 76.071 | 39.345 | -0.814 | 1.00 | 22.16 | C |
|---|---|---|---|---|---|---|---|---|---|---|---|
| ATOM | 7084 | CG | LYS | D | 56 | 76.593 | 40.488 | -0.008 | 1.00 | 23.51 | C |
| ATOM | 7085 | CD | LYS | D | 56 | 77.189 | 40.048 | 1.316 | 1.00 | 25.32 | C |
| ATOM | 7086 | CE | LYS | D | 56 | 77.918 | 41.214 | 1.934 | 1.00 | 31.98 | C |
| ATOM | 7087 | NZ | LYS | D | 56 | 78.976 | 41.748 | 0.999 | 1.00 | 38.19 | N |
| ATOM | 7088 | C | LYS | D | 56 | 76.373 | 37.196 | -1.939 | 1.00 | 20.74 | C |
| ATOM | 7089 | O | LYS | D | 56 | 75.437 | 36.546 | -1.497 | 1.00 | 22.55 | O |
| ATOM | 7090 | N | ASN | D | 57 | 76.810 | 37.074 | -3.181 | 1.00 | 19.41 | N |
| ATOM | 7091 | CA | ASN | D | 57 | 76.145 | 36.140 | -4.056 | 1.00 | 18.56 | C |
| ATOM | 7092 | CB | ASN | D | 57 | 76.460 | 36.485 | -5.507 | 1.00 | 19.79 | C |
| ATOM | 7093 | CG | ASN | D | 57 | 77.859 | 36.128 | -5.911 | 1.00 | 22.53 | C |
| ATOM | 7094 | OD1 | ASN | D | 57 | 78.177 | 34.964 | -6.126 | 1.00 | 24.99 | O |
| ATOM | 7095 | ND2 | ASN | D | 57 | 78.708 | 37.137 | -6.031 | 1.00 | 24.56 | N |
| ATOM | 7096 | C | ASN | D | 57 | 76.449 | 34.678 | -3.743 | 1.00 | 16.96 | C |
| ATOM | 7097 | O | ASN | D | 57 | 77.519 | 34.345 | -3.263 | 1.00 | 15.69 | O |
| ATOM | 7098 | N | ALA | D | 58 | 75.480 | 33.805 | -3.992 | 1.00 | 16.84 | N |
| ATOM | 7099 | CA | ALA | D | 58 | 75.638 | 32.379 | -3.731 | 1.00 | 17.56 | C |
| ATOM | 7100 | CB | ALA | D | 58 | 74.494 | 31.615 | -4.325 | 1.00 | 18.35 | C |
| ATOM | 7101 | C | ALA | D | 58 | 76.940 | 31.899 | -4.346 | 1.00 | 17.82 | C |
| ATOM | 7102 | O | ALA | D | 58 | 77.169 | 32.064 | -5.534 | 1.00 | 17.51 | O |
| ATOM | 7103 | N | ILE | D | 59 | 77.787 | 31.285 | -3.529 | 1.00 | 16.23 | N |
| ATOM | 7104 | CA | ILE | D | 59 | 79.065 | 30.825 | -4.012 | 1.00 | 16.22 | C |
| ATOM | 7105 | CB | ILE | D | 59 | 79.923 | 30.204 | -2.850 | 1.00 | 15.04 | C |
| ATOM | 7106 | CG1 | ILE | D | 59 | 81.329 | 29.944 | -3.344 | 1.00 | 11.98 | C |
| ATOM | 7107 | CD1 | ILE | D | 59 | 82.165 | 29.271 | -2.368 | 1.00 | 13.01 | C |
| ATOM | 7108 | CG2 | ILE | D | 59 | 79.297 | 28.941 | -2.327 | 1.00 | 14.91 | C |
| ATOM | 7109 | C | ILE | D | 59 | 78.871 | 29.825 | -5.142 | 1.00 | 18.23 | C |
| ATOM | 7110 | O | ILE | D | 59 | 79.733 | 29.701 | -6.013 | 1.00 | 18.55 | O |
| ATOM | 7111 | N | ILE | D | 60 | 77.735 | 29.126 | -5.143 | 1.00 | 20.14 | N |
| ATOM | 7112 | CA | ILE | D | 60 | 77.455 | 28.133 | -6.187 | 1.00 | 21.17 | C |
| ATOM | 7113 | CB | ILE | D | 60 | 76.186 | 27.325 | -5.912 | 1.00 | 20.15 | C |
| ATOM | 7114 | CG1 | ILE | D | 60 | 75.016 | 28.273 | -5.682 | 1.00 | 20.72 | C |
| ATOM | 7115 | CD1 | ILE | D | 60 | 73.679 | 27.540 | -5.611 | 1.00 | 25.48 | C |
| ATOM | 7116 | CG2 | ILE | D | 60 | 76.394 | 26.386 | -4.763 | 1.00 | 18.87 | C |
| ATOM | 7117 | C | ILE | D | 60 | 77.262 | 28.762 | -7.556 | 1.00 | 23.49 | C |
| ATOM | 7118 | O | ILE | D | 60 | 77.165 | 28.061 | -8.551 | 1.00 | 24.36 | O |
| ATOM | 7119 | N | ASP | D | 61 | 77.170 | 30.081 | -7.610 | 1.00 | 26.30 | N |
| ATOM | 7120 | CA | ASP | D | 61 | 77.007 | 30.741 | -8.880 | 1.00 | 29.36 | C |
| ATOM | 7121 | CB | ASP | D | 61 | 76.603 | 32.194 | -8.730 | 1.00 | 30.81 | C |
| ATOM | 7122 | CG | ASP | D | 61 | 75.196 | 32.368 | -8.234 | 1.00 | 37.72 | C |
| ATOM | 7123 | OD1 | ASP | D | 61 | 74.813 | 33.547 | -8.079 | 1.00 | 43.84 | O |
| ATOM | 7124 | OD2 | ASP | D | 61 | 74.479 | 31.359 | -8.005 | 1.00 | 43.22 | O |
| ATOM | 7125 | C | ASP | D | 61 | 78.343 | 30.732 | -9.545 | 1.00 | 29.41 | C |
| ATOM | 7126 | O | ASP | D | 61 | 78.413 | 30.831 | -10.760 | 1.00 | 31.21 | O |
| ATOM | 7127 | N | ASP | D | 62 | 79.411 | 30.609 | -8.775 | 1.00 | 28.91 | N |
| ATOM | 7128 | CA | ASP | D | 62 | 80.719 | 30.646 | -9.391 | 1.00 | 28.09 | C |

FIG. 2A-155

| ATOM | 7129 | CB  | ASP | D | 62 | 81.459 | 31.897 | -8.929  | 1.00 | 27.70 | C |
| ---- | ---- | --- | --- | - | -- | ------ | ------ | ------- | ---- | ----- | - |
| ATOM | 7130 | CG  | ASP | D | 62 | 80.629 | 33.165 | -9.122  | 1.00 | 29.79 | C |
| ATOM | 7131 | OD1 | ASP | D | 62 | 79.763 | 33.200 | -10.028 | 1.00 | 32.48 | O |
| ATOM | 7132 | OD2 | ASP | D | 62 | 80.839 | 34.140 | -8.368  | 1.00 | 33.46 | O |
| ATOM | 7133 | C   | ASP | D | 62 | 81.609 | 29.427 | -9.249  | 1.00 | 27.90 | C |
| ATOM | 7134 | O   | ASP | D | 62 | 82.530 | 29.252 | -10.030 | 1.00 | 28.66 | O |
| ATOM | 7135 | N   | TYR | D | 63 | 81.359 | 28.576 | -8.272  | 1.00 | 27.62 | N |
| ATOM | 7136 | CA  | TYR | D | 63 | 82.196 | 27.397 | -8.135  | 1.00 | 25.90 | C |
| ATOM | 7137 | CB  | TYR | D | 63 | 83.067 | 27.470 | -6.880  | 1.00 | 26.15 | C |
| ATOM | 7138 | CG  | TYR | D | 63 | 84.046 | 28.614 | -6.839  | 1.00 | 28.62 | C |
| ATOM | 7139 | CD1 | TYR | D | 63 | 85.352 | 28.467 | -7.299  | 1.00 | 30.45 | C |
| ATOM | 7140 | CE1 | TYR | D | 63 | 86.253 | 29.525 | -7.261  | 1.00 | 29.45 | C |
| ATOM | 7141 | CZ  | TYR | D | 63 | 85.838 | 30.747 | -6.761  | 1.00 | 34.55 | C |
| ATOM | 7142 | OH  | TYR | D | 63 | 86.663 | 31.857 | -6.730  | 1.00 | 34.27 | O |
| ATOM | 7143 | CE2 | TYR | D | 63 | 84.544 | 30.902 | -6.304  | 1.00 | 33.72 | C |
| ATOM | 7144 | CD2 | TYR | D | 63 | 83.662 | 29.841 | -6.346  | 1.00 | 29.87 | C |
| ATOM | 7145 | C   | TYR | D | 63 | 81.273 | 26.213 | -8.008  | 1.00 | 25.20 | C |
| ATOM | 7146 | O   | TYR | D | 63 | 80.080 | 26.367 | -7.774  | 1.00 | 25.11 | O |
| ATOM | 7147 | N   | ALA | D | 64 | 81.826 | 25.025 | -8.191  | 1.00 | 24.36 | N |
| ATOM | 7148 | CA  | ALA | D | 64 | 81.039 | 23.823 | -8.038  | 1.00 | 24.19 | C |
| ATOM | 7149 | CB  | ALA | D | 64 | 81.412 | 22.764 | -9.090  | 1.00 | 23.92 | C |
| ATOM | 7150 | C   | ALA | D | 64 | 81.475 | 23.376 | -6.670  | 1.00 | 24.33 | C |
| ATOM | 7151 | O   | ALA | D | 64 | 82.653 | 23.111 | -6.428  | 1.00 | 24.18 | O |
| ATOM | 7152 | N   | VAL | D | 65 | 80.536 | 23.313 | -5.759  | 1.00 | 23.88 | N |
| ATOM | 7153 | CA  | VAL | D | 65 | 80.918 | 22.892 | -4.446  | 1.00 | 22.67 | C |
| ATOM | 7154 | CB  | VAL | D | 65 | 80.110 | 23.700 | -3.396  | 1.00 | 22.88 | C |
| ATOM | 7155 | CG1 | VAL | D | 65 | 80.385 | 23.178 | -1.952  | 1.00 | 19.56 | C |
| ATOM | 7156 | CG2 | VAL | D | 65 | 80.486 | 25.194 | -3.555  | 1.00 | 17.95 | C |
| ATOM | 7157 | C   | VAL | D | 65 | 80.718 | 21.391 | -4.347  | 1.00 | 24.03 | C |
| ATOM | 7158 | O   | VAL | D | 65 | 79.650 | 20.881 | -4.619  | 1.00 | 25.27 | O |
| ATOM | 7159 | N   | THR | D | 66 | 81.771 | 20.669 | -4.005  | 1.00 | 24.21 | N |
| ATOM | 7160 | CA  | THR | D | 66 | 81.667 | 19.229 | -3.882  | 1.00 | 25.66 | C |
| ATOM | 7161 | CB  | THR | D | 66 | 82.795 | 18.558 | -4.599  | 1.00 | 25.53 | C |
| ATOM | 7162 | OG1 | THR | D | 66 | 83.822 | 18.222 | -3.651  | 1.00 | 23.83 | O |
| ATOM | 7163 | CG2 | THR | D | 66 | 83.323 | 19.484 | -5.671  | 1.00 | 26.54 | C |
| ATOM | 7164 | C   | THR | D | 66 | 81.691 | 18.783 | -2.418  | 1.00 | 27.11 | C |
| ATOM | 7165 | O   | THR | D | 66 | 81.921 | 19.576 | -1.513  | 1.00 | 27.97 | O |
| ATOM | 7166 | N   | SER | D | 67 | 81.487 | 17.493 | -2.197  | 1.00 | 27.60 | N |
| ATOM | 7167 | CA  | SER | D | 67 | 81.432 | 16.970 | -0.847  | 1.00 | 28.76 | C |
| ATOM | 7168 | CB  | SER | D | 67 | 80.177 | 16.131 | -0.743  | 1.00 | 28.85 | C |
| ATOM | 7169 | OG  | SER | D | 67 | 80.021 | 15.429 | -1.967  | 1.00 | 31.65 | O |
| ATOM | 7170 | C   | SER | D | 67 | 82.668 | 16.170 | -0.435  | 1.00 | 28.98 | C |
| ATOM | 7171 | O   | SER | D | 67 | 82.661 | 15.423 | 0.550   | 1.00 | 28.94 | O |
| ATOM | 7172 | N   | GLN | D | 68 | 83.731 | 16.314 | -1.211  | 1.00 | 29.43 | N |
| ATOM | 7173 | CA  | GLN | D | 68 | 85.008 | 15.718 | -0.838  | 1.00 | 29.37 | C |
| ATOM | 7174 | CB  | GLN | D | 68 | 85.850 | 15.554 | -2.103  | 1.00 | 30.15 | C |

FIG. 2A-156

| ATOM | 7175 | CG | GLN | D | 68 | 87.143 | 14.782 | -1.837 | 1.00 | 34.63 | C |
|---|---|---|---|---|---|---|---|---|---|---|---|
| ATOM | 7176 | CD | GLN | D | 68 | 88.071 | 14.944 | -3.013 | 1.00 | 41.71 | C |
| ATOM | 7177 | OE1 | GLN | D | 68 | 88.841 | 14.066 | -3.376 | 1.00 | 43.64 | O |
| ATOM | 7178 | NE2 | GLN | D | 68 | 87.970 | 16.141 | -3.628 | 1.00 | 40.94 | N |
| ATOM | 7179 | C | GLN | D | 68 | 85.752 | 16.578 | 0.180 | 1.00 | 28.39 | C |
| ATOM | 7180 | O | GLN | D | 68 | 86.361 | 17.593 | -0.135 | 1.00 | 28.73 | O |
| ATOM | 7181 | N | VAL | D | 69 | 85.651 | 16.154 | 1.450 | 1.00 | 27.54 | N |
| ATOM | 7182 | CA | VAL | D | 69 | 86.252 | 16.930 | 2.517 | 1.00 | 27.47 | C |
| ATOM | 7183 | CB | VAL | D | 69 | 85.638 | 16.488 | 3.844 | 1.00 | 28.11 | C |
| ATOM | 7184 | CG1 | VAL | D | 69 | 86.350 | 17.188 | 4.999 | 1.00 | 28.68 | C |
| ATOM | 7185 | CG2 | VAL | D | 69 | 84.164 | 16.845 | 3.879 | 1.00 | 29.78 | C |
| ATOM | 7186 | C | VAL | D | 69 | 87.763 | 16.738 | 2.578 | 1.00 | 25.88 | C |
| ATOM | 7187 | O | VAL | D | 69 | 88.275 | 15.673 | 2.889 | 1.00 | 25.23 | O |
| ATOM | 7188 | N | LEU | D | 70 | 88.484 | 17.811 | 2.220 | 1.00 | 24.77 | N |
| ATOM | 7189 | CA | LEU | D | 70 | 89.920 | 17.773 | 2.424 | 1.00 | 24.46 | C |
| ATOM | 7190 | CB | LEU | D | 70 | 90.496 | 19.118 | 1.987 | 1.00 | 24.44 | C |
| ATOM | 7191 | CG | LEU | D | 70 | 90.498 | 19.283 | 0.466 | 1.00 | 23.99 | C |
| ATOM | 7192 | CD1 | LEU | D | 70 | 90.922 | 20.686 | 0.037 | 1.00 | 22.34 | C |
| ATOM | 7193 | CD2 | LEU | D | 70 | 91.455 | 18.316 | -0.234 | 1.00 | 26.18 | C |
| ATOM | 7194 | C | LEU | D | 70 | 90.237 | 17.522 | 3.898 | 1.00 | 24.07 | C |
| ATOM | 7195 | O | LEU | D | 70 | 91.019 | 16.647 | 4.250 | 1.00 | 24.31 | O |
| ATOM | 7196 | N | GLY | D | 71 | 89.621 | 18.341 | 4.739 | 1.00 | 23.99 | N |
| ATOM | 7197 | CA | GLY | D | 71 | 89.890 | 18.215 | 6.156 | 1.00 | 24.19 | C |
| ATOM | 7198 | C | GLY | D | 71 | 88.950 | 18.972 | 7.070 | 1.00 | 24.76 | C |
| ATOM | 7199 | O | GLY | D | 71 | 87.842 | 19.355 | 6.680 | 1.00 | 25.36 | O |
| ATOM | 7200 | N | LEU | D | 72 | 89.406 | 19.171 | 8.303 | 1.00 | 24.98 | N |
| ATOM | 7201 | CA | LEU | D | 72 | 88.656 | 19.876 | 9.319 | 1.00 | 25.47 | C |
| ATOM | 7202 | CB | LEU | D | 72 | 88.173 | 18.900 | 10.357 | 1.00 | 25.07 | C |
| ATOM | 7203 | CG | LEU | D | 72 | 87.463 | 17.707 | 9.743 | 1.00 | 27.31 | C |
| ATOM | 7204 | CD1 | LEU | D | 72 | 87.410 | 16.583 | 10.773 | 1.00 | 30.31 | C |
| ATOM | 7205 | CD2 | LEU | D | 72 | 86.076 | 18.139 | 9.236 | 1.00 | 25.90 | C |
| ATOM | 7206 | C | LEU | D | 72 | 89.582 | 20.849 | 9.987 | 1.00 | 26.00 | C |
| ATOM | 7207 | O | LEU | D | 72 | 90.362 | 20.458 | 10.830 | 1.00 | 24.57 | O |
| ATOM | 7208 | N | GLY | D | 73 | 89.499 | 22.118 | 9.598 | 1.00 | 28.03 | N |
| ATOM | 7209 | CA | GLY | D | 73 | 90.342 | 23.147 | 10.181 | 1.00 | 29.49 | C |
| ATOM | 7210 | C | GLY | D | 73 | 89.707 | 23.620 | 11.462 | 1.00 | 31.23 | C |
| ATOM | 7211 | O | GLY | D | 73 | 88.771 | 22.997 | 11.942 | 1.00 | 28.21 | O |
| ATOM | 7212 | N | ILE | D | 74 | 90.212 | 24.710 | 12.026 | 1.00 | 33.63 | N |
| ATOM | 7213 | CA | ILE | D | 74 | 89.650 | 25.238 | 13.267 | 1.00 | 34.53 | C |
| ATOM | 7214 | CB | ILE | D | 74 | 90.535 | 26.318 | 13.884 | 1.00 | 34.83 | C |
| ATOM | 7215 | CG1 | ILE | D | 74 | 91.894 | 25.740 | 14.217 | 1.00 | 34.95 | C |
| ATOM | 7216 | CD1 | ILE | D | 74 | 92.859 | 26.790 | 14.561 | 1.00 | 44.08 | C |
| ATOM | 7217 | CG2 | ILE | D | 74 | 89.890 | 26.860 | 15.121 | 1.00 | 33.09 | C |
| ATOM | 7218 | C | ILE | D | 74 | 88.298 | 25.871 | 12.972 | 1.00 | 34.83 | C |
| ATOM | 7219 | O | ILE | D | 74 | 88.215 | 26.873 | 12.252 | 1.00 | 35.57 | O |
| ATOM | 7220 | N | ASN | D | 75 | 87.249 | 25.270 | 13.522 | 1.00 | 35.14 | N |

FIG. 2A-157

| ATOM | 7221 | CA | ASN | D | 75 | 85.890 | 25.766 | 13.350 | 1.00 | 36.17 | C |
| --- | --- | --- | --- | --- | --- | --- | --- | --- | --- | --- | --- |
| ATOM | 7222 | CB | ASN | D | 75 | 85.828 | 27.251 | 13.684 | 1.00 | 36.45 | C |
| ATOM | 7223 | CG | ASN | D | 75 | 86.450 | 27.565 | 15.024 | 1.00 | 39.35 | C |
| ATOM | 7224 | OD1 | ASN | D | 75 | 86.134 | 26.939 | 16.042 | 1.00 | 37.01 | O |
| ATOM | 7225 | ND2 | ASN | D | 75 | 87.339 | 28.548 | 15.035 | 1.00 | 40.11 | N |
| ATOM | 7226 | C | ASN | D | 75 | 85.279 | 25.545 | 11.979 | 1.00 | 35.60 | C |
| ATOM | 7227 | O | ASN | D | 75 | 84.262 | 26.142 | 11.664 | 1.00 | 37.03 | O |
| ATOM | 7228 | N | GLY | D | 76 | 85.882 | 24.696 | 11.160 | 1.00 | 35.04 | N |
| ATOM | 7229 | CA | GLY | D | 76 | 85.310 | 24.435 | 9.857 | 1.00 | 34.39 | C |
| ATOM | 7230 | C | GLY | D | 76 | 85.998 | 23.365 | 9.020 | 1.00 | 34.30 | C |
| ATOM | 7231 | O | GLY | D | 76 | 87.216 | 23.179 | 9.063 | 1.00 | 34.40 | O |
| ATOM | 7232 | N | LYS | D | 77 | 85.210 | 22.650 | 8.236 | 1.00 | 32.76 | N |
| ATOM | 7233 | CA | LYS | D | 77 | 85.780 | 21.633 | 7.380 | 1.00 | 31.71 | C |
| ATOM | 7234 | CB | LYS | D | 77 | 84.780 | 20.515 | 7.166 | 1.00 | 32.11 | C |
| ATOM | 7235 | CG | LYS | D | 77 | 83.555 | 20.907 | 6.373 | 1.00 | 32.44 | C |
| ATOM | 7236 | CD | LYS | D | 77 | 82.554 | 19.773 | 6.470 | 1.00 | 35.34 | C |
| ATOM | 7237 | CE | LYS | D | 77 | 81.180 | 20.186 | 6.009 | 1.00 | 38.22 | C |
| ATOM | 7238 | NZ | LYS | D | 77 | 80.223 | 19.058 | 6.184 | 1.00 | 38.08 | N |
| ATOM | 7239 | C | LYS | D | 77 | 86.124 | 22.262 | 6.045 | 1.00 | 30.95 | C |
| ATOM | 7240 | O | LYS | D | 77 | 85.402 | 23.126 | 5.566 | 1.00 | 32.17 | O |
| ATOM | 7241 | N | VAL | D | 78 | 87.237 | 21.848 | 5.451 | 1.00 | 29.31 | N |
| ATOM | 7242 | CA | VAL | D | 78 | 87.631 | 22.379 | 4.157 | 1.00 | 27.28 | C |
| ATOM | 7243 | CB | VAL | D | 78 | 89.164 | 22.522 | 4.027 | 1.00 | 27.49 | C |
| ATOM | 7244 | CG1 | VAL | D | 78 | 89.526 | 22.963 | 2.632 | 1.00 | 26.31 | C |
| ATOM | 7245 | CG2 | VAL | D | 78 | 89.669 | 23.529 | 5.039 | 1.00 | 25.60 | C |
| ATOM | 7246 | C | VAL | D | 78 | 87.128 | 21.378 | 3.147 | 1.00 | 27.20 | C |
| ATOM | 7247 | O | VAL | D | 78 | 87.336 | 20.171 | 3.288 | 1.00 | 27.48 | O |
| ATOM | 7248 | N | LEU | D | 79 | 86.451 | 21.898 | 2.140 | 1.00 | 26.80 | N |
| ATOM | 7249 | CA | LEU | D | 79 | 85.859 | 21.099 | 1.085 | 1.00 | 26.17 | C |
| ATOM | 7250 | CB | LEU | D | 79 | 84.365 | 21.457 | 0.961 | 1.00 | 24.42 | C |
| ATOM | 7251 | CG | LEU | D | 79 | 83.349 | 21.178 | 2.083 | 1.00 | 23.67 | C |
| ATOM | 7252 | CD1 | LEU | D | 79 | 81.994 | 21.714 | 1.731 | 1.00 | 23.02 | C |
| ATOM | 7253 | CD2 | LEU | D | 79 | 83.277 | 19.680 | 2.349 | 1.00 | 24.72 | C |
| ATOM | 7254 | C | LEU | D | 79 | 86.576 | 21.401 | -0.221 | 1.00 | 26.15 | C |
| ATOM | 7255 | O | LEU | D | 79 | 87.203 | 22.447 | -0.362 | 1.00 | 24.71 | O |
| ATOM | 7256 | N | GLN | D | 80 | 86.493 | 20.452 | -1.159 | 1.00 | 27.05 | N |
| ATOM | 7257 | CA | GLN | D | 80 | 87.095 | 20.587 | -2.488 | 1.00 | 27.50 | C |
| ATOM | 7258 | CB | GLN | D | 80 | 87.498 | 19.222 | -3.053 | 1.00 | 27.88 | C |
| ATOM | 7259 | CG | GLN | D | 80 | 88.196 | 19.293 | -4.419 | 1.00 | 35.55 | C |
| ATOM | 7260 | CD | GLN | D | 80 | 89.720 | 19.283 | -4.311 | 1.00 | 43.29 | C |
| ATOM | 7261 | OE1 | GLN | D | 80 | 90.299 | 18.375 | -3.697 | 1.00 | 45.54 | O |
| ATOM | 7262 | NE2 | GLN | D | 80 | 90.379 | 20.287 | -4.909 | 1.00 | 46.44 | N |
| ATOM | 7263 | C | GLN | D | 80 | 86.039 | 21.216 | -3.402 | 1.00 | 25.94 | C |
| ATOM | 7264 | O | GLN | D | 80 | 84.915 | 20.729 | -3.482 | 1.00 | 26.42 | O |
| ATOM | 7265 | N | ILE | D | 81 | 86.386 | 22.305 | -4.066 | 1.00 | 23.92 | N |
| ATOM | 7266 | CA | ILE | D | 81 | 85.433 | 22.939 | -4.939 | 1.00 | 24.44 | C |

FIG. 2A-158

| ATOM | 7267 | CB | ILE | D | 81 | 84.911 | 24.246 | -4.335 | 1.00 | 23.51 | C |
|---|---|---|---|---|---|---|---|---|---|---|---|
| ATOM | 7268 | CG1 | ILE | D | 81 | 86.066 | 25.227 | -4.152 | 1.00 | 24.40 | C |
| ATOM | 7269 | CD1 | ILE | D | 81 | 85.617 | 26.679 | -4.112 | 1.00 | 27.32 | C |
| ATOM | 7270 | CG2 | ILE | D | 81 | 84.240 | 23.983 | -3.016 | 1.00 | 23.66 | C |
| ATOM | 7271 | C | ILE | D | 81 | 86.123 | 23.242 | -6.259 | 1.00 | 25.17 | C |
| ATOM | 7272 | O | ILE | D | 81 | 87.349 | 23.396 | -6.299 | 1.00 | 25.90 | O |
| ATOM | 7273 | N | PHE | D | 82 | 85.350 | 23.324 | -7.338 | 1.00 | 24.75 | N |
| ATOM | 7274 | CA | PHE | D | 82 | 85.944 | 23.609 | -8.634 | 1.00 | 25.09 | C |
| ATOM | 7275 | CB | PHE | D | 82 | 85.818 | 22.415 | -9.575 | 1.00 | 23.71 | C |
| ATOM | 7276 | CG | PHE | D | 82 | 86.340 | 21.138 | -8.993 | 1.00 | 23.17 | C |
| ATOM | 7277 | CD1 | PHE | D | 82 | 85.596 | 20.432 | -8.061 | 1.00 | 24.66 | C |
| ATOM | 7278 | CE1 | PHE | D | 82 | 86.087 | 19.293 | -7.478 | 1.00 | 26.03 | C |
| ATOM | 7279 | CZ | PHE | D | 82 | 87.335 | 18.836 | -7.817 | 1.00 | 27.37 | C |
| ATOM | 7280 | CE2 | PHE | D | 82 | 88.091 | 19.524 | -8.747 | 1.00 | 28.38 | C |
| ATOM | 7281 | CD2 | PHE | D | 82 | 87.592 | 20.669 | -9.331 | 1.00 | 24.27 | C |
| ATOM | 7282 | C | PHE | D | 82 | 85.300 | 24.814 | -9.262 | 1.00 | 26.88 | C |
| ATOM | 7283 | O | PHE | D | 82 | 84.076 | 24.954 | -9.236 | 1.00 | 27.23 | O |
| ATOM | 7284 | N | ASN | D | 83 | 86.145 | 25.685 | -9.813 | 1.00 | 28.05 | N |
| ATOM | 7285 | CA | ASN | D | 83 | 85.699 | 26.897 | -10.470 | 1.00 | 28.51 | C |
| ATOM | 7286 | CB | ASN | D | 83 | 86.894 | 27.712 | -10.924 | 1.00 | 28.55 | C |
| ATOM | 7287 | CG | ASN | D | 83 | 86.483 | 28.910 | -11.731 | 1.00 | 30.07 | C |
| ATOM | 7288 | OD1 | ASN | D | 83 | 85.687 | 28.788 | -12.648 | 1.00 | 31.01 | O |
| ATOM | 7289 | ND2 | ASN | D | 83 | 87.015 | 30.076 | -11.396 | 1.00 | 29.70 | N |
| ATOM | 7290 | C | ASN | D | 83 | 84.900 | 26.485 | -11.685 | 1.00 | 28.98 | C |
| ATOM | 7291 | O | ASN | D | 83 | 85.398 | 25.707 | -12.495 | 1.00 | 28.19 | O |
| ATOM | 7292 | N | LYS | D | 84 | 83.681 | 27.005 | -11.830 | 1.00 | 30.18 | N |
| ATOM | 7293 | CA | LYS | D | 84 | 82.821 | 26.649 | -12.964 | 1.00 | 31.78 | C |
| ATOM | 7294 | CB | LYS | D | 84 | 81.436 | 27.240 | -12.764 | 1.00 | 31.62 | C |
| ATOM | 7295 | CG | LYS | D | 84 | 80.651 | 26.582 | -11.663 | 1.00 | 34.07 | C |
| ATOM | 7296 | CD | LYS | D | 84 | 79.396 | 27.370 | -11.403 | 1.00 | 38.92 | C |
| ATOM | 7297 | CE | LYS | D | 84 | 78.171 | 26.505 | -11.488 | 1.00 | 40.54 | C |
| ATOM | 7298 | NZ | LYS | D | 84 | 76.999 | 27.407 | -11.400 | 1.00 | 41.76 | N |
| ATOM | 7299 | C | LYS | D | 84 | 83.344 | 27.045 | -14.354 | 1.00 | 33.04 | C |
| ATOM | 7300 | O | LYS | D | 84 | 83.092 | 26.348 | -15.351 | 1.00 | 32.49 | O |
| ATOM | 7301 | N | ALA | D | 85 | 84.050 | 28.171 | -14.419 | 1.00 | 34.44 | N |
| ATOM | 7302 | CA | ALA | D | 85 | 84.632 | 28.638 | -15.666 | 1.00 | 35.49 | C |
| ATOM | 7303 | CB | ALA | D | 85 | 84.778 | 30.164 | -15.662 | 1.00 | 35.30 | C |
| ATOM | 7304 | C | ALA | D | 85 | 85.995 | 27.971 | -15.778 | 1.00 | 36.34 | C |
| ATOM | 7305 | O | ALA | D | 85 | 86.074 | 26.800 | -16.151 | 1.00 | 36.21 | O |
| ATOM | 7306 | N | THR | D | 86 | 87.055 | 28.700 | -15.425 | 1.00 | 37.36 | N |
| ATOM | 7307 | CA | THR | D | 86 | 88.423 | 28.169 | -15.498 | 1.00 | 37.79 | C |
| ATOM | 7308 | CB | THR | D | 86 | 89.376 | 28.805 | -14.447 | 1.00 | 38.14 | C |
| ATOM | 7309 | OG1 | THR | D | 86 | 89.149 | 28.215 | -13.161 | 1.00 | 39.17 | O |
| ATOM | 7310 | CG2 | THR | D | 86 | 89.141 | 30.300 | -14.356 | 1.00 | 42.16 | C |
| ATOM | 7311 | C | THR | D | 86 | 88.421 | 26.668 | -15.265 | 1.00 | 36.59 | C |
| ATOM | 7312 | O | THR | D | 86 | 89.051 | 25.902 | -16.007 | 1.00 | 36.68 | O |

FIG. 2A-159

| ATOM | 7313 | N | GLN | D | 87 | 87.709 | 26.257 | -14.225 | 1.00 | 35.54 | N |
| --- | --- | --- | --- | --- | --- | --- | --- | --- | --- | --- | --- |
| ATOM | 7314 | CA | GLN | D | 87 | 87.595 | 24.852 | -13.877 | 1.00 | 35.30 | C |
| ATOM | 7315 | CB | GLN | D | 87 | 87.429 | 24.011 | -15.133 | 1.00 | 35.28 | C |
| ATOM | 7316 | CG | GLN | D | 87 | 86.949 | 22.614 | -14.853 | 1.00 | 39.79 | C |
| ATOM | 7317 | CD | GLN | D | 87 | 85.881 | 22.210 | -15.826 | 1.00 | 49.11 | C |
| ATOM | 7318 | OE1 | GLN | D | 87 | 85.444 | 21.055 | -15.851 | 1.00 | 53.73 | O |
| ATOM | 7319 | NE2 | GLN | D | 87 | 85.440 | 23.166 | -16.643 | 1.00 | 50.00 | N |
| ATOM | 7320 | C | GLN | D | 87 | 88.743 | 24.299 | -13.050 | 1.00 | 34.29 | C |
| ATOM | 7321 | O | GLN | D | 87 | 88.956 | 23.089 | -13.017 | 1.00 | 32.92 | O |
| ATOM | 7322 | N | GLU | D | 88 | 89.481 | 25.183 | -12.381 | 1.00 | 34.07 | N |
| ATOM | 7323 | CA | GLU | D | 88 | 90.563 | 24.728 | -11.527 | 1.00 | 33.92 | C |
| ATOM | 7324 | CB | GLU | D | 88 | 91.692 | 25.739 | -11.500 | 1.00 | 34.33 | C |
| ATOM | 7325 | CG | GLU | D | 88 | 91.246 | 27.157 | -11.445 | 1.00 | 40.94 | C |
| ATOM | 7326 | CD | GLU | D | 88 | 92.394 | 28.124 | -11.675 | 1.00 | 48.11 | C |
| ATOM | 7327 | OE1 | GLU | D | 88 | 93.408 | 28.027 | -10.947 | 1.00 | 43.46 | O |
| ATOM | 7328 | OE2 | GLU | D | 88 | 92.280 | 28.977 | -12.587 | 1.00 | 53.04 | O |
| ATOM | 7329 | C | GLU | D | 88 | 90.059 | 24.454 | -10.115 | 1.00 | 32.89 | C |
| ATOM | 7330 | O | GLU | D | 88 | 88.995 | 24.915 | -9.700 | 1.00 | 32.84 | O |
| ATOM | 7331 | N | ALA | D | 89 | 90.830 | 23.668 | -9.382 | 1.00 | 31.78 | N |
| ATOM | 7332 | CA | ALA | D | 89 | 90.468 | 23.288 | -8.037 | 1.00 | 31.01 | C |
| ATOM | 7333 | CB | ALA | D | 89 | 91.088 | 21.916 | -7.702 | 1.00 | 30.65 | C |
| ATOM | 7334 | C | ALA | D | 89 | 90.896 | 24.324 | -7.005 | 1.00 | 30.93 | C |
| ATOM | 7335 | O | ALA | D | 89 | 91.937 | 24.974 | -7.133 | 1.00 | 31.76 | O |
| ATOM | 7336 | N | PHE | D | 90 | 90.064 | 24.472 | -5.985 | 1.00 | 29.95 | N |
| ATOM | 7337 | CA | PHE | D | 90 | 90.320 | 25.380 | -4.890 | 1.00 | 28.07 | C |
| ATOM | 7338 | CB | PHE | D | 90 | 89.579 | 26.699 | -5.091 | 1.00 | 27.21 | C |
| ATOM | 7339 | CG | PHE | D | 90 | 90.149 | 27.562 | -6.178 | 1.00 | 23.85 | C |
| ATOM | 7340 | CD1 | PHE | D | 90 | 89.727 | 27.427 | -7.482 | 1.00 | 20.25 | C |
| ATOM | 7341 | CE1 | PHE | D | 90 | 90.211 | 28.262 | -8.462 | 1.00 | 20.72 | C |
| ATOM | 7342 | CZ | PHE | D | 90 | 91.129 | 29.241 | -8.156 | 1.00 | 23.19 | C |
| ATOM | 7343 | CE2 | PHE | D | 90 | 91.570 | 29.388 | -6.856 | 1.00 | 20.71 | C |
| ATOM | 7344 | CD2 | PHE | D | 90 | 91.082 | 28.554 | -5.878 | 1.00 | 22.47 | C |
| ATOM | 7345 | C | PHE | D | 90 | 89.815 | 24.716 | -3.623 | 1.00 | 28.31 | C |
| ATOM | 7346 | O | PHE | D | 90 | 88.920 | 23.864 | -3.665 | 1.00 | 29.83 | O |
| ATOM | 7347 | N | ALA | D | 91 | 90.394 | 25.086 | -2.492 | 1.00 | 27.08 | N |
| ATOM | 7348 | CA | ALA | D | 91 | 89.929 | 24.543 | -1.238 | 1.00 | 25.92 | C |
| ATOM | 7349 | CB | ALA | D | 91 | 91.093 | 24.343 | -0.292 | 1.00 | 25.25 | C |
| ATOM | 7350 | C | ALA | D | 91 | 88.930 | 25.576 | -0.687 | 1.00 | 25.41 | C |
| ATOM | 7351 | O | ALA | D | 91 | 89.046 | 26.776 | -0.963 | 1.00 | 25.59 | O |
| ATOM | 7352 | N | LEU | D | 92 | 87.935 | 25.103 | 0.055 | 1.00 | 24.66 | N |
| ATOM | 7353 | CA | LEU | D | 92 | 86.942 | 25.985 | 0.643 | 1.00 | 24.15 | C |
| ATOM | 7354 | CB | LEU | D | 92 | 85.602 | 25.816 | -0.087 | 1.00 | 23.27 | C |
| ATOM | 7355 | CG | LEU | D | 92 | 84.372 | 26.563 | 0.447 | 1.00 | 18.97 | C |
| ATOM | 7356 | CD1 | LEU | D | 92 | 84.451 | 28.026 | 0.065 | 1.00 | 14.33 | C |
| ATOM | 7357 | CD2 | LEU | D | 92 | 83.114 | 25.926 | -0.103 | 1.00 | 20.53 | C |
| ATOM | 7358 | C | LEU | D | 92 | 86.746 | 25.700 | 2.131 | 1.00 | 24.61 | C |

FIG. 2A-160

| | | | | | | | | | | | |
|---|---|---|---|---|---|---|---|---|---|---|---|
| ATOM | 7359 | O | LEU | D | 92 | 86.584 | 24.560 | 2.518 | 1.00 | 25.09 | O |
| ATOM | 7360 | N | LYS | D | 93 | 86.776 | 26.737 | 2.957 | 1.00 | 25.27 | N |
| ATOM | 7361 | CA | LYS | D | 93 | 86.541 | 26.569 | 4.390 | 1.00 | 26.72 | C |
| ATOM | 7362 | CB | LYS | D | 93 | 87.620 | 27.237 | 5.224 | 1.00 | 27.09 | C |
| ATOM | 7363 | CG | LYS | D | 93 | 87.518 | 26.919 | 6.704 | 1.00 | 32.20 | C |
| ATOM | 7364 | CD | LYS | D | 93 | 88.621 | 27.613 | 7.487 | 1.00 | 29.31 | C |
| ATOM | 7365 | CE | LYS | D | 93 | 88.720 | 27.082 | 8.895 | 1.00 | 30.24 | C |
| ATOM | 7366 | NZ | LYS | D | 93 | 89.702 | 27.858 | 9.703 | 1.00 | 32.52 | N |
| ATOM | 7367 | C | LYS | D | 93 | 85.212 | 27.226 | 4.714 | 1.00 | 27.35 | C |
| ATOM | 7368 | O | LYS | D | 93 | 85.014 | 28.412 | 4.461 | 1.00 | 29.60 | O |
| ATOM | 7369 | N | MSED | | 94 | 84.292 | 26.447 | 5.254 | 1.00 | 27.29 | N |
| ATOM | 7370 | CA | MSED | | 94 | 82.984 | 26.962 | 5.592 | 1.00 | 26.80 | C |
| ATOM | 7371 | CB | MSED | | 94 | 81.920 | 25.933 | 5.303 | 1.00 | 26.17 | C |
| ATOM | 7372 | CG | MSED | | 94 | 81.956 | 25.416 | 3.888 | 1.00 | 29.42 | C |
| ATOM | 7373 | SE | MSED | | 94 | 80.367 | 24.365 | 3.522 | 1.00 | 43.91 | S |
| ATOM | 7374 | CE | MSED | | 94 | 79.047 | 25.303 | 4.639 | 1.00 | 34.50 | C |
| ATOM | 7375 | C | MSED | | 94 | 82.985 | 27.251 | 7.056 | 1.00 | 26.87 | C |
| ATOM | 7376 | O | MSED | | 94 | 83.217 | 26.352 | 7.865 | 1.00 | 27.63 | O |
| ATOM | 7377 | N | LEU | D | 95 | 82.740 | 28.506 | 7.404 | 1.00 | 26.04 | N |
| ATOM | 7378 | CA | LEU | D | 95 | 82.692 | 28.906 | 8.788 | 1.00 | 25.33 | C |
| ATOM | 7379 | CB | LEU | D | 95 | 83.757 | 29.966 | 9.051 | 1.00 | 24.77 | C |
| ATOM | 7380 | CG | LEU | D | 95 | 85.231 | 29.561 | 8.944 | 1.00 | 24.08 | C |
| ATOM | 7381 | CD1 | LEU | D | 95 | 86.134 | 30.747 | 9.252 | 1.00 | 19.29 | C |
| ATOM | 7382 | CD2 | LEU | D | 95 | 85.518 | 28.430 | 9.920 | 1.00 | 28.52 | C |
| ATOM | 7383 | C | LEU | D | 95 | 81.309 | 29.491 | 9.026 | 1.00 | 25.93 | C |
| ATOM | 7384 | O | LEU | D | 95 | 80.697 | 30.017 | 8.093 | 1.00 | 27.01 | O |
| ATOM | 7385 | N | GLN | D | 96 | 80.797 | 29.377 | 10.255 | 1.00 | 27.26 | N |
| ATOM | 7386 | CA | GLN | D | 96 | 79.502 | 29.965 | 10.602 | 1.00 | 28.39 | C |
| ATOM | 7387 | CB | GLN | D | 96 | 78.910 | 29.307 | 11.835 | 1.00 | 28.49 | C |
| ATOM | 7388 | CG | GLN | D | 96 | 77.587 | 29.922 | 12.243 | 1.00 | 38.93 | C |
| ATOM | 7389 | CD | GLN | D | 96 | 76.531 | 28.880 | 12.614 | 1.00 | 51.49 | C |
| ATOM | 7390 | OE1 | GLN | D | 96 | 75.364 | 29.226 | 12.880 | 1.00 | 51.60 | O |
| ATOM | 7391 | NE2 | GLN | D | 96 | 76.936 | 27.594 | 12.636 | 1.00 | 53.61 | N |
| ATOM | 7392 | C | GLN | D | 96 | 79.830 | 31.414 | 10.910 | 1.00 | 27.10 | C |
| ATOM | 7393 | O | GLN | D | 96 | 80.746 | 31.682 | 11.643 | 1.00 | 24.67 | O |
| ATOM | 7394 | N | ASP | D | 97 | 79.097 | 32.351 | 10.340 | 1.00 | 27.79 | N |
| ATOM | 7395 | CA | ASP | D | 97 | 79.417 | 33.742 | 10.567 | 1.00 | 28.90 | C |
| ATOM | 7396 | CB | ASP | D | 97 | 78.592 | 34.648 | 9.670 | 1.00 | 30.58 | C |
| ATOM | 7397 | CG | ASP | D | 97 | 79.065 | 36.077 | 9.720 | 1.00 | 35.08 | C |
| ATOM | 7398 | OD1 | ASP | D | 97 | 80.041 | 36.306 | 10.442 | 1.00 | 39.19 | O |
| ATOM | 7399 | OD2 | ASP | D | 97 | 78.481 | 36.971 | 9.063 | 1.00 | 43.48 | O |
| ATOM | 7400 | C | ASP | D | 97 | 79.224 | 34.161 | 12.005 | 1.00 | 28.51 | C |
| ATOM | 7401 | O | ASP | D | 97 | 78.138 | 34.029 | 12.559 | 1.00 | 30.07 | O |
| ATOM | 7402 | N | CYS | D | 98 | 80.282 | 34.682 | 12.608 | 1.00 | 28.14 | N |
| ATOM | 7403 | CA | CYS | D | 98 | 80.240 | 35.115 | 13.988 | 1.00 | 26.41 | C |
| ATOM | 7404 | CB | CYS | D | 98 | 80.135 | 33.900 | 14.871 | 1.00 | 26.58 | C |

FIG. 2A-161

| ATOM | 7405 | SG | CYS | D | 98 | 81.645 | 32.940 | 14.809 | 1.00 | 23.56 | S |
| --- | --- | --- | --- | --- | --- | --- | --- | --- | --- | --- | --- |
| ATOM | 7406 | C | CYS | D | 98 | 81.565 | 35.820 | 14.256 | 1.00 | 27.29 | C |
| ATOM | 7407 | O | CYS | D | 98 | 82.545 | 35.617 | 13.514 | 1.00 | 24.62 | O |
| ATOM | 7408 | N | PRO | D | 99 | 81.633 | 36.617 | 15.350 | 1.00 | 27.78 | N |
| ATOM | 7409 | CA | PRO | D | 99 | 82.835 | 37.355 | 15.716 | 1.00 | 27.32 | C |
| ATOM | 7410 | CB | PRO | D | 99 | 82.563 | 37.729 | 17.173 | 1.00 | 26.72 | C |
| ATOM | 7411 | CG | PRO | D | 99 | 81.122 | 37.955 | 17.180 | 1.00 | 26.80 | C |
| ATOM | 7412 | CD | PRO | D | 99 | 80.656 | 36.713 | 16.449 | 1.00 | 28.43 | C |
| ATOM | 7413 | C | PRO | D | 99 | 84.134 | 36.600 | 15.510 | 1.00 | 26.56 | C |
| ATOM | 7414 | O | PRO | D | 99 | 85.048 | 37.163 | 14.941 | 1.00 | 27.57 | O |
| ATOM | 7415 | N | LYS | D | 100 | 84.233 | 35.349 | 15.961 | 1.00 | 26.50 | N |
| ATOM | 7416 | CA | LYS | D | 100 | 85.471 | 34.599 | 15.760 | 1.00 | 25.77 | C |
| ATOM | 7417 | CB | LYS | D | 100 | 85.389 | 33.148 | 16.241 | 1.00 | 25.96 | C |
| ATOM | 7418 | CG | LYS | D | 100 | 85.478 | 32.887 | 17.701 | 1.00 | 31.37 | C |
| ATOM | 7419 | CD | LYS | D | 100 | 86.381 | 33.830 | 18.404 | 1.00 | 40.51 | C |
| ATOM | 7420 | CE | LYS | D | 100 | 86.179 | 33.667 | 19.924 | 1.00 | 47.80 | C |
| ATOM | 7421 | NZ | LYS | D | 100 | 86.477 | 34.932 | 20.685 | 1.00 | 51.29 | N |
| ATOM | 7422 | C | LYS | D | 100 | 85.749 | 34.529 | 14.273 | 1.00 | 25.30 | C |
| ATOM | 7423 | O | LYS | D | 100 | 86.784 | 34.978 | 13.810 | 1.00 | 26.26 | O |
| ATOM | 7424 | N | ALA | D | 101 | 84.810 | 33.934 | 13.544 | 1.00 | 26.23 | N |
| ATOM | 7425 | CA | ALA | D | 101 | 84.929 | 33.750 | 12.105 | 1.00 | 25.08 | C |
| ATOM | 7426 | CB | ALA | D | 101 | 83.589 | 33.352 | 11.507 | 1.00 | 25.52 | C |
| ATOM | 7427 | C | ALA | D | 101 | 85.449 | 35.000 | 11.429 | 1.00 | 25.04 | C |
| ATOM | 7428 | O | ALA | D | 101 | 86.467 | 34.961 | 10.749 | 1.00 | 24.14 | O |
| ATOM | 7429 | N | ARG | D | 102 | 84.731 | 36.096 | 11.617 | 1.00 | 25.70 | N |
| ATOM | 7430 | CA | ARG | D | 102 | 85.112 | 37.366 | 11.062 | 1.00 | 27.61 | C |
| ATOM | 7431 | CB | ARG | D | 102 | 84.114 | 38.433 | 11.487 | 1.00 | 27.49 | C |
| ATOM | 7432 | CG | ARG | D | 102 | 82.727 | 38.231 | 10.866 | 1.00 | 31.29 | C |
| ATOM | 7433 | CD | ARG | D | 102 | 82.474 | 39.160 | 9.691 | 1.00 | 36.29 | C |
| ATOM | 7434 | NE | ARG | D | 102 | 81.153 | 38.987 | 9.070 | 1.00 | 39.58 | N |
| ATOM | 7435 | CZ | ARG | D | 102 | 80.696 | 39.679 | 8.030 | 1.00 | 42.02 | C |
| ATOM | 7436 | NH1AR | G | D | 102 | 79.692 | 39.214 | 7.301 | 1.00 | 46.04 | N |
| ATOM | 7437 | NH2AR | G | D | 102 | 81.251 | 40.840 | 7.714 | 1.00 | 50.00 | N |
| ATOM | 7438 | C | ARG | D | 102 | 86.547 | 37.821 | 11.403 | 1.00 | 29.00 | C |
| ATOM | 7439 | O | ARG | D | 102 | 87.203 | 38.479 | 10.586 | 1.00 | 30.39 | O |
| ATOM | 7440 | N | ALA | D | 103 | 87.054 | 37.497 | 12.586 | 1.00 | 29.21 | N |
| ATOM | 7441 | CA | ALA | D | 103 | 88.422 | 37.887 | 12.892 | 1.00 | 29.68 | C |
| ATOM | 7442 | CB | ALA | D | 103 | 88.733 | 37.624 | 14.355 | 1.00 | 30.19 | C |
| ATOM | 7443 | C | ALA | D | 103 | 89.369 | 37.076 | 12.010 | 1.00 | 28.98 | C |
| ATOM | 7444 | O | ALA | D | 103 | 90.312 | 37.591 | 11.431 | 1.00 | 28.66 | O |
| ATOM | 7445 | N | GLU | D | 104 | 89.096 | 35.790 | 11.931 | 1.00 | 28.08 | N |
| ATOM | 7446 | CA | GLU | D | 104 | 89.899 | 34.872 | 11.145 | 1.00 | 28.17 | C |
| ATOM | 7447 | CB | GLU | D | 104 | 89.292 | 33.481 | 11.199 | 1.00 | 27.22 | C |
| ATOM | 7448 | CG | GLU | D | 104 | 90.136 | 32.446 | 10.566 | 1.00 | 26.07 | C |
| ATOM | 7449 | CD | GLU | D | 104 | 89.395 | 31.158 | 10.434 | 1.00 | 35.22 | C |
| ATOM | 7450 | OE1 | GLU | D | 104 | 88.679 | 30.819 | 11.407 | 1.00 | 42.37 | O |

FIG. 2A-162

| ATOM | 7451 | OE2 | GLU | D | 104 | 89.512 | 30.480 | 9.375 | 1.00 | 35.82 | O |
|------|------|-----|-----|---|-----|--------|--------|-------|------|-------|---|
| ATOM | 7452 | C | GLU | D | 104 | 90.058 | 35.289 | 9.690 | 1.00 | 28.76 | C |
| ATOM | 7453 | O | GLU | D | 104 | 91.142 | 35.181 | 9.150 | 1.00 | 28.21 | O |
| ATOM | 7454 | N | VAL | D | 105 | 88.973 | 35.738 | 9.064 | 1.00 | 27.53 | N |
| ATOM | 7455 | CA | VAL | D | 105 | 88.985 | 36.171 | 7.681 | 1.00 | 25.12 | C |
| ATOM | 7456 | CB | VAL | D | 105 | 87.502 | 36.371 | 7.159 | 1.00 | 24.83 | C |
| ATOM | 7457 | CG1 | VAL | D | 105 | 87.411 | 37.410 | 6.059 | 1.00 | 25.51 | C |
| ATOM | 7458 | CG2 | VAL | D | 105 | 86.982 | 35.076 | 6.619 | 1.00 | 24.63 | C |
| ATOM | 7459 | C | VAL | D | 105 | 89.782 | 37.469 | 7.599 | 1.00 | 24.89 | C |
| ATOM | 7460 | O | VAL | D | 105 | 90.557 | 37.649 | 6.688 | 1.00 | 25.22 | O |
| ATOM | 7461 | N | ALA | D | 106 | 89.625 | 38.378 | 8.555 | 1.00 | 23.61 | N |
| ATOM | 7462 | CA | ALA | D | 106 | 90.384 | 39.617 | 8.465 | 1.00 | 23.19 | C |
| ATOM | 7463 | CB | ALA | D | 106 | 89.876 | 40.653 | 9.473 | 1.00 | 21.00 | C |
| ATOM | 7464 | C | ALA | D | 106 | 91.854 | 39.333 | 8.714 | 1.00 | 23.33 | C |
| ATOM | 7465 | O | ALA | D | 106 | 92.727 | 39.794 | 8.001 | 1.00 | 23.18 | O |
| ATOM | 7466 | N | LEU | D | 107 | 92.126 | 38.559 | 9.736 | 1.00 | 23.11 | N |
| ATOM | 7467 | CA | LEU | D | 107 | 93.481 | 38.262 | 10.056 | 1.00 | 23.13 | C |
| ATOM | 7468 | CB | LEU | D | 107 | 93.507 | 37.518 | 11.376 | 1.00 | 24.09 | C |
| ATOM | 7469 | CG | LEU | D | 107 | 93.036 | 38.282 | 12.615 | 1.00 | 27.35 | C |
| ATOM | 7470 | CD1 | LEU | D | 107 | 93.011 | 37.406 | 13.877 | 1.00 | 31.65 | C |
| ATOM | 7471 | CD2 | LEU | D | 107 | 93.926 | 39.470 | 12.765 | 1.00 | 23.83 | C |
| ATOM | 7472 | C | LEU | D | 107 | 94.155 | 37.467 | 8.946 | 1.00 | 24.87 | C |
| ATOM | 7473 | O | LEU | D | 107 | 95.252 | 37.815 | 8.507 | 1.00 | 25.66 | O |
| ATOM | 7474 | N | HIS | D | 108 | 93.509 | 36.403 | 8.474 | 1.00 | 25.39 | N |
| ATOM | 7475 | CA | HIS | D | 108 | 94.090 | 35.579 | 7.412 | 1.00 | 22.78 | C |
| ATOM | 7476 | CB | HIS | D | 108 | 93.163 | 34.403 | 7.088 | 1.00 | 23.23 | C |
| ATOM | 7477 | CG | HIS | D | 108 | 93.763 | 33.365 | 6.187 | 1.00 | 23.78 | C |
| ATOM | 7478 | ND1 | HIS | D | 108 | 94.761 | 33.647 | 5.278 | 1.00 | 22.59 | N |
| ATOM | 7479 | CE1 | HIS | D | 108 | 95.051 | 32.558 | 4.589 | 1.00 | 17.99 | C |
| ATOM | 7480 | NE2 | HIS | D | 108 | 94.282 | 31.576 | 5.018 | 1.00 | 20.68 | N |
| ATOM | 7481 | CD2 | HIS | D | 108 | 93.468 | 32.053 | 6.018 | 1.00 | 21.95 | C |
| ATOM | 7482 | C | HIS | D | 108 | 94.277 | 36.492 | 6.195 | 1.00 | 23.28 | C |
| ATOM | 7483 | O | HIS | D | 108 | 95.296 | 36.439 | 5.518 | 1.00 | 21.50 | O |
| ATOM | 7484 | N | TRP | D | 109 | 93.297 | 37.343 | 5.931 | 1.00 | 21.63 | N |
| ATOM | 7485 | CA | TRP | D | 109 | 93.411 | 38.254 | 4.806 | 1.00 | 20.57 | C |
| ATOM | 7486 | CB | TRP | D | 109 | 92.187 | 39.179 | 4.733 | 1.00 | 20.48 | C |
| ATOM | 7487 | CG | TRP | D | 109 | 92.281 | 40.105 | 3.593 | 1.00 | 18.57 | C |
| ATOM | 7488 | CD1 | TRP | D | 109 | 92.520 | 41.438 | 3.639 | 1.00 | 16.97 | C |
| ATOM | 7489 | NE1 | TRP | D | 109 | 92.653 | 41.945 | 2.374 | 1.00 | 16.09 | N |
| ATOM | 7490 | CE2 | TRP | D | 109 | 92.493 | 40.926 | 1.477 | 1.00 | 18.55 | C |
| ATOM | 7491 | CD2 | TRP | D | 109 | 92.254 | 39.748 | 2.214 | 1.00 | 21.66 | C |
| ATOM | 7492 | CE3 | TRP | D | 109 | 92.057 | 38.544 | 1.532 | 1.00 | 22.74 | C |
| ATOM | 7493 | CZ3 | TRP | D | 109 | 92.100 | 38.563 | 0.146 | 1.00 | 24.24 | C |
| ATOM | 7494 | CH2 | TRP | D | 109 | 92.343 | 39.762 | -0.566 | 1.00 | 18.55 | C |
| ATOM | 7495 | CZ2 | TRP | D | 109 | 92.542 | 40.942 | 0.081 | 1.00 | 21.59 | C |
| ATOM | 7496 | C | TRP | D | 109 | 94.695 | 39.111 | 4.855 | 1.00 | 20.80 | C |

FIG. 2A-163

| ATOM | 7497 | O | TRP | D | 109 | 95.424 | 39.230 | 3.871 | 1.00 | 20.32 | O |
|---|---|---|---|---|---|---|---|---|---|---|---|
| ATOM | 7498 | N | ARG | D | 110 | 94.974 | 39.725 | 5.985 | 1.00 | 21.11 | N |
| ATOM | 7499 | CA | ARG | D | 110 | 96.162 | 40.522 | 6.077 | 1.00 | 21.22 | C |
| ATOM | 7500 | CB | ARG | D | 110 | 96.181 | 41.268 | 7.418 | 1.00 | 21.89 | C |
| ATOM | 7501 | CG | ARG | D | 110 | 95.014 | 42.173 | 7.642 | 1.00 | 26.86 | C |
| ATOM | 7502 | CD | ARG | D | 110 | 95.366 | 43.261 | 8.628 | 1.00 | 24.79 | C |
| ATOM | 7503 | NE | ARG | D | 110 | 95.299 | 42.808 | 10.001 | 1.00 | 32.84 | N |
| ATOM | 7504 | CZ | ARG | D | 110 | 96.290 | 42.936 | 10.872 | 1.00 | 37.29 | C |
| ATOM | 7505 | NH1AR | G | D | 110 | 97.430 | 43.503 | 10.505 | 1.00 | 39.05 | N |
| ATOM | 7506 | NH2AR | G | D | 110 | 96.135 | 42.514 | 12.117 | 1.00 | 42.61 | N |
| ATOM | 7507 | C | ARG | D | 110 | 97.416 | 39.626 | 5.962 | 1.00 | 22.11 | C |
| ATOM | 7508 | O | ARG | D | 110 | 98.380 | 39.940 | 5.262 | 1.00 | 22.36 | O |
| ATOM | 7509 | N | ALA | D | 111 | 97.403 | 38.509 | 6.664 | 1.00 | 23.62 | N |
| ATOM | 7510 | CA | ALA | D | 111 | 98.548 | 37.615 | 6.651 | 1.00 | 26.05 | C |
| ATOM | 7511 | CB | ALA | D | 111 | 98.275 | 36.425 | 7.570 | 1.00 | 26.83 | C |
| ATOM | 7512 | C | ALA | D | 111 | 98.818 | 37.115 | 5.247 | 1.00 | 27.65 | C |
| ATOM | 7513 | O | ALA | D | 111 | 99.897 | 36.639 | 4.929 | 1.00 | 27.57 | O |
| ATOM | 7514 | N | SER | D | 112 | 97.803 | 37.230 | 4.414 | 1.00 | 28.84 | N |
| ATOM | 7515 | CA | SER | D | 112 | 97.854 | 36.749 | 3.059 | 1.00 | 27.58 | C |
| ATOM | 7516 | CB | SER | D | 112 | 96.463 | 36.854 | 2.473 | 1.00 | 28.20 | C |
| ATOM | 7517 | OG | SER | D | 112 | 96.299 | 35.933 | 1.424 | 1.00 | 33.42 | O |
| ATOM | 7518 | C | SER | D | 112 | 98.859 | 37.436 | 2.136 | 1.00 | 27.42 | C |
| ATOM | 7519 | O | SER | D | 112 | 99.242 | 36.877 | 1.112 | 1.00 | 26.39 | O |
| ATOM | 7520 | N | ALA | D | 113 | 99.302 | 38.634 | 2.455 | 1.00 | 28.75 | N |
| ATOM | 7521 | CA | ALA | D | 113 | 100.234 | 39.246 | 1.541 | 1.00 | 28.65 | C |
| ATOM | 7522 | CB | ALA | D | 113 | 100.525 | 40.697 | 1.962 | 1.00 | 29.67 | C |
| ATOM | 7523 | C | ALA | D | 113 | 101.514 | 38.409 | 1.495 | 1.00 | 28.12 | C |
| ATOM | 7524 | O | ALA | D | 113 | 102.207 | 38.345 | 0.490 | 1.00 | 28.03 | O |
| ATOM | 7525 | N | CYS | D | 114 | 101.826 | 37.751 | 2.587 | 1.00 | 27.91 | N |
| ATOM | 7526 | CA | CYS | D | 114 | 103.017 | 36.929 | 2.622 | 1.00 | 27.35 | C |
| ATOM | 7527 | CB | CYS | D | 114 | 103.240 | 36.460 | 4.055 | 1.00 | 27.96 | C |
| ATOM | 7528 | SG | CYS | D | 114 | 104.653 | 35.435 | 4.301 | 1.00 | 30.07 | S |
| ATOM | 7529 | C | CYS | D | 114 | 102.821 | 35.741 | 1.681 | 1.00 | 26.87 | C |
| ATOM | 7530 | O | CYS | D | 114 | 101.787 | 35.086 | 1.719 | 1.00 | 28.72 | O |
| ATOM | 7531 | N | PRO | D | 115 | 103.813 | 35.455 | 0.812 | 1.00 | 27.16 | N |
| ATOM | 7532 | CA | PRO | D | 115 | 103.755 | 34.347 | -0.143 | 1.00 | 27.59 | C |
| ATOM | 7533 | CB | PRO | D | 115 | 105.037 | 34.484 | -0.926 | 1.00 | 24.08 | C |
| ATOM | 7534 | CG | PRO | D | 115 | 105.337 | 35.859 | -0.815 | 1.00 | 26.08 | C |
| ATOM | 7535 | CD | PRO | D | 115 | 105.059 | 36.193 | 0.615 | 1.00 | 27.28 | C |
| ATOM | 7536 | C | PRO | D | 115 | 103.736 | 33.027 | 0.581 | 1.00 | 28.34 | C |
| ATOM | 7537 | O | PRO | D | 115 | 103.141 | 32.054 | 0.095 | 1.00 | 29.33 | O |
| ATOM | 7538 | N | HIS | D | 116 | 104.403 | 32.996 | 1.734 | 1.00 | 27.62 | N |
| ATOM | 7539 | CA | HIS | D | 116 | 104.494 | 31.795 | 2.523 | 1.00 | 26.69 | C |
| ATOM | 7540 | CB | HIS | D | 116 | 105.743 | 31.870 | 3.377 | 1.00 | 27.32 | C |
| ATOM | 7541 | CG | HIS | D | 116 | 106.985 | 31.556 | 2.612 | 1.00 | 28.54 | C |
| ATOM | 7542 | ND1 | HIS | D | 116 | 107.246 | 30.296 | 2.114 | 1.00 | 29.76 | N |

FIG. 2A-164

| ATOM | 7543 | CE1 | HIS | D | 116 | 108.352 | 30.337 | 1.393 | 1.00 | 26.90 | C |
| --- | --- | --- | --- | --- | --- | --- | --- | --- | --- | --- | --- |
| ATOM | 7544 | NE2 | HIS | D | 116 | 108.821 | 31.573 | 1.412 | 1.00 | 26.77 | N |
| ATOM | 7545 | CD2 | HIS | D | 116 | 107.986 | 32.354 | 2.173 | 1.00 | 29.92 | C |
| ATOM | 7546 | C | HIS | D | 116 | 103.254 | 31.477 | 3.348 | 1.00 | 26.34 | C |
| ATOM | 7547 | O | HIS | D | 116 | 103.283 | 30.671 | 4.291 | 1.00 | 25.63 | O |
| ATOM | 7548 | N | ILE | D | 117 | 102.147 | 32.079 | 2.948 | 1.00 | 25.05 | N |
| ATOM | 7549 | CA | ILE | D | 117 | 100.888 | 31.845 | 3.609 | 1.00 | 25.48 | C |
| ATOM | 7550 | CB | ILE | D | 117 | 100.592 | 33.075 | 4.534 | 1.00 | 25.92 | C |
| ATOM | 7551 | CG1 | ILE | D | 117 | 101.330 | 32.875 | 5.848 | 1.00 | 26.31 | C |
| ATOM | 7552 | CD1 | ILE | D | 117 | 101.578 | 34.115 | 6.566 | 1.00 | 29.95 | C |
| ATOM | 7553 | CG2 | ILE | D | 117 | 99.124 | 33.251 | 4.795 | 1.00 | 23.57 | C |
| ATOM | 7554 | C | ILE | D | 117 | 99.843 | 31.591 | 2.503 | 1.00 | 25.49 | C |
| ATOM | 7555 | O | ILE | D | 117 | 99.834 | 32.302 | 1.510 | 1.00 | 26.35 | O |
| ATOM | 7556 | N | VAL | D | 118 | 99.004 | 30.562 | 2.636 | 1.00 | 25.94 | N |
| ATOM | 7557 | CA | VAL | D | 118 | 97.996 | 30.301 | 1.603 | 1.00 | 27.03 | C |
| ATOM | 7558 | CB | VAL | D | 118 | 96.925 | 29.278 | 2.015 | 1.00 | 25.72 | C |
| ATOM | 7559 | CG1 | VAL | D | 118 | 96.039 | 29.855 | 3.071 | 1.00 | 29.10 | C |
| ATOM | 7560 | CG2 | VAL | D | 118 | 96.131 | 28.871 | 0.828 | 1.00 | 28.79 | C |
| ATOM | 7561 | C | VAL | D | 118 | 97.233 | 31.545 | 1.220 | 1.00 | 27.38 | C |
| ATOM | 7562 | O | VAL | D | 118 | 96.702 | 32.248 | 2.077 | 1.00 | 27.57 | O |
| ATOM | 7563 | N | ARG | D | 119 | 97.163 | 31.789 | -0.082 | 1.00 | 27.11 | N |
| ATOM | 7564 | CA | ARG | D | 119 | 96.474 | 32.939 | -0.636 | 1.00 | 27.86 | C |
| ATOM | 7565 | CB | ARG | D | 119 | 96.900 | 33.128 | -2.093 | 1.00 | 27.67 | C |
| ATOM | 7566 | CG | ARG | D | 119 | 96.144 | 34.219 | -2.827 | 1.00 | 33.95 | C |
| ATOM | 7567 | CD | ARG | D | 119 | 96.646 | 34.402 | -4.274 | 1.00 | 44.79 | C |
| ATOM | 7568 | NE | ARG | D | 119 | 95.816 | 35.364 | -5.013 | 1.00 | 57.06 | N |
| ATOM | 7569 | CZ | ARG | D | 119 | 96.170 | 35.974 | -6.151 | 1.00 | 66.99 | C |
| ATOM | 7570 | NH1AR | G | D | 119 | 97.354 | 35.739 | -6.716 | 1.00 | 68.49 | N |
| ATOM | 7571 | NH2AR | G | D | 119 | 95.324 | 36.828 | -6.728 | 1.00 | 69.50 | N |
| ATOM | 7572 | C | ARG | D | 119 | 94.967 | 32.743 | -0.556 | 1.00 | 27.23 | C |
| ATOM | 7573 | O | ARG | D | 119 | 94.484 | 31.619 | -0.657 | 1.00 | 28.05 | O |
| ATOM | 7574 | N | ILE | D | 120 | 94.232 | 33.836 | -0.360 | 1.00 | 26.34 | N |
| ATOM | 7575 | CA | ILE | D | 120 | 92.775 | 33.781 | -0.301 | 1.00 | 25.74 | C |
| ATOM | 7576 | CB | ILE | D | 120 | 92.210 | 34.585 | 0.929 | 1.00 | 26.09 | C |
| ATOM | 7577 | CG1 | ILE | D | 120 | 92.422 | 33.777 | 2.210 | 1.00 | 25.39 | C |
| ATOM | 7578 | CD1 | ILE | D | 120 | 92.035 | 34.517 | 3.465 | 1.00 | 22.54 | C |
| ATOM | 7579 | CG2 | ILE | D | 120 | 90.727 | 34.897 | 0.748 | 1.00 | 22.27 | C |
| ATOM | 7580 | C | ILE | D | 120 | 92.248 | 34.364 | -1.615 | 1.00 | 27.01 | C |
| ATOM | 7581 | O | ILE | D | 120 | 92.569 | 35.497 | -1.997 | 1.00 | 28.04 | O |
| ATOM | 7582 | N | VAL | D | 121 | 91.464 | 33.551 | -2.317 | 1.00 | 27.22 | N |
| ATOM | 7583 | CA | VAL | D | 121 | 90.868 | 33.936 | -3.595 | 1.00 | 27.55 | C |
| ATOM | 7584 | CB | VAL | D | 121 | 90.395 | 32.727 | -4.378 | 1.00 | 28.49 | C |
| ATOM | 7585 | CG1 | VAL | D | 121 | 89.739 | 33.185 | -5.608 | 1.00 | 26.93 | C |
| ATOM | 7586 | CG2 | VAL | D | 121 | 91.562 | 31.799 | -4.680 | 1.00 | 28.85 | C |
| ATOM | 7587 | C | VAL | D | 121 | 89.655 | 34.817 | -3.414 | 1.00 | 28.20 | C |
| ATOM | 7588 | O | VAL | D | 121 | 89.544 | 35.857 | -4.028 | 1.00 | 30.04 | O |

FIG. 2A-165

| ATOM | 7589 | N   | ASP | D | 122 | 88.737 | 34.376 | -2.577 | 1.00 | 28.54 | N |
| ---- | ---- | --- | --- | - | --- | ------ | ------ | ------ | ---- | ----- | - |
| ATOM | 7590 | CA  | ASP | D | 122 | 87.529 | 35.122 | -2.303 | 1.00 | 30.41 | C |
| ATOM | 7591 | CB  | ASP | D | 122 | 86.434 | 34.815 | -3.335 | 1.00 | 31.00 | C |
| ATOM | 7592 | CG  | ASP | D | 122 | 86.600 | 35.555 | -4.644 | 1.00 | 34.42 | C |
| ATOM | 7593 | OD1 | ASP | D | 122 | 86.736 | 36.808 | -4.633 | 1.00 | 38.21 | O |
| ATOM | 7594 | OD2 | ASP | D | 122 | 86.562 | 34.867 | -5.695 | 1.00 | 36.55 | O |
| ATOM | 7595 | C   | ASP | D | 122 | 86.982 | 34.695 | -0.954 | 1.00 | 30.44 | C |
| ATOM | 7596 | O   | ASP | D | 122 | 87.365 | 33.653 | -0.411 | 1.00 | 29.84 | O |
| ATOM | 7597 | N   | VAL | D | 123 | 86.061 | 35.512 | -0.444 | 1.00 | 30.04 | N |
| ATOM | 7598 | CA  | VAL | D | 123 | 85.350 | 35.257 | 0.800  | 1.00 | 29.38 | C |
| ATOM | 7599 | CB  | VAL | D | 123 | 85.793 | 36.153 | 1.941  | 1.00 | 30.69 | C |
| ATOM | 7600 | CG1 | VAL | D | 123 | 85.177 | 35.644 | 3.249  | 1.00 | 32.38 | C |
| ATOM | 7601 | CG2 | VAL | D | 123 | 87.298 | 36.192 | 2.015  | 1.00 | 30.20 | C |
| ATOM | 7602 | C   | VAL | D | 123 | 83.918 | 35.619 | 0.470  | 1.00 | 28.81 | C |
| ATOM | 7603 | O   | VAL | D | 123 | 83.623 | 36.723 | 0.017  | 1.00 | 28.82 | O |
| ATOM | 7604 | N   | TYR | D | 124 | 83.026 | 34.679 | 0.700  | 1.00 | 28.54 | N |
| ATOM | 7605 | CA  | TYR | D | 124 | 81.613 | 34.872 | 0.403  | 1.00 | 28.31 | C |
| ATOM | 7606 | CB  | TYR | D | 124 | 81.102 | 33.701 | -0.454 | 1.00 | 28.21 | C |
| ATOM | 7607 | CG  | TYR | D | 124 | 81.600 | 33.650 | -1.874 | 1.00 | 26.17 | C |
| ATOM | 7608 | CD1 | TYR | D | 124 | 82.791 | 33.029 | -2.208 | 1.00 | 25.49 | C |
| ATOM | 7609 | CE1 | TYR | D | 124 | 83.229 | 33.017 | -3.526 | 1.00 | 29.49 | C |
| ATOM | 7610 | CZ  | TYR | D | 124 | 82.463 | 33.641 | -4.499 | 1.00 | 28.46 | C |
| ATOM | 7611 | OH  | TYR | D | 124 | 82.873 | 33.758 | -5.799 | 1.00 | 31.78 | O |
| ATOM | 7612 | CE2 | TYR | D | 124 | 81.290 | 34.242 | -4.175 | 1.00 | 28.07 | C |
| ATOM | 7613 | CD2 | TYR | D | 124 | 80.867 | 34.247 | -2.880 | 1.00 | 29.31 | C |
| ATOM | 7614 | C   | TYR | D | 124 | 80.777 | 34.899 | 1.663  | 1.00 | 26.50 | C |
| ATOM | 7615 | O   | TYR | D | 124 | 80.950 | 34.050 | 2.525  | 1.00 | 25.27 | O |
| ATOM | 7616 | N   | GLU | D | 125 | 79.857 | 35.848 | 1.761  | 1.00 | 25.61 | N |
| ATOM | 7617 | CA  | GLU | D | 125 | 78.944 | 35.899 | 2.904  | 1.00 | 24.24 | C |
| ATOM | 7618 | CB  | GLU | D | 125 | 78.706 | 37.327 | 3.348  | 1.00 | 25.41 | C |
| ATOM | 7619 | CG  | GLU | D | 125 | 78.035 | 37.445 | 4.670  | 1.00 | 29.23 | C |
| ATOM | 7620 | CD  | GLU | D | 125 | 77.431 | 38.808 | 4.836  | 1.00 | 39.83 | C |
| ATOM | 7621 | OE1 | GLU | D | 125 | 76.221 | 38.950 | 4.528  | 1.00 | 46.32 | O |
| ATOM | 7622 | OE2 | GLU | D | 125 | 78.153 | 39.746 | 5.250  | 1.00 | 38.00 | O |
| ATOM | 7623 | C   | GLU | D | 125 | 77.646 | 35.310 | 2.354  | 1.00 | 22.36 | C |
| ATOM | 7624 | O   | GLU | D | 125 | 76.929 | 35.958 | 1.595  | 1.00 | 22.83 | O |
| ATOM | 7625 | N   | ASN | D | 126 | 77.361 | 34.070 | 2.731  | 1.00 | 21.17 | N |
| ATOM | 7626 | CA  | ASN | D | 126 | 76.200 | 33.350 | 2.235  | 1.00 | 20.98 | C |
| ATOM | 7627 | CB  | ASN | D | 126 | 76.639 | 32.215 | 1.313  | 1.00 | 20.90 | C |
| ATOM | 7628 | CG  | ASN | D | 126 | 77.084 | 32.691 | -0.045 | 1.00 | 23.47 | C |
| ATOM | 7629 | OD1 | ASN | D | 126 | 77.488 | 31.890 | -0.883 | 1.00 | 22.40 | O |
| ATOM | 7630 | ND2 | ASN | D | 126 | 76.997 | 33.995 | -0.282 | 1.00 | 27.03 | N |
| ATOM | 7631 | C   | ASN | D | 126 | 75.338 | 32.729 | 3.313  | 1.00 | 20.55 | C |
| ATOM | 7632 | O   | ASN | D | 126 | 75.708 | 32.632 | 4.498  | 1.00 | 19.47 | O |
| ATOM | 7633 | N   | LEU | D | 127 | 74.185 | 32.264 | 2.858  | 1.00 | 19.04 | N |
| ATOM | 7634 | CA  | LEU | D | 127 | 73.220 | 31.610 | 3.719  | 1.00 | 18.43 | C |

FIG. 2A-166

| ATOM | 7635 | CB | LEU | D | 127 | 71.847 | 32.195 | 3.433 | 1.00 | 17.48 | C |
|---|---|---|---|---|---|---|---|---|---|---|---|
| ATOM | 7636 | CG | LEU | D | 127 | 71.185 | 33.064 | 4.497 | 1.00 | 15.36 | C |
| ATOM | 7637 | CD1 | LEU | D | 127 | 72.202 | 33.743 | 5.388 | 1.00 | 15.17 | C |
| ATOM | 7638 | CD2 | LEU | D | 127 | 70.302 | 34.064 | 3.783 | 1.00 | 18.08 | C |
| ATOM | 7639 | C | LEU | D | 127 | 73.232 | 30.103 | 3.416 | 1.00 | 19.27 | C |
| ATOM | 7640 | O | LEU | D | 127 | 73.078 | 29.711 | 2.270 | 1.00 | 20.46 | O |
| ATOM | 7641 | N | TYR | D | 128 | 73.480 | 29.267 | 4.421 | 1.00 | 18.56 | N |
| ATOM | 7642 | CA | TYR | D | 128 | 73.443 | 27.815 | 4.226 | 1.00 | 17.46 | C |
| ATOM | 7643 | CB | TYR | D | 128 | 74.753 | 27.120 | 4.554 | 1.00 | 17.65 | C |
| ATOM | 7644 | CG | TYR | D | 128 | 74.577 | 25.629 | 4.482 | 1.00 | 22.93 | C |
| ATOM | 7645 | CD1 | TYR | D | 128 | 74.787 | 24.933 | 3.296 | 1.00 | 27.26 | C |
| ATOM | 7646 | CE1 | TYR | D | 128 | 74.456 | 23.570 | 3.187 | 1.00 | 29.39 | C |
| ATOM | 7647 | CZ | TYR | D | 128 | 73.912 | 22.909 | 4.274 | 1.00 | 32.65 | C |
| ATOM | 7648 | OH | TYR | D | 128 | 73.538 | 21.579 | 4.195 | 1.00 | 36.23 | O |
| ATOM | 7649 | CE2 | TYR | D | 128 | 73.709 | 23.586 | 5.458 | 1.00 | 29.71 | C |
| ATOM | 7650 | CD2 | TYR | D | 128 | 74.047 | 24.931 | 5.557 | 1.00 | 28.20 | C |
| ATOM | 7651 | C | TYR | D | 128 | 72.408 | 27.282 | 5.186 | 1.00 | 16.06 | C |
| ATOM | 7652 | O | TYR | D | 128 | 72.557 | 27.416 | 6.393 | 1.00 | 15.12 | O |
| ATOM | 7653 | N | ALA | D | 129 | 71.363 | 26.662 | 4.653 | 1.00 | 16.33 | N |
| ATOM | 7654 | CA | ALA | D | 129 | 70.297 | 26.149 | 5.402 | 1.00 | 17.53 | C |
| ATOM | 7655 | CB | ALA | D | 129 | 70.782 | 24.960 | 6.294 | 1.00 | 18.90 | C |
| ATOM | 7656 | C | ALA | D | 129 | 69.738 | 27.240 | 6.431 | 1.00 | 17.62 | C |
| ATOM | 7657 | O | ALA | D | 129 | 69.406 | 26.974 | 7.595 | 1.00 | 17.51 | O |
| ATOM | 7658 | N | GLY | D | 130 | 69.640 | 28.458 | 5.905 | 1.00 | 17.24 | N |
| ATOM | 7659 | CA | GLY | D | 130 | 69.080 | 29.555 | 6.667 | 1.00 | 18.15 | C |
| ATOM | 7660 | C | GLY | D | 130 | 69.997 | 30.183 | 7.694 | 1.00 | 19.01 | C |
| ATOM | 7661 | O | GLY | D | 130 | 69.643 | 31.199 | 8.340 | 1.00 | 17.59 | O |
| ATOM | 7662 | N | ALA | D | 131 | 71.186 | 29.595 | 7.822 | 1.00 | 19.27 | N |
| ATOM | 7663 | CA | ALA | D | 131 | 72.169 | 30.079 | 8.777 | 1.00 | 20.65 | C |
| ATOM | 7664 | CB | ALA | D | 131 | 72.768 | 28.891 | 9.553 | 1.00 | 22.74 | C |
| ATOM | 7665 | C | ALA | D | 131 | 73.263 | 30.876 | 8.092 | 1.00 | 21.01 | C |
| ATOM | 7666 | O | ALA | D | 131 | 73.915 | 30.375 | 7.190 | 1.00 | 22.64 | O |
| ATOM | 7667 | N | ALA | D | 132 | 73.471 | 32.112 | 8.524 | 1.00 | 21.67 | N |
| ATOM | 7668 | CA | ALA | D | 132 | 74.495 | 32.969 | 7.931 | 1.00 | 21.34 | C |
| ATOM | 7669 | CB | ALA | D | 132 | 74.449 | 34.378 | 8.575 | 1.00 | 20.30 | C |
| ATOM | 7670 | C | ALA | D | 132 | 75.876 | 32.361 | 8.094 | 1.00 | 21.74 | C |
| ATOM | 7671 | O | ALA | D | 132 | 76.233 | 31.989 | 9.190 | 1.00 | 21.49 | O |
| ATOM | 7672 | N | CYS | D | 133 | 76.650 | 32.260 | 7.013 | 1.00 | 22.78 | N |
| ATOM | 7673 | CA | CYS | D | 133 | 78.011 | 31.690 | 7.099 | 1.00 | 24.44 | C |
| ATOM | 7674 | CB | CYS | D | 133 | 77.986 | 30.201 | 6.752 | 1.00 | 24.76 | C |
| ATOM | 7675 | SG | CYS | D | 133 | 77.503 | 29.963 | 5.019 | 1.00 | 38.58 | S |
| ATOM | 7676 | C | CYS | D | 133 | 79.037 | 32.389 | 6.191 | 1.00 | 22.64 | C |
| ATOM | 7677 | O | CYS | D | 133 | 78.692 | 32.971 | 5.171 | 1.00 | 23.04 | O |
| ATOM | 7678 | N | LEU | D | 134 | 80.308 | 32.288 | 6.566 | 1.00 | 22.07 | N |
| ATOM | 7679 | CA | LEU | D | 134 | 81.421 | 32.901 | 5.838 | 1.00 | 21.94 | C |
| ATOM | 7680 | CB | LEU | D | 134 | 82.328 | 33.607 | 6.824 | 1.00 | 22.66 | C |

FIG. 2A-167

| ATOM | 7681 | CG | LEU | D | 134 | 82.476 | 35.115 | 6.805 | 1.00 | 21.38 | C |
|---|---|---|---|---|---|---|---|---|---|---|---|
| ATOM | 7682 | CD1 | LEU | D | 134 | 81.283 | 35.799 | 6.231 | 1.00 | 29.01 | C |
| ATOM | 7683 | CD2 | LEU | D | 134 | 82.699 | 35.537 | 8.215 | 1.00 | 21.40 | C |
| ATOM | 7684 | C | LEU | D | 134 | 82.208 | 31.812 | 5.137 | 1.00 | 22.65 | C |
| ATOM | 7685 | O | LEU | D | 134 | 82.651 | 30.864 | 5.768 | 1.00 | 24.44 | O |
| ATOM | 7686 | N | LEU | D | 135 | 82.401 | 31.950 | 3.840 | 1.00 | 22.10 | N |
| ATOM | 7687 | CA | LEU | D | 135 | 83.112 | 30.926 | 3.090 | 1.00 | 22.38 | C |
| ATOM | 7688 | CB | LEU | D | 135 | 82.198 | 30.405 | 1.968 | 1.00 | 22.37 | C |
| ATOM | 7689 | CG | LEU | D | 135 | 80.766 | 29.989 | 2.360 | 1.00 | 24.58 | C |
| ATOM | 7690 | CD1 | LEU | D | 135 | 79.957 | 29.693 | 1.131 | 1.00 | 23.09 | C |
| ATOM | 7691 | CD2 | LEU | D | 135 | 80.794 | 28.779 | 3.256 | 1.00 | 25.69 | C |
| ATOM | 7692 | C | LEU | D | 135 | 84.440 | 31.400 | 2.491 | 1.00 | 22.76 | C |
| ATOM | 7693 | O | LEU | D | 135 | 84.469 | 32.239 | 1.590 | 1.00 | 21.35 | O |
| ATOM | 7694 | N | ILE | D | 136 | 85.554 | 30.878 | 2.986 | 1.00 | 22.28 | N |
| ATOM | 7695 | CA | ILE | D | 136 | 86.813 | 31.305 | 2.403 | 1.00 | 24.23 | C |
| ATOM | 7696 | CB | ILE | D | 136 | 87.993 | 31.360 | 3.425 | 1.00 | 23.95 | C |
| ATOM | 7697 | CG1 | ILE | D | 136 | 87.646 | 32.239 | 4.629 | 1.00 | 25.67 | C |
| ATOM | 7698 | CD1 | ILE | D | 136 | 86.870 | 31.570 | 5.714 | 1.00 | 28.57 | C |
| ATOM | 7699 | CG2 | ILE | D | 136 | 89.156 | 32.068 | 2.799 | 1.00 | 22.53 | C |
| ATOM | 7700 | C | ILE | D | 136 | 87.204 | 30.349 | 1.294 | 1.00 | 25.78 | C |
| ATOM | 7701 | O | ILE | D | 136 | 87.097 | 29.142 | 1.446 | 1.00 | 27.17 | O |
| ATOM | 7702 | N | VAL | D | 137 | 87.616 | 30.912 | 0.162 | 1.00 | 26.29 | N |
| ATOM | 7703 | CA | VAL | D | 137 | 88.090 | 30.139 | -0.983 | 1.00 | 25.65 | C |
| ATOM | 7704 | CB | VAL | D | 137 | 87.497 | 30.696 | -2.282 | 1.00 | 25.59 | C |
| ATOM | 7705 | CG1 | VAL | D | 137 | 88.003 | 29.917 | -3.485 | 1.00 | 23.25 | C |
| ATOM | 7706 | CG2 | VAL | D | 137 | 85.990 | 30.642 | -2.208 | 1.00 | 25.90 | C |
| ATOM | 7707 | C | VAL | D | 137 | 89.620 | 30.334 | -0.992 | 1.00 | 26.75 | C |
| ATOM | 7708 | O | VAL | D | 137 | 90.099 | 31.470 | -0.990 | 1.00 | 26.45 | O |
| ATOM | 7709 | N | MSED | | 138 | 90.390 | 29.249 | -0.995 | 1.00 | 27.32 | N |
| ATOM | 7710 | CA | MSED | | 138 | 91.840 | 29.386 | -0.993 | 1.00 | 27.23 | C |
| ATOM | 7711 | CB | MSED | | 138 | 92.377 | 28.889 | 0.346 | 1.00 | 27.50 | C |
| ATOM | 7712 | CG | MSED | | 138 | 91.876 | 29.675 | 1.564 | 1.00 | 30.53 | C |
| ATOM | 7713 | SE | MSED | | 138 | 92.052 | 28.696 | 3.249 | 1.00 | 28.89 | S |
| ATOM | 7714 | CE | MSED | | 138 | 90.618 | 27.447 | 2.909 | 1.00 | 20.04 | C |
| ATOM | 7715 | C | MSED | | 138 | 92.543 | 28.639 | -2.154 | 1.00 | 27.97 | C |
| ATOM | 7716 | O | MSED | | 138 | 91.961 | 27.729 | -2.766 | 1.00 | 27.25 | O |
| ATOM | 7717 | N | GLU | D | 139 | 93.776 | 29.041 | -2.463 | 1.00 | 28.41 | N |
| ATOM | 7718 | CA | GLU | D | 139 | 94.558 | 28.379 | -3.503 | 1.00 | 28.93 | C |
| ATOM | 7719 | CB | GLU | D | 139 | 95.926 | 29.073 | -3.652 | 1.00 | 28.75 | C |
| ATOM | 7720 | CG | GLU | D | 139 | 96.953 | 28.766 | -2.569 | 1.00 | 30.16 | C |
| ATOM | 7721 | CD | GLU | D | 139 | 98.212 | 29.673 | -2.589 | 1.00 | 32.55 | C |
| ATOM | 7722 | OE1 | GLU | D | 139 | 98.856 | 29.825 | -3.643 | 1.00 | 30.32 | O |
| ATOM | 7723 | OE2 | GLU | D | 139 | 98.585 | 30.226 | -1.536 | 1.00 | 29.17 | O |
| ATOM | 7724 | C | GLU | D | 139 | 94.722 | 26.909 | -3.057 | 1.00 | 30.35 | C |
| ATOM | 7725 | O | GLU | D | 139 | 94.742 | 26.625 | -1.864 | 1.00 | 31.53 | O |
| ATOM | 7726 | N | CYS | D | 140 | 94.819 | 25.959 | -3.985 | 1.00 | 31.60 | N |

FIG. 2A-168

| ATOM | 7727 | CA  | CYS | D | 140 | 94.962  | 24.565 | -3.555 | 1.00 | 33.32 | C |
| ---- | ---- | --- | --- | - | --- | ------- | ------ | ------ | ---- | ----- | - |
| ATOM | 7728 | CB  | CYS | D | 140 | 94.294  | 23.596 | -4.537 | 1.00 | 33.33 | C |
| ATOM | 7729 | SG  | CYS | D | 140 | 93.844  | 21.982 | -3.741 | 1.00 | 43.99 | S |
| ATOM | 7730 | C   | CYS | D | 140 | 96.410  | 24.162 | -3.391 | 1.00 | 32.65 | C |
| ATOM | 7731 | O   | CYS | D | 140 | 97.250  | 24.529 | -4.200 | 1.00 | 32.91 | O |
| ATOM | 7732 | N   | LEU | D | 141 | 96.707  | 23.421 | -2.330 | 1.00 | 30.92 | N |
| ATOM | 7733 | CA  | LEU | D | 141 | 98.068  | 22.969 | -2.096 | 1.00 | 30.19 | C |
| ATOM | 7734 | CB  | LEU | D | 141 | 98.600  | 23.467 | -0.750 | 1.00 | 28.83 | C |
| ATOM | 7735 | CG  | LEU | D | 141 | 98.386  | 24.893 | -0.231 | 1.00 | 29.79 | C |
| ATOM | 7736 | CD1 | LEU | D | 141 | 98.669  | 24.878 | 1.260  | 1.00 | 26.85 | C |
| ATOM | 7737 | CD2 | LEU | D | 141 | 99.275  | 25.893 | -0.945 | 1.00 | 25.51 | C |
| ATOM | 7738 | C   | LEU | D | 141 | 98.038  | 21.452 | -2.082 | 1.00 | 29.84 | C |
| ATOM | 7739 | O   | LEU | D | 141 | 97.607  | 20.822 | -1.103 | 1.00 | 30.29 | O |
| ATOM | 7740 | N   | ASP | D | 142 | 98.485  | 20.857 | -3.176 | 1.00 | 28.86 | N |
| ATOM | 7741 | CA  | ASP | D | 142 | 98.507  | 19.410 | -3.271 | 1.00 | 30.51 | C |
| ATOM | 7742 | CB  | ASP | D | 142 | 97.974  | 18.967 | -4.622 | 1.00 | 32.15 | C |
| ATOM | 7743 | CG  | ASP | D | 142 | 98.453  | 19.846 | -5.731 | 1.00 | 35.82 | C |
| ATOM | 7744 | OD1 | ASP | D | 142 | 99.673  | 19.836 | -5.987 | 1.00 | 41.36 | O |
| ATOM | 7745 | OD2 | ASP | D | 142 | 97.614  | 20.545 | -6.345 | 1.00 | 41.34 | O |
| ATOM | 7746 | C   | ASP | D | 142 | 99.904  | 18.846 | -3.041 | 1.00 | 29.59 | C |
| ATOM | 7747 | O   | ASP | D | 142 | 100.113 | 17.639 | -3.135 | 1.00 | 29.34 | O |
| ATOM | 7748 | N   | GLY | D | 143 | 100.856 | 19.710 | -2.726 | 1.00 | 28.85 | N |
| ATOM | 7749 | CA  | GLY | D | 143 | 102.192 | 19.230 | -2.464 | 1.00 | 27.58 | C |
| ATOM | 7750 | C   | GLY | D | 143 | 102.226 | 18.270 | -1.284 | 1.00 | 26.84 | C |
| ATOM | 7751 | O   | GLY | D | 143 | 103.097 | 17.405 | -1.220 | 1.00 | 25.38 | O |
| ATOM | 7752 | N   | GLY | D | 144 | 101.290 | 18.403 | -0.347 | 1.00 | 27.87 | N |
| ATOM | 7753 | CA  | GLY | D | 144 | 101.285 | 17.521 | 0.823  | 1.00 | 27.91 | C |
| ATOM | 7754 | C   | GLY | D | 144 | 101.929 | 18.114 | 2.080  | 1.00 | 28.35 | C |
| ATOM | 7755 | O   | GLY | D | 144 | 102.619 | 19.137 | 2.023  | 1.00 | 26.63 | O |
| ATOM | 7756 | N   | GLU | D | 145 | 101.711 | 17.468 | 3.224  | 1.00 | 29.01 | N |
| ATOM | 7757 | CA  | GLU | D | 145 | 102.273 | 17.959 | 4.491  | 1.00 | 29.69 | C |
| ATOM | 7758 | CB  | GLU | D | 145 | 101.778 | 17.122 | 5.676  | 1.00 | 29.73 | C |
| ATOM | 7759 | CG  | GLU | D | 145 | 100.272 | 17.009 | 5.806  | 1.00 | 38.41 | C |
| ATOM | 7760 | CD  | GLU | D | 145 | 99.836  | 16.498 | 7.181  | 1.00 | 46.80 | C |
| ATOM | 7761 | OE1 | GLU | D | 145 | 100.666 | 15.866 | 7.881  | 1.00 | 46.66 | O |
| ATOM | 7762 | OE2 | GLU | D | 145 | 98.656  | 16.725 | 7.557  | 1.00 | 50.19 | O |
| ATOM | 7763 | C   | GLU | D | 145 | 103.794 | 17.925 | 4.494  | 1.00 | 28.64 | C |
| ATOM | 7764 | O   | GLU | D | 145 | 104.398 | 16.953 | 4.044  | 1.00 | 28.23 | O |
| ATOM | 7765 | N   | LEU | D | 146 | 104.405 | 18.976 | 5.022  | 1.00 | 28.30 | N |
| ATOM | 7766 | CA  | LEU | D | 146 | 105.861 | 19.065 | 5.102  | 1.00 | 26.96 | C |
| ATOM | 7767 | CB  | LEU | D | 146 | 106.253 | 19.993 | 6.253  | 1.00 | 27.02 | C |
| ATOM | 7768 | CG  | LEU | D | 146 | 107.724 | 20.002 | 6.657  | 1.00 | 24.33 | C |
| ATOM | 7769 | CD1 | LEU | D | 146 | 108.555 | 20.418 | 5.497  | 1.00 | 17.56 | C |
| ATOM | 7770 | CD2 | LEU | D | 146 | 107.939 | 20.957 | 7.809  | 1.00 | 25.96 | C |
| ATOM | 7771 | C   | LEU | D | 146 | 106.575 | 17.717 | 5.288  | 1.00 | 27.59 | C |
| ATOM | 7772 | O   | LEU | D | 146 | 107.399 | 17.307 | 4.468  | 1.00 | 27.20 | O |

FIG. 2A-169

| ATOM | 7773 | N | PHE | D | 147 | 106.250 | 17.036 | 6.379 | 1.00 | 28.60 | N |
|---|---|---|---|---|---|---|---|---|---|---|---|
| ATOM | 7774 | CA | PHE | D | 147 | 106.867 | 15.757 | 6.694 | 1.00 | 29.58 | C |
| ATOM | 7775 | CB | PHE | D | 147 | 106.566 | 15.399 | 8.146 | 1.00 | 29.57 | C |
| ATOM | 7776 | CG | PHE | D | 147 | 107.313 | 16.242 | 9.119 | 1.00 | 30.37 | C |
| ATOM | 7777 | CD1 | PHE | D | 147 | 106.739 | 16.637 | 10.310 | 1.00 | 33.24 | C |
| ATOM | 7778 | CE1 | PHE | D | 147 | 107.434 | 17.457 | 11.193 | 1.00 | 34.87 | C |
| ATOM | 7779 | CZ | PHE | D | 147 | 108.704 | 17.881 | 10.887 | 1.00 | 34.01 | C |
| ATOM | 7780 | CE2 | PHE | D | 147 | 109.284 | 17.490 | 9.705 | 1.00 | 33.73 | C |
| ATOM | 7781 | CD2 | PHE | D | 147 | 108.589 | 16.673 | 8.825 | 1.00 | 32.29 | C |
| ATOM | 7782 | C | PHE | D | 147 | 106.493 | 14.621 | 5.747 | 1.00 | 30.51 | C |
| ATOM | 7783 | O | PHE | D | 147 | 107.271 | 13.674 | 5.567 | 1.00 | 29.73 | O |
| ATOM | 7784 | N | SER | D | 148 | 105.323 | 14.699 | 5.127 | 1.00 | 31.81 | N |
| ATOM | 7785 | CA | SER | D | 148 | 104.984 | 13.649 | 4.187 | 1.00 | 33.38 | C |
| ATOM | 7786 | CB | SER | D | 148 | 103.652 | 13.907 | 3.522 | 1.00 | 33.43 | C |
| ATOM | 7787 | OG | SER | D | 148 | 103.438 | 12.903 | 2.544 | 1.00 | 37.98 | O |
| ATOM | 7788 | C | SER | D | 148 | 106.061 | 13.616 | 3.109 | 1.00 | 33.79 | C |
| ATOM | 7789 | O | SER | D | 148 | 106.527 | 12.557 | 2.720 | 1.00 | 33.27 | O |
| ATOM | 7790 | N | ARG | D | 149 | 106.450 | 14.783 | 2.615 | 1.00 | 34.57 | N |
| ATOM | 7791 | CA | ARG | D | 149 | 107.483 | 14.829 | 1.602 | 1.00 | 34.83 | C |
| ATOM | 7792 | CB | ARG | D | 149 | 107.759 | 16.264 | 1.148 | 1.00 | 35.87 | C |
| ATOM | 7793 | CG | ARG | D | 149 | 106.781 | 16.843 | 0.148 | 1.00 | 37.87 | C |
| ATOM | 7794 | CD | ARG | D | 149 | 107.060 | 16.356 | -1.258 | 1.00 | 40.42 | C |
| ATOM | 7795 | NE | ARG | D | 149 | 106.356 | 17.171 | -2.240 | 1.00 | 41.36 | N |
| ATOM | 7796 | CZ | ARG | D | 149 | 106.675 | 18.430 | -2.513 | 1.00 | 41.39 | C |
| ATOM | 7797 | NH1AR | G | D | 149 | 107.683 | 19.003 | -1.886 | 1.00 | 37.25 | N |
| ATOM | 7798 | NH2AR | G | D | 149 | 105.974 | 19.120 | -3.400 | 1.00 | 43.35 | N |
| ATOM | 7799 | C | ARG | D | 149 | 108.754 | 14.243 | 2.170 | 1.00 | 34.31 | C |
| ATOM | 7800 | O | ARG | D | 149 | 109.285 | 13.288 | 1.619 | 1.00 | 34.97 | O |
| ATOM | 7801 | N | ILE | D | 150 | 109.241 | 14.814 | 3.267 | 1.00 | 34.51 | N |
| ATOM | 7802 | CA | ILE | D | 150 | 110.482 | 14.324 | 3.864 | 1.00 | 34.45 | C |
| ATOM | 7803 | CB | ILE | D | 150 | 110.672 | 14.809 | 5.301 | 1.00 | 35.06 | C |
| ATOM | 7804 | CG1 | ILE | D | 150 | 111.299 | 16.193 | 5.318 | 1.00 | 33.19 | C |
| ATOM | 7805 | CD1 | ILE | D | 150 | 110.278 | 17.289 | 5.336 | 1.00 | 37.50 | C |
| ATOM | 7806 | CG2 | ILE | D | 150 | 111.581 | 13.828 | 6.035 | 1.00 | 34.78 | C |
| ATOM | 7807 | C | ILE | D | 150 | 110.510 | 12.813 | 3.888 | 1.00 | 33.90 | C |
| ATOM | 7808 | O | ILE | D | 150 | 111.500 | 12.198 | 3.531 | 1.00 | 32.50 | O |
| ATOM | 7809 | N | GLN | D | 151 | 109.418 | 12.216 | 4.326 | 1.00 | 34.93 | N |
| ATOM | 7810 | CA | GLN | D | 151 | 109.336 | 10.768 | 4.361 | 1.00 | 37.34 | C |
| ATOM | 7811 | CB | GLN | D | 151 | 107.923 | 10.352 | 4.748 | 1.00 | 37.43 | C |
| ATOM | 7812 | CG | GLN | D | 151 | 107.706 | 8.875 | 4.912 | 1.00 | 40.25 | C |
| ATOM | 7813 | CD | GLN | D | 151 | 106.492 | 8.601 | 5.776 | 1.00 | 44.18 | C |
| ATOM | 7814 | OE1 | GLN | D | 151 | 106.439 | 9.027 | 6.930 | 1.00 | 42.62 | O |
| ATOM | 7815 | NE2 | GLN | D | 151 | 105.504 | 7.895 | 5.220 | 1.00 | 47.57 | N |
| ATOM | 7816 | C | GLN | D | 151 | 109.686 | 10.254 | 2.965 | 1.00 | 38.90 | C |
| ATOM | 7817 | O | GLN | D | 151 | 110.816 | 9.831 | 2.721 | 1.00 | 40.67 | O |
| ATOM | 7818 | N | ASP | D | 152 | 108.718 | 10.329 | 2.054 | 1.00 | 39.71 | N |

FIG. 2A-170

| ATOM | 7819 | CA | ASP | D | 152 | 108.863 | 9.886 | 0.661 | 1.00 | 40.43 | C |
| --- | --- | --- | --- | --- | --- | --- | --- | --- | --- | --- | --- |
| ATOM | 7820 | CB | ASP | D | 152 | 107.725 | 10.466 | -0.178 | 1.00 | 40.90 | C |
| ATOM | 7821 | CG | ASP | D | 152 | 106.365 | 10.112 | 0.377 | 1.00 | 43.89 | C |
| ATOM | 7822 | OD1 | ASP | D | 152 | 105.343 | 10.598 | -0.163 | 1.00 | 46.40 | O |
| ATOM | 7823 | OD2 | ASP | D | 152 | 106.321 | 9.339 | 1.366 | 1.00 | 45.94 | O |
| ATOM | 7824 | C | ASP | D | 152 | 110.185 | 10.183 | -0.047 | 1.00 | 40.15 | C |
| ATOM | 7825 | O | ASP | D | 152 | 110.463 | 9.589 | -1.086 | 1.00 | 39.71 | O |
| ATOM | 7826 | N | ARG | D | 153 | 110.988 | 11.094 | 0.498 | 1.00 | 40.72 | N |
| ATOM | 7827 | CA | ARG | D | 153 | 112.275 | 11.464 | -0.100 | 1.00 | 41.70 | C |
| ATOM | 7828 | CB | ARG | D | 153 | 113.202 | 12.059 | 0.961 | 1.00 | 42.15 | C |
| ATOM | 7829 | CG | ARG | D | 153 | 114.070 | 13.209 | 0.475 | 1.00 | 42.43 | C |
| ATOM | 7830 | CD | ARG | D | 153 | 113.275 | 14.504 | 0.421 | 1.00 | 46.66 | C |
| ATOM | 7831 | NE | ARG | D | 153 | 114.086 | 15.643 | -0.004 | 1.00 | 50.65 | N |
| ATOM | 7832 | CZ | ARG | D | 153 | 113.610 | 16.875 | -0.170 | 1.00 | 56.37 | C |
| ATOM | 7833 | NH1AR | G | D | 153 | 112.329 | 17.131 | 0.058 | 1.00 | 57.89 | N |
| ATOM | 7834 | NH2AR | G | D | 153 | 114.405 | 17.853 | -0.583 | 1.00 | 57.67 | N |
| ATOM | 7835 | C | ARG | D | 153 | 112.963 | 10.252 | -0.740 | 1.00 | 42.43 | C |
| ATOM | 7836 | O | ARG | D | 153 | 113.246 | 9.282 | 0.001 | 1.00 | 42.70 | O |
| ATOM | 7837 | OXT | ARG | D | 153 | 113.211 | 10.287 | -1.972 | 1.00 | 42.67 | O |
| ATOM | 7838 | N | PHE | D | 158 | 117.763 | 13.714 | 2.672 | 1.00 | 30.11 | N |
| ATOM | 7839 | CA | PHE | D | 158 | 117.376 | 14.928 | 3.388 | 1.00 | 30.40 | C |
| ATOM | 7840 | CB | PHE | D | 158 | 116.209 | 14.584 | 4.310 | 1.00 | 30.46 | C |
| ATOM | 7841 | CG | PHE | D | 158 | 115.466 | 15.840 | 4.665 | 1.00 | 29.60 | C |
| ATOM | 7842 | CD1 | PHE | D | 158 | 114.668 | 16.456 | 3.711 | 1.00 | 31.01 | C |
| ATOM | 7843 | CE1 | PHE | D | 158 | 114.016 | 17.644 | 4.020 | 1.00 | 33.84 | C |
| ATOM | 7844 | CZ | PHE | D | 158 | 114.158 | 18.216 | 5.279 | 1.00 | 32.65 | C |
| ATOM | 7845 | CE2 | PHE | D | 158 | 114.958 | 17.589 | 6.226 | 1.00 | 30.64 | C |
| ATOM | 7846 | CD2 | PHE | D | 158 | 115.615 | 16.399 | 5.923 | 1.00 | 26.98 | C |
| ATOM | 7847 | C | PHE | D | 158 | 118.539 | 15.490 | 4.212 | 1.00 | 30.19 | C |
| ATOM | 7848 | O | PHE | D | 158 | 118.852 | 15.031 | 5.303 | 1.00 | 30.44 | O |
| ATOM | 7849 | N | THR | D | 159 | 119.215 | 16.499 | 3.632 | 1.00 | 30.17 | N |
| ATOM | 7850 | CA | THR | D | 159 | 120.381 | 17.057 | 4.305 | 1.00 | 29.77 | C |
| ATOM | 7851 | CB | THR | D | 159 | 121.299 | 17.677 | 3.250 | 1.00 | 29.77 | C |
| ATOM | 7852 | OG1 | THR | D | 159 | 120.638 | 18.799 | 2.657 | 1.00 | 31.47 | O |
| ATOM | 7853 | CG2 | THR | D | 159 | 121.623 | 16.652 | 2.161 | 1.00 | 31.57 | C |
| ATOM | 7854 | C | THR | D | 159 | 120.002 | 18.119 | 5.341 | 1.00 | 29.10 | C |
| ATOM | 7855 | O | THR | D | 159 | 118.877 | 18.598 | 5.413 | 1.00 | 28.72 | O |
| ATOM | 7856 | N | GLU | D | 160 | 120.991 | 18.453 | 6.190 | 1.00 | 28.37 | N |
| ATOM | 7857 | CA | GLU | D | 160 | 120.776 | 19.498 | 7.182 | 1.00 | 28.21 | C |
| ATOM | 7858 | CB | GLU | D | 160 | 121.944 | 19.454 | 8.169 | 1.00 | 27.26 | C |
| ATOM | 7859 | CG | GLU | D | 160 | 122.015 | 20.695 | 9.060 | 1.00 | 28.81 | C |
| ATOM | 7860 | CD | GLU | D | 160 | 123.279 | 20.639 | 9.888 | 1.00 | 34.20 | C |
| ATOM | 7861 | OE1 | GLU | D | 160 | 123.654 | 21.658 | 10.452 | 1.00 | 33.40 | O |
| ATOM | 7862 | OE2 | GLU | D | 160 | 123.889 | 19.572 | 9.951 | 1.00 | 37.13 | O |
| ATOM | 7863 | C | GLU | D | 160 | 120.700 | 20.875 | 6.524 | 1.00 | 28.46 | C |
| ATOM | 7864 | O | GLU | D | 160 | 120.031 | 21.789 | 6.990 | 1.00 | 28.78 | O |

FIG. 2A-171

| ATOM | 7865 | N | ALA | D | 161 | 121.346 | 21.029 | 5.353 | 1.00 | 28.27 | N |
| --- | --- | --- | --- | --- | --- | --- | --- | --- | --- | --- | --- |
| ATOM | 7866 | CA | ALA | D | 161 | 121.225 | 22.291 | 4.626 | 1.00 | 28.99 | C |
| ATOM | 7867 | CB | ALA | D | 161 | 122.255 | 22.287 | 3.497 | 1.00 | 28.22 | C |
| ATOM | 7868 | C | ALA | D | 161 | 119.820 | 22.484 | 4.051 | 1.00 | 29.40 | C |
| ATOM | 7869 | O | ALA | D | 161 | 119.439 | 23.569 | 3.632 | 1.00 | 31.99 | O |
| ATOM | 7870 | N | ALA | D | 162 | 119.003 | 21.447 | 4.028 | 1.00 | 28.78 | N |
| ATOM | 7871 | CA | ALA | D | 162 | 117.655 | 21.621 | 3.539 | 1.00 | 27.94 | C |
| ATOM | 7872 | CB | ALA | D | 162 | 117.233 | 20.434 | 2.697 | 1.00 | 27.98 | C |
| ATOM | 7873 | C | ALA | D | 162 | 116.744 | 21.783 | 4.734 | 1.00 | 27.50 | C |
| ATOM | 7874 | O | ALA | D | 162 | 115.656 | 22.325 | 4.614 | 1.00 | 29.33 | O |
| ATOM | 7875 | N | ALA | D | 163 | 117.179 | 21.287 | 5.888 | 1.00 | 27.08 | N |
| ATOM | 7876 | CA | ALA | D | 163 | 116.373 | 21.637 | 7.057 | 1.00 | 26.29 | C |
| ATOM | 7877 | CB | ALA | D | 163 | 117.011 | 20.987 | 8.285 | 1.00 | 25.59 | C |
| ATOM | 7878 | C | ALA | D | 163 | 116.327 | 23.145 | 7.256 | 1.00 | 27.15 | C |
| ATOM | 7879 | O | ALA | D | 163 | 115.279 | 23.782 | 7.294 | 1.00 | 27.35 | O |
| ATOM | 7880 | N | SER | D | 164 | 117.528 | 23.699 | 7.448 | 1.00 | 27.26 | N |
| ATOM | 7881 | CA | SER | D | 164 | 117.709 | 25.141 | 7.576 | 1.00 | 29.26 | C |
| ATOM | 7882 | CB | SER | D | 164 | 119.178 | 25.464 | 7.319 | 1.00 | 28.46 | C |
| ATOM | 7883 | OG | SER | D | 164 | 119.329 | 26.876 | 7.175 | 1.00 | 28.90 | O |
| ATOM | 7884 | C | SER | D | 164 | 116.825 | 25.912 | 6.594 | 1.00 | 30.08 | C |
| ATOM | 7885 | O | SER | D | 164 | 116.190 | 26.905 | 6.924 | 1.00 | 32.67 | O |
| ATOM | 7886 | N | GLU | D | 165 | 116.826 | 25.441 | 5.333 | 1.00 | 29.65 | N |
| ATOM | 7887 | CA | GLU | D | 165 | 115.976 | 26.079 | 4.337 | 1.00 | 30.13 | C |
| ATOM | 7888 | CB | GLU | D | 165 | 116.184 | 25.364 | 3.003 | 1.00 | 30.95 | C |
| ATOM | 7889 | CG | GLU | D | 165 | 117.347 | 25.955 | 2.207 | 1.00 | 33.51 | C |
| ATOM | 7890 | CD | GLU | D | 165 | 117.765 | 24.985 | 1.128 | 1.00 | 41.63 | C |
| ATOM | 7891 | OE1 | GLU | D | 165 | 116.948 | 24.169 | 0.725 | -1.00 | 46.53 | O |
| ATOM | 7892 | OE2 | GLU | D | 165 | 118.914 | 25.056 | 0.691 | 1.00 | 37.36 | O |
| ATOM | 7893 | C | GLU | D | 165 | 114.506 | 26.014 | 4.750 | 1.00 | 29.53 | C |
| ATOM | 7894 | O | GLU | D | 165 | 113.847 | 27.018 | 4.990 | 1.00 | 32.43 | O |
| ATOM | 7895 | N | ILE | D | 166 | 113.984 | 24.777 | 4.790 | 1.00 | 27.75 | N |
| ATOM | 7896 | CA | ILE | D | 166 | 112.630 | 24.600 | 5.285 | 1.00 | 26.29 | C |
| ATOM | 7897 | CB | ILE | D | 166 | 112.448 | 23.123 | 5.645 | 1.00 | 25.94 | C |
| ATOM | 7898 | CG1 | ILE | D | 166 | 112.351 | 22.275 | 4.375 | 1.00 | 23.46 | C |
| ATOM | 7899 | CD1 | ILE | D | 166 | 112.647 | 20.796 | 4.641 | 1.00 | 19.15 | C |
| ATOM | 7900 | CG2 | ILE | D | 166 | 111.144 | 22.938 | 6.440 | 1.00 | 24.51 | C |
| ATOM | 7901 | C | ILE | D | 166 | 112.390 | 25.462 | 6.523 | 1.00 | 25.36 | C |
| ATOM | 7902 | O | ILE | D | 166 | 111.357 | 26.100 | 6.677 | 1.00 | 25.22 | O |
| ATOM | 7903 | N | MSE | D | 167 | 113.341 | 25.464 | 7.477 | 1.00 | 23.55 | N |
| ATOM | 7904 | CA | MSE | D | 167 | 113.126 | 26.212 | 8.715 | 1.00 | 23.12 | C |
| ATOM | 7905 | CB | MSE | D | 167 | 114.171 | 25.758 | 9.739 | 1.00 | 22.07 | C |
| ATOM | 7906 | CG | MSE | D | 167 | 113.819 | 24.417 | 10.388 | 1.00 | 16.82 | C |
| ATOM | 7907 | SE | MSE | D | 167 | 112.140 | 24.392 | 11.031 | 1.00 | 28.36 | S |
| ATOM | 7908 | CE | MSE | D | 167 | 112.158 | 25.987 | 11.863 | 1.00 | 35.50 | C |
| ATOM | 7909 | C | MSE | D | 167 | 113.218 | 27.728 | 8.507 | 1.00 | 24.71 | C |
| ATOM | 7910 | O | MSE | D | 167 | 112.842 | 28.531 | 9.352 | 1.00 | 28.59 | O |

FIG. 2A-172

| ATOM | 7911 | N | LYS | D | 168 | 113.786 | 28.116 | 7.349 | 1.00 | 24.38 | N |
|---|---|---|---|---|---|---|---|---|---|---|---|
| ATOM | 7912 | CA | LYS | D | 168 | 113.919 | 29.539 | 7.062 | 1.00 | 25.43 | C |
| ATOM | 7913 | CB | LYS | D | 168 | 115.175 | 29.753 | 6.223 | 1.00 | 25.22 | C |
| ATOM | 7914 | CG | LYS | D | 168 | 115.129 | 31.075 | 5.452 | 1.00 | 23.97 | C |
| ATOM | 7915 | CD | LYS | D | 168 | 116.304 | 31.226 | 4.489 | 1.00 | 34.85 | C |
| ATOM | 7916 | CE | LYS | D | 168 | 116.483 | 32.672 | 4.014 | 1.00 | 40.15 | C |
| ATOM | 7917 | NZ | LYS | D | 168 | 116.394 | 33.582 | 5.158 | 1.00 | 46.25 | N |
| ATOM | 7918 | C | LYS | D | 168 | 112.706 | 30.088 | 6.314 | 1.00 | 26.80 | C |
| ATOM | 7919 | O | LYS | D | 168 | 112.452 | 31.285 | 6.270 | 1.00 | 28.73 | O |
| ATOM | 7920 | N | SER | D | 169 | 111.967 | 29.172 | 5.668 | 1.00 | 27.29 | N |
| ATOM | 7921 | CA | SER | D | 169 | 110.776 | 29.613 | 4.952 | 1.00 | 28.27 | C |
| ATOM | 7922 | CB | SER | D | 169 | 110.556 | 28.679 | 3.763 | 1.00 | 28.29 | C |
| ATOM | 7923 | OG | SER | D | 169 | 110.417 | 27.338 | 4.237 | 1.00 | 35.88 | O |
| ATOM | 7924 | C | SER | D | 169 | 109.545 | 29.614 | 5.862 | 1.00 | 27.61 | C |
| ATOM | 7925 | O | SER | D | 169 | 108.638 | 30.425 | 5.722 | 1.00 | 30.09 | O |
| ATOM | 7926 | N | ILE | D | 170 | 109.601 | 28.723 | 6.853 | 1.00 | 25.88 | N |
| ATOM | 7927 | CA | ILE | D | 170 | 108.549 | 28.689 | 7.864 | 1.00 | 25.24 | C |
| ATOM | 7928 | CB | ILE | D | 170 | 108.674 | 27.489 | 8.825 | 1.00 | 25.10 | C |
| ATOM | 7929 | CG1 | ILE | D | 170 | 108.411 | 26.183 | 8.106 | 1.00 | 20.13 | C |
| ATOM | 7930 | CD1 | ILE | D | 170 | 108.693 | 25.013 | 8.975 | 1.00 | 15.71 | C |
| ATOM | 7931 | CG2 | ILE | D | 170 | 107.653 | 27.618 | 9.941 | 1.00 | 21.50 | C |
| ATOM | 7932 | C | ILE | D | 170 | 108.712 | 29.942 | 8.703 | 1.00 | 26.80 | C |
| ATOM | 7933 | O | ILE | D | 170 | 107.752 | 30.624 | 9.033 | 1.00 | 28.53 | O |
| ATOM | 7934 | N | GLY | D | 171 | 109.949 | 30.237 | 9.048 | 1.00 | 27.84 | N |
| ATOM | 7935 | CA | GLY | D | 171 | 110.206 | 31.417 | 9.844 | 1.00 | 27.80 | C |
| ATOM | 7936 | C | GLY | D | 171 | 109.755 | 32.676 | 9.128 | 1.00 | 28.44 | C |
| ATOM | 7937 | O | GLY | D | 171 | 109.350 | 33.665 | 9.767 | 1.00 | 30.22 | O |
| ATOM | 7938 | N | GLU | D | 172 | 109.814 | 32.642 | 7.799 | 1.00 | 28.11 | N |
| ATOM | 7939 | CA | GLU | D | 172 | 109.431 | 33.796 | 7.019 | 1.00 | 28.47 | C |
| ATOM | 7940 | CB | GLU | D | 172 | 109.696 | 33.569 | 5.554 | 1.00 | 30.36 | C |
| ATOM | 7941 | CG | GLU | D | 172 | 111.117 | 33.750 | 5.156 | 1.00 | 38.06 | C |
| ATOM | 7942 | CD | GLU | D | 172 | 111.226 | 33.970 | 3.669 | 1.00 | 52.90 | C |
| ATOM | 7943 | OE1 | GLU | D | 172 | 110.814 | 35.074 | 3.228 | 1.00 | 59.83 | O |
| ATOM | 7944 | OE2 | GLU | D | 172 | 111.692 | 33.051 | 2.940 | 1.00 | 54.16 | O |
| ATOM | 7945 | C | GLU | D | 172 | 107.979 | 34.098 | 7.214 | 1.00 | 26.69 | C |
| ATOM | 7946 | O | GLU | D | 172 | 107.591 | 35.255 | 7.314 | 1.00 | 26.04 | O |
| ATOM | 7947 | N | ALA | D | 173 | 107.162 | 33.057 | 7.259 | 1.00 | 25.29 | N |
| ATOM | 7948 | CA | ALA | D | 173 | 105.753 | 33.277 | 7.465 | 1.00 | 24.58 | C |
| ATOM | 7949 | CB | ALA | D | 173 | 105.024 | 31.990 | 7.332 | 1.00 | 23.48 | C |
| ATOM | 7950 | C | ALA | D | 173 | 105.574 | 33.878 | 8.878 | 1.00 | 25.31 | C |
| ATOM | 7951 | O | ALA | D | 173 | 104.826 | 34.855 | 9.075 | 1.00 | 26.62 | O |
| ATOM | 7952 | N | ILE | D | 174 | 106.286 | 33.325 | 9.860 | 1.00 | 24.99 | N |
| ATOM | 7953 | CA | ILE | D | 174 | 106.133 | 33.844 | 11.201 | 1.00 | 25.11 | C |
| ATOM | 7954 | CB | ILE | D | 174 | 106.921 | 33.058 | 12.260 | 1.00 | 23.45 | C |
| ATOM | 7955 | CG1 | ILE | D | 174 | 106.524 | 31.585 | 12.260 | 1.00 | 23.59 | C |
| ATOM | 7956 | CD1 | ILE | D | 174 | 105.043 | 31.354 | 12.218 | 1.00 | 27.05 | C |

FIG. 2A-173

| | | | | | | | | | | |
|---|---|---|---|---|---|---|---|---|---|---|
| ATOM | 7957 | CG2 | ILE | D | 174 | 106.653 | 33.670 | 13.634 | 1.00 | 23.12 | C |
| ATOM | 7958 | C | ILE | D | 174 | 106.593 | 35.279 | 11.310 | 1.00 | 25.02 | C |
| ATOM | 7959 | O | ILE | D | 174 | 105.967 | 36.075 | 11.990 | 1.00 | 27.77 | O |
| ATOM | 7960 | N | GLN | D | 175 | 107.683 | 35.618 | 10.652 | 1.00 | 23.77 | N |
| ATOM | 7961 | CA | GLN | D | 175 | 108.188 | 36.964 | 10.772 | 1.00 | 24.55 | C |
| ATOM | 7962 | CB | GLN | D | 175 | 109.503 | 37.090 | 10.039 | 1.00 | 25.69 | C |
| ATOM | 7963 | CG | GLN | D | 175 | 110.453 | 38.066 | 10.674 | 1.00 | 27.51 | C |
| ATOM | 7964 | CD | GLN | D | 175 | 111.432 | 38.614 | 9.674 | 1.00 | 34.53 | C |
| ATOM | 7965 | OE1 | GLN | D | 175 | 112.514 | 39.077 | 10.039 | 1.00 | 36.08 | O |
| ATOM | 7966 | NE2 | GLN | D | 175 | 111.057 | 38.569 | 8.389 | 1.00 | 36.47 | N |
| ATOM | 7967 | C | GLN | D | 175 | 107.195 | 37.977 | 10.245 | 1.00 | 25.14 | C |
| ATOM | 7968 | O | GLN | D | 175 | 106.937 | 39.006 | 10.867 | 1.00 | 26.64 | O |
| ATOM | 7969 | N | TYR | D | 176 | 106.621 | 37.692 | 9.091 | 1.00 | 23.92 | N |
| ATOM | 7970 | CA | TYR | D | 176 | 105.640 | 38.603 | 8.537 | 1.00 | 21.50 | C |
| ATOM | 7971 | CB | TYR | D | 176 | 105.084 | 38.061 | 7.216 | 1.00 | 20.05 | C |
| ATOM | 7972 | CG | TYR | D | 176 | 104.247 | 39.113 | 6.556 | 1.00 | 19.97 | C |
| ATOM | 7973 | CD1 | TYR | D | 176 | 104.792 | 40.343 | 6.277 | 1.00 | 17.96 | C |
| ATOM | 7974 | CE1 | TYR | D | 176 | 104.022 | 41.364 | 5.875 | 1.00 | 24.16 | C |
| ATOM | 7975 | CZ | TYR | D | 176 | 102.660 | 41.197 | 5.728 | 1.00 | 25.46 | C |
| ATOM | 7976 | OH | TYR | D | 176 | 101.894 | 42.307 | 5.402 | 1.00 | 32.93 | O |
| ATOM | 7977 | CE2 | TYR | D | 176 | 102.084 | 39.976 | 5.970 | 1.00 | 20.22 | C |
| ATOM | 7978 | CD2 | TYR | D | 176 | 102.876 | 38.944 | 6.378 | 1.00 | 18.32 | C |
| ATOM | 7979 | C | TYR | D | 176 | 104.503 | 38.791 | 9.550 | 1.00 | 21.21 | C |
| ATOM | 7980 | O | TYR | D | 176 | 104.150 | 39.914 | 9.871 | 1.00 | 22.02 | O |
| ATOM | 7981 | N | LEU | D | 177 | 103.961 | 37.683 | 10.069 | 1.00 | 21.34 | N |
| ATOM | 7982 | CA | LEU | D | 177 | 102.846 | 37.718 | 11.022 | 1.00 | 23.35 | C |
| ATOM | 7983 | CB | LEU | D | 177 | 102.420 | 36.308 | 11.451 | 1.00 | 22.77 | C |
| ATOM | 7984 | CG | LEU | D | 177 | 101.884 | 35.382 | 10.355 | 1.00 | 22.65 | C |
| ATOM | 7985 | CD1 | LEU | D | 177 | 101.370 | 34.104 | 10.948 | 1.00 | 23.00 | C |
| ATOM | 7986 | CD2 | LEU | D | 177 | 100.790 | 36.052 | 9.599 | 1.00 | 28.50 | C |
| ATOM | 7987 | C | LEU | D | 177 | 103.162 | 38.533 | 12.247 | 1.00 | 24.99 | C |
| ATOM | 7988 | O | LEU | D | 177 | 102.416 | 39.464 | 12.598 | 1.00 | 26.97 | O |
| ATOM | 7989 | N | HIS | D | 178 | 104.270 | 38.203 | 12.896 | 1.00 | 23.21 | N |
| ATOM | 7990 | CA | HIS | D | 178 | 104.639 | 38.947 | 14.071 | 1.00 | 22.22 | C |
| ATOM | 7991 | CB | HIS | D | 178 | 105.827 | 38.283 | 14.759 | 1.00 | 19.99 | C |
| ATOM | 7992 | CG | HIS | D | 178 | 105.500 | 36.941 | 15.336 | 1.00 | 17.71 | C |
| ATOM | 7993 | ND1 | HIS | D | 178 | 106.328 | 36.278 | 16.210 | 1.00 | 13.39 | N |
| ATOM | 7994 | CE1 | HIS | D | 178 | 105.772 | 35.132 | 16.559 | 1.00 | 13.89 | C |
| ATOM | 7995 | NE2 | HIS | D | 178 | 104.611 | 35.029 | 15.943 | 1.00 | 15.89 | N |
| ATOM | 7996 | CD2 | HIS | D | 178 | 104.418 | 36.145 | 15.171 | 1.00 | 18.54 | C |
| ATOM | 7997 | C | HIS | D | 178 | 104.912 | 40.408 | 13.721 | 1.00 | 22.49 | C |
| ATOM | 7998 | O | HIS | D | 178 | 104.551 | 41.307 | 14.461 | 1.00 | 24.52 | O |
| ATOM | 7999 | N | SER | D | 179 | 105.503 | 40.669 | 12.571 | 1.00 | 21.36 | N |
| ATOM | 8000 | CA | SER | D | 179 | 105.766 | 42.044 | 12.235 | 1.00 | 19.03 | C |
| ATOM | 8001 | CB | SER | D | 179 | 106.559 | 42.144 | 10.942 | 1.00 | 18.11 | C |
| ATOM | 8002 | OG | SER | D | 179 | 105.786 | 41.724 | 9.843 | 1.00 | 19.81 | O |

FIG. 2A-174

| ATOM | 8003 | C | SER | D | 179 | 104.473 | 42.819 | 12.114 | 1.00 | 20.23 | C |
| ATOM | 8004 | O | SER | D | 179 | 104.468 | 44.024 | 12.392 | 1.00 | 21.29 | O |
| ATOM | 8005 | N | ILE | D | 180 | 103.377 | 42.184 | 11.692 | 1.00 | 20.07 | N |
| ATOM | 8006 | CA | ILE | D | 180 | 102.123 | 42.956 | 11.611 | 1.00 | 21.18 | C |
| ATOM | 8007 | CB | ILE | D | 180 | 101.262 | 42.723 | 10.311 | 1.00 | 21.93 | C |
| ATOM | 8008 | CG1 | ILE | D | 180 | 100.716 | 41.300 | 10.261 | 1.00 | 20.94 | C |
| ATOM | 8009 | CD1 | ILE | D | 180 | 99.815 | 41.053 | 9.041 | 1.00 | 18.00 | C |
| ATOM | 8010 | CG2 | ILE | D | 180 | 102.072 | 43.025 | 9.062 | 1.00 | 21.90 | C |
| ATOM | 8011 | C | ILE | D | 180 | 101.237 | 42.686 | 12.814 | 1.00 | 22.17 | C |
| ATOM | 8012 | O | ILE | D | 180 | 100.036 | 42.920 | 12.765 | 1.00 | 21.29 | O |
| ATOM | 8013 | N | ASN | D | 181 | 101.862 | 42.195 | 13.881 | 1.00 | 22.76 | N |
| ATOM | 8014 | CA | ASN | D | 181 | 101.191 | 41.897 | 15.146 | 1.00 | 24.91 | C |
| ATOM | 8015 | CB | ASN | D | 181 | 100.488 | 43.150 | 15.667 | 1.00 | 24.88 | C |
| ATOM | 8016 | CG | ASN | D | 181 | 101.453 | 44.227 | 16.024 | 1.00 | 28.36 | C |
| ATOM | 8017 | OD1 | ASN | D | 181 | 102.233 | 44.100 | 16.962 | 1.00 | 27.45 | O |
| ATOM | 8018 | ND2 | ASN | D | 181 | 101.428 | 45.291 | 15.261 | 1.00 | 31.94 | N |
| ATOM | 8019 | C | ASN | D | 181 | 100.204 | 40.722 | 15.214 | 1.00 | 24.36 | C |
| ATOM | 8020 | O | ASN | D | 181 | 99.183 | 40.807 | 15.885 | 1.00 | 26.54 | O |
| ATOM | 8021 | N | ILE | D | 182 | 100.517 | 39.626 | 14.543 | 1.00 | 22.25 | N |
| ATOM | 8022 | CA | ILE | D | 182 | 99.635 | 38.501 | 14.590 | 1.00 | 22.79 | C |
| ATOM | 8023 | CB | ILE | D | 182 | 99.009 | 38.225 | 13.187 | 1.00 | 22.06 | C |
| ATOM | 8024 | CG1 | ILE | D | 182 | 98.149 | 39.406 | 12.746 | 1.00 | 20.78 | C |
| ATOM | 8025 | CD1 | ILE | D | 182 | 97.402 | 39.142 | 11.432 | 1.00 | 26.23 | C |
| ATOM | 8026 | CG2 | ILE | D | 182 | 98.147 | 36.980 | 13.234 | 1.00 | 20.86 | C |
| ATOM | 8027 | C | ILE | D | 182 | 100.370 | 37.249 | 15.092 | 1.00 | 24.45 | C |
| ATOM | 8028 | O | ILE | D | 182 | 101.498 | 36.936 | 14.672 | 1.00 | 23.85 | O |
| ATOM | 8029 | N | ALA | D | 183 | 99.725 | 36.539 | 16.007 | 1.00 | 24.07 | N |
| ATOM | 8030 | CA | ALA | D | 183 | 100.220 | 35.224 | 16.399 | 1.00 | 24.44 | C |
| ATOM | 8031 | CB | ALA | D | 183 | 100.202 | 35.143 | 17.925 | 1.00 | 23.72 | C |
| ATOM | 8032 | C | ALA | D | 183 | 99.371 | 34.091 | 15.813 | 1.00 | 26.84 | C |
| ATOM | 8033 | O | ALA | D | 183 | 98.153 | 34.064 | 15.926 | 1.00 | 28.84 | O |
| ATOM | 8034 | N | HIS | D | 184 | 100.060 | 33.154 | 15.132 | 1.00 | 26.43 | N |
| ATOM | 8035 | CA | HIS | D | 184 | 99.362 | 31.981 | 14.618 | 1.00 | 26.91 | C |
| ATOM | 8036 | CB | HIS | D | 184 | 100.363 | 31.121 | 13.839 | 1.00 | 27.29 | C |
| ATOM | 8037 | CG | HIS | D | 184 | 99.626 | 30.214 | 12.885 | 1.00 | 26.91 | C |
| ATOM | 8038 | ND1 | HIS | D | 184 | 99.375 | 28.908 | 13.148 | 1.00 | 24.80 | N |
| ATOM | 8039 | CE1 | HIS | D | 184 | 98.681 | 28.452 | 12.088 | 1.00 | 25.94 | C |
| ATOM | 8040 | NE2 | HIS | D | 184 | 98.483 | 29.403 | 11.170 | 1.00 | 23.19 | N |
| ATOM | 8041 | CD2 | HIS | D | 184 | 99.072 | 30.532 | 11.640 | 1.00 | 21.47 | C |
| ATOM | 8042 | C | HIS | D | 184 | 98.748 | 31.164 | 15.757 | 1.00 | 27.71 | C |
| ATOM | 8043 | O | HIS | D | 184 | 97.570 | 30.832 | 15.770 | 1.00 | 30.61 | O |
| ATOM | 8044 | N | ARG | D | 185 | 99.616 | 30.796 | 16.723 | 1.00 | 27.92 | N |
| ATOM | 8045 | CA | ARG | D | 185 | 99.135 | 30.102 | 17.916 | 1.00 | 27.20 | C |
| ATOM | 8046 | CB | ARG | D | 185 | 97.892 | 30.832 | 18.424 | 1.00 | 24.94 | C |
| ATOM | 8047 | CG | ARG | D | 185 | 98.221 | 32.224 | 18.970 | 1.00 | 26.46 | C |
| ATOM | 8048 | CD | ARG | D | 185 | 96.988 | 32.917 | 19.562 | 1.00 | 33.27 | C |

FIG. 2A-175

| ATOM | 8049 | NE | ARG | D | 185 | 96.018 | 31.921 | 20.019 | 1.00 | 42.07 | N |
|------|------|------|------|---|-----|---------|--------|--------|------|-------|---|
| ATOM | 8050 | CZ | ARG | D | 185 | 94.872 | 32.370 | 20.564 | 1.00 | 45.93 | C |
| ATOM | 8051 | NH1AR | G | D | 185 | 94.640 | 33.668 | 20.662 | 1.00 | 49.14 | N |
| ATOM | 8052 | NH2AR | G | D | 185 | 93.966 | 31.494 | 21.008 | 1.00 | 53.68 | N |
| ATOM | 8053 | C | ARG | D | 185 | 98.815 | 28.626 | 17.648 | 1.00 | 27.70 | C |
| ATOM | 8054 | O | ARG | D | 185 | 98.512 | 27.853 | 18.549 | 1.00 | 30.54 | O |
| ATOM | 8055 | N | ASP | D | 186 | 98.852 | 28.254 | 16.353 | 1.00 | 27.52 | N |
| ATOM | 8056 | CA | ASP | D | 186 | 98.633 | 26.852 | 15.995 | 1.00 | 28.38 | C |
| ATOM | 8057 | CB | ASP | D | 186 | 97.182 | 26.699 | 15.543 | 1.00 | 30.27 | C |
| ATOM | 8058 | CG | ASP | D | 186 | 96.819 | 25.220 | 15.501 | 1.00 | 34.09 | C |
| ATOM | 8059 | OD1 | ASP | D | 186 | 97.044 | 24.546 | 16.509 | 1.00 | 32.46 | O |
| ATOM | 8060 | OD2 | ASP | D | 186 | 96.299 | 24.768 | 14.487 | 1.00 | 37.12 | O |
| ATOM | 8061 | C | ASP | D | 186 | 99.577 | 26.397 | 14.878 | 1.00 | 27.24 | C |
| ATOM | 8062 | O | ASP | D | 186 | 99.180 | 25.809 | 13.880 | 1.00 | 26.71 | O |
| ATOM | 8063 | N | VAL | D | 187 | 100.868 | 26.730 | 15.057 | 1.00 | 27.16 | N |
| ATOM | 8064 | CA | VAL | D | 187 | 101.857 | 26.351 | 14.054 | 1.00 | 25.53 | C |
| ATOM | 8065 | CB | VAL | D | 187 | 103.009 | 27.350 | 14.125 | 1.00 | 25.44 | C |
| ATOM | 8066 | CG1 | VAL | D | 187 | 104.245 | 26.771 | 13.437 | 1.00 | 22.22 | C |
| ATOM | 8067 | CG2 | VAL | D | 187 | 102.611 | 28.651 | 13.448 | 1.00 | 20.48 | C |
| ATOM | 8068 | C | VAL | D | 187 | 102.388 | 24.930 | 14.275 | 1.00 | 26.92 | C |
| ATOM | 8069 | O | VAL | D | 187 | 103.267 | 24.679 | 15.088 | 1.00 | 28.82 | O |
| ATOM | 8070 | N | LYS | D | 188 | 101.793 | 23.973 | 13.537 | 1.00 | 26.97 | N |
| ATOM | 8071 | CA | LYS | D | 188 | 102.250 | 22.591 | 13.641 | 1.00 | 24.73 | C |
| ATOM | 8072 | CB | LYS | D | 188 | 101.142 | 21.773 | 14.305 | 1.00 | 24.25 | C |
| ATOM | 8073 | CG | LYS | D | 188 | 99.746 | 22.239 | 13.883 | 1.00 | 24.09 | C |
| ATOM | 8074 | CD | LYS | D | 188 | 98.659 | 21.755 | 14.843 | 1.00 | 36.70 | C |
| ATOM | 8075 | CE | LYS | D | 188 | 97.337 | 21.465 | 14.125 | 1.00 | 40.07 | C |
| ATOM | 8076 | NZ | LYS | D | 188 | 96.352 | 20.968 | 15.085 | 1.00 | 44.15 | N |
| ATOM | 8077 | C | LYS | D | 188 | 102.584 | 22.001 | 12.265 | 1.00 | 25.02 | C |
| ATOM | 8078 | O | LYS | D | 188 | 102.173 | 22.508 | 11.228 | 1.00 | 25.30 | O |
| ATOM | 8079 | N | PRO | D | 189 | 103.375 | 20.926 | 12.255 | 1.00 | 25.56 | N |
| ATOM | 8080 | CA | PRO | D | 189 | 103.768 | 20.306 | 10.999 | 1.00 | 24.68 | C |
| ATOM | 8081 | CB | PRO | D | 189 | 104.525 | 19.060 | 11.452 | 1.00 | 24.35 | C |
| ATOM | 8082 | CG | PRO | D | 189 | 104.071 | 18.837 | 12.891 | 1.00 | 26.10 | C |
| ATOM | 8083 | CD | PRO | D | 189 | 103.938 | 20.207 | 13.412 | 1.00 | 25.23 | C |
| ATOM | 8084 | C | PRO | D | 189 | 102.597 | 20.000 | 10.093 | 1.00 | 25.19 | C |
| ATOM | 8085 | O | PRO | D | 189 | 102.704 | 20.128 | 8.881 | 1.00 | 25.87 | O |
| ATOM | 8086 | N | GLU | D | 190 | 101.470 | 19.615 | 10.674 | 1.00 | 25.05 | N |
| ATOM | 8087 | CA | GLU | D | 190 | 100.284 | 19.275 | 9.891 | 1.00 | 25.05 | C |
| ATOM | 8088 | CB | GLU | D | 190 | 99.218 | 18.649 | 10.786 | 1.00 | 26.11 | C |
| ATOM | 8089 | CG | GLU | D | 190 | 99.687 | 17.549 | 11.736 | 1.00 | 31.14 | C |
| ATOM | 8090 | CD | GLU | D | 190 | 100.691 | 18.031 | 12.775 | 1.00 | 32.06 | C |
| ATOM | 8091 | OE1 | GLU | D | 190 | 100.639 | 19.213 | 13.176 | 1.00 | 31.93 | O |
| ATOM | 8092 | OE2 | GLU | D | 190 | 101.532 | 17.207 | 13.205 | 1.00 | 29.83 | O |
| ATOM | 8093 | C | GLU | D | 190 | 99.671 | 20.498 | 9.211 | 1.00 | 25.01 | C |
| ATOM | 8094 | O | GLU | D | 190 | 98.768 | 20.365 | 8.375 | 1.00 | 25.70 | O |

FIG. 2A-176

| ATOM | 8095 | N | ASN | D | 191 | 100.137 | 21.686 | 9.581 | 1.00 | 24.08 | N |
|---|---|---|---|---|---|---|---|---|---|---|---|
| ATOM | 8096 | CA | ASN | D | 191 | 99.610 | 22.909 | 8.998 | 1.00 | 26.46 | C |
| ATOM | 8097 | CB | ASN | D | 191 | 99.307 | 23.939 | 10.074 | 1.00 | 26.97 | C |
| ATOM | 8098 | CG | ASN | D | 191 | 97.901 | 23.842 | 10.554 | 1.00 | 31.69 | C |
| ATOM | 8099 | OD1 | ASN | D | 191 | 97.089 | 23.165 | 9.930 | 1.00 | 39.10 | O |
| ATOM | 8100 | ND2 | ASN | D | 191 | 97.583 | 24.520 | 11.653 | 1.00 | 28.98 | N |
| ATOM | 8101 | C | ASN | D | 191 | 100.493 | 23.554 | 7.949 | 1.00 | 27.23 | C |
| ATOM | 8102 | O | ASN | D | 191 | 100.248 | 24.698 | 7.547 | 1.00 | 27.76 | O |
| ATOM | 8103 | N | LEU | D | 192 | 101.516 | 22.827 | 7.510 | 1.00 | 25.72 | N |
| ATOM | 8104 | CA | LEU | D | 192 | 102.417 | 23.323 | 6.497 | 1.00 | 24.68 | C |
| ATOM | 8105 | CB | LEU | D | 192 | 103.842 | 23.320 | 7.043 | 1.00 | 24.05 | C |
| ATOM | 8106 | CG | LEU | D | 192 | 104.140 | 24.144 | 8.297 | 1.00 | 22.84 | C |
| ATOM | 8107 | CD1 | LEU | D | 192 | 105.555 | 23.893 | 8.737 | 1.00 | 17.64 | C |
| ATOM | 8108 | CD2 | LEU | D | 192 | 103.936 | 25.608 | 8.016 | 1.00 | 26.87 | C |
| ATOM | 8109 | C | LEU | D | 192 | 102.282 | 22.401 | 5.278 | 1.00 | 24.55 | C |
| ATOM | 8110 | O | LEU | D | 192 | 102.769 | 21.271 | 5.291 | 1.00 | 24.46 | O |
| ATOM | 8111 | N | LEU | D | 193 | 101.599 | 22.892 | 4.242 | 1.00 | 22.96 | N |
| ATOM | 8112 | CA | LEU | D | 193 | 101.356 | 22.154 | 3.001 | 1.00 | 22.36 | C |
| ATOM | 8113 | CB | LEU | D | 193 | 99.875 | 22.158 | 2.664 | 1.00 | 22.25 | C |
| ATOM | 8114 | CG | LEU | D | 193 | 98.925 | 21.777 | 3.794 | 1.00 | 24.24 | C |
| ATOM | 8115 | CD1 | LEU | D | 193 | 97.531 | 21.536 | 3.217 | 1.00 | 25.02 | C |
| ATOM | 8116 | CD2 | LEU | D | 193 | 99.454 | 20.521 | 4.514 | 1.00 | 25.03 | C |
| ATOM | 8117 | C | LEU | D | 193 | 102.099 | 22.755 | 1.820 | 1.00 | 21.78 | C |
| ATOM | 8118 | O | LEU | D | 193 | 102.232 | 23.973 | 1.729 | 1.00 | 21.80 | O |
| ATOM | 8119 | N | TYR | D | 194 | 102.556 | 21.891 | 0.906 | 1.00 | 21.68 | N |
| ATOM | 8120 | CA | TYR | D | 194 | 103.293 | 22.298 | -0.282 | 1.00 | 20.75 | C |
| ATOM | 8121 | CB | TYR | D | 194 | 104.228 | 21.161 | -0.694 | 1.00 | 19.91 | C |
| ATOM | 8122 | CG | TYR | D | 194 | 105.542 | 21.143 | 0.022 | 1.00 | 18.86 | C |
| ATOM | 8123 | CD1 | TYR | D | 194 | 106.490 | 22.121 | -0.217 | 1.00 | 18.77 | C |
| ATOM | 8124 | CE1 | TYR | D | 194 | 107.665 | 22.155 | 0.474 | 1.00 | 16.63 | C |
| ATOM | 8125 | CZ | TYR | D | 194 | 107.920 | 21.202 | 1.428 | 1.00 | 17.63 | C |
| ATOM | 8126 | OH | TYR | D | 194 | 109.122 | 21.213 | 2.082 | 1.00 | 13.05 | O |
| ATOM | 8127 | CE2 | TYR | D | 194 | 107.005 | 20.212 | 1.698 | 1.00 | 21.52 | C |
| ATOM | 8128 | CD2 | TYR | D | 194 | 105.819 | 20.188 | 0.983 | 1.00 | 22.70 | C |
| ATOM | 8129 | C | TYR | D | 194 | 102.315 | 22.622 | -1.423 | 1.00 | 22.51 | C |
| ATOM | 8130 | O | TYR | D | 194 | 101.241 | 22.029 | -1.506 | 1.00 | 23.00 | O |
| ATOM | 8131 | N | THR | D | 195 | 102.673 | 23.567 | -2.291 | 1.00 | 24.29 | N |
| ATOM | 8132 | CA | THR | D | 195 | 101.817 | 23.943 | -3.423 | 1.00 | 26.33 | C |
| ATOM | 8133 | CB | THR | D | 195 | 102.477 | 24.996 | -4.236 | 1.00 | 25.65 | C |
| ATOM | 8134 | OG1 | THR | D | 195 | 103.863 | 24.990 | -3.904 | 1.00 | 29.05 | O |
| ATOM | 8135 | CG2 | THR | D | 195 | 101.908 | 26.358 | -3.937 | 1.00 | 27.71 | C |
| ATOM | 8136 | C | THR | D | 195 | 101.650 | 22.746 | -4.323 | 1.00 | 26.35 | C |
| ATOM | 8137 | O | THR | D | 195 | 100.720 | 21.955 | -4.177 | 1.00 | 28.27 | O |
| ATOM | 8138 | N | SER | D | 196 | 102.593 | 22.637 | -5.254 | 1.00 | 27.20 | N |
| ATOM | 8139 | CA | SER | D | 196 | 102.696 | 21.554 | -6.235 | 1.00 | 28.28 | C |
| ATOM | 8140 | CB | SER | D | 196 | 103.345 | 22.067 | -7.497 | 1.00 | 27.80 | C |

FIG. 2A-177

| ATOM | 8141 | OG | SER | D | 196 | 104.358 | 23.004 | -7.190 | 1.00 | 27.00 | O |
|---|---|---|---|---|---|---|---|---|---|---|---|
| ATOM | 8142 | C | SER | D | 196 | 103.558 | 20.434 | -5.691 | 1.00 | 29.05 | C |
| ATOM | 8143 | O | SER | D | 196 | 104.159 | 20.566 | -4.609 | 1.00 | 29.27 | O |
| ATOM | 8144 | N | ALA | D | 197 | 103.615 | 19.330 | -6.444 | 1.00 | 29.56 | N |
| ATOM | 8145 | CA | ALA | D | 197 | 104.422 | 18.176 | -6.039 | 1.00 | 30.49 | C |
| ATOM | 8146 | CB | ALA | D | 197 | 103.765 | 16.883 | -6.445 | 1.00 | 30.14 | C |
| ATOM | 8147 | C | ALA | D | 197 | 105.754 | 18.319 | -6.714 | 1.00 | 31.42 | C |
| ATOM | 8148 | O | ALA | D | 197 | 106.588 | 17.441 | -6.633 | 1.00 | 30.08 | O |
| ATOM | 8149 | N | ALA | D | 198 | 105.931 | 19.454 | -7.383 | 1.00 | 34.03 | N |
| ATOM | 8150 | CA | ALA | D | 198 | 107.166 | 19.779 | -8.083 | 1.00 | 35.72 | C |
| ATOM | 8151 | CB | ALA | D | 198 | 107.003 | 21.104 | -8.829 | 1.00 | 35.82 | C |
| ATOM | 8152 | C | ALA | D | 198 | 108.249 | 19.901 | -7.025 | 1.00 | 36.72 | C |
| ATOM | 8153 | O | ALA | D | 198 | 107.956 | 19.834 | -5.835 | 1.00 | 38.06 | O |
| ATOM | 8154 | N | PRO | D | 199 | 109.520 | 20.074 | -7.436 | 1.00 | 37.35 | N |
| ATOM | 8155 | CA | PRO | D | 199 | 110.587 | 20.195 | -6.447 | 1.00 | 37.33 | C |
| ATOM | 8156 | CB | PRO | D | 199 | 111.817 | 19.755 | -7.224 | 1.00 | 37.46 | C |
| ATOM | 8157 | CG | PRO | D | 199 | 111.553 | 20.354 | -8.554 | 1.00 | 37.95 | C |
| ATOM | 8158 | CD | PRO | D | 199 | 110.097 | 19.959 | -8.787 | 1.00 | 37.77 | C |
| ATOM | 8159 | C | PRO | D | 199 | 110.713 | 21.610 | -5.891 | 1.00 | 37.06 | C |
| ATOM | 8160 | O | PRO | D | 199 | 110.902 | 21.781 | -4.696 | 1.00 | 38.71 | O |
| ATOM | 8161 | N | ALA | D | 200 | 110.601 | 22.624 | -6.735 | 1.00 | 35.81 | N |
| ATOM | 8162 | CA | ALA | D | 200 | 110.716 | 23.992 | -6.235 | 1.00 | 35.37 | C |
| ATOM | 8163 | CB | ALA | D | 200 | 111.302 | 24.919 | -7.333 | 1.00 | 35.72 | C |
| ATOM | 8164 | C | ALA | D | 200 | 109.397 | 24.582 | -5.677 | 1.00 | 33.86 | C |
| ATOM | 8165 | O | ALA | D | 200 | 109.236 | 25.803 | -5.580 | 1.00 | 33.15 | O |
| ATOM | 8166 | N | ALA | D | 201 | 108.460 | 23.713 | -5.311 | 1.00 | 32.53 | N |
| ATOM | 8167 | CA | ALA | D | 201 | 107.182 | 24.161 | -4.744 | 1.00 | 32.43 | C |
| ATOM | 8168 | CB | ALA | D | 201 | 106.280 | 22.937 | -4.462 | 1.00 | 32.39 | C |
| ATOM | 8169 | C | ALA | D | 201 | 107.450 | 24.942 | -3.443 | 1.00 | 31.29 | C |
| ATOM | 8170 | O | ALA | D | 201 | 108.464 | 24.716 | -2.787 | 1.00 | 32.37 | O |
| ATOM | 8171 | N | ILE | D | 202 | 106.559 | 25.852 | -3.062 | 1.00 | 29.88 | N |
| ATOM | 8172 | CA | ILE | D | 202 | 106.796 | 26.589 | -1.827 | 1.00 | 29.97 | C |
| ATOM | 8173 | CB | ILE | D | 202 | 106.551 | 28.100 | -2.008 | 1.00 | 29.62 | C |
| ATOM | 8174 | CG1 | ILE | D | 202 | 105.648 | 28.620 | -0.909 | 1.00 | 32.22 | C |
| ATOM | 8175 | CD1 | ILE | D | 202 | 105.644 | 30.122 | -0.834 | 1.00 | 45.60 | C |
| ATOM | 8176 | CG2 | ILE | D | 202 | 105.888 | 28.357 | -3.317 | 1.00 | 31.42 | C |
| ATOM | 8177 | C | ILE | D | 202 | 105.950 | 26.097 | -0.646 | 1.00 | 28.76 | C |
| ATOM | 8178 | O | ILE | D | 202 | 104.817 | 25.649 | -0.839 | 1.00 | 29.41 | O |
| ATOM | 8179 | N | LEU | D | 203 | 106.517 | 26.153 | 0.566 | 1.00 | 26.96 | N |
| ATOM | 8180 | CA | LEU | D | 203 | 105.798 | 25.741 | 1.780 | 1.00 | 25.07 | C |
| ATOM | 8181 | CB | LEU | D | 203 | 106.752 | 25.479 | 2.934 | 1.00 | 25.71 | C |
| ATOM | 8182 | CG | LEU | D | 203 | 106.186 | 24.747 | 4.142 | 1.00 | 26.68 | C |
| ATOM | 8183 | CD1 | LEU | D | 203 | 105.455 | 23.489 | 3.671 | 1.00 | 21.81 | C |
| ATOM | 8184 | CD2 | LEU | D | 203 | 107.300 | 24.416 | 5.099 | 1.00 | 25.18 | C |
| ATOM | 8185 | C | LEU | D | 203 | 104.870 | 26.872 | 2.196 | 1.00 | 24.01 | C |
| ATOM | 8186 | O | LEU | D | 203 | 105.193 | 28.065 | 2.027 | 1.00 | 22.91 | O |

FIG. 2A-178

| ATOM | 8187 | N | LYS | D | 204 | 103.719 | 26.518 | 2.741 | 1.00 | 23.63 | N |
|---|---|---|---|---|---|---|---|---|---|---|---|
| ATOM | 8188 | CA | LYS | D | 204 | 102.790 | 27.555 | 3.156 | 1.00 | 24.39 | C |
| ATOM | 8189 | CB | LYS | D | 204 | 101.805 | 27.848 | 2.028 | 1.00 | 24.90 | C |
| ATOM | 8190 | CG | LYS | D | 204 | 102.462 | 28.493 | 0.826 | 1.00 | 21.08 | C |
| ATOM | 8191 | CD | LYS | D | 204 | 101.433 | 28.964 | -0.154 | 1.00 | 26.45 | C |
| ATOM | 8192 | CE | LYS | D | 204 | 102.020 | 29.942 | -1.153 | 1.00 | 27.81 | C |
| ATOM | 8193 | NZ | LYS | D | 204 | 101.010 | 30.300 | -2.201 | 1.00 | 32.06 | N |
| ATOM | 8194 | C | LYS | D | 204 | 102.048 | 27.276 | 4.451 | 1.00 | 25.54 | C |
| ATOM | 8195 | O | LYS | D | 204 | 101.666 | 26.146 | 4.709 | 1.00 | 26.62 | O |
| ATOM | 8196 | N | LEU | D | 205 | 101.900 | 28.320 | 5.273 | 1.00 | 25.67 | N |
| ATOM | 8197 | CA | LEU | D | 205 | 101.180 | 28.231 | 6.542 | 1.00 | 25.76 | C |
| ATOM | 8198 | CB | LEU | D | 205 | 101.558 | 29.401 | 7.448 | 1.00 | 26.93 | C |
| ATOM | 8199 | CG | LEU | D | 205 | 100.971 | 29.439 | 8.856 | 1.00 | 31.45 | C |
| ATOM | 8200 | CD1 | LEU | D | 205 | 101.452 | 28.260 | 9.633 | 1.00 | 25.38 | C |
| ATOM | 8201 | CD2 | LEU | D | 205 | 101.373 | 30.722 | 9.537 | 1.00 | 33.80 | C |
| ATOM | 8202 | C | LEU | D | 205 | 99.671 | 28.299 | 6.269 | 1.00 | 25.95 | C |
| ATOM | 8203 | O | LEU | D | 205 | 99.221 | 29.062 | 5.416 | 1.00 | 27.83 | O |
| ATOM | 8204 | N | THR | D | 206 | 98.886 | 27.512 | 6.987 | 1.00 | 25.34 | N |
| ATOM | 8205 | CA | THR | D | 206 | 97.433 | 27.528 | 6.801 | 1.00 | 24.60 | C |
| ATOM | 8206 | CB | THR | D | 206 | 96.926 | 26.308 | 6.054 | 1.00 | 23.65 | C |
| ATOM | 8207 | OG1 | THR | D | 206 | 97.226 | 25.140 | 6.831 | 1.00 | 20.81 | O |
| ATOM | 8208 | CG2 | THR | D | 206 | 97.544 | 26.230 | 4.685 | 1.00 | 20.99 | C |
| ATOM | 8209 | C | THR | D | 206 | 96.671 | 27.525 | 8.111 | 1.00 | 26.19 | C |
| ATOM | 8210 | O | THR | D | 206 | 97.228 | 27.316 | 9.180 | 1.00 | 29.26 | O |
| ATOM | 8211 | N | ASP | D | 207 | 95.370 | 27.696 | 7.994 | 1.00 | 26.35 | N |
| ATOM | 8212 | CA | ASP | D | 207 | 94.476 | 27.725 | 9.140 | 1.00 | 28.01 | C |
| ATOM | 8213 | CB | ASP | D | 207 | 94.417 | 26.378 | 9.834 | 1.00 | 27.03 | C |
| ATOM | 8214 | CG | ASP | D | 207 | 93.138 | 26.224 | 10.631 | 1.00 | 32.49 | C |
| ATOM | 8215 | OD1 | ASP | D | 207 | 92.435 | 27.239 | 10.812 | 1.00 | 35.77 | O |
| ATOM | 8216 | OD2 | ASP | D | 207 | 92.825 | 25.105 | 11.079 | 1.00 | 36.89 | O |
| ATOM | 8217 | C | ASP | D | 207 | 94.734 | 28.789 | 10.200 | 1.00 | 26.74 | C |
| ATOM | 8218 | O | ASP | D | 207 | 95.539 | 28.592 | 11.098 | 1.00 | 27.28 | O |
| ATOM | 8219 | N | PHE | D | 208 | 94.013 | 29.904 | 10.093 | 1.00 | 27.35 | N |
| ATOM | 8220 | CA | PHE | D | 208 | 94.137 | 30.984 | 11.036 | 1.00 | 25.91 | C |
| ATOM | 8221 | CB | PHE | D | 208 | 94.145 | 32.315 | 10.300 | 1.00 | 25.19 | C |
| ATOM | 8222 | CG | PHE | D | 208 | 95.470 | 32.632 | 9.699 | 1.00 | 24.70 | C |
| ATOM | 8223 | CD1 | PHE | D | 208 | 95.987 | 31.856 | 8.693 | 1.00 | 21.83 | C |
| ATOM | 8224 | CE1 | PHE | D | 208 | 97.253 | 32.087 | 8.208 | 1.00 | 25.99 | C |
| ATOM | 8225 | CZ | PHE | D | 208 | 98.028 | 33.107 | 8.725 | 1.00 | 28.44 | C |
| ATOM | 8226 | CE2 | PHE | D | 208 | 97.527 | 33.892 | 9.722 | 1.00 | 27.38 | C |
| ATOM | 8227 | CD2 | PHE | D | 208 | 96.251 | 33.654 | 10.206 | 1.00 | 28.65 | C |
| ATOM | 8228 | C | PHE | D | 208 | 93.064 | 30.929 | 12.112 | 1.00 | 25.92 | C |
| ATOM | 8229 | O | PHE | D | 208 | 92.661 | 31.954 | 12.662 | 1.00 | 28.77 | O |
| ATOM | 8230 | N | GLY | D | 209 | 92.637 | 29.703 | 12.427 | 1.00 | 26.11 | N |
| ATOM | 8231 | CA | GLY | D | 209 | 91.627 | 29.468 | 13.452 | 1.00 | 24.70 | C |
| ATOM | 8232 | C | GLY | D | 209 | 91.931 | 30.033 | 14.841 | 1.00 | 25.00 | C |

FIG. 2A-179

| | | | | | | | | | | |
|---|---|---|---|---|---|---|---|---|---|---|
| ATOM | 8233 | O | GLY | D | 209 | 91.031 | 30.508 | 15.510 | 1.00 | 26.66 | O |
| ATOM | 8234 | N | PHE | D | 210 | 93.181 | 29.984 | 15.276 | 1.00 | 24.72 | N |
| ATOM | 8235 | CA | PHE | D | 210 | 93.542 | 30.526 | 16.563 | 1.00 | 24.74 | C |
| ATOM | 8236 | CB | PHE | D | 210 | 94.396 | 29.526 | 17.333 | 1.00 | 25.19 | C |
| ATOM | 8237 | CG | PHE | D | 210 | 93.710 | 28.237 | 17.615 | 1.00 | 29.74 | C |
| ATOM | 8238 | CD1 | PHE | D | 210 | 92.429 | 28.227 | 18.148 | 1.00 | 32.80 | C |
| ATOM | 8239 | CE1 | PHE | D | 210 | 91.792 | 27.051 | 18.411 | 1.00 | 36.46 | C |
| ATOM | 8240 | CZ | PHE | D | 210 | 92.418 | 25.854 | 18.149 | 1.00 | 32.84 | C |
| ATOM | 8241 | CE2 | PHE | D | 210 | 93.693 | 25.843 | 17.619 | 1.00 | 36.27 | C |
| ATOM | 8242 | CD2 | PHE | D | 210 | 94.337 | 27.028 | 17.354 | 1.00 | 32.84 | C |
| ATOM | 8243 | C | PHE | D | 210 | 94.322 | 31.844 | 16.440 | 1.00 | 23.97 | C |
| ATOM | 8244 | O | PHE | D | 210 | 94.782 | 32.387 | 17.433 | 1.00 | 22.74 | O |
| ATOM | 8245 | N | ALA | D | 211 | 94.502 | 32.350 | 15.234 | 1.00 | 22.58 | N |
| ATOM | 8246 | CA | ALA | D | 211 | 95.244 | 33.583 | 15.070 | 1.00 | 22.40 | C |
| ATOM | 8247 | CB | ALA | D | 211 | 95.209 | 34.010 | 13.599 | 1.00 | 24.06 | C |
| ATOM | 8248 | C | ALA | D | 211 | 94.668 | 34.683 | 15.957 | 1.00 | 23.37 | C |
| ATOM | 8249 | O | ALA | D | 211 | 93.480 | 34.770 | 16.136 | 1.00 | 23.60 | O |
| ATOM | 8250 | N | LYS | D | 212 | 95.514 | 35.536 | 16.502 | 1.00 | 23.95 | N |
| ATOM | 8251 | CA | LYS | D | 212 | 95.055 | 36.601 | 17.372 | 1.00 | 26.63 | C |
| ATOM | 8252 | CB | LYS | D | 212 | 95.142 | 36.160 | 18.833 | 1.00 | 27.10 | C |
| ATOM | 8253 | CG | LYS | D | 212 | 94.339 | 37.025 | 19.784 | 1.00 | 34.37 | C |
| ATOM | 8254 | CD | LYS | D | 212 | 94.751 | 36.825 | 21.250 | 1.00 | 40.48 | C |
| ATOM | 8255 | CE | LYS | D | 212 | 93.881 | 37.692 | 22.208 | 1.00 | 41.37 | C |
| ATOM | 8256 | NZ | LYS | D | 212 | 94.400 | 37.753 | 23.616 | 1.00 | 38.53 | N |
| ATOM | 8257 | C | LYS | D | 212 | 95.932 | 37.820 | 17.205 | 1.00 | 27.22 | C |
| ATOM | 8258 | O | LYS | D | 212 | 97.141 | 37.690 | 17.017 | 1.00 | 26.50 | O |
| ATOM | 8259 | N | GLU | D | 213 | 95.320 | 38.998 | 17.278 | 1.00 | 30.17 | N |
| ATOM | 8260 | CA | GLU | D | 213 | 96.048 | 40.246 | 17.186 | 1.00 | 32.14 | C |
| ATOM | 8261 | CB | GLU | D | 213 | 95.104 | 41.427 | 17.063 | 1.00 | 34.22 | C |
| ATOM | 8262 | CG | GLU | D | 213 | 94.278 | 41.554 | 15.795 | 1.00 | 39.55 | C |
| ATOM | 8263 | CD | GLU | D | 213 | 94.094 | 43.032 | 15.436 | 1.00 | 47.39 | C |
| ATOM | 8264 | OE1 | GLU | D | 213 | 93.123 | 43.374 | 14.725 | 1.00 | 51.69 | O |
| ATOM | 8265 | OE2 | GLU | D | 213 | 94.939 | 43.854 | 15.872 | 1.00 | 44.86 | O |
| ATOM | 8266 | C | GLU | D | 213 | 96.782 | 40.420 | 18.501 | 1.00 | 33.27 | C |
| ATOM | 8267 | O | GLU | D | 213 | 96.155 | 40.324 | 19.541 | 1.00 | 32.87 | O |
| ATOM | 8268 | N | THR | D | 214 | 98.085 | 40.690 | 18.465 | 1.00 | 35.29 | N |
| ATOM | 8269 | CA | THR | D | 214 | 98.861 | 40.883 | 19.688 | 1.00 | 38.49 | C |
| ATOM | 8270 | CB | THR | D | 214 | 100.370 | 40.842 | 19.438 | 1.00 | 38.25 | C |
| ATOM | 8271 | OG1 | THR | D | 214 | 100.737 | 41.860 | 18.506 | 1.00 | 40.88 | O |
| ATOM | 8272 | CG2 | THR | D | 214 | 100.774 | 39.502 | 18.900 | 1.00 | 36.69 | C |
| ATOM | 8273 | C | THR | D | 214 | 98.510 | 42.221 | 20.298 | 1.00 | 41.99 | C |
| ATOM | 8274 | O | THR | D | 214 | 99.048 | 42.605 | 21.323 | 1.00 | 42.72 | O |
| ATOM | 8275 | N | THR | D | 215 | 97.599 | 42.935 | 19.652 | 1.00 | 47.07 | N |
| ATOM | 8276 | CA | THR | D | 215 | 97.110 | 44.211 | 20.164 | 1.00 | 51.92 | C |
| ATOM | 8277 | CB | THR | D | 215 | 97.921 | 45.391 | 19.675 | 1.00 | 51.47 | C |
| ATOM | 8278 | OG1 | THR | D | 215 | 97.787 | 45.486 | 18.252 | 1.00 | 53.53 | O |

FIG. 2A-180

| ATOM | 8279 | CG2 | THR | D | 215 | 99.368 | 45.221 | 20.035 | 1.00 | 49.34 | C |
|---|---|---|---|---|---|---|---|---|---|---|---|
| ATOM | 8280 | C | THR | D | 215 | 95.685 | 44.405 | 19.641 | 1.00 | 55.47 | C |
| ATOM | 8281 | O | THR | D | 215 | 95.499 | 45.376 | 18.857 | 1.00 | 58.59 | O |
| ATOM | 8282 | OXT | THR | D | 215 | 94.780 | 43.593 | 19.994 | 1.00 | 55.99 | O |
| ATOM | 8283 | N | ALA | D | 224 | 100.834 | 59.867 | 19.253 | 1.00 | 58.55 | N |
| ATOM | 8284 | CA | ALA | D | 224 | 101.197 | 59.539 | 17.878 | 1.00 | 58.21 | C |
| ATOM | 8285 | CB | ALA | D | 224 | 100.230 | 60.268 | 16.944 | 1.00 | 58.26 | C |
| ATOM | 8286 | C | ALA | D | 224 | 102.632 | 59.959 | 17.574 | 1.00 | 57.55 | C |
| ATOM | 8287 | O | ALA | D | 224 | 103.025 | 60.186 | 16.437 | 1.00 | 58.87 | O |
| ATOM | 8288 | N | TYR | D | 225 | 103.415 | 60.100 | 18.658 | 1.00 | 55.10 | N |
| ATOM | 8289 | CA | TYR | D | 225 | 104.780 | 60.589 | 18.527 | 1.00 | 51.68 | C |
| ATOM | 8290 | CB | TYR | D | 225 | 105.059 | 61.474 | 19.743 | 1.00 | 51.43 | C |
| ATOM | 8291 | CG | TYR | D | 225 | 106.498 | 61.834 | 19.821 | 1.00 | 51.74 | C |
| ATOM | 8292 | CD1 | TYR | D | 225 | 107.249 | 61.966 | 18.659 | 1.00 | 53.51 | C |
| ATOM | 8293 | CE1 | TYR | D | 225 | 108.550 | 62.436 | 18.723 | 1.00 | 54.28 | C |
| ATOM | 8294 | CZ | TYR | D | 225 | 109.115 | 62.758 | 19.957 | 1.00 | 53.80 | C |
| ATOM | 8295 | OH | TYR | D | 225 | 110.402 | 63.256 | 20.005 | 1.00 | 55.14 | O |
| ATOM | 8296 | CE2 | TYR | D | 225 | 108.375 | 62.619 | 21.116 | 1.00 | 53.75 | C |
| ATOM | 8297 | CD2 | TYR | D | 225 | 107.073 | 62.155 | 21.053 | 1.00 | 54.23 | C |
| ATOM | 8298 | C | TYR | D | 225 | 105.786 | 59.433 | 18.462 | 1.00 | 49.02 | C |
| ATOM | 8299 | O | TYR | D | 225 | 106.114 | 58.919 | 17.399 | 1.00 | 49.03 | O |
| ATOM | 8300 | N | THR | D | 226 | 106.249 | 59.041 | 19.659 | 1.00 | 45.36 | N |
| ATOM | 8301 | CA | THR | D | 226 | 107.135 | 57.887 | 19.745 | 1.00 | 41.79 | C |
| ATOM | 8302 | CB | THR | D | 226 | 106.729 | 56.903 | 18.648 | 1.00 | 41.86 | C |
| ATOM | 8303 | OG1 | THR | D | 226 | 105.344 | 56.589 | 18.786 | 1.00 | 44.20 | O |
| ATOM | 8304 | CG2 | THR | D | 226 | 107.546 | 55.611 | 18.770 | 1.00 | 41.41 | C |
| ATOM | 8305 | C | THR | D | 226 | 108.602 | 58.279 | 19.559 | 1.00 | 37.60 | C |
| ATOM | 8306 | O | THR | D | 226 | 109.124 | 58.328 | 18.453 | 1.00 | 36.28 | O |
| ATOM | 8307 | N | PRO | D | 227 | 109.261 | 58.604 | 20.688 | 1.00 | 33.85 | N |
| ATOM | 8308 | CA | PRO | D | 227 | 110.685 | 58.910 | 20.683 | 1.00 | 30.71 | C |
| ATOM | 8309 | CB | PRO | D | 227 | 111.071 | 59.346 | 22.100 | 1.00 | 30.75 | C |
| ATOM | 8310 | CG | PRO | D | 227 | 109.786 | 59.555 | 22.900 | 1.00 | 33.18 | C |
| ATOM | 8311 | CD | PRO | D | 227 | 108.733 | 58.718 | 22.039 | 1.00 | 33.10 | C |
| ATOM | 8312 | C | PRO | D | 227 | 111.510 | 57.690 | 20.263 | 1.00 | 26.92 | C |
| ATOM | 8313 | O | PRO | D | 227 | 111.228 | 56.565 | 20.658 | 1.00 | 26.59 | O |
| ATOM | 8314 | N | TYR | D | 228 | 112.490 | 57.959 | 19.413 | 1.00 | 21.89 | N |
| ATOM | 8315 | CA | TYR | D | 228 | 113.360 | 56.929 | 18.860 | 1.00 | 17.42 | C |
| ATOM | 8316 | CB | TYR | D | 228 | 114.415 | 57.573 | 17.935 | 1.00 | 14.67 | C |
| ATOM | 8317 | CG | TYR | D | 228 | 115.514 | 58.281 | 18.688 | 1.00 | 8.29 | C |
| ATOM | 8318 | CD1 | TYR | D | 228 | 116.597 | 57.569 | 19.210 | 1.00 | 8.00 | C |
| ATOM | 8319 | CE1 | TYR | D | 228 | 117.543 | 58.179 | 19.973 | 1.00 | 2.81 | C |
| ATOM | 8320 | CZ | TYR | D | 228 | 117.426 | 59.530 | 20.245 | 1.00 | 2.59 | C |
| ATOM | 8321 | OH | TYR | D | 228 | 118.353 | 60.140 | 21.068 | 1.00 | 13.13 | O |
| ATOM | 8322 | CE2 | TYR | D | 228 | 116.373 | 60.266 | 19.741 | 1.00 | 5.06 | C |
| ATOM | 8323 | CD2 | TYR | D | 228 | 115.428 | 59.638 | 18.964 | 1.00 | 7.26 | C |
| ATOM | 8324 | C | TYR | D | 228 | 114.060 | 56.145 | 19.970 | 1.00 | 15.79 | C |

FIG. 2A-181

| ATOM | 8325 | O   | TYR | D | 228 | 114.640 | 55.118 | 19.715 | 1.00 | 15.89 | O |
|------|------|-----|-----|---|-----|---------|--------|--------|------|-------|---|
| ATOM | 8326 | N   | TYR | D | 229 | 114.012 | 56.610 | 21.205 | 1.00 | 14.07 | N |
| ATOM | 8327 | CA  | TYR | D | 229 | 114.697 | 55.881 | 22.264 | 1.00 | 14.24 | C |
| ATOM | 8328 | CB  | TYR | D | 229 | 115.652 | 56.823 | 22.953 | 1.00 | 10.92 | C |
| ATOM | 8329 | CG  | TYR | D | 229 | 114.906 | 57.955 | 23.568 | 1.00 | 15.37 | C |
| ATOM | 8330 | CD1 | TYR | D | 229 | 114.274 | 57.802 | 24.801 | 1.00 | 17.39 | C |
| ATOM | 8331 | CE1 | TYR | D | 229 | 113.503 | 58.817 | 25.340 | 1.00 | 16.25 | C |
| ATOM | 8332 | CZ  | TYR | D | 229 | 113.365 | 59.993 | 24.640 | 1.00 | 19.64 | C |
| ATOM | 8333 | OH  | TYR | D | 229 | 112.596 | 61.006 | 25.162 | 1.00 | 24.12 | O |
| ATOM | 8334 | CE2 | TYR | D | 229 | 113.988 | 60.170 | 23.421 | 1.00 | 17.67 | C |
| ATOM | 8335 | CD2 | TYR | D | 229 | 114.751 | 59.158 | 22.893 | 1.00 | 16.87 | C |
| ATOM | 8336 | C   | TYR | D | 229 | 113.787 | 55.220 | 23.317 | 1.00 | 14.54 | C |
| ATOM | 8337 | O   | TYR | D | 229 | 114.267 | 54.674 | 24.292 | 1.00 | 15.02 | O |
| ATOM | 8338 | N   | VAL | D | 230 | 112.479 | 55.281 | 23.116 | 1.00 | 15.27 | N |
| ATOM | 8339 | CA  | VAL | D | 230 | 111.509 | 54.694 | 24.041 | 1.00 | 17.02 | C |
| ATOM | 8340 | CB  | VAL | D | 230 | 110.085 | 55.057 | 23.588 | 1.00 | 18.01 | C |
| ATOM | 8341 | CG1 | VAL | D | 230 | 109.803 | 54.367 | 22.254 | 1.00 | 17.69 | C |
| ATOM | 8342 | CG2 | VAL | D | 230 | 109.061 | 54.672 | 24.639 | 1.00 | 20.92 | C |
| ATOM | 8343 | C   | VAL | D | 230 | 111.642 | 53.173 | 24.003 | 1.00 | 16.49 | C |
| ATOM | 8344 | O   | VAL | D | 230 | 112.023 | 52.640 | 22.984 | 1.00 | 18.51 | O |
| ATOM | 8345 | N   | ALA | D | 231 | 111.329 | 52.483 | 25.097 | 1.00 | 16.03 | N |
| ATOM | 8346 | CA  | ALA | D | 231 | 111.411 | 51.011 | 25.143 | 1.00 | 14.03 | C |
| ATOM | 8347 | CB  | ALA | D | 231 | 111.725 | 50.548 | 26.543 | 1.00 | 13.16 | C |
| ATOM | 8348 | C   | ALA | D | 231 | 110.107 | 50.361 | 24.664 | 1.00 | 13.01 | C |
| ATOM | 8349 | O   | ALA | D | 231 | 109.038 | 50.951 | 24.730 | 1.00 | 13.47 | O |
| ATOM | 8350 | N   | PRO | D | 232 | 110.182 | 49.127 | 24.167 | 1.00 | 12.84 | N |
| ATOM | 8351 | CA  | PRO | D | 232 | 108.949 | 48.489 | 23.700 | 1.00 | 13.43 | C |
| ATOM | 8352 | CB  | PRO | D | 232 | 109.451 | 47.167 | 23.128 | 1.00 | 13.91 | C |
| ATOM | 8353 | CG  | PRO | D | 232 | 110.748 | 46.926 | 23.812 | 1.00 | 10.50 | C |
| ATOM | 8354 | CD  | PRO | D | 232 | 111.361 | 48.269 | 23.981 | 1.00 | 11.62 | C |
| ATOM | 8355 | C   | PRO | D | 232 | 107.867 | 48.374 | 24.792 | 1.00 | 14.01 | C |
| ATOM | 8356 | O   | PRO | D | 232 | 106.718 | 48.698 | 24.574 | 1.00 | 16.75 | O |
| ATOM | 8357 | N   | GLU | D | 233 | 108.236 | 47.923 | 25.976 | 1.00 | 16.73 | N |
| ATOM | 8358 | CA  | GLU | D | 233 | 107.317 | 47.850 | 27.124 | 1.00 | 16.30 | C |
| ATOM | 8359 | CB  | GLU | D | 233 | 108.147 | 47.776 | 28.414 | 1.00 | 16.74 | C |
| ATOM | 8360 | CG  | GLU | D | 233 | 109.582 | 47.427 | 28.072 | 1.00 | 18.11 | C |
| ATOM | 8361 | CD  | GLU | D | 233 | 110.596 | 48.073 | 28.956 | 1.00 | 20.10 | C |
| ATOM | 8362 | OE1 | GLU | D | 233 | 111.742 | 48.114 | 28.512 | 1.00 | 20.24 | O |
| ATOM | 8363 | OE2 | GLU | D | 233 | 110.290 | 48.522 | 30.079 | 1.00 | 27.25 | O |
| ATOM | 8364 | C   | GLU | D | 233 | 106.477 | 49.133 | 27.181 | 1.00 | 16.83 | C |
| ATOM | 8365 | O   | GLU | D | 233 | 105.322 | 49.109 | 27.524 | 1.00 | 18.68 | O |
| ATOM | 8366 | N   | VAL | D | 234 | 107.091 | 50.264 | 26.876 | 1.00 | 17.65 | N |
| ATOM | 8367 | CA  | VAL | D | 234 | 106.395 | 51.535 | 26.918 | 1.00 | 20.00 | C |
| ATOM | 8368 | CB  | VAL | D | 234 | 107.387 | 52.701 | 27.040 | 1.00 | 18.85 | C |
| ATOM | 8369 | CG1 | VAL | D | 234 | 106.670 | 54.010 | 26.981 | 1.00 | 19.60 | C |
| ATOM | 8370 | CG2 | VAL | D | 234 | 108.121 | 52.593 | 28.342 | 1.00 | 19.75 | C |

FIG. 2A-182

| ATOM | 8371 | C | VAL | D | 234 | 105.514 | 51.737 | 25.700 | 1.00 | 22.00 | C |
| --- | --- | --- | --- | --- | --- | --- | --- | --- | --- | --- | --- |
| ATOM | 8372 | O | VAL | D | 234 | 104.432 | 52.302 | 25.798 | 1.00 | 23.27 | O |
| ATOM | 8373 | N | LEU | D | 235 | 105.958 | 51.275 | 24.548 | 1.00 | 24.89 | N |
| ATOM | 8374 | CA | LEU | D | 235 | 105.147 | 51.437 | 23.372 | 1.00 | 29.26 | C |
| ATOM | 8375 | CB | LEU | D | 235 | 105.871 | 50.943 | 22.132 | 1.00 | 27.37 | C |
| ATOM | 8376 | CG | LEU | D | 235 | 106.814 | 52.011 | 21.617 | 1.00 | 28.44 | C |
| ATOM | 8377 | CD1 | LEU | D | 235 | 107.302 | 51.664 | 20.243 | 1.00 | 33.10 | C |
| ATOM | 8378 | CD2 | LEU | D | 235 | 106.078 | 53.331 | 21.589 | 1.00 | 32.67 | C |
| ATOM | 8379 | C | LEU | D | 235 | 103.834 | 50.718 | 23.525 | 1.00 | 34.40 | C |
| ATOM | 8380 | O | LEU | D | 235 | 102.878 | 51.059 | 22.848 | 1.00 | 36.88 | O |
| ATOM | 8381 | N | GLY | D | 236 | 103.761 | 49.728 | 24.408 | 1.00 | 39.09 | N |
| ATOM | 8382 | CA | GLY | D | 236 | 102.493 | 49.036 | 24.574 | 1.00 | 44.08 | C |
| ATOM | 8383 | C | GLY | D | 236 | 102.414 | 47.798 | 25.459 | 1.00 | 47.30 | C |
| ATOM | 8384 | O | GLY | D | 236 | 103.323 | 47.471 | 26.213 | 1.00 | 47.80 | O |
| ATOM | 8385 | N | PRO | D | 237 | 101.288 | 47.079 | 25.374 | 1.00 | 49.26 | N |
| ATOM | 8386 | CA | PRO | D | 237 | 100.992 | 45.865 | 26.129 | 1.00 | 49.83 | C |
| ATOM | 8387 | CB | PRO | D | 237 | 99.478 | 45.679 | 26.163 | 1.00 | 51.07 | C |
| ATOM | 8388 | CG | PRO | D | 237 | 98.834 | 46.927 | 25.571 | 1.00 | 51.90 | C |
| ATOM | 8389 | CD | PRO | D | 237 | 100.057 | 47.566 | 24.766 | 1.00 | 49.42 | C |
| ATOM | 8390 | C | PRO | D | 237 | 101.660 | 44.632 | 25.513 | 1.00 | 50.22 | C |
| ATOM | 8391 | O | PRO | D | 237 | 102.821 | 44.327 | 25.754 | 1.00 | 49.39 | O |
| ATOM | 8392 | N | ALA | D | 238 | 100.865 | 43.882 | 24.726 | 1.00 | 51.06 | N |
| ATOM | 8393 | CA | ALA | D | 238 | 101.398 | 42.668 | 24.113 | 1.00 | 52.64 | C |
| ATOM | 8394 | CB | ALA | D | 238 | 102.576 | 43.067 | 23.223 | 1.00 | 51.72 | C |
| ATOM | 8395 | C | ALA | D | 238 | 101.857 | 41.656 | 25.166 | 1.00 | 53.32 | C |
| ATOM | 8396 | O | ALA | D | 238 | 102.752 | 41.904 | 25.963 | 1.00 | 53.91 | O |
| ATOM | 8397 | N | ALA | D | 239 | 101.175 | 40.492 | 25.178 | 1.00 | 53.70 | N |
| ATOM | 8398 | CA | ALA | D | 239 | 101.501 | 39.473 | 26.171 | 1.00 | 53.07 | C |
| ATOM | 8399 | CB | ALA | D | 239 | 100.238 | 38.663 | 26.457 | 1.00 | 52.93 | C |
| ATOM | 8400 | C | ALA | D | 239 | 102.621 | 38.546 | 25.692 | 1.00 | 52.97 | C |
| ATOM | 8401 | O | ALA | D | 239 | 103.784 | 38.916 | 25.610 | 1.00 | 53.86 | O |
| ATOM | 8402 | N | TYR | D | 240 | 102.244 | 37.282 | 25.410 | 1.00 | 51.58 | N |
| ATOM | 8403 | CA | TYR | D | 240 | 103.240 | 36.317 | 24.952 | 1.00 | 50.44 | C |
| ATOM | 8404 | CB | TYR | D | 240 | 103.806 | 35.597 | 26.176 | 1.00 | 51.83 | C |
| ATOM | 8405 | CG | TYR | D | 240 | 104.520 | 36.570 | 27.043 | 1.00 | 54.15 | C |
| ATOM | 8406 | CD1 | TYR | D | 240 | 103.894 | 37.077 | 28.178 | 1.00 | 57.11 | C |
| ATOM | 8407 | CE1 | TYR | D | 240 | 104.540 | 38.013 | 28.971 | 1.00 | 57.65 | C |
| ATOM | 8408 | CZ | TYR | D | 240 | 105.814 | 38.457 | 28.618 | 1.00 | 58.54 | C |
| ATOM | 8409 | OH | TYR | D | 240 | 106.437 | 39.411 | 29.396 | 1.00 | 61.37 | O |
| ATOM | 8410 | CE2 | TYR | D | 240 | 106.441 | 37.951 | 27.496 | 1.00 | 60.02 | C |
| ATOM | 8411 | CD2 | TYR | D | 240 | 105.799 | 37.008 | 26.707 | 1.00 | 56.24 | C |
| ATOM | 8412 | C | TYR | D | 240 | 102.638 | 35.300 | 23.983 | 1.00 | 49.23 | C |
| ATOM | 8413 | O | TYR | D | 240 | 103.060 | 34.153 | 23.901 | 1.00 | 50.13 | O |
| ATOM | 8414 | N | ASP | D | 241 | 101.656 | 35.711 | 23.191 | 1.00 | 45.84 | N |
| ATOM | 8415 | CA | ASP | D | 241 | 101.096 | 34.780 | 22.241 | 1.00 | 41.86 | C |
| ATOM | 8416 | CB | ASP | D | 241 | 99.790 | 35.318 | 21.685 | 1.00 | 42.73 | C |

FIG. 2A-183

| ATOM | 8417 | CG | ASP | D | 241 | 98.700 | 35.371 | 22.738 | 1.00 | 47.26 | C |
| ATOM | 8418 | OD1 | ASP | D | 241 | 98.318 | 34.287 | 23.238 | 1.00 | 49.94 | O |
| ATOM | 8419 | OD2 | ASP | D | 241 | 98.229 | 36.489 | 23.074 | 1.00 | 51.95 | O |
| ATOM | 8420 | C | ASP | D | 241 | 102.072 | 34.495 | 21.121 | 1.00 | 38.43 | C |
| ATOM | 8421 | O | ASP | D | 241 | 102.151 | 33.368 | 20.639 | 1.00 | 36.24 | O |
| ATOM | 8422 | N | LYS | D | 242 | 102.830 | 35.511 | 20.717 | 1.00 | 33.98 | N |
| ATOM | 8423 | CA | LYS | D | 242 | 103.793 | 35.358 | 19.634 | 1.00 | 32.08 | C |
| ATOM | 8424 | CB | LYS | D | 242 | 104.537 | 36.652 | 19.414 | 1.00 | 30.15 | C |
| ATOM | 8425 | CG | LYS | D | 242 | 103.898 | 37.551 | 18.414 | 1.00 | 28.65 | C |
| ATOM | 8426 | CD | LYS | D | 242 | 104.298 | 38.960 | 18.644 | 1.00 | 28.33 | C |
| ATOM | 8427 | CE | LYS | D | 242 | 103.811 | 39.807 | 17.523 | 1.00 | 35.11 | C |
| ATOM | 8428 | NZ | LYS | D | 242 | 103.427 | 41.187 | 17.960 | 1.00 | 40.66 | N |
| ATOM | 8429 | C | LYS | D | 242 | 104.771 | 34.310 | 20.030 | 1.00 | 31.15 | C |
| ATOM | 8430 | O | LYS | D | 242 | 105.278 | 33.531 | 19.225 | 1.00 | 32.04 | O |
| ATOM | 8431 | N | SER | D | 243 | 104.996 | 34.303 | 21.325 | 1.00 | 30.03 | N |
| ATOM | 8432 | CA | SER | D | 243 | 105.928 | 33.427 | 21.989 | 1.00 | 27.60 | C |
| ATOM | 8433 | CB | SER | D | 243 | 105.900 | 33.765 | 23.460 | 1.00 | 27.29 | C |
| ATOM | 8434 | OG | SER | D | 243 | 107.122 | 33.433 | 24.027 | 1.00 | 28.52 | O |
| ATOM | 8435 | C | SER | D | 243 | 105.697 | 31.950 | 21.776 | 1.00 | 26.87 | C |
| ATOM | 8436 | O | SER | D | 243 | 106.637 | 31.184 | 21.661 | 1.00 | 25.36 | O |
| ATOM | 8437 | N | CYS | D | 244 | 104.456 | 31.515 | 21.721 | 1.00 | 25.82 | N |
| ATOM | 8438 | CA | CYS | D | 244 | 104.292 | 30.110 | 21.525 | 1.00 | 26.13 | C |
| ATOM | 8439 | CB | CYS | D | 244 | 102.944 | 29.645 | 22.014 | 1.00 | 25.47 | C |
| ATOM | 8440 | SG | CYS | D | 244 | 101.647 | 30.503 | 21.242 | 1.00 | 38.36 | S |
| ATOM | 8441 | C | CYS | D | 244 | 104.494 | 29.758 | 20.080 | 1.00 | 24.95 | C |
| ATOM | 8442 | O | CYS | D | 244 | 104.671 | 28.584 | 19.784 | 1.00 | 25.62 | O |
| ATOM | 8443 | N | ASP | D | 245 | 104.456 | 30.733 | 19.167 | 1.00 | 24.03 | N |
| ATOM | 8444 | CA | ASP | D | 245 | 104.733 | 30.405 | 17.758 | 1.00 | 21.06 | C |
| ATOM | 8445 | CB | ASP | D | 245 | 104.584 | 31.613 | 16.821 | 1.00 | 17.87 | C |
| ATOM | 8446 | CG | ASP | D | 245 | 103.126 | 31.982 | 16.511 | 1.00 | 18.21 | C |
| ATOM | 8447 | OD1 | ASP | D | 245 | 102.232 | 31.145 | 16.553 | 1.00 | 19.89 | O |
| ATOM | 8448 | OD2 | ASP | D | 245 | 102.851 | 33.134 | 16.181 | 1.00 | 21.43 | O |
| ATOM | 8449 | C | ASP | D | 245 | 106.216 | 29.955 | 17.746 | 1.00 | 20.28 | C |
| ATOM | 8450 | O | ASP | D | 245 | 106.587 | 29.027 | 17.053 | 1.00 | 20.71 | O |
| ATOM | 8451 | N | MSED | | 246 | 107.052 | 30.601 | 18.556 | 1.00 | 19.81 | N |
| ATOM | 8452 | CA | MSED | | 246 | 108.462 | 30.258 | 18.612 | 1.00 | 21.76 | C |
| ATOM | 8453 | CB | MSED | | 246 | 109.229 | 31.305 | 19.418 | 1.00 | 21.93 | C |
| ATOM | 8454 | CG | MSED | | 246 | 109.130 | 32.695 | 18.809 | 1.00 | 24.04 | C |
| ATOM | 8455 | SE | MSED | | 246 | 109.374 | 32.713 | 16.907 | 1.00 | 28.82 | S |
| ATOM | 8456 | CE | MSED | | 246 | 111.242 | 32.386 | 16.890 | 1.00 | 14.88 | C |
| ATOM | 8457 | C | MSED | | 246 | 108.701 | 28.872 | 19.176 | 1.00 | 21.15 | C |
| ATOM | 8458 | O | MSED | | 246 | 109.570 | 28.130 | 18.697 | 1.00 | 20.43 | O |
| ATOM | 8459 | N | TRP | D | 247 | 107.941 | 28.522 | 20.204 | 1.00 | 20.54 | N |
| ATOM | 8460 | CA | TRP | D | 247 | 108.051 | 27.198 | 20.779 | 1.00 | 17.53 | C |
| ATOM | 8461 | CB | TRP | D | 247 | 107.053 | 27.055 | 21.914 | 1.00 | 17.76 | C |
| ATOM | 8462 | CG | TRP | D | 247 | 106.975 | 25.672 | 22.403 | 1.00 | 15.68 | C |

FIG. 2A-184

| ATOM | 8463 | CD1 | TRP | D | 247 | 106.225 | 24.662 | 21.889 | 1.00 | 13.77 | C |
|------|------|-----|-----|---|-----|---------|--------|--------|------|-------|---|
| ATOM | 8464 | NE1 | TRP | D | 247 | 106.506 | 23.497 | 22.531 | 1.00 | 10.96 | N |
| ATOM | 8465 | CE2 | TRP | D | 247 | 107.447 | 23.732 | 23.494 | 1.00 | 13.81 | C |
| ATOM | 8466 | CD2 | TRP | D | 247 | 107.769 | 25.093 | 23.441 | 1.00 | 16.82 | C |
| ATOM | 8467 | CE3 | TRP | D | 247 | 108.728 | 25.598 | 24.328 | 1.00 | 15.51 | C |
| ATOM | 8468 | CZ3 | TRP | D | 247 | 109.311 | 24.754 | 25.212 | 1.00 | 16.65 | C |
| ATOM | 8469 | CH2 | TRP | D | 247 | 108.974 | 23.398 | 25.248 | 1.00 | 18.81 | C |
| ATOM | 8470 | CZ2 | TRP | D | 247 | 108.041 | 22.870 | 24.394 | 1.00 | 16.42 | C |
| ATOM | 8471 | C   | TRP | D | 247 | 107.737 | 26.184 | 19.656 | 1.00 | 17.69 | C |
| ATOM | 8472 | O   | TRP | D | 247 | 108.446 | 25.201 | 19.442 | 1.00 | 15.66 | O |
| ATOM | 8473 | N   | SER | D | 248 | 106.685 | 26.431 | 18.901 | 1.00 | 20.13 | N |
| ATOM | 8474 | CA  | SER | D | 248 | 106.365 | 25.498 | 17.845 | 1.00 | 23.17 | C |
| ATOM | 8475 | CB  | SER | D | 248 | 105.119 | 25.943 | 17.131 | 1.00 | 22.66 | C |
| ATOM | 8476 | OG  | SER | D | 248 | 104.034 | 25.669 | 17.984 | 1.00 | 25.80 | O |
| ATOM | 8477 | C   | SER | D | 248 | 107.494 | 25.324 | 16.861 | 1.00 | 23.83 | C |
| ATOM | 8478 | O   | SER | D | 248 | 107.785 | 24.214 | 16.429 | 1.00 | 25.53 | O |
| ATOM | 8479 | N   | LEU | D | 249 | 108.134 | 26.423 | 16.507 | 1.00 | 23.03 | N |
| ATOM | 8480 | CA  | LEU | D | 249 | 109.227 | 26.366 | 15.568 | 1.00 | 22.37 | C |
| ATOM | 8481 | CB  | LEU | D | 249 | 109.802 | 27.757 | 15.364 | 1.00 | 20.56 | C |
| ATOM | 8482 | CG  | LEU | D | 249 | 109.785 | 28.190 | 13.911 | 1.00 | 21.21 | C |
| ATOM | 8483 | CD1 | LEU | D | 249 | 108.400 | 28.096 | 13.371 | 1.00 | 22.59 | C |
| ATOM | 8484 | CD2 | LEU | D | 249 | 110.317 | 29.600 | 13.800 | 1.00 | 24.86 | C |
| ATOM | 8485 | C   | LEU | D | 249 | 110.284 | 25.443 | 16.146 | 1.00 | 22.80 | C |
| ATOM | 8486 | O   | LEU | D | 249 | 110.864 | 24.617 | 15.425 | 1.00 | 24.34 | O |
| ATOM | 8487 | N   | GLY | D | 250 | 110.526 | 25.569 | 17.449 | 1.00 | 21.51 | N |
| ATOM | 8488 | CA  | GLY | D | 250 | 111.536 | 24.742 | 18.060 | 1.00 | 20.03 | C |
| ATOM | 8489 | C   | GLY | D | 250 | 111.192 | 23.280 | 17.903 | 1.00 | 21.08 | C |
| ATOM | 8490 | O   | GLY | D | 250 | 112.079 | 22.433 | 17.738 | 1.00 | 21.93 | O |
| ATOM | 8491 | N   | VAL | D | 251 | 109.897 | 22.978 | 17.945 | 1.00 | 19.34 | N |
| ATOM | 8492 | CA  | VAL | D | 251 | 109.428 | 21.595 | 17.841 | 1.00 | 16.86 | C |
| ATOM | 8493 | CB  | VAL | D | 251 | 107.980 | 21.426 | 18.431 | 1.00 | 16.10 | C |
| ATOM | 8494 | CG1 | VAL | D | 251 | 107.444 | 20.054 | 18.167 | 1.00 | 6.86  | C |
| ATOM | 8495 | CG2 | VAL | D | 251 | 108.009 | 21.653 | 19.943 | 1.00 | 16.09 | C |
| ATOM | 8496 | C   | VAL | D | 251 | 109.471 | 21.077 | 16.426 | 1.00 | 18.65 | C |
| ATOM | 8497 | O   | VAL | D | 251 | 109.730 | 19.907 | 16.216 | 1.00 | 21.48 | O |
| ATOM | 8498 | N   | ILE | D | 252 | 109.242 | 21.933 | 15.443 | 1.00 | 17.90 | N |
| ATOM | 8499 | CA  | ILE | D | 252 | 109.306 | 21.478 | 14.051 | 1.00 | 17.61 | C |
| ATOM | 8500 | CB  | ILE | D | 252 | 108.646 | 22.511 | 13.078 | 1.00 | 16.82 | C |
| ATOM | 8501 | CG1 | ILE | D | 252 | 107.136 | 22.551 | 13.323 | 1.00 | 15.53 | C |
| ATOM | 8502 | CD1 | ILE | D | 252 | 106.414 | 23.575 | 12.499 | 1.00 | 15.38 | C |
| ATOM | 8503 | CG2 | ILE | D | 252 | 108.929 | 22.144 | 11.661 | 1.00 | 12.53 | C |
| ATOM | 8504 | C   | ILE | D | 252 | 110.762 | 21.222 | 13.628 | 1.00 | 18.67 | C |
| ATOM | 8505 | O   | ILE | D | 252 | 111.089 | 20.174 | 13.069 | 1.00 | 18.36 | O |
| ATOM | 8506 | N   | MSED |   | 253 | 111.634 | 22.176 | 13.921 | 1.00 | 20.06 | N |
| ATOM | 8507 | CA  | MSED |   | 253 | 113.040 | 22.049 | 13.574 | 1.00 | 21.16 | C |
| ATOM | 8508 | CB  | MSED |   | 253 | 113.808 | 23.216 | 14.191 | 1.00 | 20.79 | C |

FIG. 2A-185

| ATOM | 8509 | CG | MSED | | 253 | 114.985 | 23.626 | 13.372 | 1.00 | 26.49 | C |
|---|---|---|---|---|---|---|---|---|---|---|---|
| ATOM | 8510 | SE | MSED | | 253 | 116.033 | 24.849 | 14.325 | 1.00 | 28.90 | S |
| ATOM | 8511 | CE | MSED | | 253 | 115.601 | 26.483 | 13.435 | 1.00 | 37.40 | C |
| ATOM | 8512 | C | MSED | | 253 | 113.619 | 20.702 | 14.067 | 1.00 | 21.31 | C |
| ATOM | 8513 | O | MSED | | 253 | 114.259 | 19.959 | 13.324 | 1.00 | 21.68 | O |
| ATOM | 8514 | N | TYR | D | 254 | 113.381 | 20.416 | 15.340 | 1.00 | 21.94 | N |
| ATOM | 8515 | CA | TYR | D | 254 | 113.822 | 19.203 | 15.988 | 1.00 | 21.98 | C |
| ATOM | 8516 | CB | TYR | D | 254 | 113.289 | 19.219 | 17.415 | 1.00 | 20.76 | C |
| ATOM | 8517 | CG | TYR | D | 254 | 113.700 | 18.045 | 18.258 | 1.00 | 19.96 | C |
| ATOM | 8518 | CD1 | TYR | D | 254 | 113.176 | 16.792 | 18.032 | 1.00 | 23.78 | C |
| ATOM | 8519 | CE1 | TYR | D | 254 | 113.547 | 15.719 | 18.783 | 1.00 | 22.18 | C |
| ATOM | 8520 | CZ | TYR | D | 254 | 114.454 | 15.877 | 19.773 | 1.00 | 24.33 | C |
| ATOM | 8521 | OH | TYR | D | 254 | 114.838 | 14.768 | 20.498 | 1.00 | 26.08 | O |
| ATOM | 8522 | CE2 | TYR | D | 254 | 114.992 | 17.107 | 20.023 | 1.00 | 20.78 | C |
| ATOM | 8523 | CD2 | TYR | D | 254 | 114.613 | 18.183 | 19.271 | 1.00 | 18.07 | C |
| ATOM | 8524 | C | TYR | D | 254 | 113.284 | 17.999 | 15.211 | 1.00 | 23.56 | C |
| ATOM | 8525 | O | TYR | D | 254 | 114.044 | 17.198 | 14.653 | 1.00 | 24.54 | O |
| ATOM | 8526 | N | ILE | D | 255 | 111.969 | 17.873 | 15.158 | 1.00 | 24.16 | N |
| ATOM | 8527 | CA | ILE | D | 255 | 111.386 | 16.769 | 14.433 | 1.00 | 24.80 | C |
| ATOM | 8528 | CB | ILE | D | 255 | 109.871 | 16.867 | 14.378 | 1.00 | 25.30 | C |
| ATOM | 8529 | CG1 | ILE | D | 255 | 109.292 | 16.824 | 15.796 | 1.00 | 26.62 | C |
| ATOM | 8530 | CD1 | ILE | D | 255 | 107.850 | 17.242 | 15.889 | 1.00 | 18.51 | C |
| ATOM | 8531 | CG2 | ILE | D | 255 | 109.334 | 15.730 | 13.543 | 1.00 | 25.65 | C |
| ATOM | 8532 | C | ILE | D | 255 | 111.905 | 16.733 | 13.007 | 1.00 | 24.85 | C |
| ATOM | 8533 | O | ILE | D | 255 | 111.853 | 15.698 | 12.364 | 1.00 | 27.61 | O |
| ATOM | 8534 | N | LEU | D | 256 | 112.403 | 17.855 | 12.501 | 1.00 | 23.61 | N |
| ATOM | 8535 | CA | LEU | D | 256 | 112.931 | 17.889 | 11.132 | 1.00 | 22.96 | C |
| ATOM | 8536 | CB | LEU | D | 256 | 112.877 | 19.303 | 10.545 | 1.00 | 22.86 | C |
| ATOM | 8537 | CG | LEU | D | 256 | 112.142 | 19.649 | 9.244 | 1.00 | 24.03 | C |
| ATOM | 8538 | CD1 | LEU | D | 256 | 112.934 | 20.754 | 8.564 | 1.00 | 20.67 | C |
| ATOM | 8539 | CD2 | LEU | D | 256 | 112.002 | 18.464 | 8.326 | 1.00 | 22.64 | C |
| ATOM | 8540 | C | LEU | D | 256 | 114.387 | 17.436 | 11.097 | 1.00 | 23.17 | C |
| ATOM | 8541 | O | LEU | D | 256 | 114.911 | 17.171 | 10.028 | 1.00 | 22.14 | O |
| ATOM | 8542 | N | LEU | D | 257 | 115.057 | 17.376 | 12.247 | 1.00 | 23.67 | N |
| ATOM | 8543 | CA | LEU | D | 257 | 116.456 | 16.953 | 12.236 | 1.00 | 25.38 | C |
| ATOM | 8544 | CB | LEU | D | 257 | 117.339 | 17.901 | 13.061 | 1.00 | 24.37 | C |
| ATOM | 8545 | CG | LEU | D | 257 | 117.527 | 19.343 | 12.576 | 1.00 | 23.85 | C |
| ATOM | 8546 | CD1 | LEU | D | 257 | 118.590 | 20.008 | 13.375 | 1.00 | 20.04 | C |
| ATOM | 8547 | CD2 | LEU | D | 257 | 117.916 | 19.368 | 11.136 | 1.00 | 19.90 | C |
| ATOM | 8548 | C | LEU | D | 257 | 116.672 | 15.527 | 12.734 | 1.00 | 27.95 | C |
| ATOM | 8549 | O | LEU | D | 257 | 117.799 | 15.027 | 12.690 | 1.00 | 28.24 | O |
| ATOM | 8550 | N | CYS | D | 258 | 115.610 | 14.859 | 13.182 | 1.00 | 29.74 | N |
| ATOM | 8551 | CA | CYS | D | 258 | 115.780 | 13.502 | 13.695 | 1.00 | 31.23 | C |
| ATOM | 8552 | CB | CYS | D | 258 | 115.916 | 13.531 | 15.222 | 1.00 | 30.84 | C |
| ATOM | 8553 | SG | CYS | D | 258 | 114.305 | 13.653 | 16.030 | 1.00 | 39.67 | S |
| ATOM | 8554 | C | CYS | D | 258 | 114.649 | 12.551 | 13.320 | 1.00 | 30.87 | C |

FIG. 2A-186

| | | | | | | | | | | |
|---|---|---|---|---|---|---|---|---|---|---|
| ATOM | 8555 | O | CYS | D | 258 | 114.849 | 11.335 | 13.269 | 1.00 | 30.46 | O |
| ATOM | 8556 | N | GLY | D | 259 | 113.454 | 13.086 | 13.100 | 1.00 | 29.84 | N |
| ATOM | 8557 | CA | GLY | D | 259 | 112.354 | 12.229 | 12.713 | 1.00 | 29.24 | C |
| ATOM | 8558 | C | GLY | D | 259 | 111.291 | 12.043 | 13.752 | 1.00 | 28.97 | C |
| ATOM | 8559 | O | GLY | D | 259 | 110.210 | 11.550 | 13.430 | 1.00 | 30.13 | O |
| ATOM | 8560 | N | TYR | D | 260 | 111.587 | 12.424 | 14.994 | 1.00 | 28.67 | N |
| ATOM | 8561 | CA | TYR | D | 260 | 110.628 | 12.303 | 16.101 | 1.00 | 28.53 | C |
| ATOM | 8562 | CB | TYR | D | 260 | 110.980 | 11.090 | 16.971 | 1.00 | 27.96 | C |
| ATOM | 8563 | CG | TYR | D | 260 | 112.433 | 11.064 | 17.372 | 1.00 | 27.41 | C |
| ATOM | 8564 | CD1 | TYR | D | 260 | 112.852 | 11.617 | 18.580 | 1.00 | 25.14 | C |
| ATOM | 8565 | CE1 | TYR | D | 260 | 114.192 | 11.696 | 18.890 | 1.00 | 23.95 | C |
| ATOM | 8566 | CZ | TYR | D | 260 | 115.122 | 11.215 | 17.989 | 1.00 | 24.56 | C |
| ATOM | 8567 | OH | TYR | D | 260 | 116.456 | 11.352 | 18.253 | 1.00 | 27.67 | O |
| ATOM | 8568 | CE2 | TYR | D | 260 | 114.733 | 10.653 | 16.800 | 1.00 | 27.00 | C |
| ATOM | 8569 | CD2 | TYR | D | 260 | 113.402 | 10.578 | 16.495 | 1.00 | 26.93 | C |
| ATOM | 8570 | C | TYR | D | 260 | 110.607 | 13.560 | 16.967 | 1.00 | 28.22 | C |
| ATOM | 8571 | O | TYR | D | 260 | 111.533 | 14.356 | 16.942 | 1.00 | 28.27 | O |
| ATOM | 8572 | N | PRO | D | 261 | 109.541 | 13.744 | 17.747 | 1.00 | 28.39 | N |
| ATOM | 8573 | CA | PRO | D | 261 | 109.308 | 14.871 | 18.654 | 1.00 | 28.99 | C |
| ATOM | 8574 | CB | PRO | D | 261 | 107.831 | 14.734 | 18.980 | 1.00 | 28.84 | C |
| ATOM | 8575 | CG | PRO | D | 261 | 107.631 | 13.256 | 18.967 | 1.00 | 28.91 | C |
| ATOM | 8576 | CD | PRO | D | 261 | 108.375 | 12.849 | 17.724 | 1.00 | 28.58 | C |
| ATOM | 8577 | C | PRO | D | 261 | 110.168 | 14.820 | 19.899 | 1.00 | 29.09 | C |
| ATOM | 8578 | O | PRO | D | 261 | 110.614 | 13.767 | 20.306 | 1.00 | 29.66 | O |
| ATOM | 8579 | N | PRO | D | 262 | 110.397 | 15.961 | 20.538 | 1.00 | 29.65 | N |
| ATOM | 8580 | CA | PRO | D | 262 | 111.220 | 15.979 | 21.748 | 1.00 | 30.09 | C |
| ATOM | 8581 | CB | PRO | D | 262 | 111.638 | 17.443 | 21.874 | 1.00 | 31.22 | C |
| ATOM | 8582 | CG | PRO | D | 262 | 111.333 | 18.043 | 20.536 | 1.00 | 31.27 | C |
| ATOM | 8583 | CD | PRO | D | 262 | 110.101 | 17.321 | 20.085 | 1.00 | 29.77 | C |
| ATOM | 8584 | C | PRO | D | 262 | 110.464 | 15.519 | 22.986 | 1.00 | 30.80 | C |
| ATOM | 8585 | O | PRO | D | 262 | 111.061 | 15.007 | 23.936 | 1.00 | 32.57 | O |
| ATOM | 8586 | N | PHE | D | 263 | 109.151 | 15.716 | 22.981 | 1.00 | 31.48 | N |
| ATOM | 8587 | CA | PHE | D | 263 | 108.321 | 15.325 | 24.110 | 1.00 | 32.83 | C |
| ATOM | 8588 | CB | PHE | D | 263 | 107.610 | 16.539 | 24.679 | 1.00 | 31.19 | C |
| ATOM | 8589 | CG | PHE | D | 263 | 108.539 | 17.615 | 25.095 | 1.00 | 27.92 | C |
| ATOM | 8590 | CD1 | PHE | D | 263 | 108.697 | 18.747 | 24.322 | 1.00 | 24.11 | C |
| ATOM | 8591 | CE1 | PHE | D | 263 | 109.584 | 19.719 | 24.692 | 1.00 | 23.38 | C |
| ATOM | 8592 | CZ | PHE | D | 263 | 110.323 | 19.569 | 25.844 | 1.00 | 25.25 | C |
| ATOM | 8593 | CE2 | PHE | D | 263 | 110.174 | 18.450 | 26.619 | 1.00 | 27.00 | C |
| ATOM | 8594 | CD2 | PHE | D | 263 | 109.288 | 17.482 | 26.247 | 1.00 | 28.86 | C |
| ATOM | 8595 | C | PHE | D | 263 | 107.306 | 14.279 | 23.714 | 1.00 | 35.47 | C |
| ATOM | 8596 | O | PHE | D | 263 | 106.693 | 14.367 | 22.659 | 1.00 | 36.09 | O |
| ATOM | 8597 | N | TYR | D | 264 | 107.117 | 13.297 | 24.582 | 1.00 | 38.64 | N |
| ATOM | 8598 | CA | TYR | D | 264 | 106.192 | 12.207 | 24.316 | 1.00 | 42.11 | C |
| ATOM | 8599 | CB | TYR | D | 264 | 106.923 | 11.118 | 23.541 | 1.00 | 43.28 | C |
| ATOM | 8600 | CG | TYR | D | 264 | 108.159 | 10.604 | 24.253 | 1.00 | 49.24 | C |

FIG. 2A-187

| ATOM | 8601 | CD1 | TYR | D | 264 | 109.167 | 11.475 | 24.667 | 1.00 | 51.58 | C |
|---|---|---|---|---|---|---|---|---|---|---|---|
| ATOM | 8602 | CE1 | TYR | D | 264 | 110.312 | 10.996 | 25.288 | 1.00 | 53.88 | C |
| ATOM | 8603 | CZ | TYR | D | 264 | 110.458 | 9.633 | 25.501 | 1.00 | 56.24 | C |
| ATOM | 8604 | OH | TYR | D | 264 | 111.593 | 9.120 | 26.109 | 1.00 | 58.03 | O |
| ATOM | 8605 | CE2 | TYR | D | 264 | 109.467 | 8.761 | 25.099 | 1.00 | 54.70 | C |
| ATOM | 8606 | CD2 | TYR | D | 264 | 108.332 | 9.245 | 24.483 | 1.00 | 52.21 | C |
| ATOM | 8607 | C | TYR | D | 264 | 105.671 | 11.627 | 25.619 | 1.00 | 42.70 | C |
| ATOM | 8608 | O | TYR | D | 264 | 105.932 | 12.162 | 26.697 | 1.00 | 43.03 | O |
| ATOM | 8609 | N | SER | D | 265 | 104.933 | 10.523 | 25.518 | 1.00 | 44.46 | N |
| ATOM | 8610 | CA | SER | D | 265 | 104.394 | 9.872 | 26.710 | 1.00 | 45.56 | C |
| ATOM | 8611 | CB | SER | D | 265 | 102.979 | 9.361 | 26.447 | 1.00 | 46.54 | C |
| ATOM | 8612 | OG | SER | D | 265 | 102.232 | 9.355 | 27.658 | 1.00 | 48.78 | O |
| ATOM | 8613 | C | SER | D | 265 | 105.286 | 8.710 | 27.139 | 1.00 | 44.81 | C |
| ATOM | 8614 | O | SER | D | 265 | 105.653 | 7.854 | 26.323 | 1.00 | 44.49 | O |
| ATOM | 8615 | N | ASN | D | 266 | 105.634 | 8.677 | 28.420 | 1.00 | 44.01 | N |
| ATOM | 8616 | CA | ASN | D | 266 | 106.499 | 7.621 | 28.917 | 1.00 | 44.52 | C |
| ATOM | 8617 | CB | ASN | D | 266 | 107.961 | 7.985 | 28.693 | 1.00 | 44.54 | C |
| ATOM | 8618 | CG | ASN | D | 266 | 108.815 | 6.778 | 28.365 | 1.00 | 46.82 | C |
| ATOM | 8619 | OD1 | ASN | D | 266 | 108.833 | 6.319 | 27.224 | 1.00 | 47.62 | O |
| ATOM | 8620 | ND2 | ASN | D | 266 | 109.513 | 6.247 | 29.361 | 1.00 | 46.51 | N |
| ATOM | 8621 | C | ASN | D | 266 | 106.286 | 7.379 | 30.396 | 1.00 | 44.71 | C |
| ATOM | 8622 | O | ASN | D | 266 | 106.978 | 7.954 | 31.231 | 1.00 | 44.43 | O |
| ATOM | 8623 | N | HIS | D | 267 | 105.332 | 6.522 | 30.725 | 1.00 | 45.87 | N |
| ATOM | 8624 | CA | HIS | D | 267 | 105.063 | 6.212 | 32.124 | 1.00 | 47.46 | C |
| ATOM | 8625 | CB | HIS | D | 267 | 103.663 | 5.614 | 32.276 | 1.00 | 48.86 | C |
| ATOM | 8626 | CG | HIS | D | 267 | 102.577 | 6.642 | 32.265 | 1.00 | 54.67 | C |
| ATOM | 8627 | ND1 | HIS | D | 267 | 102.518 | 7.667 | 33.184 | 1.00 | 58.10 | N |
| ATOM | 8628 | CE1 | HIS | D | 267 | 101.489 | 8.449 | 32.909 | 1.00 | 59.25 | C |
| ATOM | 8629 | NE2 | HIS | D | 267 | 100.875 | 7.962 | 31.844 | 1.00 | 60.79 | N |
| ATOM | 8630 | CD2 | HIS | D | 267 | 101.534 | 6.831 | 31.424 | 1.00 | 59.13 | C |
| ATOM | 8631 | C | HIS | D | 267 | 106.112 | 5.267 | 32.697 | 1.00 | 45.97 | C |
| ATOM | 8632 | O | HIS | D | 267 | 106.211 | 5.091 | 33.908 | 1.00 | 45.70 | O |
| ATOM | 8633 | N | GLY | D | 268 | 106.897 | 4.664 | 31.817 | 1.00 | 44.52 | N |
| ATOM | 8634 | CA | GLY | D | 268 | 107.925 | 3.761 | 32.272 | 1.00 | 42.64 | C |
| ATOM | 8635 | C | GLY | D | 268 | 109.032 | 4.529 | 32.953 | 1.00 | 41.28 | C |
| ATOM | 8636 | O | GLY | D | 268 | 109.900 | 3.940 | 33.595 | 1.00 | 41.48 | O |
| ATOM | 8637 | N | LEU | D | 269 | 109.008 | 5.851 | 32.816 | 1.00 | 39.96 | N |
| ATOM | 8638 | CA | LEU | D | 269 | 110.028 | 6.685 | 33.426 | 1.00 | 39.14 | C |
| ATOM | 8639 | CB | LEU | D | 269 | 109.948 | 8.107 | 32.871 | 1.00 | 38.78 | C |
| ATOM | 8640 | CG | LEU | D | 269 | 110.409 | 8.258 | 31.416 | 1.00 | 40.00 | C |
| ATOM | 8641 | CD1 | LEU | D | 269 | 110.151 | 9.667 | 30.900 | 1.00 | 39.24 | C |
| ATOM | 8642 | CD2 | LEU | D | 269 | 111.887 | 7.917 | 31.336 | 1.00 | 41.75 | C |
| ATOM | 8643 | C | LEU | D | 269 | 109.891 | 6.709 | 34.943 | 1.00 | 39.18 | C |
| ATOM | 8644 | O | LEU | D | 269 | 108.946 | 6.150 | 35.507 | 1.00 | 39.25 | O |
| ATOM | 8645 | N | ALA | D | 270 | 110.873 | 7.329 | 35.596 | 1.00 | 39.04 | N |
| ATOM | 8646 | CA | ALA | D | 270 | 110.900 | 7.475 | 37.051 | 1.00 | 38.60 | C |

FIG. 2A-188

| ATOM | 8647 | CB | ALA | D | 270 | 112.305 | 7.228 | 37.582 | 1.00 | 38.12 | C |
|---|---|---|---|---|---|---|---|---|---|---|---|
| ATOM | 8648 | C | ALA | D | 270 | 110.490 | 8.915 | 37.303 | 1.00 | 38.08 | C |
| ATOM | 8649 | O | ALA | D | 270 | 109.570 | 9.190 | 38.059 | 1.00 | 38.21 | O |
| ATOM | 8650 | N | ILE | D | 271 | 111.182 | 9.829 | 36.638 | 1.00 | 37.21 | N |
| ATOM | 8651 | CA | ILE | D | 271 | 110.886 | 11.244 | 36.762 | 1.00 | 37.21 | C |
| ATOM | 8652 | CB | ILE | D | 271 | 112.152 | 12.103 | 36.922 | 1.00 | 37.64 | C |
| ATOM | 8653 | CG1 | ILE | D | 271 | 112.588 | 12.073 | 38.383 | 1.00 | 37.46 | C |
| ATOM | 8654 | CD1 | ILE | D | 271 | 111.431 | 11.806 | 39.356 | 1.00 | 38.03 | C |
| ATOM | 8655 | CG2 | ILE | D | 271 | 111.898 | 13.524 | 36.413 | 1.00 | 36.60 | C |
| ATOM | 8656 | C | ILE | D | 271 | 110.137 | 11.747 | 35.557 | 1.00 | 37.14 | C |
| ATOM | 8657 | O | ILE | D | 271 | 110.535 | 11.520 | 34.413 | 1.00 | 36.70 | O |
| ATOM | 8658 | N | SER | D | 272 | 109.042 | 12.437 | 35.833 | 1.00 | 36.75 | N |
| ATOM | 8659 | CA | SER | D | 272 | 108.216 | 12.991 | 34.788 | 1.00 | 35.92 | C |
| ATOM | 8660 | CB | SER | D | 272 | 108.931 | 14.173 | 34.125 | 1.00 | 36.37 | C |
| ATOM | 8661 | OG | SER | D | 272 | 109.314 | 15.169 | 35.068 | 1.00 | 39.50 | O |
| ATOM | 8662 | C | SER | D | 272 | 107.898 | 11.934 | 33.739 | 1.00 | 34.30 | C |
| ATOM | 8663 | O | SER | D | 272 | 108.531 | 11.894 | 32.682 | 1.00 | 33.02 | O |
| ATOM | 8664 | N | PRO | D | 273 | 106.944 | 11.028 | 34.036 | 1.00 | 33.21 | N |
| ATOM | 8665 | CA | PRO | D | 273 | 106.599 | 10.005 | 33.044 | 1.00 | 32.28 | C |
| ATOM | 8666 | CB | PRO | D | 273 | 105.838 | 8.963 | 33.859 | 1.00 | 31.21 | C |
| ATOM | 8667 | CG | PRO | D | 273 | 106.218 | 9.259 | 35.281 | 1.00 | 31.46 | C |
| ATOM | 8668 | CD | PRO | D | 273 | 106.266 | 10.753 | 35.308 | 1.00 | 32.33 | C |
| ATOM | 8669 | C | PRO | D | 273 | 105.674 | 10.758 | 32.094 | 1.00 | 31.80 | C |
| ATOM | 8670 | O | PRO | D | 273 | 105.633 | 10.509 | 30.890 | 1.00 | 32.01 | O |
| ATOM | 8671 | N | GLY | D | 274 | 104.955 | 11.717 | 32.673 | 1.00 | 30.86 | N |
| ATOM | 8672 | CA | GLY | D | 274 | 104.034 | 12.521 | 31.906 | 1.00 | 28.22 | C |
| ATOM | 8673 | C | GLY | D | 274 | 104.649 | 13.398 | 30.842 | 1.00 | 27.21 | C |
| ATOM | 8674 | O | GLY | D | 274 | 105.586 | 14.153 | 31.082 | 1.00 | 27.17 | O |
| ATOM | 8675 | N | MSED | | 275 | 104.089 | 13.286 | 29.650 | 1.00 | 25.82 | N |
| ATOM | 8676 | CA | MSED | | 275 | 104.518 | 14.124 | 28.542 | 1.00 | 23.64 | C |
| ATOM | 8677 | CB | MSED | | 275 | 103.727 | 13.721 | 27.300 | 1.00 | 24.01 | C |
| ATOM | 8678 | CG | MSED | | 275 | 103.761 | 14.802 | 26.215 | 1.00 | 29.98 | C |
| ATOM | 8679 | SE | MSED | | 275 | 103.267 | 14.167 | 24.607 | 1.00 | 36.64 | S |
| ATOM | 8680 | CE | MSED | | 275 | 101.704 | 15.052 | 24.464 | 1.00 | 35.90 | C |
| ATOM | 8681 | C | MSED | | 275 | 104.281 | 15.601 | 28.844 | 1.00 | 21.20 | C |
| ATOM | 8682 | O | MSED | | 275 | 105.028 | 16.484 | 28.446 | 1.00 | 22.14 | O |
| ATOM | 8683 | N | ALA | D | 276 | 103.158 | 15.853 | 29.542 | 1.00 | 19.44 | N |
| ATOM | 8684 | CA | ALA | D | 276 | 102.878 | 17.203 | 30.008 | 1.00 | 20.04 | C |
| ATOM | 8685 | CB | ALA | D | 276 | 101.495 | 17.203 | 30.655 | 1.00 | 18.82 | C |
| ATOM | 8686 | C | ALA | D | 276 | 103.928 | 17.660 | 31.021 | 1.00 | 19.41 | C |
| ATOM | 8687 | O | ALA | D | 276 | 104.410 | 18.787 | 31.000 | 1.00 | 20.42 | O |
| ATOM | 8688 | N | THR | D | 277 | 104.249 | 16.743 | 31.958 | 1.00 | 18.92 | N |
| ATOM | 8689 | CA | THR | D | 277 | 105.283 | 17.045 | 32.941 | 1.00 | 18.38 | C |
| ATOM | 8690 | CB | THR | D | 277 | 105.402 | 15.856 | 33.894 | 1.00 | 17.11 | C |
| ATOM | 8691 | OG1 | THR | D | 277 | 104.161 | 15.668 | 34.572 | 1.00 | 19.12 | O |
| ATOM | 8692 | CG2 | THR | D | 277 | 106.499 | 16.128 | 34.930 | 1.00 | 16.69 | C |

FIG. 2A-189

| | | | | | | | | | | |
|---|---|---|---|---|---|---|---|---|---|---|
| ATOM | 8693 | C | THR | D | 277 | 106.633 | 17.284 | 32.269 | 1.00 | 18.09 | C |
| ATOM | 8694 | O | THR | D | 277 | 107.412 | 18.151 | 32.649 | 1.00 | 19.52 | O |
| ATOM | 8695 | N | ARG | D | 278 | 106.918 | 16.441 | 31.261 | 1.00 | 16.94 | N |
| ATOM | 8696 | CA | ARG | D | 278 | 108.190 | 16.561 | 30.567 | 1.00 | 15.91 | C |
| ATOM | 8697 | CB | ARG | D | 278 | 108.378 | 15.321 | 29.692 | 1.00 | 15.40 | C |
| ATOM | 8698 | CG | ARG | D | 278 | 108.939 | 14.138 | 30.483 | 1.00 | 17.26 | C |
| ATOM | 8699 | CD | ARG | D | 278 | 109.912 | 13.298 | 29.650 | 1.00 | 16.85 | C |
| ATOM | 8700 | NE | ARG | D | 278 | 109.218 | 12.678 | 28.524 | 1.00 | 22.97 | N |
| ATOM | 8701 | CZ | ARG | D | 278 | 108.314 | 11.728 | 28.810 | 1.00 | 30.00 | C |
| ATOM | 8702 | NH1AR | G | D | 278 | 108.095 | 11.375 | 30.067 | 1.00 | 31.30 | N |
| ATOM | 8703 | NH2AR | G | D | 278 | 107.650 | 11.129 | 27.822 | 1.00 | 35.38 | N |
| ATOM | 8704 | C | ARG | D | 278 | 108.245 | 17.825 | 29.707 | 1.00 | 15.98 | C |
| ATOM | 8705 | O | ARG | D | 278 | 109.287 | 18.441 | 29.530 | 1.00 | 15.69 | O |
| ATOM | 8706 | N | ILE | D | 279 | 107.112 | 18.294 | 29.180 | 1.00 | 16.11 | N |
| ATOM | 8707 | CA | ILE | D | 279 | 107.053 | 19.536 | 28.418 | 1.00 | 15.67 | C |
| ATOM | 8708 | CB | ILE | D | 279 | 105.708 | 19.708 | 27.743 | 1.00 | 16.24 | C |
| ATOM | 8709 | CG1 | ILE | D | 279 | 105.623 | 18.810 | 26.518 | 1.00 | 11.74 | C |
| ATOM | 8710 | CD1 | ILE | D | 279 | 104.273 | 18.871 | 25.861 | 1.00 | 11.27 | C |
| ATOM | 8711 | CG2 | ILE | D | 279 | 105.468 | 21.170 | 27.444 | 1.00 | 12.71 | C |
| ATOM | 8712 | C | ILE | D | 279 | 107.233 | 20.723 | 29.356 | 1.00 | 17.38 | C |
| ATOM | 8713 | O | ILE | D | 279 | 108.043 | 21.611 | 29.104 | 1.00 | 17.87 | O |
| ATOM | 8714 | N | ARG | D | 280 | 106.460 | 20.742 | 30.437 | 1.00 | 17.95 | N |
| ATOM | 8715 | CA | ARG | D | 280 | 106.545 | 21.811 | 31.425 | 1.00 | 20.38 | C |
| ATOM | 8716 | CB | ARG | D | 280 | 105.591 | 21.566 | 32.585 | 1.00 | 21.42 | C |
| ATOM | 8717 | CG | ARG | D | 280 | 104.149 | 21.937 | 32.361 | 1.00 | 28.05 | C |
| ATOM | 8718 | CD | ARG | D | 280 | 103.358 | 21.732 | 33.646 | 1.00 | 34.55 | C |
| ATOM | 8719 | NE | ARG | D | 280 | 101.930 | 21.943 | 33.429 | 1.00 | 42.79 | N |
| ATOM | 8720 | CZ | ARG | D | 280 | 100.982 | 21.154 | 33.921 | 1.00 | 47.78 | C |
| ATOM | 8721 | NH1AR | G | D | 280 | 101.310 | 20.093 | 34.659 | 1.00 | 46.68 | N |
| ATOM | 8722 | NH2AR | G | D | 280 | 99.705 | 21.428 | 33.687 | 1.00 | 51.88 | N |
| ATOM | 8723 | C | ARG | D | 280 | 107.921 | 21.791 | 32.003 | 1.00 | 19.44 | C |
| ATOM | 8724 | O | ARG | D | 280 | 108.555 | 22.805 | 32.205 | 1.00 | 17.96 | O |
| ATOM | 8725 | N | MSE | D | 281 | 108.357 | 20.590 | 32.313 | 1.00 | 20.90 | N |
| ATOM | 8726 | CA | MSE | D | 281 | 109.644 | 20.393 | 32.907 | 1.00 | 23.44 | C |
| ATOM | 8727 | CB | MSE | D | 281 | 109.734 | 18.973 | 33.419 | 1.00 | 25.51 | C |
| ATOM | 8728 | CG | MSE | D | 281 | 108.779 | 18.684 | 34.515 | 1.00 | 28.41 | C |
| ATOM | 8729 | SE | MSE | D | 281 | 109.149 | 19.586 | 36.165 | 1.00 | 40.00 | S |
| ATOM | 8730 | CE | MSE | D | 281 | 110.635 | 18.656 | 36.950 | 1.00 | 33.41 | C |
| ATOM | 8731 | C | MSE | D | 281 | 110.784 | 20.675 | 31.956 | 1.00 | 24.45 | C |
| ATOM | 8732 | O | MSE | D | 281 | 111.913 | 20.818 | 32.394 | 1.00 | 25.48 | O |
| ATOM | 8733 | N | GLY | D | 282 | 110.466 | 20.771 | 30.662 | 1.00 | 25.79 | N |
| ATOM | 8734 | CA | GLY | D | 282 | 111.452 | 21.011 | 29.618 | 1.00 | 24.07 | C |
| ATOM | 8735 | C | GLY | D | 282 | 112.509 | 19.914 | 29.501 | 1.00 | 24.09 | C |
| ATOM | 8736 | O | GLY | D | 282 | 113.651 | 20.166 | 29.140 | 1.00 | 23.97 | O |
| ATOM | 8737 | N | ALA | D | 283 | 112.129 | 18.687 | 29.807 | 1.00 | 23.44 | N |
| ATOM | 8738 | CA | ALA | D | 283 | 113.080 | 17.604 | 29.766 | 1.00 | 22.48 | C |

FIG. 2A-190

| ATOM | 8739 | CB | ALA | D | 283 | 112.828 | 16.625 | 30.911 | 1.00 | 21.69 | C |
| ATOM | 8740 | C | ALA | D | 283 | 112.991 | 16.881 | 28.463 | 1.00 | 23.01 | C |
| ATOM | 8741 | O | ALA | D | 283 | 111.995 | 16.214 | 28.196 | 1.00 | 23.89 | O |
| ATOM | 8742 | N | TYR | D | 284 | 114.031 | 17.018 | 27.647 | 1.00 | 23.42 | N |
| ATOM | 8743 | CA | TYR | D | 284 | 114.104 | 16.345 | 26.362 | 1.00 | 24.24 | C |
| ATOM | 8744 | CB | TYR | D | 284 | 113.455 | 17.163 | 25.236 | 1.00 | 23.57 | C |
| ATOM | 8745 | CG | TYR | D | 284 | 114.104 | 18.489 | 24.978 | 1.00 | 21.71 | C |
| ATOM | 8746 | CD1 | TYR | D | 284 | 113.876 | 19.554 | 25.814 | 1.00 | 24.66 | C |
| ATOM | 8747 | CE1 | TYR | D | 284 | 114.478 | 20.748 | 25.614 | 1.00 | 22.41 | C |
| ATOM | 8748 | CZ | TYR | D | 284 | 115.325 | 20.904 | 24.575 | 1.00 | 20.59 | C |
| ATOM | 8749 | OH | TYR | D | 284 | 115.907 | 22.135 | 24.398 | 1.00 | 21.44 | O |
| ATOM | 8750 | CE2 | TYR | D | 284 | 115.582 | 19.868 | 23.725 | 1.00 | 21.76 | C |
| ATOM | 8751 | CD2 | TYR | D | 284 | 114.970 | 18.667 | 23.926 | 1.00 | 19.68 | C |
| ATOM | 8752 | C | TYR | D | 284 | 115.575 | 16.188 | 26.093 | 1.00 | 25.12 | C |
| ATOM | 8753 | O | TYR | D | 284 | 116.380 | 16.829 | 26.729 | 1.00 | 25.15 | O |
| ATOM | 8754 | N | GLU | D | 285 | 115.917 | 15.347 | 25.131 | 1.00 | 26.39 | N |
| ATOM | 8755 | CA | GLU | D | 285 | 117.301 | 15.096 | 24.822 | 1.00 | 27.21 | C |
| ATOM | 8756 | CB | GLU | D | 285 | 117.686 | 13.750 | 25.455 | 1.00 | 28.62 | C |
| ATOM | 8757 | CG | GLU | D | 285 | 119.170 | 13.419 | 25.391 | 1.00 | 37.62 | C |
| ATOM | 8758 | CD | GLU | D | 285 | 119.542 | 12.265 | 26.309 | 1.00 | 49.52 | C |
| ATOM | 8759 | OE1 | GLU | D | 285 | 120.663 | 11.698 | 26.162 | 1.00 | 52.03 | O |
| ATOM | 8760 | OE2 | GLU | D | 285 | 118.701 | 11.938 | 27.185 | 1.00 | 53.83 | O |
| ATOM | 8761 | C | GLU | D | 285 | 117.588 | 15.109 | 23.309 | 1.00 | 25.94 | C |
| ATOM | 8762 | O | GLU | D | 285 | 116.685 | 15.281 | 22.492 | 1.00 | 26.27 | O |
| ATOM | 8763 | N | PHE | D | 286 | 118.859 | 14.953 | 22.947 | 1.00 | 24.96 | N |
| ATOM | 8764 | CA | PHE | D | 286 | 119.271 | 14.921 | 21.560 | 1.00 | 23.89 | C |
| ATOM | 8765 | CB | PHE | D | 286 | 120.214 | 16.078 | 21.255 | 1.00 | 21.69 | C |
| ATOM | 8766 | CG | PHE | D | 286 | 119.567 | 17.448 | 21.329 | 1.00 | 18.86 | C |
| ATOM | 8767 | CD1 | PHE | D | 286 | 120.109 | 18.449 | 22.149 | 1.00 | 15.18 | C |
| ATOM | 8768 | CE1 | PHE | D | 286 | 119.602 | 19.728 | 22.157 | 1.00 | 14.82 | C |
| ATOM | 8769 | CZ | PHE | D | 286 | 118.534 | 20.027 | 21.337 | 1.00 | 16.99 | C |
| ATOM | 8770 | CE2 | PHE | D | 286 | 117.981 | 19.041 | 20.524 | 1.00 | 15.94 | C |
| ATOM | 8771 | CD2 | PHE | D | 286 | 118.490 | 17.770 | 20.524 | 1.00 | 15.50 | C |
| ATOM | 8772 | C | PHE | D | 286 | 119.997 | 13.595 | 21.373 | 1.00 | 25.19 | C |
| ATOM | 8773 | O | PHE | D | 286 | 121.204 | 13.564 | 21.146 | 1.00 | 26.64 | O |
| ATOM | 8774 | N | PRO | D | 287 | 119.263 | 12.478 | 21.457 | 1.00 | 25.07 | N |
| ATOM | 8775 | CA | PRO | D | 287 | 119.706 | 11.077 | 21.322 | 1.00 | 25.52 | C |
| ATOM | 8776 | CB | PRO | D | 287 | 118.405 | 10.301 | 21.430 | 1.00 | 25.98 | C |
| ATOM | 8777 | CG | PRO | D | 287 | 117.391 | 11.266 | 20.862 | 1.00 | 25.97 | C |
| ATOM | 8778 | CD | PRO | D | 287 | 117.795 | 12.548 | 21.527 | 1.00 | 25.06 | C |
| ATOM | 8779 | C | PRO | D | 287 | 120.530 | 10.636 | 20.089 | 1.00 | 25.81 | C |
| ATOM | 8780 | O | PRO | D | 287 | 120.342 | 11.150 | 18.979 | 1.00 | 26.08 | O |
| ATOM | 8781 | N | ASN | D | 288 | 121.435 | 9.671 | 20.317 | 1.00 | 25.36 | N |
| ATOM | 8782 | CA | ASN | D | 288 | 122.298 | 9.077 | 19.274 | 1.00 | 25.18 | C |
| ATOM | 8783 | CB | ASN | D | 288 | 123.593 | 8.498 | 19.861 | 1.00 | 25.58 | C |
| ATOM | 8784 | CG | ASN | D | 288 | 124.641 | 9.549 | 20.138 | 1.00 | 26.33 | C |

FIG. 2A-191

| ATOM | 8785 | OD1 | ASN | D | 288 | 124.984 | 10.339 | 19.265 | 1.00 | 29.28 | O |
|---|---|---|---|---|---|---|---|---|---|---|---|
| ATOM | 8786 | ND2 | ASN | D | 288 | 125.171 | 9.552 | 21.357 | 1.00 | 23.44 | N |
| ATOM | 8787 | C | ASN | D | 288 | 121.513 | 7.915 | 18.681 | 1.00 | 25.13 | C |
| ATOM | 8788 | O | ASN | D | 288 | 120.717 | 7.283 | 19.373 | 1.00 | 25.59 | O |
| ATOM | 8789 | N | PRO | D | 289 | 121.758 | 7.584 | 17.415 | 1.00 | 24.69 | N |
| ATOM | 8790 | CA | PRO | D | 289 | 122.691 | 8.169 | 16.463 | 1.00 | 24.44 | C |
| ATOM | 8791 | CB | PRO | D | 289 | 122.875 | 7.051 | 15.467 | 1.00 | 25.20 | C |
| ATOM | 8792 | CG | PRO | D | 289 | 121.476 | 6.532 | 15.361 | 1.00 | 25.23 | C |
| ATOM | 8793 | CD | PRO | D | 289 | 121.060 | 6.441 | 16.808 | 1.00 | 25.16 | C |
| ATOM | 8794 | C | PRO | D | 289 | 122.166 | 9.411 | 15.770 | 1.00 | 24.22 | C |
| ATOM | 8795 | O | PRO | D | 289 | 122.937 | 10.296 | 15.434 | 1.00 | 25.26 | O |
| ATOM | 8796 | N | GLU | D | 290 | 120.859 | 9.462 | 15.528 | 1.00 | 23.33 | N |
| ATOM | 8797 | CA | GLU | D | 290 | 120.259 | 10.599 | 14.848 | 1.00 | 22.66 | C |
| ATOM | 8798 | CB | GLU | D | 290 | 118.814 | 10.785 | 15.275 | 1.00 | 22.61 | C |
| ATOM | 8799 | CG | GLU | D | 290 | 117.922 | 9.625 | 14.977 | 1.00 | 24.13 | C |
| ATOM | 8800 | CD | GLU | D | 290 | 118.253 | 8.436 | 15.825 | 1.00 | 28.57 | C |
| ATOM | 8801 | OE1 | GLU | D | 290 | 118.752 | 8.628 | 16.963 | 1.00 | 29.99 | O |
| ATOM | 8802 | OE2 | GLU | D | 290 | 117.995 | 7.310 | 15.352 | 1.00 | 31.76 | O |
| ATOM | 8803 | C | GLU | D | 290 | 120.960 | 11.924 | 15.047 | 1.00 | 22.11 | C |
| ATOM | 8804 | O | GLU | D | 290 | 121.243 | 12.618 | 14.085 | 1.00 | 21.95 | O |
| ATOM | 8805 | N | TRP | D | 291 | 121.244 | 12.278 | 16.289 | 1.00 | 21.99 | N |
| ATOM | 8806 | CA | TRP | D | 291 | 121.871 | 13.561 | 16.550 | 1.00 | 22.28 | C |
| ATOM | 8807 | CB | TRP | D | 291 | 121.424 | 14.110 | 17.925 | 1.00 | 21.67 | C |
| ATOM | 8808 | CG | TRP | D | 291 | 119.977 | 14.497 | 17.930 | 1.00 | 20.12 | C |
| ATOM | 8809 | CD1 | TRP | D | 291 | 118.919 | 13.676 | 18.173 | 1.00 | 20.42 | C |
| ATOM | 8810 | NE1 | TRP | D | 291 | 117.745 | 14.311 | 17.868 | 1.00 | 23.69 | N |
| ATOM | 8811 | CE2 | TRP | D | 291 | 118.021 | 15.579 | 17.430 | 1.00 | 23.52 | C |
| ATOM | 8812 | CD2 | TRP | D | 291 | 119.420 | 15.736 | 17.461 | 1.00 | 21.36 | C |
| ATOM | 8813 | CE3 | TRP | D | 291 | 119.971 | 16.959 | 17.058 | 1.00 | 22.45 | C |
| ATOM | 8814 | CZ3 | TRP | D | 291 | 119.114 | 17.971 | 16.645 | 1.00 | 22.07 | C |
| ATOM | 8815 | CH2 | TRP | D | 291 | 117.731 | 17.780 | 16.625 | 1.00 | 24.18 | C |
| ATOM | 8816 | CZ2 | TRP | D | 291 | 117.164 | 16.595 | 17.013 | 1.00 | 26.10 | C |
| ATOM | 8817 | C | TRP | D | 291 | 123.372 | 13.595 | 16.437 | 1.00 | 23.10 | C |
| ATOM | 8818 | O | TRP | D | 291 | 123.938 | 14.639 | 16.145 | 1.00 | 23.94 | O |
| ATOM | 8819 | N | SER | D | 292 | 124.005 | 12.448 | 16.655 | 1.00 | 24.02 | N |
| ATOM | 8820 | CA | SER | D | 292 | 125.461 | 12.275 | 16.608 | 1.00 | 25.00 | C |
| ATOM | 8821 | CB | SER | D | 292 | 125.765 | 10.860 | 16.140 | 1.00 | 24.97 | C |
| ATOM | 8822 | OG | SER | D | 292 | 124.891 | 9.950 | 16.803 | 1.00 | 29.62 | O |
| ATOM | 8823 | C | SER | D | 292 | 126.282 | 13.264 | 15.796 | 1.00 | 24.73 | C |
| ATOM | 8824 | O | SER | D | 292 | 127.302 | 13.766 | 16.267 | 1.00 | 24.10 | O |
| ATOM | 8825 | N | GLU | D | 293 | 125.861 | 13.560 | 14.580 | 1.00 | 25.34 | N |
| ATOM | 8826 | CA | GLU | D | 293 | 126.643 | 14.498 | 13.794 | 1.00 | 26.64 | C |
| ATOM | 8827 | CB | GLU | D | 293 | 126.820 | 13.985 | 12.362 | 1.00 | 27.47 | C |
| ATOM | 8828 | CG | GLU | D | 293 | 127.831 | 12.838 | 12.212 | 1.00 | 31.27 | C |
| ATOM | 8829 | CD | GLU | D | 293 | 129.224 | 13.217 | 12.703 | 1.00 | 37.92 | C |
| ATOM | 8830 | OE1 | GLU | D | 293 | 129.740 | 14.273 | 12.262 | 1.00 | 40.17 | O |

FIG. 2A-192

| ATOM | 8831 | OE2 | GLU | D | 293 | 129.798 | 12.454 | 13.525 | 1.00 | 39.18 | O |
|---|---|---|---|---|---|---|---|---|---|---|---|
| ATOM | 8832 | C | GLU | D | 293 | 126.069 | 15.905 | 13.768 | 1.00 | 26.56 | C |
| ATOM | 8833 | O | GLU | D | 293 | 126.687 | 16.816 | 13.226 | 1.00 | 26.58 | O |
| ATOM | 8834 | N | VAL | D | 294 | 124.892 | 16.095 | 14.348 | 1.00 | 26.43 | N |
| ATOM | 8835 | CA | VAL | D | 294 | 124.283 | 17.422 | 14.365 | 1.00 | 26.95 | C |
| ATOM | 8836 | CB | VAL | D | 294 | 122.806 | 17.360 | 14.849 | 1.00 | 27.58 | C |
| ATOM | 8837 | CG1 | VAL | D | 294 | 122.151 | 18.742 | 14.675 | 1.00 | 27.68 | C |
| ATOM | 8838 | CG2 | VAL | D | 294 | 122.037 | 16.267 | 14.076 | 1.00 | 24.12 | C |
| ATOM | 8839 | C | VAL | D | 294 | 125.089 | 18.346 | 15.285 | 1.00 | 28.02 | C |
| ATOM | 8840 | O | VAL | D | 294 | 125.312 | 18.025 | 16.461 | 1.00 | 29.02 | O |
| ATOM | 8841 | N | SER | D | 295 | 125.521 | 19.485 | 14.743 | 1.00 | 28.13 | N |
| ATOM | 8842 | CA | SER | D | 295 | 126.361 | 20.466 | 15.414 | 1.00 | 28.65 | C |
| ATOM | 8843 | CB | SER | D | 295 | 126.555 | 21.651 | 14.470 | 1.00 | 28.19 | C |
| ATOM | 8844 | OG | SER | D | 295 | 125.694 | 22.716 | 14.873 | 1.00 | 32.09 | O |
| ATOM | 8845 | C | SER | D | 295 | 125.738 | 20.937 | 16.728 | 1.00 | 29.52 | C |
| ATOM | 8846 | O | SER | D | 295 | 124.533 | 20.864 | 16.945 | 1.00 | 29.40 | O |
| ATOM | 8847 | N | GLU | D | 296 | 126.620 | 21.394 | 17.635 | 1.00 | 30.42 | N |
| ATOM | 8848 | CA | GLU | D | 296 | 126.156 | 21.914 | 18.915 | 1.00 | 32.68 | C |
| ATOM | 8849 | CB | GLU | D | 296 | 127.357 | 21.948 | 19.859 | 1.00 | 33.54 | C |
| ATOM | 8850 | CG | GLU | D | 296 | 126.959 | 22.254 | 21.305 | 1.00 | 39.68 | C |
| ATOM | 8851 | CD | GLU | D | 296 | 125.868 | 21.303 | 21.734 | 1.00 | 47.41 | C |
| ATOM | 8852 | OE1 | GLU | D | 296 | 126.034 | 20.095 | 21.570 | 1.00 | 49.88 | O |
| ATOM | 8853 | OE2 | GLU | D | 296 | 124.811 | 21.786 | 22.135 | 1.00 | 47.83 | O |
| ATOM | 8854 | C | GLU | D | 296 | 125.564 | 23.318 | 18.770 | 1.00 | 32.37 | C |
| ATOM | 8855 | O | GLU | D | 296 | 124.980 | 23.883 | 19.690 | 1.00 | 34.02 | O |
| ATOM | 8856 | N | GLU | D | 297 | 125.762 | 23.912 | 17.572 | 1.00 | 31.69 | N |
| ATOM | 8857 | CA | GLU | D | 297 | 125.159 | 25.221 | 17.296 | 1.00 | 30.19 | C |
| ATOM | 8858 | CB | GLU | D | 297 | 125.903 | 25.870 | 16.132 | 1.00 | 30.58 | C |
| ATOM | 8859 | CG | GLU | D | 297 | 124.938 | 26.654 | 15.237 | 1.00 | 36.40 | C |
| ATOM | 8860 | CD | GLU | D | 297 | 125.717 | 27.566 | 14.325 | 1.00 | 42.60 | C |
| ATOM | 8861 | OE1 | GLU | D | 297 | 126.335 | 28.501 | 14.819 | 1.00 | 41.50 | O |
| ATOM | 8862 | OE2 | GLU | D | 297 | 125.686 | 27.341 | 13.114 | 1.00 | 47.60 | O |
| ATOM | 8863 | C | GLU | D | 297 | 123.679 | 25.099 | 16.922 | 1.00 | 28.16 | C |
| ATOM | 8864 | O | GLU | D | 297 | 122.876 | 26.003 | 17.129 | 1.00 | 28.83 | O |
| ATOM | 8865 | N | VAL | D | 298 | 123.308 | 23.962 | 16.346 | 1.00 | 25.88 | N |
| ATOM | 8866 | CA | VAL | D | 298 | 121.928 | 23.771 | 16.003 | 1.00 | 24.51 | C |
| ATOM | 8867 | CB | VAL | D | 298 | 121.724 | 22.608 | 15.056 | 1.00 | 24.11 | C |
| ATOM | 8868 | CG1 | VAL | D | 298 | 120.253 | 22.487 | 14.742 | 1.00 | 22.93 | C |
| ATOM | 8869 | CG2 | VAL | D | 298 | 122.489 | 22.825 | 13.787 | 1.00 | 21.67 | C |
| ATOM | 8870 | C | VAL | D | 298 | 121.220 | 23.439 | 17.292 | 1.00 | 24.63 | C |
| ATOM | 8871 | O | VAL | D | 298 | 120.153 | 23.962 | 17.580 | 1.00 | 24.60 | O |
| ATOM | 8872 | N | LYS | D | 299 | 121.835 | 22.556 | 18.070 | 1.00 | 24.25 | N |
| ATOM | 8873 | CA | LYS | D | 299 | 121.285 | 22.122 | 19.354 | 1.00 | 24.47 | C |
| ATOM | 8874 | CB | LYS | D | 299 | 122.239 | 21.128 | 20.032 | 1.00 | 23.71 | C |
| ATOM | 8875 | CG | LYS | D | 299 | 122.373 | 19.772 | 19.337 | 1.00 | 22.34 | C |
| ATOM | 8876 | CD | LYS | D | 299 | 123.371 | 18.906 | 20.079 | 1.00 | 21.11 | C |

FIG. 2A-193

| ATOM | 8877 | CE | LYS | D | 299 | 123.554 | 17.552 | 19.390 | 1.00 | 25.03 | C |
|---|---|---|---|---|---|---|---|---|---|---|---|
| ATOM | 8878 | NZ | LYS | D | 299 | 124.576 | 16.665 | 20.058 | 1.00 | 25.38 | N |
| ATOM | 8879 | C | LYS | D | 299 | 121.055 | 23.307 | 20.270 | 1.00 | 25.05 | C |
| ATOM | 8880 | O | LYS | D | 299 | 120.091 | 23.354 | 21.013 | 1.00 | 27.55 | O |
| ATOM | 8881 | N | MSED | | 300 | 121.987 | 24.316 | 20.150 | 1.00 | 24.71 | N |
| ATOM | 8882 | CA | MSED | | 300 | 121.759 | 25.384 | 21.090 | 1.00 | 26.34 | C |
| ATOM | 8883 | CB | MSED | | 300 | 123.047 | 26.179 | 21.259 | 1.00 | 28.49 | C |
| ATOM | 8884 | CG | MSED | | 300 | 123.147 | 26.944 | 22.552 | 1.00 | 37.99 | C |
| ATOM | 8885 | SE | MSED | | 300 | 122.759 | 25.791 | 24.052 | 1.00 | 61.78 | S |
| ATOM | 8886 | CE | MSED | | 300 | 120.986 | 26.522 | 24.410 | 1.00 | 52.58 | C |
| ATOM | 8887 | C | MSED | | 300 | 120.634 | 26.281 | 20.577 | 1.00 | 25.64 | C |
| ATOM | 8888 | O | MSED | | 300 | 119.927 | 26.922 | 21.360 | 1.00 | 28.30 | O |
| ATOM | 8889 | N | LEU | D | 301 | 120.355 | 26.179 | 19.239 | 1.00 | 24.06 | N |
| ATOM | 8890 | CA | LEU | D | 301 | 119.276 | 26.935 | 18.619 | 1.00 | 23.03 | C |
| ATOM | 8891 | CB | LEU | D | 301 | 119.448 | 26.925 | 17.090 | 1.00 | 22.84 | C |
| ATOM | 8892 | CG | LEU | D | 301 | 118.468 | 27.685 | 16.175 | 1.00 | 24.52 | C |
| ATOM | 8893 | CD1 | LEU | D | 301 | 118.385 | 29.152 | 16.550 | 1.00 | 24.28 | C |
| ATOM | 8894 | CD2 | LEU | D | 301 | 118.920 | 27.536 | 14.748 | 1.00 | 26.35 | C |
| ATOM | 8895 | C | LEU | D | 301 | 117.931 | 26.331 | 19.033 | 1.00 | 22.99 | C |
| ATOM | 8896 | O | LEU | D | 301 | 116.981 | 27.038 | 19.363 | 1.00 | 27.05 | O |
| ATOM | 8897 | N | ILE | D | 302 | 117.848 | 25.016 | 19.019 | 1.00 | 21.24 | N |
| ATOM | 8898 | CA | ILE | D | 302 | 116.634 | 24.365 | 19.428 | 1.00 | 20.51 | C |
| ATOM | 8899 | CB | ILE | D | 302 | 116.745 | 22.870 | 19.107 | 1.00 | 19.87 | C |
| ATOM | 8900 | CG1 | ILE | D | 302 | 116.628 | 22.742 | 17.586 | 1.00 | 17.35 | C |
| ATOM | 8901 | CD1 | ILE | D | 302 | 116.571 | 21.341 | 17.083 | 1.00 | 12.54 | C |
| ATOM | 8902 | CG2 | ILE | D | 302 | 115.742 | 22.023 | 19.930 | 1.00 | 19.02 | C |
| ATOM | 8903 | C | ILE | D | 302 | 116.443 | 24.673 | 20.911 | 1.00 | 20.72 | C |
| ATOM | 8904 | O | ILE | D | 302 | 115.335 | 24.904 | 21.394 | 1.00 | 21.91 | O |
| ATOM | 8905 | N | ARG | D | 303 | 117.525 | 24.733 | 21.646 | 1.00 | 19.82 | N |
| ATOM | 8906 | CA | ARG | D | 303 | 117.379 | 25.053 | 23.057 | 1.00 | 22.39 | C |
| ATOM | 8907 | CB | ARG | D | 303 | 118.720 | 24.878 | 23.775 | 1.00 | 20.56 | C |
| ATOM | 8908 | CG | ARG | D | 303 | 119.153 | 23.469 | 23.900 | 1.00 | 17.36 | C |
| ATOM | 8909 | CD | ARG | D | 303 | 120.378 | 23.401 | 24.737 | 1.00 | 16.89 | C |
| ATOM | 8910 | NE | ARG | D | 303 | 121.000 | 22.095 | 24.567 | 1.00 | 28.75 | N |
| ATOM | 8911 | CZ | ARG | D | 303 | 122.156 | 21.874 | 23.937 | 1.00 | 32.35 | C |
| ATOM | 8912 | NH1AR | G | D | 303 | 122.844 | 22.888 | 23.404 | 1.00 | 32.75 | N |
| ATOM | 8913 | NH2AR | G | D | 303 | 122.621 | 20.627 | 23.846 | 1.00 | 31.27 | N |
| ATOM | 8914 | C | ARG | D | 303 | 116.843 | 26.479 | 23.315 | 1.00 | 24.61 | C |
| ATOM | 8915 | O | ARG | D | 303 | 116.272 | 26.753 | 24.348 | 1.00 | 26.12 | O |
| ATOM | 8916 | N | ASN | D | 304 | 117.038 | 27.398 | 22.395 | 1.00 | 26.82 | N |
| ATOM | 8917 | CA | ASN | D | 304 | 116.563 | 28.743 | 22.649 | 1.00 | 31.39 | C |
| ATOM | 8918 | CB | ASN | D | 304 | 117.505 | 29.760 | 22.020 | 1.00 | 32.00 | C |
| ATOM | 8919 | CG | ASN | D | 304 | 118.789 | 29.878 | 22.790 | 1.00 | 36.74 | C |
| ATOM | 8920 | OD1 | ASN | D | 304 | 119.779 | 30.409 | 22.306 | 1.00 | 42.37 | O |
| ATOM | 8921 | ND2 | ASN | D | 304 | 118.774 | 29.376 | 24.016 | 1.00 | 42.31 | N |
| ATOM | 8922 | C | ASN | D | 304 | 115.158 | 28.972 | 22.165 | 1.00 | 32.39 | C |

FIG. 2A-194

| ATOM | 8923 | O | ASN | D | 304 | 114.653 | 30.097 | 22.205 | 1.00 | 36.24 | O |
|---|---|---|---|---|---|---|---|---|---|---|---|
| ATOM | 8924 | N | LEU | D | 305 | 114.533 | 27.894 | 21.705 | 1.00 | 31.80 | N |
| ATOM | 8925 | CA | LEU | D | 305 | 113.167 | 27.942 | 21.221 | 1.00 | 30.22 | C |
| ATOM | 8926 | CB | LEU | D | 305 | 113.109 | 27.405 | 19.810 | 1.00 | 30.84 | C |
| ATOM | 8927 | CG | LEU | D | 305 | 113.663 | 28.400 | 18.795 | 1.00 | 29.42 | C |
| ATOM | 8928 | CD1 | LEU | D | 305 | 113.842 | 27.665 | 17.481 | 1.00 | 31.12 | C |
| ATOM | 8929 | CD2 | LEU | D | 305 | 112.724 | 29.571 | 18.601 | 1.00 | 30.34 | C |
| ATOM | 8930 | C | LEU | D | 305 | 112.298 | 27.101 | 22.130 | 1.00 | 29.31 | C |
| ATOM | 8931 | O | LEU | D | 305 | 111.133 | 27.412 | 22.336 | 1.00 | 30.61 | O |
| ATOM | 8932 | N | LEU | D | 306 | 112.893 | 26.036 | 22.660 | 1.00 | 27.21 | N |
| ATOM | 8933 | CA | LEU | D | 306 | 112.223 | 25.107 | 23.551 | 1.00 | 26.71 | C |
| ATOM | 8934 | CB | LEU | D | 306 | 112.711 | 23.682 | 23.279 | 1.00 | 25.25 | C |
| ATOM | 8935 | CG | LEU | D | 306 | 112.243 | 23.332 | 21.866 | 1.00 | 25.85 | C |
| ATOM | 8936 | CD1 | LEU | D | 306 | 112.610 | 21.915 | 21.482 | 1.00 | 24.64 | C |
| ATOM | 8937 | CD2 | LEU | D | 306 | 110.716 | 23.549 | 21.817 | 1.00 | 26.76 | C |
| ATOM | 8938 | C | LEU | D | 306 | 112.463 | 25.513 | 24.995 | 1.00 | 26.58 | C |
| ATOM | 8939 | O | LEU | D | 306 | 112.412 | 24.698 | 25.931 | 1.00 | 26.74 | O |
| ATOM | 8940 | N | LYS | D | 307 | 112.733 | 26.800 | 25.161 | 1.00 | 25.78 | N |
| ATOM | 8941 | CA | LYS | D | 307 | 112.934 | 27.358 | 26.477 | 1.00 | 23.73 | C |
| ATOM | 8942 | CB | LYS | D | 307 | 113.452 | 28.792 | 26.383 | 1.00 | 23.64 | C |
| ATOM | 8943 | CG | LYS | D | 307 | 114.971 | 28.861 | 26.312 | 1.00 | 24.68 | C |
| ATOM | 8944 | CD | LYS | D | 307 | 115.510 | 29.291 | 27.654 | 1.00 | 32.86 | C |
| ATOM | 8945 | CE | LYS | D | 307 | 117.013 | 29.286 | 27.733 | 1.00 | 33.25 | C |
| ATOM | 8946 | NZ | LYS | D | 307 | 117.513 | 27.901 | 27.848 | 1.00 | 36.09 | N |
| ATOM | 8947 | C | LYS | D | 307 | 111.548 | 27.316 | 27.063 | 1.00 | 23.21 | C |
| ATOM | 8948 | O | LYS | D | 307 | 110.558 | 27.579 | 26.407 | 1.00 | 26.29 | O |
| ATOM | 8949 | N | THR | D | 308 | 111.481 | 26.955 | 28.317 | 1.00 | 21.84 | N |
| ATOM | 8950 | CA | THR | D | 308 | 110.222 | 26.824 | 28.989 | 1.00 | 19.96 | C |
| ATOM | 8951 | CB | THR | D | 308 | 110.406 | 25.880 | 30.146 | 1.00 | 18.46 | C |
| ATOM | 8952 | OG1 | THR | D | 308 | 109.710 | 24.676 | 29.838 | 1.00 | 21.95 | O |
| ATOM | 8953 | CG2 | THR | D | 308 | 109.954 | 26.484 | 31.445 | 1.00 | 19.43 | C |
| ATOM | 8954 | C | THR | D | 308 | 109.612 | 28.112 | 29.424 | 1.00 | 19.11 | C |
| ATOM | 8955 | O | THR | D | 308 | 108.415 | 28.216 | 29.470 | 1.00 | 21.76 | O |
| ATOM | 8956 | N | GLU | D | 309 | 110.414 | 29.108 | 29.759 | 1.00 | 18.48 | N |
| ATOM | 8957 | CA | GLU | D | 309 | 109.834 | 30.382 | 30.159 | 1.00 | 17.82 | C |
| ATOM | 8958 | CB | GLU | D | 309 | 110.722 | 31.082 | 31.172 | 1.00 | 18.50 | C |
| ATOM | 8959 | CG | GLU | D | 309 | 109.984 | 32.159 | 31.937 | 1.00 | 25.78 | C |
| ATOM | 8960 | CD | GLU | D | 309 | 108.979 | 31.575 | 32.929 | 1.00 | 38.75 | C |
| ATOM | 8961 | OE1 | GLU | D | 309 | 109.401 | 30.794 | 33.829 | 1.00 | 38.62 | O |
| ATOM | 8962 | OE2 | GLU | D | 309 | 107.767 | 31.900 | 32.809 | 1.00 | 46.55 | O |
| ATOM | 8963 | C | GLU | D | 309 | 109.728 | 31.235 | 28.897 | 1.00 | 17.38 | C |
| ATOM | 8964 | O | GLU | D | 309 | 110.719 | 31.490 | 28.240 | 1.00 | 16.54 | O |
| ATOM | 8965 | N | PRO | D | 310 | 108.521 | 31.669 | 28.536 | 1.00 | 17.50 | N |
| ATOM | 8966 | CA | PRO | D | 310 | 108.346 | 32.491 | 27.333 | 1.00 | 17.47 | C |
| ATOM | 8967 | CB | PRO | D | 310 | 106.929 | 32.991 | 27.458 | 1.00 | 18.57 | C |
| ATOM | 8968 | CG | PRO | D | 310 | 106.254 | 31.905 | 28.205 | 1.00 | 19.35 | C |

FIG. 2A-195

| ATOM | 8969 | CD | PRO | D | 310 | 107.240 | 31.429 | 29.212 | 1.00 | 16.16 | C |
|---|---|---|---|---|---|---|---|---|---|---|---|
| ATOM | 8970 | C | PRO | D | 310 | 109.321 | 33.649 | 27.180 | 1.00 | 18.10 | C |
| ATOM | 8971 | O | PRO | D | 310 | 109.940 | 33.798 | 26.132 | 1.00 | 20.90 | O |
| ATOM | 8972 | N | THR | D | 311 | 109.472 | 34.482 | 28.203 | 1.00 | 18.62 | N |
| ATOM | 8973 | CA | THR | D | 311 | 110.378 | 35.617 | 28.064 | 1.00 | 18.97 | C |
| ATOM | 8974 | CB | THR | D | 311 | 110.289 | 36.581 | 29.244 | 1.00 | 18.28 | C |
| ATOM | 8975 | OG1 | THR | D | 311 | 110.717 | 35.925 | 30.438 | 1.00 | 20.66 | O |
| ATOM | 8976 | CG2 | THR | D | 311 | 108.870 | 37.100 | 29.395 | 1.00 | 14.59 | C |
| ATOM | 8977 | C | THR | D | 311 | 111.820 | 35.201 | 27.846 | 1.00 | 21.16 | C |
| ATOM | 8978 | O | THR | D | 311 | 112.616 | 35.996 | 27.357 | 1.00 | 24.06 | O |
| ATOM | 8979 | N | GLN | D | 312 | 112.145 | 33.956 | 28.194 | 1.00 | 21.02 | N |
| ATOM | 8980 | CA | GLN | D | 312 | 113.486 | 33.407 | 27.976 | 1.00 | 21.45 | C |
| ATOM | 8981 | CB | GLN | D | 312 | 113.786 | 32.222 | 28.910 | 1.00 | 20.73 | C |
| ATOM | 8982 | CG | GLN | D | 312 | 114.775 | 32.484 | 30.023 | 1.00 | 26.21 | C |
| ATOM | 8983 | CD | GLN | D | 312 | 115.289 | 31.204 | 30.682 | 1.00 | 35.50 | C |
| ATOM | 8984 | OE1 | GLN | D | 312 | 114.547 | 30.236 | 30.892 | 1.00 | 37.33 | O |
| ATOM | 8985 | NE2 | GLN | D | 312 | 116.565 | 31.200 | 31.027 | 1.00 | 39.78 | N |
| ATOM | 8986 | C | GLN | D | 312 | 113.572 | 32.846 | 26.564 | 1.00 | 22.51 | C |
| ATOM | 8987 | O | GLN | D | 312 | 114.591 | 32.304 | 26.174 | 1.00 | 22.92 | O |
| ATOM | 8988 | N | ARG | D | 313 | 112.520 | 32.970 | 25.775 | 1.00 | 23.47 | N |
| ATOM | 8989 | CA | ARG | D | 313 | 112.544 | 32.336 | 24.462 | 1.00 | 23.87 | C |
| ATOM | 8990 | CB | ARG | D | 313 | 111.208 | 31.651 | 24.242 | 1.00 | 24.43 | C |
| ATOM | 8991 | CG | ARG | D | 313 | 111.240 | 30.573 | 23.229 | 1.00 | 26.35 | C |
| ATOM | 8992 | CD | ARG | D | 313 | 109.874 | 29.933 | 23.155 | 1.00 | 25.21 | C |
| ATOM | 8993 | NE | ARG | D | 313 | 109.516 | 29.284 | 24.401 | 1.00 | 15.68 | N |
| ATOM | 8994 | CZ | ARG | D | 313 | 108.273 | 29.110 | 24.802 | 1.00 | 15.19 | C |
| ATOM | 8995 | NH1AR | G | D | 313 | 107.281 | 29.555 | 24.041 | 1.00 | 13.60 | N |
| ATOM | 8996 | NH2AR | G | D | 313 | 108.035 | 28.487 | 25.949 | 1.00 | 13.02 | N |
| ATOM | 8997 | C | ARG | D | 313 | 112.890 | 33.233 | 23.311 | 1.00 | 24.69 | C |
| ATOM | 8998 | O | ARG | D | 313 | 112.494 | 34.380 | 23.282 | 1.00 | 27.77 | O |
| ATOM | 8999 | N | MSED | | 314 | 113.620 | 32.689 | 22.352 | 1.00 | 25.05 | N |
| ATOM | 9000 | CA | MSED | | 314 | 114.095 | 33.441 | 21.190 | 1.00 | 26.79 | C |
| ATOM | 9001 | CB | MSED | | 314 | 114.882 | 32.499 | 20.281 | 1.00 | 26.60 | C |
| ATOM | 9002 | CG | MSED | | 314 | 115.368 | 33.055 | 18.948 | 1.00 | 35.58 | C |
| ATOM | 9003 | SE | MSED | | 314 | 116.683 | 31.821 | 18.161 | 1.00 | 35.93 | S |
| ATOM | 9004 | CE | MSED | | 314 | 115.527 | 30.632 | 17.266 | 1.00 | 42.17 | C |
| ATOM | 9005 | C | MSED | | 314 | 112.999 | 34.120 | 20.416 | 1.00 | 25.92 | C |
| ATOM | 9006 | O | MSED | | 314 | 111.922 | 33.590 | 20.275 | 1.00 | 29.26 | O |
| ATOM | 9007 | N | THR | D | 315 | 113.264 | 35.312 | 19.930 | 1.00 | 24.63 | N |
| ATOM | 9008 | CA | THR | D | 315 | 112.281 | 36.040 | 19.153 | 1.00 | 24.80 | C |
| ATOM | 9009 | CB | THR | D | 315 | 112.485 | 37.538 | 19.361 | 1.00 | 25.84 | C |
| ATOM | 9010 | OG1 | THR | D | 315 | 113.700 | 37.990 | 18.718 | 1.00 | 25.95 | O |
| ATOM | 9011 | CG2 | THR | D | 315 | 112.557 | 37.798 | 20.848 | 1.00 | 26.07 | C |
| ATOM | 9012 | C | THR | D | 315 | 112.403 | 35.695 | 17.664 | 1.00 | 25.42 | C |
| ATOM | 9013 | O | THR | D | 315 | 113.453 | 35.243 | 17.226 | 1.00 | 26.09 | O |
| ATOM | 9014 | N | ILE | D | 316 | 111.358 | 35.879 | 16.872 | 1.00 | 23.28 | N |

FIG. 2A-196

| ATOM | 9015 | CA | ILE | D | 316 | 111.538 | 35.550 | 15.468 | 1.00 | 20.80 | C |
|---|---|---|---|---|---|---|---|---|---|---|---|
| ATOM | 9016 | CB | ILE | D | 316 | 110.195 | 35.627 | 14.644 | 1.00 | 19.94 | C |
| ATOM | 9017 | CG1 | ILE | D | 316 | 110.433 | 35.008 | 13.263 | 1.00 | 19.49 | C |
| ATOM | 9018 | CD1 | ILE | D | 316 | 110.695 | 33.521 | 13.290 | 1.00 | 17.79 | C |
| ATOM | 9019 | CG2 | ILE | D | 316 | 109.716 | 37.058 | 14.437 | 1.00 | 15.08 | C |
| ATOM | 9020 | C | ILE | D | 316 | 112.633 | 36.412 | 14.792 | 1.00 | 23.71 | C |
| ATOM | 9021 | O | ILE | D | 316 | 113.293 | 35.949 | 13.872 | 1.00 | 23.51 | O |
| ATOM | 9022 | N | THR | D | 317 | 112.845 | 37.651 | 15.235 | 1.00 | 25.02 | N |
| ATOM | 9023 | CA | THR | D | 317 | 113.883 | 38.471 | 14.620 | 1.00 | 24.38 | C |
| ATOM | 9024 | CB | THR | D | 317 | 113.889 | 39.862 | 15.188 | 1.00 | 23.76 | C |
| ATOM | 9025 | OG1 | THR | D | 317 | 112.682 | 40.514 | 14.820 | 1.00 | 29.05 | O |
| ATOM | 9026 | CG2 | THR | D | 317 | 115.020 | 40.645 | 14.673 | 1.00 | 19.81 | C |
| ATOM | 9027 | C | THR | D | 317 | 115.205 | 37.839 | 14.940 | 1.00 | 23.80 | C |
| ATOM | 9028 | O | THR | D | 317 | 116.046 | 37.641 | 14.088 | 1.00 | 22.61 | O |
| ATOM | 9029 | N | GLU | D | 318 | 115.386 | 37.526 | 16.203 | 1.00 | 24.87 | N |
| ATOM | 9030 | CA | GLU | D | 318 | 116.605 | 36.884 | 16.635 | 1.00 | 24.81 | C |
| ATOM | 9031 | CB | GLU | D | 318 | 116.485 | 36.581 | 18.147 | 1.00 | 25.55 | C |
| ATOM | 9032 | CG | GLU | D | 318 | 116.826 | 37.808 | 19.055 | 1.00 | 27.20 | C |
| ATOM | 9033 | CD | GLU | D | 318 | 116.445 | 37.653 | 20.517 | 1.00 | 35.08 | C |
| ATOM | 9034 | OE1 | GLU | D | 318 | 116.845 | 38.490 | 21.353 | 1.00 | 34.31 | O |
| ATOM | 9035 | OE2 | GLU | D | 318 | 115.722 | 36.699 | 20.860 | 1.00 | 43.36 | O |
| ATOM | 9036 | C | GLU | D | 318 | 116.779 | 35.624 | 15.777 | 1.00 | 24.62 | C |
| ATOM | 9037 | O | GLU | D | 318 | 117.829 | 35.350 | 15.236 | 1.00 | 26.39 | O |
| ATOM | 9038 | N | PHE | D | 319 | 115.707 | 34.880 | 15.617 | 1.00 | 25.13 | N |
| ATOM | 9039 | CA | PHE | D | 319 | 115.714 | 33.652 | 14.846 | 1.00 | 22.49 | C |
| ATOM | 9040 | CB | PHE | D | 319 | 114.330 | 33.042 | 14.854 | 1.00 | 23.21 | C |
| ATOM | 9041 | CG | PHE | D | 319 | 114.205 | 31.822 | 14.045 | 1.00 | 18.77 | C |
| ATOM | 9042 | CD1 | PHE | D | 319 | 114.569 | 30.615 | 14.560 | 1.00 | 16.05 | C |
| ATOM | 9043 | CE1 | PHE | D | 319 | 114.381 | 29.471 | 13.843 | 1.00 | 16.64 | C |
| ATOM | 9044 | CZ | PHE | D | 319 | 113.826 | 29.524 | 12.592 | 1.00 | 12.09 | C |
| ATOM | 9045 | CE2 | PHE | D | 319 | 113.463 | 30.740 | 12.052 | 1.00 | 16.43 | C |
| ATOM | 9046 | CD2 | PHE | D | 319 | 113.657 | 31.879 | 12.785 | 1.00 | 20.00 | C |
| ATOM | 9047 | C | PHE | D | 319 | 116.103 | 33.832 | 13.423 | 1.00 | 22.19 | C |
| ATOM | 9048 | O | PHE | D | 319 | 116.861 | 33.022 | 12.894 | 1.00 | 22.53 | O |
| ATOM | 9049 | N | MSED | | 320 | 115.555 | 34.859 | 12.774 | 1.00 | 22.56 | N |
| ATOM | 9050 | CA | MSED | | 320 | 115.857 | 35.073 | 11.367 | 1.00 | 21.45 | C |
| ATOM | 9051 | CB | MSED | | 320 | 114.897 | 36.075 | 10.755 | 1.00 | 21.40 | C |
| ATOM | 9052 | CG | MSED | | 320 | 113.529 | 35.524 | 10.469 | 1.00 | 23.69 | C |
| ATOM | 9053 | SE | MSED | | 320 | 113.476 | 33.842 | 9.500 | 1.00 | 25.07 | S |
| ATOM | 9054 | CE | MSED | | 320 | 112.964 | 34.503 | 7.801 | 1.00 | 17.44 | C |
| ATOM | 9055 | C | MSED | | 320 | 117.287 | 35.520 | 11.142 | 1.00 | 22.52 | C |
| ATOM | 9056 | O | MSED | | 320 | 117.786 | 35.396 | 10.034 | 1.00 | 24.45 | O |
| ATOM | 9057 | N | ASN | D | 321 | 117.940 | 36.023 | 12.191 | 1.00 | 22.71 | N |
| ATOM | 9058 | CA | ASN | D | 321 | 119.311 | 36.475 | 12.130 | 1.00 | 23.08 | C |
| ATOM | 9059 | CB | ASN | D | 321 | 119.522 | 37.680 | 13.012 | 1.00 | 23.29 | C |
| ATOM | 9060 | CG | ASN | D | 321 | 118.849 | 38.883 | 12.484 | 1.00 | 29.90 | C |

FIG. 2A-197

| ATOM | 9061 | OD1 | ASN | D | 321 | 119.026 | 39.231 | 11.314 | 1.00 | 33.74 | O |
| --- | --- | --- | --- | --- | --- | --- | --- | --- | --- | --- | --- |
| ATOM | 9062 | ND2 | ASN | D | 321 | 118.059 | 39.547 | 13.327 | 1.00 | 36.49 | N |
| ATOM | 9063 | C | ASN | D | 321 | 120.258 | 35.411 | 12.614 | 1.00 | 22.95 | C |
| ATOM | 9064 | O | ASN | D | 321 | 121.435 | 35.665 | 12.818 | 1.00 | 23.20 | O |
| ATOM | 9065 | N | HIS | D | 322 | 119.778 | 34.214 | 12.850 | 1.00 | 22.91 | N |
| ATOM | 9066 | CA | HIS | D | 322 | 120.710 | 33.199 | 13.300 | 1.00 | 22.15 | C |
| ATOM | 9067 | CB | HIS | D | 322 | 119.980 | 32.076 | 14.027 | 1.00 | 22.20 | C |
| ATOM | 9068 | CG | HIS | D | 322 | 120.870 | 31.189 | 14.836 | 1.00 | 19.46 | C |
| ATOM | 9069 | ND1 | HIS | D | 322 | 121.812 | 30.359 | 14.267 | 1.00 | 14.87 | N |
| ATOM | 9070 | CE1 | HIS | D | 322 | 122.401 | 29.653 | 15.215 | 1.00 | 10.09 | C |
| ATOM | 9071 | NE2 | HIS | D | 322 | 121.882 | 29.998 | 16.376 | 1.00 | 11.78 | N |
| ATOM | 9072 | CD2 | HIS | D | 322 | 120.925 | 30.962 | 16.167 | 1.00 | 15.46 | C |
| ATOM | 9073 | C | HIS | D | 322 | 121.407 | 32.664 | 12.060 | 1.00 | 22.34 | C |
| ATOM | 9074 | O | HIS | D | 322 | 120.761 | 32.332 | 11.052 | 1.00 | 23.16 | O |
| ATOM | 9075 | N | PRO | D | 323 | 122.745 | 32.603 | 12.114 | 1.00 | 21.82 | N |
| ATOM | 9076 | CA | PRO | D | 323 | 123.674 | 32.134 | 11.081 | 1.00 | 20.12 | C |
| ATOM | 9077 | CB | PRO | D | 323 | 124.907 | 31.807 | 11.890 | 1.00 | 19.35 | C |
| ATOM | 9078 | CG | PRO | D | 323 | 124.908 | 32.895 | 12.862 | 1.00 | 19.37 | C |
| ATOM | 9079 | CD | PRO | D | 323 | 123.483 | 32.938 | 13.340 | 1.00 | 21.54 | C |
| ATOM | 9080 | C | PRO | D | 323 | 123.121 | 30.911 | 10.367 | 1.00 | 19.83 | C |
| ATOM | 9081 | O | PRO | D | 323 | 123.121 | 30.816 | 9.137 | 1.00 | 20.27 | O |
| ATOM | 9082 | N | TRP | D | 324 | 122.638 | 29.964 | 11.151 | 1.00 | 19.22 | N |
| ATOM | 9083 | CA | TRP | D | 324 | 122.103 | 28.773 | 10.569 | 1.00 | 18.71 | C |
| ATOM | 9084 | CB | TRP | D | 324 | 121.673 | 27.808 | 11.653 | 1.00 | 17.78 | C |
| ATOM | 9085 | CG | TRP | D | 324 | 121.576 | 26.402 | 11.184 | 1.00 | 12.34 | C |
| ATOM | 9086 | CD1 | TRP | D | 324 | 122.596 | 25.596 | 10.855 | 1.00 | 5.51 | C |
| ATOM | 9087 | NE1 | TRP | D | 324 | 122.129 | 24.350 | 10.503 | 1.00 | 6.83 | N |
| ATOM | 9088 | CE2 | TRP | D | 324 | 120.771 | 24.339 | 10.601 | 1.00 | 9.69 | C |
| ATOM | 9089 | CD2 | TRP | D | 324 | 120.378 | 25.619 | 11.029 | 1.00 | 12.68 | C |
| ATOM | 9090 | CE3 | TRP | D | 324 | 119.018 | 25.876 | 11.222 | 1.00 | 14.90 | C |
| ATOM | 9091 | CZ3 | TRP | D | 324 | 118.113 | 24.860 | 10.988 | 1.00 | 17.54 | C |
| ATOM | 9092 | CH2 | TRP | D | 324 | 118.544 | 23.594 | 10.558 | 1.00 | 17.43 | C |
| ATOM | 9093 | CZ2 | TRP | D | 324 | 119.870 | 23.321 | 10.359 | 1.00 | 14.17 | C |
| ATOM | 9094 | C | TRP | D | 324 | 120.934 | 29.150 | 9.670 | 1.00 | 20.57 | C |
| ATOM | 9095 | O | TRP | D | 324 | 120.894 | 28.756 | 8.523 | 1.00 | 23.19 | O |
| ATOM | 9096 | N | ILE | D | 325 | 119.980 | 29.934 | 10.149 | 1.00 | 22.55 | N |
| ATOM | 9097 | CA | ILE | D | 325 | 118.861 | 30.249 | 9.270 | 1.00 | 23.90 | C |
| ATOM | 9098 | CB | ILE | D | 325 | 117.622 | 30.799 | 10.045 | 1.00 | 22.74 | C |
| ATOM | 9099 | CG1 | ILE | D | 325 | 116.805 | 29.634 | 10.586 | 1.00 | 24.48 | C |
| ATOM | 9100 | CD1 | ILE | D | 325 | 117.604 | 28.709 | 11.418 | 1.00 | 25.81 | C |
| ATOM | 9101 | CG2 | ILE | D | 325 | 116.723 | 31.607 | 9.118 | 1.00 | 21.65 | C |
| ATOM | 9102 | C | ILE | D | 325 | 119.269 | 31.227 | 8.197 | 1.00 | 25.82 | C |
| ATOM | 9103 | O | ILE | D | 325 | 118.864 | 31.103 | 7.045 | 1.00 | 26.34 | O |
| ATOM | 9104 | N | MSED | | 326 | 120.093 | 32.192 | 8.564 | 1.00 | 28.45 | N |
| ATOM | 9105 | CA | MSED | | 326 | 120.538 | 33.180 | 7.601 | 1.00 | 31.56 | C |
| ATOM | 9106 | CB | MSED | | 326 | 121.171 | 34.324 | 8.340 | 1.00 | 32.12 | C |

FIG. 2A-198

| ATOM | 9107 | CG | MSED |   | 326 | 121.407 | 35.496 | 7.492 | 1.00 | 37.46 | C |
|------|------|-----|------|---|-----|---------|--------|-------|------|-------|---|
| ATOM | 9108 | SE | MSED |   | 326 | 121.581 | 36.914 | 8.722 | 1.00 | 54.55 | S |
| ATOM | 9109 | CE | MSED |   | 326 | 120.161 | 38.032 | 8.006 | 1.00 | 55.73 | C |
| ATOM | 9110 | C | MSED |   | 326 | 121.507 | 32.622 | 6.555 | 1.00 | 32.89 | C |
| ATOM | 9111 | O | MSED |   | 326 | 121.247 | 32.704 | 5.364 | 1.00 | 33.44 | O |
| ATOM | 9112 | N | GLN | D | 327 | 122.626 | 32.058 | 6.987 | 1.00 | 35.50 | N |
| ATOM | 9113 | CA | GLN | D | 327 | 123.586 | 31.477 | 6.060 | 1.00 | 37.54 | C |
| ATOM | 9114 | CB | GLN | D | 327 | 124.955 | 31.353 | 6.725 | 1.00 | 37.86 | C |
| ATOM | 9115 | CG | GLN | D | 327 | 125.923 | 32.481 | 6.433 | 1.00 | 40.60 | C |
| ATOM | 9116 | CD | GLN | D | 327 | 125.938 | 33.577 | 7.486 | 1.00 | 46.74 | C |
| ATOM | 9117 | OE1 | GLN | D | 327 | 125.065 | 34.444 | 7.520 | 1.00 | 50.02 | O |
| ATOM | 9118 | NE2 | GLN | D | 327 | 126.944 | 33.543 | 8.351 | 1.00 | 47.46 | N |
| ATOM | 9119 | C | GLN | D | 327 | 123.085 | 30.089 | 5.657 | 1.00 | 38.37 | C |
| ATOM | 9120 | O | GLN | D | 327 | 123.811 | 29.102 | 5.759 | 1.00 | 38.28 | O |
| ATOM | 9121 | N | SER | D | 328 | 121.842 | 30.019 | 5.199 | 1.00 | 39.88 | N |
| ATOM | 9122 | CA | SER | D | 328 | 121.232 | 28.746 | 4.801 | 1.00 | 41.42 | C |
| ATOM | 9123 | CB | SER | D | 328 | 119.810 | 28.977 | 4.281 | 1.00 | 41.51 | C |
| ATOM | 9124 | OG | SER | D | 328 | 118.943 | 29.365 | 5.331 | 1.00 | 46.45 | O |
| ATOM | 9125 | C | SER | D | 328 | 122.012 | 28.008 | 3.731 | 1.00 | 41.71 | C |
| ATOM | 9126 | O | SER | D | 328 | 121.817 | 26.818 | 3.504 | 1.00 | 41.63 | O |
| ATOM | 9127 | N | THR | D | 329 | 122.901 | 28.741 | 3.084 | 1.00 | 42.43 | N |
| ATOM | 9128 | CA | THR | D | 329 | 123.716 | 28.231 | 1.997 | 1.00 | 43.78 | C |
| ATOM | 9129 | CB | THR | D | 329 | 123.425 | 29.058 | 0.747 | 1.00 | 44.87 | C |
| ATOM | 9130 | OG1 | THR | D | 329 | 123.732 | 30.436 | 1.020 | 1.00 | 45.43 | O |
| ATOM | 9131 | CG2 | THR | D | 329 | 121.928 | 28.943 | 0.378 | 1.00 | 46.20 | C |
| ATOM | 9132 | C | THR | D | 329 | 125.192 | 28.332 | 2.354 | 1.00 | 43.08 | C |
| ATOM | 9133 | O | THR | D | 329 | 126.010 | 28.843 | 1.591 | 1.00 | 42.52 | O |
| ATOM | 9134 | N | ALA | D | 330 | 125.505 | 27.849 | 3.544 | 1.00 | 41.91 | N |
| ATOM | 9135 | CA | ALA | D | 330 | 126.863 | 27.861 | 4.067 | 1.00 | 40.91 | C |
| ATOM | 9136 | CB | ALA | D | 330 | 127.177 | 29.213 | 4.697 | 1.00 | 40.87 | C |
| ATOM | 9137 | C | ALA | D | 330 | 126.802 | 26.790 | 5.127 | 1.00 | 40.07 | C |
| ATOM | 9138 | O | ALA | D | 330 | 127.721 | 26.599 | 5.918 | 1.00 | 40.09 | O |
| ATOM | 9139 | N | VAL | D | 331 | 125.669 | 26.108 | 5.123 | 1.00 | 38.71 | N |
| ATOM | 9140 | CA | VAL | D | 331 | 125.410 | 25.034 | 6.076 | 1.00 | 37.54 | C |
| ATOM | 9141 | CB | VAL | D | 331 | 123.935 | 25.102 | 6.457 | 1.00 | 37.82 | C |
| ATOM | 9142 | CG1 | VAL | D | 331 | 123.077 | 25.080 | 5.195 | 1.00 | 40.27 | C |
| ATOM | 9143 | CG2 | VAL | D | 331 | 123.568 | 23.914 | 7.329 | 1.00 | 35.92 | C |
| ATOM | 9144 | C | VAL | D | 331 | 125.736 | 23.658 | 5.478 | 1.00 | 35.95 | C |
| ATOM | 9145 | O | VAL | D | 331 | 125.395 | 23.341 | 4.347 | 1.00 | 34.49 | O |
| ATOM | 9146 | N | PRO | D | 332 | 126.455 | 22.840 | 6.272 | 1.00 | 35.28 | N |
| ATOM | 9147 | CA | PRO | D | 332 | 126.934 | 21.539 | 5.811 | 1.00 | 34.71 | C |
| ATOM | 9148 | CB | PRO | D | 332 | 127.857 | 20.973 | 6.888 | 1.00 | 34.90 | C |
| ATOM | 9149 | CG | PRO | D | 332 | 128.100 | 22.068 | 7.926 | 1.00 | 35.56 | C |
| ATOM | 9150 | CD | PRO | D | 332 | 126.877 | 23.062 | 7.643 | 1.00 | 35.40 | C |
| ATOM | 9151 | C | PRO | D | 332 | 125.794 | 20.554 | 5.536 | 1.00 | 33.91 | C |
| ATOM | 9152 | O | PRO | D | 332 | 124.742 | 20.582 | 6.159 | 1.00 | 35.22 | O |

FIG. 2A-199

| | | | | | | | | | | |
|---|---|---|---|---|---|---|---|---|---|---|
| ATOM | 9153 | N | GLN | D | 333 | 126.019 | 19.672 | 4.539 | 1.00 | 32.73 | N |
| ATOM | 9154 | CA | GLN | D | 333 | 124.954 | 18.770 | 4.125 | 1.00 | 31.62 | C |
| ATOM | 9155 | CB | GLN | D | 333 | 125.008 | 18.602 | 2.606 | 1.00 | 31.49 | C |
| ATOM | 9156 | CG | GLN | D | 333 | 125.420 | 19.873 | 1.873 | 1.00 | 33.78 | C |
| ATOM | 9157 | CD | GLN | D | 333 | 125.370 | 19.602 | 0.391 | 1.00 | 40.83 | C |
| ATOM | 9158 | OE1 | GLN | D | 333 | 125.902 | 20.320 | -0.437 | 1.00 | 45.47 | O |
| ATOM | 9159 | NE2 | GLN | D | 333 | 124.708 | 18.474 | 0.075 | 1.00 | 42.76 | N |
| ATOM | 9160 | C | GLN | D | 333 | 125.046 | 17.391 | 4.789 | 1.00 | 30.63 | C |
| ATOM | 9161 | O | GLN | D | 333 | 124.833 | 16.361 | 4.163 | 1.00 | 31.06 | O |
| ATOM | 9162 | N | THR | D | 334 | 125.403 | 17.379 | 6.086 | 1.00 | 29.59 | N |
| ATOM | 9163 | CA | THR | D | 334 | 125.426 | 16.098 | 6.781 | 1.00 | 28.56 | C |
| ATOM | 9164 | CB | THR | D | 334 | 125.734 | 16.344 | 8.259 | 1.00 | 28.55 | C |
| ATOM | 9165 | OG1 | THR | D | 334 | 124.741 | 15.699 | 9.055 | 1.00 | 31.38 | O |
| ATOM | 9166 | CG2 | THR | D | 334 | 125.718 | 17.845 | 8.564 | 1.00 | 29.77 | C |
| ATOM | 9167 | C | THR | D | 334 | 124.087 | 15.369 | 6.644 | 1.00 | 27.38 | C |
| ATOM | 9168 | O | THR | D | 334 | 123.015 | 15.956 | 6.739 | 1.00 | 26.53 | O |
| ATOM | 9169 | N | PRO | D | 335 | 124.078 | 14.084 | 6.284 | 1.00 | 27.03 | N |
| ATOM | 9170 | CA | PRO | D | 335 | 122.812 | 13.385 | 6.119 | 1.00 | 27.37 | C |
| ATOM | 9171 | CB | PRO | D | 335 | 123.121 | 11.977 | 5.629 | 1.00 | 26.89 | C |
| ATOM | 9172 | CG | PRO | D | 335 | 124.497 | 12.018 | 4.982 | 1.00 | 27.58 | C |
| ATOM | 9173 | CD | PRO | D | 335 | 125.150 | 13.279 | 5.713 | 1.00 | 26.34 | C |
| ATOM | 9174 | C | PRO | D | 335 | 122.013 | 13.338 | 7.422 | 1.00 | 27.55 | C |
| ATOM | 9175 | O | PRO | D | 335 | 122.541 | 13.495 | 8.519 | 1.00 | 28.82 | O |
| ATOM | 9176 | N | LEU | D | 336 | 120.687 | 13.149 | 7.265 | 1.00 | 26.87 | N |
| ATOM | 9177 | CA | LEU | D | 336 | 119.785 | 13.197 | 8.411 | 1.00 | 26.40 | C |
| ATOM | 9178 | CB | LEU | D | 336 | 118.951 | 14.477 | 8.287 | 1.00 | 25.38 | C |
| ATOM | 9179 | CG | LEU | D | 336 | 119.454 | 15.613 | 9.184 | 1.00 | 22.63 | C |
| ATOM | 9180 | CD1 | LEU | D | 336 | 120.980 | 15.669 | 9.261 | 1.00 | 19.90 | C |
| ATOM | 9181 | CD2 | LEU | D | 336 | 119.000 | 16.995 | 8.704 | 1.00 | 22.84 | C |
| ATOM | 9182 | C | LEU | D | 336 | 118.841 | 11.991 | 8.420 | 1.00 | 27.52 | C |
| ATOM | 9183 | O | LEU | D | 336 | 118.122 | 11.724 | 7.467 | 1.00 | 29.60 | O |
| ATOM | 9184 | N | HIS | D | 337 | 118.882 | 11.224 | 9.532 | 1.00 | 27.11 | N |
| ATOM | 9185 | CA | HIS | D | 337 | 118.009 | 10.054 | 9.643 | 1.00 | 27.47 | C |
| ATOM | 9186 | CB | HIS | D | 337 | 118.104 | 9.506 | 11.072 | 1.00 | 27.51 | C |
| ATOM | 9187 | CG | HIS | D | 337 | 119.469 | 8.921 | 11.313 | 1.00 | 30.76 | C |
| ATOM | 9188 | ND1 | HIS | D | 337 | 120.610 | 9.529 | 10.921 | 1.00 | 31.73 | N |
| ATOM | 9189 | CE1 | HIS | D | 337 | 121.611 | 8.767 | 11.395 | 1.00 | 29.41 | C |
| ATOM | 9190 | NE2 | HIS | D | 337 | 121.158 | 7.703 | 12.064 | 1.00 | 30.75 | N |
| ATOM | 9191 | CD2 | HIS | D | 337 | 119.805 | 7.765 | 12.032 | 1.00 | 29.40 | C |
| ATOM | 9192 | C | HIS | D | 337 | 116.542 | 10.393 | 9.335 | 1.00 | 27.54 | C |
| ATOM | 9193 | O | HIS | D | 337 | 115.720 | 9.534 | 9.044 | 1.00 | 27.34 | O |
| ATOM | 9194 | N | THR | D | 338 | 116.213 | 11.692 | 9.450 | 1.00 | 27.60 | N |
| ATOM | 9195 | CA | THR | D | 338 | 114.812 | 12.094 | 9.362 | 1.00 | 27.91 | C |
| ATOM | 9196 | CB | THR | D | 338 | 114.751 | 13.539 | 8.879 | 1.00 | 28.36 | C |
| ATOM | 9197 | OG1 | THR | D | 338 | 115.434 | 14.362 | 9.824 | 1.00 | 29.33 | O |
| ATOM | 9198 | CG2 | THR | D | 338 | 113.290 | 13.995 | 8.799 | 1.00 | 27.86 | C |

FIG. 2A-200

| ATOM | 9199 | C | THR | D | 338 | 113.998 | 11.182 | 8.439 | 1.00 | 28.55 | C |
|---|---|---|---|---|---|---|---|---|---|---|---|
| ATOM | 9200 | O | THR | D | 338 | 113.273 | 10.300 | 8.871 | 1.00 | 29.21 | O |
| ATOM | 9201 | N | SER | D | 339 | 114.112 | 11.453 | 7.122 | 1.00 | 29.32 | N |
| ATOM | 9202 | CA | SER | D | 339 | 113.311 | 10.711 | 6.153 | 1.00 | 30.06 | C |
| ATOM | 9203 | CB | SER | D | 339 | 114.022 | 10.784 | 4.801 | 1.00 | 29.95 | C |
| ATOM | 9204 | OG | SER | D | 339 | 114.356 | 12.147 | 4.525 | 1.00 | 36.17 | O |
| ATOM | 9205 | C | SER | D | 339 | 113.100 | 9.250 | 6.559 | 1.00 | 28.80 | C |
| ATOM | 9206 | O | SER | D | 339 | 111.990 | 8.740 | 6.587 | 1.00 | 28.43 | O |
| ATOM | 9207 | N | ALA | D | 340 | 114.214 | 8.590 | 6.857 | 1.00 | 28.93 | N |
| ATOM | 9208 | CA | ALA | D | 340 | 114.211 | 7.185 | 7.261 | 1.00 | 30.13 | C |
| ATOM | 9209 | CB | ALA | D | 340 | 115.649 | 6.694 | 7.472 | 1.00 | 30.03 | C |
| ATOM | 9210 | C | ALA | D | 340 | 113.397 | 7.020 | 8.540 | 1.00 | 30.09 | C |
| ATOM | 9211 | O | ALA | D | 340 | 112.345 | 6.388 | 8.532 | 1.00 | 30.35 | O |
| ATOM | 9212 | N | VAL | D | 341 | 113.892 | 7.591 | 9.633 | 1.00 | 29.86 | N |
| ATOM | 9213 | CA | VAL | D | 341 | 113.201 | 7.536 | 10.912 | 1.00 | 29.77 | C |
| ATOM | 9214 | CB | VAL | D | 341 | 113.819 | 8.522 | 11.906 | 1.00 | 29.58 | C |
| ATOM | 9215 | CG1 | VAL | D | 341 | 112.954 | 8.607 | 13.152 | 1.00 | 30.44 | C |
| ATOM | 9216 | CG2 | VAL | D | 341 | 115.236 | 8.088 | 12.249 | 1.00 | 32.02 | C |
| ATOM | 9217 | C | VAL | D | 341 | 111.746 | 7.943 | 10.708 | 1.00 | 29.70 | C |
| ATOM | 9218 | O | VAL | D | 341 | 110.822 | 7.307 | 11.204 | 1.00 | 28.25 | O |
| ATOM | 9219 | N | LEU | D | 342 | 111.564 | 9.023 | 9.956 | 1.00 | 31.08 | N |
| ATOM | 9220 | CA | LEU | D | 342 | 110.247 | 9.568 | 9.676 | 1.00 | 31.90 | C |
| ATOM | 9221 | CB | LEU | D | 342 | 110.387 | 10.863 | 8.884 | 1.00 | 31.62 | C |
| ATOM | 9222 | CG | LEU | D | 342 | 109.147 | 11.747 | 8.787 | 1.00 | 31.69 | C |
| ATOM | 9223 | CD1 | LEU | D | 342 | 108.499 | 11.902 | 10.169 | 1.00 | 26.66 | C |
| ATOM | 9224 | CD2 | LEU | D | 342 | 109.569 | 13.101 | 8.213 | 1.00 | 35.89 | C |
| ATOM | 9225 | C | LEU | D | 342 | 109.392 | 8.584 | 8.907 | 1.00 | 31.71 | C |
| ATOM | 9226 | O | LEU | D | 342 | 109.806 | 8.262 | 7.774 | 1.00 | 32.11 | O |
| ATOM | 9227 | OXT | LEU | D | 342 | 108.338 | 8.161 | 9.445 | 1.00 | 31.45 | O |
| ATOM | 9228 | O5 | STU | E | 1 | 115.906 | 14.254 | 62.941 | 1.00 | 48.70 | O |
| ATOM | 9229 | C8 | STU | E | 1 | 115.036 | 14.908 | 62.419 | 1.00 | 46.69 | C |
| ATOM | 9230 | N1 | STU | E | 1 | 114.086 | 14.499 | 61.605 | 1.00 | 45.39 | N |
| ATOM | 9231 | C7 | STU | E | 1 | 114.777 | 16.355 | 62.532 | 1.00 | 42.78 | C |
| ATOM | 9232 | C6 | STU | E | 1 | 115.567 | 17.303 | 63.332 | 1.00 | 41.91 | C |
| ATOM | 9233 | C5 | STU | E | 1 | 116.671 | 17.224 | 64.159 | 1.00 | 42.80 | C |
| ATOM | 9234 | C20 | STU | E | 1 | 116.923 | 18.567 | 64.625 | 1.00 | 42.29 | C |
| ATOM | 9235 | C1 | STU | E | 1 | 117.996 | 18.861 | 65.523 | 1.00 | 44.81 | C |
| ATOM | 9236 | C2 | STU | E | 1 | 118.807 | 17.801 | 65.944 | 1.00 | 41.41 | C |
| ATOM | 9237 | C3 | STU | E | 1 | 118.570 | 16.465 | 65.477 | 1.00 | 43.70 | C |
| ATOM | 9238 | C4 | STU | E | 1 | 117.523 | 16.193 | 64.605 | 1.00 | 42.74 | C |
| ATOM | 9239 | N3 | STU | E | 1 | 115.995 | 19.407 | 64.082 | 1.00 | 40.29 | N |
| ATOM | 9240 | C19 | STU | E | 1 | 115.110 | 18.672 | 63.263 | 1.00 | 39.30 | C |
| ATOM | 9241 | C25 | STU | E | 1 | 115.790 | 20.811 | 64.523 | 1.00 | 44.07 | C |
| ATOM | 9242 | O4 | STU | E | 1 | 114.475 | 21.270 | 64.179 | 1.00 | 49.59 | O |
| ATOM | 9243 | C10 | STU | E | 1 | 113.741 | 16.707 | 61.811 | 1.00 | 40.69 | C |
| ATOM | 9244 | C9 | STU | E | 1 | 113.161 | 15.501 | 61.113 | 1.00 | 43.77 | C |

FIG. 2A-201

| ATOM | 9245 | C11 | STU | E | 1 | 113.281 | 18.058 | 61.733 | 1.00 | 39.02 | C |
|---|---|---|---|---|---|---|---|---|---|---|---|
| ATOM | 9246 | C12 | STU | E | 1 | 112.240 | 18.725 | 61.057 | 1.00 | 42.47 | C |
| ATOM | 9247 | C13 | STU | E | 1 | 111.250 | 18.276 | 60.189 | 1.00 | 41.06 | C |
| ATOM | 9248 | C14 | STU | E | 1 | 110.317 | 19.150 | 59.639 | 1.00 | 43.66 | C |
| ATOM | 9249 | C15 | STU | E | 1 | 110.391 | 20.559 | 59.994 | 1.00 | 43.71 | C |
| ATOM | 9250 | C17 | STU | E | 1 | 112.296 | 20.148 | 61.388 | 1.00 | 39.88 | C |
| ATOM | 9251 | C16 | STU | E | 1 | 111.362 | 21.018 | 60.842 | 1.00 | 39.66 | C |
| ATOM | 9252 | C18 | STU | E | 1 | 114.034 | 19.045 | 62.511 | 1.00 | 38.15 | C |
| ATOM | 9253 | N2 | STU | E | 1 | 113.395 | 20.313 | 62.257 | 1.00 | 38.18 | N |
| ATOM | 9254 | C21 | STU | E | 1 | 113.966 | 21.569 | 62.895 | 1.00 | 39.56 | C |
| ATOM | 9255 | C26 | STU | E | 1 | 112.886 | 22.627 | 63.165 | 1.00 | 32.64 | C |
| ATOM | 9256 | C22 | STU | E | 1 | 115.081 | 22.169 | 61.924 | 1.00 | 43.87 | C |
| ATOM | 9257 | O6 | STU | E | 1 | 115.781 | 21.120 | 61.197 | 1.00 | 36.51 | O |
| ATOM | 9258 | C27 | STU | E | 1 | 115.411 | 21.064 | 59.841 | 1.00 | 37.70 | C |
| ATOM | 9259 | C23 | STU | E | 1 | 116.150 | 22.795 | 62.882 | 1.00 | 46.65 | C |
| ATOM | 9260 | C24 | STU | E | 1 | 116.831 | 21.701 | 63.756 | 1.00 | 41.96 | C |
| ATOM | 9261 | N4 | STU | E | 1 | 117.297 | 23.529 | 62.085 | 1.00 | 53.52 | N |
| ATOM | 9262 | C28 | STU | E | 1 | 116.690 | 24.528 | 61.116 | 1.00 | 55.34 | C |
| ATOM | 9263 | O5 | STU | F | 1 | 70.504 | 8.670 | 77.792 | 1.00 | 39.31 | O |
| ATOM | 9264 | C8 | STU | F | 1 | 70.809 | 9.513 | 76.990 | 1.00 | 43.38 | C |
| ATOM | 9265 | N1 | STU | F | 1 | 72.027 | 9.771 | 76.513 | 1.00 | 41.00 | N |
| ATOM | 9266 | C7 | STU | F | 1 | 69.933 | 10.530 | 76.306 | 1.00 | 40.24 | C |
| ATOM | 9267 | C6 | STU | F | 1 | 68.456 | 10.732 | 76.466 | 1.00 | 38.46 | C |
| ATOM | 9268 | C5 | STU | F | 1 | 67.442 | 10.149 | 77.203 | 1.00 | 40.48 | C |
| ATOM | 9269 | C20 | STU | F | 1 | 66.208 | 10.877 | 76.888 | 1.00 | 40.51 | C |
| ATOM | 9270 | C1 | STU | F | 1 | 64.970 | 10.543 | 77.482 | 1.00 | 41.11 | C |
| ATOM | 9271 | C2 | STU | F | 1 | 64.979 | 9.498 | 78.382 | 1.00 | 42.69 | C |
| ATOM | 9272 | C3 | STU | F | 1 | 66.184 | 8.783 | 78.689 | 1.00 | 38.42 | C |
| ATOM | 9273 | C4 | STU | F | 1 | 67.370 | 9.111 | 78.109 | 1.00 | 40.31 | C |
| ATOM | 9274 | N3 | STU | F | 1 | 66.479 | 11.854 | 75.977 | 1.00 | 41.15 | N |
| ATOM | 9275 | C19 | STU | F | 1 | 67.886 | 11.825 | 75.668 | 1.00 | 38.82 | C |
| ATOM | 9276 | C25 | STU | F | 1 | 65.425 | 12.605 | 75.225 | 1.00 | 42.40 | C |
| ATOM | 9277 | O4 | STU | F | 1 | 65.947 | 13.175 | 74.004 | 1.00 | 45.77 | O |
| ATOM | 9278 | C10 | STU | F | 1 | 70.649 | 11.280 | 75.504 | 1.00 | 38.27 | C |
| ATOM | 9279 | C9 | STU | F | 1 | 72.135 | 10.840 | 75.564 | 1.00 | 40.41 | C |
| ATOM | 9280 | C11 | STU | F | 1 | 70.059 | 12.363 | 74.716 | 1.00 | 36.41 | C |
| ATOM | 9281 | C12 | STU | F | 1 | 70.564 | 13.297 | 73.809 | 1.00 | 40.01 | C |
| ATOM | 9282 | C13 | STU | F | 1 | 71.856 | 13.529 | 73.321 | 1.00 | 37.12 | C |
| ATOM | 9283 | C14 | STU | F | 1 | 72.123 | 14.520 | 72.425 | 1.00 | 41.21 | C |
| ATOM | 9284 | C15 | STU | F | 1 | 71.041 | 15.347 | 71.974 | 1.00 | 40.56 | C |
| ATOM | 9285 | C17 | STU | F | 1 | 69.504 | 14.128 | 73.354 | 1.00 | 41.82 | C |
| ATOM | 9286 | C16 | STU | F | 1 | 69.777 | 15.147 | 72.436 | 1.00 | 43.38 | C |
| ATOM | 9287 | C18 | STU | F | 1 | 68.640 | 12.586 | 74.849 | 1.00 | 36.67 | C |
| ATOM | 9288 | N2 | STU | F | 1 | 68.336 | 13.687 | 74.004 | 1.00 | 38.69 | N |
| ATOM | 9289 | C21 | STU | F | 1 | 66.895 | 14.236 | 73.911 | 1.00 | 42.25 | C |
| ATOM | 9290 | C26 | STU | F | 1 | 66.623 | 14.878 | 72.559 | 1.00 | 39.00 | C |

FIG. 2A-202

| ATOM | 9291 | C22 | STU | F | 1 | 66.686 | 15.337 | 75.033 | 1.00 | 43.87 | C |
|---|---|---|---|---|---|---|---|---|---|---|---|
| ATOM | 9292 | O6 | STU | F | 1 | 67.499 | 15.025 | 76.184 | 1.00 | 41.77 | O |
| ATOM | 9293 | C27 | STU | F | 1 | 68.473 | 16.018 | 76.458 | 1.00 | 45.20 | C |
| ATOM | 9294 | C23 | STU | F | 1 | 65.209 | 15.177 | 75.495 | 1.00 | 43.58 | C |
| ATOM | 9295 | C24 | STU | F | 1 | 64.978 | 13.781 | 76.145 | 1.00 | 37.24 | C |
| ATOM | 9296 | N4 | STU | F | 1 | 64.825 | 16.268 | 76.569 | 1.00 | 50.54 | N |
| ATOM | 9297 | C28 | STU | F | 1 | 63.340 | 16.503 | 76.662 | 1.00 | 59.30 | C |
| ATOM | 9298 | O5 | STU | G | 1 | 83.052 | -4.320 | 33.318 | 1.00 | 48.39 | O |
| ATOM | 9299 | C8 | STU | G | 1 | 82.942 | -3.165 | 33.629 | 1.00 | 45.58 | C |
| ATOM | 9300 | N1 | STU | G | 1 | 82.646 | -2.668 | 34.829 | 1.00 | 51.88 | N |
| ATOM | 9301 | C7 | STU | G | 1 | 83.095 | -1.957 | 32.790 | 1.00 | 41.11 | C |
| ATOM | 9302 | C6 | STU | G | 1 | 83.429 | -1.926 | 31.336 | 1.00 | 42.31 | C |
| ATOM | 9303 | C5 | STU | G | 1 | 83.699 | -2.867 | 30.339 | 1.00 | 40.25 | C |
| ATOM | 9304 | C20 | STU | G | 1 | 83.939 | -2.114 | 29.113 | 1.00 | 42.26 | C |
| ATOM | 9305 | C1 | STU | G | 1 | 84.261 | -2.766 | 27.866 | 1.00 | 43.04 | C |
| ATOM | 9306 | C2 | STU | G | 1 | 84.327 | -4.160 | 27.878 | 1.00 | 37.57 | C |
| ATOM | 9307 | C3 | STU | G | 1 | 84.080 | -4.917 | 29.104 | 1.00 | 39.08 | C |
| ATOM | 9308 | C4 | STU | G | 1 | 83.780 | -4.279 | 30.280 | 1.00 | 38.20 | C |
| ATOM | 9309 | N3 | STU | G | 1 | 83.819 | -0.793 | 29.384 | 1.00 | 41.84 | N |
| ATOM | 9310 | C19 | STU | G | 1 | 83.503 | -0.606 | 30.769 | 1.00 | 41.51 | C |
| ATOM | 9311 | C25 | STU | G | 1 | 84.260 | 0.270 | 28.456 | 1.00 | 41.15 | C |
| ATOM | 9312 | O4 | STU | G | 1 | 84.529 | 1.499 | 29.151 | 1.00 | 43.73 | O |
| ATOM | 9313 | C10 | STU | G | 1 | 82.891 | -0.870 | 33.502 | 1.00 | 42.00 | C |
| ATOM | 9314 | C9 | STU | G | 1 | 82.569 | -1.239 | 34.952 | 1.00 | 47.81 | C |
| ATOM | 9315 | C11 | STU | G | 1 | 82.967 | 0.449 | 32.938 | 1.00 | 41.33 | C |
| ATOM | 9316 | C12 | STU | G | 1 | 82.802 | 1.745 | 33.426 | 1.00 | 40.79 | C |
| ATOM | 9317 | C13 | STU | G | 1 | 82.506 | 2.243 | 34.693 | 1.00 | 41.88 | C |
| ATOM | 9318 | C14 | STU | G | 1 | 82.386 | 3.612 | 34.959 | 1.00 | 35.56 | C |
| ATOM | 9319 | C15 | STU | G | 1 | 82.573 | 4.535 | 33.873 | 1.00 | 44.60 | C |
| ATOM | 9320 | C17 | STU | G | 1 | 82.994 | 2.683 | 32.350 | 1.00 | 40.84 | C |
| ATOM | 9321 | C16 | STU | G | 1 | 82.868 | 4.066 | 32.610 | 1.00 | 41.25 | C |
| ATOM | 9322 | C18 | STU | G | 1 | 83.283 | 0.528 | 31.518 | 1.00 | 39.70 | C |
| ATOM | 9323 | N2 | STU | G | 1 | 83.282 | 1.925 | 31.202 | 1.00 | 36.28 | N |
| ATOM | 9324 | C21 | STU | G | 1 | 83.566 | 2.368 | 29.776 | 1.00 | 38.57 | C |
| ATOM | 9325 | C26 | STU | G | 1 | 84.273 | 3.719 | 29.741 | 1.00 | 35.46 | C |
| ATOM | 9326 | C22 | STU | G | 1 | 82.189 | 2.439 | 28.993 | 1.00 | 37.61 | C |
| ATOM | 9327 | O6 | STU | G | 1 | 81.286 | 1.433 | 29.523 | 1.00 | 33.44 | O |
| ATOM | 9328 | C27 | STU | G | 1 | 80.255 | 1.946 | 30.328 | 1.00 | 31.98 | C |
| ATOM | 9329 | C23 | STU | G | 1 | 82.559 | 2.011 | 27.526 | 1.00 | 41.96 | C |
| ATOM | 9330 | C24 | STU | G | 1 | 83.077 | 0.530 | 27.474 | 1.00 | 43.72 | C |
| ATOM | 9331 | N4 | STU | G | 1 | 81.338 | 2.090 | 26.562 | 1.00 | 53.82 | N |
| ATOM | 9332 | C28 | STU | G | 1 | 81.098 | 3.502 | 26.176 | 1.00 | 57.41 | C |
| ATOM | 9333 | O5 | STU | H | 1 | 94.788 | 22.684 | -0.870 | 1.00 | 64.49 | O |
| ATOM | 9334 | C8 | STU | H | 1 | 94.439 | 23.347 | 0.096 | 1.00 | 64.32 | C |
| ATOM | 9335 | N1 | STU | H | 1 | 94.340 | 24.686 | 0.183 | 1.00 | 62.67 | N |
| ATOM | 9336 | C7 | STU | H | 1 | 94.024 | 22.891 | 1.463 | 1.00 | 58.66 | C |

FIG. 2A-203

| | | | | | | | | | | | |
|---|---|---|---|---|---|---|---|---|---|---|---|
| ATOM | 9337 | C6 | STU | H | 1 | 93.945 | 21.482 | 1.960 | 1.00 | 60.23 | C |
| ATOM | 9338 | C5 | STU | H | 1 | 94.188 | 20.214 | 1.432 | 1.00 | 62.78 | C |
| ATOM | 9339 | C20 | STU | H | 1 | 93.909 | 19.270 | 2.485 | 1.00 | 64.07 | C |
| ATOM | 9340 | C1 | STU | H | 1 | 94.054 | 17.847 | 2.281 | 1.00 | 66.20 | C |
| ATOM | 9341 | C2 | STU | H | 1 | 94.476 | 17.399 | 1.034 | 1.00 | 63.64 | C |
| ATOM | 9342 | C3 | STU | H | 1 | 94.757 | 18.336 | -0.016 | 1.00 | 64.10 | C |
| ATOM | 9343 | C4 | STU | H | 1 | 94.615 | 19.698 | 0.189 | 1.00 | 63.08 | C |
| ATOM | 9344 | N3 | STU | H | 1 | 93.502 | 19.953 | 3.598 | 1.00 | 60.52 | N |
| ATOM | 9345 | C19 | STU | H | 1 | 93.507 | 21.341 | 3.341 | 1.00 | 59.27 | C |
| ATOM | 9346 | C25 | STU | H | 1 | 92.844 | 19.296 | 4.774 | 1.00 | 59.72 | C |
| ATOM | 9347 | O4 | STU | H | 1 | 92.071 | 20.234 | 5.544 | 1.00 | 64.64 | O |
| ATOM | 9348 | C10 | STU | H | 1 | 93.720 | 23.925 | 2.223 | 1.00 | 57.19 | C |
| ATOM | 9349 | C9 | STU | H | 1 | 93.901 | 25.241 | 1.443 | 1.00 | 54.41 | C |
| ATOM | 9350 | C11 | STU | H | 1 | 93.294 | 23.777 | 3.597 | 1.00 | 59.47 | C |
| ATOM | 9351 | C12 | STU | H | 1 | 92.932 | 24.677 | 4.617 | 1.00 | 61.32 | C |
| ATOM | 9352 | C13 | STU | H | 1 | 92.856 | 26.090 | 4.654 | 1.00 | 61.55 | C |
| ATOM | 9353 | C14 | STU | H | 1 | 92.467 | 26.777 | 5.787 | 1.00 | 58.53 | C |
| ATOM | 9354 | C15 | STU | H | 1 | 92.137 | 26.000 | 6.954 | 1.00 | 56.99 | C |
| ATOM | 9355 | C17 | STU | H | 1 | 92.593 | 23.921 | 5.815 | 1.00 | 58.53 | C |
| ATOM | 9356 | C16 | STU | H | 1 | 92.204 | 24.619 | 6.952 | 1.00 | 55.80 | C |
| ATOM | 9357 | C18 | STU | H | 1 | 93.199 | 22.408 | 4.125 | 1.00 | 56.80 | C |
| ATOM | 9358 | N2 | STU | H | 1 | 92.764 | 22.534 | 5.498 | 1.00 | 57.53 | N |
| ATOM | 9359 | C21 | STU | H | 1 | 92.575 | 21.261 | 6.361 | 1.00 | 58.32 | C |
| ATOM | 9360 | C26 | STU | H | 1 | 91.515 | 21.450 | 7.401 | 1.00 | 60.27 | C |
| ATOM | 9361 | C22 | STU | H | 1 | 93.903 | 20.855 | 7.085 | 1.00 | 55.37 | C |
| ATOM | 9362 | O6 | STU | H | 1 | 95.016 | 21.265 | 6.263 | 1.00 | 52.82 | O |
| ATOM | 9363 | C27 | STU | H | 1 | 95.829 | 22.185 | 6.927 | 1.00 | 50.68 | C |
| ATOM | 9364 | C23 | STU | H | 1 | 93.878 | 19.263 | 7.127 | 1.00 | 56.43 | C |
| ATOM | 9365 | C24 | STU | H | 1 | 93.951 | 18.691 | 5.693 | 1.00 | 55.39 | C |
| ATOM | 9366 | N4 | STU | H | 1 | 95.103 | 18.608 | 7.876 | 1.00 | 57.92 | N |
| ATOM | 9367 | C28 | STU | H | 1 | 95.290 | 19.183 | 9.255 | 1.00 | 65.16 | C |
| ATOM | 9368 | S | SO4 | I | 1 | 76.247 | 5.577 | 87.122 | 1.00 | 96.44 | S |
| ATOM | 9369 | O5 | SO4 | I | 1 | 77.606 | 6.076 | 87.174 | 1.00 | 90.43 | O |
| ATOM | 9370 | O2 | SO4 | I | 1 | 76.075 | 4.438 | 87.964 | 1.00 | 94.27 | O |
| ATOM | 9371 | O3 | SO4 | I | 1 | 75.406 | 6.709 | 87.295 | 1.00 | 86.42 | O |
| ATOM | 9372 | O4 | SO4 | I | 1 | 76.086 | 5.114 | 85.651 | 1.00 | 91.13 | O |
| ATOM | 9373 | S | SO4 | I | 2 | 88.533 | 8.309 | 57.336 | | 1.00 | S |
| ATOM | 9374 | O5 | SO4 | I | 2 | 89.507 | 8.302 | 58.411 | 1.00 | 98.80 | O |
| ATOM | 9375 | O2 | SO4 | I | 2 | 87.580 | 9.356 | 57.498 | 1.00 | 91.50 | O |
| ATOM | 9376 | O3 | SO4 | I | 2 | 89.279 | 8.225 | 56.130 | 1.00 | 95.40 | O |
| ATOM | 9377 | O4 | SO4 | I | 2 | 87.793 | 6.954 | 57.508 | | 1.00 | O |
| ATOM | 9378 | O | HOH | W | 1 | 88.552 | 7.879 | 68.343 | 1.00 | 69.53 | O |
| ATOM | 9379 | O | HOH | W | 2 | 116.511 | 3.959 | 72.077 | 1.00 | 69.91 | O |
| ATOM | 9380 | O | HOH | W | 3 | 101.490 | 25.908 | 21.522 | 1.00 | 60.43 | O |
| ATOM | 9381 | O | HOH | W | 4 | 108.855 | 24.868 | 53.448 | 1.00 | 54.53 | O |
| ATOM | 9382 | O | HOH | W | 5 | 114.672 | 35.597 | 30.139 | 1.00 | 56.50 | O |

FIG. 2A-204

| ATOM | 9383 | O | HOH | W | 6 | 112.819 | 24.583 | 38.076 | 1.00 | 52.34 | O |
| --- | --- | --- | --- | --- | --- | --- | --- | --- | --- | --- | --- |
| ATOM | 9384 | O | HOH | W | 7 | 68.159 | -8.708 | 77.281 | 1.00 | 79.66 | O |
| ATOM | 9385 | O | HOH | W | 8 | 74.739 | 16.415 | 70.398 | 1.00 | 38.62 | O |
| ATOM | 9386 | O | HOH | W | 9 | 81.177 | 22.244 | 59.027 | 1.00 | 72.97 | O |
| ATOM | 9387 | O | HOH | W | 10 | 81.756 | 2.014 | 75.891 | 1.00 | 50.79 | O |
| ATOM | 9388 | O | HOH | W | 11 | 61.694 | 21.179 | 83.008 | 1.00 | 81.69 | O |
| ATOM | 9389 | O | HOH | W | 12 | 81.962 | 34.944 | 73.525 | 1.00 | 68.80 | O |
| ATOM | 9390 | O | HOH | W | 13 | 104.799 | 44.316 | 15.999 | 1.00 | 54.24 | O |
| ATOM | 9391 | O | HOH | W | 14 | 91.964 | 44.959 | 16.575 | 1.00 | 79.05 | O |
| ATOM | 9392 | O | HOH | W | 15 | 81.532 | 36.391 | -8.994 | 1.00 | 75.24 | O |
| ATOM | 9393 | O | HOH | W | 16 | 112.222 | 60.612 | 18.164 | 1.00 | 47.83 | O |
| ATOM | 9394 | O | HOH | W | 17 | 61.713 | 12.029 | 37.353 | 1.00 | 41.31 | O |
| ATOM | 9395 | O | HOH | W | 18 | 77.573 | 2.179 | 2.782 | 1.00 | 74.11 | O |
| ATOM | 9396 | O | HOH | W | 19 | 85.019 | -0.271 | 68.266 | 1.00 | 85.27 | O |
| ATOM | 9397 | O | HOH | W | 20 | 86.098 | 6.714 | 68.812 | 1.00 | 64.70 | O |
| ATOM | 9398 | O | HOH | W | 21 | 114.216 | 7.044 | 63.020 | 1.00 | 64.46 | O |
| ATOM | 9399 | O | HOH | W | 22 | 99.551 | 7.408 | 59.415 | 1.00 | 49.06 | O |
| ATOM | 9400 | O | HOH | W | 23 | 92.642 | 5.873 | 63.048 | 1.00 | 63.63 | O |
| ATOM | 9401 | O | HOH | W | 24 | 92.326 | 17.927 | 74.815 | 1.00 | 57.59 | O |
| ATOM | 9402 | O | HOH | W | 25 | 126.712 | 24.806 | 61.097 | 1.00 | 87.27 | O |
| ATOM | 9403 | O | HOH | W | 26 | 86.583 | 4.342 | 64.970 | 1.00 | 75.48 | O |
| ATOM | 9404 | O | HOH | W | 27 | 84.841 | 1.859 | 59.156 | 1.00 | 64.83 | O |
| ATOM | 9405 | O | HOH | W | 28 | 68.153 | 24.161 | 63.600 | 1.00 | 84.88 | O |
| ATOM | 9406 | O | HOH | W | 29 | 72.305 | 28.915 | 76.949 | 1.00 | 67.63 | O |
| ATOM | 9407 | O | HOH | W | 30 | 89.574 | -5.925 | 49.012 | 1.00 | 87.37 | O |
| ATOM | 9408 | O | HOH | W | 31 | 77.041 | 14.231 | 46.353 | 1.00 | 82.31 | O |
| ATOM | 9409 | O | HOH | W | 32 | 76.704 | 1.397 | 90.525 | 1.00 | 57.49 | O |
| ATOM | 9410 | O | HOH | W | 33 | 47.502 | 3.215 | 28.347 | 1.00 | 84.94 | O |
| ATOM | 9411 | O | HOH | W | 34 | 84.439 | 35.065 | -9.128 | 1.00 | 78.38 | O |
| ATOM | 9412 | O | HOH | W | 35 | 75.708 | -2.192 | 54.576 | 1.00 | 46.00 | O |
| ATOM | 9413 | O | HOH | W | 36 | 69.586 | -7.400 | 73.310 | 1.00 | 79.51 | O |
| ATOM | 9414 | O | HOH | W | 37 | 75.436 | 2.603 | 78.615 | 1.00 | 90.62 | O |
| ATOM | 9415 | O | HOH | W | 38 | 89.784 | 29.931 | 75.336 | 1.00 | 62.70 | O |
| ATOM | 9416 | O | HOH | W | 39 | 113.642 | 27.900 | 48.298 | 1.00 | 59.35 | O |
| ATOM | 9417 | O | HOH | W | 40 | 81.366 | 5.710 | 37.575 | 1.00 | 62.32 | O |
| ATOM | 9418 | O | HOH | W | 41 | 60.482 | 12.328 | 39.581 | 1.00 | 56.87 | O |
| ATOM | 9419 | O | HOH | W | 42 | 52.035 | 8.096 | 26.644 | 1.00 | 73.17 | O |
| ATOM | 9420 | O | HOH | W | 43 | 73.477 | 27.919 | 14.765 | 1.00 | 76.90 | O |

FIG. 3

| | | Atom Type | Res. | Mol. | Res. No. | X | Y | Z | OCC | B | |
|---|---|---|---|---|---|---|---|---|---|---|---|
| ATOM | 1 | N | PHE | A | 46 | 214.820 | 109.707 | 179.069 | 1.00 | 118.35 | N |
| ATOM | 2 | CA | PHE | A | 46 | 214.336 | 108.388 | 178.678 | 1.00 | 109.39 | C |
| ATOM | 3 | CB | PHE | A | 46 | 213.617 | 108.523 | 177.335 | 1.00 | 106.31 | C |
| ATOM | 4 | CG | PHE | A | 46 | 212.712 | 107.345 | 177.122 | 1.00 | 100.53 | C |
| ATOM | 5 | CD1 | PHE | A | 46 | 213.246 | 106.138 | 176.688 | 1.00 | 94.28 | C |
| ATOM | 6 | CE1 | PHE | A | 46 | 212.408 | 105.049 | 176.480 | 1.00 | 71.80 | C |
| ATOM | 7 | CZ | PHE | A | 46 | 211.041 | 105.159 | 176.704 | 1.00 | 54.26 | C |
| ATOM | 8 | CE2 | PHE | A | 46 | 210.515 | 106.370 | 177.135 | 1.00 | 83.85 | C |
| ATOM | 9 | CD2 | PHE | A | 46 | 211.347 | 107.468 | 177.345 | 1.00 | 81.06 | C |
| ATOM | 10 | C | PHE | A | 46 | 215.483 | 107.382 | 178.556 | 1.00 | 92.52 | C |
| ATOM | 11 | O | PHE | A | 46 | 216.008 | 107.116 | 177.483 | 1.00 | 93.11 | O |
| ATOM | 12 | N | HIS | A | 47 | 215.896 | 106.847 | 179.719 | 1.00 | 99.95 | N |
| ATOM | 13 | CA | HIS | A | 47 | 216.976 | 105.867 | 179.715 | 1.00 | 110.68 | C |
| ATOM | 14 | CB | HIS | A | 47 | 217.598 | 105.835 | 181.111 | 1.00 | 128.34 | C |
| ATOM | 15 | CG | HIS | A | 47 | 217.973 | 107.234 | 181.527 | 1.00 | 172.75 | C |
| ATOM | 16 | ND1 | HIS | A | 47 | 219.157 | 107.813 | 181.211 | 1.00 | 209.78 | N |
| ATOM | 17 | CE1 | HIS | A | 47 | 219.113 | 109.047 | 181.749 | 1.00 | 214.52 | C |
| ATOM | 18 | NE2 | HIS | A | 47 | 217.963 | 109.275 | 182.389 | 1.00 | 216.85 | N |
| ATOM | 19 | CD2 | HIS | A | 47 | 217.216 | 108.147 | 182.270 | 1.00 | 195.55 | C |
| ATOM | 20 | C | HIS | A | 47 | 216.467 | 104.473 | 179.342 | 1.00 | 99.74 | C |
| ATOM | 21 | O | HIS | A | 47 | 215.591 | 103.903 | 179.979 | 1.00 | 108.34 | O |
| ATOM | 22 | N | VAL | A | 48 | 217.023 | 103.942 | 178.238 | 1.00 | 93.29 | N |
| ATOM | 23 | CA | VAL | A | 48 | 216.620 | 102.613 | 177.798 | 1.00 | 69.76 | C |
| ATOM | 24 | CB | VAL | A | 48 | 215.510 | 102.770 | 176.757 | 1.00 | 60.38 | C |
| ATOM | 25 | CG1 | VAL | A | 48 | 215.345 | 101.470 | 175.973 | 1.00 | 76.52 | C |
| ATOM | 26 | CG2 | VAL | A | 48 | 214.200 | 103.110 | 177.443 | 1.00 | 87.98 | C |
| ATOM | 27 | C | VAL | A | 48 | 217.795 | 101.841 | 177.194 | 1.00 | 72.39 | C |
| ATOM | 28 | O | VAL | A | 48 | 218.595 | 102.370 | 176.434 | 1.00 | 67.87 | O |
| ATOM | 29 | N | LYS | A | 49 | 217.962 | 100.570 | 177.519 | 1.00 | 63.04 | N |
| ATOM | 30 | CA | LYS | A | 49 | 219.047 | 99.811 | 176.921 | 1.00 | 61.31 | C |
| ATOM | 31 | CB | LYS | A | 49 | 219.741 | 98.923 | 177.947 | 1.00 | 46.86 | C |
| ATOM | 32 | CG | LYS | A | 49 | 220.349 | 99.673 | 179.103 | 1.00 | 52.81 | C |
| ATOM | 33 | CD | LYS | A | 49 | 221.201 | 100.796 | 178.607 | 1.00 | 52.94 | C |
| ATOM | 34 | CE | LYS | A | 49 | 222.255 | 101.150 | 179.627 | 1.00 | 106.42 | C |
| ATOM | 35 | NZ | LYS | A | 49 | 223.200 | 102.166 | 179.091 | 1.00 | 117.49 | N |
| ATOM | 36 | C | LYS | A | 49 | 218.424 | 98.945 | 175.833 | 1.00 | 56.33 | C |
| ATOM | 37 | O | LYS | A | 49 | 217.205 | 98.904 | 175.688 | 1.00 | 61.95 | O |
| ATOM | 38 | N | SER | A | 50 | 219.258 | 98.248 | 175.073 | 1.00 | 67.67 | N |
| ATOM | 39 | CA | SER | A | 50 | 218.768 | 97.403 | 173.994 | 1.00 | 61.19 | C |
| ATOM | 40 | CB | SER | A | 50 | 219.875 | 97.119 | 172.994 | 1.00 | 59.19 | C |
| ATOM | 41 | OG | SER | A | 50 | 220.167 | 98.279 | 172.248 | 1.00 | 125.35 | O |
| ATOM | 42 | C | SER | A | 50 | 218.240 | 96.087 | 174.484 | 1.00 | 62.93 | C |
| ATOM | 43 | O | SER | A | 50 | 218.661 | 95.592 | 175.528 | 1.00 | 78.88 | O |
| ATOM | 44 | N | GLY | A | 51 | 217.318 | 95.516 | 173.718 | 1.00 | 62.13 | N |
| ATOM | 45 | CA | GLY | A | 51 | 216.773 | 94.223 | 174.070 | 1.00 | 45.10 | C |
| ATOM | 46 | C | GLY | A | 51 | 217.728 | 93.155 | 173.571 | 1.00 | 32.66 | C |
| ATOM | 47 | O | GLY | A | 51 | 218.558 | 93.420 | 172.709 | 1.00 | 72.20 | O |
| ATOM | 48 | N | LEU | A | 52 | 217.634 | 91.951 | 174.114 | 1.00 | 65.04 | N |
| ATOM | 49 | CA | LEU | A | 52 | 218.509 | 90.868 | 173.671 | 1.00 | 48.78 | C |
| ATOM | 50 | CB | LEU | A | 52 | 218.420 | 89.677 | 174.635 | 1.00 | 67.84 | C |
| ATOM | 51 | CG | LEU | A | 52 | 219.214 | 88.431 | 174.227 | 1.00 | 72.80 | C |

FIG. 3A-1

| ATOM | 52 | CD1 | LEU | A | 52 | 220.719 | 88.700 | 174.309 | 1.00 | 57.35 | C |
|---|---|---|---|---|---|---|---|---|---|---|---|
| ATOM | 53 | CD2 | LEU | A | 52 | 218.844 | 87.283 | 175.128 | 1.00 | 66.63 | C |
| ATOM | 54 | C | LEU | A | 52 | 218.154 | 90.388 | 172.252 | 1.00 | 54.66 | C |
| ATOM | 55 | O | LEU | A | 52 | 216.986 | 90.340 | 171.866 | 1.00 | 70.19 | O |
| ATOM | 56 | N | GLN | A | 53 | 219.170 | 90.031 | 171.477 | 1.00 | 68.12 | N |
| ATOM | 57 | CA | GLN | A | 53 | 218.958 | 89.546 | 170.125 | 1.00 | 54.88 | C |
| ATOM | 58 | CB | GLN | A | 53 | 219.372 | 90.588 | 169.115 | 1.00 | 47.08 | C |
| ATOM | 59 | CG | GLN | A | 53 | 219.428 | 90.042 | 167.731 | 1.00 | 60.85 | C |
| ATOM | 60 | CD | GLN | A | 53 | 220.160 | 90.974 | 166.832 | 1.00 | 80.61 | C |
| ATOM | 61 | OE1 | GLN | A | 53 | 220.236 | 90.753 | 165.627 | 1.00 | 99.15 | O |
| ATOM | 62 | NE2 | GLN | A | 53 | 220.723 | 92.031 | 167.411 | 1.00 | 83.94 | N |
| ATOM | 63 | C | GLN | A | 53 | 219.752 | 88.291 | 169.858 | 1.00 | 40.76 | C |
| ATOM | 64 | O | GLN | A | 53 | 220.978 | 88.278 | 169.936 | 1.00 | 66.36 | O |
| ATOM | 65 | N | ILE | A | 54 | 219.050 | 87.233 | 169.508 | 1.00 | 60.15 | N |
| ATOM | 66 | CA | ILE | A | 54 | 219.705 | 85.971 | 169.238 | 1.00 | 52.14 | C |
| ATOM | 67 | CB | ILE | A | 54 | 218.743 | 84.814 | 169.552 | 1.00 | 64.06 | C |
| ATOM | 68 | CG1 | ILE | A | 54 | 218.312 | 84.924 | 171.010 | 1.00 | 33.87 | C |
| ATOM | 69 | CD1 | ILE | A | 54 | 217.727 | 83.680 | 171.535 | 1.00 | 82.78 | C |
| ATOM | 70 | CG2 | ILE | A | 54 | 219.412 | 83.479 | 169.315 | 1.00 | 39.67 | C |
| ATOM | 71 | C | ILE | A | 54 | 220.190 | 85.896 | 167.802 | 1.00 | 51.88 | C |
| ATOM | 72 | O | ILE | A | 54 | 219.433 | 85.575 | 166.893 | 1.00 | 58.79 | O |
| ATOM | 73 | N | LYS | A | 55 | 221.464 | 86.197 | 167.611 | 1.00 | 48.72 | N |
| ATOM | 74 | CA | LYS | A | 55 | 222.064 | 86.182 | 166.287 | 1.00 | 49.52 | C |
| ATOM | 75 | CB | LYS | A | 55 | 223.512 | 86.661 | 166.383 | 1.00 | 51.25 | C |
| ATOM | 76 | CG | LYS | A | 55 | 223.628 | 88.111 | 166.815 | 1.00 | 49.44 | C |
| ATOM | 77 | CD | LYS | A | 55 | 225.059 | 88.584 | 166.817 | 1.00 | 89.37 | C |
| ATOM | 78 | CE | LYS | A | 55 | 225.114 | 90.085 | 167.040 | 1.00 | 73.14 | C |
| ATOM | 79 | NZ | LYS | A | 55 | 226.521 | 90.612 | 167.008 | 1.00 | 123.08 | N |
| ATOM | 80 | C | LYS | A | 55 | 222.019 | 84.808 | 165.633 | 1.00 | 56.72 | C |
| ATOM | 81 | O | LYS | A | 55 | 222.270 | 83.808 | 166.283 | 1.00 | 70.19 | O |
| ATOM | 82 | N | LYS | A | 56 | 221.710 | 84.758 | 164.343 | 1.00 | 41.46 | N |
| ATOM | 83 | CA | LYS | A | 56 | 221.644 | 83.482 | 163.643 | 1.00 | 66.57 | C |
| ATOM | 84 | CB | LYS | A | 56 | 220.379 | 83.413 | 162.793 | 1.00 | 48.95 | C |
| ATOM | 85 | CG | LYS | A | 56 | 219.242 | 82.751 | 163.486 | 1.00 | 57.91 | C |
| ATOM | 86 | CD | LYS | A | 56 | 219.248 | 83.157 | 164.927 | 1.00 | 78.89 | C |
| ATOM | 87 | CE | LYS | A | 56 | 217.907 | 82.899 | 165.554 | 1.00 | 71.88 | C |
| ATOM | 88 | NZ | LYS | A | 56 | 216.873 | 83.764 | 164.935 | 1.00 | 82.07 | N |
| ATOM | 89 | C | LYS | A | 56 | 222.839 | 83.118 | 162.767 | 1.00 | 55.67 | C |
| ATOM | 90 | O | LYS | A | 56 | 223.028 | 81.945 | 162.455 | 1.00 | 66.55 | O |
| ATOM | 91 | N | ASN | A | 57 | 223.640 | 84.096 | 162.361 | 1.00 | 48.62 | N |
| ATOM | 92 | CA | ASN | A | 57 | 224.788 | 83.802 | 161.508 | 1.00 | 52.30 | C |
| ATOM | 93 | CB | ASN | A | 57 | 225.380 | 85.083 | 161.004 | 1.00 | 42.83 | C |
| ATOM | 94 | CG | ASN | A | 57 | 225.743 | 86.007 | 162.123 | 1.00 | 73.68 | C |
| ATOM | 95 | OD1 | ASN | A | 57 | 224.859 | 86.577 | 162.794 | 1.00 | 48.52 | O |
| ATOM | 96 | ND2 | ASN | A | 57 | 227.056 | 86.182 | 162.340 | 1.00 | 36.35 | N |
| ATOM | 97 | C | ASN | A | 57 | 225.851 | 83.039 | 162.261 | 1.00 | 40.32 | C |
| ATOM | 98 | O | ASN | A | 57 | 225.977 | 83.197 | 163.467 | 1.00 | 58.36 | O |
| ATOM | 99 | N | ALA | A | 58 | 226.627 | 82.223 | 161.558 | 1.00 | 41.49 | N |
| ATOM | 100 | CA | ALA | A | 58 | 227.661 | 81.432 | 162.214 | 1.00 | 44.46 | C |
| ATOM | 101 | CB | ALA | A | 58 | 228.438 | 80.641 | 161.194 | 1.00 | 32.48 | C |
| ATOM | 102 | C | ALA | A | 58 | 228.613 | 82.283 | 163.040 | 1.00 | 44.31 | C |
| ATOM | 103 | O | ALA | A | 58 | 229.267 | 83.173 | 162.516 | 1.00 | 45.45 | O |
| ATOM | 104 | N | ILE | A | 59 | 228.694 | 81.998 | 164.334 | 1.00 | 46.98 | N |
| ATOM | 105 | CA | ILE | A | 59 | 229.569 | 82.753 | 165.228 | 1.00 | 54.79 | C |
| ATOM | 106 | CB | ILE | A | 59 | 229.605 | 82.094 | 166.638 | 1.00 | 53.52 | C |

FIG. 3A-2

| | | | | | | | | | | |
|---|---|---|---|---|---|---|---|---|---|---|
| ATOM | 107 | CG1 | ILE | A | 59 | 230.284 | 83.012 | 167.644 | 1.00 | 55.42 C |
| ATOM | 108 | CD1 | ILE | A | 59 | 230.311 | 82.446 | 169.038 | 1.00 | 57.36 C |
| ATOM | 109 | CG2 | ILE | A | 59 | 230.376 | 80.791 | 166.588 | 1.00 | 40.15 C |
| ATOM | 110 | C | ILE | A | 59 | 231.007 | 82.870 | 164.670 | 1.00 | 63.43 C |
| ATOM | 111 | O | ILE | A | 59 | 231.766 | 83.777 | 165.035 | 1.00 | 47.27 O |
| ATOM | 112 | N | ILE | A | 60 | 231.375 | 81.956 | 163.777 | 1.00 | 43.08 N |
| ATOM | 113 | CA | ILE | A | 60 | 232.743 | 81.902 | 163.274 | 1.00 | 57.78 C |
| ATOM | 114 | CB | ILE | A | 60 | 232.866 | 80.659 | 162.393 | 1.00 | 38.44 C |
| ATOM | 115 | CG1 | ILE | A | 60 | 231.615 | 80.513 | 161.518 | 1.00 | 50.72 C |
| ATOM | 116 | CD1 | ILE | A | 60 | 231.798 | 79.479 | 160.407 | 1.00 | 46.70 C |
| ATOM | 117 | CG2 | ILE | A | 60 | 232.965 | 79.403 | 163.277 | 1.00 | 49.86 C |
| ATOM | 118 | C | ILE | A | 60 | 233.086 | 83.151 | 162.458 | 1.00 | 60.65 C |
| ATOM | 119 | O | ILE | A | 60 | 234.226 | 83.590 | 162.377 | 1.00 | 72.20 O |
| ATOM | 120 | N | ASP | A | 61 | 232.044 | 83.704 | 161.811 | 1.00 | 32.79 N |
| ATOM | 121 | CA | ASP | A | 61 | 232.254 | 84.863 | 160.953 | 1.00 | 58.81 C |
| ATOM | 122 | CB | ASP | A | 61 | 230.972 | 85.093 | 160.149 | 1.00 | 36.95 C |
| ATOM | 123 | CG | ASP | A | 61 | 230.476 | 83.758 | 159.608 | 1.00 | 91.42 C |
| ATOM | 124 | OD1 | ASP | A | 61 | 229.268 | 83.636 | 159.400 | 1.00 | 76.09 O |
| ATOM | 125 | OD2 | ASP | A | 61 | 231.293 | 82.864 | 159.405 | 1.00 | 122.26 O |
| ATOM | 126 | C | ASP | A | 61 | 232.607 | 86.117 | 161.758 | 1.00 | 50.10 C |
| ATOM | 127 | O | ASP | A | 61 | 233.397 | 86.956 | 161.346 | 1.00 | 78.45 O |
| ATOM | 128 | N | ASP | A | 62 | 231.954 | 86.250 | 162.929 | 1.00 | 62.40 N |
| ATOM | 129 | CA | ASP | A | 62 | 232.213 | 87.422 | 163.761 | 1.00 | 63.46 C |
| ATOM | 130 | CB | ASP | A | 62 | 230.918 | 87.786 | 164.492 | 1.00 | 33.21 C |
| ATOM | 131 | CG | ASP | A | 62 | 229.843 | 88.135 | 163.473 | 1.00 | 76.80 C |
| ATOM | 132 | OD1 | ASP | A | 62 | 230.116 | 88.979 | 162.618 | 1.00 | 99.65 O |
| ATOM | 133 | OD2 | ASP | A | 62 | 228.754 | 87.573 | 163.546 | 1.00 | 84.30 O |
| ATOM | 134 | C | ASP | A | 62 | 233.328 | 87.164 | 164.778 | 1.00 | 43.90 C |
| ATOM | 135 | O | ASP | A | 62 | 233.994 | 88.071 | 165.261 | 1.00 | 74.39 O |
| ATOM | 136 | N | TYR | A | 63 | 233.493 | 85.877 | 165.132 | 1.00 | 44.70 N |
| ATOM | 137 | CA | TYR | A | 63 | 234.482 | 85.539 | 166.148 | 1.00 | 62.53 C |
| ATOM | 138 | CB | TYR | A | 63 | 233.742 | 84.965 | 167.358 | 1.00 | 50.79 C |
| ATOM | 139 | CG | TYR | A | 63 | 233.100 | 86.068 | 168.120 | 1.00 | 44.26 C |
| ATOM | 140 | CD1 | TYR | A | 63 | 233.802 | 86.709 | 169.136 | 1.00 | 34.66 C |
| ATOM | 141 | CE1 | TYR | A | 63 | 233.220 | 87.758 | 169.831 | 1.00 | 27.94 C |
| ATOM | 142 | CZ | TYR | A | 63 | 231.916 | 88.158 | 169.519 | 1.00 | 56.82 C |
| ATOM | 143 | OH | TYR | A | 63 | 231.353 | 89.224 | 170.192 | 1.00 | 41.90 O |
| ATOM | 144 | CE2 | TYR | A | 63 | 231.215 | 87.521 | 168.512 | 1.00 | 34.56 C |
| ATOM | 145 | CD2 | TYR | A | 63 | 231.800 | 86.477 | 167.811 | 1.00 | 37.87 C |
| ATOM | 146 | C | TYR | A | 63 | 235.502 | 84.519 | 165.641 | 1.00 | 58.43 C |
| ATOM | 147 | O | TYR | A | 63 | 235.388 | 83.956 | 164.561 | 1.00 | 79.42 O |
| ATOM | 148 | N | LYS | A | 64 | 236.554 | 84.325 | 166.455 | 1.00 | 69.78 N |
| ATOM | 149 | CA | LYS | A | 64 | 237.542 | 83.306 | 166.129 | 1.00 | 60.63 C |
| ATOM | 150 | CB | LYS | A | 64 | 238.825 | 84.004 | 165.673 | 1.00 | 85.98 C |
| ATOM | 151 | CG | LYS | A | 64 | 240.084 | 83.232 | 166.078 | 1.00 | 68.10 C |
| ATOM | 152 | CD | LYS | A | 64 | 240.235 | 81.914 | 165.315 | 1.00 | 96.02 C |
| ATOM | 153 | CE | LYS | A | 64 | 241.289 | 80.993 | 165.941 | 1.00 | 159.06 C |
| ATOM | 154 | NZ | LYS | A | 64 | 241.422 | 79.778 | 165.141 | 1.00 | 151.29 N |
| ATOM | 155 | C | LYS | A | 64 | 237.831 | 82.420 | 167.340 | 1.00 | 67.37 C |
| ATOM | 156 | O | LYS | A | 64 | 238.259 | 82.882 | 168.389 | 1.00 | 66.71 O |
| ATOM | 157 | N | VAL | A | 65 | 237.271 | 81.240 | 167.130 | 1.00 | 54.82 N |
| ATOM | 158 | CA | VAL | A | 65 | 237.148 | 80.288 | 168.220 | 1.00 | 65.09 C |
| ATOM | 159 | CB | VAL | A | 65 | 235.960 | 79.329 | 168.000 | 1.00 | 53.30 C |
| ATOM | 160 | CG1 | VAL | A | 65 | 235.948 | 78.263 | 169.075 | 1.00 | 68.94 C |
| ATOM | 161 | CG2 | VAL | A | 65 | 234.659 | 80.104 | 168.039 | 1.00 | 50.00 C |

FIG. 3A-3

| ATOM | 162 | C | VAL | A | 65 | 238.437 | 79.492 | 168.298 | 1.00 | 65.21 | C |
|---|---|---|---|---|---|---|---|---|---|---|---|
| ATOM | 163 | O | VAL | A | 65 | 238.945 | 79.029 | 167.282 | 1.00 | 79.23 | O |
| ATOM | 164 | N | THR | A | 66 | 238.971 | 79.338 | 169.502 | 1.00 | 60.78 | N |
| ATOM | 165 | CA | THR | A | 66 | 240.214 | 78.602 | 169.680 | 1.00 | 73.39 | C |
| ATOM | 166 | CB | THR | A | 66 | 241.267 | 79.462 | 170.376 | 1.00 | 65.28 | C |
| ATOM | 167 | OG1 | THR | A | 66 | 241.150 | 79.289 | 171.798 | 1.00 | 71.85 | O |
| ATOM | 168 | CG2 | THR | A | 66 | 241.067 | 80.944 | 170.016 | 1.00 | 64.31 | C |
| ATOM | 169 | C | THR | A | 66 | 240.032 | 77.346 | 170.515 | 1.00 | 76.31 | C |
| ATOM | 170 | O | THR | A | 66 | 238.969 | 77.107 | 171.080 | 1.00 | 77.40 | O |
| ATOM | 171 | N | SER | A | 67 | 241.092 | 76.554 | 170.602 | 1.00 | 86.86 | N |
| ATOM | 172 | CA | SER | A | 67 | 241.065 | 75.318 | 171.369 | 1.00 | 86.84 | C |
| ATOM | 173 | CB | SER | A | 67 | 242.082 | 74.338 | 170.818 | 1.00 | 77.74 | C |
| ATOM | 174 | OG | SER | A | 67 | 241.681 | 73.901 | 169.540 | 1.00 | 131.17 | O |
| ATOM | 175 | C | SER | A | 67 | 241.359 | 75.528 | 172.838 | 1.00 | 78.98 | C |
| ATOM | 176 | O | SER | A | 67 | 241.140 | 74.631 | 173.646 | 1.00 | 92.44 | O |
| ATOM | 177 | N | GLN | A | 68 | 241.868 | 76.702 | 173.185 | 1.00 | 65.34 | N |
| ATOM | 178 | CA | GLN | A | 68 | 242.187 | 76.981 | 174.571 | 1.00 | 79.87 | C |
| ATOM | 179 | CB | GLN | A | 68 | 242.760 | 78.387 | 174.704 | 1.00 | 76.67 | C |
| ATOM | 180 | CG | GLN | A | 68 | 243.238 | 78.724 | 176.100 | 1.00 | 86.58 | C |
| ATOM | 181 | CD | GLN | A | 68 | 244.346 | 79.757 | 176.087 | 1.00 | 151.90 | C |
| ATOM | 182 | OE1 | GLN | A | 68 | 244.745 | 80.271 | 177.134 | 1.00 | 147.03 | O |
| ATOM | 183 | NE2 | GLN | A | 68 | 244.860 | 80.060 | 174.895 | 1.00 | 166.06 | N |
| ATOM | 184 | C | GLN | A | 68 | 240.955 | 76.819 | 175.448 | 1.00 | 75.61 | C |
| ATOM | 185 | O | GLN | A | 68 | 239.849 | 77.197 | 175.067 | 1.00 | 70.47 | O |
| ATOM | 186 | N | VAL | A | 69 | 241.155 | 76.244 | 176.625 | 1.00 | 70.23 | N |
| ATOM | 187 | CA | VAL | A | 69 | 240.064 | 76.013 | 177.552 | 1.00 | 73.71 | C |
| ATOM | 188 | CB | VAL | A | 69 | 240.064 | 74.564 | 178.023 | 1.00 | 69.41 | C |
| ATOM | 189 | CG1 | VAL | A | 69 | 238.896 | 74.324 | 178.952 | 1.00 | 51.08 | C |
| ATOM | 190 | CG2 | VAL | A | 69 | 240.017 | 73.648 | 176.830 | 1.00 | 57.48 | C |
| ATOM | 191 | C | VAL | A | 69 | 240.157 | 76.908 | 178.775 | 1.00 | 65.57 | C |
| ATOM | 192 | O | VAL | A | 69 | 241.009 | 76.704 | 179.639 | 1.00 | 83.31 | O |
| ATOM | 193 | N | LEU | A | 70 | 239.276 | 77.899 | 178.847 | 1.00 | 74.02 | N |
| ATOM | 194 | CA | LEU | A | 70 | 239.259 | 78.816 | 179.977 | 1.00 | 88.16 | C |
| ATOM | 195 | CB | LEU | A | 70 | 238.268 | 79.956 | 179.718 | 1.00 | 80.15 | C |
| ATOM | 196 | CG | LEU | A | 70 | 238.660 | 81.015 | 178.680 | 1.00 | 66.85 | C |
| ATOM | 197 | CD1 | LEU | A | 70 | 237.420 | 81.668 | 178.097 | 1.00 | 90.30 | C |
| ATOM | 198 | CD2 | LEU | A | 70 | 239.553 | 82.049 | 179.322 | 1.00 | 79.20 | C |
| ATOM | 199 | C | LEU | A | 70 | 238.865 | 78.039 | 181.227 | 1.00 | 94.93 | C |
| ATOM | 200 | O | LEU | A | 70 | 239.171 | 78.458 | 182.343 | 1.00 | 86.96 | O |
| ATOM | 201 | N | GLY | A | 71 | 238.194 | 76.903 | 181.035 | 1.00 | 87.34 | N |
| ATOM | 202 | CA | GLY | A | 71 | 237.781 | 76.089 | 182.166 | 1.00 | 87.75 | C |
| ATOM | 203 | C | GLY | A | 71 | 236.707 | 75.077 | 181.825 | 1.00 | 83.77 | C |
| ATOM | 204 | O | GLY | A | 71 | 236.158 | 75.111 | 180.730 | 1.00 | 84.32 | O |
| ATOM | 205 | N | LEU | A | 72 | 236.405 | 74.175 | 182.757 | 1.00 | 88.68 | N |
| ATOM | 206 | CA | LEU | A | 72 | 235.381 | 73.155 | 182.534 | 1.00 | 82.29 | C |
| ATOM | 207 | CB | LEU | A | 72 | 235.976 | 71.751 | 182.621 | 1.00 | 77.46 | C |
| ATOM | 208 | CG | LEU | A | 72 | 236.877 | 71.305 | 181.473 | 1.00 | 94.19 | C |
| ATOM | 209 | CD1 | LEU | A | 72 | 237.217 | 69.818 | 181.595 | 1.00 | 139.26 | C |
| ATOM | 210 | CD2 | LEU | A | 72 | 236.150 | 71.568 | 180.172 | 1.00 | 109.03 | C |
| ATOM | 211 | C | LEU | A | 72 | 234.225 | 73.239 | 183.509 | 1.00 | 73.28 | C |
| ATOM | 212 | O | LEU | A | 72 | 234.318 | 73.871 | 184.557 | 1.00 | 95.04 | O |
| ATOM | 213 | N | GLY | A | 73 | 233.133 | 72.577 | 183.158 | 1.00 | 77.98 | N |
| ATOM | 214 | CA | GLY | A | 73 | 231.963 | 72.592 | 184.013 | 1.00 | 71.81 | C |
| ATOM | 215 | C | GLY | A | 73 | 230.762 | 71.853 | 183.446 | 1.00 | 99.78 | C |
| ATOM | 216 | O | GLY | A | 73 | 230.843 | 71.171 | 182.418 | 1.00 | 93.36 | O |

FIG. 3A-4

| ATOM | 217 | N | ILE | A | 74 | 229.635 | 72.004 | 184.136 | 1.00 | 112.58 | N |
|---|---|---|---|---|---|---|---|---|---|---|---|
| ATOM | 218 | CA | ILE | A | 74 | 228.376 | 71.365 | 183.765 | 1.00 | 114.50 | C |
| ATOM | 219 | CB | ILE | A | 74 | 227.189 | 72.085 | 184.439 | 1.00 | 120.25 | C |
| ATOM | 220 | CG1 | ILE | A | 74 | 227.145 | 71.707 | 185.921 | 1.00 | 127.29 | C |
| ATOM | 221 | CD1 | ILE | A | 74 | 225.968 | 72.285 | 186.673 | 1.00 | 178.93 | C |
| ATOM | 222 | CG2 | ILE | A | 74 | 225.889 | 71.745 | 183.724 | 1.00 | 110.29 | C |
| ATOM | 223 | C | ILE | A | 74 | 228.103 | 71.259 | 182.270 | 1.00 | 110.24 | C |
| ATOM | 224 | O | ILE | A | 74 | 227.890 | 70.162 | 181.750 | 1.00 | 94.78 | O |
| ATOM | 225 | N | ASN | A | 75 | 228.106 | 72.393 | 181.580 | 1.00 | 113.84 | N |
| ATOM | 226 | CA | ASN | A | 75 | 227.844 | 72.395 | 180.148 | 1.00 | 108.71 | C |
| ATOM | 227 | CB | ASN | A | 75 | 227.303 | 73.756 | 179.736 | 1.00 | 95.22 | C |
| ATOM | 228 | CG | ASN | A | 75 | 225.898 | 73.967 | 180.225 | 1.00 | 84.98 | C |
| ATOM | 229 | OD1 | ASN | A | 75 | 224.966 | 73.315 | 179.749 | 1.00 | 88.40 | O |
| ATOM | 230 | ND2 | ASN | A | 75 | 225.730 | 74.858 | 181.199 | 1.00 | 112.62 | N |
| ATOM | 231 | C | ASN | A | 75 | 229.044 | 72.005 | 179.296 | 1.00 | 100.52 | C |
| ATOM | 232 | O | ASN | A | 75 | 228.935 | 71.858 | 178.079 | 1.00 | 102.09 | O |
| ATOM | 233 | N | GLY | A | 76 | 230.186 | 71.820 | 179.940 | 1.00 | 99.31 | N |
| ATOM | 234 | CA | GLY | A | 76 | 231.360 | 71.428 | 179.198 | 1.00 | 93.20 | C |
| ATOM | 235 | C | GLY | A | 76 | 232.489 | 72.428 | 179.282 | 1.00 | 96.95 | C |
| ATOM | 236 | O | GLY | A | 76 | 232.666 | 73.117 | 180.285 | 1.00 | 101.12 | O |
| ATOM | 237 | N | ALA | A | 77 | 233.258 | 72.506 | 178.205 | 1.00 | 82.50 | N |
| ATOM | 238 | CA | ALA | A | 77 | 234.386 | 73.409 | 178.146 | 1.00 | 79.18 | C |
| ATOM | 239 | CB | ALA | A | 77 | 235.410 | 72.872 | 177.160 | 1.00 | 78.70 | C |
| ATOM | 240 | C | ALA | A | 77 | 233.986 | 74.820 | 177.757 | 1.00 | 66.93 | C |
| ATOM | 241 | O | ALA | A | 77 | 233.189 | 75.025 | 176.852 | 1.00 | 79.35 | O |
| ATOM | 242 | N | VAL | A | 78 | 234.523 | 75.794 | 178.470 | 1.00 | 57.33 | N |
| ATOM | 243 | CA | VAL | A | 78 | 234.267 | 77.179 | 178.150 | 1.00 | 49.75 | C |
| ATOM | 244 | CB | VAL | A | 78 | 234.138 | 78.020 | 179.386 | 1.00 | 54.95 | C |
| ATOM | 245 | CG1 | VAL | A | 78 | 234.267 | 79.482 | 179.023 | 1.00 | 45.00 | C |
| ATOM | 246 | CG2 | VAL | A | 78 | 232.810 | 77.742 | 180.029 | 1.00 | 52.90 | C |
| ATOM | 247 | C | VAL | A | 78 | 235.512 | 77.620 | 177.410 | 1.00 | 79.35 | C |
| ATOM | 248 | O | VAL | A | 78 | 236.545 | 77.888 | 178.028 | 1.00 | 64.43 | O |
| ATOM | 249 | N | LEU | A | 79 | 235.414 | 77.692 | 176.087 | 1.00 | 70.72 | N |
| ATOM | 250 | CA | LEU | A | 79 | 236.538 | 78.073 | 175.245 | 1.00 | 61.89 | C |
| ATOM | 251 | CB | LEU | A | 79 | 236.292 | 77.599 | 173.825 | 1.00 | 51.24 | C |
| ATOM | 252 | CG | LEU | A | 79 | 235.907 | 76.149 | 173.599 | 1.00 | 64.90 | C |
| ATOM | 253 | CD1 | LEU | A | 79 | 235.543 | 75.983 | 172.139 | 1.00 | 49.75 | C |
| ATOM | 254 | CD2 | LEU | A | 79 | 237.052 | 75.236 | 173.978 | 1.00 | 80.17 | C |
| ATOM | 255 | C | LEU | A | 79 | 236.825 | 79.563 | 175.185 | 1.00 | 64.76 | C |
| ATOM | 256 | O | LEU | A | 79 | 235.930 | 80.394 | 175.360 | 1.00 | 63.50 | O |
| ATOM | 257 | N | GLN | A | 80 | 238.090 | 79.889 | 174.919 | 1.00 | 72.17 | N |
| ATOM | 258 | CA | GLN | A | 80 | 238.505 | 81.274 | 174.765 | 1.00 | 77.62 | C |
| ATOM | 259 | CB | GLN | A | 80 | 239.955 | 81.486 | 175.167 | 1.00 | 52.97 | C |
| ATOM | 260 | CG | GLN | A | 80 | 240.390 | 82.913 | 174.863 | 1.00 | 93.41 | C |
| ATOM | 261 | CD | GLN | A | 80 | 241.715 | 83.310 | 175.494 | 1.00 | 115.14 | C |
| ATOM | 262 | OE1 | GLN | A | 80 | 242.038 | 84.502 | 175.567 | 1.00 | 116.65 | O |
| ATOM | 263 | NE2 | GLN | A | 80 | 242.490 | 82.322 | 175.949 | 1.00 | 117.09 | N |
| ATOM | 264 | C | GLN | A | 80 | 238.376 | 81.604 | 173.288 | 1.00 | 66.11 | C |
| ATOM | 265 | O | GLN | A | 80 | 238.775 | 80.813 | 172.437 | 1.00 | 64.63 | O |
| ATOM | 266 | N | ILE | A | 81 | 237.792 | 82.754 | 172.982 | 1.00 | 57.33 | N |
| ATOM | 267 | CA | ILE | A | 81 | 237.629 | 83.150 | 171.596 | 1.00 | 57.32 | C |
| ATOM | 268 | CB | ILE | A | 81 | 236.160 | 83.072 | 171.114 | 1.00 | 62.17 | C |
| ATOM | 269 | CG1 | ILE | A | 81 | 235.289 | 84.050 | 171.897 | 1.00 | 51.03 | C |
| ATOM | 270 | CD1 | ILE | A | 81 | 233.852 | 84.088 | 171.391 | 1.00 | 59.46 | C |
| ATOM | 271 | CG2 | ILE | A | 81 | 235.628 | 81.679 | 171.285 | 1.00 | 42.99 | C |

FIG. 3A-5

| ATOM | 272 | C | ILE | A | 81 | 238.109 | 84.571 | 171.400 | 1.00 | 54.90 | C |
|---|---|---|---|---|---|---|---|---|---|---|---|
| ATOM | 273 | O | ILE | A | 81 | 238.310 | 85.320 | 172.362 | 1.00 | 61.04 | O |
| ATOM | 274 | N | PHE | A | 82 | 238.287 | 84.930 | 170.131 | 1.00 | 70.25 | N |
| ATOM | 275 | CA | PHE | A | 82 | 238.753 | 86.251 | 169.763 | 1.00 | 55.36 | C |
| ATOM | 276 | CB | PHE | A | 82 | 240.145 | 86.152 | 169.152 | 1.00 | 42.74 | C |
| ATOM | 277 | CG | PHE | A | 82 | 241.197 | 85.862 | 170.151 | 1.00 | 59.25 | C |
| ATOM | 278 | CD1 | PHE | A | 82 | 241.639 | 86.857 | 170.999 | 1.00 | 44.66 | C |
| ATOM | 279 | CE1 | PHE | A | 82 | 242.552 | 86.576 | 171.999 | 1.00 | 57.81 | C |
| ATOM | 280 | CZ | PHE | A | 82 | 243.032 | 85.287 | 172.156 | 1.00 | 58.83 | C |
| ATOM | 281 | CE2 | PHE | A | 82 | 242.604 | 84.286 | 171.315 | 1.00 | 54.82 | C |
| ATOM | 282 | CD2 | PHE | A | 82 | 241.687 | 84.576 | 170.314 | 1.00 | 37.34 | C |
| ATOM | 283 | C | PHE | A | 82 | 237.815 | 86.911 | 168.787 | 1.00 | 62.80 | C |
| ATOM | 284 | O | PHE | A | 82 | 237.287 | 86.260 | 167.874 | 1.00 | 65.67 | O |
| ATOM | 285 | N | ASN | A | 83 | 237.592 | 88.205 | 168.997 | 1.00 | 52.27 | N |
| ATOM | 286 | CA | ASN | A | 83 | 236.746 | 88.954 | 168.104 | 1.00 | 66.04 | C |
| ATOM | 287 | CB | ASN | A | 83 | 236.093 | 90.099 | 168.830 | 1.00 | 47.48 | C |
| ATOM | 288 | CG | ASN | A | 83 | 235.214 | 90.902 | 167.924 | 1.00 | 67.70 | C |
| ATOM | 289 | OD1 | ASN | A | 83 | 235.689 | 91.744 | 167.160 | 1.00 | 72.99 | O |
| ATOM | 290 | ND2 | ASN | A | 83 | 233.915 | 90.632 | 167.977 | 1.00 | 70.38 | N |
| ATOM | 291 | C | ASN | A | 83 | 237.605 | 89.492 | 166.971 | 1.00 | 53.09 | C |
| ATOM | 292 | O | ASN | A | 83 | 238.453 | 90.346 | 167.171 | 1.00 | 64.85 | O |
| ATOM | 293 | N | LYS | A | 84 | 237.383 | 88.974 | 165.774 | 1.00 | 63.87 | N |
| ATOM | 294 | CA | LYS | A | 84 | 238.133 | 89.376 | 164.590 | 1.00 | 68.20 | C |
| ATOM | 295 | CB | LYS | A | 84 | 237.412 | 88.859 | 163.345 | 1.00 | 55.26 | C |
| ATOM | 296 | CG | LYS | A | 84 | 237.312 | 87.343 | 163.283 | 1.00 | 33.38 | C |
| ATOM | 297 | CD | LYS | A | 84 | 236.425 | 86.918 | 162.154 | 1.00 | 30.89 | C |
| ATOM | 298 | CE | LYS | A | 84 | 236.759 | 85.521 | 161.719 | 1.00 | 46.41 | C |
| ATOM | 299 | NZ | LYS | A | 84 | 236.028 | 85.182 | 160.476 | 1.00 | 72.55 | N |
| ATOM | 300 | C | LYS | A | 84 | 238.366 | 90.876 | 164.450 | 1.00 | 61.51 | C |
| ATOM | 301 | O | LYS | A | 84 | 239.492 | 91.340 | 164.537 | 1.00 | 74.81 | O |
| ATOM | 302 | N | ARG | A | 85 | 237.290 | 91.622 | 164.235 | 1.00 | 63.12 | N |
| ATOM | 303 | CA | ARG | A | 85 | 237.359 | 93.066 | 164.043 | 1.00 | 51.69 | C |
| ATOM | 304 | CB | ARG | A | 85 | 235.978 | 93.589 | 163.647 | 1.00 | 60.23 | C |
| ATOM | 305 | CG | ARG | A | 85 | 235.862 | 95.086 | 163.509 | 1.00 | 76.93 | C |
| ATOM | 306 | CD | ARG | A | 85 | 235.516 | 95.725 | 164.835 | 1.00 | 84.92 | C |
| ATOM | 307 | NE | ARG | A | 85 | 234.121 | 96.140 | 164.907 | 1.00 | 93.42 | N |
| ATOM | 308 | CZ | ARG | A | 85 | 233.541 | 96.634 | 165.997 | 1.00 | 103.30 | C |
| ATOM | 309 | NH1 | ARG | A | 85 | 234.224 | 96.777 | 167.128 | 1.00 | 54.02 | N |
| ATOM | 310 | NH2 | ARG | A | 85 | 232.268 | 96.998 | 165.949 | 1.00 | 119.53 | N |
| ATOM | 311 | C | ARG | A | 85 | 237.905 | 93.905 | 165.183 | 1.00 | 58.02 | C |
| ATOM | 312 | O | ARG | A | 85 | 238.197 | 95.075 | 164.991 | 1.00 | 86.09 | O |
| ATOM | 313 | N | THR | A | 86 | 238.050 | 93.339 | 166.370 | 1.00 | 64.72 | N |
| ATOM | 314 | CA | THR | A | 86 | 238.565 | 94.123 | 167.489 | 1.00 | 54.27 | C |
| ATOM | 315 | CB | THR | A | 86 | 237.468 | 94.392 | 168.536 | 1.00 | 58.63 | C |
| ATOM | 316 | OG1 | THR | A | 86 | 236.471 | 95.246 | 167.968 | 1.00 | 54.24 | O |
| ATOM | 317 | CG2 | THR | A | 86 | 238.045 | 95.084 | 169.743 | 1.00 | 98.48 | C |
| ATOM | 318 | C | THR | A | 86 | 239.717 | 93.398 | 168.140 | 1.00 | 52.40 | C |
| ATOM | 319 | O | THR | A | 86 | 240.520 | 93.980 | 168.856 | 1.00 | 57.78 | O |
| ATOM | 320 | N | GLN | A | 87 | 239.772 | 92.106 | 167.883 | 1.00 | 54.70 | N |
| ATOM | 321 | CA | GLN | A | 87 | 240.819 | 91.260 | 168.397 | 1.00 | 49.69 | C |
| ATOM | 322 | CB | GLN | A | 87 | 242.148 | 91.761 | 167.854 | 1.00 | 44.04 | C |
| ATOM | 323 | CG | GLN | A | 87 | 243.145 | 90.675 | 167.561 | 1.00 | 87.54 | C |
| ATOM | 324 | CD | GLN | A | 87 | 242.722 | 89.811 | 166.413 | 1.00 | 70.54 | C |
| ATOM | 325 | OE1 | GLN | A | 87 | 243.394 | 88.840 | 166.083 | 1.00 | 95.76 | O |
| ATOM | 326 | NE2 | GLN | A | 87 | 241.601 | 90.157 | 165.789 | 1.00 | 75.13 | N |

FIG. 3A-6

| ATOM | 327 | C | GLN | A | 87 | 240.875 | 91.131 | 169.927 | 1.00 | 63.54 | C |
|---|---|---|---|---|---|---|---|---|---|---|---|
| ATOM | 328 | O | GLN | A | 87 | 241.936 | 90.881 | 170.491 | 1.00 | 78.48 | O |
| ATOM | 329 | N | GLU | A | 88 | 239.746 | 91.291 | 170.608 | 1.00 | 57.33 | N |
| ATOM | 330 | CA | GLU | A | 88 | 239.751 | 91.135 | 172.060 | 1.00 | 69.04 | C |
| ATOM | 331 | CB | GLU | A | 88 | 238.816 | 92.138 | 172.708 | 1.00 | 73.60 | C |
| ATOM | 332 | CG | GLU | A | 88 | 239.325 | 93.535 | 172.526 | 1.00 | 111.93 | C |
| ATOM | 333 | CD | GLU | A | 88 | 238.419 | 94.564 | 173.132 | 1.00 | 130.01 | C |
| ATOM | 334 | OE1 | GLU | A | 88 | 237.255 | 94.664 | 172.674 | 1.00 | 151.01 | O |
| ATOM | 335 | OE2 | GLU | A | 88 | 238.874 | 95.270 | 174.062 | 1.00 | 169.07 | O |
| ATOM | 336 | C | GLU | A | 88 | 239.352 | 89.723 | 172.442 | 1.00 | 68.23 | C |
| ATOM | 337 | O | GLU | A | 88 | 238.622 | 89.060 | 171.702 | 1.00 | 70.57 | O |
| ATOM | 338 | N | ALA | A | 89 | 239.837 | 89.261 | 173.592 | 1.00 | 80.21 | N |
| ATOM | 339 | CA | ALA | A | 89 | 239.543 | 87.904 | 174.047 | 1.00 | 67.45 | C |
| ATOM | 340 | CB | ALA | A | 89 | 240.632 | 87.424 | 175.013 | 1.00 | 46.26 | C |
| ATOM | 341 | C | ALA | A | 89 | 238.171 | 87.815 | 174.709 | 1.00 | 67.74 | C |
| ATOM | 342 | O | ALA | A | 89 | 237.719 | 88.752 | 175.355 | 1.00 | 71.95 | O |
| ATOM | 343 | N | PHE | A | 90 | 237.504 | 86.681 | 174.537 | 1.00 | 68.69 | N |
| ATOM | 344 | CA | PHE | A | 90 | 236.195 | 86.481 | 175.128 | 1.00 | 63.31 | C |
| ATOM | 345 | CB | PHE | A | 90 | 235.100 | 86.935 | 174.169 | 1.00 | 52.49 | C |
| ATOM | 346 | CG | PHE | A | 90 | 234.975 | 88.434 | 174.031 | 1.00 | 61.34 | C |
| ATOM | 347 | CD1 | PHE | A | 90 | 235.523 | 89.091 | 172.952 | 1.00 | 63.36 | C |
| ATOM | 348 | CE1 | PHE | A | 90 | 235.330 | 90.429 | 172.781 | 1.00 | 38.41 | C |
| ATOM | 349 | CZ | PHE | A | 90 | 234.591 | 91.155 | 173.683 | 1.00 | 50.60 | C |
| ATOM | 350 | CE2 | PHE | A | 90 | 234.048 | 90.529 | 174.762 | 1.00 | 57.58 | C |
| ATOM | 351 | CD2 | PHE | A | 90 | 234.238 | 89.170 | 174.942 | 1.00 | 60.92 | C |
| ATOM | 352 | C | PHE | A | 90 | 235.957 | 85.019 | 175.477 | 1.00 | 70.09 | C |
| ATOM | 353 | O | PHE | A | 90 | 236.571 | 84.121 | 174.892 | 1.00 | 76.39 | O |
| ATOM | 354 | N | ALA | A | 91 | 235.055 | 84.788 | 176.431 | 1.00 | 67.69 | N |
| ATOM | 355 | CA | ALA | A | 91 | 234.692 | 83.444 | 176.853 | 1.00 | 44.28 | C |
| ATOM | 356 | CB | ALA | A | 91 | 234.360 | 83.443 | 178.302 | 1.00 | 52.11 | C |
| ATOM | 357 | C | ALA | A | 91 | 233.480 | 83.000 | 176.052 | 1.00 | 45.25 | C |
| ATOM | 358 | O | ALA | A | 91 | 232.569 | 83.788 | 175.795 | 1.00 | 60.93 | O |
| ATOM | 359 | N | LEU | A | 92 | 233.477 | 81.736 | 175.653 | 1.00 | 48.94 | N |
| ATOM | 360 | CA | LEU | A | 92 | 232.381 | 81.179 | 174.882 | 1.00 | 50.98 | C |
| ATOM | 361 | CB | LEU | A | 92 | 232.886 | 80.710 | 173.536 | 1.00 | 39.13 | C |
| ATOM | 362 | CG | LEU | A | 92 | 231.838 | 79.857 | 172.839 | 1.00 | 52.58 | C |
| ATOM | 363 | CD1 | LEU | A | 92 | 230.636 | 80.726 | 172.548 | 1.00 | 48.33 | C |
| ATOM | 364 | CD2 | LEU | A | 92 | 232.404 | 79.256 | 171.557 | 1.00 | 58.60 | C |
| ATOM | 365 | C | LEU | A | 92 | 231.771 | 79.995 | 175.610 | 1.00 | 66.99 | C |
| ATOM | 366 | O | LEU | A | 92 | 232.467 | 79.045 | 175.939 | 1.00 | 82.82 | O |
| ATOM | 367 | N | LYS | A | 93 | 230.469 | 80.053 | 175.856 | 1.00 | 66.30 | N |
| ATOM | 368 | CA | LYS | A | 93 | 229.650 | 79.022 | 176.486 | 1.00 | 62.11 | C |
| ATOM | 369 | CB | LYS | A | 93 | 228.936 | 79.645 | 177.689 | 1.00 | 79.47 | C |
| ATOM | 370 | CG | LYS | A | 93 | 228.640 | 78.617 | 178.785 | 1.00 | 69.18 | C |
| ATOM | 371 | CD | LYS | A | 93 | 227.896 | 79.231 | 179.974 | 1.00 | 74.19 | C |
| ATOM | 372 | CE | LYS | A | 93 | 227.871 | 78.303 | 181.194 | 1.00 | 107.78 | C |
| ATOM | 373 | NZ | LYS | A | 93 | 228.986 | 78.626 | 182.083 | 1.00 | 92.73 | N |
| ATOM | 374 | C | LYS | A | 93 | 228.624 | 78.440 | 175.508 | 1.00 | 61.26 | C |
| ATOM | 375 | O | LYS | A | 93 | 227.945 | 79.148 | 174.774 | 1.00 | 77.67 | O |
| ATOM | 376 | N | MET | A | 94 | 228.551 | 77.095 | 175.489 | 1.00 | 53.94 | N |
| ATOM | 377 | CA | MET | A | 94 | 227.639 | 76.436 | 174.560 | 1.00 | 63.34 | C |
| ATOM | 378 | CB | MET | A | 94 | 228.447 | 75.451 | 173.713 | 1.00 | 54.57 | C |
| ATOM | 379 | CG | MET | A | 94 | 229.751 | 76.056 | 173.188 | 1.00 | 66.95 | C |
| ATOM | 380 | SD | MET | A | 94 | 230.855 | 74.810 | 172.511 | 1.00 | 128.32 | S |
| ATOM | 381 | CE | MET | A | 94 | 231.935 | 75.912 | 171.587 | 1.00 | 110.84 | C |

FIG. 3A-7

| ATOM | 382 | C | MET | A | 94 | 226.517 | 75.693 | 175.290 | 1.00 | 67.05 | C |
| --- | --- | --- | --- | --- | --- | --- | --- | --- | --- | --- | --- |
| ATOM | 383 | O | MET | A | 94 | 226.740 | 74.805 | 176.101 | 1.00 | 77.93 | O |
| ATOM | 384 | N | LEU | A | 95 | 225.273 | 76.116 | 174.999 | 1.00 | 76.30 | N |
| ATOM | 385 | CA | LEU | A | 95 | 224.126 | 75.468 | 175.626 | 1.00 | 47.37 | C |
| ATOM | 386 | CB | LEU | A | 95 | 223.276 | 76.549 | 176.295 | 1.00 | 56.39 | C |
| ATOM | 387 | CG | LEU | A | 95 | 224.057 | 77.342 | 177.346 | 1.00 | 78.66 | C |
| ATOM | 388 | CD1 | LEU | A | 95 | 223.138 | 78.105 | 178.302 | 1.00 | 71.39 | C |
| ATOM | 389 | CD2 | LEU | A | 95 | 224.941 | 76.453 | 178.221 | 1.00 | 68.93 | C |
| ATOM | 390 | C | LEU | A | 95 | 223.284 | 74.703 | 174.601 | 1.00 | 61.07 | C |
| ATOM | 391 | O | LEU | A | 95 | 223.143 | 75.102 | 173.452 | 1.00 | 66.44 | O |
| ATOM | 392 | N | ALA | A | 96 | 222.574 | 73.621 | 174.890 | 1.00 | 60.77 | N |
| ATOM | 393 | CA | ALA | A | 96 | 221.662 | 73.075 | 173.906 | 1.00 | 63.29 | C |
| ATOM | 394 | CB | ALA | A | 96 | 221.193 | 71.700 | 174.326 | 1.00 | 70.27 | C |
| ATOM | 395 | C | ALA | A | 96 | 220.493 | 74.049 | 173.876 | 1.00 | 63.17 | C |
| ATOM | 396 | O | ALA | A | 96 | 219.998 | 74.481 | 174.915 | 1.00 | 63.30 | O |
| ATOM | 397 | N | ASP | A | 97 | 220.056 | 74.415 | 172.686 | 1.00 | 59.87 | N |
| ATOM | 398 | CA | ASP | A | 97 | 218.950 | 75.343 | 172.589 | 1.00 | 58.98 | C |
| ATOM | 399 | CB | ASP | A | 97 | 218.831 | 75.843 | 171.157 | 1.00 | 68.14 | C |
| ATOM | 400 | CG | ASP | A | 97 | 217.933 | 77.038 | 171.045 | 1.00 | 73.65 | C |
| ATOM | 401 | OD1 | ASP | A | 97 | 217.516 | 77.567 | 172.096 | 1.00 | 68.14 | O |
| ATOM | 402 | OD2 | ASP | A | 97 | 217.647 | 77.451 | 169.906 | 1.00 | 80.65 | O |
| ATOM | 403 | C | ASP | A | 97 | 217.669 | 74.640 | 173.022 | 1.00 | 73.48 | C |
| ATOM | 404 | O | ASP | A | 97 | 217.277 | 73.626 | 172.448 | 1.00 | 75.22 | O |
| ATOM | 405 | N | CYS | A | 98 | 217.023 | 75.189 | 174.041 | 1.00 | 67.24 | N |
| ATOM | 406 | CA | CYS | A | 98 | 215.801 | 74.626 | 174.586 | 1.00 | 52.14 | C |
| ATOM | 407 | CB | CYS | A | 98 | 216.122 | 73.415 | 175.421 | 1.00 | 52.47 | C |
| ATOM | 408 | SG | CYS | A | 98 | 216.922 | 73.906 | 176.969 | 1.00 | 68.25 | S |
| ATOM | 409 | C | CYS | A | 98 | 215.258 | 75.697 | 175.510 | 1.00 | 75.99 | C |
| ATOM | 410 | O | CYS | A | 98 | 216.018 | 76.483 | 176.068 | 1.00 | 86.44 | O |
| ATOM | 411 | N | PRO | A | 99 | 213.939 | 75.722 | 175.717 | 1.00 | 81.29 | N |
| ATOM | 412 | CA | PRO | A | 99 | 213.283 | 76.705 | 176.578 | 1.00 | 85.87 | C |
| ATOM | 413 | CB | PRO | A | 99 | 211.926 | 76.073 | 176.821 | 1.00 | 94.07 | C |
| ATOM | 414 | CG | PRO | A | 99 | 211.642 | 75.452 | 175.492 | 1.00 | 91.19 | C |
| ATOM | 415 | CD | PRO | A | 99 | 212.959 | 74.756 | 175.201 | 1.00 | 93.97 | C |
| ATOM | 416 | C | PRO | A | 99 | 213.996 | 77.083 | 177.868 | 1.00 | 82.76 | C |
| ATOM | 417 | O | PRO | A | 99 | 214.153 | 78.268 | 178.149 | 1.00 | 67.85 | O |
| ATOM | 418 | N | ALA | A | 100 | 214.435 | 76.098 | 178.648 | 1.00 | 67.78 | N |
| ATOM | 419 | CA | ALA | A | 100 | 215.100 | 76.408 | 179.912 | 1.00 | 66.60 | C |
| ATOM | 420 | CB | ALA | A | 100 | 215.473 | 75.088 | 180.595 | 1.00 | 84.50 | C |
| ATOM | 421 | C | ALA | A | 100 | 216.341 | 77.236 | 179.702 | 1.00 | 80.42 | C |
| ATOM | 422 | O | ALA | A | 100 | 216.622 | 78.158 | 180.472 | 1.00 | 69.23 | O |
| ATOM | 423 | N | ALA | A | 101 | 217.085 | 76.885 | 178.656 | 1.00 | 76.33 | N |
| ATOM | 424 | CA | ALA | A | 101 | 218.320 | 77.570 | 178.319 | 1.00 | 66.38 | C |
| ATOM | 425 | CB | ALA | A | 101 | 219.022 | 76.849 | 177.175 | 1.00 | 55.84 | C |
| ATOM | 426 | C | ALA | A | 101 | 218.055 | 79.028 | 177.964 | 1.00 | 67.87 | C |
| ATOM | 427 | O | ALA | A | 101 | 218.639 | 79.922 | 178.563 | 1.00 | 70.18 | O |
| ATOM | 428 | N | ARG | A | 102 | 217.163 | 79.277 | 177.014 | 1.00 | 63.42 | N |
| ATOM | 429 | CA | ARG | A | 102 | 216.852 | 80.646 | 176.622 | 1.00 | 64.85 | C |
| ATOM | 430 | CB | ARG | A | 102 | 215.764 | 80.665 | 175.541 | 1.00 | 58.29 | C |
| ATOM | 431 | CG | ARG | A | 102 | 216.118 | 79.877 | 174.290 | 1.00 | 87.87 | C |
| ATOM | 432 | CD | ARG | A | 102 | 215.938 | 80.688 | 173.003 | 1.00 | 113.57 | C |
| ATOM | 433 | NE | ARG | A | 102 | 216.532 | 80.000 | 171.853 | 1.00 | 149.75 | N |
| ATOM | 434 | CZ | ARG | A | 102 | 216.645 | 80.517 | 170.626 | 1.00 | 161.97 | C |
| ATOM | 435 | NH1 | ARG | A | 102 | 216.200 | 81.742 | 170.361 | 1.00 | 169.18 | N |
| ATOM | 436 | NH2 | ARG | A | 102 | 217.209 | 79.808 | 169.658 | 1.00 | 123.53 | N |

FIG. 3A-8

| | | | | | | | | | | | |
|---|---|---|---|---|---|---|---|---|---|---|---|
| ATOM | 437 | C | ARG | A | 102 | 216.409 | 81.491 | 177.812 | 1.00 | 68.04 | C |
| ATOM | 438 | O | ARG | A | 102 | 216.523 | 82.715 | 177.785 | 1.00 | 87.14 | O |
| ATOM | 439 | N | ARG | A | 103 | 215.900 | 80.848 | 178.856 | 1.00 | 68.81 | N |
| ATOM | 440 | CA | ARG | A | 103 | 215.456 | 81.579 | 180.040 | 1.00 | 80.79 | C |
| ATOM | 441 | CB | ARG | A | 103 | 214.620 | 80.684 | 180.943 | 1.00 | 100.01 | C |
| ATOM | 442 | CG | ARG | A | 103 | 214.334 | 81.302 | 182.299 | 1.00 | 140.54 | C |
| ATOM | 443 | CD | ARG | A | 103 | 213.451 | 80.396 | 183.152 | 1.00 | 186.85 | C |
| ATOM | 444 | NE | ARG | A | 103 | 214.159 | 79.246 | 183.721 | 1.00 | 183.90 | N |
| ATOM | 445 | CZ | ARG | A | 103 | 213.851 | 77.974 | 183.469 | 1.00 | 163.96 | C |
| ATOM | 446 | NH1 | ARG | A | 103 | 212.848 | 77.669 | 182.641 | 1.00 | 83.48 | N |
| ATOM | 447 | NH2 | ARG | A | 103 | 214.523 | 77.008 | 184.082 | 1.00 | 172.74 | N |
| ATOM | 448 | C | ARG | A | 103 | 216.664 | 82.065 | 180.812 | 1.00 | 74.21 | C |
| ATOM | 449 | O | ARG | A | 103 | 216.757 | 83.229 | 181.192 | 1.00 | 79.04 | O |
| ATOM | 450 | N | GLU | A | 104 | 217.584 | 81.143 | 181.047 | 1.00 | 62.81 | N |
| ATOM | 451 | CA | GLU | A | 104 | 218.821 | 81.431 | 181.750 | 1.00 | 74.19 | C |
| ATOM | 452 | CB | GLU | A | 104 | 219.722 | 80.210 | 181.633 | 1.00 | 84.57 | C |
| ATOM | 453 | CG | GLU | A | 104 | 221.043 | 80.286 | 182.342 | 1.00 | 113.52 | C |
| ATOM | 454 | CD | GLU | A | 104 | 221.832 | 79.002 | 182.167 | 1.00 | 109.63 | C |
| ATOM | 455 | OE1 | GLU | A | 104 | 222.923 | 78.879 | 182.757 | 1.00 | 143.02 | O |
| ATOM | 456 | OE2 | GLU | A | 104 | 221.358 | 78.112 | 181.430 | 1.00 | 133.75 | O |
| ATOM | 457 | C | GLU | A | 104 | 219.481 | 82.643 | 181.094 | 1.00 | 76.22 | C |
| ATOM | 458 | O | GLU | A | 104 | 219.642 | 83.699 | 181.711 | 1.00 | 64.24 | O |
| ATOM | 459 | N | VAL | A | 105 | 219.845 | 82.462 | 179.828 | 1.00 | 72.46 | N |
| ATOM | 460 | CA | VAL | A | 105 | 220.488 | 83.485 | 179.010 | 1.00 | 67.75 | C |
| ATOM | 461 | CB | VAL | A | 105 | 220.450 | 83.096 | 177.524 | 1.00 | 70.64 | C |
| ATOM | 462 | CG1 | VAL | A | 105 | 221.057 | 84.183 | 176.695 | 1.00 | 60.07 | C |
| ATOM | 463 | CG2 | VAL | A | 105 | 221.196 | 81.796 | 177.312 | 1.00 | 75.62 | C |
| ATOM | 464 | C | VAL | A | 105 | 219.830 | 84.846 | 179.164 | 1.00 | 71.54 | C |
| ATOM | 465 | O | VAL | A | 105 | 220.506 | 85.851 | 179.366 | 1.00 | 75.44 | O |
| ATOM | 466 | N | GLU | A | 106 | 218.511 | 84.879 | 179.055 | 1.00 | 56.08 | N |
| ATOM | 467 | CA | GLU | A | 106 | 217.795 | 86.126 | 179.198 | 1.00 | 58.27 | C |
| ATOM | 468 | CB | GLU | A | 106 | 216.301 | 85.893 | 179.081 | 1.00 | 60.31 | C |
| ATOM | 469 | CG | GLU | A | 106 | 215.588 | 86.837 | 178.156 | 1.00 | 75.77 | C |
| ATOM | 470 | CD | GLU | A | 106 | 215.465 | 86.257 | 176.774 | 1.00 | 90.69 | C |
| ATOM | 471 | OE1 | GLU | A | 106 | 216.490 | 86.211 | 176.072 | 1.00 | 127.18 | O |
| ATOM | 472 | OE2 | GLU | A | 106 | 214.352 | 85.823 | 176.393 | 1.00 | 144.79 | O |
| ATOM | 473 | C | GLU | A | 106 | 218.087 | 86.715 | 180.569 | 1.00 | 62.94 | C |
| ATOM | 474 | O | GLU | A | 106 | 218.474 | 87.873 | 180.682 | 1.00 | 69.82 | O |
| ATOM | 475 | N | LEU | A | 107 | 217.896 | 85.921 | 181.617 | 1.00 | 59.54 | N |
| ATOM | 476 | CA | LEU | A | 107 | 218.132 | 86.409 | 182.964 | 1.00 | 60.25 | C |
| ATOM | 477 | CB | LEU | A | 107 | 218.013 | 85.269 | 183.967 | 1.00 | 82.80 | C |
| ATOM | 478 | CG | LEU | A | 107 | 216.618 | 84.741 | 184.297 | 1.00 | 74.03 | C |
| ATOM | 479 | CD1 | LEU | A | 107 | 216.740 | 83.679 | 185.368 | 1.00 | 68.79 | C |
| ATOM | 480 | CD2 | LEU | A | 107 | 215.731 | 85.866 | 184.783 | 1.00 | 64.45 | C |
| ATOM | 481 | C | LEU | A | 107 | 219.503 | 87.050 | 183.098 | 1.00 | 79.14 | C |
| ATOM | 482 | O | LEU | A | 107 | 219.649 | 88.148 | 183.623 | 1.00 | 55.44 | O |
| ATOM | 483 | N | HIS | A | 108 | 220.514 | 86.351 | 182.614 | 1.00 | 68.47 | N |
| ATOM | 484 | CA | HIS | A | 108 | 221.875 | 86.840 | 182.691 | 1.00 | 60.51 | C |
| ATOM | 485 | CB | HIS | A | 108 | 222.817 | 85.732 | 182.252 | 1.00 | 74.21 | C |
| ATOM | 486 | CG | HIS | A | 108 | 224.261 | 86.055 | 182.447 | 1.00 | 58.20 | C |
| ATOM | 487 | ND1 | HIS | A | 108 | 225.260 | 85.149 | 182.176 | 1.00 | 56.15 | N |
| ATOM | 488 | CE1 | HIS | A | 108 | 226.429 | 85.699 | 182.446 | 1.00 | 52.10 | C |
| ATOM | 489 | NE2 | HIS | A | 108 | 226.224 | 86.928 | 182.881 | 1.00 | 52.02 | N |
| ATOM | 490 | CD2 | HIS | A | 108 | 224.875 | 87.176 | 182.891 | 1.00 | 56.76 | C |
| ATOM | 491 | C | HIS | A | 108 | 222.058 | 88.075 | 181.819 | 1.00 | 51.27 | C |

FIG. 3A-9

| ATOM | 492 | O | HIS | A | 108 | 222.721 | 89.035 | 182.208 | 1.00 | 70.90 | O |
|---|---|---|---|---|---|---|---|---|---|---|---|
| ATOM | 493 | N | TRPA | | 109 | 221.480 | 88.046 | 180.628 | 1.00 | 57.29 | N |
| ATOM | 494 | CA | TRPA | | 109 | 221.633 | 89.219 | 179.779 | 1.00 | 60.60 | C |
| ATOM | 495 | CB | TRPA | | 109 | 221.000 | 88.905 | 178.423 | 1.00 | 58.21 | C |
| ATOM | 496 | CG | TRPA | | 109 | 220.711 | 90.158 | 177.691 | 1.00 | 62.11 | C |
| ATOM | 497 | CD1 | TRPA | | 109 | 219.493 | 90.874 | 177.686 | 1.00 | 77.34 | C |
| ATOM | 498 | NE1 | TRPA | | 109 | 219.557 | 92.006 | 176.931 | 1.00 | 78.01 | N |
| ATOM | 499 | CE2 | TRPA | | 109 | 220.933 | 92.041 | 176.375 | 1.00 | 87.90 | C |
| ATOM | 500 | CD2 | TRPA | | 109 | 221.631 | 90.902 | 176.855 | 1.00 | 77.76 | C |
| ATOM | 501 | CE3 | TRPA | | 109 | 222.954 | 90.700 | 176.473 | 1.00 | 105.10 | C |
| ATOM | 502 | CZ3 | TRPA | | 109 | 223.594 | 91.606 | 175.640 | 1.00 | 107.99 | C |
| ATOM | 503 | CH2 | TRPA | | 109 | 222.895 | 92.731 | 175.167 | 1.00 | 111.87 | C |
| ATOM | 504 | CZ2 | TRPA | | 109 | 221.572 | 92.943 | 175.540 | 1.00 | 127.04 | C |
| ATOM | 505 | C | TRPA | | 109 | 220.952 | 90.440 | 180.401 | 1.00 | 49.86 | C |
| ATOM | 506 | O | TRPA | | 109 | 221.365 | 91.583 | 180.231 | 1.00 | 77.39 | O |
| ATOM | 507 | N | ARG | A | 110 | 219.845 | 90.163 | 181.113 | 1.00 | 63.80 | N |
| ATOM | 508 | CA | ARG | A | 110 | 219.102 | 91.243 | 181.753 | 1.00 | 60.39 | C |
| ATOM | 509 | CB | ARG | A | 110 | 217.714 | 90.704 | 182.108 | 1.00 | 55.11 | C |
| ATOM | 510 | CG | ARG | A | 110 | 216.630 | 91.781 | 182.038 | 1.00 | 70.18 | C |
| ATOM | 511 | CD | ARG | A | 110 | 215.241 | 91.177 | 181.803 | 1.00 | 129.88 | C |
| ATOM | 512 | NE | ARG | A | 110 | 214.340 | 91.500 | 182.914 | 1.00 | 98.93 | N |
| ATOM | 513 | CZ | ARG | A | 110 | 214.072 | 90.515 | 183.794 | 1.00 | 97.18 | C |
| ATOM | 514 | NH1 | ARG | A | 110 | 213.537 | 90.802 | 184.969 | 1.00 | 106.39 | N |
| ATOM | 515 | NH2 | ARG | A | 110 | 214.325 | 89.245 | 183.464 | 1.00 | 84.21 | N |
| ATOM | 516 | C | ARG | A | 110 | 219.807 | 91.738 | 183.019 | 1.00 | 56.74 | C |
| ATOM | 517 | O | ARG | A | 110 | 219.416 | 92.713 | 183.648 | 1.00 | 72.39 | O |
| ATOM | 518 | N | ALA | A | 111 | 220.864 | 90.997 | 183.409 | 1.00 | 61.92 | N |
| ATOM | 519 | CA | ALA | A | 111 | 221.578 | 91.358 | 184.628 | 1.00 | 62.44 | C |
| ATOM | 520 | CB | ALA | A | 111 | 221.559 | 90.151 | 185.567 | 1.00 | 53.16 | C |
| ATOM | 521 | C | ALA | A | 111 | 223.023 | 91.776 | 184.343 | 1.00 | 78.96 | C |
| ATOM | 522 | O | ALA | A | 111 | 223.808 | 92.067 | 185.237 | 1.00 | 57.41 | O |
| ATOM | 523 | N | SER | A | 112 | 223.377 | 91.758 | 183.046 | 1.00 | 76.17 | N |
| ATOM | 524 | CA | SER | A | 112 | 224.737 | 92.128 | 182.670 | 1.00 | 71.16 | C |
| ATOM | 525 | CB | SER | A | 112 | 224.963 | 91.711 | 181.216 | 1.00 | 45.39 | C |
| ATOM | 526 | OG | SER | A | 112 | 224.992 | 90.282 | 181.135 | 1.00 | 81.43 | O |
| ATOM | 527 | C | SER | A | 112 | 224.979 | 93.632 | 182.825 | 1.00 | 64.82 | C |
| ATOM | 528 | O | SER | A | 112 | 226.104 | 94.113 | 182.806 | 1.00 | 63.34 | O |
| ATOM | 529 | N | GLN | A | 113 | 223.918 | 94.403 | 182.989 | 1.00 | 73.53 | N |
| ATOM | 530 | CA | GLN | A | 113 | 224.071 | 95.835 | 183.163 | 1.00 | 77.61 | C |
| ATOM | 531 | CB | GLN | A | 113 | 222.716 | 96.537 | 183.006 | 1.00 | 79.72 | C |
| ATOM | 532 | CG | GLN | A | 113 | 221.947 | 96.134 | 181.754 | 1.00 | 117.37 | C |
| ATOM | 533 | CD | GLN | A | 113 | 222.616 | 96.582 | 180.448 | 1.00 | 132.38 | C |
| ATOM | 534 | OE1 | GLN | A | 113 | 222.305 | 96.060 | 179.363 | 1.00 | 85.14 | O |
| ATOM | 535 | NE2 | GLN | A | 113 | 223.522 | 97.558 | 180.542 | 1.00 | 73.13 | N |
| ATOM | 536 | C | GLN | A | 113 | 224.644 | 96.132 | 184.545 | 1.00 | 70.17 | C |
| ATOM | 537 | O | GLN | A | 113 | 224.884 | 97.280 | 184.884 | 1.00 | 88.91 | O |
| ATOM | 538 | N | CYS | A | 114 | 224.854 | 95.098 | 185.348 | 1.00 | 77.28 | N |
| ATOM | 539 | CA | CYS | A | 114 | 225.395 | 95.280 | 186.692 | 1.00 | 65.33 | C |
| ATOM | 540 | CB | CYS | A | 114 | 224.699 | 94.346 | 187.679 | 1.00 | 68.99 | C |
| ATOM | 541 | SG | CYS | A | 114 | 225.606 | 94.158 | 189.225 | 1.00 | 70.19 | S |
| ATOM | 542 | C | CYS | A | 114 | 226.896 | 95.029 | 186.750 | 1.00 | 66.81 | C |
| ATOM | 543 | O | CYS | A | 114 | 227.365 | 93.910 | 186.553 | 1.00 | 70.94 | O |
| ATOM | 544 | N | PRO | A | 115 | 227.665 | 96.073 | 187.058 | 1.00 | 57.36 | N |
| ATOM | 545 | CA | PRO | A | 115 | 229.123 | 96.082 | 187.171 | 1.00 | 46.75 | C |
| ATOM | 546 | CB | PRO | A | 115 | 229.382 | 97.226 | 188.140 | 1.00 | 46.54 | C |

FIG. 3A-10

| ATOM | 547 | CG | PRO | A | 115 | 228.325 | 98.199 | 187.764 | 1.00 | 65.08 | C |
| ATOM | 548 | CD | PRO | A | 115 | 227.093 | 97.329 | 187.569 | 1.00 | 53.52 | C |
| ATOM | 549 | C | PRO | A | 115 | 229.770 | 94.790 | 187.650 | 1.00 | 60.90 | C |
| ATOM | 550 | O | PRO | A | 115 | 230.735 | 94.315 | 187.046 | 1.00 | 79.32 | O |
| ATOM | 551 | N | HIS | A | 116 | 229.242 | 94.217 | 188.726 | 1.00 | 50.47 | N |
| ATOM | 552 | CA | HIS | A | 116 | 229.827 | 93.015 | 189.294 | 1.00 | 62.43 | C |
| ATOM | 553 | CB | HIS | A | 116 | 229.709 | 93.085 | 190.804 | 1.00 | 66.18 | C |
| ATOM | 554 | CG | HIS | A | 116 | 230.547 | 94.163 | 191.405 | 1.00 | 74.19 | C |
| ATOM | 555 | ND1 | HIS | A | 116 | 231.923 | 94.104 | 191.422 | 1.00 | 58.68 | N |
| ATOM | 556 | CE1 | HIS | A | 116 | 232.404 | 95.220 | 191.945 | 1.00 | 106.08 | C |
| ATOM | 557 | NE2 | HIS | A | 116 | 231.386 | 95.999 | 192.269 | 1.00 | 97.40 | N |
| ATOM | 558 | CD2 | HIS | A | 116 | 230.214 | 95.360 | 191.945 | 1.00 | 50.93 | C |
| ATOM | 559 | C | HIS | A | 116 | 229.336 | 91.675 | 188.787 | 1.00 | 62.85 | C |
| ATOM | 560 | O | HIS | A | 116 | 229.654 | 90.634 | 189.366 | 1.00 | 86.03 | O |
| ATOM | 561 | N | ILE | A | 117 | 228.574 | 91.693 | 187.703 | 1.00 | 58.07 | N |
| ATOM | 562 | CA | ILE | A | 117 | 228.075 | 90.472 | 187.097 | 1.00 | 51.42 | C |
| ATOM | 563 | CB | ILE | A | 117 | 226.586 | 90.572 | 186.848 | 1.00 | 60.05 | C |
| ATOM | 564 | CG1 | ILE | A | 117 | 225.867 | 90.676 | 188.193 | 1.00 | 65.42 | C |
| ATOM | 565 | CD1 | ILE | A | 117 | 224.420 | 91.064 | 188.100 | 1.00 | 76.80 | C |
| ATOM | 566 | CG2 | ILE | A | 117 | 226.111 | 89.371 | 186.050 | 1.00 | 56.83 | C |
| ATOM | 567 | C | ILE | A | 117 | 228.790 | 90.375 | 185.769 | 1.00 | 57.68 | C |
| ATOM | 568 | O | ILE | A | 117 | 228.912 | 91.381 | 185.056 | 1.00 | 72.95 | O |
| ATOM | 569 | N | VAL | A | 118 | 229.275 | 89.188 | 185.427 | 1.00 | 60.67 | N |
| ATOM | 570 | CA | VAL | A | 118 | 229.979 | 89.028 | 184.160 | 1.00 | 56.50 | C |
| ATOM | 571 | CB | VAL | A | 118 | 230.469 | 87.583 | 183.975 | 1.00 | 59.65 | C |
| ATOM | 572 | CG1 | VAL | A | 118 | 229.288 | 86.642 | 183.812 | 1.00 | 58.62 | C |
| ATOM | 573 | CG2 | VAL | A | 118 | 231.389 | 87.503 | 182.776 | 1.00 | 72.68 | C |
| ATOM | 574 | C | VAL | A | 118 | 229.008 | 89.416 | 183.044 | 1.00 | 62.86 | C |
| ATOM | 575 | O | VAL | A | 118 | 227.844 | 89.008 | 183.071 | 1.00 | 61.80 | O |
| ATOM | 576 | N | ALA | A | 119 | 229.483 | 90.204 | 182.075 | 1.00 | 59.87 | N |
| ATOM | 577 | CA | ALA | A | 119 | 228.635 | 90.694 | 180.988 | 1.00 | 63.38 | C |
| ATOM | 578 | CB | ALA | A | 119 | 229.083 | 92.079 | 180.566 | 1.00 | 37.88 | C |
| ATOM | 579 | C | ALA | A | 119 | 228.551 | 89.821 | 179.763 | 1.00 | 57.05 | C |
| ATOM | 580 | O | ALA | A | 119 | 229.546 | 89.276 | 179.314 | 1.00 | 63.34 | O |
| ATOM | 581 | N | ILE | A | 120 | 227.348 | 89.698 | 179.217 | 1.00 | 52.84 | N |
| ATOM | 582 | CA | ILE | A | 120 | 227.135 | 88.928 | 178.002 | 1.00 | 55.21 | C |
| ATOM | 583 | CB | ILE | A | 120 | 225.742 | 88.298 | 177.985 | 1.00 | 63.39 | C |
| ATOM | 584 | CG1 | ILE | A | 120 | 225.707 | 87.100 | 178.931 | 1.00 | 59.03 | C |
| ATOM | 585 | CD1 | ILE | A | 120 | 224.390 | 86.384 | 178.896 | 1.00 | 71.76 | C |
| ATOM | 586 | CG2 | ILE | A | 120 | 225.368 | 87.898 | 176.570 | 1.00 | 45.00 | C |
| ATOM | 587 | C | ILE | A | 120 | 227.227 | 89.914 | 176.847 | 1.00 | 56.02 | C |
| ATOM | 588 | O | ILE | A | 120 | 226.375 | 90.801 | 176.719 | 1.00 | 61.19 | O |
| ATOM | 589 | N | VAL | A | 121 | 228.259 | 89.766 | 176.013 | 1.00 | 69.54 | N |
| ATOM | 590 | CA | VAL | A | 121 | 228.440 | 90.647 | 174.863 | 1.00 | 53.54 | C |
| ATOM | 591 | CB | VAL | A | 121 | 229.875 | 90.482 | 174.354 | 1.00 | 52.53 | C |
| ATOM | 592 | CG1 | VAL | A | 121 | 230.153 | 91.471 | 173.224 | 1.00 | 91.60 | C |
| ATOM | 593 | CG2 | VAL | A | 121 | 230.854 | 90.737 | 175.486 | 1.00 | 71.15 | C |
| ATOM | 594 | C | VAL | A | 121 | 227.432 | 90.354 | 173.743 | 1.00 | 53.36 | C |
| ATOM | 595 | O | VAL | A | 121 | 226.823 | 91.254 | 173.173 | 1.00 | 67.91 | O |
| ATOM | 596 | N | ASP | A | 122 | 227.299 | 89.060 | 173.389 | 1.00 | 45.30 | N |
| ATOM | 597 | CA | ASP | A | 122 | 226.149 | 88.676 | 172.567 | 1.00 | 76.20 | C |
| ATOM | 598 | CB | ASP | A | 122 | 226.337 | 89.280 | 171.173 | 1.00 | 81.39 | C |
| ATOM | 599 | CG | ASP | A | 122 | 227.687 | 88.850 | 170.615 | 1.00 | 72.92 | C |
| ATOM | 600 | OD1 | ASP | A | 122 | 228.224 | 87.860 | 171.115 | 1.00 | 121.42 | O |
| ATOM | 601 | OD2 | ASP | A | 122 | 228.183 | 89.500 | 169.698 | 1.00 | 55.20 | O |

FIG. 3A-11

| ATOM | 602 | C | ASP | A | 122 | 225.984 | 87.152 | 172.459 | 1.00 | 52.20 | C |
|---|---|---|---|---|---|---|---|---|---|---|---|
| ATOM | 603 | O | ASP | A | 122 | 226.852 | 86.378 | 172.842 | 1.00 | 62.83 | O |
| ATOM | 604 | N | VAL | A | 123 | 224.777 | 86.769 | 171.999 | 1.00 | 50.00 | N |
| ATOM | 605 | CA | VAL | A | 123 | 224.398 | 85.361 | 171.982 | 1.00 | 55.40 | C |
| ATOM | 606 | CB | VAL | A | 123 | 223.215 | 85.196 | 172.943 | 1.00 | 45.71 | C |
| ATOM | 607 | CG1 | VAL | A | 123 | 222.819 | 83.726 | 173.058 | 1.00 | 66.35 | C |
| ATOM | 608 | CG2 | VAL | A | 123 | 223.581 | 85.730 | 174.316 | 1.00 | 57.34 | C |
| ATOM | 609 | C | VAL | A | 123 | 223.988 | 84.917 | 170.574 | 1.00 | 50.66 | C |
| ATOM | 610 | O | VAL | A | 123 | 223.350 | 85.650 | 169.830 | 1.00 | 50.76 | O |
| ATOM | 611 | N | TYR | A | 124 | 224.384 | 83.682 | 170.271 | 1.00 | 54.76 | N |
| ATOM | 612 | CA | TYR | A | 124 | 224.108 | 83.092 | 168.964 | 1.00 | 59.15 | C |
| ATOM | 613 | CB | TYR | A | 124 | 225.412 | 82.768 | 168.216 | 1.00 | 54.42 | C |
| ATOM | 614 | CG | TYR | A | 124 | 226.292 | 83.973 | 167.929 | 1.00 | 64.97 | C |
| ATOM | 615 | CD1 | TYR | A | 124 | 227.031 | 84.574 | 168.941 | 1.00 | 36.17 | C |
| ATOM | 616 | CE1 | TYR | A | 124 | 227.793 | 85.681 | 168.700 | 1.00 | 56.00 | C |
| ATOM | 617 | CZ | TYR | A | 124 | 227.835 | 86.220 | 167.428 | 1.00 | 51.06 | C |
| ATOM | 618 | OH | TYR | A | 124 | 228.608 | 87.330 | 167.202 | 1.00 | 71.62 | O |
| ATOM | 619 | CE2 | TYR | A | 124 | 227.117 | 85.653 | 166.393 | 1.00 | 49.47 | C |
| ATOM | 620 | CD2 | TYR | A | 124 | 226.352 | 84.532 | 166.649 | 1.00 | 68.56 | C |
| ATOM | 621 | C | TYR | A | 124 | 223.286 | 81.813 | 169.047 | 1.00 | 61.11 | C |
| ATOM | 622 | O | TYR | A | 124 | 223.356 | 81.063 | 170.021 | 1.00 | 77.18 | O |
| ATOM | 623 | N | GLU | A | 125 | 222.497 | 81.576 | 168.010 | 1.00 | 65.81 | N |
| ATOM | 624 | CA | GLU | A | 125 | 221.697 | 80.374 | 167.910 | 1.00 | 49.40 | C |
| ATOM | 625 | CB | GLU | A | 125 | 220.210 | 80.728 | 167.851 | 1.00 | 56.44 | C |
| ATOM | 626 | CG | GLU | A | 125 | 219.285 | 79.525 | 167.952 | 1.00 | 64.02 | C |
| ATOM | 627 | CD | GLU | A | 125 | 218.600 | 79.176 | 166.637 | 1.00 | 103.79 | C |
| ATOM | 628 | OE1 | GLU | A | 125 | 217.665 | 79.900 | 166.223 | 1.00 | 113.21 | O |
| ATOM | 629 | OE2 | GLU | A | 125 | 219.002 | 78.172 | 166.009 | 1.00 | 118.03 | O |
| ATOM | 630 | C | GLU | A | 125 | 222.164 | 79.747 | 166.601 | 1.00 | 50.33 | C |
| ATOM | 631 | O | GLU | A | 125 | 221.610 | 80.007 | 165.535 | 1.00 | 63.99 | O |
| ATOM | 632 | N | ASN | A | 126 | 223.217 | 78.948 | 166.675 | 1.00 | 57.09 | N |
| ATOM | 633 | CA | ASN | A | 126 | 223.752 | 78.304 | 165.480 | 1.00 | 63.39 | C |
| ATOM | 634 | CB | ASN | A | 126 | 225.271 | 78.413 | 165.451 | 1.00 | 53.33 | C |
| ATOM | 635 | CG | ASN | A | 126 | 225.738 | 79.824 | 165.237 | 1.00 | 50.86 | C |
| ATOM | 636 | OD1 | ASN | A | 126 | 226.934 | 80.105 | 165.254 | 1.00 | 53.47 | O |
| ATOM | 637 | ND2 | ASN | A | 126 | 224.786 | 80.732 | 165.026 | 1.00 | 57.45 | N |
| ATOM | 638 | C | ASN | A | 126 | 223.370 | 76.842 | 165.453 | 1.00 | 68.35 | C |
| ATOM | 639 | O | ASN | A | 126 | 222.770 | 76.334 | 166.393 | 1.00 | 78.79 | O |
| ATOM | 640 | N | LEU | A | 127 | 223.729 | 76.167 | 164.370 | 1.00 | 72.36 | N |
| ATOM | 641 | CA | LEU | A | 127 | 223.431 | 74.753 | 164.222 | 1.00 | 56.01 | C |
| ATOM | 642 | CB | LEU | A | 127 | 222.926 | 74.467 | 162.817 | 1.00 | 57.56 | C |
| ATOM | 643 | CG | LEU | A | 127 | 221.810 | 73.443 | 162.741 | 1.00 | 56.21 | C |
| ATOM | 644 | CD1 | LEU | A | 127 | 220.660 | 73.944 | 163.564 | 1.00 | 63.97 | C |
| ATOM | 645 | CD2 | LEU | A | 127 | 221.386 | 73.235 | 161.311 | 1.00 | 50.73 | C |
| ATOM | 646 | C | LEU | A | 127 | 224.712 | 73.983 | 164.467 | 1.00 | 63.01 | C |
| ATOM | 647 | O | LEU | A | 127 | 225.637 | 74.025 | 163.663 | 1.00 | 79.72 | O |
| ATOM | 648 | N | TYR | A | 128 | 224.768 | 73.281 | 165.588 | 1.00 | 85.19 | N |
| ATOM | 649 | CA | TYR | A | 128 | 225.949 | 72.511 | 165.932 | 1.00 | 78.91 | C |
| ATOM | 650 | CB | TYR | A | 128 | 226.513 | 72.996 | 167.259 | 1.00 | 73.34 | C |
| ATOM | 651 | CG | TYR | A | 128 | 227.849 | 72.396 | 167.562 | 1.00 | 113.80 | C |
| ATOM | 652 | CD1 | TYR | A | 128 | 229.000 | 72.939 | 167.024 | 1.00 | 118.71 | C |
| ATOM | 653 | CE1 | TYR | A | 128 | 230.223 | 72.372 | 167.247 | 1.00 | 148.93 | C |
| ATOM | 654 | CZ | TYR | A | 128 | 230.316 | 71.239 | 168.018 | 1.00 | 162.93 | C |
| ATOM | 655 | OH | TYR | A | 128 | 231.559 | 70.688 | 168.244 | 1.00 | 162.00 | O |
| ATOM | 656 | CE2 | TYR | A | 128 | 229.183 | 70.667 | 168.569 | 1.00 | 160.37 | C |

FIG. 3A-12

| ATOM | 657 | CD2 | TYR | A | 128 | 227.959 | 71.253 | 168.341 | 1.00 | 128.83 | C |
|---|---|---|---|---|---|---|---|---|---|---|---|
| ATOM | 658 | C | TYR | A | 128 | 225.657 | 71.015 | 166.036 | 1.00 | 99.93 | C |
| ATOM | 659 | O | TYR | A | 128 | 224.960 | 70.571 | 166.956 | 1.00 | 83.06 | O |
| ATOM | 660 | N | ALA | A | 129 | 226.204 | 70.240 | 165.098 | 1.00 | 112.77 | N |
| ATOM | 661 | CA | ALA | A | 129 | 226.016 | 68.788 | 165.077 | 1.00 | 119.60 | C |
| ATOM | 662 | CB | ALA | A | 129 | 226.482 | 68.181 | 166.398 | 1.00 | 105.12 | C |
| ATOM | 663 | C | ALA | A | 129 | 224.556 | 68.445 | 164.843 | 1.00 | 117.04 | C |
| ATOM | 664 | O | ALA | A | 129 | 223.981 | 67.637 | 165.575 | 1.00 | 102.48 | O |
| ATOM | 665 | N | GLY | A | 130 | 223.957 | 69.056 | 163.823 | 1.00 | 115.24 | N |
| ATOM | 666 | CA | GLY | A | 130 | 222.550 | 68.810 | 163.553 | 1.00 | 115.49 | C |
| ATOM | 667 | C | GLY | A | 130 | 221.728 | 69.250 | 164.756 | 1.00 | 107.44 | C |
| ATOM | 668 | O | GLY | A | 130 | 220.501 | 69.259 | 164.722 | 1.00 | 95.78 | O |
| ATOM | 669 | N | ALA | A | 131 | 222.425 | 69.616 | 165.828 | 1.00 | 89.82 | N |
| ATOM | 670 | CA | ALA | A | 131 | 221.791 | 70.067 | 167.055 | 1.00 | 92.75 | C |
| ATOM | 671 | CB | ALA | A | 131 | 222.546 | 69.516 | 168.271 | 1.00 | 79.11 | C |
| ATOM | 672 | C | ALA | A | 131 | 221.754 | 71.593 | 167.105 | 1.00 | 80.22 | C |
| ATOM | 673 | O | ALA | A | 131 | 222.756 | 72.265 | 166.892 | 1.00 | 63.19 | O |
| ATOM | 674 | N | LYS | A | 132 | 220.574 | 72.121 | 167.381 | 1.00 | 68.38 | N |
| ATOM | 675 | CA | LYS | A | 132 | 220.349 | 73.553 | 167.487 | 1.00 | 64.95 | C |
| ATOM | 676 | CB | LYS | A | 132 | 218.839 | 73.782 | 167.429 | 1.00 | 50.70 | C |
| ATOM | 677 | CG | LYS | A | 132 | 218.340 | 75.188 | 167.516 | 1.00 | 60.30 | C |
| ATOM | 678 | CD | LYS | A | 132 | 216.821 | 75.123 | 167.476 | 1.00 | 72.13 | C |
| ATOM | 679 | CE | LYS | A | 132 | 216.171 | 76.486 | 167.371 | 1.00 | 106.61 | C |
| ATOM | 680 | NZ | LYS | A | 132 | 214.692 | 76.354 | 167.313 | 1.00 | 65.96 | N |
| ATOM | 681 | C | LYS | A | 132 | 220.944 | 74.013 | 168.828 | 1.00 | 56.62 | C |
| ATOM | 682 | O | LYS | A | 132 | 220.449 | 73.648 | 169.889 | 1.00 | 63.01 | O |
| ATOM | 683 | N | CYS | A | 133 | 222.011 | 74.805 | 168.787 | 1.00 | 77.15 | N |
| ATOM | 684 | CA | CYS | A | 133 | 222.648 | 75.263 | 170.022 | 1.00 | 74.16 | C |
| ATOM | 685 | CB | CYS | A | 133 | 224.114 | 74.877 | 170.024 | 1.00 | 92.23 | C |
| ATOM | 686 | SG | CYS | A | 133 | 224.343 | 73.126 | 169.850 | 1.00 | 106.91 | S |
| ATOM | 687 | C | CYS | A | 133 | 222.555 | 76.745 | 170.320 | 1.00 | 65.05 | C |
| ATOM | 688 | O | CYS | A | 133 | 222.157 | 77.543 | 169.471 | 1.00 | 81.10 | O |
| ATOM | 689 | N | LEU | A | 134 | 222.947 | 77.099 | 171.540 | 1.00 | 67.21 | N |
| ATOM | 690 | CA | LEU | A | 134 | 222.921 | 78.478 | 171.986 | 1.00 | 67.45 | C |
| ATOM | 691 | CB | LEU | A | 134 | 221.953 | 78.634 | 173.152 | 1.00 | 51.96 | C |
| ATOM | 692 | CG | LEU | A | 134 | 221.107 | 79.902 | 173.189 | 1.00 | 72.36 | C |
| ATOM | 693 | CD1 | LEU | A | 134 | 220.129 | 79.885 | 172.025 | 1.00 | 66.47 | C |
| ATOM | 694 | CD2 | LEU | A | 134 | 220.342 | 79.981 | 174.503 | 1.00 | 63.46 | C |
| ATOM | 695 | C | LEU | A | 134 | 224.326 | 78.865 | 172.431 | 1.00 | 63.74 | C |
| ATOM | 696 | O | LEU | A | 134 | 224.804 | 78.446 | 173.488 | 1.00 | 71.31 | O |
| ATOM | 697 | N | LEU | A | 135 | 224.992 | 79.663 | 171.608 | 1.00 | 69.76 | N |
| ATOM | 698 | CA | LEU | A | 135 | 226.338 | 80.103 | 171.910 | 1.00 | 48.46 | C |
| ATOM | 699 | CB | LEU | A | 135 | 227.130 | 80.192 | 170.609 | 1.00 | 69.61 | C |
| ATOM | 700 | CG | LEU | A | 135 | 227.191 | 78.851 | 169.873 | 1.00 | 59.09 | C |
| ATOM | 701 | CD1 | LEU | A | 135 | 227.585 | 79.058 | 168.425 | 1.00 | 80.07 | C |
| ATOM | 702 | CD2 | LEU | A | 135 | 228.173 | 77.943 | 170.579 | 1.00 | 92.22 | C |
| ATOM | 703 | C | LEU | A | 135 | 226.262 | 81.450 | 172.608 | 1.00 | 60.20 | C |
| ATOM | 704 | O | LEU | A | 135 | 225.639 | 82.381 | 172.101 | 1.00 | 49.35 | O |
| ATOM | 705 | N | ILE | A | 136 | 226.896 | 81.530 | 173.775 | 1.00 | 39.79 | N |
| ATOM | 706 | CA | ILE | A | 136 | 226.913 | 82.744 | 174.581 | 1.00 | 48.18 | C |
| ATOM | 707 | CB | ILE | A | 136 | 226.398 | 82.453 | 176.006 | 1.00 | 57.17 | C |
| ATOM | 708 | CG1 | ILE | A | 136 | 224.997 | 81.864 | 175.934 | 1.00 | 54.12 | C |
| ATOM | 709 | CD1 | ILE | A | 136 | 224.893 | 80.475 | 176.545 | 1.00 | 94.13 | C |
| ATOM | 710 | CG2 | ILE | A | 136 | 226.364 | 83.720 | 176.829 | 1.00 | 45.37 | C |
| ATOM | 711 | C | ILE | A | 136 | 228.321 | 83.324 | 174.691 | 1.00 | 54.20 | C |

FIG. 3A-13

| ATOM | 712 | O | ILE | A | 136 | 229.219 | 82.672 | 175.204 | 1.00 | 63.12 | O |
|---|---|---|---|---|---|---|---|---|---|---|---|
| ATOM | 713 | N | VAL | A | 137 | 228.527 | 84.539 | 174.200 | 1.00 | 47.11 | N |
| ATOM | 714 | CA | VAL | A | 137 | 229.812 | 85.185 | 174.376 | 1.00 | 51.92 | C |
| ATOM | 715 | CB | VAL | A | 137 | 230.091 | 85.979 | 173.099 | 1.00 | 55.29 | C |
| ATOM | 716 | CG1 | VAL | A | 137 | 231.461 | 86.640 | 173.162 | 1.00 | 49.20 | C |
| ATOM | 717 | CG2 | VAL | A | 137 | 230.064 | 85.035 | 171.910 | 1.00 | 33.49 | C |
| ATOM | 718 | C | VAL | A | 137 | 229.827 | 86.081 | 175.615 | 1.00 | 62.30 | C |
| ATOM | 719 | O | VAL | A | 137 | 228.925 | 86.871 | 175.875 | 1.00 | 65.38 | O |
| ATOM | 720 | N | MET | A | 138 | 230.893 | 85.889 | 176.417 | 1.00 | 63.64 | N |
| ATOM | 721 | CA | MET | A | 138 | 231.026 | 86.598 | 177.685 | 1.00 | 47.48 | C |
| ATOM | 722 | CB | MET | A | 138 | 231.044 | 85.548 | 178.796 | 1.00 | 76.63 | C |
| ATOM | 723 | CG | MET | A | 138 | 229.707 | 84.836 | 178.965 | 1.00 | 72.52 | C |
| ATOM | 724 | SD | MET | A | 138 | 229.779 | 83.570 | 180.236 | 1.00 | 81.89 | S |
| ATOM | 725 | CE | MET | A | 138 | 228.109 | 82.937 | 180.029 | 1.00 | 180.26 | C |
| ATOM | 726 | C | MET | A | 138 | 232.339 | 87.381 | 177.769 | 1.00 | 63.41 | C |
| ATOM | 727 | O | MET | A | 138 | 233.371 | 86.975 | 177.246 | 1.00 | 60.31 | O |
| ATOM | 728 | N | GLU | A | 139 | 232.281 | 88.555 | 178.427 | 1.00 | 44.14 | N |
| ATOM | 729 | CA | GLU | A | 139 | 233.550 | 89.154 | 178.798 | 1.00 | 46.81 | C |
| ATOM | 730 | CB | GLU | A | 139 | 233.291 | 90.346 | 179.732 | 1.00 | 40.20 | C |
| ATOM | 731 | CG | GLU | A | 139 | 233.444 | 89.999 | 181.216 | 1.00 | 70.67 | C |
| ATOM | 732 | CD | GLU | A | 139 | 233.140 | 91.231 | 182.059 | 1.00 | 76.30 | C |
| ATOM | 733 | OE1 | GLU | A | 139 | 231.972 | 91.501 | 182.306 | 1.00 | 89.15 | O |
| ATOM | 734 | OE2 | GLU | A | 139 | 234.079 | 91.912 | 182.459 | 1.00 | 100.67 | O |
| ATOM | 735 | C | GLU | A | 139 | 234.381 | 88.099 | 179.511 | 1.00 | 61.98 | C |
| ATOM | 736 | O | GLU | A | 139 | 233.876 | 87.285 | 180.272 | 1.00 | 68.61 | O |
| ATOM | 737 | N | CYS | A | 140 | 235.664 | 88.142 | 179.172 | 1.00 | 69.16 | N |
| ATOM | 738 | CA | CYS | A | 140 | 236.625 | 87.167 | 179.666 | 1.00 | 69.69 | C |
| ATOM | 739 | CB | CYS | A | 140 | 237.676 | 86.903 | 178.587 | 1.00 | 74.24 | C |
| ATOM | 740 | SG | CYS | A | 140 | 238.996 | 85.811 | 179.117 | 1.00 | 73.10 | S |
| ATOM | 741 | C | CYS | A | 140 | 237.322 | 87.529 | 180.968 | 1.00 | 60.14 | C |
| ATOM | 742 | O | CYS | A | 140 | 238.227 | 88.349 | 180.990 | 1.00 | 82.48 | O |
| ATOM | 743 | N | LEU | A | 141 | 236.912 | 86.895 | 182.055 | 1.00 | 71.80 | N |
| ATOM | 744 | CA | LEU | A | 141 | 237.524 | 87.159 | 183.348 | 1.00 | 79.00 | C |
| ATOM | 745 | CB | LEU | A | 141 | 236.523 | 86.847 | 184.462 | 1.00 | 81.97 | C |
| ATOM | 746 | CG | LEU | A | 141 | 235.203 | 87.610 | 184.350 | 1.00 | 76.77 | C |
| ATOM | 747 | CD1 | LEU | A | 141 | 234.214 | 87.100 | 185.382 | 1.00 | 96.50 | C |
| ATOM | 748 | CD2 | LEU | A | 141 | 235.469 | 89.086 | 184.535 | 1.00 | 47.85 | C |
| ATOM | 749 | C | LEU | A | 141 | 238.785 | 86.304 | 183.509 | 1.00 | 76.59 | C |
| ATOM | 750 | O | LEU | A | 141 | 238.736 | 85.081 | 183.360 | 1.00 | 77.59 | O |
| ATOM | 751 | N | ASP | A | 142 | 239.913 | 86.940 | 183.818 | 1.00 | 90.64 | N |
| ATOM | 752 | CA | ASP | A | 142 | 241.158 | 86.197 | 183.977 | 1.00 | 92.77 | C |
| ATOM | 753 | CB | ASP | A | 142 | 242.202 | 86.698 | 182.984 | 1.00 | 92.82 | C |
| ATOM | 754 | CG | ASP | A | 142 | 241.951 | 86.182 | 181.586 | 1.00 | 110.94 | C |
| ATOM | 755 | OD1 | ASP | A | 142 | 241.710 | 84.961 | 181.450 | 1.00 | 82.18 | O |
| ATOM | 756 | OD2 | ASP | A | 142 | 242.003 | 86.987 | 180.632 | 1.00 | 115.53 | O |
| ATOM | 757 | C | ASP | A | 142 | 241.771 | 86.152 | 185.366 | 1.00 | 84.21 | C |
| ATOM | 758 | O | ASP | A | 142 | 242.387 | 85.153 | 185.725 | 1.00 | 120.09 | O |
| ATOM | 759 | N | GLY | A | 143 | 241.616 | 87.220 | 186.142 | 1.00 | 76.67 | N |
| ATOM | 760 | CA | GLY | A | 143 | 242.178 | 87.249 | 187.486 | 1.00 | 84.99 | C |
| ATOM | 761 | C | GLY | A | 143 | 242.128 | 85.940 | 188.269 | 1.00 | 83.56 | C |
| ATOM | 762 | O | GLY | A | 143 | 242.909 | 85.744 | 189.194 | 1.00 | 94.38 | O |
| ATOM | 763 | N | GLY | A | 144 | 241.216 | 85.040 | 187.913 | 1.00 | 81.49 | N |
| ATOM | 764 | CA | GLY | A | 144 | 241.132 | 83.778 | 188.621 | 1.00 | 72.81 | C |
| ATOM | 765 | C | GLY | A | 144 | 240.064 | 83.784 | 189.700 | 1.00 | 88.08 | C |
| ATOM | 766 | O | GLY | A | 144 | 239.527 | 84.839 | 190.045 | 1.00 | 76.11 | O |

FIG. 3A-14

| ATOM | 767 | N | GLU | A | 145 | 239.759 | 82.603 | 190.235 | 1.00 | 72.60 | N |
|---|---|---|---|---|---|---|---|---|---|---|---|
| ATOM | 768 | CA | GLU | A | 145 | 238.746 | 82.464 | 191.268 | 1.00 | 80.92 | C |
| ATOM | 769 | CB | GLU | A | 145 | 238.543 | 80.993 | 191.605 | 1.00 | 61.62 | C |
| ATOM | 770 | CG | GLU | A | 145 | 237.861 | 80.199 | 190.509 | 1.00 | 89.57 | C |
| ATOM | 771 | CD | GLU | A | 145 | 237.725 | 78.732 | 190.876 | 1.00 | 126.57 | C |
| ATOM | 772 | OE1 | GLU | A | 145 | 237.118 | 77.967 | 190.092 | 1.00 | 97.67 | O |
| ATOM | 773 | OE2 | GLU | A | 145 | 238.236 | 78.346 | 191.955 | 1.00 | 103.63 | O |
| ATOM | 774 | C | GLU | A | 145 | 239.050 | 83.249 | 192.539 | 1.00 | 85.24 | C |
| ATOM | 775 | O | GLU | A | 145 | 240.206 | 83.446 | 192.908 | 1.00 | 76.66 | O |
| ATOM | 776 | N | LEU | A | 146 | 237.988 | 83.679 | 193.210 | 1.00 | 97.07 | N |
| ATOM | 777 | CA | LEU | A | 146 | 238.095 | 84.479 | 194.419 | 1.00 | 86.04 | C |
| ATOM | 778 | CB | LEU | A | 146 | 236.743 | 84.530 | 195.138 | 1.00 | 83.71 | C |
| ATOM | 779 | CG | LEU | A | 146 | 236.768 | 85.402 | 196.395 | 1.00 | 84.94 | C |
| ATOM | 780 | CD1 | LEU | A | 146 | 237.338 | 86.754 | 196.044 | 1.00 | 92.90 | C |
| ATOM | 781 | CD2 | LEU | A | 146 | 235.382 | 85.551 | 196.975 | 1.00 | 116.24 | C |
| ATOM | 782 | C | LEU | A | 146 | 239.174 | 84.065 | 195.402 | 1.00 | 75.32 | C |
| ATOM | 783 | O | LEU | A | 146 | 240.049 | 84.852 | 195.732 | 1.00 | 72.90 | O |
| ATOM | 784 | N | PHE | A | 147 | 239.127 | 82.829 | 195.867 | 1.00 | 80.55 | N |
| ATOM | 785 | CA | PHE | A | 147 | 240.104 | 82.385 | 196.847 | 1.00 | 87.51 | C |
| ATOM | 786 | CB | PHE | A | 147 | 239.611 | 81.094 | 197.495 | 1.00 | 62.88 | C |
| ATOM | 787 | CG | PHE | A | 147 | 238.388 | 81.297 | 198.330 | 1.00 | 83.58 | C |
| ATOM | 788 | CD1 | PHE | A | 147 | 237.514 | 80.260 | 198.589 | 1.00 | 80.71 | C |
| ATOM | 789 | CE1 | PHE | A | 147 | 236.375 | 80.476 | 199.342 | 1.00 | 93.95 | C |
| ATOM | 790 | CZ | PHE | A | 147 | 236.105 | 81.740 | 199.844 | 1.00 | 97.28 | C |
| ATOM | 791 | CE2 | PHE | A | 147 | 236.971 | 82.778 | 199.596 | 1.00 | 50.19 | C |
| ATOM | 792 | CD2 | PHE | A | 147 | 238.102 | 82.557 | 198.845 | 1.00 | 82.88 | C |
| ATOM | 793 | C | PHE | A | 147 | 241.526 | 82.244 | 196.332 | 1.00 | 92.39 | C |
| ATOM | 794 | O | PHE | A | 147 | 242.478 | 82.546 | 197.051 | 1.00 | 104.70 | O |
| ATOM | 795 | N | SER | A | 148 | 241.680 | 81.805 | 195.090 | 1.00 | 81.24 | N |
| ATOM | 796 | CA | SER | A | 148 | 243.008 | 81.657 | 194.525 | 1.00 | 74.75 | C |
| ATOM | 797 | CB | SER | A | 148 | 242.902 | 81.301 | 193.051 | 1.00 | 76.50 | C |
| ATOM | 798 | OG | SER | A | 148 | 242.158 | 80.106 | 192.902 | 1.00 | 74.94 | O |
| ATOM | 799 | C | SER | A | 148 | 243.758 | 82.970 | 194.714 | 1.00 | 83.42 | C |
| ATOM | 800 | O | SER | A | 148 | 244.679 | 83.053 | 195.529 | 1.00 | 88.34 | O |
| ATOM | 801 | N | ARG | A | 149 | 243.347 | 83.999 | 193.978 | 1.00 | 81.76 | N |
| ATOM | 802 | CA | ARG | A | 149 | 243.974 | 85.316 | 194.077 | 1.00 | 102.63 | C |
| ATOM | 803 | CB | ARG | A | 149 | 243.038 | 86.396 | 193.537 | 1.00 | 92.17 | C |
| ATOM | 804 | CG | ARG | A | 149 | 242.950 | 86.427 | 192.033 | 1.00 | 96.27 | C |
| ATOM | 805 | CD | ARG | A | 149 | 244.278 | 86.851 | 191.433 | 1.00 | 127.89 | C |
| ATOM | 806 | NE | ARG | A | 149 | 244.141 | 88.079 | 190.656 | 1.00 | 105.03 | N |
| ATOM | 807 | CZ | ARG | A | 149 | 243.698 | 89.227 | 191.155 | 1.00 | 106.80 | C |
| ATOM | 808 | NH1 | ARG | A | 149 | 243.350 | 89.307 | 192.434 | 1.00 | 91.41 | N |
| ATOM | 809 | NH2 | ARG | A | 149 | 243.597 | 90.293 | 190.377 | 1.00 | 81.30 | N |
| ATOM | 810 | C | ARG | A | 149 | 244.325 | 85.650 | 195.512 | 1.00 | 107.57 | C |
| ATOM | 811 | O | ARG | A | 149 | 245.399 | 86.169 | 195.796 | 1.00 | 115.11 | O |
| ATOM | 812 | N | ILE | A | 150 | 243.410 | 85.352 | 196.423 | 1.00 | 117.64 | N |
| ATOM | 813 | CA | ILE | A | 150 | 243.658 | 85.636 | 197.821 | 1.00 | 111.89 | C |
| ATOM | 814 | CB | ILE | A | 150 | 242.447 | 85.262 | 198.691 | 1.00 | 102.67 | C |
| ATOM | 815 | CG1 | ILE | A | 150 | 241.501 | 86.458 | 198.783 | 1.00 | 81.93 | C |
| ATOM | 816 | CD1 | ILE | A | 150 | 241.279 | 87.159 | 197.457 | 1.00 | 131.92 | C |
| ATOM | 817 | CG2 | ILE | A | 150 | 242.900 | 84.866 | 200.081 | 1.00 | 93.62 | C |
| ATOM | 818 | C | ILE | A | 150 | 244.890 | 84.907 | 198.320 | 1.00 | 111.27 | C |
| ATOM | 819 | O | ILE | A | 150 | 245.841 | 85.543 | 198.769 | 1.00 | 125.08 | O |
| ATOM | 820 | N | GLN | A | 151 | 244.898 | 83.583 | 198.221 | 1.00 | 93.05 | N |
| ATOM | 821 | CA | GLN | A | 151 | 246.045 | 82.836 | 198.708 | 1.00 | 112.82 | C |

FIG. 3A-15

| ATOM | 822 | CB | GLN | A | 151 | 245.825 | 81.329 | 198.565 | 1.00 | 96.24 | C |
|---|---|---|---|---|---|---|---|---|---|---|---|
| ATOM | 823 | CG | GLN | A | 151 | 246.123 | 80.751 | 197.203 | 1.00 | 107.91 | C |
| ATOM | 824 | CD | GLN | A | 151 | 246.134 | 79.231 | 197.224 | 1.00 | 135.63 | C |
| ATOM | 825 | OE1 | GLN | A | 151 | 246.326 | 78.584 | 196.193 | 1.00 | 152.64 | O |
| ATOM | 826 | NE2 | GLN | A | 151 | 245.929 | 78.654 | 198.406 | 1.00 | 63.64 | N |
| ATOM | 827 | C | GLN | A | 151 | 247.325 | 83.240 | 197.992 | 1.00 | 130.96 | C |
| ATOM | 828 | O | GLN | A | 151 | 248.373 | 83.378 | 198.624 | 1.00 | 146.77 | O |
| ATOM | 829 | N | ASP | A | 152 | 247.241 | 83.452 | 196.682 | 1.00 | 131.86 | N |
| ATOM | 830 | CA | ASP | A | 152 | 248.416 | 83.833 | 195.898 | 1.00 | 121.88 | C |
| ATOM | 831 | CB | ASP | A | 152 | 248.226 | 83.420 | 194.436 | 1.00 | 120.82 | C |
| ATOM | 832 | CG | ASP | A | 152 | 247.643 | 82.015 | 194.296 | 1.00 | 145.66 | C |
| ATOM | 833 | OD1 | ASP | A | 152 | 248.152 | 81.088 | 194.964 | 1.00 | 161.64 | O |
| ATOM | 834 | OD2 | ASP | A | 152 | 246.679 | 81.834 | 193.515 | 1.00 | 172.99 | O |
| ATOM | 835 | C | ASP | A | 152 | 248.697 | 85.331 | 195.974 | 1.00 | 119.03 | C |
| ATOM | 836 | O | ASP | A | 152 | 249.617 | 85.765 | 196.678 | 1.00 | 108.04 | O |
| ATOM | 837 | N | THR | A | 159 | 244.002 | 91.956 | 205.011 | 1.00 | 65.30 | N |
| ATOM | 838 | CA | THR | A | 159 | 243.414 | 92.956 | 205.898 | 1.00 | 99.51 | C |
| ATOM | 839 | CB | THR | A | 159 | 243.790 | 94.404 | 205.473 | 1.00 | 95.19 | C |
| ATOM | 840 | OG1 | THR | A | 159 | 243.610 | 94.560 | 204.061 | 1.00 | 103.02 | O |
| ATOM | 841 | CG2 | THR | A | 159 | 245.229 | 94.718 | 205.831 | 1.00 | 121.85 | C |
| ATOM | 842 | C | THR | A | 159 | 241.893 | 92.871 | 205.964 | 1.00 | 87.22 | C |
| ATOM | 843 | O | THR | A | 159 | 241.221 | 92.755 | 204.944 | 1.00 | 90.56 | O |
| ATOM | 844 | N | GLU | A | 160 | 241.360 | 92.931 | 207.178 | 1.00 | 90.46 | N |
| ATOM | 845 | CA | GLU | A | 160 | 239.921 | 92.876 | 207.395 | 1.00 | 95.08 | C |
| ATOM | 846 | CB | GLU | A | 160 | 239.606 | 93.302 | 208.836 | 1.00 | 84.05 | C |
| ATOM | 847 | CG | GLU | A | 160 | 238.135 | 93.255 | 209.218 | 1.00 | 102.30 | C |
| ATOM | 848 | CD | GLU | A | 160 | 237.888 | 93.636 | 210.675 | 1.00 | 107.68 | C |
| ATOM | 849 | OE1 | GLU | A | 160 | 238.512 | 93.022 | 211.566 | 1.00 | 102.89 | O |
| ATOM | 850 | OE2 | GLU | A | 160 | 237.063 | 94.542 | 210.931 | 1.00 | 116.03 | O |
| ATOM | 851 | C | GLU | A | 160 | 239.243 | 93.816 | 206.400 | 1.00 | 97.10 | C |
| ATOM | 852 | O | GLU | A | 160 | 238.191 | 93.498 | 205.844 | 1.00 | 77.77 | O |
| ATOM | 853 | N | ARG | A | 161 | 239.872 | 94.966 | 206.169 | 1.00 | 91.94 | N |
| ATOM | 854 | CA | ARG | A | 161 | 239.359 | 95.979 | 205.252 | 1.00 | 98.89 | C |
| ATOM | 855 | CB | ARG | A | 161 | 240.276 | 97.204 | 205.245 | 1.00 | 94.61 | C |
| ATOM | 856 | CG | ARG | A | 161 | 239.886 | 98.251 | 204.206 | 1.00 | 116.99 | C |
| ATOM | 857 | CD | ARG | A | 161 | 240.724 | 99.506 | 204.347 | 1.00 | 131.31 | C |
| ATOM | 858 | NE | ARG | A | 161 | 240.601 | 100.069 | 205.688 | 1.00 | 142.10 | N |
| ATOM | 859 | CZ | ARG | A | 161 | 241.205 | 101.180 | 206.092 | 1.00 | 132.03 | C |
| ATOM | 860 | NH1 | ARG | A | 161 | 241.982 | 101.855 | 205.257 | 1.00 | 142.54 | N |
| ATOM | 861 | NH2 | ARG | A | 161 | 241.026 | 101.620 | 207.330 | 1.00 | 138.86 | N |
| ATOM | 862 | C | ARG | A | 161 | 239.188 | 95.480 | 203.826 | 1.00 | 94.53 | C |
| ATOM | 863 | O | ARG | A | 161 | 238.251 | 95.874 | 203.129 | 1.00 | 84.43 | O |
| ATOM | 864 | N | GLU | A | 162 | 240.107 | 94.628 | 203.389 | 1.00 | 86.92 | N |
| ATOM | 865 | CA | GLU | A | 162 | 240.040 | 94.067 | 202.050 | 1.00 | 96.77 | C |
| ATOM | 866 | CB | GLU | A | 162 | 241.360 | 93.385 | 201.699 | 1.00 | 101.33 | C |
| ATOM | 867 | CG | GLU | A | 162 | 242.463 | 94.360 | 201.317 | 1.00 | 125.60 | C |
| ATOM | 868 | CD | GLU | A | 162 | 243.848 | 93.755 | 201.448 | 1.00 | 135.51 | C |
| ATOM | 869 | OE1 | GLU | A | 162 | 244.823 | 94.405 | 201.011 | 1.00 | 144.57 | O |
| ATOM | 870 | OE2 | GLU | A | 162 | 243.959 | 92.636 | 201.999 | 1.00 | 130.61 | O |
| ATOM | 871 | C | GLU | A | 162 | 238.899 | 93.063 | 201.991 | 1.00 | 93.54 | C |
| ATOM | 872 | O | GLU | A | 162 | 238.101 | 93.078 | 201.052 | 1.00 | 98.52 | O |
| ATOM | 873 | N | ALA | A | 163 | 238.822 | 92.199 | 203.002 | 1.00 | 93.78 | N |
| ATOM | 874 | CA | ALA | A | 163 | 237.772 | 91.187 | 203.071 | 1.00 | 86.54 | C |
| ATOM | 875 | CB | ALA | A | 163 | 237.871 | 90.419 | 204.371 | 1.00 | 72.07 | C |
| ATOM | 876 | C | ALA | A | 163 | 236.426 | 91.889 | 202.976 | 1.00 | 87.93 | C |

FIG. 3A-16

| ATOM | 877 | O   | ALA | A | 163 | 235.509 | 91.418  | 202.297 | 1.00 | 94.67  | O |
|------|-----|-----|-----|---|-----|---------|---------|---------|------|--------|---|
| ATOM | 878 | N   | SER | A | 164 | 236.319 | 93.021  | 203.662 | 1.00 | 75.33  | N |
| ATOM | 879 | CA  | SER | A | 164 | 235.098 | 93.809  | 203.651 | 1.00 | 81.45  | C |
| ATOM | 880 | CB  | SER | A | 164 | 235.281 | 95.057  | 204.511 | 1.00 | 61.52  | C |
| ATOM | 881 | OG  | SER | A | 164 | 234.233 | 95.977  | 204.289 | 1.00 | 85.01  | O |
| ATOM | 882 | C   | SER | A | 164 | 234.765 | 94.222  | 202.223 | 1.00 | 92.32  | C |
| ATOM | 883 | O   | SER | A | 164 | 233.708 | 93.892  | 201.679 | 1.00 | 89.51  | O |
| ATOM | 884 | N   | GLU | A | 165 | 235.696 | 94.949  | 201.622 | 1.00 | 106.88 | N |
| ATOM | 885 | CA  | GLU | A | 165 | 235.537 | 95.436  | 200.259 | 1.00 | 107.60 | C |
| ATOM | 886 | CB  | GLU | A | 165 | 236.834 | 96.102  | 199.807 | 1.00 | 117.73 | C |
| ATOM | 887 | CG  | GLU | A | 165 | 237.296 | 97.198  | 200.763 | 1.00 | 121.43 | C |
| ATOM | 888 | CD  | GLU | A | 165 | 238.640 | 97.776  | 200.381 | 1.00 | 129.44 | C |
| ATOM | 889 | OE1 | GLU | A | 165 | 239.620 | 96.998  | 200.285 | 1.00 | 132.54 | O |
| ATOM | 890 | OE2 | GLU | A | 165 | 238.711 | 99.007  | 200.172 | 1.00 | 114.59 | O |
| ATOM | 891 | C   | GLU | A | 165 | 235.138 | 94.312  | 199.306 | 1.00 | 98.22  | C |
| ATOM | 892 | O   | GLU | A | 165 | 234.309 | 94.509  | 198.421 | 1.00 | 80.74  | O |
| ATOM | 893 | N   | ILE | A | 166 | 235.722 | 93.134  | 199.483 | 1.00 | 87.57  | N |
| ATOM | 894 | CA  | ILE | A | 166 | 235.354 | 92.020  | 198.628 | 1.00 | 78.81  | C |
| ATOM | 895 | CB  | ILE | A | 166 | 236.207 | 90.755  | 198.905 | 1.00 | 76.17  | C |
| ATOM | 896 | CG1 | ILE | A | 166 | 237.628 | 90.972  | 198.376 | 1.00 | 76.65  | C |
| ATOM | 897 | CD1 | ILE | A | 166 | 238.532 | 89.759  | 198.515 | 1.00 | 56.87  | C |
| ATOM | 898 | CG2 | ILE | A | 166 | 235.567 | 89.534  | 198.255 | 1.00 | 77.07  | C |
| ATOM | 899 | C   | ILE | A | 166 | 233.887 | 91.705  | 198.905 | 1.00 | 85.13  | C |
| ATOM | 900 | O   | ILE | A | 166 | 233.068 | 91.644  | 197.975 | 1.00 | 86.94  | O |
| ATOM | 901 | N   | MET | A | 167 | 233.546 | 91.520  | 200.179 | 1.00 | 80.82  | N |
| ATOM | 902 | CA  | MET | A | 167 | 232.166 | 91.195  | 200.521 | 1.00 | 77.70  | C |
| ATOM | 903 | CB  | MET | A | 167 | 231.978 | 91.110  | 202.035 | 1.00 | 67.42  | C |
| ATOM | 904 | CG  | MET | A | 167 | 232.544 | 89.845  | 202.620 | 1.00 | 65.04  | C |
| ATOM | 905 | SD  | MET | A | 167 | 232.087 | 88.398  | 201.648 | 1.00 | 75.11  | S |
| ATOM | 906 | CE  | MET | A | 167 | 230.294 | 88.399  | 201.807 | 1.00 | 53.41  | C |
| ATOM | 907 | C   | MET | A | 167 | 231.228 | 92.224  | 199.941 | 1.00 | 73.89  | C |
| ATOM | 908 | O   | MET | A | 167 | 230.152 | 91.895  | 199.452 | 1.00 | 72.21  | O |
| ATOM | 909 | N   | LYS | A | 168 | 231.659 | 93.472  | 199.962 | 1.00 | 54.97  | N |
| ATOM | 910 | CA  | LYS | A | 168 | 230.830 | 94.534  | 199.449 | 1.00 | 60.76  | C |
| ATOM | 911 | CB  | LYS | A | 168 | 231.502 | 95.876  | 199.659 | 1.00 | 65.32  | C |
| ATOM | 912 | CG  | LYS | A | 168 | 230.616 | 97.027  | 199.293 | 1.00 | 49.49  | C |
| ATOM | 913 | CD  | LYS | A | 168 | 231.208 | 98.313  | 199.780 | 1.00 | 103.77 | C |
| ATOM | 914 | CE  | LYS | A | 168 | 230.191 | 99.429  | 199.714 | 1.00 | 87.12  | C |
| ATOM | 915 | NZ  | LYS | A | 168 | 230.644 | 100.674 | 200.407 | 1.00 | 118.45 | N |
| ATOM | 916 | C   | LYS | A | 168 | 230.456 | 94.386  | 197.990 | 1.00 | 70.78  | C |
| ATOM | 917 | O   | LYS | A | 168 | 229.307 | 94.607  | 197.629 | 1.00 | 66.11  | O |
| ATOM | 918 | N   | SER | A | 169 | 231.403 | 94.023  | 197.136 | 1.00 | 82.60  | N |
| ATOM | 919 | CA  | SER | A | 169 | 231.061 | 93.885  | 195.723 | 1.00 | 89.11  | C |
| ATOM | 920 | CB  | SER | A | 169 | 232.327 | 93.796  | 194.863 | 1.00 | 73.74  | C |
| ATOM | 921 | OG  | SER | A | 169 | 233.058 | 92.620  | 195.165 | 1.00 | 77.68  | O |
| ATOM | 922 | C   | SER | A | 169 | 230.176 | 92.665  | 195.484 | 1.00 | 81.07  | C |
| ATOM | 923 | O   | SER | A | 169 | 229.262 | 92.726  | 194.657 | 1.00 | 75.01  | O |
| ATOM | 924 | N   | ILE | A | 170 | 230.448 | 91.560  | 196.191 | 1.00 | 75.29  | N |
| ATOM | 925 | CA  | ILE | A | 170 | 229.630 | 90.349  | 196.034 | 1.00 | 74.32  | C |
| ATOM | 926 | CB  | ILE | A | 170 | 230.053 | 89.177  | 196.951 | 1.00 | 68.61  | C |
| ATOM | 927 | CG1 | ILE | A | 170 | 231.437 | 88.663  | 196.571 | 1.00 | 59.95  | C |
| ATOM | 928 | CD1 | ILE | A | 170 | 231.768 | 87.318  | 197.192 | 1.00 | 76.19  | C |
| ATOM | 929 | CG2 | ILE | A | 170 | 229.091 | 88.015  | 196.782 | 1.00 | 46.17  | C |
| ATOM | 930 | C   | ILE | A | 170 | 228.232 | 90.743  | 196.437 | 1.00 | 63.33  | C |
| ATOM | 931 | O   | ILE | A | 170 | 227.255 | 90.334  | 195.818 | 1.00 | 57.44  | O |

FIG. 3A-17

| | | | | | | | | | | |
|---|---|---|---|---|---|---|---|---|---|---|
| ATOM | 932 | N | GLY | A | 171 | 228.154 | 91.560 | 197.484 | 1.00 | 56.09 N |
| ATOM | 933 | CA | GLY | A | 171 | 226.870 | 92.026 | 197.958 | 1.00 | 75.47 C |
| ATOM | 934 | C | GLY | A | 171 | 226.110 | 92.700 | 196.835 | 1.00 | 69.45 C |
| ATOM | 935 | O | GLY | A | 171 | 224.947 | 92.390 | 196.568 | 1.00 | 76.12 O |
| ATOM | 936 | N | GLU | A | 172 | 226.792 | 93.621 | 196.166 | 1.00 | 71.58 N |
| ATOM | 937 | CA | GLU | A | 172 | 226.212 | 94.368 | 195.066 | 1.00 | 73.09 C |
| ATOM | 938 | CB | GLU | A | 172 | 227.243 | 95.332 | 194.499 | 1.00 | 62.80 C |
| ATOM | 939 | CG | GLU | A | 172 | 228.028 | 96.080 | 195.547 | 1.00 | 91.94 C |
| ATOM | 940 | CD | GLU | A | 172 | 228.717 | 97.298 | 194.973 | 1.00 | 112.10 C |
| ATOM | 941 | OE1 | GLU | A | 172 | 228.051 | 98.349 | 194.825 | 1.00 | 116.39 O |
| ATOM | 942 | OE2 | GLU | A | 172 | 229.919 | 97.199 | 194.649 | 1.00 | 121.47 O |
| ATOM | 943 | C | GLU | A | 172 | 225.715 | 93.446 | 193.960 | 1.00 | 69.34 C |
| ATOM | 944 | O | GLU | A | 172 | 224.645 | 93.653 | 193.396 | 1.00 | 74.21 O |
| ATOM | 945 | N | ALA | A | 173 | 226.487 | 92.427 | 193.635 | 1.00 | 50.91 N |
| ATOM | 946 | CA | ALA | A | 173 | 226.039 | 91.525 | 192.599 | 1.00 | 55.42 C |
| ATOM | 947 | CB | ALA | A | 173 | 227.036 | 90.392 | 192.429 | 1.00 | 59.45 C |
| ATOM | 948 | C | ALA | A | 173 | 224.666 | 90.969 | 192.995 | 1.00 | 69.00 C |
| ATOM | 949 | O | ALA | A | 173 | 223.779 | 90.793 | 192.156 | 1.00 | 68.62 O |
| ATOM | 950 | N | ILE | A | 174 | 224.491 | 90.709 | 194.287 | 1.00 | 59.68 N |
| ATOM | 951 | CA | ILE | A | 174 | 223.240 | 90.163 | 194.793 | 1.00 | 55.23 C |
| ATOM | 952 | CB | ILE | A | 174 | 223.439 | 89.528 | 196.157 | 1.00 | 72.24 C |
| ATOM | 953 | CG1 | ILE | A | 174 | 224.492 | 88.438 | 196.055 | 1.00 | 44.08 C |
| ATOM | 954 | CD1 | ILE | A | 174 | 224.090 | 87.355 | 195.102 | 1.00 | 105.89 C |
| ATOM | 955 | CG2 | ILE | A | 174 | 222.132 | 88.924 | 196.636 | 1.00 | 52.34 C |
| ATOM | 956 | C | ILE | A | 174 | 222.137 | 91.199 | 194.912 | 1.00 | 66.27 C |
| ATOM | 957 | O | ILE | A | 174 | 220.991 | 90.943 | 194.542 | 1.00 | 59.24 O |
| ATOM | 958 | N | GLN | A | 175 | 222.473 | 92.368 | 195.444 | 1.00 | 46.22 N |
| ATOM | 959 | CA | GLN | A | 175 | 221.477 | 93.407 | 195.586 | 1.00 | 60.91 C |
| ATOM | 960 | CB | GLN | A | 175 | 222.121 | 94.674 | 196.144 | 1.00 | 49.40 C |
| ATOM | 961 | CG | GLN | A | 175 | 221.309 | 95.931 | 195.912 | 1.00 | 71.12 C |
| ATOM | 962 | CD | GLN | A | 175 | 221.661 | 97.042 | 196.892 | 1.00 | 104.15 C |
| ATOM | 963 | OE1 | GLN | A | 175 | 222.825 | 97.446 | 197.017 | 1.00 | 76.77 O |
| ATOM | 964 | NE2 | GLN | A | 175 | 220.645 | 97.544 | 197.600 | 1.00 | 111.29 N |
| ATOM | 965 | C | GLN | A | 175 | 220.804 | 93.676 | 194.240 | 1.00 | 48.25 C |
| ATOM | 966 | O | GLN | A | 175 | 219.581 | 93.742 | 194.155 | 1.00 | 62.61 O |
| ATOM | 967 | N | TYR | A | 176 | 221.602 | 93.798 | 193.184 | 1.00 | 72.76 N |
| ATOM | 968 | CA | TYR | A | 176 | 221.025 | 94.078 | 191.873 | 1.00 | 74.81 C |
| ATOM | 969 | CB | TYR | A | 176 | 222.168 | 94.255 | 190.874 | 1.00 | 79.19 C |
| ATOM | 970 | CG | TYR | A | 176 | 221.628 | 94.703 | 189.563 | 1.00 | 53.89 C |
| ATOM | 971 | CD1 | TYR | A | 176 | 221.692 | 96.048 | 189.209 | 1.00 | 73.14 C |
| ATOM | 972 | CE1 | TYR | A | 176 | 221.197 | 96.471 | 187.985 | 1.00 | 58.55 C |
| ATOM | 973 | CZ | TYR | A | 176 | 220.616 | 95.546 | 187.115 | 1.00 | 70.05 C |
| ATOM | 974 | OH | TYR | A | 176 | 220.124 | 95.975 | 185.898 | 1.00 | 98.35 O |
| ATOM | 975 | CE2 | TYR | A | 176 | 220.550 | 94.209 | 187.463 | 1.00 | 60.19 C |
| ATOM | 976 | CD2 | TYR | A | 176 | 221.054 | 93.785 | 188.683 | 1.00 | 78.08 C |
| ATOM | 977 | C | TYR | A | 176 | 220.105 | 92.946 | 191.416 | 1.00 | 74.26 C |
| ATOM | 978 | O | TYR | A | 176 | 218.933 | 93.142 | 191.122 | 1.00 | 61.26 O |
| ATOM | 979 | N | LEU | A | 177 | 220.626 | 91.729 | 191.357 | 1.00 | 69.60 N |
| ATOM | 980 | CA | LEU | A | 177 | 219.824 | 90.582 | 190.986 | 1.00 | 65.69 C |
| ATOM | 981 | CB | LEU | A | 177 | 220.562 | 89.297 | 191.333 | 1.00 | 59.94 C |
| ATOM | 982 | CG | LEU | A | 177 | 221.671 | 88.955 | 190.357 | 1.00 | 54.02 C |
| ATOM | 983 | CD1 | LEU | A | 177 | 222.252 | 87.585 | 190.679 | 1.00 | 59.89 C |
| ATOM | 984 | CD2 | LEU | A | 177 | 221.078 | 88.962 | 188.964 | 1.00 | 77.33 C |
| ATOM | 985 | C | LEU | A | 177 | 218.485 | 90.616 | 191.705 | 1.00 | 62.46 C |
| ATOM | 986 | O | LEU | A | 177 | 217.437 | 90.563 | 191.057 | 1.00 | 73.48 O |

FIG. 3A-18

| ATOM | 987  | N   | HIS | A | 178 | 218.518 | 90.708 | 193.035 | 1.00 | 61.49 | N |
| ATOM | 988  | CA  | HIS | A | 178 | 217.285 | 90.746 | 193.816 | 1.00 | 57.69 | C |
| ATOM | 989  | CB  | HIS | A | 178 | 217.590 | 90.741 | 195.313 | 1.00 | 58.67 | C |
| ATOM | 990  | CG  | HIS | A | 178 | 218.154 | 89.446 | 195.805 | 1.00 | 66.35 | C |
| ATOM | 991  | ND1 | HIS | A | 178 | 218.554 | 89.259 | 197.110 | 1.00 | 49.65 | N |
| ATOM | 992  | CE1 | HIS | A | 178 | 219.068 | 88.049 | 197.241 | 1.00 | 77.64 | C |
| ATOM | 993  | NE2 | HIS | A | 178 | 219.010 | 87.442 | 196.069 | 1.00 | 44.53 | N |
| ATOM | 994  | CD2 | HIS | A | 178 | 218.437 | 88.292 | 195.154 | 1.00 | 50.67 | C |
| ATOM | 995  | C   | HIS | A | 178 | 216.419 | 91.952 | 193.466 | 1.00 | 56.16 | C |
| ATOM | 996  | O   | HIS | A | 178 | 215.204 | 91.831 | 193.368 | 1.00 | 71.55 | O |
| ATOM | 997  | N   | SER | A | 179 | 217.037 | 93.107 | 193.259 | 1.00 | 62.56 | N |
| ATOM | 998  | CA  | SER | A | 179 | 216.270 | 94.292 | 192.906 | 1.00 | 56.93 | C |
| ATOM | 999  | CB  | SER | A | 179 | 217.160 | 95.518 | 192.803 | 1.00 | 41.33 | C |
| ATOM | 1000 | OG  | SER | A | 179 | 217.835 | 95.504 | 191.554 | 1.00 | 86.61 | O |
| ATOM | 1001 | C   | SER | A | 179 | 215.575 | 94.094 | 191.567 | 1.00 | 44.23 | C |
| ATOM | 1002 | O   | SER | A | 179 | 214.830 | 94.956 | 191.136 | 1.00 | 68.45 | O |
| ATOM | 1003 | N   | ILE | A | 180 | 215.842 | 92.997 | 190.876 | 1.00 | 60.70 | N |
| ATOM | 1004 | CA  | ILE | A | 180 | 215.135 | 92.778 | 189.629 | 1.00 | 66.56 | C |
| ATOM | 1005 | CB  | ILE | A | 180 | 216.041 | 92.928 | 188.368 | 1.00 | 65.72 | C |
| ATOM | 1006 | CG1 | ILE | A | 180 | 217.061 | 91.804 | 188.280 | 1.00 | 98.00 | C |
| ATOM | 1007 | CD1 | ILE | A | 180 | 217.787 | 91.783 | 186.962 | 1.00 | 42.99 | C |
| ATOM | 1008 | CG2 | ILE | A | 180 | 216.766 | 94.248 | 188.413 | 1.00 | 65.05 | C |
| ATOM | 1009 | C   | ILE | A | 180 | 214.483 | 91.409 | 189.667 | 1.00 | 76.38 | C |
| ATOM | 1010 | O   | ILE | A | 180 | 214.223 | 90.783 | 188.641 | 1.00 | 67.28 | O |
| ATOM | 1011 | N   | ASN | A | 181 | 214.229 | 90.940 | 190.880 | 1.00 | 62.76 | N |
| ATOM | 1012 | CA  | ASN | A | 181 | 213.556 | 89.672 | 191.081 | 1.00 | 64.37 | C |
| ATOM | 1013 | CB  | ASN | A | 181 | 212.156 | 89.726 | 190.464 | 1.00 | 52.97 | C |
| ATOM | 1014 | CG  | ASN | A | 181 | 211.274 | 90.765 | 191.118 | 1.00 | 91.87 | C |
| ATOM | 1015 | OD1 | ASN | A | 181 | 210.607 | 91.549 | 190.435 | 1.00 | 70.51 | O |
| ATOM | 1016 | ND2 | ASN | A | 181 | 211.261 | 90.779 | 192.456 | 1.00 | 66.84 | N |
| ATOM | 1017 | C   | ASN | A | 181 | 214.257 | 88.447 | 190.552 | 1.00 | 64.72 | C |
| ATOM | 1018 | O   | ASN | A | 181 | 213.624 | 87.605 | 189.919 | 1.00 | 76.26 | O |
| ATOM | 1019 | N   | ILE | A | 182 | 215.550 | 88.325 | 190.800 | 1.00 | 69.03 | N |
| ATOM | 1020 | CA  | ILE | A | 182 | 216.251 | 87.140 | 190.343 | 1.00 | 58.61 | C |
| ATOM | 1021 | CB  | ILE | A | 182 | 217.217 | 87.452 | 189.175 | 1.00 | 67.77 | C |
| ATOM | 1022 | CG1 | ILE | A | 182 | 216.498 | 88.204 | 188.058 | 1.00 | 51.81 | C |
| ATOM | 1023 | CD1 | ILE | A | 182 | 217.397 | 88.520 | 186.870 | 1.00 | 51.04 | C |
| ATOM | 1024 | CG2 | ILE | A | 182 | 217.765 | 86.162 | 188.604 | 1.00 | 71.00 | C |
| ATOM | 1025 | C   | ILE | A | 182 | 217.060 | 86.582 | 191.510 | 1.00 | 64.49 | C |
| ATOM | 1026 | O   | ILE | A | 182 | 217.652 | 87.335 | 192.289 | 1.00 | 75.24 | O |
| ATOM | 1027 | N   | ALA | A | 183 | 217.068 | 85.261 | 191.639 | 1.00 | 74.62 | N |
| ATOM | 1028 | CA  | ALA | A | 183 | 217.907 | 84.570 | 192.612 | 1.00 | 86.67 | C |
| ATOM | 1029 | CB  | ALA | A | 183 | 217.006 | 83.691 | 193.480 | 1.00 | 82.75 | C |
| ATOM | 1030 | C   | ALA | A | 183 | 218.970 | 83.710 | 191.924 | 1.00 | 88.25 | C |
| ATOM | 1031 | O   | ALA | A | 183 | 218.683 | 82.841 | 191.110 | 1.00 | 87.52 | O |
| ATOM | 1032 | N   | HIS | A | 184 | 220.241 | 84.008 | 192.248 | 1.00 | 80.72 | N |
| ATOM | 1033 | CA  | HIS | A | 184 | 221.331 | 83.245 | 191.654 | 1.00 | 76.94 | C |
| ATOM | 1034 | CB  | HIS | A | 184 | 222.652 | 83.872 | 192.102 | 1.00 | 71.67 | C |
| ATOM | 1035 | CG  | HIS | A | 184 | 223.777 | 83.319 | 191.264 | 1.00 | 61.47 | C |
| ATOM | 1036 | ND1 | HIS | A | 184 | 224.599 | 84.095 | 190.515 | 1.00 | 83.49 | N |
| ATOM | 1037 | CE1 | HIS | A | 184 | 225.456 | 83.245 | 189.918 | 1.00 | 77.60 | C |
| ATOM | 1038 | NE2 | HIS | A | 184 | 225.215 | 81.974 | 190.250 | 1.00 | 94.64 | N |
| ATOM | 1039 | CD2 | HIS | A | 184 | 224.158 | 81.983 | 191.101 | 1.00 | 84.93 | C |
| ATOM | 1040 | C   | HIS | A | 184 | 221.282 | 81.775 | 192.077 | 1.00 | 80.75 | C |
| ATOM | 1041 | O   | HIS | A | 184 | 221.411 | 80.858 | 191.277 | 1.00 | 72.26 | O |

FIG. 3A-19

| ATOM | 1042 | N   | ARG | A | 185 | 221.128 | 81.570 | 193.401 | 1.00 | 76.53  | N |
|------|------|-----|-----|---|-----|---------|--------|---------|------|--------|---|
| ATOM | 1043 | CA  | ARG | A | 185 | 221.070 | 80.207 | 193.915 | 1.00 | 77.64  | C |
| ATOM | 1044 | CB  | ARG | A | 185 | 219.805 | 79.546 | 193.368 | 1.00 | 60.05  | C |
| ATOM | 1045 | CG  | ARG | A | 185 | 218.538 | 80.313 | 193.747 | 1.00 | 69.87  | C |
| ATOM | 1046 | CD  | ARG | A | 185 | 217.293 | 79.421 | 193.714 | 1.00 | 88.79  | C |
| ATOM | 1047 | NE  | ARG | A | 185 | 216.984 | 79.018 | 192.339 | 1.00 | 74.62  | N |
| ATOM | 1048 | CZ  | ARG | A | 185 | 216.704 | 77.720 | 192.125 | 1.00 | 102.74 | C |
| ATOM | 1049 | NH1 | ARG | A | 185 | 216.704 | 76.865 | 193.132 | 1.00 | 105.16 | N |
| ATOM | 1050 | NH2 | ARG | A | 185 | 216.428 | 77.299 | 190.884 | 1.00 | 124.15 | N |
| ATOM | 1051 | C   | ARG | A | 185 | 222.301 | 79.398 | 193.501 | 1.00 | 85.59  | C |
| ATOM | 1052 | O   | ARG | A | 185 | 222.247 | 78.190 | 193.308 | 1.00 | 76.00  | O |
| ATOM | 1053 | N   | ASP | A | 186 | 223.476 | 80.000 | 193.397 | 1.00 | 85.17  | N |
| ATOM | 1054 | CA  | ASP | A | 186 | 224.677 | 79.238 | 193.128 | 1.00 | 65.94  | C |
| ATOM | 1055 | CB  | ASP | A | 186 | 224.651 | 78.670 | 191.712 | 1.00 | 64.22  | C |
| ATOM | 1056 | CG  | ASP | A | 186 | 225.560 | 77.461 | 191.555 | 1.00 | 69.83  | C |
| ATOM | 1057 | OD1 | ASP | A | 186 | 225.629 | 76.654 | 192.503 | 1.00 | 114.36 | O |
| ATOM | 1058 | OD2 | ASP | A | 186 | 226.197 | 77.304 | 190.492 | 1.00 | 103.36 | O |
| ATOM | 1059 | C   | ASP | A | 186 | 225.857 | 80.161 | 193.327 | 1.00 | 63.69  | C |
| ATOM | 1060 | O   | ASP | A | 186 | 226.821 | 80.122 | 192.573 | 1.00 | 76.80  | O |
| ATOM | 1061 | N   | VAL | A | 187 | 225.757 | 80.991 | 194.364 | 1.00 | 65.08  | N |
| ATOM | 1062 | CA  | VAL | A | 187 | 226.794 | 81.952 | 194.717 | 1.00 | 62.87  | C |
| ATOM | 1063 | CB  | VAL | A | 187 | 226.218 | 83.132 | 195.539 | 1.00 | 56.36  | C |
| ATOM | 1064 | CG1 | VAL | A | 187 | 227.311 | 84.156 | 195.831 | 1.00 | 45.04  | C |
| ATOM | 1065 | CG2 | VAL | A | 187 | 225.099 | 83.791 | 194.774 | 1.00 | 49.15  | C |
| ATOM | 1066 | C   | VAL | A | 187 | 227.923 | 81.305 | 195.507 | 1.00 | 61.46  | C |
| ATOM | 1067 | O   | VAL | A | 187 | 228.134 | 81.605 | 196.677 | 1.00 | 76.23  | O |
| ATOM | 1068 | N   | LYS | A | 188 | 228.644 | 80.407 | 194.852 | 1.00 | 71.26  | N |
| ATOM | 1069 | CA  | LYS | A | 188 | 229.766 | 79.731 | 195.482 | 1.00 | 71.74  | C |
| ATOM | 1070 | CB  | LYS | A | 188 | 229.770 | 78.246 | 195.123 | 1.00 | 59.58  | C |
| ATOM | 1071 | CG  | LYS | A | 188 | 229.709 | 77.962 | 193.639 | 1.00 | 61.04  | C |
| ATOM | 1072 | CD  | LYS | A | 188 | 228.939 | 76.679 | 193.367 | 1.00 | 96.00  | C |
| ATOM | 1073 | CE  | LYS | A | 188 | 228.669 | 76.509 | 191.869 | 1.00 | 141.45 | C |
| ATOM | 1074 | NZ  | LYS | A | 188 | 227.746 | 75.371 | 191.579 | 1.00 | 122.86 | N |
| ATOM | 1075 | C   | LYS | A | 188 | 231.033 | 80.392 | 194.985 | 1.00 | 71.11  | C |
| ATOM | 1076 | O   | LYS | A | 188 | 231.049 | 80.975 | 193.905 | 1.00 | 76.85  | O |
| ATOM | 1077 | N   | PRO | A | 189 | 232.115 | 80.318 | 195.776 | 1.00 | 66.86  | N |
| ATOM | 1078 | CA  | PRO | A | 189 | 233.409 | 80.911 | 195.433 | 1.00 | 82.94  | C |
| ATOM | 1079 | CB  | PRO | A | 189 | 234.359 | 80.199 | 196.381 | 1.00 | 77.38  | C |
| ATOM | 1080 | CG  | PRO | A | 189 | 233.511 | 80.063 | 197.620 | 1.00 | 79.38  | C |
| ATOM | 1081 | CD  | PRO | A | 189 | 232.197 | 79.582 | 197.049 | 1.00 | 84.38  | C |
| ATOM | 1082 | C   | PRO | A | 189 | 233.746 | 80.698 | 193.967 | 1.00 | 81.19  | C |
| ATOM | 1083 | O   | PRO | A | 189 | 233.989 | 81.641 | 193.231 | 1.00 | 92.51  | O |
| ATOM | 1084 | N   | GLU | A | 190 | 233.743 | 79.447 | 193.553 | 1.00 | 79.12  | N |
| ATOM | 1085 | CA  | GLU | A | 190 | 234.019 | 79.080 | 192.178 | 1.00 | 82.41  | C |
| ATOM | 1086 | CB  | GLU | A | 190 | 233.432 | 77.689 | 191.920 | 1.00 | 94.71  | C |
| ATOM | 1087 | CG  | GLU | A | 190 | 233.784 | 76.609 | 192.978 | 1.00 | 121.01 | C |
| ATOM | 1088 | CD  | GLU | A | 190 | 233.527 | 77.030 | 194.444 | 1.00 | 135.59 | C |
| ATOM | 1089 | OE1 | GLU | A | 190 | 232.488 | 77.674 | 194.727 | 1.00 | 113.86 | O |
| ATOM | 1090 | OE2 | GLU | A | 190 | 234.363 | 76.700 | 195.321 | 1.00 | 133.59 | O |
| ATOM | 1091 | C   | GLU | A | 190 | 233.441 | 80.092 | 191.159 | 1.00 | 81.32  | C |
| ATOM | 1092 | O   | GLU | A | 190 | 234.121 | 80.487 | 190.213 | 1.00 | 102.09 | O |
| ATOM | 1093 | N   | ASN | A | 191 | 232.196 | 80.527 | 191.350 | 1.00 | 80.04  | N |
| ATOM | 1094 | CA  | ASN | A | 191 | 231.584 | 81.457 | 190.405 | 1.00 | 59.50  | C |
| ATOM | 1095 | CB  | ASN | A | 191 | 230.068 | 81.364 | 190.471 | 1.00 | 59.13  | C |
| ATOM | 1096 | CG  | ASN | A | 191 | 229.566 | 79.975 | 190.189 | 1.00 | 57.02  | C |

FIG. 3A-20

| ATOM | 1097 | OD1 | ASN | A | 191 | 228.797 | 79.413 | 190.959 | 1.00 | 107.48 | O |
|---|---|---|---|---|---|---|---|---|---|---|---|
| ATOM | 1098 | ND2 | ASN | A | 191 | 230.005 | 79.406 | 189.077 | 1.00 | 62.85 | N |
| ATOM | 1099 | C | ASN | A | 191 | 231.991 | 82.905 | 190.569 | 1.00 | 72.63 | C |
| ATOM | 1100 | O | ASN | A | 191 | 231.360 | 83.796 | 189.998 | 1.00 | 60.72 | O |
| ATOM | 1101 | N | LEU | A | 192 | 233.042 | 83.149 | 191.342 | 1.00 | 64.74 | N |
| ATOM | 1102 | CA | LEU | A | 192 | 233.524 | 84.514 | 191.552 | 1.00 | 58.75 | C |
| ATOM | 1103 | CB | LEU | A | 192 | 233.512 | 84.856 | 193.047 | 1.00 | 64.92 | C |
| ATOM | 1104 | CG | LEU | A | 192 | 232.127 | 84.840 | 193.709 | 1.00 | 76.84 | C |
| ATOM | 1105 | CD1 | LEU | A | 192 | 232.285 | 84.706 | 195.207 | 1.00 | 63.79 | C |
| ATOM | 1106 | CD2 | LEU | A | 192 | 231.350 | 86.108 | 193.349 | 1.00 | 49.09 | C |
| ATOM | 1107 | C | LEU | A | 192 | 234.931 | 84.655 | 190.987 | 1.00 | 67.25 | C |
| ATOM | 1108 | O | LEU | A | 192 | 235.906 | 84.314 | 191.644 | 1.00 | 63.30 | O |
| ATOM | 1109 | N | LEU | A | 193 | 235.022 | 85.173 | 189.767 | 1.00 | 76.60 | N |
| ATOM | 1110 | CA | LEU | A | 193 | 236.299 | 85.334 | 189.077 | 1.00 | 68.12 | C |
| ATOM | 1111 | CB | LEU | A | 193 | 236.165 | 84.801 | 187.657 | 1.00 | 57.38 | C |
| ATOM | 1112 | CG | LEU | A | 193 | 235.346 | 83.517 | 187.573 | 1.00 | 67.03 | C |
| ATOM | 1113 | CD1 | LEU | A | 193 | 235.242 | 83.061 | 186.137 | 1.00 | 74.99 | C |
| ATOM | 1114 | CD2 | LEU | A | 193 | 235.985 | 82.449 | 188.445 | 1.00 | 80.12 | C |
| ATOM | 1115 | C | LEU | A | 193 | 236.765 | 86.779 | 189.008 | 1.00 | 67.18 | C |
| ATOM | 1116 | O | LEU | A | 193 | 235.957 | 87.700 | 189.001 | 1.00 | 70.12 | O |
| ATOM | 1117 | N | TYR | A | 194 | 238.073 | 86.982 | 188.950 | 1.00 | 66.38 | N |
| ATOM | 1118 | CA | TYR | A | 194 | 238.603 | 88.333 | 188.846 | 1.00 | 70.20 | C |
| ATOM | 1119 | CB | TYR | A | 194 | 239.903 | 88.449 | 189.636 | 1.00 | 71.53 | C |
| ATOM | 1120 | CG | TYR | A | 194 | 239.692 | 88.807 | 191.085 | 1.00 | 83.55 | C |
| ATOM | 1121 | CD1 | TYR | A | 194 | 239.221 | 90.068 | 191.446 | 1.00 | 60.55 | C |
| ATOM | 1122 | CE1 | TYR | A | 194 | 239.026 | 90.402 | 192.766 | 1.00 | 77.54 | C |
| ATOM | 1123 | CZ | TYR | A | 194 | 239.300 | 89.472 | 193.749 | 1.00 | 80.69 | C |
| ATOM | 1124 | OH | TYR | A | 194 | 239.118 | 89.812 | 195.068 | 1.00 | 97.12 | O |
| ATOM | 1125 | CE2 | TYR | A | 194 | 239.764 | 88.216 | 193.423 | 1.00 | 72.23 | C |
| ATOM | 1126 | CD2 | TYR | A | 194 | 239.959 | 87.889 | 192.095 | 1.00 | 54.69 | C |
| ATOM | 1127 | C | TYR | A | 194 | 238.833 | 88.697 | 187.382 | 1.00 | 65.05 | C |
| ATOM | 1128 | O | TYR | A | 194 | 239.219 | 87.856 | 186.578 | 1.00 | 55.59 | O |
| ATOM | 1129 | N | THR | A | 195 | 238.585 | 89.952 | 187.035 | 1.00 | 56.71 | N |
| ATOM | 1130 | CA | THR | A | 195 | 238.754 | 90.389 | 185.660 | 1.00 | 63.48 | C |
| ATOM | 1131 | CB | THR | A | 195 | 238.334 | 91.865 | 185.494 | 1.00 | 66.82 | C |
| ATOM | 1132 | OG1 | THR | A | 195 | 239.028 | 92.668 | 186.452 | 1.00 | 70.80 | O |
| ATOM | 1133 | CG2 | THR | A | 195 | 236.829 | 92.022 | 185.688 | 1.00 | 54.17 | C |
| ATOM | 1134 | C | THR | A | 195 | 240.193 | 90.206 | 185.176 | 1.00 | 82.40 | C |
| ATOM | 1135 | O | THR | A | 195 | 240.436 | 89.542 | 184.164 | 1.00 | 96.10 | O |
| ATOM | 1136 | N | SER | A | 196 | 241.145 | 90.790 | 185.897 | 1.00 | 84.27 | N |
| ATOM | 1137 | CA | SER | A | 196 | 242.552 | 90.672 | 185.532 | 1.00 | 77.62 | C |
| ATOM | 1138 | CB | SER | A | 196 | 243.089 | 92.019 | 185.033 | 1.00 | 78.67 | C |
| ATOM | 1139 | OG | SER | A | 196 | 243.063 | 92.995 | 186.055 | 1.00 | 92.46 | O |
| ATOM | 1140 | C | SER | A | 196 | 243.388 | 90.202 | 186.716 | 1.00 | 88.08 | C |
| ATOM | 1141 | O | SER | A | 196 | 242.865 | 89.980 | 187.805 | 1.00 | 101.07 | O |
| ATOM | 1142 | N | ALA | A | 197 | 244.688 | 90.038 | 186.490 | 1.00 | 106.23 | N |
| ATOM | 1143 | CA | ALA | A | 197 | 245.601 | 89.609 | 187.542 | 1.00 | 100.72 | C |
| ATOM | 1144 | CB | ALA | A | 197 | 246.792 | 88.882 | 186.936 | 1.00 | 90.18 | C |
| ATOM | 1145 | C | ALA | A | 197 | 246.055 | 90.885 | 188.230 | 1.00 | 93.19 | C |
| ATOM | 1146 | O | ALA | A | 197 | 246.509 | 90.870 | 189.373 | 1.00 | 91.43 | O |
| ATOM | 1147 | N | ARG | A | 198 | 245.911 | 91.985 | 187.500 | 1.00 | 76.02 | N |
| ATOM | 1148 | CA | ARG | A | 198 | 246.275 | 93.318 | 187.959 | 1.00 | 111.08 | C |
| ATOM | 1149 | CB | ARG | A | 198 | 245.582 | 94.345 | 187.048 | 1.00 | 118.16 | C |
| ATOM | 1150 | CG | ARG | A | 198 | 246.321 | 95.666 | 186.798 | 1.00 | 144.07 | C |
| ATOM | 1151 | CD | ARG | A | 198 | 245.911 | 96.211 | 185.435 | 1.00 | 152.31 | C |

FIG. 3A-21

| ATOM | 1152 | NE | ARG | A | 198 | 246.262 | 97.611 | 185.210 | 1.00 | 171.50 | N |
| ATOM | 1153 | CZ | ARG | A | 198 | 245.920 | 98.290 | 184.115 | 1.00 | 162.32 | C |
| ATOM | 1154 | NH1 | ARG | A | 198 | 245.223 | 97.692 | 183.152 | 1.00 | 96.38 | N |
| ATOM | 1155 | NH2 | ARG | A | 198 | 246.265 | 99.565 | 183.984 | 1.00 | 146.82 | N |
| ATOM | 1156 | C | ARG | A | 198 | 245.815 | 93.469 | 189.412 | 1.00 | 105.33 | C |
| ATOM | 1157 | O | ARG | A | 198 | 244.993 | 92.696 | 189.885 | 1.00 | 104.59 | O |
| ATOM | 1158 | N | PRO | A | 199 | 246.347 | 94.461 | 190.144 | 1.00 | 115.43 | N |
| ATOM | 1159 | CA | PRO | A | 199 | 245.943 | 94.653 | 191.545 | 1.00 | 123.33 | C |
| ATOM | 1160 | CB | PRO | A | 199 | 247.061 | 95.524 | 192.105 | 1.00 | 121.70 | C |
| ATOM | 1161 | CG | PRO | A | 199 | 247.387 | 96.397 | 190.921 | 1.00 | 133.24 | C |
| ATOM | 1162 | CD | PRO | A | 199 | 247.411 | 95.409 | 189.775 | 1.00 | 125.16 | C |
| ATOM | 1163 | C | PRO | A | 199 | 244.581 | 95.315 | 191.719 | 1.00 | 123.60 | C |
| ATOM | 1164 | O | PRO | A | 199 | 243.991 | 95.259 | 192.794 | 1.00 | 135.30 | O |
| ATOM | 1165 | N | ALA | A | 200 | 244.090 | 95.943 | 190.656 | 1.00 | 122.57 | N |
| ATOM | 1166 | CA | ALA | A | 200 | 242.810 | 96.629 | 190.719 | 1.00 | 108.91 | C |
| ATOM | 1167 | CB | ALA | A | 200 | 242.923 | 98.019 | 190.090 | 1.00 | 118.71 | C |
| ATOM | 1168 | C | ALA | A | 200 | 241.726 | 95.826 | 190.023 | 1.00 | 95.83 | C |
| ATOM | 1169 | O | ALA | A | 200 | 240.606 | 96.310 | 189.835 | 1.00 | 73.96 | O |
| ATOM | 1170 | N | ALA | A | 201 | 242.059 | 94.598 | 189.637 | 1.00 | 75.18 | N |
| ATOM | 1171 | CA | ALA | A | 201 | 241.093 | 93.725 | 188.979 | 1.00 | 84.90 | C |
| ATOM | 1172 | CB | ALA | A | 201 | 241.579 | 92.278 | 189.022 | 1.00 | 81.83 | C |
| ATOM | 1173 | C | ALA | A | 201 | 239.789 | 93.860 | 189.751 | 1.00 | 91.91 | C |
| ATOM | 1174 | O | ALA | A | 201 | 239.800 | 94.214 | 190.929 | 1.00 | 89.51 | O |
| ATOM | 1175 | N | ILE | A | 202 | 238.660 | 93.607 | 189.097 | 1.00 | 78.80 | N |
| ATOM | 1176 | CA | ILE | A | 202 | 237.378 | 93.698 | 189.795 | 1.00 | 91.70 | C |
| ATOM | 1177 | CB | ILE | A | 202 | 236.454 | 94.707 | 189.121 | 1.00 | 76.30 | C |
| ATOM | 1178 | CG1 | ILE | A | 202 | 235.623 | 94.029 | 188.059 | 1.00 | 78.45 | C |
| ATOM | 1179 | CD1 | ILE | A | 202 | 234.681 | 94.991 | 187.390 | 1.00 | 169.28 | C |
| ATOM | 1180 | CG2 | ILE | A | 202 | 237.278 | 95.772 | 188.468 | 1.00 | 61.72 | C |
| ATOM | 1181 | C | ILE | A | 202 | 236.697 | 92.326 | 189.886 | 1.00 | 95.28 | C |
| ATOM | 1182 | O | ILE | A | 202 | 236.837 | 91.488 | 188.995 | 1.00 | 88.21 | O |
| ATOM | 1183 | N | LEU | A | 203 | 235.975 | 92.102 | 190.981 | 1.00 | 93.25 | N |
| ATOM | 1184 | CA | LEU | A | 203 | 235.308 | 90.821 | 191.231 | 1.00 | 66.28 | C |
| ATOM | 1185 | CB | LEU | A | 203 | 235.195 | 90.599 | 192.745 | 1.00 | 73.90 | C |
| ATOM | 1186 | CG | LEU | A | 203 | 234.947 | 89.189 | 193.273 | 1.00 | 52.16 | C |
| ATOM | 1187 | CD1 | LEU | A | 203 | 236.016 | 88.244 | 192.783 | 1.00 | 61.94 | C |
| ATOM | 1188 | CD2 | LEU | A | 203 | 234.956 | 89.228 | 194.779 | 1.00 | 85.31 | C |
| ATOM | 1189 | C | LEU | A | 203 | 233.935 | 90.746 | 190.587 | 1.00 | 67.61 | C |
| ATOM | 1190 | O | LEU | A | 203 | 233.137 | 91.681 | 190.695 | 1.00 | 68.70 | O |
| ATOM | 1191 | N | LYS | A | 204 | 233.665 | 89.628 | 189.919 | 1.00 | 58.34 | N |
| ATOM | 1192 | CA | LYS | A | 204 | 232.392 | 89.434 | 189.243 | 1.00 | 58.89 | C |
| ATOM | 1193 | CB | LYS | A | 204 | 232.540 | 89.740 | 187.750 | 1.00 | 68.02 | C |
| ATOM | 1194 | CG | LYS | A | 204 | 232.844 | 91.199 | 187.461 | 1.00 | 64.40 | C |
| ATOM | 1195 | CD | LYS | A | 204 | 232.603 | 91.552 | 186.008 | 1.00 | 62.63 | C |
| ATOM | 1196 | CE | LYS | A | 204 | 232.786 | 93.033 | 185.788 | 1.00 | 71.16 | C |
| ATOM | 1197 | NZ | LYS | A | 204 | 232.247 | 93.468 | 184.487 | 1.00 | 94.63 | N |
| ATOM | 1198 | C | LYS | A | 204 | 231.788 | 88.047 | 189.423 | 1.00 | 73.88 | C |
| ATOM | 1199 | O | LYS | A | 204 | 232.490 | 87.027 | 189.406 | 1.00 | 67.59 | O |
| ATOM | 1200 | N | LEU | A | 205 | 230.472 | 88.023 | 189.586 | 1.00 | 66.05 | N |
| ATOM | 1201 | CA | LEU | A | 205 | 229.750 | 86.781 | 189.782 | 1.00 | 63.28 | C |
| ATOM | 1202 | CB | LEU | A | 205 | 228.540 | 87.024 | 190.680 | 1.00 | 64.69 | C |
| ATOM | 1203 | CG | LEU | A | 205 | 227.514 | 85.905 | 190.813 | 1.00 | 47.19 | C |
| ATOM | 1204 | CD1 | LEU | A | 205 | 228.150 | 84.657 | 191.394 | 1.00 | 81.96 | C |
| ATOM | 1205 | CD2 | LEU | A | 205 | 226.397 | 86.387 | 191.695 | 1.00 | 64.88 | C |
| ATOM | 1206 | C | LEU | A | 205 | 229.296 | 86.241 | 188.452 | 1.00 | 53.73 | C |

FIG. 3A-22

| ATOM | 1207 | O | LEU | A | 205 | 228.884 | 87.001 | 187.583 | 1.00 | 55.72 | O |
|---|---|---|---|---|---|---|---|---|---|---|---|
| ATOM | 1208 | N | THR | A | 206 | 229.374 | 84.926 | 188.300 | 1.00 | 53.81 | N |
| ATOM | 1209 | CA | THR | A | 206 | 228.976 | 84.363 | 187.015 | 1.00 | 65.26 | C |
| ATOM | 1210 | CB | THR | A | 206 | 230.241 | 84.083 | 186.203 | 1.00 | 61.13 | C |
| ATOM | 1211 | OG1 | THR | A | 206 | 230.968 | 83.019 | 186.821 | 1.00 | 57.86 | O |
| ATOM | 1212 | CG2 | THR | A | 206 | 231.129 | 85.331 | 186.165 | 1.00 | 74.17 | C |
| ATOM | 1213 | C | THR | A | 206 | 228.175 | 83.071 | 187.188 | 1.00 | 53.82 | C |
| ATOM | 1214 | O | THR | A | 206 | 227.988 | 82.556 | 188.283 | 1.00 | 71.37 | O |
| ATOM | 1215 | N | ASP | A | 207 | 227.657 | 82.569 | 186.051 | 1.00 | 79.42 | N |
| ATOM | 1216 | CA | ASP | A | 207 | 226.909 | 81.318 | 186.086 | 1.00 | 59.92 | C |
| ATOM | 1217 | CB | ASP | A | 207 | 227.599 | 80.372 | 187.069 | 1.00 | 60.66 | C |
| ATOM | 1218 | CG | ASP | A | 207 | 227.153 | 78.944 | 186.787 | 1.00 | 80.61 | C |
| ATOM | 1219 | OD1 | ASP | A | 207 | 226.302 | 78.773 | 185.913 | 1.00 | 83.40 | O |
| ATOM | 1220 | OD2 | ASP | A | 207 | 227.653 | 78.029 | 187.436 | 1.00 | 77.29 | O |
| ATOM | 1221 | C | ASP | A | 207 | 225.453 | 81.534 | 186.504 | 1.00 | 58.53 | C |
| ATOM | 1222 | O | ASP | A | 207 | 225.143 | 81.930 | 187.620 | 1.00 | 80.39 | O |
| ATOM | 1223 | N | PHE | A | 208 | 224.545 | 81.298 | 185.539 | 1.00 | 57.58 | N |
| ATOM | 1224 | CA | PHE | A | 208 | 223.124 | 81.428 | 185.838 | 1.00 | 65.42 | C |
| ATOM | 1225 | CB | PHE | A | 208 | 222.547 | 82.534 | 184.954 | 1.00 | 41.42 | C |
| ATOM | 1226 | CG | PHE | A | 208 | 222.872 | 83.876 | 185.540 | 1.00 | 55.64 | C |
| ATOM | 1227 | CD1 | PHE | A | 208 | 224.196 | 84.290 | 185.613 | 1.00 | 30.42 | C |
| ATOM | 1228 | CE1 | PHE | A | 208 | 224.499 | 85.545 | 186.122 | 1.00 | 68.91 | C |
| ATOM | 1229 | CZ | PHE | A | 208 | 223.486 | 86.389 | 186.558 | 1.00 | 56.42 | C |
| ATOM | 1230 | CE2 | PHE | A | 208 | 222.165 | 85.964 | 186.486 | 1.00 | 47.56 | C |
| ATOM | 1231 | CD2 | PHE | A | 208 | 221.853 | 84.706 | 185.978 | 1.00 | 49.87 | C |
| ATOM | 1232 | C | PHE | A | 208 | 222.380 | 80.116 | 185.581 | 1.00 | 55.77 | C |
| ATOM | 1233 | O | PHE | A | 208 | 221.168 | 80.082 | 185.411 | 1.00 | 71.33 | O |
| ATOM | 1234 | N | GLYA | | 209 | 223.139 | 79.032 | 185.556 | 1.00 | 61.07 | N |
| ATOM | 1235 | CA | GLYA | | 209 | 222.547 | 77.727 | 185.313 | 1.00 | 72.68 | C |
| ATOM | 1236 | C | GLYA | | 209 | 221.409 | 77.412 | 186.261 | 1.00 | 73.62 | C |
| ATOM | 1237 | O | GLYA | | 209 | 220.608 | 76.525 | 185.988 | 1.00 | 77.98 | O |
| ATOM | 1238 | N | PHE | A | 210 | 221.352 | 78.128 | 187.382 | 1.00 | 83.69 | N |
| ATOM | 1239 | CA | PHE | A | 210 | 220.290 | 77.940 | 188.362 | 1.00 | 69.57 | C |
| ATOM | 1240 | CB | PHE | A | 210 | 220.841 | 77.442 | 189.694 | 1.00 | 67.31 | C |
| ATOM | 1241 | CG | PHE | A | 210 | 221.563 | 76.143 | 189.608 | 1.00 | 73.06 | C |
| ATOM | 1242 | CD1 | PHE | A | 210 | 220.948 | 75.034 | 189.064 | 1.00 | 114.78 | C |
| ATOM | 1243 | CE1 | PHE | A | 210 | 221.599 | 73.816 | 189.010 | 1.00 | 109.98 | C |
| ATOM | 1244 | CZ | PHE | A | 210 | 222.883 | 73.702 | 189.504 | 1.00 | 132.84 | C |
| ATOM | 1245 | CE2 | PHE | A | 210 | 223.512 | 74.806 | 190.050 | 1.00 | 108.27 | C |
| ATOM | 1246 | CD2 | PHE | A | 210 | 222.851 | 76.019 | 190.099 | 1.00 | 90.32 | C |
| ATOM | 1247 | C | PHE | A | 210 | 219.538 | 79.240 | 188.621 | 1.00 | 81.37 | C |
| ATOM | 1248 | O | PHE | A | 210 | 218.671 | 79.281 | 189.485 | 1.00 | 58.29 | O |
| ATOM | 1249 | N | ALA | A | 211 | 219.886 | 80.302 | 187.897 | 1.00 | 81.89 | N |
| ATOM | 1250 | CA | ALA | A | 211 | 219.212 | 81.589 | 188.060 | 1.00 | 69.02 | C |
| ATOM | 1251 | CB | ALA | A | 211 | 219.636 | 82.550 | 186.968 | 1.00 | 73.43 | C |
| ATOM | 1252 | C | ALA | A | 211 | 217.727 | 81.332 | 187.960 | 1.00 | 58.89 | C |
| ATOM | 1253 | O | ALA | A | 211 | 217.302 | 80.474 | 187.198 | 1.00 | 66.98 | O |
| ATOM | 1254 | N | LYS | A | 212 | 216.934 | 82.068 | 188.724 | 1.00 | 66.85 | N |
| ATOM | 1255 | CA | LYS | A | 212 | 215.497 | 81.865 | 188.688 | 1.00 | 74.67 | C |
| ATOM | 1256 | CB | LYS | A | 212 | 215.120 | 80.722 | 189.638 | 1.00 | 70.15 | C |
| ATOM | 1257 | CG | LYS | A | 212 | 213.648 | 80.362 | 189.598 | 1.00 | 104.51 | C |
| ATOM | 1258 | CD | LYS | A | 212 | 213.266 | 79.331 | 190.660 | 1.00 | 157.53 | C |
| ATOM | 1259 | CE | LYS | A | 212 | 211.736 | 79.184 | 190.773 | 1.00 | 119.37 | C |
| ATOM | 1260 | NZ | LYS | A | 212 | 211.330 | 78.105 | 191.715 | 1.00 | 93.54 | N |
| ATOM | 1261 | C | LYS | A | 212 | 214.704 | 83.123 | 189.034 | 1.00 | 69.94 | C |

FIG. 3A-23

| ATOM | 1262 | O | LYS | A | 212 | 215.037 | 83.845 | 189.978 | 1.00 | 68.45 | O |
| --- | --- | --- | --- | --- | --- | --- | --- | --- | --- | --- | --- |
| ATOM | 1263 | N | GLU | A | 213 | 213.659 | 83.376 | 188.250 | 1.00 | 52.90 | N |
| ATOM | 1264 | CA | GLU | A | 213 | 212.688 | 84.446 | 188.476 | 1.00 | 53.07 | C |
| ATOM | 1265 | CB | GLU | A | 213 | 211.816 | 84.590 | 187.225 | 1.00 | 70.72 | C |
| ATOM | 1266 | CG | GLU | A | 213 | 211.589 | 86.052 | 186.851 | 1.00 | 92.25 | C |
| ATOM | 1267 | CD | GLU | A | 213 | 210.774 | 86.136 | 185.579 | 1.00 | 152.81 | C |
| ATOM | 1268 | OE1 | GLU | A | 213 | 211.143 | 85.485 | 184.613 | 1.00 | 137.21 | O |
| ATOM | 1269 | OE2 | GLU | A | 213 | 209.804 | 86.888 | 185.551 | 1.00 | 179.15 | O |
| ATOM | 1270 | C | GLU | A | 213 | 211.803 | 84.165 | 189.693 | 1.00 | 74.84 | C |
| ATOM | 1271 | O | GLU | A | 213 | 211.208 | 83.109 | 189.838 | 1.00 | 77.86 | O |
| ATOM | 1272 | N | THR | A | 214 | 211.753 | 85.162 | 190.590 | 1.00 | 74.12 | N |
| ATOM | 1273 | CA | THR | A | 214 | 211.087 | 84.945 | 191.872 | 1.00 | 73.32 | C |
| ATOM | 1274 | CB | THR | A | 214 | 211.904 | 85.675 | 192.944 | 1.00 | 76.21 | C |
| ATOM | 1275 | OG1 | THR | A | 214 | 211.900 | 87.072 | 192.647 | 1.00 | 75.06 | O |
| ATOM | 1276 | CG2 | THR | A | 214 | 213.355 | 85.188 | 192.940 | 1.00 | 84.21 | C |
| ATOM | 1277 | C | THR | A | 214 | 209.656 | 85.489 | 191.886 | 1.00 | 91.51 | C |
| ATOM | 1278 | O | THR | A | 214 | 208.900 | 85.288 | 192.836 | 1.00 | 84.09 | O |
| ATOM | 1279 | N | THR | A | 215 | 209.290 | 86.223 | 190.815 | 1.00 | 103.67 | N |
| ATOM | 1280 | CA | THR | A | 215 | 208.070 | 87.015 | 190.911 | 1.00 | 117.08 | C |
| ATOM | 1281 | CB | THR | A | 215 | 208.481 | 88.480 | 191.049 | 1.00 | 121.50 | C |
| ATOM | 1282 | OG1 | THR | A | 215 | 208.568 | 89.063 | 189.752 | 1.00 | 147.96 | O |
| ATOM | 1283 | CG2 | THR | A | 215 | 209.858 | 88.576 | 191.719 | 1.00 | 141.58 | C |
| ATOM | 1284 | C | THR | A | 215 | 207.090 | 86.849 | 189.731 | 1.00 | 132.47 | C |
| ATOM | 1285 | O | THR | A | 215 | 207.331 | 87.277 | 188.609 | 1.00 | 126.69 | O |
| ATOM | 1286 | N | SER | A | 216 | 205.961 | 86.157 | 190.016 | 1.00 | 158.51 | N |
| ATOM | 1287 | CA | SER | A | 216 | 204.753 | 86.381 | 189.216 | 1.00 | 179.90 | C |
| ATOM | 1288 | CB | SER | A | 216 | 204.743 | 87.849 | 188.787 | 1.00 | 182.30 | C |
| ATOM | 1289 | OG | SER | A | 216 | 203.419 | 88.370 | 188.903 | 1.00 | 180.54 | O |
| ATOM | 1290 | C | SER | A | 216 | 204.609 | 85.474 | 187.986 | 1.00 | 187.54 | C |
| ATOM | 1291 | O | SER | A | 216 | 205.573 | 84.989 | 187.407 | 1.00 | 190.38 | O |
| ATOM | 1292 | N | HIS | A | 217 | 203.321 | 85.231 | 187.632 | 1.00 | 196.43 | N |
| ATOM | 1293 | CA | HIS | A | 217 | 202.986 | 84.503 | 186.407 | 1.00 | 199.51 | C |
| ATOM | 1294 | CB | HIS | A | 217 | 202.164 | 83.261 | 186.788 | 1.00 | 203.06 | C |
| ATOM | 1295 | CG | HIS | A | 217 | 201.036 | 83.051 | 185.796 | 1.00 | 202.54 | C |
| ATOM | 1296 | ND1 | HIS | A | 217 | 199.724 | 83.206 | 186.115 | 1.00 | 209.62 | N |
| ATOM | 1297 | CE1 | HIS | A | 217 | 199.041 | 83.002 | 184.971 | 1.00 | 218.59 | C |
| ATOM | 1298 | NE2 | HIS | A | 217 | 199.850 | 82.721 | 183.948 | 1.00 | 213.16 | N |
| ATOM | 1299 | CD2 | HIS | A | 217 | 201.121 | 82.740 | 184.432 | 1.00 | 198.21 | C |
| ATOM | 1300 | C | HIS | A | 217 | 202.173 | 85.381 | 185.456 | 1.00 | 200.36 | C |
| ATOM | 1301 | O | HIS | A | 217 | 201.281 | 86.113 | 185.863 | 1.00 | 198.75 | O |
| ATOM | 1302 | N | PRO | A | 227 | 200.093 | 101.757 | 196.180 | 1.00 | 80.66 | N |
| ATOM | 1303 | CA | PRO | A | 227 | 199.610 | 102.177 | 197.501 | 1.00 | 91.16 | C |
| ATOM | 1304 | CB | PRO | A | 227 | 198.615 | 101.079 | 197.871 | 1.00 | 94.28 | C |
| ATOM | 1305 | CG | PRO | A | 227 | 198.095 | 100.647 | 196.537 | 1.00 | 102.33 | C |
| ATOM | 1306 | CD | PRO | A | 227 | 199.356 | 100.570 | 195.721 | 1.00 | 98.69 | C |
| ATOM | 1307 | C | PRO | A | 227 | 200.779 | 102.245 | 198.470 | 1.00 | 90.45 | C |
| ATOM | 1308 | O | PRO | A | 227 | 201.209 | 101.232 | 199.018 | 1.00 | 104.90 | O |
| ATOM | 1309 | N | TYR | A | 228 | 201.286 | 103.451 | 198.674 | 1.00 | 91.57 | N |
| ATOM | 1310 | CA | TYR | A | 228 | 202.437 | 103.675 | 199.536 | 1.00 | 98.53 | C |
| ATOM | 1311 | CB | TYR | A | 228 | 202.624 | 105.177 | 199.768 | 1.00 | 104.50 | C |
| ATOM | 1312 | CG | TYR | A | 228 | 201.647 | 105.749 | 200.759 | 1.00 | 100.42 | C |
| ATOM | 1313 | CD1 | TYR | A | 228 | 201.858 | 105.610 | 202.122 | 1.00 | 88.02 | C |
| ATOM | 1314 | CE1 | TYR | A | 228 | 200.913 | 106.024 | 203.046 | 1.00 | 102.20 | C |
| ATOM | 1315 | CZ | TYR | A | 228 | 199.735 | 106.586 | 202.612 | 1.00 | 124.03 | C |
| ATOM | 1316 | OH | TYR | A | 228 | 198.771 | 106.927 | 203.537 | 1.00 | 117.36 | O |

FIG. 3A-24

| ATOM | 1317 | CE2 | TYR | A | 228 | 199.504 | 106.752 | 201.257 | 1.00 | 142.48 | C |
|------|------|-----|-----|---|-----|---------|---------|---------|------|--------|---|
| ATOM | 1318 | CD2 | TYR | A | 228 | 200.464 | 106.334 | 200.337 | 1.00 | 96.43 | C |
| ATOM | 1319 | C | TYR | A | 228 | 202.339 | 102.969 | 200.883 | 1.00 | 87.42 | C |
| ATOM | 1320 | O | TYR | A | 228 | 203.355 | 102.749 | 201.542 | 1.00 | 95.70 | O |
| ATOM | 1321 | N | TYR | A | 229 | 201.127 | 102.593 | 201.280 | 1.00 | 73.60 | N |
| ATOM | 1322 | CA | TYR | A | 229 | 200.903 | 101.962 | 202.580 | 1.00 | 85.67 | C |
| ATOM | 1323 | CB | TYR | A | 229 | 199.696 | 102.629 | 203.248 | 1.00 | 73.23 | C |
| ATOM | 1324 | CG | TYR | A | 229 | 198.393 | 102.323 | 202.553 | 1.00 | 86.83 | C |
| ATOM | 1325 | CD1 | TYR | A | 229 | 197.748 | 101.111 | 202.750 | 1.00 | 115.70 | C |
| ATOM | 1326 | CE1 | TYR | A | 229 | 196.581 | 100.793 | 202.066 | 1.00 | 137.89 | C |
| ATOM | 1327 | CZ | TYR | A | 229 | 196.047 | 101.694 | 201.168 | 1.00 | 127.06 | C |
| ATOM | 1328 | OH | TYR | A | 229 | 194.889 | 101.381 | 200.477 | 1.00 | 149.86 | O |
| ATOM | 1329 | CE2 | TYR | A | 229 | 196.674 | 102.908 | 200.961 | 1.00 | 124.32 | C |
| ATOM | 1330 | CD2 | TYR | A | 229 | 197.838 | 103.216 | 201.656 | 1.00 | 102.84 | C |
| ATOM | 1331 | C | TYR | A | 229 | 200.710 | 100.443 | 202.602 | 1.00 | 89.04 | C |
| ATOM | 1332 | O | TYR | A | 229 | 200.464 | 99.872 | 203.658 | 1.00 | 98.52 | O |
| ATOM | 1333 | N | VAL | A | 230 | 200.812 | 99.785 | 201.453 | 1.00 | 92.87 | N |
| ATOM | 1334 | CA | VAL | A | 230 | 200.633 | 98.335 | 201.401 | 1.00 | 81.27 | C |
| ATOM | 1335 | CB | VAL | A | 230 | 200.116 | 97.897 | 200.008 | 1.00 | 78.39 | C |
| ATOM | 1336 | CG1 | VAL | A | 230 | 201.070 | 98.367 | 198.917 | 1.00 | 88.77 | C |
| ATOM | 1337 | CG2 | VAL | A | 230 | 199.960 | 96.396 | 199.962 | 1.00 | 93.18 | C |
| ATOM | 1338 | C | VAL | A | 230 | 201.930 | 97.587 | 201.726 | 1.00 | 75.38 | C |
| ATOM | 1339 | O | VAL | A | 230 | 203.016 | 98.069 | 201.442 | 1.00 | 80.47 | O |
| ATOM | 1340 | N | ALA | A | 231 | 201.806 | 96.411 | 202.330 | 1.00 | 74.39 | N |
| ATOM | 1341 | CA | ALA | A | 231 | 202.962 | 95.606 | 202.703 | 1.00 | 71.83 | C |
| ATOM | 1342 | CB | ALA | A | 231 | 202.629 | 94.752 | 203.906 | 1.00 | 75.67 | C |
| ATOM | 1343 | C | ALA | A | 231 | 203.429 | 94.715 | 201.564 | 1.00 | 75.14 | C |
| ATOM | 1344 | O | ALA | A | 231 | 202.628 | 94.232 | 200.767 | 1.00 | 77.29 | O |
| ATOM | 1345 | N | PRO | A | 232 | 204.743 | 94.463 | 201.498 | 1.00 | 80.99 | N |
| ATOM | 1346 | CA | PRO | A | 232 | 205.412 | 93.639 | 200.490 | 1.00 | 79.87 | C |
| ATOM | 1347 | CB | PRO | A | 232 | 206.837 | 93.544 | 201.021 | 1.00 | 77.93 | C |
| ATOM | 1348 | CG | PRO | A | 232 | 206.667 | 93.721 | 202.506 | 1.00 | 73.68 | C |
| ATOM | 1349 | CD | PRO | A | 232 | 205.675 | 94.829 | 202.576 | 1.00 | 75.44 | C |
| ATOM | 1350 | C | PRO | A | 232 | 204.769 | 92.279 | 200.303 | 1.00 | 71.74 | C |
| ATOM | 1351 | O | PRO | A | 232 | 204.797 | 91.706 | 199.222 | 1.00 | 79.81 | O |
| ATOM | 1352 | N | GLU | A | 233 | 204.185 | 91.762 | 201.367 | 1.00 | 78.47 | N |
| ATOM | 1353 | CA | GLU | A | 233 | 203.534 | 90.461 | 201.313 | 1.00 | 77.99 | C |
| ATOM | 1354 | CB | GLU | A | 233 | 203.006 | 90.120 | 202.695 | 1.00 | 67.34 | C |
| ATOM | 1355 | CG | GLU | A | 233 | 203.819 | 90.813 | 203.754 | 1.00 | 79.16 | C |
| ATOM | 1356 | CD | GLU | A | 233 | 203.074 | 91.008 | 205.036 | 1.00 | 86.62 | C |
| ATOM | 1357 | OE1 | GLU | A | 233 | 203.666 | 91.592 | 205.953 | 1.00 | 72.11 | O |
| ATOM | 1358 | OE2 | GLU | A | 233 | 201.905 | 90.581 | 205.133 | 1.00 | 107.24 | O |
| ATOM | 1359 | C | GLU | A | 233 | 202.382 | 90.567 | 200.333 | 1.00 | 77.38 | C |
| ATOM | 1360 | O | GLU | A | 233 | 202.310 | 89.824 | 199.356 | 1.00 | 88.31 | O |
| ATOM | 1361 | N | VAL | A | 234 | 201.494 | 91.523 | 200.596 | 1.00 | 86.00 | N |
| ATOM | 1362 | CA | VAL | A | 234 | 200.322 | 91.745 | 199.766 | 1.00 | 75.09 | C |
| ATOM | 1363 | CB | VAL | A | 234 | 199.552 | 92.959 | 200.249 | 1.00 | 71.61 | C |
| ATOM | 1364 | CG1 | VAL | A | 234 | 198.252 | 93.088 | 199.474 | 1.00 | 102.31 | C |
| ATOM | 1365 | CG2 | VAL | A | 234 | 199.298 | 92.832 | 201.737 | 1.00 | 93.29 | C |
| ATOM | 1366 | C | VAL | A | 234 | 200.643 | 91.931 | 198.295 | 1.00 | 83.28 | C |
| ATOM | 1367 | O | VAL | A | 234 | 199.859 | 91.542 | 197.436 | 1.00 | 78.54 | O |
| ATOM | 1368 | N | LEU | A | 235 | 201.793 | 92.528 | 198.003 | 1.00 | 93.82 | N |
| ATOM | 1369 | CA | LEU | A | 235 | 202.204 | 92.740 | 196.619 | 1.00 | 91.56 | C |
| ATOM | 1370 | CB | LEU | A | 235 | 203.640 | 93.253 | 196.557 | 1.00 | 95.45 | C |
| ATOM | 1371 | CG | LEU | A | 235 | 203.876 | 94.717 | 196.884 | 1.00 | 75.77 | C |

FIG. 3A-25

| ATOM | 1372 | CD1 | LEU | A | 235 | 204.496 | 95.392 | 195.686 | 1.00 | 96.15 | C |
| --- | --- | --- | --- | --- | --- | --- | --- | --- | --- | --- | --- |
| ATOM | 1373 | CD2 | LEU | A | 235 | 202.569 | 95.369 | 197.252 | 1.00 | 112.18 | C |
| ATOM | 1374 | C | LEU | A | 235 | 202.115 | 91.432 | 195.842 | 1.00 | 110.37 | C |
| ATOM | 1375 | O | LEU | A | 235 | 202.120 | 91.419 | 194.606 | 1.00 | 122.67 | O |
| ATOM | 1376 | N | GLY | A | 236 | 202.045 | 90.324 | 196.571 | 1.00 | 110.40 | N |
| ATOM | 1377 | CA | GLY | A | 236 | 201.954 | 89.038 | 195.920 | 1.00 | 118.60 | C |
| ATOM | 1378 | C | GLY | A | 236 | 202.944 | 88.043 | 196.484 | 1.00 | 125.02 | C |
| ATOM | 1379 | O | GLY | A | 236 | 203.917 | 88.425 | 197.138 | 1.00 | 106.36 | O |
| ATOM | 1380 | N | PRO | A | 237 | 202.703 | 86.743 | 196.250 | 1.00 | 136.19 | N |
| ATOM | 1381 | CA | PRO | A | 237 | 203.541 | 85.638 | 196.713 | 1.00 | 143.31 | C |
| ATOM | 1382 | CB | PRO | A | 237 | 202.554 | 84.492 | 196.808 | 1.00 | 142.67 | C |
| ATOM | 1383 | CG | PRO | A | 237 | 201.742 | 84.717 | 195.577 | 1.00 | 137.14 | C |
| ATOM | 1384 | CD | PRO | A | 237 | 201.458 | 86.216 | 195.657 | 1.00 | 142.83 | C |
| ATOM | 1385 | C | PRO | A | 237 | 204.631 | 85.327 | 195.712 | 1.00 | 149.24 | C |
| ATOM | 1386 | O | PRO | A | 237 | 204.352 | 84.852 | 194.610 | 1.00 | 159.46 | O |
| ATOM | 1387 | N | ALA | A | 238 | 205.870 | 85.588 | 196.100 | 1.00 | 152.17 | N |
| ATOM | 1388 | CA | ALA | A | 238 | 207.009 | 85.317 | 195.240 | 1.00 | 151.75 | C |
| ATOM | 1389 | CB | ALA | A | 238 | 207.756 | 86.612 | 194.947 | 1.00 | 159.51 | C |
| ATOM | 1390 | C | ALA | A | 238 | 207.915 | 84.333 | 195.970 | 1.00 | 146.33 | C |
| ATOM | 1391 | O | ALA | A | 238 | 208.569 | 84.693 | 196.947 | 1.00 | 140.83 | O |
| ATOM | 1392 | N | ALA | A | 239 | 207.946 | 83.088 | 195.505 | 1.00 | 149.80 | N |
| ATOM | 1393 | CA | ALA | A | 239 | 208.766 | 82.065 | 196.149 | 1.00 | 156.32 | C |
| ATOM | 1394 | CB | ALA | A | 239 | 208.073 | 80.713 | 196.060 | 1.00 | 165.04 | C |
| ATOM | 1395 | C | ALA | A | 239 | 210.185 | 81.967 | 195.586 | 1.00 | 150.12 | C |
| ATOM | 1396 | O | ALA | A | 239 | 210.716 | 82.933 | 195.040 | 1.00 | 143.93 | O |
| ATOM | 1397 | N | ALA | A | 240 | 210.788 | 80.789 | 195.728 | 1.00 | 145.44 | N |
| ATOM | 1398 | CA | ALA | A | 240 | 212.161 | 80.541 | 195.280 | 1.00 | 128.29 | C |
| ATOM | 1399 | CB | ALA | A | 240 | 212.293 | 80.806 | 193.785 | 1.00 | 114.46 | C |
| ATOM | 1400 | C | ALA | A | 240 | 213.107 | 81.446 | 196.059 | 1.00 | 128.18 | C |
| ATOM | 1401 | O | ALA | A | 240 | 214.257 | 81.626 | 195.673 | 1.00 | 107.42 | O |
| ATOM | 1402 | N | ASP | A | 241 | 212.598 | 81.985 | 197.167 | 1.00 | 142.36 | N |
| ATOM | 1403 | CA | ASP | A | 241 | 213.317 | 82.909 | 198.046 | 1.00 | 144.32 | C |
| ATOM | 1404 | CB | ASP | A | 241 | 212.971 | 82.615 | 199.513 | 1.00 | 155.32 | C |
| ATOM | 1405 | CG | ASP | A | 241 | 213.448 | 83.712 | 200.469 | 1.00 | 166.53 | C |
| ATOM | 1406 | OD1 | ASP | A | 241 | 213.226 | 83.563 | 201.690 | 1.00 | 177.22 | O |
| ATOM | 1407 | OD2 | ASP | A | 241 | 214.026 | 84.720 | 200.004 | 1.00 | 173.19 | O |
| ATOM | 1408 | C | ASP | A | 241 | 214.836 | 82.926 | 197.861 | 1.00 | 131.50 | C |
| ATOM | 1409 | O | ASP | A | 241 | 215.496 | 81.886 | 197.846 | 1.00 | 121.60 | O |
| ATOM | 1410 | N | LYS | A | 242 | 215.369 | 84.133 | 197.716 | 1.00 | 106.74 | N |
| ATOM | 1411 | CA | LYS | A | 242 | 216.787 | 84.344 | 197.525 | 1.00 | 86.50 | C |
| ATOM | 1412 | CB | LYS | A | 242 | 217.044 | 85.758 | 197.017 | 1.00 | 97.76 | C |
| ATOM | 1413 | CG | LYS | A | 242 | 215.893 | 86.735 | 197.167 | 1.00 | 71.36 | C |
| ATOM | 1414 | CD | LYS | A | 242 | 215.009 | 86.697 | 195.932 | 1.00 | 103.00 | C |
| ATOM | 1415 | CE | LYS | A | 242 | 214.110 | 87.928 | 195.850 | 1.00 | 138.19 | C |
| ATOM | 1416 | NZ | LYS | A | 242 | 213.337 | 88.031 | 194.570 | 1.00 | 123.67 | N |
| ATOM | 1417 | C | LYS | A | 242 | 217.611 | 84.131 | 198.779 | 1.00 | 99.35 | C |
| ATOM | 1418 | O | LYS | A | 242 | 218.833 | 84.245 | 198.738 | 1.00 | 106.37 | O |
| ATOM | 1419 | N | SER | A | 243 | 216.953 | 83.831 | 199.894 | 1.00 | 97.75 | N |
| ATOM | 1420 | CA | SER | A | 243 | 217.650 | 83.624 | 201.165 | 1.00 | 84.81 | C |
| ATOM | 1421 | CB | SER | A | 243 | 216.717 | 82.963 | 202.160 | 1.00 | 77.67 | C |
| ATOM | 1422 | OG | SER | A | 243 | 215.576 | 83.776 | 202.336 | 1.00 | 121.59 | O |
| ATOM | 1423 | C | SER | A | 243 | 218.935 | 82.808 | 201.061 | 1.00 | 82.48 | C |
| ATOM | 1424 | O | SER | A | 243 | 219.947 | 83.156 | 201.672 | 1.00 | 74.56 | O |
| ATOM | 1425 | N | CYS | A | 244 | 218.906 | 81.718 | 200.304 | 1.00 | 67.22 | N |
| ATOM | 1426 | CA | CYS | A | 244 | 220.107 | 80.921 | 200.148 | 1.00 | 78.41 | C |

FIG. 3A-26

| ATOM | 1427 | CB | CYS | A | 244 | 219.885 | 79.820 | 199.117 | 1.00 | 64.99 | C |
|---|---|---|---|---|---|---|---|---|---|---|---|
| ATOM | 1428 | SG | CYS | A | 244 | 219.278 | 80.410 | 197.539 | 1.00 | 91.08 | S |
| ATOM | 1429 | C | CYS | A | 244 | 221.238 | 81.841 | 199.703 | 1.00 | 64.58 | C |
| ATOM | 1430 | O | CYS | A | 244 | 222.365 | 81.703 | 200.171 | 1.00 | 67.24 | O |
| ATOM | 1431 | N | ASP | A | 245 | 220.933 | 82.777 | 198.804 | 1.00 | 49.99 | N |
| ATOM | 1432 | CA | ASP | A | 245 | 221.931 | 83.724 | 198.319 | 1.00 | 45.00 | C |
| ATOM | 1433 | CB | ASP | A | 245 | 221.287 | 84.814 | 197.456 | 1.00 | 69.55 | C |
| ATOM | 1434 | CG | ASP | A | 245 | 220.970 | 84.352 | 196.044 | 1.00 | 60.27 | C |
| ATOM | 1435 | OD1 | ASP | A | 245 | 221.440 | 83.266 | 195.644 | 1.00 | 73.75 | O |
| ATOM | 1436 | OD2 | ASP | A | 245 | 220.261 | 85.094 | 195.327 | 1.00 | 70.27 | O |
| ATOM | 1437 | C | ASP | A | 245 | 222.627 | 84.380 | 199.510 | 1.00 | 60.39 | C |
| ATOM | 1438 | O | ASP | A | 245 | 223.856 | 84.484 | 199.532 | 1.00 | 67.65 | O |
| ATOM | 1439 | N | MET | A | 246 | 221.839 | 84.819 | 200.497 | 1.00 | 43.54 | N |
| ATOM | 1440 | CA | MET | A | 246 | 222.388 | 85.456 | 201.695 | 1.00 | 64.86 | C |
| ATOM | 1441 | CB | MET | A | 246 | 221.285 | 86.049 | 202.558 | 1.00 | 52.62 | C |
| ATOM | 1442 | CG | MET | A | 246 | 220.483 | 87.102 | 201.868 | 1.00 | 60.79 | C |
| ATOM | 1443 | SD | MET | A | 246 | 221.517 | 88.262 | 201.008 | 1.00 | 66.30 | S |
| ATOM | 1444 | CE | MET | A | 246 | 222.196 | 89.233 | 202.364 | 1.00 | 55.43 | C |
| ATOM | 1445 | C | MET | A | 246 | 223.195 | 84.479 | 202.539 | 1.00 | 67.48 | C |
| ATOM | 1446 | O | MET | A | 246 | 224.122 | 84.880 | 203.250 | 1.00 | 67.31 | O |
| ATOM | 1447 | N | TRP | A | 247 | 222.833 | 83.200 | 202.474 | 1.00 | 54.14 | N |
| ATOM | 1448 | CA | TRP | A | 247 | 223.551 | 82.177 | 203.215 | 1.00 | 62.36 | C |
| ATOM | 1449 | CB | TRP | A | 247 | 222.784 | 80.860 | 203.162 | 1.00 | 69.04 | C |
| ATOM | 1450 | CG | TRP | A | 247 | 223.544 | 79.696 | 203.717 | 1.00 | 86.20 | C |
| ATOM | 1451 | CD1 | TRP | A | 247 | 224.418 | 78.902 | 203.046 | 1.00 | 72.11 | C |
| ATOM | 1452 | NE1 | TRP | A | 247 | 224.952 | 77.958 | 203.896 | 1.00 | 81.90 | N |
| ATOM | 1453 | CE2 | TRP | A | 247 | 224.424 | 78.136 | 205.147 | 1.00 | 68.57 | C |
| ATOM | 1454 | CD2 | TRP | A | 247 | 223.529 | 79.220 | 205.076 | 1.00 | 75.65 | C |
| ATOM | 1455 | CE3 | TRP | A | 247 | 222.846 | 79.610 | 206.237 | 1.00 | 91.13 | C |
| ATOM | 1456 | CZ3 | TRP | A | 247 | 223.079 | 78.913 | 207.411 | 1.00 | 82.48 | C |
| ATOM | 1457 | CH2 | TRP | A | 247 | 223.979 | 77.841 | 207.447 | 1.00 | 74.62 | C |
| ATOM | 1458 | CZ2 | TRP | A | 247 | 224.660 | 77.438 | 206.329 | 1.00 | 68.02 | C |
| ATOM | 1459 | C | TRP | A | 247 | 224.934 | 82.015 | 202.592 | 1.00 | 62.90 | C |
| ATOM | 1460 | O | TRP | A | 247 | 225.951 | 82.071 | 203.287 | 1.00 | 62.42 | O |
| ATOM | 1461 | N | SER | A | 248 | 224.959 | 81.829 | 201.274 | 1.00 | 77.02 | N |
| ATOM | 1462 | CA | SER | A | 248 | 226.203 | 81.676 | 200.531 | 1.00 | 73.53 | C |
| ATOM | 1463 | CB | SER | A | 248 | 225.930 | 81.731 | 199.043 | 1.00 | 67.92 | C |
| ATOM | 1464 | OG | SER | A | 248 | 225.112 | 80.642 | 198.668 | 1.00 | 118.25 | O |
| ATOM | 1465 | C | SER | A | 248 | 227.156 | 82.786 | 200.892 | 1.00 | 80.75 | C |
| ATOM | 1466 | O | SER | A | 248 | 228.369 | 82.583 | 200.943 | 1.00 | 84.06 | O |
| ATOM | 1467 | N | LEU | A | 249 | 226.593 | 83.967 | 201.130 | 1.00 | 76.04 | N |
| ATOM | 1468 | CA | LEU | A | 249 | 227.378 | 85.132 | 201.506 | 1.00 | 82.09 | C |
| ATOM | 1469 | CB | LEU | A | 249 | 226.473 | 86.363 | 201.610 | 1.00 | 85.62 | C |
| ATOM | 1470 | CG | LEU | A | 249 | 227.049 | 87.629 | 200.964 | 1.00 | 77.42 | C |
| ATOM | 1471 | CD1 | LEU | A | 249 | 227.250 | 87.346 | 199.493 | 1.00 | 68.42 | C |
| ATOM | 1472 | CD2 | LEU | A | 249 | 226.119 | 88.832 | 201.153 | 1.00 | 95.64 | C |
| ATOM | 1473 | C | LEU | A | 249 | 228.081 | 84.869 | 202.845 | 1.00 | 84.27 | C |
| ATOM | 1474 | O | LEU | A | 249 | 229.298 | 85.035 | 202.960 | 1.00 | 83.90 | O |
| ATOM | 1475 | N | GLY | A | 250 | 227.318 | 84.449 | 203.851 | 1.00 | 64.22 | N |
| ATOM | 1476 | CA | GLY | A | 250 | 227.915 | 84.165 | 205.147 | 1.00 | 62.72 | C |
| ATOM | 1477 | C | GLY | A | 250 | 229.103 | 83.231 | 204.998 | 1.00 | 63.71 | C |
| ATOM | 1478 | O | GLY | A | 250 | 230.220 | 83.544 | 205.418 | 1.00 | 57.98 | O |
| ATOM | 1479 | N | VAL | A | 251 | 228.855 | 82.076 | 204.387 | 1.00 | 57.35 | N |
| ATOM | 1480 | CA | VAL | A | 251 | 229.902 | 81.091 | 204.152 | 1.00 | 72.77 | C |
| ATOM | 1481 | CB | VAL | A | 251 | 229.474 | 80.052 | 203.129 | 1.00 | 72.02 | C |

FIG. 3A-27

| | | | | | | | | | | |
|---|---|---|---|---|---|---|---|---|---|---|
| ATOM | 1482 | CG1 | VAL | A | 251 | 230.627 | 79.119 | 202.852 | 1.00 | 48.81 | C |
| ATOM | 1483 | CG2 | VAL | A | 251 | 228.255 | 79.312 | 203.617 | 1.00 | 45.51 | C |
| ATOM | 1484 | C | VAL | A | 251 | 231.130 | 81.779 | 203.587 | 1.00 | 65.76 | C |
| ATOM | 1485 | O | VAL | A | 251 | 232.239 | 81.624 | 204.093 | 1.00 | 72.08 | O |
| ATOM | 1486 | N | ILE | A | 252 | 230.927 | 82.544 | 202.525 | 1.00 | 65.58 | N |
| ATOM | 1487 | CA | ILE | A | 252 | 232.036 | 83.248 | 201.899 | 1.00 | 68.61 | C |
| ATOM | 1488 | CB | ILE | A | 252 | 231.564 | 84.008 | 200.634 | 1.00 | 65.58 | C |
| ATOM | 1489 | CG1 | ILE | A | 252 | 231.151 | 82.989 | 199.570 | 1.00 | 42.53 | C |
| ATOM | 1490 | CD1 | ILE | A | 252 | 230.557 | 83.587 | 198.355 | 1.00 | 59.04 | C |
| ATOM | 1491 | CG2 | ILE | A | 252 | 232.679 | 84.891 | 200.102 | 1.00 | 53.46 | C |
| ATOM | 1492 | C | ILE | A | 252 | 232.722 | 84.197 | 202.876 | 1.00 | 77.12 | C |
| ATOM | 1493 | O | ILE | A | 252 | 233.932 | 84.098 | 203.088 | 1.00 | 79.18 | O |
| ATOM | 1494 | N | MET | A | 253 | 231.956 | 85.091 | 203.498 | 1.00 | 72.95 | N |
| ATOM | 1495 | CA | MET | A | 253 | 232.553 | 86.028 | 204.444 | 1.00 | 81.03 | C |
| ATOM | 1496 | CB | MET | A | 253 | 231.486 | 86.866 | 205.149 | 1.00 | 64.17 | C |
| ATOM | 1497 | CG | MET | A | 253 | 232.083 | 88.081 | 205.819 | 1.00 | 54.30 | C |
| ATOM | 1498 | SD | MET | A | 253 | 230.954 | 88.969 | 206.885 | 1.00 | 85.00 | S |
| ATOM | 1499 | CE | MET | A | 253 | 229.555 | 89.250 | 205.802 | 1.00 | 83.83 | C |
| ATOM | 1500 | C | MET | A | 253 | 233.367 | 85.286 | 205.497 | 1.00 | 75.68 | C |
| ATOM | 1501 | O | MET | A | 253 | 234.460 | 85.724 | 205.883 | 1.00 | 79.62 | O |
| ATOM | 1502 | N | TYR | A | 254 | 232.829 | 84.161 | 205.960 | 1.00 | 81.14 | N |
| ATOM | 1503 | CA | TYR | A | 254 | 233.513 | 83.370 | 206.969 | 1.00 | 68.03 | C |
| ATOM | 1504 | CB | TYR | A | 254 | 232.711 | 82.107 | 207.279 | 1.00 | 66.09 | C |
| ATOM | 1505 | CG | TYR | A | 254 | 233.253 | 81.291 | 208.427 | 1.00 | 68.80 | C |
| ATOM | 1506 | CD1 | TYR | A | 254 | 234.285 | 80.388 | 208.230 | 1.00 | 93.85 | C |
| ATOM | 1507 | CE1 | TYR | A | 254 | 234.797 | 79.640 | 209.281 | 1.00 | 93.85 | C |
| ATOM | 1508 | CZ | TYR | A | 254 | 234.270 | 79.797 | 210.553 | 1.00 | 78.16 | C |
| ATOM | 1509 | OH | TYR | A | 254 | 234.780 | 79.043 | 211.592 | 1.00 | 83.85 | O |
| ATOM | 1510 | CE2 | TYR | A | 254 | 233.238 | 80.696 | 210.775 | 1.00 | 60.25 | C |
| ATOM | 1511 | CD2 | TYR | A | 254 | 232.739 | 81.434 | 209.713 | 1.00 | 66.37 | C |
| ATOM | 1512 | C | TYR | A | 254 | 234.879 | 83.008 | 206.419 | 1.00 | 74.50 | C |
| ATOM | 1513 | O | TYR | A | 254 | 235.901 | 83.519 | 206.879 | 1.00 | 78.65 | O |
| ATOM | 1514 | N | ILE | A | 255 | 234.876 | 82.148 | 205.405 | 1.00 | 71.34 | N |
| ATOM | 1515 | CA | ILE | A | 255 | 236.099 | 81.690 | 204.774 | 1.00 | 61.37 | C |
| ATOM | 1516 | CB | ILE | A | 255 | 235.810 | 81.046 | 203.443 | 1.00 | 62.35 | C |
| ATOM | 1517 | CG1 | ILE | A | 255 | 234.928 | 79.819 | 203.653 | 1.00 | 62.67 | C |
| ATOM | 1518 | CD1 | ILE | A | 255 | 234.514 | 79.131 | 202.387 | 1.00 | 57.99 | C |
| ATOM | 1519 | CG2 | ILE | A | 255 | 237.107 | 80.661 | 202.790 | 1.00 | 76.47 | C |
| ATOM | 1520 | C | ILE | A | 255 | 237.128 | 82.782 | 204.558 | 1.00 | 76.55 | C |
| ATOM | 1521 | O | ILE | A | 255 | 238.298 | 82.590 | 204.870 | 1.00 | 92.35 | O |
| ATOM | 1522 | N | LEU | A | 256 | 236.709 | 83.925 | 204.024 | 1.00 | 73.36 | N |
| ATOM | 1523 | CA | LEU | A | 256 | 237.647 | 85.022 | 203.809 | 1.00 | 76.61 | C |
| ATOM | 1524 | CB | LEU | A | 256 | 236.921 | 86.316 | 203.430 | 1.00 | 82.53 | C |
| ATOM | 1525 | CG | LEU | A | 256 | 236.503 | 86.623 | 201.991 | 1.00 | 67.94 | C |
| ATOM | 1526 | CD1 | LEU | A | 256 | 236.199 | 88.119 | 201.870 | 1.00 | 83.50 | C |
| ATOM | 1527 | CD2 | LEU | A | 256 | 237.615 | 86.248 | 201.038 | 1.00 | 61.15 | C |
| ATOM | 1528 | C | LEU | A | 256 | 238.466 | 85.295 | 205.065 | 1.00 | 80.02 | C |
| ATOM | 1529 | O | LEU | A | 256 | 239.681 | 85.116 | 205.074 | 1.00 | 95.93 | O |
| ATOM | 1530 | N | LEU | A | 257 | 237.780 | 85.718 | 206.124 | 1.00 | 64.99 | N |
| ATOM | 1531 | CA | LEU | A | 257 | 238.407 | 86.060 | 207.399 | 1.00 | 83.07 | C |
| ATOM | 1532 | CB | LEU | A | 257 | 237.331 | 86.467 | 208.402 | 1.00 | 65.07 | C |
| ATOM | 1533 | CG | LEU | A | 257 | 236.445 | 87.661 | 208.054 | 1.00 | 72.20 | C |
| ATOM | 1534 | CD1 | LEU | A | 257 | 235.475 | 87.888 | 209.185 | 1.00 | 109.20 | C |
| ATOM | 1535 | CD2 | LEU | A | 257 | 237.282 | 88.906 | 207.843 | 1.00 | 77.76 | C |
| ATOM | 1536 | C | LEU | A | 257 | 239.336 | 85.046 | 208.090 | 1.00 | 92.07 | C |

FIG. 3A-28

| | | | | | | | | | | |
|---|---|---|---|---|---|---|---|---|---|---|
| ATOM | 1537 | O | LEU | A | 257 | 240.175 | 85.450 | 208.897 | 1.00 | 79.63 O |
| ATOM | 1538 | N | CYS | A | 258 | 239.211 | 83.751 | 207.805 | 1.00 | 84.06 N |
| ATOM | 1539 | CA | CYS | A | 258 | 240.068 | 82.782 | 208.486 | 1.00 | 65.38 C |
| ATOM | 1540 | CB | CYS | A | 258 | 239.250 | 81.952 | 209.465 | 1.00 | 74.82 C |
| ATOM | 1541 | SG | CYS | A | 258 | 238.333 | 80.661 | 208.627 | 1.00 | 88.33 S |
| ATOM | 1542 | C | CYS | A | 258 | 240.811 | 81.822 | 207.572 | 1.00 | 79.35 C |
| ATOM | 1543 | O | CYS | A | 258 | 241.865 | 81.305 | 207.936 | 1.00 | 89.35 O |
| ATOM | 1544 | N | GLY | A | 259 | 240.259 | 81.552 | 206.397 | 1.00 | 77.77 N |
| ATOM | 1545 | CA | GLY | A | 259 | 240.927 | 80.636 | 205.491 | 1.00 | 86.18 C |
| ATOM | 1546 | C | GLY | A | 259 | 240.211 | 79.311 | 205.306 | 1.00 | 84.64 C |
| ATOM | 1547 | O | GLY | A | 259 | 240.562 | 78.538 | 204.415 | 1.00 | 91.47 O |
| ATOM | 1548 | N | TYR | A | 260 | 239.219 | 79.030 | 206.145 | 1.00 | 80.25 N |
| ATOM | 1549 | CA | TYR | A | 260 | 238.454 | 77.788 | 206.024 | 1.00 | 85.40 C |
| ATOM | 1550 | CB | TYR | A | 260 | 238.936 | 76.760 | 207.050 | 1.00 | 90.73 C |
| ATOM | 1551 | CG | TYR | A | 260 | 239.030 | 77.305 | 208.451 | 1.00 | 78.95 C |
| ATOM | 1552 | CD1 | TYR | A | 260 | 237.942 | 77.261 | 209.312 | 1.00 | 99.14 C |
| ATOM | 1553 | CE1 | TYR | A | 260 | 238.023 | 77.785 | 210.585 | 1.00 | 88.16 C |
| ATOM | 1554 | CZ | TYR | A | 260 | 239.201 | 78.364 | 211.007 | 1.00 | 67.63 C |
| ATOM | 1555 | OH | TYR | A | 260 | 239.298 | 78.896 | 212.269 | 1.00 | 84.01 O |
| ATOM | 1556 | CE2 | TYR | A | 260 | 240.292 | 78.420 | 210.173 | 1.00 | 97.24 C |
| ATOM | 1557 | CD2 | TYR | A | 260 | 240.204 | 77.892 | 208.904 | 1.00 | 82.37 C |
| ATOM | 1558 | C | TYR | A | 260 | 236.969 | 78.064 | 206.208 | 1.00 | 92.78 C |
| ATOM | 1559 | O | TYR | A | 260 | 236.587 | 79.064 | 206.813 | 1.00 | 109.20 O |
| ATOM | 1560 | N | PRO | A | 261 | 236.114 | 77.183 | 205.676 | 1.00 | 89.49 N |
| ATOM | 1561 | CA | PRO | A | 261 | 234.656 | 77.296 | 205.753 | 1.00 | 103.35 C |
| ATOM | 1562 | CB | PRO | A | 261 | 234.185 | 76.209 | 204.791 | 1.00 | 98.88 C |
| ATOM | 1563 | CG | PRO | A | 261 | 235.208 | 75.152 | 204.996 | 1.00 | 95.80 C |
| ATOM | 1564 | CD | PRO | A | 261 | 236.493 | 75.962 | 204.950 | 1.00 | 91.52 C |
| ATOM | 1565 | C | PRO | A | 261 | 234.107 | 77.095 | 207.161 | 1.00 | 96.36 C |
| ATOM | 1566 | O | PRO | A | 261 | 234.743 | 76.459 | 207.995 | 1.00 | 100.89 O |
| ATOM | 1567 | N | PRO | A | 262 | 232.918 | 77.653 | 207.444 | 1.00 | 94.45 N |
| ATOM | 1568 | CA | PRO | A | 262 | 232.337 | 77.488 | 208.773 | 1.00 | 85.15 C |
| ATOM | 1569 | CB | PRO | A | 262 | 231.092 | 78.368 | 208.717 | 1.00 | 75.57 C |
| ATOM | 1570 | CG | PRO | A | 262 | 230.721 | 78.337 | 207.278 | 1.00 | 64.63 C |
| ATOM | 1571 | CD | PRO | A | 262 | 232.053 | 78.504 | 206.609 | 1.00 | 99.03 C |
| ATOM | 1572 | C | PRO | A | 262 | 232.015 | 76.028 | 209.043 | 1.00 | 68.20 C |
| ATOM | 1573 | O | PRO | A | 262 | 232.519 | 75.448 | 209.998 | 1.00 | 106.94 O |
| ATOM | 1574 | N | PHE | A | 263 | 231.200 | 75.419 | 208.191 | 1.00 | 73.57 N |
| ATOM | 1575 | CA | PHE | A | 263 | 230.838 | 74.021 | 208.393 | 1.00 | 79.36 C |
| ATOM | 1576 | CB | PHE | A | 263 | 229.428 | 73.777 | 207.848 | 1.00 | 69.85 C |
| ATOM | 1577 | CG | PHE | A | 263 | 228.420 | 74.759 | 208.374 | 1.00 | 81.28 C |
| ATOM | 1578 | CD1 | PHE | A | 263 | 228.128 | 75.917 | 207.677 | 1.00 | 113.87 C |
| ATOM | 1579 | CE1 | PHE | A | 263 | 227.285 | 76.867 | 208.205 | 1.00 | 85.69 C |
| ATOM | 1580 | CZ | PHE | A | 263 | 226.729 | 76.670 | 209.437 | 1.00 | 117.73 C |
| ATOM | 1581 | CE2 | PHE | A | 263 | 227.004 | 75.520 | 210.145 | 1.00 | 108.39 C |
| ATOM | 1582 | CD2 | PHE | A | 263 | 227.845 | 74.573 | 209.613 | 1.00 | 117.67 C |
| ATOM | 1583 | C | PHE | A | 263 | 231.864 | 73.093 | 207.757 | 1.00 | 106.15 C |
| ATOM | 1584 | O | PHE | A | 263 | 231.972 | 73.009 | 206.530 | 1.00 | 105.28 O |
| ATOM | 1585 | N | TYR | A | 264 | 232.620 | 72.408 | 208.622 | 1.00 | 134.25 N |
| ATOM | 1586 | CA | TYR | A | 264 | 233.681 | 71.497 | 208.197 | 1.00 | 147.77 C |
| ATOM | 1587 | CB | TYR | A | 264 | 234.775 | 71.405 | 209.284 | 1.00 | 153.86 C |
| ATOM | 1588 | CG | TYR | A | 264 | 236.191 | 71.629 | 208.760 | 1.00 | 157.09 C |
| ATOM | 1589 | CD1 | TYR | A | 264 | 237.265 | 70.886 | 209.250 | 1.00 | 193.79 C |
| ATOM | 1590 | CE1 | TYR | A | 264 | 238.553 | 71.074 | 208.764 | 1.00 | 220.80 C |
| ATOM | 1591 | CZ | TYR | A | 264 | 238.782 | 72.015 | 207.781 | 1.00 | 222.82 C |

FIG. 3A-29

| ATOM | 1592 | OH | TYR | A | 264 | 240.069 | 72.185 | 207.307 | 1.00 | 220.52 | O |
|---|---|---|---|---|---|---|---|---|---|---|---|
| ATOM | 1593 | CE2 | TYR | A | 264 | 237.734 | 72.771 | 207.279 | 1.00 | 201.56 | C |
| ATOM | 1594 | CD2 | TYR | A | 264 | 236.448 | 72.574 | 207.768 | 1.00 | 140.55 | C |
| ATOM | 1595 | C | TYR | A | 264 | 233.192 | 70.094 | 207.848 | 1.00 | 140.09 | C |
| ATOM | 1596 | O | TYR | A | 264 | 232.006 | 69.787 | 207.979 | 1.00 | 138.93 | O |
| ATOM | 1597 | N | SER | A | 265 | 234.118 | 69.246 | 207.409 | 1.00 | 141.69 | N |
| ATOM | 1598 | CA | SER | A | 265 | 233.785 | 67.877 | 207.044 | 1.00 | 135.35 | C |
| ATOM | 1599 | CB | SER | A | 265 | 234.113 | 67.628 | 205.566 | 1.00 | 138.65 | C |
| ATOM | 1600 | OG | SER | A | 265 | 233.591 | 66.386 | 205.130 | 1.00 | 107.77 | O |
| ATOM | 1601 | C | SER | A | 265 | 234.560 | 66.896 | 207.915 | 1.00 | 131.47 | C |
| ATOM | 1602 | O | SER | A | 265 | 235.792 | 66.945 | 207.976 | 1.00 | 126.66 | O |
| ATOM | 1603 | N | GLY | A | 274 | 229.307 | 63.721 | 209.431 | 1.00 | 106.41 | N |
| ATOM | 1604 | CA | GLY | A | 274 | 228.030 | 64.307 | 209.816 | 1.00 | 119.68 | C |
| ATOM | 1605 | C | GLY | A | 274 | 227.987 | 65.812 | 209.615 | 1.00 | 113.16 | C |
| ATOM | 1606 | O | GLY | A | 274 | 227.553 | 66.551 | 210.496 | 1.00 | 95.55 | O |
| ATOM | 1607 | N | MET | A | 275 | 228.446 | 66.261 | 208.449 | 1.00 | 110.29 | N |
| ATOM | 1608 | CA | MET | A | 275 | 228.463 | 67.676 | 208.112 | 1.00 | 95.81 | C |
| ATOM | 1609 | CB | MET | A | 275 | 229.412 | 67.938 | 206.943 | 1.00 | 90.51 | C |
| ATOM | 1610 | CG | MET | A | 275 | 229.404 | 69.380 | 206.472 | 1.00 | 83.11 | C |
| ATOM | 1611 | SD | MET | A | 275 | 230.324 | 69.611 | 204.942 | 1.00 | 99.84 | S |
| ATOM | 1612 | CE | MET | A | 275 | 229.028 | 69.352 | 203.750 | 1.00 | 79.14 | C |
| ATOM | 1613 | C | MET | A | 275 | 227.067 | 68.162 | 207.746 | 1.00 | 94.19 | C |
| ATOM | 1614 | O | MET | A | 275 | 226.633 | 69.206 | 208.220 | 1.00 | 75.71 | O |
| ATOM | 1615 | N | ALA | A | 276 | 226.362 | 67.411 | 206.904 | 1.00 | 80.06 | N |
| ATOM | 1616 | CA | ALA | A | 276 | 225.018 | 67.816 | 206.511 | 1.00 | 81.42 | C |
| ATOM | 1617 | CB | ALA | A | 276 | 224.327 | 66.705 | 205.731 | 1.00 | 70.05 | C |
| ATOM | 1618 | C | ALA | A | 276 | 224.233 | 68.145 | 207.770 | 1.00 | 67.18 | C |
| ATOM | 1619 | O | ALA | A | 276 | 223.297 | 68.931 | 207.738 | 1.00 | 87.18 | O |
| ATOM | 1620 | N | THR | A | 277 | 224.641 | 67.552 | 208.886 | 1.00 | 90.20 | N |
| ATOM | 1621 | CA | THR | A | 277 | 223.982 | 67.776 | 210.167 | 1.00 | 86.79 | C |
| ATOM | 1622 | CB | THR | A | 277 | 224.316 | 66.657 | 211.170 | 1.00 | 94.65 | C |
| ATOM | 1623 | OG1 | THR | A | 277 | 223.953 | 65.387 | 210.614 | 1.00 | 124.83 | O |
| ATOM | 1624 | CG2 | THR | A | 277 | 223.559 | 66.871 | 212.464 | 1.00 | 101.58 | C |
| ATOM | 1625 | C | THR | A | 277 | 224.402 | 69.103 | 210.790 | 1.00 | 88.87 | C |
| ATOM | 1626 | O | THR | A | 277 | 223.570 | 69.987 | 211.004 | 1.00 | 90.25 | O |
| ATOM | 1627 | N | ARG | A | 278 | 225.696 | 69.224 | 211.083 | 1.00 | 83.15 | N |
| ATOM | 1628 | CA | ARG | A | 278 | 226.273 | 70.425 | 211.683 | 1.00 | 85.59 | C |
| ATOM | 1629 | CB | ARG | A | 278 | 227.792 | 70.413 | 211.479 | 1.00 | 76.56 | C |
| ATOM | 1630 | CG | ARG | A | 278 | 228.346 | 68.998 | 211.313 | 1.00 | 94.91 | C |
| ATOM | 1631 | CD | ARG | A | 278 | 229.398 | 68.600 | 212.352 | 1.00 | 109.01 | C |
| ATOM | 1632 | NE | ARG | A | 278 | 230.699 | 69.199 | 212.072 | 1.00 | 121.75 | N |
| ATOM | 1633 | CZ | ARG | A | 278 | 231.384 | 69.003 | 210.944 | 1.00 | 131.02 | C |
| ATOM | 1634 | NH1 | ARG | A | 278 | 230.892 | 68.216 | 209.988 | 1.00 | 101.83 | N |
| ATOM | 1635 | NH2 | ARG | A | 278 | 232.556 | 69.613 | 210.763 | 1.00 | 135.84 | N |
| ATOM | 1636 | C | ARG | A | 278 | 225.653 | 71.666 | 211.039 | 1.00 | 80.18 | C |
| ATOM | 1637 | O | ARG | A | 278 | 225.537 | 72.716 | 211.673 | 1.00 | 83.67 | O |
| ATOM | 1638 | N | ILE | A | 279 | 225.250 | 71.516 | 209.778 | 1.00 | 83.10 | N |
| ATOM | 1639 | CA | ILE | A | 279 | 224.615 | 72.579 | 209.001 | 1.00 | 82.30 | C |
| ATOM | 1640 | CB | ILE | A | 279 | 224.609 | 72.257 | 207.498 | 1.00 | 84.92 | C |
| ATOM | 1641 | CG1 | ILE | A | 279 | 226.006 | 72.436 | 206.913 | 1.00 | 77.12 | C |
| ATOM | 1642 | CD1 | ILE | A | 279 | 226.093 | 72.021 | 205.455 | 1.00 | 73.72 | C |
| ATOM | 1643 | CG2 | ILE | A | 279 | 223.611 | 73.144 | 206.789 | 1.00 | 57.01 | C |
| ATOM | 1644 | C | ILE | A | 279 | 223.167 | 72.765 | 209.421 | 1.00 | 76.46 | C |
| ATOM | 1645 | O | ILE | A | 279 | 222.778 | 73.847 | 209.847 | 1.00 | 90.20 | O |
| ATOM | 1646 | N | ALA | A | 280 | 222.371 | 71.709 | 209.270 | 1.00 | 68.55 | N |

FIG. 3A-30

| ATOM | 1647 | CA | ALA | A | 280 | 220.965 | 71.757 | 209.640 | 1.00 | 66.51 | C |
|---|---|---|---|---|---|---|---|---|---|---|---|
| ATOM | 1648 | CB | ALA | A | 280 | 220.326 | 70.383 | 209.475 | 1.00 | 49.45 | C |
| ATOM | 1649 | C | ALA | A | 280 | 220.886 | 72.218 | 211.090 | 1.00 | 62.26 | C |
| ATOM | 1650 | O | ALA | A | 280 | 220.039 | 73.038 | 211.456 | 1.00 | 69.34 | O |
| ATOM | 1651 | N | MET | A | 281 | 221.787 | 71.693 | 211.912 | 1.00 | 62.31 | N |
| ATOM | 1652 | CA | MET | A | 281 | 221.846 | 72.058 | 213.323 | 1.00 | 71.30 | C |
| ATOM | 1653 | CB | MET | A | 281 | 222.794 | 71.122 | 214.075 | 1.00 | 73.13 | C |
| ATOM | 1654 | CG | MET | A | 281 | 222.253 | 69.721 | 214.315 | 1.00 | 98.38 | C |
| ATOM | 1655 | SD | MET | A | 281 | 220.850 | 69.703 | 215.434 | 1.00 | 82.33 | S |
| ATOM | 1656 | CE | MET | A | 281 | 221.659 | 70.065 | 216.963 | 1.00 | 94.31 | C |
| ATOM | 1657 | C | MET | A | 281 | 222.348 | 73.489 | 213.438 | 1.00 | 78.13 | C |
| ATOM | 1658 | O | MET | A | 281 | 222.151 | 74.152 | 214.450 | 1.00 | 79.48 | O |
| ATOM | 1659 | N | GLY | A | 282 | 223.000 | 73.953 | 212.379 | 1.00 | 80.51 | N |
| ATOM | 1660 | CA | GLY | A | 282 | 223.536 | 75.298 | 212.354 | 1.00 | 70.03 | C |
| ATOM | 1661 | C | GLY | A | 282 | 224.577 | 75.481 | 213.435 | 1.00 | 89.35 | C |
| ATOM | 1662 | O | GLY | A | 282 | 224.566 | 76.482 | 214.146 | 1.00 | 77.94 | O |
| ATOM | 1663 | N | GLN | A | 283 | 225.479 | 74.514 | 213.576 | 1.00 | 81.75 | N |
| ATOM | 1664 | CA | GLN | A | 283 | 226.509 | 74.624 | 214.602 | 1.00 | 104.61 | C |
| ATOM | 1665 | CB | GLN | A | 283 | 226.421 | 73.450 | 215.583 | 1.00 | 113.16 | C |
| ATOM | 1666 | CG | GLN | A | 283 | 226.575 | 72.075 | 214.982 | 1.00 | 114.78 | C |
| ATOM | 1667 | CD | GLN | A | 283 | 226.574 | 71.002 | 216.057 | 1.00 | 133.39 | C |
| ATOM | 1668 | OE1 | GLN | A | 283 | 227.356 | 71.068 | 217.005 | 1.00 | 133.52 | O |
| ATOM | 1669 | NE2 | GLN | A | 283 | 225.691 | 70.012 | 215.922 | 1.00 | 112.55 | N |
| ATOM | 1670 | C | GLN | A | 283 | 227.939 | 74.764 | 214.094 | 1.00 | 94.71 | C |
| ATOM | 1671 | O | GLN | A | 283 | 228.503 | 73.843 | 213.505 | 1.00 | 88.07 | O |
| ATOM | 1672 | N | TYR | A | 284 | 228.516 | 75.935 | 214.347 | 1.00 | 90.04 | N |
| ATOM | 1673 | CA | TYR | A | 284 | 229.875 | 76.242 | 213.934 | 1.00 | 64.09 | C |
| ATOM | 1674 | CB | TYR | A | 284 | 229.864 | 77.002 | 212.620 | 1.00 | 82.88 | C |
| ATOM | 1675 | CG | TYR | A | 284 | 229.040 | 78.259 | 212.690 | 1.00 | 50.94 | C |
| ATOM | 1676 | CD1 | TYR | A | 284 | 227.656 | 78.208 | 212.619 | 1.00 | 72.36 | C |
| ATOM | 1677 | CE1 | TYR | A | 284 | 226.901 | 79.355 | 212.709 | 1.00 | 69.83 | C |
| ATOM | 1678 | CZ | TYR | A | 284 | 227.527 | 80.569 | 212.877 | 1.00 | 57.53 | C |
| ATOM | 1679 | OH | TYR | A | 284 | 226.778 | 81.716 | 212.978 | 1.00 | 94.22 | O |
| ATOM | 1680 | CE2 | TYR | A | 284 | 228.896 | 80.646 | 212.951 | 1.00 | 57.96 | C |
| ATOM | 1681 | CD2 | TYR | A | 284 | 229.645 | 79.496 | 212.856 | 1.00 | 79.70 | C |
| ATOM | 1682 | C | TYR | A | 284 | 230.474 | 77.137 | 215.008 | 1.00 | 65.66 | C |
| ATOM | 1683 | O | TYR | A | 284 | 229.806 | 77.468 | 215.981 | 1.00 | 88.03 | O |
| ATOM | 1684 | N | ALA | A | 285 | 231.725 | 77.538 | 214.821 | 1.00 | 80.73 | N |
| ATOM | 1685 | CA | ALA | A | 285 | 232.399 | 78.388 | 215.785 | 1.00 | 81.22 | C |
| ATOM | 1686 | CB | ALA | A | 285 | 233.113 | 77.527 | 216.807 | 1.00 | 87.46 | C |
| ATOM | 1687 | C | ALA | A | 285 | 233.397 | 79.305 | 215.101 | 1.00 | 90.67 | C |
| ATOM | 1688 | O | ALA | A | 285 | 233.713 | 79.119 | 213.926 | 1.00 | 106.16 | O |
| ATOM | 1689 | N | PHE | A | 286 | 233.875 | 80.303 | 215.839 | 1.00 | 86.81 | N |
| ATOM | 1690 | CA | PHE | A | 286 | 234.880 | 81.236 | 215.334 | 1.00 | 97.06 | C |
| ATOM | 1691 | CB | PHE | A | 286 | 234.476 | 82.697 | 215.602 | 1.00 | 78.01 | C |
| ATOM | 1692 | CG | PHE | A | 286 | 233.214 | 83.127 | 214.904 | 1.00 | 98.13 | C |
| ATOM | 1693 | CD1 | PHE | A | 286 | 232.172 | 83.698 | 215.615 | 1.00 | 92.96 | C |
| ATOM | 1694 | CE1 | PHE | A | 286 | 231.003 | 84.092 | 214.980 | 1.00 | 96.16 | C |
| ATOM | 1695 | CZ | PHE | A | 286 | 230.865 | 83.918 | 213.620 | 1.00 | 71.90 | C |
| ATOM | 1696 | CE2 | PHE | A | 286 | 231.892 | 83.353 | 212.897 | 1.00 | 82.36 | C |
| ATOM | 1697 | CD2 | PHE | A | 286 | 233.064 | 82.959 | 213.538 | 1.00 | 102.41 | C |
| ATOM | 1698 | C | PHE | A | 286 | 236.110 | 80.887 | 216.167 | 1.00 | 100.16 | C |
| ATOM | 1699 | O | PHE | A | 286 | 236.527 | 81.662 | 217.028 | 1.00 | 110.05 | O |
| ATOM | 1700 | N | PRO | A | 287 | 236.707 | 79.715 | 215.909 | 1.00 | 96.70 | N |
| ATOM | 1701 | CA | PRO | A | 287 | 237.883 | 79.170 | 216.586 | 1.00 | 103.18 | C |

FIG. 3A-31

| ATOM | 1702 | CB | PRO | A | 287 | 238.210 | 77.940 | 215.754 | 1.00 | 105.25 | C |
| ATOM | 1703 | CG | PRO | A | 287 | 237.828 | 78.359 | 214.411 | 1.00 | 92.44 | C |
| ATOM | 1704 | CD | PRO | A | 287 | 236.474 | 78.978 | 214.659 | 1.00 | 100.51 | C |
| ATOM | 1705 | C | PRO | A | 287 | 239.086 | 80.081 | 216.730 | 1.00 | 112.32 | C |
| ATOM | 1706 | O | PRO | A | 287 | 239.531 | 80.709 | 215.770 | 1.00 | 114.13 | O |
| ATOM | 1707 | N | ASN | A | 288 | 239.608 | 80.133 | 217.950 | 1.00 | 119.25 | N |
| ATOM | 1708 | CA | ASN | A | 288 | 240.796 | 80.913 | 218.239 | 1.00 | 131.90 | C |
| ATOM | 1709 | CB | ASN | A | 288 | 240.826 | 81.347 | 219.708 | 1.00 | 133.89 | C |
| ATOM | 1710 | CG | ASN | A | 288 | 239.631 | 82.211 | 220.092 | 1.00 | 158.92 | C |
| ATOM | 1711 | OD1 | ASN | A | 288 | 239.383 | 83.259 | 219.485 | 1.00 | 172.68 | O |
| ATOM | 1712 | ND2 | ASN | A | 288 | 238.890 | 81.779 | 221.114 | 1.00 | 139.14 | N |
| ATOM | 1713 | C | ASN | A | 288 | 241.953 | 79.964 | 217.949 | 1.00 | 138.51 | C |
| ATOM | 1714 | O | ASN | A | 288 | 241.808 | 78.742 | 218.021 | 1.00 | 143.95 | O |
| ATOM | 1715 | N | PRO | A | 289 | 243.119 | 80.510 | 217.602 | 1.00 | 145.89 | N |
| ATOM | 1716 | CA | PRO | A | 289 | 243.399 | 81.940 | 217.477 | 1.00 | 147.78 | C |
| ATOM | 1717 | CB | PRO | A | 289 | 244.904 | 81.967 | 217.231 | 1.00 | 160.27 | C |
| ATOM | 1718 | CG | PRO | A | 289 | 245.107 | 80.724 | 216.415 | 1.00 | 158.40 | C |
| ATOM | 1719 | CD | PRO | A | 289 | 244.286 | 79.712 | 217.185 | 1.00 | 149.68 | C |
| ATOM | 1720 | C | PRO | A | 289 | 242.632 | 82.643 | 216.367 | 1.00 | 140.12 | C |
| ATOM | 1721 | O | PRO | A | 289 | 242.027 | 83.678 | 216.608 | 1.00 | 145.48 | O |
| ATOM | 1722 | N | GLU | A | 290 | 242.665 | 82.064 | 215.166 | 1.00 | 135.89 | N |
| ATOM | 1723 | CA | GLU | A | 290 | 242.019 | 82.602 | 213.959 | 1.00 | 122.33 | C |
| ATOM | 1724 | CB | GLU | A | 290 | 241.230 | 81.502 | 213.236 | 1.00 | 121.58 | C |
| ATOM | 1725 | CG | GLU | A | 290 | 241.934 | 80.155 | 213.147 | 1.00 | 140.70 | C |
| ATOM | 1726 | CD | GLU | A | 290 | 241.650 | 79.287 | 214.360 | 1.00 | 183.86 | C |
| ATOM | 1727 | OE1 | GLU | A | 290 | 241.898 | 79.762 | 215.484 | 1.00 | 193.44 | O |
| ATOM | 1728 | OE2 | GLU | A | 290 | 241.178 | 78.137 | 214.193 | 1.00 | 182.20 | O |
| ATOM | 1729 | C | GLU | A | 290 | 241.100 | 83.810 | 214.141 | 1.00 | 111.48 | C |
| ATOM | 1730 | O | GLU | A | 290 | 241.314 | 84.858 | 213.531 | 1.00 | 94.90 | O |
| ATOM | 1731 | N | TRP | A | 291 | 240.080 | 83.655 | 214.980 | 1.00 | 102.18 | N |
| ATOM | 1732 | CA | TRP | A | 291 | 239.105 | 84.715 | 215.221 | 1.00 | 106.95 | C |
| ATOM | 1733 | CB | TRP | A | 291 | 237.712 | 84.106 | 215.295 | 1.00 | 110.40 | C |
| ATOM | 1734 | CG | TRP | A | 291 | 237.364 | 83.374 | 214.056 | 1.00 | 104.11 | C |
| ATOM | 1735 | CD1 | TRP | A | 291 | 237.782 | 82.121 | 213.692 | 1.00 | 84.92 | C |
| ATOM | 1736 | NE1 | TRP | A | 291 | 237.282 | 81.799 | 212.456 | 1.00 | 103.99 | N |
| ATOM | 1737 | CE2 | TRP | A | 291 | 236.529 | 82.848 | 211.996 | 1.00 | 102.71 | C |
| ATOM | 1738 | CD2 | TRP | A | 291 | 236.556 | 83.857 | 212.982 | 1.00 | 106.19 | C |
| ATOM | 1739 | CE3 | TRP | A | 291 | 235.857 | 85.048 | 212.753 | 1.00 | 70.56 | C |
| ATOM | 1740 | CZ3 | TRP | A | 291 | 235.165 | 85.189 | 211.578 | 1.00 | 73.88 | C |
| ATOM | 1741 | CH2 | TRP | A | 291 | 235.154 | 84.171 | 210.616 | 1.00 | 114.55 | C |
| ATOM | 1742 | CZ2 | TRP | A | 291 | 235.827 | 82.992 | 210.807 | 1.00 | 86.03 | C |
| ATOM | 1743 | C | TRP | A | 291 | 239.335 | 85.573 | 216.457 | 1.00 | 115.40 | C |
| ATOM | 1744 | O | TRP | A | 291 | 238.474 | 86.375 | 216.824 | 1.00 | 120.18 | O |
| ATOM | 1745 | N | SER | A | 292 | 240.491 | 85.404 | 217.091 | 1.00 | 129.00 | N |
| ATOM | 1746 | CA | SER | A | 292 | 240.851 | 86.158 | 218.287 | 1.00 | 124.04 | C |
| ATOM | 1747 | CB | SER | A | 292 | 242.199 | 85.658 | 218.825 | 1.00 | 125.10 | C |
| ATOM | 1748 | OG | SER | A | 292 | 243.196 | 85.669 | 217.817 | 1.00 | 135.63 | O |
| ATOM | 1749 | C | SER | A | 292 | 240.910 | 87.670 | 218.051 | 1.00 | 123.03 | C |
| ATOM | 1750 | O | SER | A | 292 | 240.661 | 88.455 | 218.966 | 1.00 | 113.67 | O |
| ATOM | 1751 | N | ALA | A | 293 | 241.237 | 88.081 | 216.829 | 1.00 | 123.41 | N |
| ATOM | 1752 | CA | ALA | A | 293 | 241.321 | 89.508 | 216.513 | 1.00 | 127.66 | C |
| ATOM | 1753 | CB | ALA | A | 293 | 242.600 | 89.792 | 215.737 | 1.00 | 138.28 | C |
| ATOM | 1754 | C | ALA | A | 293 | 240.108 | 90.026 | 215.724 | 1.00 | 121.92 | C |
| ATOM | 1755 | O | ALA | A | 293 | 240.091 | 91.178 | 215.285 | 1.00 | 115.91 | O |
| ATOM | 1756 | N | VAL | A | 294 | 239.094 | 89.181 | 215.555 | 1.00 | 111.91 | N |

FIG. 3A-32

| ATOM | 1757 | CA | VAL | A | 294 | 237.898 | 89.568 | 214.818 | 1.00 | 95.15 | C |
|---|---|---|---|---|---|---|---|---|---|---|---|
| ATOM | 1758 | CB | VAL | A | 294 | 237.322 | 88.378 | 214.066 | 1.00 | 92.93 | C |
| ATOM | 1759 | CG1 | VAL | A | 294 | 236.182 | 88.840 | 213.168 | 1.00 | 91.77 | C |
| ATOM | 1760 | CG2 | VAL | A | 294 | 238.418 | 87.705 | 213.269 | 1.00 | 94.47 | C |
| ATOM | 1761 | C | VAL | A | 294 | 236.811 | 90.136 | 215.721 | 1.00 | 103.25 | C |
| ATOM | 1762 | O | VAL | A | 294 | 236.506 | 89.573 | 216.771 | 1.00 | 98.28 | O |
| ATOM | 1763 | N | SER | A | 295 | 236.218 | 91.249 | 215.292 | 1.00 | 84.68 | N |
| ATOM | 1764 | CA | SER | A | 295 | 235.168 | 91.914 | 216.056 | 1.00 | 92.73 | C |
| ATOM | 1765 | CB | SER | A | 295 | 234.745 | 93.201 | 215.365 | 1.00 | 102.34 | C |
| ATOM | 1766 | OG | SER | A | 295 | 233.464 | 93.030 | 214.784 | 1.00 | 114.40 | O |
| ATOM | 1767 | C | SER | A | 295 | 233.919 | 91.072 | 216.244 | 1.00 | 88.74 | C |
| ATOM | 1768 | O | SER | A | 295 | 233.568 | 90.250 | 215.399 | 1.00 | 88.58 | O |
| ATOM | 1769 | N | GLU | A | 296 | 233.244 | 91.301 | 217.362 | 1.00 | 92.37 | N |
| ATOM | 1770 | CA | GLU | A | 296 | 232.008 | 90.600 | 217.658 | 1.00 | 104.61 | C |
| ATOM | 1771 | CB | GLU | A | 296 | 231.593 | 90.857 | 219.108 | 1.00 | 99.76 | C |
| ATOM | 1772 | CG | GLU | A | 296 | 230.316 | 90.154 | 219.543 | 1.00 | 121.36 | C |
| ATOM | 1773 | CD | GLU | A | 296 | 230.324 | 88.663 | 219.236 | 1.00 | 136.85 | C |
| ATOM | 1774 | OE1 | GLU | A | 296 | 231.304 | 87.970 | 219.609 | 1.00 | 131.43 | O |
| ATOM | 1775 | OE2 | GLU | A | 296 | 229.340 | 88.185 | 218.619 | 1.00 | 136.46 | O |
| ATOM | 1776 | C | GLU | A | 296 | 230.970 | 91.166 | 216.694 | 1.00 | 112.98 | C |
| ATOM | 1777 | O | GLU | A | 296 | 229.956 | 90.523 | 216.406 | 1.00 | 105.91 | O |
| ATOM | 1778 | N | GLU | A | 297 | 231.237 | 92.379 | 216.203 | 1.00 | 112.50 | N |
| ATOM | 1779 | CA | GLU | A | 297 | 230.357 | 93.045 | 215.247 | 1.00 | 99.85 | C |
| ATOM | 1780 | CB | GLU | A | 297 | 230.838 | 94.472 | 214.998 | 1.00 | 98.76 | C |
| ATOM | 1781 | CG | GLU | A | 297 | 230.226 | 95.146 | 213.787 | 1.00 | 102.64 | C |
| ATOM | 1782 | CD | GLU | A | 297 | 230.489 | 96.642 | 213.773 | 1.00 | 129.34 | C |
| ATOM | 1783 | OE1 | GLU | A | 297 | 229.777 | 97.379 | 214.497 | 1.00 | 134.48 | O |
| ATOM | 1784 | OE2 | GLU | A | 297 | 231.415 | 97.081 | 213.049 | 1.00 | 104.72 | O |
| ATOM | 1785 | C | GLU | A | 297 | 230.420 | 92.241 | 213.960 | 1.00 | 92.47 | C |
| ATOM | 1786 | O | GLU | A | 297 | 229.396 | 91.854 | 213.400 | 1.00 | 93.48 | O |
| ATOM | 1787 | N | VAL | A | 298 | 231.638 | 91.993 | 213.499 | 1.00 | 80.38 | N |
| ATOM | 1788 | CA | VAL | A | 298 | 231.843 | 91.200 | 212.305 | 1.00 | 87.49 | C |
| ATOM | 1789 | CB | VAL | A | 298 | 233.333 | 91.057 | 211.993 | 1.00 | 64.02 | C |
| ATOM | 1790 | CG1 | VAL | A | 298 | 233.542 | 89.953 | 210.980 | 1.00 | 84.65 | C |
| ATOM | 1791 | CG2 | VAL | A | 298 | 233.873 | 92.364 | 211.466 | 1.00 | 112.61 | C |
| ATOM | 1792 | C | VAL | A | 298 | 231.282 | 89.809 | 212.579 | 1.00 | 80.88 | C |
| ATOM | 1793 | O | VAL | A | 298 | 230.690 | 89.176 | 211.702 | 1.00 | 71.80 | O |
| ATOM | 1794 | N | LYS | A | 299 | 231.479 | 89.331 | 213.801 | 1.00 | 79.83 | N |
| ATOM | 1795 | CA | LYS | A | 299 | 230.990 | 88.015 | 214.162 | 1.00 | 75.16 | C |
| ATOM | 1796 | CB | LYS | A | 299 | 231.517 | 87.616 | 215.539 | 1.00 | 74.57 | C |
| ATOM | 1797 | CG | LYS | A | 299 | 232.979 | 87.229 | 215.509 | 1.00 | 75.11 | C |
| ATOM | 1798 | CD | LYS | A | 299 | 233.432 | 86.563 | 216.790 | 1.00 | 92.06 | C |
| ATOM | 1799 | CE | LYS | A | 299 | 234.841 | 86.005 | 216.623 | 1.00 | 125.81 | C |
| ATOM | 1800 | NZ | LYS | A | 299 | 235.368 | 85.378 | 217.867 | 1.00 | 126.47 | N |
| ATOM | 1801 | C | LYS | A | 299 | 229.478 | 87.983 | 214.138 | 1.00 | 80.77 | C |
| ATOM | 1802 | O | LYS | A | 299 | 228.872 | 87.052 | 213.618 | 1.00 | 62.14 | O |
| ATOM | 1803 | N | MET | A | 300 | 228.872 | 89.021 | 214.691 | 1.00 | 78.00 | N |
| ATOM | 1804 | CA | MET | A | 300 | 227.428 | 89.116 | 214.735 | 1.00 | 80.36 | C |
| ATOM | 1805 | CB | MET | A | 300 | 227.033 | 90.378 | 215.502 | 1.00 | 87.97 | C |
| ATOM | 1806 | CG | MET | A | 300 | 226.011 | 90.131 | 216.601 | 1.00 | 118.90 | C |
| ATOM | 1807 | SD | MET | A | 300 | 226.231 | 88.508 | 217.393 | 1.00 | 128.71 | S |
| ATOM | 1808 | CE | MET | A | 300 | 224.516 | 87.872 | 217.267 | 1.00 | 113.92 | C |
| ATOM | 1809 | C | MET | A | 300 | 226.822 | 89.120 | 213.327 | 1.00 | 69.48 | C |
| ATOM | 1810 | O | MET | A | 300 | 225.732 | 88.587 | 213.118 | 1.00 | 75.70 | O |
| ATOM | 1811 | N | LEU | A | 301 | 227.538 | 89.707 | 212.369 | 1.00 | 73.89 | N |

FIG. 3A-33

| ATOM | 1812 | CA | LEU | A | 301 | 227.079 | 89.782 | 210.972 | 1.00 | 63.96 | C |
|------|------|-----|-----|---|-----|---------|--------|---------|------|--------|---|
| ATOM | 1813 | CB | LEU | A | 301 | 227.977 | 90.735 | 210.177 | 1.00 | 63.62 | C |
| ATOM | 1814 | CG | LEU | A | 301 | 227.617 | 91.019 | 208.720 | 1.00 | 52.63 | C |
| ATOM | 1815 | CD1 | LEU | A | 301 | 226.130 | 91.284 | 208.596 | 1.00 | 65.57 | C |
| ATOM | 1816 | CD2 | LEU | A | 301 | 228.414 | 92.212 | 208.225 | 1.00 | 73.24 | C |
| ATOM | 1817 | C | LEU | A | 301 | 227.048 | 88.406 | 210.301 | 1.00 | 70.75 | C |
| ATOM | 1818 | O | LEU | A | 301 | 226.145 | 88.086 | 209.532 | 1.00 | 60.38 | O |
| ATOM | 1819 | N | ILE | A | 302 | 228.046 | 87.588 | 210.592 | 1.00 | 67.57 | N |
| ATOM | 1820 | CA | ILE | A | 302 | 228.090 | 86.250 | 210.037 | 1.00 | 61.70 | C |
| ATOM | 1821 | CB | ILE | A | 302 | 229.422 | 85.565 | 210.402 | 1.00 | 70.53 | C |
| ATOM | 1822 | CG1 | ILE | A | 302 | 230.562 | 86.271 | 209.659 | 1.00 | 76.98 | C |
| ATOM | 1823 | CD1 | ILE | A | 302 | 231.930 | 85.670 | 209.869 | 1.00 | 71.99 | C |
| ATOM | 1824 | CG2 | ILE | A | 302 | 229.369 | 84.086 | 210.071 | 1.00 | 65.01 | C |
| ATOM | 1825 | C | ILE | A | 302 | 226.900 | 85.455 | 210.582 | 1.00 | 75.97 | C |
| ATOM | 1826 | O | ILE | A | 302 | 226.226 | 84.741 | 209.837 | 1.00 | 58.38 | O |
| ATOM | 1827 | N | ARG | A | 303 | 226.630 | 85.611 | 211.878 | 1.00 | 73.53 | N |
| ATOM | 1828 | CA | ARG | A | 303 | 225.526 | 84.913 | 212.532 | 1.00 | 61.85 | C |
| ATOM | 1829 | CB | ARG | A | 303 | 225.461 | 85.279 | 214.009 | 1.00 | 61.93 | C |
| ATOM | 1830 | CG | ARG | A | 303 | 226.666 | 84.917 | 214.852 | 1.00 | 78.75 | C |
| ATOM | 1831 | CD | ARG | A | 303 | 226.402 | 85.392 | 216.284 | 1.00 | 71.93 | C |
| ATOM | 1832 | NE | ARG | A | 303 | 227.608 | 85.725 | 217.038 | 1.00 | 101.37 | N |
| ATOM | 1833 | CZ | ARG | A | 303 | 228.488 | 84.827 | 217.457 | 1.00 | 93.09 | C |
| ATOM | 1834 | NH1 | ARG | A | 303 | 228.286 | 83.540 | 217.191 | 1.00 | 90.11 | N |
| ATOM | 1835 | NH2 | ARG | A | 303 | 229.561 | 85.211 | 218.140 | 1.00 | 76.11 | N |
| ATOM | 1836 | C | ARG | A | 303 | 224.162 | 85.201 | 211.898 | 1.00 | 74.05 | C |
| ATOM | 1837 | O | ARG | A | 303 | 223.370 | 84.286 | 211.695 | 1.00 | 79.80 | O |
| ATOM | 1838 | N | ASN | A | 304 | 223.865 | 86.458 | 211.596 | 1.00 | 61.15 | N |
| ATOM | 1839 | CA | ASN | A | 304 | 222.575 | 86.775 | 210.982 | 1.00 | 77.76 | C |
| ATOM | 1840 | CB | ASN | A | 304 | 222.312 | 88.291 | 211.016 | 1.00 | 83.64 | C |
| ATOM | 1841 | CG | ASN | A | 304 | 222.000 | 88.806 | 212.421 | 1.00 | 112.22 | C |
| ATOM | 1842 | OD1 | ASN | A | 304 | 222.399 | 89.919 | 212.802 | 1.00 | 84.27 | O |
| ATOM | 1843 | ND2 | ASN | A | 304 | 221.269 | 88.004 | 213.197 | 1.00 | 69.02 | N |
| ATOM | 1844 | C | ASN | A | 304 | 222.517 | 86.277 | 209.535 | 1.00 | 74.95 | C |
| ATOM | 1845 | O | ASN | A | 304 | 221.449 | 86.208 | 208.929 | 1.00 | 67.98 | O |
| ATOM | 1846 | N | LEU | A | 305 | 223.671 | 85.943 | 208.973 | 1.00 | 63.99 | N |
| ATOM | 1847 | CA | LEU | A | 305 | 223.711 | 85.458 | 207.605 | 1.00 | 54.76 | C |
| ATOM | 1848 | CB | LEU | A | 305 | 225.032 | 85.860 | 206.948 | 1.00 | 52.05 | C |
| ATOM | 1849 | CG | LEU | A | 305 | 225.127 | 87.316 | 206.481 | 1.00 | 58.75 | C |
| ATOM | 1850 | CD1 | LEU | A | 305 | 226.511 | 87.621 | 205.932 | 1.00 | 69.80 | C |
| ATOM | 1851 | CD2 | LEU | A | 305 | 224.075 | 87.560 | 205.421 | 1.00 | 47.92 | C |
| ATOM | 1852 | C | LEU | A | 305 | 223.590 | 83.952 | 207.666 | 1.00 | 73.10 | C |
| ATOM | 1853 | O | LEU | A | 305 | 222.929 | 83.313 | 206.841 | 1.00 | 58.22 | O |
| ATOM | 1854 | N | LEU | A | 306 | 224.240 | 83.401 | 208.681 | 1.00 | 57.81 | N |
| ATOM | 1855 | CA | LEU | A | 306 | 224.256 | 81.975 | 208.915 | 1.00 | 59.22 | C |
| ATOM | 1856 | CB | LEU | A | 306 | 225.581 | 81.582 | 209.559 | 1.00 | 54.83 | C |
| ATOM | 1857 | CG | LEU | A | 306 | 226.752 | 81.718 | 208.599 | 1.00 | 56.28 | C |
| ATOM | 1858 | CD1 | LEU | A | 306 | 228.035 | 81.262 | 209.237 | 1.00 | 46.67 | C |
| ATOM | 1859 | CD2 | LEU | A | 306 | 226.445 | 80.883 | 207.385 | 1.00 | 50.52 | C |
| ATOM | 1860 | C | LEU | A | 306 | 223.087 | 81.525 | 209.779 | 1.00 | 70.17 | C |
| ATOM | 1861 | O | LEU | A | 306 | 223.205 | 80.586 | 210.565 | 1.00 | 86.15 | O |
| ATOM | 1862 | N | LYS | A | 307 | 221.960 | 82.212 | 209.648 | 1.00 | 70.52 | N |
| ATOM | 1863 | CA | LYS | A | 307 | 220.772 | 81.832 | 210.394 | 1.00 | 64.84 | C |
| ATOM | 1864 | CB | LYS | A | 307 | 219.720 | 82.930 | 210.337 | 1.00 | 60.26 | C |
| ATOM | 1865 | CG | LYS | A | 307 | 220.137 | 84.247 | 210.952 | 1.00 | 76.35 | C |
| ATOM | 1866 | CD | LYS | A | 307 | 219.620 | 84.411 | 212.371 | 1.00 | 75.87 | C |

FIG. 3A-34

| ATOM | 1867 | CE | LYS | A | 307 | 220.487 | 83.696 | 213.389 | 1.00 | 92.33 | C |
| ATOM | 1868 | NZ | LYS | A | 307 | 219.963 | 83.886 | 214.773 | 1.00 | 94.73 | N |
| ATOM | 1869 | C | LYS | A | 307 | 220.251 | 80.593 | 209.676 | 1.00 | 65.05 | C |
| ATOM | 1870 | O | LYS | A | 307 | 220.153 | 80.570 | 208.449 | 1.00 | 73.22 | O |
| ATOM | 1871 | N | THR | A | 308 | 219.925 | 79.558 | 210.439 | 1.00 | 87.36 | N |
| ATOM | 1872 | CA | THR | A | 308 | 219.432 | 78.314 | 209.864 | 1.00 | 86.54 | C |
| ATOM | 1873 | CB | THR | A | 308 | 219.382 | 77.198 | 210.945 | 1.00 | 80.31 | C |
| ATOM | 1874 | OG1 | THR | A | 308 | 220.615 | 76.457 | 210.929 | 1.00 | 85.50 | O |
| ATOM | 1875 | CG2 | THR | A | 308 | 218.211 | 76.265 | 210.701 | 1.00 | 108.80 | C |
| ATOM | 1876 | C | THR | A | 308 | 218.057 | 78.489 | 209.219 | 1.00 | 80.07 | C |
| ATOM | 1877 | O | THR | A | 308 | 217.722 | 77.809 | 208.248 | 1.00 | 80.48 | O |
| ATOM | 1878 | N | GLU | A | 309 | 217.264 | 79.407 | 209.755 | 1.00 | 86.56 | N |
| ATOM | 1879 | CA | GLU | A | 309 | 215.934 | 79.647 | 209.217 | 1.00 | 80.34 | C |
| ATOM | 1880 | CB | GLU | A | 309 | 214.937 | 79.945 | 210.345 | 1.00 | 79.03 | C |
| ATOM | 1881 | CG | GLU | A | 309 | 213.461 | 79.716 | 209.976 | 1.00 | 107.32 | C |
| ATOM | 1882 | CD | GLU | A | 309 | 213.028 | 78.264 | 210.160 | 1.00 | 128.86 | C |
| ATOM | 1883 | OE1 | GLU | A | 309 | 213.354 | 77.691 | 211.227 | 1.00 | 100.32 | O |
| ATOM | 1884 | OE2 | GLU | A | 309 | 212.364 | 77.699 | 209.252 | 1.00 | 91.75 | O |
| ATOM | 1885 | C | GLU | A | 309 | 215.964 | 80.820 | 208.253 | 1.00 | 80.14 | C |
| ATOM | 1886 | O | GLU | A | 309 | 216.353 | 81.933 | 208.614 | 1.00 | 72.43 | O |
| ATOM | 1887 | N | PRO | A | 310 | 215.554 | 80.585 | 207.002 | 1.00 | 69.20 | N |
| ATOM | 1888 | CA | PRO | A | 310 | 215.536 | 81.644 | 205.988 | 1.00 | 75.56 | C |
| ATOM | 1889 | CB | PRO | A | 310 | 214.675 | 81.041 | 204.888 | 1.00 | 58.28 | C |
| ATOM | 1890 | CG | PRO | A | 310 | 215.049 | 79.598 | 204.957 | 1.00 | 61.31 | C |
| ATOM | 1891 | CD | PRO | A | 310 | 215.073 | 79.312 | 206.442 | 1.00 | 64.66 | C |
| ATOM | 1892 | C | PRO | A | 310 | 214.955 | 82.953 | 206.540 | 1.00 | 73.13 | C |
| ATOM | 1893 | O | PRO | A | 310 | 215.697 | 83.886 | 206.848 | 1.00 | 70.20 | O |
| ATOM | 1894 | N | THR | A | 311 | 213.633 | 83.004 | 206.683 | 1.00 | 57.71 | N |
| ATOM | 1895 | CA | THR | A | 311 | 212.952 | 84.188 | 207.194 | 1.00 | 63.44 | C |
| ATOM | 1896 | CB | THR | A | 311 | 211.552 | 83.839 | 207.666 | 1.00 | 52.68 | C |
| ATOM | 1897 | OG1 | THR | A | 311 | 211.650 | 82.936 | 208.763 | 1.00 | 76.00 | O |
| ATOM | 1898 | CG2 | THR | A | 311 | 210.781 | 83.179 | 206.574 | 1.00 | 44.79 | C |
| ATOM | 1899 | C | THR | A | 311 | 213.671 | 84.899 | 208.338 | 1.00 | 65.40 | C |
| ATOM | 1900 | O | THR | A | 311 | 213.424 | 86.078 | 208.585 | 1.00 | 70.08 | O |
| ATOM | 1901 | N | GLN | A | 312 | 214.551 | 84.198 | 209.043 | 1.00 | 61.23 | N |
| ATOM | 1902 | CA | GLN | A | 312 | 215.271 | 84.831 | 210.145 | 1.00 | 58.30 | C |
| ATOM | 1903 | CB | GLN | A | 312 | 215.675 | 83.798 | 211.202 | 1.00 | 78.77 | C |
| ATOM | 1904 | CG | GLN | A | 312 | 215.203 | 84.120 | 212.625 | 1.00 | 101.21 | C |
| ATOM | 1905 | CD | GLN | A | 312 | 215.952 | 83.321 | 213.691 | 1.00 | 105.49 | C |
| ATOM | 1906 | OE1 | GLN | A | 312 | 217.112 | 83.612 | 214.004 | 1.00 | 110.73 | O |
| ATOM | 1907 | NE2 | GLN | A | 312 | 215.294 | 82.305 | 214.243 | 1.00 | 82.13 | N |
| ATOM | 1908 | C | GLN | A | 312 | 216.527 | 85.518 | 209.629 | 1.00 | 63.30 | C |
| ATOM | 1909 | O | GLN | A | 312 | 216.995 | 86.509 | 210.189 | 1.00 | 65.70 | O |
| ATOM | 1910 | N | ARG | A | 313 | 217.057 | 84.974 | 208.545 | 1.00 | 75.75 | N |
| ATOM | 1911 | CA | ARG | A | 313 | 218.278 | 85.463 | 207.924 | 1.00 | 58.86 | C |
| ATOM | 1912 | CB | ARG | A | 313 | 218.663 | 84.495 | 206.807 | 1.00 | 52.47 | C |
| ATOM | 1913 | CG | ARG | A | 313 | 220.131 | 84.401 | 206.516 | 1.00 | 74.86 | C |
| ATOM | 1914 | CD | ARG | A | 313 | 220.355 | 83.299 | 205.506 | 1.00 | 84.86 | C |
| ATOM | 1915 | NE | ARG | A | 313 | 219.851 | 82.018 | 205.984 | 1.00 | 53.52 | N |
| ATOM | 1916 | CZ | ARG | A | 313 | 219.467 | 81.032 | 205.186 | 1.00 | 62.95 | C |
| ATOM | 1917 | NH1 | ARG | A | 313 | 219.528 | 81.192 | 203.874 | 1.00 | 85.30 | N |
| ATOM | 1918 | NH2 | ARG | A | 313 | 219.039 | 79.888 | 205.697 | 1.00 | 49.87 | N |
| ATOM | 1919 | C | ARG | A | 313 | 218.184 | 86.894 | 207.391 | 1.00 | 51.81 | C |
| ATOM | 1920 | O | ARG | A | 313 | 217.125 | 87.341 | 206.952 | 1.00 | 85.05 | O |
| ATOM | 1921 | N | MET | A | 314 | 219.318 | 87.590 | 207.430 | 1.00 | 75.49 | N |

FIG. 3A-35

| ATOM | 1922 | CA | MET | A | 314 | 219.450 | 88.981 | 206.980 | 1.00 | 62.90 | C |
|---|---|---|---|---|---|---|---|---|---|---|---|
| ATOM | 1923 | CB | MET | A | 314 | 220.888 | 89.463 | 207.248 | 1.00 | 79.70 | C |
| ATOM | 1924 | CG | MET | A | 314 | 221.145 | 90.951 | 206.994 | 1.00 | 74.01 | C |
| ATOM | 1925 | SD | MET | A | 314 | 222.873 | 91.447 | 207.330 | 1.00 | 84.44 | S |
| ATOM | 1926 | CE | MET | A | 314 | 222.742 | 92.071 | 208.957 | 1.00 | 104.75 | C |
| ATOM | 1927 | C | MET | A | 314 | 219.115 | 89.160 | 205.496 | 1.00 | 68.20 | C |
| ATOM | 1928 | O | MET | A | 314 | 219.267 | 88.229 | 204.694 | 1.00 | 78.91 | O |
| ATOM | 1929 | N | THR | A | 315 | 218.660 | 90.357 | 205.135 | 1.00 | 63.73 | N |
| ATOM | 1930 | CA | THR | A | 315 | 218.319 | 90.652 | 203.750 | 1.00 | 64.98 | C |
| ATOM | 1931 | CB | THR | A | 315 | 217.075 | 91.545 | 203.661 | 1.00 | 62.15 | C |
| ATOM | 1932 | OG1 | THR | A | 315 | 217.322 | 92.813 | 204.286 | 1.00 | 58.05 | O |
| ATOM | 1933 | CG2 | THR | A | 315 | 215.929 | 90.868 | 204.338 | 1.00 | 61.97 | C |
| ATOM | 1934 | C | THR | A | 315 | 219.470 | 91.347 | 203.030 | 1.00 | 68.09 | C |
| ATOM | 1935 | O | THR | A | 315 | 220.317 | 91.969 | 203.658 | 1.00 | 63.59 | O |
| ATOM | 1936 | N | ILE | A | 316 | 219.498 | 91.236 | 201.707 | 1.00 | 65.76 | N |
| ATOM | 1937 | CA | ILE | A | 316 | 220.566 | 91.854 | 200.935 | 1.00 | 66.14 | C |
| ATOM | 1938 | CB | ILE | A | 316 | 220.417 | 91.583 | 199.426 | 1.00 | 60.35 | C |
| ATOM | 1939 | CG1 | ILE | A | 316 | 221.714 | 91.937 | 198.710 | 1.00 | 52.24 | C |
| ATOM | 1940 | CD1 | ILE | A | 316 | 222.942 | 91.410 | 199.405 | 1.00 | 55.83 | C |
| ATOM | 1941 | CG2 | ILE | A | 316 | 219.314 | 92.435 | 198.854 | 1.00 | 56.27 | C |
| ATOM | 1942 | C | ILE | A | 316 | 220.564 | 93.351 | 201.167 | 1.00 | 71.26 | C |
| ATOM | 1943 | O | ILE | A | 316 | 221.618 | 93.981 | 201.192 | 1.00 | 67.36 | O |
| ATOM | 1944 | N | THR | A | 317 | 219.381 | 93.926 | 201.346 | 1.00 | 60.50 | N |
| ATOM | 1945 | CA | THR | A | 317 | 219.301 | 95.356 | 201.591 | 1.00 | 58.94 | C |
| ATOM | 1946 | CB | THR | A | 317 | 217.865 | 95.875 | 201.554 | 1.00 | 68.58 | C |
| ATOM | 1947 | OG1 | THR | A | 317 | 217.301 | 95.636 | 200.259 | 1.00 | 67.56 | O |
| ATOM | 1948 | CG2 | THR | A | 317 | 217.844 | 97.364 | 201.860 | 1.00 | 50.05 | C |
| ATOM | 1949 | C | THR | A | 317 | 219.858 | 95.658 | 202.964 | 1.00 | 61.73 | C |
| ATOM | 1950 | O | THR | A | 317 | 220.533 | 96.659 | 203.161 | 1.00 | 69.91 | O |
| ATOM | 1951 | N | GLU | A | 318 | 219.577 | 94.794 | 203.923 | 1.00 | 54.23 | N |
| ATOM | 1952 | CA | GLU | A | 318 | 220.082 | 95.027 | 205.266 | 1.00 | 69.88 | C |
| ATOM | 1953 | CB | GLU | A | 318 | 219.336 | 94.138 | 206.269 | 1.00 | 82.03 | C |
| ATOM | 1954 | CG | GLU | A | 318 | 217.903 | 94.596 | 206.496 | 1.00 | 64.99 | C |
| ATOM | 1955 | CD | GLU | A | 318 | 217.152 | 93.742 | 207.486 | 1.00 | 85.92 | C |
| ATOM | 1956 | OE1 | GLU | A | 318 | 216.415 | 94.327 | 208.315 | 1.00 | 91.71 | O |
| ATOM | 1957 | OE2 | GLU | A | 318 | 217.288 | 92.497 | 207.424 | 1.00 | 88.17 | O |
| ATOM | 1958 | C | GLU | A | 318 | 221.586 | 94.796 | 205.348 | 1.00 | 72.99 | C |
| ATOM | 1959 | O | GLU | A | 318 | 222.262 | 95.329 | 206.221 | 1.00 | 64.78 | O |
| ATOM | 1960 | N | PHE | A | 319 | 222.103 | 94.005 | 204.421 | 1.00 | 75.36 | N |
| ATOM | 1961 | CA | PHE | A | 319 | 223.519 | 93.700 | 204.380 | 1.00 | 69.31 | C |
| ATOM | 1962 | CB | PHE | A | 319 | 223.744 | 92.455 | 203.523 | 1.00 | 78.91 | C |
| ATOM | 1963 | CG | PHE | A | 319 | 225.193 | 92.144 | 203.250 | 1.00 | 82.05 | C |
| ATOM | 1964 | CD1 | PHE | A | 319 | 225.978 | 91.538 | 204.210 | 1.00 | 64.69 | C |
| ATOM | 1965 | CE1 | PHE | A | 319 | 227.287 | 91.219 | 203.940 | 1.00 | 55.30 | C |
| ATOM | 1966 | CZ | PHE | A | 319 | 227.826 | 91.506 | 202.711 | 1.00 | 57.56 | C |
| ATOM | 1967 | CE2 | PHE | A | 319 | 227.060 | 92.114 | 201.744 | 1.00 | 75.06 | C |
| ATOM | 1968 | CD2 | PHE | A | 319 | 225.757 | 92.432 | 202.011 | 1.00 | 68.65 | C |
| ATOM | 1969 | C | PHE | A | 319 | 224.279 | 94.883 | 203.800 | 1.00 | 79.85 | C |
| ATOM | 1970 | O | PHE | A | 319 | 225.281 | 95.324 | 204.359 | 1.00 | 86.43 | O |
| ATOM | 1971 | N | MET | A | 320 | 223.805 | 95.404 | 202.679 | 1.00 | 64.36 | N |
| ATOM | 1972 | CA | MET | A | 320 | 224.489 | 96.527 | 202.066 | 1.00 | 69.16 | C |
| ATOM | 1973 | CB | MET | A | 320 | 223.848 | 96.889 | 200.725 | 1.00 | 73.27 | C |
| ATOM | 1974 | CG | MET | A | 320 | 224.120 | 95.877 | 199.635 | 1.00 | 72.98 | C |
| ATOM | 1975 | SD | MET | A | 320 | 225.832 | 95.315 | 199.691 | 1.00 | 87.32 | S |
| ATOM | 1976 | CE | MET | A | 320 | 226.586 | 96.413 | 198.528 | 1.00 | 70.20 | C |

FIG. 3A-36

| ATOM | 1977 | C | MET | A | 320 | 224.525 | 97.753 | 202.973 | 1.00 | 78.25 | C |
|---|---|---|---|---|---|---|---|---|---|---|---|
| ATOM | 1978 | O | MET | A | 320 | 225.304 | 98.673 | 202.745 | 1.00 | 86.13 | O |
| ATOM | 1979 | N | ASN | A | 321 | 223.695 | 97.772 | 204.006 | 1.00 | 77.28 | N |
| ATOM | 1980 | CA | ASN | A | 321 | 223.691 | 98.907 | 204.912 | 1.00 | 79.74 | C |
| ATOM | 1981 | CB | ASN | A | 321 | 222.271 | 99.296 | 205.267 | 1.00 | 79.55 | C |
| ATOM | 1982 | CG | ASN | A | 321 | 221.783 | 100.428 | 204.427 | 1.00 | 104.33 | C |
| ATOM | 1983 | OD1 | ASN | A | 321 | 222.191 | 101.578 | 204.622 | 1.00 | 115.09 | O |
| ATOM | 1984 | ND2 | ASN | A | 321 | 220.926 | 100.121 | 203.456 | 1.00 | 119.81 | N |
| ATOM | 1985 | C | ASN | A | 321 | 224.489 | 98.692 | 206.174 | 1.00 | 76.50 | C |
| ATOM | 1986 | O | ASN | A | 321 | 224.868 | 99.651 | 206.836 | 1.00 | 95.86 | O |
| ATOM | 1987 | N | HIS | A | 322 | 224.744 | 97.439 | 206.521 | 1.00 | 82.50 | N |
| ATOM | 1988 | CA | HIS | A | 322 | 225.527 | 97.179 | 207.707 | 1.00 | 80.78 | C |
| ATOM | 1989 | CB | HIS | A | 322 | 225.812 | 95.691 | 207.851 | 1.00 | 75.27 | C |
| ATOM | 1990 | CG | HIS | A | 322 | 226.690 | 95.370 | 209.013 | 1.00 | 76.67 | C |
| ATOM | 1991 | ND1 | HIS | A | 322 | 227.927 | 95.950 | 209.189 | 1.00 | 84.96 | N |
| ATOM | 1992 | CE1 | HIS | A | 322 | 228.464 | 95.502 | 210.308 | 1.00 | 85.58 | C |
| ATOM | 1993 | NE2 | HIS | A | 322 | 227.622 | 94.649 | 210.862 | 1.00 | 86.63 | N |
| ATOM | 1994 | CD2 | HIS | A | 322 | 226.504 | 94.548 | 210.070 | 1.00 | 67.42 | C |
| ATOM | 1995 | C | HIS | A | 322 | 226.837 | 97.948 | 207.555 | 1.00 | 84.39 | C |
| ATOM | 1996 | O | HIS | A | 322 | 227.483 | 97.895 | 206.506 | 1.00 | 83.28 | O |
| ATOM | 1997 | N | PRO | A | 323 | 227.234 | 98.686 | 208.603 | 1.00 | 91.61 | N |
| ATOM | 1998 | CA | PRO | A | 323 | 228.447 | 99.501 | 208.680 | 1.00 | 84.82 | C |
| ATOM | 1999 | CB | PRO | A | 323 | 228.567 | 99.772 | 210.170 | 1.00 | 74.59 | C |
| ATOM | 2000 | CG | PRO | A | 323 | 227.135 | 99.952 | 210.553 | 1.00 | 86.91 | C |
| ATOM | 2001 | CD | PRO | A | 323 | 226.484 | 98.767 | 209.868 | 1.00 | 92.14 | C |
| ATOM | 2002 | C | PRO | A | 323 | 229.697 | 98.867 | 208.087 | 1.00 | 79.23 | C |
| ATOM | 2003 | O | PRO | A | 323 | 230.318 | 99.436 | 207.193 | 1.00 | 85.59 | O |
| ATOM | 2004 | N | TRP | A | 324 | 230.066 | 97.692 | 208.578 | 1.00 | 81.53 | N |
| ATOM | 2005 | CA | TRP | A | 324 | 231.247 | 97.002 | 208.070 | 1.00 | 80.47 | C |
| ATOM | 2006 | CB | TRP | A | 324 | 231.225 | 95.553 | 208.537 | 1.00 | 79.62 | C |
| ATOM | 2007 | CG | TRP | A | 324 | 232.549 | 94.881 | 208.546 | 1.00 | 68.42 | C |
| ATOM | 2008 | CD1 | TRP | A | 324 | 233.579 | 95.118 | 209.408 | 1.00 | 97.23 | C |
| ATOM | 2009 | NE1 | TRP | A | 324 | 234.614 | 94.254 | 209.162 | 1.00 | 96.32 | N |
| ATOM | 2010 | CE2 | TRP | A | 324 | 234.268 | 93.437 | 208.120 | 1.00 | 90.15 | C |
| ATOM | 2011 | CD2 | TRP | A | 324 | 232.973 | 93.806 | 207.704 | 1.00 | 91.77 | C |
| ATOM | 2012 | CE3 | TRP | A | 324 | 232.382 | 93.118 | 206.639 | 1.00 | 85.73 | C |
| ATOM | 2013 | CZ3 | TRP | A | 324 | 233.091 | 92.099 | 206.038 | 1.00 | 78.54 | C |
| ATOM | 2014 | CH2 | TRP | A | 324 | 234.375 | 91.755 | 206.475 | 1.00 | 83.38 | C |
| ATOM | 2015 | CZ2 | TRP | A | 324 | 234.979 | 92.411 | 207.515 | 1.00 | 55.96 | C |
| ATOM | 2016 | C | TRP | A | 324 | 231.260 | 97.039 | 206.541 | 1.00 | 76.75 | C |
| ATOM | 2017 | O | TRP | A | 324 | 232.288 | 97.293 | 205.917 | 1.00 | 63.50 | O |
| ATOM | 2018 | N | ILE | A | 325 | 230.099 | 96.785 | 205.952 | 1.00 | 61.98 | N |
| ATOM | 2019 | CA | ILE | A | 325 | 229.956 | 96.764 | 204.513 | 1.00 | 63.34 | C |
| ATOM | 2020 | CB | ILE | A | 325 | 228.723 | 95.941 | 204.092 | 1.00 | 64.13 | C |
| ATOM | 2021 | CG1 | ILE | A | 325 | 229.156 | 94.621 | 203.470 | 1.00 | 57.81 | C |
| ATOM | 2022 | CD1 | ILE | A | 325 | 230.005 | 93.796 | 204.357 | 1.00 | 99.33 | C |
| ATOM | 2023 | CG2 | ILE | A | 325 | 227.909 | 96.703 | 203.076 | 1.00 | 79.69 | C |
| ATOM | 2024 | C | ILE | A | 325 | 229.832 | 98.156 | 203.920 | 1.00 | 81.46 | C |
| ATOM | 2025 | O | ILE | A | 325 | 230.518 | 98.483 | 202.956 | 1.00 | 101.97 | O |
| ATOM | 2026 | N | MET | A | 326 | 228.971 | 98.986 | 204.497 | 1.00 | 86.84 | N |
| ATOM | 2027 | CA | MET | A | 326 | 228.766 | 100.327 | 203.962 | 1.00 | 97.80 | C |
| ATOM | 2028 | CB | MET | A | 326 | 227.509 | 100.951 | 204.573 | 1.00 | 99.22 | C |
| ATOM | 2029 | CG | MET | A | 326 | 227.134 | 102.287 | 203.957 | 1.00 | 109.19 | C |
| ATOM | 2030 | SD | MET | A | 326 | 225.425 | 102.771 | 204.309 | 1.00 | 131.16 | S |
| ATOM | 2031 | CE | MET | A | 326 | 224.679 | 102.571 | 202.683 | 1.00 | 123.49 | C |

FIG. 3A-37

| ATOM | 2032 | C | MET | A | 326 | 229.941 | 101.291 | 204.108 | 1.00 | 88.82 | C |
| --- | --- | --- | --- | --- | --- | --- | --- | --- | --- | --- | --- |
| ATOM | 2033 | O | MET | A | 326 | 230.023 | 102.271 | 203.375 | 1.00 | 96.42 | O |
| ATOM | 2034 | N | GLN | A | 327 | 230.847 | 101.016 | 205.042 | 1.00 | 99.42 | N |
| ATOM | 2035 | CA | GLN | A | 327 | 232.005 | 101.880 | 205.253 | 1.00 | 100.47 | C |
| ATOM | 2036 | CB | GLN | A | 327 | 231.856 | 102.668 | 206.557 | 1.00 | 90.31 | C |
| ATOM | 2037 | CG | GLN | A | 327 | 230.780 | 103.743 | 206.538 | 1.00 | 124.03 | C |
| ATOM | 2038 | CD | GLN | A | 327 | 230.929 | 104.713 | 205.370 | 1.00 | 165.27 | C |
| ATOM | 2039 | OE1 | GLN | A | 327 | 232.047 | 105.051 | 204.958 | 1.00 | 160.87 | O |
| ATOM | 2040 | NE2 | GLN | A | 327 | 229.795 | 105.178 | 204.841 | 1.00 | 148.79 | N |
| ATOM | 2041 | C | GLN | A | 327 | 233.330 | 101.120 | 205.290 | 1.00 | 109.31 | C |
| ATOM | 2042 | O | GLN | A | 327 | 234.060 | 101.184 | 206.279 | 1.00 | 116.79 | O |
| ATOM | 2043 | N | SER | A | 328 | 233.644 | 100.406 | 204.215 | 1.00 | 109.39 | N |
| ATOM | 2044 | CA | SER | A | 328 | 234.888 | 99.643 | 204.157 | 1.00 | 117.56 | C |
| ATOM | 2045 | CB | SER | A | 328 | 235.055 | 99.008 | 202.777 | 1.00 | 106.48 | C |
| ATOM | 2046 | OG | SER | A | 328 | 233.976 | 98.139 | 202.490 | 1.00 | 101.32 | O |
| ATOM | 2047 | C | SER | A | 328 | 236.084 | 100.539 | 204.457 | 1.00 | 126.63 | C |
| ATOM | 2048 | O | SER | A | 328 | 236.892 | 100.239 | 205.332 | 1.00 | 122.39 | O |
| ATOM | 2049 | N | THR | A | 329 | 236.189 | 101.642 | 203.725 | 1.00 | 147.22 | N |
| ATOM | 2050 | CA | THR | A | 329 | 237.283 | 102.582 | 203.919 | 1.00 | 153.16 | C |
| ATOM | 2051 | CB | THR | A | 329 | 236.918 | 103.986 | 203.365 | 1.00 | 159.02 | C |
| ATOM | 2052 | OG1 | THR | A | 329 | 237.929 | 104.930 | 203.748 | 1.00 | 164.35 | O |
| ATOM | 2053 | CG2 | THR | A | 329 | 235.553 | 104.443 | 203.893 | 1.00 | 171.23 | C |
| ATOM | 2054 | C | THR | A | 329 | 237.668 | 102.713 | 205.393 | 1.00 | 151.36 | C |
| ATOM | 2055 | O | THR | A | 329 | 238.849 | 102.680 | 205.736 | 1.00 | 165.48 | O |
| ATOM | 2056 | N | ALA | A | 330 | 236.670 | 102.840 | 206.262 | 1.00 | 138.67 | N |
| ATOM | 2057 | CA | ALA | A | 330 | 236.916 | 102.994 | 207.691 | 1.00 | 128.38 | C |
| ATOM | 2058 | CB | ALA | A | 330 | 235.867 | 103.931 | 208.298 | 1.00 | 134.91 | C |
| ATOM | 2059 | C | ALA | A | 330 | 236.937 | 101.670 | 208.457 | 1.00 | 134.38 | C |
| ATOM | 2060 | O | ALA | A | 330 | 236.425 | 101.586 | 209.580 | 1.00 | 138.61 | O |
| ATOM | 2061 | N | VAL | A | 331 | 237.526 | 100.637 | 207.860 | 1.00 | 122.49 | N |
| ATOM | 2062 | CA | VAL | A | 331 | 237.608 | 99.340 | 208.531 | 1.00 | 120.28 | C |
| ATOM | 2063 | CB | VAL | A | 331 | 236.770 | 98.239 | 207.785 | 1.00 | 120.15 | C |
| ATOM | 2064 | CG1 | VAL | A | 331 | 237.342 | 97.971 | 206.422 | 1.00 | 125.69 | C |
| ATOM | 2065 | CG2 | VAL | A | 331 | 236.740 | 96.946 | 208.595 | 1.00 | 124.20 | C |
| ATOM | 2066 | C | VAL | A | 331 | 239.066 | 98.890 | 208.689 | 1.00 | 111.19 | C |
| ATOM | 2067 | O | VAL | A | 331 | 239.850 | 98.899 | 207.739 | 1.00 | 85.41 | O |
| ATOM | 2068 | N | PRO | A | 332 | 239.433 | 98.496 | 209.916 | 1.00 | 102.76 | N |
| ATOM | 2069 | CA | PRO | A | 332 | 240.737 | 98.021 | 210.385 | 1.00 | 105.52 | C |
| ATOM | 2070 | CB | PRO | A | 332 | 240.369 | 97.193 | 211.609 | 1.00 | 105.70 | C |
| ATOM | 2071 | CG | PRO | A | 332 | 239.247 | 97.970 | 212.184 | 1.00 | 122.25 | C |
| ATOM | 2072 | CD | PRO | A | 332 | 238.418 | 98.332 | 210.971 | 1.00 | 100.61 | C |
| ATOM | 2073 | C | PRO | A | 332 | 241.528 | 97.215 | 209.363 | 1.00 | 112.97 | C |
| ATOM | 2074 | O | PRO | A | 332 | 241.016 | 96.262 | 208.779 | 1.00 | 111.93 | O |
| ATOM | 2075 | N | GLN | A | 333 | 242.782 | 97.604 | 209.154 | 1.00 | 109.39 | N |
| ATOM | 2076 | CA | GLN | A | 333 | 243.645 | 96.908 | 208.206 | 1.00 | 106.56 | C |
| ATOM | 2077 | CB | GLN | A | 333 | 244.744 | 97.842 | 207.696 | 1.00 | 117.29 | C |
| ATOM | 2078 | CG | GLN | A | 333 | 244.224 | 99.042 | 206.922 | 1.00 | 121.73 | C |
| ATOM | 2079 | CD | GLN | A | 333 | 244.771 | 99.095 | 205.510 | 1.00 | 144.41 | C |
| ATOM | 2080 | OE1 | GLN | A | 333 | 244.442 | 99.996 | 204.735 | 1.00 | 153.63 | O |
| ATOM | 2081 | NE2 | GLN | A | 333 | 245.613 | 98.124 | 205.165 | 1.00 | 138.94 | N |
| ATOM | 2082 | C | GLN | A | 333 | 244.265 | 95.714 | 208.913 | 1.00 | 99.10 | C |
| ATOM | 2083 | O | GLN | A | 333 | 245.347 | 95.251 | 208.554 | 1.00 | 97.72 | O |
| ATOM | 2084 | N | THR | A | 334 | 243.565 | 95.229 | 209.931 | 1.00 | 88.60 | N |
| ATOM | 2085 | CA | THR | A | 334 | 244.023 | 94.081 | 210.693 | 1.00 | 112.85 | C |
| ATOM | 2086 | CB | THR | A | 334 | 242.989 | 93.668 | 211.738 | 1.00 | 105.19 | C |

FIG. 3A-38

| ATOM | 2087 | OG1 | THR | A | 334 | 243.011 | 92.243 | 211.887 | 1.00 | 102.93 | O |
|---|---|---|---|---|---|---|---|---|---|---|---|
| ATOM | 2088 | CG2 | THR | A | 334 | 241.607 | 94.120 | 211.315 | 1.00 | 106.97 | C |
| ATOM | 2089 | C | THR | A | 334 | 244.310 | 92.878 | 209.797 | 1.00 | 123.95 | C |
| ATOM | 2090 | O | THR | A | 334 | 243.438 | 92.392 | 209.086 | 1.00 | 128.29 | O |
| ATOM | 2091 | N | PRO | A | 335 | 245.549 | 92.372 | 209.832 | 1.00 | 124.58 | N |
| ATOM | 2092 | CA | PRO | A | 335 | 245.911 | 91.224 | 209.005 | 1.00 | 124.62 | C |
| ATOM | 2093 | CB | PRO | A | 335 | 247.383 | 91.002 | 209.358 | 1.00 | 134.66 | C |
| ATOM | 2094 | CG | PRO | A | 335 | 247.857 | 92.390 | 209.673 | 1.00 | 120.03 | C |
| ATOM | 2095 | CD | PRO | A | 335 | 246.730 | 92.881 | 210.547 | 1.00 | 120.76 | C |
| ATOM | 2096 | C | PRO | A | 335 | 245.058 | 89.999 | 209.317 | 1.00 | 119.67 | C |
| ATOM | 2097 | O | PRO | A | 335 | 244.513 | 89.878 | 210.416 | 1.00 | 108.06 | O |
| ATOM | 2098 | N | LEU | A | 336 | 244.926 | 89.110 | 208.333 | 1.00 | 110.96 | N |
| ATOM | 2099 | CA | LEU | A | 336 | 244.175 | 87.867 | 208.499 | 1.00 | 98.45 | C |
| ATOM | 2100 | CB | LEU | A | 336 | 242.909 | 87.852 | 207.632 | 1.00 | 95.92 | C |
| ATOM | 2101 | CG | LEU | A | 336 | 241.694 | 88.725 | 207.963 | 1.00 | 81.15 | C |
| ATOM | 2102 | CD1 | LEU | A | 336 | 241.641 | 88.972 | 209.461 | 1.00 | 94.01 | C |
| ATOM | 2103 | CD2 | LEU | A | 336 | 241.773 | 90.034 | 207.215 | 1.00 | 82.79 | C |
| ATOM | 2104 | C | LEU | A | 336 | 245.087 | 86.726 | 208.066 | 1.00 | 87.77 | C |
| ATOM | 2105 | O | LEU | A | 336 | 245.851 | 86.877 | 207.117 | 1.00 | 92.64 | O |
| ATOM | 2106 | N | HIS | A | 337 | 244.999 | 85.595 | 208.762 | 1.00 | 86.05 | N |
| ATOM | 2107 | CA | HIS | A | 337 | 245.813 | 84.410 | 208.469 | 1.00 | 100.05 | C |
| ATOM | 2108 | CB | HIS | A | 337 | 245.687 | 83.390 | 209.610 | 1.00 | 118.04 | C |
| ATOM | 2109 | CG | HIS | A | 337 | 246.205 | 83.874 | 210.930 | 1.00 | 151.49 | C |
| ATOM | 2110 | ND1 | HIS | A | 337 | 246.241 | 85.210 | 211.271 | 1.00 | 169.76 | N |
| ATOM | 2111 | CE1 | HIS | A | 337 | 246.713 | 85.337 | 212.502 | 1.00 | 129.99 | C |
| ATOM | 2112 | NE2 | HIS | A | 337 | 246.984 | 84.132 | 212.971 | 1.00 | 150.26 | N |
| ATOM | 2113 | CD2 | HIS | A | 337 | 246.675 | 83.198 | 212.010 | 1.00 | 160.51 | C |
| ATOM | 2114 | C | HIS | A | 337 | 245.401 | 83.709 | 207.170 | 1.00 | 103.25 | C |
| ATOM | 2115 | O | HIS | A | 337 | 246.075 | 82.782 | 206.712 | 1.00 | 110.52 | O |
| ATOM | 2116 | N | THR | A | 338 | 244.294 | 84.167 | 206.589 | 1.00 | 111.23 | N |
| ATOM | 2117 | CA | THR | A | 338 | 243.713 | 83.590 | 205.375 | 1.00 | 105.16 | C |
| ATOM | 2118 | CB | THR | A | 338 | 242.957 | 84.658 | 204.557 | 1.00 | 100.36 | C |
| ATOM | 2119 | OG1 | THR | A | 338 | 242.218 | 85.494 | 205.451 | 1.00 | 103.82 | O |
| ATOM | 2120 | CG2 | THR | A | 338 | 241.961 | 83.993 | 203.605 | 1.00 | 97.07 | C |
| ATOM | 2121 | C | THR | A | 338 | 244.649 | 82.822 | 204.440 | 1.00 | 106.58 | C |
| ATOM | 2122 | O | THR | A | 338 | 244.708 | 81.589 | 204.504 | 1.00 | 102.89 | O |
| ATOM | 2123 | N | SER | A | 339 | 245.370 | 83.532 | 203.573 | 1.00 | 100.67 | N |
| ATOM | 2124 | CA | SER | A | 339 | 246.276 | 82.877 | 202.622 | 1.00 | 106.75 | C |
| ATOM | 2125 | CB | SER | A | 339 | 247.341 | 83.855 | 202.137 | 1.00 | 100.87 | C |
| ATOM | 2126 | OG | SER | A | 339 | 246.771 | 84.880 | 201.348 | 1.00 | 116.32 | O |
| ATOM | 2127 | C | SER | A | 339 | 246.957 | 81.641 | 203.202 | 1.00 | 117.17 | C |
| ATOM | 2128 | O | SER | A | 339 | 246.862 | 80.555 | 202.634 | 1.00 | 126.71 | O |
| ATOM | 2129 | N | ARG | A | 340 | 247.643 | 81.811 | 204.329 | 1.00 | 108.64 | N |
| ATOM | 2130 | CA | ARG | A | 340 | 248.325 | 80.697 | 204.971 | 1.00 | 101.87 | C |
| ATOM | 2131 | CB | ARG | A | 340 | 248.848 | 81.112 | 206.347 | 1.00 | 117.73 | C |
| ATOM | 2132 | CG | ARG | A | 340 | 250.041 | 82.055 | 206.292 | 1.00 | 162.36 | C |
| ATOM | 2133 | CD | ARG | A | 340 | 249.770 | 83.353 | 207.068 | 1.00 | 208.75 | C |
| ATOM | 2134 | NE | ARG | A | 340 | 249.607 | 83.107 | 208.504 | 1.00 | 216.90 | N |
| ATOM | 2135 | CZ | ARG | A | 340 | 249.378 | 84.053 | 209.416 | 1.00 | 203.42 | C |
| ATOM | 2136 | NH1 | ARG | A | 340 | 249.279 | 85.330 | 209.055 | 1.00 | 186.56 | N |
| ATOM | 2137 | NH2 | ARG | A | 340 | 249.255 | 83.719 | 210.696 | 1.00 | 191.24 | N |
| ATOM | 2138 | C | ARG | A | 340 | 247.391 | 79.508 | 205.121 | 1.00 | 94.03 | C |
| ATOM | 2139 | O | ARG | A | 340 | 247.554 | 78.480 | 204.454 | 1.00 | 80.82 | O |
| ATOM | 2140 | N | VAL | A | 341 | 246.412 | 79.653 | 206.004 | 1.00 | 84.97 | N |
| ATOM | 2141 | CA | VAL | A | 341 | 245.455 | 78.585 | 206.239 | 1.00 | 88.40 | C |

FIG. 3A-39

| ATOM | 2142 | CB | VAL | A | 341 | 244.269 | 79.077 | 207.078 | 1.00 | 86.60 | C |
| --- | --- | --- | --- | --- | --- | --- | --- | --- | --- | --- | --- |
| ATOM | 2143 | CG1 | VAL | A | 341 | 243.692 | 77.928 | 207.866 | 1.00 | 93.99 | C |
| ATOM | 2144 | CG2 | VAL | A | 341 | 244.700 | 80.214 | 207.975 | 1.00 | 87.95 | C |
| ATOM | 2145 | C | VAL | A | 341 | 244.913 | 78.128 | 204.891 | 1.00 | 93.56 | C |
| ATOM | 2146 | O | VAL | A | 341 | 244.917 | 76.939 | 204.566 | 1.00 | 86.14 | O |
| ATOM | 2147 | N | LEU | A | 342 | 244.463 | 79.101 | 204.107 | 1.00 | 98.12 | N |
| ATOM | 2148 | CA | LEU | A | 342 | 243.887 | 78.847 | 202.798 | 1.00 | 97.33 | C |
| ATOM | 2149 | CB | LEU | A | 342 | 243.666 | 80.171 | 202.065 | 1.00 | 101.09 | C |
| ATOM | 2150 | CG | LEU | A | 342 | 242.513 | 80.212 | 201.065 | 1.00 | 102.01 | C |
| ATOM | 2151 | CD1 | LEU | A | 342 | 241.211 | 79.865 | 201.761 | 1.00 | 89.86 | C |
| ATOM | 2152 | CD2 | LEU | A | 342 | 242.428 | 81.595 | 200.463 | 1.00 | 76.62 | C |
| ATOM | 2153 | C | LEU | A | 342 | 244.771 | 77.929 | 201.976 | 1.00 | 103.21 | C |
| ATOM | 2154 | O | LEU | A | 342 | 244.280 | 77.134 | 201.181 | 1.00 | 108.03 | O |
| ATOM | 2155 | N | LYS | A | 343 | 246.078 | 78.031 | 202.177 | 1.00 | 118.91 | N |
| ATOM | 2156 | CA | LYS | A | 343 | 246.980 | 77.154 | 201.447 | 1.00 | 128.99 | C |
| ATOM | 2157 | CB | LYS | A | 343 | 248.308 | 77.894 | 201.320 | 1.00 | 131.78 | C |
| ATOM | 2158 | CG | LYS | A | 343 | 249.233 | 77.265 | 200.274 | 1.00 | 133.47 | C |
| ATOM | 2159 | CD | LYS | A | 343 | 250.528 | 78.061 | 200.106 | 1.00 | 161.36 | C |
| ATOM | 2160 | CE | LYS | A | 343 | 251.591 | 77.288 | 199.318 | 1.00 | 189.16 | C |
| ATOM | 2161 | NZ | LYS | A | 343 | 252.882 | 77.968 | 199.425 | 1.00 | 166.57 | N |
| ATOM | 2162 | C | LYS | A | 343 | 247.211 | 75.800 | 202.144 | 1.00 | 129.81 | C |
| ATOM | 2163 | O | LYS | A | 343 | 247.730 | 74.859 | 201.559 | 1.00 | 124.36 | O |
| ATOM | 2164 | N | GLU | A | 344 | 246.842 | 75.714 | 203.442 | 1.00 | 128.07 | N |
| ATOM | 2165 | CA | GLU | A | 344 | 247.254 | 74.549 | 204.240 | 1.00 | 135.55 | C |
| ATOM | 2166 | CB | GLU | A | 344 | 247.196 | 74.935 | 205.720 | 1.00 | 144.51 | C |
| ATOM | 2167 | CG | GLU | A | 344 | 248.480 | 74.589 | 206.485 | 1.00 | 182.52 | C |
| ATOM | 2168 | CD | GLU | A | 344 | 249.414 | 75.782 | 206.484 | 1.00 | 205.75 | C |
| ATOM | 2169 | OE1 | GLU | A | 344 | 249.252 | 76.650 | 207.336 | 1.00 | 195.59 | O |
| ATOM | 2170 | OE2 | GLU | A | 344 | 250.270 | 75.861 | 205.607 | 1.00 | 217.38 | O |
| ATOM | 2171 | C | GLU | A | 344 | 246.429 | 73.272 | 203.985 | 1.00 | 137.12 | C |
| ATOM | 2172 | O | GLU | A | 344 | 246.915 | 72.156 | 204.102 | 1.00 | 147.11 | O |
| ATOM | 2173 | N | ASP | A | 345 | 245.127 | 73.456 | 203.702 | 1.00 | 134.97 | N |
| ATOM | 2174 | CA | ASP | A | 345 | 244.310 | 72.298 | 203.321 | 1.00 | 153.39 | C |
| ATOM | 2175 | CB | ASP | A | 345 | 243.435 | 71.892 | 204.514 | 1.00 | 147.36 | C |
| ATOM | 2176 | CG | ASP | A | 345 | 242.851 | 70.495 | 204.291 | 1.00 | 174.56 | C |
| ATOM | 2177 | OD1 | ASP | A | 345 | 243.455 | 69.731 | 203.533 | 1.00 | 191.84 | O |
| ATOM | 2178 | OD2 | ASP | A | 345 | 241.820 | 70.182 | 204.883 | 1.00 | 169.86 | O |
| ATOM | 2179 | C | ASP | A | 345 | 243.429 | 72.611 | 202.107 | 1.00 | 164.28 | C |
| ATOM | 2180 | O | ASP | A | 345 | 243.779 | 73.413 | 201.250 | 1.00 | 177.09 | O |
| ATOM | 2181 | OXT | ASP | A | 345 | 242.356 | 71.976 | 201.992 | 1.00 | 173.04 | O |
| ATOM | 2182 | O1A | ADP | B | 1 | 230.276 | 79.816 | 184.543 | 1.00 | 174.47 | O |
| ATOM | 2183 | PA | ADP | B | 1 | 230.706 | 78.491 | 184.989 | 1.00 | 102.14 | P |
| ATOM | 2184 | O2A | ADP | B | 1 | 230.524 | 78.380 | 186.435 | 1.00 | 153.66 | O |
| ATOM | 2185 | O3A | ADP | B | 1 | 229.878 | 77.381 | 184.234 | 1.00 | 60.21 | O |
| ATOM | 2186 | PB | ADP | B | 1 | 229.414 | 75.930 | 184.638 | 1.00 | 144.05 | P |
| ATOM | 2187 | O3B | ADP | B | 1 | 230.444 | 74.946 | 184.218 | 1.00 | 144.86 | O |
| ATOM | 2188 | O2B | ADP | B | 1 | 229.282 | 76.005 | 186.238 | 1.00 | 122.65 | O |
| ATOM | 2189 | O1B | ADP | B | 1 | 228.095 | 75.638 | 184.020 | 1.00 | 142.49 | O |
| ATOM | 2190 | O5* | ADP | B | 1 | 232.245 | 78.264 | 184.682 | 1.00 | 117.31 | O |
| ATOM | 2191 | C5* | ADP | B | 1 | 232.874 | 77.159 | 184.030 | 1.00 | 53.55 | C |
| ATOM | 2192 | C4* | ADP | B | 1 | 234.396 | 77.400 | 184.260 | 1.00 | 67.72 | C |
| ATOM | 2193 | O4* | ADP | B | 1 | 234.874 | 78.078 | 183.094 | 1.00 | 74.41 | O |
| ATOM | 2194 | C1* | ADP | B | 1 | 235.708 | 79.212 | 183.442 | 1.00 | 75.90 | C |
| ATOM | 2195 | C2* | ADP | B | 1 | 235.912 | 79.155 | 184.952 | 1.00 | 75.95 | C |
| ATOM | 2196 | O2* | ADP | B | 1 | 237.163 | 78.609 | 185.403 | 1.00 | 92.70 | O |

FIG. 3A-40

| ATOM | 2197 | C3* | ADP | B | 1 | 234.701 | 78.366 | 185.418 | 1.00 | 57.09 | C |
|------|------|-----|-----|---|---|---------|--------|---------|------|-------|---|
| ATOM | 2198 | O3* | ADP | B | 1 | 234.973 | 77.677 | 186.650 | 1.00 | 113.37 | O |
| ATOM | 2199 | N9 | ADP | B | 1 | 234.976 | 80.439 | 182.996 | 1.00 | 81.65 | N |
| ATOM | 2200 | C8 | ADP | B | 1 | 233.649 | 80.489 | 182.770 | 1.00 | 67.80 | C |
| ATOM | 2201 | N7 | ADP | B | 1 | 233.314 | 81.705 | 182.387 | 1.00 | 84.52 | N |
| ATOM | 2202 | C5 | ADP | B | 1 | 234.401 | 82.426 | 182.294 | 1.00 | 77.01 | C |
| ATOM | 2203 | C6 | ADP | B | 1 | 234.688 | 83.726 | 181.905 | 1.00 | 74.49 | C |
| ATOM | 2204 | N6 | ADP | B | 1 | 233.702 | 84.538 | 181.513 | 1.00 | 67.62 | N |
| ATOM | 2205 | C4 | ADP | B | 1 | 235.482 | 81.611 | 182.690 | 1.00 | 72.84 | C |
| ATOM | 2206 | N3 | ADP | B | 1 | 236.742 | 82.122 | 182.681 | 1.00 | 88.25 | N |
| ATOM | 2207 | C2 | ADP | B | 1 | 237.002 | 83.396 | 182.326 | 1.00 | 72.98 | C |
| ATOM | 2208 | N1 | ADP | B | 1 | 235.979 | 84.183 | 181.928 | 1.00 | 58.39 | N |

FIG. 4

| M | G | Q | Q | F | P | Q | F | H | V |
|---|---|---|---|---|---|---|---|---|---|
| ATG | GGT | CAG | CAG | TTC | CCG | CAG | TTC | CAC | GTC |
| K | S | G | L | Q | I | K | K | N | A |
| AAG | TCC | GGC | CTG | CAG | ATC | AAG | AAG | AAC | GCC |
| I | I | D | D | Y | K | V | T | S | Q |
| ATC | ATC | GAT | GAC | TAC | AAG | GTC | ACC | AGC | CAG |
| V | L | G | L | G | I | N | G | K | V |
| GTC | CTG | GGG | CTG | GGC | ATC | AAC | GGC | AAA | GTT |
| L | Q | I | F | N | K | R | T | Q | E |
| TTG | CAG | ATC | TTC | AAC | AAG | AGG | ACC | CAG | GAG |
| K | F | A | L | K | M | L | Q | D | C |
| AAA | TTC | GCC | CTC | AAA | ATG | CTT | CAG | GAC | TGC |
| P | K | A | R | R | E | V | E | L | H |
| CCC | AAG | GCC | CGC | AGG | GAG | GTG | GAG | CTG | CAC |
| W | R | A | S | Q | C | P | H | I | V |
| TGG | CGG | GCC | TCC | CAG | TGC | CCG | CAC | ATC | GTA |
| R | I | V | D | V | Y | E | N | L | Y |
| CGG | ATC | GTG | GAT | GTG | TAC | GAG | AAT | CTG | TAC |
| A | G | R | K | C | L | L | I | V | M |
| GCA | GGG | AGG | AAG | TGC | CTG | CTG | ATT | GTC | ATG |
| E | C | L | D | G | G | E | L | F | S |
| GAA | TGT | TTG | GAC | GGT | GGA | GAA | CTC | TTT | AGC |
| R | I | Q | D | R | G | D | Q | A | F |
| CGA | ATC | CAG | GAT | CGA | GGA | GAC | CAG | GCA | TTC |
| T | E | R | E | A | S | E | I | M | K |
| ACA | GAA | AGA | GAA | GCA | TCC | GAA | ATC | ATG | AAG |
| S | I | G | E | A | I | Q | Y | L | H |
| AGC | ATC | GGT | GAG | GCC | ATC | CAG | TAT | CTG | CAT |
| S | I | N | I | A | H | R | D | V | K |
| TCA | ATC | AAC | ATT | GCC | CAT | CGG | GAT | GTC | AAG |
| P | E | N | L | L | Y | T | S | K | R |
| CCT | GAG | AAT | CTC | TTA | TAC | ACC | TCC | AAA | AGG |
| P | N | A | I | L | K | L | T | D | F |
| CCC | AAC | GCC | ATC | CTG | AAA | CTC | ACT | GAC | TTT |
| G | F | A | K | E | T | T | S | H | N |
| GGC | TTT | GCC | AAG | GAA | ACC | ACC | AGC | CAC | AAC |
| S | L | T | T | P | C | Y | T | P | Y |
| TCT | TTG | ACC | ACT | CCT | TGT | TAT | ACA | CCG | TAC |
| Y | V | A | P | E | V | L | G | P | E |
| TAT | GTG | GCT | CCA | GAA | GTG | CTG | GGT | CCA | GAG |
| K | Y | D | K | S | C | D | M | W | S |
| AAG | TAT | GAC | AAG | TCC | TGT | GAC | ATG | TGG | TCC |
| L | G | V | I | M | Y | I | L | L | C |
| CTG | GGT | GTC | ATC | ATG | TAC | ATC | CTG | CTG | TGT |

FIG. 4A-1

| G | Y | P | P | F | Y | S | N | H | G |
|---|---|---|---|---|---|---|---|---|---|
| GGG | TAT | CCC | CCC | TTC | TAC | TCC | AAC | CAC | GGC |
| L | A | I | S | P | G | M | K | T | R |
| CTT | GCC | ATC | TCT | CCG | GGC | ATG | AAG | ACT | CGC |
| I | R | M | G | Q | Y | E | F | P | N |
| ATC | CGA | ATG | GGC | CAG | TAT | GAA | TTT | CCC | AAC |
| P | E | W | S | E | V | S | E | E | V |
| CCA | GAA | TGG | TCA | GAA | GTA | TCA | GAG | GAA | GTG |
| K | M | L | I | R | N | L | L | K | T |
| AAG | ATG | CTC | ATT | CGG | AAT | CTG | CTG | AAA | ACA |
| E | P | T | Q | R | M | T | I | T | E |
| GAG | CCC | ACC | CAG | AGA | ATG | ACC | ATC | ACC | GAG |
| F | M | N | H | P | W | I | M | Q | S |
| TTT | ATG | AAC | CAC | CCT | TGG | ATC | ATG | CAA | TCA |
| T | K | V | P | Q | T | P | L | H | T |
| ACA | AAG | GTC | CCT | CAA | ACC | CCA | CTG | CAC | ACC |
| S | R | V | L | K | E | D | K | E | R |
| AGC | CGG | GTC | CTG | AAG | GAG | GAC | AAG | GAG | CGG |
| W | E | D | V | K | E | E | M | T | S |
| TGG | GAG | GAT | GTC | AAG | GAG | GAG | ATG | ACC | AGT |
| A | L | A | T | M | R |  |  |  |  |
| GCC | TTG | GCC | ACA | ATG | CGC | TGA |  |  |  | ns
METHODS FOR IDENTIFYING AGENTS THAT INTERACT WITH MAP KINASE ACTIVATED PROTEIN KINASE 2

FIELD OF THE INVENTION

The present invention relates to the identification of the crystal structures of MK2, and the use of the structures for designing new drugs.

BACKGROUND OF THE INVENTION

Mitogen activated protein (MAP) kinases are a large and diverse group of Ser/Thr kinases separated into three major subgroups, which include the extracellular signal regulated kinases (ERKs), the c-Jun N-terminal kinases (JNKs)/stress-activated protein kinases (JNKs) and p38/reactivating kinases (RK). The ERKs are activated by mitogens and growth factors, whereas the JNKs/SAPKs and p38/RK are activated by bacterial lipopolysaccharide (LPS, interleukin-1 (IL-1), tumor necrosis factor-α (TNF-α) and cellular stresses such as heat shock, osmotic shock, or UV damage. Exposure of cells to these factors results in the increased production of proinflammatory cytokines. Analysis of a specific inhibitor of p38 MAP kinase, SB203580, reveals that it inhibits LPS-induced cytokine synthesis in human monocytes, thus indicating that p38 is the MAP kinase responsible for stress-induced cytokine production (1). SB203580 also prevents the activation of MAP kinase activated protein kinase 2 (MK2), suggesting that this kinase is activated by P38 (2).

Mice engineered to be homozygously-deficient in MK2 show a reduction in TNF-α, interferon-γ, IL-1β, and IL-6 production and an increased rate of survival upon challenge with LPS, suggesting that this enzyme is a key component in the inflammatory process and a potential target for anti-inflammatory therapy (3). Activation of MK2 results in the production of cytokines by regulating the translation and or stability of the encoding mRNAs through the AU-rich elements of the 3'-untranslated regions of the gene (4). MK2 also phosphorylates the transcription factor CREB, as well as leukocyte specific protein-1 and heat shock protein 25/27, which are involved in the regulation of actin polymerization (5–8) and cell migration (9, 10).

MK2 is a multi-domain protein consisting of an N-terminal proline-rich domain, a catalytic domain, an autoinhibitory domain and at the C-terminus a nuclear export signal (NES) and nuclear localization signal (NLS) (11–15). Two isoforms of human MK2 have been characterized. One isoform consists of 400 amino acids and the other isoform 370 residues which is thought to be a splice variant missing the C-terminal NLS (11, 16, 12). MK2 is located in the nucleus of the cell and upon binding and phosphorylation by p38, the MK2 NES becomes functional and both kinases are co-transported out of the nucleus to the cytoplasm (8, 12, 13, 17). Interestingly, transport of the MK2/p38 complex does not require catalytically active MK2, as the active site mutant, Asp207Ala, is still transported to the cytoplasm (13). Phosphorylation of human MK2 by p38 on residues T222, S272 and T334 is thought to activate the enzyme by inducing a conformational change of the autoinhibitory domain thus exposing the active site for substrate binding (8, 18). Mutations of two autoinhibitory domain residues W332A and K326E in murine MK2 demonstrate an increase in basal activity and a C-terminal deletion of the autoinhibitory domain renders the enzyme constitutively active, providing additional evidence to the role of this domain in inhibition of MK2 activity (18).

Recently, Meng, et al., published the structure of the autoinhibited, inactive form of MK2 47-400. However, since MK2 47-400 used by Meng, et al. included the autoinhibitory domain and was otherwise inactive, that structure is less useful for drug design.

SUMMARY OF THE INVENTION

The present invention provides an isolated MK2 polypeptide, having an amino acid sequence corresponding to a portion of MK2, in which the N-terminus begins at amino acid 41 to 55 and the C-terminus ends at 338 to 365, or an MK2 analogue thereof. This MK2 polypeptide, unlike the MK2 polypeptide used by Meng, et al., does not include the complete autoinhibitory domain and is catalytically active.

The present invention also provides nucleic acids encoding the forgoing MK2 polypeptides or MK2 analogues thereof, vectors comprising the nucleic acids, as well as host cells transformed, transfected or infected with the vectors. Additionally, the present invention provides a method for preparing an MK2 polypeptide or an MK2 analogue that comprises transforming, transfecting or infecting a host cell with the vector, and culturing the host cell under conditions permitting the production of MK2 polypeptide or MK2 analogue by the host cell.

The present invention also provides a method for obtaining crystallized native MK2, an MK2 polypeptide or an MK2 analogue comprising contacting native MK2, an MK2 polypeptide or an MK2 analogue with a buffer solution comprising at least one of cacodylate, Tris, Tris-HCL, acetate, malonate, sodium phosphate, potassium phosphate, citrate, HEPES and MES, at a salt concentration of 0.1 M to 2.4 M, and at a pH of 4.5 to 8.5, under conditions permitting the formation of crystallized MK2, crystallized MK2 polypeptide or crystallized MK2 analogue.

The present invention also provides a crystallized complex of MK2 polypeptide and staurosporine, having four molecules of MK2 in the asymmetric unit.

Additionally, the present invention provides a crystallized complex of MK2 polypeptide and ADP, having one molecule of MK2 in the asymmetric unit.

The present invention further provides a three dimensional model of MK2, defined by the relative structural coordinates for: (i) molecules A, B, C or D of MK2 according to FIG. 2, (ii) a portion of molecules A, B, C, or D of MK2 according to FIG. 2, (iii) molecule A of MK2 according to FIG. 3, or (iv) a portion of molecule A of MK2 according to FIG. 3, ± a root mean square deviation from the backbone atoms of said amino acids of not more than 1.5 Å.

Also provided by the present invention is an active site of MK2, and particularly the site on MK2 in which staurosporine binds. The active site comprises the relative structural coordinates of amino acid resides Leu70, Gly71, Leu72, Gly73, Val78, Ala91, Val118, Mse138, Glu139, Cys140, Leu141, Glu145, Glu190, Asn191, Leu192, Thr206 and Asp207 of molecules A, B, C or D according to FIG. 2, ± a root mean square deviation from the backbone atoms of said amino acids of not more than 1.5 Å. In another embodiment, the active site further comprises, in addition to the above relative coordinates, the relative structural coordinates for amino acid residues Val69, Ile74, Gly76, Ala77, Leu79, Gln80, Lys89, Phe90, Leu92, Lys93, Leu95, Glu104, His108, Arg119, Ile136, Val137, Asp142, Gly143, Gly144, His184, Asp186, Lys188, Pro189, Leu193, Tyr194, Thr195, Lys204, Leu205, Phe208 and Gly209 of molecules A, B, C or D according to FIG. 2, ± a root mean square deviation from the backbone atoms of said amino acids of not more than 1.5 Å.

The present invention also provides an active site of MK2 in which ADP binds. Specifically, the active site comprises the relative structural coordinates of amino acid residues Leu70, Gly71, Leu72, Gly73, Ile74, Asn75, Val78, Ala91, Lys93, Met138, Glu139, Cys140, Leu141, Asn191, Thr206, Asp207 of molecule A of MK2 according to FIG. 3, ± a root mean square deviation from the backbone atoms of said amino acids of not more than 1.5 Å. In another embodiment, the active site further comprises, in addition to the above relative coordinates, the relative structural coordinates for amino acid residues Val69, Gly76, Ala77, Leu79, Gln80, Phe90, Leu92, Met94, Leu95, Glu104, His108, Val118, Ala119, Ile136, Val137, Asp142, Gly143, Gly144, Glu145, His184, Asp186, Lys188, Pro189, Glu190, Leu192, Leu193, Tyr194, Thr195, Leu205, Phe208, Gly209, Phe210 of molecule A of MK2 according to FIG. 3, ± a root mean square deviation from the backbone atoms of said amino acids of not more than 1.5 Å.

Still further, the present invention provides a method for identifying an agent that interacts with MK2, comprising the steps of: (a) generating a three dimensional model of MK2 using the relative structural coordinates of (i) molecules A, B, C or D of MK2 according to FIG. 2, (ii) a portion of molecules A, B, C or D of MK2 according to FIG. 2, (iii) molecule A of MK2 according to FIG. 3, or (iv) a portion of molecule A of MK2 according to FIG. 3, ± a root mean square deviation from the backbone atoms of said amino acids of not more than 1.5 Å; and (b) employing said three-dimensional model to identify an agent that interacts with MK2.

The present invention also provides a method for designing a putative agent that interacts with an active site of MK2, and particularly the staurosporine binding site on MK2. This method comprises the steps of: (a) generating a three dimensional model of said active site using the relative structural coordinates of amino acid residues Leu70. Gly71, Leu72, Gly73Val78, Ala91Val118, Mse138, Glu139, Cys140 , Leu141, Glu145, Glu190, Asn191, Leu192, Thr206, and Asp207 of molecules A, B, C of MK2 according to FIG. 2, ± a root mean square deviation from the backbone atoms of said amino acids of not more than 1.5 Å; and (b) designing a putative agent that interacts with said active site by performing computer fitting analysis of said putative agent with the three dimensional model generated in step (a). In another embodiment, the active site further comprises, in addition to the above relative coordinates, the relative structural coordinates for amino acid residues Val69, Ile74, Gly76, Ala77, Leu79, Gln80, Lys89, Phe90, Leu92, Lys93, Leu95, Glu104, His108, Arg119, Ile136, Val137, Asp142, Gly143, Gly144, His184, Asp186, Lys188, Pro189, Leu193, Tyr194, Thr195, Lys204, Leu205, Phe208 and Gly209of molecules A, B, C or D according to FIG. 2, ± a root mean square deviation from the backbone atoms of said amino acids of not more than 1.5 Å.

Additionally, the present invention provides a method for identifying a putative agent that interacts with an active site of MK2, and particularly the site on MK2 in which ADP binds. This method comprises the steps of: (a) generating a three dimensional model of said active site using the relative structural coordinates of amino acid residues Leu70, Gly71, Leu72, Gly73, Ile74, Asn75, Val78, Ala91, Lys93, Met138, Glu139, Cys140, Leu141, Asn191, Thr206, Asp207 of molecule A of MK2 according to FIG. 3, ± a root mean square deviation from the backbone atoms of said amino acids of not more than 1.5 Å; and (b) designing a putative agent that interacts with said active site by performing computer fitting analysis of said putative agent with the three dimensional model generated in step (a). In another embodiment, the active site further comprises, in addition to the above relative coordinates, the relative structural coordinates for amino acid residues Val69, Gly76, Ala77, Leu79, Gln80, Phe90, Leu92, Met94, Leu95, Glu104, His108, Val118, Ala119, Ile136, Val137, Asp142, Gly143, Gly144, Glu145, His184, Asp186, Lys188, Pro189, Glu190, Leu192, Leu193, Tyr194, Thr195, Leu205, Phe208, Gly209, Phe210 of molecule A of MK2 according to FIG. 3, ± a root mean square deviation from the backbone atoms of said amino acids of not more than 1.5 Å.

Finally, the present invention provides agents identified using the foregoing methods. Small molecules or other agents which activate, inhibit or otherwise interfere with substrate binding to MK2 may be useful as therapeutic agents in inflammatory based diseases.

Additional objects of the present invention will be apparent from the description which follows.

BRIEF DESCRIPTION OF THE FIGURES

FIG. 1 is a sequence alignment of MK2 (SEQ ID NO:1), MK3 (SEQ ID NO:2) and MK5 (SEQ ID NO:3). Residues highlighted in bold are identical. The GXGXXG motif (SEQ ID NO:6), the catalytic RD residues and the bipartite nuclear localization sequence (KKI . . . RKK) are boxed. The residues that are phosphorylated are donated by stars.

FIGS. 2 through 2A-204 provide the atomic structural coordinates for MK2 and staurosporine as derived by X-ray diffraction of the MK2/staurosporine crystal complex. "Atom type" refers to the atom whose coordinates are being measured. "Residue" refers to the type of residue of which each measured atom is a part —i.e., amino acid, cofactor, ligand or solvent. The "x, y and z" coordinates indicate the Cartesian coordinates of each measured atom's location in the unit cell (Å). "Occ" indicates the occupancy factor. "B" indicates the "B-value", which is a measure of how mobile the atom is in the atomic structure ($Å^2$). Under "Molecules", A, B, C, and D refer to each molecule of MK2, E, F G and H refer to each molecule of staurosporine, molecule I corresponds to $SO_4$, and W corresponds to water.

FIGS. 3 through 3A-40 provide the atomic structural coordinates for MK2 and ADP as derived by X-ray diffraction of the MK2/ADP crystal complex. "Atom type" refers to the atom whose coordinates are being measured. "Residue" refers to the type of residue of which each measured atom is a part —i.e., amino acid, cofactor, ligand or solvent. The "x, y and z" coordinates indicate the Cartesian coordinates of each measured atom's location in the unit cell (Å). "Occ" indicates the occupancy factor. "B" indicates the "B-value", which is a measure of how mobile the atom is in the atomic structure (Å2). Under "Molecule", A refers to MK2 and B corresponds to ADP.

FIGS. 4 through 4A-1 provide the nucleic acid sequence for MK2 (SEQ ID NO:5) with the corresponding MK2 amino acid sequence (SEQ ID NO:4).

DETAILED DESCRIPTION OF THE INVENTION

As used herein, the following terms and phrases shall have the meanings set forth below:

Unless otherwise noted, "MK2" includes: (i) native MK2 having the amino acid sequence (residues 1–400) set forth in FIG. 1, including conservative substitutions thereof; (ii) modeled MK2, including conservative substitutions thereof; and (iii) an MK2 polypeptide, including conservative substitutions thereof.

"Modeled MK2" corresponds to molecules A, B, C and D of MK2 according to FIG. 2, and molecule A of MK2 according to FIG. 3.

An "MK2 polypeptide" is an amino acid sequence that defines a portion or fragment of residues 1–400 of MK2 set forth in FIG. 1. An MK2 polypeptide includes but is not limited to an amino acid sequence of MK2 in which the N-terminus begins at amino acid 41 to 55 and the C-terminus ends at 338 to 365, in accordance with the residue numbering shown in FIG. 1.

An "MK2 analogue" is a polypeptide having at least 80% homology with "MK2" defined above, more preferably at least 90% homology with "MK2" defined above, and most preferably at least 95% homology with "MK2" defined above. In the preferred embodiment, an "MK2 analogue" also has MAP kinase activated protein kinase activity.

A "portion" of molecules A, B, C, or D of MK2 set forth in FIG. 2, or a "portion" of molecule A of MK2 set forth in FIG. 3, refers to the relative structural coordinates of amino acid residues that include less than all the amino acid residues shown. Preferably, the portion of molecules A, B, C or D of MK2 set forth in FIG. 2, or a portion of molecule A of MK2 set forth in FIG. 3 includes, at a minimum, a sufficient portion of the MK2 molecule to define an active site of MK2.

An "MK2 complex" is MK2 complexed to another molecule, including but not limited to staurosporine or ADP.

Unless otherwise indicated, "protein" or "molecule" shall include a protein, protein domain, polypeptide or peptide.

"Structural coordinates" are the Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The structural coordinates of the present invention may be modified from the original sets provided in FIGS. 2 and 3 by mathematical manipulation, such as by inversion or integer additions or subtractions. As such, it is recognized that the structural coordinates of the present invention are relative, and are in no way specifically limited by the actual x, y, z coordinates of FIGS. 2 and 3.

An "agent" shall include a protein, polypeptide, peptide, nucleic acid (including DNA or RNA), molecule, compound or drug.

"Root mean square deviation" is the square root of the arithmetic mean of the squares of the deviations from the mean, and is a way of expressing deviation or variation from the structural coordinates described herein. The present invention includes all embodiments comprising conservative substitutions of the noted amino acid residues resulting in same structural coordinates within the stated root mean square deviation. It will be obvious to the skilled practitioner that the numbering of the amino acid residues of MK2 may be different than that set forth herein, and may contain certain conservative amino acid substitutions that yield the, same three dimensional structures as those defined by FIGS. 2 and 3 herein. Corresponding amino acids and conservative substitutions in other isoforms or analogues are easily identified by visual inspection of the relevant amino acid sequences or by using commercially available homology software programs (e.g., MODELLAR, MSI, San Diego, Calif.).

"Conservative substitutions" are those amino acid substitutions which are functionally equivalent to the substituted amino acid residue, either by way of having similar polarity, steric arrangement, or by belonging to the same class as the substituted residue (e.g., hydrophobic, acidic or basic), and includes substitutions having an inconsequential effect on the three dimensional structure of MK2 with respect to the use of said structures for the identification and design of agents which interact with MK2, as well as for molecular replacement analyses and/or for homology modeling.

An "active site" refers to a region of a molecule or molecular complex that, as a result of its shape and charge potential, favorably interacts or associates with another agent (including, without limitation, a protein, polypeptide, peptide, nucleic acid, including DNA or RNA, molecule, compound or drug) via various covalent and/or non-covalent binding forces. As such, an active site of the present invention may include, for example, the actual site of binding, as well as accessory binding sites adjacent or proximal to the actual site of binding that nonetheless may affect MK2 activity upon interaction or association with a particular agent, either by direct interference with the actual site of substrate binding or by indirectly affecting the steric conformation or charge potential of the MK2, thereby preventing or reducing binding to MK2 at the actual site of binding. As used herein, an "active site" also includes analog residues of MK2, which exhibit observable NMR perturbations in the presence of a binding ligand. While such residues exhibiting observable NMR perturbations may not necessarily be in direct contact with or immediately proximate to ligand binding residues, they may be critical to MK2 residues for rational drug design protocols.

The present invention first provides an MK2 polypeptide having an amino acid sequence corresponding to a portion of MK2, in which the N-terminus begins at amino acid 41 to 55 and the C-terminus ends at 338 to 365. The present inventors have found that sequences which lack amino acid residues 366–400 of MK2, are active. Preferably, a MK2 polypeptide has the amino acid sequence corresponding to amino acid residues 41–364 of MK2 according to FIG. 1.

The present invention also provides an MK2 analogue of the foregoing MK2 polypeptide that is at least 80% homologous, more preferably at least 90% homologous and most preferably at least 95% homologous, with the foregoing MK2 polypeptide having an amino acid sequence corresponding to a portion of MK2, in which the N-terminus begins at amino acid 41 to 55 and the C-terminus ends at 338 to 365. In the more preferred embodiment, the MK2 analogue is at least 80% homologous, more preferably at least 90% homologous and most preferably at least 95% homologous, with the MK2 polypeptide having the amino acid sequence corresponding to amino acid residues 41–364 of MK2 according to FIG. 1.

The present invention also provides a nucleic acid encoding the MK2 polypeptide having an amino acid sequence corresponding to a portion of MK2, in which the N-terminus begins at amino acid 41 to 55 and the C-terminus ends at 338 to 365, as well as a nucleic acid encoding amino acid residues 41–364 of MK2 according to FIG. 1. The nucleic acid sequence for MK2 is known, and is shown in FIG. 4. Such nucleic acids can be introduced into the appropriate vectors, and then transformed, transfected or infected into the appropriate host cells, which can be cultured to produce recombinant MK2 polypeptide. The recombinant MK2 polypeptide can then be isolated and purified according to known techniques. Suitable vector and expression systems are well known and commercially available.

The present invention also provides a nucleic acid encoding an MK2 analogue that is at least 80% homologous, more preferably at least 90% homologous and most preferably at least 95% homologous, with the MK2 polypeptide having an amino acid sequence corresponding to a portion of MK2, in which the N-terminus begins at amino acid 41 to 55 and the C-terminus ends at 338 to 365. In the more preferred embodiment, the nucleic acid encodes an MK2 analogue that is at least 80% homologous, more preferably at least 90% homologous and most preferably at least 95% homologous, with the MK2 polypeptide having the amino acid sequence corresponding to amino acid residues 41–364 of MK2 according to FIG. 1. Such nucleic acids can be introduced into the appropriate vectors, and then transformed, transfected or infected into the appropriate host cells, which can be cultured to produce recombinant MK2 polypeptide. The recombinant MK2 analogue can then be isolated and purified according to known techniques. Suitable vector and expression systems are well known and commercially available.

The present invention also provides a method for crystallizing native MK2, an MK2 polypeptide or an MK2 analogue. The method comprises contacting native MK2, an MK2 polypeptide or an MK2 analogue with a buffer solution comprising at least one of cacodylate, Tris, Tris-HCL, acetate, malonate, sodium phosphate, potassium phosphate, citrate, HEPES and MES, at a salt concentration of 0.1 M to 2.4 M, and at a pH of 4.5 to 8.5, under conditions permitting the formation of crystallized native MK2, crystallized MK2 polypeptide or crystallized MK2 analogue. In a preferred embodiment, the salt has an anion selected from the group consisting of sulfate, citrate, chloride, acetate, phosphate, malonate and tartrate. In another preferred embodiment, the salt concentration is 0.8 M or higher. It is also within the confines of the present invention that the native MK2, the MK2 polypeptide or the MK2 analogue is contacted with the buffer solution in the presence of PEG or a PEG substitute having a molecular weight up to 3350. The PEG includes but is not limited to PEG-200, PEG-400, PEG-500-MME, PEG-1000, PEG-1500, PEG-2000MME and MEG-3350, and is preferably PEG-400. The PEG substitute includes but is not limited to Jeffamine M-600, ethylene glycol, glycerol and 1–6 hexanediol, 2-methyl-2,4-pentanediol (MPD). The more specific crystallization conditions are exemplified in example which follows, as well as in Table 4.

The present invention also provides a crystallized complex of MK2 polypeptide and staurosporine, having four molecules of MK2 polypeptide in the asymmetric unit. This crystal effectively diffracts X-rays for the determination of the structural coordinates of MK2, and is characterized as having space group $P6_3$, unit cell parameters of a=b=160.20 Å, c=133.48 Å.

Additionally, the present invention provides a crystallized complex of MK2 polypeptide and ADP, having one molecule of MK2 polypeptide in the asymmetric unit. This crystal effectively diffracts X-rays for the determination of the structural coordinates of MK2, and is characterized as having space group F4132, unit cell parameters of a=b=c=253.05 Å.

Using the crystals of the present invention, X-ray diffraction data can be collected by a variety of means in order to obtain the atomic coordinates of the molecules in the crystals. With the aid of specifically designed computer software, such crystallographic data can be used to generate a three dimensional structure. Various methods used to generate and refine a three dimensional structure of a molecular structure are well known to those skilled in the art, and include, without limitation, multiwavelength anomalous dispersion (MAD), multiple isomorphous replacement, reciprocal space solvent flattening, molecular replacement, and single isomorphous replacement with anomalous scattering (SIRAS).

Accordingly, the present invention also provides a three dimensional model of MK2 as derived by x-ray diffraction data of the MK2/staurosporine crystal. The three dimensional model of MK2 derived from the MK2/staurosporine crystal is preferably defined by the relative structural coordinates for molecules A, B, C or D of MK2 according to FIG. 2, ± a root mean square deviation from the backbone atoms of said amino acids of not more than 1.5 Å, preferably not more than 1.0 Å, and most preferably not more than 0.5 Å. The three dimensional model also includes the relative structural coordinates of a portion of molecules A, B, C or D of MK2 according to FIG. 2, ± a root mean square deviation from the backbone atoms of said amino acids of not more than 1.5 Å, preferably not more than 1.0 Å, and most preferably not more than 0.5 Å. The three dimensional model of MK2 is useful for a number of applications, including, but not limited to, the visualization, identification and characterization of various active sites of MK2. The active site structures may then be used to design agents with interact with MK2.

The present invention also provides a three dimensional model of MK2 as derived by x-ray diffraction data of the MK2/ADP crystal. The three dimensional model of MK2 derived from the MK2/ADP crystal is preferably defined by the structural coordinates for molecule A of MK2 shown in FIG. 3, ± a root mean square deviation from the backbone atoms of the amino acids of not more than 1.5 Å, preferably not more than 1.0 Å, and most preferably not more than 0.5 Å. The three dimensional model also includes the relative structural coordinates of a portion of molecule A of MK2 according to FIG. 3, ± a root mean square deviation from the backbone atoms of said amino acids of not more than 1.5 Å, preferably not more than 1.0 Å, and most preferably not more than 0.5 Å. The three dimensional model of MK2 derived from the MK2/ADP crystal is useful for a number of applications, including, but not limited to, the visualization, identification and characterization of various active sites of MK2. The active site structures may then be used to design agents with interact with MK2.

The present invention also provides a machine, such as a computer, programmed in memory with the coordinates of FIG. 2 or 3, or portions thereof, together with a program capable of converting the coordinates into a three dimensional graphical representation of the structural coordinates on a display connected to the machine. A machine having a memory containing such data aids in the rational design or selection of inhibitors or activators of MK2 activity, including the evaluation of ability of a particular chemical entity to favorably associate with MK2 or an MK2 complex as disclosed herein, as well as in the modeling of compounds, proteins, complexes, etc. related by structural or sequence homology to MK2.

For storage, transfer and use with such programs, a machine, such as a computer, is provided for that produces a three dimensional representation of the MK2 molecule, a portion thereof (such as an active site or a binding site), an MK2 molecular complex, or an MK2 analogue. The machine of the present invention comprises a machine-readable data storage medium comprising a data storage material encoded with machine-readable data. Machine-readable storage media comprising data storage material include conventional computer hard drives, floppy disks, DAT tape, CD-ROM, and other magnetic, magneto-optical, optical, and other media which may be adapted for use with a computer. The machine of the present invention also comprises a working memory for storing instructions for processing the machine-readable data, as well as a central processing unit (CPU) coupled to the working memory and to the machine-readable data storage medium for the purpose of processing the machine-readable data into the desired three dimensional representation. Finally, the machine of the present invention further comprises a display connected to the CPU so that the three dimensional representation may be visualized by the user. Accordingly, when used with a machine programmed with instructions for using said data, e.g., a computer loaded with one or more programs of the sort identified below, the machine provided for herein is capable of displaying a graphical three-dimensional representation of any of the molecules or molecular complexes, or portions of molecules of molecular complexes, described herein.

Molecular modeling methods known in the art may be used to identify an active site or binding pocket of MK2, MK2 complex or an MK2 analogue. Specifically, the structural coordinates provided by the present invention may be used to characterize a three dimensional model of the MK2, MK2 complex or MK2 analogue. From such a model, putative active sites may be computationally visualized, identified and characterized based on the surface structure of the molecule, surface charge, steric arrangement, the presence of reactive amino acids, regions of hydrophobicity or hydrophilicity, etc. Such putative active sites may be further refined using chemical shift perturbations of spectra generated from various and distinct MK2 complexes, competitive and non-competitive inhibition experiments, and/or by the generation and characterization of MK2 mutants to identify critical residues or characteristics of the active site. The identification of putative active sites of a molecule or molecular complex is of great importance, as most often the biological activity of a molecule or molecular complex results from the interaction between an agent and one or more active sites of the molecule or molecular complex. Accordingly, the active sites of a molecule or molecular complex are the best targets to use in the design or selection of activators or inhibitors that affect the activity of the molecule or molecular complex.

As such, the present invention also provides an active site of MK2, and particularly the site of binding of staurosporine to MK2. In one embodiment, the active site comprises the relative structural coordinates of amino acid residues Leu70, Gly71, Leu72, Gly73, Val78, Ala91, Val118, Mse138, Glu139, Cys140, Leu141, Glu145, Glu190, Asn191, Leu192, Thr206 and Asp207 of molecules A, B, C or D according to FIG. 2, ± a root mean square deviation from the backbone atoms of said amino acids of not more than 1.5 Å, preferably not more than 1.0 Å, and most preferably not more than 0.5 Å. In another embodiment, the active site further comprises, in addition to the above relative coordinates, the relative structural coordinates for amino acid residues Val69, Ile74, Gly76, Ala77, Leu79, Gln80, Lys89, Phe90, Leu92, Lys93, Leu95, Glu104, His108, Arg119, Ile136, Val137, Asp142, Gly143, Gly144, His184, Asp186, Lys188, Pro189, Leu193, Tyr194, Thr195, Lys204, Leu205, Phe208 and Gly209 of molecules A, B, C or D according to FIG. 2, ± a root mean square deviation from the backbone atoms of said amino acids of not more than 1.5 Å, preferably not more than 1.0 Å, and most preferably not more than 0.5 Å.

Still further, the present invention provides an active site of MK2, and particularly the site of binding of staurosporine to ADP. In one embodiment, the active site comprises the relative structural coordinates of amino acid residues Leu70, Gly71, Leu72, Gly73, Ile74, Asn75, Val78, Ala91, Lys93, Met138, Glu139, Cys140, Leu141, Asn191, Thr206, Asp207 of molecule A of MK2 according to FIG. 3, ± a root mean square deviation from the backbone atoms of said amino acids of not more than 1.5 Å, preferably not more than 1.0 Å, and most preferably not more than 0.5 Å. In another embodiment, the active site further comprises, in addition to the above relative coordinates, the relative structural coordinates for amino acid residues Val69, Gly76, Ala77, Leu79, Gln80, Phe90, Leu92, Met94, Leu95, Glu104, His108, Val118, Ala119, Ile136, Val137, Asp142, Gly143, Gly144, Glu145, His184, Asp186, Lys188, Pro189, Glu190, Leu192, Leu193, Tyr194, Thr195, Leu205, Phe208, Gly209, Phe210 of molecule A of MK2 according to FIG. 3, ± a root mean square deviation from the backbone atoms of said amino acids of not more than 1.5 Å, preferably not more than 1.0 Å, and most preferably not more than 0.5 Å.

Another aspect of the present invention is directed to a method for identifying an agent that interacts with MK2. In this method, a three dimensional model of MK2 is first generated using the relative structural coordinates of (i) molecules A, B, C or D of MK2 according to FIG. 2, (ii) a portion of molecules A, B, C or D of MK2 according to FIG. 2, (iii) molecule A of MK2 according to FIG. 3, or (iv) a portion of molecule A according to FIG. 3, ± a root mean square deviation from the backbone atoms of said amino acids of not more than 1.5 Å, preferably not more than 1.0 Å, and most preferably not more than 0.5 Å. The three-dimensional model is then used to identify an agent that interacts with MK2.

The present invention also provides a method for designing a putative agent that interacts with an active site of MK2, and particularly the site on MK2 to which staurosporine binds. In this method, a three dimensional model of the active site is first generated using the relative structural coordinates of amino acid residues Leu70, Gly71, Leu72, Gly73, Val78, Ala91, Val118, Mse138, Glu139, Cys140, Leu141, Glu145, Glu 190, Asn191, Leu192, Thr206, and Asp207of molecules A, B, C or D of MK2 according to FIG. 2, ± a root mean square deviation from the backbone atoms of said amino acids of not more than 1.5 Å, preferably not more than 1.0 Å, and most preferably not more than 0.5 Å. A putative agent that interacts with the active site is then designed, generated or identified by performing computer fitting analysis of the putative agent with the three dimensional model generated above. In another embodiment, the active site further comprises, in addition to the above relative coordinates, the relative structural coordinates for amino acid residues Val69, Ile74, Gly76, Ala77, Leu79, Gln80, Lys89, Phe90, Leu92, Lys93, Leu95, Glu104, His108, Arg119Ile136, Val137, Asp142, Gly143, Gly144, His184, Asp186, Lys188, Pro189, Leu193, Tyr194, Thr195, Lys204, Leu205, Phe208 and Gly209 of molecule A, B, C or D according to FIG. 2, ± a root mean square deviation from the backbone atoms of said amino acids of not more than 1.5 Å, preferably not more than 1.0 Å, and most preferably not more than 0.5 Å.

Additionally, the present invention provides a method for identifying a putative agent that interacts with an active site of MK2, and particularly the site on MK2 in which ADP binds. In this method, a three dimensional model of the active site is first generated using the relative structural coordinates of amino acid residues Leu70, Gly71, Leu72, Gly73, Ile74, Asn75, Val78, Ala91, Lys93, Met138, Glu139, Cys140, Leu141, Asn191, Thr206, Asp207 of molecule A of MK2 according to FIG. 3, ± a root mean square deviation from the backbone atoms of said amino acids of not more than 1.5 Å, preferably not more than 1.0 Å, and most preferably not more than 0.5 Å. A putative agent that interacts with the active site is then designed, generated or identified by performing computer fitting analysis of the putative agent with the three dimensional model. In another embodiment, the active site further comprises, in addition to the above relative coordinates, the relative structural coordinates for amino acid residues Val69, Gly76, Ala77, Leu79, Gln80, Phe90, Leu92, Met94, Leu95, Glu104, His108, Val118, Ala119, Ile136, Val137, Asp142, Gly143, Gly144, Glu145, His184, Asp186, Lys188, Pro189, Glu190, Leu192, Leu193, Tyr194, Thr195, Leu205, Phe208, Gly209, Phe210 of molecule A of MK2 according to FIG. 3, ± a root mean square deviation from the backbone atoms of said amino acids of not more than 1.5 Å, preferably not more than 1.0 Å, and most preferably not more than 0.5 Å.

Using the active site, the agent may be designed or evaluated using computer fitting analyses utilizing various computer software programs that evaluate the "fit" between the putative active site and the identified agent, by (a) generating a three dimensional model of the putative active site of a molecule or molecular complex using homology modeling or the atomic structural coordinates of the active site, and (b) determining the degree of association between the putative active site and the identified agent. The degree of association may be determined computationally by any number of commercially available software programs, or may be determined experimentally using standard binding assays.

Three dimensional models of the putative active site may be generated using any one of a number of methods known in the art, and include, but are not limited to, homology modeling as well as computer analysis of raw data generated using crystallographic or spectroscopy data. Computer programs used to generate such three dimensional models and/or perform the necessary fitting analyses include, but are not limited to: GRID (Oxford University, Oxford, UK), MCSS (Molecular Simulations, San Diego, Calif.), AUTODOCK (Scripps Research Institute, La Jolla, Calif.), DOCK (University of California, San Francisco, Calif.), Flo99 (Thistlesoft, Morris Township, N.J.), Ludi (Molecular Simulations, San Diego, Calif.), QUANTA (Molecular Simulations, San Diego, Calif.), Insight (Molecular Simulations, San Diego, Calif.), SYBYL (TRIPOS, Inc., St. Louis. Mo.) and LEAPFROG (TRIPOS, Inc., St. Louis, Mo.). The structural coordinates also may be used to visualize the three-dimensional structure of MK2 using MOLSCRIPT (Kraulis, P J, J. Appl. Crystallogr. 24: 946–950 (1991)) and RASTER3D (Bacon, D. J. and Anderson, W. F., J. Mol. Graph. 6: 219–220 (1998)), for example.

The agent, whether an inhibitor or activator, may be selected by screening an appropriate database, may designed de novo by analyzing the steric configurations and charge potentials of an empty MK2 active site in conjunction with the appropriate software programs, or may be designed using characteristics of known inhibitors or activators to MK2 or other mitogen activated protein kinases in order to create "hybrid" activators or inhibitors. The method of the present invention is preferably used to design or select inhibitors of MK2. In this case, the potential inhibitor or activator is designed to incorporate chemical or steric features favorable for association with the active site. The inhibitor or activator may be selected by screening an appropriate database, may designed de novo by analyzing the steric configurations and charge potentials of empty active sites in conjunction with the appropriate software programs, or may be designed using characteristics of known inhibitors or activators to MK2 or other mitogen activated protein kinases in order to create "hybrid" activators or inhibitors.

Once the agent has been designed or identified, it may be obtained or synthesized and further evaluated for its affect on MK2 activity. For example, the agent may be evaluated by contacting the identified agent with MK2 and measuring the effect of the agent on MK2 activity. Depending upon the action of the agent on MK2, the agent may act either as an inhibitor or activator of MK2 activity. With respect to the specific active sites identified above, the agent also may be contacted with MK2 in the presence of staurosporine or ADP in order to determine whether or not the agent inhibits binding between MK2 and staurosporine or ADP, respectively.

Various molecular analysis and rational drug design techniques are further disclosed in U.S. Pat. Nos. 5,834,228, 5,939,528 and 5,865,116, as well as in PCT Application No. PCT/US98/16879, published WO 99/09148, the contents of which are hereby incorporated by reference.

The present invention is also directed to the agents, activators or inhibitors identified using the foregoing methods. Such agents may be a protein, polypeptide, peptide, nucleic acid, including DNA or RNA, molecule, compound, or drug. Small molecules or other agents which interact with MK2 may be useful in the treatment of diseases or conditions associated with MK2.

The present invention may be better understood by reference to the following non-limiting Example. The following Example is presented in order to more fully illustrate the preferred embodiments of the invention, and should in no way be construed as limiting the scope of the present invention.

EXAMPLE 1

1. Materials and Methods.

Sequence Selection for MK2 Crystallization. Various constructs were made, expressed and the resulting MK2 were purified and crystalized. After analyzing a large number of constructs for expression of MK2 in *E. coli*, it was found that deleting the first 40 residues of the proline rich domain greatly enhanced the expression levels and solubility of the enzyme. Analyses of the resulting MK2 also indicated that constructs lacking amino acids 366 to 400 were not active in vitro. It was also found that crystals could be obtained for constructs of MK2 in which the N-terminus begins at amino acid 41 to 55 and the C-terminus ends at 338 to 365. The construct 41–364 resulted in the best crystals for determining the crystal structure of MK2, and details concerning its expression, purification and crystallization are provided below.

Cloning and expression of MK2. The MAPKAP kinase 2 gene was PCR cloned into the NcoI and XhoI sites of pET16b (Novagen) using Hot tub polymerase (Amersham Pharmacia Biotech). The expressed protein contains residues 41–364, excluding the N-terminal proline-rich sequence. To produce selenomethionine labeled MK2, the protein was expressed in BL21 (DE3) (Novagen) *E. coli* at 25° C. Precultures were grown in shake flasks in LeMaster media supplemented with L-methionine and expression cultures were grown in LeMaster media supplemented with L-selenomethionine that was replenished upon culture induction. Cultures were induced with 0.5 mM IPTG for four hours. Unlabelled MK2 was also expressed in E. coli BL21 (DE3). The culture was induced with 0.5 mM IPTG and cells were harvested 4 hours post-induction.

Purification of MK2 41-364. The purification was performed at 4° C. 5 g of bacterial cells were homogenized in 200 ml of Buffer A (50 mM Tris pH7.5, 10 mM DTT, 0.24 mg/ml AEBSF)+90 µg/ml TPCK, 2.5 mM Aminobenzamidine, 500 µL protease inhibitor cocktail (without EDTA) for use in purification of poly-(Histidine)tagged proteins (Sigma), RNase, DNase. Cells were lysed by four passages through a Microfluidics microfluidizer submerged in ice. The lysate was collected and centrifuged at 20,000×g for 30 min. The supernatant was applied to a Poros HQ column (Applied Biosystems) that was equilibrated in Buffer A. The flow through was loaded onto a Poros HS column (Applied Biosystems) and the bound protein was eluted with a gradient of Buffer A+1M NaCl. Ammonium sulfate to 0.8 M was added to the peak fraction and the protein was loaded onto a polypropyl aspartamide column (Nest Group) equilibrated with Buffer B (50 mM Hepes pH 7.5, 10 mM DTT, 0.8 M ammonium sulfate). The protein was eluted with a gradient and the peak fraction was concentrated in a Millipore Ultrafree concentrator. The protein was applied to a Superdex 200 column (Amersham Pharmacia Biotech) equilibrated with 20 mM Hepes pH 7.5, 200 mM NaCl, 10 mM DTT. Protein purity was >95%.

Kinetic Analysis.

Materials. ATP, ADP, phosphoenolpyruvate (PEP), NADH, and pyruvate kinase/lactate dehydrogenase enzymes were purchased from Sigma Chemical Co. (St. Louis, Mo.). Activated p38 MAP kinase was purchased from Upstate Biotech (Lake Placid, N.Y.). LSP-1 peptide (RTPKLARQASIELPSM) (SEQ ID NO: 10) was purchased from AnaSpec Inc. (San Jose, Calif.).

Activation of MK2 Constructs. The MK2 constructs 41–400 and 41–364 were activated by the phosphorylation of the constructs by p38 MAP kinase. The activation was done in 20 mM HEPES (pH 7.5), 10 mM MgCl$_2$, 2 mM DTT, 0.50 mM ATP, 0.2 mg/ml MK2 and 0.125 µg activated p38. The reaction was incubated at 25° C. for 1–2 hour then placed on ice to be used for kinetic analysis.

Kinase Kinetics. The rate of MK2 kinase was characterized in 20 mM HEPES (pH 7.5), 10 mM MgCl$_2$, 2 mM DTT and 100 mM NaCl. The kinetics was followed by linking the turnover of ATP is to the turnover of NADH to NAD. This was followed spectrophotometrically at 340 nm. The continuos assay contained 20 units pyruvate kinase, 30 units lactate dehydrogenase, 0.25 mM NADH, 2 mM PEP and 1.6 to 8.0 µg/mL MK2. For determining the apparent $K_m$ for ATP, the ATP concentration was varied from 0.005 to 0.25 mM while the peptide was held constant at 0.2 mM for activated MK-2 or 1.0 mM for the constitutively active form of MK-2 (41–364). For determining the apparent $K_m$ for LSP-1, the LSP-1 concentration was varied from 0.01 to 0.5 mM while ATP was held constant at 2 mM. The kinetic analysis was carried out in a 96-well plate at 25° C., on a Molecular Devices spectrophotometer.

Substrate Kinetics. Peptide LSP, based on the protein substrate of MK-2 lymphocyte/leukocyte specific protein, was used for the investigation of the kinetic mechanism for the enzyme MK-2. Data was fit to equation 1 for normal Michaelis-Menten kinetics.

$$v = V_{max}[S]/K_m + [S] \quad (1)$$

where [S] is the substrate, $V_{max}$ is the maximum enzyme velocity, $K_m$ is the Michaelis constant.

Crystallization. The selenomethionine labeled protein was concentrated to ~5 mg/mL according to the Bradford method (31) in a solution containing 20 mM HEPES pH 7.5, 200 mM NaCl, 10 mM DTT, and 5 mM MgCl$_2$. Prior to crystallization, staurosporine (0.375 mM) was added from a DMSO stock. Diffraction quality conical crystals were obtained at 18° C. from 2M ammonium sulfate, 100 mM HEPES pH 7.5, 2% PEG 400. These crystals, which appeared in 7–10 days, belonged to space group P6$_3$ with cell dimensions of a=b=160.20 Å, c=133.48 Å and contained four molecules of MK2 in the asymmetric unit. Native MK2 was crystallized in the presence of ADP and the protein solution was prepared as above except that 5 mM ADP was added instead of the staurosporine. Diffraction quality native MK2/ADP co-crystals were obtained at 18° C. from 2.0M ammonium sulfate. These bipyramidal crystals belonged to space group F4132 with cell dimensions a=b=c=253.05 Å and contained one molecule of MK2 and one molecule of ADP in the asymmetric unit.

MK2 41-364 also was successfully crystallized using the various conditions described in Table 4. Based on these experiments, it was discovered that MK2 could be crystallized over a broad pH range (4.5 to 8.5). It also was discovered that over that pH range, MK2 could crystallize using a variety of buffers (Cacodylate, Tris, Tris-HCL, Acetate, Malonate, Sodium/Potassium Phosphate, Citrate, HEPES, MES). Additionally, salts of the anions (Sulfate, Citrate, Chloride, Acetate, Phosphate, Malonate and Tartrate) were preferred for crystallization. Still further, the amount of salt needed to crystallize MK2 ranged from 0.1 M to 2.4 M, with less salt required in the presence of polyethylene glycol. However, MK2 preferred to crystallize in the presence of high salt concentrations, defined as 0.8 M or higher, as only three conditions (#1, #14 and #16) have an organic (PEG 400) as the precipitant. Finally, it was discovered that PEG-400, in the range of 2 to 30%, could aid in the crystallization of MK2. It is envisioned that any PEG (39) or its equivalent (e.g., PEG MME, MPD) up to a molecular weight of 3350 could be substituted for PEG 400.

Data Collection.

MK2—Staurosporine. MAD data were collected on beamline 5.0.2 at the ALS, Berkley using an ADSC Quantum-4 CCD detector from a single crystal of the hexagonal SeMet-MK2. The crystal was cooled to −180° C. for data collection and in order to minimize the exposure of the crystal to x-rays, the strategy option within MOSFLM (32) was used to determine the settings that gave the most complete MAD data using the shortest total exposure time. The wavelengths used can be found in Table 2. These data were then used as input to the programs Shake and Bake (33) and ShelX (34) for determination of the Selenium atom positions. Heavy atom parameters for each were refined with SHARP (35). In addition to the MAD data, a higher resolution data set was collected at 1.1 Å.

MK2—ADP. Single-wavelength (1.0 Å) data for the MK2/ADP co-crystals were collected on beamline 5.0.1 at the ALS, Berkley using an ADSC Quantum-4 CCD detector. A single crystal, cooled to −180° C., was used to collect the data set. The data were processed using DENZO/Scalepack (HKL Research, Inc., Charlottesville, Va.) and the statistics from refinement are given in Table II.

Model Building and Refinement.

MK2—Staurosporine. The structure of the MK2 was built into the original 3.1 Å resolution solvent flattened symmetry-averaged MAD map using the X-AUTOFIT features within QUANTA (Molecular Simulations Inc., San Diego, Calif.). The phases were then extended from 3.1 Å to 2.7 Å with symmetry averaging in DM. This model was then used as the initial model for refinement using the program CNX (35) against the 2.7 Å data. Prior to refinement, 5% of the data were randomly selected and designated as a $R_{free}$ test set to monitor the progress of the refinement. Following seven cycles of refining and rebuilding the refinement converged with a model which contained four molecules of MK2, four staurosporine molecules, 43 water molecules, and two sulfate ions at an $R_{cryst}$ of 23.9% ($R_{free}$ 27.4%). The refinement statistics are given in Table 2.

MK2—ADP. The structure of the MK2/ADP complex was solved using molecular replacement. A composite consisting of the overlapped MK2 monomers from the staurosporine structure was utilized as a molecular replacement probe with AMORE (37). The molecular replacement solution was then rebuilt into a 3.2 Å resolution solvent averaged map. After the initial placement of the protein chain into density, the model was rebuilt utilizing omit maps calculated with BUSTER (38) in order to eliminate the bias from the molecular replacement solution. The structure was refined in CNX using methods as described above. Refinement converged after six rebuilding cycles with a $R_{cryst}$ of 25.9% and a $R_{free}$ of 29.2%. The final model consisted of residues 46–152, 159–217, 227–265, 274–345, and the ADP moiety. The refinement statistics are given in Table 2.

2. Results and Discussion

Alignment of homologues. Map Kap kinase 2 (MK2) is an enzyme that belongs to a family of Map kinase activated protein kinases. Human members of this family include MK2, MK3 and MK5 (23, 24). There is also a MK4 from sea urchin (25). These proteins are highly homologous and, in addition, all have shown to be activated by the Map kinase p38, although to date the only well studied enzyme is MK2 (26, 24). MK2 is phosphorylated on T222, S272, and T334 by p38 and has a putative autophosphorylation site at T338. All four of the phosphorylation sites are conserved in MK3 but only T222 is present in MK5. All of the isozymes have the ATP binding site motif GXGXXG (SEQ ID NO:6), (residues 71–76 in MK2), but only MK2 has the bipartite nuclear localization signal KKLEDDASNPLLLKRRKK (SEQ ID NO:7) (residues 373–389). The putative activation segment is highly conserved in all three isozymes (residues 207–233 in MK2), including the conserved motifs found to flank the activation segments of many kinases, DFG and APE, with the latter being APQ in MK5 (27). Interestingly, the conserved p38 phosphorylation site, T222, is in the activation loop. MK2 and MK3 contain an N-terminal proline rich domain that is absent in MK5 and the C-terminal extension thought to contain the autoinhibitory domain in MK2 is elongated in MK5. Overall, MK2 shares 75% identity with MK3 and 42% identity with MK5.

Analysis of protein constructs. MK2 is a 400 amino acid protein consisting of five domains, an N-terminal proline rich domain, a kinase catalytic domain, a C-terminal kinase autoinhibitory domain, a nuclear export signal, and a nuclear localization sequence, which also the postulated site for p38 binding (28). After analyzing a large number of constructs for expression of MK2 in E. coli, it was found that deleting the first 40 residues of the proline rich domain greatly enhanced the expression levels and solubility of the enzyme. MK2 41–364, a constitutively active form of the enzyme in which a portion of the C-terminal autoinhibitory domain was removed, was purified and produced crystals that diffracted to 2.7 Å. As shown in Table 1, the $K_m$ for ATP is very similar for MK2 41-364 as compared to p38 activated MK2 41-400, 7 µM versus 15 µM, respectively. However, binding of the peptide substrate, leukocyte specific protein 1, to MK2 41-364 is more than 40-fold weaker than to the p38 activated MK2 41-400, 584 µM vs. 13 µM $K_m$. In addition, the $V_{max}$ for MK2 41-364 is also much lower when compared to the p38 activated MK2 41-400 (0.076 vs. 8.9 µmol/min/mg, respectively). These data indicate that MK2 41–364, which lacks a portion of the autoinhibitory domain, binds ATP normally but peptide substrate binding has been affected dramatically. However, when MK2 41-364 is phosphorylated by p38, the $V_{max}$ of the enzyme is greatly increased to 11 µmol/min/mg, which is comparable to the $V_{max}$ of p38 activated MK2 41-400, 8.9 µmol/min/mg. Phosphorylation of MK2 41-364 also alters the $K_m$ for peptide substrate such that the $K_m$ decreases from 584 µM to 20 µM, similar to the $K_m$ observed in activated MK2 41-400. These data suggest that for optimal substrate binding and activity MK2 must be phosphorylated. Clearly, phosphorylation of key residues within the autoinhibitory C-terminal α helix and T222 in the activation segment induce conformational changes in the enzyme that allow highly efficient binding of peptide substrate (22). Analysis of the MK2 structures in conjunction with other known Ser/THR kinase structures suggests how this may occur.

Analysis of MK2 structures. The MK2 kinase core domain contains an overall fold that is very similar to the structures of other protein kinases. It is bilobal, consisting of a smaller N-terminal domain that is largely β sheet and a larger C-terminal domain dominated by a helices. MK2 shares two structural features within the N-terminal lobe that have been shown to be important in the regulation of many protein kinases (29). These structural elements are the highly conserved αC helix (residues 99–113), and the β1–β2 loop (residues 13–32), that has been termed the phosphate binding loop or "P loop". The P loop contains the hlghiy conserved ATP binding motif, GXGXXG (SEQ ID NO:6).

The C-terminal lobe contains another important regulatory feature, the MK2 activation segment (residues 207–233), which extends outward from the surface of the catalytic domain into solvent. Electron density was not observed for part of the segment, residues 216–226 including T222, which is one of the p38 phosphorylation sites. The activation segment is likely to be dynamic due to the role the loop is expected to play in the regulation of the enzyme. As discussed previously, MK2 41-364 is a constitutively active truncated version of the enzyme and lacks part of the C-terminal autoinhibitory sequence. Of the four MK2 structures in the asymmetric unit, C-terminal residues 345–364 are disordered in three and residues 358–364 are disordered in the fourth structure. The additional residues ordered in the latter structure are in contact with a symmetry related molecule.

Comparison of the MK2 binary ADP and staurosporine complex structures reveals a conformation change in the P loop where the loop shifts inward to bind to staurosporine and shifts outward to accommodate ADP.

Comparison with other kinases. Although the overall structure of the catalytic domain is highly conserved in many protein kinases, the mechanisms of regulation are quite diverse and in some cases, require dramatic conformational changes (29). The N-terminal and C-terminal lobes of many protein kinases are connected by a flexible hinge (residues 142–145, DGGE (SEQ ID NO:9) in MK2) thus the relative positions of the domains determine whether the kinase is in the "open" or inactive state versus the "closed" or active conformation (29). MK2 can be classified as an "RD" kinase as the catalytic aspartate, D186, is immediately preceded by an arginine, R185. Activation of a number of RD kinases requires phosphorylation on one or more threonine, serine, or tyrosine residues within the activation segment. Activation of MK2 requires phosphorylation, by p38, of the activation segment residue T222. Three protein kinases closely related to MK2, both by structure and shared regulatory mechanisms, are cAMP dependent protein kinase (PKA) (25), $Ca^{++}$/calmodulin dependent protein kinase (cAMK) (19) and Titin (21). All are Ser/Thr kinases and all require phosphorylation of a residue within the activation segment for activation of the kinase. Like MK2, all share an additional level of negative regulation by either a C-terminal autoinhibitory domain or a regulatory subunit. Although PKA lacks an autoinhibitory domain, a bound regulatory subunit maintains the kinase in an inactive conformation. Activation of PKA requires binding of an allosteric regulator, cAMP, to the regulatory subunit resulting in a conformation change and release of the catalytically active kinase subunit. cAMK is maintained in an inactive conformation by a C-terminal autoinhibitory domain that blocks both substrate and ATP binding. Activation of cAMK requires $Ca^{++}$/calmodulin binding which is thought to induce a conformation change resulting in the displacement of the autoinhibitory domain from the peptide and ATP binding sites. Titin also contains a C-terminal autoinhibitory domain that sterically blocks both substrate and ATP binding. Titin activation also requires $Ca^{++}$/calmodulin binding which is also thought to induce a conformation change resulting in the displacement of the autoinhibitory domain from the peptide and ATP binding sites.

The recently published structure of the autoinhibited, inactive form of MK2 47-400 reveals a unique mechanism of kinase regulation (22). The C-terminal autoinhibitory α helix extends along the entire surface of one face of the C-terminal lobe towards the active site and binds, hypothetically, as a pseudosubstrate. Asp366 acts as a phosphothreonine mimetic by coordinating with the basic residues R185 and K212 within the active site of the enzyme. This "pseudosubstrate" region is thought to be positioned in a manner that would effectively block binding of both protein and peptide substrates. The N-terminal lobe of the kinase domain has significant structural differences when compared to the active MK2 structures presented here. The β-2 strand in the MK2 structures of the present invention is replaced by an α helix which effectively disrupts the 5 strand β sheet observed in the structures of the present invention and many other kinases. Additionally, the αC and αD helices are shorter by 1.5 and 1.0 turns, respectively, in the autoinhibited structure.

Analysis of the MK2 active site. The ATP binding site of protein kinases is located in a deep cleft between the N-terminal and C-terminal lobes of the catalytic domain. The β1 and β2 strands in the N-terminal lobe constitute the P loop, which contains a glycine rich motif, GXGXXG (SEQ ID NO:6), is highly conserved in all protein kinases. The conserved glycines confer two important structural properties to the P loop, lack of side chains, which allow loop backbone amides to interact with ATP phosphates without steric hindrance, and backbone flexibility, which allows the P loop to adopt multiple conformations. Conformational flexibility of the P loop is an important factor in the regulation of many protein kinases. The structure of the MK2 P loop, within the context of a 5 strand β-sheet, and the spatial relationship of the αC2 helix are highly consistent with the structures of many protein kinases and also constitute an important part of the kinase active site.

A number of catalytic residues conserved in all protein kinases are spatially oriented to allow efficient transfer of phosphate from ATP to a protein substrate. The binary complex structure of MK2 41-364 and staurosporine is highly consistent with the ternary complex structure of PKA, PKI inhibitor peptide and staurosporine (30) thus forms the basis for a comparative analysis of the MK2 and PKA active sites. The analysis revealed that all active site residues discussed below are spatially conserved. Arg-185 and Asp-186 (R165, D166 in PKA) are catalytic loop residues that are invariant in all "RD" kinases. The catalytic aspartate, D186, is thought to act as a base to remove a proton from the protein substrate hydroxyl group. The phosphates of ATP are positioned for hydrolysis by interactions with backbone amide protons in the P loop and by ionic interactions with K93 (K72 in PKA), which is positioned and stabilized properly by E104 (E91 from PKA), a residue from the αC helix.

The MK2 activation segment, residues 207–233, extends outward from the kinase catalytic domain in a conformation partially stabilized by interactions with another symmetry related MK2 C-terminal domain. The activation segment is also disordered in the structure of the autoinhibited form of MK2 (22). The structural data suggest that the activation segment in unphosphorylated MK2 is highly dynamic and solvent accessible.

The MK2 structures of the present invention are of unphosphorylated enzyme. Although unphosphorylated MK2 41-364 is catalytically active and shows normal binding of ATP, the $K_m$ for LSP-1 peptide substrate 45-fold higher and the $V_{max}$ is 100-fold lower when compared to p38 phosphorylated MK2 41-400 (See Table 1). MK2 41-364 phosphorylated by p38, however, exhibits virtually identical peptide substrate binding and catalytic rates as compared to phosphorylated MK2 41-400. These data suggest that p38 phosphorylation of the activation segment residue T222 shifts the equilibrium of the activation segment from an unbound highly dynamic state, as observed in the MK2 structures of the present invention and in the inactive MK2 (22), to a more stable bound state required for efficient binding of peptide substrate and a high catalytic rate. Constitutively active MK2 41-364, however, lacks key residues within the pseudosubstrate region and as observed in the structures of the present invention, the majority of the autoinhibitory C-terminal helix is disordered and probably highly mobile thus allowing a lower level of peptide substrate binding and catalysis. Phosphorylation of MK2 41-364 by p38 restores full enzymatic activity presumably by shifting the equilibrium of the phosphorylated activation segment to the bound state allowing efficient binding of peptide substrate. These data also clearly show that residues 365–400 are not required for full catalytic activity in vitro.

As observed in many other RD kinases, including PKA, that require phosphorylation of a threonine residue within the activation segment for activation and efficient catalysis, two basic residues, R165 and K189 in PKA, are required for coordination and charge neutralization of the phosphoryl threonine. These residues are also spatially conserved in the MK2 structures (R185 and K212).

Differences in ADP and staurosporine structures. Comparison of the MK2 structures co-crystallized with ADP and staurosporine show that the only significant differences lie in the β-sheet containing the GKGING (SEQ ID NO:8) (71–76) loop. This loop, between β strand 1 and 2, and the loop on the other side of β strand 2 that connects to β strand 3 (residues 83–88) move extensively. Ile74 moves 4.7A closer to Gly209 in the activation loop when bound with staurosporine as compared to ADP where the loop is shifter outward to accommodate ADP. Conversely in the structure with ADP Thr86, found in the loop between β strand 2 and 3, moves closer to the protein core by 2.5A as compared to the loop in the structure with staurosporine. This coupled movement of the loops connecting strands 1, 2 and 3 allows the structural integrity of the b-sheet to remain while moving to accommodate different entities in the active site. Excluding the residues in the glycine rich loop, Asp207 and Lys93 make the only significant movement of residues in the active site. In the structure with ADP, these residues adopt orientations in close proximity to the ADP moiety thereby revealing their importance in the catalytic mechanism (29).

Biological implications. Cells exposed to heat shock, cytokines (TNF, IL-1β) or ultraviolet light display an increase in p38 MAP kinase activity due to phosphorylation by the upstream kinases MKK3 and MKK6. p38 in turn phosphorylates a variety of substrates including the transcription factors ATF-2 and CHOP-1, and other kinases such as MK2 and MK3. The p38/MK2 signal transduction cascade plays a pivotal role in the production of proinflammatory cytokines. Mice homozygously deficient in MK2 show a reduction in TNF, IL1β, IL-6 and IFN-γ synthesis and an increased rate of survival upon exposure to LPS, as compared to wild-type mice. MK2 controls the synthesis of cytokines by regulating the translation and/or stability of the encoding mRNAs through the AU-rich elements of the 3'-untranslated regions of the gene. These data indicate that MK2 is a vitally important enzyme in inflammatory based diseases and is a target for anti-inflammatory drug design.

The present invention is based on the determination of a catalytically active MK2 41-364 in complex with ADP and staurosporine. From the structures of the present invention, as well as the previous structure of the inactive enzyme 47-400 (22), it is observed that MK2 is regulated quite differently from other kinases that have a similar fold. Specifically, the autoinhibitory domain of MK2 does not block the nucleotide binding site and that phosphorylation of the residues in the activation domain are necessary for optimal binding of the substrate and activity of the enzyme. The structures of the present invention will permit the design of inhibitors to MK2.

TABLE 1

| Construct | p38 | Apparent $K_m$ (ATP) (μM) | Apparent $K_m$ (LSP-1) (μM) | $V_{max}$ μmole/min/mg |
|---|---|---|---|---|
| 41-400 | − | not determined | not determined | no activity |
| 41-400 | + | 7.0 + 0.7 | 13 + 1 | 8.9 + 0.1 |
| 41-364 | − | 15 + 1.5 | 584 + 50 | 0.076 + 0.004 |
| 41-364 | + | not determined | 20 + 2 | 11 + 14 |

Conditions: p38 (1.25 μg/ml), MK-2 (200 μg/mL), ATP (500 μM), incubate 1–2 hours at 25° C.

TABLE 2

Statistics for data collection and phase determination

| | MK2-Staurosporine | | | MK2-Staurosporine SeMet | MK2-ADP Native |
|---|---|---|---|---|---|
| | Remote | Peak | Inflection | | |
| Wavelength (Å) | λ3 = 0.95666 | λ1 = 0.97926 | λ2 = 0.97955 | 1.1 | 1.0 |
| Resolution Range (Å) | 50–3.1 | 50–3.1 | 50–3.1 | 50–2.7 | 25–3.1 |
| $R_{merge}$*(%) | 6.7(49.2) | 6.6(37.7) | 6.0(37.9) | 4.7(48.1) | 5.5(63.1) |
| Completeness (%) | 99.6(99.4) | 100(100) | 100(100) | 100(100) | 99.3(100.0) |
| Total Reflections | 255,756 | 427,587 | 449,393 | 215,726 | 90,852 |
| Unique Reflections | 82,015 | 42,754 | 42,927 | 52,352 | 12,997 |
| I/σ(I) | 10.8(1.7) | 16.2(3.4) | 18.0(3.6) | 20.2(1.6) | 34.9(3.3) |
| F'(e-)† | −2.95 | −4.60 | −7.21 | | |
| F"(e-) | 3.70 | 6.44 | 1.81 | | |

| | MAD phasing Statistics for MK2-Staurosporine | | | | | | | |
|---|---|---|---|---|---|---|---|---|
| Resolution limits (A) | 6.92 | 5.24 | 4.62 | 4.00 | 3.70 | 3.46 | 3.27 | 3.10 Overall |

Phasing power‡

| | | | | | | | | |
|---|---|---|---|---|---|---|---|---|
| λ3 anomalous | 3.36 | 2.08 | 1.72 | 1.07 | 0.82 | 0.68 | 0.55 | 0.52  1.08 |
| λ1 isomorphous | 0 | 0 | 0 | 0 | 0 | 0 | 0 | 0  0 |
| λ1 anomalous | 5.48 | 4.36 | 3.58 | 2.57 | 1.99 | 1.64 | 1.34 | 1.12  2.39 |
| λ2 isomorphous | 2.72 | 2.35 | 1.96 | 1.59 | 1.35 | 1.14 | 0.93 | 0.80  1.57 |
| λ2 anomalous | 2.99 | 1.67 | 1.33 | 0.83 | 0.62 | 0.53 | 0.40 | 0.36  0.80 |
| Mean FOM§ | 0.85 | 0.75 | 0.70 | 0.60 | 0.55 | 0.48 | 0.42 | 0.39  0.59 |

*$R_{merge} = \Sigma|I_h - \langle I_h \rangle|/\Sigma I_h$ where $\langle I_h \rangle$ is the average intensity over symmetry equivalents. Numbers in parentheses reflect statistics for the last shell.
†F' and F" reported values were refined by SHARP.
‡Phasing power = $\Sigma|F_h|/\Sigma||F_{PHobs}|-|F_{PHcalc}||$, where $F_h$ is the calculated heavy atom structure-factor amplitude.
§Figure of Merit = $\langle \Sigma P(\alpha)e^{i\alpha}/\Sigma P(\alpha)|\rangle$, where α is the phase and P(α) is the phase probability distribution.

TABLE 3

Residues of MK2 within 4 Å of staurosporin in MK2/staurosorin complex

Leu70, Gly71, Leu72, Gly73, Val78, Ala91, Val118, Mse138, Glu139, Cys140, Leu141, Glu145, Glu190, Asn191, Leu192, Thr206, Asp207

Residues of MK2 within 8 Å of staurosporin in MK2/staurosorin complex

Val69, Leu70, Gly71, Leu72, Gly73, Ile74, Gly76, Ala77, Val78, Leu79, Gln80, Lys89, Phe90, Ala91, Leu92, Lys93, Leu95, Glu104, His108, Val118, Arg119, Ile136, Val137, Mse138, Glu139, Cys140, Leu141, Asp142, Gly143, Gly144, Glu145, His184, Asp186, Lys188, Pro189, Glu190, Asn191, Leu192, Leu193, Tyr194, Thr195, Lys204, Leu205, Thr206, Asp207, Phe208, Gly209

Residues of MK2 within 4 Å of ADP in MK2/ADP complex

Leu70, Gly71, Leu72, Gly73, Ile74, Asn75, Val78, Ala91, Lys93, Met138, Glu139, Cys140, Leu141, Asn191, Thr206, Asp207

Residues of MK2 within 8 Å of ADP in MK2/ADP complex

Val69, Leu70, Gly71, Leu72, Gly73, Ile74, Asn75, Gly76, Ala77, Val78, Leu79, Gln80, Phe90, Ala91, Leu92, Lys93, Met94, Leu95, Glu104, His108, Val118, Ala119, Ile136, Val137, Met138, Glu139, Cys140, Leu141, Asp142, Gly143, Gly144, Glu145, His184, Asp186, Lys188, Pro189, Glu190, Asn191, Leu192, Leu193, Tyr194, Thr195, Leu205, Thr206, Asp207, Phe208, Gly209, Phe210

TABLE 4

| | Precipitant | Buffer | Additional Salt |
|---|---|---|---|
| #1 | 30% (v/v) polyethyleneglycol-400 | 0.1 M Cacodylate pH 6.5 | 0.2 M Lithium Sulfate |
| #2 | 1.0 M sodium citrate | 0.1 M Tris pH 7.0 | 0.2 M Sodium chloride |
| #3 | 0.8 M sodium dihydrogen phosphate 1.2 M K$_2$HPO$_4$ dipotassium hydrogen phosphate | 0.2 M Acetate pH 4.5 | |
| #4 | 1.0 M sodium citrate | 0.1 M Cacodylate pH 6.5 | |
| #5 | | 1.9 M sodium malonate pH 5.0 | |
| #6 | | 1.5 M sodium malonate pH 6.0 | |
| #7 | | 1.5 M sodium malonate pH 7.0 | |
| #8 | 2.0 M ammonium Sulfate | | |
| #9 | | 1/17 M NaH$_2$PO$_4$ 0.63 M K$_2$HPO$_4$ (Final: 1.8 M Sodium/ Pottassium Phosphate pH 6.3) | |
| #10 | | 0.27 M NaH$_2$PO$_4$ 1.53 M K$_2$HPO$_4$ (Final: 1.8 M Sodium/ Pottassium Phosphate pH 7.5) | |
| #11 | | 0.072 M NaH$_2$PO$_4$ 1.728 M K$_2$HPO$_4$ (Final: 1.8 M Sodium/ Pottassium Phosphate pH 8.2) | |
| #12 | 1.6 M ammonium sulfate | 0.1 M citric acid pH 5.0 | |
| #13 | 2.4 M ammonium sulfate | 0.1 M HEPES pH 7.0 | |
| #14 | 30% v/v polyethyleneglycol-400 | 0.1 M Tris hydrochloride pH 8.5 | 0.2 M tri-Sodium citrate dihydrate |
| #15 | 1 M potassium sodium tartrate tetrahydrate | 0.1 M HEPES-Na pH 7.5 | |
| #16 | 18% v/v polyethyleneglycol-400 | 0.1 M HEPES-Na pH 7.5 | 0.1 M ammonium sulfate |
| #17 | 1 M tri-sodium citrate dihydrate | 0.1 M HEPES-Na pH 7.5 | |
| #18 | 1.6 M Sodium/Potassium Tartrate | 0.1 M MES pH 6.5 | |
| #19 | 2.0 M Ammonium Sulfate | 0.1 M HEPES pH 7.5 | 2% PEG 400 |

REFERENCES

1. Lee, J. C., Laydon, J. T., McDonnel, P. C., Gallagher, T. F., Kumar, S., Green, D., McNulty, D., Blumenthal, M. J., Heys, J. R., Landvatter, S. W., al., e. (1994) A protein kinase involved in the regulation of inflammatory cytokine biosynthesis. *Nature* 372, 739–746.

2. Cuenda, A., Rouse, J., Doza, Y. N., Meier, R., Cohen, P., Gallagher, T. F., Young, P. R., Lee, J. C. (1995) SB 203580 is a specific inhibitor of a MAP kinase homologue which is stimulated by cellular stresses and interleukin-1. *FEBS Letters* 364, 229–233.

3. Kotlyarov, A., Neininger, A., Schubert, C., Eckert, R., Birchmeier, C., Volk, H.-D., Gaestel, M. (1999) MAP-KAP kinase 2 is essential for LPS-induced TNF-biosynthesis. *Nat. Cell. Biol.* 1, 94–97.

4. Neininger, A., Kontoyiannis, D., Kotlyarov, A., Winzen, R., Eckert, R., Volk, H.-D., Holtmann, H., Kollias, G., Gaestel, M. (2002) MK2 Targets AU-rich Elements and Regulates Biosynthesis of Tumor Necrosis Factor and Interleukin-6 Independently at Different Post-transcriptional Levels. *J. Biol. Chem.* 277, 3065–3068.

5. Tan, Y., Rouse, J., Zhang, A., Cariati, S., Cohen, P., Comb, M. (1996) FGF and stress regulate CREB and ATF-1 via a pathway involving p38 MAP kinase and MAPKAP kinase-2. *EMBO J.* 15, 4629–4642.

6. Lavoie, J., Hickey, E., Weber, L., Landry, J. (1993) Modulation of actin microfilament dynamics and fluid phase pinocytosis by phosphorylation of heat shock protein 27. *J. Biol. Chem.* 268, 24210–24214.

7. Stokoe, D., Engel, K., Campbell, D. G., Cohen, P., Gaestel, M. (1992) Identification of MAPKAP kinase 2 as a major enzyme responsible for the phosphorylation of the small mammalian heat shock proteins. *FEBS Letters* 313, 307–313.

8. Ben-Levy, R., Leighton, I., Doza, Y., Attwood, P., Morrice, N., Marshall, C., Cohen, P. (1995) Identification of novel phosphorylation sites required for activation of MAPKAP kinase-2. *EMBO J.* 14, 5920–5930.
9. Hedges, J. C., Dechert, M. A., Yamboliev, I. A., Martin, J. L., Hickey, E., Weber, L. A., Gerthoffer, W. T. (1999) A Role for p38MAPK/HSP27 Pathway in Smooth Muscle Cell Migration. *J. Biol. Chem.* 274, 24211–24219.
10. Kotlyarov, A., Yannoni, Y., Fritz, S., Laass, K., Telliez, J.-B., Pitman, D., Lin, L.-L., Gaestel, M. (2002) Distinct Cellular Functions of MK2. *Mol. Cell. Biol.* 22, 4827–4835.
11. Stokoe, D., Caudwell, B., Cohen, P. T., Cohen, P. (1993) The substrate specificity and structure of mitogen-activated protein (MAP) kinase-activated protein kinase-2. *Biochem. J.* 296, 843–849.
12. Engel, K., Kotlyarov, A., Gaestel, M. (1998) Leptomycin B-sensitive nuclear export of MAPKAP kinase 2 is regulated by phosphorylation. *EMBO J.* 17, 3363–3371.
13. Ben-Levy, R., Hooper, S., Wilson, R., Paterson, H. F., Marshall, C. J. (1998) Nuclear export of the stress-activated protein kinase p38 mediated by its substrate MAPKAP kinase-2. *Curr. Biol.* 8, 1049–1057.
14. Engel, K., Plath, K., Gaestel, M. (1993) The MAP kinase-activated protein kinase 2 contains a proline-rich SH3-binding domain. *FEBS Letters* 336, 143–147.
15. Veron, M., Radzio-Andzelm, E., Tsigelny, I., Eyck, L., Taylor, S. (1993) A Conserved Helix Motif Complements the Protein Kinase Core. *Proc. Natl. Acad. Sci.* 90, 10618–10622.
16. Zu, Y.-L., Wu, F., Gilchrist, A., Ai, Y., Labadia, M. E., Huang, C.-K. (1994) The Primary Structure of a Human MAP Kinase Activated Protein Kinase 2. *Biochem. Biophys. Res. Commun.* 200, 1118–1124.
17. Stokoe, D., Campbell, D., Nakielny, S., Hidaka, H., Leevers, S., Marshall, C., Cohen, P. (1992) MAPKAP kinase-2; a novel protein kinase activated by mitogen-activated protein kinase. *EMBO J.* 11, 3985–3994.
18. Engel, K., Schultz, H., Martin, F., Kotlyarov, A., Plath, K., Hahn, M., Heinemann, U., Gaestel, M. (1995) Constitutive Activation of Mitogen-activated Protein Kinase-activated Protein Kinase 2 by Mutation of Phosphorylation Sites and an A-helix Motif. *J. Biol. Chem.* 270, 27213–27221.
19. Zheng, J. H., Trafny, E. A., Knighton, D. R., Xuong, N. H., Taylor, S. S., Teneyck, L. F., Sowadski, J. M. (1993) Crystal structure of the catalytic subunit of cAMP-dependent protein kinase complexed with magnesium-ATP and peptide inhibitor. *Biochemistry* 32, 2154–61.
20. Goldberg, J., Nairn, A. C., Kuriyan, J. (1996) Structural basis for the autoinhibition of calcium/calmodulin-dependent protein kinase I. *Cell* 84, 875–87.
21. Mayans, O., van der Ven, P. F. M., Wilm, M., Mues, A., Young, P., Furst, D. O., Wilmanns, M., Gautel, M. (1998) Structural basis for activation of the titin kinase doamin during myofibrillogenesis. *Nature* 395, 863–869.
22. Meng, W., Swenson, L. L., Fitzgibbon, M. J., Hayakawa, K., Haar, E. t., Behrens, A. E., Fulghum, J. R., Lippke, J. A. (2002) Structure of MAPKAP kinase 2 suggests a bifunctional switch that couples kinase ativation with nuclear export. *J. Biol. Chem.,* 37401–37405.
23. McLaughlin, M. M., Kumar, S., McDonnell, P. C., Van Horn, S., Lee, J. C., Livi, G. P., Young, P. R. (1996) Identification of Mitogen-activated Protein (MAP) Kinase-activated Protein Kinase-3, a Novel Substrate of CSBP p38 MAP Kinase. *J. Biol. Chem.* 271, 8488–8492.
24. Ni, H., Wang, X. S., Diener, K., Yao, Z. (1998) MAP-KAPK5, a Novel Mitogen-Activated Protein Kinase (MAPK)-Activated Protein Kinase, Is a Substrate of the Extracellular-Regulated Kinase (ERK) and p38 Kinase. *Biochem. Biophys. Res. Commun.* 243, 492–496.
25. Komatsu, S., Murai, N., Totsukawa, G., Abe, M., Akasaka, K., Shimada, H., Hosoya, H. (1997) Identification of MAPKAPK homolog (MAPKAPK-4) as a myosin II regulatory light-chain kinase in sea urchin egg extracts. *Arch. Biochem. Biophys.* 343, 55–62.
26. Clifton, A. D., Young, P. R., Cohen, P. (1996) A comparison of the substrate specificity of MAPKAP kinase-2 and MAPKAP kinase-3 and their activation by cytokines and cellular stress. *FEBS Letters* 392, 209–214.
27. Johnson, L. N., Noble, M. E. M., Owen, D. J. (1996) Active and Inactive Protein Kinases: Structural Basis for Regulation. *Cell* 85, 149–158.
28. Tanoue, T., Adachi, M. Moriguchi, T., Nishida, E. (2000) A conserved docking motif in MAP kinases common to substrates, activators and regulators. *Nat. Cell. Biol.* 2, 110–116.
29. Huse, M., Kuriyan, J. (2002) The Conformational Plasticity of Protein Kinases. *Cell* 109, 275–282.
30. Prade, L., Engh, R. A., Girod, A., Kinzel, V., Huber, R., Bossemeyer, D. (1997) Staurosporine-induced conformational changes of cAMP-dependent protein kinase catalytic subunit explain inhibitory potential. *Structure* 5, 1627–37.
31. Bradford, M. M. (1976) A Rapid and Sensitive Method for the Quantitation of Microgram Quantities of Protein Utilizing the Principle of Protein-Dye Binding. *Analytical Biochemistry* 72, 248–254.
32. Leslie, A. G. W. (1992) Recent changes to the MOSFLM package for processing film and image plate data. *Joint CCP4+ESF-EAMCB Newsletter on Protein Crystallography* 26.
33. Weeks, C. M., Miller, R. (1999) The design and implementation of SnB v2.0. *J. App. Crystallogr.* 32, 120–124.
34. Sheldrick, G. M. (1997) Patterson Superposition and ab Initio Phasing. *Methods in Enzymol.* 276, 628–641.
35. De La Fortelle, E., Bricogne, G. (1997) Maximum-likelihood heavy atom parameter refinement and multiwavelength anomalous diffraction methods. *Methods Enzymol.* 276, 472–494.
36. Brunger, A. T., Adams, P. D., Clore, G. M., DeLano, W. L., Gros, P., Grosse-Kunstleve, R. W., Jiang, J. S., Kuszewski, J., Nilges, M., Pannu, N. S. (1998) Crystallography & NMR system: A new software suite for macromolecular structure determination. *Acta Crystallogr. D*54, 905–921.
37. CCP4 (1994) The CCP-4 suite: programs for X-ray crystallography. *Acta Crystallogr. D*50, 760–763.
38. Bricogne, G. (1993) Direct phase determination by entropy maximization and likelihood ranking; status report and perspectives. Acta Crystallogr. D54, 905–921.
39. McPherson, A. (1999) Crystallization of Biological Macromolecules, Cold Spring Harbor Press, Cold Spring Harbor.

All publications mentioned herein above, whether to issued patents, pending applications, published articles, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for identifying an agent that interacts with MAP Kinase Activated Protein Kinase 2 (MK2), comprising:

provinding a crystallized MK2;

determining the three dimensional structure of MK2;

generating a three dimensional model of MK2 using the structural coordinates of (i) molecules A, B, C, or D of MK2 according to FIGS. 2 through 2A-204, (ii) a portion of molecules A, B, C, or D of MK2 according to FIGS. 2 through 2A-204, (iii) molecule A of MK2 according to FIGS. 3 through 3A-40, or (iv) a portion of molecule A according to FIGS. 3 through 3A-40, ± a root mean square deviation from the backbone atoms of said amino acids of not more than 1.5 Å;
identifying a putative agent that interacts with MK2 by performing computer fitting analysis of the putative agent with said three dimensional model; and
obtaining the agent.

2. The method of claim 1, wherein the ± a root mean square deviation from the backbone atoms of said amino acids is not more than 1.0 Å.

3. The method of claim 1, wherein the ± a root mean square deviation from the backbone atoms of said amino acids is not more than 0.5 Å.

4. The method of claim 1, wherein obtaining the agent comprises synthesizing the agent.

5. A method for designing a putative agent that interacts with an active site of MK2, said method comprising:
providing a crystallized MK2;
determining the three dimensional structure of MK2;
generating a three dimensional model of said active site using the relative structural coordinates of amino acid residues Leu70, Gly71, Leu72, Gly73, Val78, Ala91, Val118, Mse138, Glu139, Cys140, Leu141, Glu145, Glu190, Asn191, Leu192, Thr206, and Asp207 of molecules A, B, C or D of MK2 according to FIGS. 2 through 2A-204, ± a root mean square deviation from the backbone atoms of said amino acids of not more than 1.5 Å;
designing a putative agent that interacts with said active site by performing computer fitting analysis of said putative agent with the three dimensional model; and
obtaining the agent.

6. The method of claim 5, wherein the ± a root mean square deviation from the backbone atoms of said amino acids is not more than 1.0 Å.

7. The method of claim 5, wherein the ± a root mean square deviation from the backbone atoms of said amino acids is not more than 0.5 Å.

8. The method of claim 5, wherein the three dimensional model further comprises the relative structural coordinates for amino acid residues Val69, Ile74, Gly76, Ala77, Leu79, Gln80, Lys89, Phe90, Leu92, Lys93, Leu95, Glu104, His108, Arg119, Ile136, Val137, Asp142, Gly143, Gly144, His184, Asp186, Lys188, Pro189, Leu193, Tyr194, Thr195, Lys204, Leu205, Phe208, and Gly209 of molecules A, B, C, or D according to FIGS. 2 through 2A-204, ± a root mean square deviation from the backbone atoms of said amino acids of not more than 1.5 Å.

9. The method of claim 8, wherein the ± a root mean square deviation from the backbone atoms of said amino acids is not more than 1.0 Å.

10. The method of claim 8, wherein the ± a root mean square deviation from the backbone atoms of said amino acids is not more than 0.5 Å.

11. The method of claim 5, wherein obtaining the agent comprises synthesizing the agent.

12. A method for identifying a putative agent that interacts with an active site of MK2, said method comprising:
providing a crystallized MK2;
determining the three dimensional structure of MK2;
generating a three dimensional model of said active site using the relative structural coordinates of amino acid residues Leu70, Gly71, Leu72, Gly73, Ile74, Asn75, Val 78, Ala91, Lys93, Met138, Glu139, Cys140, Leu141, Asn191, Thr206, and Asp207 of molecule A of MK2 according to FIGS. 3 through 3A-40, ± a root mean square deviation from the backbone atoms of said of not more than 1.5 Å;
designing a putative agent that interacts with said active site by performing computer fitting analysis of said putative agent with the three dimemensional model; and
obtaining the agent.

13. The method of claim 12, wherein the ± a root mean square deviation from the backbone atoms of said amino acids is not more than 1.0 Å.

14. The method of claim 12, wherein the ± a root mean square deviation from the backbone atoms of said amino acids is not more than 0.5 Å.

15. The method of claim 12 wherein the three dimensional model further comprises the relative structural coordinates for amino acid residues Val69, Gly76, Ala77, Leu79, Gln80, Phe90, Leu92, Met94, Leu95, Glu104, His108, Val118, Ala119, Ile136, Val137, Asp142, Gly143, Gly144, Glu145, His184, Asp186, Lys188, Pro189, Glu190, Leu192, Leu193, Tyr194, Thr195, Leu205, Phe208, Gly209, and Phe210 of molecule A of MK2 according to FIGS. 3 through 3A-40, ± a root mean square deviation from the backbone atoms of said amino acids of not more than 1.5 Å.

16. The method of claim 15, wherein the ± a root mean square deviation from the backbone atoms of said amino acids is not more than 1.0 Å.

17. The method of claim 15, wherein the ± a root mean square deviation from the backbone atoms of said amino acids is not more than 0.5 Å.

18. The method of claim 12, wherein obtaining the agent comprises synthesizing the agent.

* * * * *

SEQUENCE LISTING

<160> NUMBER OF SEQ ID NOS: 10

<210> SEQ ID NO 1
<211> LENGTH: 400
<212> TYPE: PRT
<213> ORGANISM: Homo sapiens
<220> FEATURE:
<221> NAME/KEY: MISC_FEATURE
<223> OTHER INFORMATION: MK2

<400> SEQUENCE: 1

```
Met Leu Ser Asn Ser Gln Gly Gln Ser Pro Val Pro Phe Pro Ala
1               5                   10                  15

Pro Ala Pro Pro Gln Pro Pro Thr Pro Ala Leu Pro His Pro Pro
            20                  25                  30

Ala Gln Pro Pro Pro Pro Pro Gln Gln Phe Pro Gln Phe His Val
            35                  40                  45

Lys Ser Gly Leu Gln Ile Lys Lys Asn Ala Ile Ile Asp Asp Tyr Lys
    50                  55                  60

Val Thr Ser Gln Val Leu Gly Leu Gly Ile Asn Gly Lys Val Leu Gln
65                  70                  75                  80

Ile Phe Asn Lys Arg Thr Gln Glu Lys Phe Ala Leu Lys Met Leu Gln
                85                  90                  95

Asp Cys Pro Lys Ala Arg Arg Glu Val Glu Leu His Trp Arg Ala Ser
                100                 105                 110

Gln Cys Pro His Ile Val Arg Ile Val Asp Val Tyr Glu Asn Leu Tyr
            115                 120                 125

Ala Gly Arg Lys Cys Leu Leu Ile Val Met Glu Cys Leu Asp Gly Gly
        130                 135                 140

Glu Leu Phe Ser Arg Ile Gln Asp Arg Gly Asp Gln Ala Phe Thr Glu
145                 150                 155                 160

Arg Glu Ala Ser Glu Ile Met Lys Ser Ile Gly Glu Ala Ile Gln Tyr
                165                 170                 175

Leu His Ser Ile Asn Ile Ala His Arg Asp Val Lys Pro Glu Asn Leu
            180                 185                 190

Leu Tyr Thr Ser Lys Arg Pro Asn Ala Ile Leu Lys Leu Thr Asp Phe
        195                 200                 205

Gly Phe Ala Lys Glu Thr Thr Ser His Asn Ser Leu Thr Thr Pro Cys
210                 215                 220

Tyr Thr Pro Tyr Tyr Val Ala Pro Glu Val Leu Gly Pro Glu Lys Tyr
225                 230                 235                 240

Asp Lys Ser Cys Asp Met Trp Ser Leu Gly Val Ile Met Tyr Ile Leu
                245                 250                 255

Leu Cys Gly Tyr Pro Pro Phe Tyr Ser Asn His Gly Leu Ala Ile Ser
            260                 265                 270

Pro Gly Met Lys Thr Arg Ile Arg Met Gly Gln Tyr Glu Phe Pro Asn
        275                 280                 285

Pro Glu Trp Ser Glu Val Ser Glu Glu Val Lys Met Leu Ile Arg Asn
        290                 295                 300

Leu Leu Lys Thr Glu Pro Thr Gln Arg Met Thr Ile Thr Glu Phe Met
305                 310                 315                 320

Asn His Pro Trp Ile Met Gln Ser Thr Lys Val Pro Gln Thr Pro Leu
                325                 330                 335
```

-continued

His Thr Ser Arg Val Leu Lys Glu Asp Lys Glu Arg Trp Glu Asp Val
                340                 345                 350

Lys Glu Glu Met Thr Ser Ala Leu Ala Thr Met Arg Val Asp Tyr Glu
            355                 360                 365

Gln Ile Lys Ile Lys Ile Glu Asp Ala Ser Asn Pro Leu Leu
        370                 375                 380

Lys Arg Arg Lys Lys Ala Arg Ala Leu Glu Ala Ala Leu Ala His
385                 390                 395                 400

<210> SEQ ID NO 2
<211> LENGTH: 382
<212> TYPE: PRT
<213> ORGANISM: Homo sapiens
<220> FEATURE:
<221> NAME/KEY: MISC_FEATURE
<223> OTHER INFORMATION: MK3

<400> SEQUENCE: 2

Met Asp Gly Glu Thr Ala Glu Glu Gln Gly Gly Pro Val Pro Pro Pro
1               5                   10                  15

Val Ala Pro Gly Gly Pro Gly Leu Gly Gly Ala Pro Gly Gly Arg Arg
            20                  25                  30

Glu Pro Lys Lys Tyr Ala Val Thr Asp Asp Tyr Gln Leu Ser Lys Gln
        35                  40                  45

Val Leu Gly Leu Gly Val Asn Gly Lys Val Leu Glu Cys Phe His Arg
    50                  55                  60

Arg Thr Gly Gln Lys Cys Ala Leu Lys Leu Leu Tyr Asp Ser Pro Lys
65                  70                  75                  80

Ala Arg Gln Glu Val Asp His His Trp Gln Ala Ser Gly Gly Pro His
                85                  90                  95

Ile Val Cys Ile Leu Asp Val Tyr Glu Asn Met His His Gly Lys Arg
            100                 105                 110

Cys Leu Leu Ile Ile Met Glu Cys Met Glu Gly Gly Glu Leu Phe Ser
        115                 120                 125

Arg Ile Gln Glu Arg Gly Asp Gln Ala Phe Thr Glu Arg Glu Ala Ala
    130                 135                 140

Glu Ile Met Arg Asp Ile Gly Thr Ala Ile Gln Phe Leu His Ser His
145                 150                 155                 160

Asn Ile Ala His Arg Asp Val Lys Pro Glu Asn Leu Leu Tyr Thr Ser
                165                 170                 175

Lys Glu Lys Asp Ala Val Leu Lys Leu Thr Asp Phe Gly Phe Ala Lys
            180                 185                 190

Glu Thr Thr Gln Asn Ala Leu Gln Thr Pro Cys Tyr Thr Pro Tyr Tyr
        195                 200                 205

Val Ala Pro Glu Val Leu Gly Pro Glu Lys Tyr Asp Lys Ser Cys Asp
    210                 215                 220

Met Trp Ser Leu Gly Val Ile Met Tyr Ile Leu Leu Cys Gly Phe Pro
225                 230                 235                 240

Pro Phe Tyr Ser Asn Thr Gly Gln Ala Ile Ser Pro Gly Met Lys Arg
                245                 250                 255

Arg Ile Arg Leu Gly Gln Tyr Gly Phe Pro Asn Pro Glu Trp Ser Glu
            260                 265                 270

Val Ser Glu Asp Ala Lys Gln Leu Ile Arg Leu Leu Leu Lys Thr Asp
        275                 280                 285

Pro Thr Glu Arg Leu Thr Ile Thr Gln Phe Met Asn His Pro Trp Ile
    290                 295                 300

-continued

```
Asn Gln Ser Met Val Val Pro Gln Thr Pro Leu His Thr Ala Arg Val
305                 310                 315                 320

Leu Gln Glu Asp Lys Asp His Trp Asp Glu Val Lys Glu Met Thr
            325                 330                 335

Ser Ala Leu Ala Thr Met Arg Val Asp Tyr Asp Gln Val Lys Ile Lys
            340                 345                 350

Asp Leu Lys Thr Ser Asn Asn Arg Leu Leu Asn Lys Arg Arg Lys Lys
            355                 360                 365

Gln Ala Gly Ser Ser Ser Ala Ser Gln Gly Cys Asn Asn Gln
    370                 375                 380

<210> SEQ ID NO 3
<211> LENGTH: 473
<212> TYPE: PRT
<213> ORGANISM: Homo sapiens
<220> FEATURE:
<221> NAME/KEY: MISC_FEATURE
<223> OTHER INFORMATION: MK5

<400> SEQUENCE: 3

Met Ser Glu Glu Ser Asp Met Asp Lys Ala Ile Lys Glu Thr Ser Ile
1               5                   10                  15

Leu Glu Glu Tyr Ser Ile Asn Trp Thr Gln Lys Leu Gly Ala Gly Ile
            20                  25                  30

Ser Gly Pro Val Arg Val Cys Val Lys Lys Ser Thr Gln Glu Arg Phe
        35                  40                  45

Ala Leu Lys Ile Leu Leu Asp Arg Pro Lys Ala Arg Asn Glu Val Arg
    50                  55                  60

Leu His Met Met Cys Ala Thr His Pro Asn Ile Val Gln Ile Ile Glu
65                  70                  75                  80

Val Phe Ala Asn Ser Val Gln Phe Pro His Glu Ser Ser Pro Arg Ala
                85                  90                  95

Arg Leu Leu Ile Val Met Glu Met Met Glu Gly Gly Glu Leu Phe His
                100                 105                 110

Arg Ile Ser Gln His Arg His Phe Thr Glu Lys Gln Ala Ser Gln Val
            115                 120                 125

Thr Lys Gln Ile Ala Leu Ala Leu Arg His Cys His Leu Leu Asn Ile
    130                 135                 140

Ala His Arg Asp Leu Lys Pro Glu Asn Leu Leu Phe Lys Asp Asn Ser
145                 150                 155                 160

Leu Asp Ala Pro Val Lys Leu Cys Asp Phe Gly Phe Ala Lys Ile Asp
                165                 170                 175

Gln Gly Asp Leu Met Thr Pro Gln Phe Thr Pro Tyr Tyr Val Ala Pro
            180                 185                 190

Gln Val Leu Glu Ala Gln Arg Arg His Gln Lys Glu Lys Ser Gly Ile
        195                 200                 205

Ile Pro Thr Ser Pro Thr Pro Tyr Thr Tyr Asn Lys Ser Cys Asp Leu
    210                 215                 220

Trp Ser Leu Gly Val Ile Ile Tyr Val Met Leu Cys Gly Tyr Pro Pro
225                 230                 235                 240

Phe Tyr Ser Lys His His Ser Arg Thr Ile Pro Lys Asp Met Arg Arg
                245                 250                 255

Lys Ile Met Thr Gly Ser Phe Glu Phe Pro Glu Glu Glu Trp Ser Gln
            260                 265                 270

Ile Ser Glu Met Ala Lys Asp Val Val Arg Lys Leu Leu Lys Val Lys
        275                 280                 285
```

```
Pro Glu Glu Arg Leu Thr Ile Glu Gly Val Leu Asp His Pro Trp Leu
    290                 295                 300

Asn Ser Thr Glu Ala Leu Asp Asn Val Leu Pro Ser Ala Gln Leu Met
305                 310                 315                 320

Met Asp Lys Ala Val Val Ala Gly Ile Gln Gln Ala His Ala Glu Gln
                325                 330                 335

Leu Ala Asn Met Arg Ile Gln Asp Leu Lys Val Ser Leu Lys Pro Leu
            340                 345                 350

His Ser Val Asn Asn Pro Ile Leu Arg Lys Lys Leu Leu Gly Thr
        355                 360                 365

Lys Pro Lys Asp Ser Val Tyr Ile His Asp His Glu Asn Gly Ala Glu
370                 375                 380

Asp Ser Asn Val Ala Leu Glu Lys Leu Arg Asp Val Ile Ala Gln Cys
385                 390                 395                 400

Ile Leu Pro Gln Ala Gly Lys Gly Glu Asn Glu Asp Glu Lys Leu Asn
                405                 410                 415

Glu Val Met Gln Glu Ala Trp Lys Tyr Asn Arg Glu Cys Lys Leu Leu
            420                 425                 430

Arg Asp Thr Leu Gln Ser Phe Ser Trp Asn Gly Arg Gly Phe Thr Asp
        435                 440                 445

Lys Val Asp Arg Leu Lys Leu Ala Glu Ile Val Lys Gln Val Ile Glu
450                 455                 460

Glu Gln Thr Thr Ser His Glu Ser Gln
465                 470

<210> SEQ ID NO 4
<211> LENGTH: 326
<212> TYPE: PRT
<213> ORGANISM: Homo sapiens

<400> SEQUENCE: 4

Met Gly Gln Gln Phe Pro Gln Phe His Val Lys Ser Gly Leu Gln Ile
1               5                   10                  15

Lys Lys Asn Ala Ile Ile Asp Asp Tyr Lys Val Thr Ser Gln Val Leu
            20                  25                  30

Gly Leu Gly Ile Asn Gly Lys Val Leu Gln Ile Phe Asn Lys Arg Thr
        35                  40                  45

Gln Glu Lys Phe Ala Leu Lys Met Leu Gln Asp Cys Pro Lys Ala Arg
    50                  55                  60

Arg Glu Val Glu Leu His Trp Arg Ala Ser Gln Cys Pro His Ile Val
65                  70                  75                  80

Arg Ile Val Asp Val Tyr Glu Asn Leu Tyr Ala Gly Arg Lys Cys Leu
                85                  90                  95

Leu Ile Val Met Glu Cys Leu Asp Gly Gly Glu Leu Phe Ser Arg Ile
            100                 105                 110

Gln Asp Arg Gly Asp Gln Ala Phe Thr Glu Arg Glu Ala Ser Glu Ile
        115                 120                 125

Met Lys Ser Ile Gly Glu Ala Ile Gln Tyr Leu His Ser Ile Asn Ile
    130                 135                 140

Ala His Arg Asp Val Lys Pro Glu Asn Leu Leu Tyr Thr Ser Lys Arg
145                 150                 155                 160

Pro Asn Ala Ile Leu Lys Leu Thr Asp Phe Gly Phe Ala Lys Glu Thr
                165                 170                 175

Thr Ser His Asn Ser Leu Thr Thr Pro Cys Tyr Thr Pro Tyr Tyr Val
            180                 185                 190
```

```
Ala Pro Glu Val Leu Gly Pro Glu Lys Tyr Asp Lys Ser Cys Asp Met
        195                 200                 205

Trp Ser Leu Gly Val Ile Met Tyr Ile Leu Leu Cys Gly Tyr Pro Pro
210                 215                 220

Phe Tyr Ser Asn His Gly Leu Ala Ile Ser Pro Gly Met Lys Thr Arg
225                 230                 235                 240

Ile Arg Met Gly Gln Tyr Glu Phe Pro Asn Pro Glu Trp Ser Glu Val
                245                 250                 255

Ser Glu Glu Val Lys Met Leu Ile Arg Asn Leu Leu Lys Thr Glu Pro
            260                 265                 270

Thr Gln Arg Met Thr Ile Thr Glu Phe Met Asn His Pro Trp Ile Met
        275                 280                 285

Gln Ser Thr Lys Val Pro Gln Thr Pro Leu His Thr Ser Arg Val Leu
    290                 295                 300

Lys Glu Asp Lys Glu Arg Trp Glu Asp Val Lys Glu Glu Met Thr Ser
305                 310                 315                 320

Ala Leu Ala Thr Met Arg
                325

<210> SEQ ID NO 5
<211> LENGTH: 981
<212> TYPE: DNA
<213> ORGANISM: Homo sapiens

<400> SEQUENCE: 5
atgggtcagc agttcccgca gttccacgtc aagtccggcc tgcagatcaa gaagaacgcc      60
atcatcgatg actacaaggt caccagccag gtcctggggc tgggcatcaa cggcaaagtt     120
ttgcagatct tcaacaagag gacccaggag aaattcgccc tcaaaatgct tcaggactgc     180
cccaaggccc gcagggaggt ggagctgcac tggcgggcct cccagtgccc gcacatcgta     240
cggatcgtgg atgtgtacga gaatctgtac gcagggagga agtgcctgct gattgtcatg     300
gaatgtttgg acggtggaga actctttagc cgaatccagg atcgaggaga ccaggcattc     360
acagaaagag aagcatccga atcatgaag agcatcggtg aggccatcca gtatctgcat     420
tcaatcaaca ttgcccatcg ggatgtcaag cctgagaatc tcttatacac ctccaaaagg     480
cccaacgcca tcctgaaact cactgacttt ggctttgcca aggaaaccac cagccacaac     540
tctttgacca ctccttgtta tacaccgtac tatgtggctc agaagtgct gggtccagag     600 aagtatgaca gtcctgtga catgtggtcc ctgggtgtca tcatgtacat cctgctgtgt     660
gggtatcccc ccttctactc caaccacggc cttgccatct ctccgggcat gaagactcgc     720
atccgaatgg gccagtatga atttcccaac ccagaatggt cagaagtatc agaggaagtg     780
aagatgctca ttcggaatct gctgaaaaca gagcccaccc agagaatgac catcaccgag     840
tttatgaacc acccttggat catgcaatca acaaaggtcc ctcaaacccc actgcacacc     900
agccgggtcc tgaaggagga caaggagcgg tgggaggatg tcaaggagga gatgaccagt     960
gccttggcca caatgcgctg a                                                981

<210> SEQ ID NO 6
<211> LENGTH: 6
<212> TYPE: PRT
<213> ORGANISM: Homo sapiens
<220> FEATURE:
<221> NAME/KEY: MISC_FEATURE
<223> OTHER INFORMATION: X = any amino acid;
      ATP binding site motiff
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 6

Gly Xaa Gly Xaa Xaa Gly
1               5

<210> SEQ ID NO 7
<211> LENGTH: 18
<212> TYPE: PRT
<213> ORGANISM: Homo sapiens
<220> FEATURE:
<221> NAME/KEY: MISC_FEATURE
<223> OTHER INFORMATION: MK2 bipartite nuclear localization signal

<400> SEQUENCE: 7

Lys Lys Ile Glu Asp Asp Ala Ser Asn Pro Leu Leu Leu Lys Arg Arg
1               5                   10                  15

Lys Lys

<210> SEQ ID NO 8
<211> LENGTH: 6
<212> TYPE: PRT
<213> ORGANISM: Homo sapiens

<400> SEQUENCE: 8

Gly Lys Gly Ile Asn Gly
1               5

<210> SEQ ID NO 9
<211> LENGTH: 4
<212> TYPE: PRT
<213> ORGANISM: Homo sapiens
<220> FEATURE:
<221> NAME/KEY: MISC_FEATURE
<223> OTHER INFORMATION: MK2 flexible hinge

<400> SEQUENCE: 9

Asp Gly Gly Glu
1

<210> SEQ ID NO 10
<211> LENGTH: 16
<212> TYPE: PRT
<213> ORGANISM: Salmonella typhosa
<220> FEATURE:
<221> NAME/KEY: MISC_FEATURE
<223> OTHER INFORMATION: LSP-1 peptide

<400> SEQUENCE: 10

Arg Thr Pro Lys Leu Ala Arg Gln Ala Ser Ile Glu Leu Pro Ser Met
1               5                   10                  15
```